United States Patent
Kotian et al.

(10) Patent No.: US 12,054,492 B2
(45) Date of Patent: Aug. 6, 2024

(54) IMIDAZOLE-CONTAINING INHIBITORS OF ALK2 KINASE

(71) Applicant: BioCryst Pharmaceuticals, Inc., Durham, NC (US)

(72) Inventors: Pravin L. Kotian, Hoover, AL (US); Yarlagadda S. Babu, Birmingham, AL (US); V. Satish Kumar, Birmingham, AL (US); Weihe Zhang, Vestavia Hills, AL (US); Peng-Cheng Lu, Vestavia Hills, AL (US); Krishnan Raman, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 18/168,055

(22) Filed: Feb. 13, 2023

(65) Prior Publication Data
US 2023/0271975 A1 Aug. 31, 2023

Related U.S. Application Data

(63) Continuation of application No. 16/622,816, filed as application No. PCT/US2018/037503 on Jun. 14, 2018, now Pat. No. 11,661,426.
(Continued)

(51) Int. Cl.
*C07D 491/048* (2006.01)
*C07D 401/14* (2006.01)
(Continued)

(52) U.S. Cl.
CPC ....... *C07D 491/048* (2013.01); *C07D 401/14* (2013.01); *C07D 403/12* (2013.01);
(Continued)

(58) Field of Classification Search
CPC .. C07D 401/14; C07D 403/12; C07D 403/14; C07D 405/12; C07D 405/14;
(Continued)

(56) References Cited

U.S. PATENT DOCUMENTS 5,693,652 A 12/1997 Takase et al.
6,919,338 B2 7/2005 Mortlock et al.
(Continued)

FOREIGN PATENT DOCUMENTS

EP 2058314 A1 5/2009
EP 2226315 A1 9/2010
(Continued)

OTHER PUBLICATIONS

"4-Quinazolinamine, 6-methoxy-N-(5-phenyl-2-thiazolyl)-2-(3-pyridinyl)," RN 1314071-05-0, STN Entry date Jul. 29, 2011.
(Continued)

*Primary Examiner* — Deepak R Rao
(74) *Attorney, Agent, or Firm* — Foley Hoag LLP; Dana M. Gordon; Laura A. Wzorek

(57) ABSTRACT

Disclosed are compounds of formula I, II, III, and IV, and pharmaceutically acceptable salts thereof. The compounds are inhibitors of ALK2 kinase. Also provided are pharmaceutical compositions comprising a compound of formula I, II, III, or IV, or pharmaceutically acceptable salt thereof, and methods involving use of the compounds or pharmaceutically acceptable salts thereof and compositions in the treatment and prevention of various diseases and conditions, such as fibrodysplasia ossificans progressiva.

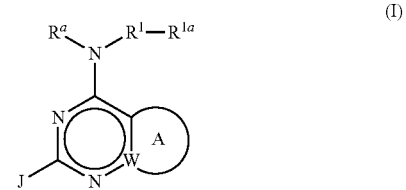

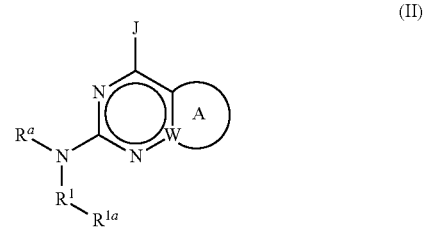

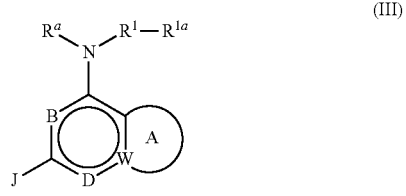

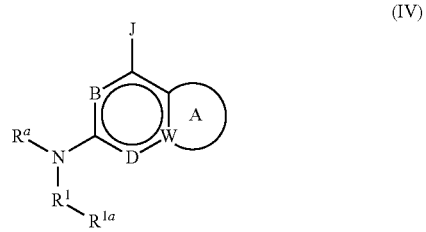

37 Claims, No Drawings

Related U.S. Application Data

(60) Provisional application No. 62/520,150, filed on Jun. 15, 2017.

(51) Int. Cl.
  *C07D 403/12*   (2006.01)
  *C07D 403/14*   (2006.01)
  *C07D 405/12*   (2006.01)
  *C07D 405/14*   (2006.01)
  *C07D 471/04*   (2006.01)
  *C07D 487/04*   (2006.01)
  *C07D 495/04*   (2006.01)
  *C07D 513/04*   (2006.01)

(52) U.S. Cl.
  CPC ......... *C07D 403/14* (2013.01); *C07D 405/12* (2013.01); *C07D 405/14* (2013.01); *C07D 471/04* (2013.01); *C07D 487/04* (2013.01); *C07D 495/04* (2013.01); *C07D 513/04* (2013.01)

(58) Field of Classification Search
  CPC ................ C07D 471/04; C07D 487/04; C07D 491/048; C07D 495/04; C07D 513/04
  See application file for complete search history.

(56) References Cited

U.S. PATENT DOCUMENTS

| | | | |
|---|---|---|---|
| 9,073,890 B2 | 7/2015 | Suzuki et al. | |
| 11,661,426 B2 * | 5/2023 | Kotian | A61P 19/00 514/210.21 |
| 2006/0258658 A1 | 11/2006 | Bebbington et al. | |
| 2007/0244114 A1 | 10/2007 | Cai et al. | |
| 2008/0045496 A1 | 2/2008 | Fink et al. | |
| 2011/0201628 A1 | 8/2011 | Chuaqui et al. | |
| 2014/0179668 A1 | 6/2014 | Chakravarty et al. | |
| 2022/0332723 A1 | 10/2022 | Kotian et al. | |

FOREIGN PATENT DOCUMENTS

| | | |
|---|---|---|
| JP | 2013/032343 A | 2/2013 |
| WO | WO-1993/007124 A1 | 4/1993 |
| WO | WO-2001/038315 A1 | 5/2001 |
| WO | WO-2002/000649 A1 | 1/2002 |
| WO | WO-2002/022601 A1 | 3/2002 |
| WO | WO-2002/022608 A1 | 3/2002 |
| WO | WO-2003/078423 A1 | 9/2003 |
| WO | WO-2004/081000 A1 | 9/2004 |
| WO | WO-2006/067614 A2 | 6/2006 |
| WO | WO-2007/071348 A1 | 6/2007 |
| WO | WO-2008/005956 A2 | 1/2008 |
| WO | WO-2009/084695 A1 | 7/2009 |
| WO | WO-2010/038060 A1 | 4/2010 |
| WO | WO-2010/143168 A2 | 12/2010 |
| WO | WO-2011/082337 A1 | 7/2011 |
| WO | WO-2014/151871 A2 | 9/2014 |
| WO | WO-2018/121400 A1 | 7/2018 |
| WO | WO-2018/232094 A1 | 12/2018 |

OTHER PUBLICATIONS

Acute Leukemia, Merck Manual (Online Edition) 1-6 (2013).
Australian Examination Report for AU Application No. 2018283053 dated Nov. 25, 2021.
CAS Registry No. 1797159-90-0; Date Entered STN: Jul. 8, 2015; Chemical name: N-(1-methyl-1H-pyrazolo[3,4-d]pyrimidin-4-yl)-5-phenylthiazol-2-amine.
Extended European Search Report for EP Application No. 18816547.6 dated Feb. 2, 2021.
Gellibert et al., "Design of novel quinazoline derivatives and related analogues as potent and selective ALK5 inhibitors," Bioorganic & Medicinal Chemistry Letters, 19(8): 2277-2281 (2009).
Gura et al., "Systems for Identifying New Drugs Are Often Faulty" Science, 278: 1041-1042 (1997).
Hao et al., "Structure-Based Design of 6-Chloro-4-aminoquinazoline-2-carboxamide Derivatives as Potent and Selective p21-Activated Kinase 4 (PAK4) Inhibitors," Journal of Medicinal Chemistry, 61(1): 265-285 (2018).
Hopkins., "Inhibitors of the bone morphogenetic protein (BMP) signaling pathway: a patent review (2008-2015 )," Expert Opinion on Therapeutic Patents, 26(10): 1115-1128 (2016).
International Search Report and Written Opinion for International Application No. PCT/US2018/037503 dated Oct. 1, 2018.
Johnson et al., "Relationships between drug activity in NCI preclinical in vitro and in vivo models and early clinical trials," British Journal of Cancer, 84(10):1424-1431 (2001).
Lim et al., "Discovery of 1-(1H-Pyrazolo[4,3-c]pyridin-6-yl)urea Inhibitors of Extracellular Signal-Regulated Kinase (ERK) for the Treatment of Cancers," Journal of Medicinal Chemistry, 59(13): 6501-6511 (2016).
Luo et al., "Development of New Therapeutic Agents for Fibrodysplasia Ossificans Progressiva," Current Molecular Medicine, 16(1): 4-11 (2016).
National Center for Biotechnology Information. PubChem Substance Database; SID=232516042, <https://pubchem.ncbi.nlm.nih.gov/substance/232516042> (accessed Aug. 13, 2018).
Pearce et al., "Failure modes in anticancer drug discovery and development" Cancer Drug Design and Discovery Edited by Stephen Neidle, Chapter 18: 424-435 (2008).
PubChem CID 75431703: 9 pages create date Jul. 12, 2014.
PubChem SID: 232516042, "N-Pyridin-2-ylquinazolin-4-amine," dated Feb. 12, 2015.
Search Report and Written Opinion for SG Application No. 11201911289W dated Jan. 4, 2021.
Simone, Oncology: Introduction: Cecil Textbook of Medicine, 20th Edition, vol. 1 1004-1010 (1995).
Taylor et al., "ACVR1 mutations in DIPG: lessons learned from FOP," Cancer Research, 74(17): 4565-4570 (2014).
Buczkowicz et al., "Genomic analysis of diffuse intrinsic pontine gliomas identifies three molecular subgroups and recurrent activating ACVR1 mutations." *Nature genetics* 46.5: 451-456 (2014).
Carvalho et al., "ALK2 inhibitors display beneficial effects in preclinical models of ACVR1 mutant diffuse intrinsic pontine glioma", *Communications biology* 2.1: 156 (2019).
Taylor et al. "Recurrent activating ACVR1 mutations in diffuse intrinsic pontine glioma", *Nature genetics* 46.5: 457-461 (2014).

* cited by examiner

IMIDAZOLE-CONTAINING INHIBITORS OF ALK2 KINASE

RELATED APPLICATIONS

This application is a continuation of U.S. patent application Ser. No. 16/622,816, filed Dec. 13, 2019; which is a U.S. National Stage Application of International Patent Application No. PCT/US2018/037503, filed Jun. 14, 2018; which claims the benefit of priority to U.S. Provisional Patent Application Ser. No. 62/520,150, filed Jun. 15, 2017.

BACKGROUND OF THE INVENTION

A single mutation (R206H) within the kinase domain of one (ACVR1/ALK2) of the four human bone morphogenetic protein (BMP) receptors has been linked to a catastrophic disorder of secondary (heterotopic) bone formation. As a result of the mutation, all children presenting with features of classic Fibrodysplasia Ossificans Progressiva (FOP) eventually become encased in, and their movement blocked by, a second heterotopic skeleton. The disorder has long been associated with dysregulation of BMP signaling in soft tissues (skeletal muscle, tendon, ligament, fascia) that were transformed into ribbons, sheets and plates of heterotopic bone via an endochondral process. In addition to the common R206H mutation linked to the classic form of FOP, other dysregulating mutations have been identified in ACVR1/ALK2 that lead to atypical and variant forms of FOP. Further, compounds effective in regulating BMP signaling based on their ability to inhibit ALK2 have been shown also to inhibit kinases from multiple signaling pathways.

Thus, there remains a need for additional compounds that inhibit the ALK2 kinase which will be suitable for various important therapeutic applications.

SUMMARY OF THE INVENTION

In certain aspects, the invention provides a compound of formula (I) or formula (II):

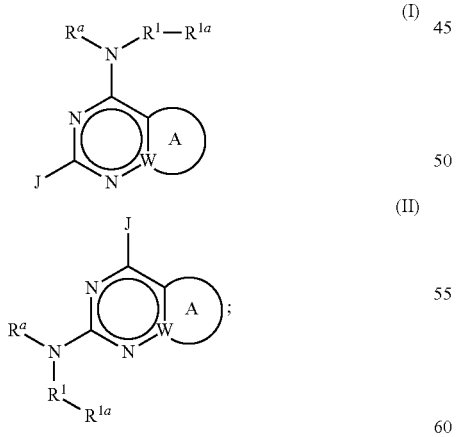

or a pharmaceutically acceptable salt thereof,
wherein:
A is a fused optionally substituted aromatic ring, heteroaromatic ring, partially unsaturated cycloalkyl ring, or partially unsaturated heterocycloalkyl ring;
W is C or N;
$R_a$ represents H or alkyl;
$R^1$ represents heteroarylene;
$R^{1a}$ represents H or optionally substituted —C(O)alkyl, —C(O)O(alkyl), —C(O)(heterocyclyl), —C(O)(aryl), —C(O)(heteroaryl), —C(O)NR$^x$R$^y$, alkyl, cycloalkyl, heterocycloalkyl, aryl, or heteroaryl;
J represents H, halo, —OR$^2$, —NR$^2$R$^3$, —C(O)NR$^2$R$^3$, —C(O)O(alkyl), —C(O)OH, aryl, or heteroaryl, wherein aryl or heteroaryl is optionally substituted by one or more occurrences of $R^{2a}$;
$R^2$ represents optionally substituted alkyl, aralkyl, heteroaralkyl, cycloalkyl, heterocycloalkyl, (cycloalkyl)alkyl, (heterocycloalkyl)alkyl, or hydroxyalkyl;
$R^3$ represents H or alkyl; or
$R^2$ and $R^3$, taken together, form a heterocycloalkyl ring, optionally substituted by one or more occurrences of $R^{2a}$;
$R^{2a}$, independently for each occurrence, represents halo, hydroxyl, —C(O)H, oxo, —NH$_2$, —C(O)NH$_2$, —C(O)OH, —C(O)R$^5$, —C(O)OR$^5$, —C(O)NH(R$^5$), or optionally substituted alkyl, alkoxyl, hydroxyalkyl, heteroaryl, aryl, or —N(alkyl)$_2$;
or any two germinal or vicinal occurrences of $R^{2a}$, taken together, may form a spiro or fused cycloalkyl ring;
$R^5$, independently for each occurrence, represents optionally substituted alkyl, aralkyl, aryl, heteroaralkyl, heteroaryl, cycloalkyl, heterocycloalkyl, (cycloalkyl)alkyl, or (heterocycloalkyl)alkyl; and
$R^x$ and $R^y$ each independently represent H, alkyl, aralkyl, heteroaralkyl, aryl, heteroaryl, cycloalkyl, heterocycloalkyl, (cycloalkyl)alkyl, (heterocycloalkyl)alkyl, or hydroxyalkyl.

In further aspects, the invention provides a compound of formula (III) or formula (IV):

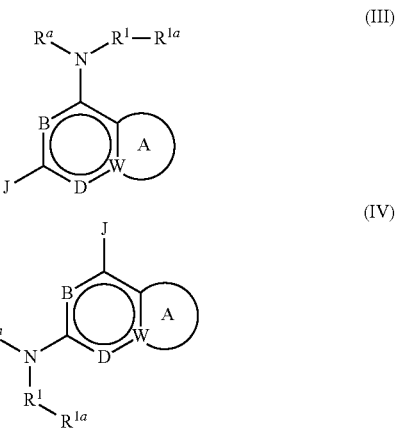

or a pharmaceutically acceptable salt thereof,
wherein:
A is a fused optionally substituted aromatic ring, heteroaromatic ring, partially unsaturated cycloalkyl ring, or partially unsaturated heterocycloalkyl ring;
W is C or N;
B is CH or N;
D is CH or N;
provided that when B is CH, then D is N; or when D is CH, then B is N;
$R^a$ represents H or alkyl;
$R^1$ represents heteroarylene;

$R^{1a}$ represents H or optionally substituted —C(O)alkyl, —C(O)aryl, —C(O)heteroaryl, —C(O)O(alkyl), —C(O)(heterocyclyl), —C(O)$NR^xR^y$, alkyl, cycloalkyl, heterocycloalkyl, aryl, or heteroaryl;

J represents H, halo, —$OR^2$, —$NR^2R^3$, —C(O)$NR^2R^3$, —C(O)O(alkyl), —C(O)OH, aryl, or heteroaryl, wherein aryl or heteroaryl is optionally substituted by one or more occurrences of $R^{2a}$;

$R^2$ represents optionally substituted alkyl, aralkyl, heteroaralkyl, cycloalkyl, heterocycloalkyl, (cycloalkyl)alkyl, (heterocycloalkyl)alkyl, or hydroxyalkyl;

$R^3$ represents H or alkyl; or $R^2$ and $R^3$, taken together, form a heterocycloalkyl ring, optionally substituted by one or more occurrences of $R^{2a}$;

$R^{2a}$, independently for each occurrence, represents halo, hydroxyl, —C(O)H, oxo, —$NH_2$, —C(O)$NH_2$, —C(O)OH, —C(O)$R^5$, —C(O)$OR^5$, —C(O)NH($R^5$), or optionally substituted alkyl, alkoxyl, hydroxyalkyl, heteroaryl, aryl, aryloxy, heteroaryloxy, arylalkyloxy, heteroarylalkyloxy, or —N(alkyl)$_2$;

or any two germinal or vicinal occurrences of $R^{2a}$, taken together, may form a spiro or fused cycloalkyl ring;

$R^5$, independently for each occurrence, represents optionally substituted alkyl, aralkyl, aryl, heteroaralkyl, heteroaryl, cycloalkyl, heterocycloalkyl, (cycloalkyl)alkyl, or (heterocycloalkyl)alkyl; and $R^x$ and $R^y$ each independently represent H, alkyl, aralkyl, heteroaralkyl, aryl, heteroaryl, cycloalkyl, heterocycloalkyl, (cycloalkyl)alkyl, (heterocycloalkyl)alkyl, or hydroxyalkyl.

In still further aspects, the invention provides a compound, or a pharmaceutically acceptable salt thereof, selected from the group consisting of:

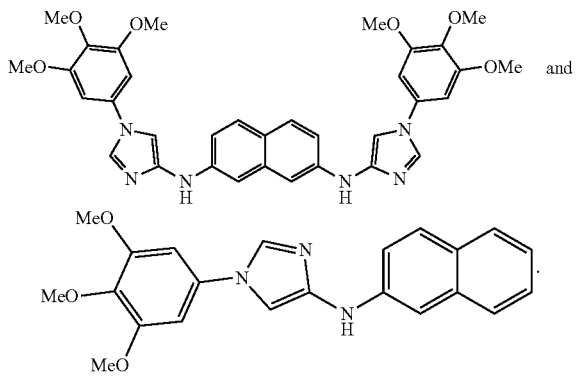

In certain aspects, the invention provides a pharmaceutical composition, comprising a compound of the invention, or a pharmaceutically acceptable salt thereof; and a pharmaceutically acceptable excipient.

In certain aspects, the invention provides methods of inhibiting ALK2 kinase, comprising administering to a subject in need thereof an effective amount of a compound of the invention, or a pharmaceutically acceptable salt thereof.

The present invention also provides methods of treating fibrodysplasia ossificans progressiva, comprising administering to a subject in need thereof an effective amount of a compound of the invention, or a pharmaceutically acceptable salt thereof.

In further aspects, the invention provides methods of treating cancer, comprising administering to a subject in need thereof a therapeutically effective amount of a compound of the invention, or a pharmaceutically acceptable salt thereof. In certain embodiments, the cancer is a glioma.

DETAILED DESCRIPTION

Provided herein are compounds of formulae (I), (II), (III), and (IV), and pharmaceutically acceptable salts thereof, that are useful for inhibiting ALK2 kinase, and useful in the treatment or prevention of a disease or condition that would benefit from inhibition of ALK2 kinase. For example, the disclosed inhibitors of ALK2 kinase are useful in therapeutic methods and compositions suitable for use in treating cancer or fibrodysplasia ossificans progressiva.

Definitions

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium, and alternatively oxygen, nitrogen or sulfur.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ alkyl group. In certain embodiments, the term "alkyl" refers to a $C_1$-$C_6$ alkyl group, for example a $C_1$-$C_6$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, isobutyl, tert-butyl, n-pentyl, isopentyl, neopentyl, and n-hexyl.

The term "cycloalkyl" means mono- or bicyclic or bridged saturated carbocyclic rings, each having from 3 to 12 carbon atoms. Certain cycloalkyls have from 5-12 carbon atoms in their ring structure, and may have 6-10 carbons in the ring structure. Preferably, cycloalkyl is ($C_3$-$C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "(cycloalkyl)alkyl" as used herein refers to an alkyl group substituted with one or more cycloalkyl groups. An example of (cycloalkyl)alkyl is cyclohexylmethyl group.

The term "heterocycloalkyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocycloalkyl group is optionally substituted by one or more substituents as described below.

The term "(heterocycloalkyl)alkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

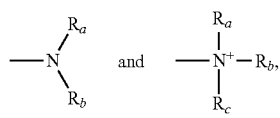

wherein $R_a$, $R_b$, and $R_c$ each independently represent a hydrogen, an alkyl, an alkenyl, $-(CH_2)_x-R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or $-(CH_2)_x-R_d$. In certain embodiments, the term "amino" refers to $-NH_2$.

In certain embodiments, the term "alkylamino" refers to $-NH(alkyl)$.

In certain embodiments, the term "dialkylamino" refers to $-N(alkyl)_2$.

The term "amido", as used herein, means $-NHC(=O)-$, wherein the amido group is bound to the parent molecular moiety through the nitrogen. Examples of amido include alkylamido such as $CH_3C(=O)N(H)-$ and $CH_3CH_2C(=O)N(H)-$.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

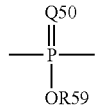

wherein Q50 represents S or O, and R59 represents hydrogen, a lower alkyl or an aryl; for example, $-P(O)(OMe)-$ or $-P(O)(OH)_2$. When used to substitute, e.g., an alkyl, the phosphoryl group of the phosphorylalkyl may be represented by the general formulas:

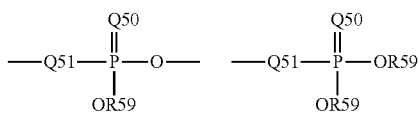

wherein Q50 and R59, each independently, are defined above, and Q51 represents O, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an —N$_3$ group.

The term "carbonyl" as used herein refers to —C(=O)—.

The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—. The term "(alkylthio)alkyl" refers to an alkyl group substituted by an alkylthio group.

The term "carboxy", as used herein, means a —CO$_2$H group.

The term "aryl" is a term of art and as used herein refers to includes monocyclic, bicyclic and polycyclic aromatic hydrocarbon groups, for example, benzene, naphthalene, anthracene, and pyrene. Typically, an aryl group contains from 6-10 carbon ring atoms (i.e., (C$_6$-C$_{10}$)aryl). The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group.

The term "arylene" means a diradical obtained by removing two hydrogen atoms of an aryl group, as defined above. In certain embodiments an arylene refers to a disubstituted arene, i.e., an arene substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluoromethyl), cyano, or the like. That is, in certain embodiments, a "substituted aryl" is an "arylene".

The term "heteroaryl" is a term of art and as used herein refers to a monocyclic, bicyclic, and polycyclic aromatic group having 3 to 12 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "heteroarylene" means a diradical obtained by removing two hydrogen atoms of a heteroaryl group, as defined above. In certain embodiments an heteroarylene refers to a disubstituted heteroarene, i.e., a heteroarene substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluoromethyl), cyano, or the like. That is, in certain embodiments, a "substituted heteroaryl" is an "heteroarylene".

The term "aralkyl" or "arylalkyl" is a term of art and as used herein refers to an alkyl group substituted with an aryl group, wherein the moiety is appended to the parent molecule through the alkyl group.

The term "heteroaralkyl" or "heteroarylalkyl" is a term of art and as used herein refers to an alkyl group substituted with a heteroaryl group, appended to the parent molecular moiety through the alkyl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" refers to an alkyl group substituted by an alkoxy group.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH-CH_2-O-$) and vinyloxy (i.e., $CH_2=CH-O-$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to —CN.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si-$) group (i.e., (hydrocarbyl)$_3Si-$), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

In certain embodiments, the optional substituents can include, for example, halogen, haloalkyl, hydroxyl, carbonyl (such as carboxyl, alkoxycarbonyl, formyl, or acyl), thiocarbonyl (such as thioester, thioacetate, or thioformate), alkoxyl, alkenyloxy, alkynyloxy, phosphoryl, phosphate, phosphonate, phosphinate, amino (including alkyl- and dialkylamino), amido, amidine, imine, cyano, nitro, azido, sulfhydryl, alkylthio, sulfate, sulfonate, sulfamoyl, sulfonamido, sulfonyl, silyl, silyloxy, heterocycloalkyl, cycloalkyl, alkyl, alkenyl, alkynyl, aryl, heteroaryl, aralkyl, or heteroaralkyl group.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$ ed.*; Wiley: New York, 1991). Protected forms of the inventive compounds are included within the scope of this invention.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I, II, III, or IV. As another example, the salt may comprise less than one inorganic or organic acid molecule per molecule of base, such as two molecules of compound of Formula I, II, III, or IV per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Compounds

The present invention provides a compound of Formula (I) or (II):

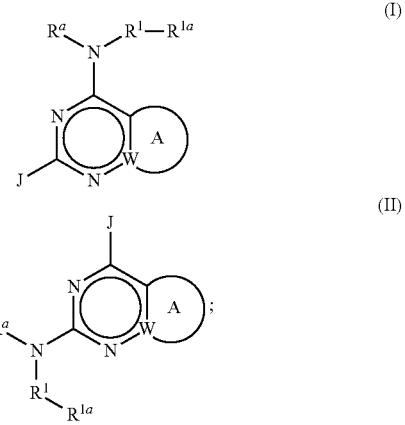

or a pharmaceutically acceptable salt thereof, wherein:

A is a fused optionally substituted aromatic ring, heteroaromatic ring, partially unsaturated cycloalkyl ring, or partially unsaturated heterocycloalkyl ring;

W is C or N;

$R^a$ represents H or alkyl;

$R^1$ represents heteroarylene;

$R^{1a}$ represents H or optionally substituted —C(O)alkyl, —C(O)aryl, —C(O)heteroaryl, —C(O)O(alkyl), —C(O)(heterocyclyl), —C(O)NR$^x$R$^y$, alkyl, cycloalkyl, heterocycloalkyl, aryl, or heteroaryl;

J represents H, halo, —OR$^2$, —NR$^2$R$^3$, —C(O)NR$^2$R$^3$, —C(O)O(alkyl), —C(O)OH, aryl, or heteroaryl, wherein aryl or heteroaryl is optionally substituted by one or more occurrences of R$^{2a}$;

$R^2$ represents optionally substituted alkyl, aralkyl, heteroaralkyl, cycloalkyl, heterocycloalkyl, (cycloalkyl)alkyl, (heterocycloalkyl)alkyl, or hydroxyalkyl;

$R^3$ represents H or alkyl; or $R^2$ and $R^3$, taken together, form a heterocycloalkyl ring, optionally substituted by one or more occurrences of $R^{2a}$;

$R^{2a}$, independently for each occurrence, represents halo, hydroxyl, —C(O)H, oxo, —NH$_2$, —C(O)NH$_2$, —C(O)OH, —C(O)R$^5$, —C(O)OR$^5$, —C(O)NH(R$^5$), or optionally substituted alkyl, alkoxyl, hydroxyalkyl, heteroaryl, aryl, aryloxy, heteroaryloxy, arylalkyloxy, heteroarylalkyloxy, or —N(alkyl)$_2$;

or any two germinal or vicinal occurrences of $R^{2a}$, taken together, may form a spiro or fused cycloalkyl ring;

$R^5$, independently for each occurrence, represents optionally substituted alkyl, aralkyl, aryl, heteroaralkyl, heteroaryl, cycloalkyl, heterocycloalkyl, (cycloalkyl)alkyl, or (heterocycloalkyl)alkyl; and $R^x$ and $R^y$ each independently represent H, alkyl, aralkyl, heteroaralkyl, aryl, heteroaryl, cycloalkyl, heterocycloalkyl, (cycloalkyl)alkyl, (heterocycloalkyl)alkyl, or hydroxyalkyl.

In certain embodiments, the compound of the invention is represented by formula (Ia) or formula (IIa):

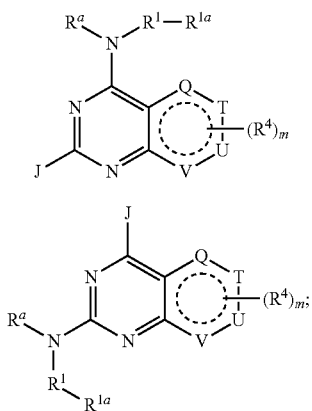

(Ia)

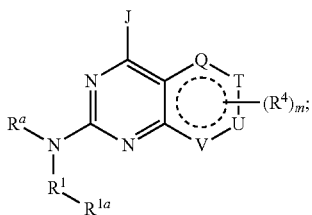

(IIa)

wherein:

- valence permitting, Q, T, U, and V each independently represent CH, CH$_2$, N, NH, O, or SO$_2$, wherein any hydrogen of a CH, CH$_2$, or NH group is optionally replaced by an occurrence of R$^4$;
- R$^4$, independently for each occurrence, represents halo, cyano, or optionally substituted alkyl, alkenyl, haloalkyl, hydroxyalkyl, aminoalkyl, alkoxy, aryl, aralkyl, heteroaryl, heteroaralkyl, heterocycloalkyl, heterocycloalkenyl, (heterocycloalkyl)alkyl, cycloalkyl, (cycloalkyl)alkyl, halocycloalkyl, hydroxycycloalkyl, aminocycloalkyl, aryloxy, heteroaryloxy, arylalkyloxy, heteroarylalkyloxy, —CH$_2$C(O)NH$_2$, —C(O)R$^5$, —C(O)OR$^5$, or —S(O)$_2$R$^5$;
- m is an integer from 0-4, as permitted by valence.

In certain embodiments, the compound of the invention is represented by formula (Ib) or formula (IIb):

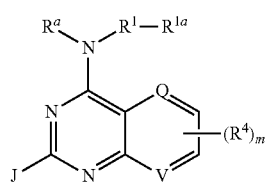

(Ib)

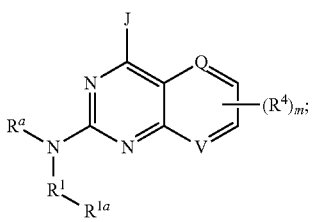

(IIb)

wherein Q represents CH or N; and V represents CH or N. In certain embodiments, Q is N and V is CH. In alternative embodiments, Q is CH and V is N.

In certain embodiments, the compound of the invention is represented by formula (Ic) or formula (IIc):

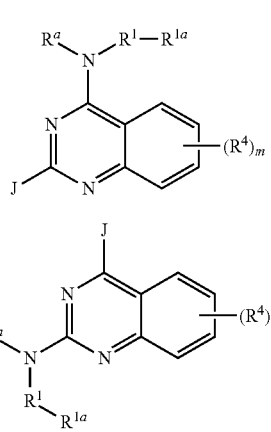

(Ic)

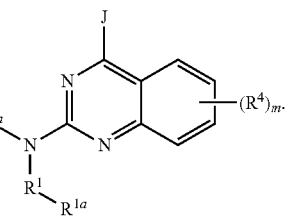

(IIc)

In certain embodiments, the compound of the invention is represented by formula (Id) or formula (IId):

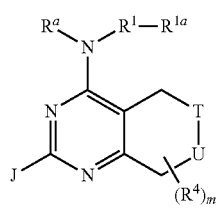

(Id)

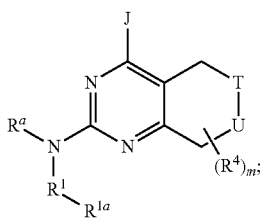

(IId)

wherein T represents CH$_2$, NH, O, or SO$_2$; and U represents CH$_2$, NH, O, or SO$_2$. In certain embodiments, T is NH; and U is CH$_2$. In other embodiments, T is CH$_2$ and U is NH.

In certain embodiments, the compound of the invention is represented by formula (Ie) or formula (IIe):

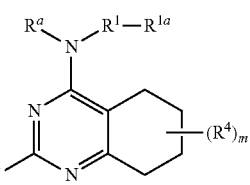

(Ie)

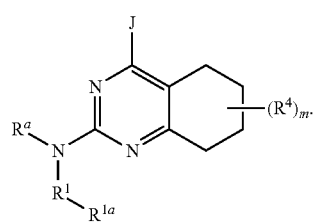

(IIe)

In any one of formulae (Ia), (IIa), (Ib), (IIb), (Ic), (IIc), (Id), (IId), (Ie), and (IIe), in certain embodiments, m is 0 or 1.

In certain embodiments, the compound of the invention is represented by formula (Ij) or (IIj):

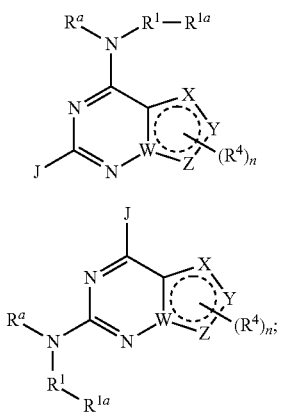

wherein:

W is C or N;

valence permitting, X, Y, and Z each independently represent CH, $CH_2$, CO, N, NH, O, S, or $SO_2$, wherein any hydrogen of a CH, $CH_2$, or NH group is optionally replaced by an occurrence of $R^4$;

$R^4$, independently for each occurrence, represents cyano, halo, or optionally substituted alkyl, alkenyl, haloalkyl, hydroxyalkyl, aminoalkyl, alkoxy, aryl, aralkyl, heteroaryl, heteroaralkyl, heterocycloalkyl, heterocycloalkenyl, (heterocycloalkyl)alkyl, cycloalkyl, (cycloalkyl)alkyl, halocycloalkyl, hydroxycycloalkyl, aminocycloalkyl, aryloxy, heteroaryloxy, arylalkyloxy, heteroarylalkyloxy, —$CH_2C(O)NH_2$, —$C(O)R^5$, —$C(O)OR^5$, or —$S(O)_2R^5$;

n is an integer from 0-4, as permitted by valence.

In certain embodiments, $R^4$, independently for each occurrence, represents halo, or optionally substituted alkyl, alkenyl, haloalkyl, hydroxyalkyl, aminoalkyl, alkoxy, aryl, aralkyl, heteroaryl, heteroaralkyl, heterocycloalkyl, heterocycloalkenyl, (heterocycloalkyl)alkyl, cycloalkyl, (cycloalkyl)alkyl, —$CH_2C(O)NH_2$, —$C(O)R^5$, —$C(O)OR^5$, or —$S(O)_2R^5$.

In certain embodiments, $R^4$, independently for each occurrence, represents halocycloalkyl, hydroxycycloalkyl, aminocycloalkyl, aryloxy, heteroaryloxy, arylalkyloxy, or heteroarylalkyloxy.

In certain embodiments, one of X, Y, or Z is $NR^4$.

In certain such embodiments, $R^4$ is selected from the group consisting of:

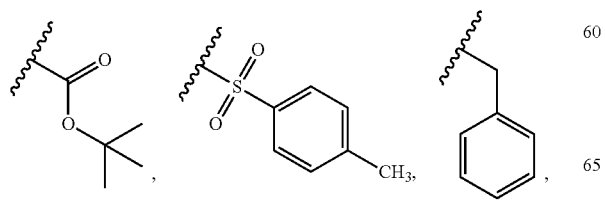

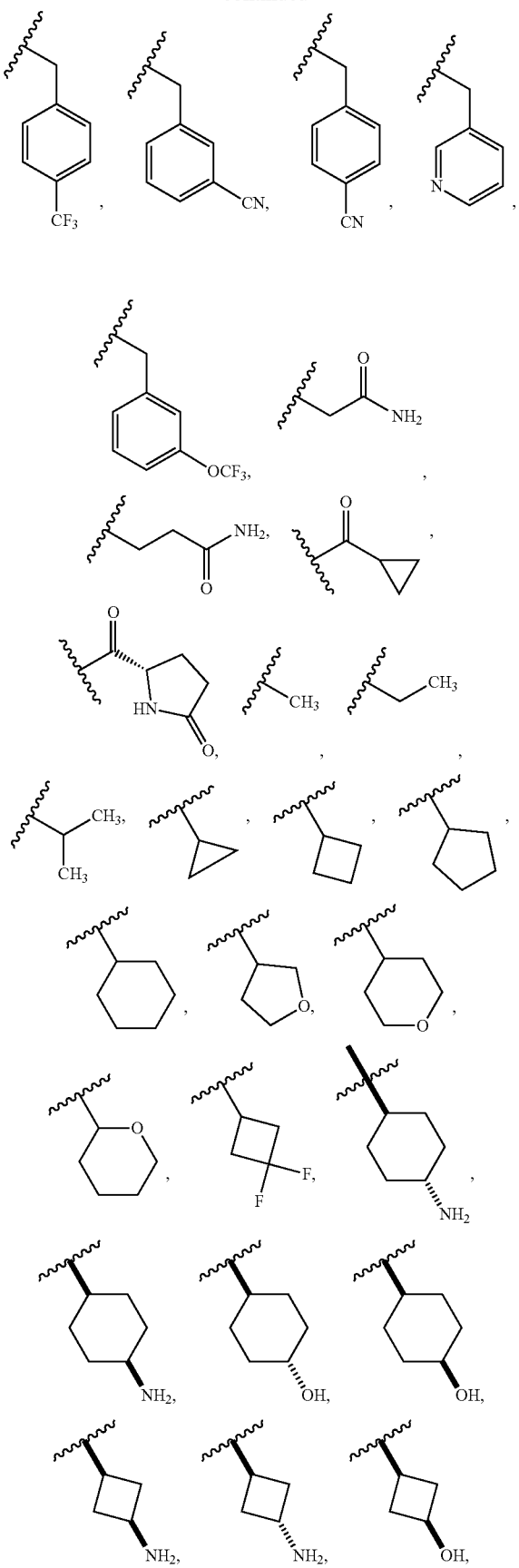

-continued

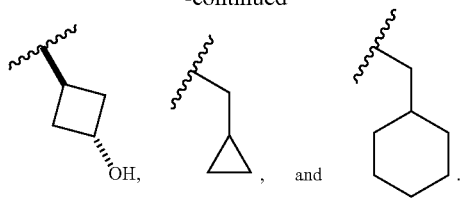
OH, , and .

In certain embodiments, the compound of the invention is represented by formula (Ik) or (IIk):

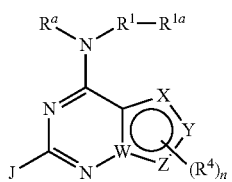
(Ik)

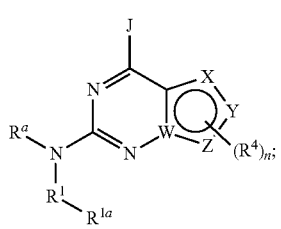
(IIk)

wherein X, Y, and Z each independently represent CH, N, NH, O, S, or $SO_2$.

In certain embodiments, the compound of the invention is represented by formula

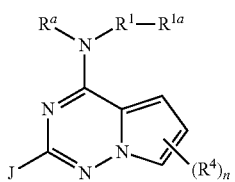
(Ik')

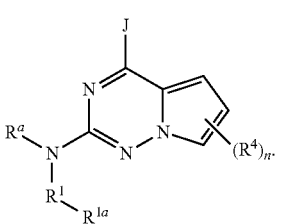
(IIk')

Alternatively, in certain embodiments, the compound of the invention is represented by formula (Ik") or (IIk"):

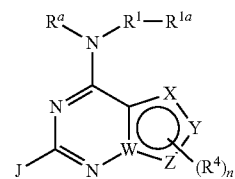
(Ik")

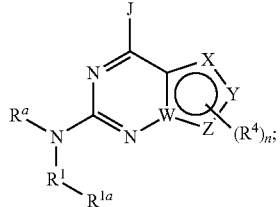
(IIk")

wherein at least one of X and Z is selected from the group consisting of O, N, NH, and S.

In certain embodiments of the compounds of formula (Ik") and (IIk"), one of X and Z is selected from the group consisting of O, NH, and S; and the other of X and Z is CH. For example, X may be selected from the group consisting of O, NH, and S. Alternatively, Z may be selected from the group consisting of O, NH, and S.

In other embodiments of the compounds of formula (Ik") and (IIk"), each of X and Z are selected from the group consisting of O, N, NH, and S. For example, one of X and Z may be N and the other of X and Z may be NH.

In certain embodiments, the compound of the invention is represented by formula (In) or (IIn):

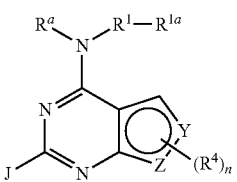
(In)

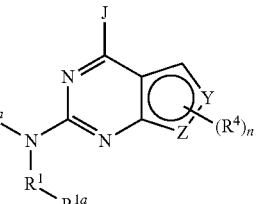
(IIn)

wherein each of Y and Z are selected from the group consisting of O, N, NH, and S.

In certain such embodiments, Y is N and Z is NH.

In certain embodiments, the compound of the invention is represented by formula (Im) or (IIm):

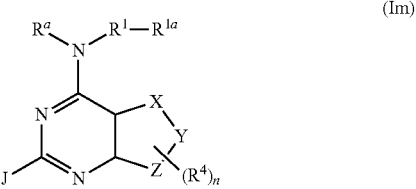
(Im)

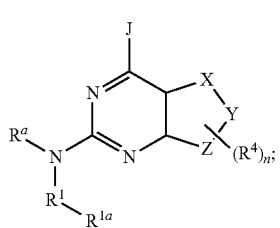

(IIm)

wherein X, Y, and Z each independently represent $CH_2$, CO, NH, O, S, or $SO_2$.

In certain embodiments of the compounds of formula (Im) or (IIm), each of X, Y, and Z is $CH_2$. In alternative embodiments, one of X, Y, and Z is N or O.

In any one of formulae (Ij), (IIj), (Ik), (IIk), (Ik'), (IIk'), (Ik"), (IIk"), (Im), and (IIm), in certain embodiments, n is 0 or 1.

In any of the foregoing embodiments, $R^4$, if present, may be selected from the group consisting of optionally substituted alkyl, hydroxyalkyl, aminoalkyl, alkoxy, aryl, aralkyl, and (heterocycloalkyl)alkyl.

In any of the foregoing embodiments, $R^a$ may be H.

In certain embodiments, $R^1$ is a nitrogen-containing heteroarylene, such as a 5-membered nitrogen-containing heteroarylene. In certain embodiments, $R^1$ is imidazolene.

In some embodiments, $—R^1-R^{1a}$ represents

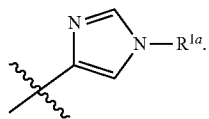

In certain embodiments, $R^{1a}$ is H.

Alternatively, $R^{1a}$ may be optionally substituted phenyl. Specifically, $R^{1a}$ may be phenyl, substituted by one or more occurrences of halo, hydroxyl, cyano, —C(O)NH$_2$, hydroxyalkyl, haloalkyl, alkoxy, haloalkoxy, cycloalkyl, —C(O)alkyl, —C(O)O-alkyl, heterocycloalkyl, —C(O)NH(alkyl), —C(O)N(alkyl)$_2$, —C(O)heterocycloalkyl, —C(O)(prolinol), —C(O)NH((cycloalkyl)alkyl), or —C(O)NH(cycloalkyl). In certain embodiments, $R^{1a}$ is phenyl, substituted by two or more occurrences of alkoxy. Preferably, $R^{1a}$ is 3,4,5-trimethoxyphenyl.

In certain embodiments, $R^{1a}$ is substituted phenyl, wherein two adjacent substituents on the phenyl, taken together with the intervening atoms, form an optionally substituted cycloalkyl or heterocycloalkyl ring. For example, $R^{1a}$ may be phenyl, wherein two adjacent substituents form a fused optionally substituted heterocyclic ring such as 1,4-dioxane or 1,3-dioxolane.

In certain embodiments, $R^{1a}$ is optionally substituted heteroaryl, such as quinoline.

In certain embodiments, J is aryl, optionally substituted by one or more occurrences of $R^{2a}$.

In alternative embodiments, J is —$NR^2R^3$.

In certain such embodiments, $R^2$ and $R^3$, taken together, form a heterocycloalkyl ring, for example, a pyrrolidine ring, optionally substituted by one or more occurrences of $R^{2a}$.

In certain such embodiments, $R^{2a}$, independently for each occurrence, may represent —C(O)NH$_2$, —C(O)R$^5$, hydroxyalkyl, heteroaryl, or aryl; preferably —C(O)NH$_2$, or hydroxyalkyl.

In certain embodiments, A represents a fused optionally substituted cycloalkyl ring, such as an optionally substituted cyclohexane or cycloheptane ring.

In certain embodiments, A represents a fused optionally substituted heterocycloalkyl ring, such as an optionally substituted tetrahydrofuran or pyrrolidine ring.

In certain embodiments, the compound of the invention is selected from the group consisting of the compounds depicted in the following tables, or a pharmaceutically acceptable salt thereof:

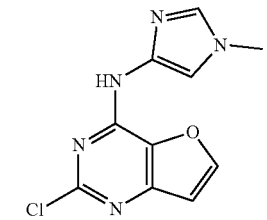 [SMILES: Cn1cnc(Nc2nc(Cl)nc3ccoc23)c1]

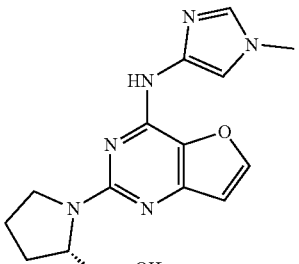

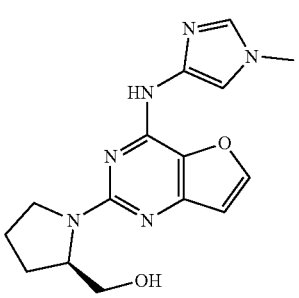 [SMILES: Cn1cnc(Nc2nc(N3CCC[C@@H]3CO)nc3ccoc23)c1]

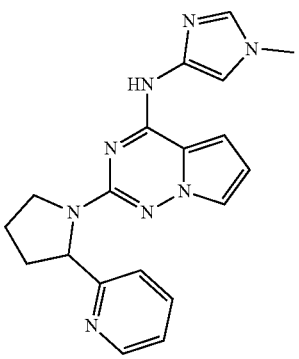 [SMILES: Cn1cnc(Nc2nc(N3CCCC3c3ccccn3)nn3cccc23)c1]

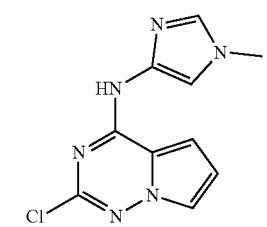 [SMILES: Cn1cnc(Nc2nc(Cl)nn3cccc23)c1]

-continued
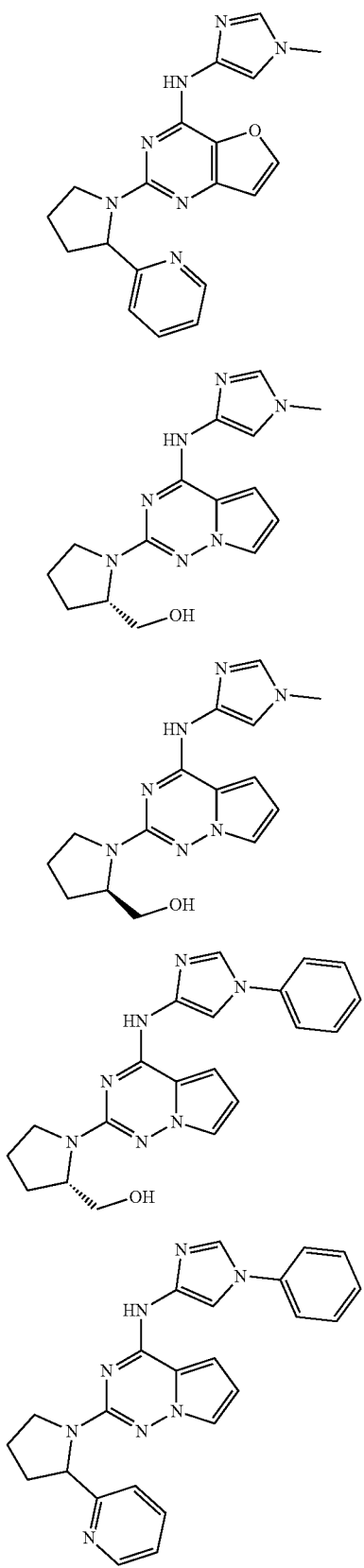
-continued
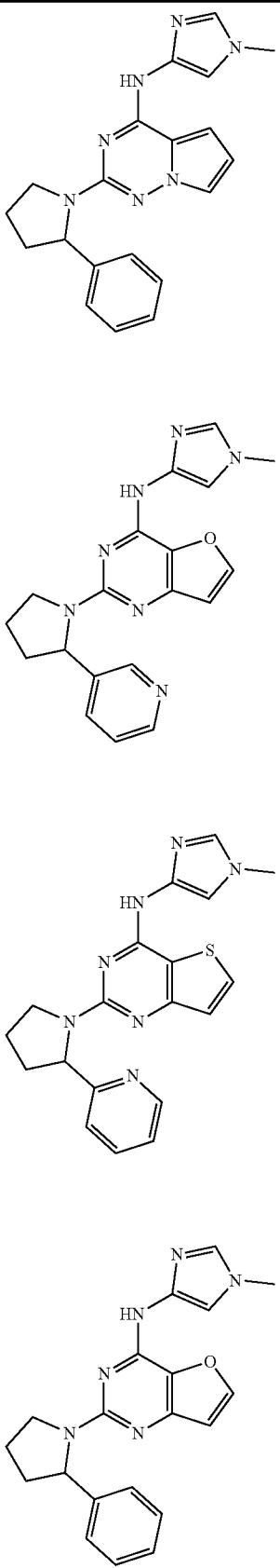

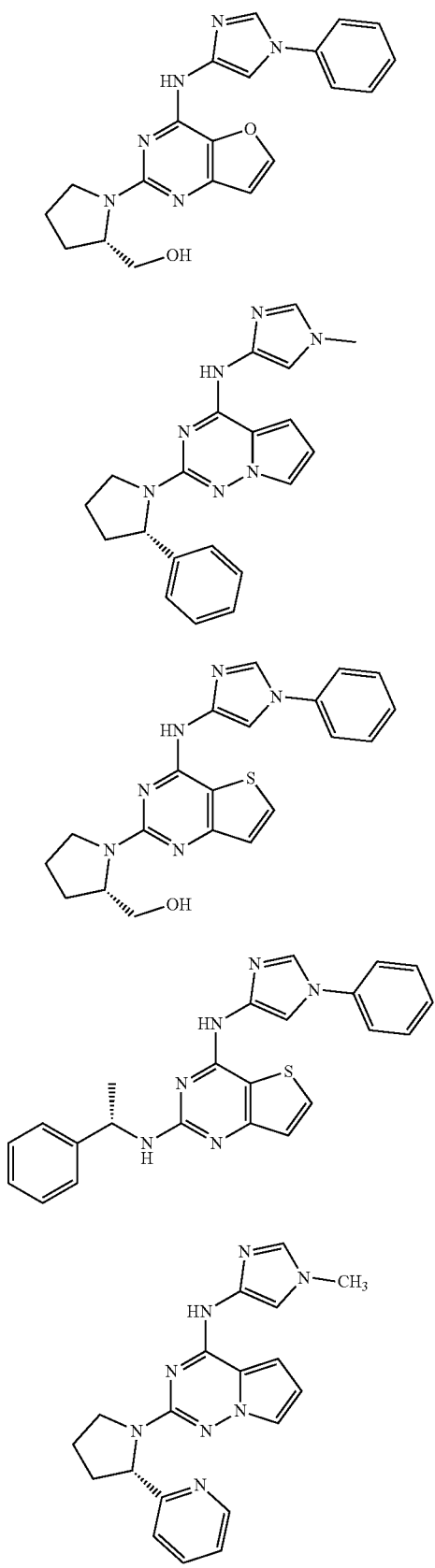
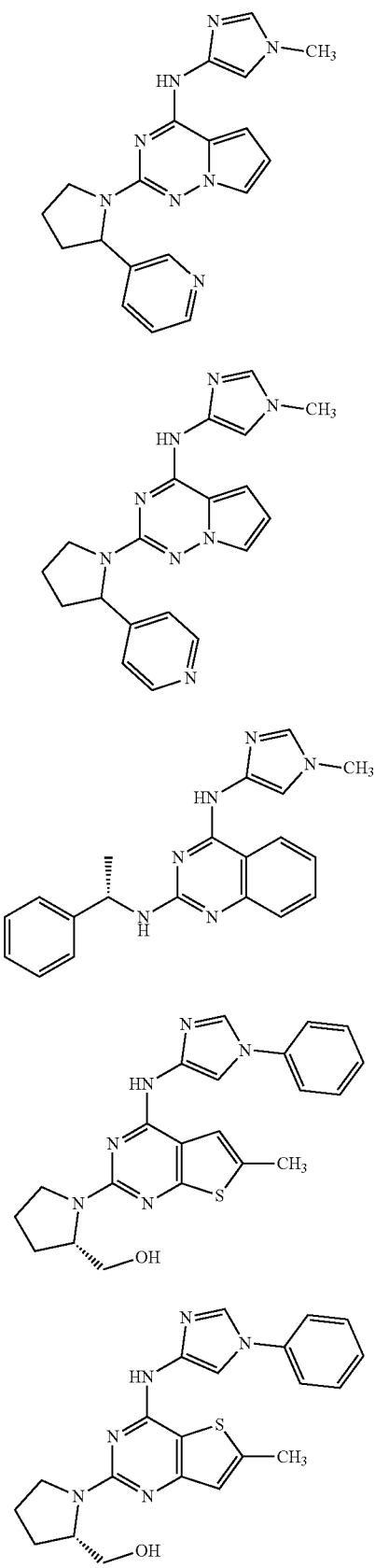

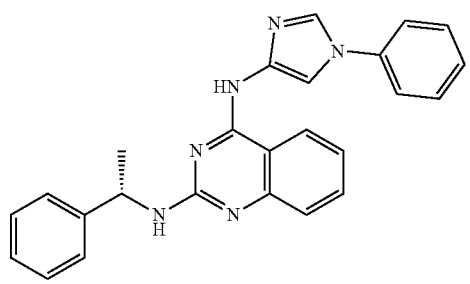 [SMILES: C[C@H](Nc1nc(Nc2cn(-c3ccccc3)cn2)c2ccccc2n1)c1ccccc1]
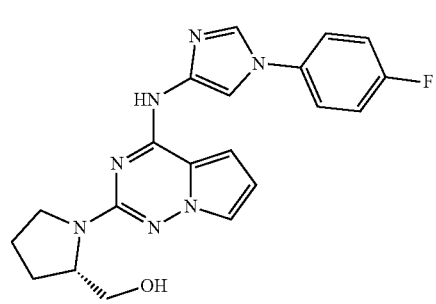 [SMILES: OC[C@@H]1CCCN1c1nc(Nc2cn(-c3ccc(F)cc3)cn2)c2cccn2n1]
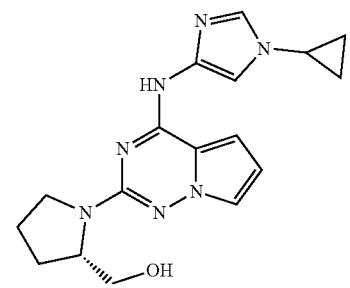 [SMILES: OC[C@@H]1CCCN1c1nc(Nc2cn(C3CC3)cn2)c2cccn2n1]
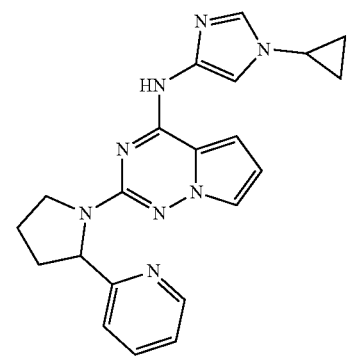 [SMILES: c1ccc(C2CCCN2c2nc(Nc3cn(C4CC4)cn3)c3cccn3n2)nc1]
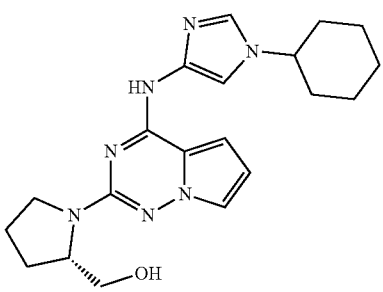 [SMILES: OC[C@@H]1CCCN1c1nc(Nc2cn(C3CCCCC3)cn2)c2cccn2n1]
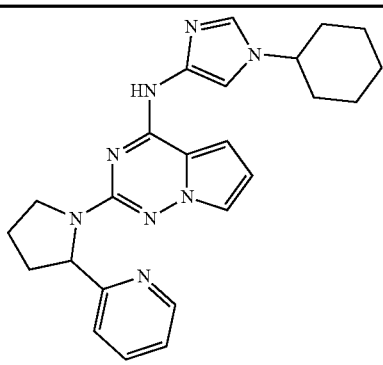
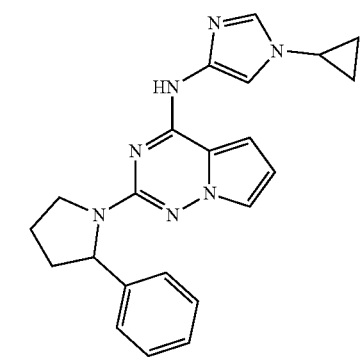 [SMILES: c1ccc(C2CCCN2c2nc(Nc3cn(C4CC4)cn3)c3cccn3n2)cc1]
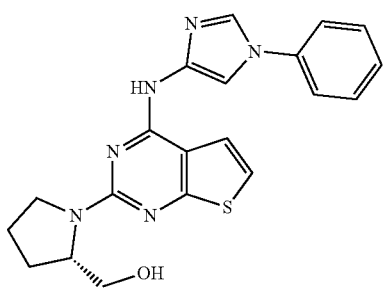 [SMILES: OC[C@@H]1CCCN1c1nc(Nc2cn(-c3ccccc3)cn2)c2ccsc2n1]
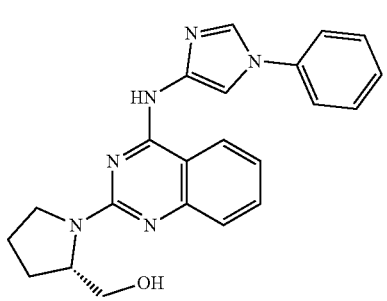 [SMILES: OC[C@@H]1CCCN1c1nc(Nc2cn(-c3ccccc3)cn2)c2ccccc2n1]
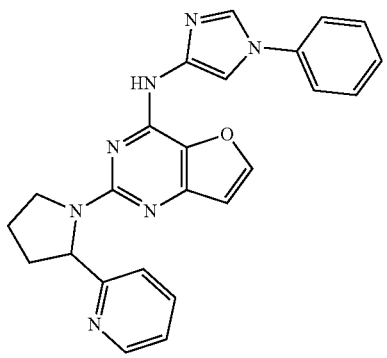 [SMILES: c1ccc(-n2cnc(Nc3nc(N4CCCC4c4ccccn4)nc4ccoc34)c2)cc1]

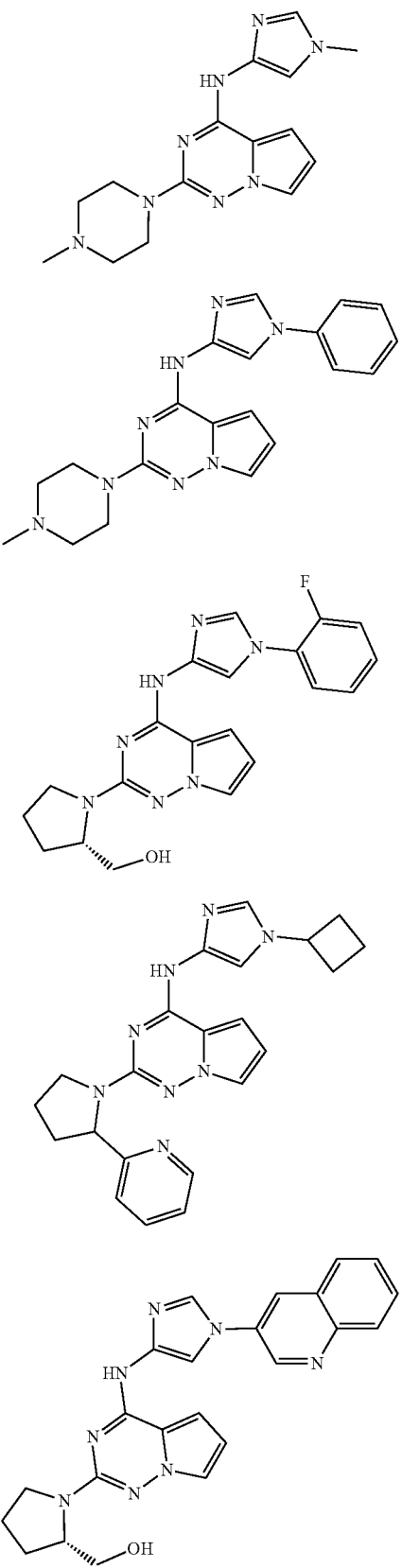
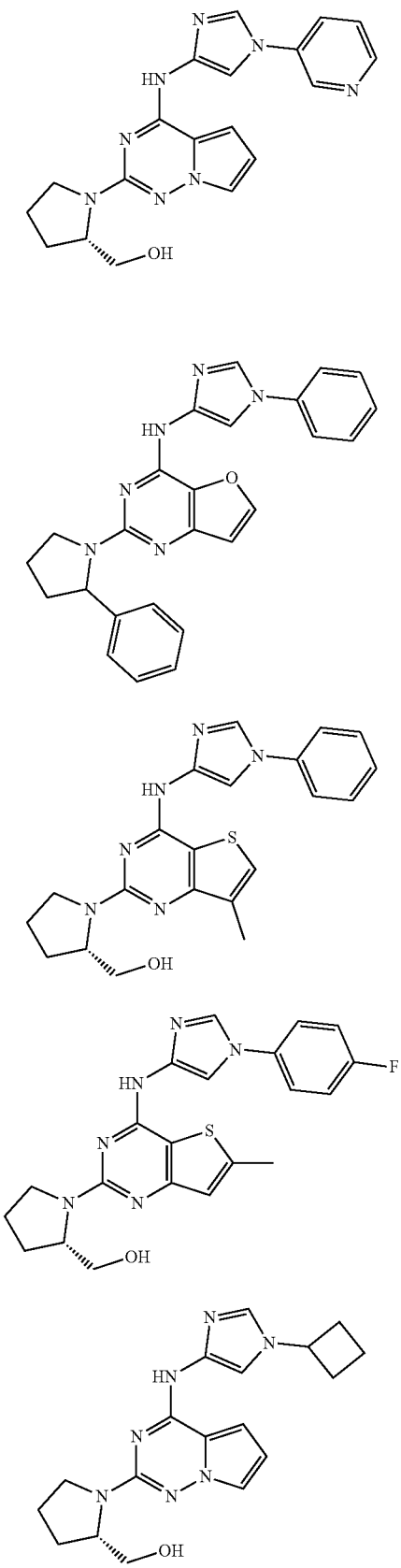

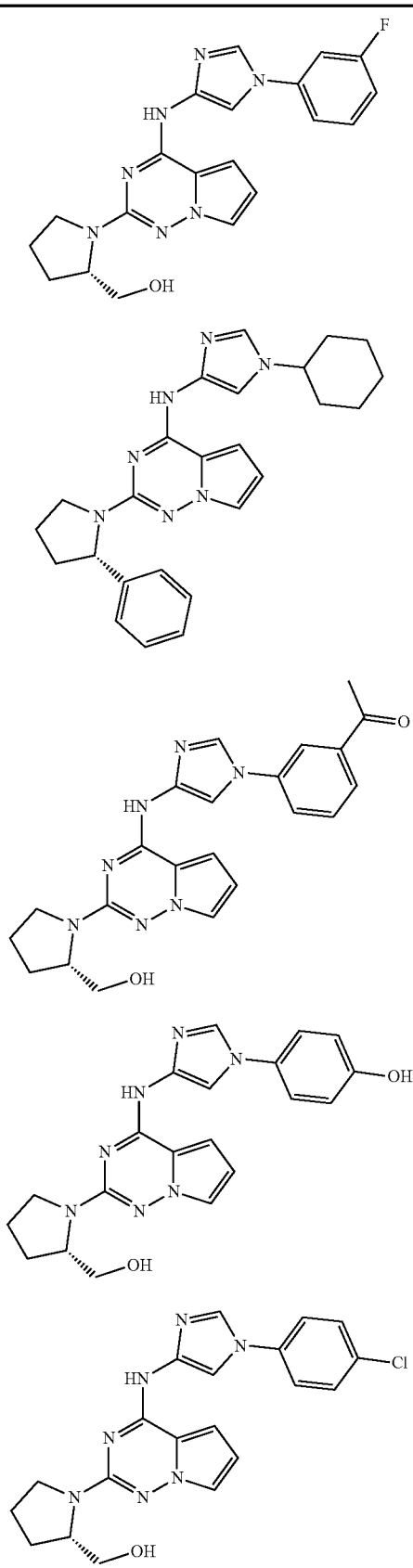
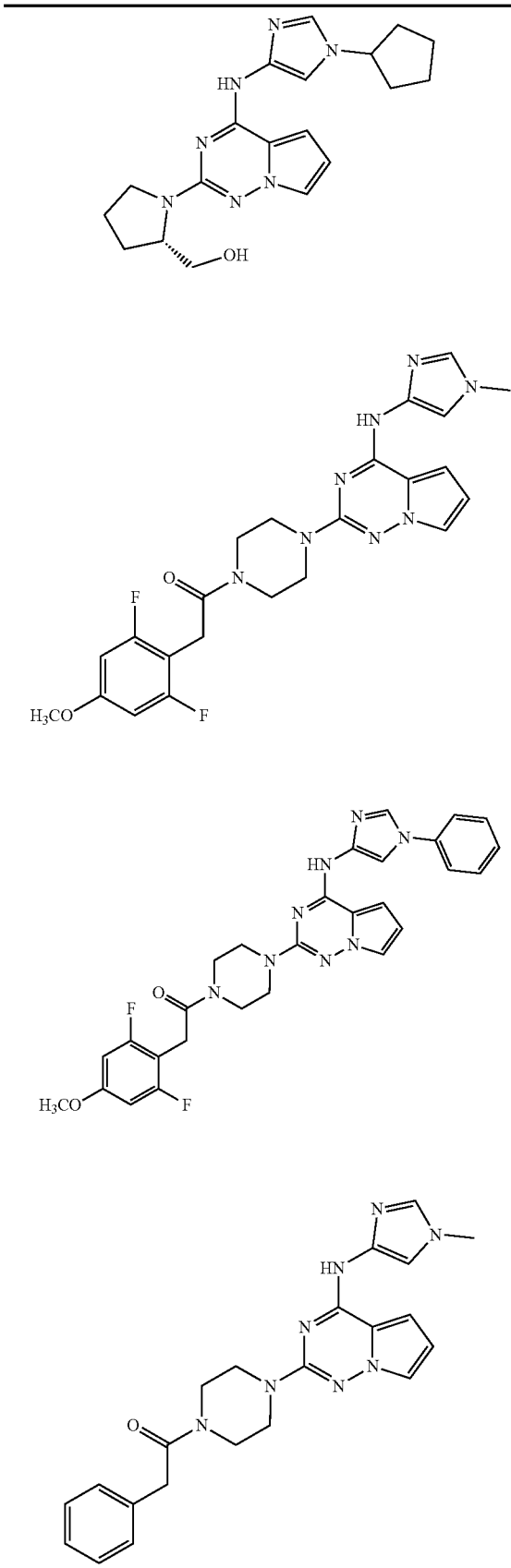

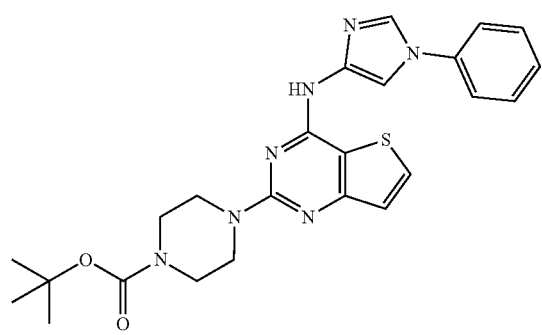 [SMILES: CC(C)(C)OC(=O)N1CCN(c2nc(Nc3cn(-c4ccccc4)cn3)c3sccc3n2)CC1]
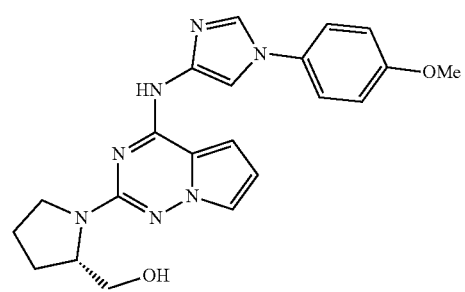 [SMILES: COc1ccc(-n2cnc(Nc3nc(N4CCC[C@H]4CO)nn4cccc34)c2)cc1]
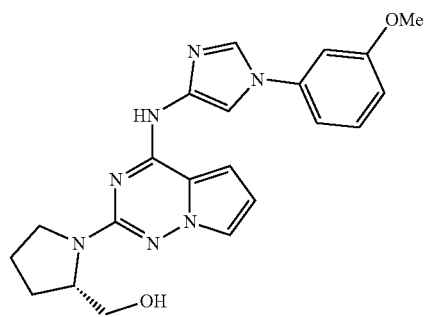 [SMILES: COc1cccc(-n2cnc(Nc3nc(N4CCC[C@H]4CO)nn4cccc34)c2)c1]
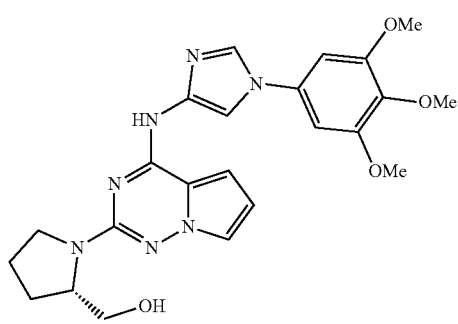 [SMILES: COc1cc(-n2cnc(Nc3nc(N4CCC[C@H]4CO)nn4cccc34)c2)cc(OC)c1OC]
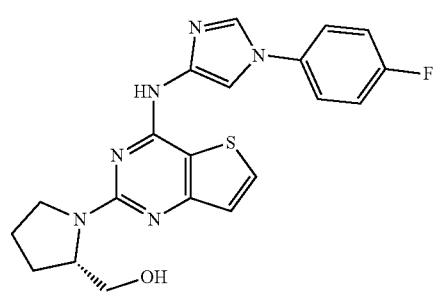 [SMILES: OC[C@@H]1CCCN1c1nc(Nc2cn(-c3ccc(F)cc3)cn2)c2sccc2n1]
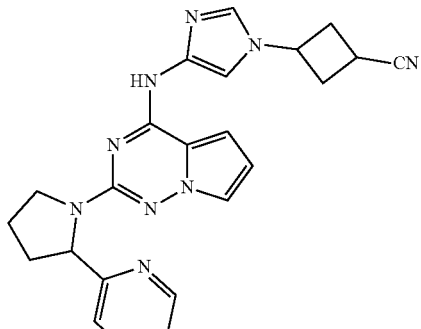
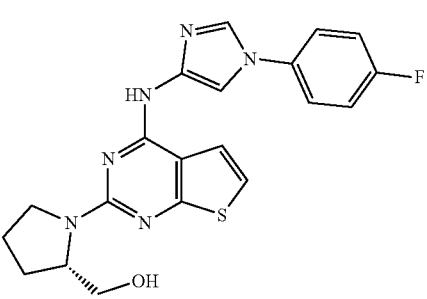 [SMILES: OC[C@@H]1CCCN1c1nc(Nc2cn(-c3ccc(F)cc3)cn2)c2ccsc2n1]
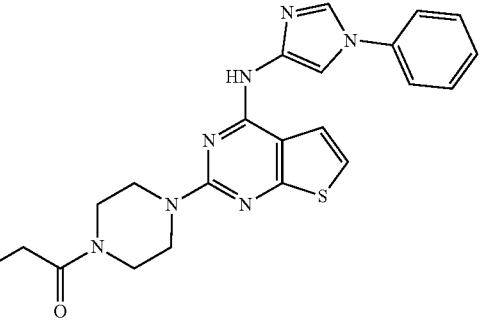
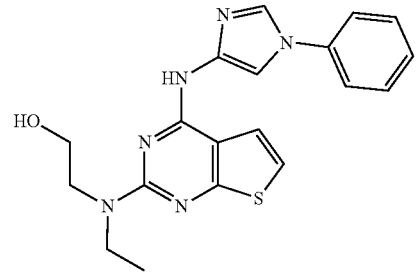 [SMILES: CCN(CCO)c1nc(Nc2cn(-c3ccccc3)cn2)c2ccsc2n1]
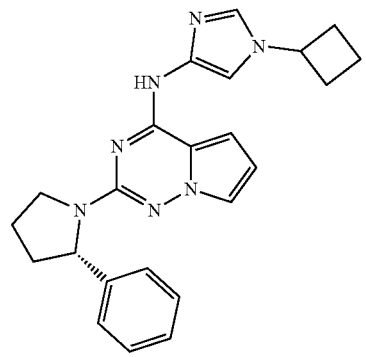 [SMILES: c1ccc([C@@H]2CCCN2c2nc(Nc3cn(C4CCC4)cn3)c3cccn3n2)cc1]

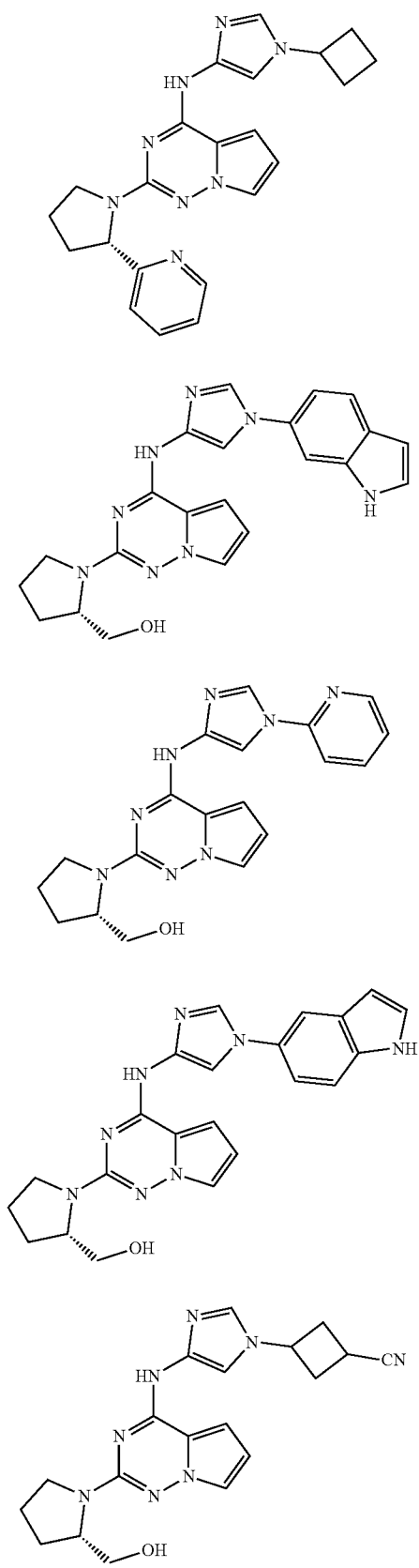
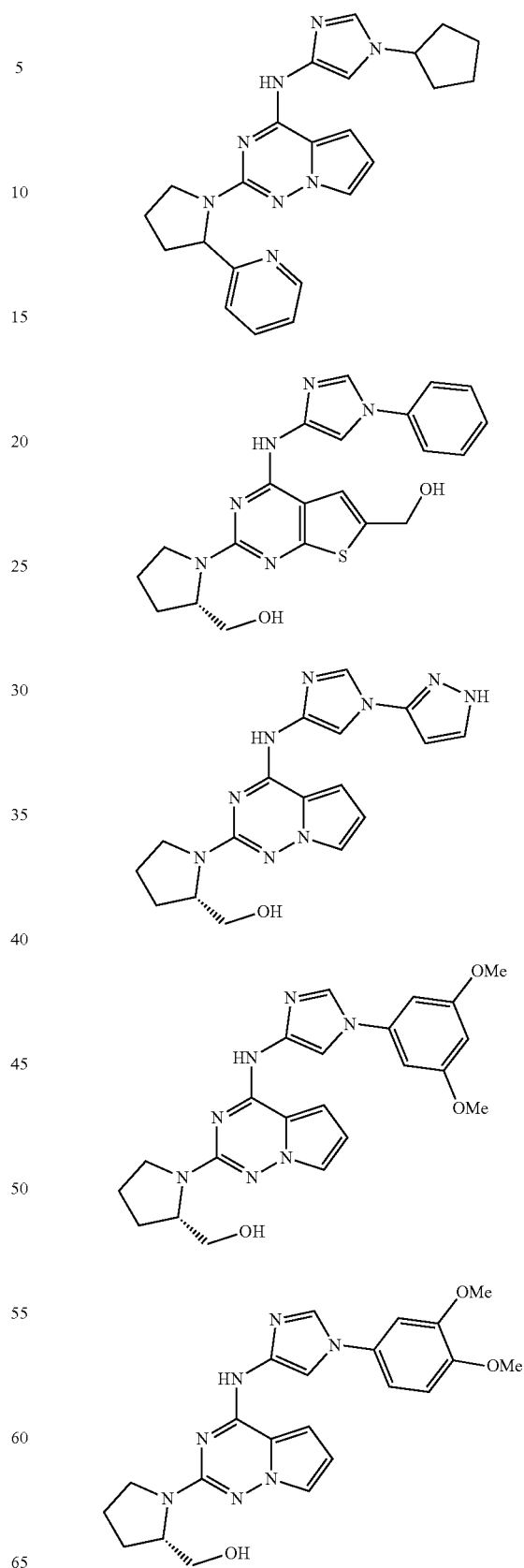

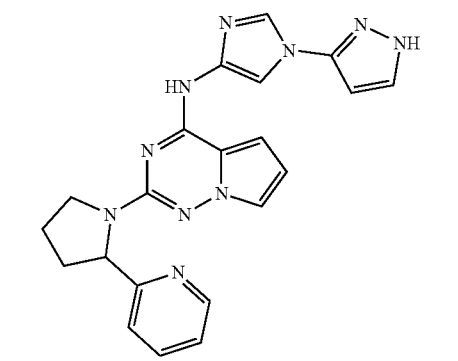 [SMILES: c1ccc(C2CCCN2c2nc(Nc3cn(-c4cc[nH]n4)cn3)c3cccn3n2)nc1]
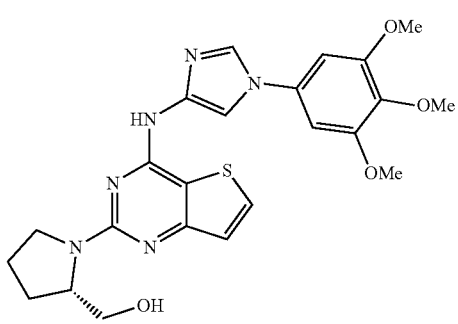 [SMILES: COc1cc(-n2cnc(Nc3nc(N4CCC[C@H]4CO)nc4ccsc34)c2)cc(OC)c1OC]
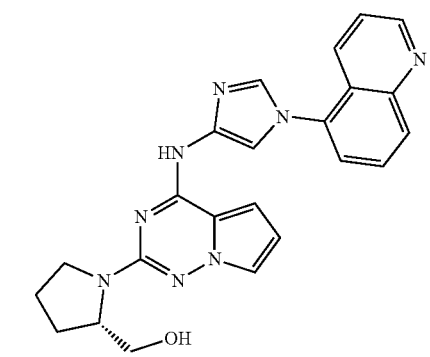 [SMILES: OC[C@@H]1CCCN1c1nc(Nc2cn(-c3cccc4ncccc34)cn2)c2cccn2n1]
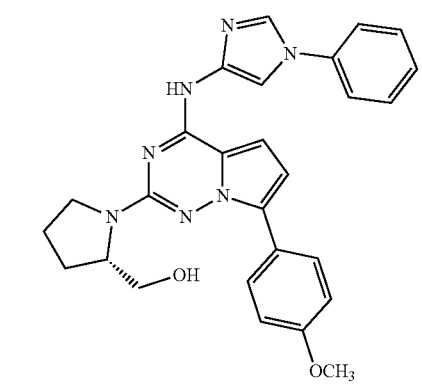 [SMILES: COc1ccc(-c2ccc3c(Nc4cn(-c5ccccc5)cn4)nc(N4CCC[C@H]4CO)nn23)cc1]
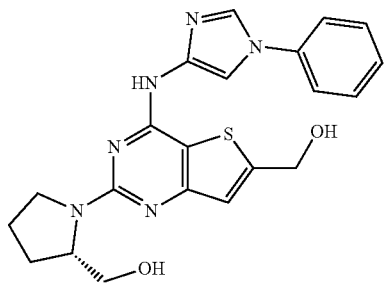 [SMILES: OCc1cc2nc(N3CCC[C@H]3CO)nc(Nc3cn(-c4ccccc4)cn3)c2s1]
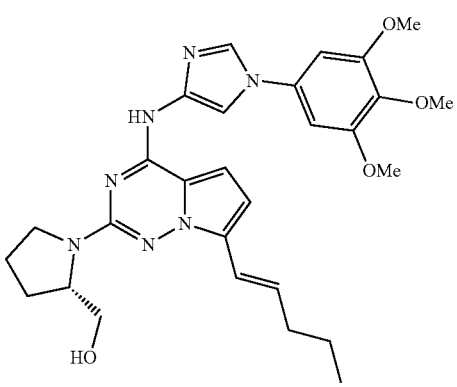 [SMILES: CCC/C=C/c1ccc2c(Nc3cn(-c4cc(OC)c(OC)c(OC)c4)cn3)nc(N3CCC[C@H]3CO)nn12]
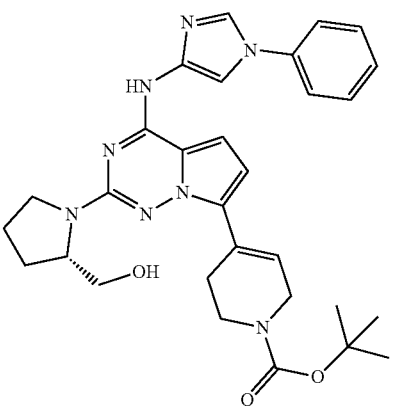 [SMILES: CC(C)(C)OC(=O)N1CC=C(c2ccc3c(Nc4cn(-c5ccccc5)cn4)nc(N4CCC[C@H]4CO)nn23)CC1]
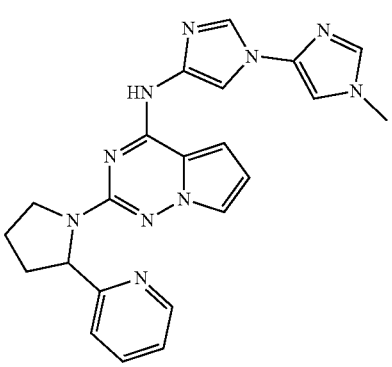 [SMILES: Cn1cnc(-n2cnc(Nc3nc(N4CCCC4c4ccccn4)nn4cccc34)c2)c1]

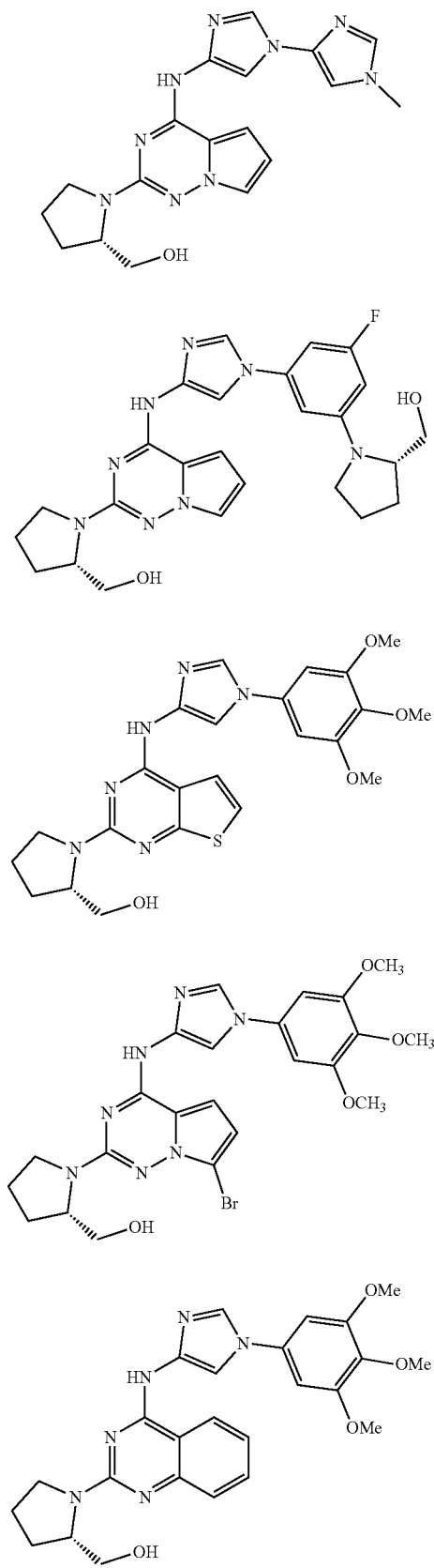
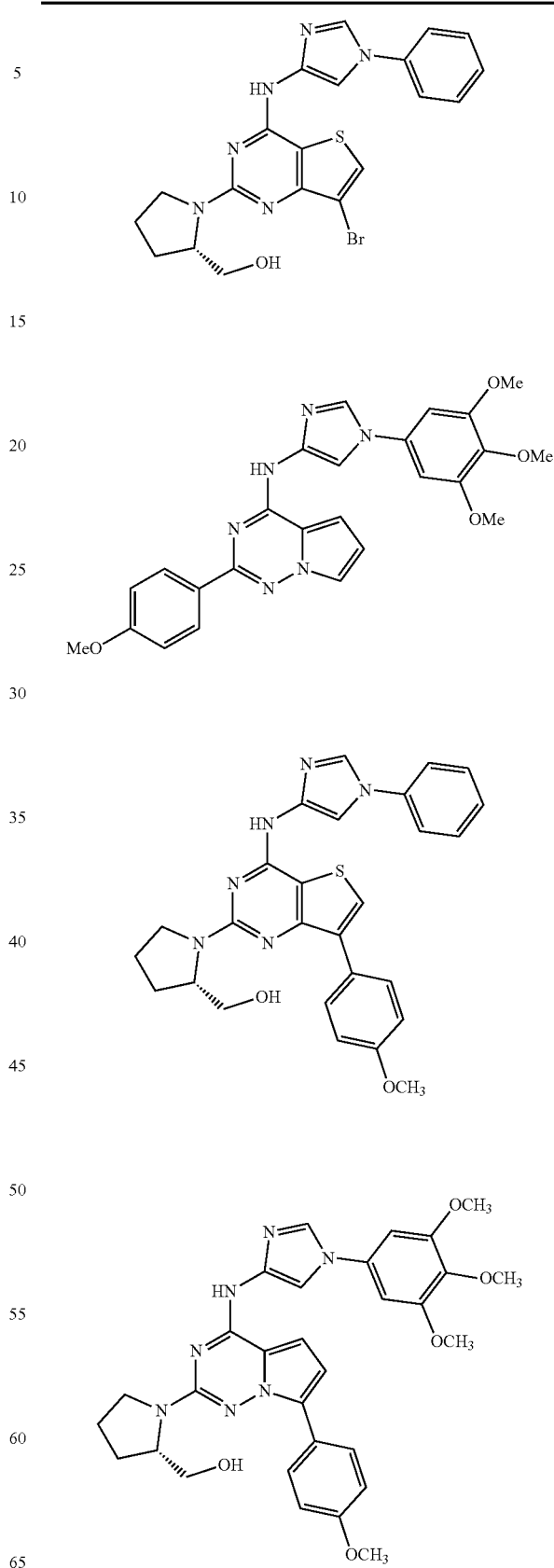

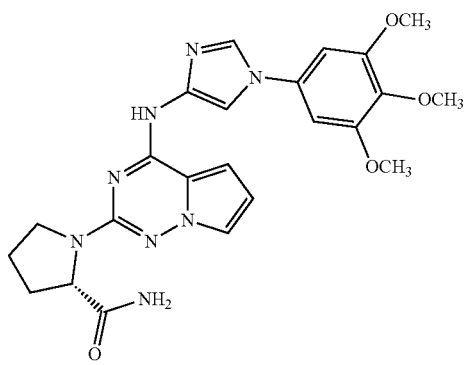 [SMILES: COc1cc(-n2cnc(Nc3nc(N4CCC[C@H]4C(N)=O)nn4cccc34)c2)cc(OC)c1OC]
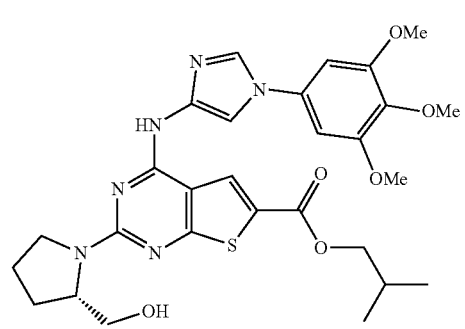 [SMILES: COc1cc(-n2cnc(Nc3nc(N4CCC[C@H]4CO)nc4sc(C(=O)OCC(C)C)cc34)c2)cc(OC)c1OC]
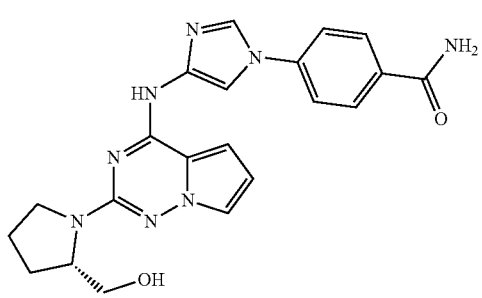 [SMILES: NC(=O)c1ccc(-n2cnc(Nc3nc(N4CCC[C@H]4CO)nn4cccc34)c2)cc1]
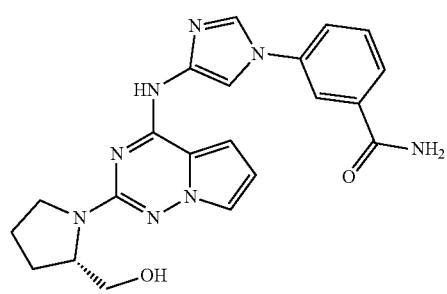 [SMILES: NC(=O)c1cccc(-n2cnc(Nc3nc(N4CCC[C@H]4CO)nn4cccc34)c2)c1]
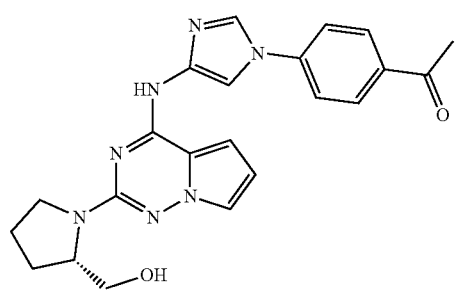 [SMILES: CC(=O)c1ccc(-n2cnc(Nc3nc(N4CCC[C@H]4CO)nn4cccc34)c2)cc1]
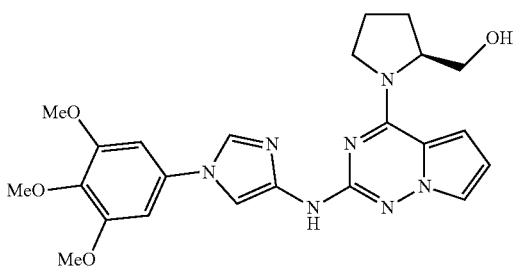 [SMILES: COc1cc(-n2cnc(Nc3nc(N4CCC[C@H]4CO)c4cccn4n3)c2)cc(OC)c1OC]
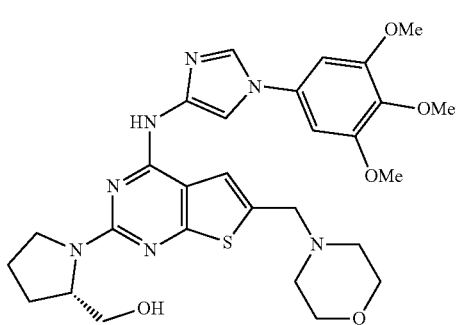 [SMILES: COc1cc(-n2cnc(Nc3nc(N4CCC[C@H]4CO)nc4sc(CN5CCOCC5)cc34)c2)cc(OC)c1OC]
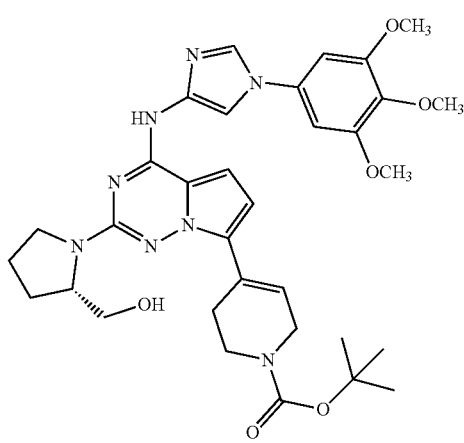 [SMILES: COc1cc(-n2cnc(Nc3nc(N4CCC[C@H]4CO)nn4c(C5=CCN(C(=O)OC(C)(C)C)CC5)ccc34)c2)cc(OC)c1OC]
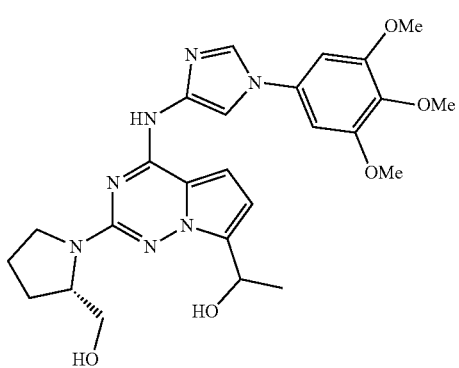 [SMILES: COc1cc(-n2cnc(Nc3nc(N4CCC[C@H]4CO)nn4c(C(C)O)ccc34)c2)cc(OC)c1OC]

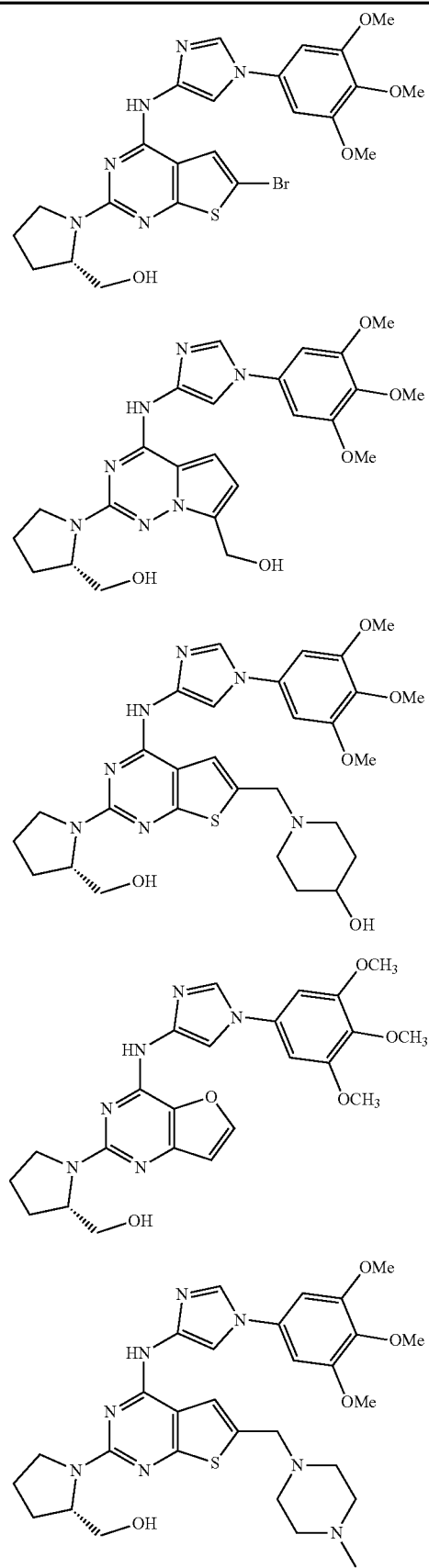
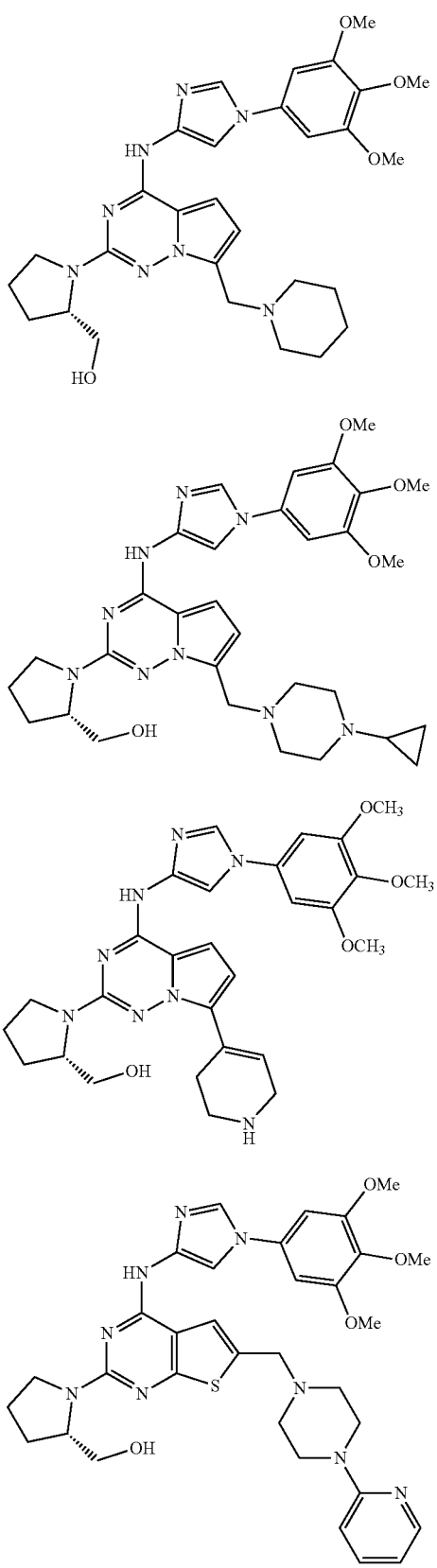

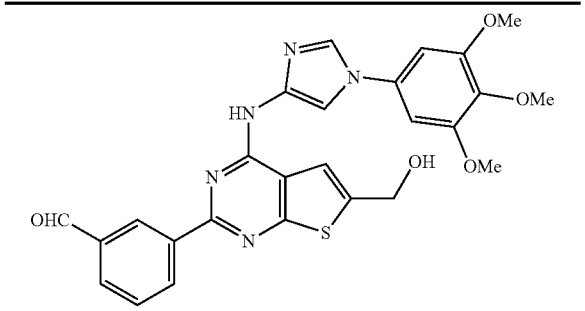
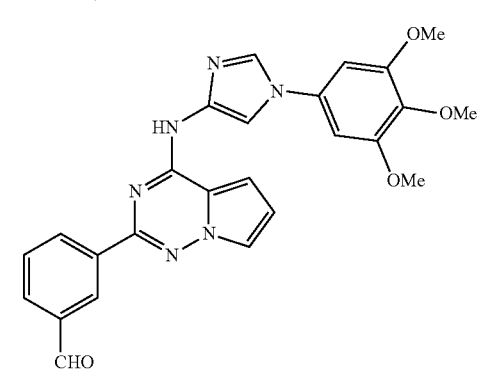 [SMILES: COc1cc(-n2cnc(Nc3nc(-c4cccc(C=O)c4)nn4cccc34)c2)cc(OC)c1OC]
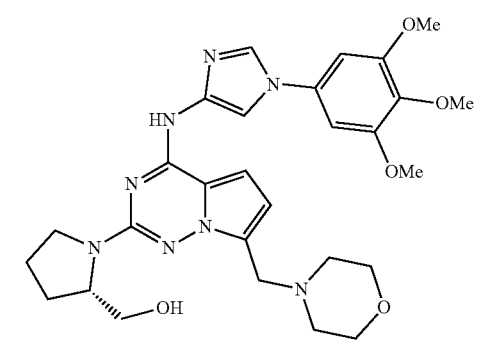 [SMILES: COc1cc(-n2cnc(Nc3nc(N4CCC[C@H]4CO)nn4c(CN5CCOCC5)ccc34)c2)cc(OC)c1OC]
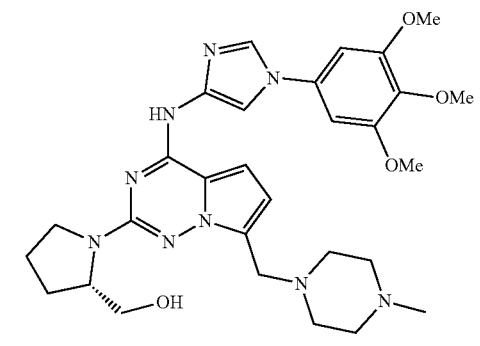 [SMILES: COc1cc(-n2cnc(Nc3nc(N4CCC[C@H]4CO)nn4c(CN5CCN(C)CC5)ccc34)c2)cc(OC)c1OC]
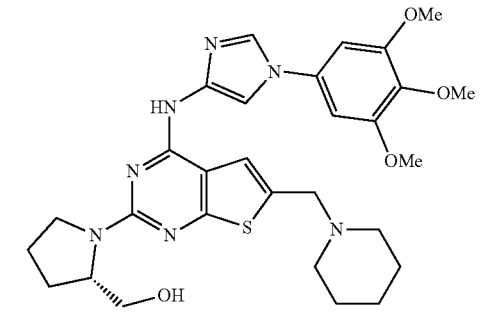 [SMILES: COc1cc(-n2cnc(Nc3nc(N4CCC[C@H]4CO)nc4sc(CN5CCCCC5)cc34)c2)cc(OC)c1OC]
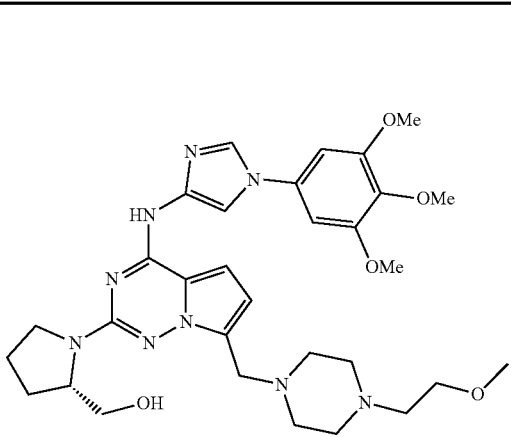
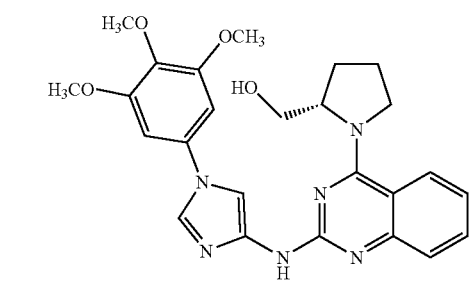 [SMILES: COc1cc(-n2cnc(Nc3nc(N4CCC[C@H]4CO)c4ccccc4n3)c2)cc(OC)c1OC]
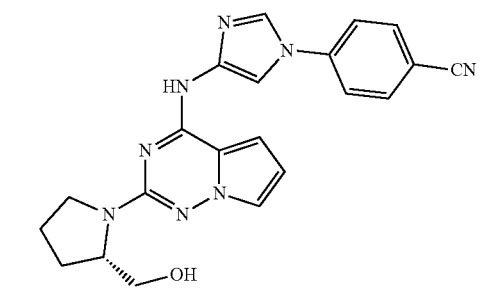 [SMILES: N#Cc1ccc(-n2cnc(Nc3nc(N4CCC[C@H]4CO)nn4cccc34)c2)cc1]
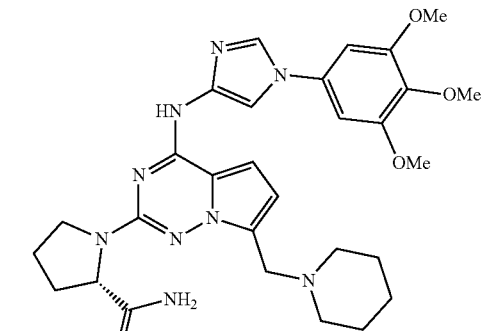

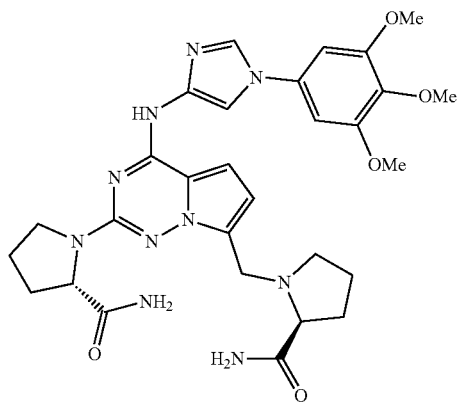 [SMILES: COc1cc(-n2cnc(Nc3nc(N4CCC[C@H]4C(N)=O)nn4c(CN5CCC[C@H]5C(N)=O)ccc34)c2)cc(OC)c1OC]
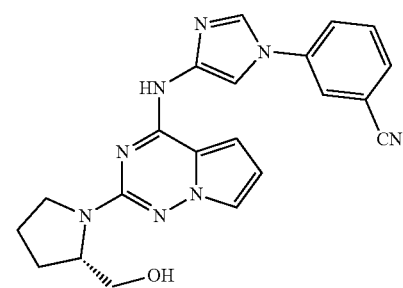 [SMILES: N#Cc1cccc(-n2cnc(Nc3nc(N4CCC[C@H]4CO)nn4cccc34)c2)c1]
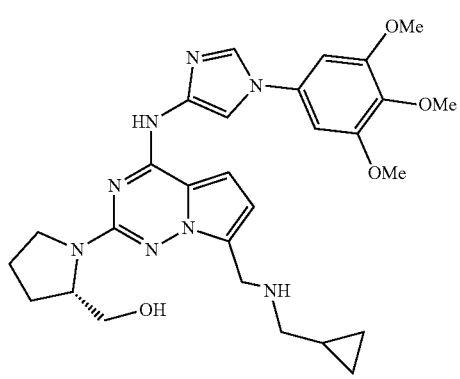 [SMILES: COc1cc(-n2cnc(Nc3nc(N4CCC[C@H]4CO)nn4c(CNCC5CC5)ccc34)c2)cc(OC)c1OC]
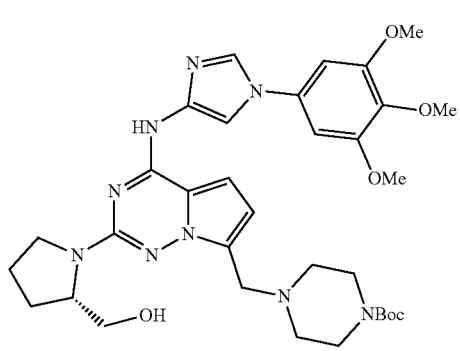 [SMILES: COc1cc(-n2cnc(Nc3nc(N4CCC[C@H]4CO)nn4c(CN5CCN(C(=O)OC(C)(C)C)CC5)ccc34)c2)cc(OC)c1OC]
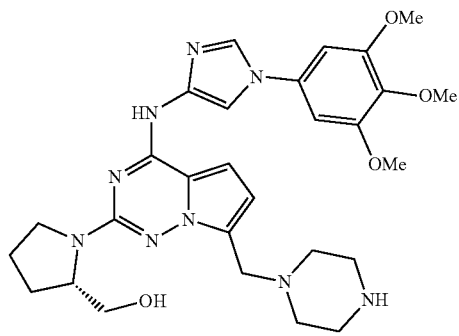 [SMILES: COc1cc(-n2cnc(Nc3nc(N4CCC[C@H]4CO)nn4c(CN5CCNCC5)ccc34)c2)cc(OC)c1OC]
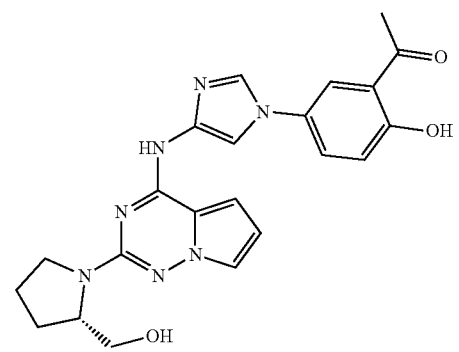 [SMILES: CC(=O)c1cc(-n2cnc(Nc3nc(N4CCC[C@H]4CO)nn4cccc34)c2)ccc1O]
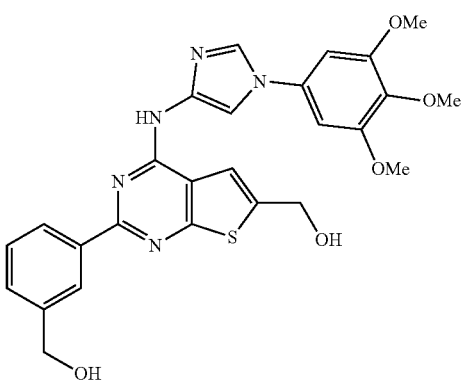 [SMILES: COc1cc(-n2cnc(Nc3nc(-c4cccc(CO)c4)nc4sc(CO)cc34)c2)cc(OC)c1OC]
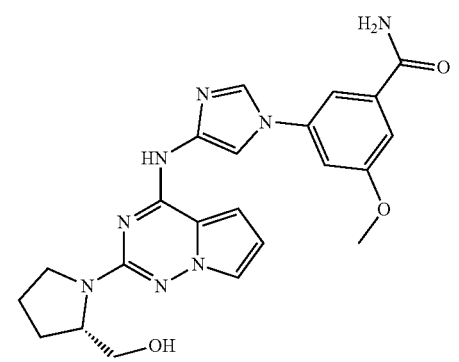 [SMILES: COc1cc(C(N)=O)cc(-n2cnc(Nc3nc(N4CCC[C@H]4CO)nn4cccc34)c2)c1]

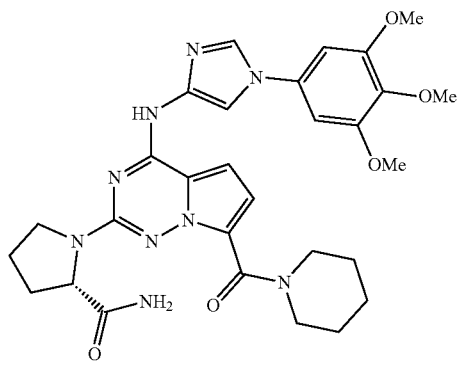 [SMILES: COc1cc(-n2cnc(Nc3nc(N4CCC[C@H]4C(N)=O)nn4c(C(=O)N5CCCCC5)ccc34)c2)cc(OC)c1OC]
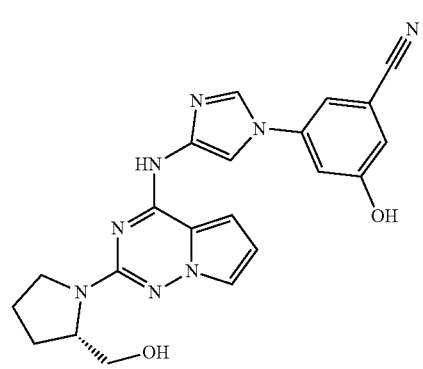 [SMILES: N#Cc1cc(O)cc(-n2cnc(Nc3nc(N4CCC[C@H]4CO)nn4cccc34)c2)c1]
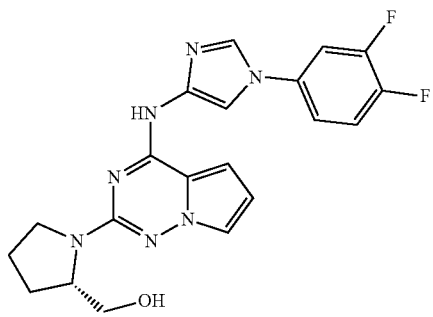 [SMILES: OC[C@@H]1CCCN1c1nc(Nc2cn(-c3ccc(F)c(F)c3)cn2)c2cccn2n1]
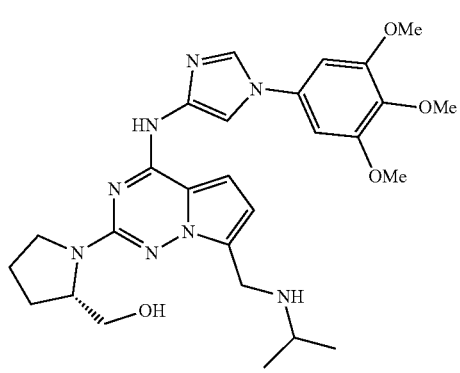 [SMILES: COc1cc(-n2cnc(Nc3nc(N4CCC[C@H]4CO)nn4c(CNC(C)C)ccc34)c2)cc(OC)c1OC]
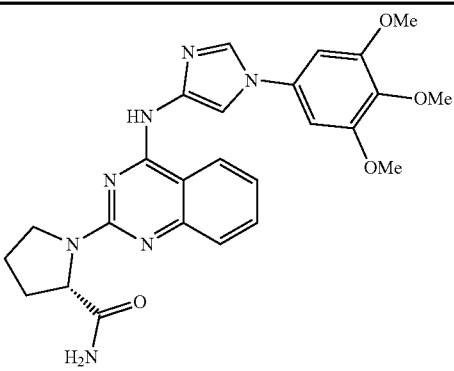
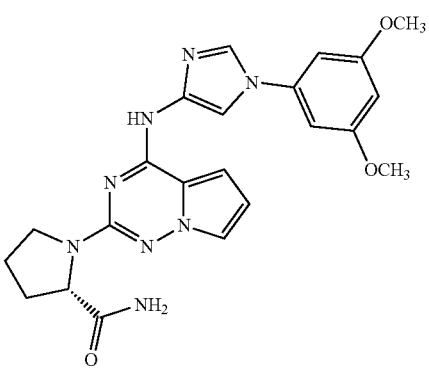 [SMILES: COc1cc(OC)cc(-n2cnc(Nc3nc(N4CCC[C@H]4C(N)=O)nn4cccc34)c2)c1]
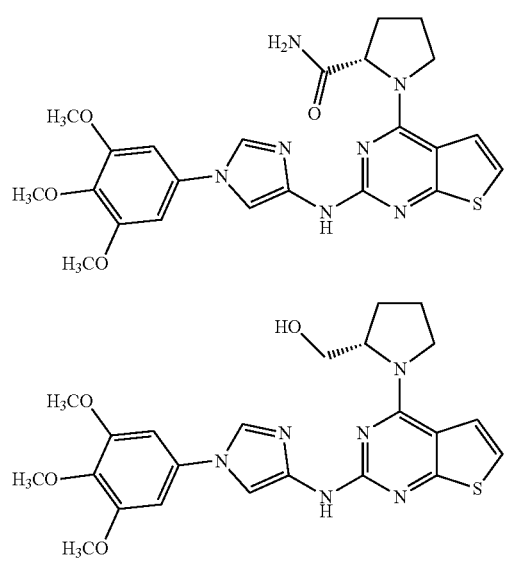
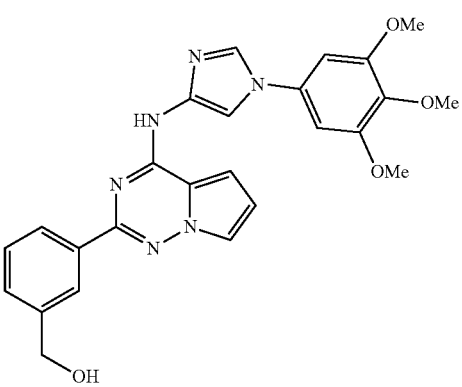 [SMILES: COc1cc(-n2cnc(Nc3nc(-c4cccc(CO)c4)nn4cccc34)c2)cc(OC)c1OC]

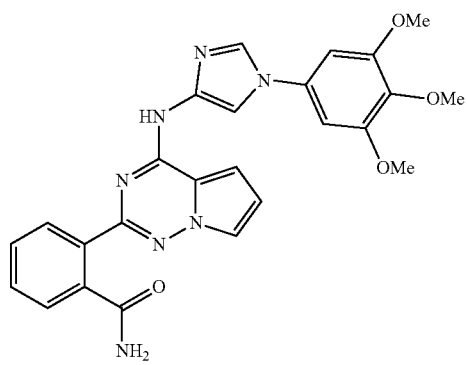 [SMILES: COc1cc(-n2cnc(Nc3nc(-c4ccccc4C(N)=O)nn4cccc34)c2)cc(OC)c1OC]
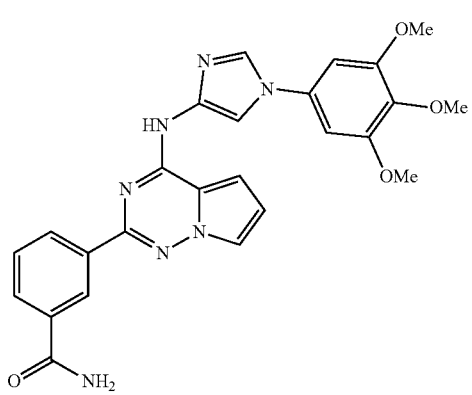 [SMILES: COc1cc(-n2cnc(Nc3nc(-c4cccc(C(N)=O)c4)nn4cccc34)c2)cc(OC)c1OC]
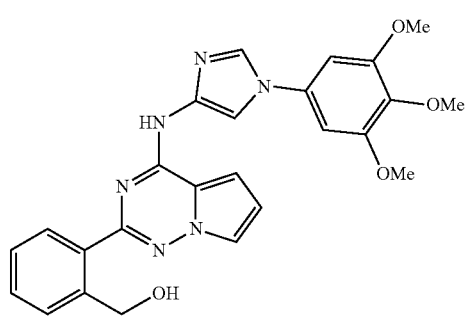 [SMILES: COc1cc(-n2cnc(Nc3nc(-c4ccccc4CO)nn4cccc34)c2)cc(OC)c1OC]
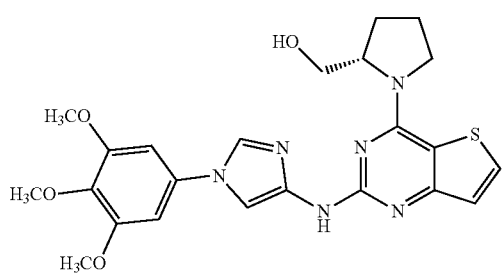 [SMILES: COc1cc(-n2cnc(Nc3nc(N4CCC[C@H]4CO)c4sccc4n3)c2)cc(OC)c1OC]
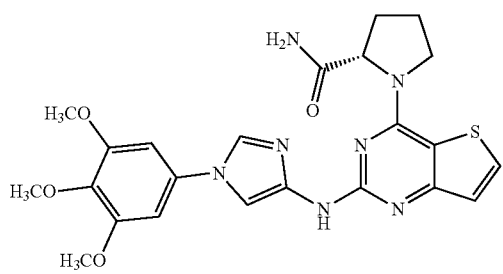 [SMILES: COc1cc(-n2cnc(Nc3nc(N4CCC[C@H]4C(N)=O)c4sccc4n3)c2)cc(OC)c1OC]
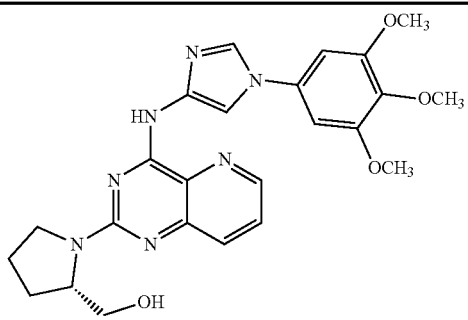
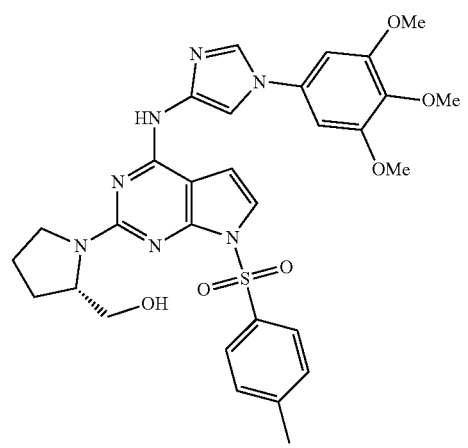 [SMILES: COc1cc(-n2cnc(Nc3nc(N4CCC[C@H]4CO)nc4c3ccn4S(=O)(=O)c3ccc(C)cc3)c2)cc(OC)c1OC]
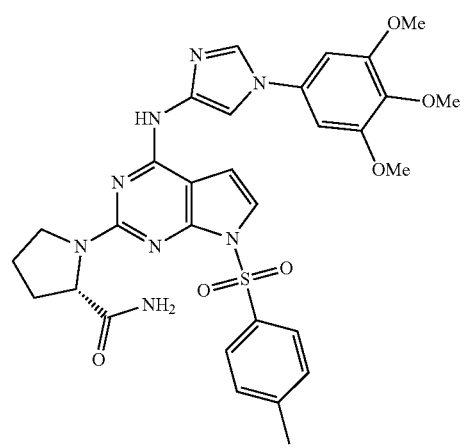 [SMILES: COc1cc(-n2cnc(Nc3nc(N4CCC[C@H]4C(N)=O)nc4c3ccn4S(=O)(=O)c3ccc(C)cc3)c2)cc(OC)c1OC]
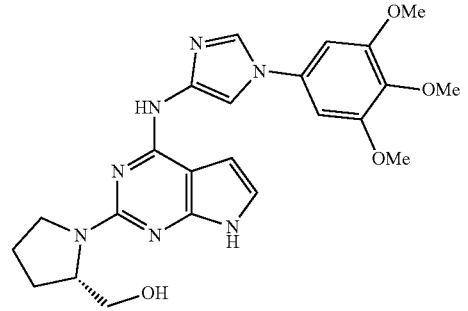 [SMILES: COc1cc(-n2cnc(Nc3nc(N4CCC[C@H]4CO)nc4[nH]ccc34)c2)cc(OC)c1OC]

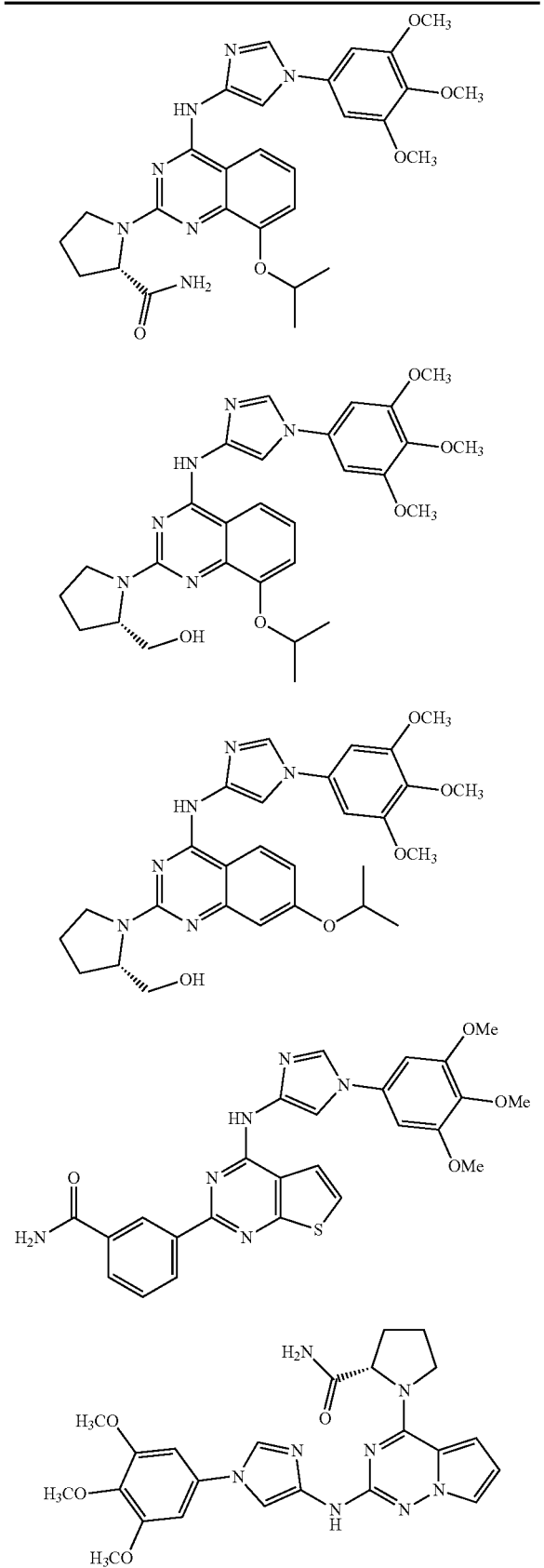
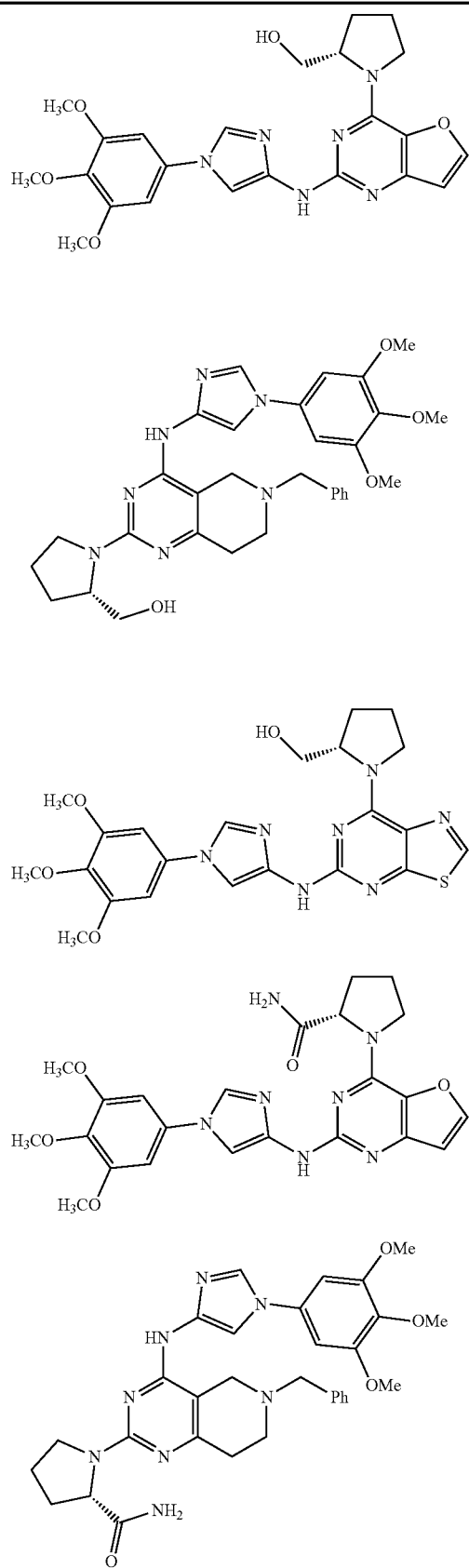

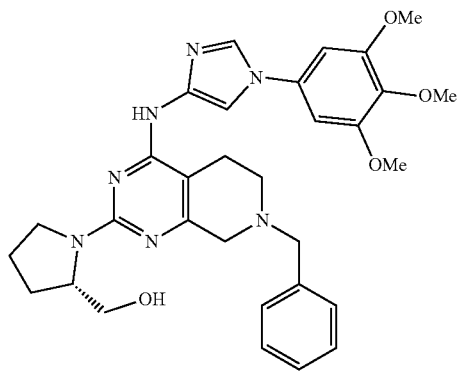 [SMILES: COc1cc(-n2cnc(Nc3nc(N4CCC[C@H]4CO)nc4c3CCN(Cc3ccccc3)C4)c2)cc(OC)c1OC]
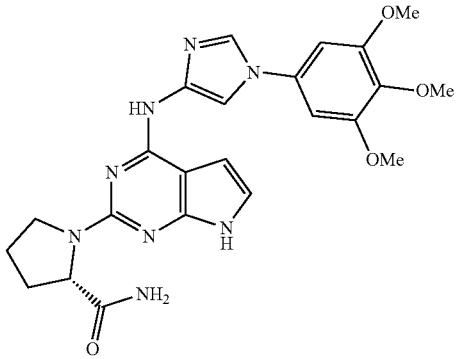
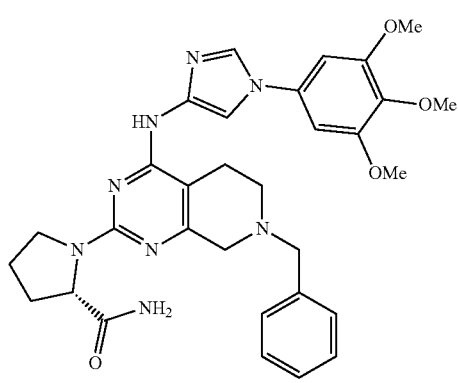 [SMILES: COc1cc(-n2cnc(Nc3nc(N4CCC[C@H]4C(N)=O)nc4c3CCN(Cc3ccccc3)C4)c2)cc(OC)c1OC]
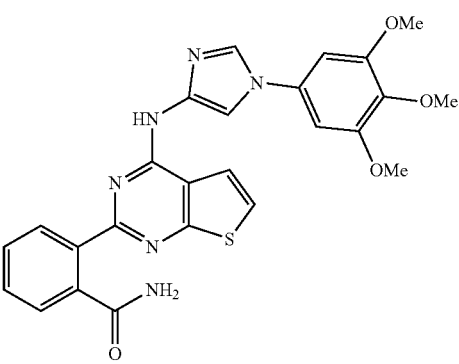
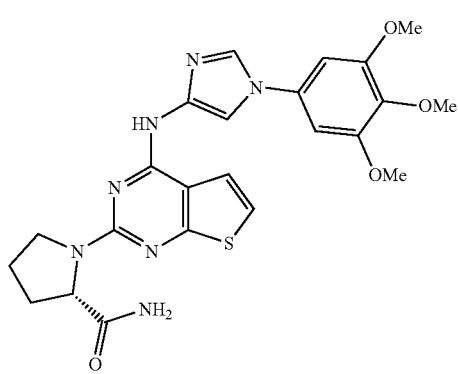 [SMILES: COc1cc(-n2cnc(Nc3nc(N4CCC[C@H]4C(N)=O)nc4sccc34)c2)cc(OC)c1OC]
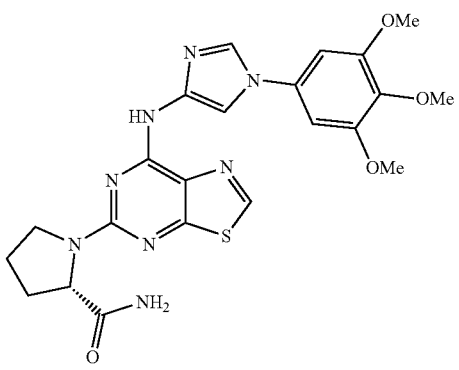
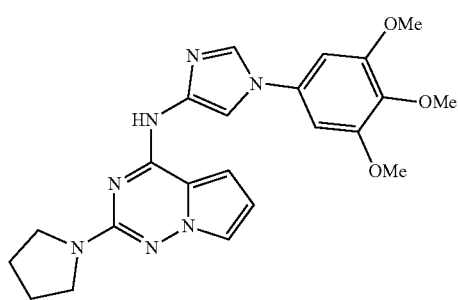 [SMILES: COc1cc(-n2cnc(Nc3nc(N4CCCC4)nn4cccc34)c2)cc(OC)c1OC]
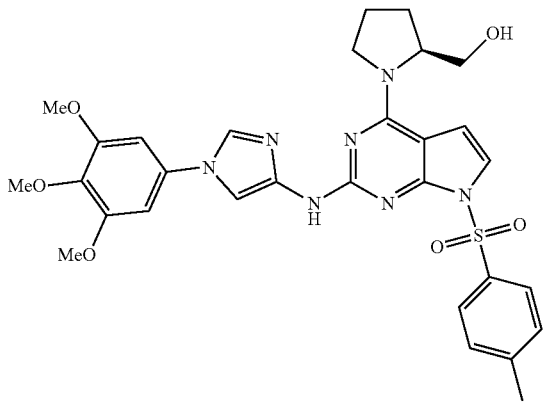 [SMILES: COc1cc(-n2cnc(Nc3nc(N4CCC[C@H]4CO)c4ccn(S(=O)(=O)c5ccc(C)cc5)c4n3)c2)cc(OC)c1OC]

55
-continued
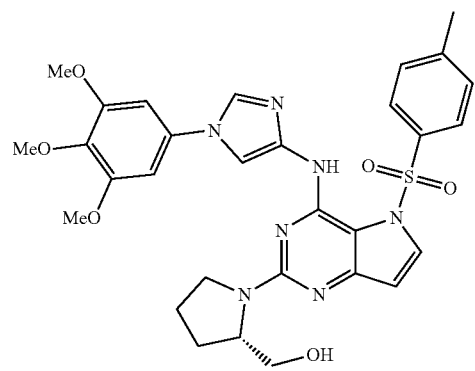 [SMILES: COc1cc(-n2cnc(Nc3nc(N4CCC[C@H]4CO)nc4ccn(S(=O)(=O)c5ccc(C)cc5)c34)c2)cc(OC)c1OC]
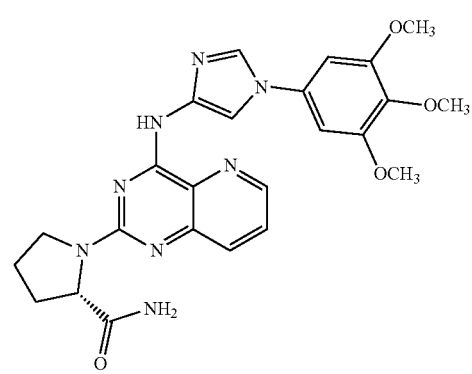 [SMILES: COc1cc(-n2cnc(Nc3nc(N4CCC[C@H]4C(N)=O)nc4cccnc34)c2)cc(OC)c1OC]
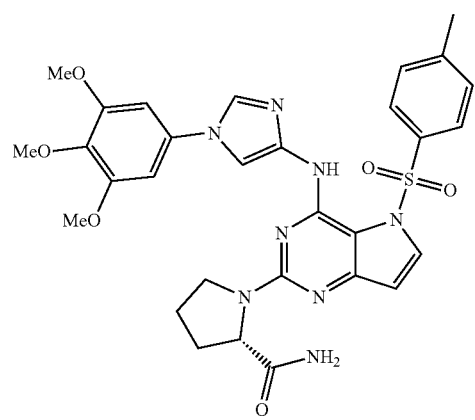 [SMILES: COc1cc(-n2cnc(Nc3nc(N4CCC[C@H]4C(N)=O)nc4ccn(S(=O)(=O)c5ccc(C)cc5)c34)c2)cc(OC)c1OC]
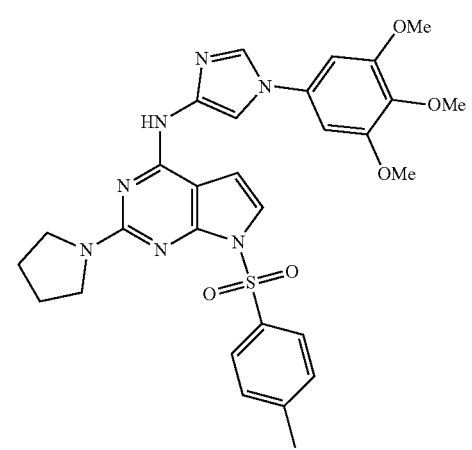 [SMILES: COc1cc(-n2cnc(Nc3nc(N4CCCC4)nc4c3ccn4S(=O)(=O)c3ccc(C)cc3)c2)cc(OC)c1OC]
56
-continued
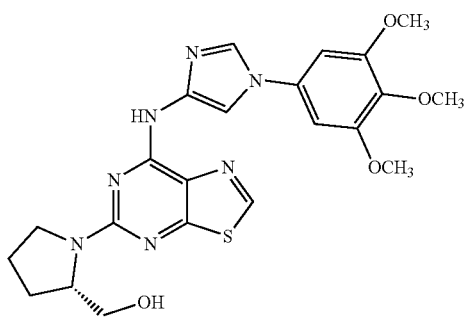 [SMILES: COc1cc(-n2cnc(Nc3nc(N4CCC[C@H]4CO)nc4scnc34)c2)cc(OC)c1OC]
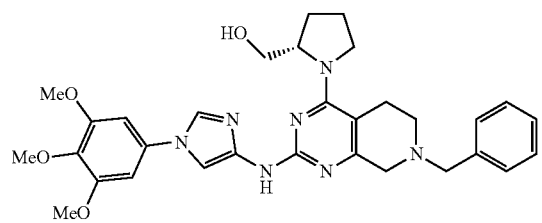 [SMILES: COc1cc(-n2cnc(Nc3nc4c(c(N5CCC[C@H]5CO)n3)CCN(Cc3ccccc3)C4)c2)cc(OC)c1OC]
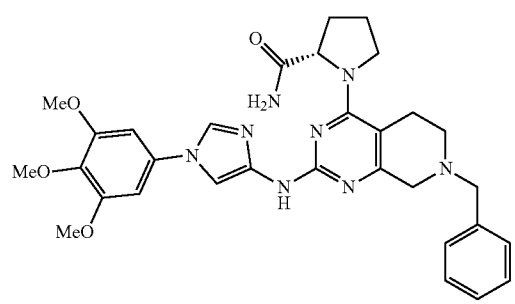 [SMILES: COc1cc(-n2cnc(Nc3nc4c(c(N5CCC[C@H]5C(N)=O)n3)CCN(Cc3ccccc3)C4)c2)cc(OC)c1OC]
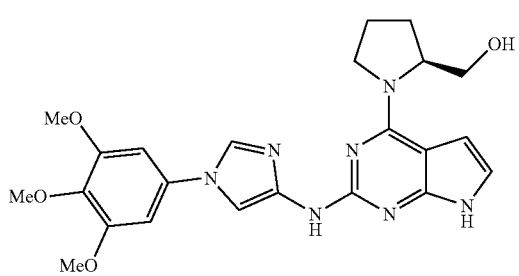 [SMILES: COc1cc(-n2cnc(Nc3nc(N4CCC[C@H]4CO)c4cc[nH]c4n3)c2)cc(OC)c1OC]
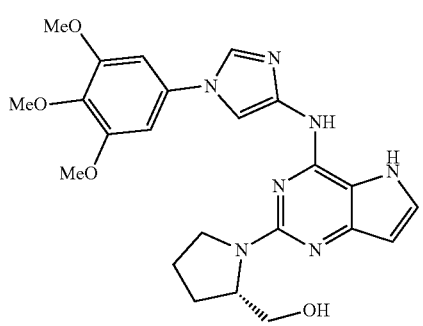 [SMILES: COc1cc(-n2cnc(Nc3nc(N4CCC[C@H]4CO)nc4cc[nH]c34)c2)cc(OC)c1OC]

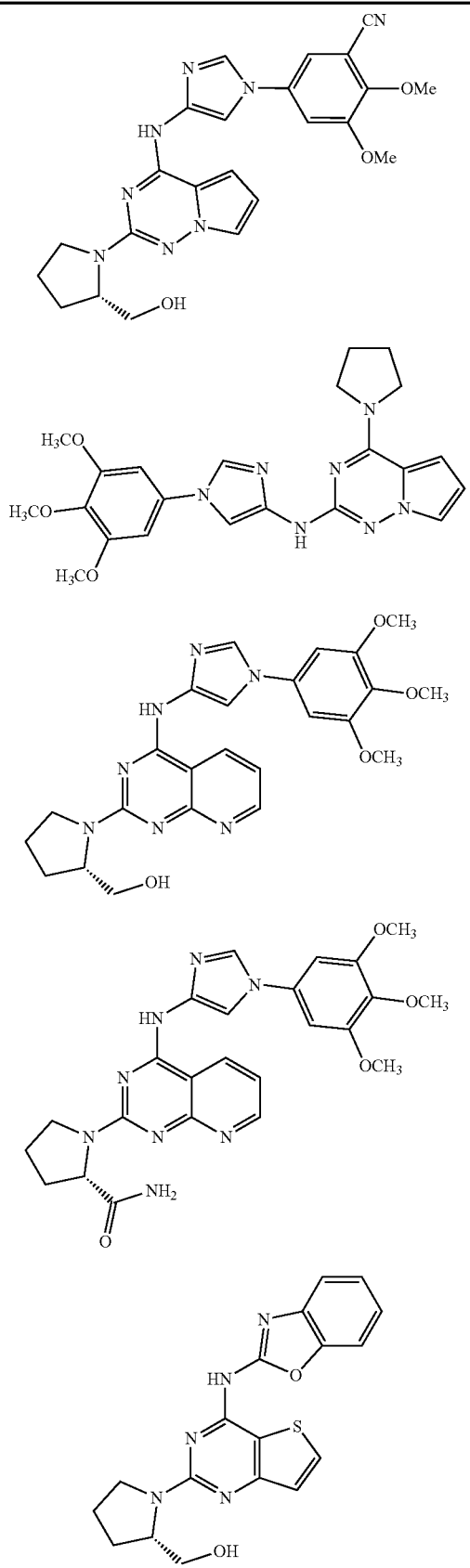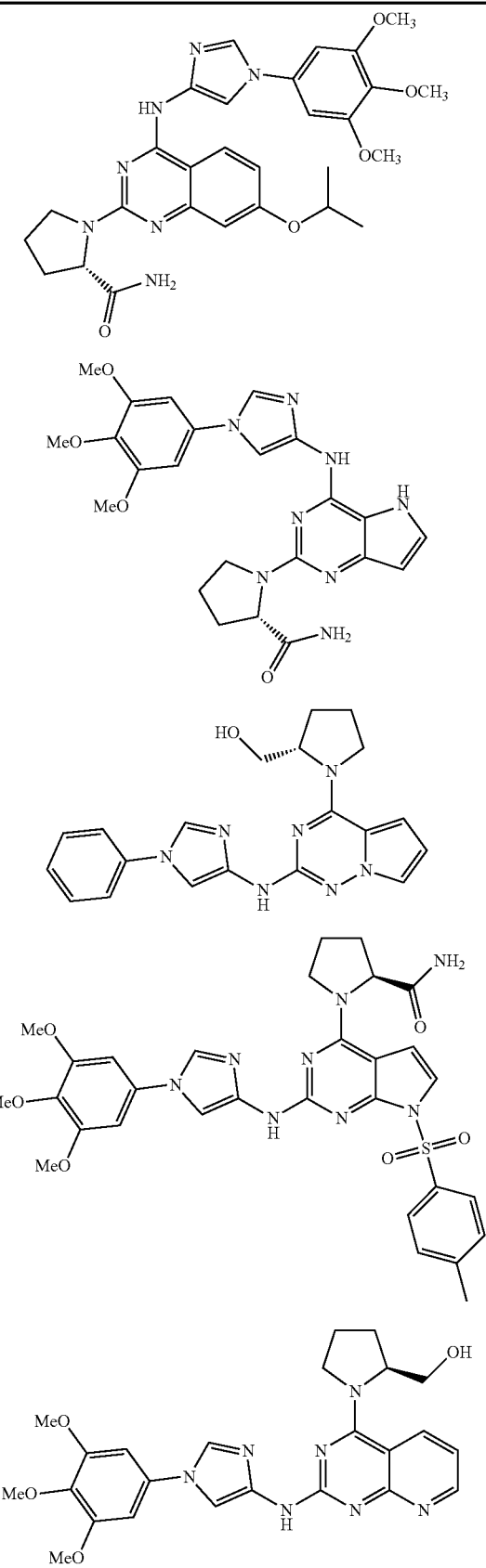

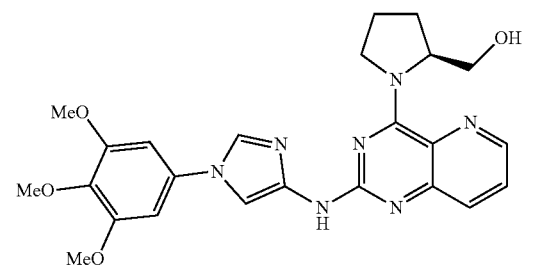 [SMILES: COc1cc(-n2cnc(Nc3nc(N4CCC[C@H]4CO)c4ncccc4n3)c2)cc(OC)c1OC]
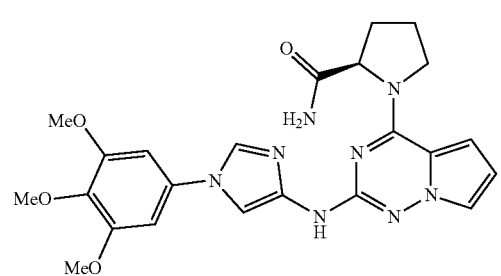 [SMILES: COc1cc(-n2cnc(Nc3nc(N4CCC[C@@H]4C(N)=O)c4cccn4n3)c2)cc(OC)c1OC]
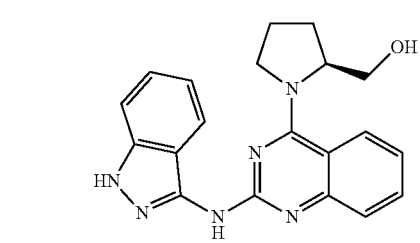 [SMILES: OC[C@@H]1CCCN1c1nc(Nc2n[nH]c3ccccc23)nc2ccccc12]
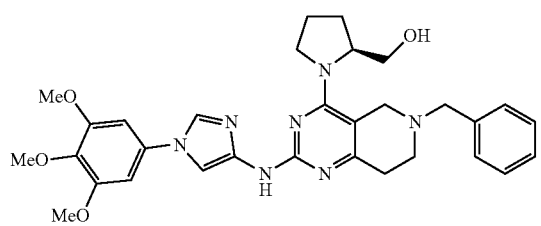 [SMILES: COc1cc(-n2cnc(Nc3nc4c(c(N5CCC[C@H]5CO)n3)CN(Cc3ccccc3)CC4)c2)cc(OC)c1OC]
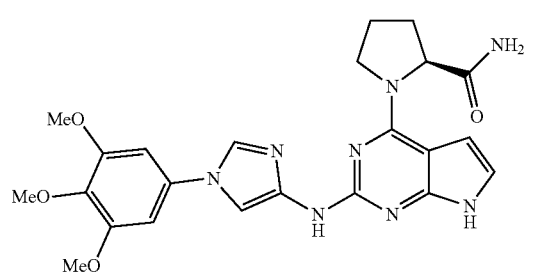 [SMILES: COc1cc(-n2cnc(Nc3nc(N4CCC[C@H]4C(N)=O)c4cc[nH]c4n3)c2)cc(OC)c1OC]
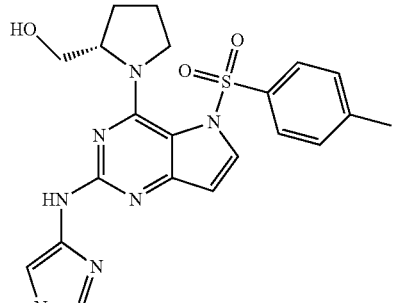
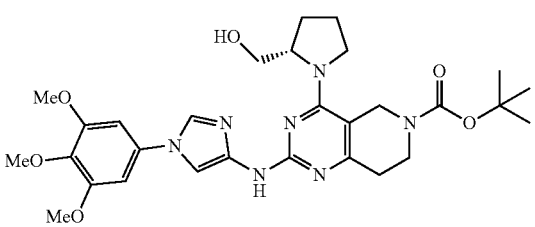 [SMILES: COc1cc(-n2cnc(Nc3nc4c(c(N5CCC[C@H]5CO)n3)CN(C(=O)OC(C)(C)C)CC4)c2)cc(OC)c1OC]
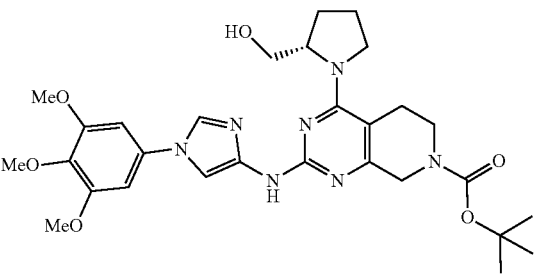 [SMILES: COc1cc(-n2cnc(Nc3nc4c(c(N5CCC[C@H]5CO)n3)CCN(C(=O)OC(C)(C)C)C4)c2)cc(OC)c1OC]
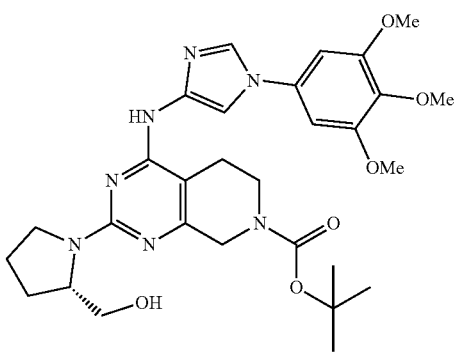 [SMILES: COc1cc(-n2cnc(Nc3nc(N4CCC[C@H]4CO)nc4c3CCN(C(=O)OC(C)(C)C)C4)c2)cc(OC)c1OC]

-continued
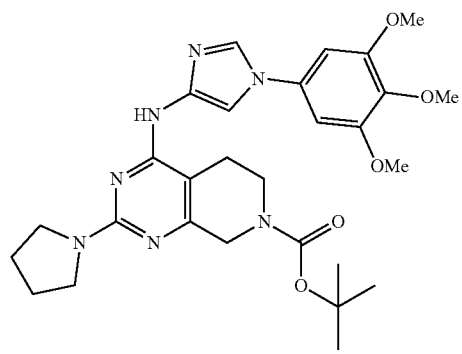 [SMILES: COc1cc(-n2cnc(Nc3nc(N4CCCC4)nc4c3CCN(C(=O)OC(C)(C)C)C4)c2)cc(OC)c1OC]
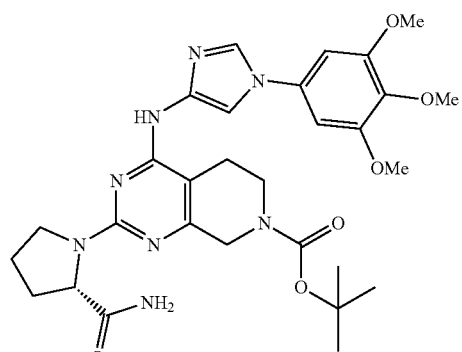
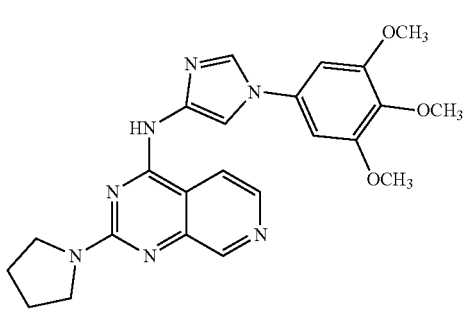 [SMILES: COc1cc(-n2cnc(Nc3nc(N4CCCC4)nc4cnccc34)c2)cc(OC)c1OC]
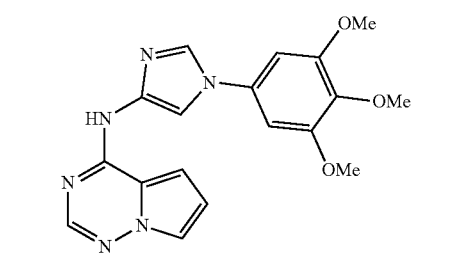 [SMILES: COc1cc(-n2cnc(Nc3ncnn4cccc34)c2)cc(OC)c1OC]
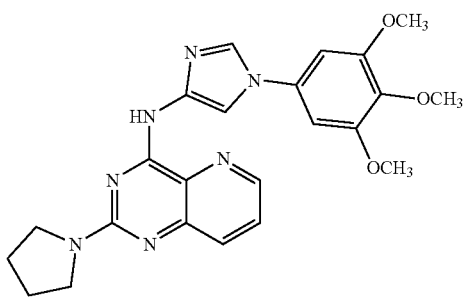 [SMILES: COc1cc(-n2cnc(Nc3nc(N4CCCC4)nc4cccnc34)c2)cc(OC)c1OC]
-continued
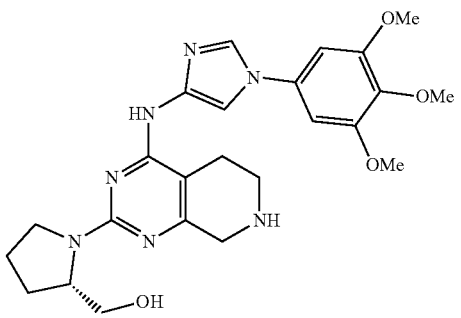 [SMILES: COc1cc(-n2cnc(Nc3nc(N4CCC[C@H]4CO)nc4c3CCNC4)c2)cc(OC)c1OC]
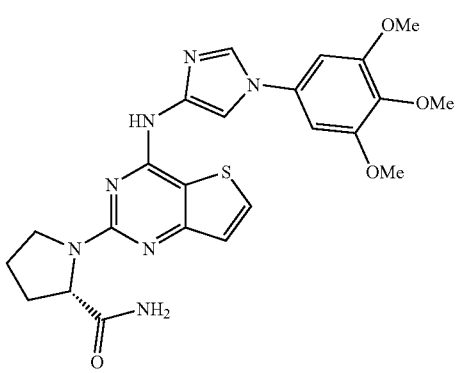 [SMILES: COc1cc(-n2cnc(Nc3nc(N4CCC[C@H]4C(N)=O)nc4ccsc34)c2)cc(OC)c1OC]
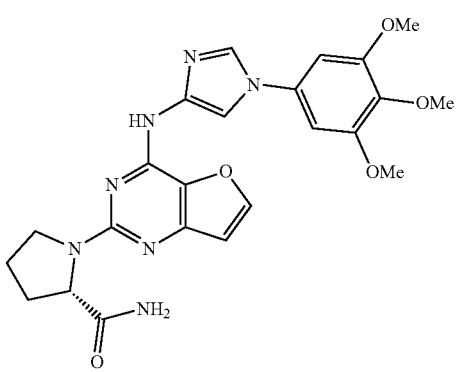 [SMILES: COc1cc(-n2cnc(Nc3nc(N4CCC[C@H]4C(N)=O)nc4ccoc34)c2)cc(OC)c1OC]
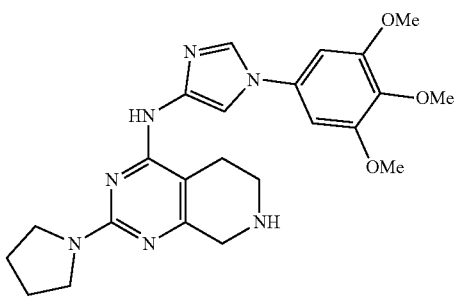 [SMILES: COc1cc(-n2cnc(Nc3nc(N4CCCC4)nc4c3CCNC4)c2)cc(OC)c1OC]

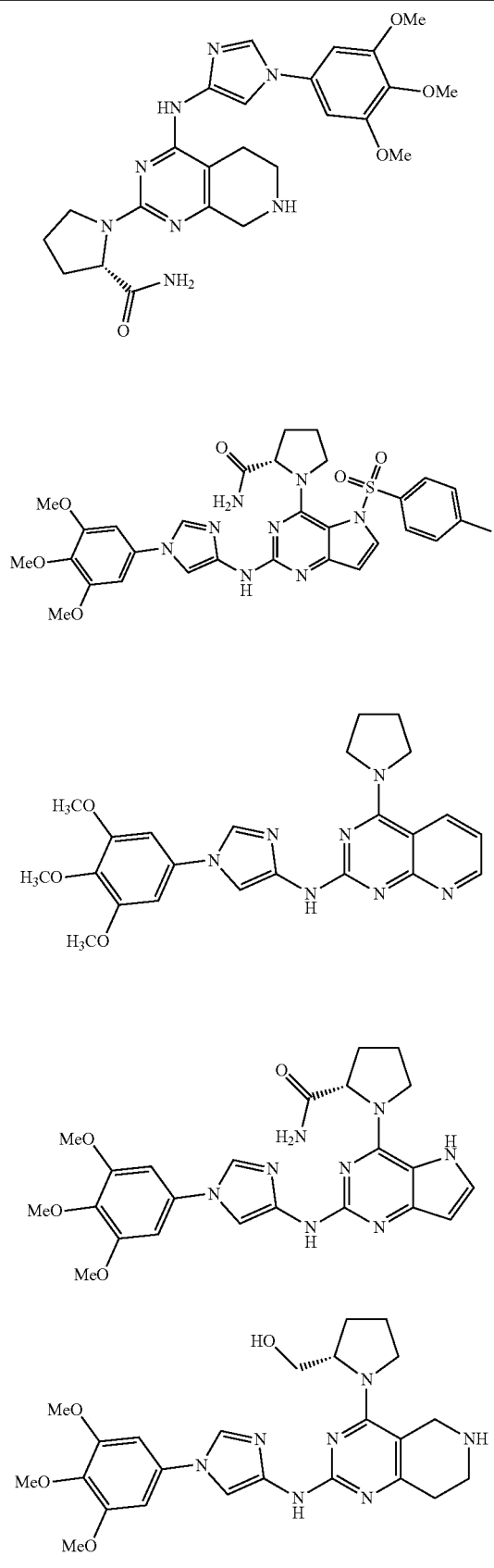
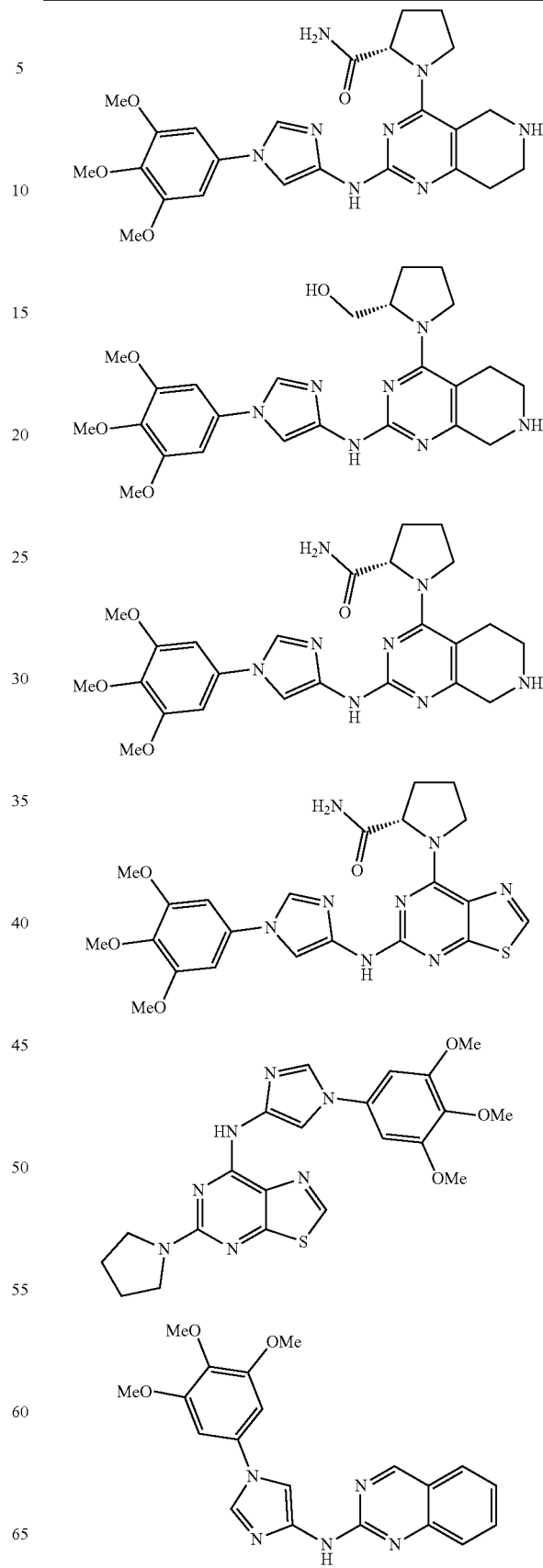

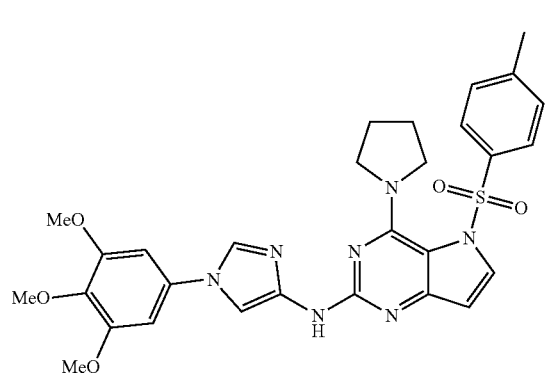 [SMILES: COc1cc(-n2cnc(Nc3nc(N4CCCC4)c4c(ccn4S(=O)(=O)c4ccc(C)cc4)n3)c2)cc(OC)c1OC]
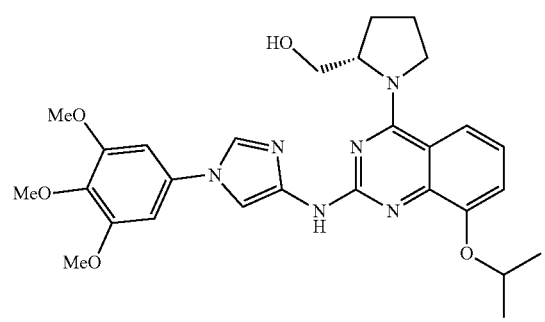 [SMILES: COc1cc(-n2cnc(Nc3nc(N4CCC[C@H]4CO)c4cccc(OC(C)C)c4n3)c2)cc(OC)c1OC]
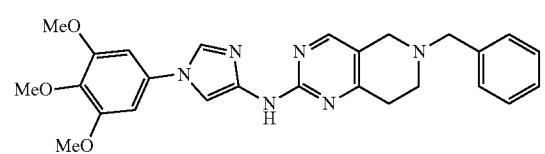 [SMILES: COc1cc(-n2cnc(Nc3ncc4c(n3)CCN(Cc3ccccc3)C4)c2)cc(OC)c1OC]
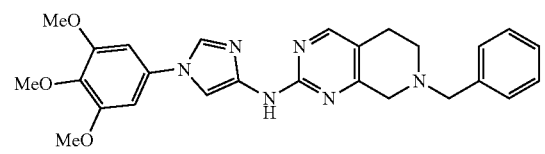 [SMILES: COc1cc(-n2cnc(Nc3ncc4c(n3)CN(Cc3ccccc3)CC4)c2)cc(OC)c1OC]
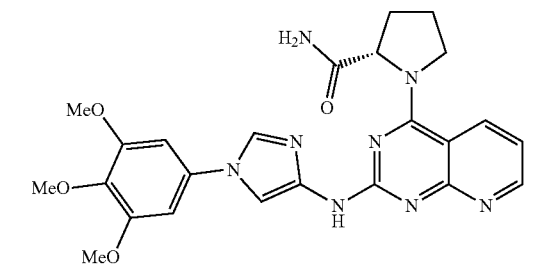 [SMILES: COc1cc(-n2cnc(Nc3nc(N4CCC[C@H]4C(N)=O)c4cccnc4n3)c2)cc(OC)c1OC]
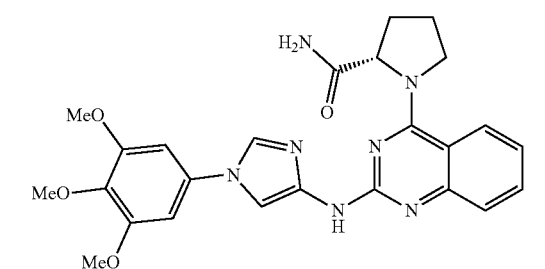 [SMILES: COc1cc(-n2cnc(Nc3nc(N4CCC[C@H]4C(N)=O)c4ccccc4n3)c2)cc(OC)c1OC]
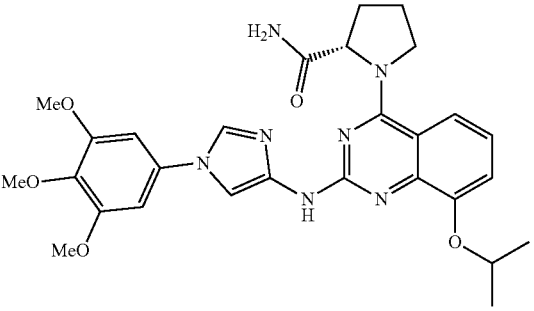 [SMILES: COc1cc(-n2cnc(Nc3nc(N4CCC[C@H]4C(N)=O)c4cccc(OC(C)C)c4n3)c2)cc(OC)c1OC]
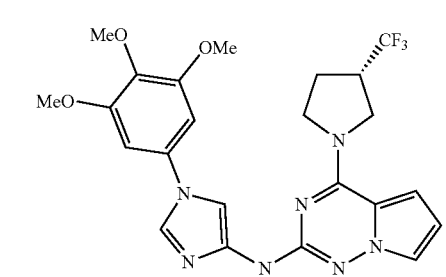
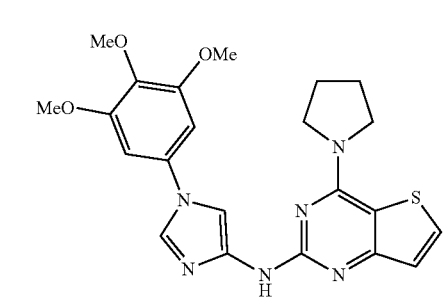 [SMILES: COc1cc(-n2cnc(Nc3nc(N4CCCC4)c4sccc4n3)c2)cc(OC)c1OC]
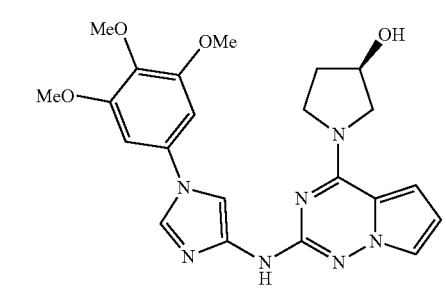 [SMILES: COc1cc(-n2cnc(Nc3nc(N4CC[C@@H](O)C4)c4cccn4n3)c2)cc(OC)c1OC]
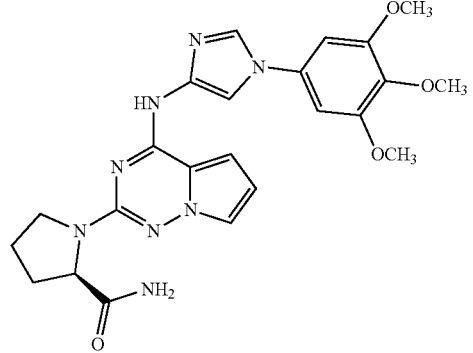 [SMILES: COc1cc(-n2cnc(Nc3nc(N4CCC[C@@H]4C(N)=O)nn4cccc34)c2)cc(OC)c1OC]

-continued

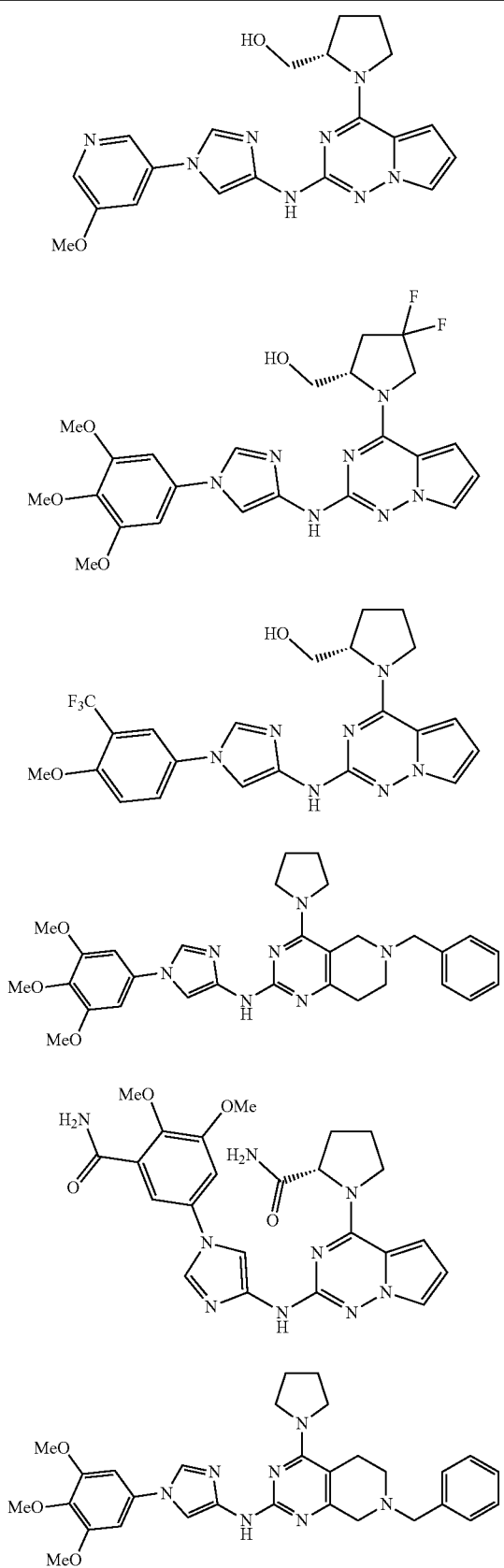
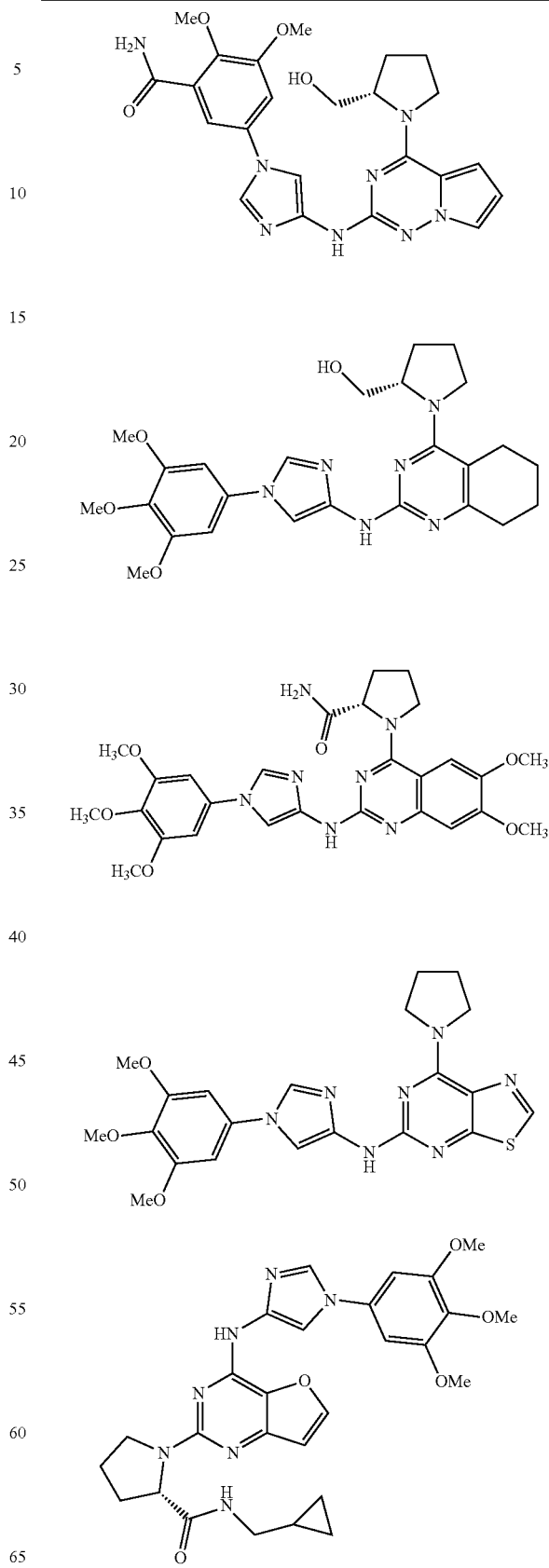

-continued
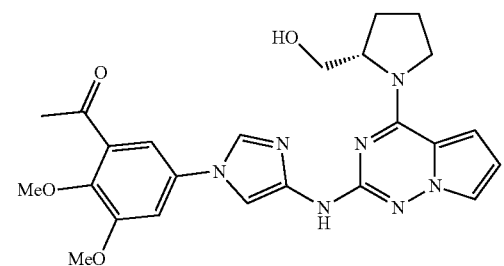 [SMILES: COc1cc(-n2cnc(Nc3nc(N4CCC[C@H]4CO)c4cccn4n3)c2)cc(C(C)=O)c1OC]
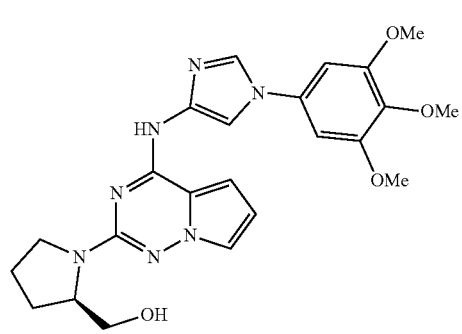 [SMILES: COc1cc(-n2cnc(Nc3nc(N4CCC[C@@H]4CO)nn4cccc34)c2)cc(OC)c1OC]
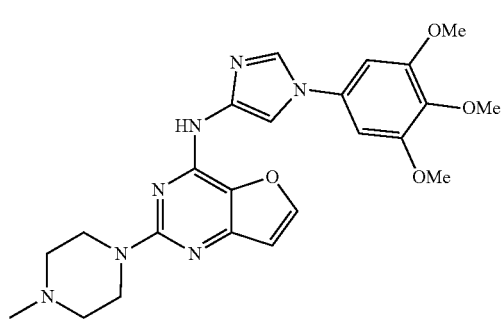 [SMILES: COc1cc(-n2cnc(Nc3nc(N4CCN(C)CC4)nc4ccoc34)c2)cc(OC)c1OC]
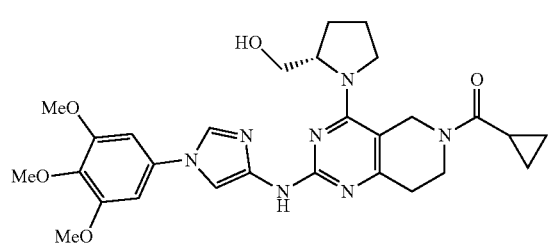 [SMILES: COc1cc(-n2cnc(Nc3nc4c(c(N5CCC[C@H]5CO)n3)CN(C(=O)C3CC3)CC4)c2)cc(OC)c1OC]
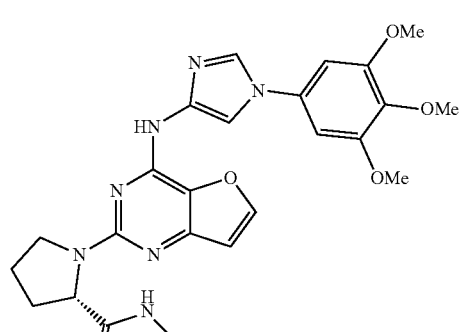
-continued
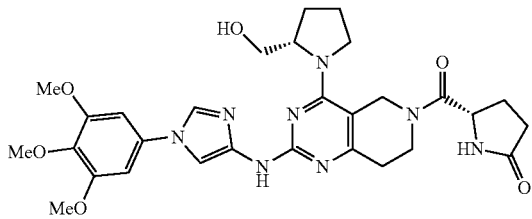 [SMILES: COc1cc(-n2cnc(Nc3nc4c(c(N5CCC[C@H]5CO)n3)CN(C(=O)[C@@H]3CCC(=O)N3)CC4)c2)cc(OC)c1OC]
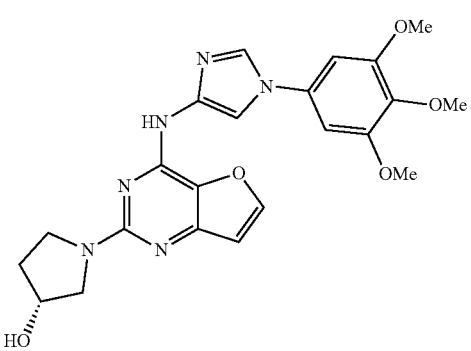 [SMILES: COc1cc(-n2cnc(Nc3nc(N4CC[C@@H](O)C4)nc4ccoc34)c2)cc(OC)c1OC]
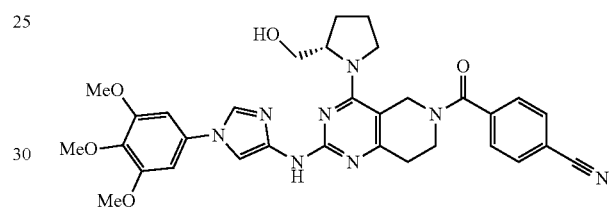
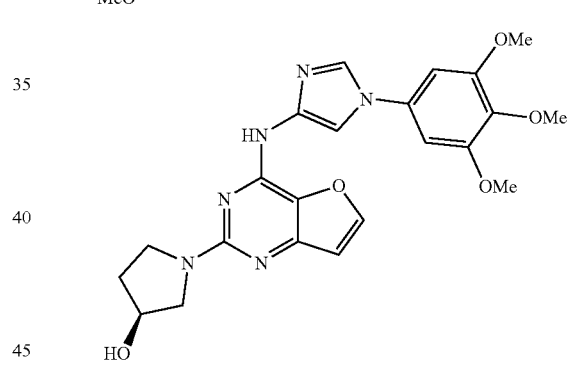
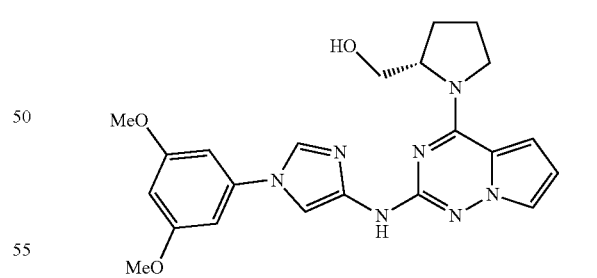
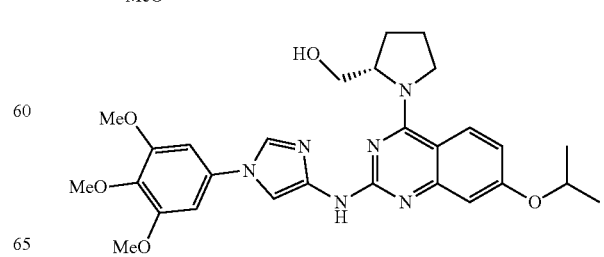

73
-continued
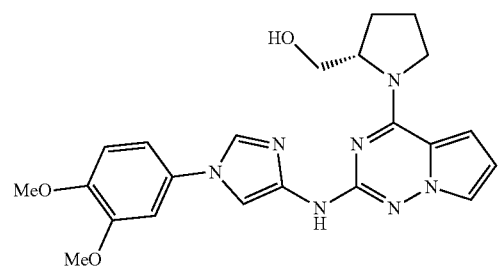 [SMILES: COc1ccc(-n2cnc(Nc3nc(N4CCC[C@H]4CO)c4cccn4n3)c2)cc1OC]
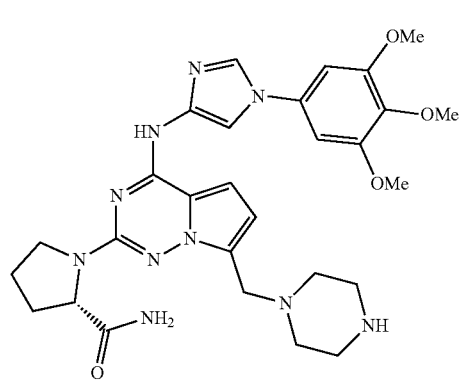 [SMILES: COc1cc(-n2cnc(Nc3nc(N4CCC[C@H]4C(N)=O)nn4c(CN5CCNCC5)ccc34)c2)cc(OC)c1OC]
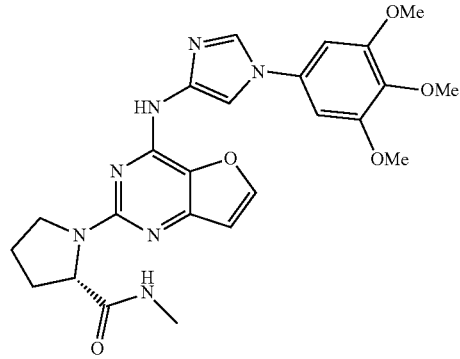 [SMILES: CNC(=O)[C@@H]1CCCN1c1nc(Nc2cn(-c3cc(OC)c(OC)c(OC)c3)cn2)c2occc2n1]
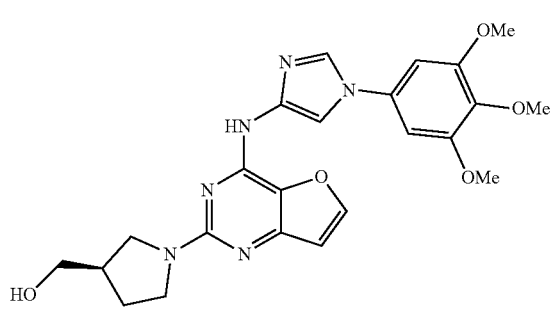 [SMILES: COc1cc(-n2cnc(Nc3nc(N4CC[C@@H](CO)C4)nc4ccoc34)c2)cc(OC)c1OC]
74
-continued
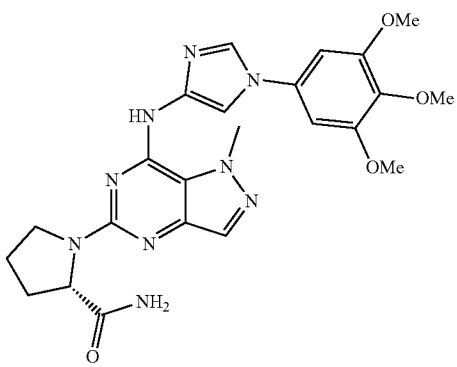 [SMILES: COc1cc(-n2cnc(Nc3nc(N4CCC[C@H]4C(N)=O)nc4cnn(C)c34)c2)cc(OC)c1OC]
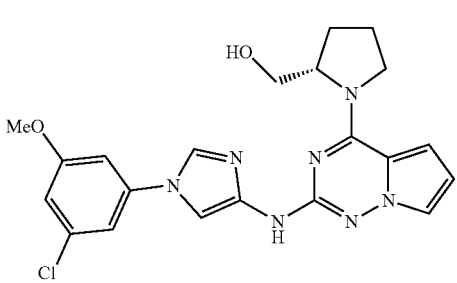 [SMILES: COc1cc(Cl)cc(-n2cnc(Nc3nc(N4CCC[C@H]4CO)c4cccn4n3)c2)c1]
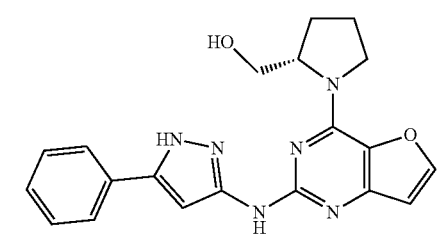 [SMILES: OC[C@@H]1CCCN1c1nc(Nc2cc(-c3ccccc3)[nH]n2)nc2ccoc12]
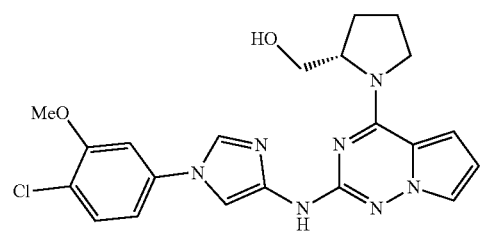 [SMILES: COc1cc(-n2cnc(Nc3nc(N4CCC[C@H]4CO)c4cccn4n3)c2)ccc1Cl]
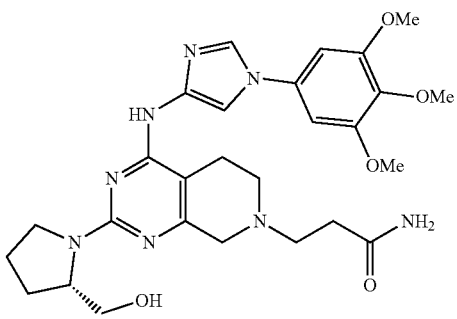 [SMILES: COc1cc(-n2cnc(Nc3nc(N4CCC[C@H]4CO)nc4c3CCN(CCC(N)=O)C4)c2)cc(OC)c1OC]

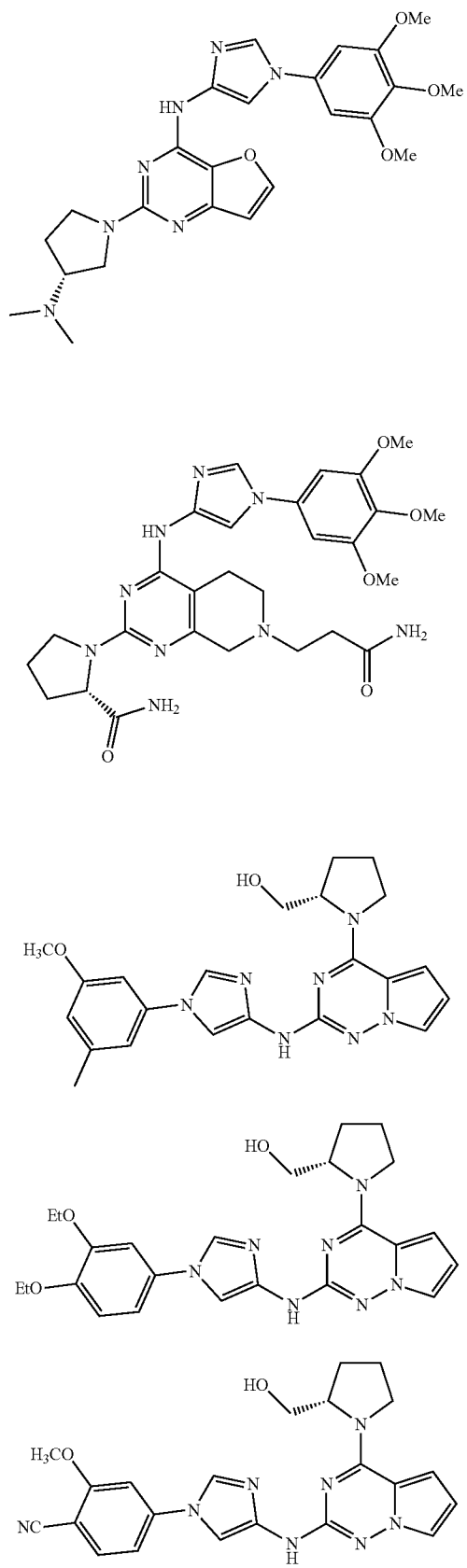
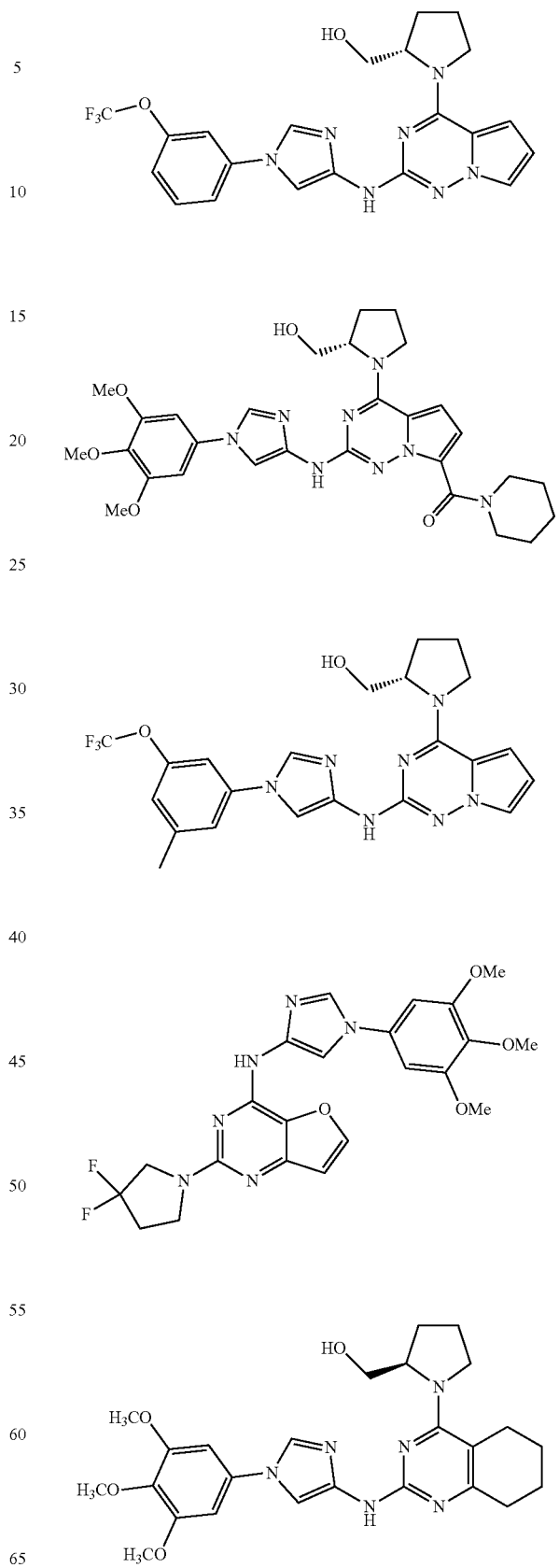

77
-continued
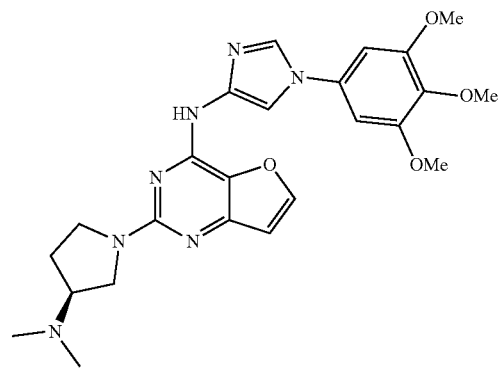 [SMILES: COc1cc(-n2cnc(Nc3nc(N4CC[C@H](N(C)C)C4)nc4ccoc34)c2)cc(OC)c1OC]
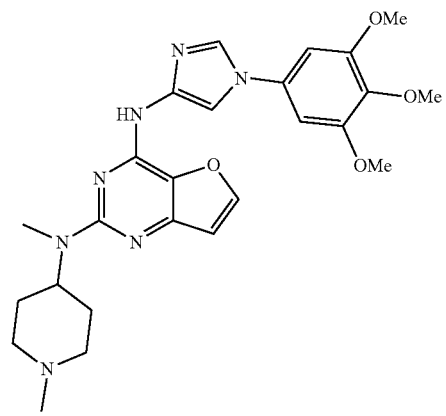 [SMILES: COc1cc(-n2cnc(Nc3nc(N(C)C4CCN(C)CC4)nc4ccoc34)c2)cc(OC)c1OC]
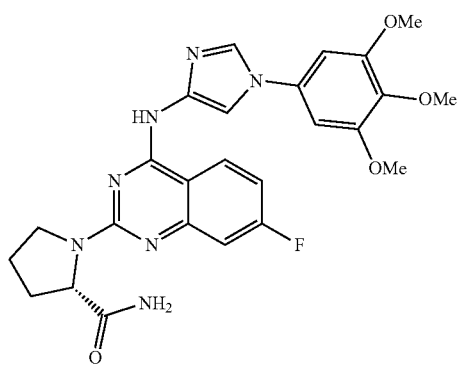 [SMILES: COc1cc(-n2cnc(Nc3nc(N4CCC[C@H]4C(N)=O)nc4cc(F)ccc34)c2)cc(OC)c1OC]
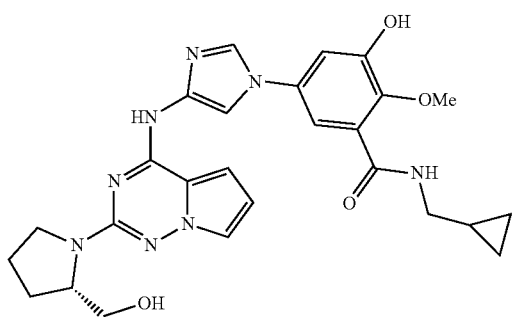 [SMILES: COc1c(O)cc(-n2cnc(Nc3nc(N4CCC[C@H]4CO)nn4cccc34)c2)cc1C(=O)NCC1CC1]
78
-continued
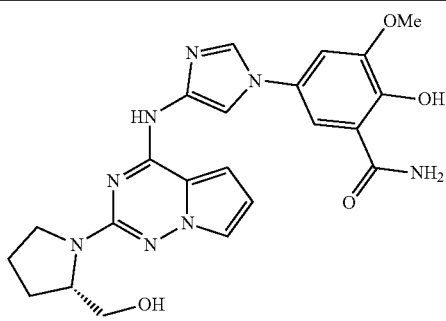
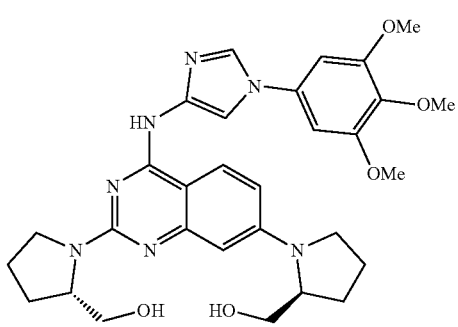 [SMILES: COc1cc(-n2cnc(Nc3nc(N4CCC[C@H]4CO)nc4cc(N5CCC[C@H]5CO)ccc34)c2)cc(OC)c1OC]
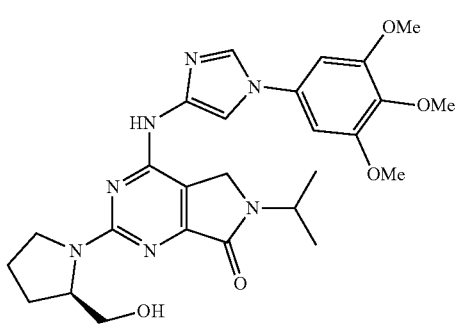 [SMILES: COc1cc(-n2cnc(Nc3nc(N4CCC[C@@H]4CO)nc4c3CN(C(C)C)C4=O)c2)cc(OC)c1OC]
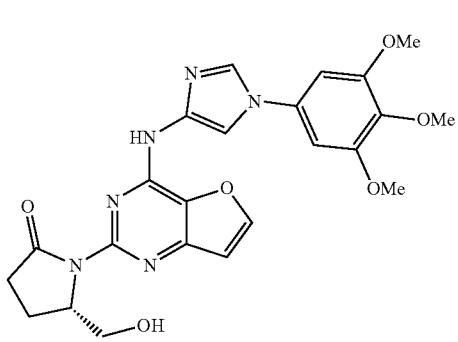 [SMILES: COc1cc(-n2cnc(Nc3nc(N4C(=O)CC[C@H]4CO)nc4ccoc34)c2)cc(OC)c1OC]
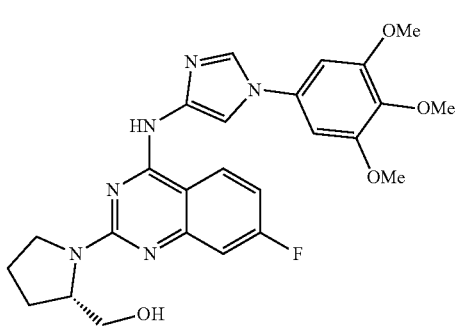 [SMILES: COc1cc(-n2cnc(Nc3nc(N4CCC[C@H]4CO)nc4cc(F)ccc34)c2)cc(OC)c1OC]

-continued
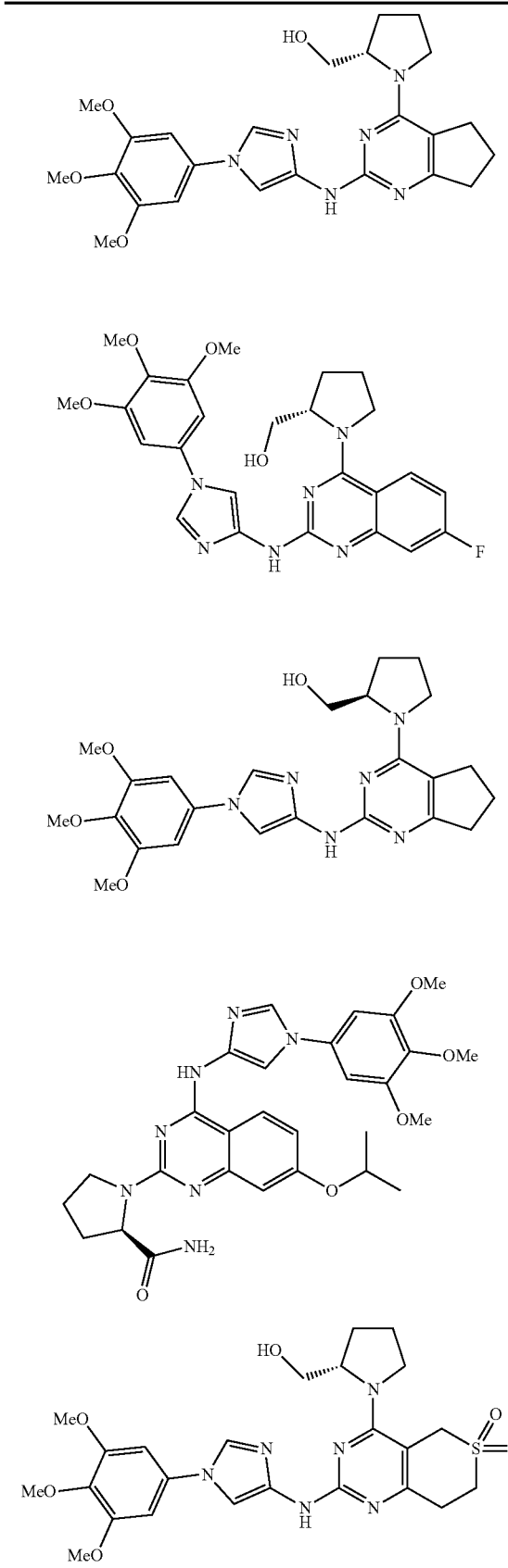
-continued
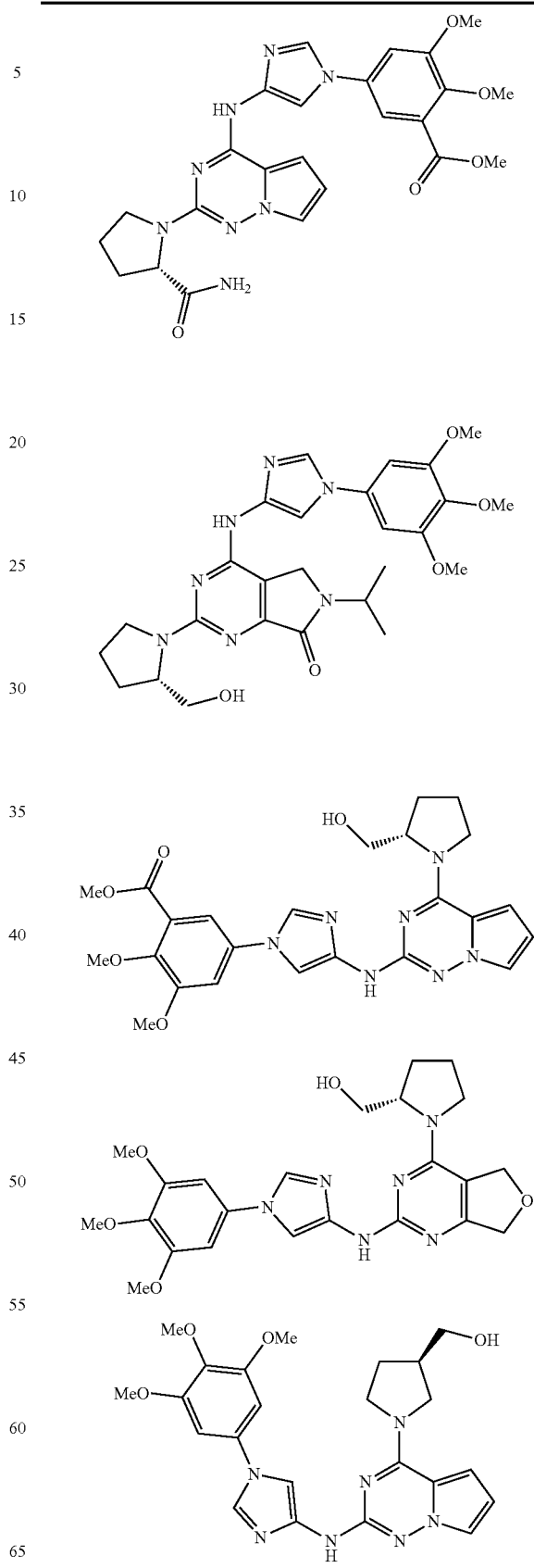

81
-continued
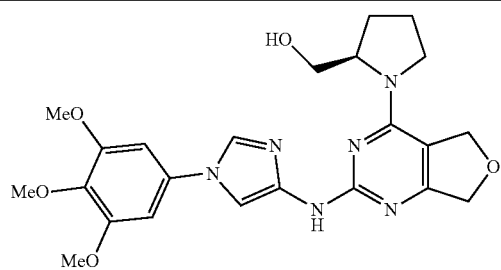
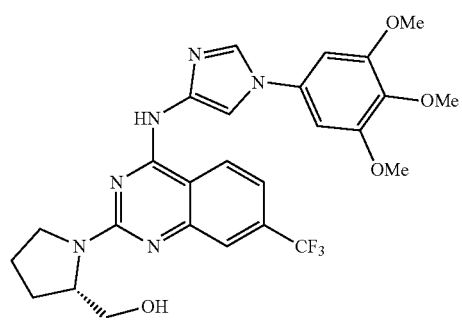 [SMILES: COc1cc(-n2cnc(Nc3nc(N4CCC[C@H]4CO)nc4cc(C(F)(F)F)ccc34)c2)cc(OC)c1OC]
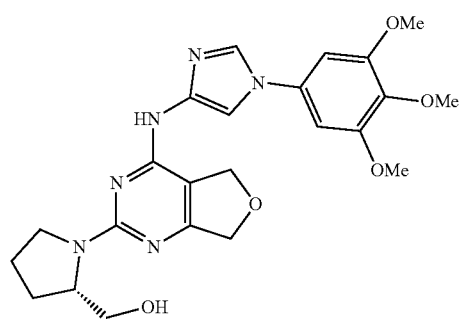 [SMILES: COc1cc(-n2cnc(Nc3nc(N4CCC[C@H]4CO)nc4c3COC4)c2)cc(OC)c1OC]
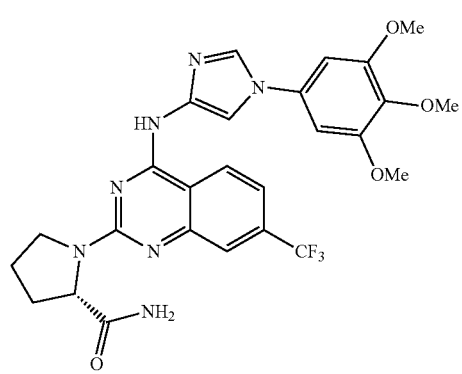 [SMILES: COc1cc(-n2cnc(Nc3nc(N4CCC[C@H]4C(N)=O)nc4cc(C(F)(F)F)ccc34)c2)cc(OC)c1OC]
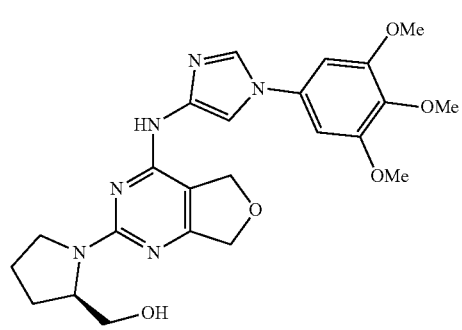 [SMILES: COc1cc(-n2cnc(Nc3nc(N4CCC[C@@H]4CO)nc4c3COC4)c2)cc(OC)c1OC]
82
-continued
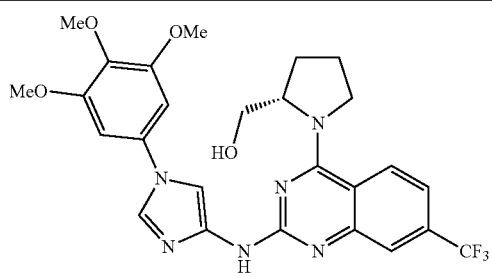
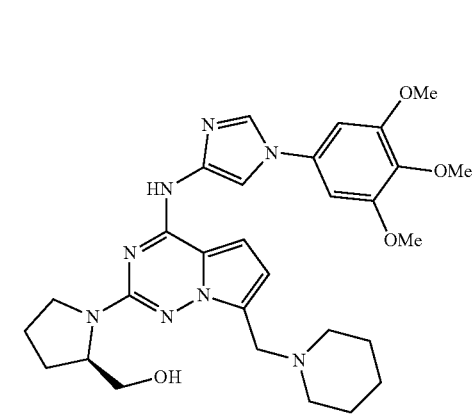 [SMILES: COc1cc(-n2cnc(Nc3nc(N4CCC[C@@H]4CO)nn4c(CN5CCCCC5)ccc34)c2)cc(OC)c1OC]
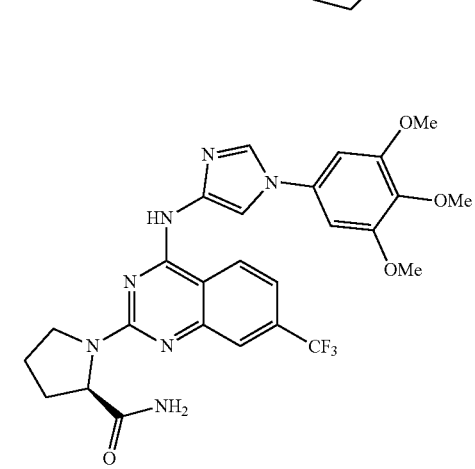
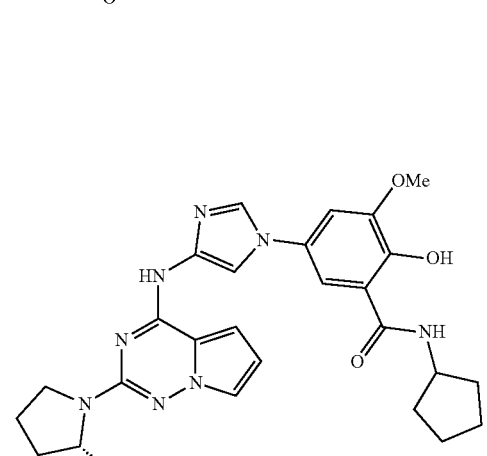

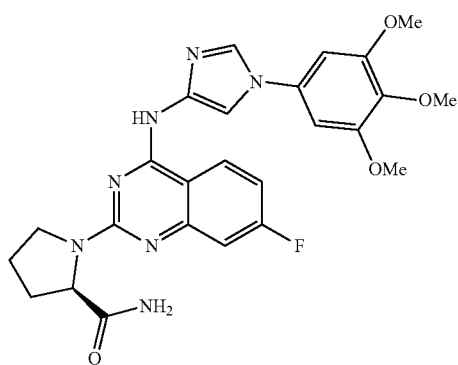 [SMILES: COc1cc(-n2cnc(Nc3nc(N4CCC[C@@H]4C(N)=O)nc4cc(F)ccc34)c2)cc(OC)c1OC]
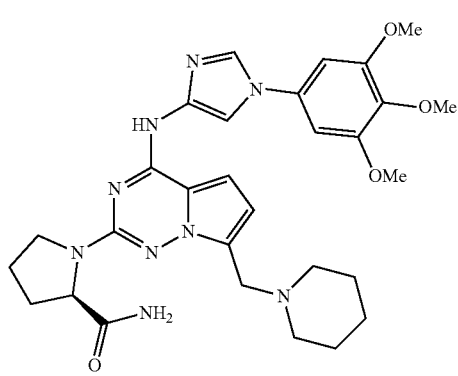 [SMILES: COc1cc(-n2cnc(Nc3nc(N4CCC[C@@H]4C(N)=O)nn4c(CN5CCCCC5)ccc34)c2)cc(OC)c1OC]
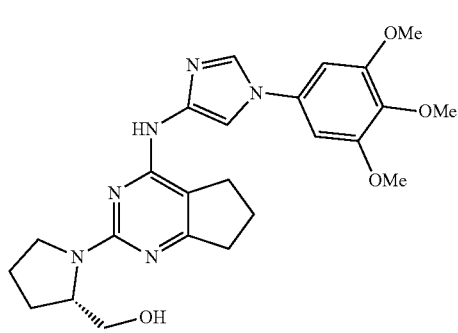 [SMILES: COc1cc(-n2cnc(Nc3nc(N4CCC[C@H]4CO)nc4c3CCC4)c2)cc(OC)c1OC]
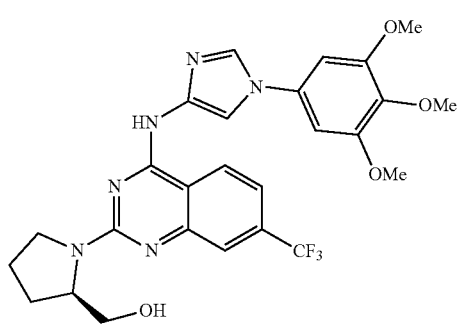
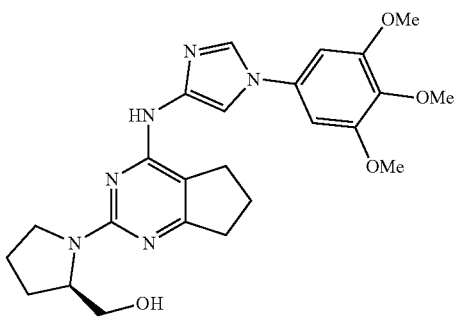 [SMILES: COc1cc(-n2cnc(Nc3nc(N4CCC[C@@H]4CO)nc4c3CCC4)c2)cc(OC)c1OC]
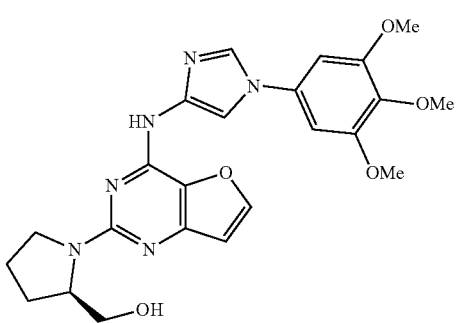 [SMILES: COc1cc(-n2cnc(Nc3nc(N4CCC[C@@H]4CO)nc4ccoc34)c2)cc(OC)c1OC]
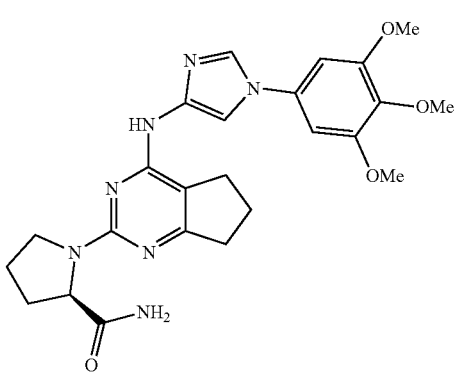 [SMILES: COc1cc(-n2cnc(Nc3nc(N4CCC[C@@H]4C(N)=O)nc4c3CCC4)c2)cc(OC)c1OC]
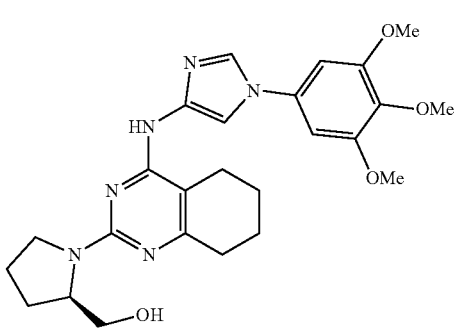 [SMILES: COc1cc(-n2cnc(Nc3nc(N4CCC[C@@H]4CO)nc4c3CCCC4)c2)cc(OC)c1OC]

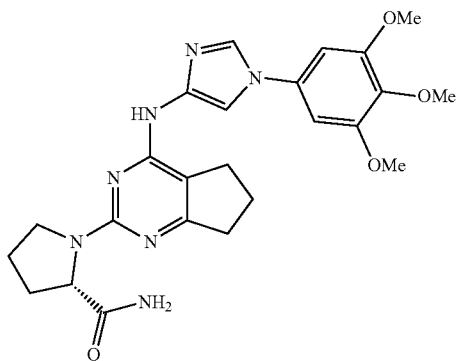 [SMILES: COc1cc(-n2cnc(Nc3nc(N4CCC[C@H]4C(N)=O)nc4c3CCC4)c2)cc(OC)c1OC]
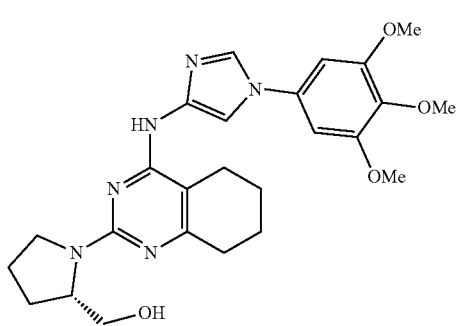 [SMILES: COc1cc(-n2cnc(Nc3nc(N4CCC[C@H]4CO)nc4c3CCCC4)c2)cc(OC)c1OC]
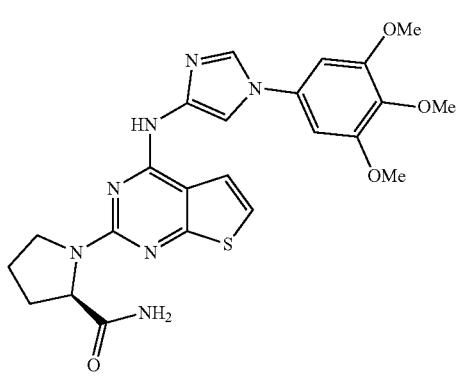 [SMILES: COc1cc(-n2cnc(Nc3nc(N4CCC[C@@H]4C(N)=O)nc4sccc34)c2)cc(OC)c1OC]
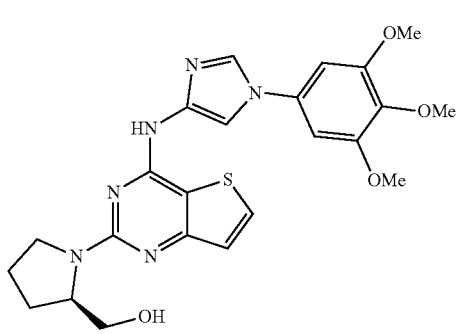 [SMILES: COc1cc(-n2cnc(Nc3nc(N4CCC[C@@H]4CO)nc4ccsc34)c2)cc(OC)c1OC]
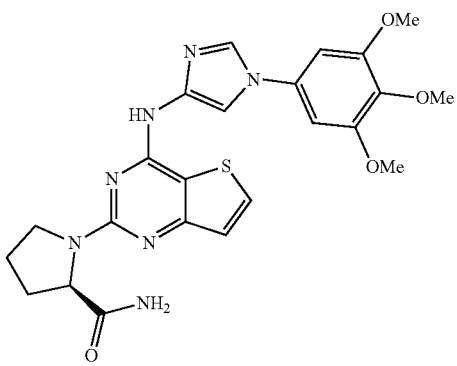 [SMILES: COc1cc(-n2cnc(Nc3nc(N4CCC[C@@H]4C(N)=O)nc4ccsc34)c2)cc(OC)c1OC]
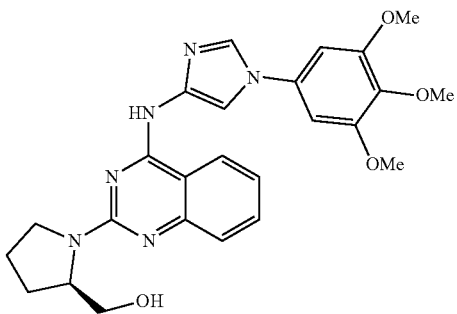 [SMILES: COc1cc(-n2cnc(Nc3nc(N4CCC[C@@H]4CO)nc4ccccc34)c2)cc(OC)c1OC]
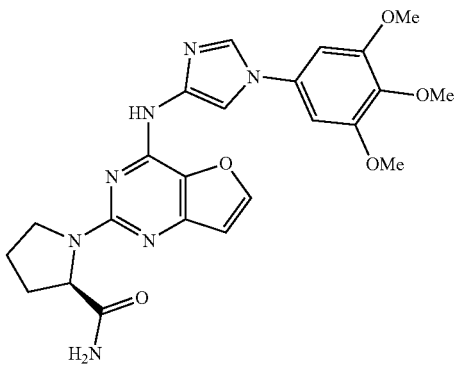 [SMILES: COc1cc(-n2cnc(Nc3nc(N4CCC[C@@H]4C(N)=O)nc4ccoc34)c2)cc(OC)c1OC]
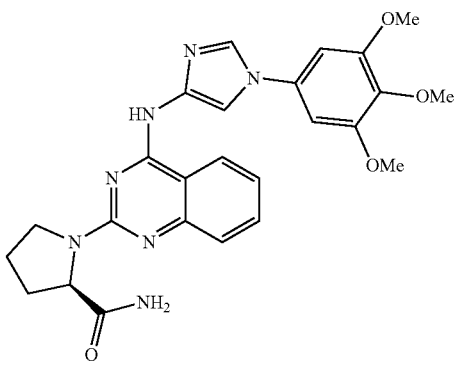 [SMILES: COc1cc(-n2cnc(Nc3nc(N4CCC[C@@H]4C(N)=O)nc4ccccc34)c2)cc(OC)c1OC]

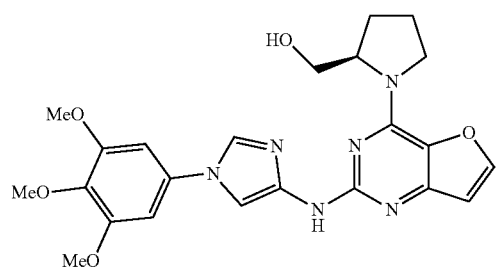 [SMILES: COc1cc(-n2cnc(Nc3nc(N4CCC[C@@H]4CO)c4occc4n3)c2)cc(OC)c1OC]
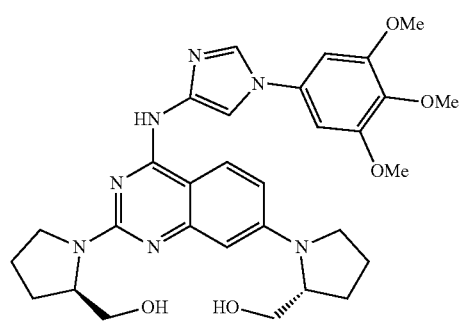 [SMILES: COc1cc(-n2cnc(Nc3nc(N4CCC[C@@H]4CO)nc4cc(N5CCC[C@@H]5CO)ccc34)c2)cc(OC)c1OC]
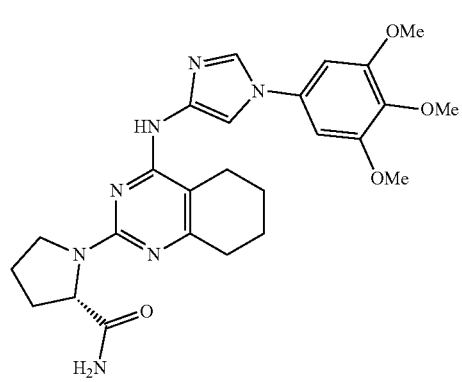 [SMILES: COc1cc(-n2cnc(Nc3nc(N4CCC[C@H]4C(N)=O)nc4c3CCCC4)c2)cc(OC)c1OC]
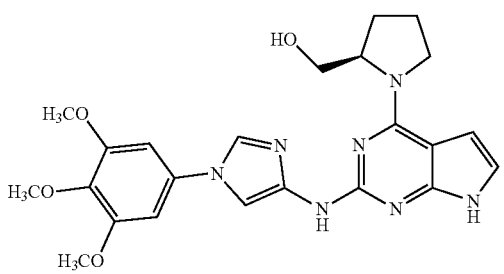 [SMILES: COc1cc(-n2cnc(Nc3nc(N4CCC[C@@H]4CO)c4cc[nH]c4n3)c2)cc(OC)c1OC]
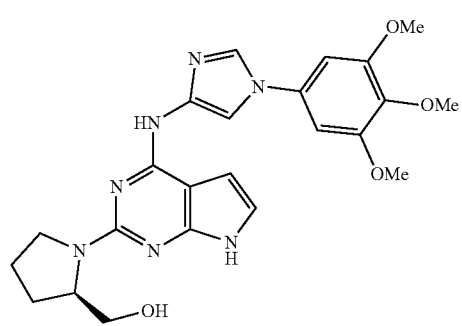 [SMILES: COc1cc(-n2cnc(Nc3nc(N4CCC[C@@H]4CO)nc4[nH]ccc34)c2)cc(OC)c1OC]
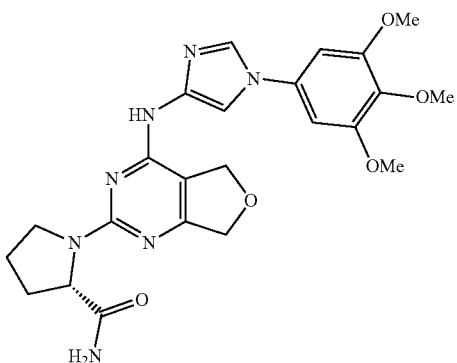
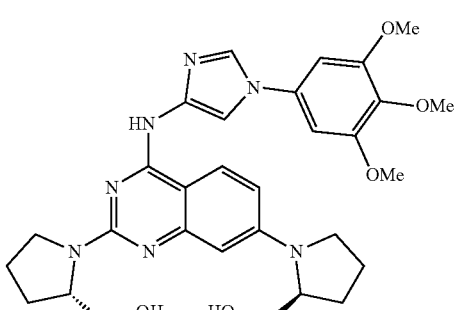
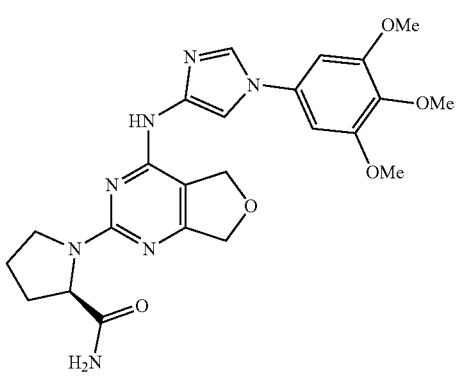 [SMILES: COc1cc(-n2cnc(Nc3nc(N4CCC[C@@H]4C(N)=O)nc4c3COC4)c2)cc(OC)c1OC]
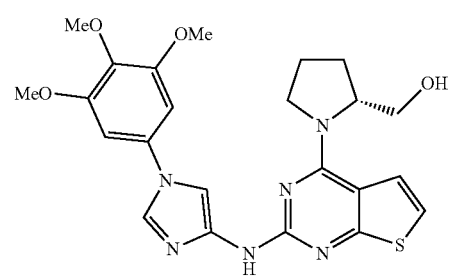 [SMILES: COc1cc(-n2cnc(Nc3nc(N4CCC[C@@H]4CO)c4ccsc4n3)c2)cc(OC)c1OC]

89
-continued
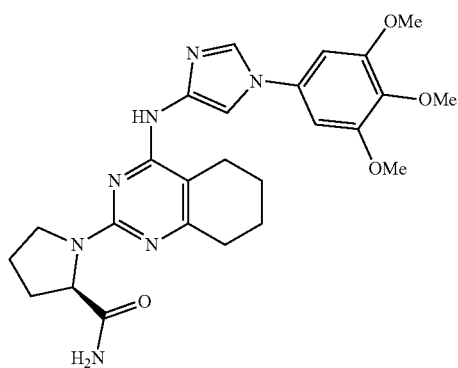 [SMILES: COc1cc(-n2cnc(Nc3nc(N4CCC[C@@H]4C(N)=O)nc4c3CCCC4)c2)cc(OC)c1OC]
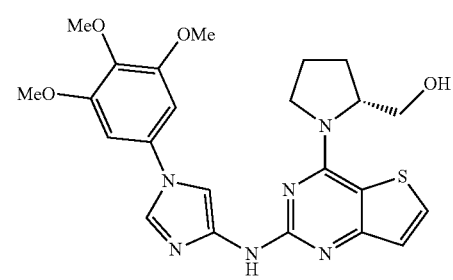 [SMILES: COc1cc(-n2cnc(Nc3nc(N4CCC[C@@H]4CO)c4sccc4n3)c2)cc(OC)c1OC]
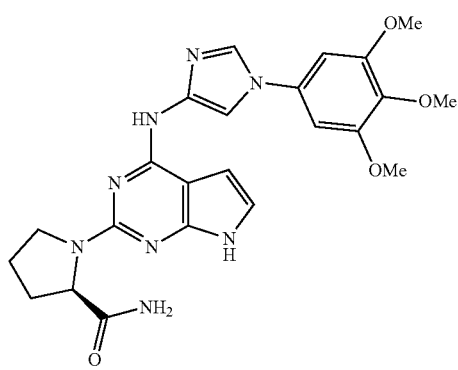 [SMILES: COc1cc(-n2cnc(Nc3nc(N4CCC[C@@H]4C(N)=O)nc4[nH]ccc34)c2)cc(OC)c1OC]
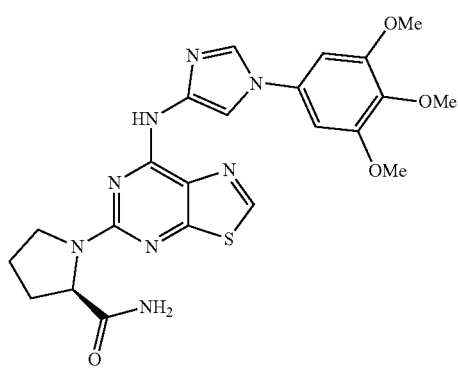 [SMILES: COc1cc(-n2cnc(Nc3nc(N4CCC[C@@H]4C(N)=O)nc4scnc34)c2)cc(OC)c1OC]
90
-continued
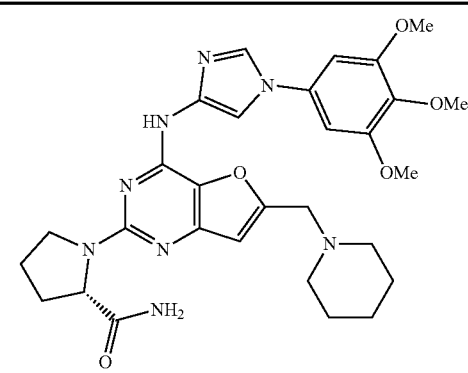
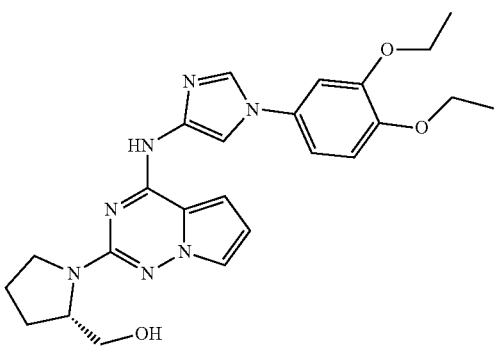 [SMILES: CCOc1ccc(-n2cnc(Nc3nc(N4CCC[C@H]4CO)nn4cccc34)c2)cc1OCC]
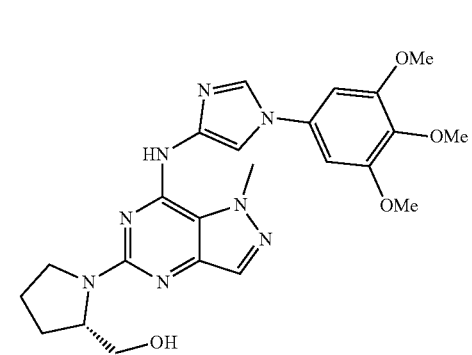 [SMILES: COc1cc(-n2cnc(Nc3nc(N4CCC[C@H]4CO)nc4cnn(C)c34)c2)cc(OC)c1OC]
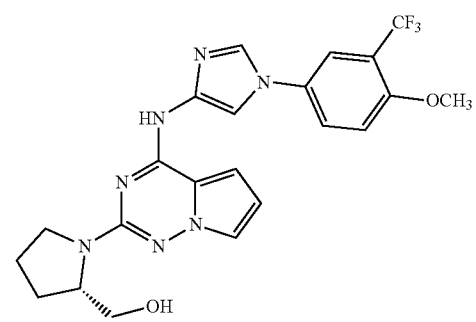 [SMILES: COc1ccc(-n2cnc(Nc3nc(N4CCC[C@H]4CO)nn4cccc34)c2)cc1C(F)(F)F]

91
-continued
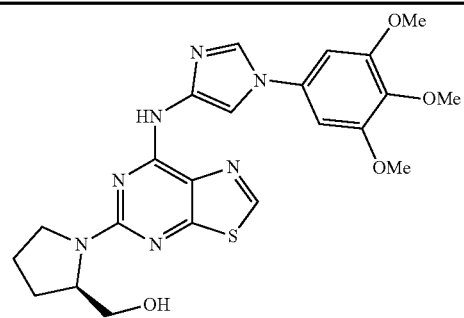
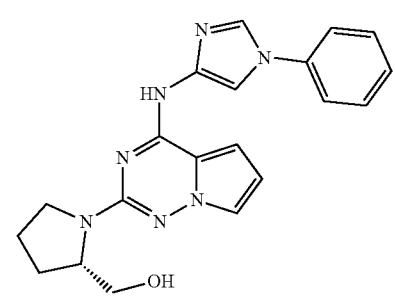 [SMILES: OC[C@@H]1CCCN1c1nc(Nc2cn(-c3ccccc3)cn2)c2cccn2n1]
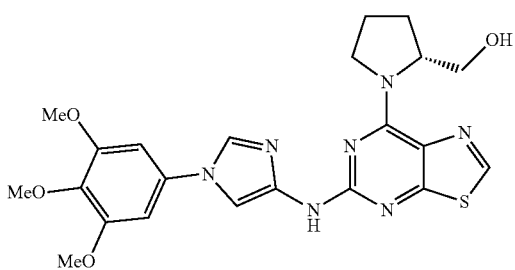 [SMILES: COc1cc(-n2cnc(Nc3nc(N4CCC[C@@H]4CO)c4ncsc4n3)c2)cc(OC)c1OC]
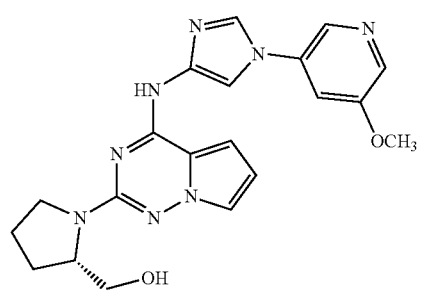 [SMILES: COc1cncc(-n2cnc(Nc3nc(N4CCC[C@H]4CO)nn4cccc34)c2)c1]
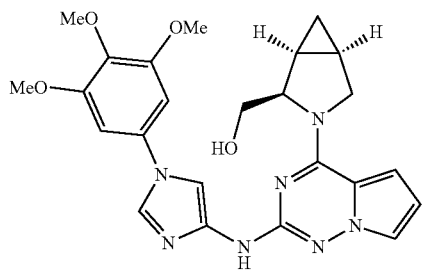 [SMILES: COc1cc(-n2cnc(Nc3nc(N4C[C@@H]5C[C@@H]5[C@@H]4CO)c4cccn4n3)c2)cc(OC)c1OC]
92
-continued
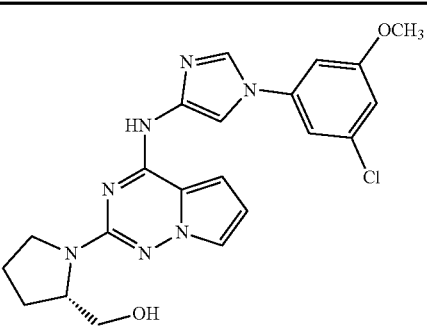
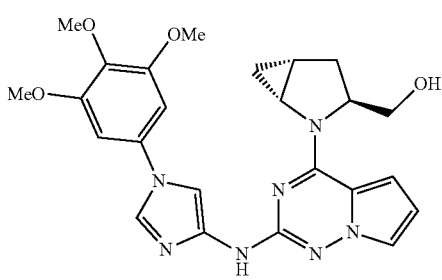 [SMILES: COc1cc(-n2cnc(Nc3nc(N4[C@H](CO)C[C@H]5C[C@H]54)c4cccn4n3)c2)cc(OC)c1OC]
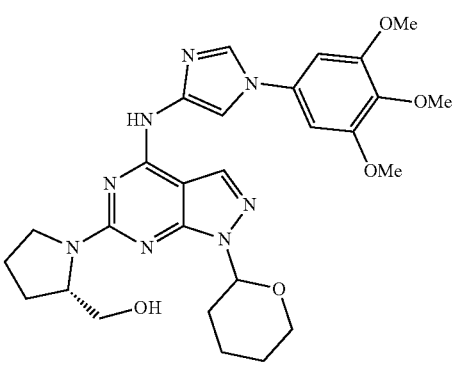 [SMILES: COc1cc(-n2cnc(Nc3nc(N4CCC[C@H]4CO)nc4c3cnn4C3CCCCO3)c2)cc(OC)c1OC]
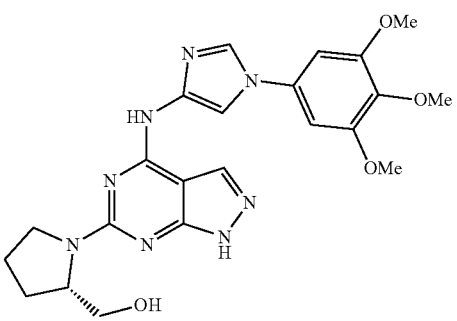 [SMILES: COc1cc(-n2cnc(Nc3nc(N4CCC[C@H]4CO)nc4[nH]ncc34)c2)cc(OC)c1OC]
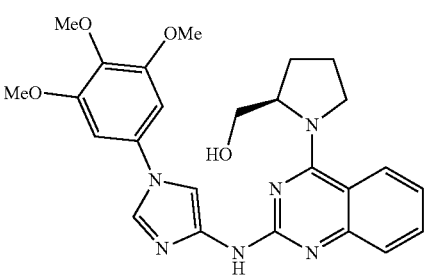 [SMILES: COc1cc(-n2cnc(Nc3nc(N4CCC[C@@H]4CO)c4ccccc4n3)c2)cc(OC)c1OC]

93
-continued
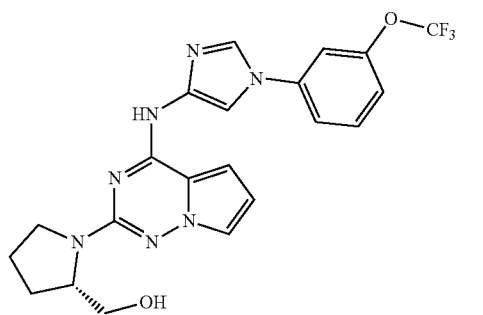 [SMILES: OC[C@@H]1CCCN1c1nc(Nc2cn(-c3cccc(OC(F)(F)F)c3)cn2)c2cccn2n1]
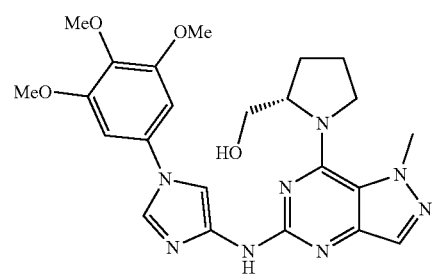 [SMILES: COc1cc(-n2cnc(Nc3nc(N4CCC[C@H]4CO)c4c(cnn4C)n3)c2)cc(OC)c1OC]
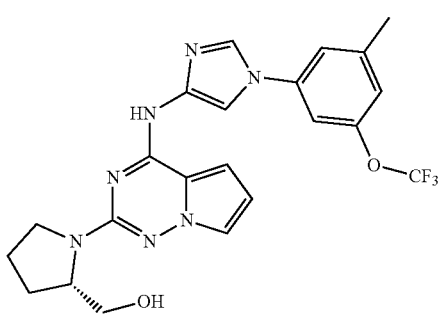 [SMILES: Cc1cc(OC(F)(F)F)cc(-n2cnc(Nc3nc(N4CCC[C@H]4CO)nn4cccc34)c2)c1]
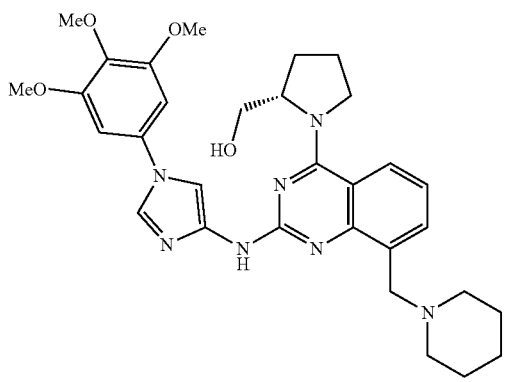 [SMILES: COc1cc(-n2cnc(Nc3nc(N4CCC[C@H]4CO)c4cccc(CN5CCCCC5)c4n3)c2)cc(OC)c1OC]
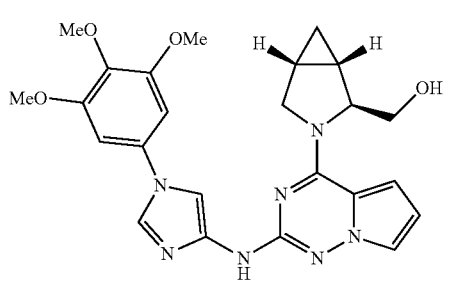 [SMILES: COc1cc(-n2cnc(Nc3nc(N4C[C@@H]5C[C@@H]5[C@H]4CO)c4cccn4n3)c2)cc(OC)c1OC]
94
-continued
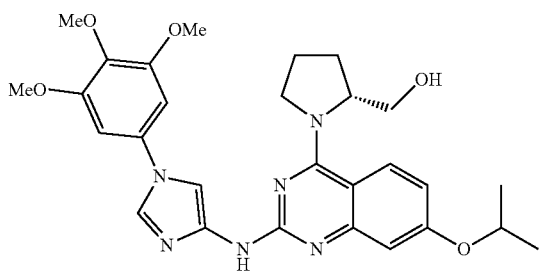 [SMILES: COc1cc(-n2cnc(Nc3nc(N4CCC[C@@H]4CO)c4ccc(OC(C)C)cc4n3)c2)cc(OC)c1OC]
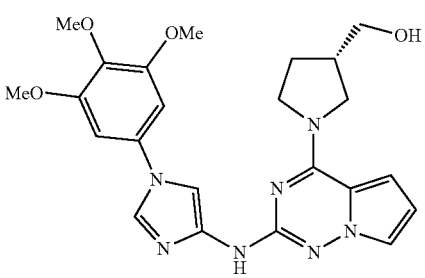 [SMILES: COc1cc(-n2cnc(Nc3nc(N4CC[C@H](CO)C4)c4cccn4n3)c2)cc(OC)c1OC]
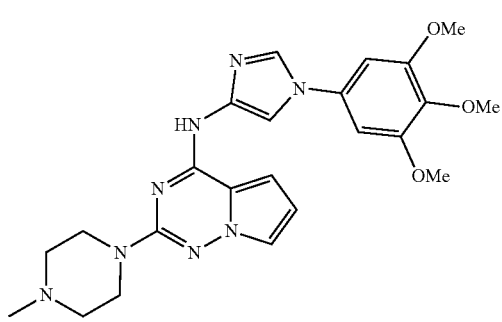 [SMILES: COc1cc(-n2cnc(Nc3nc(N4CCN(C)CC4)nn4cccc34)c2)cc(OC)c1OC]
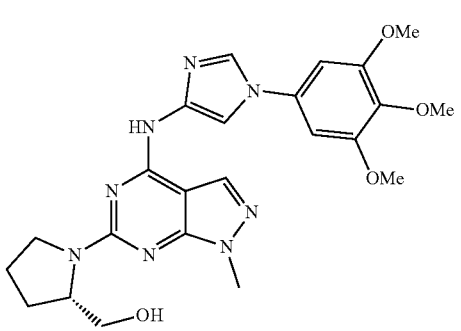 [SMILES: COc1cc(-n2cnc(Nc3nc(N4CCC[C@H]4CO)nc4c3cnn4C)c2)cc(OC)c1OC]
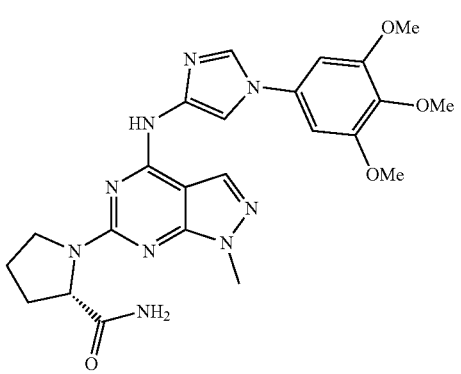 [SMILES: COc1cc(-n2cnc(Nc3nc(N4CCC[C@H]4C(N)=O)nc4c3cnn4C)c2)cc(OC)c1OC]

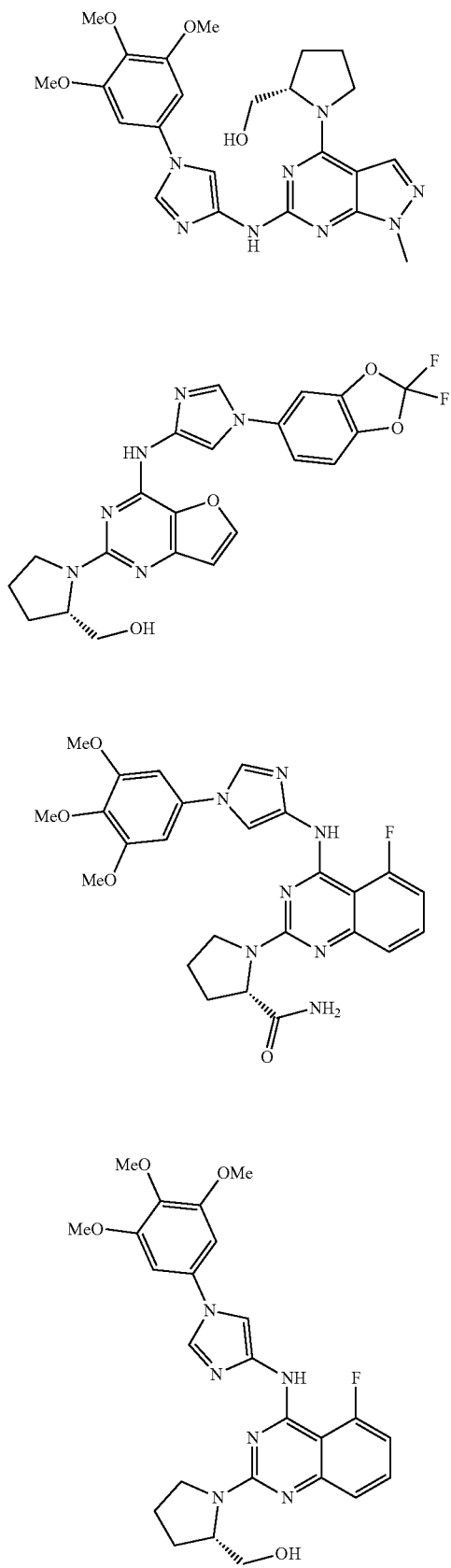
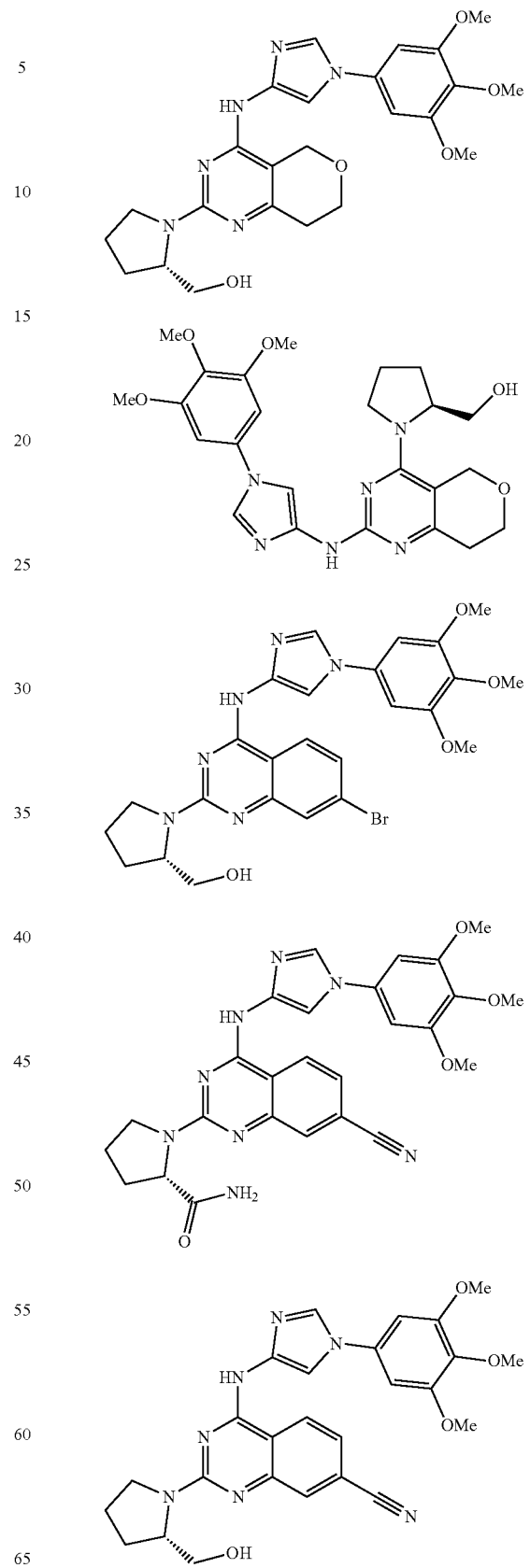

97
-continued
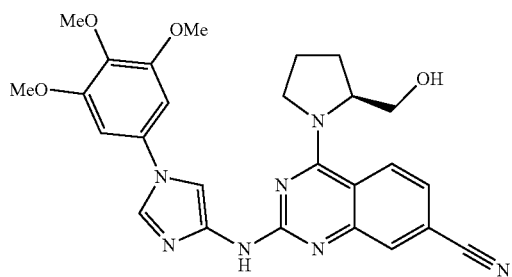 [SMILES: COc1cc(-n2cnc(Nc3nc(N4CCC[C@H]4CO)c4ccc(C#N)cc4n3)c2)cc(OC)c1OC]
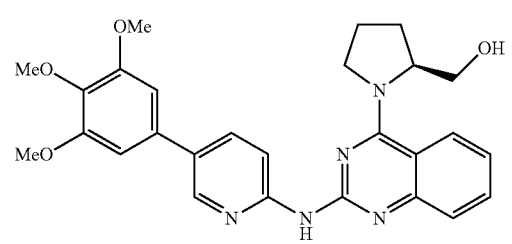 [SMILES: COc1cc(-c2ccc(Nc3nc(N4CCC[C@H]4CO)c4ccccc4n3)nc2)cc(OC)c1OC]
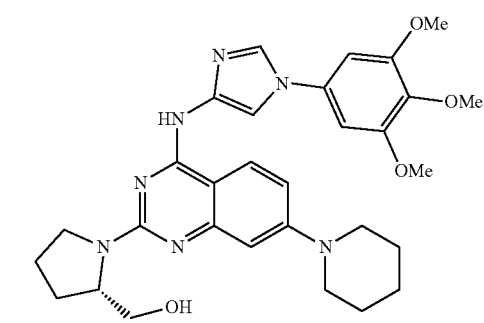 [SMILES: COc1cc(-n2cnc(Nc3nc(N4CCC[C@H]4CO)nc4cc(N5CCCCC5)ccc34)c2)cc(OC)c1OC]
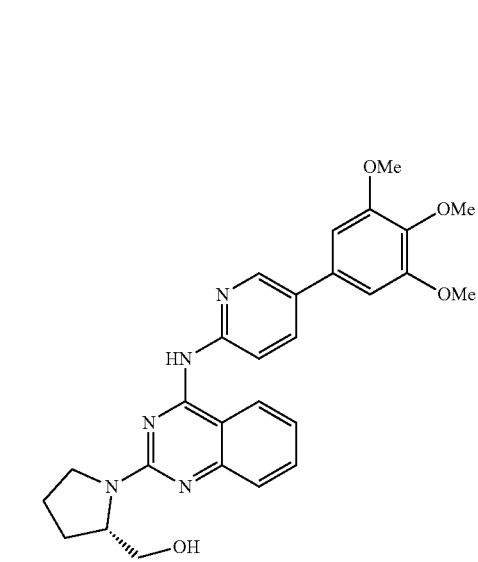 [SMILES: COc1cc(-c2ccc(Nc3nc(N4CCC[C@H]4CO)nc4ccccc34)nc2)cc(OC)c1OC]
98
-continued
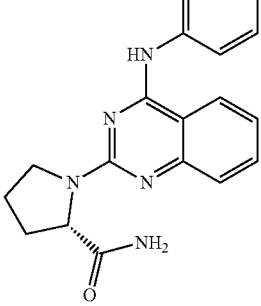
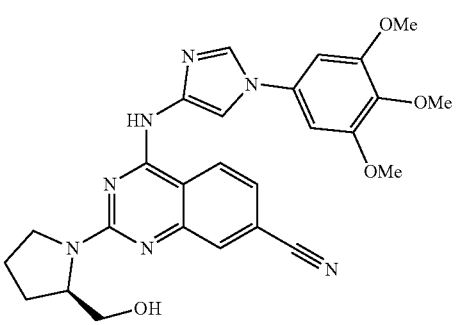 [SMILES: COc1cc(-n2cnc(Nc3nc(N4CCC[C@@H]4CO)nc4cc(C#N)ccc34)c2)cc(OC)c1OC]
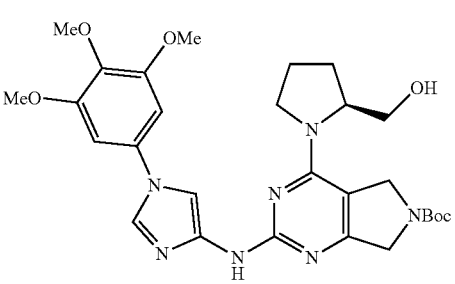 [SMILES: COc1cc(-n2cnc(Nc3nc4c(c(N5CCC[C@H]5CO)n3)CN(C(=O)OC(C)(C)C)C4)c2)cc(OC)c1OC]
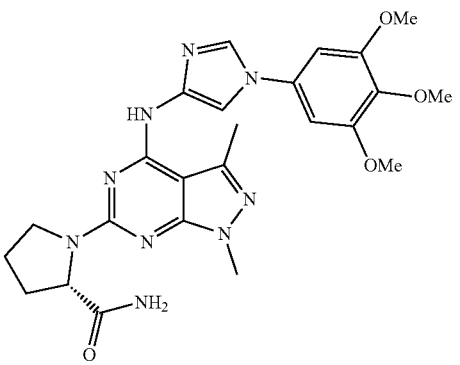 [SMILES: COc1cc(-n2cnc(Nc3nc(N4CCC[C@H]4C(N)=O)nc4c3c(C)nn4C)c2)cc(OC)c1OC]

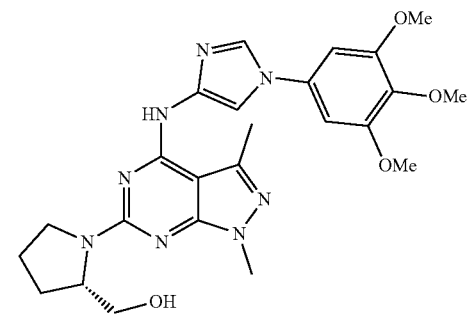 [SMILES: COc1cc(-n2cnc(Nc3nc(N4CCC[C@H]4CO)nc4c3c(C)nn4C)c2)cc(OC)c1OC]
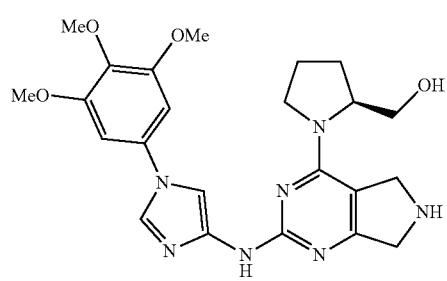 [SMILES: COc1cc(-n2cnc(Nc3nc4c(c(N5CCC[C@H]5CO)n3)CNC4)c2)cc(OC)c1OC]
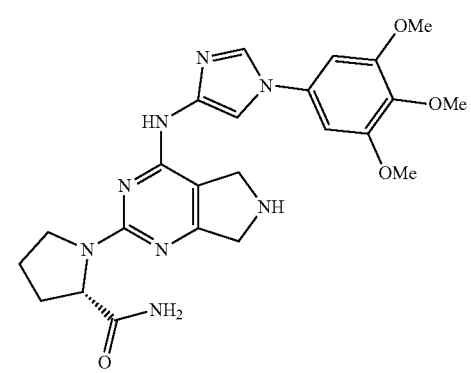 [SMILES: COc1cc(-n2cnc(Nc3nc(N4CCC[C@H]4C(N)=O)nc4c3CNC4)c2)cc(OC)c1OC]
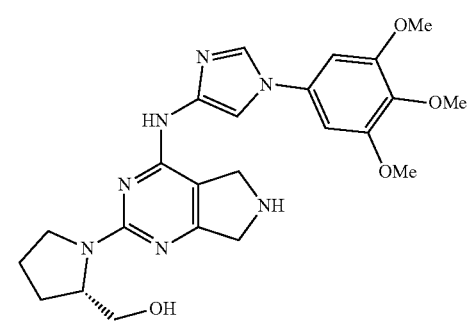 [SMILES: COc1cc(-n2cnc(Nc3nc(N4CCC[C@H]4CO)nc4c3CNC4)c2)cc(OC)c1OC]
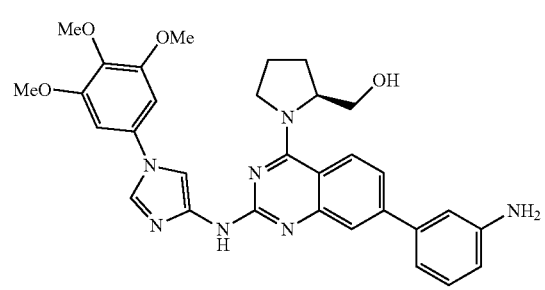 [SMILES: COc1cc(-n2cnc(Nc3nc(N4CCC[C@H]4CO)c4ccc(-c5cccc(N)c5)cc4n3)c2)cc(OC)c1OC]
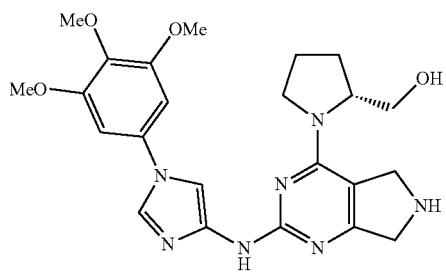 [SMILES: COc1cc(-n2cnc(Nc3nc4c(c(N5CCC[C@@H]5CO)n3)CNC4)c2)cc(OC)c1OC]
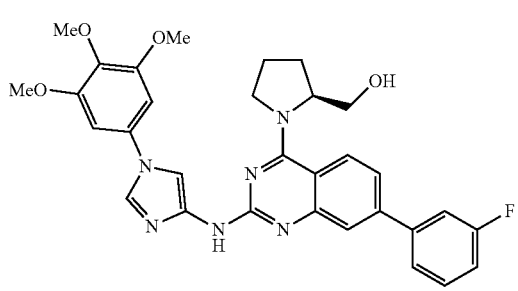 [SMILES: COc1cc(-n2cnc(Nc3nc(N4CCC[C@H]4CO)c4ccc(-c5cccc(F)c5)cc4n3)c2)cc(OC)c1OC]
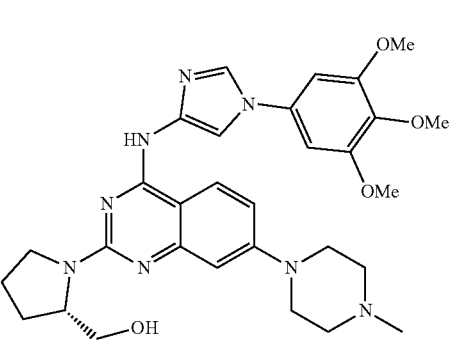 [SMILES: COc1cc(-n2cnc(Nc3nc(N4CCC[C@H]4CO)nc4cc(N5CCN(C)CC5)ccc34)c2)cc(OC)c1OC]
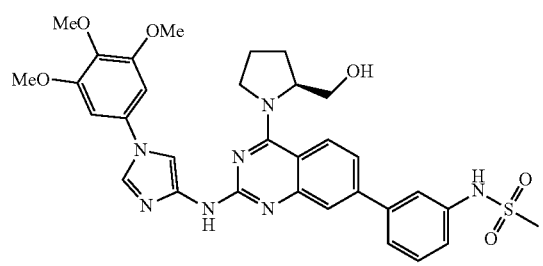 [SMILES: COc1cc(-n2cnc(Nc3nc(N4CCC[C@H]4CO)c4ccc(-c5cccc(NS(C)(=O)=O)c5)cc4n3)c2)cc(OC)c1OC]
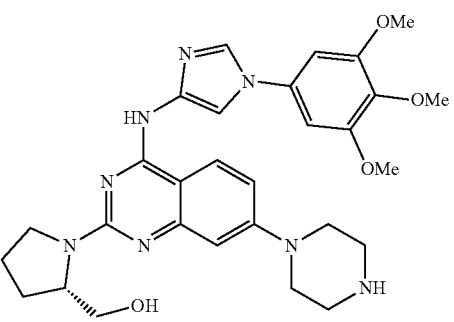 [SMILES: COc1cc(-n2cnc(Nc3nc(N4CCC[C@H]4CO)nc4cc(N5CCNCC5)ccc34)c2)cc(OC)c1OC]

101
-continued
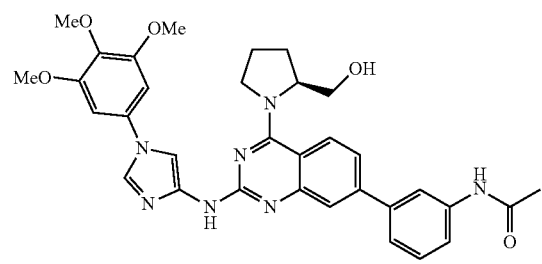 [SMILES: COc1cc(-n2cnc(Nc3nc(N4CCC[C@H]4CO)c4ccc(-c5cccc(NC(C)=O)c5)cc4n3)c2)cc(OC)c1OC]
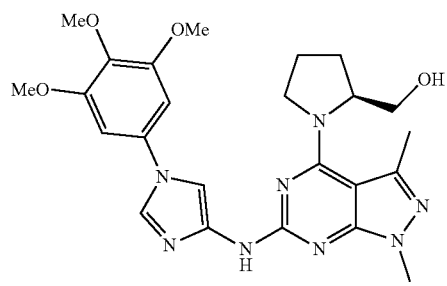 [SMILES: COc1cc(-n2cnc(Nc3nc(N4CCC[C@H]4CO)c4c(C)nn(C)c4n3)c2)cc(OC)c1OC]
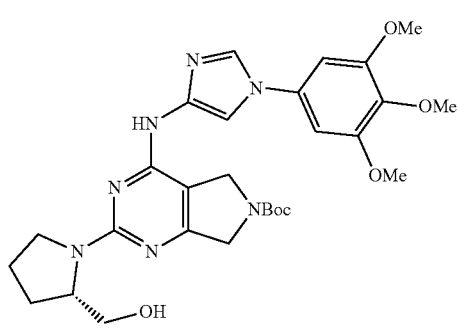 [SMILES: COc1cc(-n2cnc(Nc3nc(N4CCC[C@H]4CO)nc4c3CN(C(=O)OC(C)(C)C)C4)c2)cc(OC)c1OC]
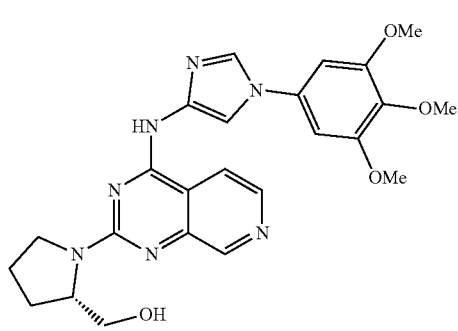 [SMILES: COc1cc(-n2cnc(Nc3nc(N4CCC[C@H]4CO)nc4cnccc34)c2)cc(OC)c1OC]
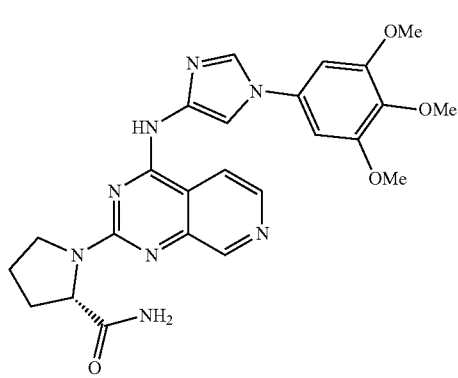 [SMILES: COc1cc(-n2cnc(Nc3nc(N4CCC[C@H]4C(N)=O)nc4cnccc34)c2)cc(OC)c1OC]
102
-continued
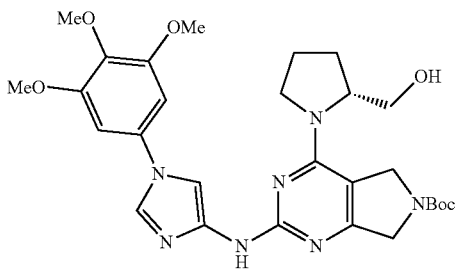 [SMILES: COc1cc(-n2cnc(Nc3nc4c(c(N5CCC[C@@H]5CO)n3)CN(C(=O)OC(C)(C)C)C4)c2)cc(OC)c1OC]
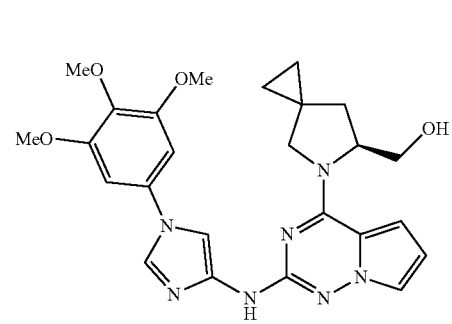 [SMILES: COc1cc(-n2cnc(Nc3nc(N4CC5(CC5)C[C@H]4CO)c4cccn4n3)c2)cc(OC)c1OC]
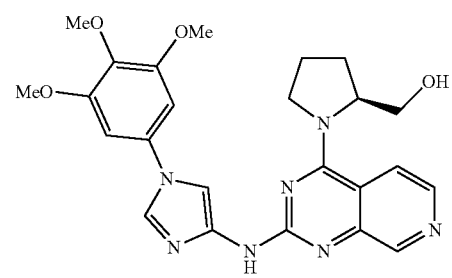 [SMILES: COc1cc(-n2cnc(Nc3nc(N4CCC[C@H]4CO)c4ccncc4n3)c2)cc(OC)c1OC]
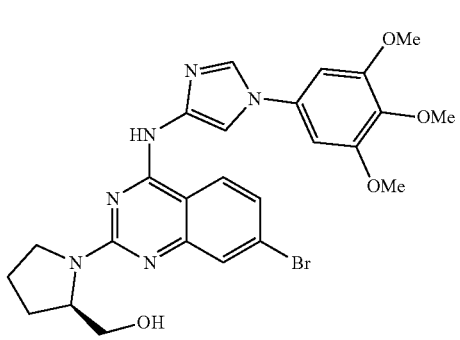 [SMILES: COc1cc(-n2cnc(Nc3nc(N4CCC[C@@H]4CO)nc4cc(Br)ccc34)c2)cc(OC)c1OC]
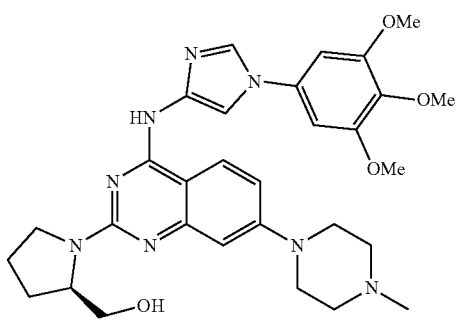 [SMILES: COc1cc(-n2cnc(Nc3nc(N4CCC[C@@H]4CO)nc4cc(N5CCN(C)CC5)ccc34)c2)cc(OC)c1OC]

-continued
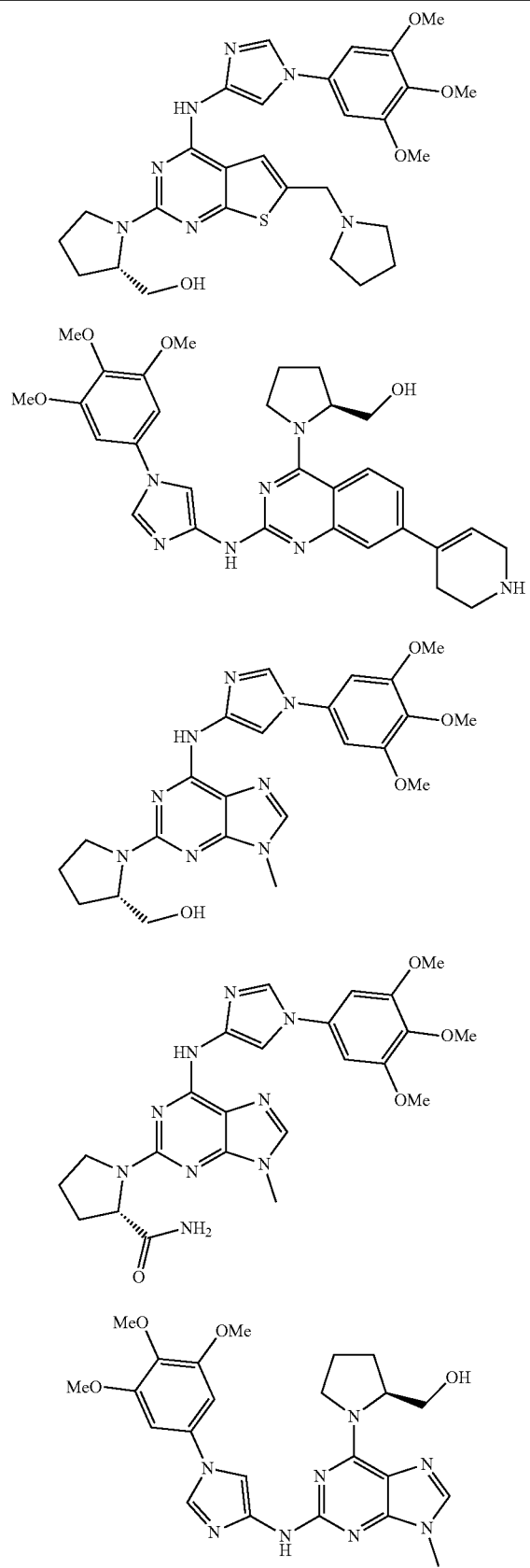
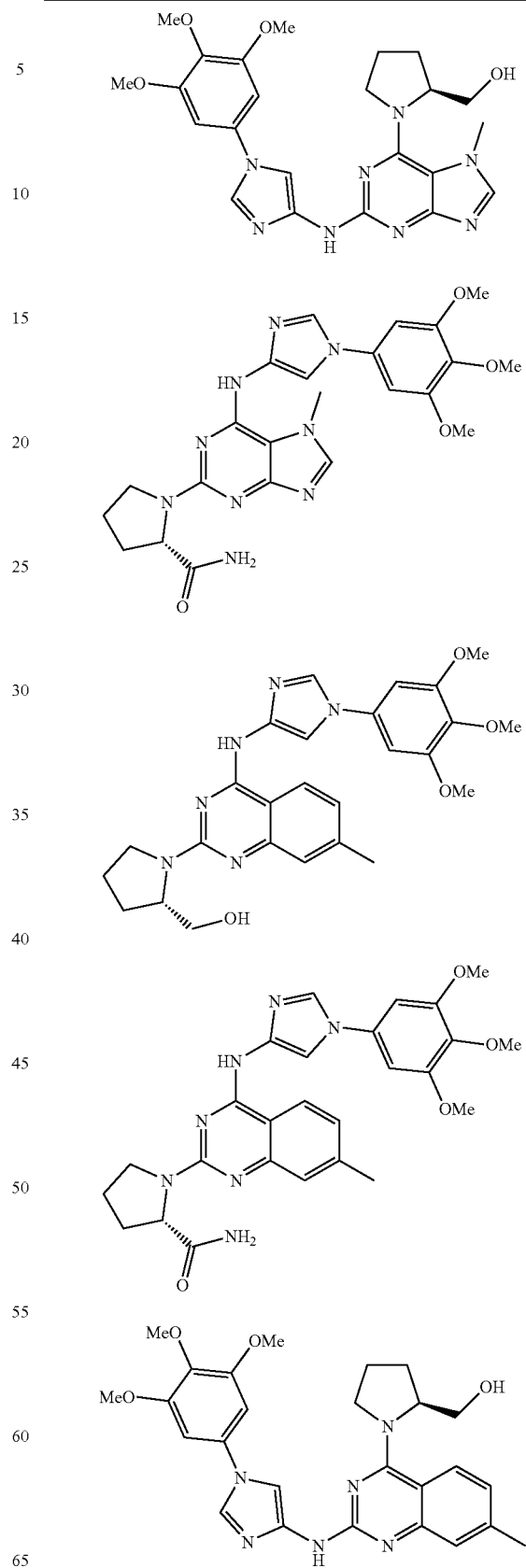

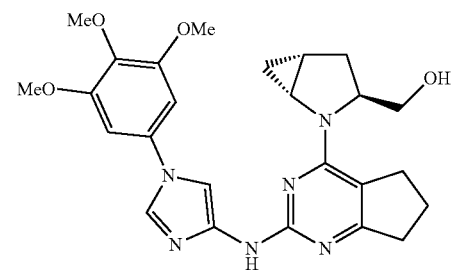 [SMILES: COc1cc(-n2cnc(Nc3nc4c(c(N5[C@H](CO)C[C@H]6C[C@H]65)n3)CCC4)c2)cc(OC)c1OC]
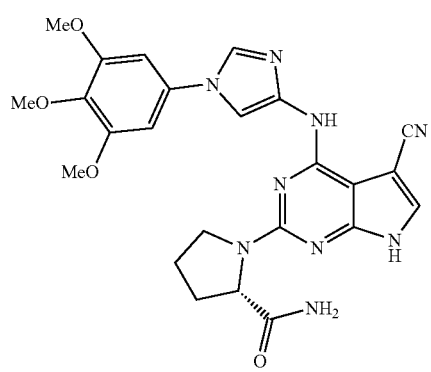 [SMILES: COc1cc(-n2cnc(Nc3nc(N4CCC[C@H]4C(N)=O)nc4[nH]cc(C#N)c34)c2)cc(OC)c1OC]
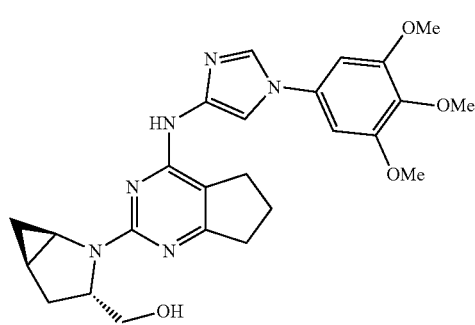 [SMILES: COc1cc(-n2cnc(Nc3nc(N4[C@H](CO)C[C@H]5C[C@H]54)nc4c3CCC4)c2)cc(OC)c1OC]
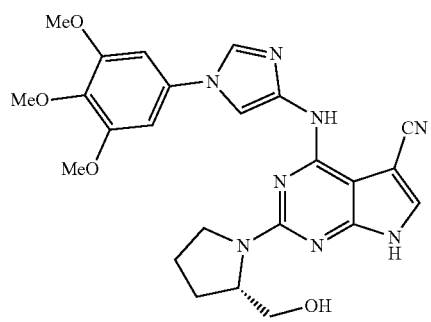 [SMILES: COc1cc(-n2cnc(Nc3nc(N4CCC[C@H]4CO)nc4[nH]cc(C#N)c34)c2)cc(OC)c1OC]
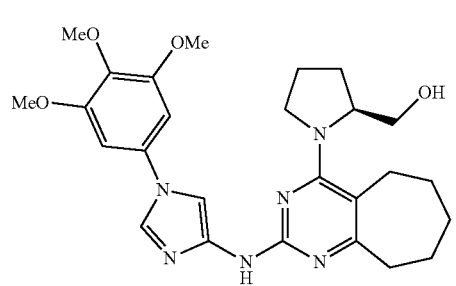 [SMILES: COc1cc(-n2cnc(Nc3nc4c(c(N5CCC[C@H]5CO)n3)CCCCC4)c2)cc(OC)c1OC]
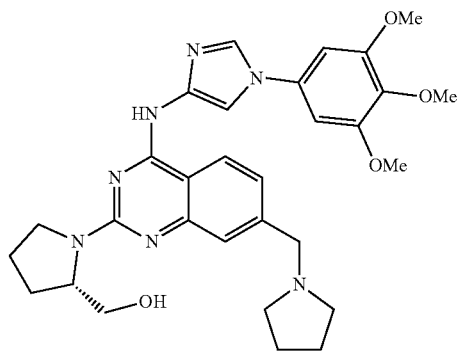 [SMILES: COc1cc(-n2cnc(Nc3nc(N4CCC[C@H]4CO)nc4cc(CN5CCCC5)ccc34)c2)cc(OC)c1OC]
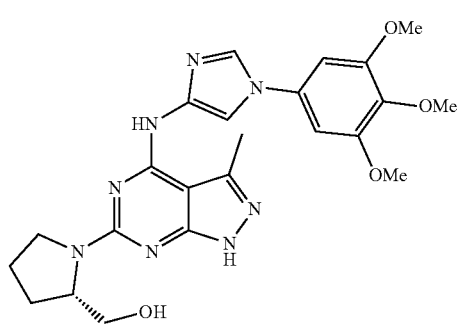 [SMILES: COc1cc(-n2cnc(Nc3nc(N4CCC[C@H]4CO)nc4[nH]nc(C)c34)c2)cc(OC)c1OC]
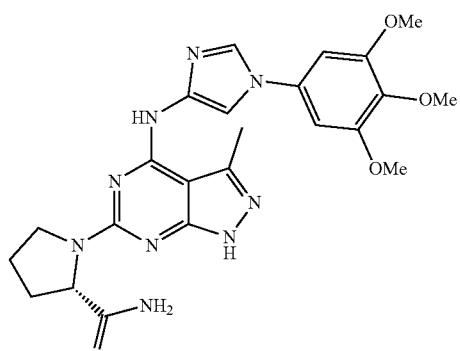
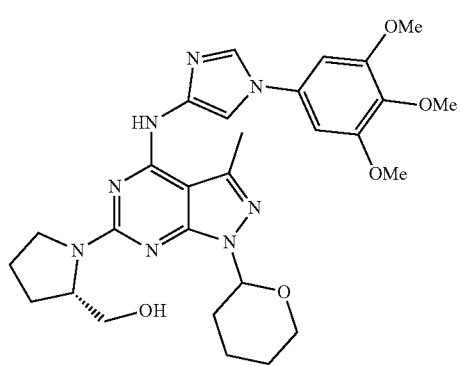 [SMILES: COc1cc(-n2cnc(Nc3nc(N4CCC[C@H]4CO)nc4c3c(C)nn4C3CCCCO3)c2)cc(OC)c1OC]

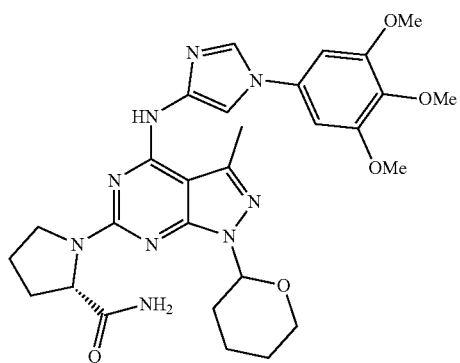 [SMILES: COc1cc(-n2cnc(Nc3nc(N4CCC[C@H]4C(N)=O)nc4c3c(C)nn4C3CCCCO3)c2)cc(OC)c1OC]
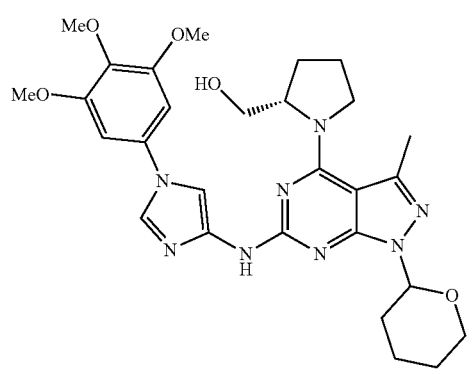 [SMILES: COc1cc(-n2cnc(Nc3nc(N4CCC[C@H]4CO)c4c(C)nn(C5CCCCO5)c4n3)c2)cc(OC)c1OC]
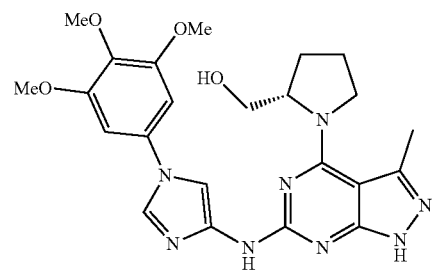 [SMILES: COc1cc(-n2cnc(Nc3nc(N4CCC[C@H]4CO)c4c(C)n[nH]c4n3)c2)cc(OC)c1OC]
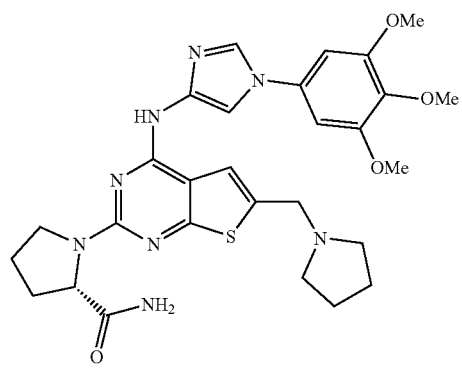 [SMILES: COc1cc(-n2cnc(Nc3nc(N4CCC[C@H]4C(N)=O)nc4sc(CN5CCCC5)cc34)c2)cc(OC)c1OC]
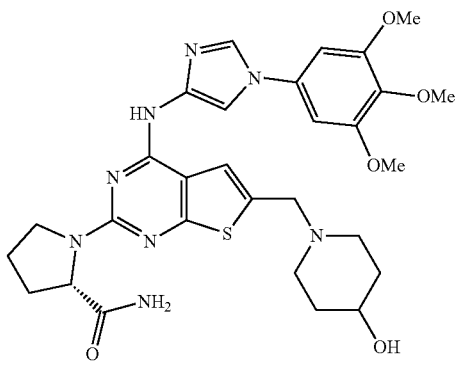 [SMILES: COc1cc(-n2cnc(Nc3nc(N4CCC[C@H]4C(N)=O)nc4sc(CN5CCC(O)CC5)cc34)c2)cc(OC)c1OC]
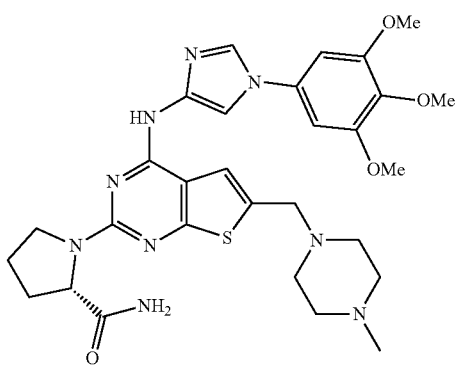 [SMILES: COc1cc(-n2cnc(Nc3nc(N4CCC[C@H]4C(N)=O)nc4sc(CN5CCN(C)CC5)cc34)c2)cc(OC)c1OC]
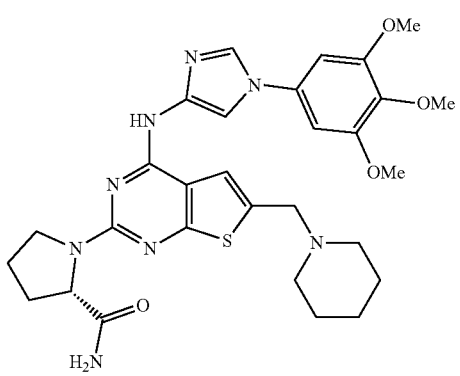 [SMILES: COc1cc(-n2cnc(Nc3nc(N4CCC[C@H]4C(N)=O)nc4sc(CN5CCCCC5)cc34)c2)cc(OC)c1OC]
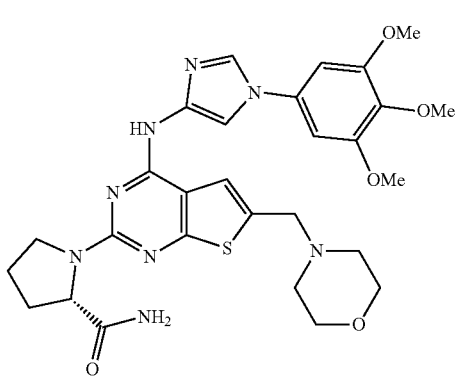 [SMILES: COc1cc(-n2cnc(Nc3nc(N4CCC[C@H]4C(N)=O)nc4sc(CN5CCOCC5)cc34)c2)cc(OC)c1OC]

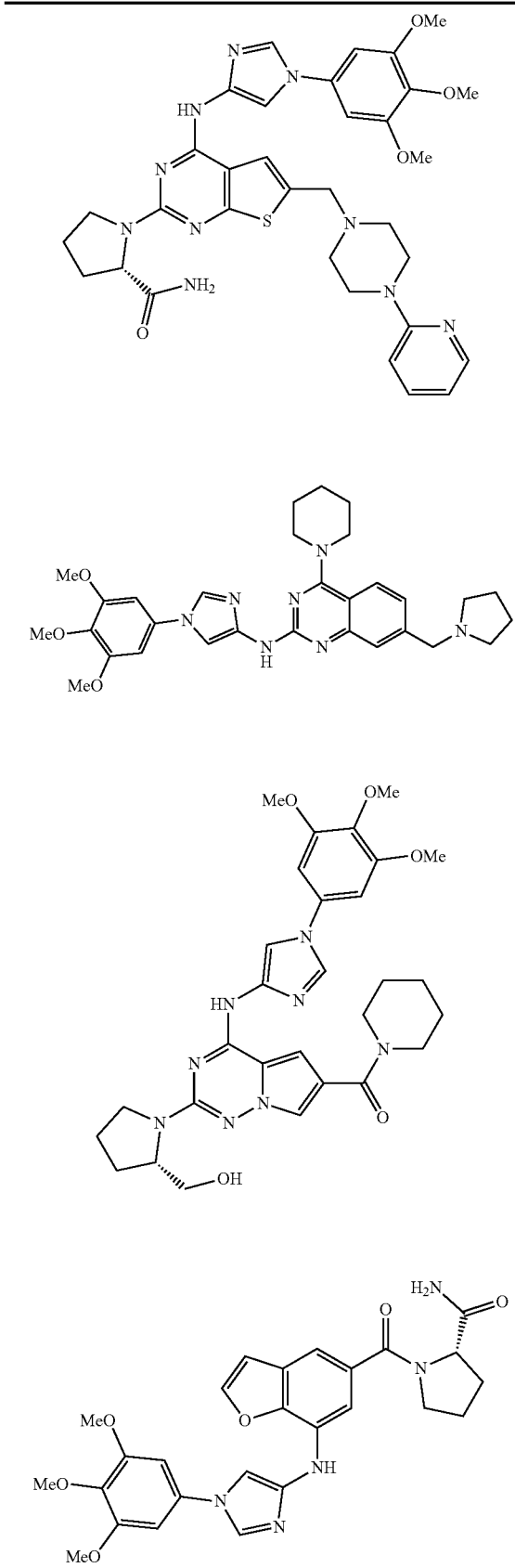
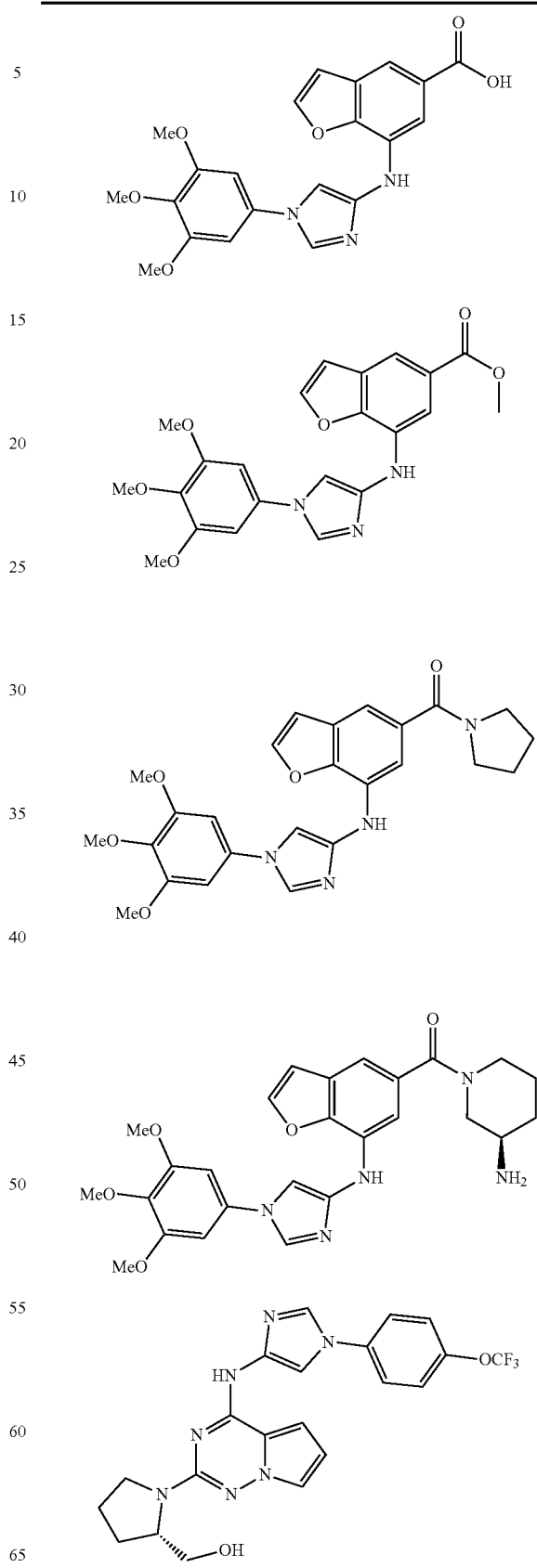

111
-continued
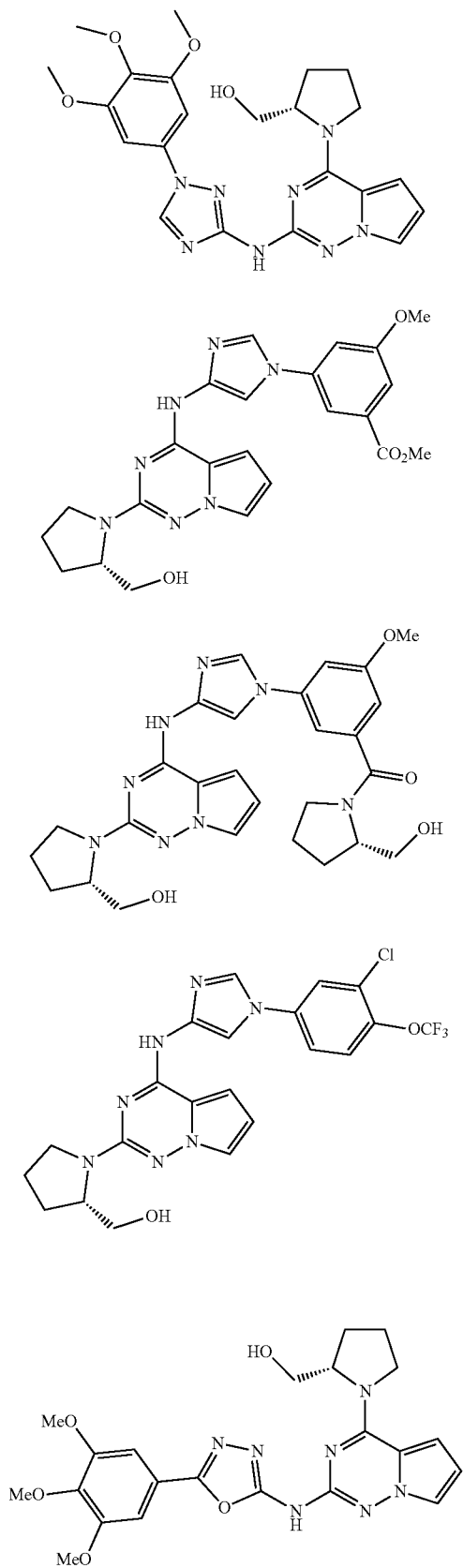
112
-continued
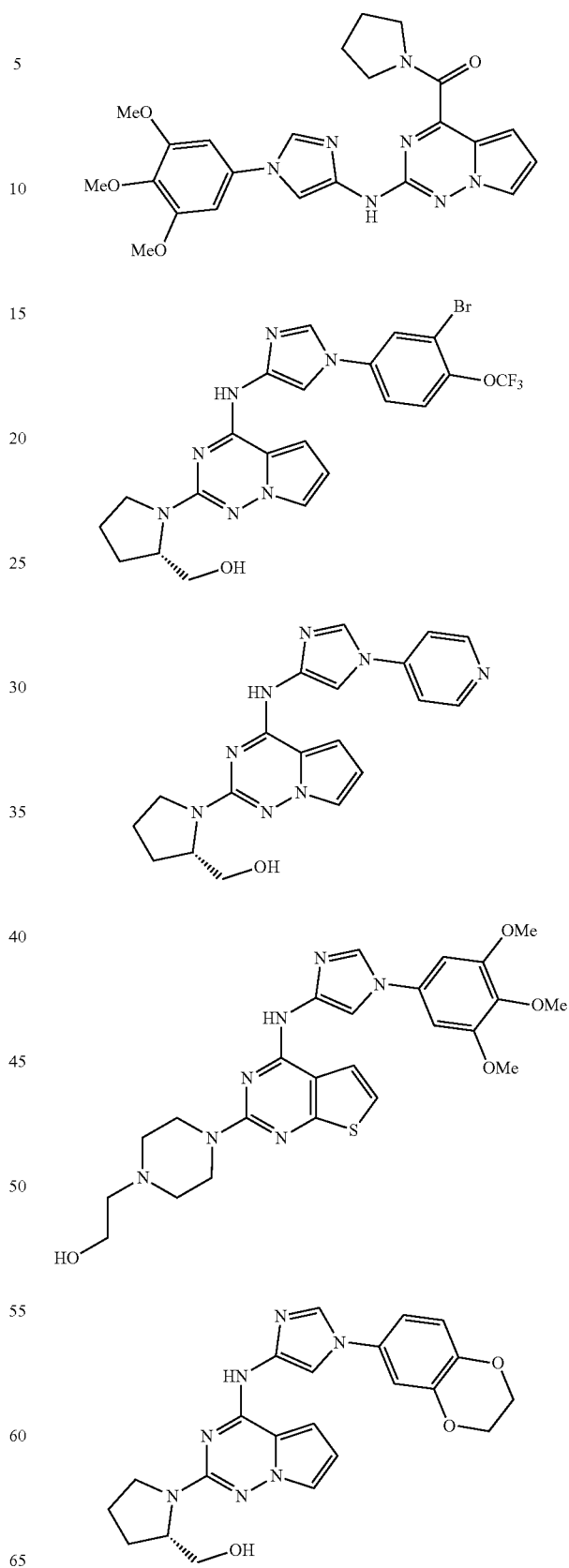

113
-continued
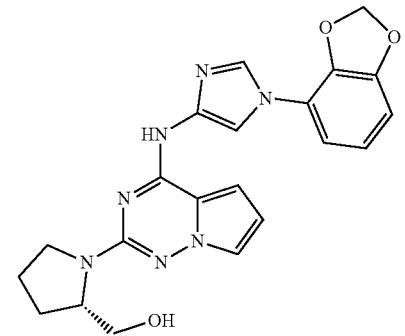 [SMILES: OC[C@@H]1CCCN1c1nc(Nc2cn(-c3cccc4c3OCO4)cn2)c2cccn2n1]
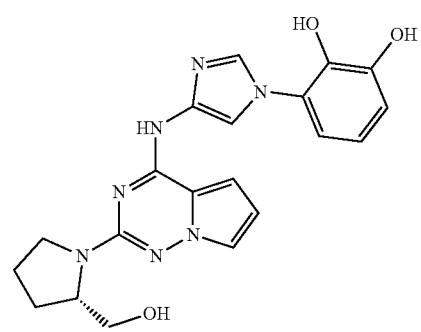 [SMILES: OC[C@@H]1CCCN1c1nc(Nc2cn(-c3cccc(O)c3O)cn2)c2cccn2n1]
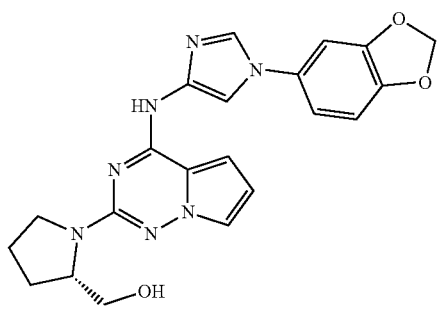 [SMILES: OC[C@@H]1CCCN1c1nc(Nc2cn(-c3ccc4c(c3)OCO4)cn2)c2cccn2n1]
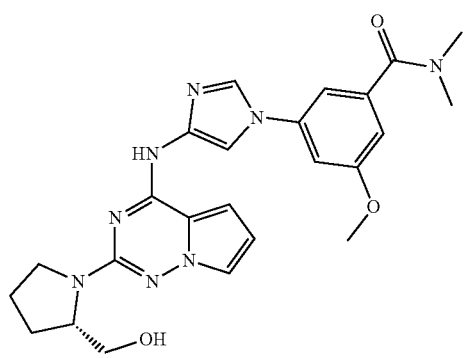 [SMILES: COc1cc(C(=O)N(C)C)cc(-n2cnc(Nc3nc(N4CCC[C@H]4CO)nn4cccc34)c2)c1]
114
-continued
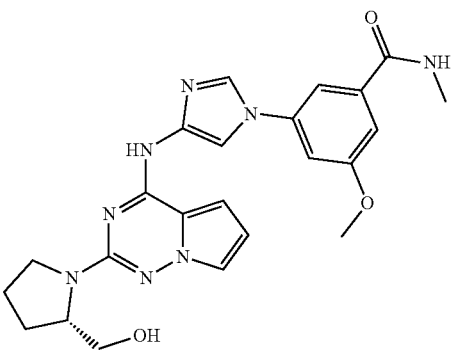 [SMILES: CNC(=O)c1cc(OC)cc(-n2cnc(Nc3nc(N4CCC[C@H]4CO)nn4cccc34)c2)c1]
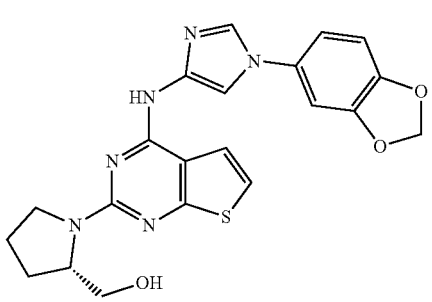 [SMILES: OC[C@@H]1CCCN1c1nc(Nc2cn(-c3ccc4c(c3)OCO4)cn2)c2ccsc2n1]
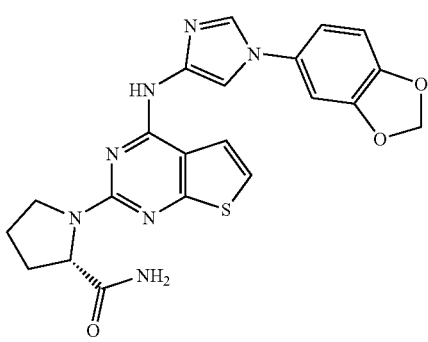 [SMILES: NC(=O)[C@@H]1CCCN1c1nc(Nc2cn(-c3ccc4c(c3)OCO4)cn2)c2ccsc2n1]
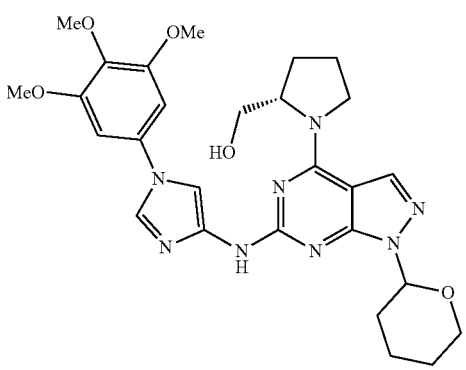 [SMILES: COc1cc(-n2cnc(Nc3nc(N4CCC[C@H]4CO)c4cnn(C5CCCCO5)c4n3)c2)cc(OC)c1OC]

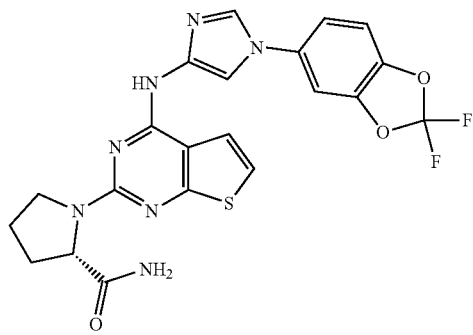 [SMILES: NC(=O)[C@@H]1CCCN1c1nc(Nc2cn(-c3ccc4c(c3)OC(F)(F)O4)cn2)c2ccsc2n1]
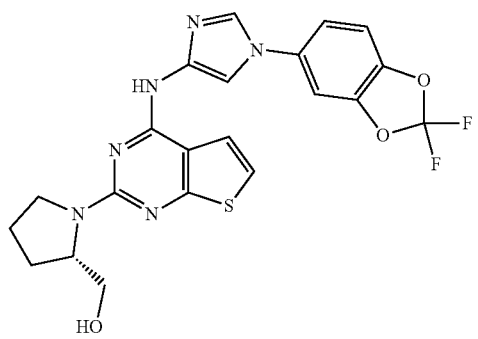 [SMILES: OC[C@@H]1CCCN1c1nc(Nc2cn(-c3ccc4c(c3)OC(F)(F)O4)cn2)c2ccsc2n1]
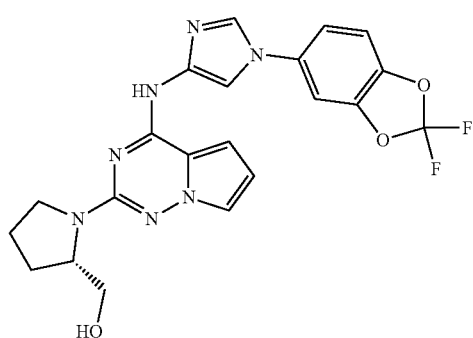 [SMILES: OC[C@@H]1CCCN1c1nc(Nc2cn(-c3ccc4c(c3)OC(F)(F)O4)cn2)c2cccn2n1]
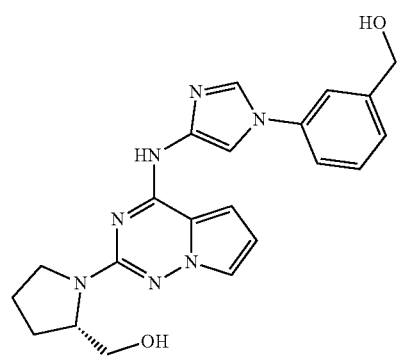 [SMILES: OCc1cccc(-n2cnc(Nc3nc(N4CCC[C@H]4CO)nn4cccc34)c2)c1]
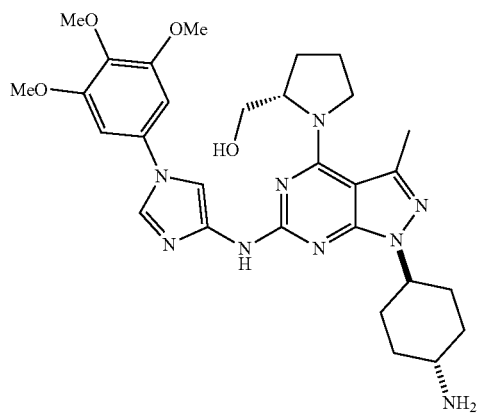
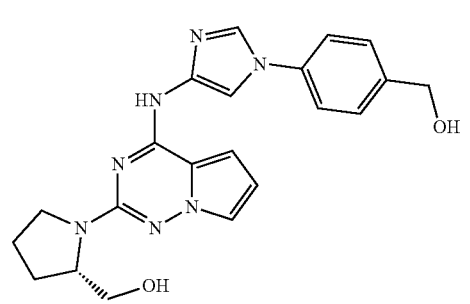 [SMILES: OCc1ccc(-n2cnc(Nc3nc(N4CCC[C@H]4CO)nn4cccc34)c2)cc1]
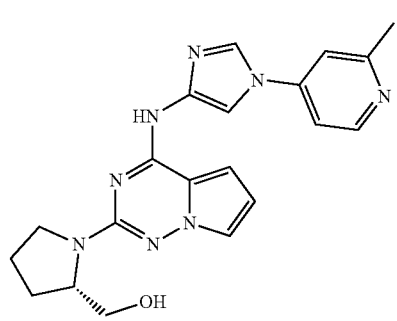 [SMILES: Cc1cc(-n2cnc(Nc3nc(N4CCC[C@H]4CO)nn4cccc34)c2)ccn1]
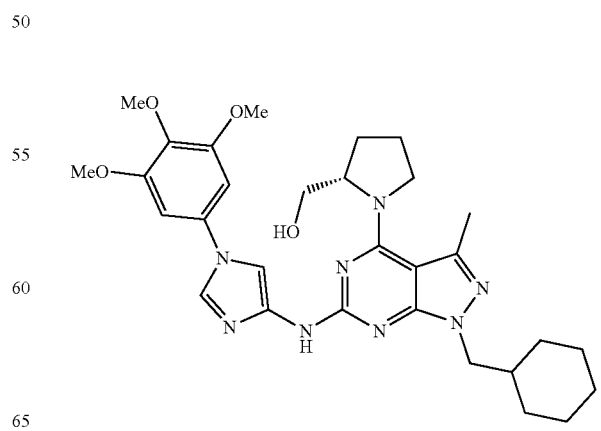

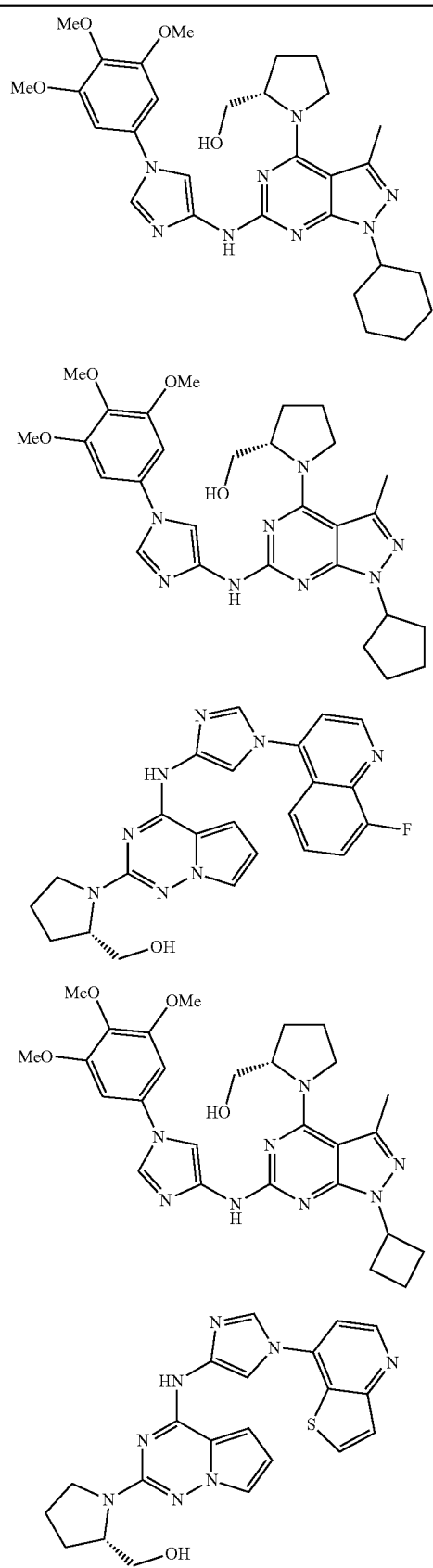
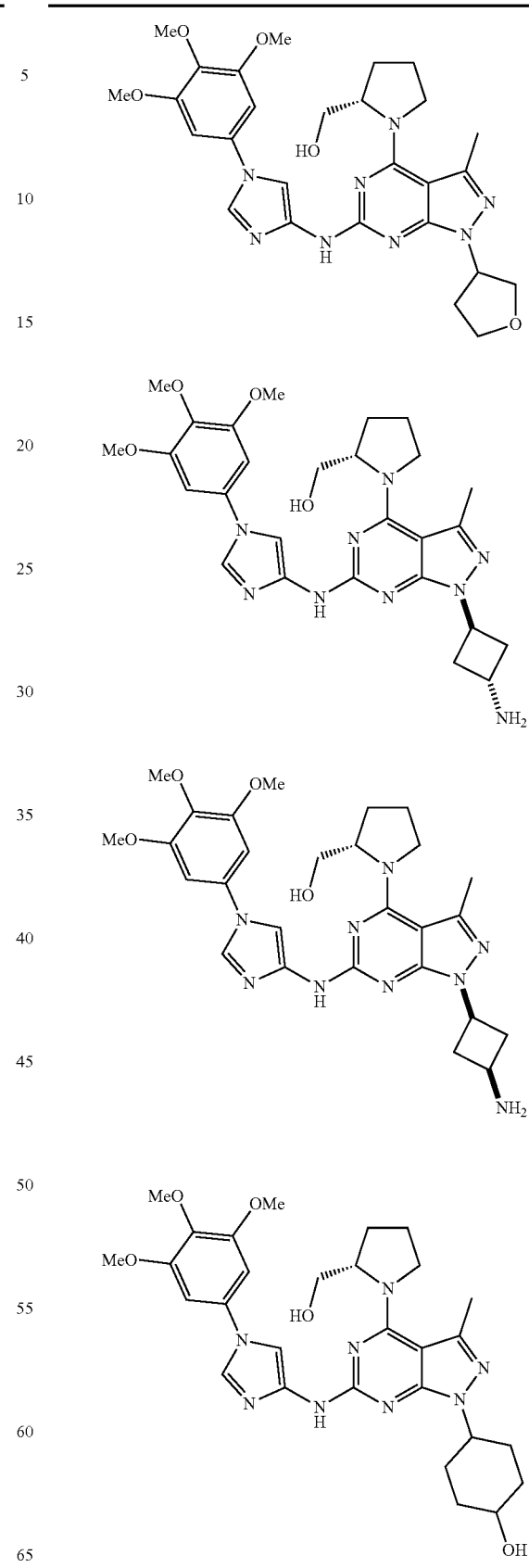

119
-continued
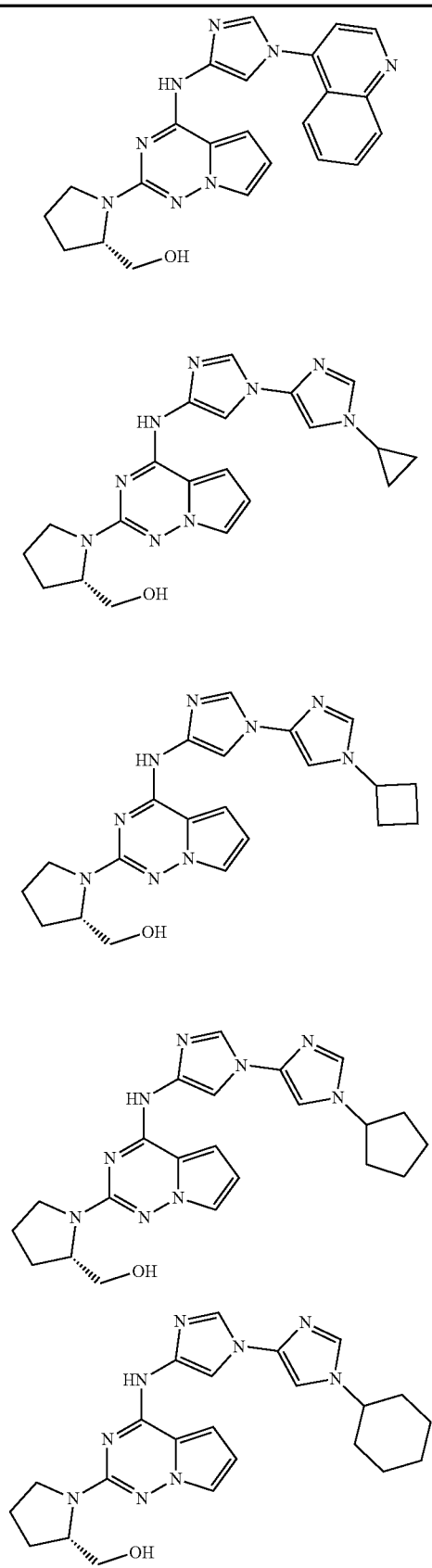
120
-continued
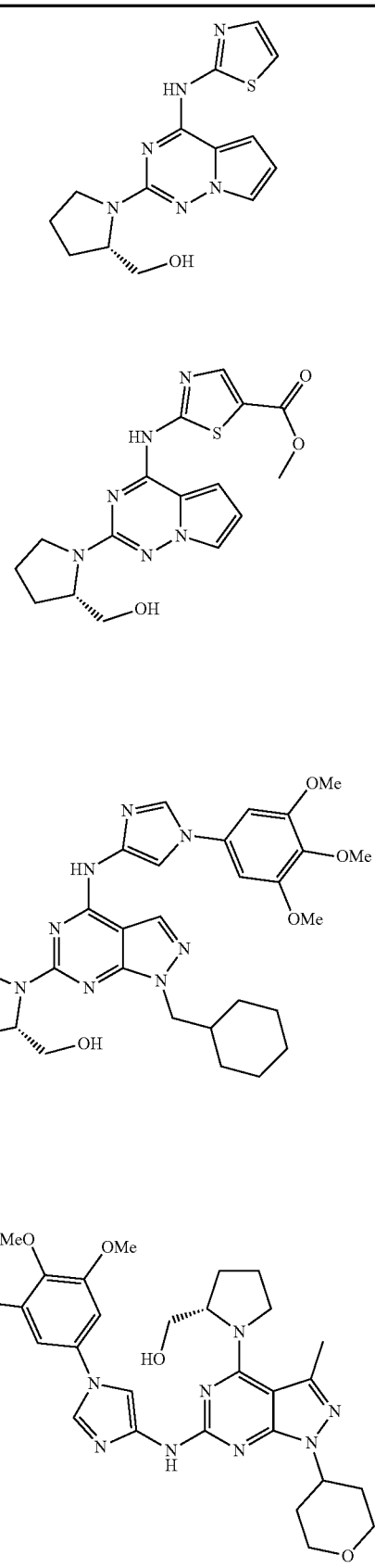

-continued
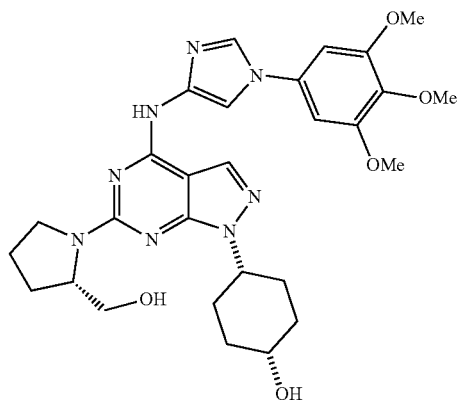
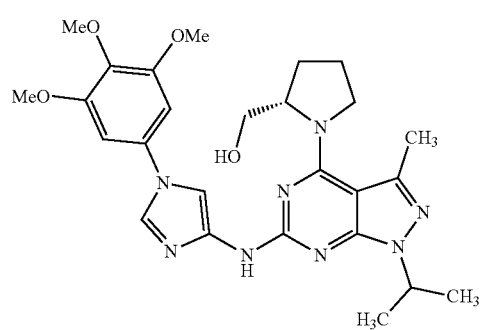 [SMILES: COc1cc(-n2cnc(Nc3nc(N4CCC[C@H]4CO)c4c(C)nn(C(C)C)c4n3)c2)cc(OC)c1OC]
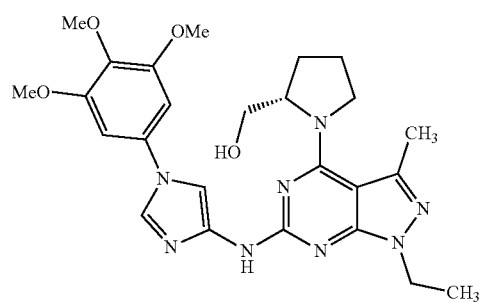 [SMILES: CCn1nc(C)c2c(N3CCC[C@H]3CO)nc(Nc3cn(-c4cc(OC)c(OC)c(OC)c4)cn3)nc21]
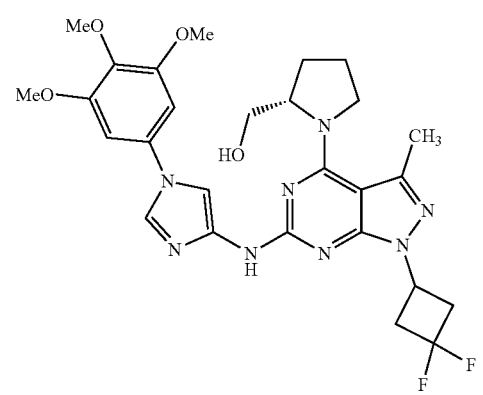 [SMILES: COc1cc(-n2cnc(Nc3nc(N4CCC[C@H]4CO)c4c(C)nn(C5CC(F)(F)C5)c4n3)c2)cc(OC)c1OC]
-continued
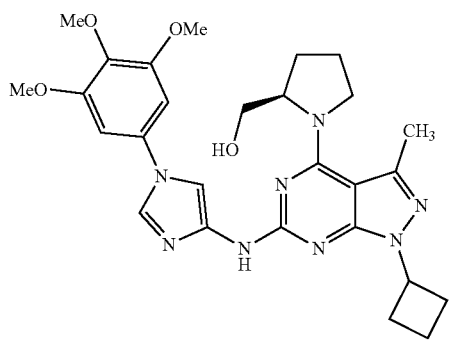 [SMILES: COc1cc(-n2cnc(Nc3nc(N4CCC[C@@H]4CO)c4c(C)nn(C5CCC5)c4n3)c2)cc(OC)c1OC]
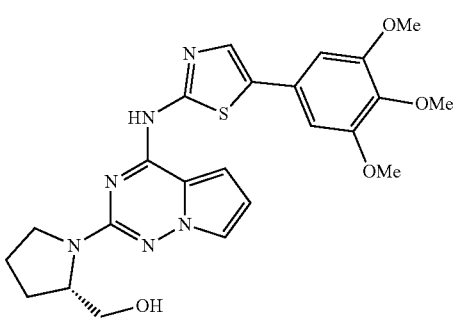 [SMILES: COc1cc(-c2cnc(Nc3nc(N4CCC[C@H]4CO)nn4cccc34)s2)cc(OC)c1OC]
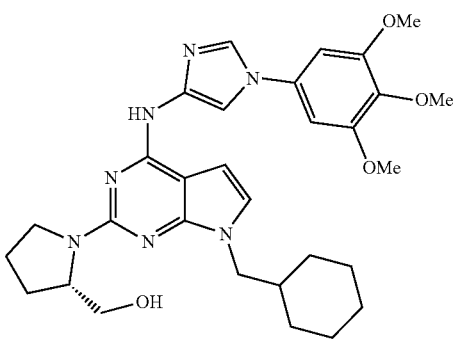 [SMILES: COc1cc(-n2cnc(Nc3nc(N4CCC[C@H]4CO)nc4c3ccn4CC3CCCCC3)c2)cc(OC)c1OC]
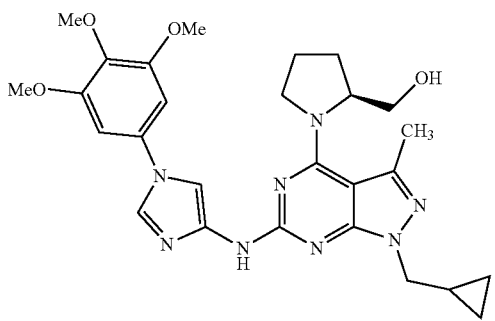 [SMILES: COc1cc(-n2cnc(Nc3nc(N4CCC[C@H]4CO)c4c(C)nn(CC5CC5)c4n3)c2)cc(OC)c1OC]

| 123 -continued | 124 -continued |
|---|---|
| 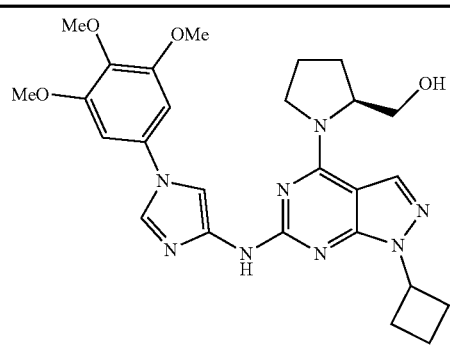 | 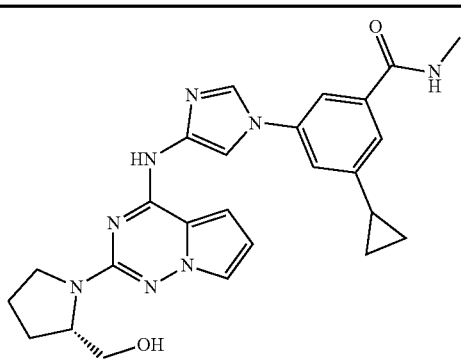 |
| 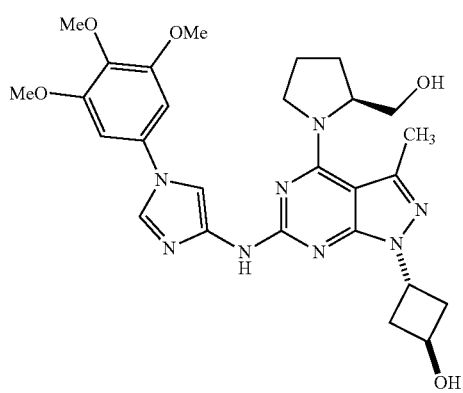 | 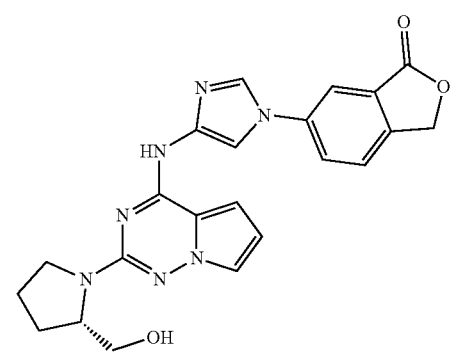 |
| 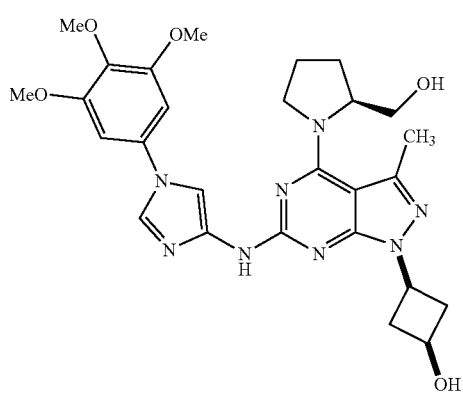 | 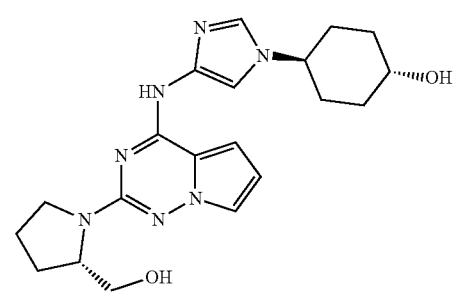 [SMILES: OC[C@@H]1CCCN1c1nc(Nc2cn([C@H]3CC[C@H](O)CC3)cn2)c2cccn2n1] |
| | 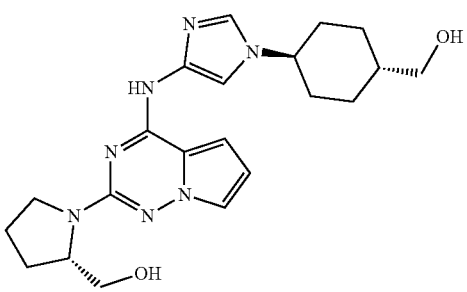 [SMILES: OC[C@@H]1CCCN1c1nc(Nc2cn([C@H]3CC[C@H](CO)CC3)cn2)c2cccn2n1] |
| 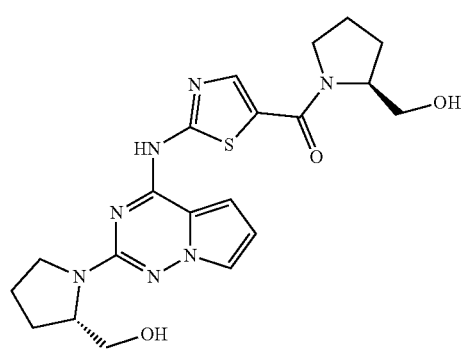 | 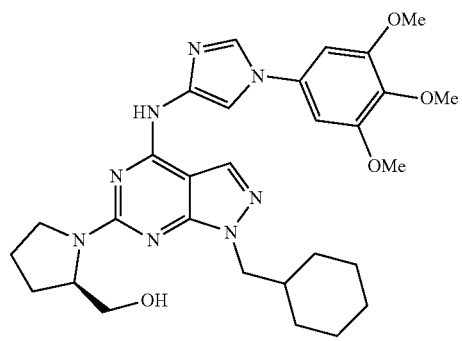 [SMILES: COc1cc(-n2cnc(Nc3nc(N4CCC[C@@H]4CO)nc4c3cnn4CC3CCCCC3)c2)cc(OC)c1OC] |

125
-continued
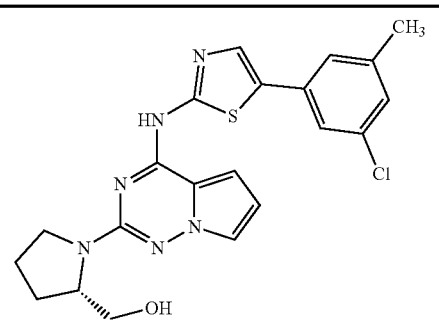
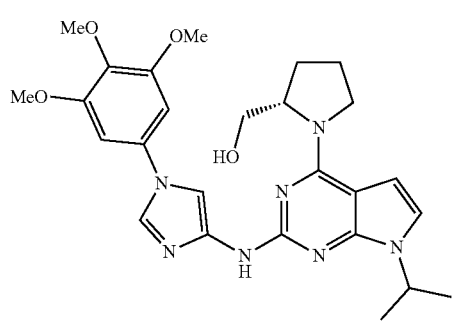 [SMILES: COc1cc(-n2cnc(Nc3nc(N4CCC[C@H]4CO)c4ccn(C(C)C)c4n3)c2)cc(OC)c1OC]
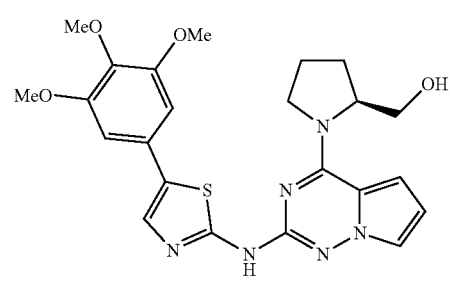 [SMILES: COc1cc(-c2cnc(Nc3nc(N4CCC[C@H]4CO)c4cccn4n3)s2)cc(OC)c1OC]
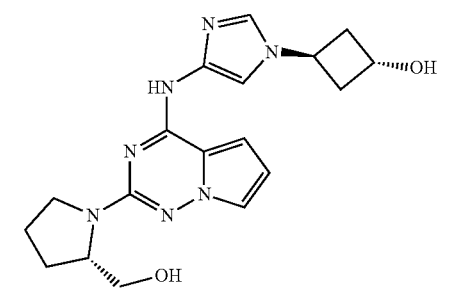 [SMILES: OC[C@@H]1CCCN1c1nc(Nc2cn([C@H]3C[C@H](O)C3)cn2)c2cccn2n1]
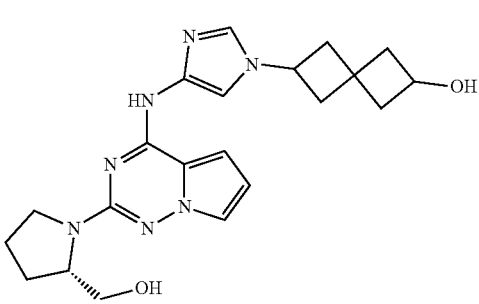 [SMILES: OC[C@@H]1CCCN1c1nc(Nc2cn(C3CC4(CC(O)C4)C3)cn2)c2cccn2n1]
126
-continued
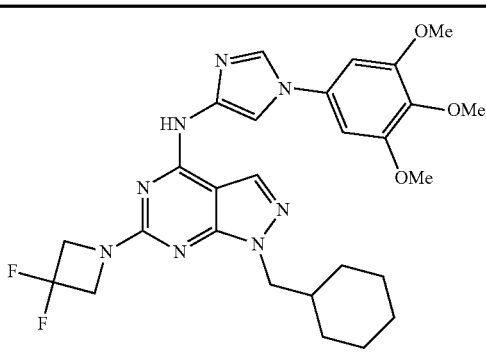
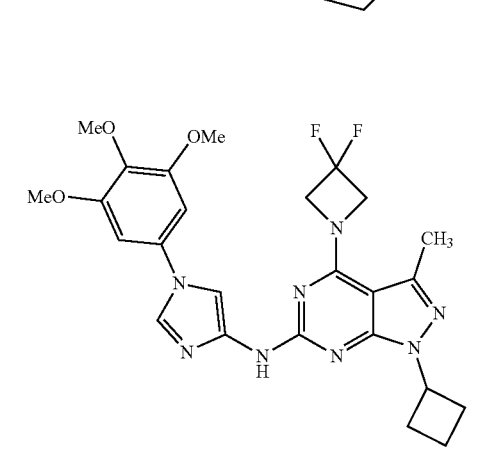
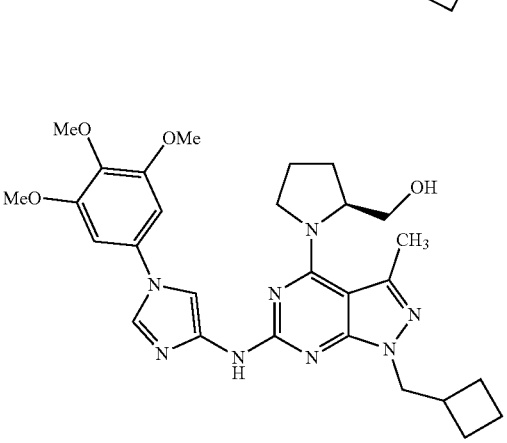
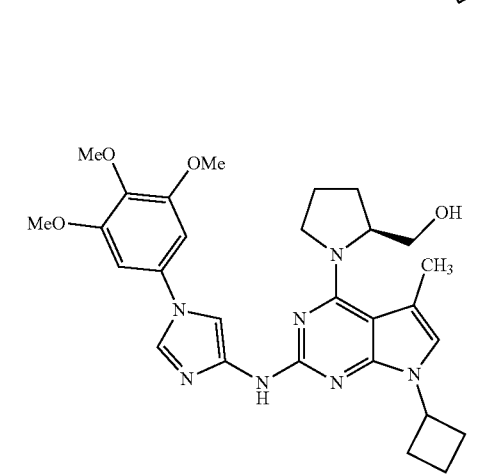

127
-continued

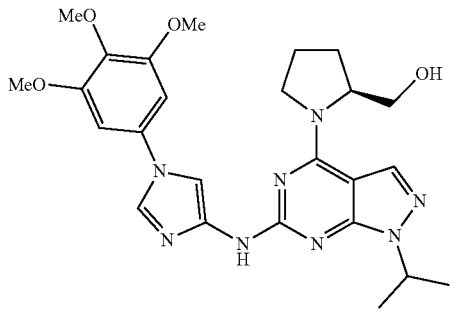 [SMILES: COc1cc(-n2cnc(Nc3nc(N4CCC[C@H]4CO)c4cnn(C(C)C)c4n3)c2)cc(OC)c1OC]

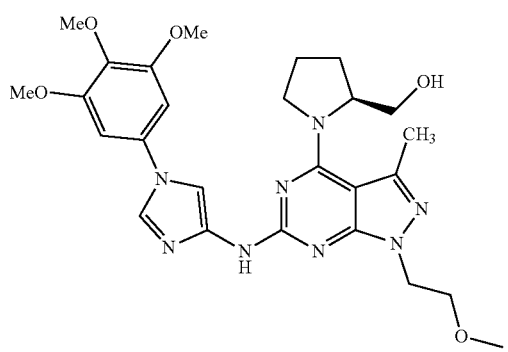 [SMILES: COCCn1nc(C)c2c(N3CCC[C@H]3CO)nc(Nc3cn(-c4cc(OC)c(OC)c(OC)c4)cn3)nc21]

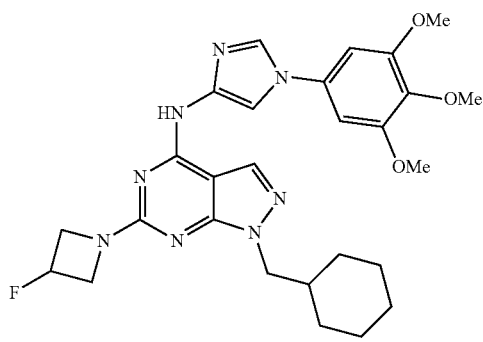 [SMILES: COc1cc(-n2cnc(Nc3nc(N4CC(F)C4)nc4c3cnn4CC3CCCCC3)c2)cc(OC)c1OC]

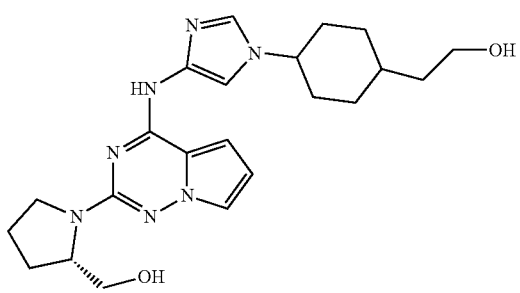 [SMILES: OCCC1CCC(n2cnc(Nc3nc(N4CCC[C@H]4CO)nn4cccc34)c2)CC1]

128
-continued

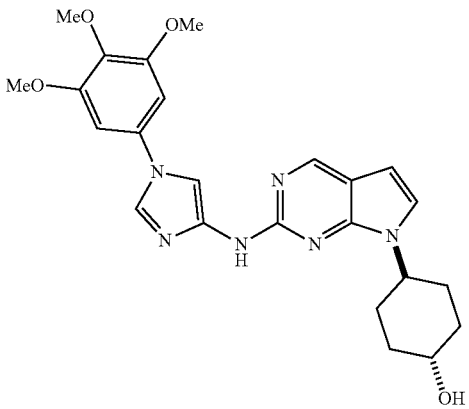

In further aspects, the invention provides a compound represented by formula (III) or formula (IV):

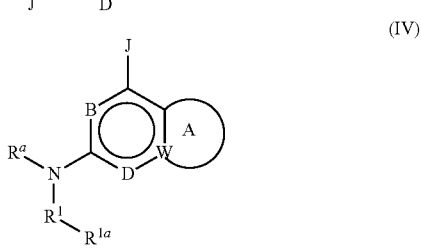

or a pharmaceutically acceptable salt thereof,
wherein:
A is a fused optionally substituted aromatic ring, heteroaromatic ring, partially unsaturated cycloalkyl ring, or partially unsaturated heterocycloalkyl ring;
W is C or N;
B is CH or N;
D is CH or N;
provided that when B is CH, then D is N; or when D is CH, then B is N;
$R^a$ represents H or alkyl;
$R^1$ represents heteroarylene;
$R^{1a}$ represents H or optionally substituted —C(O)alkyl, —C(O)aryl, —C(O)heteroaryl, —C(O)O(alkyl), —C(O)(heterocyclyl), —C(O)NR$^x$R$^y$, alkyl, cycloalkyl, heterocycloalkyl, aryl, or heteroaryl;
J represents H, halo, —OR$^2$, —NR$^2$R$^3$, —C(O)NR$^2$R$^3$, —C(O)O(alkyl), —C(O)OH, aryl, or heteroaryl, wherein aryl or heteroaryl is optionally substituted by one or more occurrences of R$^{2a}$;
$R^2$ represents optionally substituted alkyl, aralkyl, heteroaralkyl, cycloalkyl, heterocycloalkyl, (cycloalkyl)alkyl, (heterocycloalkyl)alkyl, or hydroxyalkyl;
$R^3$ represents H or alkyl; or
$R^2$ and $R^3$, taken together, form a heterocycloalkyl ring, optionally substituted by one or more occurrences of R$^{2a}$;

$R^{2a}$, independently for each occurrence, represents halo, hydroxyl, —C(O)H, oxo, —NH$_2$, —C(O)NH$_2$, —C(O)OH, —C(O)R$^5$, —C(O)OR$^5$, —C(O)NH(R$^5$), or optionally substituted alkyl, alkoxyl, hydroxyalkyl, heteroaryl, aryl, aryloxy, heteroaryloxy, arylalkyloxy, heteroarylalkyloxy, or —N(alkyl)$_2$;

or any two germinal or vicinal occurrences of $R^{2a}$, taken together, may form a spiro or fused cycloalkyl ring;

$R^5$, independently for each occurrence, represents optionally substituted alkyl, aralkyl, aryl, heteroaralkyl, heteroaryl, cycloalkyl, heterocycloalkyl, (cycloalkyl)alkyl, or (heterocycloalkyl)alkyl; and $R^x$ and $R^y$ each independently represent H, alkyl, aralkyl, heteroaralkyl, aryl, heteroaryl, cycloalkyl, heterocycloalkyl, (cycloalkyl)alkyl, (heterocycloalkyl)alkyl, or hydroxyalkyl.

In certain embodiments, the compound is represented by formula (IIIa) or formula (IVa):

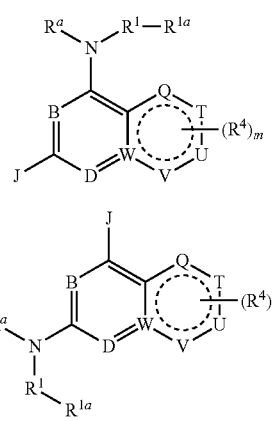

wherein:

valence permitting, Q, T, U, and V each independently represent CH, CH$_2$, N, NH, O, or SO$_2$, wherein any hydrogen of a CH, CH$_2$, or NH group is optionally replaced by an occurrence of R$^4$;

$R^4$, independently for each occurrence, represents halo, cyano, or optionally substituted alkyl, alkenyl, haloalkyl, hydroxyalkyl, aminoalkyl, alkoxy, aryl, aralkyl, heteroaryl, heteroaralkyl, heterocycloalkyl, heterocycloalkenyl, (heterocycloalkyl)alkyl, cycloalkyl, (cycloalkyl)alkyl, halocycloalkyl, hydroxycycloalkyl, aminocycloalkyl, aryloxy, heteroaryloxy, arylalkyloxy, heteroarylalkyloxy, —CH$_2$C(O)NH$_2$, —C(O)R$^5$, —C(O)OR$^5$, or —S(O)$_2$R$^5$;

m is an integer from 0-4, as permitted by valence.

In certain embodiments, the compound is represented by formula (IIIb) or formula

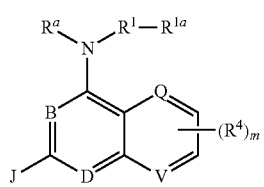

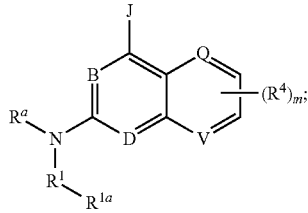

wherein Q represents CH or N; and V represents CH or N. In certain embodiments, Q is N and V is CH. In alternative embodiments, Q is CH and V is N.

In certain embodiments, the compound is represented by formula (IIIc) or formula (IVc):

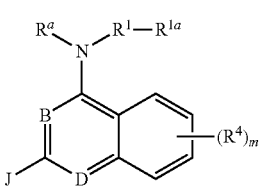

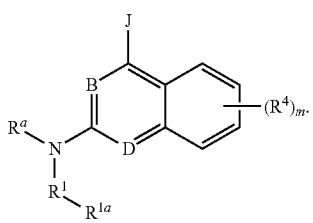

In certain embodiments, the compound is represented by formula (IIId) or formula

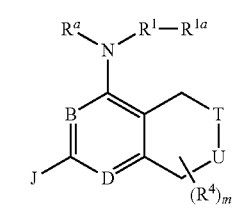

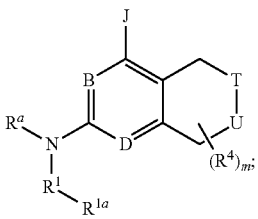

wherein T represents CH$_2$, NH, O, or SO$_2$; and U represents CH$_2$, NH, O, or SO$_2$. In certain embodiments, T is NH; and U is CH$_2$. In other embodiments, T is CH$_2$ and U is NH.

In certain embodiments, the compound is represented by formula (IIIe) or formula (IVe):

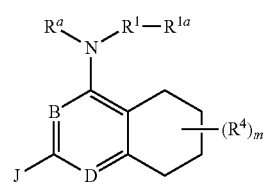

(IIIe)

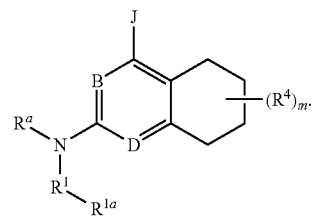

(IVe)

In any one of formulae (IIIa), (IVa), (IIIb), (IVb), (IIIc), (IVc), (IIId), (IVd), (IIIe), and (IVe), in certain embodiments, m is 0 or 1.

In certain embodiments, the compound is represented by formula (IIIj) or formula (IVj):

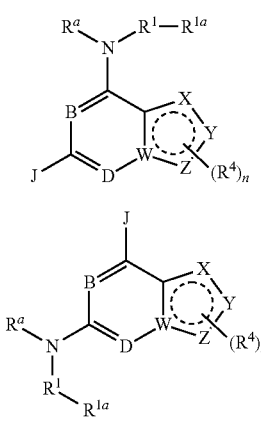

(IIIj)

(IVj)

wherein:
W is C or N;
valence permitting, X, Y, and Z each independently represent CH, CH$_2$, CO, N, NH, O, S, or SO$_2$, wherein any hydrogen of a CH, CH$_2$, or NH group is optionally replaced by an occurrence of R$^4$;
R$^4$, independently for each occurrence, represents halo, cyano, or optionally substituted alkyl, alkenyl, haloalkyl, hydroxyalkyl, aminoalkyl, alkoxy, aryl, aralkyl, heteroaryl, heteroaralkyl, heterocycloalkyl, heterocycloalkenyl, (heterocycloalkyl)alkyl, cycloalkyl, (cycloalkyl)alkyl, halocycloalkyl, hydroxycycloalkyl, aminocycloalkyl, aryloxy, heteroaryloxy, arylalkyloxy, heteroarylalkyloxy, —CH$_2$C(O)NH$_2$, —C(O)R$^5$, —C(O)OR$^5$, or —S(O)$_2$R$^5$;
n is an integer from 0-4, as permitted by valence.

In certain embodiments, R$^4$, independently for each occurrence, represents halo, or optionally substituted alkyl, alkenyl, haloalkyl, hydroxyalkyl, aminoalkyl, alkoxy, aryl, aralkyl, heteroaryl, heteroaralkyl, heterocycloalkyl, heterocycloalkenyl, (heterocycloalkyl)alkyl, cycloalkyl, (cycloalkyl)alkyl, —CH$_2$C(O)NH$_2$, —C(O)R$^5$, —C(O)OR$^5$, or —S(O)$_2$R$^5$.

In certain embodiments, R$^4$, independently for each occurrence, represents halocycloalkyl, hydroxycycloalkyl, aminocycloalkyl, aryloxy, heteroaryloxy, arylalkyloxy, or heteroarylalkyloxy.

In certain embodiments, one of X, Y, or Z is NR$^4$.

In certain such embodiments, R$^4$ is selected from the group consisting of:

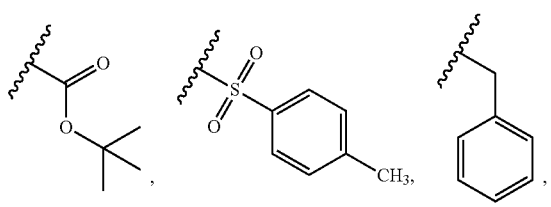

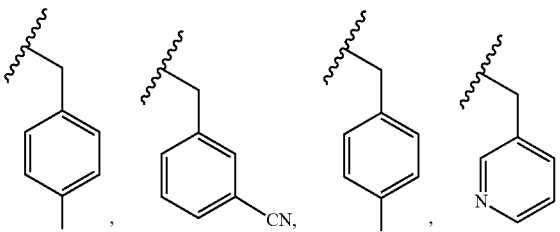

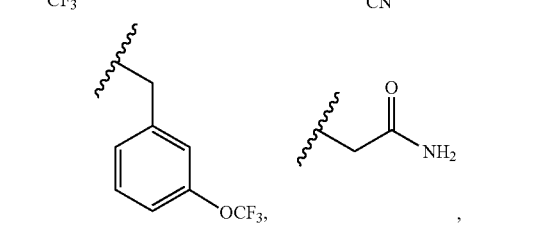

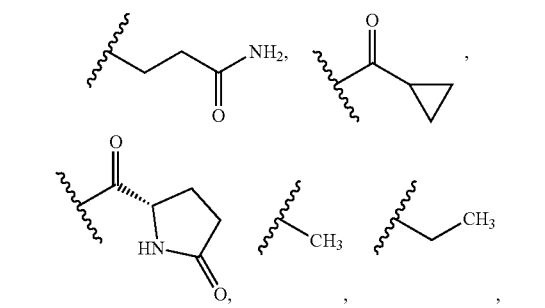

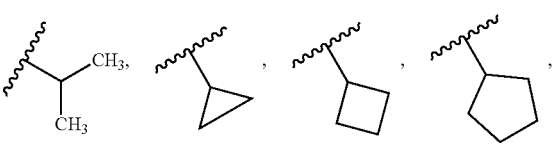

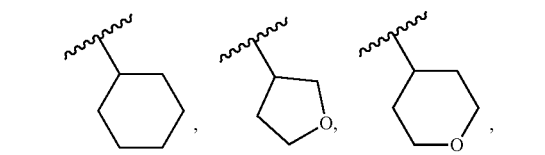

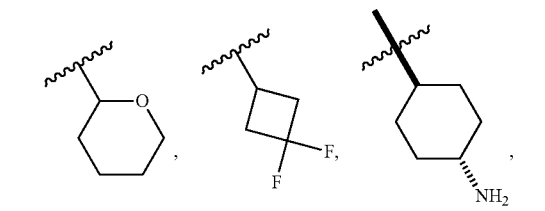

-continued

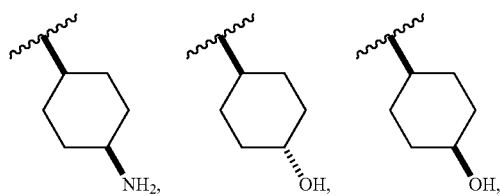

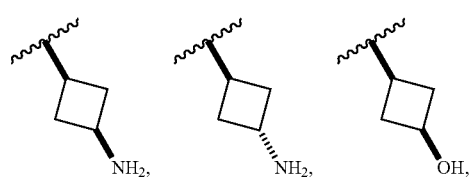

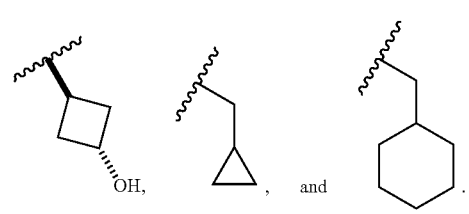

In certain embodiments, the compound is represented by formula (IIIk) or (IVk):

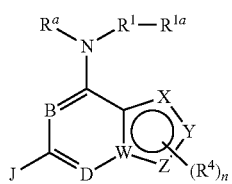

(IIIk)

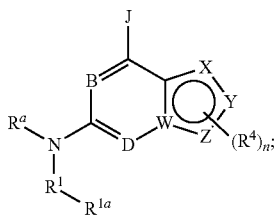

(IVk)

wherein X, Y, and Z each independently represent CH, N, NH, O, S, or $SO_2$.

In further embodiments, the compound is represented by formula (IIIk') or (IVk'):

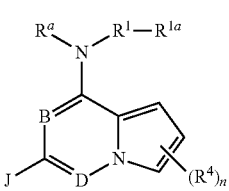

(IIIk')

-continued

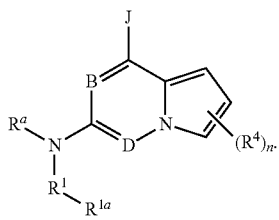

(IVk')

In certain embodiments, the compound is represented by formula (IIIk") or (IVk"):

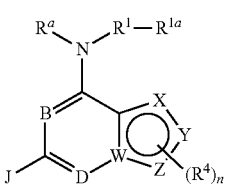

(IIIk")

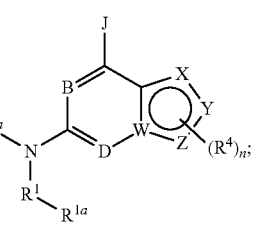

(IVk")

wherein at least one of X and Z is selected from the group consisting of O, N, NH, and S.

In certain embodiments of the compounds of formula (IIIk") and (IVk"), one of X and Z is selected from the group consisting of O, NH, and S; and the other of X and Z is CH. For example, X may be selected from the group consisting of O, NH, and S. Alternatively, Z may be selected from the group consisting of O, NH, and S.

In further embodiments of the compounds of formula (IIIk") and (IVk"), each of X and Z are selected from the group consisting of O, N, NH, and S. For example, one of X and Z is N and the other of X and Z is NH.

In certain embodiments, the compound of the invention is represented by wherein the compound is represented by formula (IIIn) or (IVn):

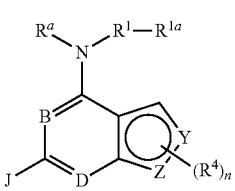

(IIIn)

-continued

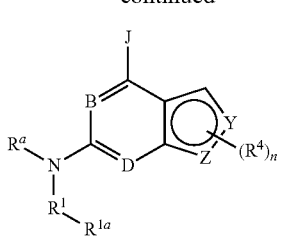
(IVn)

wherein each of Y and Z are selected from the group consisting of O, N, NH, and S.

In certain embodiments, Y is N and Z is NH.

In certain embodiments, the compound of the invention is represented by formula (IIIm) or (IVm):

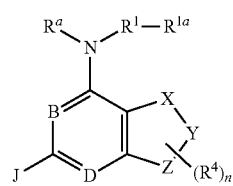
(IIIm)

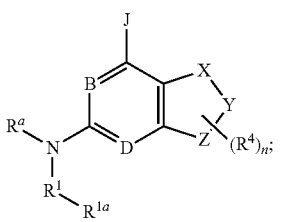
(IVm)

wherein X, Y, and Z each independently represent $CH_2$, CO, NH, O, S, or $SO_2$.

In certain embodiments of the compounds of formula (IIIm) or (IVm), each of X, Y, and Z is $CH_2$. In alternative embodiments, one of X, Y, and Z is N or O.

In any one of formulae (IIIj), (IVj), (IIIk), (IVk), (IIIk'), (IVk'), (IIIk"), (IVk"), (IIIm), and (IVm), in certain embodiments, n is 0 or 1.

In any of the foregoing embodiments, $R^4$, if present, may be selected from the group consisting of optionally substituted alkyl, hydroxyalkyl, aminoalkyl, alkoxy, aryl, aralkyl, and (heterocycloalkyl)alkyl.

In any of the foregoing embodiments, $R^a$ may be H.

In certain embodiments, $R^1$ is a nitrogen-containing heteroarylene, such as a 5-membered nitrogen-containing heteroarylene. In certain embodiments, $R^1$ is imidazolene.

In some embodiments, —$R^1$-$R^{1a}$ represents.

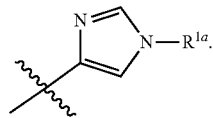

In certain embodiments, $R^{1a}$ is H.

Alternatively, $R^{1a}$ may be optionally substituted phenyl. Specifically, $R^{1a}$ may be phenyl, substituted by one or more occurrences of halo, hydroxyl, cyano, —$C(O)NH_2$, hydroxlalkyl, haloalkyl, alkoxy, haloalkoxy, cycloalkyl, —C(O)alkyl, —C(O)O-alkyl, heterocycloalkyl, —C(O)NH (alkyl), —$C(O)N(alkyl)_2$, —C(O)heterocycloalkyl, —C(O)(prolinol), —C(O)NH((cycloalkyl)alkyl), or —C(O)NH(cycloalkyl). In certain embodiments, $R^{1a}$ is phenyl, substituted by two or more occurrences of alkoxy. Preferably, $R^{1a}$ is 3,4,5-trimethoxyphenyl.

In certain embodiments, $R^{1a}$ is substituted phenyl, wherein two adjacent substituents on the phenyl, taken together with the intervening atoms, form an optionally substituted cycloalkyl or heterocycloalkyl ring. For example, $R^{1a}$ may be phenyl, wherein two adjacent substituents form a fused optionally substituted heterocyclic ring such as 1,4-dioxane or 1,3-dioxolane.

In certain embodiments, $R^{1a}$ is optionally substituted heteroaryl, such as quinoline.

In certain embodiments, J is aryl, optionally substituted by one or more occurrences of $R^{2a}$.

In alternative embodiments, J is —$NR^2R^3$.

In certain such embodiments, $R^2$ and $R^3$, taken together, form a heterocycloalkyl ring, for example, a pyrrolidine ring, optionally substituted by one or more occurrences of $R^{2a}$.

In certain such embodiments, $R^{2a}$, independently for each occurrence, may represent —$C(O)NH_2$, —$C(O)R^5$, hydroxyalkyl, heteroaryl, or aryl; preferably —$C(O)NH_2$, or hydroxyalkyl.

In certain embodiments, the compound of the invention is selected from the group consisting of the compounds depicted in the following table:

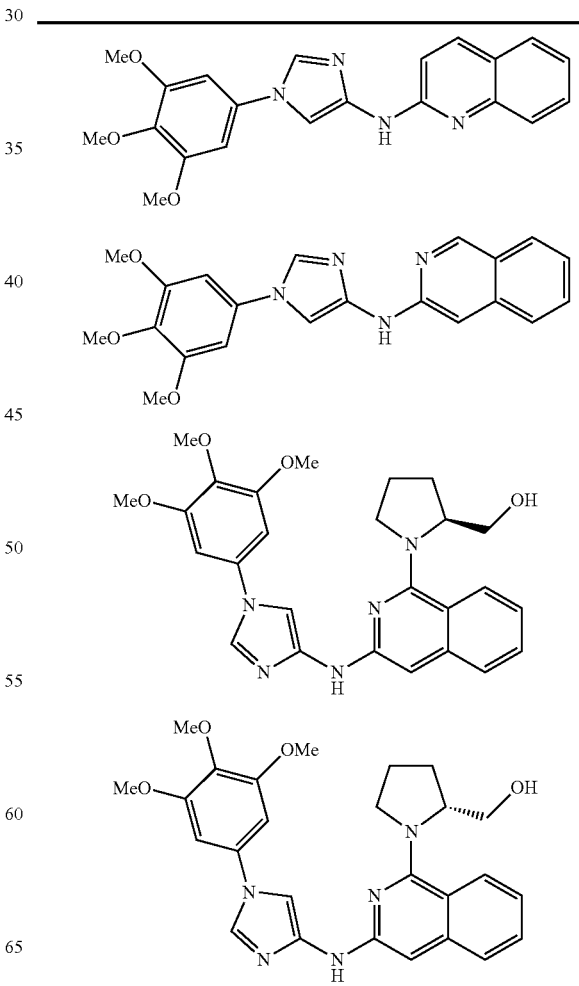

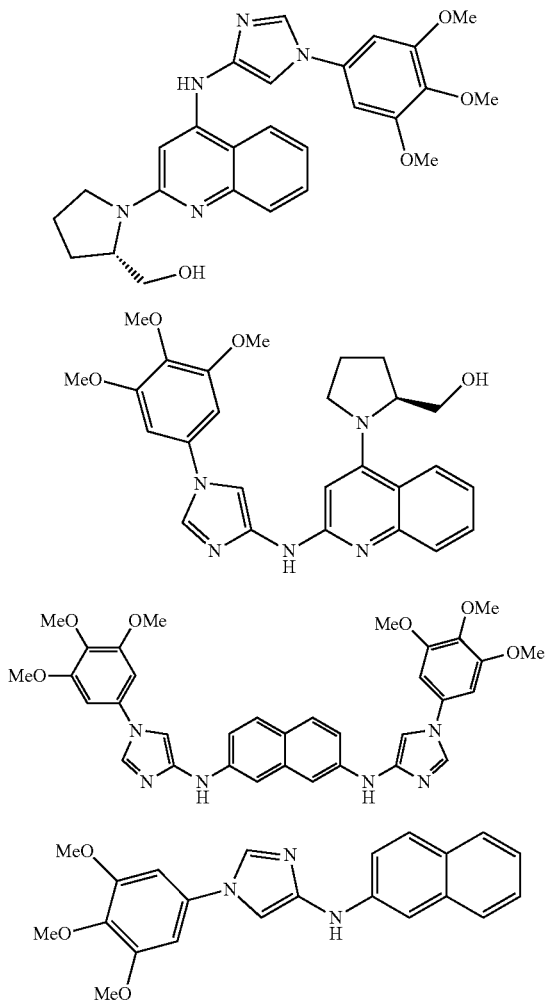

Pharmaceutical Compositions

The invention provides pharmaceutical compositions, each comprising one or more compounds of the invention, or pharmaceutically acceptable salts thereof, and a pharmaceutically acceptable carrier. In certain embodiments, the pharmaceutical composition comprises a compound of the invention and a pharmaceutically acceptable carrier. In certain embodiments, the pharmaceutical composition comprises a plurality of compounds of the invention, or pharmaceutically acceptable salts thereof, and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of a disease or condition that would be benefitted by inhibition of ALK2 kinase.

Pharmaceutical compositions of the invention can be prepared by combining one or more compounds of the invention, or pharmaceutically acceptable salts thereof, with a pharmaceutically acceptable carrier and, optionally, one or more additional pharmaceutically active agents.

Methods of Use

The present invention provides compounds, and pharmaceutically acceptable salts thereof, that are useful for treating or preventing a disease or condition whose treatment would benefit from ALK2 kinase inhibition.

In certain aspects, the invention provides a method of inhibiting ALK2 kinase, comprising administering to a subject in need thereof an effective amount of a compound of the invention (e.g., a compound of formula (I), (II), (III), or (IV)), or a pharmaceutically acceptable salt thereof.

In certain aspects, the invention provides a compound of the invention, or a pharmaceutically acceptable salt thereof, for use as a medicament.

In certain aspects, the invention provides methods of treating fibrodysplasia ossificans progressive, comprising the step of administering to a subject in need thereof a therapeutically effective amount of a compound of the invention, or a pharmaceutically acceptable salt thereof.

The present invention also provides a method of treating cancer, comprising the step of administering to a subject in need thereof a therapeutically effective amount of a compound of the invention, or a pharmaceutically acceptable salt thereof.

In certain embodiments, the cancer comprises tumors of the central nervous system, breast cancer, prostate cancer, skin cancer (including basal cell carcinoma cell carcinoma, squamous cell carcinoma and melanoma), cervical cancer, uterine cancer, lung cancer, ovarian cancer, testicular cancer, thyroid cancer, astrocytoma, glioma, pancreatic cancer, stomach cancer, liver cancer, colon cancer, renal cancer, bladder cancer, oesophageal cancer, cancer of the larynx, cancer of the parotid, cancer of the biliary tract, rectal cancer, endometrial cancer, adenocarcinomas, small cell carcinomas, neuroblastomas, mesotheliomas, adrenocortical carcinomas, epithelial carcinomas, desmoid tumors, desmoplastic small round cell tumors, endocrine tumors, Ewing sarcoma family tumors, germ cell tumors, hepatoblastomas, hepatocellular carcinomas, non-rhabdomyosarcoma, soft tissue sarcomas, osteosarcomas, peripheral primitive neuroectodermal tumors, retinoblastomas, rhabdomyosarcomas, and Wilms tumors.

In certain embodiments, the cancer is a glioma, such as diffuse intrinsic pontine glioma.

The compounds of the invention are useful in treating any disease or condition whose treatment would benefit from ALK2 kinase inhibition, meaning that in such disease or condition it would be desirable to reduce ALK2 kinase activity. For example, it may be desirable to reduce ALK2 kinase activity in the setting of inappropriate activation or hyperactivation of ALK2 kinase.

Formulations, Routes of Administration, and Dosing

The compounds of the invention, and pharmaceutically acceptable salts thereof, can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the present compounds or pharmaceutically acceptable salts thereof may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound (i.e., a compound of the invention or a pharmaceutically acceptable salt thereof) may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active compound which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active compound plus any additional desired ingredient present in the previously sterile-filtered solutions.

For topical administration, the present compounds or pharmaceutically acceptable salts thereof may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds or pharmaceutically acceptable salts thereof can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention, or pharmaceutically acceptable salts thereof, to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention, or pharmaceutically acceptable salts thereof, can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the compound, or pharmaceutically acceptable salt thereof, required for use in treatment will vary not only with the particular compound or salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Compounds of the invention, or pharmaceutically acceptable salts thereof, can be conveniently formulated in unit dosage form; for example, containing 5 to 1000 mg, 10 to 750 mg, or 50 to 500 mg of active compound per unit dosage form. In one embodiment, the invention provides a composition comprising a compound of the invention, or pharmaceutically acceptable salt thereof, formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Compounds of the invention, or pharmaceutically acceptable salts thereof, can also be administered in combination with other therapeutic agents, for example, other agents that are useful for treating or preventing a disease or condition whose treatment would benefit from ALK2 kinase inhibition.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active compound for at least 30 days, and preferably 60 days.

In certain embodiments, a compound of the invention, or pharmaceutically acceptable salt thereof, is formulated for intraocular administration, for example direct injection or insertion within or in association with an intraocular medical device.

The compounds of the invention, or pharmaceutically acceptable salts thereof, may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver compounds of the invention, or pharmaceutically acceptable salts thereof, to the region of a body which has been treated by interventional technique.

In exemplary embodiments, a compound of the invention, or pharmaceutically acceptable salt thereof, may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the active compound is coated, adsorbed, placed, or otherwise incorporated into the device by methods known in the art. For example, the active compound may be embedded and released from within ("matrix type") or surrounded by and released through ("reservoir type") polymer materials that coat or span the medical device. In the latter example, the active compound may be entrapped within the polymer materials or coupled to the polymer materials using one or more the techniques for generating such materials known in the art. In other formulations, the active compound may be linked to the surface of the medical device without the need for a coating, for example by means of detachable bonds, and release with time or can be removed by active mechanical or chemical processes. In other formulations, the active compound may be in a permanently immobilized form that presents the active compound at the implantation site.

In certain embodiments, the active compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is suitable for this embodiment because, unlike a biostable polymer, it will typically not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D, L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, poly-epsilon caprolactone, polyhydroxy butyric acid, polyorthoesters, polyacetals, polydihydropyrans, polycyanoacrylates, cross linked or amphipathic block copolymers of hydrogels, and other suitable bioabsorbable polymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the compound of the invention, or pharmaceutically acceptable salt thereof, is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the compound of the invention, or pharmaceutically acceptable salt thereof, is formulated for release from the polymer coating into the environment in which the medical device is placed. Preferably, the active compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the active compound from the polymer coating can be controlled. For example, the diffusion coefficient of the one or more polymer coatings can be modulated to control the release of the active compound from the polymer coating. In a variation on this theme, the diffusion coefficient of the one or more polymer coatings can be controlled to modulate the ability of an analyte that is present in the environment in which the medical device is placed (e.g., an analyte that facilitates the breakdown or hydrolysis of some portion of the polymer) to access one or more components within the polymer composition (and for example, thereby modulate the release of the active compound from the polymer coating). Yet another embodiment of the invention includes a device having a plurality of polymer coatings, each having a plurality of diffusion coefficients. In such embodiments of the invention, the release of the active compound from the polymer coating can be modulated by the plurality of polymer coatings.

In yet another embodiment of the invention, the release of the active compound from the polymer coating is controlled by modulating one or more of the properties of the polymer composition, such as the presence of one or more endogenous or exogenous compounds, or alternatively, the pH of the polymer composition. For example, certain polymer compositions can be designed to release an active compound in response to a decrease in the pH of the polymer composition.

Kits

The invention also provides a kit, comprising a compound of the invention, or a pharmaceutically acceptable salt thereof, at least one other therapeutic agent, packaging material, and instructions for administering the compound of the invention or the pharmaceutically acceptable salt thereof and the other therapeutic agent or agents to a mammal to treat or prevent a disease or condition that would benefit from ALK2 inhibition. In one embodiment, the mammal is a human.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

Examples

Having now described the present invention in detail, the same will be more clearly understood by reference to the following examples, which are included herewith for purposes of illustration only and are not intended to be limiting of the invention. Part 1 shows the synthesis of exemplary compounds of the invention. Part 2 shows the preparation of various exemplary 3-substituted-(4-amino-1H-imidazol-1-yl) reagents. Part 3 presents biological assay data for the exemplary compounds of the invention.

For purposes of the present invention, the numerical descriptors "pyrrolo[2,1-f][1,2,4]triazine" and "pyrrolo[1,2-f][1,2,4]triazine" and the like in the context of a chemical name provided for a compound disclosed herein are understood to be synonymous and, therefore, may be and sometimes are used interchangeably. As a non-limiting example, the chemical names "2,4-dichloropyrrolo[2,1-f][1,2,4]triazine" and "2,4-dichloropyrrolo[1,2-f][1,2,4]triazine" are both understood to refer to a compound having the following structure:

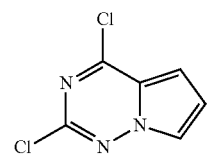

4a

As another non-limiting example, the chemical names "2-chloro-N-(1-methyl-1H-imidazol-4-yl)pyrrolo[2,1-f][1,2,4]triazin-4-amine" and "2-chloro-N-(1-methyl-1H-imidazol-4-yl)pyrrolo[1,2-f][1,2,4]triazin-4-amine" are both understood to refer to a compound having the following structure.

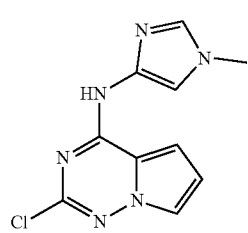

4b

Part 1: Synthesis of Imidazole-Containing Inhibitors of ALK2 Kinase

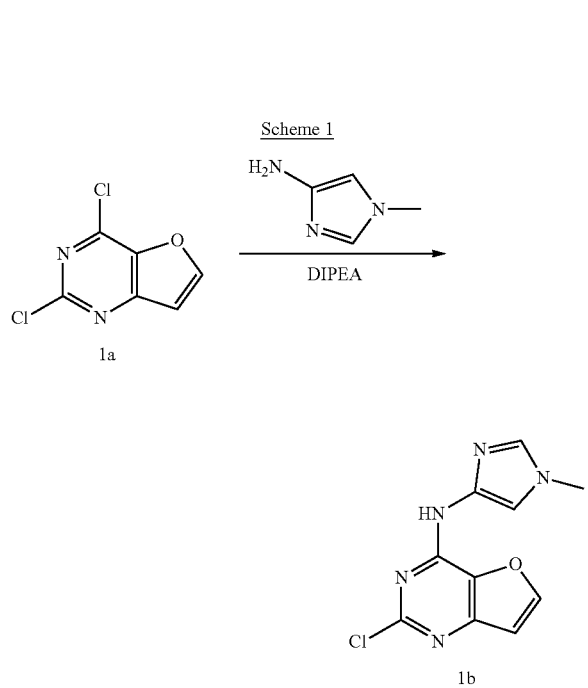

Preparation of 2-chloro-N-(1-methyl-1H-imidazol-4-yl)furo[3,2-d]pyrimidin-4-amine (1b)

To a solution of 2,4-dichlorofuro[3,2-d]pyrimidine (1a) (0.71 g, 3.74 mmol; CAS #956034-07-4) in 2-Propanol (20 mL) was added DIPEA (1.63 mL, 9.36 mmol), 1-methyl-1H-imidazol-4-amine hydrochloride (0.5 g, 3.74 mmol) and heated at reflux for 24 h. The reaction mixture was concentrated in vacuum to dryness and the residue obtained was triturated with water. The solid obtained was collected by filtration and dried in vacuum to afford 2-chloro-N-(1-methyl-1H-imidazol-4-yl)furo[3,2-d]pyrimidin-4-amine (1b) (550 mg, 59% yield) as brown solid; H NMR (300 MHz, DMSO-$d_6$) δ 10.89 (s, 1H, $D_2O$ exchangeable), 8.35 (d, J=2.1 Hz, 1H), 7.52 (d, J=1.6 Hz, 1H), 7.39 (d, J=1.3 Hz, 1H), 7.03 (d, J=2.1 Hz, 1H), 3.71 (s, 3H); MS (ES+): 250.3 (M+1), 272.3, 274.3 (M+Na), (ES−): 248.2 (M−1).

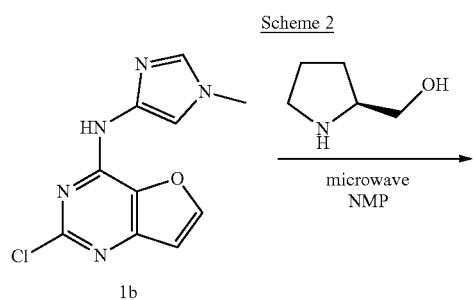

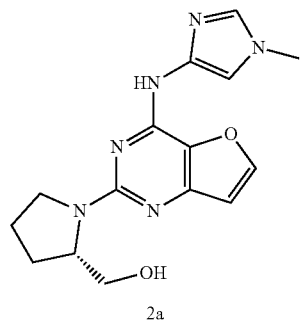

Preparation of (S)-(1-(4-((1-methyl-1H-imidazol-4-yl)amino)furo[3,2-d]pyrimidin-2-yl)pyrrolidin-2-yl)methanol (2a)

A stirred suspension of 2-chloro-N-(1-methyl-1H-imidazol-4-yl)furo[3,2-d]pyrimidin-4-amine (1b) (100 mg, 0.40 mmol), (S)-pyrrolidin-2-ylmethanol (122 mg, 1.20 mmol) in N-Methyl-2-pyrrolidinone (1 mL) was subjected to microwave irradiation at 150° C. for 2 h. The reaction mixture was diluted with ethyl acetate (50 mL), washed with brine (2×20 mL), dried, filtered and concentrated in vacuum. The crude residue was purified by combiflash (silica gel, 12 g, eluting with chloroform/CMA-80) to afford (S)-(1-(4-((1-methyl-1H-imidazol-4-yl)amino)furo[3,2-d]pyrimidin-2-yl)pyrrolidin-2-yl)methanol (2a) (43 mg, 34% yield) as a light yellow solid; $^1$H NMR (300 MHz, DMSO-$d_6$) δ 9.90 (s, 1H, $D_2O$ exchangeable), 8.00 (d, J=2.1 Hz, 1H), 7.44 (s, 1H), 7.42 (d, J=1.4 Hz, 1H), 6.71 (d, J=2.1 Hz, 1H), 4.94 (s, 1H, $D_2O$ exchangeable), 4.13 (s, 1H), 3.83-3.69 (m, 1H), 3.64 (s, 3H), 3.62-3.49 (m, 1H), 3.48-3.23 (m, 2H), 2.07-1.83 (m, 4H); MS (ES+): 315.4 (M+1), 337.5 (M+Na), (ES−): 313.4 (M−1). HPLC purity: 98.70%.

Preparation of (R)-(1-(4-((1-methyl-1H-imidazol-4-yl)amino)furo[3,2-d]pyrimidin-2-yl)pyrrolidin-2-yl)methanol (3a)

Reaction of 2-chloro-N-(1-methyl-1H-imidazol-4-yl)furo[3,2-d]pyrimidin-4-amine (1b) (100 mg, 0.40 mmol) with (R)-pyrrolidin-2-ylmethanol (122 mg, 1.20 mmol) in NMP (1 mL) according to the procedure as reported in Scheme 2 gave after workup and purification (R)-(1-(4-((1-methyl-1H-imidazol-4-yl)amino)furo[3,2-d]pyrimidin-2-yl)pyrrolidin-2-yl)methanol (3a) (65 mg, 52% yield) as a buff color solid; $^1$H NMR (300 MHz, DMSO-$d_6$) δ 9.91 (s, 1H, $D_2O$ exchangeable), 8.00 (d, J=2.2 Hz, 1H), 7.44 (s, 1H), 7.42 (d, J=1.4 Hz, 1H), 6.71 (d, J=2.1 Hz, 1H), 4.93 (s, 1H, $D_2O$ exchangeable), 4.13 (s, 1H), 3.82-3.69 (m, 1H), 3.64 (s, 3H), 3.61-3.48 (m, 1H), 3.48-3.23 (m, 2H), 2.06-1.80 (m, 4H); MS (ES+): 315.4 (M+1), 337.4 (M+Na), (ES−): 313.3 (M−1).

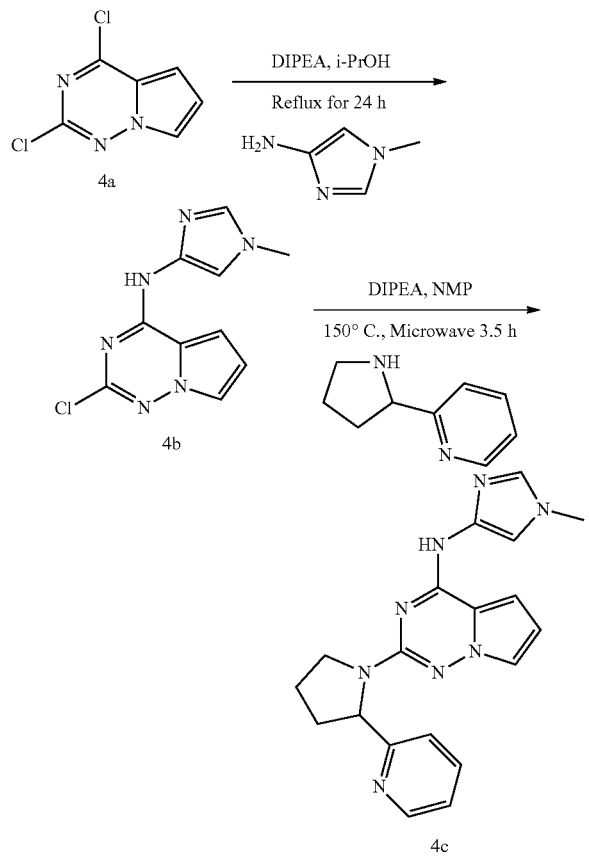

Scheme 4

Preparation of N-(1-methyl-1H-imidazol-4-yl)-2-(2-(pyridin-2-yl)pyrrolidin-1-yl)pyrrolo[1,2-f][1,2,4]triazin-4-amine (4c)

Step-1: Preparation of 2-chloro-N-(1-methyl-1H-imidazol-4-yl)pyrrolo[2,1-f][1,2,4]triazin-4-amine (4b) Compound 4b was prepared from compound 4a according to the procedure reported by Mastalerz, Harold et al; in PCT Int. Appl., WO 2008/005956, 10 Jan. 2008 (incorporated by reference). This gave 2-chloro-N-(1-methyl-1H-imidazol-4-yl)pyrrolo[2,1-f][1,2,4]triazin-4-amine (4b) as a pale-off colored solid; $^1$H NMR (300 MHz, DMSO-$d_6$) δ 11.15 (s, 1H), 7.75-7.67 (m, 1H), 7.54 (s, 1H), 7.44 (s, 1H), 7.35 (dd, J=4.5, 1.5 Hz, 1H), 6.68 (dd, J=4.4, 2.6 Hz, 1H), 3.70 (s, 3H); MS (ES+): 249.3 (M+1), 271.3 (M+Na); MS (ES−): 247.2 (M−1).

Step-2: Preparation of N-(1-methyl-1H-imidazol-4-yl)-2-(2-(pyridin-2-yl)pyrrolidin-1-yl)pyrrolo[1,2-f][1,2,4]triazin-4-amine (4c)

Compound 4c was prepared from 2-chloro-N-(1-methyl-1H-imidazol-4-yl)pyrrolo[1,2-f][1,2,4]triazin-4-amine (4b) (100 mg, 0.40 mmol), 2-(pyrrolidin-2-yl)pyridine (179 mg, 1.21 mmol), and DIPEA (0.21 mL, 1.21 mmol) in NMP (1 mL) according to the procedure reported in Scheme 2. This gave after workup and purification by flash chromatography [silica (24 g), eluting with CMA80 in $CHCl_3$ from 0 to 20%]] N-(1-methyl-1H-imidazol-4-yl)-2-(2-(pyridin-2-yl)pyrrolidin-1-yl)pyrrolo[1,2-f][1,2,4]triazin-4-amine (4c) (50 mg, 35% yield) as a yellow solid; $^1$H NMR (300 MHz, DMSO-d6) δ 10.24 (s, 1H), 8.67-8.56 (m, 1H), 7.67 (td, J=7.7, 1.8 Hz, 1H), 7.44-7.32 (m, 2H), 7.28-7.15 (m, 2H), 7.06 (dd, J=4.4, 1.7 Hz, 1H), 6.86-6.67 (m, 1H), 6.36 (dd, J=4.4, 2.5 Hz, 1H), 5.29 (d, J=8.3 Hz, 1H), 3.81 (t, J=9.0 Hz, 1H), 3.67-3.54 (m, 1H), 3.53 (s, 3H), 2.46-2.24 (m, 1H), 2.09-1.75 (m, 3H); MS (ES+): 361.5 (M+1); MS (ES−) 359.4 (M−1).

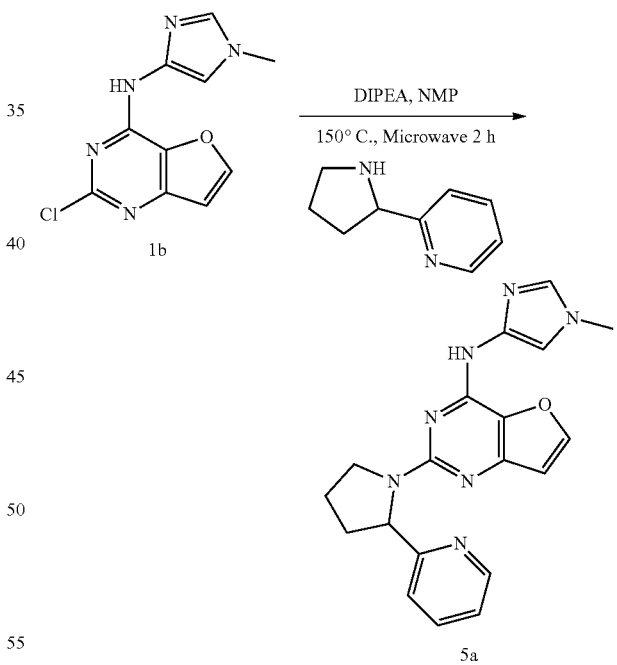

Scheme 5

Preparation of N-(1-methyl-1H-imidazol-4-yl)-2-(2-(pyridin-2-yl)pyrrolidin-1-yl)furo[3,2-d]pyrimidin-4-amine (5a)

Compound 5a was prepared from 2-chloro-N-(1-methyl-1H-imidazol-4-yl)furo[3,2-d]pyrimidin-4-amine (1b) (100 mg, 0.40 mmol), DIPEA (155 mg, 1.20 mmol) and 2-(pyrrolidin-2-yl)pyridine hydrochloride (148 mg, 0.8 mmol) in NMP (1 mL) according to the procedure reported in Scheme 2. This gave after workup and purification by flash chromatography [silica (12 g), eluting with CMA80 in CHCl₃ from 0 to 20%] N-(1-methyl-1H-imidazol-4-yl)-2-(2-(pyridin-2-yl)pyrrolidin-1-yl)furo[3,2-d]pyrimidin-4-amine (5a) (22 mg, 15% yield) as an off white solid; H NMR (300 MHz, DMSO-d₆) δ 9.83 (s, 1H, D₂O exchangeable), 8.61 (s, 1H), 8.00 (s, 1H), 7.66 (td, J=7.6, 1.8 Hz, 1H), 7.38-7.27 (m, 1H), 7.26-7.18 (m, 1H), 7.15 (d, J=7.8 Hz, 1H), 6.84-6.67 (m, 1H), 6.67-6.44 (m, 1H), 5.29 (d, J=8.2 Hz, 1H), 3.99-3.81 (m, 1H), 3.78-3.60 (m, 1H), 3.52 (s, 3H), 2.46-2.27 (m, 1H), 2.06-1.74 (m, 3H); MS (ES+): 362.4 (M+1), 384.5 (M+Na).

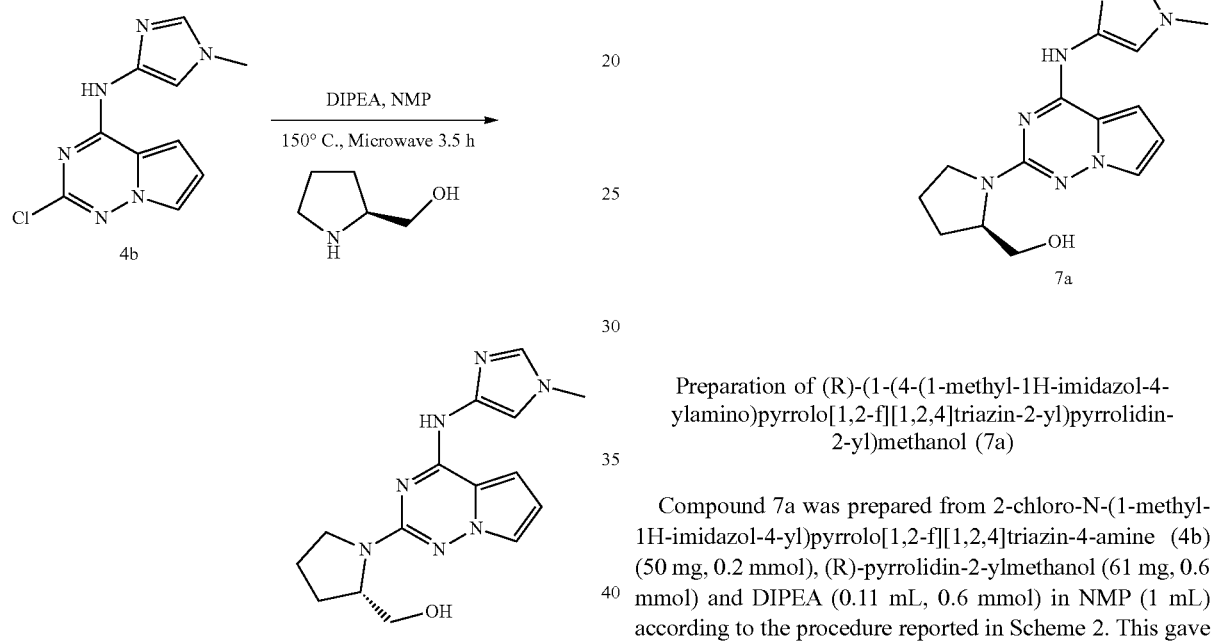

Scheme 6

Scheme 7

Preparation of (S)-(1-(4-(1-methyl-1H-imidazol-4-ylamino)pyrrolo[1,2-f][1,2,4]triazin-2-yl)pyrrolidin-2-yl)methanol (6a)

Compound 6a was prepared from 2-chloro-N-(1-methyl-1H-imidazol-4-yl)pyrrolo[1,2-f][1,2,4]triazin-4-amine (4b) (50 mg, 0.2 mmol), (S)-pyrrolidin-2-ylmethanol (61 mg, 0.6 mmol) and DIPEA (0.11 mL, 0.6 mmol) in NMP (1 mL) according to the procedure reported in Scheme 2. This gave after workup and purification by flash chromatography [silica (24 g), eluting with CMA-80 in CHCl₃ from 0 to 40%] (S)-(1-(4-(1-methyl-1H-imidazol-4-ylamino)pyrrolo[1,2-f][1,2,4]triazin-2-yl)pyrrolidin-2-yl)methanol (6a) (34 mg, 54% yield); ¹H NMR (300 MHz, DMSO-d₆) δ 10.32 (s, 1H), 7.47 (s, 2H), 7.35 (dd, J=2.4, 1.7 Hz, 1H), 7.08 (d, J=3.5 Hz, 1H), 6.36 (dd, J=4.4, 2.4 Hz, 1H), 4.81 (t, J=5.0 Hz, 1H), 4.16-4.07 (m, 1H), 3.82-3.70 (m, 1H), 3.65 (s, 3H), 3.54-3.42 (m, 1H), 3.36-3.25 (m, 2H), 2.12-1.79 (m, 4H); MS (ES+): 314.4 (M+1); MS (ES−): 312.4 (M−1).

Preparation of (R)-(1-(4-(1-methyl-1H-imidazol-4-ylamino)pyrrolo[1,2-f][1,2,4]triazin-2-yl)pyrrolidin-2-yl)methanol (7a)

Compound 7a was prepared from 2-chloro-N-(1-methyl-1H-imidazol-4-yl)pyrrolo[1,2-f][1,2,4]triazin-4-amine (4b) (50 mg, 0.2 mmol), (R)-pyrrolidin-2-ylmethanol (61 mg, 0.6 mmol) and DIPEA (0.11 mL, 0.6 mmol) in NMP (1 mL) according to the procedure reported in Scheme 2. This gave after workup and purification by flash chromatography [silica (24 g), eluting with CMA-80 in CHCl₃ from 0 to 40%] (R)-(1-(4-(1-methyl-1H-imidazol-4-ylamino)pyrrolo[1,2-f][1,2,4]triazin-2-yl)pyrrolidin-2-yl)methanol (7a) (27 mg, 43% yield); ¹H NMR (300 MHz, DMSO-d₆) δ 10.32 (s, 1H), 7.47 (s, 2H), 7.35 (dd, J=2.5, 1.7 Hz, 1H), 7.08 (dd, J=4.5, 1.7 Hz, 1H), 6.36 (dd, J=4.4, 2.4 Hz, 1H), 4.81 (t, J=5.0 Hz, 1H), 4.20-4.04 (m, 1H), 3.82-3.69 (m, 1H), 3.65 (s, 3H), 3.54-3.42 (m, 1H), 3.35-3.24 (m, 2H), 2.11-1.78 (m, 4H); MS (ES+): 314.5 (M+1), 336.5 (M+Na).

Scheme 8

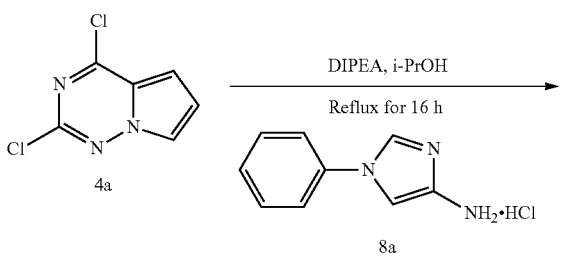

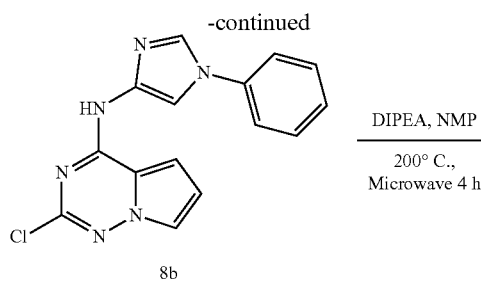

7.98 (s, 1H), 7.76 (d, J=7.8 Hz, 2H), 7.51 (t, J=7.7 Hz, 2H), 7.43-7.37 (m, 1H), 7.37-7.31 (m, 1H), 7.23-7.09 (m, 2H), 7.00 (s, 1H), 6.48-6.31 (m, 1H), 4.26-4.09 (m, 1H), 3.84-3.68 (m, 1H), 3.59-3.44 (m, 1H), 3.44-3.28 (m, 2H), 2.15-1.78 (m, 4H); $^{19}$F NMR (282 MHz, DMSO-d$_6$)) δ −74.29; MS (ES+): 376.5 (M+1); MS (ES−): 374.4 (M−1), 410.4 (M+Cl).

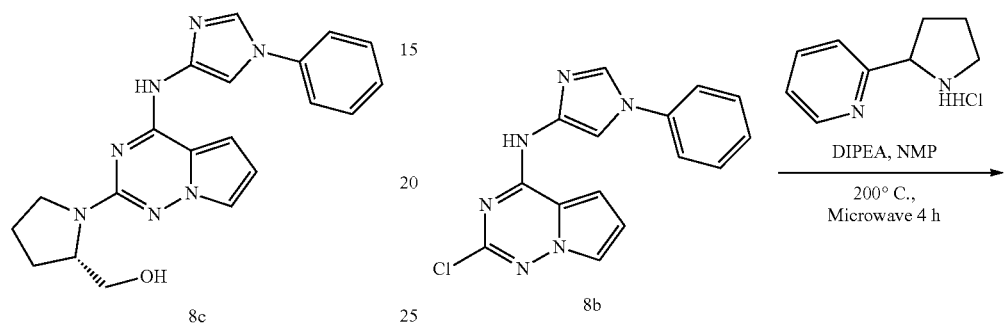

Scheme 9

Preparation of (S)-(1-(4-((1-phenyl-1H-imidazol-4-yl)amino)pyrrolo[2,1-f][1,2,4]triazin-2-yl)pyrrolidin-2-yl)methanol (8c)

Step-1: Preparation of 2-chloro-N-(1-phenyl-1H-imidazol-4-yl)pyrrolo[2,1-f][1,2,4]triazin-4-amine (8b) Compound 8b was prepared according to the procedure reported in Scheme 1 from 2,4-dichloropyrrolo[1,2-f][1,2,4]triazine (4a) (240 mg, 1.28 mmol; CAS #918538-05-3) in 2-Propanol (5 mL) using DIPEA (0.67 mL, 3.83 mmol) and 1-phenyl-1H-imidazol-4-amine, HCl (8a) (250 mg, 1.28 mmol; prepared according to the procedure reported by Sakamoto, Toshihiro et al in Bioorganic & Medicinal Chemistry, 17(14), 5015-5026; 2009 and Francini, Cinzia Maria et al; in Chem. Med. Chem, 10(12), 2027-2041). This gave 2-chloro-N-(1-phenyl-1H-imidazol-4-yl)pyrrolo[1,2-f][1,2,4]triazin-4-amine (8b) (302 mg, 76% yield); $^1$H NMR (300 MHz, DMSO-d$_6$) δ 11.35 (s, 1H), 8.35-8.18 (m, 1H), 7.95-7.87 (m, 1H), 7.81-7.73 (m, 1H), 7.65 (d, J=7.9 Hz, 2H), 7.56 (t, J=7.7 Hz, 2H), 7.46-7.35 (m, 2H), 6.80-6.66 (m, 1H); MS (ES+): 311.3 (M+1); MS (ES−): 309.3 (M−1).

Step-2: Preparation of (S)-(1-(4-((1-phenyl-1H-imidazol-4-yl)amino)pyrrolo[2,1-f][1,2,4]triazin-2-yl)pyrrolidin-2-yl)methanol (8c)

Compound 8c was prepared from 2-chloro-N-(1-phenyl-1H-imidazol-4-yl)pyrrolo[2,1-f][1,2,4]triazin-4-amine (8b) (100 mg, 0.32 mmol), (S)-pyrrolidin-2-ylmethanol (98 mg, 0.97 mmol), and DIPEA (0.17 mL, 0.97 mmol) in NMP (1 mL) according to the procedure reported in Scheme 2. This gave after workup and purification by flash chromatography [silica (24 g), eluting with CMA-80 in CHCl$_3$ from 0 to 40%] (S)-(1-(4-((1-phenyl-1H-imidazol-4-yl)amino)pyrrolo[2,1-f][1,2,4]triazin-2-yl)pyrrolidin-2-yl)methanol (8c) (29 mg, 24% yield) TFA salt as a pale off-white solid (obtained by reverse phase column purification of final compound using 0.1% TFA in acetonitrile/water as a mobile phase); $^1$H NMR (300 MHz, DMSO-d$_6$) δ 10.58 (s, 1H), 8.32 (s, 1H),

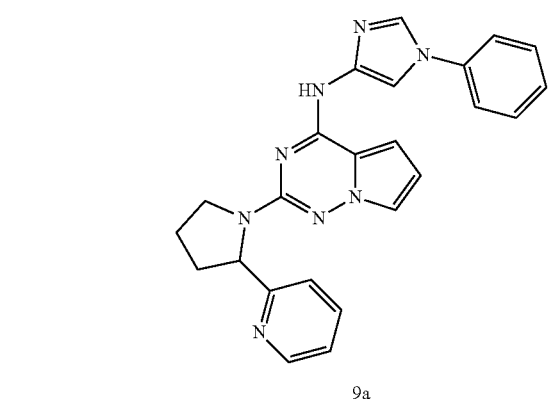

Preparation of N-(1-phenyl-1H-imidazol-4-yl)-2-(2-(pyridin-2-yl)pyrrolidin-1-yl)pyrrolo[2,1-f][1,2,4]triazin-4-amine (9a)

Compound 9a was prepared from 2-chloro-N-(1-phenyl-1H-imidazol-4-yl)pyrrolo[2,1-f][1,2,4]triazin-4-amine (8b) (100 mg, 0.32 mmol), 2-(pyrrolidin-2-yl)pyridine hydrochloride (149 mg, 0.81 mmol), and DIPEA (0.28 mL, 1.61 mmol) in NMP (1 mL) according to the procedure reported in Scheme 2. This gave after workup and purification by flash chromatography [silica (24 g), eluting with CMA-80 in CHCl$_3$ from 0 to 40%] N-(1-phenyl-1H-imidazol-4-yl)-2-(2-(pyridin-2-yl)pyrrolidin-1-yl)pyrrolo[2,1-f][1,2,4]triazin-4-amine (9a) (27 mg, 20% yield) as a light brown solid; $^1$H NMR (300 MHz, DMSO-d$_6$) δ 10.55 (s, 1H), 8.43 (s, 1H), 8.26-8.08 (m, 1H), 8.04-7.76 (m, 1H), 7.67-7.52 (m, 6H), 7.49-7.34 (m, 3H), 7.20-7.10 (m, 1H), 6.42 (dd, J=4.4, 2.5 Hz, 1H), 5.47 (d, J=8.3 Hz, 1H), 3.91-3.78 (m, 1H), 3.70-3.62 (m, 1H), 2.53-2.36 (m, 1H), 2.14-1.73 (m, 3H); $^{19}$F NMR (282 MHz, DMSO-d$_6$) δ −74.26; MS (ES+): 423.5 (M+1), 445.5 (M+Na); MS (ES−): 421.4 (M−1).

Scheem 10

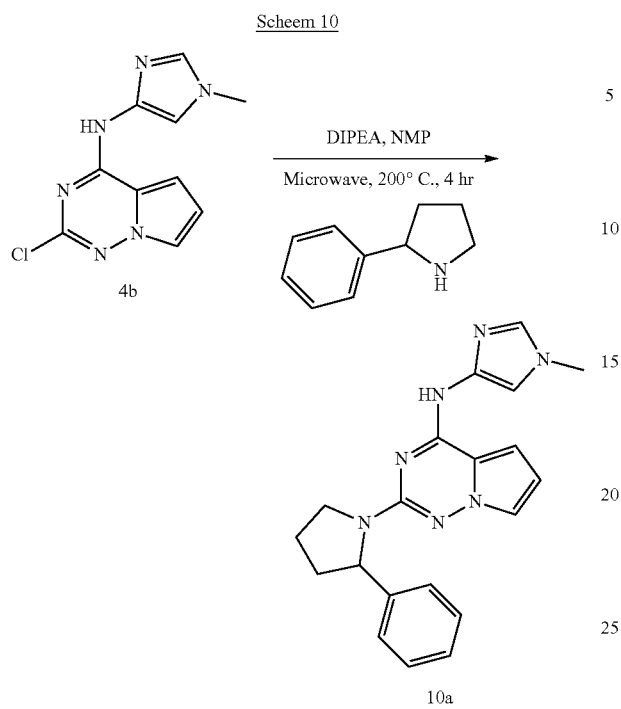

Preparation of N-(1-methyl-1H-imidazol-4-yl)-2-(2-phenylpyrrolidin-1-yl)pyrrolo[2,1-f][1,2,4]triazin-4-amine (10a)

Compound 10a was prepared from 2-chloro-N-(1-methyl-1H-imidazol-4-yl)pyrrolo[1,2-f][1,2,4]triazin-4-amine (4b) (80 mg, 0.32 mmol), 2-phenylpyrrolidine (142 mg, 0.97 mmol), and DIPEA (0.17 mL, 0.97 mmol) in NMP (1 mL) according to the procedure reported in Scheme 2. This gave after workup and purification by flash chromatography [silica (24 g), eluting with CMA-80 in CHCl$_3$ from 0 to 40%] N-(1-methyl-1H-imidazol-4-yl)-2-(2-phenylpyrrolidin-1-yl)pyrrolo[2,1-f][1,2,4]triazin-4-amine (10a) (31 mg, 27% yield) as a pale-off white solid; $^1$H NMR (300 MHz, DMSO-d$_6$) δ 10.20 (s, 1H), 7.41-7.25 (m, 6H), 7.24-7.15 (m, 1H), 7.05 (dd, J=4.4, 1.7 Hz, 1H), 6.78-6.66 (m, 1H), 6.35 (dd, J=4.4, 2.4 Hz, 1H), 5.32 (d, J=8.0 Hz, 1H), 3.84-3.70 (m, 1H), 3.64-3.54 (m, 1H), 3.49 (s, 3H), 2.41-2.30 (m, 1H), 2.01-1.76 (m, 3H); MS (ES+): 360.5 (M+1), 382.5 (M+Na); MS (ES−): 358.4 (M−1), 394.5 (M+Cl); HPLC purity: 95.75%.

Scheme 11

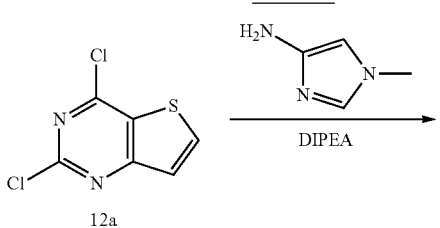

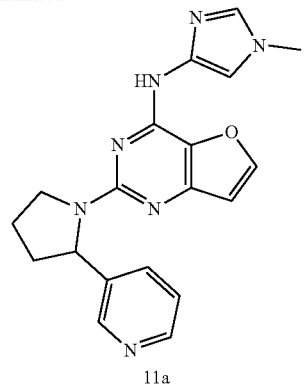

Preparation of N-(1-methyl-1H-imidazol-4-yl)-2-(2-(pyridin-3-yl)pyrrolidin-1-yl)furo[3,2-d]pyrimidin-4-amine (11a)

Compound 11a was prepared from 2-chloro-N-(1-methyl-1H-imidazol-4-yl)furo[3,2-d]pyrimidin-4-amine (1b) (100 mg, 0.4 mmol), 3-(pyrrolidin-2-yl)pyridine (119 mg, 0.8 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water 0-100%] N-(1-methyl-1H-imidazol-4-yl)-2-(2-(pyridin-3-yl)pyrrolidin-1-yl)furo[3,2-d]pyrimidin-4-amine (11a) (23 mg, 16% yield) as an off white solid; H NMR (300 MHz, DMSO-d$_6$) δ 9.83 (s, 1H, D$_2$O exchangeable), 8.54 (s, 1H), 8.41 (dd, J=4.8, 1.6 Hz, 1H), 8.01 (d, J=2.2 Hz, 1H), 7.62 (d, J=8.0 Hz, 1H), 7.32 (dd, J=7.8, 4.7 Hz, 2H), 6.72 (s, 1H), 6.70-6.30 (m, 1H), 5.35 (d, J=7.9 Hz, 1H), 3.98-3.81 (m, 1H), 3.77-3.60 (m, 1H), 3.51 (s, 3H), 2.47-2.33 (m, 1H), 2.02-1.73 (m, 3H); MS (ES+): 362.5 (M+1), 384.5 (M+Na), 745.8 (2M+Na), (ES−): 360.4 (M−1).

Scheme 12

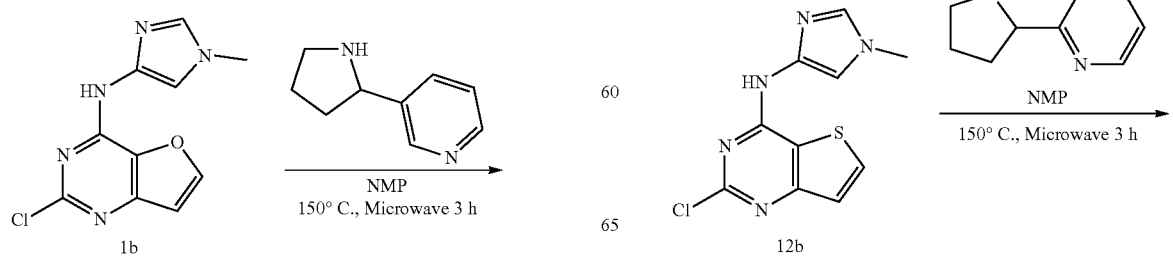

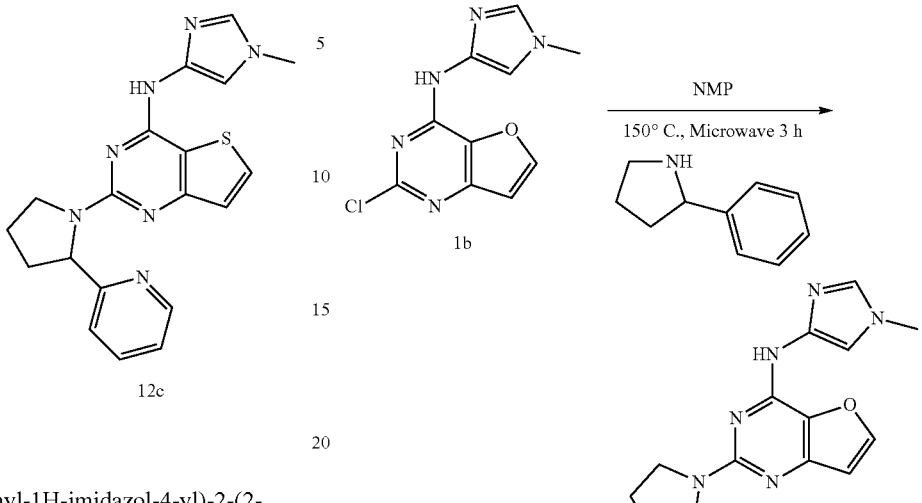

12c

Preparation of N-(1-methyl-1H-imidazol-4-yl)-2-(2-(pyridin-2-yl)pyrrolidin-1-yl)thieno[3,2-d]pyrimidin-4-amine (12c)

Step-1: Preparation of 2-chloro-N-(1-methyl-1H-imidazol-4-yl)thieno[3,2-d]pyrimidin-4-amine (12b)

Compound 12b was prepared from 2,4-dichlorothieno[3,2-d]pyrimidine (12a) (0.31 g, 1.5 mmol; CAS #16234-14-3) in 2-Propanol (10 mL) using 1-methyl-1H-imidazol-4-amine hydrochloride (0.2 g, 1.5 mmol) and DIPEA (0.65 mL, 3.74 mmol) according to the procedure reported in Scheme 1. This gave after workup and purification by flash column chromatography (silica gel, 24 g eluting with CMA-80 in chloroform) 2-chloro-N-(1-methyl-1H-imidazol-4-yl)thieno[3,2-d]pyrimidin-4-amine (12b) (165 mg, 42% yield) as a yellow solid; $^1$H NMR (300 MHz, DMSO-$d_6$) δ 10.82 (s, 1H), 8.21 (d, J=5.4 Hz, 1H), 7.55 (s, 1H), 7.41 (s, 1H), 7.36 (d, J=5.4 Hz, 1H), 3.71 (s, 3H); MS (ES+): 266.3 (M+1), 288.3 (M+Na), (ES−): 264.2 (M−1).

Step-2: Preparation of N-(1-methyl-1H-imidazol-4-yl)-2-(2-(pyridin-2-yl)pyrrolidin-1-yl)thieno[3,2-d]pyrimidin-4-amine (12c)

Compound 12c was prepared from 2-chloro-N-(1-methyl-1H-imidazol-4-yl)thieno[3,2-d]pyrimidin-4-amine (12b) (100 mg, 0.38 mmol), 2-(pyrrolidin-2-yl)pyridine (167 mg, 1.13 mmol) in NMP (1 mL) according to the procedure reported in Scheme 2. This gave after workup and purification by reverse phase flash chromatography [(silica C-18, 30 g), eluting with 0.1% TFA in acetonitrile and 0.1% TFA in water] N-(1-methyl-1H-imidazol-4-yl)-2-(2-(pyridin-2-yl)pyrrolidin-1-yl)thieno[3,2-d]pyrimidin-4-amine (12c) (86 mg, 61% yield) as an off-white solid; H NMR (300 MHz, DMSO-$d_6$) δ 9.81 (s, 1H, D$_2$O exchangeable), 8.62 (s, 1H), 8.02-7.80 (m, 1H), 7.66 (td, J=7.6, 1.8 Hz, 1H), 7.31 (s, 1H), 7.27-7.05 (m, 3H), 6.62 (s, 1H), 5.34 (d, J=8.2 Hz, 1H), 4.01-3.84 (m, 1H), 3.79-3.64 (m, 1H), 3.64-3.43 (m, 3H), 2.44 (s, 1H), 2.08-1.77 (m, 3H); MS (ES+): 378.5 (M+1), 400.5 (M+Na), (ES−): 376.4 (M−1).

Scheme 13

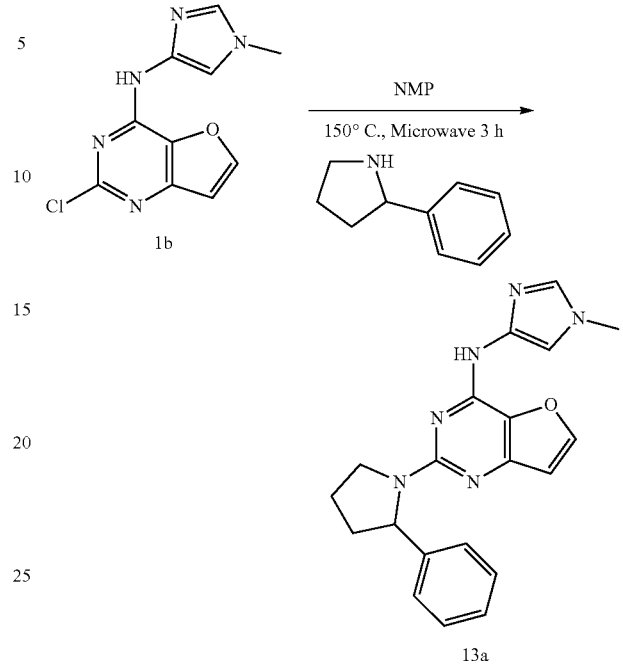

13a

Preparation of N-(1-methyl-1H-imidazol-4-yl)-2-(2-phenylpyrrolidin-1-yl)furo[3,2-d]pyrimidin-4-amine (13a)

Compound 13a was prepared from 2-chloro-N-(1-methyl-1H-imidazol-4-yl)furo[3,2-d]pyrimidin-4-amine (1b) (100 mg, 0.4 mmol), 2-phenylpyrrolidine (147 mg, 1.0 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-methyl-1H-imidazol-4-yl)-2-(2-phenylpyrrolidin-1-yl)furo[3,2-d]pyrimidin-4-amine (13a) (8 mg, 6% yield) as a colorless solid; H NMR (300 MHz, DMSO-$d_6$) δ 11.50 (s, 1H, D$_2$O exchangeable), 8.33 (s, 1H), 7.68 (s, 1H), 7.36 (d, J=5.6 Hz, 4H), 7.32-7.20 (m, 1H), 6.97 (s, 1H), 6.58 (s, 1H), 5.47 (d, J=7.2 Hz, 1H), 3.96 (s, 1H), 3.74-3.63 (m, 1H), 3.54 (s, 3H), 2.49-2.34 (m, 1H), 2.08 (s, 1H), 2.01-1.83 (m, 2H); MS (ES+): 361.5 (M+1).

Scheme 14

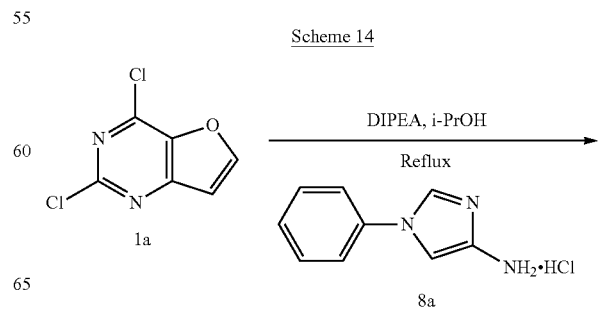

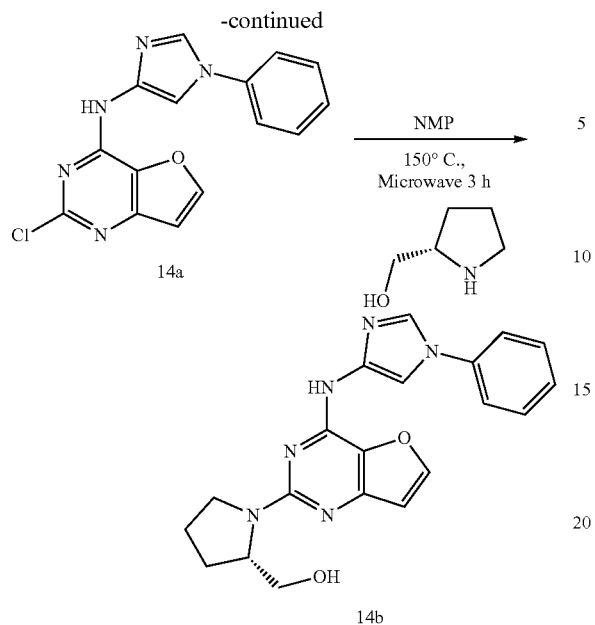

14a

14b

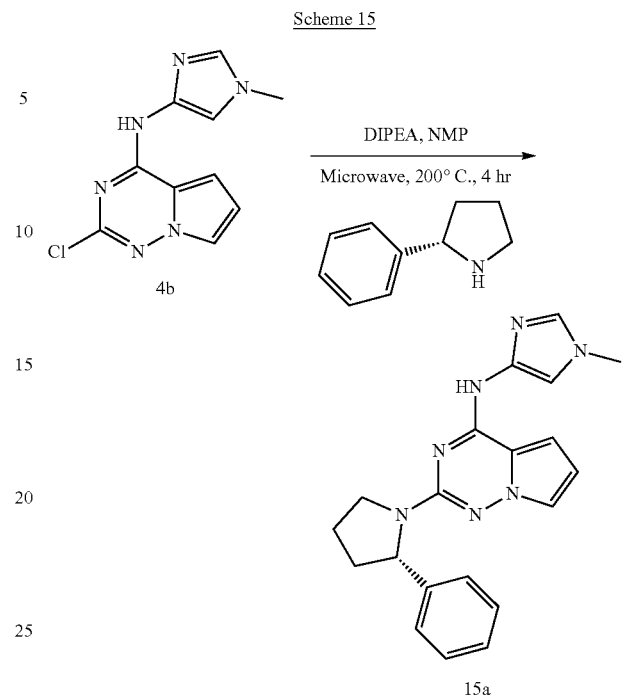

Scheme 15

4b

15a

Preparation of (S)-(1-(44(1-phenyl-1H-imidazol-4-yl)amino)furo[3,2-d]pyrimidin-2-yl)pyrrolidin-2-yl)methanol (14b)

Step-1: Preparation of 2-chloro-N-(1-phenyl-1H-imidazol-4-yl)furo[3,2-d]pyrimidin-4-amine (14a)

Compound 14a was prepared according to the procedure reported in Scheme 1 from 2,4-dichlorofuro[3,2-d]pyrimidine (1a) (400 mg, 2.12 mmol) in 2-Propanol (30 mL) using DIPEA (0.92 mL, 5.29 mmol) and 1-phenyl-1H-imidazol-4-amine, HCl (8a) (414 mg, 2.12 mmol). This gave 2-chloro-N-(1-phenyl-1H-imidazol-4-yl)furo[3,2-d]pyrimidin-4-amine (14a) (267 mg, 41% yield) as a light brown solid; $^1$H NMR (300 MHz, DMSO-d$_6$) δ 11.01 (s, 1H), 8.38 (d, J=2.2 Hz, 1H), 8.23 (d, J=1.6 Hz, 1H), 7.88 (d, J=1.7 Hz, 1H), 7.70-7.63 (m, 2H), 7.63-7.50 (m, 2H), 7.45-7.35 (m, 1H), 7.06 (d, J=2.2 Hz, 1H); MS (ES+): 312.3 (M+1), 334.3 (M+Na), 310.3 (M−1).

Step-2: Preparation of (S)-(1-(4-((1-phenyl-1H-imidazol-4-yl)amino)furo[3,2-d]pyrimidin-2-yl)pyrrolidin-2-yl)methanol (14b)

Compound 14b was prepared from 2-chloro-N-(1-phenyl-1H-imidazol-4-yl)furo[3,2-d]pyrimidin-4-amine (14a) (100 mg, 0.32 mmol), (S)-pyrrolidin-2-ylmethanol (81 mg, 0.8 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-phenyl-1H-imidazol-4-yl)amino)furo[3,2-d]pyrimidin-2-yl)pyrrolidin-2-yl)methanol (14b) (65 mg, 54% yield) as a brown solid; 1H NMR (300 MHz, DMSO-d$_6$) δ 10.13 (s, 1H, D$_2$O exchangeable), 8.18 (d, J=1.6 Hz, 1H), 8.04 (d, J=2.1 Hz, 1H), 7.95 (d, J=1.7 Hz, 1H), 7.80-7.64 (m, 2H), 7.51 (t, J=7.7 Hz, 2H), 7.34 (t, J=7.4 Hz, 1H), 6.74 (d, J=2.1 Hz, 1H), 5.00 (s, 1H, D$_2$O exchangeable), 4.20 (s, 1H), 3.85-3.69 (m, 1H), 3.66-3.54 (m, 1H), 3.55-3.41 (m, 2H), 2.09-1.83 (m, 4H); MS (ES+): 377.5 (M+1), (ES−): 375.4 (M−1).

Preparation of (S)—N-(1-methyl-1H-imidazol-4-yl)-2-(2-phenylpyrrolidin-1-yl)pyrrolo[2,1-f][1,2,4]triazin-4-amine (15a)

Compound 15a was prepared from 2-chloro-N-(1-methyl-1H-imidazol-4-yl)pyrrolo[1,2-f][1,2,4]triazin-4-amine (4b) (80 mg, 0.32 mmol), (S)-2-phenylpyrrolidine (142 mg, 0.97 mmol), DIPEA (0.17 mL, 0.97 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)—N-(1-methyl-1H-imidazol-4-yl)-2-(2-phenylpyrrolidin-1-yl)pyrrolo[2,1-f][1,2,4]triazin-4-amine (15a) (42 mg, 36% yield) as an off white solid; H NMR (300 MHz, DMSO-d$_6$) δ 10.20 (s, 1H, D$_2$O exchangeable), 7.40-7.34 (m, 2H), 7.34-7.26 (m, 4H), 7.25-7.15 (m, 1H), 7.05 (dd, J=4.3, 1.7 Hz, 1H), 6.73 (s, 1H), 6.36 (dd, J=4.4, 2.4 Hz, 1H), 5.33 (d, J=8.0 Hz, 1H), 3.86-3.70 (m, 1H), 3.66-3.50 (m, 1H), 3.49 (s, 3H), 2.42-2.28 (m, 1H), 2.02-1.71 (m, 3H); MS (ES+): 360.5 (M+1), (ES−): 358.5 (M−1).

Scheme 16

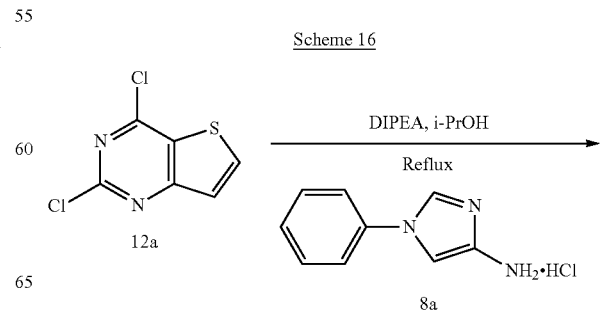

12a

8a

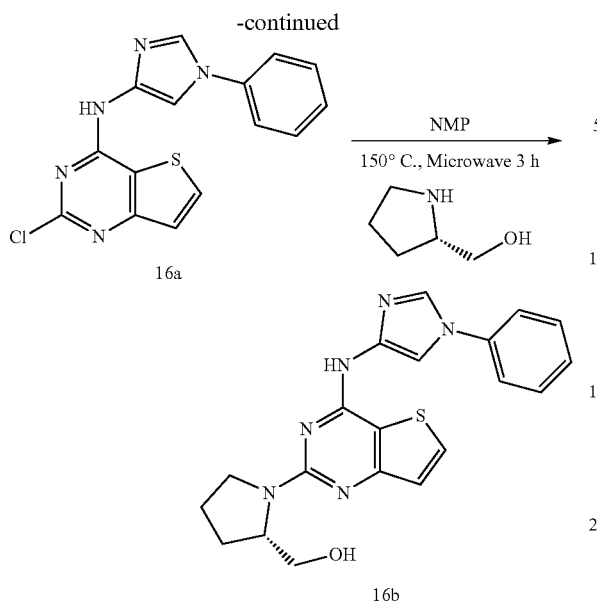

16a

16b

Preparation of (S)-(1-(4-((1-phenyl-1H-imidazol-4-yl)amino)thieno[3,2-d]pyrimidin-2-yl)pyrrolidin-2-yl)methanol (16b)

Step-1: Preparation of 2-chloro-N-(1-phenyl-1H-imidazol-4-yl)thieno[3,2-d]pyrimidin-4-amine (16a)

Compound 16a was prepared according to the procedure reported in Scheme 1 from 2,4-dichlorothieno[3,2-d]pyrimidine (12a) (500 mg, 2.44 mmol) in 2-Propanol (30 mL) using DIPEA (1.07 mL, 6.1 mmol) and 1-phenyl-1H-imidazol-4-amine, HCl (8a) (477 mg, 2.45 mmol). This gave 2-chloro-N-(1-phenyl-1H-imidazol-4-yl)thieno[3,2-d]pyrimidin-4-amine (16a) (340 mg, 43% yield) as a light pink solid; $^1$H NMR (300 MHz, DMSO-$d_6$) δ 10.97 (s, 1H, D$_2$O exchangeable), 8.27 (s, 1H), 8.24 (d, J=5.4 Hz, 1H), 7.96 (d, J=1.7 Hz, 1H), 7.73-7.65 (m, 2H), 7.62-7.52 (m, 2H), 7.46-7.36 (m, 2H); MS (ES+): 328.3 (M+1) (ES−): 326.3 (M−1).

Step-2: Preparation of (S)-(1-(4-((1-phenyl-1H-imidazol-4-yl)amino)thieno[3,2-d]pyrimidin-2-yl)pyrrolidin-2-yl)methanol (16b)

Compound 16b was prepared from 2-chloro-N-(1-phenyl-1H-imidazol-4-yl)thieno[3,2-d]pyrimidin-4-amine (16a) (100 mg, 0.31 mmol), (S)-pyrrolidin-2-ylmethanol (77 mg, 0.76 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-(1-phenyl-1H-imidazol-4-yl)amino)thieno[3,2-d]pyrimidin-2-yl)pyrrolidin-2-yl)methanol (16b) (95 mg, 79% yield) as a brown solid; $^1$H NMR (300 MHz, DMSO-$d_6$) δ 10.14 (s, 1H, D$_2$O exchangeable), 8.20 (d, J=1.6 Hz, 1H), 7.98 (d, J=1.6 Hz, 1H), 7.93 (d, J=5.4 Hz, 1H), 7.72 (s, 2H), 7.51 (t, J=7.8 Hz, 2H), 7.35 (t, J=7.4 Hz, 1H), 7.10 (d, J=5.4 Hz, 1H), 5.03 (s, 1H, D$_2$O exchangeable), 4.24 (s, 1H), 3.87-3.70 (m, 1H), 3.70-3.45 (m, 1H), 3.43-3.36 (m, 2H), 2.12-1.78 (m, 4H); MS (ES+): 393.5 (M+1), 415.5 (M+Na), (ES−): 391.4 (M−1).

Scheme 17

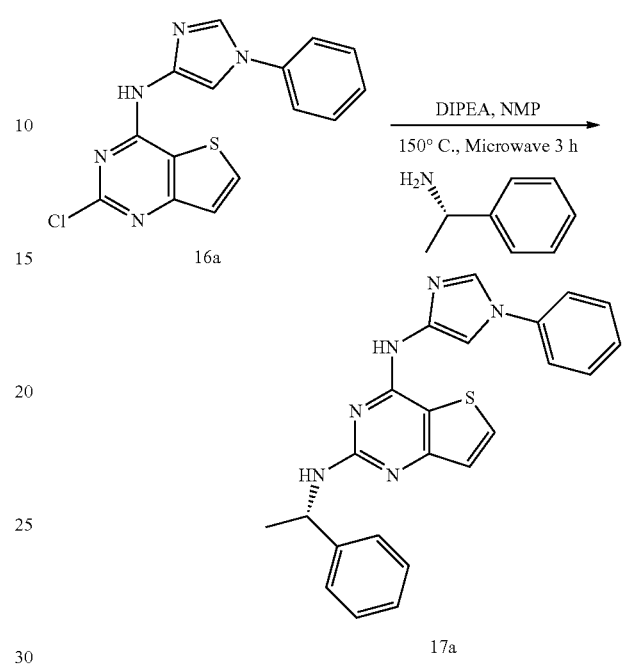

17a

Preparation of (S)-N4-(1-phenyl-1H-imidazol-4-yl)-N2-(1-phenylethyl)thieno[3,2-d]pyrimidine-2,4-diamine (17a)

Compound 17a was prepared from 2-chloro-N-(1-phenyl-1H-imidazol-4-yl)thieno[3,2-d]pyrimidin-4-amine (16a) (100 mg, 0.31 mmol), (S)-1-phenylethanamine (111 mg, 0.92 mmol) and DIPEA (0.2 mL, 1.2 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-N4-(1-phenyl-1H-imidazol-4-yl)-N2-(1-phenylethyl)thieno[3,2-d]pyrimidine-2,4-diamine (17a) (65 mg, 52% yield) as an off white solid; $^1$H NMR (300 MHz, DMSO-$d_6$) δ 10.10 (s, 1H, D$_2$O exchangeable), 8.33-8.16 (m, 1H), 8.14 (s, 1H), 7.97-7.87 (m, 1H), 7.76-7.63 (m, 2H), 7.57 (t, J=7.8 Hz, 2H), 7.48-7.30 (m, 3H), 7.33-7.19 (m, 3H), 7.22-7.07 (m, 1H), 7.04 (d, J=5.4 Hz, 1H), 5.32-5.16 (m, 1H), 1.50 (d, J=7.0 Hz, 3H); MS (ES+): 413.5 (M+1), (ES−): 411.5 (M−1); HPLC purity: 91.57%.

Scheme 18

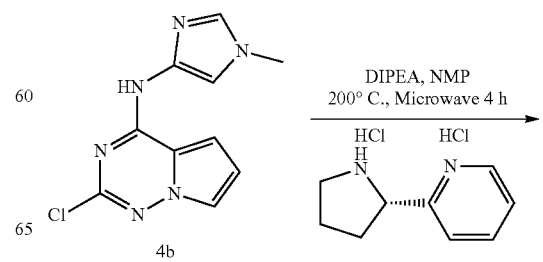

4b

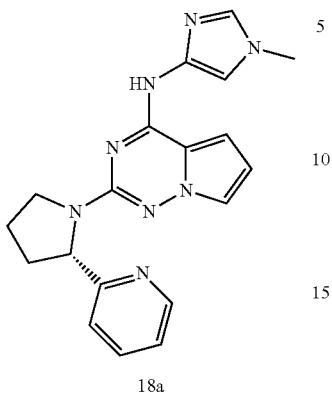

18a

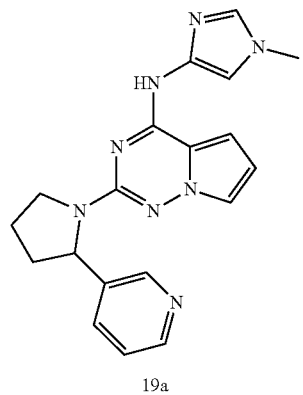

19a

Preparation of (S)—N-(1-methyl-1H-imidazol-4-yl)-2-(2-(pyridin-2-yl)pyrrolidin-1-yl)pyrrolo[2,1-f][1,2,4]triazin-4-amine (18a)

Compound 18a was prepared from 2-chloro-N-(1-methyl-1H-imidazol-4-yl)pyrrolo[2,1-f][1,2,4]triazin-4-amine (4b) (100 mg, 0.4 mmol), (S)-2-(pyrrolidin-2-yl)pyridine dihydrochloride (98 mg, 0.44 mmol) and DIPEA (0.17 mL, 0.97 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)—N-(1-methyl-1H-imidazol-4-yl)-2-(2-(pyridin-2-yl)pyrrolidin-1-yl)pyrrolo[2,1-f][1,2,4]triazin-4-amine (18a) (11 mg, 8% yield) as a light yellow solid; 1H NMR (300 MHz, DMSO-d$_6$) δ 10.24 (s, 1H, D$_2$O exchangeable), 8.66-8.56 (m, 1H), 7.67 (td, J=7.7, 1.8 Hz, 1H), 7.43-7.31 (m, 2H), 7.27-7.16 (m, 2H), 7.06 (dd, J=4.5, 1.7 Hz, 1H), 6.75 (bs, 1H), 6.36 (dd, J=4.4, 2.4 Hz, 1H), 5.29 (d, J=8.2 Hz, 1H), 3.87-3.74 (m, 1H), 3.66-3.56 (m, 1H), 3.53 (s, 3H), 2.44-2.31 (m, 1H), 2.05-1.79 (m, 3H); MS (ES+). 361.5 (M+1), 383.5 (M+Na).

Preparation of N-(1-methyl-1H-imidazol-4-yl)-2-(2-(pyridin-3-yl)pyrrolidin-1-yl)pyrrolo[2,1-f][1,2,4]triazin-4-amine (19a)

Compound 19a was prepared from 2-chloro-N-(1-methyl-1H-imidazol-4-yl)pyrrolo[2,1-f][1,2,4]triazin-4-amine (4b) (100 mg, 0.4 mmol), 3-(pyrrolidin-2-yl)pyridine (119 mg, 0.804 mmol), and DIPEA (0.21 mL, 1.21 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-methyl-1H-imidazol-4-yl)-2-(2-(pyridin-3-yl)pyrrolidin-1-yl)pyrrolo[2,1-f][1,2,4]triazin-4-amine (19a) (11 mg, 8% yield) as a light yellow solid; $^1$H NMR (300 MHz, DMSO-d$_6$) δ 10.24 (s, 1H, D$_2$O exchangeable), 8.66-8.56 (m, 1H), 7.67 (td, J=7.7, 1.8 Hz, 1H), 7.43-7.31 (m, 2H), 7.27-7.16 (m, 2H), 7.06 (dd, J=4.5, 1.7 Hz, 1H), 6.75 (bs, 1H), 6.36 (dd, J=4.4, 2.4 Hz, 1H), 5.29 (d, J=8.2 Hz, 1H), 3.87-3.74 (m, 1H), 3.66-3.56 (m, 1H), 3.53 (s, 3H), 2.44-2.31 (m, 1H), 2.05-1.79 (m, 3H); MS (ES+): 361.5 (M+1), 383.5 (M+Na).

Scheme 19

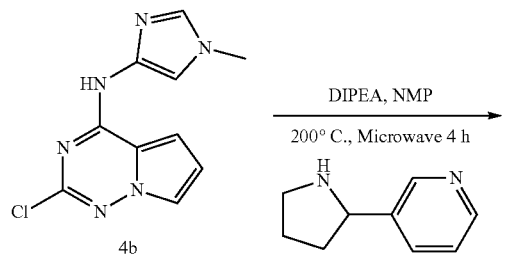

Scheme 20

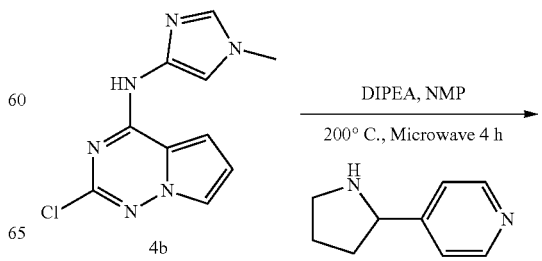

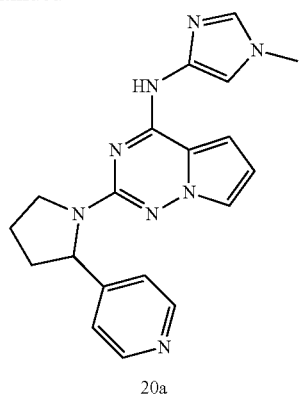

20a

Preparation of N-(1-methyl-1H-imidazol-4-yl)-2-(2-(pyridin-4-yl)pyrrolidin-1-yl)pyrrolo[2,1-f][1,2,4]triazin-4-amine (20a)

Compound 20a was prepared from 2-chloro-N-(1-methyl-1H-imidazol-4-yl)pyrrolo[2,1-f][1,2,4]triazin-4-amine (4b) (100 mg, 0.4 mmol), 4-(pyrrolidin-2-yl)pyridine (119 mg, 0.8 mmol) and DIPEA (0.21 mL, 1.21 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using $NaHCO_3$, N-(1-methyl-1H-imidazol-4-yl)-2-(2-(pyridin-4-yl)pyrrolidin-1-yl)pyrrolo[2,1-f][1,2,4]triazin-4-amine (20a) (23 mg, 16% yield) as a light brown solid; H NMR (300 MHz, DMSO-$d_6$) δ 10.26 (s, 1H, $D_2O$ exchangeable), 8.55-8.42 (m, 2H), 7.37 (s, 2H), 7.34-7.30 (m, 2H), 7.07 (dd, J=4.4, 1.7 Hz, 1H), 6.74 (s, 1H), 6.36 (dd, J=4.5, 2.4 Hz, 1H), 5.30 (d, J=8.3 Hz, 1H), 3.86-3.73 (m, 1H), 3.68-3.58 (m, 1H), 3.52 (s, 3H), 2.47-2.30 (m, 1H), 2.01-1.73 (m, 3H); MS (ES+): 361.5 (M+1), 383.5 (M+Na), (ES−): 359.4 (M−1).

Preparation of (S)-N4-(1-methyl-1H-imidazol-4-yl)-N2-(1-phenylethyl)quinazoline-2,4-diamine (21c)

Step-1: Preparation of 2-chloro-N-(1-methyl-1H-imidazol-4-yl)quinazolin-4-amine (21b)

Compound 21b was prepared according to the procedure reported by Su, Qibin et al in Journal of Medicinal Chemistry, 57(1), 144-158; 2014. This gave 2-chloro-N-(1-methyl-1H-imidazol-4-yl)quinazolin-4-amine (21b) as a light brown solid; $^1$H NMR (300 MHz, DMSO-$d_6$) δ 10.97 (s, 1H, $D_2O$ exchangeable), 8.72 (dd, J=8.3, 1.3 Hz, 1H), 7.84 (ddd, J=8.3, 6.9, 1.3 Hz, 1H), 7.68 (dd, J=8.4, 1.2 Hz, 1H), 7.62-7.50 (m, 3H), 3.73 (s, 3H); MS (ES+): 260.3 (M+1), 282.3 (M+Na), (ES−): 258.3 (M−1).

Step-2: Preparation of (S)-N4-(1-methyl-1H-imidazol-4-yl)-N2-(1-phenylethyl)quinazoline-2,4-diamine (21c)

Compound 21c was prepared from 2-chloro-N-(1-methyl-1H-imidazol-4-yl)quinazolin-4-amine (21b) (100 mg, 0.39 mmol), (S)-1-phenylethanamine (140 mg, 1.16 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using $NaHCO_3$, (S)-N4-(1-methyl-1H-imidazol-4-yl)-N2-(1-phenylethyl)quinazoline-2,4-diamine (21c) (24 mg, 18% yield) as a light brown solid; $^1$H NMR (300 MHz, DMSO-$d_6$) δ 9.96 (s, 1H, $D_2O$ exchangeable), 8.36 (d, J=8.2 Hz, 1H), 7.96 (s, 1H), 7.55-7.39 (m, 4H), 7.37-7.3 (m, 5H), 7.08-6.93 (m, 1H), 5.29 (s, 1H), 3.69 (s, 3H), 1.50 (d, J=7.0 Hz, 3H); MS (ES+): 345.5 (M+1), 367.5 (M+Na), (ES−): 343.4 (M−1), 379.5 (M+Cl).

Scheme 21

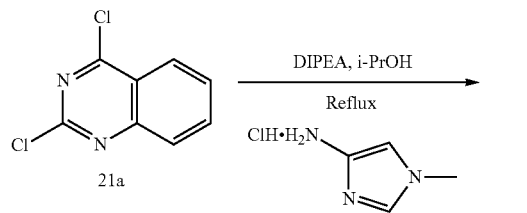

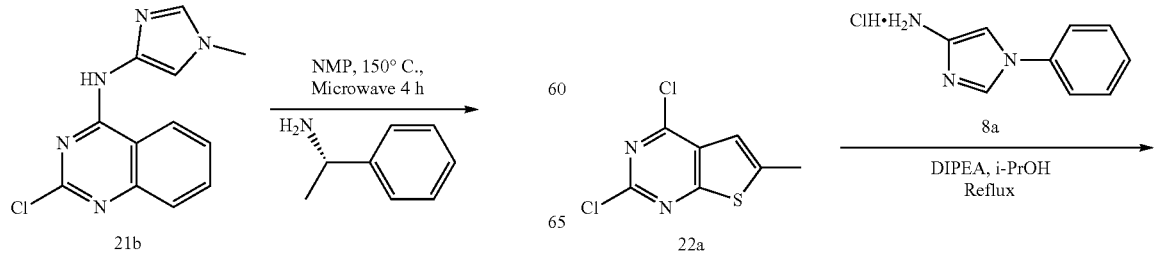

Scheme 22

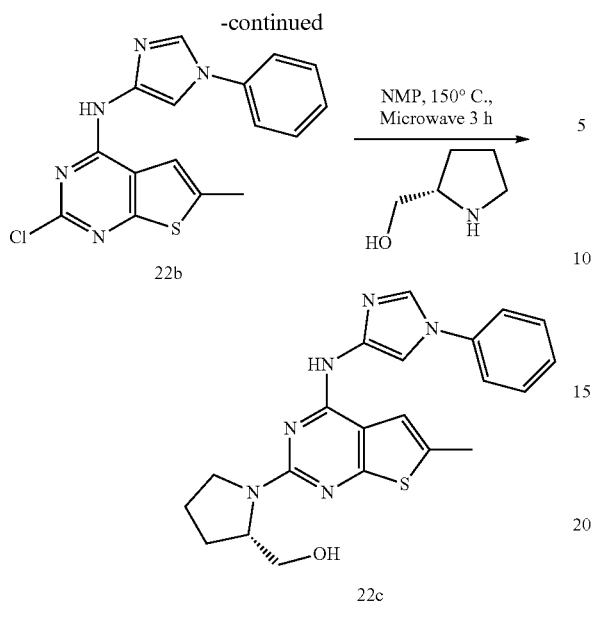

22b

22c

Preparation of (S)-(1-(6-methyl-4-((1-phenyl-1H-imidazol-4-yl)amino)thieno[2,3-d]pyrimidin-2-yl)pyrrolidin-2-yl)methanol (22c)

Step-1: Preparation of 2-chloro-6-methyl-N-(1-phenyl-1H-imidazol-4-yl)thieno[2,3-d]pyrimidin-4-amine (22b)

Compound 22b was prepared according to the procedure reported in Scheme 1 from 2,4-dichloro-6-methylthieno[2,3-d]pyrimidine (22a) (500 mg, 2.28 mmol, CAS #76872-23-6) in 2-Propanol (30 mL) using DIPEA (1.0 mL, 5.71 mmol) and 1-phenyl-1H-imidazol-4-amine, HCl (8a) (363 mg, 2.28 mmol). This gave 2-chloro-6-methyl-N-(1-phenyl-1H-imidazol-4-yl)thieno[2,3-d]pyrimidin-4-amine (22b) (340 mg, 44% yield) as light pink solid; $^1$H NMR (300 MHz, DMSO-$d_6$) δ 10.88 (s, 1H, D$_2$O exchangeable), 8.25 (d, J=1.7 Hz, 1H), 7.91 (d, J=1.7 Hz, 1H), 7.72 (s, 1H), 7.70-7.63 (m, 2H), 7.57 (dd, J=8.7, 7.1 Hz, 2H), 7.46-7.36 (m, 1H), 2.56 (d, J=1.2 Hz, 3H); MS (ES+): 364.3 (M+Na), (ES−): 340.3 (M−1).

Step-2: Preparation of (S)-(1-(6-methyl-4-((1-phenyl-1H-imidazol-4-yl)amino)thieno[2,3-d]pyrimidin-2-yl)pyrrolidin-2-yl)methanol (22c)

Compound 22c was prepared from 2-chloro-6-methyl-N-(1-phenyl-1H-imidazol-4-yl)thieno[2,3-d]pyrimidin-4-amine (22b) (100 mg, 0.29 mmol), (S)-pyrrolidin-2-ylmethanol (89 mg, 0.88 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(6-methyl-4-((1-phenyl-1H-imidazol-4-yl)amino)thieno[2,3-d]pyrimidin-2-yl)pyrrolidin-2-yl)methanol (22c) (65 mg, 55% yield) as a light brown solid; $^1$H NMR (300 MHz, DMSO-$d_6$) δ 9.98 (s, 1H, D$_2$O exchangeable), 8.20 (s, 1H), 7.96 (d, J=1.6 Hz, 1H), 7.84-7.60 (m, 2H), 7.57-7.42 (m, 3H), 7.40-7.29 (m, 1H), 4.94 (s, 1H, D$_2$O exchangeable), 4.42-4.02 (m, 1H), 3.87-3.39 (m, 2H), 2.63-2.51 (m, 1H), 2.49-2.35 (m, 4H), 2.13-1.76 (m, 4H); MS (ES+): 407.5 (M+1), 429.5 (M+Na), (ES−): 405.4.

Scheme 23

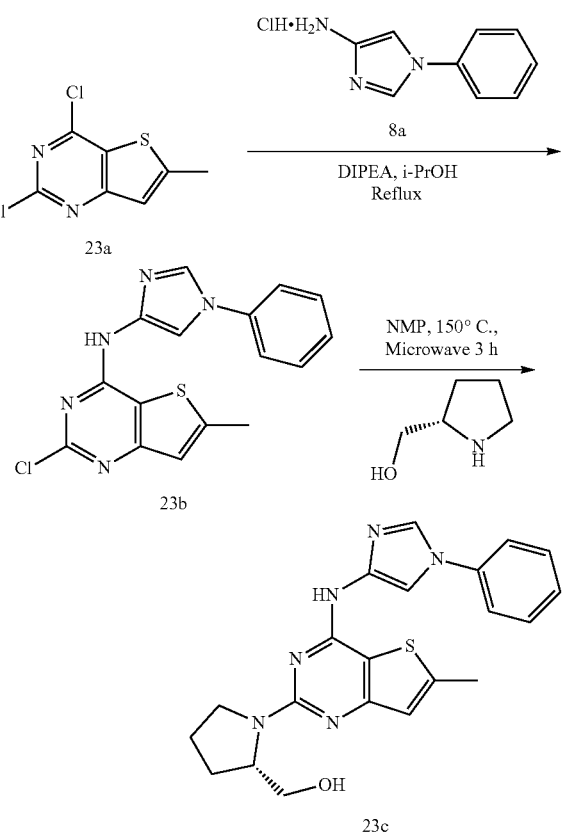

23a

23b

23c

Preparation of (S)-(1-(6-methyl-4-((1-phenyl-1H-imidazol-4-yl)amino)thieno[3,2-d]pyrimidin-2-yl)pyrrolidin-2-yl)methanol (23c)

Step-1: Preparation of 2-chloro-6-methyl-N-(1-phenyl-1H-imidazol-4-yl)thieno[3,2-d]pyrimidin-4-amine (23b)

Compound 23b was prepared according to the procedure reported in Scheme 1 from 2,4-dichloro-6-methylthieno[3,2-d]pyrimidine (23a) (500 mg, 2.28 mmol, CAS #35265-82-8) in 2-Propanol (30 mL) using DIPEA (1.00 mL, 5.71 mmol) and 1-phenyl-1H-imidazol-4-amine, HCl (8a) (363 mg, 2.28 mmol). This gave 2-chloro-6-methyl-N-(1-phenyl-1H-imidazol-4-yl)thieno[3,2-d]pyrimidin-4-amine (23b) (340 mg, 44% yield) as a light pink solid; $^1$H NMR (300 MHz, DMSO-$d_6$) δ 10.75 (s, 1H, D$_2$O exchangeable), 8.27 (d, J=1.6 Hz, 1H), 7.92 (d, J=1.6 Hz, 1H), 7.68 (dd, J=7.9, 1.6 Hz, 2H), 7.57 (dd, J=8.6, 7.1 Hz, 2H), 7.45-7.36 (m, 1H), 7.17-7.08 (m, 1H), 2.60 (s, 3H); MS (ES+): 342.3 (M+1), 364.3 (M+Na), (ES−): 340.3 (M−1).

Step-2: Preparation of (S)-(1-(6-methyl-4-((1-phenyl-1H-imidazol-4-yl)amino)thieno[3,2-d]pyrimidin-2-yl)pyrrolidin-2-yl)methanol (23c)

Compound 23c was prepared from 2-chloro-6-methyl-N-(1-phenyl-1H-imidazol-4-yl)thieno[3,2-d]pyrimidin-4- amine (23b) (100 mg, 0.29 mmol), (S)-pyrrolidin-2-yl-methanol (89 mg, 0.88 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(6-methyl-4-((1-phenyl-1H-imidazol-4-yl)amino)thieno[3,2-d]pyrimidin-2-yl)pyrrolidin-2-yl)methanol (23c) (65 mg, 55% yield) as an off-white solid; $^1$H NMR (300 MHz, DMSO-d$_6$) δ 9.95 (s, 1H, D$_2$O exchangeable), 8.19 (d, J=1.6 Hz, 1H), 7.96 (d, J=1.6 Hz, 1H), 7.72 (s, 2H), 7.51 (t, J=7.7 Hz, 2H), 7.34 (t, J=7.4 Hz, 1H), 6.83 (d, J=1.5 Hz, 1H), 5.37-4.71 (m, 1H, D$_2$O exchangeable), 4.36-4.05 (m, 1H), 3.85-3.69 (m, 1H), 3.70-3.38 (m, 3H), 2.52 (s, 3H), 2.10-1.80 (m, 4H); MS (ES+): 407.5 (M+1), 429.5 (M+Na), (ES−): 405.5 (M−1).

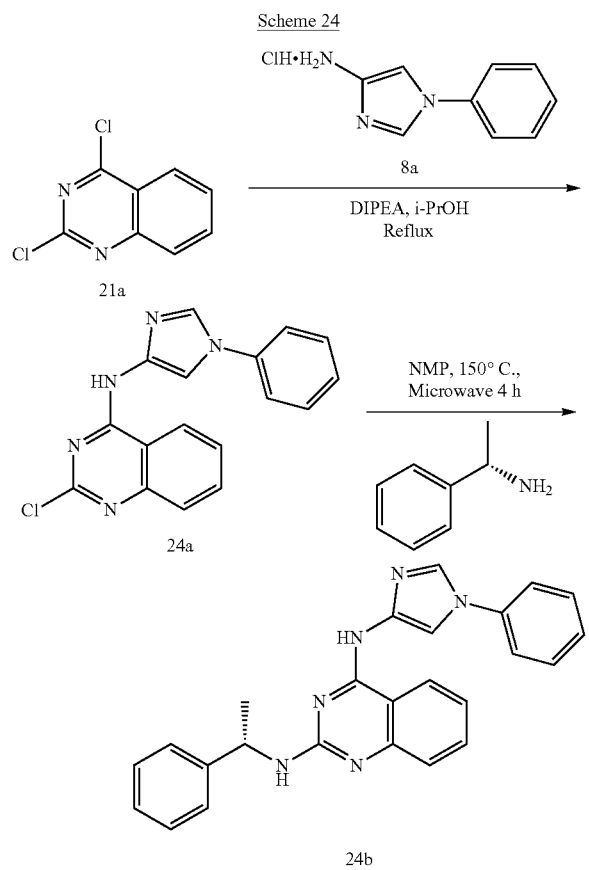

Preparation of (S)-N4-(1-phenyl-1H-imidazol-4-yl)-N2-(1-phenylethyl)quinazoline-2,4-diamine (24b)

Step-1: Preparation of 2-chloro-N-(1-phenyl-1H-imidazol-4-yl)quinazolin-4-amine (24a)

Compound 24a was prepared according to the procedure reported in Scheme 1 from 2,4-dichloroquinazoline (21a) (180 mg, 0.9 mmol; CAS #607-68-1) in 2-Propanol (5 mL) using DIPEA (0.51 mL, 2.92 mmol) and 1-phenyl-1H-imidazol-4-amine, HCl (8a) (177 mg, 0.9 mmol). This gave 2-chloro-N-(1-phenyl-1H-imidazol-4-yl)quinazolin-4-amine (24a) (125 mg, 43% yield) as an off-white solid; $^1$H NMR (300 MHz, DMSO-d$_6$) δ 11.18 (s, 1H, D$_2$O exchangeable), 8.77 (d, J=8.2 Hz, 1H), 8.29 (d, J=1.7 Hz, 1H), 8.04 (d, J=1.7 Hz, 1H), 7.87 (ddd, J=8.3, 7.0, 1.3 Hz, 1H), 7.73 (dd, J=8.4, 1.2 Hz, 1H), 7.70-7.65 (m, 2H), 7.60 (tdd, J=8.5, 6.9, 1.5 Hz, 3H), 7.46-7.37 (m, 1H); MS (ES+): 322.4 (M+1), 344.4 (M+Na), (ES−): 320.3 (M−1).

Step-2: Preparation of (S)-N4-(1-phenyl-1H-imidazol-4-yl)-N2-(1-phenylethyl)quinazoline-2,4-diamine (24b)

Compound 24b was prepared from 2-chloro-N-(1-phenyl-1H-imidazol-4-yl)quinazolin-4-amine (24a) (100 mg, 0.31 mmol), (S)-1-phenylethanamine (113 mg, 0.93 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-N4-(1-phenyl-1H-imidazol-4-yl)-N2-(1-phenylethyl)quinazoline-2,4-diamine (24b) (86 mg, 68% yield) as an off-white solid; $^1$H NMR (300 MHz, DMSO-d$_6$) δ 11.47-10.14 (m, 1H, D$_2$O exchangeable), 8.66-8.36 (m, 2H), 8.22 (d, J=1.7 Hz, 1H), 7.82-7.63 (m, 1H), 7.59 (t, J=7.6 Hz, 2H), 7.51-7.28 (m, 9H), 7.26-7.15 (m, 2H), 5.35 (q, J=7.2 Hz, 1H), 1.57 (d, J=6.9 Hz, 3H); MS (ES+): 407.5 (M+1), (ES−): 405.6 (M−1).

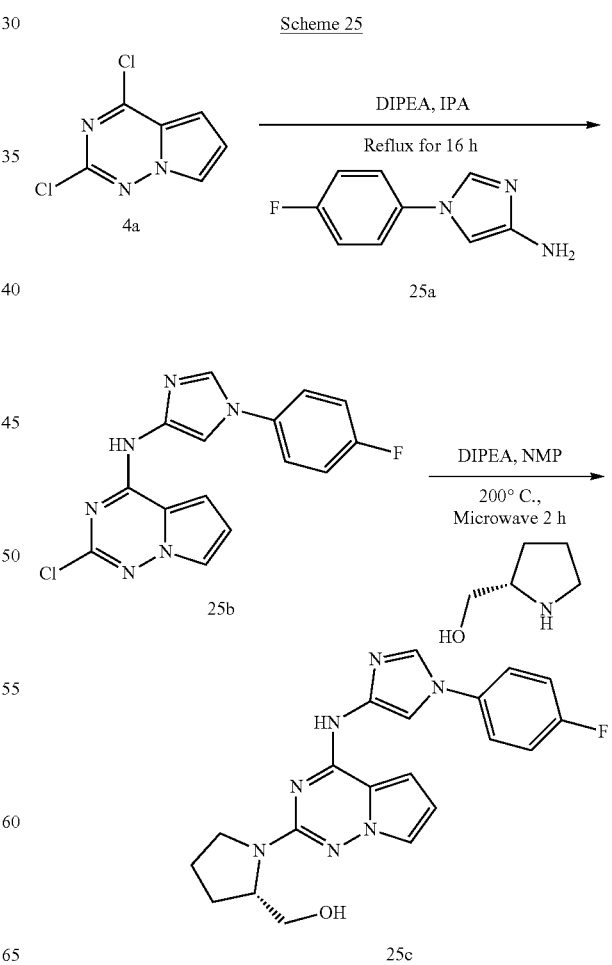

Preparation of (S)-(1-(4-((1-(4-fluorophenyl)-1H-imidazol-4-yl)amino)pyrrolo[2,1-f][1,2,4]triazin-2-yl)pyrrolidin-2-yl)methanol (25c)

Step-1: Preparation of 2-chloro-N-(1-(4-fluorophenyl)-1H-imidazol-4-yl)pyrrolo[2,1-f][1,2,4]triazin-4-amine (25b)

Compound 25b was prepared according to the procedure reported in Scheme 1 from 2,4-dichloropyrrolo[1,2-f][1,2,4]triazine (4a) (323 mg, 1.72 mmol) in 2-Propanol (20 mL) using DIPEA (0.9 mL, 5.15 mmol) and 1-(4-fluorophenyl)-1H-imidazol-4-amine (25a) (440 mg, 2.06 mmol; prepared according to the procedure reported by Sakamoto, Toshihiro et al in Bioorganic & Medicinal Chemistry, 17(14), 5015-5026; 2009 and Francini, Cinzia Maria et al; in Chem. Med. Chem, 10(12), 2027-2041). This gave 2-chloro-N-(1-(4-fluorophenyl)-1H-imidazol-4-yl)pyrrolo[2,1-f][1,2,4]triazin-4-amine (25b) (381 mg, 68% yield) as a pale off-white solid; $^1$H NMR (300 MHz, DMSO-$d_6$) δ 11.35 (s, 1H, $D_2O$ exchangeable), 8.21 (d, J=1.6 Hz, 1H), 7.87 (d, J=1.6 Hz, 1H), 7.77 (dd, J=2.6, 1.5 Hz, 1H), 7.74-7.65 (m, 2H), 7.49-7.35 (m, 3H), 6.72 (dd, J=4.5, 2.6 Hz, 1H); $^{19}$F NMR (282 MHz, DMSO) δ −114.97; MS (ES+): 329.3 (M+1); MS (ES−): 327.3 (M−1).

Step-2: Preparation of (S)-(1-(4-((1-(4-fluorophenyl)-1H-imidazol-4-yl)amino)pyrrolo[2,1-f][1,2,4]triazin-2-yl)pyrrolidin-2-yl)methanol (25c)

Compound 25c was prepared from 2-chloro-N-(1-(4-fluorophenyl)-1H-imidazol-4-yl)pyrrolo[2,1-f][1,2,4]triazin-4-amine (25b) (100 mg, 0.32 mmol), (S)-pyrrolidin-2-ylmethanol (154 mg, 1.52 mmol), and DIPEA (0.16 mL, 0.91 mmol) in NMP (1 mL) according to the procedure reported in Scheme 2. This gave after workup and purification by flash chromatography [silica (24 g), eluting with CMA-80 in CHCl$_3$ from 0 to 40%] (S)-(1-(4-((1-(4-fluorophenyl)-1H-imidazol-4-yl)amino)pyrrolo[2,1-f][1,2,4]triazin-2-yl)pyrrolidin-2-yl)methanol (25c) (40 mg, 33% yield) as white solid; $^1$H NMR (300 MHz, DMSO-$d_6$) δ 10.53 (s, 1H, $D_2O$ exchangeable), 8.20 (d, J=1.6 Hz, 1H), 7.93 (d, J=1.6 Hz, 1H), 7.86-7.74 (m, 2H), 7.39 (dd, J=2.4, 1.6 Hz, 1H), 7.38-7.29 (m, 2H), 7.15 (dd, J=4.5, 1.7 Hz, 1H), 6.39 (dd, J=4.4, 2.4 Hz, 1H), 4.91 (t, J=5.0 Hz, 1H, $D_2O$ exchangeable), 4.26-4.12 (m, 1H), 3.83-3.69 (m, 1H), 3.55-3.44 (m, 1H), 3.39-3.25 (m, 2H), 2.12-1.81 (m, 4H); $^{19}$F NMR (282 MHz, DMSO-$d_6$) δ −115.67; MS (ES+): 394.5 (M+1), 416.5 (M+Na); MS (ES−): 392.5 (M−1).

Scheme 26

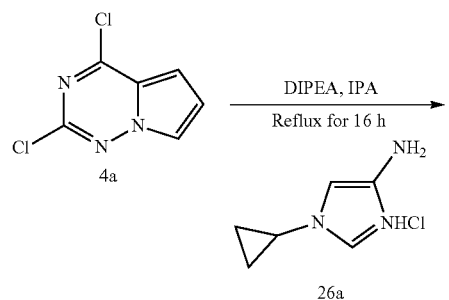

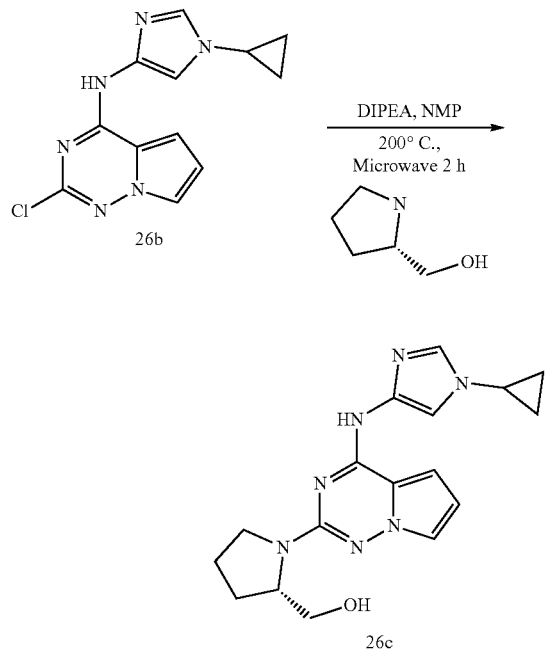

Preparation of (S)-(1-(4-((1-cyclopropyl-1H-imidazol-4-yl)amino)pyrrolo[2,1-f][1,2,4]triazin-2-yl)pyrrolidin-2-yl)methanol (26c)

Step-1: Preparation of 2-chloro-N-(1-cyclopropyl-1H-imidazol-4-yl)pyrrolo[2,1-f][1,2,4]triazin-4-amine (26b)

Compound 26b was prepared according to the procedure reported in Scheme 1 from 2,4-dichloropyrrolo[1,2-f][1,2,4]triazine (4a) (268 mg, 1.43 mmol) in 2-Propanol (5 mL) using DIPEA (1.25 mL, 7.14 mmol) and 1-cyclopropyl-1H-imidazol-4-amine hydrochloride (26a) (1.4 g, 7.14 mmol). This gave 2-chloro-N-(1-cyclopropyl-1H-imidazol-4-yl)pyrrolo[2,1-f][1,2,4]triazin-4-amine (26b) (225 mg, 57% yield) as a brownish solid; $^1$H NMR (300 MHz, DMSO-$d_6$) δ 11.19 (s, 1H, $D_2O$ exchangeable), 7.73 (dd, J=2.6, 1.5 Hz, 1H), 7.65 (d, J=1.5 Hz, 1H), 7.50 (d, J=1.5 Hz, 1H), 7.35 (dd, J=4.5, 1.6 Hz, 1H), 6.68 (dd, J=4.5, 2.6 Hz, 1H), 3.62-3.46 (m, 1H), 1.14-0.89 (m, 4H); MS (ES−): 273.3 (M−1).

Step-2: Preparation of (S)-(1-(4-((1-cyclopropyl-1H-imidazol-4-yl)amino)pyrrolo[2,1-f][1,2,4]triazin-2-yl)pyrrolidin-2-yl)methanol (26c)

Compound 26c was prepared from 2-chloro-N-(1-cyclopropyl-1H-imidazol-4-yl)pyrrolo[2,1-f][1,2,4]triazin-4-amine (26b) (70 mg, 0.26 mmol), (S)-pyrrolidin-2-ylmethanol (129 mg, 1.27 mmol), and DIPEA (0.13 mL, 0.76 mmol) in NMP (1 mL) according to the procedure reported in Scheme 2. This gave after workup and purification by flash chromatography [silica (24 g), eluting with CMA-80 in CHCl$_3$ from 0 to 40%] (S)-(1-(4-((1-cyclopropyl-1H-imidazol-4-yl)amino)pyrrolo[2,1-f][1,2,4]triazin-2-yl)pyrrolidin- 2-yl)methanol (26c) (22 mg, 25% yield) as a white solid; $^1$H NMR (300 MHz, DMSO-$d_6$) δ 10.31 (s, 1H, D$_2$O exchangeable), 7.60 (d, J=1.4 Hz, 1H), 7.49 (d, J=1.6 Hz, 1H), 7.35 (dd, J=2.4, 1.6 Hz, 1H), 7.09 (dd, J=4.5, 1.7 Hz, 1H), 6.36 (dd, J=4.4, 2.4 Hz, 1H), 4.77 (t, J=5.1 Hz, 1H, D$_2$O exchangeable), 4.21-4.01 (m, 1H), 3.80-3.64 (m, 1H), 3.59-3.38 (m, 2H), 3.39 (s, 2H), 2.13-1.77 (m, 4H), 1.07-0.83 (m, 4H); MS (ES+): 340.5 (M+1), 362.5 (M+Na).

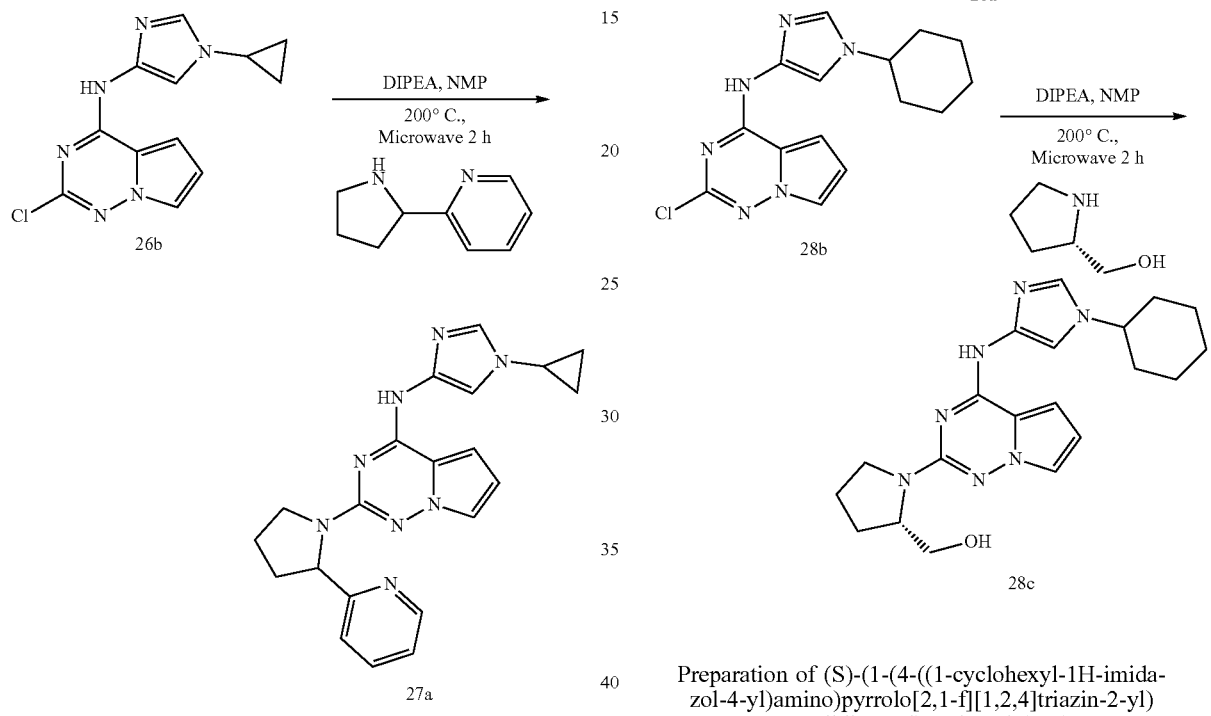

Preparation of N-(1-cyclopropyl-1H-imidazol-4-yl)-2-(2-(pyridin-2-yl)pyrrolidin-1-yl)pyrrolo[2,1-f][1,2,4]triazin-4-amine (27a)

Compound 27a was prepared from 2-chloro-N-(1-cyclopropyl-1H-imidazol-4-yl)pyrrolo[2,1-f][1,2,4]triazin-4-amine (26b) (70 mg, 0.26 mmol), 2-(pyrrolidin-2-yl)pyridine (113 mg, 0.76 mmol), and DIPEA (0.13 mL, 0.76 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-cyclopropyl-1H-imidazol-4-yl)-2-(2-(pyridin-2-yl)pyrrolidin-1-yl)pyrrolo[2,1-f][1,2,4]triazin-4-amine (27a) (48 mg, 51% yield) as a white solid; 1H NMR (300 MHz, DMSO-$d_6$) δ 10.19 (s, 1H, D$_2$O exchangeable), 8.59 (s, 1H), 7.78-7.60 (m, 1H), 7.52-7.43 (m, 1H), 7.41-7.32 (m, 1H), 7.29-7.11 (m, 2H), 7.09-6.99 (m, 1H), 6.93-6.70 (m, 1H), 6.46-6.26 (m, 1H), 5.43-5.21 (m, 1H), 3.89-3.70 (m, 1H), 3.42 (s, 1H), 3.37-3.21 (m, 1H), 2.47-2.29 (m, 1H), 2.12-1.68 (m, 3H), 1.09-0.87 (m, 3H), 0.88-0.71 (m, 1H); MS (ES+): 387.5 (M+1), 409.5 (M+Na).

Preparation of (S)-(1-(4-((1-cyclohexyl-1H-imidazol-4-yl)amino)pyrrolo[2,1-f][1,2,4]triazin-2-yl)pyrrolidin-2-yl)methanol (28c)

Step-1: Preparation of 2-chloro-N-(1-cyclohexyl-1H-imidazol-4-yl)pyrrolo[2,1-f][1,2,4]triazin-4-amine (28b)

Compound 28b was prepared according to the procedure reported in Scheme 1 from 2,4-dichloropyrrolo[1,2-f][1,2,4]triazine (4a) (376 mg, 2.0 mmol) in 2-Propanol (10 mL) using DIPEA (1.05 mL, 6.0 mmol) and 1-cyclohexyl-1H-imidazol-4-amine hydrochloride (28a) (572 mg, 2.4 mmol). This gave 2-chloro-N-(1-cyclohexyl-1H-imidazol-4-yl)pyrrolo[2,1-f][1,2,4]triazin-4-amine (28b) (381 mg, 60% yield) as a pale off-white colored solid; $^1$H NMR (300 MHz, DMSO-$d_6$) δ 11.68 (s, 1H), 8.76 (s, 1H), 7.86 (dd, J=2.6, 1.5 Hz, 1H), 7.78 (d, J=1.7 Hz, 1H), 7.36 (s, 1H), 6.79 (dd, J=4.5, 2.6 Hz, 1H), 4.28 (ddd, J=11.7, 7.9, 3.8 Hz, 1H), 2.10 (d, J=11.9 Hz, 2H), 1.85 (d, J=13.3 Hz, 2H), 1.72 (dt, J=14.9, 11.6 Hz, 3H), 1.40 (q, J=12.7 Hz, 2H), 1.24 (t, J=12.5 Hz, 1H); MS (ES+): 317.3 (M+1).

Step-2: Preparation of (S)-(1-(4-((1-cyclohexyl-1H-imidazol-4-yl)amino)pyrrolo[2,1-f][1,2,4]triazin-2-yl)pyrrolidin-2-yl)methanol (28c)

Compound 28c was prepared from 2-chloro-N-(1-cyclohexyl-1H-imidazol-4-yl)pyrrolo[2,1-f][1,2,4]triazin-4- amine (28b) (100 mg, 0.32 mmol), (S)-pyrrolidin-2-yl-methanol (160 mg, 1.56 mmol), and DIPEA (0.17 mL, 0.95 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-cyclohexyl-1H-imidazol-4-yl)amino)pyrrolo[2,1-f][1,2,4]triazin-2-yl)pyrrolidin-2-yl)methanol (28c) (25 mg, 21% yield) as a pale off-white solid; $^1$H NMR (300 MHz, DMSO-d$_6$) δ 10.31 (s, 1H, D$_2$O exchangeable), 7.66-7.51 (m, 2H), 7.43-7.28 (m, 1H), 7.18-7.01 (m, 1H), 6.45-6.22 (m, 1H), 4.93-4.76 (m, 1H, D$_2$O exchangeable), 4.20-4.07 (m, 1H), 4.07-3.92 (m, 1H), 3.83-3.65 (m, 1H), 3.54-3.20 (m, 3H), 2.13-1.84 (m, 6H), 1.89-1.70 (m, 4H), 1.72-1.54 (m, 1H), 1.47-1.12 (m, 3H); MS (ES+): 382.5 (M+1), 404.5 (M+Na); MS (ES−): 380.4 (M−1).

DMSO-d$_6$) δ 10.25 (s, 1H, D$_2$O exchangeable), 8.64-8.52 (m, 1H), 7.67 (td, J=7.7, 1.8 Hz, 1H), 7.49 (d, J=1.5 Hz, 1H), 7.38 (s, 1H), 7.26-7.21 (m, 1H), 7.19 (d, J=7.9 Hz, 1H), 7.08 (dd, J=4.4, 1.7 Hz, 1H), 6.91-6.83 (m, 1H), 6.36 (dd, J=4.4, 2.5 Hz, 1H), 5.33 (d, J=8.1 Hz, 1H), 3.87-3.70 (m, 2H), 3.66-3.50 (m, 1H), 2.42-2.28 (m, 1H), 2.15-2.03 (m, 1H), 2.03-1.78 (m, 6H), 1.81-1.64 (m, 2H), 1.67-1.51 (m, 1H), 1.51-1.37 (m, 2H), 1.37-1.15 (m, 1H). MS (ES+): 429.6 (M+1), 451.6 (M+Na).

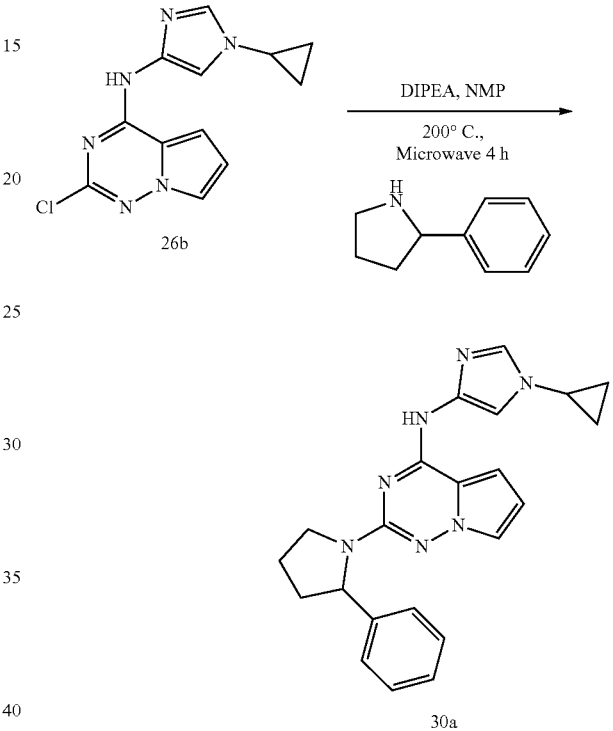

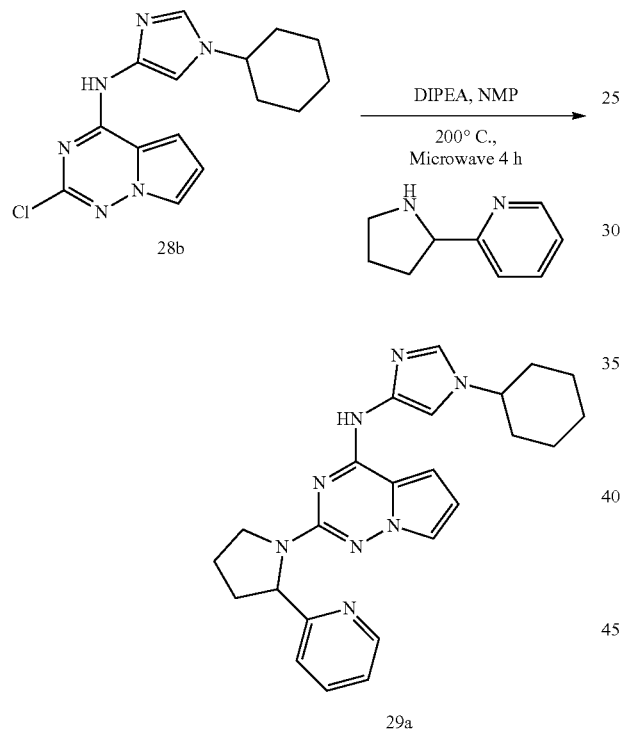

Preparation of N-(1-cyclohexyl-1H-imidazol-4-yl)-2-(2-(pyridin-2-yl)pyrrolidin-1-yl)pyrrolo[2,1-f][1,2,4]triazin-4-amine (29a)

Compound 29a was prepared from 2-chloro-N-(1-cyclohexyl-1H-imidazol-4-yl)pyrrolo[2,1-f][1,2,4]triazin-4-amine (28b) (100 mg, 0.32 mmol), 2-(pyrrolidin-2-yl)pyridine (140 mg, 0.95 mmol), and DIPEA (0.17 mL, 0.95 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-cyclohexyl-1H-imidazol-4-yl)-2-(2-(pyridin-2-yl)pyrrolidin-1-yl)pyrrolo[2,1-f][1,2,4]triazin-4-amine (29a) (47 mg, 35% oyield) as a white solid; $^1$H NMR (300 MHz,

Preparation of N-(1-cyclopropyl-1H-imidazol-4-yl)-2-(2-phenylpyrrolidin-1-yl)pyrrolo[2,1-f][1,2,4]triazin-4-amine (30a)

Compound 30a was prepared from 2-chloro-N-(1-cyclopropyl-1H-imidazol-4-yl)pyrrolo[2,1-f][1,2,4]triazin-4-amine (26b) (100 mg, 0.36 mmol), 2-phenylpyrrolidine (161 mg, 1.09 mmol), and DIPEA (0.19 mL, 1.09 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-cyclopropyl-1H-imidazol-4-yl)-2-(2-phenylpyrrolidin-1-yl)pyrrolo[2,1-f][1,2,4]triazin-4-amine (30a) (74 mg, 53% yield) as a pale off-white solid; $^1$H NMR (300 MHz, DMSO-d$_6$) δ 10.36 (s, 1H, D$_2$O exchangeable), 7.89 (s, 1H), 7.50-7.39 (m, 1H), 7.36-7.27 (m, 2H), 7.26 (d, J=7.5 Hz, 2H), 7.23-7.16 (m, 1H), 7.08-6.90 (m, 2H), 6.40 (dd, J=4.4, 2.4 Hz, 1H), 5.33 (d, J=7.9 Hz, 1H), 4.00-3.29 (m, 3H), 2.41-2.21 (m, 1H), 2.05-1.73 (m, 3H), 1.11-0.76 (m, 4H). MS (ES+): 386.5 (M+1), 408.5 (M+Na).

Scheme 31

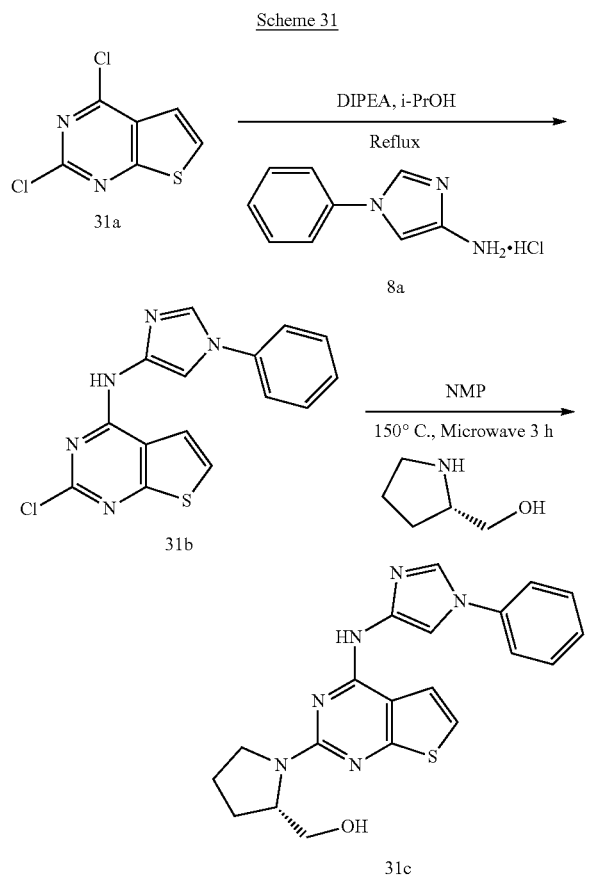

Preparation of (S)-(1-(4-((1-phenyl-1H-imidazol-4-yl)amino)thieno[2,3-d]pyrimidin-2-yl)pyrrolidin-2-yl)methanol (31c)

Step-1: Preparation of 2-chloro-N-(1-phenyl-1H-imidazol-4-yl)thieno[2,3-d]pyrimidin-4-amine (31b)

Compound 31b was prepared according to the procedure reported in Scheme 1 from 2,4-dichlorothieno[2,3-d]pyrimidine (31a) (500 mg, 2.44 mmol; CAS #18740-39-1) in 2-Propanol (10 mL) using DIPEA (1.70 mL, 9.75 mmol) and 1-phenyl-1H-imidazol-4-amine, HCl (8a) (716 mg, 3.66 mmol). This gave 2-chloro-N-(1-phenyl-1H-imidazol-4-yl)thieno[2,3-d]pyrimidin-4-amine (31b) (640 mg, 80% yield) as a light pink solid; $^1$H NMR (300 MHz, DMSO-$d_6$) δ 11.06 (s, 1H, $D_2O$ exchangeable), 8.26 (d, J=1.7 Hz, 1H), 8.04 (d, J=5.6 Hz, 1H), 7.94 (d, J=1.6 Hz, 1H), 7.71 (d, J=5.9 Hz, 1H), 7.69-7.63 (m, 2H), 7.62-7.54 (m, 2H), 7.46-7.36 (m, 1H); MS (ES+): 328.2 (M+1), 350.2 (M+Na), (ES−): 326.2 (M−1).

Step-2: Preparation of (S)-(1-(4-((1-phenyl-1H-imidazol-4-yl)amino)thieno[2,3-d]pyrimidin-2-yl)pyrrolidin-2-yl)methanol (31c)

Compound 31c was prepared from 2-chloro-N-(1-phenyl-1H-imidazol-4-yl)thieno[2,3-d]pyrimidin-4-amine (31b) (100 mg, 0.31 mmol), (S)-pyrrolidin-2-ylmethanol (93 mg, 0.92 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-phenyl-1H-imidazol-4-yl)amino)thieno[2,3-d]pyrimidin-2-yl)pyrrolidin-2-yl)methanol (31c) (95 mg, 79% yield) as a light brown solid; $^1$H NMR (300 MHz, DMSO-$d_6$) δ 10.16 (s, 1H, $D_2O$ exchangeable), 8.22 (s, 1H), 7.99 (d, J=1.7 Hz, 1H), 7.89-7.59 (m, 2H), 7.60-7.42 (m, 3H), 7.35 (t, J=7.3 Hz, 1H), 7.03 (d, J=6.0 Hz, 1H), 4.96 (s, 1H, $D_2O$ exchangeable), 4.46-4.00 (m, 1H), 3.95-3.36 (m, 4H), 2.17-1.82 (m, 4H); MS (ES+): 393.5 (M+1), 415.5 (M+Na), (ES−): 391.4 (M−1).

Scheme 32

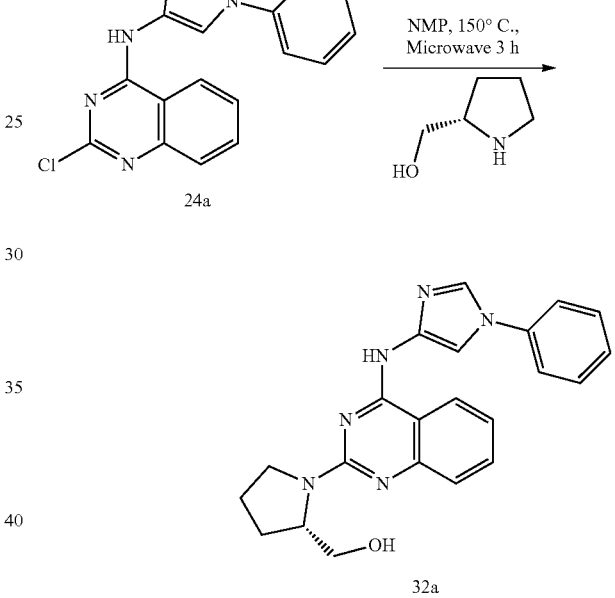

Preparation of (S)-(1-(4-((1-phenyl-1H-imidazol-4-yl)amino)quinazolin-2-yl)pyrrolidin-2-yl)methanol (32a)

Compound 32a was prepared from 2-chloro-N-(1-phenyl-1H-imidazol-4-yl)quinazolin-4-amine (24a) (100 mg, 0.31 mmol), (S)-pyrrolidin-2-ylmethanol (94 mg, 0.93 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-phenyl-1H-imidazol-4-yl)amino)quinazolin-2-yl)pyrrolidin-2-yl)methanol (32a) (75 mg, 62% yield) as light brown solid; $^1$H NMR (300 MHz, DMSO-$d_6$) δ 10.49-10.15 (m, 1H, $D_2O$ exchangeable), 8.48 (d, J=8.2 Hz, 1H), 8.25 (s, 1H), 8.07 (s, 1H), 7.93-7.63 (m, 3H), 7.61-7.43 (m, 2H), 7.43-7.24 (m, 2H), 7.09 (t, J=7.5 Hz, 1H), 5.16-4.88 (m, 1H, $D_2O$ exchangeable), 4.49-4.14 (m, 1H), 3.93-3.56 (m, 3H), 3.54-3.36 (m, 1H), 2.19-1.79 (m, 4H); MS (ES+): 387.4 (M+1), (ES−): 385.3 (M−1).

Scheme 33

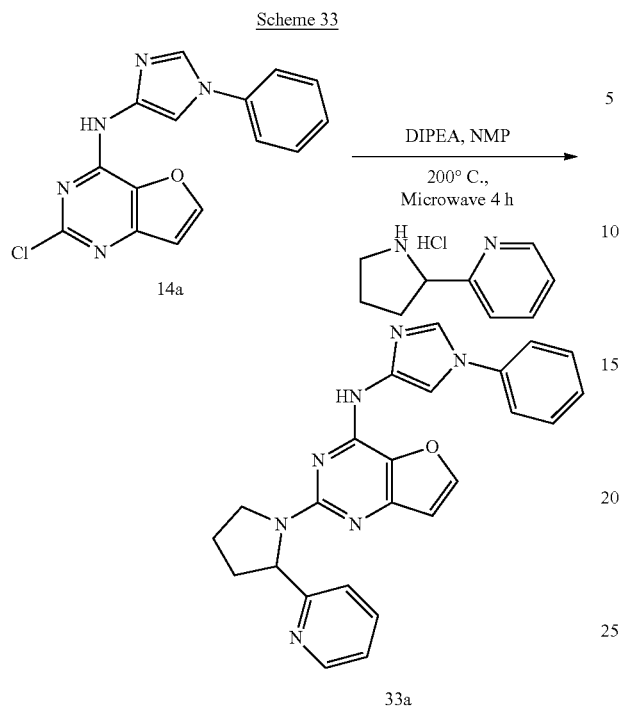

Preparation of N-(1-phenyl-1H-imidazol-4-yl)-2-(2-(pyridin-2-yl)pyrrolidin-1-yl)furo[3,2-d]pyrimidin-4-amine (33a)

Compound 33a was prepared from 2-chloro-N-(1-phenyl-1H-imidazol-4-yl)furo[3,2-d]pyrimidin-4-amine (14a) (100 mg, 0.32 mmol), 2-(pyrrolidin-2-yl)pyridine hydrochloride (148 mg, 0.8 mmol), and DIPEA (0.22 mL, 1.28 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-phenyl-1H-imidazol-4-yl)-2-(2-(pyridin-2-yl)pyrrolidin-1-yl)furo[3,2-d]pyrimidin-4-amine (33a) (61 mg, 45% yield) as a light brown solid; $^1$H NMR (300 MHz, DMSO-d$_6$) δ 10.03 (s, 1H, D$_2$O exchangeable), 8.26 (s, 1H), 8.17-7.90 (m, 2H), 7.80-7.45 (m, 5H), 7.39 (p, J=8.5, 4.2 Hz, 1H), 7.35-7.18 (m, 1H), 7.11 (d, J=7.7 Hz, 2H), 6.77 (s, 1H), 5.39 (s, 1H), 4.01-3.82 (m, 1H), 3.79-3.54 (m, 1H), 2.45-2.28 (m, 1H), 2.11-1.88 (m, 2H), 1.88-1.71 (m, 1H); MS (ES+): 424.5 (M+1), 446.5 (M+Na).

Scheme 34

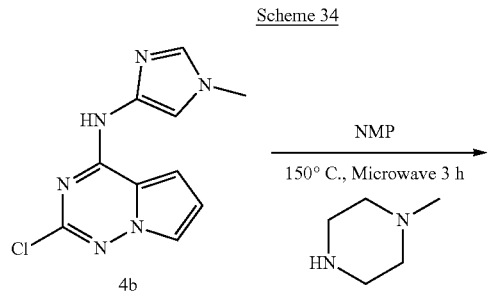

Preparation of N-(1-methyl-1H-imidazol-4-yl)-2-(4-methylpiperazin-1-yl)pyrrolo[2,1-f][1,2,4]triazin-4-amine (34a)

Compound 34a was prepared from 2-chloro-N-(1-methyl-1H-imidazol-4-yl)pyrrolo[1,2-f][1,2,4]triazin-4-amine (4b) (100 mg, 0.4 mmol), 1-methylpiperazine (0.13 mL, 1.21 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-methyl-1H-imidazol-4-yl)-2-(4-methylpiperazin-1-yl)pyrrolo[2,1-f][1,2,4]triazin-4-amine (34a) (37 mg, 30% yield) as an off-white solid; $^1$H NMR (300 MHz, DMSO-d$_6$) δ 10.32 (s, 1H, D$_2$O exchangeable), 7.49 (d, J=1.4 Hz, 1H), 7.37 (t, J=2.1 Hz, 1H), 7.30 (d, J=1.6 Hz, 1H), 7.11 (s, 1H), 6.41 (dd, J=4.5, 2.5 Hz, 1H), 3.69 (s, 3H), 3.55 (t, J=4.9 Hz, 4H), 2.41 (q, J=5.0 Hz, 4H), 2.22 (s, 3H); MS (ES+): 313.4 (M+1), 325.4 (M+Na).

Scheme 35

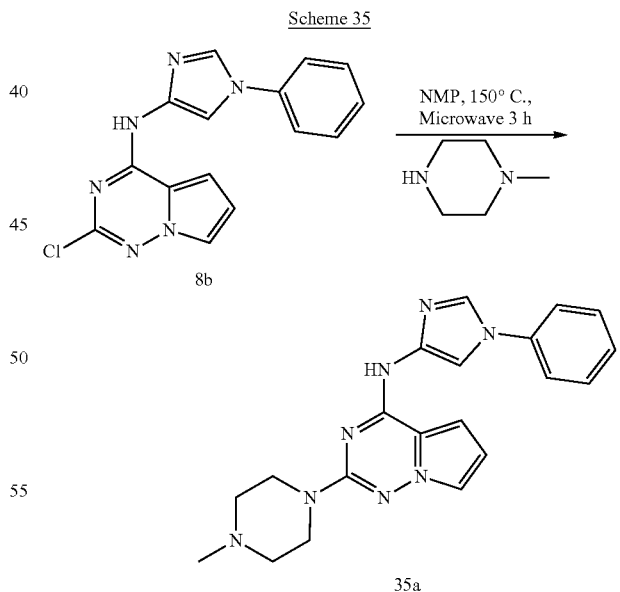

Preparation of 2-(4-methylpiperazin-1-yl)-N-(1-phenyl-1H-imidazol-4-yl)pyrrolo[2,1-f][1,2,4]triazin-4-amine (35a)

Compound 35a was prepared from 2-chloro-N-(1-phenyl-1H-imidazol-4-yl)pyrrolo[2,1-f][1,2,4]triazin-4-amine (8b)

(100 mg, 0.32 mmol), 1-methylpiperazine (0.11 mL, 0.97 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, 2-(4-methylpiperazin-1-yl)-N-(1-phenyl-1H-imidazol-4-yl)pyrrolo[2,1-f][1,2,4]triazin-4-amine (35a) (16 mg, 13% yield) as a brown solid; $^1$H NMR (300 MHz, DMSO-d$_6$) δ 10.59 (s, 1H, D$_2$O exchangeable), 8.23 (d, J=1.6 Hz, 1H), 7.83 (d, J=1.6 Hz, 1H), 7.63 (dd, J=8.5, 1.5 Hz, 2H), 7.56 (dd, J=8.7, 7.1 Hz, 2H), 7.45-7.39 (m, 1H), 7.39-7.34 (m, 1H), 7.16 (d, J=4.3 Hz, 1H), 6.45 (dd, J=4.4, 2.5 Hz, 1H), 3.66-3.52 (m, 4H), 2.50-2.36 (m, 4H), 2.23 (s, 3H); MS (ES+): 375.5 (M+1).

4]triazine (4a) (260 mg, 1.38 mmol) in 2-Propanol (20 mL) using DIPEA (0.73 mL, 4.15 mmol) and 1-(2-fluorophenyl)-1H-imidazol-4-amine hydrochloride (36a) (450 mg, 1.8 mmol). This gave 2-chloro-N-(1-(2-fluorophenyl)-1H-imidazol-4-yl)pyrrolo[2,1-f][1,2,4]triazin-4-amine (36b) (125 mg, 28% yield) as a pale-off colored solid; $^1$H NMR (300 MHz, DMSO-d$_6$) δ 11.40 (s, 1H, D$_2$O exchangeable), 8.08 (t, J=1.5 Hz, 1H), 7.83 (t, J=1.9 Hz, 1H), 7.77 (dd, J=2.6, 1.5 Hz, 2H), 7.73 (td, J=7.9, 1.6 Hz, 1H), 7.59-7.46 (m, 2H), 7.40 (ddd, J=9.1, 6.0, 2.0 Hz, 2H); $^{19}$F NMR (282 MHz, DMSO-d$_6$) δ −125.09; MS (ES+): 329.3 (M+1); MS (ES−): 363.4 (M+Cl).

Step-2: Preparation of (S)-(1-(4-((1-(2-fluorophenyl)-1H-imidazol-4-yl)amino)pyrrolo[2,1-f][1,2,4]triazin-2-yl)pyrrolidin-2-yl)methanol (36c)

Compound 36c was prepared from 2-chloro-N-(1-(2-fluorophenyl)-1H-imidazol-4-yl)pyrrolo[2,1-f][1,2,4]triazin-4-amine (36b) (70 mg, 0.21 mmol), (S)-pyrrolidin-2-ylmethanol (108 mg, 1.07 mmol), and DIPEA (0.11 mL, 0.64 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(2-fluorophenyl)-1H-imidazol-4-yl)amino)pyrrolo[2,1-f][1,2,4]triazin-2-yl)pyrrolidin-2-yl)methanol (36c) (45 mg, 54% yield) as a light yellow solid; $^1$H NMR (300 MHz, DMSO-d$_6$) δ 10.56 (s, 1H, D$_2$O exchangeable), 8.02 (t, J=1.8 Hz, 1H), 7.87 (t, J=1.7 Hz, 1H), 7.76 (td, J=7.9, 1.7 Hz, 1H), 7.55-7.41 (m, 2H), 7.40-7.31 (m, 2H), 7.15 (dd, J=4.5, 1.7 Hz, 1H), 6.39 (dd, J=4.4, 2.4 Hz, 1H), 4.74 (t, J=5.2 Hz, 1H, D$_2$O exchangeable), 4.20-4.04 (m, 1H), 3.72-3.62 (m, 1H), 3.54-3.44 (m, 1H), 3.46-3.26 (m, 2H), 2.08-1.79 (m, 4H); $^{19}$F NMR (282 MHz, DMSO-d$_6$) δ −125.10; MS (ES+): 394.5 (M+1); 416.5 (M+Na); MS (ES−): 392.5 (M−1), 428.5 (M+Cl).

Scheme 36

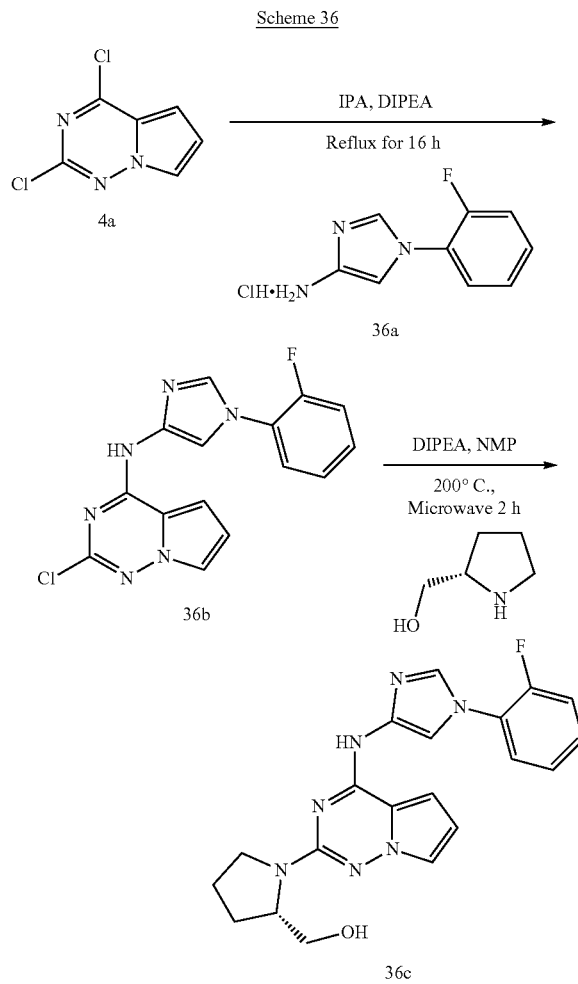

Preparation of (S)-(1-(4-((1-(2-fluorophenyl)-1H-imidazol-4-yl)amino)pyrrolo[2,1-f][1,2,4]triazin-2-yl)pyrrolidin-2-yl)methanol (36c)

Step-1: Preparation of 2-chloro-N-(1-(2-fluorophenyl)-1H-imidazol-4-yl)pyrrolo[2,1-f][1,2,4]triazin-4-amine (36b)

Compound 36b was prepared according to the procedure reported in Scheme 1 from 2,4-dichloropyrrolo[1,2-f][1,2, Scheme 37

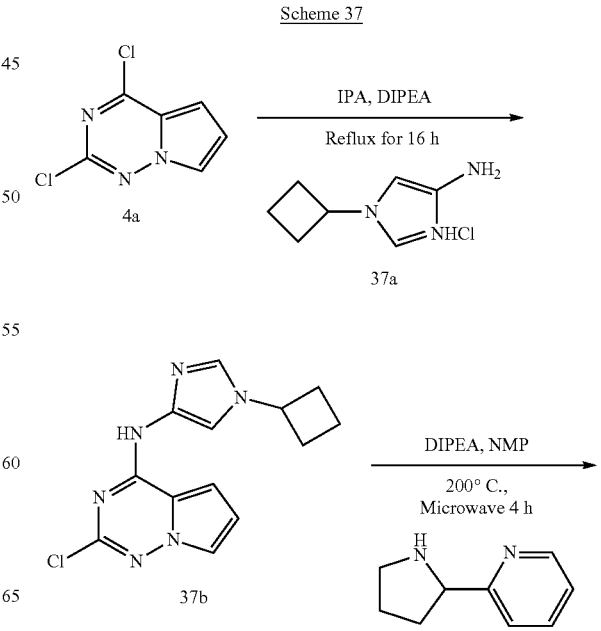

181

-continued

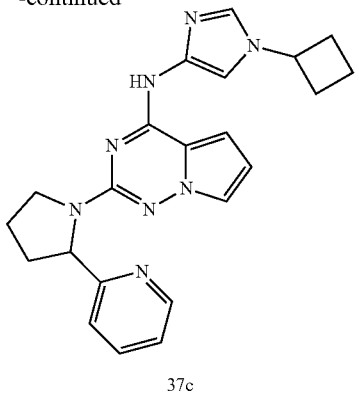

37c

Preparation of N-(1-cyclobutyl-1H-imidazol-4-yl)-2-(2-(pyridin-2-yl)pyrrolidin-1-yl)pyrrolo[2,1-f][1,2,4]triazin-4-amine (37c)

Step-1: Preparation of 2-chloro-N-(1-cyclobutyl-1H-imidazol-4-yl)pyrrolo[2,1-f][1,2,4]triazin-4-amine (37b)

Compound 37b was prepared according to the procedure reported in Scheme 1 from 2,4-dichloropyrrolo[1,2-f][1,2,4]triazine (4a) (350 mg, 1.86 mmol) in 2-Propanol (20 mL) using DIPEA (0.98 mL, 5.58 mmol) and 1-cyclobutyl-1H-imidazol-4-amine hydrochloride (37a) (420 mg, 2.42 mmol). This gave 2-chloro-N-(1-cyclobutyl-1H-imidazol-4-yl)pyrrolo[2,1-f][1,2,4]triazin-4-amine (37b) (348 mg, 65% yield) as a yellowish solid; $^1$H NMR (300 MHz, DMSO-$d_6$) δ 11.16 (s, 1H, D$_2$O exchangeable), 7.83-7.62 (m, 2H), 7.53 (d, J=1.6 Hz, 1H), 7.35 (dd, J=4.5, 1.6 Hz, 1H), 6.68 (dd, J=4.4, 2.6 Hz, 1H), 4.88-4.61 (m, 1H), 2.55-2.19 (m, 4H), 1.96-1.64 (m, 2H); MS (ES+): 289.3 (M+1), 311.3 (M+Na); MS (ES−): 287.3 (M−1).

Step-2: Preparation of N-(1-cyclobutyl-1H-imidazol-4-yl)-2-(2-(pyridin-2-yl)pyrrolidin-1-yl)pyrrolo[2,1-f][1,2,4]triazin-4-amine (37c)

Compound 37c was prepared from 2-chloro-N-(1-cyclobutyl-1H-imidazol-4-yl)pyrrolo[2,1-f][1,2,4]triazin-4-amine (37b) (70 mg, 0.24 mmol), 2-(pyrrolidin-2-yl)pyridine (108 mg, 0.73 mmol), and DIPEA (0.13 mL, 0.73 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-cyclobutyl-1H-imidazol-4-yl)-2-(2-(pyridin-2-yl)pyrrolidin-1-yl)pyrrolo[2,1-f][1,2,4]triazin-4-amine (37c) (65 mg, 67% yield) as a light yellow solid; $^1$H NMR (300 MHz, DMSO-$d_6$) δ 10.27 (s, 1H, D$_2$O exchangeable), 8.59 (d, J=4.8 Hz, 1H), 7.67 (t, J=7.7 Hz, 1H), 7.56 (s, 1H), 7.38 (s, 1H), 7.29-7.12 (m, 2H), 7.08 (d, J=4.4 Hz, 1H), 7.05-6.93 (m, 1H), 6.42-6.30 (m, 1H), 5.35 (d, J=8.2 Hz, 1H), 4.55 (q, J=8.6 Hz, 1H), 3.90-3.75 (m, 1H), 3.71-3.54 (m, 1H), 2.45-2.26 (m, 4H), 2.26-2.09 (m, 1H), 2.12-1.99 (m, 1H), 2.02-1.88 (m, 1H), 1.89-1.69 (m, 3H). MS (ES+): 401.5 (M+1); 423.5 (M+Na).

182

Scheme 38

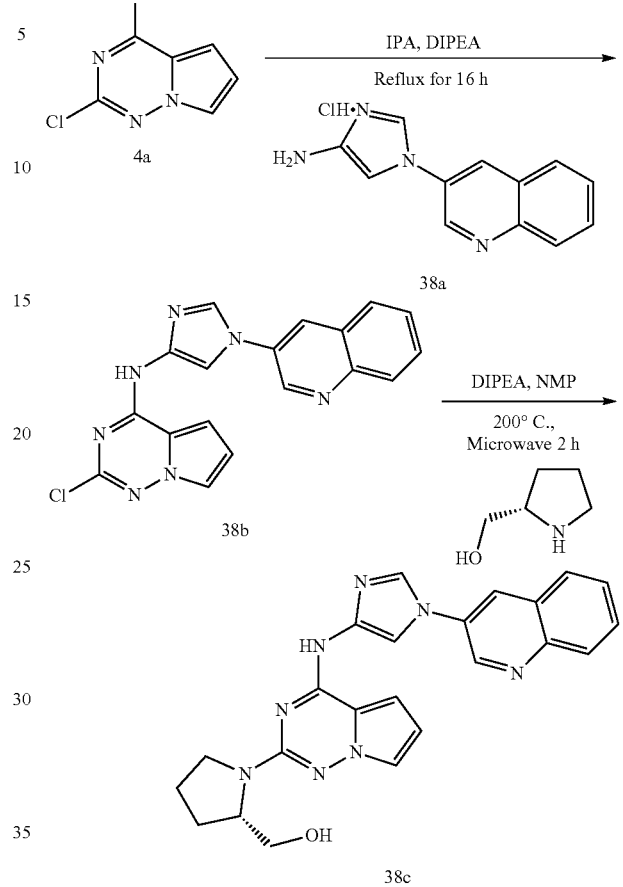

Preparation of (S)-(1-(4-((1-(quinolin-3-yl)-1H-imidazol-4-yl)amino)pyrrolo[2,1-f][1,2,4]triazin-2-yl)pyrrolidin-2-yl)methanol (38c)

Step-1: Preparation of 2-chloro-N-(1-(quinolin-3-yl)-1H-imidazol-4-yl)pyrrolo[2,1-f][1,2,4]triazin-4-amine (38b)

Compound 38b was prepared according to the procedure reported in Scheme 1 from 2,4-dichloropyrrolo[1,2-f][1,2,4]triazine (4a) (384 mg, 2.04 mmol) in 2-Propanol (20 mL) using DIPEA (1.07 mL, 6.12 mmol) and 11-(quinolin-3-yl)-1H-imidazol-4-amine hydrochloride (38a) (730 mg, 2.96 mmol). This gave 2-chloro-N-(1-(quinolin-3-yl)-1H-imidazol-4-yl)pyrrolo[2,1-f][1,2,4]triazin-4-amine (38b) (264 mg, 36% yield) as a pale off-white colored solid; $^1$H NMR (300 MHz, DMSO-$d_6$) δ 11.41 (s, 1H), 9.30 (d, J=2.7 Hz, 1H), 8.68 (d, J=2.6 Hz, 1H), 8.47 (d, J=1.6 Hz, 1H), 8.16-8.06 (m, 3H), 7.88-7.76 (m, 2H), 7.71 (t, J=7.4 Hz, 1H), 7.42 (d, J=4.3 Hz, 1H), 6.74 (dd, J=4.5, 2.6 Hz, 1H); $^1$H NMR (300 MHz, DMSO-$d_6$/D$_2$O) δ 9.24 (d, J=2.5 Hz, 1H), 8.63 (d, J=2.6 Hz, 1H), 8.41 (s, 1H), 8.16-8.00 (m, 3H), 7.80 (t, J=7.7 Hz, 1H), 7.75 (d, J=2.0 Hz, 1H), 7.69 (t, J=7.5 Hz, 1H), 7.36 (s, 1H), 6.72 (dd, J=4.4, 2.5 Hz, 1H); MS (ES+): 362.3 (M+1), 384.3 (M+Na); MS (ES−): 360.2 (M−1).

Step-2: Preparation of (S)-(1-(4-((1-(quinolin-3-yl)-1H-imidazol-4-yl)amino)pyrrolo[2,1-f][1,2,4]triazin-2-yl)pyrrolidin-2-yl)methanol (38c)

Compound 38c was prepared from 2-chloro-N-(1-(quinolin-3-yl)-1H-imidazol-4-yl)pyrrolo[2,1-f][1,2,4]triazin-4-amine (38b) (100 mg, 0.28 mmol), (S)-pyrrolidin-2-yl-methanol (140 mg, 1.38 mmol), and DIPEA (0.15 mL, 0.83 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(quinolin-3-yl)-1H-imidazol-4-yl)amino)pyrrolo[2,1-f][1,2,4]triazin-2-yl)pyrrolidin-2-yl)methanol (38c) (66 mg, 56% yield) as a yellow solid; $^1$H NMR (300 MHz, DMSO-d$_6$) δ 10.63 (s, 1H, D$_2$O exchangeable), 9.42 (d, J=2.7 Hz, 1H), 8.81 (d, J=2.6 Hz, 1H), 8.53 (d, J=1.5 Hz, 1H), 8.15 (d, J=1.6 Hz, 1H), 8.12-8.00 (m, 2H), 7.79 (ddd, J=8.4, 6.9, 1.6 Hz, 1H), 7.69 (td, J=7.5, 6.9, 1.3 Hz, 1H), 7.41 (dd, J=2.4, 1.7 Hz, 1H), 7.18 (dd, J=4.4, 1.7 Hz, 1H), 6.41 (dd, J=4.5, 2.4 Hz, 1H), 5.28-5.16 (m, 1H, D$_2$O exchangeable), 4.37-4.18 (m, 1H), 3.93-3.79 (m, 1H), 3.56-3.40 (m, 1H), 3.45-3.20 (m, 2H), 2.21-1.72 (m, 4H). MS (ES+): 427.5 (M+1); 449.5 (M+Na).

Preparation of (S)-(1-(4-((1-(pyridin-3-yl)-1H-imidazol-4-yl)amino)pyrrolo[2,1-f][1,2,4]triazin-2-yl)pyrrolidin-2-yl)methanol (39c)

Step-1: Preparation of 2-chloro-N-(1-(pyridin-3-yl)-1H-imidazol-4-yl)pyrrolo[2,1-f][1,2,4]triazin-4-amine (39b)

Compound 39b was prepared according to the procedure reported in Scheme 1 from 2,4-dichloropyrrolo[1,2-f][1,2,4]triazine (4a) (500 mg, 2.66 mmol) in 2-Propanol (20 mL) using DIPEA (1.39 mL, 7.98 mmol) and 1-(pyridin-3-yl)-1H-imidazol-4-amine (39a) (511 mg, 3.19 mmol). This gave 2-chloro-N-(1-(pyridin-3-yl)-1H-imidazol-4-yl)pyrrolo[2,1-f][1,2,4]triazin-4-amine (39b) (728 mg, 88% yield) as a brownish solid; $^1$H NMR (300 MHz, DMSO-d$_6$) δ 11.38 (s, 1H, D$_2$O exchangeable), 8.96 (d, J=2.7 Hz, 1H), 8.61 (dd, J=4.7, 1.4 Hz, 1H), 8.35 (d, J=1.6 Hz, 1H), 8.13 (ddd, J=8.3, 2.8, 1.4 Hz, 1H), 7.97 (d, J=1.6 Hz, 1H), 7.78 (dd, J=2.6, 1.5 Hz, 1H), 7.61 (dd, J=8.3, 4.7 Hz, 1H), 7.47-7.35 (m, 1H), 6.73 (dd, J=4.5, 2.6 Hz, 1H); MS (ES+): 312.3 (M+1); MS (ES−): 310.4 (M−1).

Step-2: Preparation of (S)-(1-(4-((1-(pyridin-3-yl)-1H-imidazol-4-yl)amino)pyrrolo[2,1-f][1,2,4]triazin-2-yl)pyrrolidin-2-yl)methanol (39c)

Compound 39c was prepared from 2-chloro-N-(1-(pyridin-3-yl)-1H-imidazol-4-yl)pyrrolo[2,1-f][1,2,4]triazin-4-amine (39b) (100 mg, 0.32 mmol), (S)-pyrrolidin-2-yl-methanol (162 mg, 1.60 mmol), and DIPEA (0.17 mL, 0.96 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(pyridin-3-yl)-1H-imidazol-4-yl)amino)pyrrolo[2,1-f][1,2,4]triazin-2-yl)pyrrolidin-2-yl)methanol (39c) (60 mg, 50% yield) as a brownish solid; $^1$H NMR (300 MHz, DMSO-d$_6$) δ 10.59 (s, 1H, D$_2$O exchangeable), 9.04 (d, J=2.7 Hz, 1H), 8.55 (dd, J=4.7, 1.3 Hz, 1H), 8.35 (d, J=1.5 Hz, 1H), 8.25-8.14 (m, 1H), 8.01 (d, J=1.6 Hz, 1H), 7.54 (dd, J=8.3, 4.7 Hz, 1H), 7.40 (t, J=2.1 Hz, 1H), 7.16 (dd, J=4.4, 1.7 Hz, 1H), 6.40 (dd, J=4.4, 2.5 Hz, 1H), 5.13-4.74 (m, 1H, D$_2$O exchangeable), 4.28-4.13 (m, 1H), 3.77 (dd, J=10.1, 3.4 Hz, 1H), 3.55-3.44 (m, 1H), 3.46-3.25 (m, 2H), 2.18-1.77 (m, 4H). MS (ES+): 377.5 (M+1); 399.5 (M+Na).

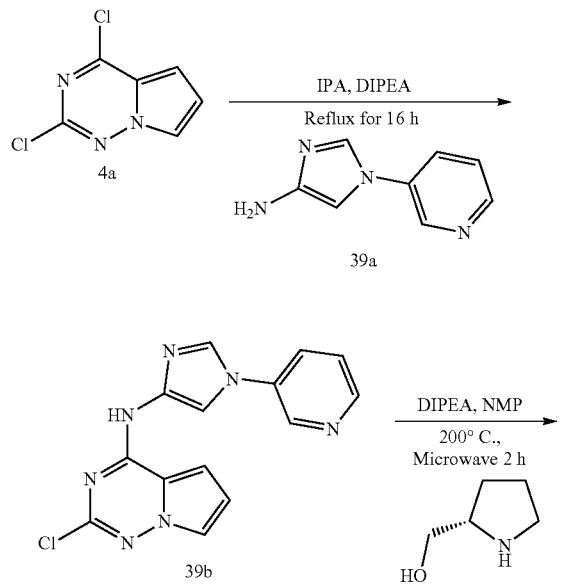

Scheme 39

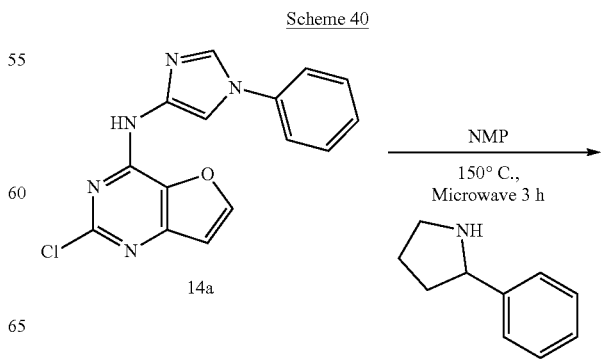

Scheme 40

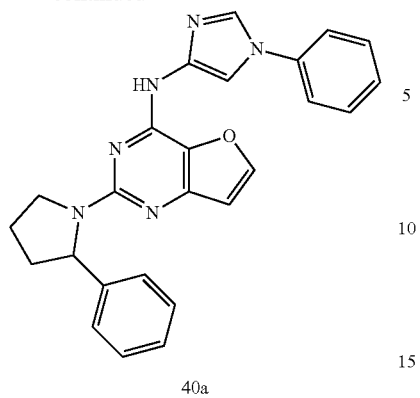

40a

Preparation of N-(1-phenyl-1H-imidazol-4-yl)-2-(2-phenylpyrrolidin-1-yl)furo[3,2-d]pyrimidin-4-amine (40a)

Compound 40a was prepared from 2-chloro-N-(1-phenyl-1H-imidazol-4-yl)furo[3,2-d]pyrimidin-4-amine (14a) (100 mg, 0.32 mmol), 2-phenylpyrrolidine (118 mg, 0.8 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-phenyl-1H-imidazol-4-yl)-2-(2-phenylpyrrolidin-1-yl)furo[3,2-d]pyrimidin-4-amine (40a) (18 mg, 13% yield) as a light yellow solid; $^1$H NMR (300 MHz, DMSO-d$_6$) δ 10.04 (s, 1H, D$_2$O exchangeable), 8.19-7.83 (m, 2H), 7.66-7.50 (m, 2H), 7.54-7.25 (m, 2H), 7.26-7.14 (m, 3H), 7.16-7.00 (m, 4H), 6.74 (s, 1H), 5.41 (s, 1H), 3.99-3.57 (m, 2H), 2.40-2.24 (m, 1H), 1.98-1.63 (m, 3H); MS (ES+) 423.5 (M+1), 445.5 (M+Na).

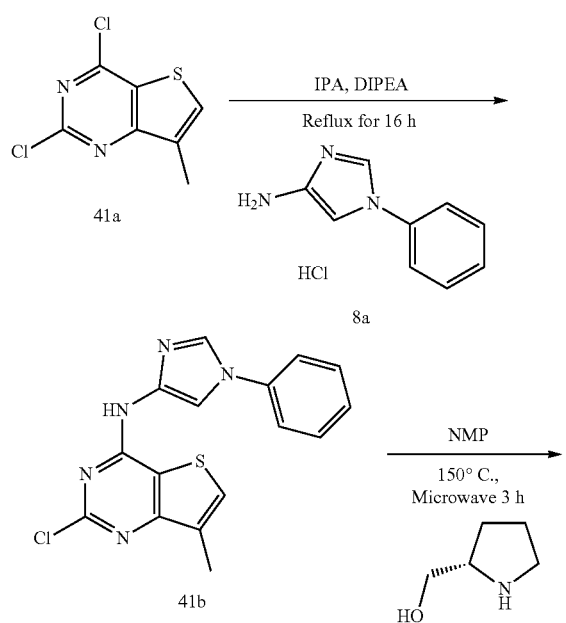

Scheme 41

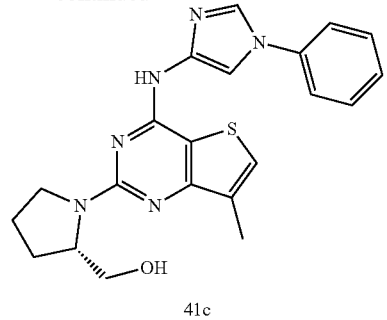

41c

Preparation of (S)-(1-(7-methyl-4-((1-phenyl-1H-imidazol-4-yl)amino)thieno[3,2-d]pyrimidin-2-yl)pyrrolidin-2-yl)methanol (41c)

Step-1: Preparation of 2-chloro-7-methyl-N-(1-phenyl-1H-imidazol-4-yl)thieno[3,2-d]pyrimidin-4-amine (41b)

Compound 41b was prepared according to the procedure reported in Scheme 1 from 2,4-dichloro-7-methylthieno[3,2-d]pyrimidine (41a) (500 mg, 2.28 mmol; CAS #35265-83-9) and DIPEA (1.59 mL, 9.13 mmol) in 2-Propanol (10 mL) using 1-phenyl-1H-imidazol-4-amine, HCl (8a) (558 mg, 2.85 mmol). This gave 2-chloro-7-methyl-N-(1-phenyl-1H-imidazol-4-yl)thieno[3,2-d]pyrimidin-4-amine (41b) (350 mg, 45% yield) as an off-white solid; $^1$H NMR (300 MHz, DMSO-d$_6$) δ 10.72 (s, 1H, D$_2$O exchangeable), 8.27 (d, J=1.6 Hz, 1H), 7.95 (d, J=1.6 Hz, 1H), 7.89 (s, 1H), 7.72-7.63 (m, 2H), 7.57 (dd, J=8.6, 7.1 Hz, 2H), 7.46-7.36 (m, 1H), 2.31 (d, J=1.2 Hz, 3H); MS (ES+): 342.3 (M+1), 364.3 (M+Na), (ES−): 340.3 (M−1).

Step-2: Preparation of (S)-(1-(7-methyl-4-((1-phenyl-1H-imidazol-4-yl)amino)thieno[3,2-d]pyrimidin-2-yl)pyrrolidin-2-yl)methanol (41c)

Compound 41c was prepared from 2-chloro-7-methyl-N-(1-phenyl-1H-imidazol-4-yl)thieno[3,2-d]pyrimidin-4-amine (41b) (100 mg, 0.29 mmol) and (S)-pyrrolidin-2-ylmethanol (89 mg, 0.88 mmol), in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(7-methyl-4-((1-phenyl-1H-imidazol-4-yl)amino)thieno[3,2-d]pyrimidin-2-yl)pyrrolidin-2-yl)methanol (41c) (82 mg, 69% yield) as an off-white solid; $^1$H NMR (300 MHz, DMSO-d$_6$) δ 10.08 (s, 1H, D$_2$O exchangeable), 8.20 (d, J=1.5 Hz, 1H), 7.99 (d, J=1.6 Hz, 1H), 7.71 (s, 2H), 7.57 (d, J=1.3 Hz, 1H), 7.51 (t, J=7.7 Hz, 2H), 7.35 (t, J=7.4 Hz, 1H), 5.65-4.81 (m, 1H, D$_2$O exchangeable), 4.26 (s, 1H), 3.86-3.52 (m, 2H), 3.51-3.24 (m, 2H), 2.22 (d, J=1.2 Hz, 3H), 2.11-1.81 (m, 4H); MS (ES+): 407.5 (M+1), 429.5 (M+Na), (ES−): 405.5 (M−1).

Scheme 42

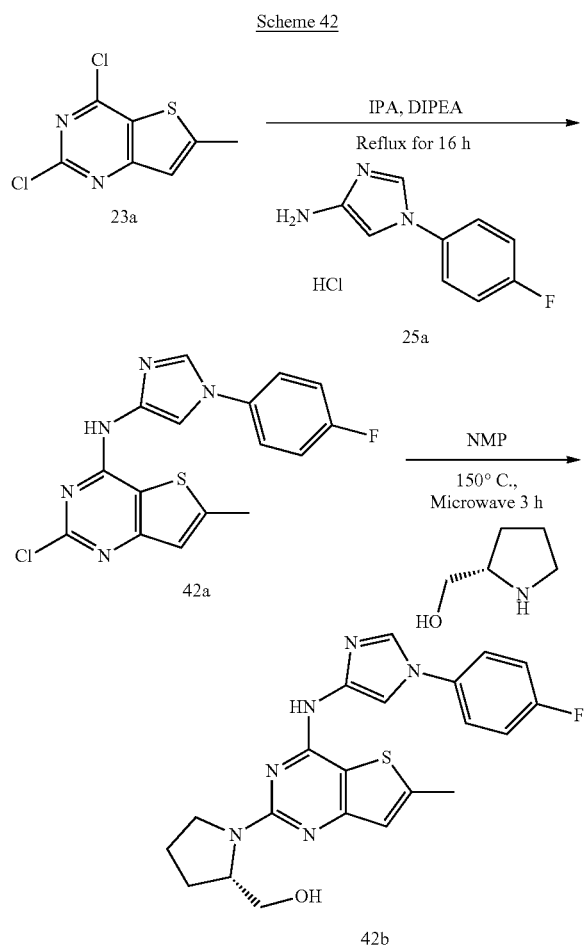

Preparation of (S)-(1-(4-((1-(4-fluorophenyl)-1H-imidazol-4-yl)amino)-6-methylthieno[3,2-d]pyrimidin-2-yl)pyrrolidin-2-yl)methanol (42b)

Step-1: Preparation of 2-chloro-N-(1-(4-fluorophenyl)-1H-imidazol-4-yl)-6-methylthieno[3,2-d]pyrimidin-4-amine (42a)

Compound 42a was prepared according to the procedure reported in Scheme 1 from 2,4-dichloro-6-methylthieno[3,2-d]pyrimidine (23a) (302 mg, 1.38 mmol) in 2-Propanol (10 mL) using DIPEA (0.96 mL, 5.51 mmol), 1-(4-fluorophenyl)-1H-imidazol-4-amine hydrochloride (25a) (368 mg, 1.72 mmol). This gave 2-chloro-N-(1-(4-fluorophenyl)-1H-imidazol-4-yl)-6-methylthieno[3,2-d]pyrimidin-4-amine (42a) (100 mg, 21% yield) as a dark brown solid; $^1$H NMR (300 MHz, DMSO-$d_6$) δ 10.74 (s, 1H, $D_2O$ exchangeable), 8.22 (d, J=1.6 Hz, 1H), 7.88 (d, J=1.6 Hz, 1H), 7.76-7.67 (m, 2H), 7.48-7.37 (m, 2H), 7.13 (d, J=1.3 Hz, 1H), 2.60 (s, 3H); $^{19}$F NMR (282 MHz, DMSO-$d_6$) δ −115.30; MS (ES+): 382.4 (M+Na), (ES−): 358.3 (M−1).

Step-2: Preparation of (S)-(1-(4-((1-(4-fluorophenyl)-1H-imidazol-4-yl)amino)-6-methylthieno[3,2-d]pyrimidin-2-yl)pyrrolidin-2-yl)methanol (42b)

Compound 42b was prepared from 2-chloro-N-(1-(4-fluorophenyl)-1H-imidazol-4-yl)-6-methylthieno[3,2-d]pyrimidin-4-amine (42a) (90 mg, 0.25 mmol) and (S)-pyrrolidin-2-ylmethanol (89 mg, 0.88 mmol), in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using $NaHCO_3$, (S)-(1-(4-((1-(4-fluorophenyl)-1H-imidazol-4-yl)amino)-6-methylthieno[3,2-d]pyrimidin-2-yl)pyrrolidin-2-yl)methanol (42b) (27 mg, 25% yield) as a brown solid; $^1$H NMR (300 MHz, DMSO-$d_6$) δ 9.95 (s, 1H, $D_2O$ exchangeable), 8.14 (d, J=1.6 Hz, 1H), 7.92 (d, J=1.7 Hz, 1H), 7.86-7.62 (m, 2H), 7.35 (t, J=8.6 Hz, 2H), 6.83 (d, J=1.3 Hz, 1H), 5.06 (s, 1H, $D_2O$ exchangeable), 4.37-4.01 (m, 1H), 3.89-3.68 (m, 1H), 3.68-3.44 (m, 3H), 2.52 (d, J=1.1 Hz, 3H), 2.16-1.72 (m, 4H); $^{19}$F NMR (282 MHz, DMSO-$d_6$) δ −73.43; MS (ES+): 425.4 (M+1), 447.4 (M+Na), (ES−): 423.4 (M−1).

Scheme 43

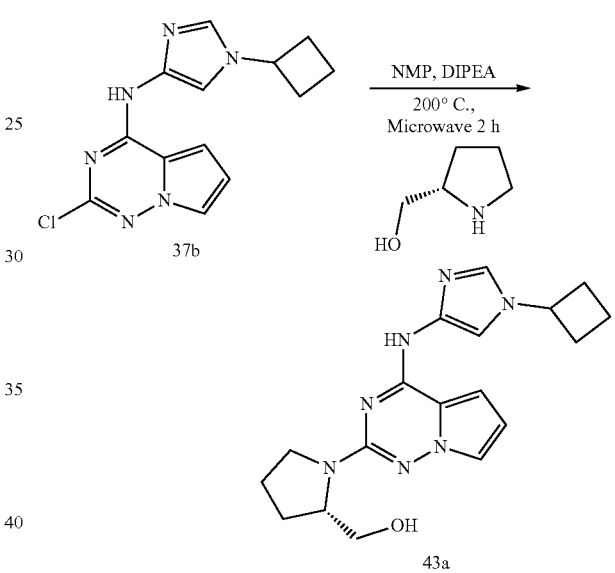

Preparation of (S)-(1-(4-((1-cyclobutyl-1H-imidazol-4-yl)amino)pyrrolo[2,1-f][1,2,4]triazin-2-yl)pyrrolidin-2-yl)methanol (43a)

Compound 43a was prepared from 2-chloro-N-(1-cyclobutyl-1H-imidazol-4-yl)pyrrolo[2,1-f][1,2,4]triazin-4-amine (37b) (100 mg, 0.35 mmol) and (S)-pyrrolidin-2-ylmethanol (175 mg, 1.73 mmol) and DIPEA (0.18 mL, 1.04 mmol) in NMP (1 mL) according to the procedure reported in Scheme 2. This gave after workup and purification by flash chromatography (silica gel 24 g, eluting with CMA-80 in Chloroform 0-40%) (S)-(1-(4-((1-cyclobutyl-1H-imidazol-4-yl)amino)pyrrolo[2,1-f][1,2,4]triazin-2-yl)pyrrolidin-2-yl)methanol (43a) (67 mg, 55% yield) as a yellow solid; $^1$H NMR (300 MHz, DMSO-$d_6$) δ 10.33 (s, 1H, $D_2O$ exchangeable), 7.67-7.56 (m, 2H), 7.42-7.29 (m, 1H), 7.09 (dd, J=4.4, 1.7 Hz, 1H), 6.36 (dd, J=4.4, 2.4 Hz, 1H), 4.97-4.76 (m, 1H, $D_2O$ exchangeable), 4.69 (p, J=8.5 Hz, 1H), 4.29-4.05 (m, 1H), 3.84-3.67 (m, 1H), 3.55-3.42 (m, 1H), 3.41-3.19 (m, 2H), 2.52-2.28 (m, 4H), 2.12-1.83 (m, 4H), 1.83-1.62 (m, 2H); $^{19}$F NMR (282 MHz, DMSO) δ −73.48; MS (ES+): 354.5 (M+1); 376.5 (M+Na); MS (ES−): 352.4 (M−1).

Scheme 44

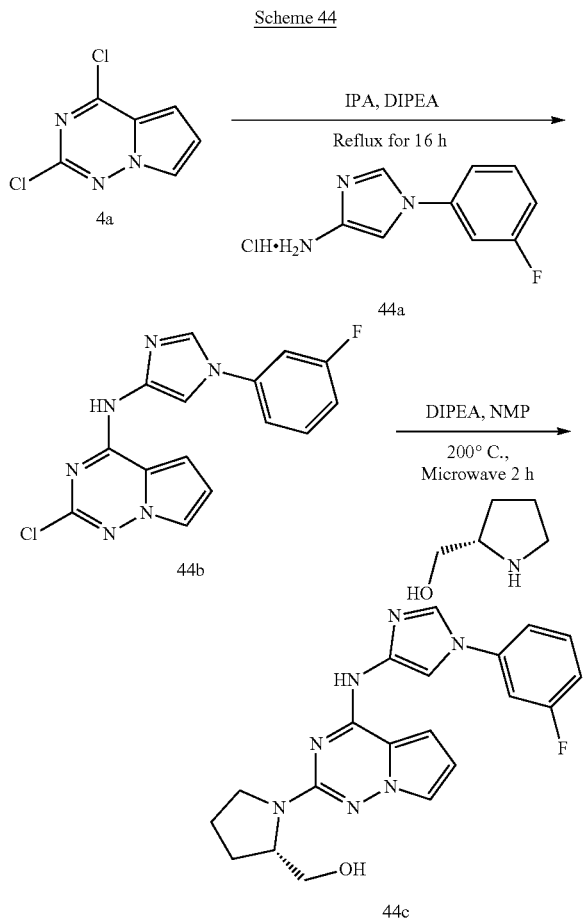

Preparation of (S)-(1-(4-((1-(3-fluorophenyl)-1H-imidazol-4-yl)amino)pyrrolo[2,1-f][1,2,4]triazin-2-yl)pyrrolidin-2-yl)methanol (44c)

Step-1: Preparation of 2-chloro-N-(1-(3-fluorophenyl)-1H-imidazol-4-yl)pyrrolo[2,1-f][1,2,4]triazin-4-amine (44b)

Compound 44b was prepared according to the procedure reported in Scheme 1 from 2,4-dichloropyrrolo[1,2-f][1,2,4]triazine (4a) (254 mg, 1.35 mmol) in 2-Propanol (20 mL) using DIPEA (0.71 mL, 4.06 mmol) and 1-(3-fluorophenyl)-1H-imidazol-4-amine hydrochloride (44a) (440 mg, 1.76 mmol). This gave 2-chloro-N-(1-(3-fluorophenyl)-1H-imidazol-4-yl)pyrrolo[2,1-f][1,2,4]triazin-4-amine (44b) (343 mg, 77% yield) as a pale-off colored solid; $^1$H NMR (300 MHz, DMSO-d6) δ 11.35 (s, 1H, D$_2$O exchangeable), 8.33 (d, J=1.6 Hz, 1H), 7.95 (d, J=1.6 Hz, 1H), 7.78 (dd, J=2.6, 1.5 Hz, 1H), 7.67 (dt, J=10.1, 2.1 Hz, 1H), 7.63-7.57 (m, 1H), 7.55-7.49 (m, 1H), 7.44-7.37 (m, 1H), 7.30-7.20 (m, 1H), 6.73 (dd, J=4.5, 2.6 Hz, 1H); MS (ES+): 329.3 (M+1), 351.3 (M+Na); MS (ES−): 327.3 (M−1).

Step-2: Preparation of (S)-(1-(4-((1-(3-fluorophenyl)-1H-imidazol-4-yl)amino)pyrrolo[2,1-f][1,2,4]triazin-2-yl)pyrrolidin-2-yl)methanol (44c)

Compound 44c was prepared from 2-chloro-N-(1-(3-fluorophenyl)-1H-imidazol-4-yl)pyrrolo[2,1-f][1,2,4]triazin-4-amine (44b) (100 mg, 0.3 mmol), (S)-pyrrolidin-2-ylmethanol (154 mg, 1.52 mmol), and DIPEA (0.16 mL, 0.91 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$ followed by flash chromatography [silica gel (24 g), eluting with CMA-80 in chloroform, 0 to 40%], (S)-(1-(4-((1-(3-fluorophenyl)-1H-imidazol-4-yl)amino)pyrrolo[2,1-f][1,2,4]triazin-2-yl)pyrrolidin-2-yl)methanol (44c) (30 mg, 25% yield) as a white solid; $^1$H NMR (300 MHz, DMSO-d$_6$) δ 10.54 (s, 1H, D$_2$O exchangeable), 8.33 (d, J=1.6 Hz, 1H), 7.97 (d, J=1.6 Hz, 1H), 7.81-7.70 (m, 1H), 7.69-7.60 (m, 1H), 7.58-7.46 (m, 1H), 7.40 (dd, J=2.4, 1.7 Hz, 1H), 7.23-7.13 (m, 2H), 6.39 (dd, J=4.4, 2.5 Hz, 1H), 5.07-4.90 (m, 1H, D$_2$O exchangeable), 4.26-4.12 (m, 1H), 3.85-3.67 (m, 1H), 3.56-3.43 (m, 1H), 3.44-3.22 (m, 2H), 2.22-1.75 (m, 4H); $^{19}$F NMR (282 MHz, DMSO) δ −110.92; MS (ES+): 394.5 (M+1); 416.5 (M+Na); MS (ES−): 392.4 (M−1).

Scheme 45

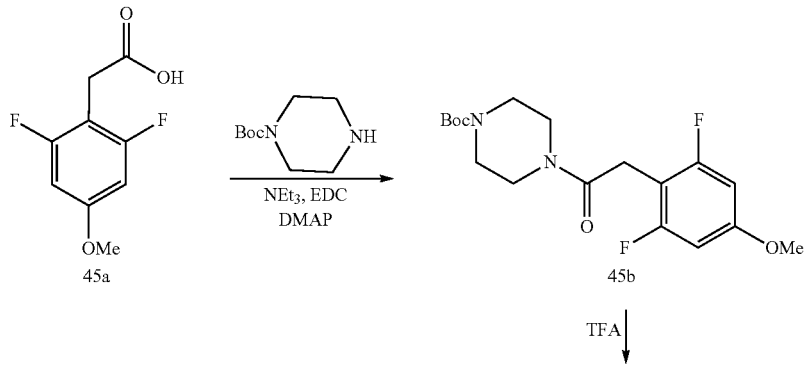

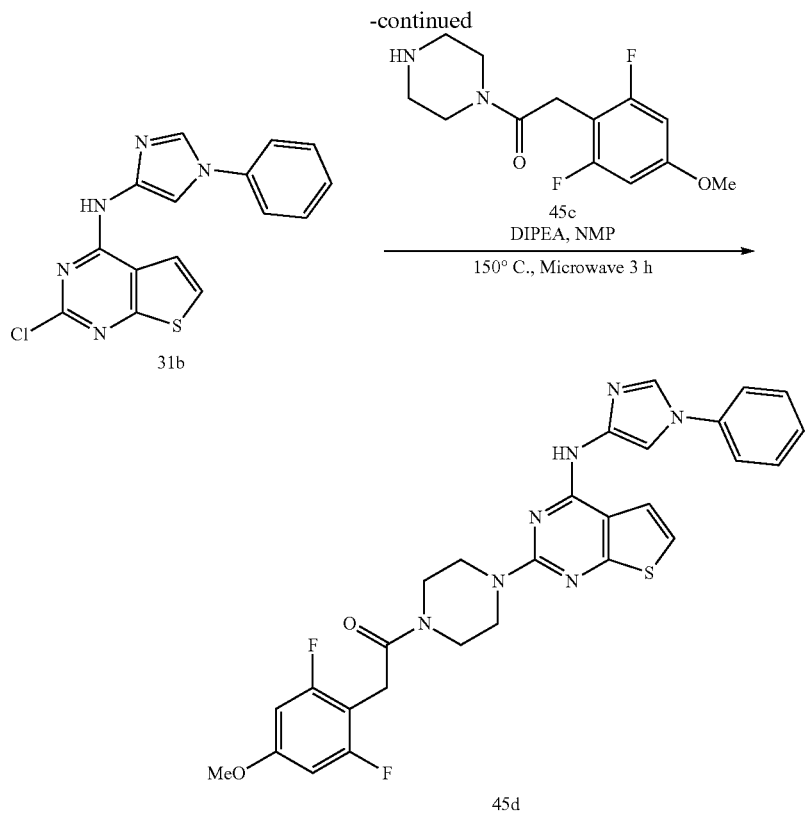

Preparation of 2-(2,6-difluoro-4-methoxyphenyl)-1-(4-(4-((1-phenyl-1H-imidazol-4-yl)amino)thieno[2,3-d]pyrimidin-2-yl)piperazin-1-yl)ethanone (45d)

Step-1: Preparation of tert-butyl 4-(2-(2,6-difluoro-4-methoxyphenyl)acetyl)piperazine-1-carboxylate (45b)

To a stirred suspension of tert-butyl piperazine-1-carboxylate (1 g, 5.37 mmol), 2-(2,6-difluoro-4-methoxyphenyl)acetic acid (45a) (1.09 g, 5.37 mmol; CAS #886498-98-2), EDC (1.24 g, 6.44 mmol), in acetonitrile (15 mL) and DMF (1 mL) was added TEA (2.25 mL, 16.11 mmol) and DMAP (33 mg, 0.27 mmol) and stirred at room temperature for 16 h. The reaction was concentrated to remove acetonitrile and diluted with ethyl acetate (100 mL), washed with iN KHSO$_4$ (2×20 mL), saturated sodium bicarbonate (2×20 mL), water (20 mL), brine (20 mL), dried and concentrated to afford tert-butyl 4-(2-(2,6-difluoro-4-methoxyphenyl)acetyl)piperazine-1-carboxylate (45b) (1.00 g, 50% yield) as a colorless solid; $^1$H NMR (300 MHz, DMSO-d$_6$) δ 6.72 (s, 1H), 6.69 (d, J=1.4 Hz, 1H), 3.77 (s, 3H), 3.66 (s, 2H), 3.57 (t, J=5.3 Hz, 2H), 3.49-3.24 (m, 6H), 1.41 (s, 9H); MS (ES+): 393.5 (+Na) (ES−): 369.3 (M−1).

Step-2: Preparation of 2-(2,6-difluoro-4-methoxyphenyl)-1-(piperazin-1-yl)ethanone 2,2,2-trifluoroacetate (45c)

To a stirred solution of tert-butyl 4-(2-(2,6-difluoro-4-methoxyphenyl)acetyl)piperazine-1-carboxylate (45b) (0.95 g, 2.56 mmol) in Dichloromethane (20 mL) was added TFA (1.98 mL, 25.6 mmol) at room temperature and stirred overnight at room temperature. The reaction was concentrated in vacuum to afford 2-(2,6-difluoro-4-methoxyphenyl)-1-(piperazin-1-yl)ethanone 2,2,2-trifluoroacetate (45c) (800 mg, 81% yield) as an oil; 1H NMR (300 MHz, DMSO-d$_6$) δ 8.94 (s, 2H), 6.88-6.43 (m, 2H), 3.77 (s, 5H), 3.72 (s, 2H), 3.63 (d, J=5.6 Hz, 2H), 3.14 (d, J=27.6 Hz, 4H); $^{19}$F NMR (282 MHz, DMSO-d$_6$) δ −74.66, −112.12-−120.42 (m); MS (ES+) 271.3 (M+1), 293.3 (M+Na), 541.6 (2M+1), 563.5 (2M+Na).

Step-3: Preparation of 2-(2,6-difluoro-4-methoxyphenyl)-1-(4-(4-((1-phenyl-1H-imidazol-4-yl)amino)thieno[2,3-d]pyrimidin-2-yl)piperazin-1-yl)ethanone (45d)

Compound 45d was prepared from 2-chloro-N-(1-phenyl-1H-imidazol-4-yl)thieno[2,3-d]pyrimidin-4-amine (31b) (100 mg, 0.31 mmol), 2-(2,6-difluoro-4-methoxyphenyl)-1-(piperazin-1-yl)ethanone 2,2,2-trifluoroacetate (45c) (371 mg, 0.97 mmol) and DIPEA (0.28 mL, 1.61 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, 2-(2,6-difluoro-4-methoxyphenyl)-1-(4-(4-((1-phenyl-1H-imidazol-4-yl)amino)thieno[2,3-d]pyrimidin-2-yl)piperazin-1-yl)ethanone (45d) (43 mg, 24% yield) as an off-white solid; $^1$H NMR (300 MHz, DMSO-d$_6$) δ 10.30 (s, 1H, D$_2$O exchangeable), 8.29 (d, J=1.7 Hz, 1H), 7.87 (d, J=1.7 Hz, 1H), 7.81 (d, J=6.0 Hz, 1H), 7.70-7.64 (m, 2H), 7.57 (t, J=7.9 Hz, 2H), 7.43-7.34 (m, 1H), 7.15 (d, J=6.0 Hz, 1H), 6.71 (d, J=9.5 Hz, 2H), 3.93-3.85 (m, 2H), 3.85-3.78 (m, 4H), 3.77 (s, 3H), 3.76-3.70 (m, 2H), 3.65-3.56 (m, 2H); $^{19}$F NMR (282 MHz, DMSO-d$_6$) δ −113.98; MS (ES+): 562.6 (M+1), 584.6 (M+Na).

Scheme 46

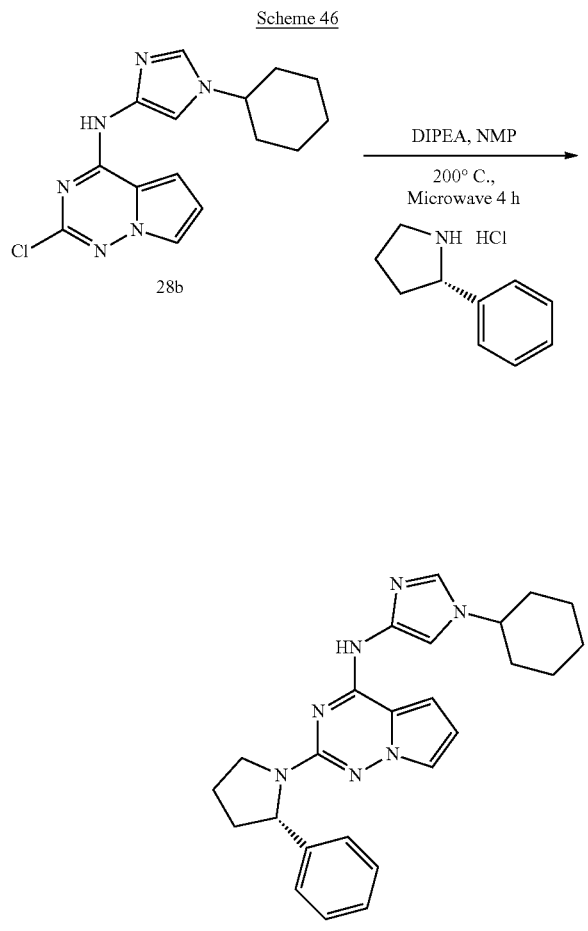

Preparation of (S)—N-(1-cyclohexyl-1H-imidazol-4-yl)-2-(2-phenylpyrrolidin-1-yl)pyrrolo[2,1-f][1,2,4]triazin-4-amine (46a)

Compound 46a was prepared from 2-chloro-N-(1-cyclohexyl-1H-imidazol-4-yl)pyrrolo[2,1-f][1,2,4]triazin-4-amine (28b) (72 mg, 0.23 mmol), (S)-2-phenylpyrrolidine hydrochloride (50 mg, 0.27 mmol) and DIPEA (0.12 mL, 0.68 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)—N-(1-cyclohexyl-1H-imidazol-4-yl)-2-(2-phenylpyrrolidin-1-yl)pyrrolo[2,1-f][1,2,4]triazin-4-amine (46a) (13 mg, 13% yield) as a pale off-white solid; $^1$H NMR (300 MHz, DMSO-d$_6$) δ 10.42 (s, 1H, D$_2$O exchangeable), 8.06 (s, 1H), 7.44 (s, 1H), 7.38-7.13 (m, 6H), 6.98 (dd, J=4.5, 1.6 Hz, 1H), 6.42 (dd, J=4.4, 2.5 Hz, 1H), 5.34 (d, J=7.8 Hz, 1H), 3.99-3.81 (m, 1H), 3.80-3.68 (m, 1H), 3.66-3.49 (m, 1H), 2.42-2.22 (m, 1H), 2.05-1.64 (m, 9H), 1.62-1.32 (m, 3H), 1.32-1.14 (m, 1H); MS (ES+): 428.6 (M+1).

Scheme 47

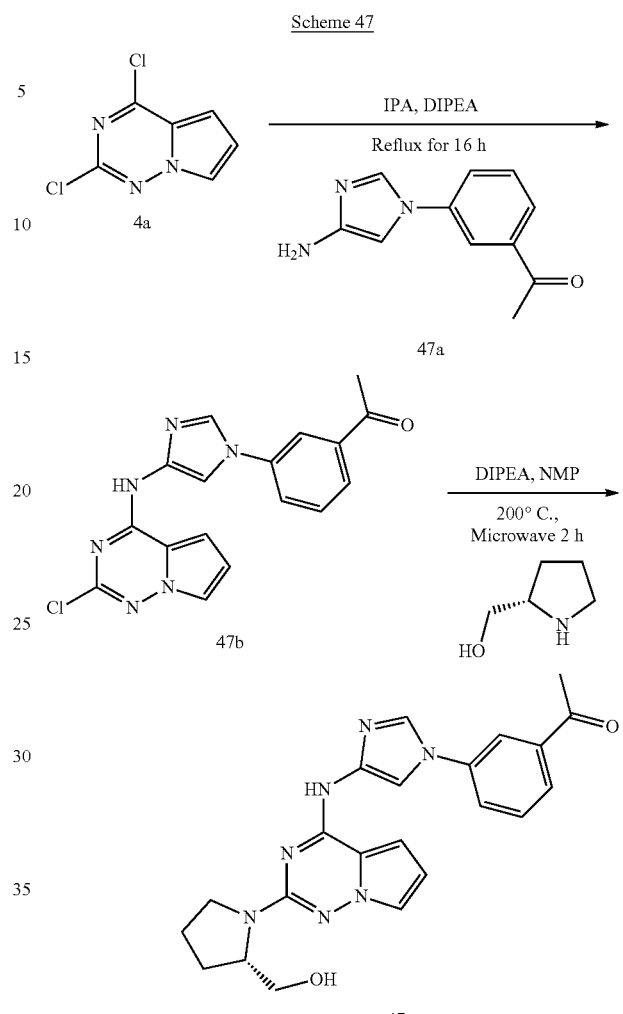

Preparation of (S)-1-(3-(4-((2-(2-(hydroxymethyl)pyrrolidin-1-yl)pyrrolo[2,1-f][1,2,4]triazin-4-yl)amino)-1H-imidazol-1-yl)phenyl)ethanone (47c)

Step-1: Preparation of 1-(3-(4-((2-chloropyrrolo[2,1-f][1,2,4]triazin-4-yl)amino)-1H-imidazol-1-yl)phenyl)ethanone (47b)

Compound 47b was prepared according to the procedure reported in Scheme 1 from 2,4-dichloropyrrolo[1,2-f][1,2,4]triazine (4a) (185 mg, 1.0 mmol) in 2-Propanol (20 mL) using DIPEA (0.52 mL, 2.96 mmol) and 1-(3-(4-amino-1H-imidazol-1-yl)phenyl)ethanone (47a) (238 mg, 1.18 mmol). This gave 1-(3-(4-((2-chloropyrrolo[2,1-f][1,2,4]triazin-4-yl)amino)-1H-imidazol-1-yl)phenyl)ethanone (47b) (282 mg, 81% yield) as a pale off-white solid; $^1$H NMR (300 MHz, DMSO-d$_6$) δ 11.37 (s, 1H, D$_2$O exchangeable), 8.38 (d, J=1.6 Hz, 1H), 8.14 (t, J=1.9 Hz, 1H), 8.01-7.97 (m, 1H), 7.97-7.89 (m, 2H), 7.78 (dd, J=2.6, 1.5 Hz, 1H), 7.72 (t, J=7.9 Hz, 1H), 7.40 (d, J=4.3 Hz, 1H), 6.73 (dd, J=4.5, 2.6 Hz, 1H), 2.68 (s, 3H); MS (ES+): 353.3 (M+1); MS (ES−): 351.4 (M−1).

Step-2: Preparation of (S)-1-(3-(4-((2-(2-(hydroxymethyl)pyrrolidin-1-yl)pyrrolo[2,1-f][1,2,4]triazin-4-yl)amino)-1H-imidazol-1-yl)phenyl)ethanone (47c)

Compound 47c was prepared from 1-(3-(4-((2-chloropyrrolo[2,1-f][1,2,4]triazin-4-yl)amino)-1H-imidazol-1-yl)phenyl)ethanone (47b) (100 mg, 0.28 mmol), (S)-pyrrolidin-2-ylmethanol (143 mg, 1.42 mmol), and DIPEA (0.15 mL, 0.85 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using $NaHCO_3$, (S)-1-(3-(4-((2-(2-(hydroxymethyl)pyrrolidin-1-yl)pyrrolo[2,1-f][1,2,4]triazin-4-yl)amino)-1H-imidazol-1-yl)phenyl)ethanone (47c) (39 mg, 33% yield) as a white solid; $^1$H NMR (300 MHz, DMSO-$d_6$) δ 10.58 (s, 1H, $D_2O$ exchangeable), 8.38 (d, J=1.5 Hz, 1H), 8.24-8.16 (m, 1H), 8.07 (d, J=1.6 Hz, 1H), 8.06-7.98 (m, 1H), 7.98-7.84 (m, 1H), 7.65 (t, J=7.9 Hz, 1H), 7.40 (dd, J=2.4, 1.6 Hz, 1H), 7.15 (dd, J=4.5, 1.6 Hz, 1H), 6.40 (dd, J=4.4, 2.5 Hz, 1H), 4.87 (t, J=5.0 Hz, 1H, $D_2O$ exchangeable), 4.29-4.03 (m, 1H), 3.84-3.70 (m, 1H), 3.63-3.46 (m, 1H), 3.47-3.22 (m, 2H), 2.68 (s, 3H), 2.10-1.85 (m, 4H); MS (ES+): 418.5 (M+1).

Preparation of (S)-4-(4-((2-(2-(hydroxymethyl)pyrrolidin-1-yl)pyrrolo[2,1-f][1,2,4]triazin-4-yl)amino)-1H-imidazol-1-yl)phenol (48c)

Step-1: Preparation of 4-(4-((2-chloropyrrolo[2,1-f][1,2,4]triazin-4-yl)amino)-1H-imidazol-1-yl)phenol (48b)

Compound 48b was prepared according to the procedure reported in Scheme 1 from 2,4-dichloropyrrolo[1,2-f][1,2,4]triazine (4a) (410 mg, 2.18 mmol) in 2-Propanol (20 mL) using DIPEA (1.14 mL, 6.54 mmol) and 4-(4-amino-1H-imidazol-1-yl)phenol (458 mg, 2.61 mmol) (48a) (238 mg, 1.18 mmol). This gave 4-(4-((2-chloropyrrolo[2,1-f][1,2,4]triazin-4-yl)amino)-1H-imidazol-1-yl)phenol (48b) (264 mg, 37% yield) as solid with a little pink color; $^1$H NMR (300 MHz, DMSO-d6) δ 11.34 (s, 1H), 9.78 (s, 1H), 8.04 (d, J=1.6 Hz, 1H), 7.77 (d, J=1.6 Hz, 1H), 7.77-7.74 (m, 1H), 7.47-7.35 (m, 3H), 6.94-6.86 (m, 2H), 6.71 (dd, J=4.5, 2.6 Hz, 1H); MS (ES+): 327.3 (M+1); MS (ES−): 325.2 (M−1), 361.2 (M+Cl).

Step-2: Preparation of (S)-4-(4-((2-(2-(hydroxymethyl)pyrrolidin-1-yl)pyrrolo[2,1-f][1,2,4]triazin-4-yl)amino)-1H-imidazol-1-yl)phenol (48c)

Compound 48c was prepared from 4-(4-((2-chloropyrrolo[2,1-f][1,2,4]triazin-4-yl)amino)-1H-imidazol-1-yl)phenol (48b) (100 mg, 0.31 mmol), (S)-pyrrolidin-2-ylmethanol (155 mg, 1.53 mmol), and DIPEA (0.16 mL, 0.92 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using $NaHCO_3$, (S)-4-(4-((2-(2-(hydroxymethyl)pyrrolidin-1-yl)pyrrolo[2,1-f][1,2,4]triazin-4-yl)amino)-1H-imidazol-1-yl)phenol (48c) (60 mg, 50% yield) as a white solid; $^1$H NMR (300 MHz, DMSO-$d_6$) δ 10.46 (s, 1H, $D_2O$ exchangeable), 9.69 (s, 1H, $D_2O$ exchangeable), 8.02 (d, J=1.5 Hz, 1H), 7.84 (d, J=1.6 Hz, 1H), 7.51 (d, J=8.8 Hz, 2H), 7.38 (dd, J=2.4, 1.6 Hz, 1H), 7.14 (dd, J=4.4, 1.7 Hz, 1H), 6.85 (d, J=8.8 Hz, 2H), 6.38 (dd, J=4.4, 2.4 Hz, 1H), 4.85 (t, J=5.0 Hz, 1H, $D_2O$ exchangeable), 4.26-4.06 (m, 1H), 3.81-3.65 (m, 1H), 3.55-3.42 (m, 1H), 3.45-3.23 (m, 2H), 2.11-1.81 (m, 4H); MS (ES+): 392.5 (M+1); 414.5 (M+Na); Analysis calculated for $C_{20}H_{21}N_7O_2$: C, 61.37; H, 5.41; N, 25.05. Found: C, 60.88; H, 5.54; N, 24.96.

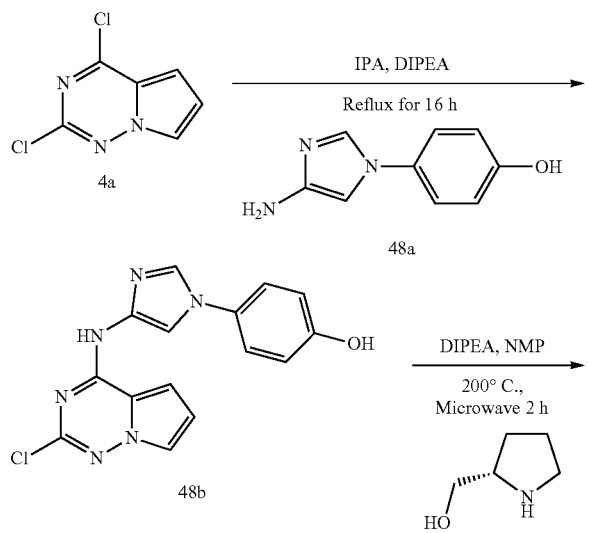

Scheme 48

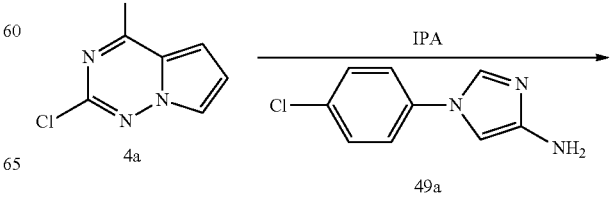

Scheme 49

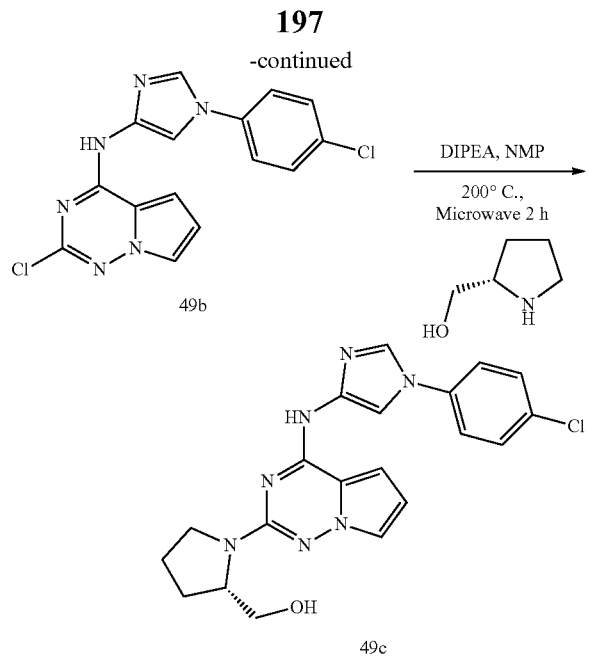

49b

49c

Preparation of (S)-(1-(4-((1-(4-chlorophenyl)-1H-imidazol-4-yl)amino)pyrrolo[2,1-f][1,2,4]triazin-2-yl)pyrrolidin-2-yl)methanol (49c)

Step-1: Preparation of 2-chloro-N-(1-(4-chlorophenyl)-1H-imidazol-4-yl)pyrrolo[2,1-f][1,2,4]triazin-4-amine (49b)

Compound 49b was prepared according to the procedure reported in Scheme 1 from 2,4-dichloropyrrolo[1,2-f][1,2,4]triazine (4a) (375 mg, 2.0 mmol) in 2-Propanol (20 mL) using DIPEA (1.05 mL, 5.99 mmol) and 1-(4-chlorophenyl)-1H-imidazol-4-amine (49a) (464 mg, 2.396 mmol). This gave 2-chloro-N-(1-(4-chlorophenyl)-1H-imidazol-4-yl)pyrrolo[2,1-f][1,2,4]triazin-4-amine (49b) (264 mg, 38% yield) as a pale-off white solid; $^1$H NMR (300 MHz, DMSO-d$_6$) δ 11.36 (s, 1H), 8.29 (d, J=1.6 Hz, 1H), 7.91 (d, J=1.7 Hz, 1H), 7.78 (dd, J=2.6, 1.5 Hz, 1H), 7.74-7.68 (m, 2H), 7.66-7.60 (m, 2H), 7.40 (d, J=4.5 Hz, 1H), 6.72 (dd, J=4.5, 2.6 Hz, 1H); 1H NMR (300 MHz, DMSO-d$_6$/D$_2$O) δ 8.19 (d, J=1.7 Hz, 1H), 7.87 (d, J=1.6 Hz, 1H), 7.73 (dd, J=2.6, 1.5 Hz, 1H), 7.70-7.64 (m, 2H), 7.62-7.56 (m, 2H), 7.32 (d, J=4.3 Hz, 1H), 6.71 (dd, J=4.5, 2.6 Hz, 1H); MS (ES+): 345.3, 347.3 (M+1).

Step-2: Preparation of (S)-(1-(4-((1-(4-chlorophenyl)-1H-imidazol-4-yl)amino)pyrrolo[2,1-f][1,2,4]triazin-2-yl)pyrrolidin-2-yl)methanol (49c)

Compound 49c was prepared from 2-chloro-N-(1-(4-chlorophenyl)-1H-imidazol-4-yl)pyrrolo[2,1-f][1,2,4]triazin-4-amine (49b) (100 mg, 0.29 mmol), (S)-pyrrolidin-2-ylmethanol (147 mg, 1.45 mmol), and DIPEA (0.15 mL, 0.87 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(4-chlorophenyl)-1H-imidazol-4-yl)amino)pyrrolo[2,1-f][1,2,4]triazin-2-yl)pyrrolidin-2-yl)methanol (49c) (55 mg, 46% yield) as a white solid; $^1$H NMR (300 MHz, DMSO-d$_6$) δ 10.55 (s, 1H, D$_2$O exchangeable), 8.27 (d, J=1.5 Hz, 1H), 7.96 (d, J=1.6 Hz, 1H), 7.86-7.77 (m, 2H), 7.63-7.50 (m, 2H), 7.39 (dd, J=2.4, 1.6 Hz, 1H), 7.15 (dd, J=4.5, 1.7 Hz, 1H), 6.39 (dd, J=4.4, 2.5 Hz, 1H), 5.03-4.80 (m, 1H, D$_2$O exchangeable), 4.31-4.07 (m, 1H), 3.87-3.67 (m, 1H), 3.53-3.35 (m, 1H), 3.42-3.23 (m, 2H), 2.11-1.83 (m, 4H). MS (ES+): 410.4 (M+1).

Scheme 50

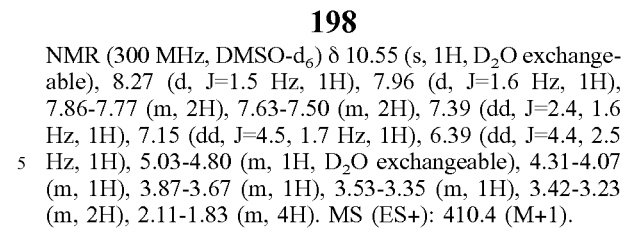

4a

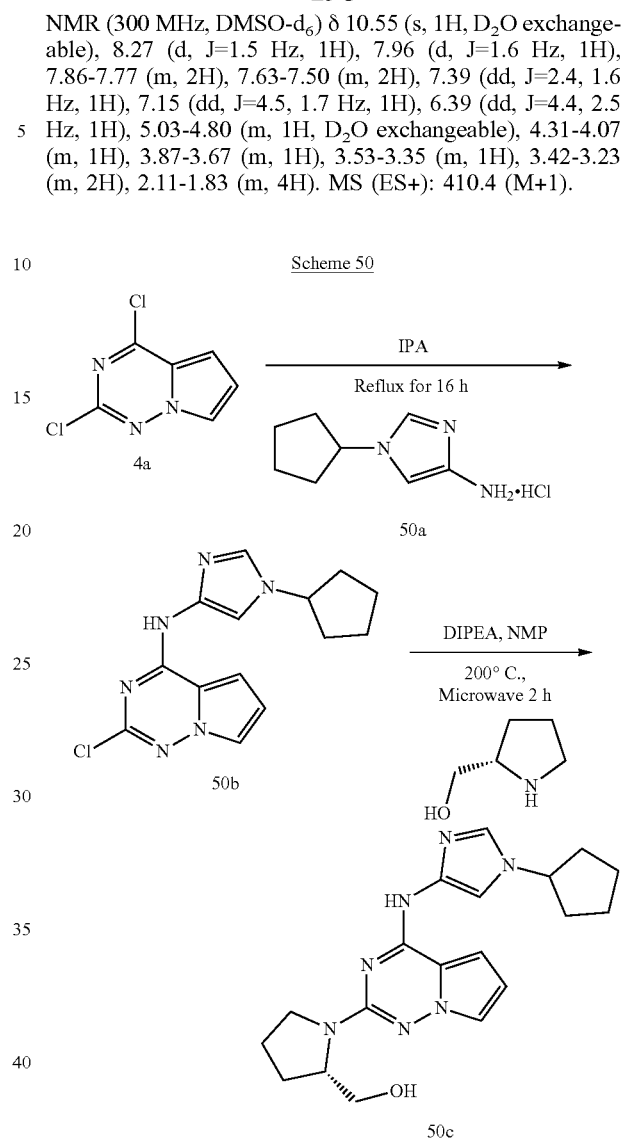

50a

50b

50c

Preparation of (S)-(1-(4-((1-cyclopentyl-1H-imidazol-4-yl)amino)pyrrolo[2,1-f][1,2,4]triazin-2-yl)pyrrolidin-2-yl)methanol (50c)

Step-1: Preparation of 2-chloro-N-(1-cyclopentyl-1H-imidazol-4-yl)pyrrolo[2,1-f][1,2,4]triazin-4-amine (50b)

Compound 50b was prepared according to the procedure reported in Scheme 1 from 2,4-dichloropyrrolo[1,2-f][1,2,4]triazine (4a) (392 mg, 2.08 mmol) in 2-Propanol (20 mL) using DIPEA (1.09 mL, 6.25 mmol) and 1-cyclopentyl-1H-imidazol-4-amine hydrochloride (50a) (469 mg, 2.499 mmol). This gave 2-chloro-N-(1-cyclopentyl-1H-imidazol-4-yl)pyrrolo[2,1-f][1,2,4]triazin-4-amine (50b) (397 mg, 63% yield) as a pale-off yellow colored solid; $^1$H NMR (300 MHz, DMSO-d$_6$) δ 11.17 (s, 1H, D$_2$O exchangeable), 7.72 (dd, J=2.6, 1.5 Hz, 1H), 7.68 (d, J=1.5 Hz, 1H), 7.50 (d, J=1.6 Hz, 1H), 7.35 (dd, J=4.5, 1.5 Hz, 1H), 6.68 (dd, J=4.5, 2.6 Hz, 1H), 4.69-4.50 (m, 1H), 2.24-2.05 (m, 2H), 1.92-1.57 (m, 6H). MS (ES+): 303.3 (M+1), 325.3 (M+Na); MS (ES−): 301.3 (M−1)

Step-2: Preparation of (S)-(1-(4-((1-cyclopentyl-1H-imidazol-4-yl)amino)pyrrolo[2,1-f][1,2,4]triazin-2-yl)pyrrolidin-2-yl)methanol (50c)

Compound 50c was prepared from 2-chloro-N-(1-cyclopentyl-1H-imidazol-4-yl)pyrrolo[2,1-f][1,2,4]triazin-4-amine (50b) (100 mg, 0.33 mmol), (S)-pyrrolidin-2-ylmethanol (33 mg, 0.33 mmol), and DIPEA (0.17 mL, 0.99 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-cyclopentyl-1H-imidazol-4-yl)amino)pyrrolo[2,1-f][1,2,4]triazin-2-yl)pyrrolidin-2-yl)methanol (50c) (80 mg, 66% yield); $^1$H NMR (300 MHz, DMSO-d$_6$) δ 10.32 (s, 1H, D$_2$O exchangeable), 7.59 (d, J=1.5 Hz, 1H), 7.54 (d, J=1.6 Hz, 1H), 7.35 (dd, J=2.4, 1.7 Hz, 1H), 7.09 (dd, J=4.6, 1.7 Hz, 1H), 6.35 (dd, J=4.4, 2.4 Hz, 1H), 4.78 (t, J=5.1 Hz, 1H, D$_2$O exchangeable), 4.52 (p, J=7.3 Hz, 1H), 4.20-4.04 (m, 1H), 3.77-3.64 (m, 1H), 3.55-3.44 (m, 1H), 3.44-3.28 (m, 2H), 2.22-1.97 (m, 2H), 1.99-1.70 (m, 9H), 1.73-1.52 (m, 1H). MS (ES+): 368.5 (M+1); 370.5 (M+Na).

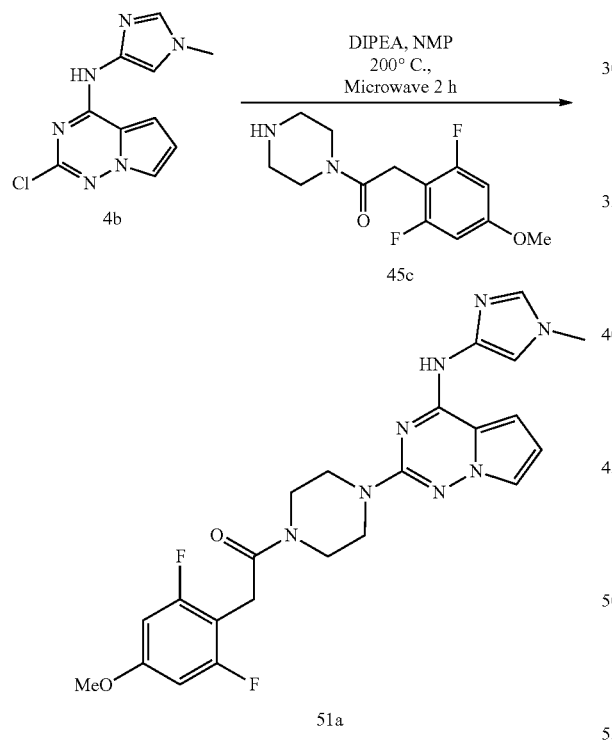

Scheme 51

Preparation of 2-(2,6-difluoro-4-methoxyphenyl)-1-(4-(4-((1-methyl-1H-imidazol-4-yl)amino)pyrrolo[2,1-f][1,2,4]triazin-2-yl)piperazin-1-yl)ethanone (51a)

Compound 51a was prepared from 2-chloro-N-(1-methyl-1H-imidazol-4-yl)pyrrolo[2,1-f][1,2,4]triazin-4-amine (4b) (100 mg, 0.4 mmol), 2-(2,6-difluoro-4-methoxyphenyl)-1-(piperazin-1-yl)ethanone 2,2,2-trifluoroacetate (45c) (170 mg, 0.44 mmol) and DIPEA (0.21 mL, 1.21 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, 2-(2,6-difluoro-4-methoxyphenyl)-1-(4-(4-((1-methyl-1H-imidazol-4-yl)amino)pyrrolo[2,1-f][1,2,4]triazin-2-yl)piperazin-1-yl)ethanone (51a) (25 mg, 13% yield) as a light brown solid; $^1$H NMR (300 MHz, DMSO-d$_6$) δ 10.54 (s, 1H, D$_2$O exchangeable), 8.10 (s, 1H), 7.54-7.40 (m, 2H), 7.11-6.97 (m, 1H), 6.72 (d, J=9.4 Hz, 2H), 6.49 (dd, J=4.5, 2.4 Hz, 1H), 3.79 (s, 3H), 3.77 (s, 4H), 3.71 (s, 3H), 3.64 (d, J=4.6 Hz, 2H), 3.57 (s, 4H); $^{19}$F NMR (282 MHz, DMSO-d$_6$) δ −114.02; MS (ES+): 483.5 (M+1), 505.5 (M+Na).

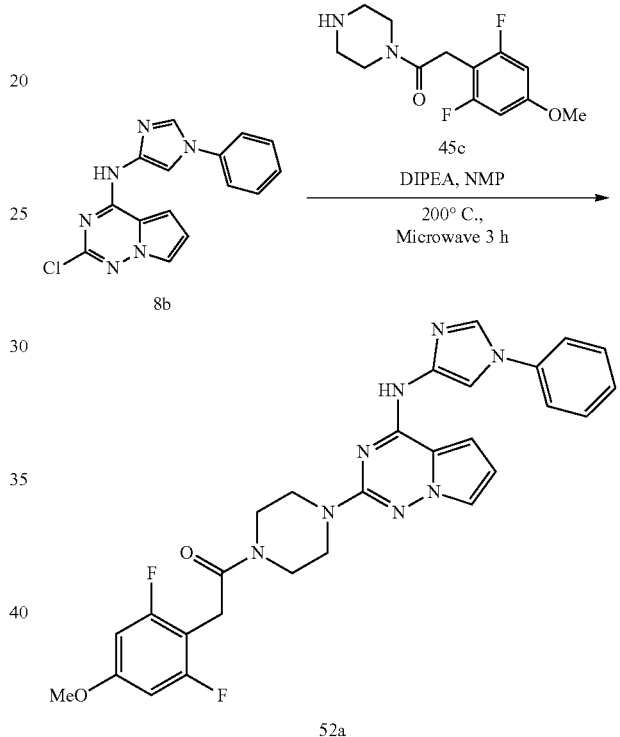

Scheme 52

Preparation of 2-(2,6-difluoro-4-methoxyphenyl)-1-(4-(4-((1-phenyl-1H-imidazol-4-yl)amino)pyrrolo[2,1-f][1,2,4]triazin-2-yl)piperazin-1-yl)ethanone (52a)

Compound 52a was prepared from 2-chloro-N-(1-phenyl-1H-imidazol-4-yl)pyrrolo[1,2-f][1,2,4]triazin-4-amine (8b) (100 mg, 0.32 mmol), 2-(2,6-difluoro-4-methoxyphenyl)-1-(piperazin-1-yl)ethanone 2,2,2-trifluoroacetate (45c) (247 mg, 0.64 mmol) and DIPEA (0.22 mL, 1.28 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, 2-(2,6-difluoro-4-methoxyphenyl)-1-(4-(4-((1-phenyl-1H-imidazol-4-yl)amino)pyrrolo[2,1-f][1,2,4]triazin-2-yl)piperazin-1-yl)ethanone (52a) (25 mg, 14% yield) as a light brown solid; $^1$H NMR (300 MHz, DMSO-d$_6$) δ 10.63 (s, 1H, D$_2$O exchangeable), 8.24 (d, J=1.6 Hz, 1H), 7.85 (d, J=1.6 Hz, 1H), 7.72-7.64 (m, 2H), 7.57 (dd, J=8.6, 7.2 Hz, 2H), 7.47 (dd, J=2.5, 1.7 Hz, 1H), 7.43-7.34 (m, 1H), 7.19 (s, 1H), 6.72 (d, J=9.5 Hz, 2H), 6.47 (dd, J=4.5, 2.5 Hz, 1H), 3.77 (s, 3H), 3.76-3.65 (m, 6H), 3.64-3.58 (m, 4H); $^{19}$F NMR (282 MHz, DMSO-d$_6$) δ −114.00 (d, J=9.4 Hz); MS (ES+): 545.6 (M+1), 567.6 (M+Na), (ES−): 543.5 (M−1).

Scheme 53

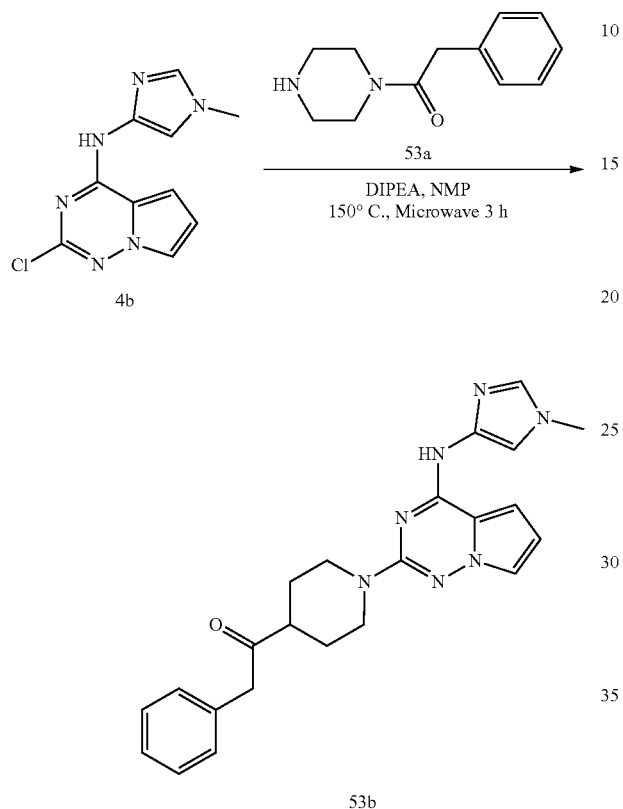

Scheme 54

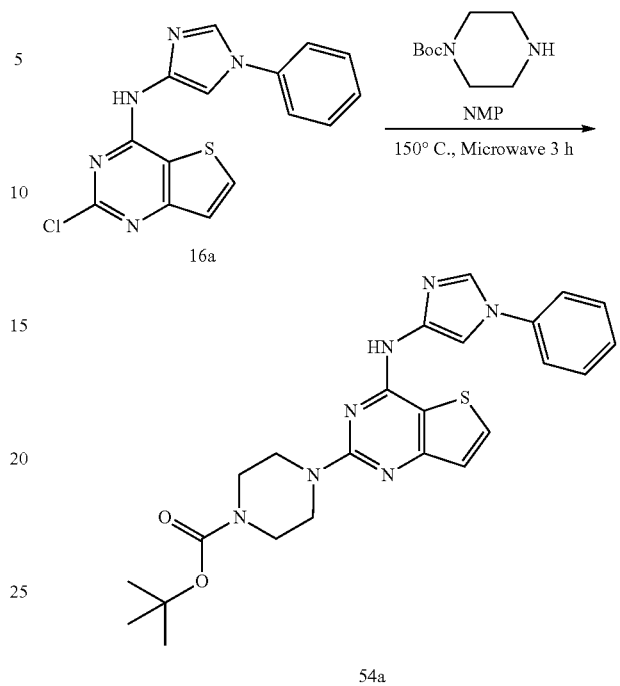

Preparation of tert-butyl 4-(4-((1-phenyl-1H-imidazol-4-yl)amino)thieno[3,2-d]pyrimidin-2-yl)piperazine-1-carboxylate (54a)

Compound 54a was prepared from 2-chloro-N-(1-phenyl-1H-imidazol-4-yl)thieno[3,2-d]pyrimidin-4-amine (16a) (100 mg, 0.31 mmol), tert-butyl piperazine-1-carboxylate (170 mg, 0.92 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, tert-butyl 4-(4-(1-phenyl-1H-imidazol-4-ylamino)thieno[3,2-d]pyrimidin-2-yl)piperazine-1-carboxylate (54a) (92 mg, 63% yield) as an off-white solid; $^1$H NMR (300 MHz, DMSO-d$_6$) δ 10.10 (s, 1H), D$_2$O exchangeable, 8.22 (d, J=1.5 Hz, 1H), 7.97 (d, J=5.4 Hz, 1H), 7.85 (d, J=1.7 Hz, 1H), 7.68 (d, J=1.4 Hz, 1H), 7.65 (dd, J=1.9, 0.9 Hz, 1H), 7.55 (dd, J=8.7, 7.1 Hz, 2H), 7.43-7.35 (m, 1H), 7.12 (d, J=5.4 Hz, 1H), 3.85-3.71 (m, 4H), 3.50-3.38 (m, 4H), 1.43 (s, 9H); MS (ES+): 478.6 (M+1), 500.5 (M+Na).

Preparation of 1-(4-(4-((1-methyl-1H-imidazol-4-yl)amino)pyrrolo[2,1-f][1,2,4]triazin-2-yl)piperazin-1-yl)-2-phenylethanone (53b)

Compound 53b was prepared from 2-chloro-N-(1-methyl-1H-imidazol-4-yl)pyrrolo[2,1-f][1,2,4]triazin-4-amine (4b) (100 mg, 0.4 mmol), 2-phenyl-1-(piperazin-1-yl)ethanone 2,2,2-trifluoroacetate (53a) (256 mg, 0.80 mmol; prepared according to the procedure reported by Levy, Daniel E. et al; in PCT Int. Appl., 2003/022214, 20 Mar. 2003) and DIPEA (0.28 mL, 1.61 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, 1-(4-(4-(1-methyl-1H-imidazol-4-ylamino)pyrrolo[1,2-f][1,2,4]triazin-2-yl)piperazin-1-yl)-2-phenylethanone (11 mg, 7% yield) as a brown solid; $^1$H NMR (300 MHz, DMSO-d$_6$) δ 10.38 (s, 1H, D$_2$O exchangeable), 7.50 (d, J=1.4 Hz, 1H), 7.45-7.36 (m, 2H), 7.36-7.29 (m, 2H), 7.29-7.19 (m, 3H), 7.18-7.09 (m, 1H), 6.42 (dd, J=4.4, 2.5 Hz, 1H), 3.78 (s, 2H), 3.70 (s, 3H), 3.67-3.59 (m, 4H), 3.60-3.43 (m, 4H); MS (ES+): 417.6 (M+1), 439.5 (M+Na), (ES−): 415.5 (M−1).

Scheme 55

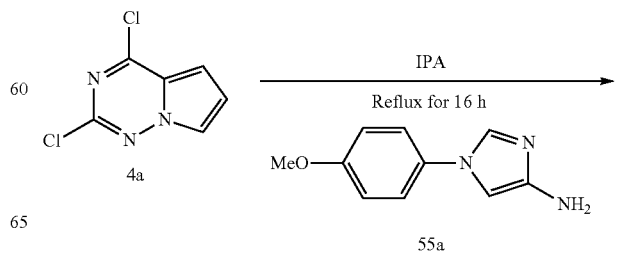

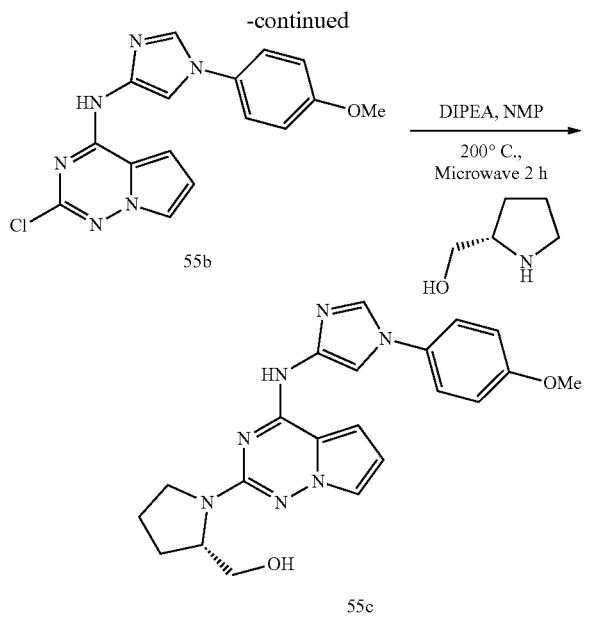

methanol (55c) (83 mg, 70% yield) as a white solid; $^1$H NMR (300 MHz, DMSO-d$_6$) δ 10.49 (s, 1H, D$_2$O exchangeable), 8.11 (d, J=1.5 Hz, 1H), 7.88 (d, J=1.6 Hz, 1H), 7.65 (d, J=9.0 Hz, 2H), 7.38 (t, J=2.0 Hz, 1H), 7.15 (dd, J=4.5, 1.7 Hz, 1H), 7.04 (d, J=9.0 Hz, 2H), 6.39 (dd, J=4.4, 2.5 Hz, 1H), 4.94-4.81 (m, 1H, D$_2$O exchangeable), 4.27-4.08 (m, 1H), 3.80 (s, 3H), 3.80-3.70 (m, 1H), 3.56-3.43 (m, 1H), 3.44-3.30 (m, 2H), 2.13-1.79 (m, 4H); MS (ES+): 406.5 (M+1).

Scheme 56

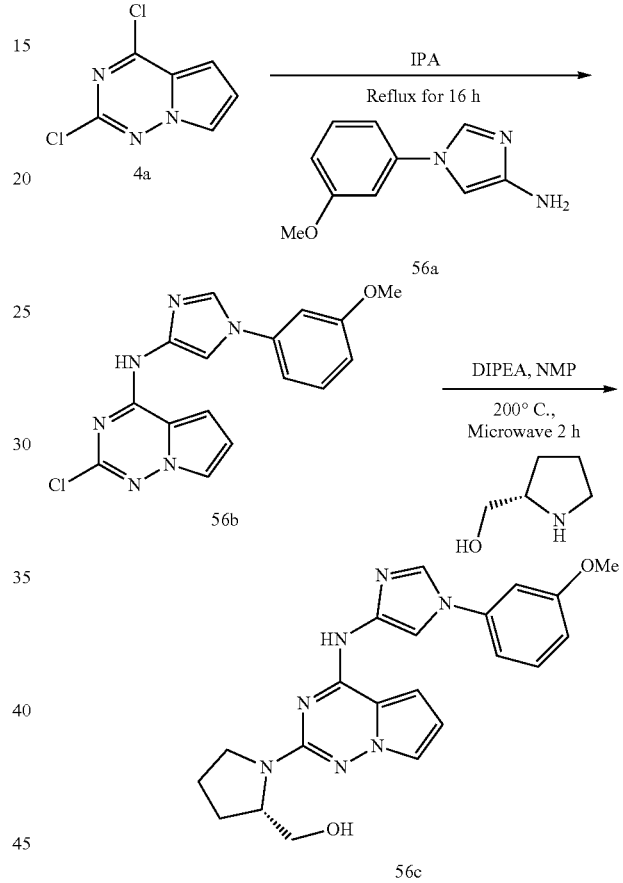

Preparation of (S)-(1-(4-((1-(3-methoxyphenyl)-1H-imidazol-4-yl)amino)pyrrolo[2,1-f][1,2,4]triazin-2-yl)pyrrolidin-2-yl)methanol (56c)

Step-1: Preparation of 2-chloro-N-(1-(3-methoxyphenyl)-1H-imidazol-4-yl)pyrrolo[2,1-f][1,2,4]triazin-4-amine (56b)

Compound 56b was prepared according to the procedure reported in Scheme 1 from 2,4-dichloropyrrolo[1,2-f][1,2,4]triazine (4a) (373 mg, 1.99 mmol) in 2-Propanol (20 mL) using DIPEA (1.04 mL, 5.96 mmol) and 1-(3-methoxyphenyl)-1H-imidazol-4-amine (56a) (451 mg, 2.38 mmol). This gave 2-chloro-N-(1-(3-methoxyphenyl)-1H-imidazol-4-yl)pyrrolo[2,1-f][1,2,4]triazin-4-amine (56b) (556 mg, 82% yield) as a pale off-yellow solid; $^1$H NMR (300 MHz, DMSO-d$_6$) δ 11.34 (s, 1H), 8.29 (d, J=1.6 Hz, 1H), 7.91 (d, J=1.6 Hz, 1H), 7.77 (dd, J=2.6, 1.5 Hz, 1H), 7.47 (t, J=8.1

---

Preparation of (S)-(1-(4-((1-(4-methoxyphenyl)-1H-imidazol-4-yl)amino)pyrrolo[2,1-f][1,2,4]triazin-2-yl)pyrrolidin-2-yl)methanol (55c)

Step-1: Preparation of 2-chloro-N-(1-(4-methoxyphenyl)-1H-imidazol-4-yl)pyrrolo[2,1-f][1,2,4]triazin-4-amine (55b)

Compound 55b was prepared according to the procedure reported in Scheme 1 from 2,4-dichloropyrrolo[1,2-f][1,2,4]triazine (4a) (423 mg, 2.25 mmol) in 2-Propanol (20 mL) using DIPEA (1.18 mL, 6.75 mmol) and 1-(4-methoxyphenyl)-1H-imidazol-4-amine (55a) (511 mg, 2.70 mmol). This gave 2-chloro-N-(1-(4-methoxyphenyl)-1H-imidazol-4-yl)pyrrolo[2,1-f][1,2,4]triazin-4-amine (55b) (635 mg, 83% yield) as a yellow solid; $^1$H NMR (300 MHz, DMSO-d$_6$) δ 11.33 (s, 1H), 8.11 (d, J=1.6 Hz, 1H), 7.82 (d, J=1.6 Hz, 1H), 7.76 (dd, J=2.6, 1.5 Hz, 1H), 7.63-7.49 (m, 2H), 7.40 (dd, J=4.6, 1.5 Hz, 1H), 7.19-7.06 (m, 2H), 6.71 (dd, J=4.5, 2.6 Hz, 1H), 3.81 (s, 3H); $^1$H NMR (300 MHz, DMSO-d-D$_2$O) δ 8.02 (d, J=1.2 Hz, 1H), 7.77 (dd, J=1.6, 0.8 Hz, 1H), 7.74-7.67 (m, 1H), 7.56-7.47 (m, 2H), 7.30 (d, J=4.4 Hz, 1H), 7.12-7.00 (m, 2H), 6.70 (dd, J=4.6, 2.7 Hz, 1H), 3.80 (s, 3H). MS (ES+): 341.3 (M+1), 363.4 (M+Na); MS (ES−): 339.3 (M−1).

Step-2: Preparation of (S)-(1-(4-((1-(4-methoxyphenyl)-1H-imidazol-4-yl)amino)pyrrolo[2,1-f][1,2,4]triazin-2-yl)pyrrolidin-2-yl)methanol (55c)

Compound 55c was prepared from 2-chloro-N-(1-(4-methoxyphenyl)-1H-imidazol-4-yl)pyrrolo[2,1-f][1,2,4]triazin-4-amine (55b) (100 mg, 0.29 mmol), (S)-pyrrolidin-2-ylmethanol (148 mg, 1.47 mmol), and DIPEA (0.15 mL, 0.87 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(4-methoxyphenyl)-1H-imidazol-4-yl)amino)pyrrolo[2,1-f][1,2,4]triazin-2-yl)pyrrolidin-2-yl)

Hz, 1H), 7.40 (d, J=4.3 Hz, 1H), 7.23 (t, J=2.2 Hz, 1H), 7.22-7.16 (m, 1H), 7.03-6.93 (m, 1H), 6.72 (dd, J=4.5, 2.6 Hz, 1H), 3.85 (s, 3H); $^1$H NMR (300 MHz, DMSO-d-D$_2$O) δ 8.22 (d, J=1.6 Hz, 1H), 7.88 (d, J=1.6 Hz, 1H), 7.74 (dd, J=2.6, 1.5 Hz, 1H), 7.53-7.41 (m, 1H), 7.34 (d, J=4.4 Hz, 1H), 7.21-7.14 (m, 2H), 7.03-6.93 (m, 1H), 6.71 (dd, J=4.5, 2.6 Hz, 1H), 3.82 (s, 3H); MS (ES+): 341.4 (M+1); MS (ES-): 339.3 (M-1).

Step-2: Preparation of (S)-(1-(4-((1-(3-methoxyphenyl)-1H-imidazol-4-yl)amino)pyrrolo[2,1-f][1,2,4]triazin-2-yl)pyrrolidin-2-yl)methanol (56c)

Compound 56c was prepared from 2-chloro-N-(1-(3-methoxyphenyl)-1H-imidazol-4-yl)pyrrolo[2,1-f][1,2,4]triazin-4-amine (56b) (100 mg, 0.29 mmol), (S)-pyrrolidin-2-ylmethanol (148 mg, 1.47 mmol), and DIPEA (0.15 mL, 0.87 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(3-methoxyphenyl)-1H-imidazol-4-yl)amino)pyrrolo[2,1-f][1,2,4]triazin-2-yl)pyrrolidin-2-yl)methanol (56c) (58 mg, 49% yield) as a white solid; $^1$H NMR (300 MHz, DMSO-d$_6$) δ 10.53 (s, 1H, D$_2$O exchangeable), 8.27 (d, J=1.5 Hz, 1H), 7.97 (d, J=1.6 Hz, 1H), 7.45-7.34 (m, 2H), 7.35-7.23 (m, 2H), 7.15 (dd, J=4.4, 1.7 Hz, 1H), 6.97-6.86 (m, 1H), 6.39 (dd, J=4.5, 2.4 Hz, 1H), 5.02-4.68 (m, 1H, D$_2$O exchangeable), 4.30-4.11 (m, 1H), 3.85 (s, 3H), 3.74 (dd, J=9.9, 3.5 Hz, 1H), 3.61-3.46 (m, 1H), 3.47-3.26 (m, 2H), 2.17-1.77 (m, 4H); MS (ES+): 406.5 (M+1).

Scheme 57

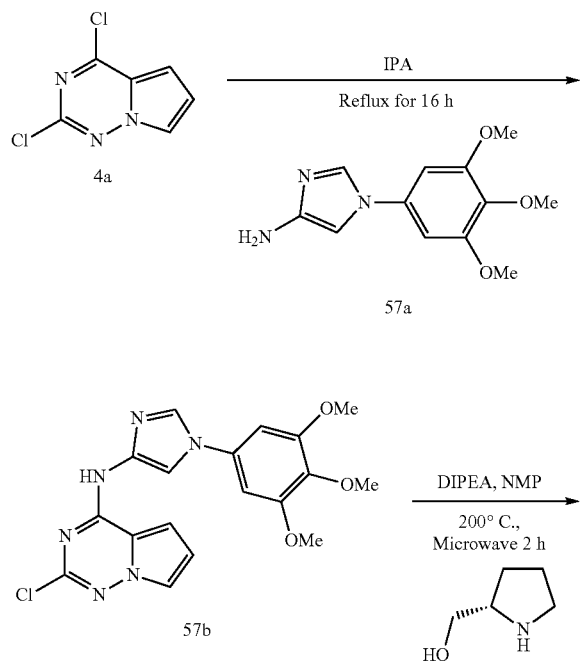

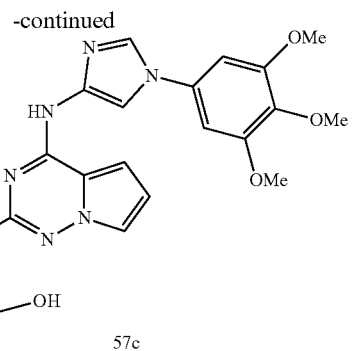

57c

Preparation of (S)-(1-(4-((1-(3,4,5-trimethoxyphenyl)-1H-imidazol-4-yl)amino)pyrrolo[2,1-f][1,2,4]triazin-2-yl)pyrrolidin-2-yl)methanol (57c)

Step-1: Preparation of 2-chloro-N-(1-(3,4,5-trimethoxyphenyl)-1H-imidazol-4-yl)pyrrolo[2,1-f][1,2,4]triazin-4-amine (57b)

Compound 57b was prepared according to the procedure reported in Scheme 1 from 2,4-dichloropyrrolo[1,2-f][1,2,4]triazine (4a) (226 mg, 1.2 mmol) in 2-Propanol (20 mL) using DIPEA (0.63 mL, 3.61 mmol) and 1-(3,4,5-trimethoxyphenyl)-1H-imidazol-4-amine (57a) (300 mg, 1.02 mmol). This gave 2-chloro-N-(1-(3,4,5-trimethoxyphenyl)-1H-imidazol-4-yl)pyrrolo[2,1-f][1,2,4]triazin-4-amine (57b) (410 mg, 85% yield) as white solid; $^1$H NMR (300 MHz, DMSO-d$_6$) δ 11.31 (s, 1H), 8.21 (d, J=1.6 Hz, 1H), 7.89 (d, J=1.6 Hz, 1H), 7.77 (dd, J=2.6, 1.6 Hz, 1H), 7.39 (d, J=4.4 Hz, 1H), 6.93 (s, 2H), 6.72 (dd, J=4.4, 2.6 Hz, 1H), 3.87 (s, 6H), 3.69 (s, 3H); $^1$H NMR (300 MHz, DMSO-d$_6$-D$_2$O) δ 8.14 (d, J=1.6 Hz, 1H), 7.86 (d, J=1.6 Hz, 1H), 7.72 (dd, J=2.6, 1.6 Hz, 1H), 7.35-7.28 (m, 1H), 6.88 (s, 2H), 6.71 (dd, J=4.5, 2.6 Hz, 1H), 3.84 (s, 6H), 3.67 (s, 3H); MS (ES+): 401.4 (M+1); MS (ES-): 399.3 (M-1).

Step-2: Preparation of (S)-(1-(4-((1-(3,4,5-trimethoxyphenyl)-1H-imidazol-4-yl)amino)pyrrolo[2,1-f][1,2,4]triazin-2-yl)pyrrolidin-2-yl)methanol (57c)

Compound 57c was prepared from 2-chloro-N-(1-(3,4,5-trimethoxyphenyl)-1H-imidazol-4-yl)pyrrolo[2,1-f][1,2,4]triazin-4-amine (57b) (100 mg, 0.25 mmol), (S)-pyrrolidin-2-ylmethanol (126 mg, 1.25 mmol), and DIPEA (0.13 mL, 0.74 mmol) in NMP (1 mL) according to the procedure reported in Scheme 2. This gave after workup and purification by reverse phase flash chromatography [silica gel C-18, 24 g), eluting with 0.1% TFA in acetonitrile and 0.1% TFA in water], followed by conversion to free base using NaHCO$_3$, (S)-(1-(4-((1-(3,4,5-trimethoxyphenyl)-1H-imidazol-4-yl)amino)pyrrolo[2,1-f][1,2,4]triazin-2-yl)pyrrolidin-2-yl)methanol (57c) (18 mg, 16% yield) as a white solid; $^1$H NMR (300 MHz, DMSO-d$_6$) δ 10.54 (s, 1H, D$_2$O exchangeable), 8.24 (d, J=1.5 Hz, 1H), 7.97 (d, J=1.6 Hz, 1H), 7.39 (dd, J=2.4, 1.6 Hz, 1H), 7.14 (dd, J=4.4, 1.7 Hz, 1H), 6.96 (s, 2H), 6.39 (dd, J=4.4, 2.4 Hz, 1H), 4.84 (t, J=5.1 Hz, 1H, D$_2$O exchangeable), 4.29-4.15 (m, 1H), 3.88 (s, 6H), 3.79-3.68 (m, 1H), 3.68 (s, 3H), 3.61-3.47 (m, 1H), 3.49-3.24 (m, 2H), 2.12-1.75 (m, 4H); MS (ES+): 466.5 (M+1), 488.5 (M+Na); Hydrochloride salt of compound 57c was obtained by purification of crude reaction mixture from step-2 above by reverse phase flash chromatography [(silica gel C-18, 24 g) eluting with acetonitrile and 0.1% HCl in water] followed by lyophilization; $^1$H NMR (300 MHz, DMSO-$d_6$): δ 10.78 (s, 1H), 8.59 (s, 1H), 8.03 (s, 1H), 7.44 (s, 1H), 7.12 (d, J=4.5 Hz, 1H), 7.02 (s, 2H), 6.43 (dd, J=4.4, 2.5 Hz, 1H), 4.26-4.13 (m, 1H), 3.88 (s, 6H), 3.78-3.21 (m, 7H), 2.08-1.80 (m, 4H). MS (ES+): 466.3 (M+1). MS (ES−): 500.2 (M+Cl).

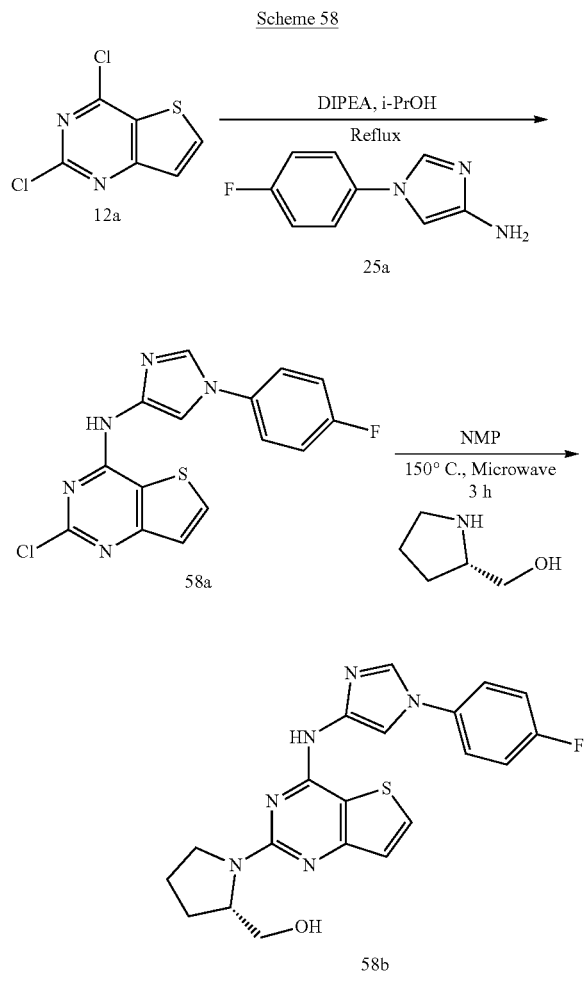

Preparation of (S)-(1-(4-((1-(4-fluorophenyl)-1H-imidazol-4-yl)amino)thieno[3,2-d]pyrimidin-2-yl)pyrrolidin-2-yl)methanol (58b)

Step-1: Preparation of 2-chloro-N-(1-(4-fluorophenyl)-1H-imidazol-4-yl)thieno[3,2-d]pyrimidin-4-amine (58a)

Compound 58a was prepared according to the procedure reported in Scheme 1 from 2,4-dichlorothieno[3,2-d]pyrimidine (12a) (261 mg, 1.27 mmol) in 2-Propanol (10 mL) using DIPEA (0.44 mL, 2.54 mmol), and 1-(4-fluorophenyl)-1H-imidazol-4-amine (25a) (225 mg, 1.27 mmol). This gave 2-chloro-N-(1-(4-fluorophenyl)-1H-imidazol-4-yl)thieno[3,2-d]pyrimidin-4-amine (58a) (268 mg, 61% yield) as a light pink solid; $^1$H NMR (300 MHz, DMSO-$d_6$) δ 10.96 (s, 1H, D$_2$O exchangeable), 8.29-8.18 (m, 2H), 7.91 (d, J=1.6 Hz, 1H), 7.78-7.65 (m, 2H), 7.48-7.35 (m, 3H); $^{19}$F NMR (282 MHz, DMSO-$d_6$) δ −115.27; MS (ES+): 346.3 (M+1), 368.3 (M+Na); (ES−): 344.2 (M−1).

Step-2: Preparation of (S)-(1-(4-((1-(4-fluorophenyl)-1H-imidazol-4-yl)amino)thieno[3,2-d]pyrimidin-2-yl)pyrrolidin-2-yl)methanol (58b)

Compound 58b was prepared from 2-chloro-N-(1-(4-fluorophenyl)-1H-imidazol-4-yl)thieno[3,2-d]pyrimidin-4-amine (58a) (100 mg, 0.29 mmol), (S)-pyrrolidin-2-ylmethanol (88 mg, 0.86 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-(1-(4-fluorophenyl)-1H-imidazol-4-ylamino)thieno[3,2-d]pyrimidin-2-yl)pyrrolidin-2-yl)methanol (58b) (69 mg, 58% yield) as a brown solid; $^1$H NMR (300 MHz, DMSO-$d_6$) δ 10.14 (s, 1H, D$_2$O exchangeable), 8.15 (d, J=1.5 Hz, 1H), 8.01-7.88 (m, 2H), 7.77 (s, 2H), 7.36 (t, J=8.4 Hz, 2H), 7.10 (d, J=5.3 Hz, 1H), 5.35-4.91 (m, 1H, D$_2$O exchangeable), 4.23 (s, 1H), 3.92-3.69 (m, 1H), 3.69-3.18 (m, 3H), 2.15-1.73 (m, 4H); $^{19}$F NMR (282 MHz, DMSO-$d_6$) δ −116.11; MS (ES+): 411.4 (M+1), 433.4 (M+Na); (ES−): 409.4 (M−1).

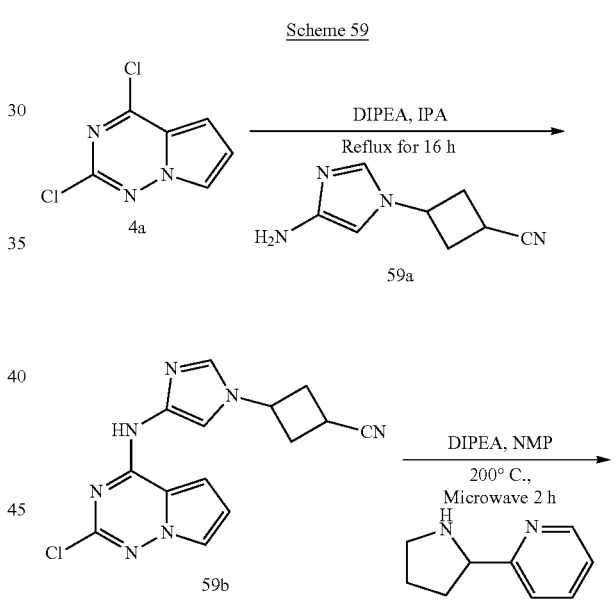

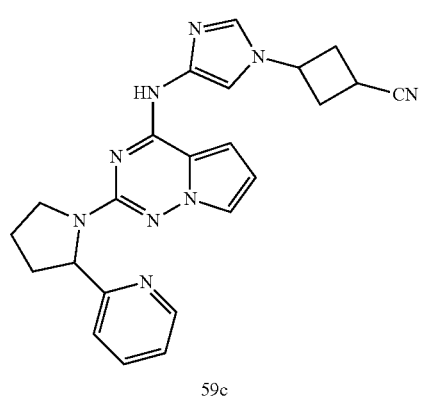

Preparation of 3-(4-((2-(2-(pyridin-2-yl)pyrrolidin-1-yl)pyrrolo[2,1-f][1,2,4]triazin-4-yl)amino)-1H-imidazol-1-yl)cyclobutanecarbonitrile (59c)

Step-1: Preparation of 3-(4-((2-chloropyrrolo[2,1-f][1,2,4]triazin-4-yl)amino)-1H-imidazol-1-yl)cyclobutanecarbonitrile (59b)

Compound 59b was prepared according to the procedure reported in Scheme 1 from 2,4-dichloropyrrolo[1,2-f][1,2,4]triazine (4a) (145 mg, 0.77 mmol) in 2-Propanol (10 mL) using DIPEA (0.4 mL, 2.31 mmol) and 3-(4-amino-1H-imidazol-1-yl)cyclobutanecarbonitrile (59a) (125 mg, 0.77 mmol). This gave 3-(4-((2-chloropyrrolo[2,1-f][1,2,4]triazin-4-yl)amino)-1H-imidazol-1-yl)cyclobutanecarbonitrile (59b) (168 mg, 70% yield) as a yellow solid; $^1$H NMR (300 MHz, DMSO-$d_6$) δ 11.17 (s, 1H), 7.86 (d, J=1.5 Hz, 1H), 7.73 (dt, J=2.9, 1.4 Hz, 1H), 7.57 (d, J=1.5 Hz, 1H), 7.35 (d, J=4.4 Hz, 1H), 6.77-6.60 (m, 1H), 4.77 (p, J=8.6 Hz, 1H), 3.31-3.12 (m, 1H), 2.96-2.81 (m, 2H), 2.79-2.63 (m, 2H); MS (ES+): 314.3 (M+1); MS (ES−): 312.3 (M−1); HPLC purity: 98.51%.

Step-2: Preparation of 3-(4-((2-(2-(pyridin-2-yl)pyrrolidin-1-yl)pyrrolo[2,1-f][1,2,4]triazin-4-yl)amino)-1H-imidazol-1-yl)cyclobutanecarbonitrile (59c)

Compound 59c was prepared from 3-(4-((2-chloropyrrolo[2,1-f][1,2,4]triazin-4-yl)amino)-1H-imidazol-1-yl)cyclobutanecarbonitrile (59b) (60 mg, 0.19 mmol), 2-(pyrrolidin-2-yl)pyridine (85 mg, 0.57 mmol), and DIPEA (0.1 mL, 0.57 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, 3-(4-((2-(2-(pyridin-2-yl)pyrrolidin-1-yl)pyrrolo[2,1-f][1,2,4]triazin-4-yl)amino)-1H-imidazol-1-yl)cyclobutanecarbonitrile (59c) (41 mg, 50% yield) as a white solid; $^1$H NMR (300 MHz, DMSO-$d_6$) δ 10.31 (s, 1H, D$_2$O exchangeable), 8.62 (d, J=4.8 Hz, 1H), 7.71 (d, J=1.5 Hz, 1H), 7.66 (td, J=7.7, 1.8 Hz, 1H), 7.37 (s, 1H), 7.25-7.19 (m, 1H), 7.17 (d, J=7.9 Hz, 1H), 7.16-6.97 (m, 2H), 6.36 (dd, J=4.4, 2.5 Hz, 1H), 5.32 (d, J=8.2 Hz, 1H), 4.68-4.40 (m, 1H), 3.96-3.76 (m, 1H), 3.76-3.50 (m, 1H), 3.33-3.21 (m, 1H), 3.02-2.61 (m, 4H), 2.44-2.26 (m, 1H), 2.16-1.71 (m, 3H); MS (ES+): 426.5 (M+1), 448.5 (M+Na).

Scheme 60

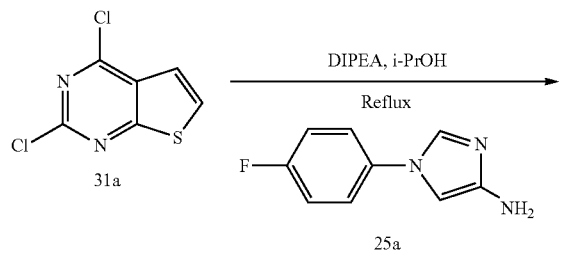

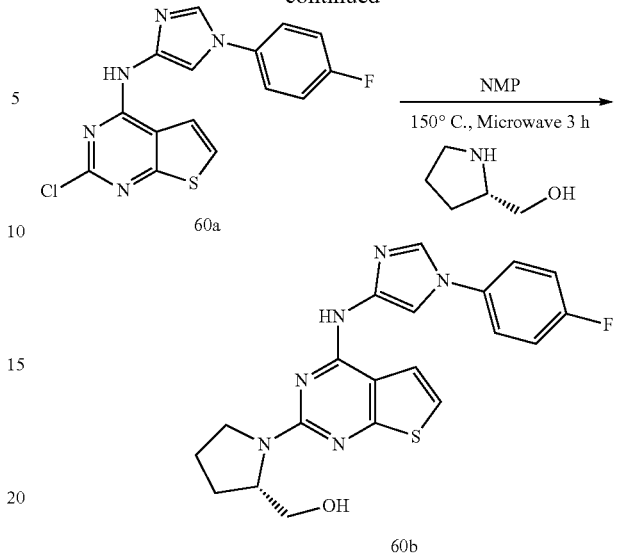

Preparation of (S)-(1-(4-((1-(4-fluorophenyl)-1H-imidazol-4-yl)amino)thieno[2,3-d]pyrimidin-2-yl)pyrrolidin-2-yl)methanol (60b)

Step-1: Preparation of 2-chloro-N-(1-(4-fluorophenyl)-1H-imidazol-4-yl)thieno[2,3-d]pyrimidin-4-amine (60a)

Compound 60a was prepared according to the procedure reported in Scheme 1 from 2,4-dichlorothieno[2,3-d]pyrimidine (31a) (261 mg, 1.27 mmol) in 2-Propanol (10 mL) using DIPEA (0.44 mL, 2.54 mmol), and 1-(4-fluorophenyl)-1H-imidazol-4-amine (25a) (225 mg, 1.27 mmol). This gave 2-chloro-N-(1-(4-fluorophenyl)-1H-imidazol-4-yl)thieno[2,3-d]pyrimidin-4-amine (60a) (270 mg, 61% yield) as a light pink solid; $^1$H NMR (300 MHz, DMSO-$d_6$) δ 11.06 (s, 1H, D$_2$O exchangeable), 8.21 (d, J=1.6 Hz, 1H), 8.04 (d, J=5.8 Hz, 1H), 7.90 (d, J=1.6 Hz, 1H), 7.76-7.67 (m, 3H), 7.48-7.37 (m, 2H); $^{19}$F NMR (282 MHz, DMSO-$d_6$) δ −115.31; MS (ES+): 346.3 (M+1), 368.3 (M+Na); (ES−): 344.3 (M−1).

Step-2: Preparation of (S)-(1-(4-((1-(4-fluorophenyl)-1H-imidazol-4-yl)amino)thieno[2,3-d]pyrimidin-2-yl)pyrrolidin-2-yl)methanol (60b)

Compound 60b was prepared from 2-chloro-N-(1-(4-fluorophenyl)-1H-imidazol-4-yl)thieno[2,3-d]pyrimidin-4-amine (60a) (100 mg, 0.29 mmol), (S)-pyrrolidin-2-ylmethanol (88 mg, 0.86 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-(1-(4-fluorophenyl)-1H-imidazol-4-ylamino)thieno[2,3-d]pyrimidin-2-yl)pyrrolidin-2-yl)methanol (60b) (25 mg, 22% yield) as a brown solid; $^1$H NMR (300 MHz, DMSO-$d_6$) δ 10.17 (s, 1H, D$_2$O exchangeable), 8.17 (s, 1H), 7.94 (d, J=1.6 Hz, 1H), 7.91-7.61 (m, 2H), 7.47-7.21 (m, 3H), 7.03 (d, J=6.0 Hz, 1H), 5.17-4.77 (m, 1H, D$_2$O exchangeable), 4.39-3.99 (m, 1H), 3.89-3.19

(m, 4H), 2.13-1.81 (m, 4H); $^{19}$F NMR (282 MHz, DMSO-$d_6$) δ −73.43; MS (ES+) 411.4 (M+1), 433.4 (M+Na).

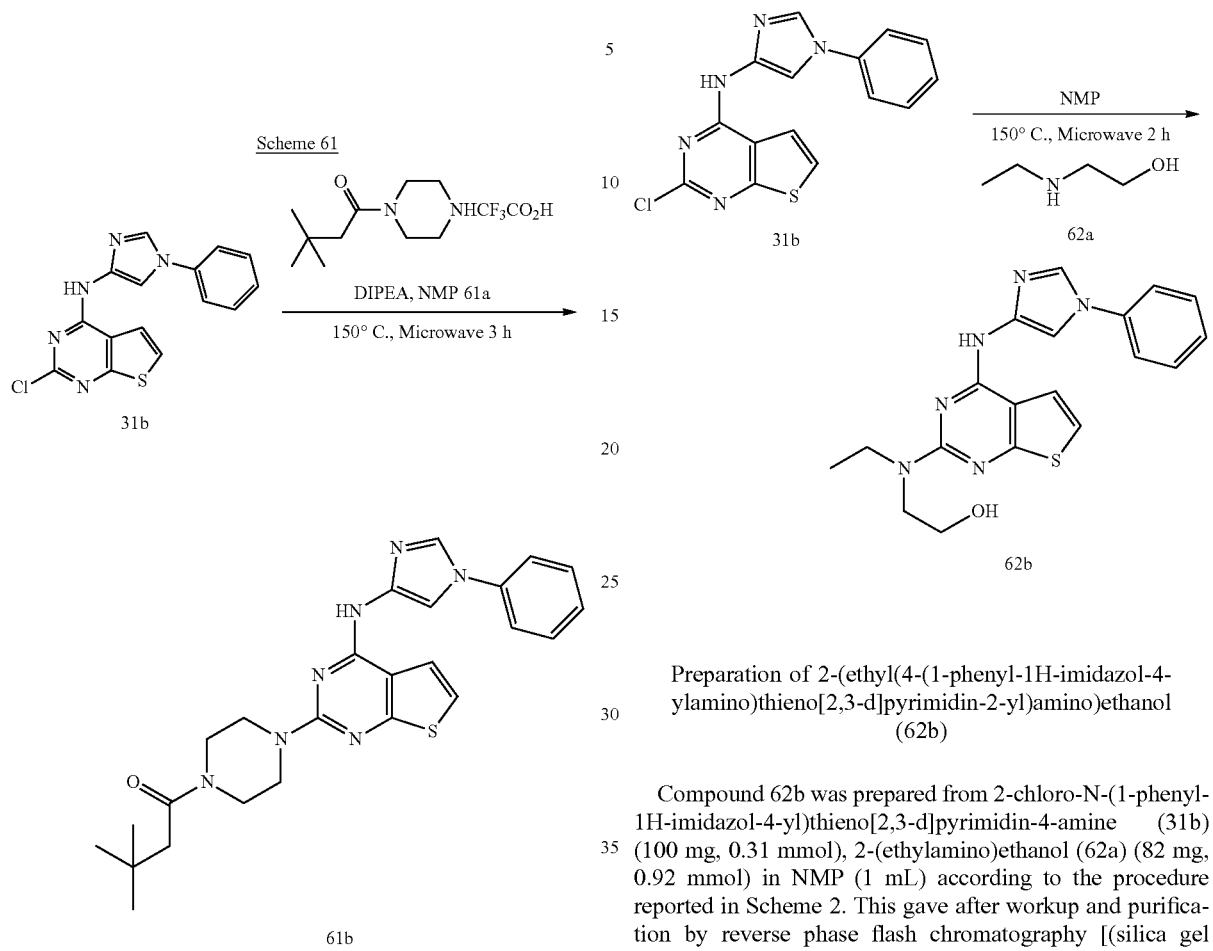

Scheme 61

31b

61b

Scheme 62

31b

62a

62b

Preparation of 3,3-dimethyl-1-(4-(4-((1-phenyl-1H-imidazol-4-yl)amino)thieno[2,3-d]pyrimidin-2-yl)piperazin-1-yl)butan-1-one (61b)

Compound 61b was prepared from 2-chloro-N-(1-phenyl-1H-imidazol-4-yl)thieno[2,3-d]pyrimidin-4-amine (31b) (100 mg, 0.31 mmol), tert-3,3-dimethyl-1-(piperazin-1-yl)butan-1-one 2,2,2-trifluoroacetate (61a) (182 mg, 0.61 mmol; prepared according to the procedure described By Bisacchi, Gregory S. et al; in U.S. Pat. No. 6,335,324) and DIPEA (0.21 mL, 1.22 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, 3,3-dimethyl-1-(4-(4-((1-phenyl-1H-imidazol-4-yl)amino)thieno[2,3-d]pyrimidin-2-yl)piperazin-1-yl)butan-1-one (61b) (95 mg, 66% yield) as a brown solid; $^1$H NMR (300 MHz, DMSO-$d_6$) δ 10.26 (s, 1H, D$_2$O exchangeable), 8.25 (d, J=1.6 Hz, 1H), 7.86 (d, J=1.6 Hz, 1H), 7.81 (d, J=6.0 Hz, 1H), 7.70-7.63 (m, 2H), 7.61-7.52 (m, 2H), 7.45-7.34 (m, 1H), 7.13 (d, J=6.0 Hz, 1H), 3.87-3.74 (m, 4H), 3.71-3.54 (m, 4H), 2.30 (s, 2H), 1.01 (s, 9H); MS (ES+): 476.6 (M+1), 498.5 (M+Na), (ES-): 474.6 (M-1).

Preparation of 2-(ethyl(4-(1-phenyl-1H-imidazol-4-ylamino)thieno[2,3-d]pyrimidin-2-yl)amino)ethanol (62b)

Compound 62b was prepared from 2-chloro-N-(1-phenyl-1H-imidazol-4-yl)thieno[2,3-d]pyrimidin-4-amine (31b) (100 mg, 0.31 mmol), 2-(ethylamino)ethanol (62a) (82 mg, 0.92 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, 2-(ethyl(4-(1-phenyl-1H-imidazol-4-ylamino)thieno[2,3-d]pyrimidin-2-yl)amino)ethanol (62b) (43 mg, 37% yield) as a light brown solid; 1H NMR (300 MHz, DMSO-$d_6$) δ 10.16 (s, 1H, D$_2$O exchangeable), 8.23 (d, J=1.5 Hz, 1H), 7.92 (d, J=1.5 Hz, 1H), 7.80 (d, J=6.0 Hz, 1H), 7.75-7.59 (m, 2H), 7.53 (t, J=7.7 Hz, 2H), 7.42-7.27 (m, 1H), 7.02 (d, J=6.0 Hz, 1H), 4.82 (s, 1H, D$_2$O exchangeable), 3.82-3.54 (m, 6H), 1.31-1.06 (m, 3H); MS (ES+): 381.4 (M+1), 403.4 (M+Na), (ES-): 379.4 (M-1).

Scheme 63

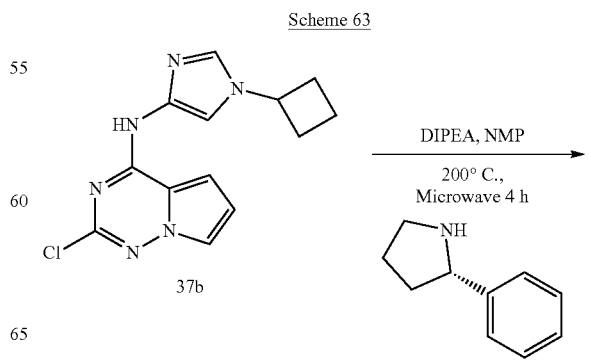

37b

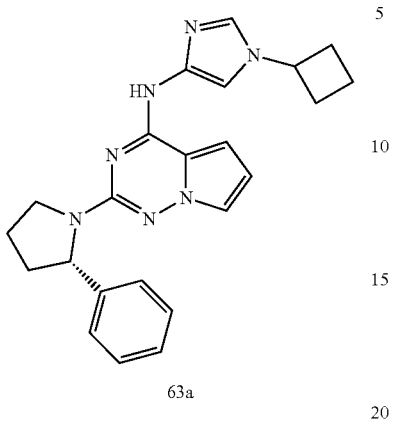

63a

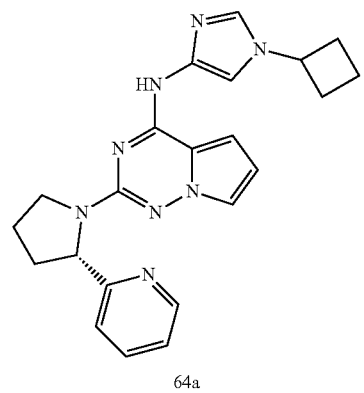

64a

Preparation of (S)—N-(1-cyclobutyl-1H-imidazol-4-yl)-2-(2-phenylpyrrolidin-1-yl)pyrrolo[2,1-f][1,2,4]triazin-4-amine (63a)

Compound 63a was prepared from 2-chloro-N-(1-cyclobutyl-1H-imidazol-4-yl)pyrrolo[2,1-f][1,2,4]triazin-4-amine (37b) (70 mg, 0.24 mmol), (S)-2-phenylpyrrolidine (54 mg, 0.36 mmol) and DIPEA (0.13 mL, 0.73 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using $NaHCO_3$, (S)—N-(1-cyclobutyl-1H-imidazol-4-yl)-2-(2-phenylpyrrolidin-1-yl)pyrrolo[2,1-f][1,2,4]triazin-4-amine (63a) (65 mg, 67% yield) as a white solid; $^1$H NMR (300 MHz, DMSO-$d_6$) δ 10.32 (s, 1H, $D_2O$ exchangeable), 7.88-7.79 (m, 1H), 7.42-7.37 (m, 1H), 7.36-7.23 (m, 4H), 7.23-7.15 (m, 1H), 7.09-6.97 (m, 2H), 6.39 (dd, J=4.4, 2.5 Hz, 1H), 5.41-5.30 (m, 1H), 4.66-4.43 (m, 1H), 3.83-3.69 (m, 1H), 3.67-3.51 (m, 1H), 2.41-2.08 (m, 6H), 2.02-1.69 (m, 4H); MS (ES+): 400.6 (M+1), 422.5 (M+Na); HPLC purity: 98.69%.

Preparation of (S)—N-(1-cyclobutyl-1H-imidazol-4-yl)-2-(2-(pyridin-2-yl)pyrrolidin-1-yl)pyrrolo[2,1-f][1,2,4]triazin-4-amine (64a)

Compound 64a was prepared from 2-chloro-N-(1-cyclobutyl-1H-imidazol-4-yl)pyrrolo[2,1-f][1,2,4]triazin-4-amine (37b) (60 mg, 0.21 mmol), (S)-2-(pyrrolidin-2-yl)pyridine dihydrochloride (55 mg, 0.25 mmol) and DIPEA (0.11 mL, 0.62 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using $NaHCO_3$, (S)—N-(1-cyclobutyl-1H-imidazol-4-yl)-2-(2-(pyridin-2-yl)pyrrolidin-1-yl)pyrrolo[2,1-f][1,2,4]triazin-4-amine (64a) (10 mg, 12% yield) as a light yellow solid; $^1$H NMR (300 MHz, DMSO-$d_6$) δ 10.26 (s, 1H, $D_2O$ exchangeable), 8.67-8.48 (m, 1H), 7.67 (td, J=7.7, 1.8 Hz, 1H), 7.56 (d, J=1.5 Hz, 1H), 7.38 (s, 1H), 7.30-7.13 (m, 2H), 7.08 (dd, J=4.4, 1.7 Hz, 1H), 7.05-6.89 (m, 1H), 6.36 (dd, J=4.4, 2.5 Hz, 1H), 5.35 (d, J=8.1 Hz, 1H), 4.65-4.36 (m, 1H), 3.90-3.72 (m, 1H), 3.68-3.49 (m, 1H), 2.47-2.25 (m, 4H), 2.26-2.11 (m, 1H), 2.12-1.99 (m, 1H), 2.01-1.90 (m, 1H), 1.90-1.65 (m, 3H). MS (ES+): 401.5 (M+1), 423.5 (M+Na); HPLC purity: 96.63%.

Scheme 64

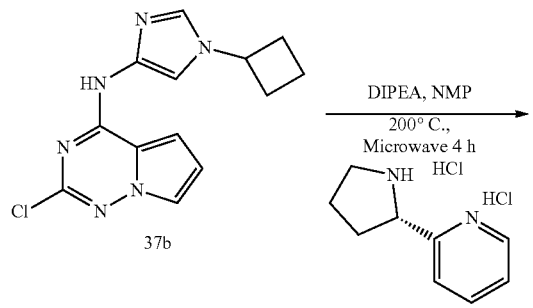

Scheme 65

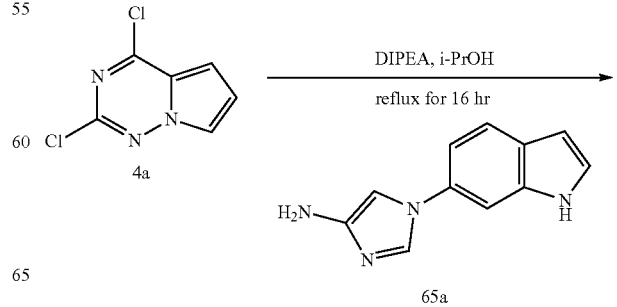

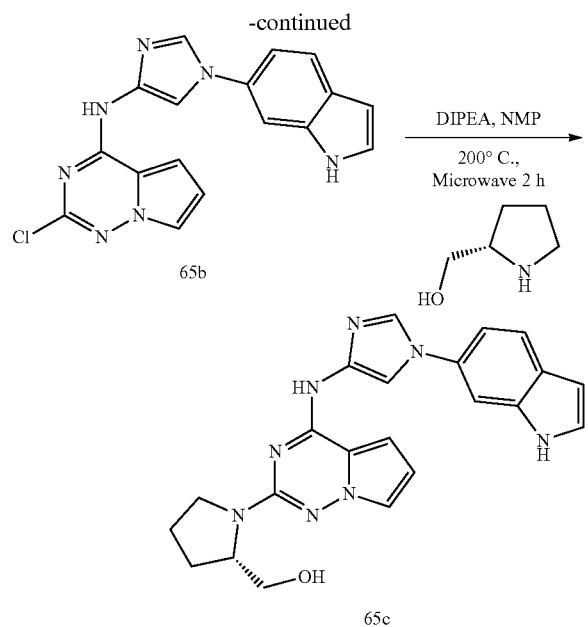

Preparation of (S)-(1-(4-((1-(1H-indol-6-yl)-1H-imidazol-4-yl)amino)pyrrolo[2,1-f][1,2,4]triazin-2-yl)pyrrolidin-2-yl)methanol (65c)

Step-1: Preparation of N-(1-(1H-indol-6-yl)-1H-imidazol-4-yl)-2-chloropyrrolo[2,1-f][1,2,4]triazin-4-amine (65b)

Compound 65b was prepared according to the procedure reported in Scheme 1 from 2,4-dichloropyrrolo[1,2-f][1,2,4]triazine (4a) (199 mg, 1.06 mmol) in 2-Propanol (20 mL) using DIPEA (0.55 mL, 3.18 mmol) and 1-(1H-indol-6-yl)-1H-imidazol-4-amine (65a) (231 mg, 1.17 mmol). This gave N-(1-(1H-indol-6-yl)-1H-imidazol-4-yl)-2-chloropyrrolo[2,1-f][1,2,4]triazin-4-amine (65b) (271 mg, 73% yield) as light pink solid; $^1$H NMR (300 MHz, DMSO-$d_6$) δ 11.36 (s, 2H), 8.18 (d, J=1.6 Hz, 1H), 7.90 (d, J=1.6 Hz, 1H), 7.77 (dd, J=2.6, 1.6 Hz, 1H), 7.70 (d, J=8.4 Hz, 1H), 7.58 (d, J=2.0 Hz, 1H), 7.46 (dd, J=3.1, 2.4 Hz, 1H), 7.41 (d, J=4.1 Hz, 1H), 7.27 (dd, J=8.4, 2.0 Hz, 1H), 6.72 (dd, J=4.4, 2.6 Hz, 1H), 6.52 (ddd, J=3.0, 2.0, 0.9 Hz, 1H); MS (ES+): 350.4 (M+1); MS (ES−): 348.3 (M−1), 384.3 (M+Cl).

Step-2: Preparation of (S)-(1-(4-((1-(1H-indol-6-yl)-1H-imidazol-4-yl)amino)pyrrolo[2,1-f][1,2,4]triazin-2-yl)pyrrolidin-2-yl)methanol (65c)

Compound 65c was prepared from N-(1-(1H-indol-6-yl)-1H-imidazol-4-yl)-2-chloropyrrolo[2,1-f][1,2,4]triazin-4-amine (65b) (100 mg, 0.29 mmol), (S)-pyrrolidin-2-ylmethanol (145 mg, 1.43 mmol), and DIPEA (0.15 mL, 0.86 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(1H-indol-6-yl)-1H-imidazol-4-yl)amino)pyrrolo[2,1-f][1,2,4]triazin-2-yl)pyrrolidin-2-yl)methanol (65c) (81 mg, 68% yield) as a white solid; $^1$H NMR (300 MHz, DMSO-$d_6$) δ 11.26 (s, 1H, D$_2$O exchangeable), 10.50 (s, 1H, D$_2$O exchangeable), 8.14 (s, 1H), 7.95 (d, J=1.6 Hz, 1H), 7.70-7.60 (m, 2H), 7.46-7.41 (m, 1H), 7.41-7.37 (m, 1H), 7.33 (dd, J=8.5, 2.0 Hz, 1H), 7.20-7.11 (m, 1H), 6.53-6.46 (m, 1H), 6.40 (dd, J=4.4, 2.4 Hz, 1H), 5.06-4.37 (m, 1H), 4.30-4.09 (m, 1H), 3.79-3.69 (m, 1H), 3.58-3.48 (m, 1H), 3.48-3.23 (m, 2H), 2.15-1.71 (m, 4H); MS (ES+): 415.5 (M+1); HPLC purity: 99.33%.

Scheme 66

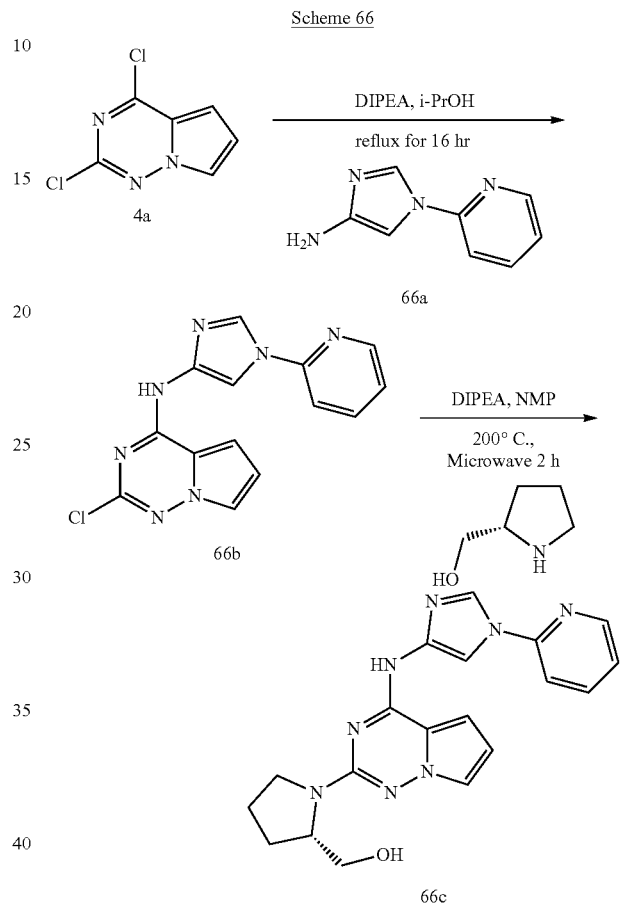

Preparation of (S)-(1-(4-((1-(pyridin-2-yl)-1H-imidazol-4-yl)amino)pyrrolo[2,1-f][1,2,4]triazin-2-yl)pyrrolidin-2-yl)methanol (66c)

Step-1: Preparation of 2-chloro-N-(1-(pyridin-2-yl)-1H-imidazol-4-yl)pyrrolo[2,1-f][1,2,4]triazin-4-amine (66b)

Compound 66b was prepared according to the procedure reported in Scheme 1 from 2,4-dichloropyrrolo[1,2-f][1,2,4]triazine (4a) (112 mg, 0.59 mmol) in 2-Propanol (10 mL) using DIPEA (0.31 mL, 1.78 mmol) and 1-(pyridin-2-yl)-1H-imidazol-4-amine (66a) (95 mg, 0.59 mmol; prepared according to the procedure reported by Bleicher, Konrad et al; in PCT Int. Appl., 2011089132, 28 Jul. 2011). This gave after purification by flash column chromatography [silica (24 g), eluting with DMA-80 in DCM from 0 to 40%] 2-chloro-N-(1-(pyridin-2-yl)-1H-imidazol-4-yl)pyrrolo[2,1-f][1,2,4]triazin-4-amine (66b) (27 mg, 15% yield) as a solid; $^1$H NMR (300 MHz, DMSO-$d_6$) δ 11.37 (s, 1H), 8.64-8.49 (m, 2H), 8.25 (d, J=1.5 Hz, 1H), 8.11-7.97 (m, 1H), 7.86 (d, J=8.2 Hz, 1H), 7.80-7.75 (m, 1H), 7.48-7.33 (m, 2H), 6.72 (dd, J=4.5, 2.6 Hz, 1H); MS (ES+): 312.3 (M+1); MS (ES−): 310.3 (M−1).

Step-2: Preparation of (S)-(1-(4-((1-(pyridin-2-yl)-1H-imidazol-4-yl)amino)pyrrolo[2,1-f][1,2,4]triazin-2-yl)pyrrolidin-2-yl)methanol (66c)

Compound 66c was prepared from 2-chloro-N-(1-(pyridin-2-yl)-1H-imidazol-4-yl)pyrrolo[2,1-f][1,2,4]triazin-4-amine (66b) (27 mg, 0.09 mmol), (S)-pyrrolidin-2-ylmethanol (44 mg, 0.43 mmol) and DIPEA (0.05 mL, 0.26 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(pyridin-2-yl)-1H-imidazol-4-yl)amino)pyrrolo[2,1-f][1,2,4]triazin-2-yl)pyrrolidin-2-yl)methanol (66c) (9 mg, 28% yield) as a white solid; $^1$H NMR (300 MHz, DMSO-d$_6$) δ 10.58 (s, 1H, D$_2$O exchangeable), 8.51 (s, 1H), 8.48 (d, J=4.4 Hz, 1H), 8.19 (s, 1H), 7.98 (t, J=7.7 Hz, 1H), 7.90 (d, J=8.2 Hz, 1H), 7.47-7.31 (m, 2H), 7.22-7.09 (m, 1H), 6.46-6.37 (m, 1H), 5.02-4.81 (m, 1H, D$_2$O exchangeable), 4.26-4.11 (m, 1H), 3.90-3.73 (m, 1H), 3.63-3.46 (m, 1H), 3.47-3.15 (m, 2H), 2.19-1.69 (m, 4H); MS (ES+): 377.4 (M+1), 399.4 (M+Na); HPLC purity: 97.04%.

Preparation of (S)-(1-(4-((1-(1H-indol-5-yl)-1H-imidazol-4-yl)amino)pyrrolo[2,1-f][1,2,4]triazin-2-yl)pyrrolidin-2-yl)methanol (67c)

Step-1: Preparation of N-(1-(1H-indol-5-yl)-1H-imidazol-4-yl)-2-chloropyrrolo[2,1-f][1,2,4]triazin-4-amine (67b)

Compound 67b was prepared according to the procedure reported in Scheme 1 from 2,4-dichloropyrrolo[1,2-f][1,2,4]triazine (4a) (215 mg, 1.14 mmol) in 2-Propanol (20 mL) using DIPEA (0.6 mL, 3.43 mmol) and 1-(1H-indol-5-yl)-1H-imidazol-4-amine (67a) (249 mg, 1.26 mmol). This gave N-(1-(1H-indol-5-yl)-1H-imidazol-4-yl)-2-chloropyrrolo[2,1-f][1,2,4]triazin-4-amine (67b) (314 mg, 79% yield) as light pink solid; $^1$H NMR (300 MHz, DMSO-d$_6$) δ 11.36 (s, 1H), 11.33 (s, 1H), 8.16-8.05 (m, 1H), 7.90-7.84 (m, 1H), 7.80-7.71 (m, 2H), 7.61-7.52 (m, 1H), 7.51-7.45 (m, 1H), 7.46-7.37 (m, 1H), 7.37-7.25 (m, 1H), 6.72 (p, J=3.4, 2.9 Hz, 1H), 6.58-6.46 (m, 1H); MS (ES+): 350.4 (M+1), 372.4 (M+Na); MS (ES−): 348.3 (M−1), 384.3 (M+Cl); HPLC purity: 98.41%.

Step-2: Preparation of (S)-(1-(4-((1-(1H-indol-5-yl)-1H-imidazol-4-yl)amino)pyrrolo[2,1-f][1,2,4]triazin-2-yl)pyrrolidin-2-yl)methanol (67c)

Compound 67c was prepared from N-(1-(1H-indol-5-yl)-1H-imidazol-4-yl)-2-chloropyrrolo[2,1-f][1,2,4]triazin-4-amine (67b) (100 mg, 0.29 mmol), (S)-pyrrolidin-2-ylmethanol (145 mg, 1.43 mmol), and DIPEA (0.15 mL, 0.86 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(1H-indol-5-yl)-1H-imidazol-4-yl)amino)pyrrolo[2,1-f][1,2,4]triazin-2-yl)pyrrolidin-2-yl)methanol (67c) (80 mg, 68% yield) as a white solid; $^1$H NMR (300 MHz, DMSO-d$_6$) δ 11.30 (s, 1H, D$_2$O exchangeable), 10.48 (s, 1H, D$_2$O exchangeable), 8.09 (d, J=1.5 Hz, 1H), 7.95 (d, J=1.6 Hz, 1H), 7.87 (d, J=2.0 Hz, 1H), 7.55-7.43 (m, 2H), 7.44-7.32 (m, 2H), 7.19-7.11 (m, 1H), 6.53-6.47 (m, 1H), 6.39 (dd, J=4.4, 2.4 Hz, 1H), 4.87 (t, J=5.1 Hz, 1H, D$_2$O exchangeable), 4.28-4.06 (m, 1H), 3.86-3.67 (m, 1H), 3.57-3.45 (m, 1H), 3.47-3.25 (m, 2H), 2.11-1.81 (m, 4H); MS (ES+): 415.5 (M+1); MS (ES−): 413.5 (M−1), 449.4 (M+Cl); HPLC purity: 99.37%.

Scheme 67

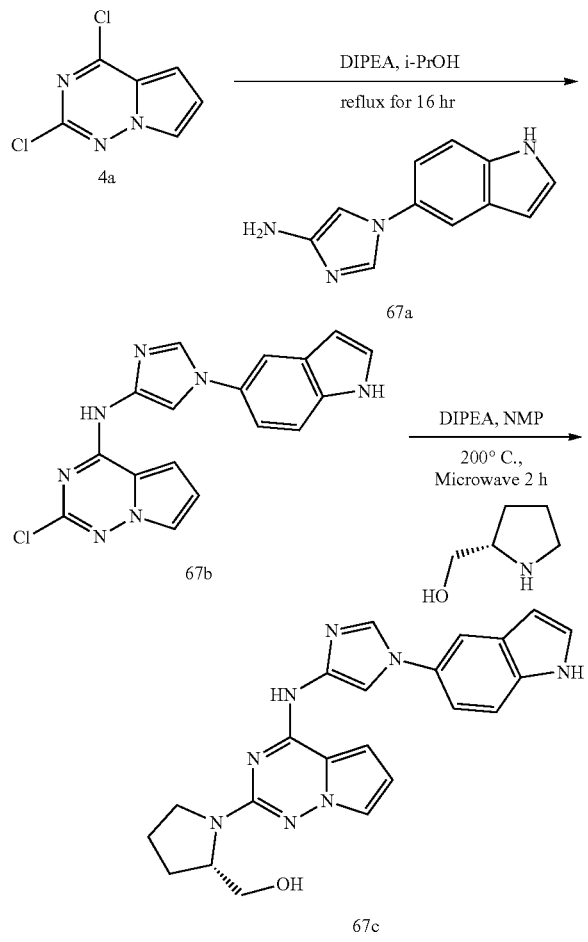

Scheme 68

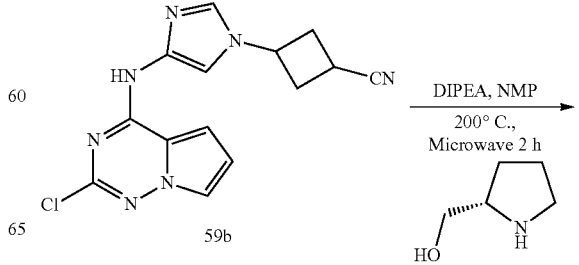

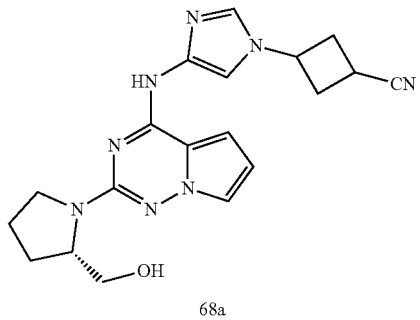

68a

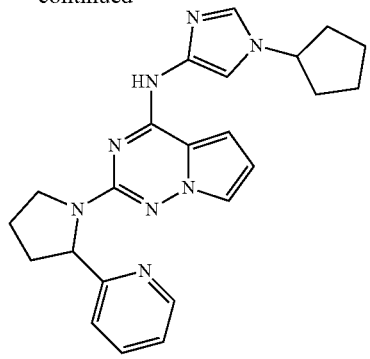

69a

Preparation of (S)-3-(4-((2-(2-(hydroxymethyl)pyrrolidin-1-yl)pyrrolo[2,1-f][1,2,4]triazin-4-yl)amino)-1H-imidazol-1-yl)cyclobutanecarbonitrile (68a)

Compound 68a was prepared from 3-(4-((2-chloropyrrolo[2,1-f][1,2,4]triazin-4-yl)amino)-1H-imidazol-1-yl)cyclobutanecarbonitrile (59b) (50 mg, 0.16 mmol), (S)-pyrrolidin-2-ylmethanol (81 mg, 0.8 mmol) and DIPEA (0.08 mL, 0.48 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-3-(4-((2-(2-(hydroxymethyl)pyrrolidin-1-yl)pyrrolo[2,1-f][1,2,4]triazin-4-yl)amino)-1H-imidazol-1-yl)cyclobutanecarbonitrile (68a) (36 mg, 60% yield) as a light yellow solid; $^1$H NMR (300 MHz, DMSO-d$_6$) δ 10.38 (s, 1H, D$_2$O exchangeable), 7.72 (d, J=1.5 Hz, 1H), 7.65 (d, J=1.6 Hz, 1H), 7.36 (dd, J=2.4, 1.6 Hz, 1H), 7.09 (dd, J=4.5, 1.7 Hz, 1H), 6.36 (dd, J=4.4, 2.4 Hz, 1H), 4.80 (t, J=5.2 Hz, 1H, D$_2$O exchangeable), 4.77-4.63 (m, 1H), 4.23-4.04 (m, 1H), 3.81-3.67 (m, 1H), 3.57-3.45 (m, 1H), 3.45-3.33 (m, 2H), 3.27-3.12 (m, 1H), 2.98-2.62 (m, 4H), 2.16-1.75 (m, 4H); MS (ES+): 379.5 (M+1); 401.5 (M+Na).

Preparation of N-(1-cyclopentyl-1H-imidazol-4-yl)-2-(2-(pyridin-2-yl)pyrrolidin-1-yl)pyrrolo[2,1-f][1,2,4]triazin-4-amine (69a)

Compound 69a was prepared from 2-chloro-N-(1-cyclopentyl-1H-imidazol-4-yl)pyrrolo[2,1-f][1,2,4]triazin-4-amine (50b) (50 mg, 0.17 mmol), 2-(pyrrolidin-2-yl)pyridine (73 mg, 0.5 mmol) and DIPEA (0.09 mL, 0.5 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-cyclopentyl-1H-imidazol-4-yl)-2-(2-(pyridin-2-yl)pyrrolidin-1-yl)pyrrolo[2,1-f][1,2,4]triazin-4-amine (69a) (48 mg, 70% yield) as a light yellow solid; $^1$H NMR (300 MHz, DMSO-d$_6$) δ 10.26 (s, 1H, D$_2$O exchangeable), 8.61-8.50 (m, 1H), 7.67 (td, J=7.7, 1.8 Hz, 1H), 7.51 (d, J=1.5 Hz, 1H), 7.37 (s, 1H), 7.26-7.13 (m, 2H), 7.13-7.05 (m, 1H), 7.04-6.89 (m, 1H), 6.36 (dd, J=4.4, 2.4 Hz, 1H), 5.31 (d, J=8.1 Hz, 1H), 4.43-4.23 (m, 1H), 3.79 (t, J=9.3 Hz, 1H), 3.68-3.50 (m, 1H), 2.41-2.29 (m, 1H), 2.18-1.87 (m, 5H), 1.89-1.53 (m, 6H); MS (ES+): 415.5 (M+1), 437.5 (M+Na); HPLC purity: 98.48%.

Scheme 70

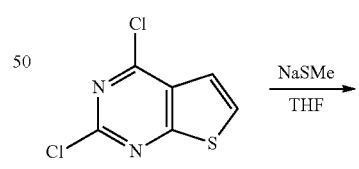

31a

Scheme 69

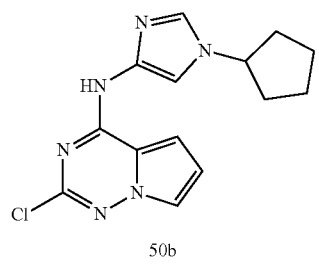

50b

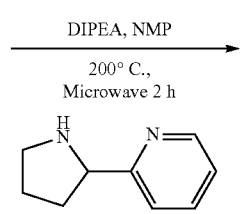

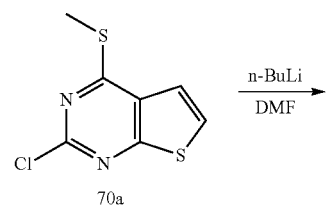

70a

221

-continued

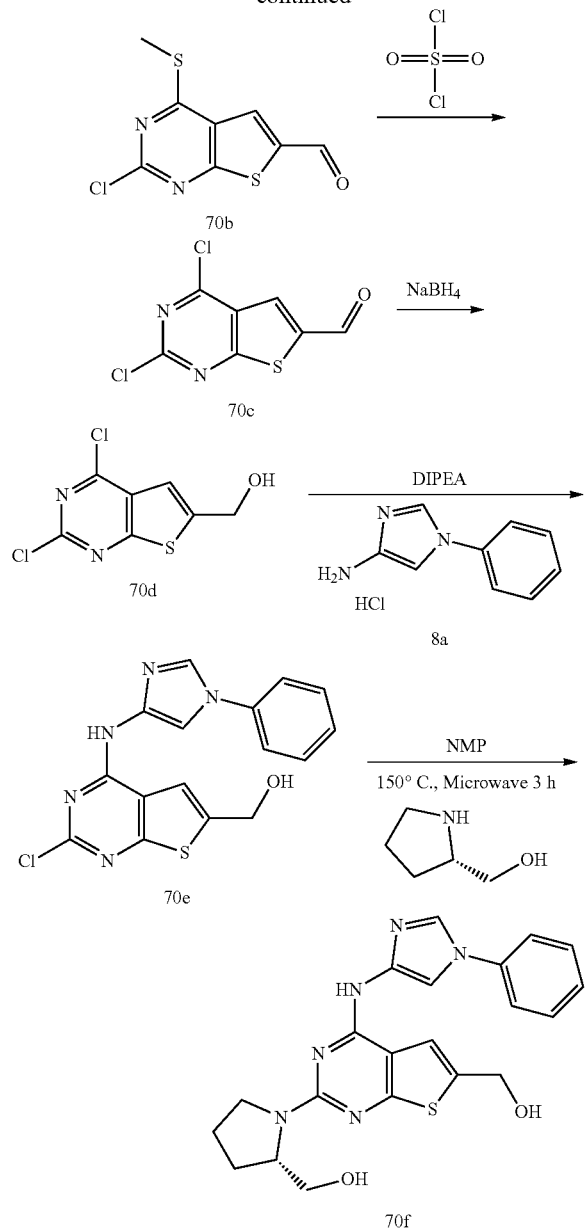

Preparation of (S)-(1-(6-(hydroxymethyl)-4-((1-phenyl-1H-imidazol-4-yl)amino)thieno[2,3-d]pyrimidin-2-yl)pyrrolidin-2-yl)methanol (70f)

Step-1: Preparation of 2-chloro-4-(methylthio)thieno[2,3-d]pyrimidine (70a)

To a solution of 2,4-dichlorothieno[2,3-d]pyrimidine (31a) (4 g, 19.51 mmol) in THF (100 mL) at 0° C. was added sodium thiomethoxide (1.418 g, 19.51 mmol) and allowed to come to room temperature. Reaction mixture was quenched by adding 1 N HCl and poured into water (200 mL). The solid separated was collected by filtration, dried in vacuum to afford 2-chloro-4-(methylthio)thieno[2,3-d]pyrimidine (70a) (3.76 g, 89% yield) as a brown solid; $^1$H NMR (300 MHz, DMSO-$d_6$) δ 7.96 (d, J=6.0 Hz, 1H), 7.50 (d, J=6.0 Hz, 1H), 2.68 (s, 3H).

222

Step-2: Preparation of 2-chloro-4-(methylthio)thieno[2,3-d]pyrimidine-6-carbaldehyde (70b)

To a solution of 2-chloro-4-(methylthio)thieno[2,3-d]pyrimidine (70a) (3.68 g, 17.0 mmol) in dry THF (100 mL) at −78° C. under nitrogen was added dropwise n-butyl lithium (1.6 M solution in hexanes, 21.25 mL, 34.0 mmol). Reaction was stirred at −78° C. for 1.5 h and quenched slowly by dropwise addition of N,N-dimethylformamide (2.63 mL, 34.0 mmol). The reaction was stirred at −78° C. for 2 h and allowed to warm to room temperature overnight. The reaction mixture was cooled to 0° C. and quenched with 1 N HCl and extracted with ethyl acetate (2×100 mL). The organic layer was separated, washed with water (2×20 mL); brine (20 mL) dried, filtered and concentrated in vacuum. The residue obtained was purified by flash column chromatography [silica gel, (40 g) eluting with 0-100% ethyl acetate in hexanes] to afford 2-chloro-4-(methylthio)thieno[2,3-d]pyrimidine-6-carbaldehyde (70b) (2.48 g, 60% yield) as a brown solid; $^1$H NMR (300 MHz, DMSO-$d_6$) δ 10.13 (s, 1H), 8.55 (s, 1H), 2.73 (s, 3H); MS (ES+): 277.2 (M+Na).

Step 3: Preparation of 2,4-dichlorothieno[2,3-d]pyrimidine-6-carbaldehyde (70c)

To a solution of 2-chloro-4-(methylthio)thieno[2,3-d]pyrimidine-6-carbaldehyde (70b) (2 g, 8.17 mmol) in acetonitrile (50 mL) and dichloromethane (20 mL) at 0° C. was added sulfuryl chloride (3.32 mL, 40.9 mmol) in dichloromethane (20 mL) over a period of 30 min. The reaction mixture was stirred for 10 min at 0° C. and quenched with saturated sodium bicarbonate solution. The reaction mixture was concentrated in vacuum to remove organic solvents and the aqueous residue was extracted with ethyl acetate (3×50 mL). The combined organic layer was washed with brine, dried, filtered, and concentrated under reduced pressure to afford 2,4-dichlorothieno[2,3-d]pyrimidine-6-carbaldehyde (70c) (1.9 g, 100% yield) as a dark brown solid; $^1$H NMR (300 MHz, DMSO-$d_6$) δ 10.19 (s, 1H), 8.62 (s, 1H).

Step 4: Preparation of (2,4-dichlorothieno[2,3-d]pyrimidin-6-yl)methanol (70d)

To a solution of 2,4-dichlorothieno[2,3-d]pyrimidine-6-carbaldehyde (70c) (1 g, 4.29 mmol) in THF (30 mL) and Water (1 mL) was added sodium borohydride (162 mg, 4.29 mmol) at room temperature and stirred for 20 min. The reaction mixture was diluted with ethyl acetate (100 mL), quenched with 1 N HCl. The organic layer was separated washed with brine, dried and concentrated. The residue obtained was purified by flash column chromatography [silica gel (25 g), eluting with 0-100% ethyl acetate in hexanes] to afford (2,4-dichlorothieno[2,3-d]pyrimidin-6-yl)methanol (70d) (450 mg, 45% yield) as a white solid; $^1$H NMR (300 MHz, DMSO-$d_6$) δ 7.43 (t, J=1.3 Hz, 1H), 6.07 (t, J=5.7 Hz, 1H, $D_2O$ exchangeable), 4.83 (dd, J=5.8, 1.3 Hz, 2H).

Step 5: Preparation of (2-chloro-4-((1-phenyl-1H-imidazol-4-yl)amino)thieno[2,3-d]pyrimidin-6-yl)methanol (70e)

Compound 70e was prepared according to the procedure reported in Scheme 1 from (2,4-dichlorothieno[2,3-d]pyrimidin-6-yl)methanol (70d) (40 mg, 0.17 mmol) in 2-Propanol (10 mL) using DIPEA (0.12 mL, 0.68 mmol), and 1-phenyl-1H-imidazol-4-amine hydrochloride (8a) (50 mg, 0.26 mmol). This gave (2-chloro-4-(1-phenyl-1H-imidazol-4-ylamino)thieno[2,3-d]pyrimidin-6-yl)methanol (70e) (25 mg, 41% yield) as light pink solid. $^1$H NMR (300 MHz, DMSO-$d_6$) δ 10.95 (s, 1H, D$_2$O exchangeable), 8.25 (d, J=1.6 Hz, 1H), 7.92 (d, J=1.6 Hz, 1H), 7.87 (s, 1H), 7.66 (dd, J=8.4, 1.4 Hz, 2H), 7.57 (t, J=7.9 Hz, 2H), 7.46-7.35 (m, 1H), 5.83 (t, J=5.8 Hz, 1H, D$_2$O exchangeable), 4.72 (d, J=5.6 Hz, 2H); MS (ES+): 380.3 (M+Na), (ES−): 356.2 (M−1).

Step 6: Preparation of (S)-(1-(6-(hydroxymethyl)-4-((1-phenyl-1H-imidazol-4-yl)amino)thieno[2,3-d]pyrimidin-2-yl)pyrrolidin-2-yl)methanol (70f)

Compound 70f was prepared from (2-chloro-4-(1-phenyl-1H-imidazol-4-ylamino)thieno[2,3-d]pyrimidin-6-yl)methanol (70e) (24 mg, 0.07 mmol), (S)-pyrrolidin-2-yl-methanol (20 mg, 0.2 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(6-(hydroxymethyl)-4-((1-phenyl-1H-imidazol-4-yl)amino)thieno[2,3-d]pyrimidin-2-yl)pyrrolidin-2-yl)methanol (70f) (10 mg, 35% yield) as a brown solid; $^1$H NMR (300 MHz, DMSO-$d_6$) δ 10.07 (s, 1H, D$_2$O exchangeable), 8.20 (s, 1H), 7.97 (d, J=1.7 Hz, 1H), 7.85-7.67 (m, 2H), 7.65 (s, 1H), 7.58-7.42 (m, 2H), 7.39-7.28 (m, 1H), 5.50 (t, J=5.7 Hz, 1H, D$_2$O exchangeable), 5.05-4.82 (m, 1H, D$_2$O exchangeable), 4.57 (d, J=5.7 Hz, 2H), 4.42-3.99 (m, 1H), 3.97-3.34 (m, 4H), 2.16-1.76 (m, 4H); MS (ES+): 423.4 (M+1), (ES−): 421.3 (M−1), 457.4 (M+Cl).

Scheme 71

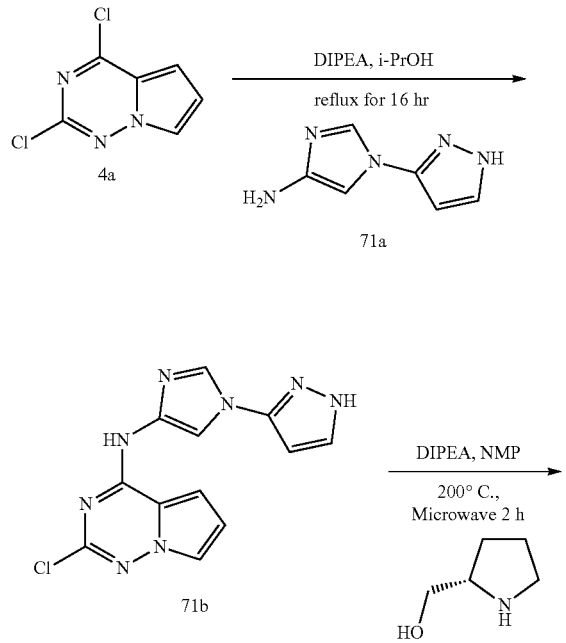

-continued

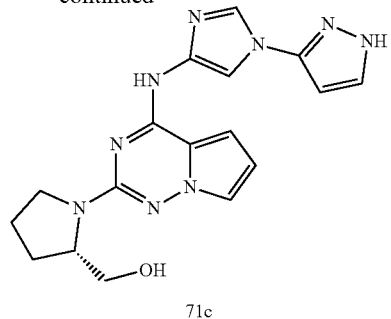

71c

Preparation of (S)-(1-(4-((1-(1H-pyrazol-3-yl)-1H-imidazol-4-yl)amino)pyrrolo[2,1-f][1,2,4]triazin-2-yl)pyrrolidin-2-yl)methanol (71c)

Step-1: Preparation of N-(1-(1H-pyrazol-3-yl)-1H-imidazol-4-yl)-2-chloropyrrolo[2,1-f][1,2,4]triazin-4-amine (71b)

Compound 71b was prepared according to the procedure reported in Scheme 1 from 2,4-dichloropyrrolo[1,2-f][1,2,4]triazine (4a) (357 mg, 1.9 mmol) in 2-Propanol (10 mL) using DIPEA (1.0 mL, 5.7 mmol) and 1-(1H-pyrazol-3-yl)-1H-imidazol-4-amine (71a) (340 mg, 2.28 mmol). This gave N-(1-(1H-pyrazol-3-yl)-1H-imidazol-4-yl)-2-chloropyrrolo[2,1-f][1,2,4]triazin-4-amine (71b) (496 mg, 87% yield) as yellow solid; $^1$H NMR (300 MHz, DMSO-$d_6$) δ 12.92 (s, 1H), 11.34 (s, 1H), 8.35-8.13 (m, 1H), 8.02-7.93 (m, 1H), 7.93-7.81 (m, 1H), 7.81-7.66 (m, 1H), 7.52-7.26 (m, 1H), 6.83-6.68 (m, 1H), 6.67-6.53 (m, 1H); $^1$H NMR (300 MHz, DMSO-$d_6$/D$_2$O) δ 8.14 (d, J=1.6 Hz, 1H), 7.92 (d, J=1.5 Hz, 1H), 7.82 (d, J=2.4 Hz, 1H), 7.72 (dd, J=2.6, 1.5 Hz, 1H), 7.33-7.26 (m, 1H), 6.71 (dd, J=4.5, 2.6 Hz, 1H), 6.60 (d, J=2.5 Hz, 1H); MS (ES+): 301.3 (M+1); MS (ES−): 299.3 (M−1); HPLC purity: 98.56%.

Step-2: Preparation of (S)-(1-(4-((1-(1H-pyrazol-3-yl)-1H-imidazol-4-yl)amino)pyrrolo[2,1-f][1,2,4]triazin-2-yl)pyrrolidin-2-yl)methanol (71c)

Compound 71c was prepared from N-(1-(1H-pyrazol-3-yl)-1H-imidazol-4-yl)-2-chloropyrrolo[2,1-f][1,2,4]triazin-4-amine (71b) (90 mg, 0.3 mmol), (S)-pyrrolidin-2-ylmethanol (151 mg, 1.5 mmol), and DIPEA (0.16 mL, 0.9 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(1H-pyrazol-3-yl)-1H-imidazol-4-yl)amino)pyrrolo[2,1-f][1,2,4]triazin-2-yl)pyrrolidin-2-yl)methanol (71c) (86 mg, 79% yield) as a white solid; $^1$H NMR (300 MHz, DMSO-$d_6$) δ 12.94 (s, 1H, D$_2$O exchangeable), 10.54 (s, 1H, D$_2$O exchangeable), 8.15 (d, J=1.5 Hz, 1H), 7.97 (d, J=1.5 Hz, 1H), 7.86 (dd, J=2.4, 1.1 Hz, 1H), 7.39 (dd, J=2.4, 1.7 Hz, 1H), 7.13 (dd, J=4.4, 1.7 Hz, 1H), 6.69 (s, 1H), 6.39 (dd, J=4.4, 2.4 Hz, 1H), 4.86 (t, J=5.6 Hz, 1H, D$_2$O exchangeable), 4.25-4.04 (m, 1H), 3.88-3.71 (m, 1H), 3.58-3.45 (m, 1H), 3.45-3.24 (m, 2H), 2.17-1.70 (m, 4H); MS (ES+): 366.5 (M+1), 388.5 (M+Na); HPLC purity: 99.33%.

Scheme 72

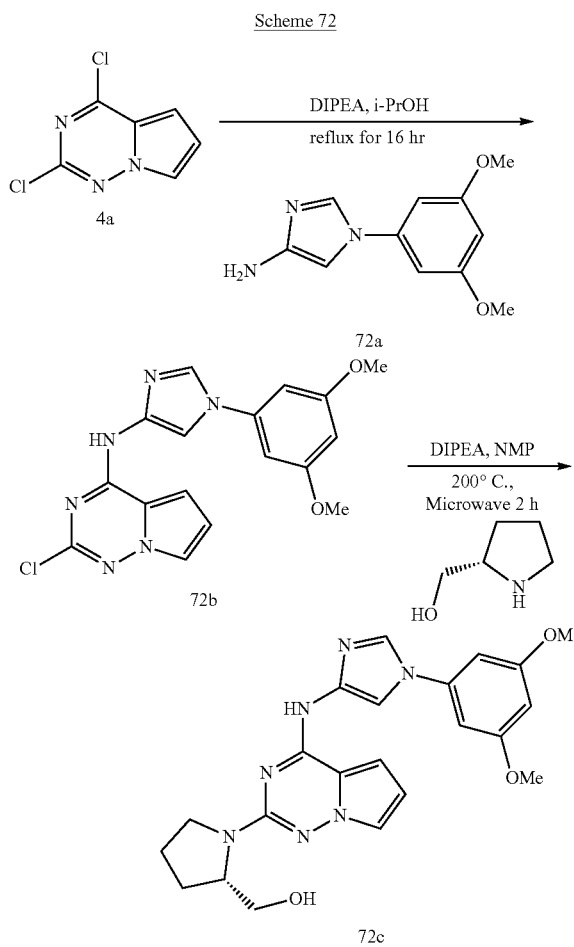

Preparation of (S)-(1-(4-((1-(3,5-dimethoxyphenyl)-1H-imidazol-4-yl)amino)pyrrolo[2,1-f][1,2,4]triazin-2-yl)pyrrolidin-2-yl)methanol (72c)

Step-1: Preparation of 2-chloro-N-(1-(3,5-dimethoxyphenyl)-1H-imidazol-4-yl)pyrrolo[2,1-f][1,2,4]triazin-4-amine (72b)

Compound 72b was prepared according to the procedure reported in Scheme 1 from 2,4-dichloropyrrolo[1,2-f][1,2,4]triazine (4a) (313 mg, 1.67 mmol) in 2-Propanol (20 mL) using DIPEA (0.87 mL, 5.0 mmol) and 1-(3,5-dimethoxyphenyl)-1H-imidazol-4-amine (72a) (365 mg, 1.67 mmol). This gave 2-chloro-N-(1-(3,5-dimethoxyphenyl)-1H-imidazol-4-yl)pyrrolo[2,1-f][1,2,4]triazin-4-amine (72b) (492 mg, 80% yield) as a solid; $^1$H NMR (300 MHz, DMSO-$d_6$) δ 11.32 (s, 1H, D$_2$O exchangeable), 8.29 (d, J=1.6 Hz, 1H), 7.90 (d, J=1.6 Hz, 1H), 7.77 (dd, J=2.6, 1.6 Hz, 1H), 7.39 (d, J=4.4 Hz, 1H), 6.80 (d, J=2.2 Hz, 2H), 6.72 (dd, J=4.5, 2.6 Hz, 1H), 6.54 (t, J=2.2 Hz, 1H), 3.83 (s, 6H); MS (ES+): 371.4 (M+1); MS (ES−): 369.3 (M−1); HPLC purity: 98.98%.

Step-2: Preparation of (S)-(1-(4-((1-(3,5-dimethoxyphenyl)-1H-imidazol-4-yl)amino)pyrrolo[2,1-f][1,2,4]triazin-2-yl)pyrrolidin-2-yl)methanol (72c)

Compound 72c was prepared from 2-chloro-N-(1-(3,5-dimethoxyphenyl)-1H-imidazol-4-yl)pyrrolo[2,1-f][1,2,4]triazin-4-amine (72b) (100 mg, 0.27 mmol), (S)-pyrrolidin-2-ylmethanol (136 mg, 1.35 mmol), and DIPEA (0.14 mL, 0.81 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(3,5-dimethoxyphenyl)-1H-imidazol-4-yl)amino)pyrrolo[2,1-f][1,2,4]triazin-2-yl)pyrrolidin-2-yl)methanol (72c) (73 mg, 62% yield) as a white solid; $^1$H NMR (300 MHz, DMSO-$d_6$) δ 10.53 (s, 1H, D$_2$O exchangeable), 8.27 (d, J=1.5 Hz, 1H), 7.97 (d, J=1.6 Hz, 1H), 7.39 (dd, J=2.4, 1.7 Hz, 1H), 7.14 (dd, J=4.5, 1.7 Hz, 1H), 6.86 (d, J=2.2 Hz, 2H), 6.47 (t, J=2.2 Hz, 1H), 6.39 (dd, J=4.4, 2.4 Hz, 1H), 4.82 (t, J=5.1 Hz, 1H, D$_2$O exchangeable), 4.27-4.13 (m, 1H), 3.82 (s, 6H), 3.78-3.65 (m, 1H), 3.62-3.48 (m, 1H), 3.49-3.24 (m, 2H), 2.10-1.79 (m, 4H); MS (ES+): 436.5 (M+1), 458.4 (M+Na); MS (ES−): 434.4 (M−1); HPLC purity: 98.94%.

Scheme 73

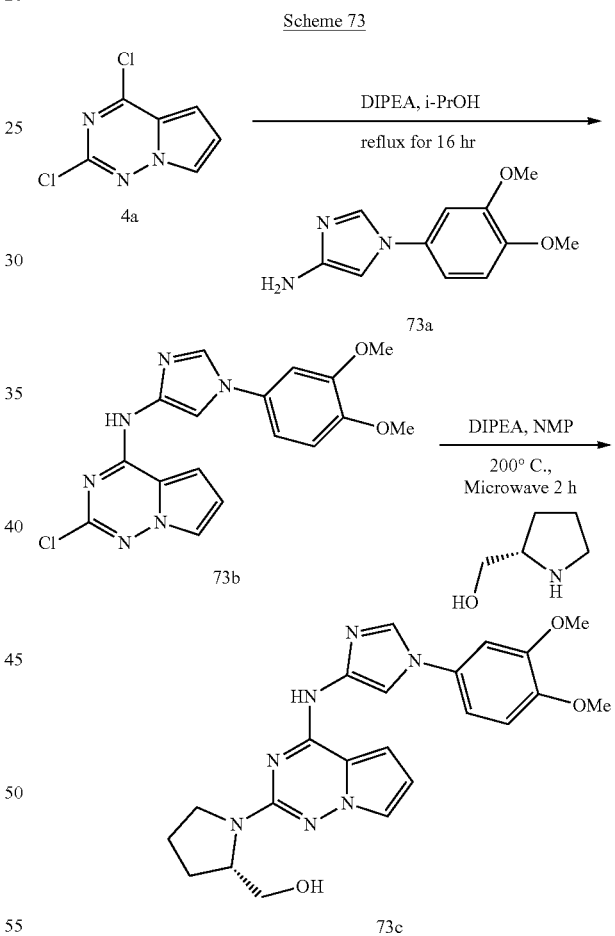

Preparation of (S)-(1-(4-((1-(3,4-dimethoxyphenyl)-1H-imidazol-4-yl)amino)pyrrolo[2,1-f][1,2,4]triazin-2-yl)pyrrolidin-2-yl)methanol (73c)

Step-1: Preparation of 2-chloro-N-(1-(3,4-dimethoxyphenyl)-1H-imidazol-4-yl)pyrrolo[2,1-f][1,2,4]triazin-4-amine (73b)

Compound 73b was prepared according to the procedure reported in Scheme 1 from 2,4-dichloropyrrolo[1,2-f][1,2, 4]triazine (4a) (313 mg, 1.67 mmol) in 2-Propanol (10 mL) using DIPEA (0.87 mL, 5.0 mmol) and 1-(3,4-dimethoxyphenyl)-1H-imidazol-4-amine (73a) (365 mg, 1.67 mmol). This gave 2-chloro-N-(1-(3,4-dimethoxyphenyl)-1H-imidazol-4-yl)pyrrolo[2,1-f][1,2,4]triazin-4-amine (73b) (513 mg, 83% yield) as a solid; $^1$H NMR (300 MHz, DMSO-$d_6$) δ 11.32 (s, 1H, $D_2O$ exchangeable), 8.16 (d, J=1.6 Hz, 1H), 7.84 (d, J=1.6 Hz, 1H), 7.76 (dd, J=2.6, 1.5 Hz, 1H), 7.49-7.34 (m, 1H), 7.25 (t, J=1.3 Hz, 1H), 7.16-7.06 (m, 2H), 6.72 (dd, J=4.4, 2.6 Hz, 1H), 3.86 (s, 3H), 3.80 (s, 3H); MS (ES+): 371.5 (M+1); MS (ES-): 369.3 (M-1); HPLC purity: 99.51%.

Step-2: Preparation of (S)-(1-(4-((1-(3,4-dimethoxyphenyl)-1H-imidazol-4-yl)amino)pyrrolo[2,1-f][1,2,4]triazin-2-yl)pyrrolidin-2-yl)methanol (73c)

Compound 73c was prepared from 2-chloro-N-(1-(3,4-dimethoxyphenyl)-1H-imidazol-4-yl)pyrrolo[2,1-f][1,2,4]triazin-4-amine (73b) (100 mg, 0.27 mmol), (S)-pyrrolidin-2-ylmethanol (136 mg, 1.35 mmol), and DIPEA (0.14 mL, 0.81 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(3,4-dimethoxyphenyl)-1H-imidazol-4-yl)amino)pyrrolo[2,1-f][1,2,4]triazin-2-yl)pyrrolidin-2-yl)methanol (73c) (38 mg, 32% yield) as a pale off-white solid; $^1$H NMR (300 MHz, DMSO-$d_6$) δ 10.51 (s, 1H, $D_2O$ exchangeable), 8.16 (d, J=1.5 Hz, 1H), 7.92 (d, J=1.6 Hz, 1H), 7.42-7.35 (m, 1H), 7.23 (d, J=8.3 Hz, 2H), 7.14 (dd, J=4.4, 1.7 Hz, 1H), 7.04 (d, J=8.3 Hz, 1H), 6.39 (dd, J=4.4, 2.4 Hz, 1H), 4.85 (t, J=5.1 Hz, 1H, $D_2O$ exchangeable), 4.19 (s, 1H), 3.87 (s, 3H), 3.80 (s, 3H), 3.80-3.67 (m, 1H), 3.60-3.47 (m, 1H), 3.47-3.25 (m, 2H), 2.09-1.80 (m, 4H); MS (ES+): 436.5 (M+1); MS (ES-): 434.4 (M-1).

Preparation of N-(1-(1H-pyrazol-3-yl)-1H-imidazol-4-yl)-2-(2-(pyridin-2-yl)pyrrolidin-1-yl)pyrrolo[2,1-f][1,2,4]triazin-4-amine (74a)

Compound 74a was prepared from N-(1-(1H-pyrazol-3-yl)-1H-imidazol-4-yl)-2-chloropyrrolo[2,1-f][1,2,4]triazin-4-amine (71b) (90 mg, 0.3 mmol), 2-(pyrrolidin-2-yl)pyridine (133 mg, 0.9 mmol) and DIPEA (0.16 mL, 0.9 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1-(1H-pyrazol-3-yl)-1H-imidazol-4-yl)-2-(2-(pyridin-2-yl)pyrrolidin-1-yl)pyrrolo[2,1-f][1,2,4]triazin-4-amine (74a) (53 mg, 43% yield) as a yellowish solid; $^1$H NMR (300 MHz, DMSO-$d_6$) δ 12.93 (s, 1H, $D_2O$ exchangeable), 10.43 (s, 1H, $D_2O$ exchangeable), 8.40 (d, J=4.8 Hz, 1H), 8.03 (s, 1H), 7.93 (t, J=2.0 Hz, 1H), 7.73-7.46 (m, 2H), 7.37 (s, 1H), 7.20 (d, J=7.9 Hz, 1H), 7.17-7.03 (m, 2H), 6.69 (t, J=2.2 Hz, 1H), 6.38 (dd, J=4.4, 2.4 Hz, 1H), 5.34 (d, J=8.1 Hz, 1H), 3.98-3.78 (m, 1H), 3.78-3.50 (m, 1H), 2.44-2.27 (m, 1H), 2.11-1.71 (m, 3H); MS (ES+): 413.5 (M+1), 435.5 (M+Na); HPLC purity: 98.54%.

Scheme 75

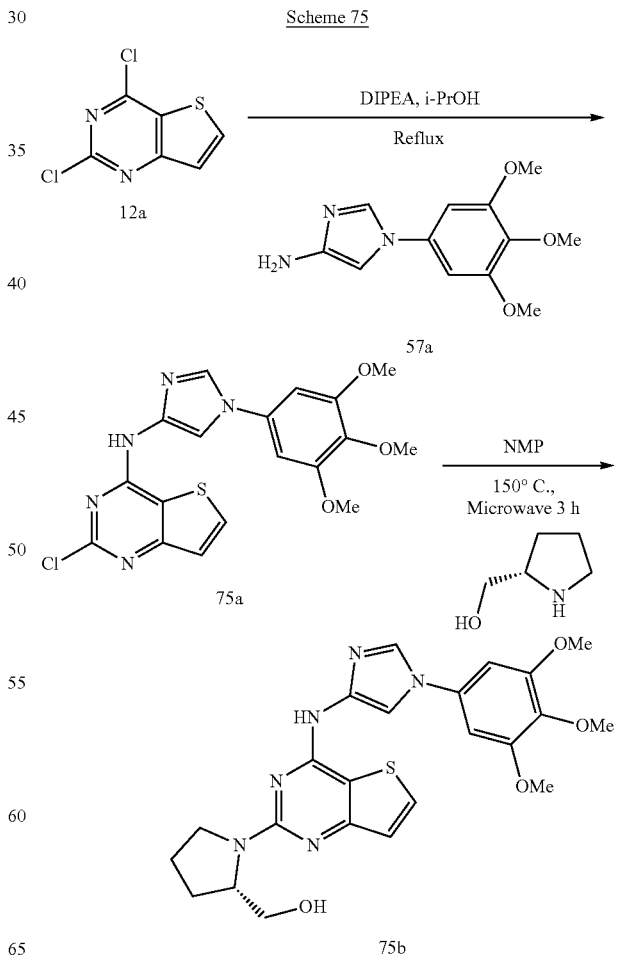

Scheme 74

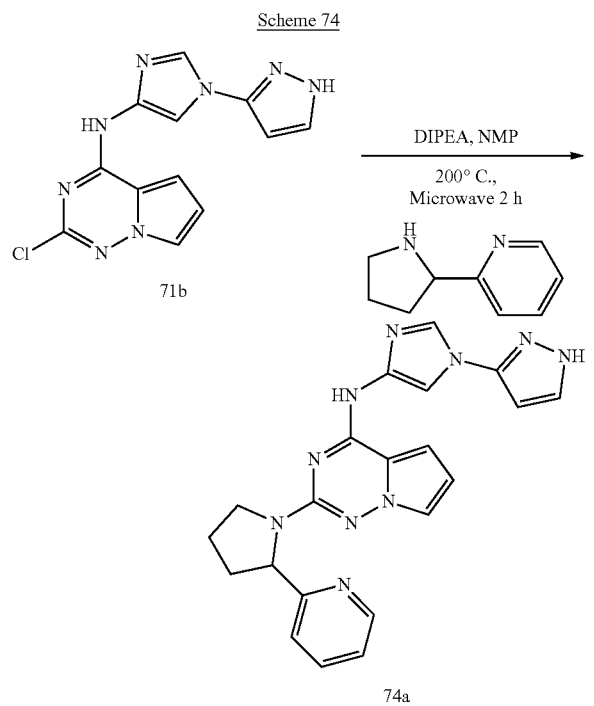

Preparation of (S)-(1-(4-((1-(3,4,5-trimethoxyphenyl)-1H-imidazol-4-yl)amino)thieno[3,2-d]pyrimidin-2-yl)pyrrolidin-2-yl)methanol (75b)

Step-1: Preparation of 2-chloro-N-(1-(3,4,5-trimethoxyphenyl)-1H-imidazol-4-yl)thieno[3,2-d]pyrimidin-4-amine (75a)

Compound 75a was prepared according to the procedure reported in Scheme 1 from 2,4-dichlorothieno[3,2-d]pyrimidine (12a) (304 mg, 1.48 mmol) in 2-Propanol (10 mL) using DIPEA (0.52 mL, 2.97 mmol) and 1-(3,4,5-trimethoxyphenyl)-1H-imidazol-4-amine (57a) (370 mg, 1.48 mmol). This gave 2-chloro-N-(1-(3,4,5-trimethoxyphenyl)-1H-imidazol-4-yl)thieno[3,2-d]pyrimidin-4-amine (75a) (403 mg, 65% yield) as a light pink solid; $^1$H NMR (300 MHz, DMSO-$d_6$) δ 10.86 (s, 1H, D$_2$O exchangeable), 8.24 (d, J=6.0 Hz, 2H), 7.95 (s, 1H), 7.39 (d, J=5.4 Hz, 1H), 6.96 (s, 2H), 3.87 (s, 6H), 3.69 (s, 3H); MS (ES+): 440.3 (M+Na), (ES−): 416.3 (M−1).

Step-2: Preparation of (S)-(1-(4-((1-(3,4,5-trimethoxyphenyl)-1H-imidazol-4-yl)amino)thieno[3,2-d]pyrimidin-2-yl)pyrrolidin-2-yl)methanol (75b)

Compound 75b was prepared from 2-chloro-N-(1-(3,4,5-trimethoxyphenyl)-1H-imidazol-4-yl)thieno[3,2-d]pyrimidin-4-amine (75a) (100 mg, 0.24 mmol), (S)-pyrrolidin-2-ylmethanol (73 mg, 0.72 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-(1-(3,4,5-trimethoxyphenyl)-1H-imidazol-4-ylamino)thieno[3,2-d]pyrimidin-2-yl)pyrrolidin-2-yl)methanol (75b) (93 mg, 81% yield) as a brown solid; $^1$H NMR (300 MHz, DMSO-$d_6$) δ 10.19 (s, 1H, D$_2$O exchangeable), 8.22 (d, J=1.5 Hz, 1H), 8.09-7.98 (m, 1H), 7.93 (d, J=5.4 Hz, 1H), 7.10 (d, J=5.3 Hz, 1H), 6.95 (s, 2H), 5.29-4.79 (m, 1H, D$_2$O exchangeable), 4.53-4.04 (m, 1H), 3.88 (s, 6H), 3.81-3.55 (m, 5H), 3.46-3.24 (m, 2H), 2.10-1.69 (m, 4H); MS (ES+): 483.5 (M+1), 505.5 (M+Na), 965.8 (2M+1), 987.8 (2M+Na), (ES−): 481.5 (M−1).

Scheme 76

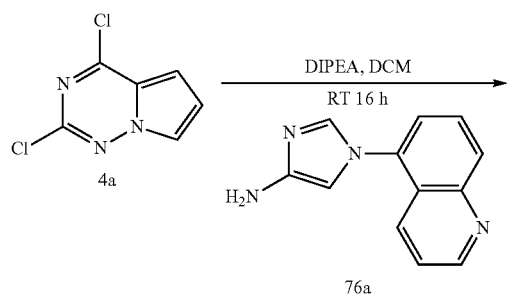

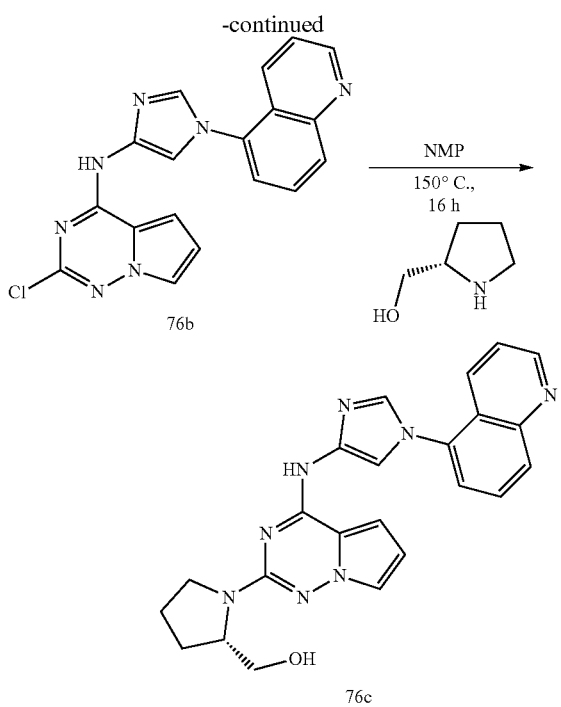

Preparation of (S)-(1-(4-((1-(quinolin-5-yl)-1H-imidazol-4-yl)amino)pyrrolo[2,1-f][1,2,4]triazin-2-yl)pyrrolidin-2-yl)methanol (76c)

Step-1: Preparation of 2-chloro-N-(1-(quinolin-5-yl)-1H-imidazol-4-yl)pyrrolo[2,1-f][1,2,4]triazin-4-amine (76b)

Compound 76b was prepared according to the procedure reported in Scheme 1 from 2,4-dichloropyrrolo[1,2-f][1,2,4]triazine (4a) (0.5 g, 2.65 mmol) in DCM (20 mL) using DIPEA (1.03 g, 7.97 mmol) and 1-(quinolin-5-yl)-1H-imidazol-4-amine (76a) (0.67 g, 3.19 mmol). This gave after work up and purification by flash column chromatography (silica gel, eluting with 0-80% ethyl acetate in hexanes) 2-chloro-N-(1-(quinolin-5-yl)-1H-imidazol-4-yl)pyrrolo[2,1-f][1,2,4]triazin-4-amine (76b) (300 mg, 31% yield) as an off white solid; $^1$H NMR (300 MHz, DMSO-$d_6$): δ 11.45 (s, 1H), 9.04-9.03 (s, 1H), 8.23-8.20 (d, 1H), 8.11-7.96 (d, 2H), 7.93-7.91 (t, 1H), 7.84-7.82 (m, 3H), 7.77-7.76 (m, 1H), 7.45-7.44 (s, 1H), 6.75-6.74 (s, 1H); MS (ES+): 362.0 (M+1).

Step-2: Preparation of (S)-(1-(4-((1-(quinolin-5-yl)-1H-imidazol-4-yl)amino)pyrrolo[2,1-f][1,2,4]triazin-2-yl)pyrrolidin-2-yl)methanol (76c)

A stirred solution of 2-chloro-N-(1-(quinolin-5-yl)-1H-imidazol-4-yl)pyrrolo[2,1-f][1,2,4]triazin-4-amine (76b) (300 mg, 0.83 mmol) and (S)-pyrrolidin-2-ylmethanol (838 mg, 8.29 mmol) in NMP (10 mL) was heated at 150° C. for 16 h. The reaction mixture was extracted with ethyl acetate (3×100 mL). The combined organic layers were washed with a brine solution (100 mL), dried, filtered and concentrated under reduced pressure. The crude product obtained was purified by flash column chromatography (silica gel, eluting with 0-10% ethyl acetate in methanol) to afford (S)-(1-(4-((1-(quinolin-5-yl)-1H-imidazol-4-yl)amino)pyrrolo[2,1-f][1,2,4]triazin-2-yl)pyrrolidin-2-yl)methanol (76c) (110 mg, 31%) as an off-white solid; ¹H NMR (300 MHz, DMSO-d6) δ 10.63 (s, 1H, D₂O exchangeable), 9.03 (dd, J=4.1, 1.6 Hz, 1H), 8.30-8.10 (m, 2H), 8.02 (d, J=1.4 Hz, 1H), 7.96-7.86 (m, 2H), 7.80 (dd, J=7.4, 1.2 Hz, 1H), 7.66 (dd, J=8.6, 4.2 Hz, 1H), 7.40 (t, J=2.0 Hz, 1H), 7.18 (dd, J=4.5, 1.7 Hz, 1H), 6.41 (dd, J=4.4, 2.4 Hz, 1H), 4.51 (t, J=5.3 Hz, 1H, D₂O exchangeable), 4.10-3.96 (m, 1H), 3.63-3.49 (m, 1H), 3.47-3.20 (m, 3H), 1.98-1.68 (m, 4H); MS (ES+) 449.5 (M+Na); HPLC purity: 94.15%.

Scheme 77

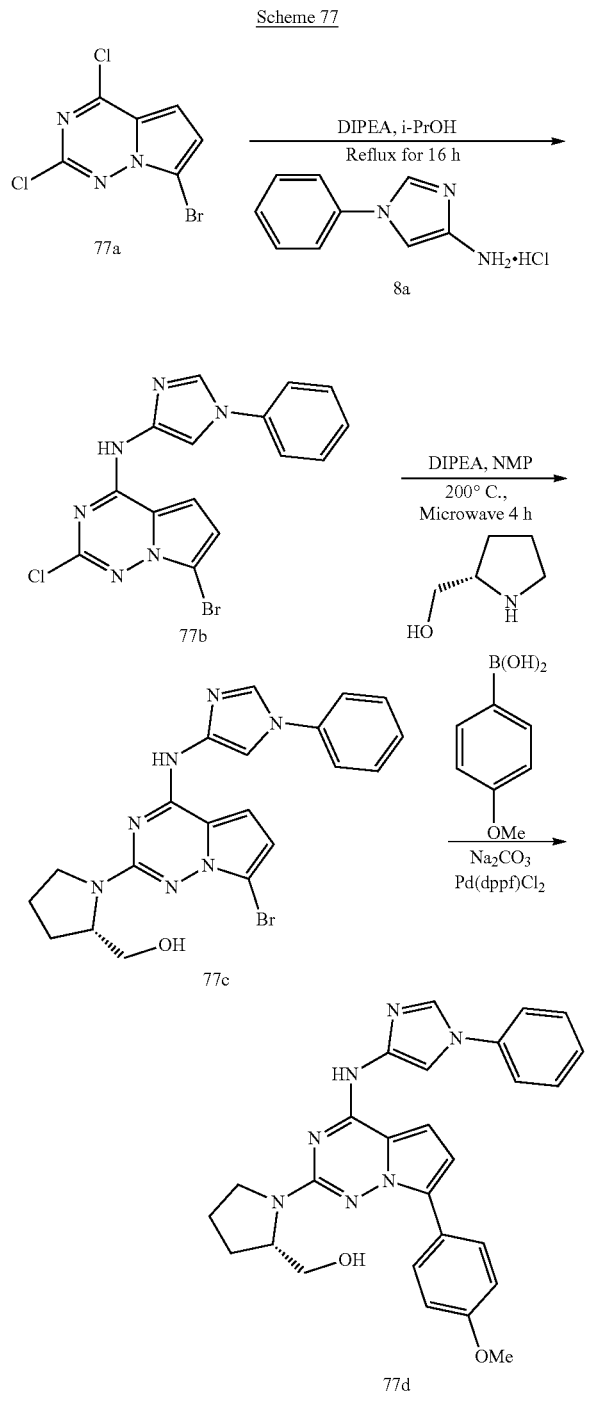

Preparation of (S)-(1-(7-(4-methoxyphenyl)-4-((1-phenyl-1H-imidazol-4-yl)amino)pyrrolo[2,1-f][1,2,4]triazin-2-yl)pyrrolidin-2-yl)methanol (77d)

Step-1: Preparation of 7-bromo-2-chloro-N-(1-phenyl-1H-imidazol-4-yl)pyrrolo[2,1-f][1,2,4]triazin-4-amine (77b)

Compound 77b was prepared according to the procedure reported in Scheme 1 from 7-bromo-2,4-dichloropyrrolo[1,2-f][1,2,4]triazine (77a) (50 mg, 0.19 mmol; CAS #1008112-03-5) in 2-Propanol (6 mL) using DIPEA (0.67 mL, 3.83 mmol) and 1-phenyl-1H-imidazol-4-amine, HCl (8a) (250 mg, 1.28 mmol). This gave after workup and purification by flash column chromatography [silica gel, 40 g eluting with a 9:1 mixture of ethyl acetate and methanol in hexanes (0 to 100%)] 7-bromo-2-chloro-N-(1-phenyl-1H-imidazol-4-yl)pyrrolo[2,1-f][1,2,4]triazin-4-amine (77b) (22 mg, 30% yield) as a white solid; ¹H NMR (300 MHz, DMSO-d₆) δ 11.50 (s, 1H, D₂O exchangeable), 8.27 (d, J=1.6 Hz, 1H), 7.92 (d, J=1.6 Hz, 1H), 7.71-7.63 (m, 2H), 7.57 (dd, J=8.8, 7.1 Hz, 2H), 7.52 (d, J=4.7 Hz, 1H), 7.46-7.37 (m, 1H), 6.91 (d, J=4.7 Hz, 1H). MS (ES+): 389.2, 391.3 (M+2); MS (ES−): 387.2, 389.1 (M+2).

Step-2: Preparation of (S)-(1-(7-bromo-4-((1-phenyl-1H-imidazol-4-yl)amino)pyrrolo[2,1-f][1,2,4]triazin-2-yl)pyrrolidin-2-yl)methanol (77c)

Compound 77c was prepared from 7-bromo-2-chloro-N-(1-phenyl-1H-imidazol-4-yl)pyrrolo[2,1-f][1,2,4]triazin-4-amine (77b) (50 mg, 0.13 mmol), (S)-pyrrolidin-2-ylmethanol (0.04 mL, 0.39 mmol), and DIPEA (0.07 mL, 0.39 mmol) in NMP (0.5 mL) according to the procedure reported in Scheme 2. This gave after workup and purification by flash chromatography [silica (4 g), eluting with DMA-80 in CHCl₃ from 0 to 20%] (S)-(1-(7-bromo-4-((1-phenyl-1H-imidazol-4-yl)amino)pyrrolo[2,1-f][1,2,4]triazin-2-yl)pyrrolidin-2-yl)methanol (77c), which was used as such in next step without further purification.

Step-3: Preparation of (S)-(1-(7-(4-methoxyphenyl)-4-((1-phenyl-1H-imidazol-4-yl)amino)pyrrolo[2,1-f][1,2,4]triazin-2-yl)pyrrolidin-2-yl)methanol (77d)

A slurry of (S)-(1-(7-bromo-4-((1-phenyl-1H-imidazol-4-yl)amino)pyrrolo[2,1-f][1,2,4]triazin-2-yl)methanol (77c) (20 mg, 0.04 mmol), 4-methoxyphenylboronic acid (33 mg, 0.22 mmol), Pd(dppf)Cl₂ (7 mg, 8.80 µmol), sodium carbonate (12 mg, 0.11 mmol) in a sealed reactor under a positive flow of nitrogen in Dioxane (3 mL) and Water (1 mL) was stirred at 90° C. for 2 h. The reaction mixture was cooled to room temperature, diluted with EtOAc (50 mL) and filtered though a Celite pad. Reaction mixture was purified by reverse phase flash column chromatography [(silica gel C-18, 24 g) eluting with 0.1% TFA in acetonitrile and 0.1% TFA in water]. The appropriate fractions containing the product were combined and concentrated to remove acetonitrile. The aqueous solution was basified with saturated sodium bicarbonate and the solid obtained was collected by filtration, dried in vacuum to afford (S)-(1-(7-(4-methoxyphenyl)-4-((1-phenyl-1H-imidazol-4-yl)amino)pyrrolo[2,1-f][1,2,4]triazin-2-yl)pyrrolidin-2-yl)methanol (77d) (6 mg, 28% yield) as a yellow solid; ¹H NMR (300 MHz, DMSO-d₆): δ 10.53 (s, 1H, D₂O exchangeable), 8.29 (d, J=1.5 Hz, 1H), 8.22-8.13 (m, 2H), 8.01 (d, J=1.7 Hz, 1H), 7.76 (d, J=7.9 Hz, 2H), 7.51 (t, J=7.8

Hz, 2H), 7.36 (t, J=7.3 Hz, 1H), 7.29 (d, J=4.6 Hz, 1H), 7.04-6.96 (m, 2H), 6.81 (d, J=4.6 Hz, 1H), 4.23 (s, 1H), 3.82 (s, 1H), 3.79 (s, 3H), 3.64-3.52 (m, 1H), 3.44 (q, J=10.0, 9.2 Hz, 2H), 2.16-1.82 (m, 4H); MS (ES+): 482.6 (M+1).

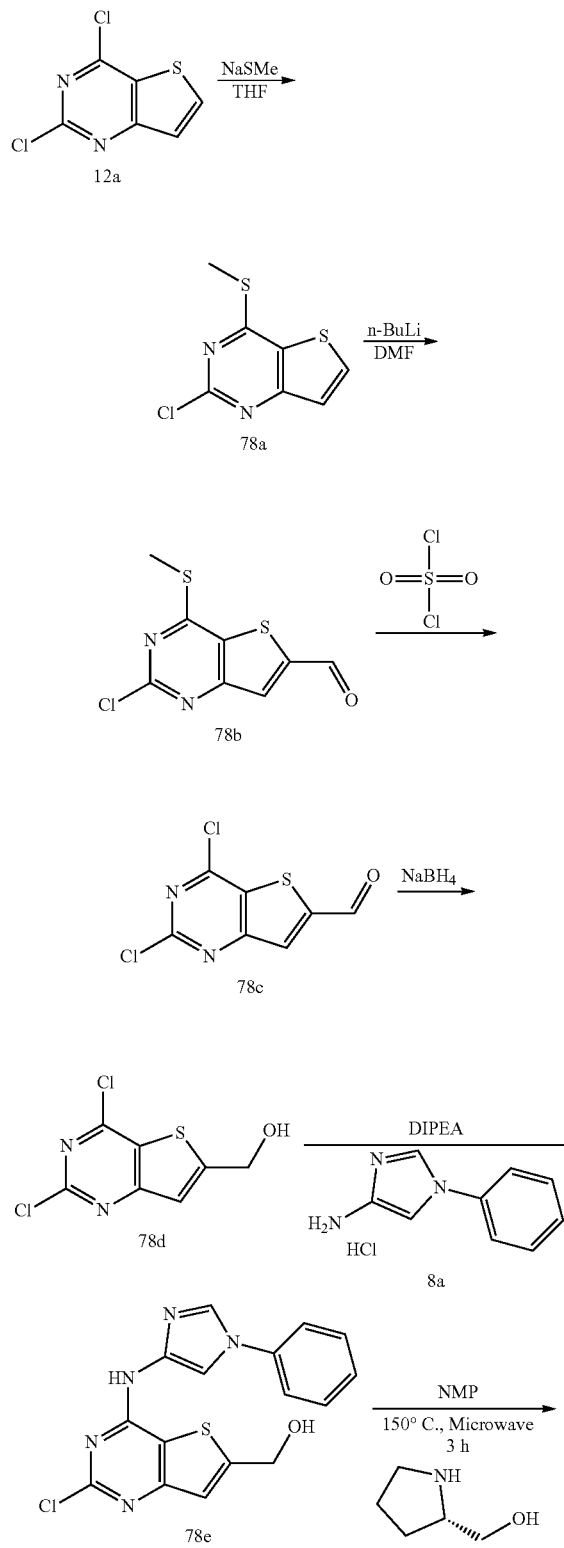

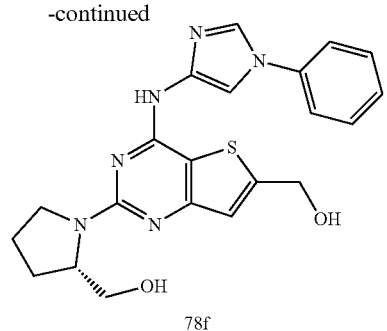

Preparation of (S)-(1-(6-(hydroxymethyl)-4-((1-phenyl-1H-imidazol-4-yl)amino)thieno[3,2-d]pyrimidin-2-yl)pyrrolidin-2-yl)methanol (78f)

Step-1: Preparation of 2-chloro-4-(methylthio)thieno[3,2-d]pyrimidine (78a)

Compound 78a was prepared from 2,4-dichlorothieno[3,2-d]pyrimidine (12a) (2 g, 9.75 mmol) and sodium thiomethoxide (0.75 g, 10.24 mmol) according to the procedure reported in step-1 of Scheme 70. This gave after workup 2-chloro-4-(methylthio)thieno[3,2-d]pyrimidine (78a) (1.85 g, 88% yield) as a brown solid; $^1$H NMR (300 MHz, DMSO-$d_6$) δ 8.47 (d, J=5.4 Hz, 1H), 7.60 (d, J=5.4 Hz, 1H), 2.75 (s, 3H).

Step-2: Preparation of 2-chloro-4-(methylthio)thieno[3,2-d]pyrimidine-6-carbaldehyde (78b)

Compound 78b was prepared from 2-chloro-4-(methylthio)thieno[3,2-d]pyrimidine (78a) (1 g, 4.61 mmol) according to the procedure reported in step-2 of Scheme 70. This gave after workup 2-chloro-4-(methylthio)thieno[3,2-d]pyrimidine-6-carbaldehyde (78b) (1.05 g, 93% yield) as a red solid; $^1$H NMR (300 MHz, DMSO-$d_6$) δ 10.25 (s, 1H), 8.50 (s, 1H), 2.77 (s, 3H).

Step 3: Preparation of 2,4-dichlorothieno[3,2-d]pyrimidine-6-carbaldehyde (78c)

Compound 78c was prepared from 2-chloro-4-(methylthio)thieno[3,2-d]pyrimidine-6-carbaldehyde (78b) (200 mg, 0.82 mmol) according to the procedure reported in step-3 of Scheme 70. This gave after workup 2,4-dichlorothieno[3,2-d]pyrimidine-6-carbaldehyde (78c) (75 mg, 39% yield) as a white solid. $^1$H NMR (300 MHz, DMSO-$d_6$) δ 10.29 (s, 1H), 8.63 (s, 1H).

Step 4: Preparation of (2,4-dichlorothieno[3,2-d]pyrimidin-6-yl)methanol (78d)

Compound 78d was prepared from 2,4-dichlorothieno[3,2-d]pyrimidine-6-carbaldehyde (78c) (70 mg, 0.3 mmol) according to the procedure reported in step-4 of Scheme 70. This gave after workup (2,4-dichlorothieno[3,2-d]pyrimidin-6-yl)methanol (78d) (95 mg) as a light orange solid; $^1$H NMR (300 MHz, DMSO-$d_6$) δ 7.43 (t, J=1.3 Hz, 1H), 6.07 (t, J=5.7 Hz, 1H, $D_2O$ exchangeable), 4.83 (dd, J=5.8, 1.3 Hz, 2H).

235

Step 5: Preparation of (2-chloro-4-((1-phenyl-1H-imidazol-4-yl)amino)thieno[3,2-d]pyrimidin-6-yl)methanol (78e)

Compound 78e was prepared according to the procedure reported in Scheme 1 from (2,4-dichlorothieno[3,2-d]pyrimidin-6-yl)methanol (78d) (90 mg, 0.38 mmol) in 2-Propanol (10 mL) using DIPEA (0.1 mL, 0.57 mmol), and 1-phenyl-1H-imidazol-4-amine hydrochloride (8a) (91 mg, 0.57 mmol). This gave (2-chloro-4-(1-phenyl-1H-imidazol-4-ylamino)thieno[3,2-d]pyrimidin-6-yl)methanol (78e) (45 mg, 33% yield) as a dark brown solid; $^1$H NMR (300 MHz, DMSO-$d_6$) δ 10.99-10.67 (m, 1H, $D_2O$ exchangeable), 8.27 (s, 1H), 7.94 (d, J=1.7 Hz, 1H), 7.68 (d, J=7.9 Hz, 2H), 7.57 (t, J=7.8 Hz, 2H), 7.41 (t, J=7.3 Hz, 1H), 7.21 (s, 1H), 5.92 (s, 1H, $D_2O$ exchangeable), 4.78 (d, J=5.4 Hz, 2H); MS (ES+): 358.3 (M+1), (ES−): 356.3 (M−1).

Step 6: Preparation of (S)-(1-(6-(hydroxymethyl)-4-((1-phenyl-1H-imidazol-4-yl)amino)thieno[3,2-d]pyrimidin-2-yl)pyrrolidin-2-yl)methanol (78f)

Compound 78f was prepared from (2-chloro-4-(1-phenyl-1H-imidazol-4-ylamino)thieno[3,2-d]pyrimidin-6-yl)methanol (78e) (39 mg, 0.11 mmol), (S)-pyrrolidin-2-ylmethanol (33 mg, 0.33 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(6-(hydroxymethyl)-4-((1-phenyl-1H-imidazol-4-yl)amino)thieno[3,2-d]pyrimidin-2-yl)pyrrolidin-2-yl)methanol (78f) (12 mg, 26% yield) as a brown solid; $^1$H NMR (300 MHz, DMSO-$d_6$) δ 10.00 (s, 1H, $D_2O$ exchangeable), 8.20 (d, J=1.7 Hz, 1H), 7.97 (d, J=1.7 Hz, 1H), 7.81-7.59 (m, 2H), 7.51 (t, J=7.7 Hz, 2H), 7.34 (t, J=7.4 Hz, 1H), 6.93 (d, J=1.1 Hz, 1H), 5.72 (t, J=5.8 Hz, 1H, $D_2O$ exchangeable), 5.04 (s, 1H, $D_2O$ exchangeable), 4.70 (dd, J=5.8, 1.2 Hz, 2H), 4.22 (s, 1H), 3.88-3.69 (m, 1H), 3.69-3.49 (m, 2H), 3.44-3.24 (m, 1H), 2.12-1.81 (m, 4H); MS (ES+): 423.4 (M+1); (ES−): 421 (M−1); HPLC purity: 95.50%.

Scheme 79

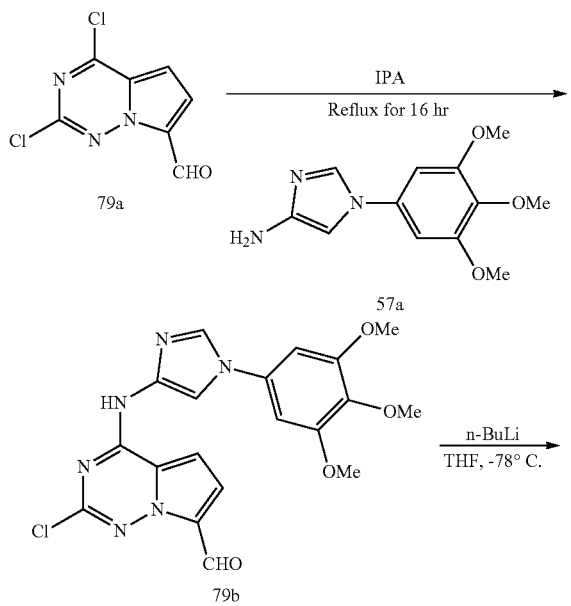

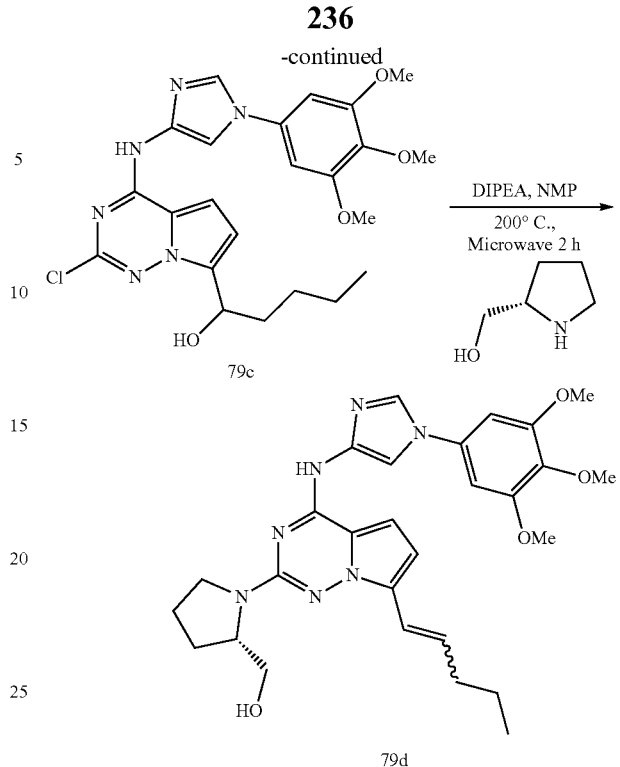

Preparation of (S)-(1-(7-(pent-1-en-1-yl)-4-((1-(3,4,5-trimethoxyphenyl)-1H-imidazol-4-yl)amino)pyrrolo[2,1-f][1,2,4]triazin-2-yl)pyrrolidin-2-yl)methanol (79d)

Step-1: Preparation of 2-chloro-4-((1-(3,4,5-trimethoxyphenyl)-1H-imidazol-4-yl)amino)pyrrolo[2,1-f][1,2,4]triazine-7-carbaldehyde (79b)

Compound 79b was prepared according to the procedure reported in Scheme 1 from 2,4-dichloropyrrolo[2,1-f][1,2,4]triazine-7-carbaldehyde (79a) (400 mg, 1.85 mmol) in 2-Propanol (20 mL) using DIPEA (0.97 mL, 5.55 mmol) and 1-(3,4,5-trimethoxyphenyl)-1H-imidazol-4-amine (57a) (635 mg, 2.22 mmol). This gave 2-chloro-4-((1-(3,4,5-trimethoxyphenyl)-1H-imidazol-4-yl)amino)pyrrolo[2,1-f][1,2,4]triazine-7-carbaldehyde (79b) (564 mg, 71% yield) as a yellow solid; $^1$H NMR (300 MHz, DMSO-$d_6$) δ 11.81 (s, 1H), 10.21 (s, 1H), 9.46 (s, OH), 8.25 (d, J=1.5 Hz, 1H), 7.93 (d, J=1.6 Hz, 1H), 7.50 (d, J=4.9 Hz, 1H), 7.35 (d, J=4.8 Hz, 1H), 6.94 (s, 2H), 3.88 (s, 6H), 3.69 (s, 3H). MS (ES+): 429.5 (M+1); MS (ES−): 427.3 (M−1).

Step 2: Preparation of 1-(2-chloro-4-(1-(3,4,5-trimethoxyphenyl)-1H-imidazol-4-ylamino)pyrrolo[1,2-f][1,2,4]triazin-7-yl)pentan-1-ol (79c)

To a solution of 2-chloro-4-((1-(3,4,5-trimethoxyphenyl)-1H-imidazol-4-yl)amino)pyrrolo[2,1-f][1,2,4]triazine-7-carbaldehyde (79b) (100 mg, 0.23 mmol) in THF (10 mL) at −78° C. was added n-BuLi (1.6 M, 0.32 mL, 0.51 mmol) and stirred at −78° C. for 4 h. The reaction mixture was quenched with Sat. NH$_4$Cl and extracted with ethyl acetate (3×30 mL).

The combined organic layers were washed with brine, dried, filtered, concentrated under vacuum and purified by flash column chromatography (Silica gel 12 g, eluting with MeOH in DCM from 0 to 20%) to afford 1-(2-chloro-4-(1-(3,4,5-trimethoxyphenyl)-1H-imidazol-4-ylamino)pyrrolo[1,2-f][1,2,4]triazin-7-yl)pentan-1-ol (79c) (65 mg, 57% yield) as yellow solid; $^1$H NMR (300 MHz, Chloroform-d) δ 10.51 (s, 1H), 7.94 (d, J=1.6 Hz, 1H), 7.65 (d, J=1.6 Hz, 1H), 6.84 (d, J=4.5 Hz, 1H), 6.65 (s, 2H), 6.58 (d, J=4.4 Hz, 1H), 5.16 (dd, J=7.5, 6.1 Hz, 1H), 3.92 (s, 6H), 3.88 (s, 3H), 2.14-1.79 (m, 2H), 1.65-1.21 (m, 4H), 0.91 (t, J=7.0 Hz, 3H); MS (ES+): 487.5 (M+1); MS (ES−): 485.5 (M−1).

Step-3: Preparation of (S)-(1-(7-(pent-1-en-1-yl)-4-((1-(3,4,5-trimethoxyphenyl)-1H-imidazol-4-yl)amino)pyrrolo[2,1-f][1,2,4]triazin-2-yl)pyrrolidin-2-yl)methanol (79d)

Compound 79d was prepared from 1-(2-chloro-4-(1-(3,4,5-trimethoxyphenyl)-1H-imidazol-4-ylamino)pyrrolo[1,2-f][1,2,4]triazin-7-yl)pentan-1-ol (79c) (65 mg, 0.13 mmol), (S)-pyrrolidin-2-ylmethanol (68 mg, 0.67 mmol), DIPEA (0.07 mL, 0.4 mmol) in NMP (2.5 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(7-(pent-1-en-1-yl)-4-((1-(3,4,5-trimethoxyphenyl)-1H-imidazol-4-yl)amino)pyrrolo[2,1-f][1,2,4]triazin-2-yl)pyrrolidin-2-yl)methanol (79d) (11 mg, 15% yield) as a white solid; $^1$H NMR (300 MHz, DMSO-d$_6$) δ 10.47 (s, 1H, D$_2$O exchangeable), 8.24 (d, J=1.6 Hz, 1H), 7.97 (d, J=1.6 Hz, 1H), 7.14 (d, J=4.6 Hz, 1H), 6.95 (s, 2H), 6.70 (d, J=16.1 Hz, 1H), 6.55 (d, J=4.6 Hz, 1H), 6.52-6.40 (m, 1H), 4.84 (t, J=5.1 Hz, 1H, D$_2$O exchangeable), 4.30-4.17 (m, 1H), 3.88 (s, 6H), 3.81-3.68 (m, 1H), 3.68 (s, 3H), 3.66-3.53 (m, 1H), 3.54-3.35 (m, 2H), 2.19 (q, J=7.1 Hz, 2H), 2.10-1.81 (m, 4H), 1.56-1.39 (m, 2H), 0.93 (t, J=7.2 Hz, 3H); MS (ES+): 534.6 (M+1); MS (ES−): 532.7 (M−1), 568.6 (M+Cl); HPLC purity: 94.02%.

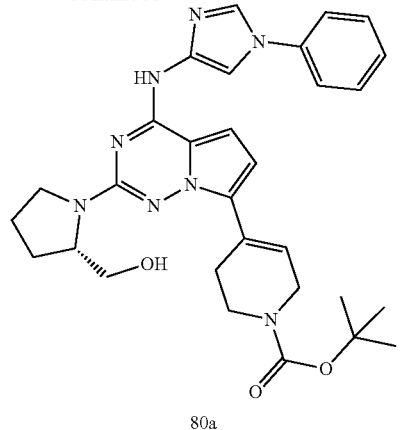

80a

Preparation of (S)-tert-butyl 4-(2-(2-(hydroxymethyl)pyrrolidin-1-yl)-4-(1-phenyl-1H-imidazol-4-ylamino)pyrrolo[1,2-f][1,2,4]triazin-7-yl)-5,6-dihydropyridine-1(2H)-carboxylate (80a)

Compound 80a was prepared from (S)-(1-(7-bromo-4-(1-phenyl-1H-imidazol-4-ylamino)pyrrolo[1,2-f][1,2,4]triazin-2-yl)pyrrolidin-2-yl)methanol (77c) (30 mg, 0.07 mmol), 1-(tert-butoxycarbonyl)-1,2,3,6-tetrahydropyridin-4-ylboronic acid (30.0 mg, 0.13 mmol), Pd(dppf)Cl$_2$ (9.69 mg, 0.01 mmol), sodium carbonate (17.50 mg, 0.17 mmol) in Dioxane (3 mL) and Water (1 mL) according to the procedure reported in step-3 of Scheme 77. This gave after purification by reverse phase flash column chromatography [(silica gel C-18, 24 g) eluting with 0.1% TFA in acetonitrile and 0.1% TFA in water] (S)-tert-butyl 4-(2-(2-(hydroxymethyl)pyrrolidin-1-yl)-4-(1-phenyl-1H-imidazol-4-ylamino)pyrrolo[1,2-f][1,2,4]triazin-7-yl)-5,6-dihydropyridine-1(2H)-carboxylate (80a) (7 mg, 19% yield) as a brown solid; $^1$H NMR (300 MHz, DMSO-d$_6$): δ 10.52 (s, 1H, D$_2$O exchangeable), 8.27 (d, J=1.6 Hz, 1H), 7.98 (d, J=1.6 Hz, 1H), 7.75 (d, J=7.9 Hz, 2H), 7.51 (t, J=7.8 Hz, 2H), 7.35 (t, J=7.3 Hz, 1H), 7.21 (d, J=4.9 Hz, 1H), 6.50 (d, J=4.7 Hz, 1H), 4.19 (s, 3H), 4.06 (s, 3H), 3.78 (d, J=9.8 Hz, 1H), 3.54 (s, 3H), 3.38 (s, 1H), 2.59-2.53 (m, 1H), 2.10-1.91 (m, 4H), 1.43 (s, 9H). $^{19}$F NMR (282 MHz, DMSO-d$_6$) δ −73.99; MS (ES+): 557.6 (M+1); 579.6 (M+Na).

Scheme 80

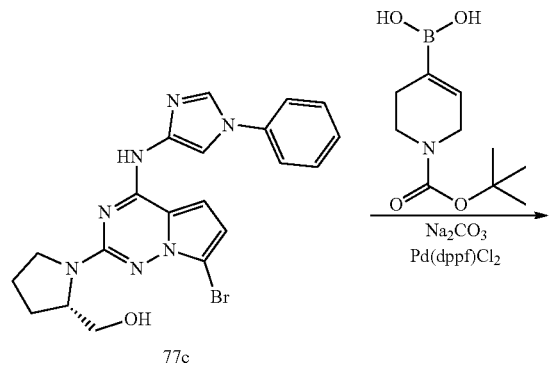

77c

Scheme 81

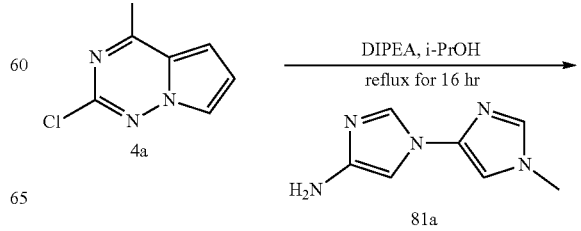

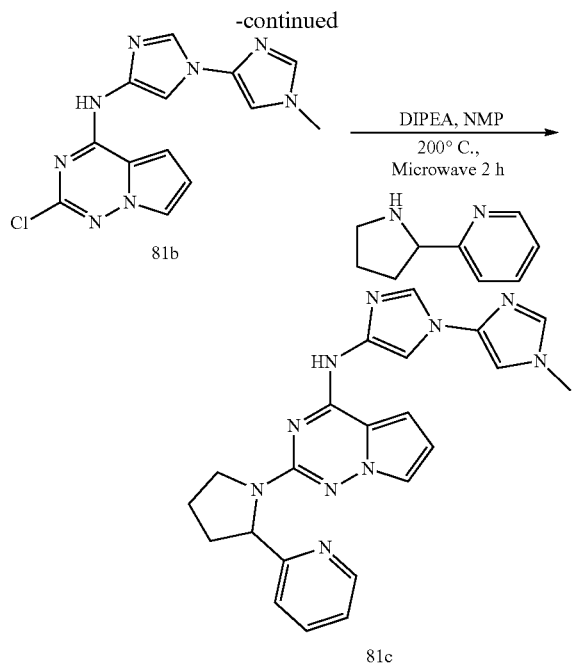

Preparation of N-(1'-methyl-1'H-[1,4'-biimidazol]-4-yl)-2-(2-(pyridin-2-yl)pyrrolidin-1-yl)pyrrolo[2,1-f][1,2,4]triazin-4-amine (81c)

Step-1: Preparation of 2-chloro-N-(1'-methyl-1'H-[1,4'-biimidazol]-4-yl)pyrrolo[2,1-f][1,2,4]triazin-4-amine (81b)

Compound 81b was prepared according to the procedure reported in Scheme 1 from 2,4-dichloropyrrolo[1,2-f][1,2,4]triazine (4a) (187 mg, 0.99 mmol) in 2-Propanol (10 mL) using DIPEA (0.52 mL, 2.98 mmol) and 1'-methyl-1'H-1,4'-biimidazol-4-amine (81a) (162 mg, 0.99 mmol). This gave 2-chloro-N-(1'-methyl-1'H-[1,4'-biimidazol]-4-yl)pyrrolo[2,1-f][1,2,4]triazin-4-amine (81b) (205 mg, 66% yield) as a pale off-white solid; $^1$H NMR (300 MHz, DMSO-$d_6$) δ 11.31 (s, 1H, D$_2$O exchangeable), 8.03 (d, J=1.5 Hz, 1H), 7.84 (d, J=1.5 Hz, 1H), 7.76 (dd, J=2.6, 1.5 Hz, 1H), 7.65 (d, J=1.4 Hz, 1H), 7.49 (d, J=1.5 Hz, 1H), 7.39 (dd, J=4.5, 1.6 Hz, 1H), 6.71 (dd, J=4.4, 2.6 Hz, 1H), 3.71 (s, 3H); MS (ES+): 315.3 (M+1), 337.3 (M+Na); MS (ES−): 313.3 (M−1); HPLC purity: 99.21%.

Step-2: Preparation of N-(1'-methyl-1'H-[1,4'-biimidazol]-4-yl)-2-(2-(pyridin-2-yl)pyrrolidin-1-yl)pyrrolo[2,1-f][1,2,4]triazin-4-amine (81c)

Compound 81c was prepared from 2-chloro-N-(1'-methyl-1'H-[1,4'-biimidazol]-4-yl)pyrrolo[2,1-f][1,2,4]triazin-4-amine (81b) (70 mg, 0.22 mmol), 2-(pyrrolidin-2-yl)pyridine (99 mg, 0.67 mmol) and DIPEA (0.12 mL, 0.67 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, N-(1'-methyl-1'H-[1,4'-biimidazol]-4-yl)-2-(2-(pyridin-2-yl)pyrrolidin-1-yl)pyrrolo[2,1-f][1,2,4]triazin-4-amine (81c) (55 mg, 58% yield) as a off-white solid; $^1$H NMR (300 MHz, DMSO-$d_6$) δ 10.40 (s, 1H, D$_2$O exchangeable), 8.44 (d, J=4.8 Hz, 1H), 7.89 (d, J=1.5 Hz, 1H), 7.65 (s, 1H), 7.64-7.55 (m, 1H), 7.44 (d, J=1.5 Hz, 1H), 7.42-7.33 (m, 2H), 7.20 (d, J=7.9 Hz, 1H), 7.21-7.10 (m, 1H), 7.12-7.08 (m, 1H), 6.38 (dd, J=4.5, 2.4 Hz, 1H), 5.34 (d, J=8.1 Hz, 1H), 3.92-3.80 (m, 1H), 3.79 (s, 3H), 3.74-3.57 (m, 1H), 2.53-2.25 (m, 1H), 2.11-1.74 (m, 3H); MS (ES+): 427.5 (M+1), 449.5 (M+Na); HPLC purity: 98.90%.

Scheme 82

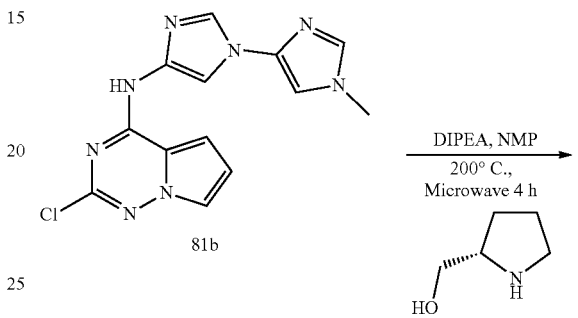

Preparation of (S)-(1-(4-((1'-methyl-1'H-[1,4'-biimidazol]-4-yl)amino)pyrrolo[2,1-f][1,2,4]triazin-2-yl)pyrrolidin-2-yl)methanol (82a)

Compound 82a was prepared from 2-chloro-N-(1'-methyl-1'H-[1,4'-biimidazol]-4-yl)pyrrolo[2,1-f][1,2,4]triazin-4-amine (81b) (70 mg, 0.22 mmol), (S)-pyrrolidin-2-ylmethanol (112 mg, 1.11 mmol) and DIPEA (0.12 mL, 0.67 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1'-methyl-1'H-[1,4'-biimidazol]-4-yl)amino)pyrrolo[2,1-f][1,2,4]triazin-2-yl)pyrrolidin-2-yl)methanol (82a) (65 mg, 77% yield) as an off-white solid; $^1$H NMR (300 MHz, DMSO-$d_6$) δ 10.52 (s, 1H), 8.01 (d, J=1.5 Hz, 1H), 7.89 (d, J=1.6 Hz, 1H), 7.71-7.58 (m, 1H), 7.54 (d, J=1.5 Hz, 1H), 7.39 (dd, J=2.4, 1.6 Hz, 1H), 7.12 (dd, J=4.4, 1.7 Hz, 1H), 6.39 (dd, J=4.4, 2.5 Hz, 1H), 5.26-4.98 (m, 1H), 4.31-4.00 (m, 1H), 3.95-3.76 (m, 1H), 3.73-3.65 (m, 3H), 3.53-3.25 (m, 3H), 2.16-1.84 (m, 4H); MS (ES+): 380.4 (M+1), 402.4 (M+Na); HPLC purity: 99.92%.

Scheme 83

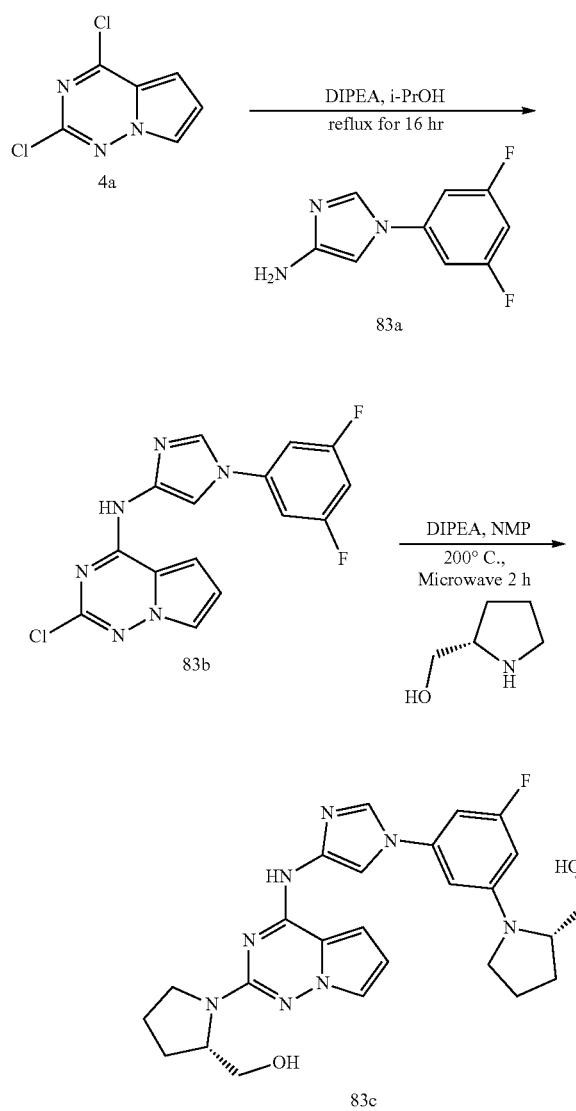

Preparation of ((S)-1-(4-((1-(3-fluoro-5-((S)-2-(hydroxymethyl)pyrrolidin-1-yl)phenyl)-1H-imidazol-4-yl)amino)pyrrolo[2,1-f][1,2,4]triazin-2-yl)pyrrolidin-2-yl)methanol (83c)

Step-1: Preparation of 2-chloro-N-(1-(3,5-difluorophenyl)-1H-imidazol-4-yl)pyrrolo[1,2-f][1,2,4]triazin-4-amine (83b)

Compound 83b was prepared according to the procedure reported in Scheme 1 from 2,4-dichloropyrrolo[1,2-f][1,2,4]triazine (4a) (365 mg, 1.94 mmol) in 2-Propanol (10 mL) using DIPEA (1.02 mL, 5.83 mmol) and 1-(3,5-difluorophenyl)-1H-imidazol-4-amine (83a) (379 mg, 1.94 mmol). This gave 2-chloro-N-(1-(3,5-difluorophenyl)-1H-imidazol-4-yl)pyrrolo[1,2-f][1,2,4]triazin-4-amine (83b) (521 mg, 77% yield) as a solid; $^1$H NMR (300 MHz, DMSO-d6) δ 11.33 (s, 1H, D$_2$O exchangeable), 8.38 (d, J=1.6 Hz, 1H), 7.97 (d, J=1.6 Hz, 1H), 7.79 (dd, J=2.6, 1.5 Hz, 1H), 7.65-7.53 (m, 2H), 7.45-7.36 (m, 1H), 7.31 (tt, J=9.3, 2.2 Hz, 1H), 6.73 (dd, J=4.5, 2.6 Hz, 1H); $^{19}$F NMR (282 MHz, DMSO-d$_6$) δ −107.50; MS (ES+): 347.3 (M+1); MS (ES−): 345.2 (M−1); HPLC purity: 98.86%.

Step-2: Preparation of ((S)-1-(4-((1-(3-fluoro-5-((S)-2-(hydroxymethyl)pyrrolidin-1-yl)phenyl)-1H-imidazol-4-yl)amino)pyrrolo[2,1-f][1,2,4]triazin-2-yl)pyrrolidin-2-yl)methanol (83c)

Compound 83c was prepared from 2-chloro-N-(1-(3,5-difluorophenyl)-1H-imidazol-4-yl)pyrrolo[1,2-f][1,2,4]triazin-4-amine (83b) (100 mg, 0.29 mmol), (S)-pyrrolidin-2-ylmethanol (146 mg, 1.44 mmol), and DIPEA (0.15 mL, 0.87 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, ((S)-1-(4-((1-(3-fluoro-5-((S)-2-(hydroxymethyl)pyrrolidin-1-yl)phenyl)-1H-imidazol-4-yl)amino)pyrrolo[2,1-f][1,2,4]triazin-2-yl)pyrrolidin-2-yl)methanol (83c) (66 mg, 47% yield) as a white solid; $^1$H NMR (300 MHz, DMSO-d$_6$) δ 10.55 (s, 1H, D$_2$O exchangeable), 8.24 (d, J=1.5 Hz, 1H), 7.95 (d, J=1.6 Hz, 1H), 7.39 (dd, J=2.5, 1.7 Hz, 1H), 7.14 (dd, J=4.5, 1.7 Hz, 1H), 6.90-6.77 (m, 1H), 6.60 (s, 1H), 6.46-6.33 (m, 2H), 4.83 (t, J=6.1 Hz, 2H, D$_2$O exchangeable), 4.27-4.08 (m, 1H), 3.83-3.75 (m, 1H), 3.74-3.64 (m, 1H), 3.61-3.55 (m, 1H), 3.53-3.29 (m, 4H), 3.27-3.21 (m, 1H), 3.18-3.05 (m, 1H), 2.22-1.72 (m, 8H); $^{19}$F NMR (282 MHz, DMSO-d$_6$) δ −110.98-111.15 (m); $^{19}$FCPD NMR (282 MHz, DMSO-d$_6$) δ −111.06; MS (ES+): 493.5 (M+1); MS (ES−): 491.4 (M−1), 527.6 (M+Cl); HPLC purity: 96.03%.

Scheme 84

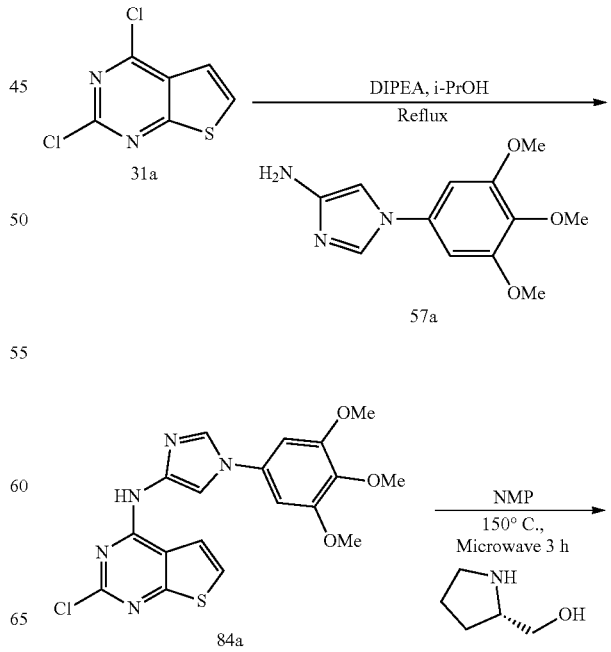

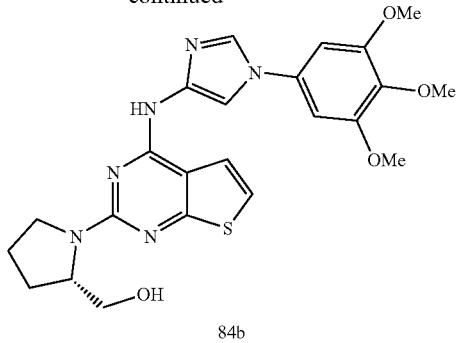

84b

Preparation of (S)-(1-(4-((1-(3,4,5-trimethoxyphenyl)-1H-imidazol-4-yl)amino)thieno[2,3-d]pyrimidin-2-yl)pyrrolidin-2-yl)methanol (84b)

Step-1: Preparation of 2-chloro-N-(1-(3,4,5-trimethoxyphenyl)-1H-imidazol-4-yl)thieno[2,3-d]pyrimidin-4-amine (84a)

Compound 84a was prepared according to the procedure reported in Scheme 1 from 2,4-dichlorothieno[2,3-d]pyrimidine (31a) (0.4 g, 1.95 mmol) in 2-Propanol (10 mL) using DIPEA (1.36 mL, 7.8 mmol) and 1-(3,4,5-trimethoxyphenyl)-1H-imidazol-4-amine (57a) (669 mg, 2.34 mmol). This gave 2-chloro-N-(1-(3,4,5-trimethoxyphenyl)-1H-imidazol-4-yl)thieno[2,3-d]pyrimidin-4-amine (84a) (275 mg, 34% yield) as a buff colored solid; $^1$H NMR (300 MHz, DMSO-$d_6$) δ 11.01 (s, 1H, D$_2$O exchangeable), 8.21 (d, J=1.6 Hz, 1H), 8.02 (s, 1H), 7.91 (d, J=1.6 Hz, 1H), 7.71 (d, J=5.9 Hz, 1H), 6.93 (s, 2H), 3.87 (s, 6H), 3.69 (s, 3H); MS (ES+): 440.3 (M+Na), (ES−): 416.2 (M−1).

Step-2: Preparation of (S)-(1-(4-((1-(3,4,5-trimethoxyphenyl)-1H-imidazol-4-yl)amino)thieno[2,3-d]pyrimidin-2-yl)pyrrolidin-2-yl)methanol (84b)

Compound 84b was prepared from 2-chloro-N-(1-(3,4,5-trimethoxyphenyl)-1H-imidazol-4-yl)thieno[2,3-d]pyrimidin-4-amine (84a) (100 mg, 0.24 mmol), (S)-pyrrolidin-2-ylmethanol (73 mg, 0.72 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-(1-(4-((1-(3,4,5-trimethoxyphenyl)-1H-imidazol-4-yl)amino)thieno[2,3-d]pyrimidin-2-yl)pyrrolidin-2-yl)methanol (84b) (65 mg, 56% yield) as a brown solid; $^1$H NMR (300 MHz, DMSO-$d_6$) δ 10.17 (s, 1H, D$_2$O exchangeable), 8.23 (d, J=1.7 Hz, 1H), 8.08-7.94 (m, 1H), 7.79 (d, J=6.0 Hz, 1H), 7.02 (d, J=6.0 Hz, 1H), 6.95 (s, 2H), 4.90 (s, 1H, D$_2$O exchangeable), 4.47-4.24 (m, 1H), 3.88 (s, 6H), 3.82-3.51 (m, 5H), 3.46-3.23 (m, 2H), 2.13-1.79 (m, 4H); MS (ES+): 483.4 (M+1), 505.4 (M+Na), (ES−): 481.4 (M−1); Hydrochloride salt of compound 84b was prepared by purification of crude reaction mixture from step-2 above by reverse phase flash chromatography [(silica gel C-18, 24 g) eluting with acetonitrile and 0.1% HCl in water; $^1$H NMR (300 MHz, DMSO-$d_6$): δ 11.36 (s, 1H), 8.45 (s, 1H), 8.20-7.84 (m, 2H), 7.37 (d, J=5.8 Hz, 1H), 6.99 (s, 2H), 4.68-4.19 (m, 1H), 4.14-3.07 (m, 13H), 2.20-1.76 (m, 4H). MS (ES+): 483.2 (M+1), 505.3 (M+Na); MS (ES−): 517.2 (M+Cl); HPLC purity; 95.11%.

Scheme 85

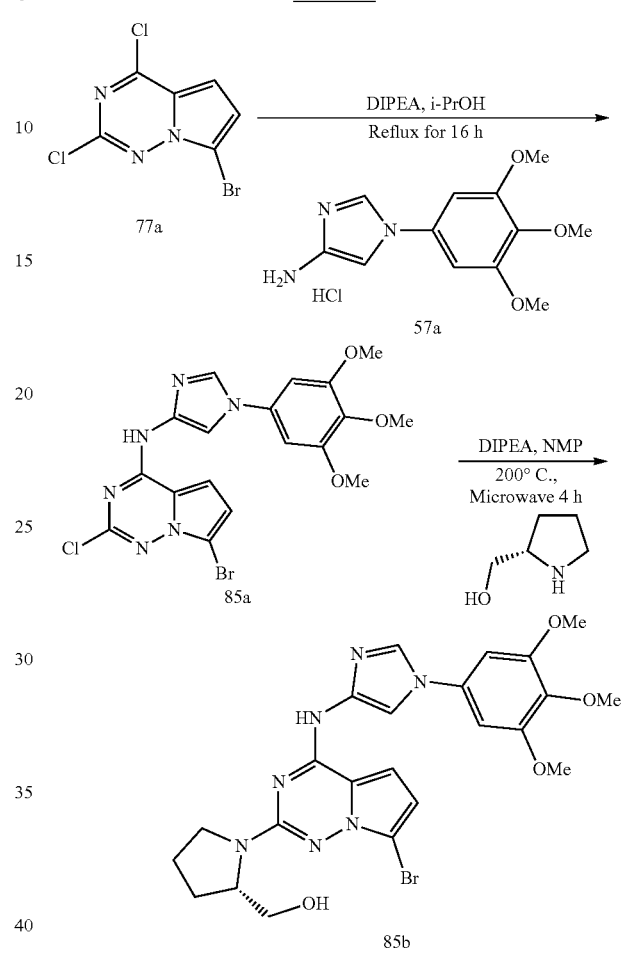

Preparation of (S)-(1-(7-bromo-4-(1-(3,4,5-trimethoxyphenyl)-1H-imidazol-4-ylamino)pyrrolo[1,2-f][1,2,4]triazin-2-yl)pyrrolidin-2-yl)methanol (85b)

Step-1: Preparation of 7-bromo-2-chloro-N-(1-(3,4,5-trimethoxyphenyl)-1H-imidazol-4-yl)pyrrolo[1,2-f][1,2,4]triazin-4-amine (85a)

Compound 85a was prepared according to the procedure reported in Scheme 1 from 7-bromo-2,4-dichloropyrrolo[1,2-f][1,2,4]triazine (77a) (500 mg, 1.87 mmol) in 2-Propanol (20 mL) using DIPEA (0.98 mL, 5.62 mmol) and 1-(3,4,5-trimethoxyphenyl)-1H-imidazol-4-amine hydrochloride (57a) (0.71 g, 2.47 mmol). This gave after workup and purification by flash column chromatography [silica gel, 40 g eluting with a DCM and methanol (0 to 30%)] 7-bromo-2-chloro-N-(1-(3,4,5-trimethoxyphenyl)-1H-imidazol-4-yl)pyrrolo[1,2-f][1,2,4]triazin-4-amine (85a) (480 mg, 53% yield) as a brown solid; $^1$H NMR (300 MHz, DMSO-$d_6$) δ 11.46 (s, 1H, D$_2$O exchangeable), 8.22 (d, J=1.6 Hz, 1H), 7.90 (d, J=1.6 Hz, 1H), 7.51 (d, J=4.7 Hz, 1H), 6.93 (s, 2H), 6.90 (d, J=4.6 Hz, 1H), 3.87 (s, 6H), 3.69 (s, 3H). MS (ES+): 481.3 (M+2); MS (ES−): 479.2, 481.2 (M+2).

Step-2: Preparation (S)-(1-(7-bromo-4-(1-(3,4,5-trimethoxyphenyl)-1H-imidazol-4-ylamino)pyrrolo[1,2-f][1,2,4]triazin-2-yl)pyrrolidin-2-yl)methanol (85b)

Compound 85b was prepared from 7-bromo-2-chloro-N-(1-(3,4,5-trimethoxyphenyl)-1H-imidazol-4-yl)pyrrolo[1,2-f][1,2,4]triazin-4-amine (85a) (50 mg, 0.1 mmol), (S)-pyrrolidin-2-ylmethanol (0.03 mL, 0.31 mmol), and DIPEA (0.06 mL, 0.31 mmol) in NMP (3 mL) according to the procedure reported in Scheme 2. This gave after workup and purification by reverse phase flash column chromatography [(silica gel C-18, 24 g) eluting with 0.1% TFA in acetonitrile and 0.1% TFA in water] followed by lyophilization (S)-(1-(7-bromo-4-(1-(3,4,5-trimethoxyphenyl)-1H-imidazol-4-ylamino)pyrrolo[1,2-f][1,2,4]triazin-2-yl)pyrrolidin-2-yl)methanol (85b) (16 mg, 28% yield) as a white solid; $^1$H NMR (300 MHz, DMSO-$d_6$): δ 10.68 (s, 1H, $D_2O$ exchangeable), 8.26 (d, J=1.5 Hz, 1H), 7.98 (d, J=1.6 Hz, 1H), 7.28 (d, J=4.6 Hz, 1H), 6.96 (s, 2H), 6.55 (d, J=4.6 Hz, 1H), 4.24 (s, 1H), 3.88 (s, 6H), 3.68 (s, 3H), 3.40-3.34 (m, 2H), 2.07-1.83 (m, 4H). $^{19}$F NMR (282 MHz, DMSO-$d_6$) δ −74.03; MS (ES+): 544.4, 546.4 (M+2); MS (ES−): 542.4, 544.3 (M+2).

Preparation of (S)-(1-(4-((1-(3,4,5-trimethoxyphenyl)-1H-imidazol-4-yl)amino)quinazolin-2-yl)pyrrolidin-2-yl)methanol (86b)

Step-1: Preparation of 2-chloro-N-(1-(3,4,5-trimethoxyphenyl)-1H-imidazol-4-yl)quinazolin-4-amine (86a)

Compound 86a was prepared according to the procedure reported in Scheme 1 from 2,4-dichloroquinazoline (21a) (0.4 g, 2.01 mmol) in 2-Propanol (10 mL) using DIPEA (1.4 mL, 8.04 mmol) and 1-(3,4,5-trimethoxyphenyl)-1H-imidazol-4-amine hydrochloride (57a) (0.69 g, 2.41 mmol). This gave 2-chloro-N-(1-(3,4,5-trimethoxyphenyl)-1H-imidazol-4-yl)quinazolin-4-amine (86a) (1.26 mmol, 63% yield) as a light pink solid; $^1$H NMR (300 MHz, DMSO-$d_6$) δ 11.12 (s, 1H, $D_2O$ exchangeable), 8.75 (d, J=8.3 Hz, 1H), 8.24 (s, 1H), 8.01 (d, J=1.7 Hz, 1H), 7.87 (t, J=7.6 Hz, 1H), 7.72 (d, J=8.2 Hz, 1H), 7.61 (t, J=7.7 Hz, 1H), 6.95 (s, 2H), 3.88 (s, 6H), 3.70 (s, 3H); MS (ES+): 412.4 (M+1), 434.3 (M+Na), (ES−): 410.3 (M−1).

Step-2: Preparation of (S)-(1-(4-((1-(3,4,5-trimethoxyphenyl)-1H-imidazol-4-yl)amino)quinazolin-2-yl)pyrrolidin-2-yl)methanol (86b)

Compound 86b was prepared from 2-chloro-N-(1-(3,4,5-trimethoxyphenyl)-1H-imidazol-4-yl)quinazolin-4-amine (86a) (100 mg, 0.24 mmol), (S)-pyrrolidin-2-ylmethanol (74 mg, 0.73 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using $NaHCO_3$, (S)-(1-(4-(1-(3,4,5-trimethoxyphenyl)-1H-imidazol-4-ylamino)quinazolin-2-yl)pyrrolidin-2-yl)methanol (86b) (55 mg, 48% yield) as a cream color solid; $^1$H NMR (300 MHz, DMSO-$d_6$) δ 10.59-10.09 (m, 1H, $D_2O$ exchangeable), 8.47 (d, J=8.1 Hz, 1H), 8.27 (s, 1H), 8.20-7.94 (m, 1H), 7.54 (t, J=7.7 Hz, 1H), 7.31 (d, J=8.4 Hz, 1H), 7.08 (t, J=7.6 Hz, 1H), 6.98 (s, 2H), 5.09-4.67 (m, 1H, $D_2O$ exchangeable), 4.56-4.14 (m, 2H), 3.89 (s, 6H), 3.69 (s, 5H), 3.57-3.17 (m, 1H), 2.18-1.79 (m, 4H); MS (ES+): 477.5 (M+1), (ES−): 475.5 (M−1).

Scheme 86

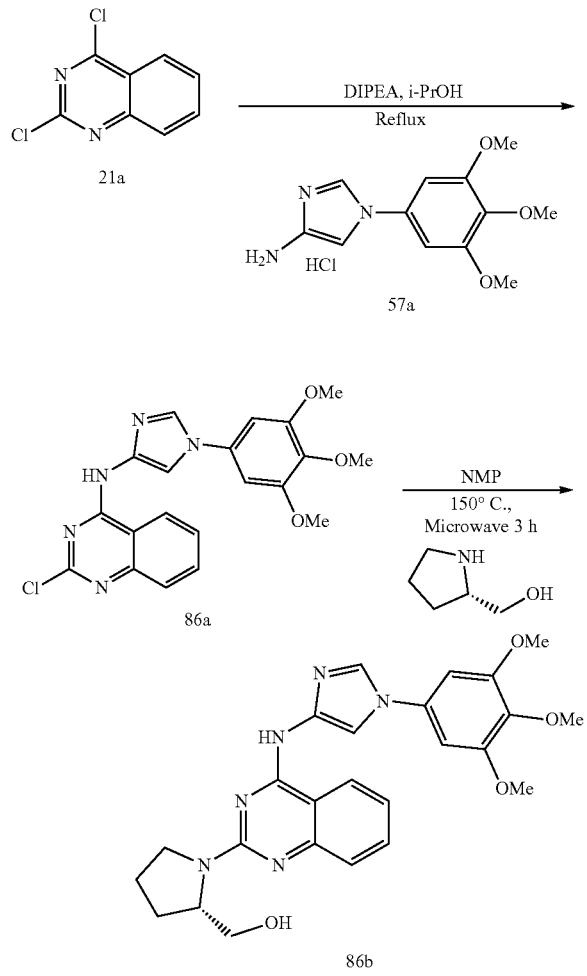

Scheme 87

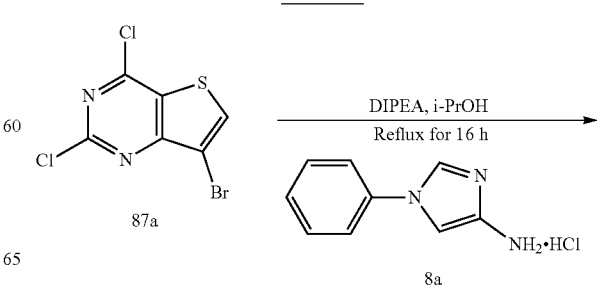

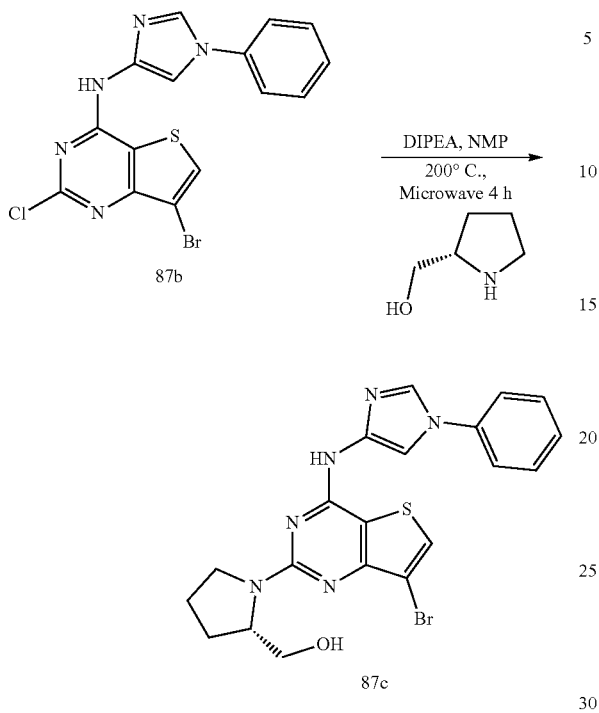

Preparation of (S)-(1-(7-bromo-4-((1-phenyl-1H-imidazol-4-yl)amino)thieno[3,2-d]pyrimidin-2-yl)pyrrolidin-2-yl)methanol (87c)

Step-1: Preparation of 7-bromo-2-chloro-N-(1-phenyl-1H-imidazol-4-yl)thieno[3,2-d]pyrimidin-4-amine (87b)

Compound 87b was prepared according to the procedure reported in Scheme 1 from 7-bromo-2,4-dichlorothieno[3,2-d]pyrimidine (87a) (0.2 g, 0.70 mmol; CAS #41102-25-4) in 2-Propanol (6 mL) using DIPEA (0.67 mL, 3.83 mmol) and 1-phenyl-1H-imidazol-4-amine, HCl (8a) (182 mg, 0.93 mmol). This gave after workup and purification by flash column chromatography [silica gel 12 g, eluting with a 9:1 mixture of ethyl acetate and methanol in hexanes (0 to 100%)] 7-bromo-2-chloro-N-(1-phenyl-1H-imidazol-4-yl)thieno[3,2-d]pyrimidin-4-amine (87b) (122 mg, 43% yield) as a brown solid; $^1$HNMR (300 MHz, DMSO-$d_6$) δ 11.34 (s, 1H, $D_2O$ exchangeable), 8.44 (s, 1H), 8.29 (s, 1H), 7.96 (s, 1H), 7.73-7.64 (m, 2H), 7.62-7.52 (m, 2H), 7.46-7.36 (m, 1H). MS (ES-): 404.1, 406.1 (M-2).

Step-2: Preparation of (S)-(1-(7-bromo-4-((1-phenyl-1H-imidazol-4-yl)amino)thieno[3,2-d]pyrimidin-2-yl)pyrrolidin-2-yl)methanol (87c)

Compound 87c was prepared from 7-bromo-2-chloro-N-(1-phenyl-1H-imidazol-4-yl)thieno[3,2-d]pyrimidin-4-amine (87b) (50 mg, 0.12 mmol), (S)-pyrrolidin-2-ylmethanol (0.04 mL, 0.39 mmol), and DIPEA (0.06 mL, 0.37 mmol) in NMP (0.5 mL) according to the procedure reported in Scheme 2. This gave after workup and purification by reverse phase flash column chromatography [(silica gel C-18, 24 g) eluting with 0.1% TFA in acetonitrile and 0.1% TFA in water] followed by lyophilization (S)-(1-(7-bromo-4-((1-phenyl-1H-imidazol-4-yl)amino)thieno[3,2-d]pyrimidin-2-yl)pyrrolidin-2-yl)methanol (87c) (22 mg, 38% yield) as a light yellow solid; $^1$H NMR (300 MHz, Methanol-$d_4$) δ 8.78-8.54 (m, 1H), 8.28 (s, 1H), 8.21-8.01 (m, 1H), 7.74-7.54 (m, 4H), 7.54-7.43 (m, 1H), 4.38-4.15 (m, 1H), 4.14-3.93 (m, 2H), 3.93-3.65 (m, 2H), 2.44-2.21 (m, 1H), 2.21-1.99 (m, 2H), 1.99-1.79 (m, 1H); $^{19}$F NMR (282 MHz, Methanol-$d_4$) δ -77.25; MS (ES+): 471.3, 473.3 (M+2). HPLC purity: 97.84%.

Scheme 88

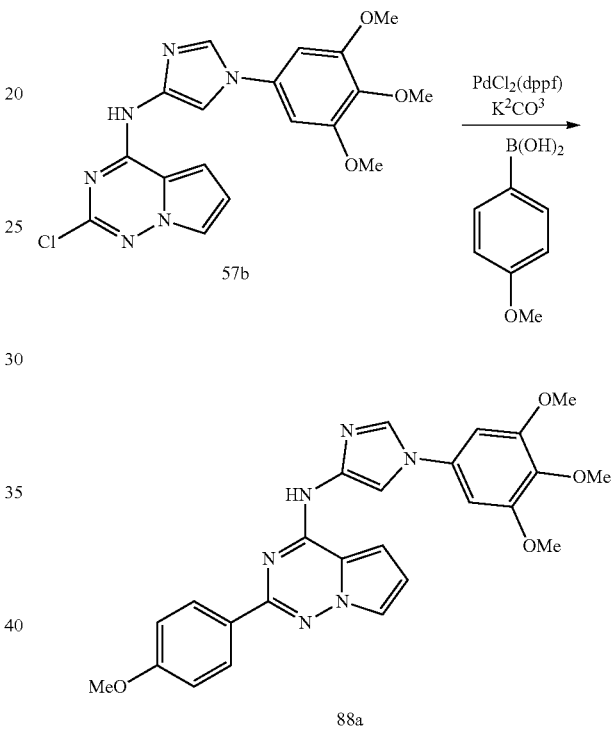

Preparation of 2-(4-methoxyphenyl)-N-(1-(3,4,5-trimethoxyphenyl)-1H-imidazol-4-yl)pyrrolo[2,1-f][1,2,4]triazin-4-amine (88a)

Compound 88a was prepared from 2-chloro-N-(1-(3,4,5-trimethoxyphenyl)-1H-imidazol-4-yl)pyrrolo[1,2-f][1,2,4]triazin-4-amine (57b) (200 mg, 0.5 mmol), 4-methoxyphenylboronic acid (114 mg, 0.75 mmol), PdCl$_2$(dppf) (73 mg, 0.100 mmol) in anhydrous 1,4-Dioxane (15 mL) and Water (1 mL) using potassium carbonate (207 mg, 1.5 mmol) according to the procedure reported in step-3 of Scheme 77. This gave after workup 2-(4-methoxyphenyl)-N-(1-(3,4,5-trimethoxyphenyl)-1H-imidazol-4-yl)pyrrolo[1,2-f][1,2,4]triazin-4-amine (88a) (52 mg, 22% yield) as a white solid; $^1$H NMR (300 MHz, DMSO-$d_6$) δ 10.89 (s, 1H, $D_2O$ exchangeable), 8.33-8.29 (m, 1H), 8.28 (s, 1H), 8.24 (s, 1H), 8.20-8.15 (m, 1H), 7.78 (s, 1H), 7.34 (s, 1H), 7.08-6.97 (m, 4H), 6.73-6.67 (m, 1H), 3.93 (s, 6H), 3.82 (s, 3H), 3.71 (s, 3H); MS (ES+): 473.5 (M+1), 495.4 (M+Na), MS (ES-): 471.4 (M-1), 507.4 (M+Cl).

Scheme 89

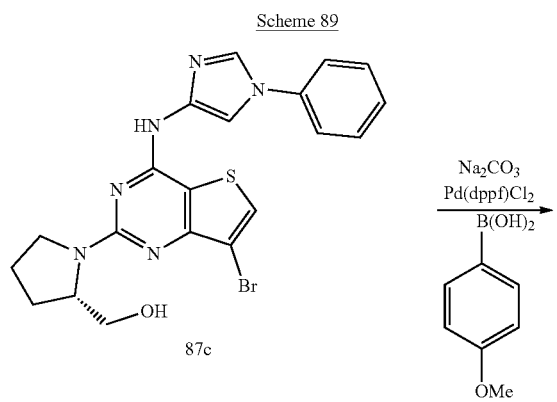

Scheme 90

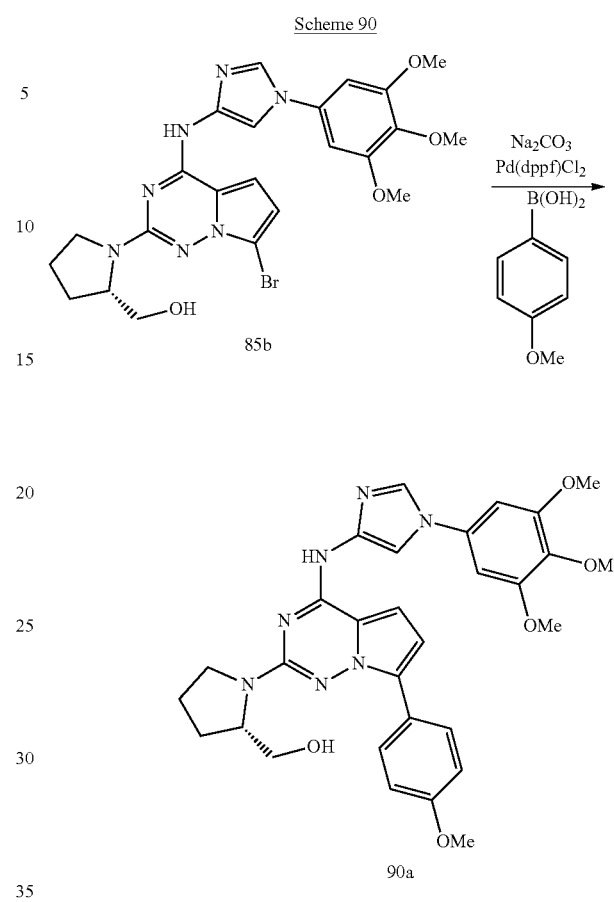

Preparation of (S)-(1-(7-(4-methoxyphenyl)-4-(1-phenyl-1H-imidazol-4-ylamino)thieno[3,2-d]pyrimidin-2-yl)pyrrolidin-2-yl)methanol (89a)

Compound 89a was prepared from (S)-(1-(7-bromo-4-(1-phenyl-1H-imidazol-4-ylamino)thieno[3,2-d]pyrimidin-2-yl)pyrrolidin-2-yl)methanol (87c) (50 mg, 0.11 mmol), 4-methoxyphenylboronic acid (81 mg, 0.53 mmol), Pd(dppf)Cl$_2$ (4 mg, 5.30 µmol) in anhydrous 1,4-Dioxane (3 mL) and Water (1 mL) using sodium carbonate (28 mg, 0.27 mmol) according to the procedure reported in step-3 of Scheme 77. This gave after workup, purification by reverse phase flash column chromatography [(silica gel C-18, 24 g) eluting with 0.1% TFA in acetonitrile and 0.1% TFA in water] and lyophilization (S)-(1-(7-(4-methoxyphenyl)-4-(1-phenyl-1H-imidazol-4-ylamino)thieno[3,2-d]pyrimidin-2-yl)pyrrolidin-2-yl)methanol (89a) (20 mg, 38% yield) as a yellow solid; $^1$H NMR (300 MHz, Methanol-d$_4$): δ 8.20 (s, 1H), 8.03 (d, J=12.4 Hz, 2H), 7.61 (dd, J=11.6, 7.7 Hz, 4H), 7.53-7.42 (m, 3H), 7.13-7.03 (m, 2H), 4.18 (s, 1H), 4.12-3.96 (m, 1H), 3.86 (s, 3H), 3.78 (dd, J=10.4, 2.4 Hz, 1H), 3.73-3.63 (m, 1H), 3.60 (s, 1H), 2.34-2.17 (m, 1H), 2.05 (s, 2H), 1.87 (s, 1H). $^{19}$F NMR (282 MHz, Methanol-d$_4$) δ −77.28; MS (ES+): 499.5 (M+1), 521.5 (M+Na); MS (ES−): 497.5 (M−1).

Preparation of (S)-(1-(7-(4-methoxyphenyl)-4-(1-(3,4,5-trimethoxyphenyl)-1H-imidazol-4-ylamino)pyrrolo[1,2-f][1,2,4]triazin-2-yl)pyrrolidin-2-yl)methanol (90a)

Compound 90a was prepared from (S)-(1-(7-bromo-4-(1-(3,4,5-trimethoxyphenyl)-1H-imidazol-4-ylamino)pyrrolo[1,2-f][1,2,4]triazin-2-yl)pyrrolidin-2-yl)methanol (85b) (70 mg, 0.13 mmol), 4-methoxyphenylboronic acid (98 mg, 0.64 mmol), Pd(dppf)Cl$_2$ (5 mg, 6.43 µmol) in anhydrous 1,4-Dioxane (3 mL) and Water (1 mL) using sodium carbonate (34 mg, 0.32 mmol) according to the procedure reported in step-3 of Scheme 77. This gave after workup, purification by reverse phase flash column chromatography [(silica gel C-18, 24 g) eluting with 0.1% TFA in acetonitrile and 0.1% TFA in water] and lyophilization (S)-(1-(7-(4-methoxyphenyl)-4-(1-(3,4,5-trimethoxyphenyl)-1H-imidazol-4-ylamino)pyrrolo[1,2-f][1,2,4]triazin-2-yl)pyrrolidin-2-yl)methanol (90a) (31 mg, 42% yield) as a yellow solid; $^1$H NMR (300 MHz, DMSO-d$_6$): δ 10.57 (s, 1H, D$_2$O exchangeable), 8.33 (s, 1H), 8.17 (d, J=8.7 Hz, 2H), 8.01 (s, 1H), 7.27 (s, 1H), 7.06-6.92 (m, 4H), 6.81 (s, 1H), 4.57 (s, 1H), 4.36-4.16 (m, 1H), 4.04 (s, 1H), 3.92-3.87 (m, 6H), 3.83-3.75 (m, 3H), 3.73-3.64 (m, 3H), 3.57-3.31 (m, 2H), 2.12-1.85 (m, 4H). $^{19}$F NMR (282 MHz, DMSO-d$_6$) δ −74.45; MS (ES+): 572.6, 594.6 (M+Na), 610.4 (M+K).

Scheme 91

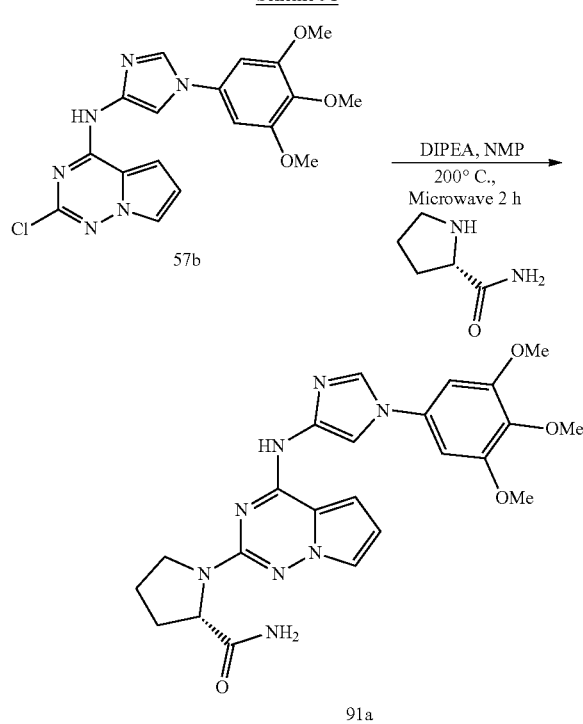

Preparation of (S)-1-(4-(1-(3,4,5-trimethoxyphenyl)-1H-imidazol-4-ylamino)pyrrolo[1,2-f][1,2,4]triazin-2-yl)pyrrolidine-2-carboxamide (91a)

Compound 91a was prepared from the stirred suspension of 2-chloro-N-(1-(3,4,5-trimethoxyphenyl)-1H-imidazol-4-yl)pyrrolo[1,2-f][1,2,4]triazin-4-amine (57b) (0.2 g, 0.5 mmol), (S)-pyrrolidine-2-carboxamide (0.17 g, 1.5 mmol) and DIPEA (0.26 mL, 1.5 mmol) in NMP (2 mL) according to the procedure reported in Scheme 2. This gave after workup and purification by reverse phase flash column chromatography [(silica gel C-18, 24 g) eluting with 0.1% TFA in acetonitrile and 0.1% TFA in water] followed by lyophilization (S)-1-(4-(1-(3,4,5-trimethoxyphenyl)-1H-imidazol-4-ylamino)pyrrolo[1,2-f][1,2,4]triazin-2-yl)pyrrolidine-2-carboxamide (91a) (50 mg, 19% yield) as a white solid; $^1$H NMR (300 MHz, DMSO-d$_6$): δ 10.50 (s, 1H, D$_2$O exchangeable), 8.22 (d, J=5.6 Hz, 1H), 7.92 (d, J=5.4 Hz, 1H), 7.42 (d, J=5.4 Hz, 1H), 7.23 (s, 1H, D$_2$O exchangeable), 7.17 (s, 1H), 7.12-7.05 (m, 2H), 7.02 (s, 1H, D$_2$O exchangeable), 6.41 (d, J=5.6 Hz, 1H), 4.41 (s, 1H), 3.93 (t, J=4.2 Hz, 6H), 3.68 (t, J=4.2 Hz, 3H), 3.35 (s, 1H), 2.19 (s, 1H), 1.95 (d, J=13.6 Hz, 4H); MS (ES+): 479.5 (M+1).

Scheme 92

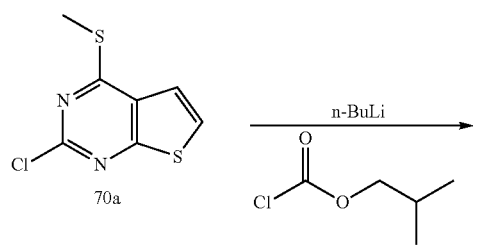

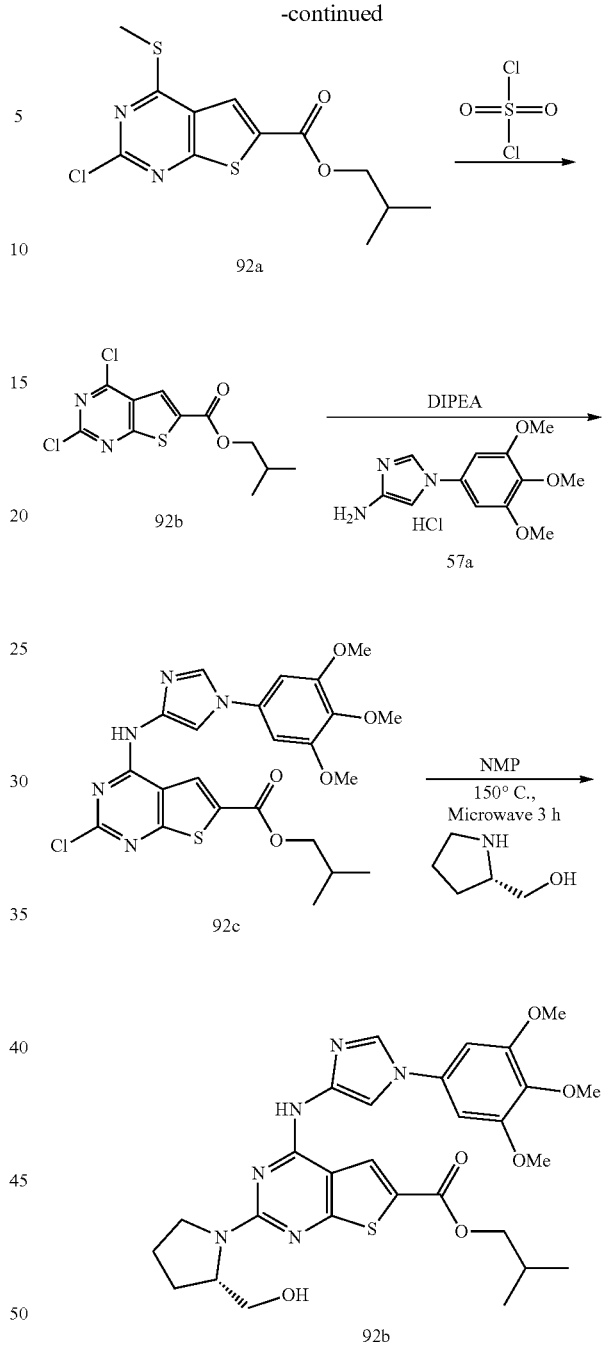

Preparation of (S)-isobutyl 2-(2-(hydroxymethyl)pyrrolidin-1-yl)-4-((1-(3,4,5-trimethoxyphenyl)-1H-imidazol-4-yl)amino)thieno[2,3-d]pyrimidine-6-carboxylate (92d)

Step-1: Preparation of isobutyl 2-chloro-4-(methylthio)thieno[2,3-d]pyrimidine-6-carboxylate (92a)

Compound 92a was prepared according to the procedure reported in step-2 of Scheme 70 from 2-chloro-4-(methylthio)thieno[2,3-d]pyrimidine (70a) (0.5 g, 2.31 mmol) in THF (20 mL) using n-butyl lithium (1.6 M solution in hexanes, 3.03 mL, 4.85 mmol) and quenching with Isobutyl chloroformate (0.6 mL, 4.61 mmol). This gave after workup and purification by flash column chromatography [silica gel, (25 g) eluting with 0-100% ethyl acetate in hexanes]isobutyl 2-chloro-4-(methylthio)thieno[2,3-d]pyrimidine-6-carboxylate (92a) (403 mg, 55% yield) as a brown solid; $^1$H NMR (300 MHz, DMSO-d$_6$) δ 8.09 (s, 1H), 4.14 (d, J=6.6 Hz, 2H), 2.70 (s, 3H), 2.04 (hept, J=6.6 Hz, 1H), 0.97 (d, J=6.7 Hz, 6H); MS (ES+): 339.2 (M+Na).

Step-2: Preparation of isobutyl 2,4-dichlorothieno [2,3-d]pyrimidine-6-carboxylate (92b)

Compound 92b was prepared according to the procedure reported in step-3 of Scheme 70 from isobutyl 2-chloro-4-(methylthio)thieno[2,3-d]pyrimidine-6-carboxylate (92a) (375 mg, 1.18 mmol) in acetonitrile (30 mL) and DCM (5 mL) using sulfuryl chloride (0.48 mL, 5.92 mmol). This gave after workup and purification by flash column chromatography [silica gel, (12 g) eluting with 0-100% ethyl acetate in hexanes] isobutyl 2,4-dichlorothieno[2,3-d]pyrimidine-6-carboxylate (92b) (174 mg, 48% yield) as a syrup; $^1$H NMR (300 MHz, DMSO-d$_6$) δ 8.21 (s, 1H), 4.17 (d, J=6.6 Hz, 2H), 2.06 (dt, J=13.4, 6.7 Hz, 1H), 0.99 (d, J=6.8 Hz, 6H).

Step 3: Preparation of isobutyl 2-chloro-4-((1-(3,4,5-trimethoxyphenyl)-1H-imidazol-4-yl)amino)thieno [2,3-d]pyrimidine-6-carboxylate (92c)

Compound 92c was prepared according to the procedure reported in Scheme 1 from isobutyl 2,4-dichlorothieno[2,3-d]pyrimidine-6-carboxylate (92b) (160 mg, 0.52 mmol) in 2-Propanol (5 mL) using DIPEA (0.27 mL, 1.57 mmol) and 1-(3,4,5-trimethoxyphenyl)-1H-imidazol-4-amine hydrochloride (57a) (0.22 g, 0.78 mmol). This gave isobutyl 2-chloro-4-(1-(3,4,5-trimethoxyphenyl)-1H-imidazol-4-ylamino)thieno[2,3-d]pyrimidine-6-carboxylate (92c) (160 mg, 59% yield) as a brown solid; $^1$H NMR (300 MHz, DMSO-d$_6$) δ 11.43 (s, 1H, D$_2$O exchangeable), 8.87 (s, 1H), 8.22 (d, J=1.6 Hz, 1H), 7.91 (d, J=1.6 Hz, 1H), 6.94 (s, 2H), 4.12 (d, J=6.5 Hz, 2H), 3.88 (s, 6H), 3.70 (s, 3H), 2.09-1.96 (m, 1H), 1.01 (d, J=6.7 Hz, 6H); MS (ES+): 540.5 (M+Na), (ES−): 516.5 (M−1).

Step 4: Preparation of (S)-isobutyl 2-(2-(hydroxymethyl)pyrrolidin-1-yl)-4-((1-(3,4,5-trimethoxyphenyl)-1H-imidazol-4-yl)amino)thieno[2,3-d]pyrimidine-6-carboxylate (92d)

Compound 92d was prepared from 2-chloro-4-(1-(3,4,5-trimethoxyphenyl)-1H-imidazol-4-ylamino)thieno[2,3-d]pyrimidine-6-carboxylate (92c) (80 mg, 0.15 mmol), (S)-pyrrolidin-2-ylmethanol (46.9 mg, 0.46 mmol) in NMP (1 mL) according to the procedure reported in Scheme 2. This gave after workup by pouring reaction the mixture into water and collecting the solid that separated out by filtration followed by drying in vacuum (S)-isobutyl 2-(2-(hydroxymethyl)pyrrolidin-1-yl)-4-(1-(3,4,5-trimethoxyphenyl)-1H-imidazol-4-ylamino)thieno[2,3-d]pyrimidine-6-carboxylate (92d) (65 mg, 72% yield) as a brown solid; $^1$H NMR (300 MHz, DMSO-d$_6$) δ 10.32 (s, 1H, D$_2$O exchangeable), 8.63 (s, 1H), 8.12 (d, J=1.7 Hz, 1H), 7.95 (s, 1H), 6.92 (s, 1H), 4.61 (s, 1H), 4.31 (s, 1H), 4.08-3.99 (m, 2H), 3.87 (s, 6H), 3.84-3.58 (m, 5H), 3.52-3.36 (m, 2H), 2.13-1.76 (m, 5H), 1.00 (dd, J=6.6, 1.6 Hz, 6H); MS (ES+): 583.6 (M+1).

Scheme 93

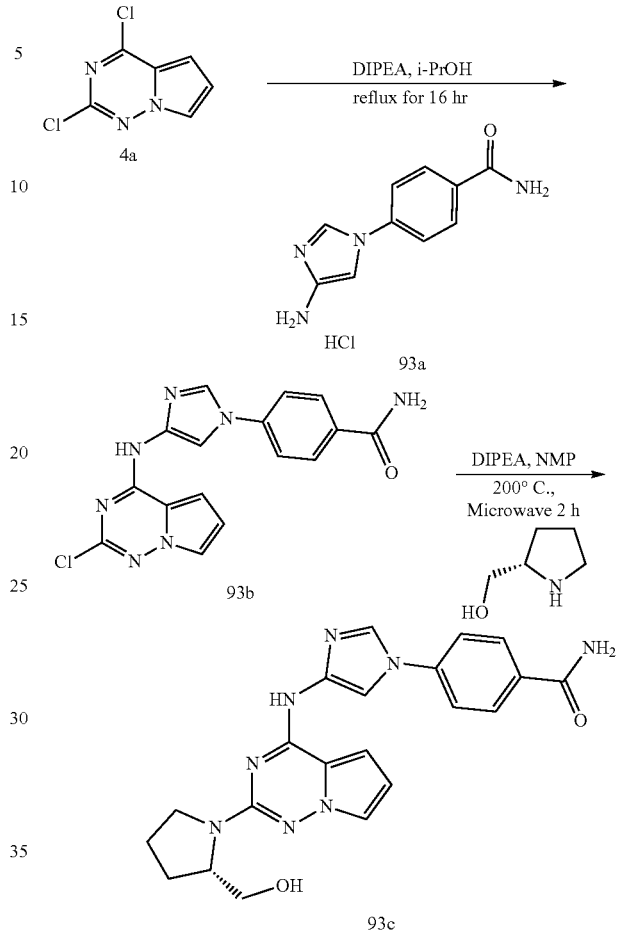

Preparation of (S)-4-(4-(2-(2-(hydroxymethyl)pyrrolidin-1-yl)pyrrolo[1,2-f][1,2,4]triazin-4-ylamino)-1H-imidazol-1-yl)benzamide (93c)

Step-1: Preparation of 4-(4-(2-chloropyrrolo[1,2-f] [1,2,4]triazin-4-ylamino)-1H-imidazol-1-yl)benzamide (93b)

Compound 93b was prepared according to the procedure reported in Scheme 1 from 2,4-dichloropyrrolo[1,2-f][1,2,4]triazine (4a) (180 mg, 0.97 mmol) in 2-Propanol (20 mL) using DIPEA (0.51 mL, 2.92 mmol) and 4-(4-amino-1H-imidazol-1-yl)benzamide hydrochloride (93a) (0.26 g, 1.29 mmol). This gave after work up and purification by flash column chromatography [silica gel, (40 g) eluting with DCM and methanol (0 to 30%)] 4-(4-(2-chloropyrrolo[1,2-f][1,2,4]triazin-4-ylamino)-1H-imidazol-1-yl)benzamide (93b) (0.26 g, 76% yield) as a brown solid; $^1$H NMR (300 MHz, DMSO-d$_6$): δ 11.37 (s, 1H, D$_2$O exchangeable), 8.38 (d, J=1.7 Hz, 1H), 8.09 (s, 1H, D$_2$O exchangeable), 8.08-8.01 (m, 2H), 7.98 (d, J=1.7 Hz, 1H), 7.78 (d, J=2.3 Hz, 2H), 7.75 (s, 1H), 7.50 (s, 1H, D$_2$O exchangeable), 7.40 (d, J=4.4 Hz, 1H), 6.73 (dd, J=4.5, 2.6 Hz, 1H). MS (ES+): 354.4; MS (ES−): 352.3.

Step-2: Preparation of (S)-4-(4-(2-(2-(hydroxymethyl)pyrrolidin-1-yl)pyrrolo[1,2-f][1,2,4]triazin-4-ylamino)-1H-imidazol-1-yl)benzamide (93c)

Compound 93c was prepared from 4-(4-(2-chloropyrrolo[1,2-f][1,2,4]triazin-4-ylamino)-1H-imidazol-1-yl)benzamide (93b) (160 mg, 0.45 mmol), (S)-pyrrolidin-2-ylmethanol (0.13 mL, 1.34 mmol), and DIPEA (0.23 mL, 1.34 mmol) in NMP (1.5 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-4-(4-(2-(2-(hydroxymethyl)pyrrolidin-1-yl)pyrrolo[1,2-f][1,2,4]triazin-4-ylamino)-1H-imidazol-1-yl)benzamide (93c) (102 mg, 55% yield) as a brown solid; $^1$H NMR (300 MHz, DMSO-d$_6$): δ 10.57 (s, 1H, D$_2$O exchangeable), 8.37 (d, J=1.5 Hz, 1H), 8.08 (s, 1H, D$_2$O exchangeable), 8.05-8.01 (m, 2H), 7.99 (s, 1H), 7.86 (d, J=8.4 Hz, 2H), 7.44 (s, 1H, D$_2$O exchangeable), 7.40 (t, J=2.0 Hz, 1H), 7.16 (dd, J=4.4, 1.7 Hz, 1H), 6.40 (dd, J=4.5, 2.4 Hz, 1H), 4.99 (s, 1H, D$_2$O exchangeable), 4.21 (s, 2H), 3.89-3.70 (m, 1H), 3.50 (s, 2H), 2.17-1.75 (m, 4H); MS (ES+): 419.4 (M+1); MS (ES-): 453.4 (M+Cl).

Preparation of (S)-3-(4-(2-(2-(hydroxymethyl)pyrrolidin-1-yl)pyrrolo[1,2-f][1,2,4]triazin-4-ylamino)-1H-imidazol-1-yl)benzamide (94c)

Step-1: Preparation of 3-(4-(2-chloropyrrolo[1,2-f][1,2,4]triazin-4-ylamino)-1H-imidazol-1-yl)benzamide (94b)

Compound 94b was prepared according to the procedure reported in Scheme 1 from 2,4-dichloropyrrolo[1,2-f][1,2,4]triazine (4a) (240 mg, 1.29 mmol) in 2-Propanol (20 mL) using DIPEA ((0.68 mL), 3.87 mmol) and 3-(4-amino-1H-imidazol-1-yl)benzamide hydrochloride (94a) (0.4 g, 1.68 mmol). This gave after work up and purification by flash column chromatography [silica gel, (40 g) eluting with DCM and methanol (0 to 30%)] 3-(4-(2-chloropyrrolo[1,2-f][1,2,4]triazin-4-ylamino)-1H-imidazol-1-yl)benzamide (94b) (0.27 g, 60% yield) as a brown solid; $^1$H NMR (300 MHz, DMSO-d$_6$): δ 11.36 (s, 1H, D$_2$O exchangeable), 8.31 (d, J=1.6 Hz, 1H), 8.18 (s, 1H), 8.11 (t, J=1.9 Hz, 1H), 7.96 (d, J=1.6 Hz, 1H), 7.89 (dt, J=7.6, 1.3 Hz, 1H), 7.86-7.80 (m, 1H), 7.78 (dd, J=2.6, 1.5 Hz, 1H), 7.65 (t, J=7.9 Hz, 1H), 7.60 (s, 1H), 7.41 (d, J=4.4 Hz, 1H), 6.73 (dd, J=4.5, 2.6 Hz, 1H). MS (ES+): 354.3 (M+1); MS (ES-): 352.3 (M-1).

Step-2: Preparation of (S)-3-(4-(2-(2-(hydroxymethyl)pyrrolidin-1-yl)pyrrolo[1,2-f][1,2,4]triazin-4-ylamino)-1H-imidazol-1-yl)benzamide (94c)

Compound 94c was prepared from 3-(4-(2-chloropyrrolo[1,2-f][1,2,4]triazin-4-ylamino)-1H-imidazol-1-yl)benzamide (94b) (150 mg, 0.42 mmol), (S)-pyrrolidin-2-ylmethanol (0.13 mL, 1.34 mmol), and DIPEA (0.22 mL, 1.27 mmol) in NMP (1.5 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-3-(4-(2-(2-(hydroxymethyl)pyrrolidin-1-yl)pyrrolo[1,2-f][1,2,4]triazin-4-ylamino)-1H-imidazol-1-yl)benzamide (94c) (0.12 g, 69% yield) as a brown solid; $^1$H NMR (300 MHz, DMSO-d$_6$): δ 10.57 (s, 1H, D$_2$O exchangeable), 8.30 (d, J=1.5 Hz, 1H), 8.15-8.08 (m, 2H), 8.04 (d, J=1.6 Hz, 1H), 7.92 (dd, J=8.0, 2.1 Hz, 1H), 7.83 (d, J=7.7 Hz, 1H), 7.69-7.53 (m, 2H), 7.39 (t, J=2.0 Hz, 1H), 7.14 (dd, J=4.4, 1.6 Hz, 1H), 6.40 (dd, J=4.5, 2.4 Hz, 1H), 4.97 (s, 1H, D$_2$O exchangeable), 4.21 (s, 1H), 3.78 (dd, J=10.0, 3.5 Hz, 1H), 3.51 (d, J=18.1 Hz, 2H), 3.35 (s, 1H), 2.11-1.82 (m, 4H). $^{19}$F NMR (282 MHz, DMSO-d$_6$) δ -73.49; MS (ES+): 419.5 (M+1); MS (ES-): 453.4 (M+Cl).

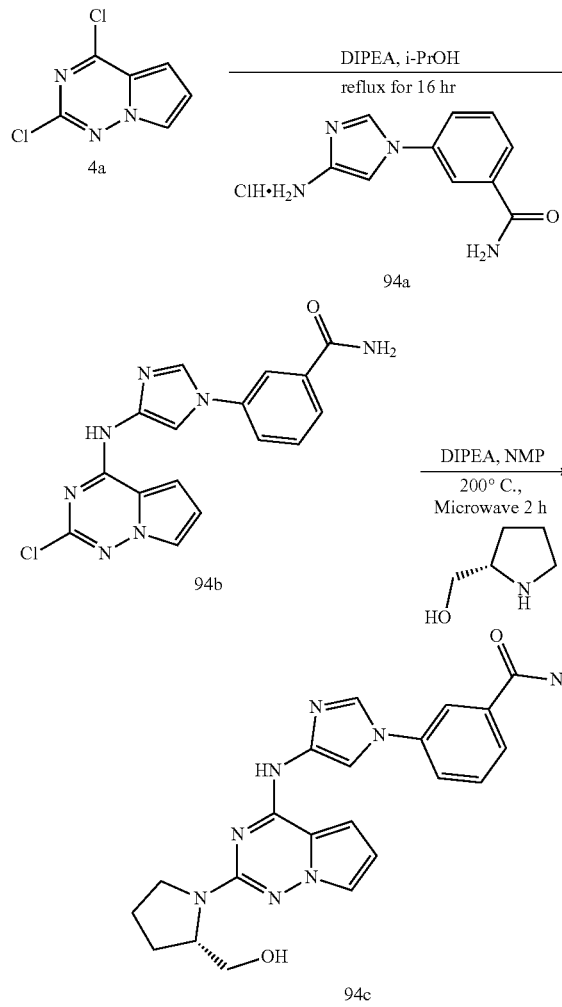

Scheme 94

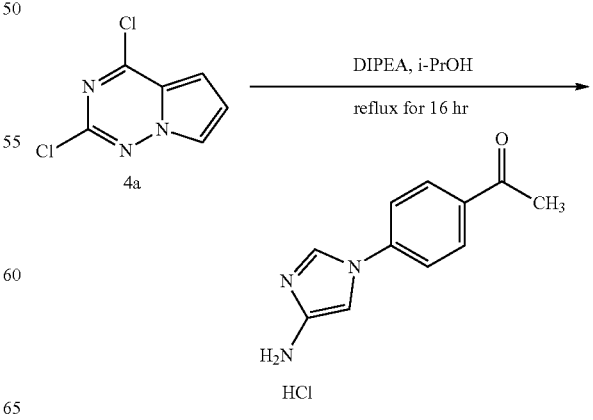

Scheme 95

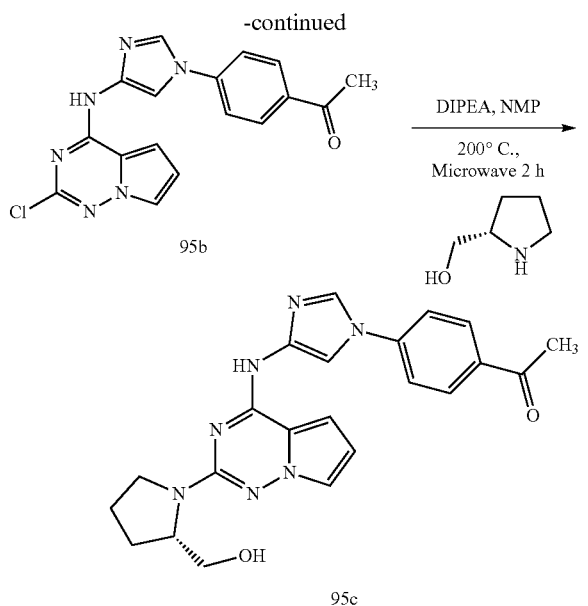

95b

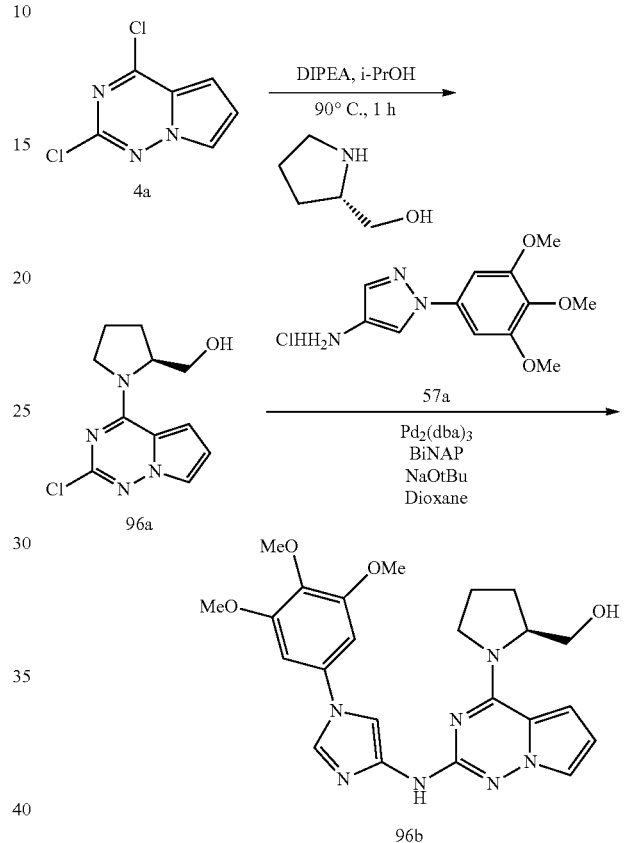

exchangeable), 8.64 (s, 1H), 8.13-8.05 (m, 3H), 7.95 (d, J=8.5 Hz, 2H), 7.44 (t, J=2.0 Hz, 1H), 7.16 (dd, J=4.5, 1.6 Hz, 1H), 6.43 (dd, J=4.4, 2.4 Hz, 1H), 4.19 (s, 1H), 3.76 (dd, J=10.0, 3.6 Hz, 1H), 3.58-3.42 (m, 1H), 3.36 (dd, J=11.7, 7.1 Hz, 2H), 2.62 (s, 3H), 2.11-1.83 (m, 4H). MS (ES+): 418.5 (M+1); MS (ES−): 452.5 (M+Cl).

Scheme 96

95c

Preparation of (S)-1-(4-(4-(2-(2-(hydroxymethyl) pyrrolidin-1-yl)pyrrolo[1,2-f][1,2,4]triazin-4-ylamino)-1H-imidazol-1-yl)phenyl)ethanone (95c)

Step-1: Preparation of 1-(4-(4-(2-chloropyrrolo[1,2-f][1,2,4]triazin-4-ylamino)-1H-imidazol-1-yl)phenyl)ethanone (95b)

Compound 95b was prepared according to the procedure reported in Scheme 1 from 2,4-dichloropyrrolo[1,2-f][1,2,4]triazine (4a) (240 mg, 1.3 mmol) in 2-Propanol (20 mL) using DIPEA (0.51 mL, 2.92 mmol) and 1-(4-(4-amino-1H-imidazol-1-yl)phenyl)ethanone hydrochloride (95a) (0.4 g, 1.68 mmol). This gave after work up and purification by flash column chromatography [silica gel, (40 g) eluting with DCM and methanol (0 to 30%)] 1-(4-(4-(2-chloropyrrolo[1,2-f][1,2,4]triazin-4-ylamino)-1H-imidazol-1-yl)phenyl)ethanone (95b) (0.26 g, 57% yield) as a brown solid; $^1$H NMR (300 MHz, DMSO-$d_6$): δ 11.40 (s, 1H, D$_2$O exchangeable), 8.45 (d, J=1.6 Hz, 1H), 8.18-8.09 (m, 2H), 8.01 (d, J=1.6 Hz, 1H), 7.86-7.80 (m, 2H), 7.79 (dd, J=2.6, 1.5 Hz, 1H), 7.41 (d, J=4.4 Hz, 1H), 6.73 (dd, J=4.5, 2.6 Hz, 1H), 2.62 (s, 3H). MS (ES−): 351.3, 353.3 (M−1).

Step-2: Preparation of (S)-1-(4-(4-(2-(2-(hydroxymethyl)pyrrolidin-1-yl)pyrrolo[1,2-f][1,2,4]triazin-4-ylamino)-1H-imidazol-1-yl)phenyl)ethanone (95c)

Compound 95c was prepared from 1-(4-(4-(2-chloropyrrolo[1,2-f][1,2,4]triazin-4-ylamino)-1H-imidazol-1-yl)phenyl)ethanone (95b) (150 mg, 0.43 mmol), (S)-pyrrolidin-2-ylmethanol (0.13 mL, 1.34 mmol), and DIPEA (0.22 mL, 1.28 mmol) in NMP (1.5 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$, (S)-1-(4-(4-(2-(2-(hydroxymethyl)pyrrolidin-1-yl)pyrrolo[1,2-f][1,2,4]triazin-4-ylamino)-1H-imidazol-1-yl)phenyl)ethanone (95c) (30 mg, 14% yield) as a brown solid; $^1$H NMR (300 MHz, DMSO-$d_6$): δ 10.79 (s, 1H, D$_2$O Preparation of (S)-(1-(2-((1-(3,4,5-trimethoxyphenyl)-1H-imidazol-4-yl)amino)pyrrolo[2,1-f][1,2,4]triazin-4-yl)pyrrolidin-2-yl)methanol (96b)

Step-1: Preparation of (S)-(1-(2-chloropyrrolo[2,1-f][1,2,4]triazin-4-yl)pyrrolidin-2-yl)methanol (96a)

To a solution of 2,4-dichloropyrrolo[1,2-f][1,2,4]triazine (4a) (0.5 g, 2.7 mmol) in 2-Propanol (6 mL) was added (S)-pyrrolidin-2-ylmethanol (0.39 mL, 4.0 mmol), DIPEA (1.39 mL, 8.0 mmol) and heated at 90° C. for 1 hr. The reaction was cooled to room temperature and solid obtained was collected by filtration to afford (S)-(1-(2-chloropyrrolo[2,1-f][1,2,4]triazin-4-yl)pyrrolidin-2-yl)methanol (96a) (0.49 g, 73% yield) as a white solid; $^1$H NMR (300 MHz, DMSO-$d_6$): δ 7.70 (dd, J=2.6, 1.4 Hz, 1H), 6.97 (dd, J=4.7, 1.6 Hz, 1H), 6.80-6.57 (m, 1H), 5.15 (t, J=5.7 Hz, 1H, D$_2$O exchangeable), 4.87 (t, J=5.7 Hz, 1H), 4.44 (d, J=17.8 Hz, 1H), 4.05-3.82 (m, 1H), 3.72-3.39 (m, 2H), 2.22-1.84 (m, 4H). MS (ES+): 253.3, 255.3 (M+2); MS (ES−): 287.2, 289.2 (M+Cl).

Step-2: Preparation of (S)-(1-(2-((1-(3,4,5-trimethoxyphenyl)-1H-imidazol-4-yl)amino)pyrrolo[2,1-f][1,2,4]triazin-4-yl)pyrrolidin-2-yl)methanol (96b)

A slurry of (S)-(1-(2-chloropyrrolo[1,2-f][1,2,4]triazin-4-yl)pyrrolidin-2-yl)methanol (96a) (0.1 g, 0.4 mmol), 1-(3,4,5-trimethoxyphenyl)-1H-imidazol-4-amine hydrochloride (57a) (0.11 g, 0.4 mmol), 2,2'-bis(diphenylphosphino)-1,1'-binaphthyl (30 mg, 0.04 mmol), sodium 2-methylpropan-2-olate (80 mg, 0.79 mmol), Pd$_2$(dba)$_3$ (40 mg, 0.04 mmol) in anhydrous Dioxane (4 mL) was heated in a sealed reactor under a positive flow of nitrogen at 90° C. for 18 h. The reaction mixture was diluted with EtOAc (100 mL) and organic layer was separated. The organic layer was washed with water (3 xs), brine, dried, filtered and concentrated in vacuum to dryness. The residue was purified by reverse phase flash column chromatography [(silica gel C-18, 24 g) eluting with acetonitrile and 0.1% HCl in water] and lyophilized to afford (S)-(1-(2-((1-(3,4,5-trimethoxyphenyl)-1H-imidazol-4-yl)amino)pyrrolo[2,1-f][1,2,4]triazin-4-yl)pyrrolidin-2-yl)methanol (96b) (21 mg, 11% yield) hydrochloride salt as a yellow solid; $^1$H NMR (300 MHz, DMSO-d$_6$): δ 9.72 (s, 1H, D$_2$O exchangeable), 9.63 (s, 1H, D$_2$O exchangeable), 9.38 (s, 1H), 7.92 (s, 1H), 7.66 (s, 1H), 7.15 (s, 2H), 6.90 (d, J=4.5 Hz, 1H), 6.56 (s, 1H), 4.54 (s, 1H), 4.07-3.93 (m, 1H), 3.89 (s, 6H), 3.77 (s, 1H), 3.71 (s, 3H), 3.68-3.62 (m, 1H), 3.60-3.47 (m, 1H), 2.23-1.88 (m, 4H). MS (ES+): 466.5 (M+1), 688.5 (M+Na); MS (ES−): 464.6 (M−1).

Scheme 97

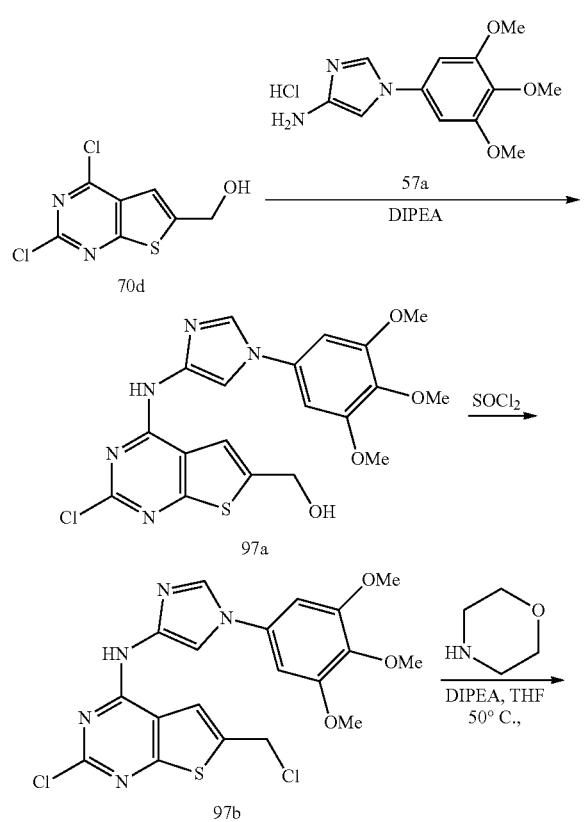

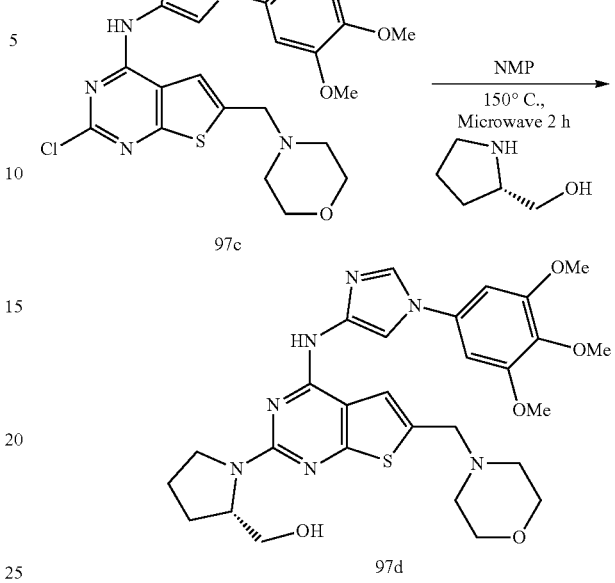

Preparation of (S)-(1-(6-(morpholinomethyl)-4-((1-(3,4,5-trimethoxyphenyl)-1H-imidazol-4-yl)amino)thieno[2,3-d]pyrimidin-2-yl)pyrrolidin-2-yl)methanol (97d)

Step-1: Preparation of (2-chloro-4-((1-(3,4,5-trimethoxyphenyl)-1H-imidazol-4-yl)amino)thieno[2,3-d]pyrimidin-6-yl)methanol (97a)

Compound 97a was prepared according to the procedure reported in Scheme 1 from (2,4-dichlorothieno[2,3-d]pyrimidin-6-yl)methanol (70d) (1.2 g, 5.1 mmol) in 2-Propanol (15 mL) using DIPEA (2.67 mL, 15.31 mmol) and 1-(3,4,5-trimethoxyphenyl)-1H-imidazol-4-amine hydrochloride (57a) (1.89 g, 6.64 mmol). This gave (2-chloro-4-(1-(3,4,5-trimethoxyphenyl)-1H-imidazol-4-ylamino)thieno[2,3-d]pyrimidin-6-yl)methanol (97a) (1.48 g, 65% yield) as light brown solid; $^1$H NMR (300 MHz, DMSO-d$_6$) δ 10.90 (s, 1H, D$_2$O exchangeable), 8.19 (d, J=1.6 Hz, 1H), 7.89 (d, J=1.6 Hz, 1H), 7.84 (s, 1H), 6.93 (s, 2H), 5.82 (t, J=5.8 Hz, 1H, D$_2$O exchangeable), 4.72 (dd, J=5.8, 1.2 Hz, 2H), 3.87 (s, 6H), 3.69 (s, 3H); MS (ES+): 448.3 (M+1), 470.3 (M+Na), (ES−): 446.3 (M−1).

Step-2: Preparation of 2-chloro-6-(chloromethyl)-N-(1-(3,4,5-trimethoxyphenyl)-1H-imidazol-4-yl)thieno[2,3-d]pyrimidin-4-amine (97b)

To a stirred suspension of (2-chloro-4-(1-(3,4,5-trimethoxyphenyl)-1H-imidazol-4-ylamino)thieno[2,3-d]pyrimidin-6-yl)methanol (97a) (0.5 g, 1.12 mmol) in DCM (50 mL) at 0° C. was added N,N-Dimethylformamide (5 mL) and thionyl chloride (0.2 mL, 2.79 mmol). The reaction mixture was allowed to warm to room temperature overnight, concentrated in vacuum to dryness triturated with hexanes and filtered to afford 2-chloro-6-(chloromethyl)-N-(1-(3,4,5-trimethoxyphenyl)-1H-imidazol-4-yl)thieno[2,3-d]pyrimidin-4-amine (97b) (520 mg, 100% yield) as a solid, which was used as such for next step; $^1$H NMR (300 MHz, DMSO-d$_6$/D$_2$O) δ 11.26 (s, 1H, D$_2$O exchangeable), 8.07 (s, 1H), 8.00 (s, 1H), 7.96 (s, 1H), 7.01 (s, 2H), 5.17 (s, 2H), 3.88 (s, 6H), 3.70 (s, 3H); MS (ES+): 466.4, 468.4 (M+1), (ES−): 464.3, 466.4 (M−1).

Step 3: Preparation of 2-chloro-6-(morpholinomethyl)-N-(1-(3,4,5-trimethoxyphenyl)-1H-imidazol-4-yl)thieno[2,3-d]pyrimidin-4-amine (97c)

To a solution of 2-chloro-6-(chloromethyl)-N-(1-(3,4,5-trimethoxyphenyl)-1H-imidazol-4-yl)thieno[2,3-d]pyrimidin-4-amine (97b) (100 mg, 0.21 mmol) in THF (3 mL) was added morpholine (0.04 mL, 0.43 mmol), DIPEA (0.15 mL, 0.86 mmol) and heated at 50° C. overnight. The reaction mixture was concentrated in vacuum and purified by flash column chromatography to afford 2-chloro-6-(morpholinomethyl)-N-(1-(3,4,5-trimethoxyphenyl)-1H-imidazol-4-yl)thieno[2,3-d]pyrimidin-4-amine (97c); $^1$H NMR (300 MHz, DMSO-d$_6$) δ 10.89 (s, 1H), 8.19 (d, J=1.6 Hz, 1H), 7.88 (d, J=1.6 Hz, 1H), 6.93 (s, 2H), 3.87 (s, 6H), 3.75 (s, 2H), 3.60 (m, 6H), 2.47 (m, 6H); MS (ES+): 539.4 (M+Na), (ES−): 515.4 (M−1).

Step 4: Preparation of (S)-(1-(6-(morpholinomethyl)-4-((1-(3,4,5-trimethoxyphenyl)-1H-imidazol-4-yl)amino)thieno[2,3-d]pyrimidin-2-yl)pyrrolidin-2-yl)methanol (97d)

Compound 97d was prepared from 2-chloro-6-(morpholinomethyl)-N-(1-(3,4,5-trimethoxyphenyl)-1H-imidazol-4-yl)thieno[2,3-d]pyrimidin-4-amine (97c) (50 mg, 0.09 mmol), (S)-pyrrolidin-2-ylmethanol (0.03 mL, 0.26 mmol) in NMP (1 mL) according to the procedure reported in Scheme 2. This gave after workup and purification by reverse phase flash chromatography [(silica gel C-18, 24 g), eluting with eluting with acetonitrile and 0.1% HCl in water] followed by lyophilization (S)-(1-(6-(morpholinomethyl)-4-(1-(3,4,5-trimethoxyphenyl)-1H-imidazol-4-ylamino)thieno[2,3-d]pyrimidin-2-yl)pyrrolidin-2-yl)methanol (97d) (21 mg, 42% yield) HCl salt as a yellow solid; $^1$H NMR (300 MHz, DMSO-d$_6$): δ 11.70 (s, 1H, D$_2$O exchangeable), 11.49 (s, 1H, D$_2$O exchangeable), 8.52 (s, 1H), 8.11 (s, 1H), 8.07 (s, 1H), 8.02 (s, 1H, D$_2$O exchangeable), 7.01 (s, 2H), 4.60 (s, 2H), 4.50 (s, 1H), 4.34 (s, 1H), 3.96 (s, 1H), 3.88 (s, 6H), 3.81 (s, 2H), 3.68 (s, 3H), 3.60-3.41 (m, 4H), 3.40-3.07 (m, 4H), 2.15-1.86 (m, 4H). MS (ES+): 582.6 (M+1); MS (ES−): 616.6 (M+Cl).

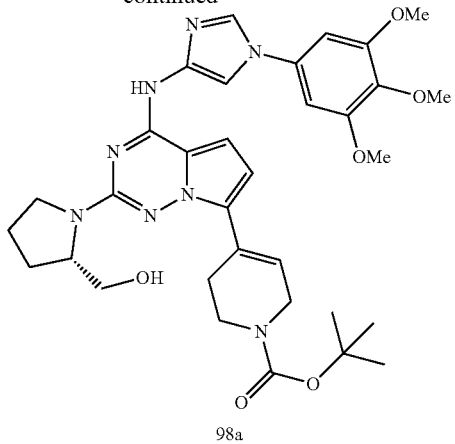

98a

Preparation of (S)-tert-butyl 4-(2-(2-(hydroxymethyl)pyrrolidin-1-yl)-4-(1-(3,4,5-trimethoxyphenyl)-1H-imidazol-4-ylamino)pyrrolo[1,2-f][1,2,4]triazin-7-yl)-5,6-dihydropyridine-1(2H)-carboxylate (98a)

Compound 98a was prepared from (S)-(1-(7-bromo-4-(1-(3,4,5-trimethoxyphenyl)-1H-imidazol-4-ylamino)pyrrolo[1,2-f][1,2,4]triazin-2-yl)pyrrolidin-2-yl)methanol (85b) (150 mg, 0.28 mmol), 1-(tert-butoxycarbonyl)-1,2,3,6-tetrahydropyridin-4-ylboronic acid (188 mg, 0.83 mmol), Pd(dppf)Cl$_2$ (10 mg, 0.01 mmol), sodium carbonate (73 mg, 0.69 mmol) in Dioxane (3 mL) and Water (1 mL) according to the procedure reported in step-3 of Scheme 77. This gave after purification by reverse phase flash column chromatography [(silica gel C-18, 24 g) eluting with 0.1% TFA in acetonitrile and 0.1% TFA in water] followed by conversion to free base using NaHCO$_3$, (S)-tert-butyl 4-(2-(2-(hydroxymethyl)pyrrolidin-1-yl)-4-(1-(3,4,5-trimethoxyphenyl)-1H-imidazol-4-ylamino)pyrrolo[1,2-f][1,2,4]triazin-7-yl)-5,6-dihydropyridine-1(2H)-carboxylate (98a) (70 mg, 38% yield) as a white solid; $^1$H NMR (300 MHz, DMSO-d$_6$): δ 10.53 (s, 1H, D$_2$O exchangeable), 8.24 (d, J=1.5 Hz, 1H), 7.98 (d, J=1.6 Hz, 1H), 7.20 (d, J=4.6 Hz, 2H), 6.96 (s, 2H), 6.50 (d, J=4.6 Hz, 1H), 4.85 (s, 1H, D$_2$O exchangeable), 4.21 (s, 2H), 4.06 (s, 2H), 3.88 (s, 6H), 3.79-3.71 (m, 1H), 3.68 (s, 3H), 3.54 (s, 2H), 3.42 (d, J=6.9 Hz, 1H), 3.28 (s, 1H), 2.54 (s, 2H), 2.09-1.86 (m, 4H), 1.43 (s, 9H). MS (ES+): 669.7 (M+Na).

Scheme 98

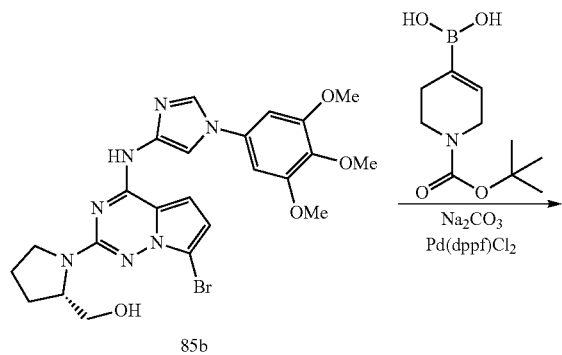

85b

Scheme 99

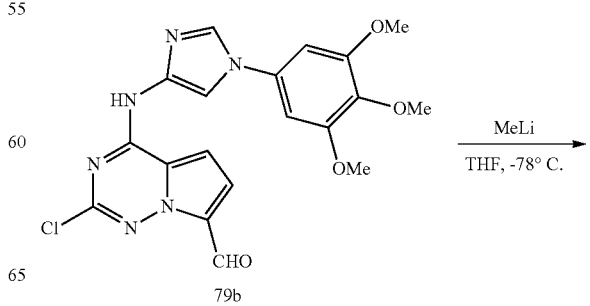

79b

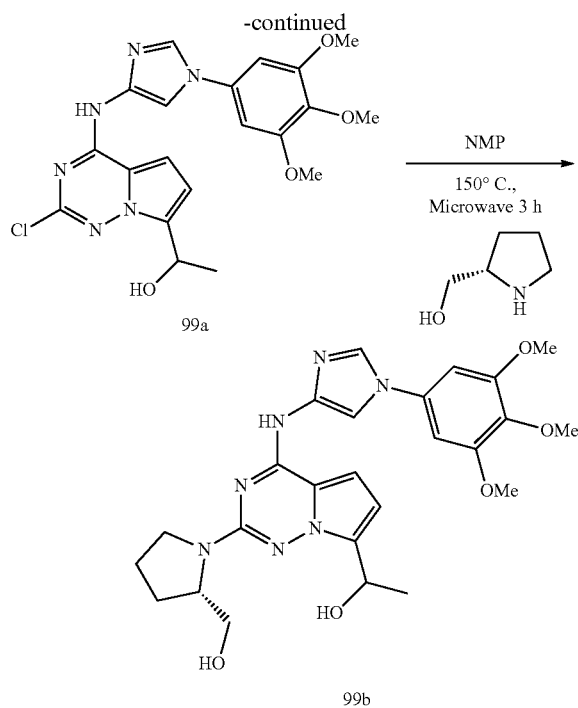

Preparation of 1-(2-((S)-2-(hydroxymethyl)pyrrolidin-1-yl)-4-((1-(3,4,5-trimethoxyphenyl)-1H-imidazol-4-yl)amino)pyrrolo[2,1-f][1,2,4]triazin-7-yl)ethanol (99b)

Step-1: Preparation of 1-(2-chloro-4-((1-(3,4,5-trimethoxyphenyl)-1H-imidazol-4-yl)amino)pyrrolo[2,1-f][1,2,4]triazin-7-yl)ethanol (99a)

Compound 99a was prepared according to the procedure reported in step-2 of Scheme 79 from 2-chloro-4-((1-(3,4,5-trimethoxyphenyl)-1H-imidazol-4-yl)amino)pyrrolo[2,1-f][1,2,4]triazine-7-carbaldehyde (79b) (200 mg, 0.47 mmol) in THF (10 mL) using MeLi (3 M in THF, 0.33 mL, 1.03 mmol). This gave after workup and purification by flash column chromatography (Silica gel 12 g, eluting with MeOH in DCM from 0 to 10%) 1-(2-chloro-4-((1-(3,4,5-trimethoxyphenyl)-1H-imidazol-4-yl)amino)pyrrolo[2,1-f][1,2,4]triazin-7-yl)ethanol (99a) (103 mg, 50% yield) as light yellow solid; $^1$H NMR (300 MHz, DMSO-$d_6$) δ 11.21 (s, 1H), 8.20 (d, J=1.6 Hz, 1H), 7.88 (d, J=1.6 Hz, 1H), 7.36 (d, J=4.5 Hz, 1H), 6.93 (s, 2H), 6.68 (d, J=4.5 Hz, 1H), 5.31 (d, J=5.0 Hz, 1H), 5.16 (p, J=6.4 Hz, 1H), 3.87 (s, 6H), 3.69 (s, 3H), 1.45 (d, J=6.5 Hz, 3H); MS (ES+): 445.5 (M+1), 467.4 (M+Na).

Step 2: Preparation of 1-(2-((S)-2-(hydroxymethyl)pyrrolidin-1-yl)-4-((1-(3,4,5-trimethoxyphenyl)-1H-imidazol-4-yl)amino)pyrrolo[2,1-f][1,2,4]triazin-7-yl)ethanol (99b)

Compound 99b was prepared from 1-(2-chloro-4-((1-(3,4,5-trimethoxyphenyl)-1H-imidazol-4-yl)amino)pyrrolo[2,1-f][1,2,4]triazin-7-yl)ethanol (99a) (35 mg, 0.08 mmol), (S)-pyrrolidin-2-ylmethanol (80 mg, 0.79 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by lyophilization 1-(2-((S)-2-(hydroxymethyl)pyrrolidin-1-yl)-4-((1-(3,4,5-trimethoxyphenyl)-1H-imidazol-4-yl)amino)pyrrolo[2,1-f][1,2,4]triazin-7-yl)ethanol (99b) (25 mg, 51% yield) TFA salt as a yellow solid; $^1$H NMR (300 MHz, DMSO-$d_6$) δ 10.79 (s, 1H, $D_2O$ exchangeable), 9.32 (s, 1H, $D_2O$ exchangeable), 9.20 (s, 1H, $D_2O$ exchangeable), 8.37-8.15 (m, 1H), 8.07-7.90 (m, 1H), 7.25 (dd, J=10.5, 4.6 Hz, 1H), 6.96 (s, 2H), 6.77 (dd, J=16.6, 4.6 Hz, 1H), 5.45-5.21 (m, 1H), 4.37-4.14 (m, 1H), 3.88 (s, 6H), 3.68 (s, 3H), 3.67-3.49 (m, 2H), 3.47-3.18 (m, 3H), 2.17-1.76 (m, 4H), 1.76-1.65 (m, 3H); MS (ES+): 492.5 (M-OH); $^{19}$F NMR (282 MHz, DMSO-$d_6$) δ −74.28; HPLC purity: 92.61%; Elemental Analysis: Calculated for: $C_{25}H_{31}N_7O_5 \cdot 2CF_3COOH \cdot 3H_2O$: C, 42.29; H, 4.77; N, 11.90; Found: C, 42.02; H, 4.79; N, 12.08.

Scheme 100

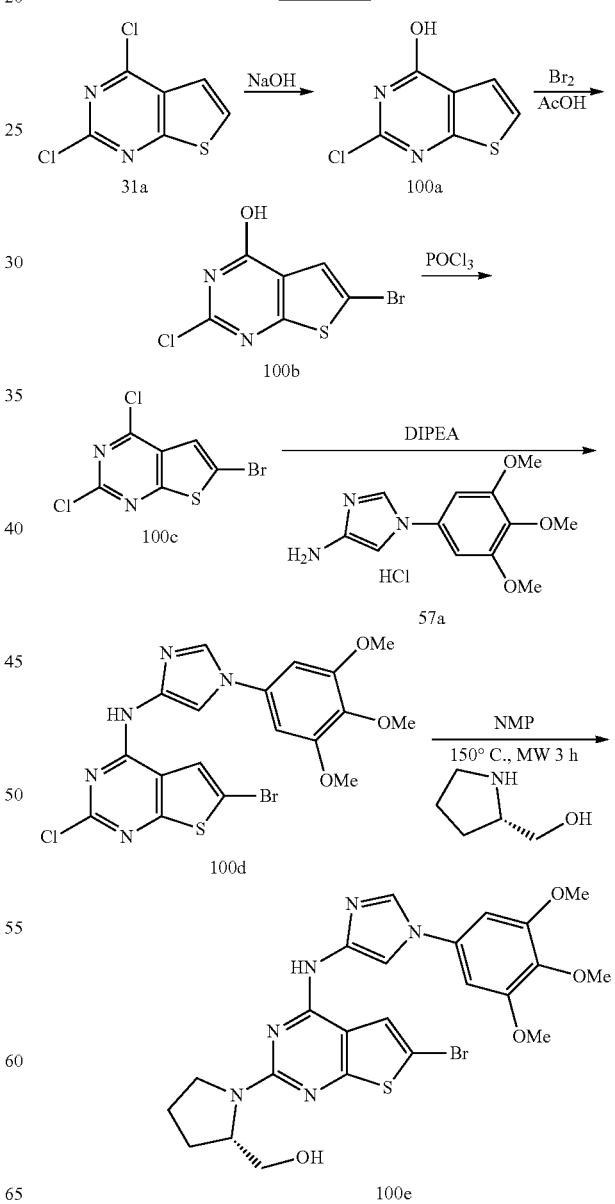

Preparation of (S)-(1-(6-bromo-4-((1-(3,4,5-trimethoxyphenyl)-1H-imidazol-4-yl)amino)thieno[2,3-d]pyrimidin-2-yl)pyrrolidin-2-yl)methanol (100e)

Step 1: Preparation of 2-chlorothieno[2,3-d]pyrimidin-4-ol (100a)

Compound 100a was prepared from 2,4-dichlorothieno[2,3-d]pyrimidine (31a) (4 g, 19.51 mmol) using the procedure reported by Deng, Jifeng et al; in European Journal of Medicinal Chemistry, 46(1), 71-76; 2010. This gave 2-chlorothieno[2,3-d]pyrimidin-4-ol (100a) (2.45 g, 13.13 mmol, 67.3% yield) as a white solid; $^1$H NMR (300 MHz, DMSO-$d_6$) δ 13.54 (s, 1H, D$_2$O exchangeable), 7.61 (d, J=5.8 Hz, 1H), 7.39 (d, J=5.8 Hz, 1H); MS (ES−): 185.1 (M−1).

Step 2: Preparation of 6-bromo-2-chlorothieno[2,3-d]pyrimidin-4-ol (100b)

To a solution of 2-chlorothieno[2,3-d]pyrimidin-4-ol (100a) (2.43 g, 13.02 mmol) in acetic acid (30 mL) was added bromine (2.01 mL, 39.1 mmol) and stirred at room temperature for 10 h. The resulting solid was collected by filtration, washed with water, and dried in vacuum to give 6-bromo-2-chlorothieno[2,3-d]pyrimidin-4-ol (100b) (2.85 g, 82% yield) as a tan solid; $^1$H NMR (300 MHz, DMSO-$d_6$) δ 7.94 (s, 1H).

Step 3: Preparation of 6-bromo-2,4-dichlorothieno[2,3-d]pyrimidine (100c)

A mixture of 6-bromo-2-chlorothieno[2,3-d]pyrimidin-4-ol (100b) (2.84 g, 10.70 mmol) and phosphorus oxychloride (9.97 mL, 107 mmol) was heated at reflux for 30 h. The mixture was concentrated to remove excess phosphorus oxychloride, diluted with ice cold water and extracted with ethyl acetate (2×100 mL). The combined organic layers were washed with water (20 mL), brine (30 mL), dried, filtered and concentrated in vacuum to afford 6-bromo-2,4-dichlorothieno[2,3-d]pyrimidine (100c) (1.4 g, 46% yield) as a white solid; $^1$H NMR (300 MHz, DMSO-$d_6$) δ 7.94 (s, 1H).

Step 4: Preparation of 6-bromo-2-chloro-N-(1-(3,4,5-trimethoxyphenyl)-1H-imidazol-4-yl)thieno[2,3-d]pyrimidin-4-amine (100d)

Compound 100d was prepared according to the procedure reported in Scheme 1 from 6-bromo-2,4-dichlorothieno[2,3-d]pyrimidine (100c) (0.5 g, 1.76 mmol) in 2-Propanol (10 mL) using DIPEA (0.92 mL, 5.28 mmol) and 1-(3,4,5-trimethoxyphenyl)-1H-imidazol-4-amine hydrochloride (57a) (654 mg, 2.29 mmol). This gave 6-bromo-2-chloro-N-(1-(3,4,5-trimethoxyphenyl)-1H-imidazol-4-yl)thieno[2,3-d]pyrimidin-4-amine (100d) (718 mg, 82% yield) as a light purple solid; $^1$H NMR (300 MHz, DMSO-$d_6$) δ 11.04 (s, 1H, D$_2$O exchangeable), 8.21 (d, J=1.6 Hz, 2H), 7.88 (d, J=1.6 Hz, 1H), 6.93 (s, 2H), 3.87 (s, 6H), 3.70 (s, 3H); MS (ES−): 494.2, 496.3 (M−1).

Step 5: Preparation of (S)-(1-(6-bromo-4-((1-(3,4,5-trimethoxyphenyl)-1H-imidazol-4-yl)amino)thieno[2,3-d]pyrimidin-2-yl)pyrrolidin-2-yl)methanol (100e)

Compound 100e was prepared from 6-bromo-2-chloro-N-(1-(3,4,5-trimethoxyphenyl)-1H-imidazol-4-yl)thieno[2,3-d]pyrimidin-4-amine (100d) (300 mg, 0.6 mmol), (S)-pyrrolidin-2-ylmethanol (18 mg, 1.81 mmol) in NMP (1 mL) according to the procedure reported in Scheme 2. This gave after workup by pouring into water and collecting the solid that separated by filtration followed by drying in vacuum (S)-(1-(6-bromo-4-((1-(3,4,5-trimethoxyphenyl)-1H-imidazol-4-yl)amino)thieno[2,3-d]pyrimidin-2-yl)pyrrolidin-2-yl)methanol (100e) (35 mg, 10% yield) as a white solid; $^1$H NMR (300 MHz, DMSO-$d_6$): δ 11.08 (s, 1H, D$_2$O exchangeable), 8.57 (s, 1H), 8.04 (d, J=15.7 Hz, 2H), 7.01 (s, 2H), 4.42 (s, 1H), 4.20 (s, 1H), 3.94 (s, 1H), 3.88 (s, 6H), 3.81 (s, 1H), 3.68 (s, 3H), 3.44 (d, J=9.3 Hz, 1H), 2.12-1.85 (m, 4H). MS (ES+): 561.3, 564.3 (M+1), (ES−) 595.3 597.4 (M+Cl).

Scheme 101

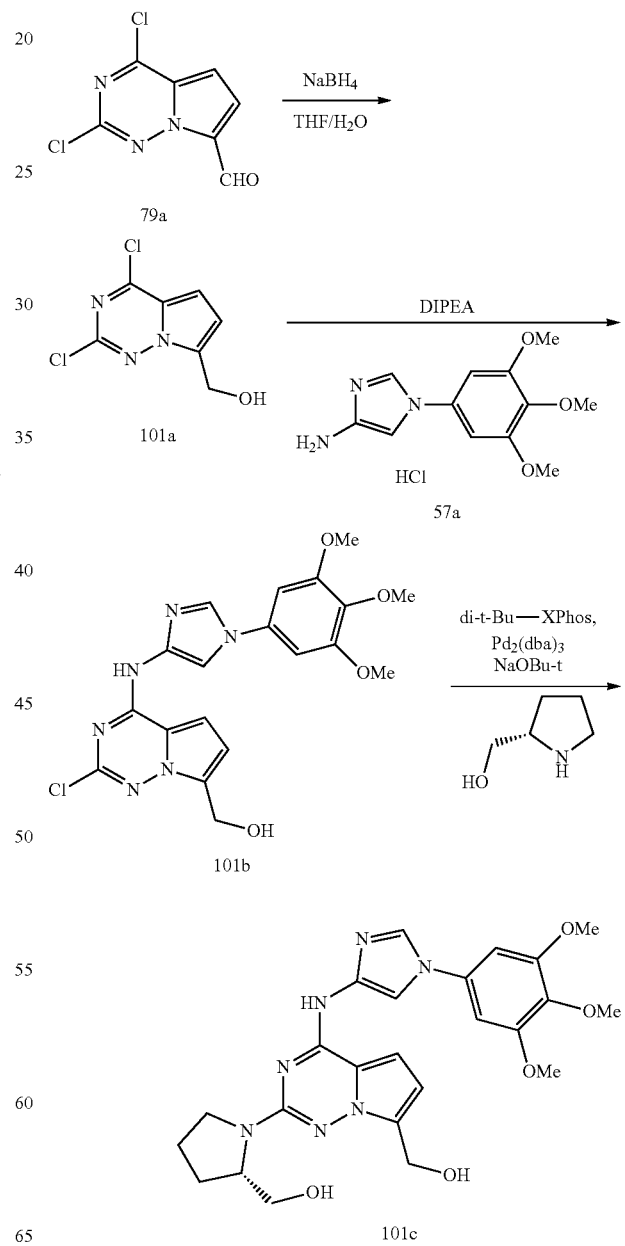

Preparation of (S)-(1-(7-(hydroxymethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (101c)

Step-1: Preparation of (2,4-dichloropyrrolo[2,1-f][1,2,4]triazin-7-yl)methanol (101a)

Compound 101a was prepared from 2,4-dichloropyrrolo[1,2-f][1,2,4]triazine-7-carbaldehyde (79a) (100 mg, 0.46 mmol) according to the procedure reported in step-4 of Scheme 70. This gave after workup (2,4-dichloropyrrolo[1,2-f][1,2,4]triazin-7-yl)methanol (101a) (100 mg, 99% yield) as an oil, which was used in the next reaction without further purification. MS (ES+): 218.1 (M+1).

Step 2: Preparation of (2-chloro-4-((1-(3,4,5-trimethoxyphenyl)-1H-imidazol-4-yl)amino)pyrrolo[2,1-f][1,2,4]triazin-7-yl)methanol (101b)

Compound 101b was prepared according to the procedure reported in Scheme 1 from (2,4-dichloropyrrolo[2,1-f][1,2,4]triazin-7-yl)methanol (101a) (100 mg, 0.46 mmol) in 2-Propanol (10 mL) using DIPEA (0.24 mL, 1.38 mmol) and 1-(3,4,5-trimethoxyphenyl)-1H-imidazol-4-amine hydrochloride (57a) (157 mg, 0.55 mmol). This gave (2-chloro-4-(1-(3,4,5-trimethoxyphenyl)-1H-imidazol-4-ylamino)pyrrolo[1,2-f][1,2,4]triazin-7-yl)methanol (101b) (85 mg, 43% yield) as a pale off-white solid; $^1$H NMR (300 MHz, DMSO-$d_6$) δ 11.24 (s, 1H, $D_2O$ exchangeable), 8.20 (d, J=1.6 Hz, 1H), 7.89 (d, J=1.6 Hz, 1H), 7.37 (d, J=4.3 Hz, 1H), 6.93 (s, 2H), 6.69 (d, J=4.4 Hz, 1H), 5.24 (t, J=5.6 Hz, 1H, $D_2O$ exchangeable), 4.70 (d, J=5.5 Hz, 2H), 3.87 (s, 6H), 3.69 (s, 3H); MS (ES+): 431.4 (M+1), 453.4 (M+Na); MS (ES−): 429.3 (M−1); HPLC: 98.24%.

Step 3: Preparation of (S)-(1-(7-(hydroxymethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (101c)

A slurry of (2-chloro-4-(1-(3,4,5-trimethoxyphenyl)-1H-imidazol-4-ylamino)pyrrolo[1,2-f][1,2,4]triazin-7-yl)methanol (101b) (97 mg, 0.23 mmol), (S)-pyrrolidin-2-ylmethanol (171 mg, 1.69 mmol), di-tert-butyl(2',4',6'-triisopropylbiphenyl-2-yl)phosphine (di-t-Bu-XPhos, 14 mg, 0.034 mmol), Pd$_2$(dba)$_3$ (14 mg, 0.016 mmol), sodium tert-butoxide (162 mg, 1.69 mmol) in PhMe (5 mL) was degassed and placed in a sealed reactor. The reaction was heated at 100° C. for 48 hr, cooled to room temperature, quenched with saturated aqueous NH$_4$Cl and extracted with ethyl acetate (3×20 mL). The organic layers were combined, washed with water, brine, dried, filtered and concentrated in vacuum to dryness. The residue obtained was purified by flash column chromatography (Silica gel 12 g, eluting with MeOH in DCM from 0 to 40%) to afford (S)-(1-(7-(hydroxymethyl)-4-(1-(3,4,5-trimethoxyphenyl)-1H-imidazol-4-ylamino)pyrrolo[1,2-f][1,2,4]triazin-2-yl)pyrrolidin-2-yl)methanol (101c) (12 mg, 11% yield) as a white solid; $^1$H NMR (300 MHz, DMSO-$d_6$) δ 10.47 (s, 1H, $D_2O$ exchangeable), 8.24 (d, J=1.5 Hz, 1H), 7.97 (s, 1H), 7.10 (d, J=4.4 Hz, 1H), 6.96 (s, 2H), 6.37 (d, J=4.4 Hz, 1H), 4.67 (s, 2H), 4.32-4.09 (m, 1H), 3.88 (s, 6H), 3.79-3.70 (m, 1H), 3.68 (s, 3H), 3.67-3.52 (m, 1H), 3.53-3.20 (m, 2H), 2.14-1.75 (m, 4H); MS (ES+): 496.5 (M+1), 518.5 (M+Na); MS (ES−): 494.4 (M−1).

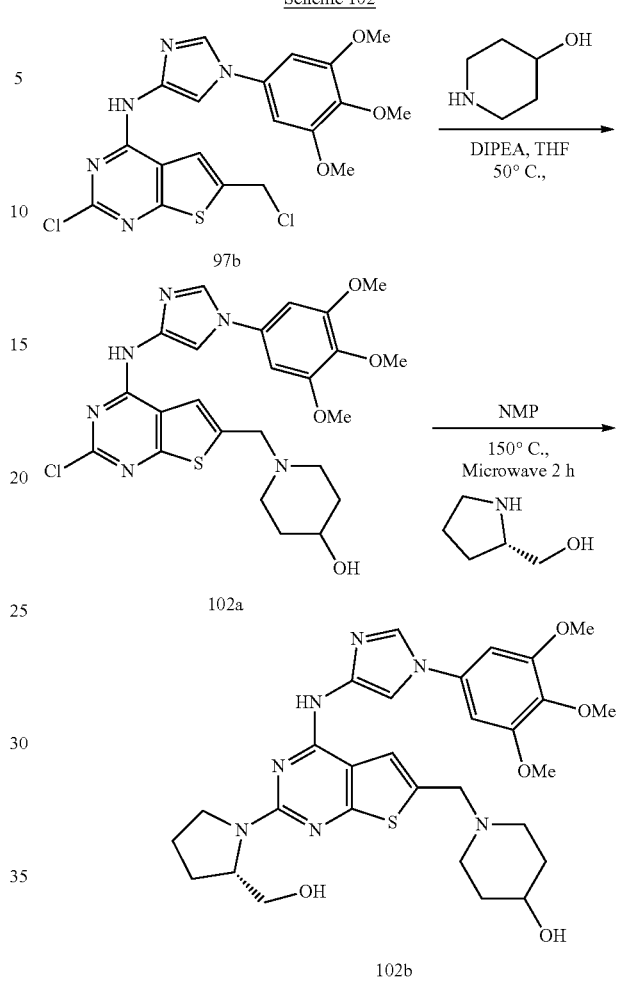

Scheme 102

Preparation of (S)-1-((2-(2-(hydroxymethyl)pyrrolidin-1-yl)-4-((1-(3,4,5-trimethoxyphenyl)-1H-imidazol-4-yl)amino)thieno[2,3-d]pyrimidin-6-yl)methyl)piperidin-4-ol (102b)

Step-1: Preparation of 1-((2-chloro-4-((1-(3,4,5-trimethoxyphenyl)-1H-imidazol-4-yl)amino)thieno[2,3-d]pyrimidin-6-yl)methyl)piperidin-4-ol (102a)

Compound 102a was prepared from 2-chloro-6-(chloromethyl)-N-(1-(3,4,5-trimethoxyphenyl)-1H-imidazol-4-yl)thieno[2,3-d]pyrimidin-4-amine (97b) (100 mg, 0.21 mmol), DIPEA (0.15 mL, 0.86 mmol) and piperidin-4-ol (43 mg, 0.43 mmol) in THF (3 mL) according to the procedure reported in step-3 of Scheme 97. This gave 1-((2-chloro-4-((1-(3,4,5-trimethoxyphenyl)-1H-imidazol-4-yl)amino)thieno[2,3-d]pyrimidin-6-yl)methyl)piperidin-4-ol (102a) (32 mg 28% yield); MS (ES+): 531.5, 533.5 (M+1), (ES−): 529.4, 531.4 (M−1).

Step-2: Preparation of (S)-1-((2-(2-(hydroxymethyl)pyrrolidin-1-yl)-4-((1-(3,4,5-trimethoxyphenyl)-1H-imidazol-4-yl)amino)thieno[2,3-d]pyrimidin-6-yl)methyl)piperidin-4-ol (102b)

Compound 102b was prepared from 1-((2-chloro-4-(1-(3,4,5-trimethoxyphenyl)-1H-imidazol-4-ylamino)thieno[2,3- d]pyrimidin-6-yl)methyl)piperidin-4-ol (102a) (0.03 g, 0.06 mmol), (S)-pyrrolidin-2-ylmethanol (0.02 mL, 0.18 mmol) in NMP (1 mL) according to the procedure reported in Scheme 2. This gave after workup and purification by reverse phase flash chromatography [(silica gel C-18, 24 g), eluting with eluting with acetonitrile and 0.1% HCl water] followed by lyophilization (S)-1-((2-(2-(hydroxymethyl) pyrrolidin-1-yl)-4-((1-(3,4,5-trimethoxyphenyl)-1H-imidazol-4-yl)amino)thieno[2,3-d]pyrimidin-6-yl)methyl)piperidin-4-ol (102b) (13 mg, 36% yield) HCl salt as a solid; $^1$H NMR (300 MHz, DMSO-d$_6$): δ 11.40 (s, 1H), 10.97 (s, 1H), 8.49 (s, 1H), 8.19-7.88 (m, 2H), 7.00 (s, 2H), 4.65-4.41 (m, 2H), 4.40-3.91 (m, 6H), 3.88 (s, 6H), 3.68 (s, 3H), 3.64-2.87 (m, 4H), 2.15-1.86 (m, 7H), 1.85-1.60 (m, 1H). MS (ES+): 596.6 (M+1); MS (ES−): 630.6 (M+Cl).

(2.06 mL, 15.87 mmol) and 1-(3,4,5-trimethoxyphenyl)-1H-imidazol-4-ylamine hydrochloride (57a) (1.81 g, 6.34 mmol). This gave after work up (2-chloro-furo[3,2-d]pyrimidin-4-yl)-[1-(3,4,5-trimethoxy-phenyl)-1H-imidazol-4-yl]-amine (103a) (1.0 g, 47%) as an off-white solid; MS (ES+): 402.0 (M+1); MS (ES−): 400.0 (M+1).

Step-2: Preparation of (S)-(1-(4-((1-(3,4,5-trimethoxyphenyl)-1H-imidazol-4-yl)amino)furo[3,2-d]pyrimidin-2-yl)pyrrolidin-2-yl)methanol (103b)

Compound 103b was prepared according to the procedure reported in step-2 of Scheme 76 from (2-chloro-furo[3,2-d] pyrimidin-4-yl)-[1-(3,4,5-trimethoxy-phenyl)-1H-imidazol-4-yl]-amine (103a) (300 mg, 0.75 mmol) and (S)-pyrrolidin-2-ylmethanol (0.76 g, 7.5 mmol) in NMP (20 mL). This gave after workup and purification by flash chromatography (silica gel, eluting with 0-10% methanol in ethyl acetate) (S)-(1-(4-((1-(3,4,5-trimethoxyphenyl)-1H-imidazol-4-yl) amino)furo[3,2-d]pyrimidin-2-yl)pyrrolidin-2-yl)methanol (103b) (100 mg, 29%) free base as a white solid. The free base was re-purified by reverse phase flash column chromatography [(silica gel C-18 column, 24 g) eluting with acetonitrile and 0.1% HCl water (0-50%)] followed by lyophilization to afford (S)-(1-(4-((1-(3,4,5-trimethoxyphenyl)-1H-imidazol-4-yl)amino)furo[3,2-d]pyrimidin-2-yl) pyrrolidin-2-yl)methanol (103b) (25 mgs) HCl salt as a light yellow solid; $^1$H NMR (300 MHz, DMSO-d$_6$): δ 13.40 (s, 1H), 11.91 (s, 1H), 8.54 (s, 1H), 8.35 (s, 1H), 8.04 (s, 1H), 7.01 (d, J=10.6 Hz, 3H), 4.44 (s, 1H), 3.87 (d, J=3.8 Hz, 6H), 3.75 (s, 1H), 3.68 (d, J=3.7 Hz, 3H), 3.58-3.34 (m, 3H), 2.02 (s, 4H). MS (ES+): 467.5 (M+1), 489.5 (M+Na); MS (ES−): 501.5 (M+Cl); HPLC purity: 98.60%.

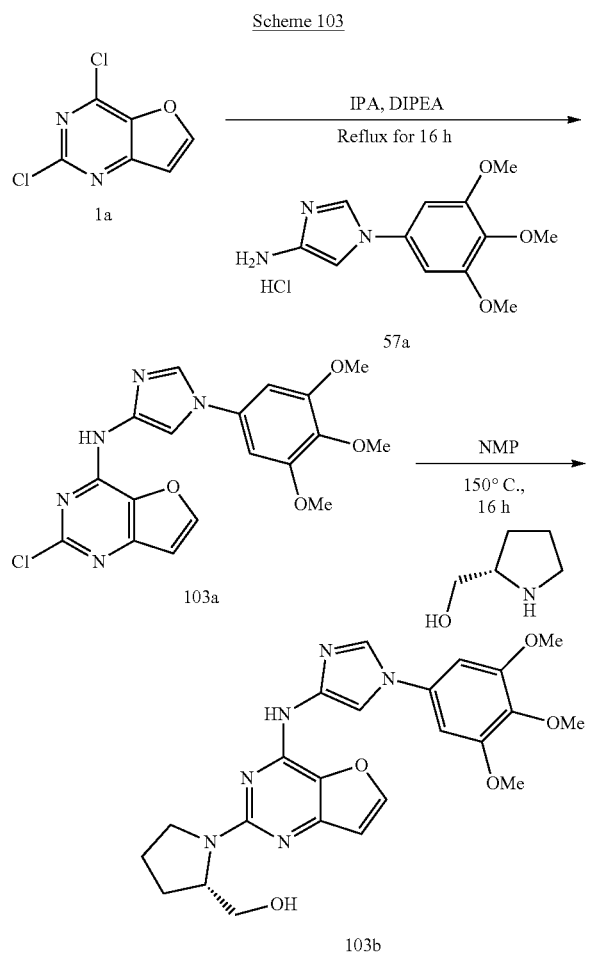

Scheme 103

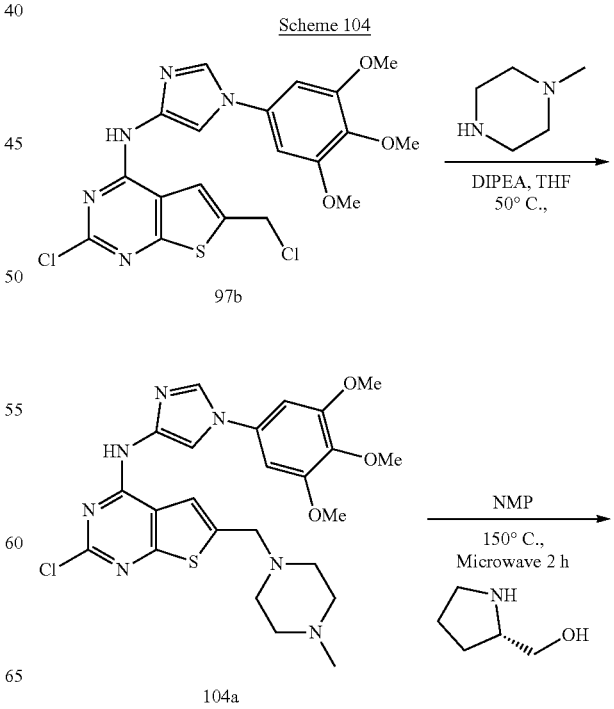

Scheme 104

Preparation of (S)-(1-(4-((1-(3,4,5-trimethoxyphenyl)-1H-imidazol-4-yl)amino)furo[3,2-d]pyrimidin-2-yl)pyrrolidin-2-yl)methanol (103b)

Step-1: Preparation of(2-chloro-furo[3,2-d]pyrimidin-4-yl)-[1-(3,4,5-trimethoxy-phenyl)-1H-imidazol-4-yl]-amine (103a)

Compound 103a was prepared according to the procedure reported in Scheme 1 from 2,4-dichloro-furo[3,2-d]pyrimidine (1a) (1.0 g, 5.29 mmol) in IPA (30 mL) using DIPEA

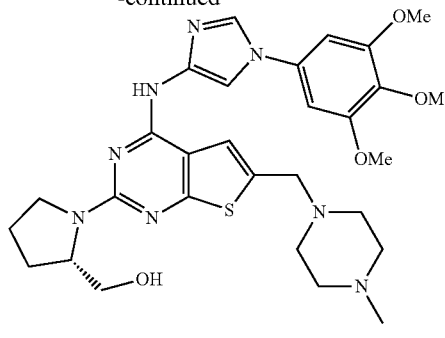

104b

Preparation of (S)-(1-(6-((4-methylpiperazin-1-yl)methyl)-4-((1-(3,4,5-trimethoxyphenyl)-1H-imidazol-4-yl)amino)thieno[2,3-d]pyrimidin-2-yl)pyrrolidin-2-yl)methanol (104b)

Step-1: Preparation of 2-chloro-6-((4-methylpiperazin-1-yl)methyl)-N-(1-(3,4,5-trimethoxyphenyl)-1H-imidazol-4-yl)thieno[2,3-d]pyrimidin-4-amine (104a)

Compound 104a was prepared from 2-chloro-6-(chloromethyl)-N-(1-(3,4,5-trimethoxyphenyl)-1H-imidazol-4-yl)thieno[2,3-d]pyrimidin-4-amine (97b) (100 mg, 0.21 mmol), DIPEA (0.15 mL, 0.86 mmol) and 1-methylpiperazine (0.048 mL, 0.43 mmol) in THF (3 mL) according to the procedure reported in step-3 of Scheme 97. This gave 2-chloro-6-((4-methylpiperazin-1-yl)methyl)-N-(1-(3,4,5-trimethoxyphenyl)-1H-imidazol-4-yl)thieno[2,3-d]pyrimidin-4-amine (104a) (32 mg, 28% yield); MS (ES+): 530.5, 532.5 (M+1), (ES−): 528.4 (M−1), 564.4, 566.4 (M+Cl).

Step-2: Preparation of (S)-(1-(6-((4-methylpiperazin-1-yl)methyl)-4-((1-(3,4,5-trimethoxyphenyl)-1H-imidazol-4-yl)amino)thieno[2,3-d]pyrimidin-2-yl)pyrrolidin-2-yl)methanol (104b)

Compound 104b was prepared from 2-chloro-6-((4-methylpiperazin-1-yl)methyl)-N-(1-(3,4,5-trimethoxyphenyl)-1H-imidazol-4-yl)thieno[2,3-d]pyrimidin-4-amine (104a) (0.05 g, 0.09 mmol), (S)-pyrrolidin-2-ylmethanol (0.03 mL, 0.26 mmol) in NMP (1 mL) according to the procedure reported in Scheme 2. This gave after workup and purification by reverse phase flash chromatography [(silica gel C-18, 24 g), eluting with eluting with acetonitrile and 0.1% HCl water] followed by lyophilization (S)-(1-(6-((4-methylpiperazin-1-yl)methyl)-4-((1-(3,4,5-trimethoxyphenyl)-1H-imidazol-4-yl)amino)thieno[2,3-d]pyrimidin-2-yl)pyrrolidin-2-yl)methanol (104b) (10 mg, 24% yield) HCl salt as a tan colored solid; $^1$H NMR (300 MHz, DMSO-$d_6$): δ 11.14 (s, 1H), 8.43 (s, 1H), 8.07-7.85 (m, 2H), 6.98 (d, J=4.6 Hz, 2H), 4.48 (s, 1H), 4.27 (s, 2H), 3.94 (s, 1H), 3.88 (s, 6H), 3.86 (s, 2H), 3.81 (s, 1H), 3.68 (s, 3H), 3.61-3.40 (m, 4H), 3.40-3.12 (m, 4H), 2.79 (s, 3H), 2.11-1.85 (m, 4H). MS (ES+): 595.6 (M+1).

Scheme 105

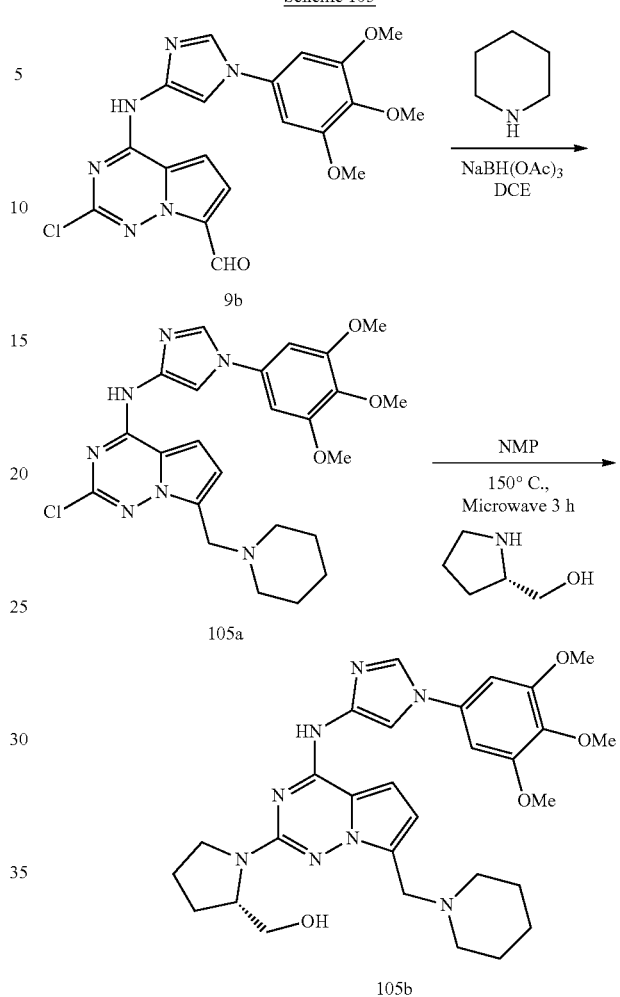

Preparation of (S)-(1-(7-(piperidin-1-ylmethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (105b)

Step-1: Preparation of 2-chloro-7-(piperidin-1-ylmethyl)-N-(1-(3,4,5-trimethoxyphenyl)-1H-imidazol-4-yl)pyrrolo[2,1-f][1,2,4]triazin-4-amine (105a)

To a solution of 2-chloro-4-(1-(3,4,5-trimethoxyphenyl)-1H-imidazol-4-ylamino)pyrrolo[1,2-f][1,2,4]triazine-7-carbaldehyde (79b) (100 mg, 0.23 mmol) in dichloroethane (5 mL) was added piperidine (0.025 mL, 0.26 mmol) and acetic acid (0.03 mL). To this suspension was added NaBH(OAc)$_3$ (64 mg, 0.3 mmol) and the reaction was stirred for 8 h. An additional amount of NaBH(OAc)$_3$ (64 mg, 0.3) was added and the reaction was allowed to stir for 8 h. The reaction was quenched with 1 N NaOH (2 mL), the organic layer was separated and the aqueous layer was extracted with CH$_2$Cl$_2$ (3×10 mL). The combined organic layers were dried, filtered and concentrated in vacuum. The crude product was purified by flash column chromatography (Silica gel 12 g, eluting with MeOH in DCM from 0% to 10%) to afford 2-chloro-7-(piperidin-1-ylmethyl)-N-(1-(3,4,5-trimethoxyphenyl)-1H-imidazol-4-yl)pyrrolo[2,1-f][1,2,4]triazin-4-amine (105a) (43 mg, 37% yield) as a pale off-white solid; $^1$H NMR (300 MHz, Chloroform-d) δ 10.56 (s, 1H), 7.95 (s, 1H), 7.66 (s, 1H), 7.07-6.81 (m, 1H), 6.84-6.40 (m, 3H), 4.10-3.73 (m, 11H), 2.61-2.41 (m, 4H), 1.67-1.49 (m, 4H), 1.48-1.33 (m, 2H); MS (ES+): 498.5 (M+1); MS (ES−): 496.5 (M−1).

Step 2: Preparation of (S)-(1-(7-(piperidin-1-ylmethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (105b)

Compound 105b was prepared from 2-chloro-7-(piperidin-1-ylmethyl)-N-(1-(3,4,5-trimethoxyphenyl)-1H-imidazol-4-yl)pyrrolo[2,1-f][1,2,4]triazin-4-amine (105a) (43 mg, 0.09 mmol), (S)-pyrrolidin-2-ylmethanol (87 mg, 0.86 mmol) in NMP (1 mL) according to the procedure reported in Scheme 2. This gave after workup and purification by flash chromatography (Silica gel 4 g, eluting with MeOH in DCM from 0% to 10%) (S)-(1-(7-(piperidin-1-ylmethyl)-4-(1-(3,4,5-trimethoxyphenyl)-1H-imidazol-4-ylamino)pyrrolo[1,2-f][1,2,4]triazin-2-yl)pyrrolidin-2-yl)methanol (105b) (6 mg, 13% yield) as a white solid; $^1$H NMR (300 MHz, Methanol-d$_4$) δ 7.98 (d, J=1.6 Hz, 1H), 7.93 (d, J=1.6 Hz, 1H), 6.88-6.83 (m, 3H), 6.45 (d, J=4.5 Hz, 1H), 4.33-4.16 (m, 1H), 3.91 (s, 6H), 3.87 (s, 2H), 3.88-3.78 (m, 1H), 3.79 (s, 3H), 3.75-3.50 (m, 2H), 3.40-3.25 (m, 1H), 2.64-2.45 (m, 4H), 2.14-1.86 (m, 4H), 1.72-1.53 (m, 4H), 1.49-1.36 (m, 2H); MS (ES+): 563.6 (M+1), 585.6 (M+Na). Hydrochloride salt of compound 105b was obtained by purification of crude reaction mixture from step-2 above by reverse phase flash chromatography [(silica gel C-18, 24 g) eluting with acetonitrile and 0.1% HCl in water] followed by lyophilization as a yellow solid. $^1$H NMR (300 MHz, DMSO-d$_6$): δ 10.90 (s, 1H), 10.36 (s, 1H), 8.46 (s, 1H), 8.01 (s, 1H), 7.23 (d, J=4.6 Hz, 1H), 6.99 (s, 2H), 6.72 (d, J=4.5 Hz, 1H), 4.49 (s, 2H), 4.29-4.14 (m, 1H), 3.88 (s, 6H), 3.84-3.26 (m, 9H), 2.86 (d, J=11.4 Hz, 2H), 2.13-1.16 (m, 10H). MS (ES+): 563.3 (M+1); MS (ES−): 597.4 (M+Cl). HPLC purity: 95.10%.

Scheme 106

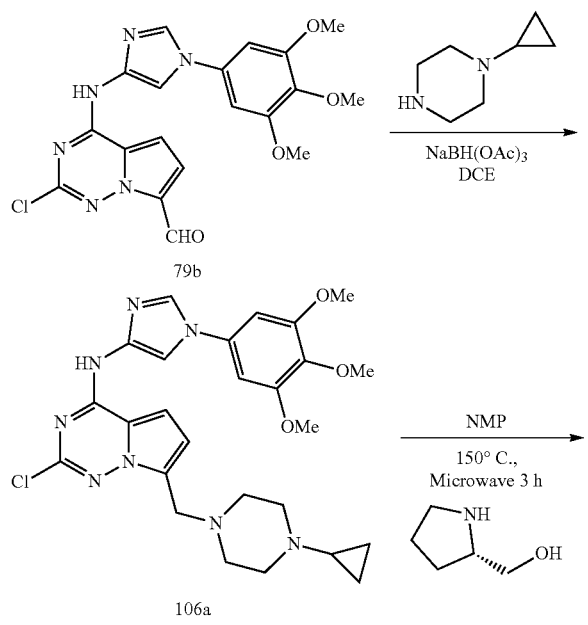

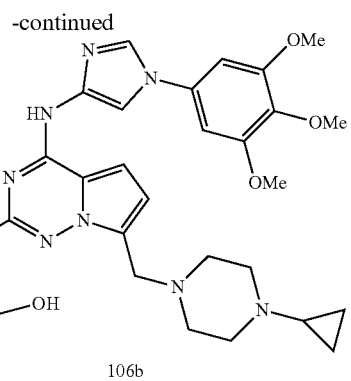

106b

Preparation of (S)-(1-(7-((4-cyclopropylpiperazin-1-yl)methyl)-4-((1-(3,4,5-trimethoxyphenyl)-1H-imidazol-4-yl)amino)pyrrolo[2,1-f][1,2,4]triazin-2-yl) pyrrolidin-2-yl)methanol (106b)

Step-1: Preparation of 2-chloro-7-((4-cyclopropylpiperazin-1-yl)methyl)-N-(1-(3,4,5-trimethoxyphenyl)-1H-imidazol-4-yl)pyrrolo[2,1-f][1,2,4]triazin-4-amine (106a)

Compound 106a was prepared according to the procedure reported for reductive amination in step-1 of Scheme 105 from 2-chloro-4-(1-(3,4,5-trimethoxyphenyl)-1H-imidazol-4-ylamino)pyrrolo[1,2-f][1,2,4]triazine-7-carbaldehyde (79b) (100 mg, 0.23 mmol) in dichloroethane (3 mL) using 1-cyclopropylpiperazine (44 mg, 0.35 mmol), acetic acid (0.03 mL) and NaBH(OAc)$_3$ (74 mg, 0.35 mmol). This gave after workup and purification by flash column chromatography (Silica gel 12 g, eluting with DMA-80 in DCM from 0% to 10%) to afford 2-chloro-7-((4-cyclopropylpiperazin-1-yl)methyl)-N-(1-(3,4,5-trimethoxyphenyl)-1H-imidazol-4-yl)pyrrolo[2,1-f][1,2,4]triazin-4-amine (106a) (46 mg, 37% yield) as a solid; $^1$H NMR (300 MHz, Chloroform-d) δ 10.64 (s, 1H), 7.95 (s, 1H), 7.65 (s, 1H), 6.91 (d, J=4.5 Hz, 1H), 6.66 (s, 2H), 6.61 (d, J=4.5 Hz, 1H), 4.18-3.61 (m, 11H), 3.36-2.11 (m, 8H), 1.68-1.47 (m, 1H), 0.62-0.15 (m, 4H); MS (ES+): 539.5 (M+1), 561.5 (M+Na); MS (ES−): 537.5 (M−1).

Step 2: Preparation of (S)-(1-(7-((4-cyclopropylpiperazin-1-yl)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (106b)

Compound 106b was prepared from 2-chloro-7-((4-cyclopropylpiperazin-1-yl)methyl)-N-(1-(3,4,5-trimethoxyphenyl)-1H-imidazol-4-yl)pyrrolo[2,1-f][1,2,4]triazin-4-amine (106a) (46 mg, 0.09 mmol), (S)-pyrrolidin-2-ylmethanol (86 mg, 0.85 mmol) in NMP (1 mL) according to the procedure reported in Scheme 2. This gave after workup and purification by reverse phase flash chromatography [(silica gel C-18, 24 g) eluting with 0.1% TFA of acetonitrile and 0.1% TFA water] followed by lyophilization (S)-(1-(7-((4-cyclopropylpiperazin-1-yl)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (106b) (14 mg, 27% yield) as a solid; $^1$H NMR (300 MHz, DMSO-d$_6$) δ 10.47 (s, 1H, D$_2$O exchangeable), 8.24 (d, J=1.5 Hz, 1H), 7.97 (d, J=1.6 Hz, 1H), 7.13 (d, J=4.4 Hz, 1H), 6.95 (s, 2H), 6.33 (d, J=4.5 Hz, 1H), 4.89-4.79 (m, 1H, D$_2$O exchangeable), 4.26-4.08 (m, 1H), 3.87 (s, 6H), 3.85-3.66 (m, 3H), 3.68 (s, 3H), 3.64-3.54 (m, 1H), 3.52-3.38 (m, 2H), 2.67-2.25 (m, 8H), 2.11-1.81 (m, 4H), 1.65-1.49 (m, 1H), 0.37 (s, 2H), 0.28-0.18 (m, 2H); MS (ES+): 604.7 (M+1), 626.6 (M+Na); Hydrochloride salt of compound 106b was obtained by purification of crude reaction mixture from step-2 above by reverse phase flash chromatography [(silica gel C-18, 24 g) eluting with acetonitrile and 0.1% HCl water] followed by lyophilization as a yellow solid. $^1$H NMR (300 MHz, DMSO-d$_6$): δ 10.49 (s, 1H), 8.23 (s, 1H), 7.97 (s, 1H), 7.13 (d, J=4.4 Hz, 1H), 6.95 (s, 2H), 6.34 (d, J=4.2 Hz, 1H), 4.83 (s, 1H), 4.19 (s, 1H), 3.87 (s, 6H), 3.79 (s, 2H), 3.68 (s, 3H), 3.58 (s, 1H), 3.52-3.42 (m, 2H), 3.42-3.20 (m, 9H), 2.11-1.71 (m, 4H), 1.67-1.40 (m, 1H), 0.44-0.13 (m, 4H). MS (ES-): 602.6 (M−1). HPLC purity: 93.61%.

dropyridine-1(2H)-carboxylate (98a) (0.06 g, 0.05 mmol) in DCM (5 mL) was added 2,2,2-trifluoroacetic acid (0.04 mL, 0.54 mmol) and stirred at room temperature overnight. The reaction mixture was diluted with EtOAc (50 mL), washed with water (3×), brine, dried, filtered and concentrated in vacuum. The residue was purified by reverse phase flash column chromatography [(silica gel C-18, 24 g) eluting with acetonitrile and 0.1% HCl water] and lyophilized to afford (S)-(1-(7-(1,2,3,6-tetrahydropyridin-4-yl)-4-(1-(3,4,5-trimethoxyphenyl)-1H-imidazol-4-ylamino)pyrrolo[1,2-f][1,2,4]triazin-2-yl)pyrrolidin-2-yl)methanol (107a) (8 mg, 27% yield) as a HCl salt; $^1$H NMR (300 MHz, DMSO-d$_6$) δ 10.68 (s, 1H), 9.16 (s, 2H), 8.37 (s, 1H), 8.01 (s, 1H), 7.29 (s, 1H), 7.22 (d, J=4.6 Hz, 1H), 6.98 (s, 2H), 6.58 (d, J=4.7 Hz, 1H), 4.20 (s, 1H), 4.00-3.25 (m, 17H), 2.83-2.68 (m, 2H), 2.11-1.83 (m, 4H); MS (ES+): 547.6. HPLC purity: 96.94%.

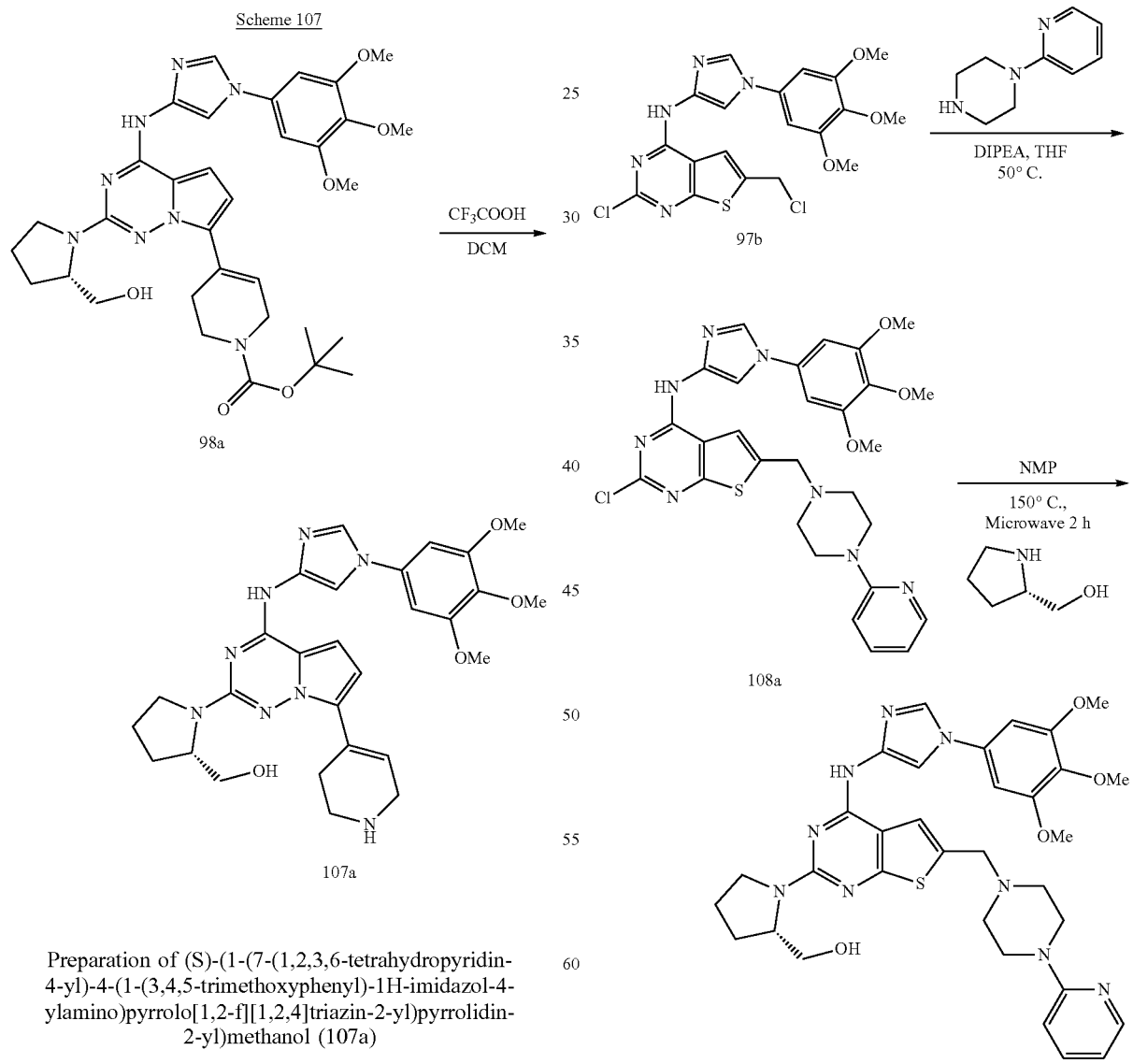

Preparation of (S)-(1-(7-(1,2,3,6-tetrahydropyridin-4-yl)-4-(1-(3,4,5-trimethoxyphenyl)-1H-imidazol-4-ylamino)pyrrolo[1,2-f][1,2,4]triazin-2-yl)pyrrolidin-2-yl)methanol (107a)

To a solution of (S)-tert-butyl 4-(2-(2-(hydroxymethyl) pyrrolidin-1-yl)-4-(1-(3,4,5-trimethoxyphenyl)-1H-imidazol-4-ylamino)pyrrolo[1,2-f][1,2,4]triazin-7-yl)-5,6-dihy-

Preparation of (S)-(1-(6-((4-(pyridin-2-yl)piperazin-1-yl)methyl)-4-((1-(3,4,5-trimethoxyphenyl)-1H-imidazol-4-yl)amino)thieno[2,3-d]pyrimidin-2-yl)pyrrolidin-2-yl)methanol (108b)

Step-1: Preparation of 2-chloro-6-((4-(pyridin-2-yl)piperazin-1-yl)methyl)-N-(1-(3,4,5-trimethoxyphenyl)-1H-imidazol-4-yl)thieno[2,3-d]pyrimidin-4-amine (108a)

Compound 108a was prepared from 2-chloro-6-(chloromethyl)-N-(1-(3,4,5-trimethoxyphenyl)-1H-imidazol-4-yl)thieno[2,3-d]pyrimidin-4-amine (97b) (100 mg, 0.21 mmol), DIPEA (0.15 mL, 0.86 mmol) and 1-(pyridin-2-yl)piperazine (0.065 mL, 0.43 mmol) in THF (3 mL) according to the procedure reported in step-3 of Scheme 97. This gave 2-chloro-6-((4-(pyridin-2-yl)piperazin-1-yl)methyl)-N-(1-(3,4,5-trimethoxyphenyl)-1H-imidazol-4-yl)thieno[2,3-d]pyrimidin-4-amine (108a) (60 mgs, 47%) as a solid. MS (ES+): 593.5 (M+1), (ES−): 591.4 (M−1), 627.5, 629.5 (M+Cl).

Step-2: Preparation of (S)-(1-(6-((4-(pyridin-2-yl)piperazin-1-yl)methyl)-4-((1-(3,4,5-trimethoxyphenyl)-1H-imidazol-4-yl)amino)thieno[2,3-d]pyrimidin-2-yl)pyrrolidin-2-yl)methanol (108b)

Compound 108b was prepared from 2-chloro-6-((4-(pyridin-2-yl)piperazin-1-yl)methyl)-N-(1-(3,4,5-trimethoxyphenyl)-1H-imidazol-4-yl)thieno[2,3-d]pyrimidin-4-amine (108a) (0.06 g, 0.1 mmol), (S)-pyrrolidin-2-ylmethanol (0.03 mL, 0.3 mmol) in NMP (1 mL) according to the procedure reported in Scheme 2. This gave after workup and purification by reverse phase flash chromatography [(silica gel 18, 24 g), eluting with eluting with acetonitrile and 0.1% HCl water] followed by lyophilization (S)-(1-(6-((4-(pyridin-2-yl)piperazin-1-yl)methyl)-4-((1-(3,4,5-trimethoxyphenyl)-1H-imidazol-4-yl)amino)thieno[2,3-d]pyrimidin-2-yl)pyrrolidin-2-yl)methanol (108b) (10 mg, 15% yield) HCl salt as a white solid; $^1$H NMR (300 MHz, DMSO-$d_6$) δ 12.16 (s, 1H), 11.60 (s, 1H), 8.58 (s, 1H), 8.19-7.93 (m, 5H), 7.37 (d, J=8.9 Hz, 1H), 7.00 (d, J=8.5 Hz, 2H), 4.74-4.30 (m, 4H), 3.88 (s, 6H), 3.81-3.19 (m, 13H), 2.16-1.89 (m, 4H). MS (ES+): 658.5; MS (ES−): 692.5 (M+Cl). HPLC purity: 97.78%.

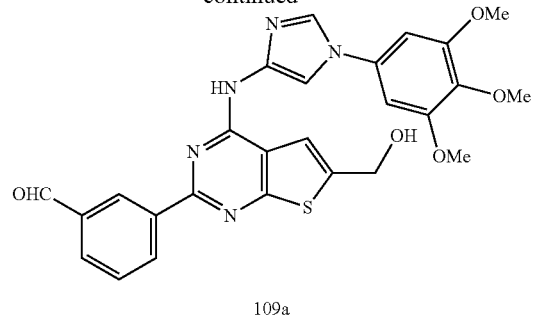

109a

Preparation of 3-(6-(hydroxymethyl)-4-((1-(3,4,5-trimethoxyphenyl)-1H-imidazol-4-yl)amino)thieno[2,3-d]pyrimidin-2-yl)benzaldehyde (109a)

Compound 109a was prepared from (2-chloro-4-(1-(3,4,5-trimethoxyphenyl)-1H-imidazol-4-ylamino)thieno[2,3-d]pyrimidin-6-yl)methanol (97a) (0.2 g, 0.44 mmol), using 3-formylphenylboronic acid (0.1 g, 0.67 mmol), PdCl$_2$(dppf) (65 mg, 0.09 mmol), potassium carbonate (185 mg, 1.34 mmol) in 1,4-Dioxane (10 mL) and Water (1 mL) according to the procedure reported in step-3 of Scheme 77. This gave after workup, purification by flash column chromatography [(silica gel, 12 g) eluting with DMA 80 in dichloromethane] 3-(6-(hydroxymethyl)-4-((1-(3,4,5-trimethoxyphenyl)-1H-imidazol-4-yl)amino)thieno[2,3-d]pyrimidin-2-yl)benzaldehyde (109a) (134 mg, 58% yield) as a yellow solid; $^1$H NMR (300 MHz, DMSO-$d_6$) δ 10.63 (s, 1H, D$_2$O exchangeable), 10.14 (s, 1H), 8.95 (d, J=1.9 Hz, 1H), 8.76 (d, J=7.8 Hz, 1H), 8.28 (d, J=1.6 Hz, 1H), 8.18 (d, J=1.6 Hz, 1H), 8.03 (d, J=7.6 Hz, 1H), 7.94 (s, 1H), 7.73 (t, J=7.7 Hz, 1H), 7.03 (s, 2H), 5.84 (s, 1H, D$_2$O exchangeable), 4.76 (s, 2H), 3.90 (s, 6H), 3.71 (s, 3H); MS (ES+): 518.5 (M+1), 540.3 (M+Na), (ES−): 516.5 (M-1).

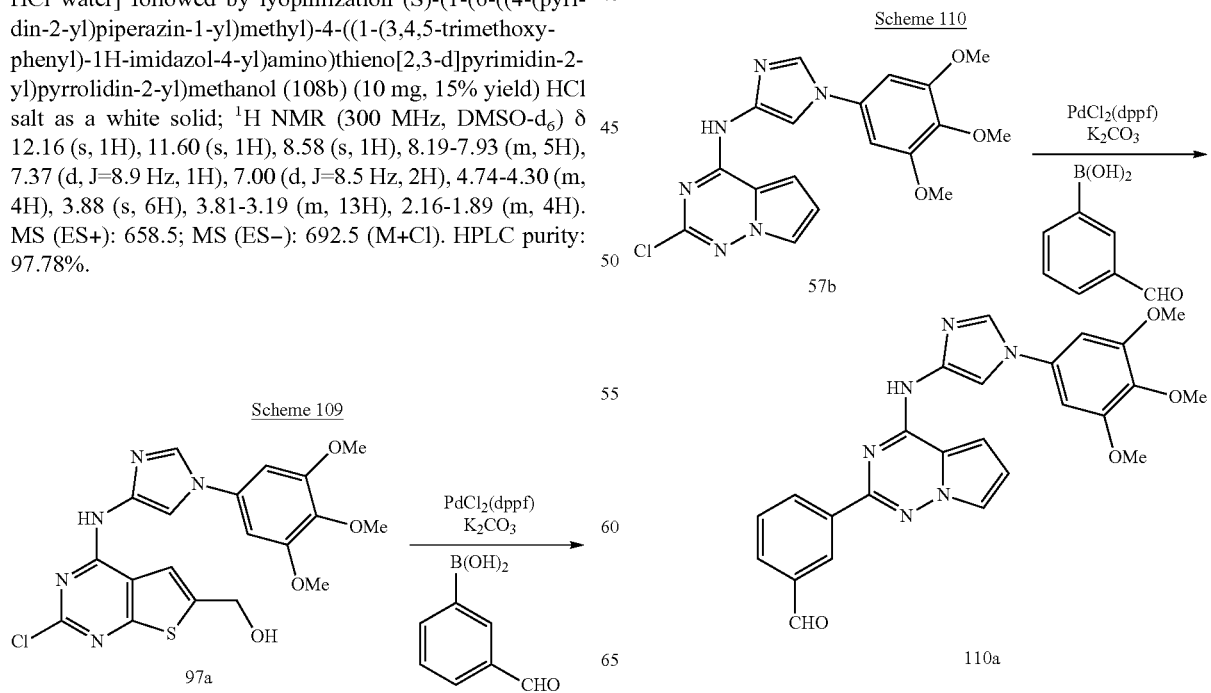

Preparation of 3-(4-((1-(3,4,5-trimethoxyphenyl)-1H-imidazol-4-yl)amino)pyrrolo[2,1-f][1,2,4]triazin-2-yl)benzaldehyde (110a)

Compound 110a was prepared from 2-chloro-N-(1-(3,4,5-trimethoxyphenyl)-1H-imidazol-4-yl)pyrrolo[2,1-f][1,2,4]triazin-4-amine (57b) (0.2 g, 0.5 mmol), using 3-formylphenylboronic acid (112 mg, 0.75 mmol), PdCl$_2$(dppf) (73 mg, 0.1 mmol), potassium carbonate (207 mg, 1.5 mmol) in 1,4-Dioxane (10 mL) and Water (1 mL) according to the procedure reported in step-3 of Scheme 77. This gave after workup, purification by flash column chromatography [(silica gel, 12 g) eluting with DMA 80 in dichloromethane] 3-(4-((1-(3,4,5-trimethoxyphenyl)-1H-imidazol-4-yl)amino)pyrrolo[2,1-f][1,2,4]triazin-2-yl)benzaldehyde (110a) (45 mg, 19% yield) as a white solid; $^1$H NMR (300 MHz, DMSO-d$_6$) δ 11.02 (s, 1H, D$_2$O exchangeable), 10.13 (s, 1H), 8.82 (t, J=1.7 Hz, 1H), 8.64 (dt, J=7.8, 1.5 Hz, 1H), 8.30 (d, J=1.6 Hz, 1H), 8.18 (d, J=1.7 Hz, 1H), 8.04 (dt, J=7.7, 1.4 Hz, 1H), 7.88 (dd, J=2.6, 1.6 Hz, 1H), 7.73 (t, J=7.7 Hz, 1H), 7.51-7.25 (m, 1H), 7.03 (s, 2H), 6.77 (dd, J=4.4, 2.6 Hz, 1H), 3.90 (s, 6H), 3.71 (s, 3H); MS (ES+): 471.4 (M+1), (ES−): 469.4 (M−1).

Scheme 111

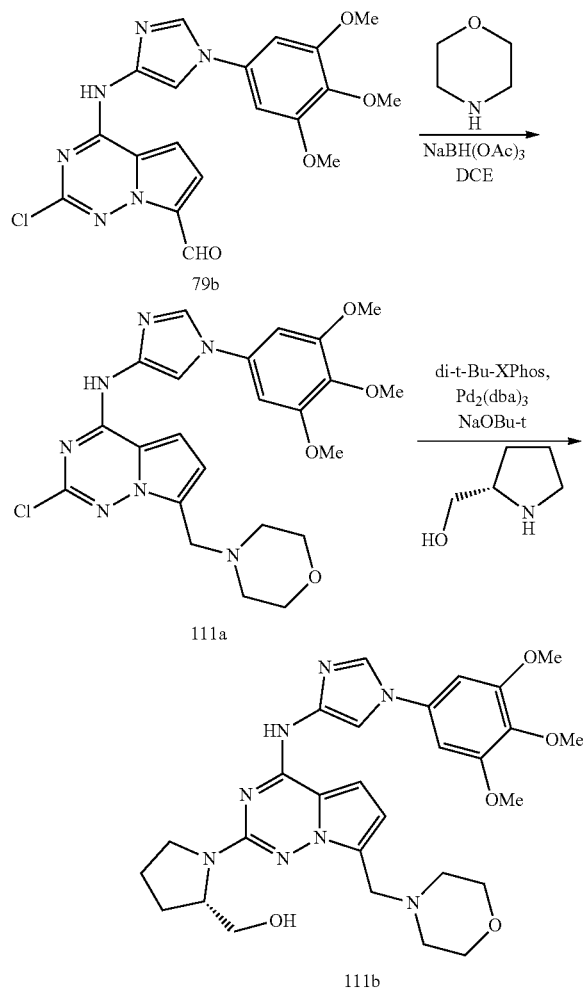

Preparation of (S)-(1-(7-(morpholinomethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (111b)

Step-1: Preparation of 2-chloro-7-(morpholinomethyl)-N-(1-(3,4,5-trimethoxyphenyl)-1H-imidazol-4-yl)pyrrolo[2,1-f][1,2,4]triazin-4-amine (111a)

Compound 111a was prepared according to the procedure reported for reductive amination in step-1 of Scheme 105 from 2-chloro-4-(1-(3,4,5-trimethoxyphenyl)-1H-imidazol-4-ylamino)pyrrolo[1,2-f][1,2,4]triazine-7-carbaldehyde (79b) (200 mg, 0.47 mmol) in dichloroethane (3 mL) using 1-morpholine (0.045 mL, 0.51 mmol), acetic acid (0.05 mL) and NaBH(OAc)$_3$ (129 mg, 0.61 mmol). This gave after workup and purification by flash column chromatography (Silica gel 12 g, eluting with MeOH in DCM from 0% to 10%) 2-chloro-7-(morpholinomethyl)-N-(1-(3,4,5-trimethoxyphenyl)-1H-imidazol-4-yl)pyrrolo[1,2-f][1,2,4]triazin-4-amine (111a) (131 mg, 56% yield) as a little pink solid; $^1$H NMR (300 MHz, DMSO-d$_6$) δ 11.24 (s, 1H, D$_2$O exchangeable), 8.20 (d, J=1.6 Hz, 1H), 7.88 (d, J=1.6 Hz, 1H), 7.40 (d, J=4.4 Hz, 1H), 6.93 (s, 2H), 6.67 (d, J=4.5 Hz, 1H), 3.87 (s, 6H), 3.78 (s, 2H), 3.69 (s, 3H), 3.56 (t, J=4.6 Hz, 4H), 2.47-2.37 (m, 4H); MS (ES+): 500.4 (M+1), 522.4 (M+Na); HPLC purity: 95.21%.

Step 2: Preparation of(S)-(1-(7-(morpholinomethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (111b)

Compound 111b was prepared from 2-chloro-7-(morpholinomethyl)-N-(1-(3,4,5-trimethoxyphenyl)-1H-imidazol-4-yl)pyrrolo[2,1-f][1,2,4]triazin-4-amine (111a) (106 mg, 0.21 mmol), (S)-pyrrolidin-2-ylmethanol (161 mg, 1.59 mmol), di-tert-butyl(2',4',6'-triisopropylbiphenyl-2-yl)phosphine (di-t-Bu-XPhos) (14 mg, 0.032 mmol), Pd$_2$(dba)$_3$ (14 mg, 0.015 mmol) and sodium tert-butoxide (153 mg, 1.59 mmol) in toluene (5 mL) according to the procedure reported in step-3 on Scheme 101. This gave after workup and purification by flash chromatography (Silica gel 24 g, eluting with MeOH in DCM from 0% to 10%) (S)-(1-(7-(morpholinomethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (111b) (75 mg, 63% yield) as a solid; $^1$H NMR (300 MHz, DMSO-d$_6$) δ 10.48 (s, 1H, D$_2$O exchangeable), 8.24 (s, 1H), 7.98 (s, 1H), 7.14 (d, J=4.4 Hz, 1H), 6.95 (s, 2H), 6.35 (d, J=4.4 Hz, 1H), 4.83 (t, J=5.2 Hz, 1H, D$_2$O exchangeable), 4.31-4.07 (m, 1H), 3.87 (s, 6H), 3.85-3.63 (m, 5H), 3.65-3.43 (m, 4H), 3.42-3.23 (m, 4H), 2.46-2.29 (m, 4H), 2.13-1.74 (m, 4H); MS (ES+): 565.6 (M+1), 587.4 (M+Na); MS (ES−): 563.6 (M−1); HPLC purity: 84.98%. Hydrochloride salt of compound 111b was obtained by purification of crude reaction mixture from step-2 above by reverse phase flash chromatography [(silica gel C-18, 24 g) eluting with acetonitrile and 0.1% HCl in water] followed by lyophilization; $^1$H NMR (300 MHz, DMSO-d$_6$): δ 11.51 (s, 1H), 11.15 (s, 1H), 8.77 (s, 1H), 8.09 (s, 1H), 7.25 (d, J=4.5 Hz, 1H), 7.04 (s, 2H), 6.78 (d, J=4.4 Hz, 1H), 4.58 (s, 2H), 4.20 (s, 1H), 3.99-3.90 (m, 1H), 3.88 (s, 6H), 3.85-3.71 (m, 2H), 3.69 (s, 3H), 3.47 (s, 1H), 3.37-3.21 (m, 4H), 3.19-2.96 (m, 4H), 2.09-1.78 (m, 4H). MS (ES+): 565.4 (M+1), 587.3 (M+Na). MS (ES−): 599.5 (M+Cl). HPLC purity: 94.30%.

Scheme 112

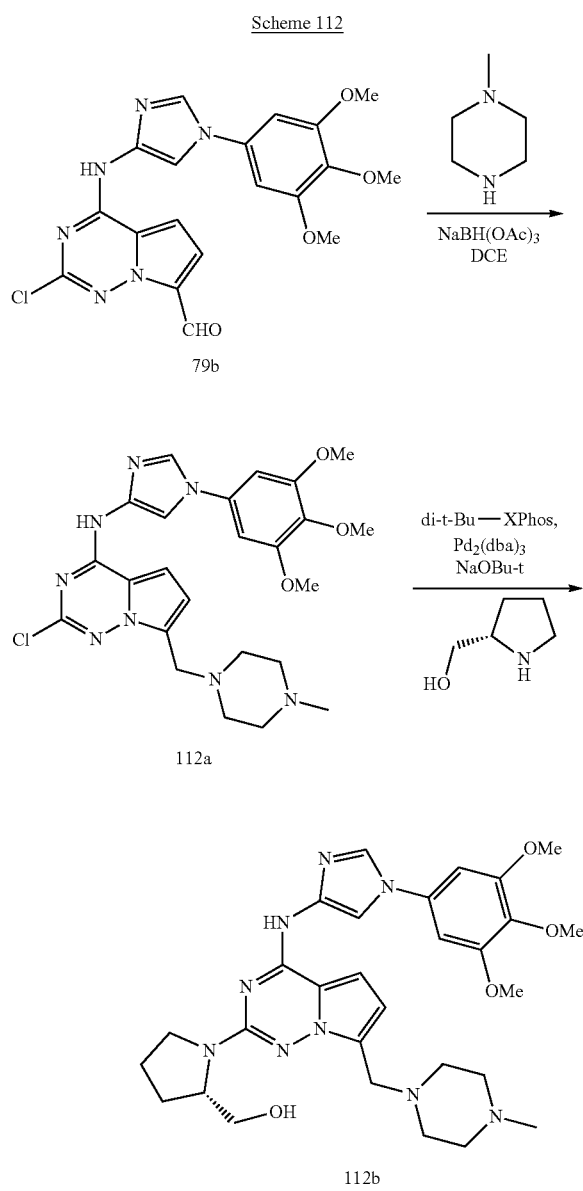

Preparation of (S)-(1-(7-((4-methylpiperazin-1-yl)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (112b)

Step-1: Preparation of 2-chloro-7-((4-methylpiperazin-1-yl)methyl)-N-(1-(3,4,5-trimethoxyphenyl)-1H-imidazol-4-yl)pyrrolo[2,1-f][1,2,4]triazin-4-amine (112a)

Compound 112a was prepared according to the procedure reported for reductive amination in step-1 of Scheme 105 from 2-chloro-4-(1-(3,4,5-trimethoxyphenyl)-1H-imidazol-4-ylamino)pyrrolo[1,2-f][1,2,4]triazine-7-carbaldehyde (79b) (200 mg, 0.47 mmol) in dichloroethane (10 mL) using 1-methylpiperazine (0.078 mL, 0.7 mmol), acetic acid (0.05 mL) and NaBH(OAc)₃ (148 mg, 0.7 mmol).

The combined organic layers were dried, filtered and concentrated in vacuum. This gave after workup and purification by flash column chromatography (Silica gel 12 g, eluting with DMA-80 in DCM from 0 to 50%) to afford 2-chloro-7-((4-methylpiperazin-1-yl)methyl)-N-(1-(3,4,5-trimethoxyphenyl)-1H-imidazol-4-yl)pyrrolo[1,2-f][1,2,4]triazin-4-amine (112a) (122 mg, 51.0% yield) as a solid; $^1$H NMR (300 MHz, Chloroform-d) δ 10.13 (s, 1H), 7.94 (d, J=1.5 Hz, 1H), 7.65 (d, J=1.6 Hz, 1H), 6.87 (d, J=4.5 Hz, 1H), 6.66 (s, 2H), 6.63 (d, J=4.5 Hz, 1H), 4.25-3.56 (m, 11H), 2.86-2.37 (m, 8H), 2.29 (s, 3H); MS (ES+): 513.5 (M+1); MS (ES-): 511.5 (M-1).

Step 2: Preparation of (S)-(1-(7-((4-methylpiperazin-1-yl)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (112b)

Compound 112b was prepared from 2-chloro-7-((4-methylpiperazin-1-yl)methyl)-N-(1-(3,4,5-trimethoxyphenyl)-1H-imidazol-4-yl)pyrrolo[1,2-f][1,2,4]triazin-4-amine (112a) (106 mg, 0.21 mmol), (S)-pyrrolidin-2-ylmethanol (157 mg, 1.55 mmol), (di-t-Bu-XPhos) (13 mg, 0.031 mmol), Pd₂(dba)₃ (13 mg, 0.015 mmol) and sodium tert-butoxide (149 mg, 1.55 mmol) in toluene (5 mL) according to the procedure reported in step-3 on Scheme 101. This gave after workup and purification by flash chromatography (Silica gel 12 g, eluting with MeOH in DCM from 0 to 40%) (S)-(1-(7-((4-methylpiperazin-1-yl)methyl)-4-(1-(3,4,5-trimethoxyphenyl)-1H-imidazol-4-ylamino)pyrrolo[1,2-f][1,2,4]triazin-2-yl)pyrrolidin-2-yl)methanol (112b) (31 mg, 26.0% yield) as a white solid; $^1$H NMR (300 MHz, DMSO-d₆) δ 10.47 (s, 1H, D₂O exchangeable), 8.24 (d, J=1.5 Hz, 1H), 7.97 (d, J=1.6 Hz, 1H), 7.13 (d, J=4.4 Hz, 1H), 6.95 (s, 2H), 6.33 (d, J=4.4 Hz, 1H), 4.83 (t, J=5.2 Hz, 1H, D₂O exchangeable), 4.28-4.06 (m, 1H), 3.87 (s, 6H), 3.82-3.69 (m, 1H), 3.76 (s, 2H), 3.68 (s, 3H), 3.65-3.54 (m, 1H), 3.54-3.37 (m, 2H), 2.55-2.18 (m, 8H), 2.15 (s, 3H), 2.11-1.79 (m, 4H); MS (ES+): 578.6 (M+1), 600.6 (M+Na); HPLC purity: 88.41%.

Scheme 113

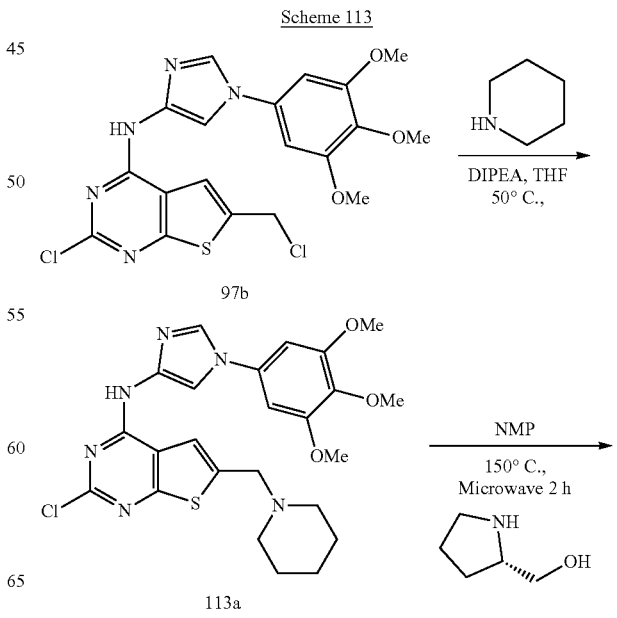

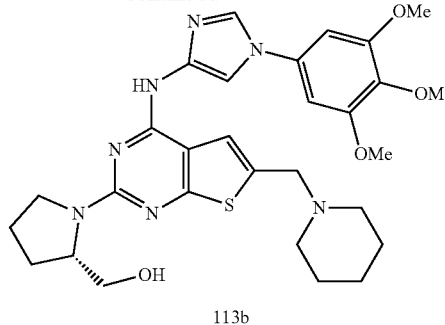

113b

Preparation of (S)-(1-(6-(piperidin-1-ylmethyl)-4-((1-(3,4,5-trimethoxyphenyl)-1H-imidazol-4-yl)amino)thieno[2,3-d]pyrimidin-2-yl)pyrrolidin-2-yl)methanol (113b)

Step-1: Preparation of 2-chloro-6-(piperidin-1-ylmethyl)-N-(1-(3,4,5-trimethoxyphenyl)-1H-imidazol-4-yl)thieno[2,3-d]pyrimidin-4-amine (113a)

Compound 113a was prepared from 2-chloro-6-(chloromethyl)-N-(1-(3,4,5-trimethoxyphenyl)-1H-imidazol-4-yl)thieno[2,3-d]pyrimidin-4-amine (97b) (150 mg, 0.32 mmol), DIPEA (0.23 mL, 1.29 mmol) and piperidine (0.04 mL, 0.64 mmol) in THF (3 mL) according to the procedure reported in step-3 of Scheme 97. This gave 2-chloro-6-(piperidin-1-ylmethyl)-N-(1-(3,4,5-trimethoxyphenyl)-1H-imidazol-4-yl)thieno[2,3-d]pyrimidin-4-amine (113a) (100 mgs, 60%) as a solid, which was used for next step without further purification; MS (ES−): 514.4 (M−1).

Step-2: Preparation of (S)-(1-(6-(piperidin-1-ylmethyl)-4-((1-(3,4,5-trimethoxyphenyl)-1H-imidazol-4-yl)amino)thieno[2,3-d]pyrimidin-2-yl)pyrrolidin-2-yl)methanol (113b)

Compound 113b was prepared from 2-chloro-6-(piperidin-1-ylmethyl)-N-(1-(3,4,5-trimethoxyphenyl)-1H-imidazol-4-yl)thieno[2,3-d]pyrimidin-4-amine (113a) (0.1 g, 0.19 mmol), (S)-pyrrolidin-2-ylmethanol (0.1 mL, 0.97 mmol) in NMP (1 mL) according to the procedure reported in Scheme 2. This gave after workup and purification by flash chromatography [silica (4 g), eluting with DMA 80 in CH$_2$Cl$_2$ from 0 to 30%] (S)-(1-(6-(piperidin-1-ylmethyl)-4-(1-(3,4,5-trimethoxyphenyl)-1H-imidazol-4-ylamino)thieno[2,3-d]pyrimidin-2-yl)pyrrolidin-2-yl)methanol (113b) (15 mg, 13% yield) as a white solid; $^1$H NMR (300 MHz, Chloroform-d) δ 7.88 (d, J=1.6 Hz, 1H), 7.75 (s, 1H), 7.62 (d, J=1.6 Hz, 1H), 6.93 (s, 1H), 6.67 (s, 2H), 4.42 (s, 1H), 3.92 (s, 6H), 3.89 (s, 3H), 3.83-3.69 (m, 2H), 3.65 (s, 2H), 2.55-2.37 (m, 4H), 2.22-1.51 (m, 9H), 1.52-1.35 (m, 3H). MS (ES+): 580.6 (M+1); MS (ES−): 578.6 (M−1); Hydrochloride salt of compound 113b was obtained by purification of crude reaction mixture from step-2 above by reverse phase flash chromatography [(silica gel C-18, 24 g) eluting with acetonitrile and 0.1% HCl in water] followed by lyophilization; $^1$H NMR (300 MHz, DMSO-d$_6$) δ 11.36 (s, 1H), 10.85 (s, 1H), 8.49 (s, 1H), 8.07 (s, 2H), 7.00 (s, 2H), 4.51 (s, 2H), 4.39-4.06 (m, 1H), 3.88 (s, 6H), 3.79-3.62 (m, 4H), 3.58-3.28 (m, 3H), 3.06-2.78 (m, 4H), 2.19-1.88 (m, 4H), 1.88-1.56 (m, 4H), 1.51-1.19 (m, 2H); MS (ES+): 580.4; MS (ES−): 614.5 (M+Cl). HPLC purity: 98.49%.

Scheme 114

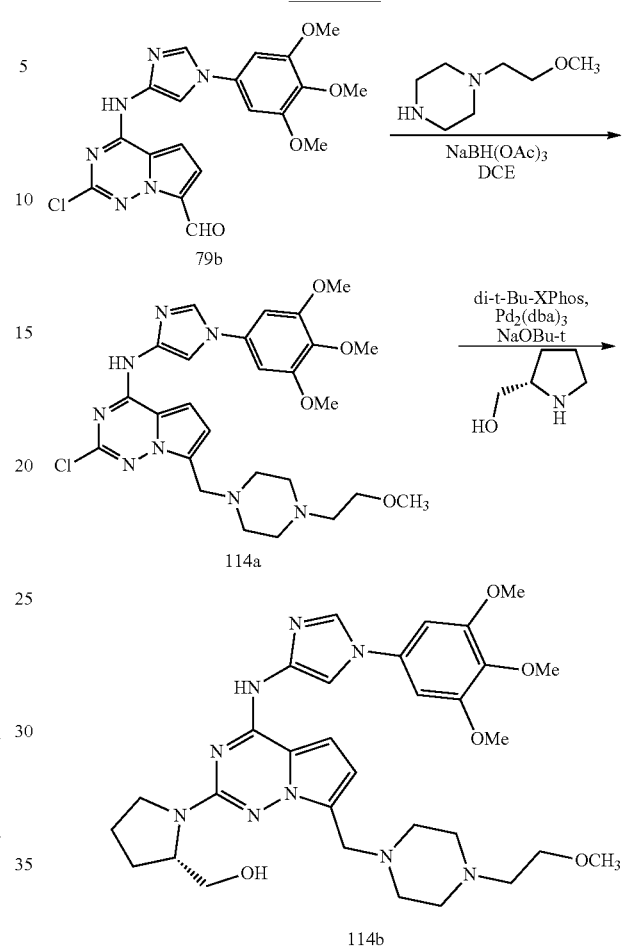

Preparation of (S)-(1-(7-((4-(2-methoxyethyl)piperazin-1-yl)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (114b)

Step-1: Preparation of 2-chloro-7-((4-(2-methoxyethyl)piperazin-1-yl)methyl)-N-(1-(3,4,5-trimethoxyphenyl)-1H-imidazol-4-yl)pyrrolo[2,1-f][1,2,4]triazin-4-amine (114a)

Compound 114a was prepared according to the procedure reported for reductive amination in step-1 of Scheme 105 from 2-chloro-4-(1-(3,4,5-trimethoxyphenyl)-1H-imidazol-4-ylamino)pyrrolo[1,2-f][1,2,4]triazine-7-carbaldehyde (79b) (200 mg, 0.47 mmol) in dichloroethane (8 mL) using 1-(2-methoxyethyl)piperazine (101 mg, 0.7 mmol), acetic acid (0.05 mL) and NaBH(OAc)$_3$ (148 mg, 0.7 mmol). This gave after workup and purification by flash column chromatography (Silica gel 12 g, eluting with DMA-80 in DCM from 0 to 50%) 2-chloro-7-((4-(2-methoxyethyl)piperazin-1-yl)methyl)-N-(1-(3,4,5-trimethoxyphenyl)-1H-imidazol-4-yl)pyrrolo[2,1-f][1,2,4]triazin-4-amine (114a) (72 mg, 28% yield) as a yellow solid; MS (ES+): 557.5, 579.5 (M+1); MS (ES−): 555.5 (M−1).

Step 2: Preparation of (S)-(1-(7-((4-(2-methoxy-ethyl)piperazin-1-yl)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (114b)

Compound 114b was prepared from 2-chloro-7-((4-(2-methoxyethyl)piperazin-1-yl)methyl)-N-(1-(3,4,5-trimethoxyphenyl)-1H-imidazol-4-yl)pyrrolo[2,1-f][1,2,4]triazin-4-amine (114a) (72 mg, 0.13 mmol), (S)-pyrrolidin-2-ylmethanol (98 mg, 0.97 mmol), (di-t-Bu-XPhos) (8 mg, 0.019 mmol), $Pd_2(dba)_3$ (8 mg, 0.009 mmol) and sodium tert-butoxide (93 mg, 0.97 mmol) in PhMe (5 mL) according to the procedure reported in step-3 on Scheme 101. This gave after workup and purification by flash chromatography (Silica gel 12 g, eluting with MeOH in DCM from 0 to 50%) (S)-(1-(7-((4-(2-methoxyethyl)piperazin-1-yl)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (114b) (16 mg, 20% yield) as a solid; $^1$H NMR (300 MHz, DMSO-$d_6$) δ 10.50 (s, 1H, $D_2O$ exchangeable), 8.24 (d, J=1.6 Hz, 1H), 7.97 (s, 1H), 7.14 (d, J=4.4 Hz, 1H), 6.95 (s, 2H), 6.35 (s, 1H), 4.96-4.75 (m, 1H, $D_2O$ exchangeable), 4.30-4.06 (m, 1H), 3.54-3.25 (m, 4H), 3.87 (s, 6H), 3.84-3.68 (m, 1H), 3.68 (s, 3H), 3.67-3.52 (m, 1H), 3.31-3.14 (m, 3H), 2.76-2.24 (m, 10H), 2.10-1.79 (m, 4H); MS (ES+): 622.7 (M+1); MS (ES−): 656.7 (M+Cl).

Preparation of (S)-(1-(2-((1-(3,4,5-trimethoxyphenyl)-1H-imidazol-4-yl)amino)quinazolin-4-yl)pyrrolidin-2-yl)methanol (115b)

Step-1: Preparation of (S)-(1-(2-chloroquinazolin-4-yl)pyrrolidin-2-yl)methanol (115a)

To a solution of 2,4-dichloroquinazoline (21a) (2.0 g, 10.04 mmol) in DCM (30 mL) was added (S)-pyrrolidin-2-ylmethanol (2.0 mL, 19.77 mmol), DIPEA (3.5 mL, 27.15 mmol) and stirred at room temperature for 1 h. The reaction was diluted with water (50 mL) extracted with DCM (2×100 mL). The organic layers were combined dried, filtered and concentrated in vacuum. The residue obtained was purified by flash column chromatography (silica gel, eluting with ethyl acetate in hexanes 0-40%) to afford (S)-(1-(2-chloroquinazolin-4-yl)pyrrolidin-2-yl)methanol (115a) (1.4 g, 54% yield) as an off white solid; $^1$H NMR (300 MHz, DMSO-$d_6$): δ 8.33-8.22 (m, 1H), 7.78 (ddd, J=8.2, 6.9, 1.2 Hz, 1H), 7.62 (dd, J=8.4, 1.3 Hz, 1H), 7.47 (ddd, J=8.4, 6.9, 1.4 Hz, 1H), 4.85 (t, J=5.8 Hz, 1H), 4.57 (t, J=5.7 Hz, 1H), 4.11-3.87 (m, 2H), 3.64 (t, J=5.2 Hz, 2H), 2.16-1.78 (m, 4H). MS (ES−): 264.3 (M+1), 286.3 (M+Na); MS (ES−): 262.3 (M−1), 298.3 (M+Cl).

Step-2: Preparation of (S)-(1-(2-((1-(3,4,5-trimethoxyphenyl)-1H-imidazol-4-yl)amino)quinazolin-4-yl)pyrrolidin-2-yl)methanol (115b)

Compound 115b was prepared from (S)-(1-(2-chloroquinazolin-4-yl)pyrrolidin-2-yl)methanol (115a) (250 mg, 0.95 mmol), 1-(3,4,5-trimethoxyphenyl)-1H-imidazol-4-amine hydrochloride (57a) (0.41 g, 1.42 mmol), 2,2'-bis(diphenylphosphino)-1,1'-binaphthyl (BiNAP, 0.07 g, 0.11 mmol), $Pd_2(dba)_3$ (0.09 g, 0.1 mmol) and sodium tert-butoxide (0.18 g, 1.9 mmol) in PhMe (4 mL) according to the procedure reported in step-2 on Scheme 96. This gave after workup and purification by flash column chromatography [silica (4 g), eluting with DMA 80 in $CH_2Cl_2$ from 0 to 30%] (S)-(1-(2-((1-(3,4,5-trimethoxyphenyl)-1H-imidazol-4-yl)amino)quinazolin-4-yl)pyrrolidin-2-yl)methanol (115b) (169 mg, 37% yield) as a yellow solid; $^1$H NMR (300 MHz, DMSO-$d_6$) δ 9.01 (s, 1H), 8.08 (d, J=1.6 Hz, 1H), 8.05 (s, 1H), 7.80 (s, 1H), 7.56 (td, J=7.4, 6.8, 1.2 Hz, 1H), 7.48 (s, 1H), 7.10 (t, J=7.6 Hz, 1H), 6.93 (s, 2H), 4.87 (s, 1H), 4.72 (s, 1H), 4.10-3.97 (m, 1H), 3.96 (s, 1H), 3.89 (s, 6H), 3.85-3.73 (m, 1H), 3.68 (s, 3H), 3.63-3.50 (m, 1H), 2.12-1.78 (m, 4H). MS (ES+): 477.5 (M+1); MS (ES−): 511.5 (M+Cl).

Scheme 115

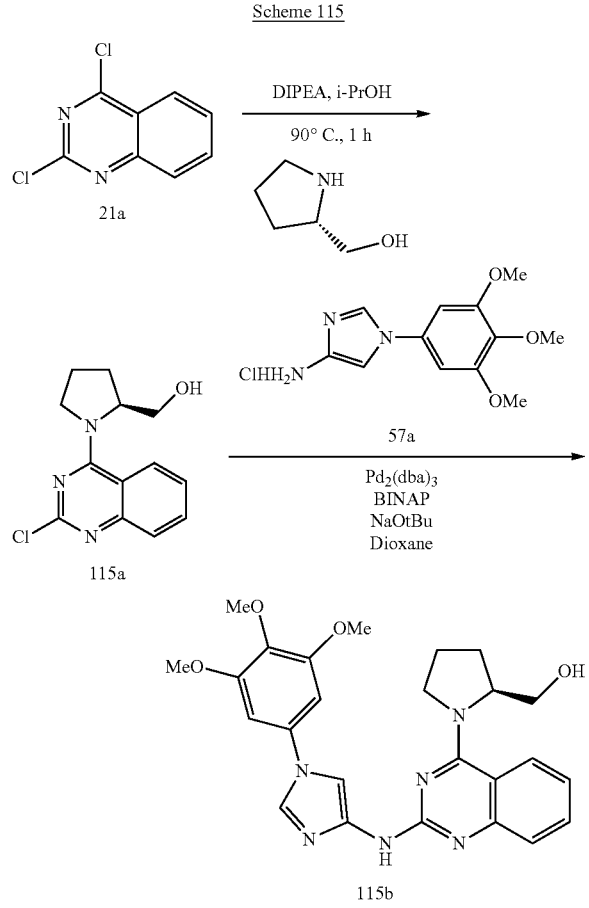

Scheme 116

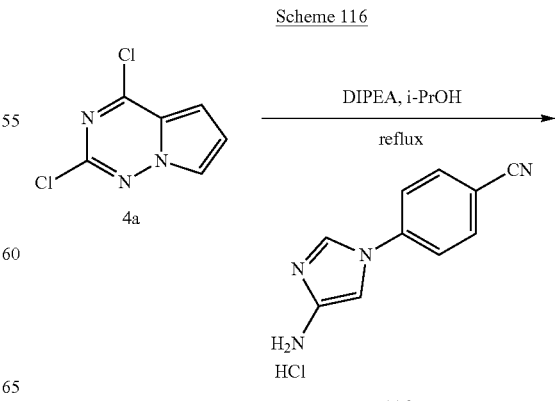

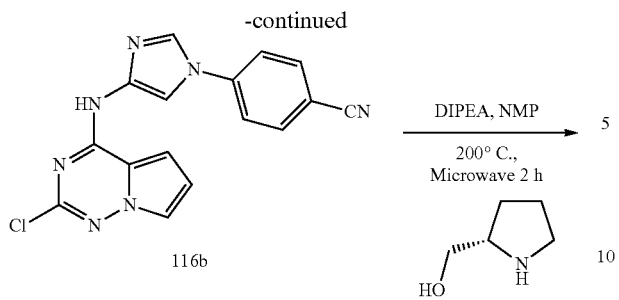

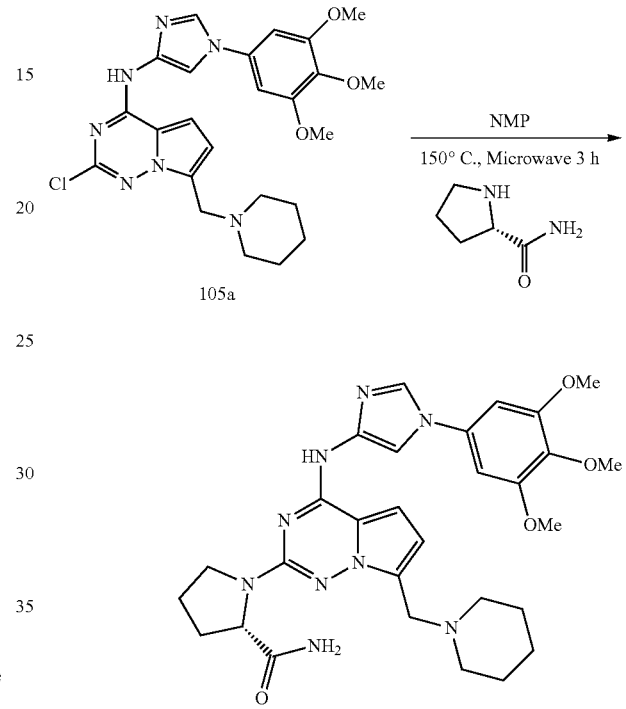

Preparation of (S)-4-(4-((2-(2-(hydroxymethyl)pyrrolidin-1-yl)pyrrolo[2,1-f][1,2,4]triazin-4-yl)amino)-1H-imidazol-1-yl)benzonitrile (116c)

Step-1: Preparation of 4-(4-((2-chloropyrrolo[2,1-f][1,2,4]triazin-4-yl)amino)-1H-imidazol-1-yl)benzonitrile (116b)

Compound 116b was prepared according to the procedure reported in Scheme 1 from 2,4-dichloropyrrolo[1,2-f][1,2,4]triazine (4a) (340 mg, 1.81 mmol) in 2-Propanol (10 mL) using DIPEA (0.95 mL, 5.44 mmol) and 4-(4-amino-1H-imidazol-1-yl)benzonitrile hydrochloride (116a) (0.4 g, 1.81 mmol; prepared according to the procedure reported in Jones, Alison et al; in PCT Int. Appl., 2016046530, 31 Mar. 2016). This gave after work up and purification by flash column chromatography [silica gel, (12 g) eluting with DCM and methanol (0 to 50%)]4-(4-((2-chloropyrrolo[2,1-f][1,2,4]triazin-4-yl)amino)-1H-imidazol-1-yl)benzonitrile (116b) (0.55 g, 91% yield) as a brown solid; $^1$H NMR (300 MHz, DMSO-$d_6$): δ 11.39 (s, 1H), 8.47 (d, J=1.6 Hz, 1H), 8.09-8.02 (m, 2H), 8.01 (d, J=1.6 Hz, 1H), 7.94-7.87 (m, 2H), 7.79 (dd, J=2.6, 1.6 Hz, 1H), 7.40 (s, 1H), 6.73 (dd, J=4.5, 2.6 Hz, 1H). MS (ES−): 334.3, 336.3 (M+2).

Step-2: Preparation of (S)-4-(4-((2-(2-(hydroxymethyl)pyrrolidin-1-yl)pyrrolo[2,1-f][1,2,4]triazin-4-yl)amino)-1H-imidazol-1-yl)benzonitrile (116c)

Compound 116c was prepared from 4-(4-((2-chloropyrrolo[2,1-f][1,2,4]triazin-4-yl)amino)-1H-imidazol-1-yl)benzonitrile (116b) (100 mg, 0.3 mmol), (S)-pyrrolidin-2-ylmethanol (0.09 mL, 0.9 mmol), and DIPEA (0.16 mL, 0.9 mmol) in NMP (1.5 mL) according to the procedure reported in Scheme 2. This gave after workup and purification by reverse phase flash chromatography [(silica gel C-18, 24 g), eluting with eluting with acetonitrile and 0.1% HCl water], followed by lyophilization (S)-4-(4-((2-(2-(hydroxymethyl)pyrrolidin-1-yl)pyrrolo[2,1-f][1,2,4]triazin-4-yl)amino)-1H-imidazol-1-yl)benzonitrile (116c) (20 mg, 18% yield) HCl salt as a white solid; $^1$H NMR (300 MHz, DMSO-$d_6$) δ 10.67 (s, 1H), 8.53 (s, 1H), 8.15-7.92 (m, 5H), 7.42 (s, 1H), 7.15 (d, J=4.2 Hz, 1H), 6.41 (d, J=4.4 Hz, 1H), 4.18 (s, 1H), 3.56-3.43 (m, 1H), 3.42-3.27 (m, 2H), 2.13-1.81 (m, 4H); MS (ES+): 401.5. IR (film): 2230 cm$^{-1}$. HPLC purity: 94.20%.

Preparation of (S)-1-(7-(piperidin-1-ylmethyl)-4-((1-(3,4,5-trimethoxyphenyl)-1H-imidazol-4-yl)amino)pyrrolo[2,1-f][1,2,4]triazin-2-yl)pyrrolidine-2-carboxamide (117a)

Compound 117a was prepared from 2-chloro-7-(piperidin-1-ylmethyl)-N-(1-(3,4,5-trimethoxyphenyl)-1H-imidazol-4-yl)pyrrolo[2,1-f][1,2,4]triazin-4-amine (105a) (52 mg, 0.104 mmol), (S)-pyrrolidine-2-carboxamide (119 mg, 1.04 mmol) in NMP (1 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using NaHCO$_3$ (S)-1-(7-(piperidin-1-ylmethyl)-4-((1-(3,4,5-trimethoxyphenyl)-1H-imidazol-4-yl)amino)pyrrolo[2,1-f][1,2,4]triazin-2-yl)pyrrolidine-2-carboxamide (117a) (7 mg, 12% yield) as a pale off-white solid; $^1$H NMR (300 MHz, Chloroform-d) δ 8.04 (s, 1H), 7.80 (s, 1H), 7.69-7.58 (m, 1H), 6.76 (s, 2H), 6.63 (d, J=4.4 Hz, 1H), 6.51 (d, J=4.5 Hz, 1H), 5.54-5.32 (m, 1H), 4.66-4.54 (m, 1H), 4.28-3.67 (m, 12H), 3.70-3.57 (m, 1H), 2.77-2.43 (m, 4H), 2.40-2.14 (m, 2H), 2.16-1.93 (m, 2H), 1.81-1.50 (m, 4H), 1.52-1.35 (m, 2H); MS (ES+): 576.6 (M+1).

Scheme 118

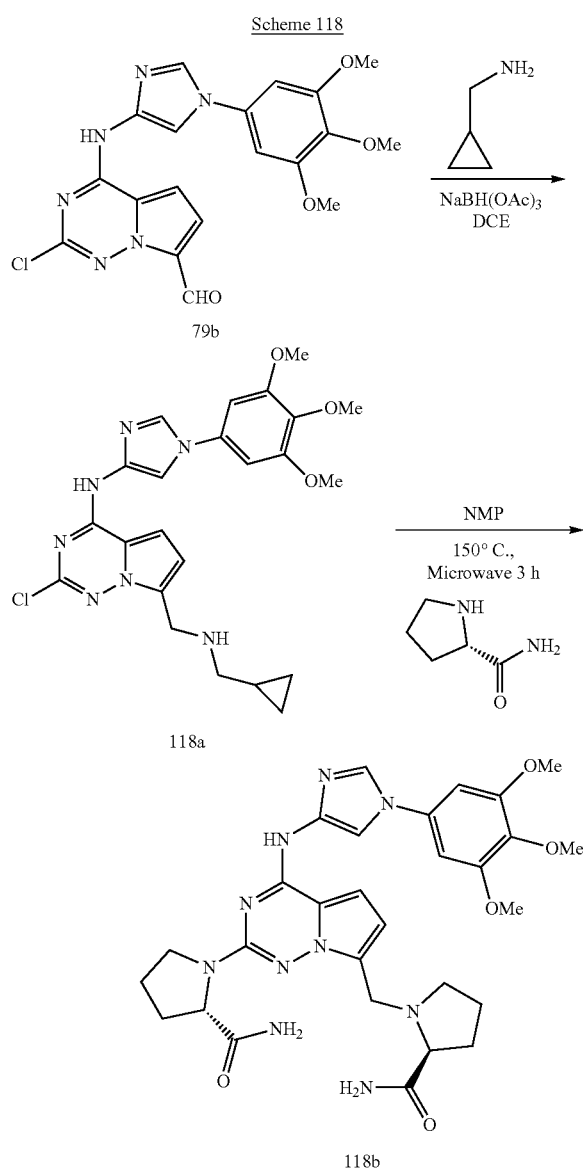

Preparation of (S)-1-((2-((S)-2-carbamoylpyrrolidin-1-yl)-4-((1-(3,4,5-trimethoxyphenyl)-1H-imidazol-4-yl)amino)pyrrolo[2,1-f][1,2,4]triazin-7-yl)methyl)pyrrolidine-2-carboxamide (118b)

Step-1: Preparation of 2-chloro-7-(((cyclopropylmethyl)amino)methyl)-N-(1-(3,4,5-trimethoxyphenyl)-1H-imidazol-4-yl)pyrrolo[2,1-f][1,2,4]triazin-4-amine (118a)

Compound 118a was prepared according to the procedure reported for reductive amination in step-1 of Scheme 105 from 2-chloro-4-(1-(3,4,5-trimethoxyphenyl)-1H-imidazol-4-ylamino)pyrrolo[1,2-f][1,2,4]triazine-7-carbaldehyde (79b) (400 mg, 0.93 mmol) in dichloroethane (10 mL) using 1-cyclopropylmethylamine (0.24 mL, 2.8 mmol), acetic acid (0.11 mL) and NaBH(OAc)₃ (297 mg, 1.4 mmol). This gave after workup and purification by flash column chromatography (Silica gel 12 g, eluting with MeOH in DCM from 0% to 40%) 2-chloro-7-(((cyclopropylmethyl)amino)methyl)-N-(1-(3,4,5-trimethoxyphenyl)-1H-imidazol-4-yl)pyrrolo[2,1-f][1,2,4]triazin-4-amine (118a) (218 mg, 48% yield) as a solid; ¹H NMR (300 MHz, DMSO-d₆) δ 11.20 (s, 1H), 8.20 (d, J=1.6 Hz, 1H), 7.88 (d, J=1.6 Hz, 1H), 7.35 (d, J=4.4 Hz, 1H), 6.93 (s, 2H), 6.65 (d, J=4.4 Hz, 1H), 3.96 (s, 2H), 3.87 (s, 6H), 3.69 (s, 3H), 2.39 (d, J=6.7 Hz, 2H), 0.99-0.78 (m, 1H), 0.46-0.31 (m, 2H), 0.14-0.02 (m, 2H); MS (ES+): 484.4 (M+1), 506.4 (M+Na); MS (ES−): 482.4 (M−1), 518.4 (M+Cl).

Step 2: Preparation of (S)-1-((2-((S)-2-carbamoylpyrrolidin-1-yl)-4-((1-(3,4,5-trimethoxyphenyl)-1H-imidazol-4-yl)amino)pyrrolo[2,1-f][1,2,4]triazin-7-yl)methyl)pyrrolidine-2-carboxamide (118b)

Compound 118b was prepared from 2-chloro-7-(((cyclopropylmethyl)amino)methyl)-N-(1-(3,4,5-trimethoxyphenyl)-1H-imidazol-4-yl)pyrrolo[2,1-f][1,2,4]triazin-4-amine (118a) (98 mg, 0.2 mmol), (S)-pyrrolidine-2-carboxamide (0.462 g, 4.1 mmol) in NMP (1.5 mL) according to the procedure reported in Scheme 2. This gave after workup and purification by flash chromatography [silica gel (12 g), eluting with MeOH in DCM from 0% to 40%] (S)-1-((2-((S)-2-carbamoylpyrrolidin-1-yl)-4-((1-(3,4,5-trimethoxyphenyl)-1H-imidazol-4-yl)amino)pyrrolo[2,1-f][1,2,4]triazin-7-yl)methyl)pyrrolidine-2-carboxamide (118b) (10 mg, 8% yield) as a yellow solid; ¹H NMR (300 MHz, DMSO-d₆) δ 10.43 (s, 1H, D₂O exchangeable), 8.21 (d, J=1.5 Hz, 1H), 7.91 (s, 1H), 7.63-7.43 (m, 1H, D₂O exchangeable), 7.37-7.15 (m, 2H, D₂O exchangeable), 7.16 (d, J=4.4 Hz, 1H), 7.08 (s, 2H), 7.04 (s, 1H, D₂O exchangeable), 6.39 (d, J=4.4 Hz, 1H), 4.49-4.35 (m, 1H), 4.23-4.06 (m, 1H), 3.93 (s, 6H), 3.68 (s, 3H), 3.64-3.52 (m, 1H), 3.02-2.89 (m, 1H), 2.89-2.78 (m, 1H), 2.45-2.30 (m, 1H), 2.32-1.98 (m, 2H), 2.00-1.85 (m, 4H), 1.81-1.48 (m, 4H); MS (ES+): 605.6 (M+1), 627.6 (M+Na); HPLC purity: 95.61%.

Scheme 119

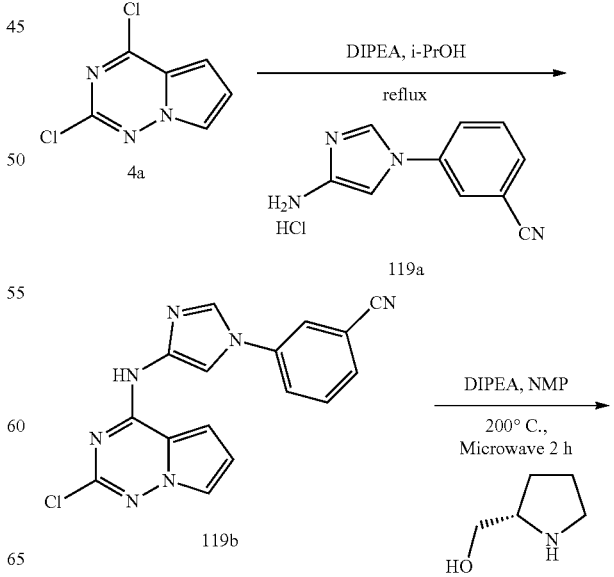

-continued

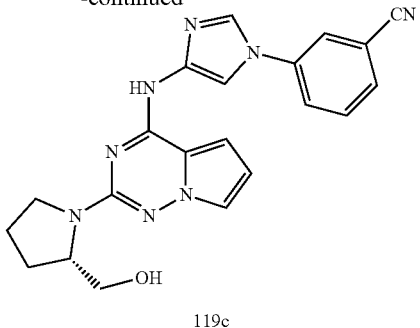

119c

Preparation of (S)-3-(4-((2-(2-(hydroxymethyl)pyrrolidin-1-yl)pyrrolo[2,1-f][1,2,4]triazin-4-yl)amino)-1H-imidazol-1-yl)benzonitrile (119c)

Step-1: Preparation of 3-(4-((2-chloropyrrolo[2,1-f][1,2,4]triazin-4-yl)amino)-1H-imidazol-1-yl)benzonitrile (119b)

Compound 119b was prepared according to the procedure reported in Scheme 1 from 2,4-dichloropyrrolo[1,2-f][1,2,4]triazine (4a) (852 mg, 4.53 mmol) in 2-Propanol (10 mL) using DIPEA (2.38 mL, 13.6 mmol) and 3-(4-amino-1H-imidazol-1-yl)benzonitrile hydrochloride (119a) (1 g, 4.53 mmol; can be prepared according to the procedure reported by Jones, Alison et al; in PCT Int. Appl., 2016046530, 31 Mar. 2016). This gave after work up and purification by flash column chromatography [silica gel, (40 g) eluting with DCM and methanol (0 to 30%)]3-(4-((2-chloropyrrolo[2,1-f][1,2,4]triazin-4-yl)amino)-1H-imidazol-1-yl)benzonitrile (119b) (0.9 g, 59% yield) as a yellow solid; $^1$H NMR (300 MHz, DMSO-$d_6$) δ 11.35 (s, 1H), 8.37 (d, J=1.6 Hz, 1H), 8.29 (t, J=1.8 Hz, 1H), 8.02 (ddd, J=8.1, 2.4, 1.1 Hz, 1H), 7.98 (d, J=1.6 Hz, 1H), 7.86 (dt, J=7.7, 1.3 Hz, 1H), 7.80-7.72 (m, 2H), 7.40 (d, J=4.4 Hz, 1H), 6.73 (dd, J=4.5, 2.6 Hz, 1H); MS (ES−): 335.3, 337.3 (M+2).

Step-2: Preparation of (S)-3-(4-((2-(2-(hydroxymethyl)pyrrolidin-1-yl)pyrrolo[2,1-f][1,2,4]triazin-4-yl)amino)-1H-imidazol-1-yl)benzonitrile (119c)

Compound 119c was prepared from 3-(4-((2-chloropyrrolo[2,1-f][1,2,4]triazin-4-yl)amino)-1H-imidazol-1-yl)benzonitrile (119b) (300 mg, 0.89 mmol), (S)-pyrrolidin-2-ylmethanol (0.27 mL, 2.68 mmol), and DIPEA (0.47 mL, 2.68 mmol) in NMP (1.5 mL) according to the procedure reported in Scheme 2. This gave after workup and purification by reverse phase flash chromatography [(silica gel C-18, 24 g), eluting with eluting with acetonitrile and 0.1% HCl water], followed by lyophilization (S)-3-(4-((2-(2-(hydroxymethyl)pyrrolidin-1-yl)pyrrolo[2,1-f][1,2,4]triazin-4-yl)amino)-1H-imidazol-1-yl)benzonitrile (119c) (22 mg, 6% yield) HCl salt as a white solid; $^1$H NMR (300 MHz, DMSO-$d_6$) δ 11.28 (s, 1H), 8.94 (s, 1H), 8.37 (s, 1H), 8.25-8.06 (m, 2H), 7.90 (d, J=6.6 Hz, 1H), 7.83-7.68 (m, 1H), 7.49 (s, 1H), 7.17 (s, 1H), 6.46 (s, 1H), 4.15 (s, 1H), 3.77-3.63 (m, 1H), 3.55-3.19 (m, 3H), 2.10-1.73 (m, 4H); MS (ES+): 401.5; MS (ES−): 399.5 (M−1), 435.5 (M+Cl). HPLC purity: 96.43%.

Scheme 120

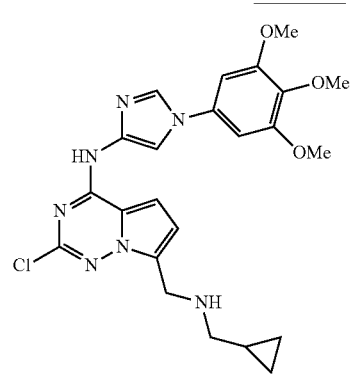

118a

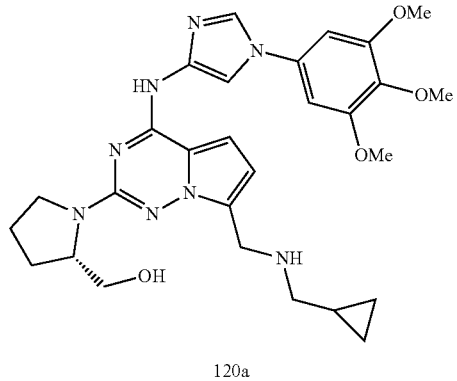

120a

Preparation of (S)-(1-(7-((((cyclopropylmethyl)amino)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (120a)

Compound 120a was prepared from 2-chloro-7-((((cyclopropylmethyl)amino)methyl)-N-(1-(3,4,5-trimethoxyphenyl)-1H-imidazol-4-yl)pyrrolo[2,1-f][1,2,4]triazin-4-amine (118a) (103 mg, 0.21 mmol), (S)-pyrrolidin-2-ylmethanol (431 mg, 4.26 mmol) in NMP (1.5 mL) according to the procedure reported in Scheme 2. This gave after workup and purification by reverse phase flash chromatography [(silica gel C-18, 24 g) eluting with 0.1% TFA in acetonitrile and 0.1% TFA in water] (S)-(1-(7-((((cyclopropylmethyl)amino)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (120a) (10 mg, 7% yield) TFA salt as a yellow solid; $^1$H NMR (300 MHz, DMSO-$d_6$) δ 10.76 (s, 1H, D$_2$O exchangeable), 8.79 (s, 2H, D$_2$O exchangeable), 8.28 (d, J=1.5 Hz, 1H), 7.98 (d, J=1.6 Hz, 1H), 7.20 (d, J=4.5 Hz, 1H), 6.96 (s, 2H), 6.60 (d, J=4.5 Hz, 1H), 4.48-4.39 (m, 2H), 4.31-4.20 (m, 1H), 3.88 (s, 6H), 3.81-3.70 (m, 1H), 3.68 (s, 3H), 3.67-3.56 (m, 1H), 3.56-3.43 (m, 1H), 3.35 (t, J=9.3 Hz, 1H), 2.88 (q, J=6.1 Hz, 2H), 2.20-1.75 (m, 4H), 1.21-1.01 (m, 1H), 0.69-0.52 (m, 2H), 0.48-0.30 (m, 2H); $^{19}$F NMR (282 MHz, DMSO-$d_6$) δ −74.16; MS (ES+): 549.5 (M+1), 571.6 (M+Na); HPLC purity: 94.26%.

Scheme 121

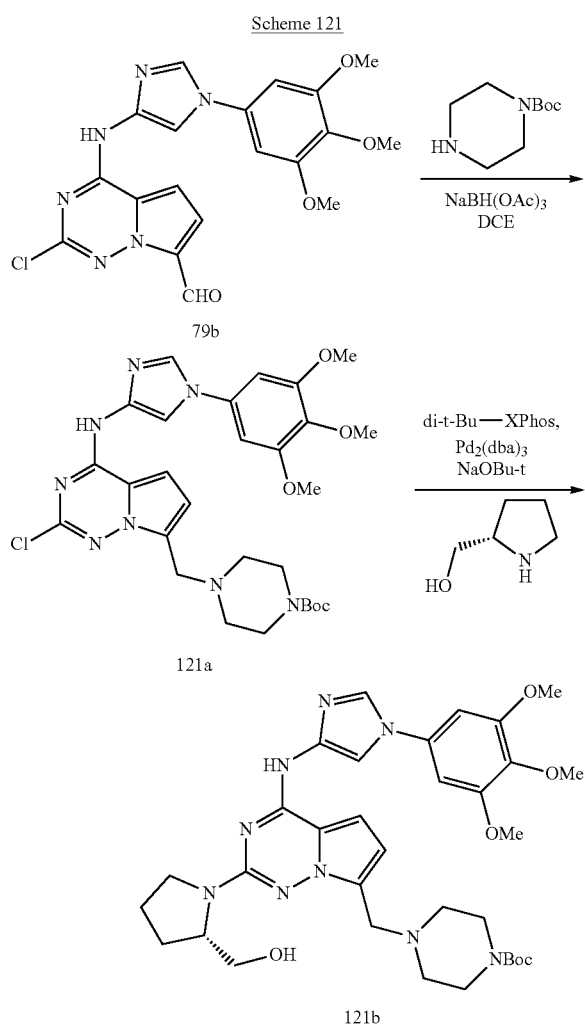

Preparation of (S)-tert-butyl 4-((2-(2-(hydroxymethyl)pyrrolidin-1-yl)-4-(1-(3,4,5-trimethoxyphenyl)-1H-imidazol-4-yl)amino)pyrrolo[2,1-f][1,2,4]triazin-7-yl)methyl)piperazine-1-carboxylate (121b)

Step-1: Preparation of tert-butyl 4-((2-chloro-4-((1-(3,4,5-trimethoxyphenyl)-1H-imidazol-4-yl)amino)pyrrolo[2,1-f][1,2,4]triazin-7-yl)methyl)piperazine-1-carboxylate (121a)

Compound 121a was prepared according to the procedure reported for reductive amination in step-1 of Scheme 105 from 2-chloro-4-(1-(3,4,5-trimethoxyphenyl)-1H-imidazol-4-ylamino)pyrrolo[1,2-f][1,2,4]triazine-7-carbaldehyde (79b) (400 mg, 0.93 mmol) in dichloroethane (10 mL) using tert-butyl piperazine-1-carboxylate (521 mg, 2.8 mmol), acetic acid (0.064 mL) and NaBH(OAc)$_3$ (297 mg, 1.4 mmol). This gave after workup and purification by flash column chromatography (Silica gel 12 g, eluting with MeOH in DCM from 0 to 40%) tert-butyl 4-((2-chloro-4-((1-(3,4,5-trimethoxyphenyl)-1H-imidazol-4-yl)amino)pyrrolo[2,1-f][1,2,4]triazin-7-yl)methyl)piperazine-1-carboxylate (121a) (218 mg, 39% yield) as a solid; $^1$H NMR (300 MHz, CDCl$_3$) δ 7.90 (s, 1H), 7.64 (d, J=1.6 Hz, 1H), 6.79 (s, 1H), 6.74-6.58 (m, 3H), 4.09-3.79 (m, 11H), 3.53-3.34 (m, 4H), 2.65-2.39 (m, 4H), 1.44 (s, 9H); MS (ES+): 599.6 (M+1), 621.6 (M+Na); MS (ES−): 597.5 (M−1).

Step 2: Preparation of (S)-tert-butyl 4-((2-(2-(hydroxymethyl)pyrrolidin-1-yl)-4-((1-(3,4,5-trimethoxyphenyl)-1H-imidazol-4-yl)amino)pyrrolo[2,1-f][1,2,4]triazin-7-yl)methyl)piperazine-1-carboxylate (121b)

Compound 121b was prepared from tert-butyl 4-((2-chloro-4-((1-(3,4,5-trimethoxyphenyl)-1H-imidazol-4-yl)amino)pyrrolo[2,1-f][1,2,4]triazin-7-yl)methyl)piperazine-1-carboxylate (121a) (148 mg, 0.25 mmol), (S)-pyrrolidin-2-ylmethanol (187 mg, 1.85 mmol), (di-t-Bu-XPhos) (16 mg, 0.087 mmol), Pd$_2$(dba)$_3$ (16 mg, 0.087 mmol) and sodium tert-butoxide (178 mg, 1.85 mmol) in PhMe (5 mL) according to the procedure reported in step-3 on Scheme 101. This gave after workup and purification by flash chromatography (Silica gel 24 g, eluting with MeOH in DCM from 0 to 50%) (S)-tert-butyl 4-((2-(2-(hydroxymethyl)pyrrolidin-1-yl)-4-((1-(3,4,5-trimethoxyphenyl)-1H-imidazol-4-yl)amino)pyrrolo[2,1-f][1,2,4]triazin-7-yl)methyl)piperazine-1-carboxylate (121b) (86 mg, 52% yield) as a yellow solid; $^1$H NMR (300 MHz, DMSO-d$_6$) δ 10.49 (s, 1H, D$_2$O exchangeable), 8.24 (d, J=1.5 Hz, 1H), 7.97 (d, J=1.6 Hz, 1H), 7.13 (d, J=4.5 Hz, 1H), 6.95 (s, 2H), 6.34 (d, J=4.4 Hz, 1H), 4.84 (t, J=5.2 Hz, 1H, D$_2$O exchangeable), 4.26-4.12 (m, 1H), 3.87 (s, 6H), 3.87-3.71 (m, 2H), 3.80-3.67 (m, 1H), 3.68 (s, 3H), 3.66-3.53 (m, 1H), 3.51-3.22 (m, 6H), 2.38 (s, 4H), 2.12-1.69 (m, 4H), 1.36 (s, 9H); MS (ES+): 664.7 (M+1), 686.7 (M+Na); MS (ES−): 662.7 (M+1), 698.8 (M+Cl); HPLC purity: 88.43%.

Scheme 122

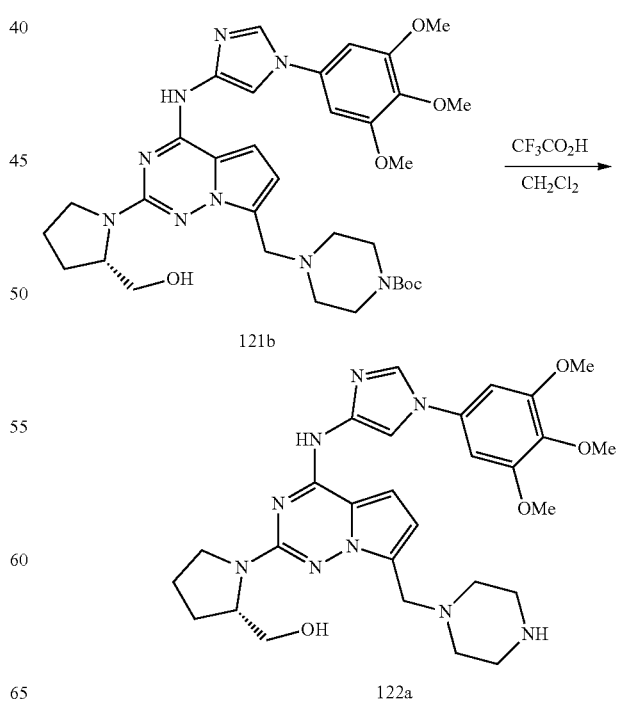

Preparation of (S)-(1-(7-(piperazin-1-ylmethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (122a)

To a solution of (S)-tert-butyl 4-((2-(2-(hydroxymethyl)pyrrolidin-1-yl)-4-(1-(3,4,5-trimethoxyphenyl)-1H-imidazol-4-ylamino)pyrrolo[2,1-f][1,2,4]triazin-7-yl)methyl)piperazine-1-carboxylate (121b) (66 mg, 0.1 mmol) in DCM (5 mL) was added TFA (0.15 mL, 1.99 mmol) and stirred at room temperature for 3 h. The reaction mixture was concentrated in vacuum and the residue was dissolved in DCM, washed with saturated aqueous $NaHCO_3$, brine, dried, and concentrated in vacuum. The residue obtained was purified by flash column chromatography (silica gel 12 g, eluting with DMA80 in DCM 0-50%) to afford (S)-(1-(7-(piperazin-1-ylmethyl)-4-(1-(3,4,5-trimethoxyphenyl)-1H-imidazol-4-ylamino)pyrrolo[1,2-f][1,2,4]triazin-2-yl)pyrrolidin-2-yl)methanol (122a) (22 mg, 39% yield) as a yellow solid; $^1$H NMR (300 MHz, DMSO-$d_6$) δ 10.45 (s, 1H, $D_2O$ exchangeable), 8.23 (d, J=1.5 Hz, 1H), 7.97 (d, J=1.7 Hz, 1H), 7.12 (dd, J=4.5, 2.1 Hz, 1H), 6.95 (s, 2H), 6.32 (d, J=4.4 Hz, 1H), 4.93-4.72 (m, 1H, $D_2O$ exchangeable), 4.32-4.13 (m, 1H), 3.87 (s, 6H), 3.80-3.70 (m, 3H), 3.68 (s, 3H), 3.66-3.52 (m, 1H), 3.54-3.24 (m, 2H), 2.71-2.59 (m, 4H), 2.41-2.27 (m, 4H), 2.10-1.82 (m, 4H); MS (ES+): 564.7 (M+1); MS (ES−): 598.9 (M+Cl); HPLC purity: 98.11%.

Preparation of (S)-1-(2-hydroxy-5-(4-((2-(2-(hydroxymethyl)pyrrolidin-1-yl)pyrrolo[2,1-f][1,2,4]triazin-4-yl)amino)-1H-imidazol-1-yl)phenyl)ethanone (123c)

Step-1: Preparation of 1-(5-(4-((2-chloropyrrolo[2,1-f][1,2,4]triazin-4-yl)amino)-1H-imidazol-1-yl)-2-methoxyphenyl)ethanone (123b)

Compound 123b was prepared according to the procedure reported in Scheme 1 from 2,4-dichloropyrrolo[1,2-f][1,2,4]triazine (4a) (240 mg, 1.30 mmol) in 2-Propanol (10 mL) using DIPEA (0.68 mL, 3.89 mmol) and 1-(5-(4-amino-1H-imidazol-1-yl)-2-methoxyphenyl)ethanone hydrochloride (123a) (0.3 g, 1.3 mmol). This gave after work up and purification by flash column chromatography [silica gel, (12 g) eluting with DCM and methanol (0 to 50%)] 1-(5-(4-((2-chloropyrrolo[2,1-f][1,2,4]triazin-4-yl)amino)-1H-imidazol-1-yl)-2-methoxyphenyl)ethanone (123b) (0.35 g, 71% yield) as a brown solid; $^1$H NMR (300 MHz, DMSO-$d_6$): δ 11.41-11.28 (m, 1H), 8.19 (t, J=2.1 Hz, 1H), 7.91-7.79 (m, 2H), 7.76 (dt, J=5.9, 2.4 Hz, 2H), 7.45-7.31 (m, 2H), 6.72 (q, J=2.6 Hz, 1H), 3.96 (d, J=2.5 Hz, 3H), 2.59 (d, J=2.6 Hz, 3H). MS (ES+): 405.4 (M+Na); MS (ES−): 381.4, 383.4 (M−1).

Step-2: Preparation of (S)-1-(2-hydroxy-5-(4-((2-(2-(hydroxymethyl)pyrrolidin-1-yl)pyrrolo[2,1-f][1,2,4]triazin-4-yl)amino)-1H-imidazol-1-yl)phenyl)ethanone (123c)

Compound 123c was prepared from 1-(5-(4-((2-chloropyrrolo[2,1-f][1,2,4]triazin-4-yl)amino)-1H-imidazol-1-yl)-2-methoxyphenyl)ethanone (123b) (100 mg, 0.26 mmol), (S)-pyrrolidin-2-ylmethanol (0.08 mL, 0.78 mmol), and DIPEA (0.14 mL, 0.78 mmol) in NMP (1.5 mL) according to the procedure reported in Scheme 2. This gave after workup and purification by reverse phase flash chromatography [(silica gel C-18, 24 g), eluting with acetonitrile and 0.1% HCl water], followed by lyophilization (S)-1-(2-hydroxy-5-(4-((2-(2-(hydroxymethyl)pyrrolidin-1-yl)pyrrolo[2,1-f][1,2,4]triazin-4-yl)amino)-1H-imidazol-1-yl)phenyl)ethanone (123c) (10 mg, 10% yield) HCl salt as a white solid; $^1$H NMR (300 MHz, DMSO-$d_6$) δ 11.92 (s, 1H), 10.63 (s, 1H), 8.37 (s, 1H), 8.09 (d, J=2.8 Hz, 1H), 8.00 (s, 1H), 7.92 (dd, J=8.9, 2.7 Hz, 1H), 7.41 (t, J=2.0 Hz, 1H), 7.17-7.07 (m, 2H), 6.41 (dd, J=4.4, 2.4 Hz, 1H), 4.27-4.12 (m, 2H), 3.73 (dd, J=10.0, 3.5 Hz, 1H), 3.50 (s, 1H), 3.45-3.26 (m, 2H), 2.75 (s, 3H), 2.10-1.81 (m, 4H). MS (ES+): 434.5 (M+1); MS (ES−): 432.5 (M−1), 468.6 (M+Cl). HPLC purity: 88.85%.

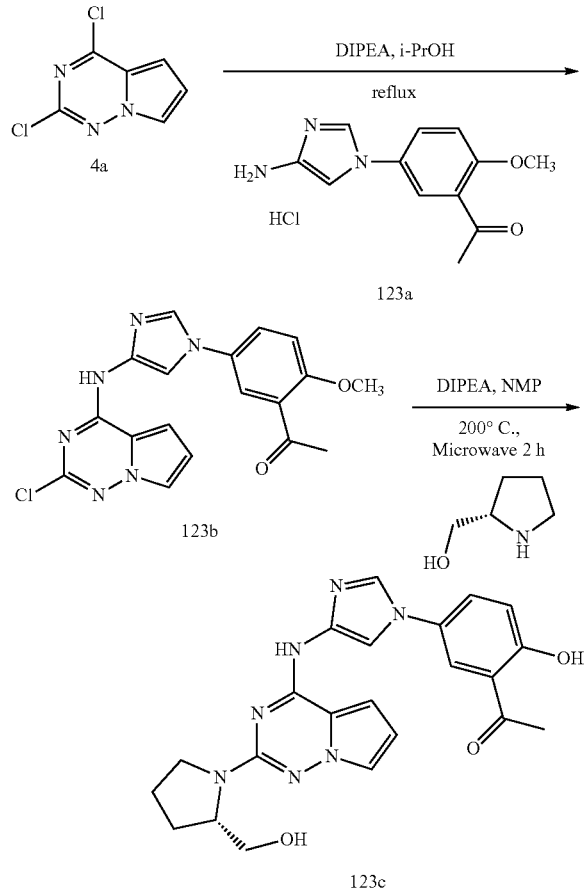

Scheme 123

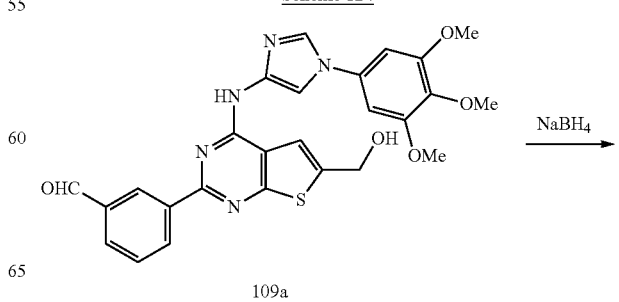

Scheme 124

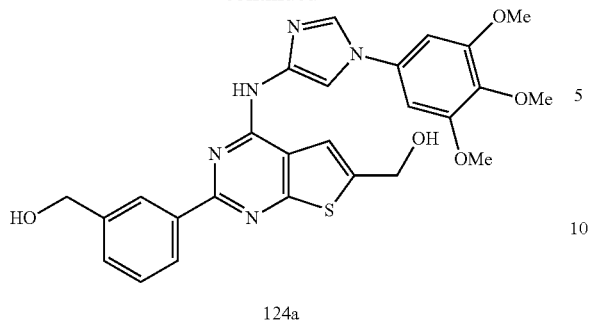

124a

Preparation of (3-(6-(hydroxymethyl)-4-((1-(3,4,5-trimethoxyphenyl)-1H-imidazol-4-yl)amino)thieno[2,3-d]pyrimidin-2-yl)phenyl)methanol (124a)

Compound 124a was prepared from 3-(6-(hydroxymethyl)-4-((1-(3,4,5-trimethoxyphenyl)-1H-imidazol-4-yl)amino)thieno[2,3-d]pyrimidin-2-yl)benzaldehyde (109a) (50 mg, 0.1 mmol) according to the procedure reported in step-4 of Scheme 70 using NaBH$_4$ (4 mg, 0.1 mmol) in MeOH (10 mL). This gave after workup (3-(6-(hydroxymethyl)-4-((1-(3,4,5-trimethoxyphenyl)-1H-imidazol-4-yl)amino)thieno[2,3-d]pyrimidin-2-yl)phenyl)methanol (124a) (0.03 g, 58% yield) as a white solid; $^1$H NMR (300 MHz, DMSO-d$_6$) δ 10.54 (s, 1H), 8.41 (s, 1H), 8.33 (s, 1H), 8.26 (d, J=1.7 Hz, 1H), 8.18 (s, 1H), 7.91 (s, 1H), 7.44 (d, J=4.5 Hz, 2H), 7.01 (s, 2H), 5.79 (s, 1H), 5.30 (s, 1H), 4.74 (s, 2H), 4.59 (s, 2H), 3.91 (s, 6H), 3.71 (s, 3H); MS (ES+): 501.6 (M−18); HPLC purity: 93.11%.

Scheme 125

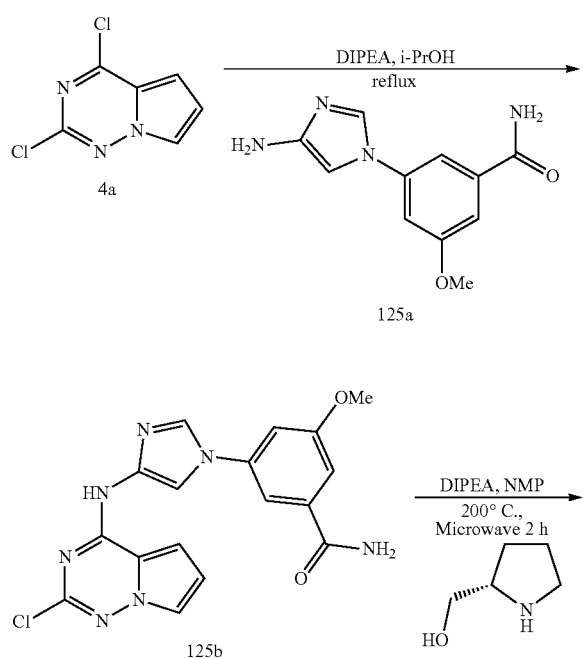

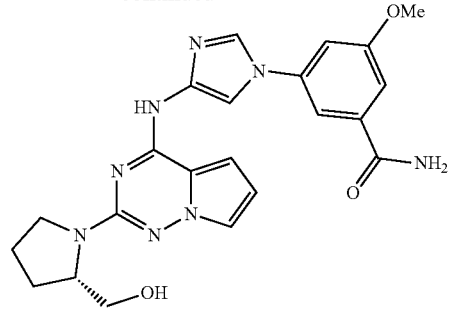

125c

Preparation of (S)-3-(4-((2-(2-(hydroxymethyl)pyrrolidin-1-yl)pyrrolo[2,1-f][1,2,4]triazin-4-yl)amino)-1H-imidazol-1-yl)-5-methoxybenzamide (125c)

Step-1: Preparation of 3-(4-((2-chloropyrrolo[2,1-f][1,2,4]triazin-4-yl)amino)-1H-imidazol-1-yl)-5-methoxybenzamide (125b)

Compound 125b was prepared according to the procedure reported in Scheme 1 from 2,4-dichloropyrrolo[1,2-f][1,2,4]triazine (4a) (350 mg, 1.86 mmol) in 2-Propanol (10 mL) using DIPEA (0.98 mL, 5.58 mmol) and 3-(4-amino-1H-imidazol-1-yl)-5-methoxybenzamide (125a) (0.4 g, 1.86 mmol). This gave after work up and purification by flash column chromatography [silica gel, (12 g) eluting with DCM and methanol (0 to 50%)] 3-(4-((2-chloropyrrolo[2,1-f][1,2,4]triazin-4-yl)amino)-1H-imidazol-1-yl)-5-methoxybenzamide (125b) (0.52 g, 75% yield) as a white solid; $^1$H NMR (300 MHz, DMSO-d$_6$): δ 11.34 (s, 1H), 8.38-8.28 (m, 1H), 8.17 (s, 1H), 7.95 (d, J=1.5 Hz, 1H), 7.78 (dd, J=2.6, 1.5 Hz, 1H), 7.69 (t, J=1.6 Hz, 1H), 7.60 (s, 1H), 7.45 (t, J=1.7 Hz, 1H), 7.40 (t, J=2.3 Hz, 2H), 6.73 (dd, J=4.4, 2.6 Hz, 1H), 3.90 (s, 3H). MS (ES+): 384.2, 386.5 (M+1), 406.3 (M+Na); MS (ES−): 382.4, 384.4 (M−1).

Step-2: Preparation of (S)-3-(4-((2-(2-(hydroxymethyl)pyrrolidin-1-yl)pyrrolo[2,1-f][1,2,4]triazin-4-yl)amino)-1H-imidazol-1-yl)-5-methoxybenzamide (125c)

Compound 125c was prepared from 3-(4-((2-chloropyrrolo[2,1-f][1,2,4]triazin-4-yl)amino)-1H-imidazol-1-yl)-5-methoxybenzamide (125b) (100 mg, 0.26 mmol), (S)-pyrrolidin-2-ylmethanol (0.08 mL, 0.78 mmol), and DIPEA (0.14 mL, 0.78 mmol) in NMP (1.5 mL) according to the procedure reported in Scheme 2. This gave after workup and purification by flash chromatography [silica gel (4 g), eluting with ethyl acetate/methanol (9:1) in hexane from 0 to 100%], (S)-3-(4-((2-(2-(hydroxymethyl)pyrrolidin-1-yl)pyrrolo[2,1-f][1,2,4]triazin-4-yl)amino)-1H-imidazol-1-yl)-5-methoxybenzamide (125c) (14 mg, 12% yield) as a white solid; $^1$H NMR (300 MHz, DMSO-d$_6$) δ 10.56 (s, 1H), 8.32 (dd, J=4.5, 1.6 Hz, 1H), 8.10-8.00 (m, 2H), 7.70 (t, J=1.7 Hz, 1H), 7.59 (s, 1H), 7.47-7.33 (m, 3H), 7.14 (dd, J=4.4, 1.7 Hz, 1H), 6.40 (dd, J=4.4, 2.5 Hz, 1H), 4.89 (t, J=5.0 Hz, 1H), 4.28-4.15 (m, 1H), 3.89 (s, 3H), 3.82-3.69 (m, 1H), 3.61-3.47 (m, 1H), 3.48-3.34 (m, 2H), 2.11-1.82 (m, 4H); MS (ES+): 449.5 (M+1); MS (ES−): 447.5 (M−1). HPLC purity: 87.51%.

Scheme 126

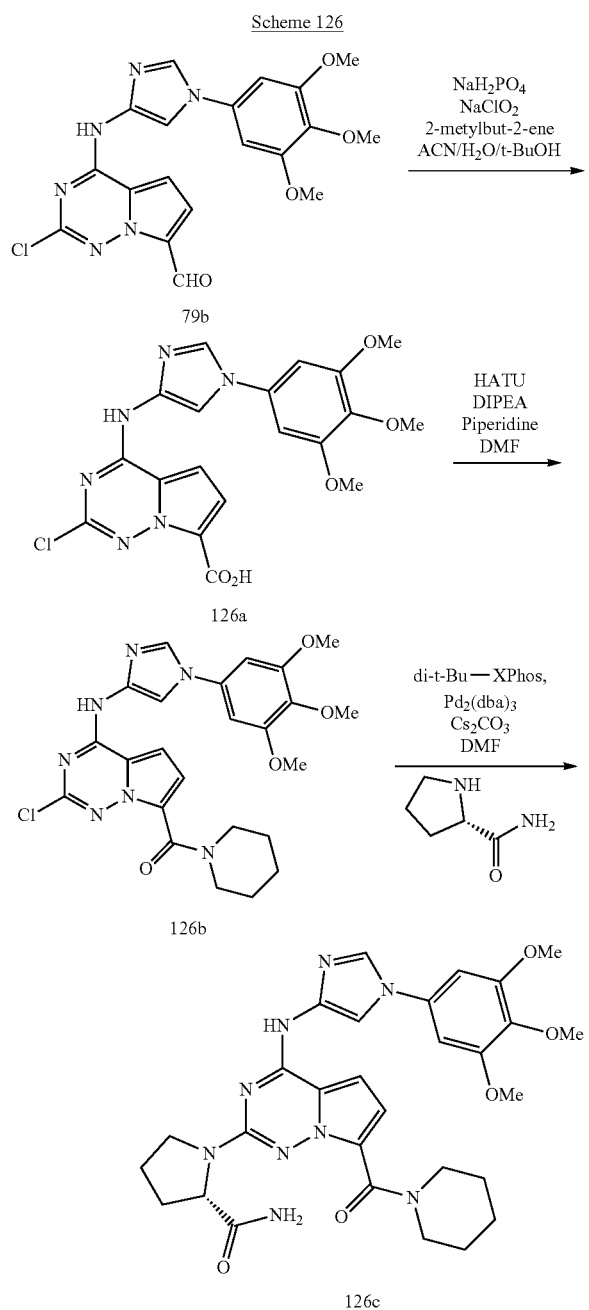

Preparation of (S)-1-(7-(piperidine-1-carbonyl)-4-((1-(3,4,5-trimethoxyphenyl)-1H-imidazol-4-yl)amino)pyrrolo[2,1-f][1,2,4]triazin-2-yl)pyrrolidine-2-carboxamide (126c)

Step-1: Preparation of 2-chloro-4-((1-(3,4,5-trimethoxyphenyl)-1H-imidazol-4-yl)amino)pyrrolo[2,1-f][1,2,4]triazine-7-carboxylic acid (126a)

To a solution of 2-chloro-4-(1-(3,4,5-trimethoxyphenyl)-1H-imidazol-4-ylamino)pyrrolo[1,2-f][1,2,4]triazine-7-carbaldehyde (79b) (1 g, 2.33 mmol) in acetonitrile (4 ml), t-BuOH (28 mL), Water (4 mL) was added sodium dihydrogenphosphate (0.56 g, 4.66 mmol) and 2-methylbut-2-ene (2.63 mL, 23.32 mmol). The reaction mixture was cooled with ice-water bath and added a solution of sodium chlorite (1.055 g, 11.66 mmol) in Water (4 mL). The reaction mixture was allowed to warm to room temperature overnight and diluted with water. The solid obtained was collected by filtration dried in air to afford 2-chloro-4-((1-(3,4,5-trimethoxyphenyl)-1H-imidazol-4-yl)amino)pyrrolo[2,1-f][1,2,4]triazine-7-carboxylic acid (126a) (1.037 g, 100% yield, contaminated with 30% starting material 79b based on NMR data) as a white solid, which was used directly for next step without further purification; $^1$H NMR (300 MHz, DMSO-$d_6$) δ 11.77, 11.55 (2s, 1H), 8.25 (dd, J=4.8, 1.6 Hz, 1H), 7.93 (dd, J=5.2, 1.6 Hz, 1H), 7.49 (dd, J=14.2, 4.8 Hz, 1H), 7.32 (dd, J=20.8, 4.8 Hz, 1H), 6.95 (s, 2H), 3.88 (s, 6H), 3.70 (s, 3H).

Step 2: Preparation of (2-chloro-4-((1-(3,4,5-trimethoxyphenyl)-1H-imidazol-4-yl)amino)pyrrolo[2,1-f][1,2,4]triazin-7-yl)(piperidin-1-yl)methanone (126b)

To a solution of 2-chloro-4-((1-(3,4,5-trimethoxyphenyl)-1H-imidazol-4-yl)amino)pyrrolo[2,1-f][1,2,4]triazine-7-carboxylic acid (126a) (0.75 g, 1.69 mmol) and piperidine (0.2 mL, 2.02 mmol) in DMF (50 mL) was added HATU (769 mg, 2.02 mmol) and DIPEA (0.883 mL, 5.06 mmol), stirred at room temperature overnight and diluted with EtOAc (200 mL). The organic layer was washed with water, brine, dried, filtered and concentrated in vacuum. The residue obtained was purified twice by flash column chromatography [silica (40 g), eluting with DMA80 in DCM from 0 to 30%] followed by [silica (40 g), eluting with EtOAc/MeOH (9:1) in hexane from 0 to 100%] to afford (2-chloro-4-((1-(3,4,5-trimethoxyphenyl)-1H-imidazol-4-yl)amino)pyrrolo[2,1-f][1,2,4]triazin-7-yl)(piperidin-1-yl)methanone (126b) (219 mg, 25% yield) as a yellow solid; $^1$H NMR (300 MHz, DMSO-$d_6$) δ 11.46 (s, 1H), 8.22 (d, J=1.6 Hz, 1H), 7.90 (d, J=1.6 Hz, 1H), 7.44 (d, J=4.6 Hz, 1H), 6.94 (s, 2H), 6.85 (d, J=4.6 Hz, 1H), 3.87 (s, 6H), 3.69 (s, 3H), 3.69-3.58 (m, 2H), 3.26-3.04 (m, 2H), 1.77-1.39 (m, 6H); MS (ES+): 512.5 (M+1), 534.5 (M+1); MS (ES-): 510.5 (M-1).

Step 3: Preparation of (S)-1-(7-(piperidine-1-carbonyl)-4-((1-(3,4,5-trimethoxyphenyl)-1H-imidazol-4-yl)amino)pyrrolo[2,1-f][1,2,4]triazin-2-yl)pyrrolidine-2-carboxamide (126c)

Compound 126c was prepared from (2-chloro-4-((1-(3,4,5-trimethoxyphenyl)-1H-imidazol-4-yl)amino)pyrrolo[2,1-f][1,2,4]triazin-7-yl)(piperidin-1-yl)methanone (126b) (253 mg, 0.49 mmol), (S)-pyrrolidine-2-carboxamide (169 mg, 1.48 mmol), (di-t-Bu-XPhos) (32 mg, 0.074 mmol), Pd$_2$(dba)$_3$ (32 mg, 0.035 mmol) and Cs$_2$CO$_3$ (483 mg, 1.48 mmol) in PhMe (5 mL) according to the procedure reported in step-3 of Scheme 101. This gave after workup and purification by flash chromatography (Silica gel 24 g, eluting with MeOH in DCM from 0 to 10%), followed by purification by reverse phase chromatography [(silica gel C-18, 24 g) eluting with 0.1% TFA in acetonitrile and 0.1% TFA in water] (S)-1-(7-(piperidine-1-carbonyl)-4-((1-(3,4,5-trimethoxyphenyl)-1H-imidazol-4-yl)amino)pyrrolo[2,1-f][1,2,4]triazin-2-yl)pyrrolidine-2-carboxamide (126c) (6 mg, 2% yield) TFA salt as a white solid; $^1$H NMR (300 MHz, DMSO-$d_6$) δ 10.65 (s, 1H, D$_2$O exchangeable), 8.26 (s, 1H), 7.95 (s, 1H), 7.24 (s, 2H, 1H D$_2$O exchangeable), 7.15-6.95 (m, 3H, 1H D$_2$O exchangeable), 6.55 (s, 1H), 4.52-4.27 (m, 1H), 3.92 (s, 6H), 3.86-3.70 (m, 2H), 3.68 (s, 3H), 3.64-3.36

(m, 2H), 3.34-3.01 (m, 2H), 2.31-1.79 (m, 4H), 1.72-1.29 (m, 6H); $^{19}$F NMR (282 MHz, DMSO-d$_6$) δ −74.12; MS (ES+): 590.6 (M+1), 612.6 (M+Na); MS (ES−): 624.0 (M+Cl); HPLC purity: 83.3%; Hydrochloride salt of compound 126c was obtained by purification of crude reaction mixture from step-2 above by reverse phase flash chromatography [(silica gel C-18, 24 g) eluting with acetonitrile and 0.1% HCl in water] followed by lyophilization; $^1$H NMR (300 MHz, DMSO-d$_6$): δ 11.10 (s, 1H), 8.83 (s, 1H), 8.04 (s, 1H), 7.29 (s, 1H), 7.22 (d, J=4.6 Hz, 1H), 7.17 (s, 2H), 7.03 (s, 1H), 6.60 (d, J=4.5 Hz, 1H), 4.38 (d, J=8.6 Hz, 1H), 4.06-2.97 (m, 15H), 2.28-1.79 (m, 4H), 1.69-1.32 (m, 6H). MS (ES−): 588.3 (M−1). HPLC purity: 94.09%.

added saturated aqueous NaHCO$_3$ (20 mL) and extracted with chloroform (2×30 mL). The organic layers were combined washed with brine (30 mL), dried, filtered and concentrated in vacuum. The residue obtained was purified by flash column chromatography [silica gel, eluting with hexanes/ethyl acetate (1:0 to 2:1)] to afford 3-(4-((2-chloropyrrolo[2,1-f][1,2,4]triazin-4-yl)amino)-1H-imidazol-1-yl)-5-methoxybenzonitrile (127a) (31 mg, 59% yield) as a white solid; $^1$H NMR (300 MHz, DMSO-d$_6$): δ 11.32 (s, 1H), 8.38 (d, J=1.6 Hz, 1H), 7.98 (d, J=1.6 Hz, 1H), 7.88-7.73 (m, 2H), 7.59 (d, J=2.1 Hz, 1H), 7.49 (t, J=1.6 Hz, 1H), 7.39 (s, 1H), 6.73 (dd, J=4.4, 2.6 Hz, 1H), 3.91 (s, 3H). MS (ES+): 366.4; MS (ES−): 364.4.

Step-2: Preparation of (S)-3-hydroxy-5-(4-((2-(2-(hydroxymethyl)pyrrolidin-1-yl)pyrrolo[2,1-f][1,2,4]triazin-4-yl)amino)-1H-imidazol-1-yl)benzonitrile (127b)

Compound 127b was prepared from 3-(4-((2-chloropyrrolo[2,1-f][1,2,4]triazin-4-yl)amino)-1H-imidazol-1-yl)-5-methoxybenzonitrile (127a) (100 mg, 0.27 mmol), (S)-pyrrolidin-2-ylmethanol (0.08 mL, 0.78 mmol), and DIPEA (0.14 mL, 0.78 mmol) in NMP (1.5 mL) according to the procedure reported in Scheme 2. This gave after workup and purification by flash chromatography [silica (4 g), eluting with ethyl acetate/methanol (9:1) in hexane from 0 to 100%] (S)-3-hydroxy-5-(4-((2-(2-(hydroxymethyl)pyrrolidin-1-yl)pyrrolo[2,1-f][1,2,4]triazin-4-yl)amino)-1H-imidazol-1-yl)benzonitrile (127b) (10 mg, 9% yield) as a white solid; $^1$H NMR (300 MHz, DMSO-d$_6$) δ 10.76-10.58 (m, 1H), 10.54 (s, 1H), 8.29 (s, 1H), 7.93 (s, 1H), 7.70 (s, 1H), 7.45-7.35 (m, 2H), 7.19-7.07 (m, 2H), 6.44-6.34 (m, 1H), 4.96-4.81 (m, 1H), 4.25-4.08 (m, 1H), 3.81-3.68 (m, 1H), 3.58-3.42 (m, 1H), 3.44-3.33 (m, 1H), 2.23-1.82 (m, 4H); MS (ES+): 417.5 (M+1), 439.5 (M+Na); MS (ES−): 415.5 (M−1).

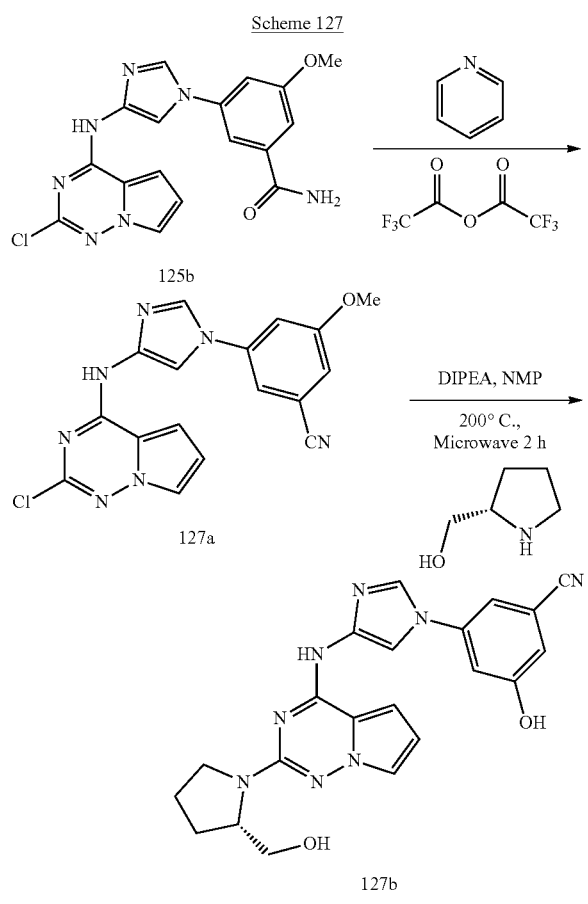

Preparation of (S)-3-hydroxy-5-(4-((2-(2-(hydroxymethyl)pyrrolidin-1-yl)pyrrolo[2,1-f][1,2,4]triazin-4-yl)amino)-1H-imidazol-1-yl)benzonitrile (127b)

Step-1: Preparation of 3-(4-((2-chloropyrrolo[2,1-f][1,2,4]triazin-4-yl)amino)-1H-imidazol-1-yl)-5-methoxybenzonitrile (127a)

To a solution of 3-(4-((2-chloropyrrolo[2,1-f][1,2,4]triazin-4-yl)amino)-1H-imidazol-1-yl)-5-methoxybenzamide (125b) (0.06 g, 0.14 mmol) in THF (5 mL) was added pyridine (0.02 mL, 0.29 mmol), 2,2,2-trifluoroacetic anhydride (0.02 mL, 0.17 mmol) and stirred at room temperature for 1 h. The mixture was quenched with water (1 mL) and concentrated in vacuum to dryness. To the residue was

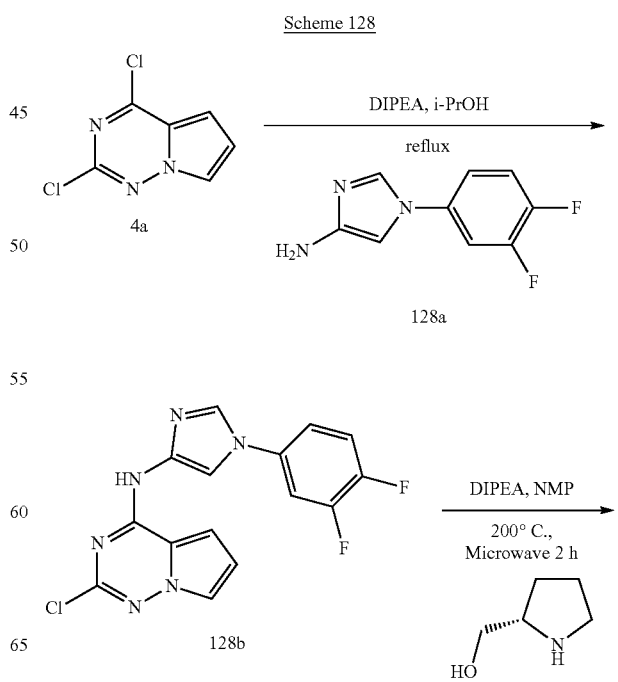

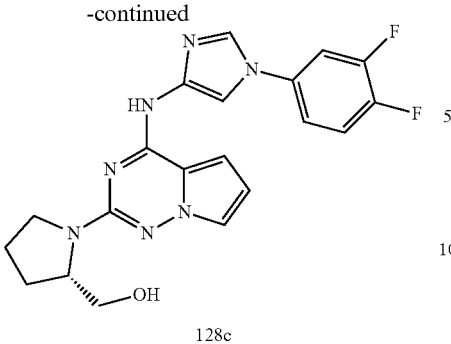

128c

Preparation of (S)-(1-(4-((1-(3,4-difluorophenyl)-1H-imidazol-4-yl)amino)pyrrolo[2,1-f][1,2,4]triazin-2-yl)pyrrolidin-2-yl)methanol (128c)

Step-1: Preparation of 2-chloro-N-(1-(3,4-difluorophenyl)-1H-imidazol-4-yl)pyrrolo[2,1-f][1,2,4]triazin-4-amine (128b)

Compound 128b was prepared according to the procedure reported in Scheme 1 from 2,4-dichloropyrrolo[1,2-f][1,2,4]triazine (4a) (366 mg, 1.95 mmol) in 2-Propanol (10 mL) using DIPEA (1.02 mL, 5.84 mmol) and 1-(3,4-difluorophenyl)-1H-imidazol-4-amine (128a) (0.38 g, 1.95 mmol). This gave after work up 2-chloro-N-(1-(3,4-difluorophenyl)-1H-imidazol-4-yl)pyrrolo[2,1-f][1,2,4]triazin-4-amine (128b) (566 mg, 84% yield) as an off-white solid; $^1$H NMR (300 MHz, DMSO-$d_6$) δ 11.34 (s, 1H, D$_2$O exchangeable), 8.26 (d, J=1.6 Hz, 1H), 7.95 (ddd, J=11.9, 7.0, 2.8 Hz, 1H), 7.90 (d, J=1.7 Hz, 1H), 7.78 (dd, J=2.6, 1.5 Hz, 1H), 7.65 (dt, J=10.4, 8.8 Hz, 1H), 7.58-7.48 (m, 1H), 7.40 (d, J=4.4 Hz, 1H), 6.72 (dd, J=4.4, 2.6 Hz, 1H); $^{19}$F NMR (282 MHz, DMSO-$d_6$) δ −135.50, −135.68 (m), −139.73, −141.11 (m); $^{19}$F CPD NMR (282 MHz, DMSO-$d_6$) δ −135.59 (d, J=22.9 Hz), −140.48 (d, J=22.9 Hz); MS (ES+): 347.3 (M+1); MS (ES−): 345.3 (M−1); HPLC purity: 99.39%.

Step-2: Preparation of (S)-(1-(4-((1-(3,4-difluorophenyl)-1H-imidazol-4-yl)amino)pyrrolo[2,1-f][1,2,4]triazin-2-yl)pyrrolidin-2-yl)methanol (128c)

Compound 128c was prepared from 2-chloro-N-(1-(3,4-difluorophenyl)-1H-imidazol-4-yl)pyrrolo[2,1-f][1,2,4]triazin-4-amine (128b) (100 mg, 0.29 mmol), (S)-pyrrolidin-2-ylmethanol (146 mg, 1.44 mmol), and DIPEA (0.15 mL, 0.87 mmol) in NMP (1.5 mL) according to the procedure reported in Scheme 2. This gave after workup and purification by reverse phase flash chromatography [(silica gel C-18, 24 g), eluting with 0.1% TFA in acetonitrile and 0.1% TFA in water], followed by conversion to free base using saturated sodium bicarbonate gave (S)-(1-(4-((1-(3,4-difluorophenyl)-1H-imidazol-4-yl)amino)pyrrolo[2,1-f][1,2,4]triazin-2-yl)pyrrolidin-2-yl)methanol (128c) (24 mg, 20% yield) as a yellow solid; $^1$H NMR (300 MHz, DMSO-$d_6$) δ 10.55 (s, 1H, D$_2$O exchangeable), 8.27 (d, J=1.6 Hz, 1H), 8.07-7.96 (m, 1H), 7.93 (d, J=1.6 Hz, 1H), 7.65 (dt, J=5.7, 2.9 Hz, 1H), 7.63-7.47 (m, 1H), 7.40 (dd, J=2.4, 1.6 Hz, 1H), 7.15 (dd, J=4.4, 1.7 Hz, 1H), 6.39 (dd, J=4.4, 2.4 Hz, 1H), 5.01 (t, J=4.7 Hz, 1H, D$_2$O exchangeable), 4.30-4.08 (m, 1H), 3.88-3.69 (m, 1H), 3.58-3.43 (m, 1H), 3.45-3.20 (m, 2H), 2.17-1.77 (m, 4H); $^{19}$F NMR (282 MHz, DMSO-$d_6$) δ −133.86--137.91 (m), −139.79--143.07 (m); $^{19}$FCPD NMR (282 MHz, DMSO-$d_6$) δ −135.89 (d, J=22.6 Hz), −141.35 (d, J=22.6 Hz); MS (ES+): 412.4 (M+1); MS (ES−): 410.4 (M−1), 446.3 (M+Cl); HPLC purity: 97.91%.

Scheme 129

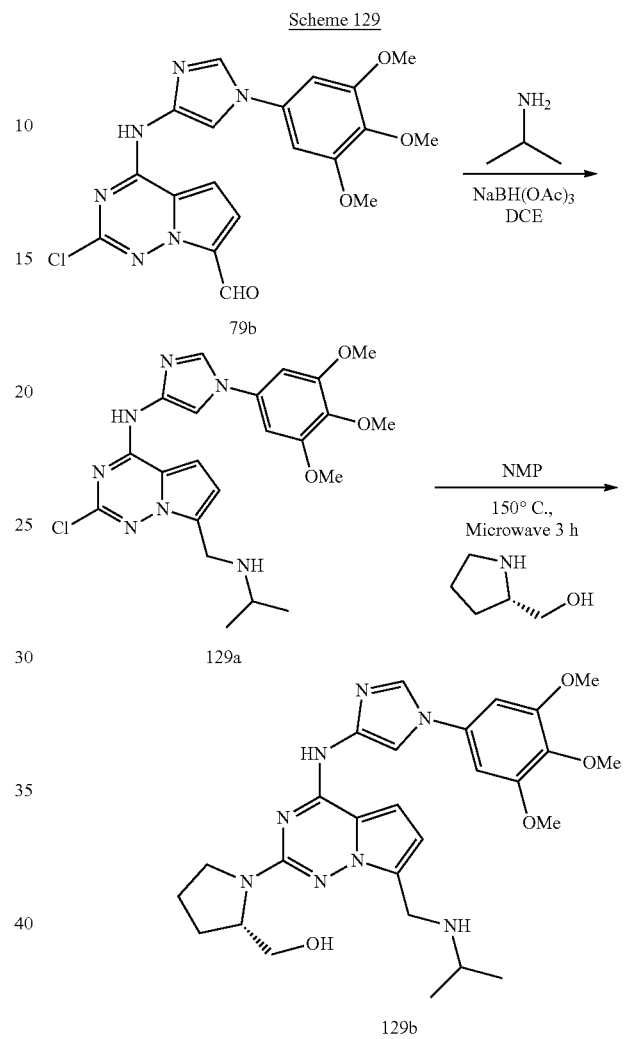

Preparation of (S)-(1-(7-((isopropylamino)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (129b)

Step-1: Preparation of 2-chloro-7-((isopropylamino)methyl)-N-(1-(3,4,5-trimethoxyphenyl)-1H-imidazol-4-yl)pyrrolo[2,1-f][1,2,4]triazin-4-amine (129a)

Compound 129a was prepared according to the procedure reported for reductive amination in step-1 of Scheme 105 from 2-chloro-4-(1-(3,4,5-trimethoxyphenyl)-1H-imidazol-4-ylamino)pyrrolo[1,2-f][1,2,4]triazine-7-carbaldehyde (79b) (400 mg, 0.93 mmol) in dichloroethane (10 mL) using 1-isopropylamine (0.24 mL, 2.8 mmol), acetic acid (0.064 mL) and NaBH(OAc)$_3$ (297 mg, 1.4 mmol). This gave after workup and purification by flash column chromatography (Silica gel 12 g, eluting with MeOH in DCM from 0% to 50%) 2-chloro-7-((isopropylamino)methyl)-N-(1-(3,4,5-trimethoxyphenyl)-1H-imidazol-4-yl)pyrrolo[2,1-f][1,2,4]

triazin-4-amine (129a) (217 mg, 49% yield) as a solid; $^1$HNMR (300 MHz, CDCl$_3$) δ 8.98 (br, s, 1H), 7.91 (d, J=1.3 Hz, 1H), 7.72-7.57 (m, 1H), 6.80 (d, J=4.5 Hz, 1H), 6.66 (d, J=0.9 Hz, 2H), 6.63 (d, J=4.5 Hz, 1H), 4.13 (s, 2H), 3.94 (s, 6H), 3.89 (s, 3H), 2.95-2.74 (m, 1H), 1.79 (br, s, 1H), 1.13 (d, J=6.2 Hz, 6H); MS (ES+): 472.5 (M+1), 494.5 (M+Na); MS (ES−): 470.5 (M−1).

Step 2: Preparation of (S)-(1-(7-((isopropylamino)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (129b)

Compound 129b was prepared from 2-chloro-7-((isopropylamino)methyl)-N-(1-(3,4,5-trimethoxyphenyl)-1H-imidazol-4-yl)pyrrolo[2,1-f][1,2,4]triazin-4-amine (129a) (103 mg, 0.22 mmol), (S)-pyrrolidin-2-ylmethanol (221 mg, 2.18 mmol) in NMP (1.5 mL) according to the procedure reported in Scheme 2. This gave after workup and purification by flash chromatography [silica gel (4 g), eluting with DMA80 in DCM from 0 to 50%], followed by purification by reverse phase flash chromatography [(silica gel C-18, 24 g) eluting with acetonitrile and 0.1% HCl in water] (S)-(1-(7-((isopropylamino)methyl)-4-((1-(3,4,5-trimethoxyphenyl)-1H-imidazol-4-yl)amino)pyrrolo[2,1-f][1,2,4]triazin-2-yl)pyrrolidin-2-yl)methanol (129b) (8 mg, 7% yield) HCl salt as a yellow solid; $^1$H NMR (300 MHz, DMSO-d$_6$) (a mixture of two rotamers) δ 11.21 and 11.18 (2s, 1H), 9.17 (s, 1H), 8.85 and 8.82 (2s, 1H), 8.12-8.05 (m, 1H), 7.24 and 7.20 (2d, J=4.5 Hz, 1H), 7.10-7.01 (m, 2H), 6.77 and 6.73 (d, J=4.5 Hz, 1H), 4.66-4.52 (m, 1H), 4.45-4.29 (m, 2H), 4.22 (s, 1H), 3.98-3.12 (m, 13H), 2.13-1.68 (m, 4H), 1.35-1.28 (m, 6H); MS (ES+): 559.5 (M+Na); MS (ES−): 571.6 (M+Cl). HPLC purity: 96.89%.

Preparation (S)-1-(4-((1-(3,4,5-trimethoxyphenyl)-1H-imidazol-4-yl)amino)quinazolin-2-yl)pyrrolidine-2-carboxamide (130a)

Compound 130a was prepared according to the procedure reported in step-2 of Scheme 76 from 2-chloro-N-(1-(3,4,5-trimethoxyphenyl)-1H-imidazol-4-yl)quinazolin-4-amine (86a) (100 mg, 0.24 mmol), DIPEA (0.11 mL, 0.85 mmol), and (S)-pyrrolidine-2-carboxamide (0.15 g, 1.31 mmol) in NMP (10 mL). This gave after workup and purification by flash chromatography (silica gel, eluting with 0-80% ethyl acetate in hexanes) (S)-1-(4-((1-(3,4,5-trimethoxyphenyl)-1H-imidazol-4-yl)amino)quinazolin-2-yl)pyrrolidine-2-carboxamide (130a) (50 mg, 43%) free base as a white solid. This was re-purified by reverse phase flash column chromatography [(silica gel C-18 column 24 g), eluting with acetonitrile and 0.1% HCl water (0-50%)] followed by lyophilization to afford (S)-1-(4-((1-(3,4,5-trimethoxyphenyl)-1H-imidazol-4-yl)amino)quinazolin-2-yl)pyrrolidine-2-carboxamide (130a) (20 mgs) HCl salt as a light yellow solid; $^1$H NMR (300 MHz, DMSO-d$_6$) δ 12.29 (s, 1H), 11.65 (s, 1H), 8.77 (d, J=8.0 Hz, 1H), 8.38 (s, 1H), 8.13-7.99 (m, 1H), 7.99-7.81 (m, 1H), 7.62 (s, 1H), 7.57-7.40 (m, 2H), 7.37-7.24 (m, 1H), 7.14 (s, 2H), 4.75 (d, J=9.0 Hz, 1H), 4.10-4.01 (m, 2H), 3.94 (s, 6H), 3.69 (s, 3H), 2.40-1.95 (m, 4H) MS (ES+): 490.5 (M+1), 512.5 (M+Na); MS (ES−): 524.5 (M+Cl). HPLC purity: 98.13%.

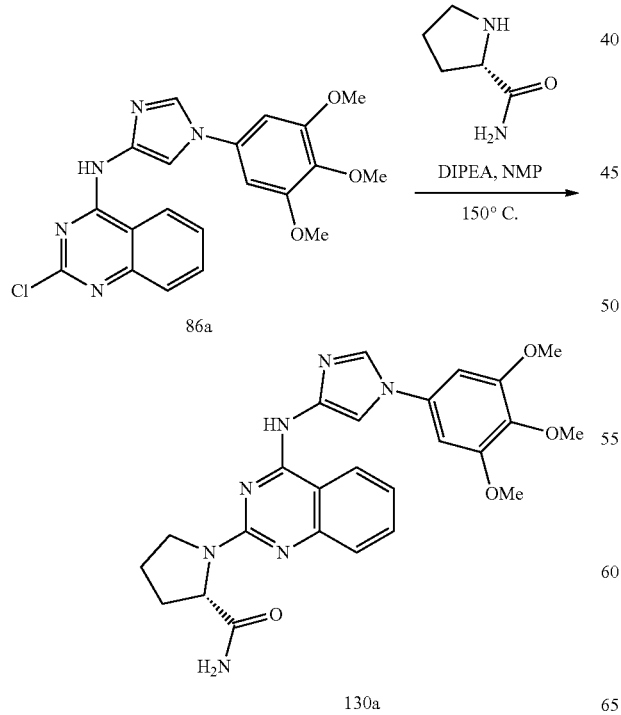

Scheme 130

86a

130a

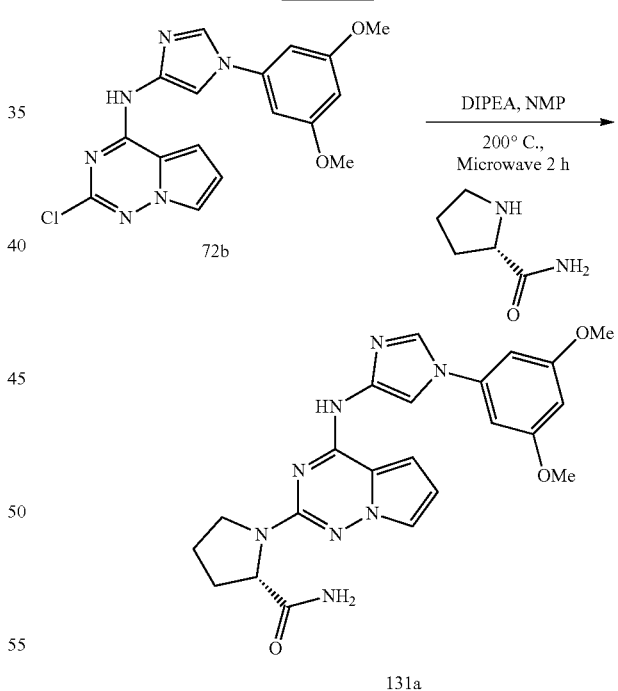

Scheme 131

72b

131a

Preparation of (S)-1-(4-((1-(3,5-dimethoxyphenyl)-1H-imidazol-4-yl)amino)pyrrolo[2,1-f][1,2,4]triazin-2-yl)pyrrolidine-2-carboxamide (131a)

Compound 131a was prepared from 2-chloro-N-(1-(3,5-dimethoxyphenyl)-1H-imidazol-4-yl)pyrrolo[2,1-f][1,2,4]triazin-4-amine (72b) (150 mg, 0.41 mmol), (S)-pyrrolidine-2-carboxamide (0.14 g, 1.21 mmol), and DIPEA (0.21 mL, 1.21 mmol) in NMP (2 mL) according to the procedure reported in Scheme 2. This gave after workup and purification by reverse phase flash chromatography [(silica gel C-18, 24 g), eluting with acetonitrile and 0.1% HCl in water], followed by lyophilization (S)-1-(4-((1-(3,5-dimethoxyphenyl)-1H-imidazol-4-yl)amino)pyrrolo[2,1-f][1,2,4]triazin-2-yl)pyrrolidine-2-carboxamide (131a) (50 mg, 25% yield) HCl salt as a white solid; $^1$H NMR (300 MHz, DMSO-$d_6$): δ 10.53 (s, 1H), 8.35 (d, J=1.5 Hz, 1H), 7.95 (s, 1H), 7.48-7.37 (m, 1H), 7.22 (s, 1H), 7.16 (dd, J=4.6, 1.7 Hz, 1H), 7.00 (s, 3H), 6.47 (t, J=2.2 Hz, 1H), 6.43 (dd, J=4.4, 2.4 Hz, 1H), 4.39 (d, J=9.0 Hz, 1H), 3.86 (s, 6H), 3.78 (m, 1H), 3.48 (m, 1H), 2.31-1.82 (m, 4H). MS (ES+): 449.4; MS (ES−): 483.3 (M+Cl). HPLC purity: 94.06%.

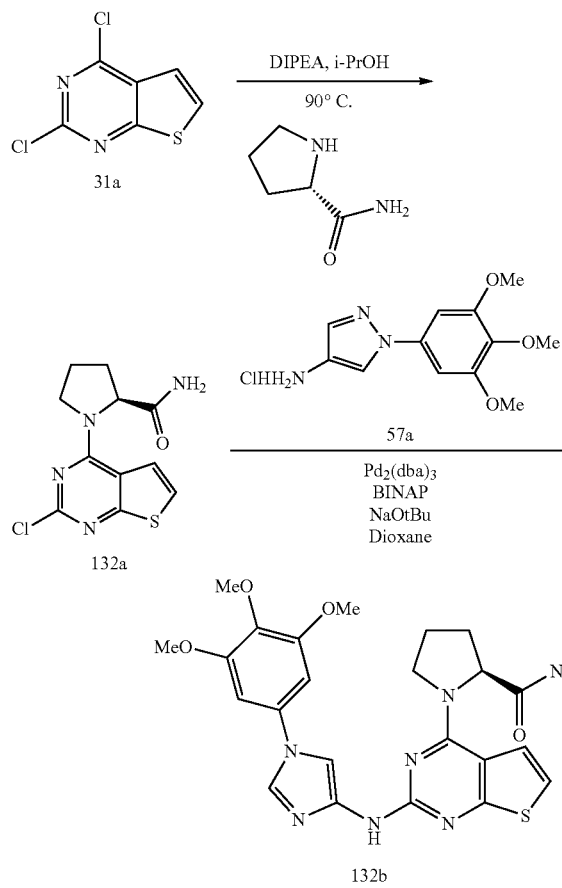

Scheme 132

Preparation of (S)-1-(2-((1-(3,4,5-trimethoxyphenyl)-1H-imidazol-4-yl)amino)thieno[2,3-d]pyrimidin-4-yl)pyrrolidine-2-carboxamide (132b)

Step-1: Preparation of (S)-1-(2-chlorothieno[2,3-d]pyrimidin-4-yl)pyrrolidine-2-carboxamide (132a)

Compound 132a was prepared from 2,4-dichlorothieno[2,3-d]pyrimidine (31a) (2 g, 9.75 mmol) in 2-Propanol (20 mL) was added (S)-pyrrolidine-2-carboxamide (1.11 g, 9.75 mmol), DIPEA (5.11 mL, 29.3 mmol) according to the procedure reported in step-1 of Scheme 96. This gave (S)-1-(2-chlorothieno[2,3-d]pyrimidin-4-yl)pyrrolidine-2-carboxamide (132a) (1.28 g, 46% yield) as a yellow solid; $^1$H NMR (300 MHz, DMSO-$d_6$): δ 7.71-7.66 (m, 1H), 7.58 (d, J=6.0 Hz, 1H), 7.52 (s, 1H), 7.07-6.97 (m, 1H), 4.63 (s, 1H), 4.19-3.77 (m, 2H), 2.25-1.86 (m, 4H). MS (ES−): 281.3, 317.3 (M+Cl).

Step-2: Preparation of (S)-1-(2-((1-(3,4,5-trimethoxyphenyl)-1H-imidazol-4-yl)amino)thieno[2,3-d]pyrimidin-4-yl)pyrrolidine-2-carboxamide (132b)

Compound 132b was prepared from (S)-1-(2-chlorothieno[2,3-d]pyrimidin-4-yl)pyrrolidine-2-carboxamide (132a) (0.3 g, 1.06 mmol), 1-(3,4,5-trimethoxyphenyl)-1H-imidazol-4-amine hydrochloride (57a) (0.3 g, 1.06 mmol), di-tert-butyl(2',4',6'-triisopropylbiphenyl-2-yl)phosphine (50 mg, 0.13 mmol), sodium 2-methylpropan-2-olate (610 mg, 6.4 mmol), Pd$_2$(dba)$_3$ (60 mg, 0.06 mmol) in anhydrous Dioxane (15 mL) according to the procedure reported in step-3 of Scheme 101. This gave after workup and purification by reverse phase flash column chromatography [(silica gel C-18, 24 g) eluting with acetonitrile and 0.1% HCl water] followed by lyophilization (S)-1-(2-((1-(3,4,5-trimethoxyphenyl)-1H-imidazol-4-yl)amino)thieno[2,3-d]pyrimidin-4-yl)pyrrolidine-2-carboxamide (132b) (0.03 g, 6% yield) HCl salt as a yellow solid; $^1$H NMR (300 MHz, DMSO-$d_6$): δ 10.18 (s, 1H), 9.29 (s, 1H), 7.96 (s, 1H), 7.60 (s, 1H), 7.48 (s, 1H), 7.31 (d, J=6.0 Hz, 1H), 7.28 (s, 2H), 7.08 (s, 1H), 4.73 (s, 1H), 4.25 (m, 1H), 4.03-3.84 (m, 7H), 3.71 (s, 3H), 2.34-1.86 (m, 4H). MS (ES+): 496.3; MS (ES−): 530.3 (M+Cl).

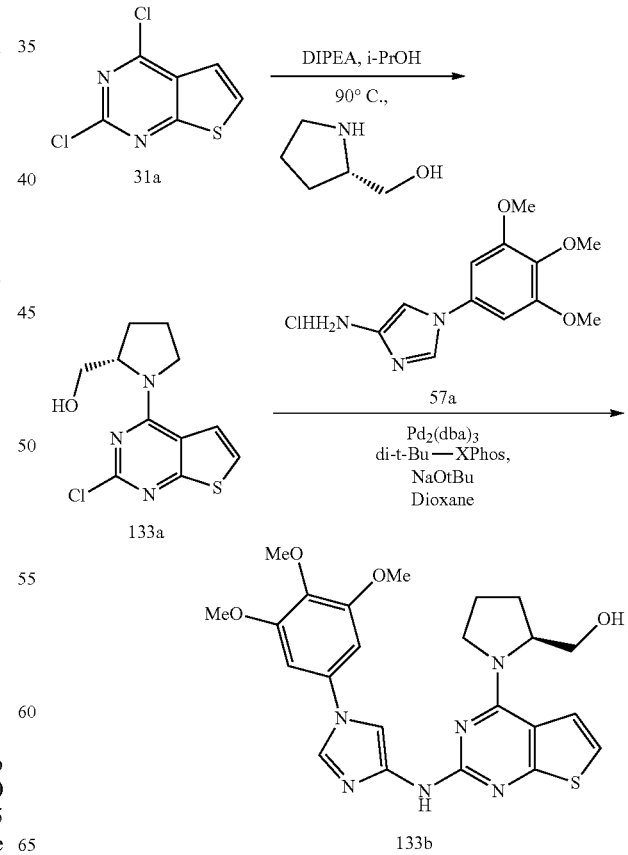

Scheme 133

Preparation of (S)-(1-(2-((1-(3,4,5-trimethoxyphenyl)-1H-imidazol-4-yl)amino)thieno[2,3-d]pyrimidin-4-yl)pyrrolidin-2-yl)methanol (133b)

Step-1: Preparation of (S)-(1-(2-chlorothieno[2,3-d]pyrimidin-4-yl)pyrrolidin-2-yl)methanol (133a) Compound 133a was prepared from 2,4-dichlorothieno[2,3-d]pyrimidine (31a) (2 g, 9.75 mmol) in 2-Propanol (20 mL), (S)-pyrrolidin-2-ylmethanol (0.96 mL, 9.75 mmol), DIPEA (5.11 mL, 29.3 mmol) according to the procedure reported in step-1 of Scheme 96. This gave (S)-(1-(2-chlorothieno[2,3-d]pyrimidin-4-yl)pyrrolidin-2-yl)methanol (133a) (1.52 g, 58% yield) as a yellow solid; $^1$H NMR (300 MHz, DMSO-$d_6$): δ 7.61 (d, J=5.3 Hz, 1H), 7.55 (d, J=6.2 Hz, 1H), 4.96-4.73 (m, 1H), 4.48-4.34 (m, 1H), 4.05-3.67 (m, 2H), 3.66-3.38 (m, 2H), 2.22-1.81 (m, 4H). MS (ES+): 292.2 (M+Na). MS (ES−): 268.3 (M−1), 304.3 (M+Cl).

Step-2: Preparation of (S)-(1-(2-((1-(3,4,5-trimethoxyphenyl)-1H-imidazol-4-yl)amino)thieno[2,3-d]pyrimidin-4-yl)pyrrolidin-2-yl)methanol (133b)

Compound 133b was prepared from (S)-(1-(2-chlorothieno[2,3-d]pyrimidin-4-yl)pyrrolidin-2-yl)methanol (133a) (0.5 g, 1.85 mmol), 1-(3,4,5-trimethoxyphenyl)-1H-imidazol-4-amine hydrochloride (57a) (0.53 g, 1.85 mmol), di-tert-butyl(2',4',6'-triisopropylbiphenyl-2-yl)phosphine (0.094 g, 0.22 mmol), sodium 2-methylpropan-2-olate (1.07 g, 11.12 mmol), Pd$_2$(dba)$_3$ (0.1 g, 0.11 mmol) in anhydrous Dioxane (15 mL) according to the procedure reported in step-3 of Scheme 101. This gave after workup and purification by reverse phase flash column chromatography [(silica gel C-18, 24 g) eluting with acetonitrile and 0.1% HCl water] followed by lyophilization (S)-(1-(2-((1-(3,4,5-trimethoxyphenyl)-1H-imidazol-4-yl)amino)thieno[2,3-d]pyrimidin-4-yl)pyrrolidin-2-yl)methanol (133b) (100 mg, 12% yield) HCl salt as a yellow solid; $^1$H NMR (300 MHz, DMSO-$d_6$): δ 10.26 (s, 1H), 9.15 (s, 1H), 7.92 (s, 1H), 7.57 (d, J=6.1 Hz, 1H), 7.32 (d, J=5.9 Hz, 1H), 7.12 (s, 2H), 4.68-4.50 (m, 1H), 4.07-3.93 (m, 1H), 3.89 (s, 6H), 3.85-3.76 (m, 1H), 3.70 (s, 3H), 3.66-3.58 (m, 1H), 3.47 (t, J=9.3 Hz, 1H), 2.20-1.83 (m, 4H). MS (ES+): 483.4 (M+1); MS (ES−): 517.3 (M+Cl). HPLC purity: 98.94%.

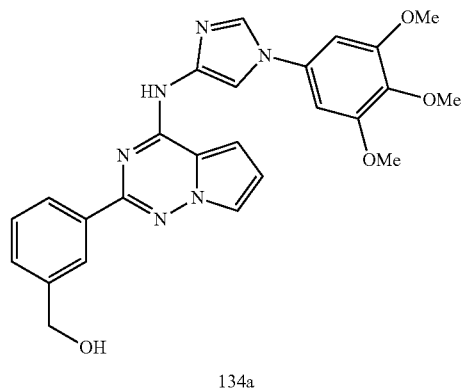

134a

Preparation of (3-(4-((1-(3,4,5-trimethoxyphenyl)-1H-imidazol-4-yl)amino)pyrrolo[2,1-f][1,2,4]triazin-2-yl)phenyl)methanol (134a)

Compound 134a was prepared from 2-chloro-N-(1-(3,4,5-trimethoxyphenyl)-1H-imidazol-4-yl)pyrrolo[2,1-f][1,2,4]triazin-4-amine (57b) (0.3 g, 0.75 mmol), using 3-(hydroxymethyl)phenylboronic acid (171 mg, 1.10 mmol), Pd(Ph$_3$P)$_4$ (86 mg, 0.075 mmol), potassium carbonate (207 mg, 1.5 mmol) in 1,4-Dioxane (8 mL) and Water (2 mL) according to the procedure reported in step-3 of Scheme 77. This gave after workup, purification by flash column chromatography [(silica gel, 12 g) eluting with ethyl acetate/MeOH (9:1) in hexane from 0-100%] then [(silica, 12 g), eluting with MeOH in DCM from 0-15%] (3-(4-((1-(3,4,5-trimethoxyphenyl)-1H-imidazol-4-yl)amino)pyrrolo[2,1-f][1,2,4]triazin-2-yl)phenyl)methanol (134a) (54 mg, 15% yield) as a white solid. $^1$H NMR (300 MHz, DMSO-$d_6$) δ 10.93 (s, 1H, D$_2$O exchangeable), 8.28 (s, 2H), 8.24-8.15 (m, 2H), 7.83 (t, J=2.0 Hz, 1H), 7.43 (d, J=4.7 Hz, 2H), 7.41-7.34 (m, 1H), 7.01 (s, 2H), 6.76-6.68 (m, 1H), 5.30 (t, J=5.7 Hz, 1H, D$_2$O exchangeable), 4.58 (d, J=5.8 Hz, 2H), 3.88 (s, 6H), 3.71 (s, 3H); MS (ES+): 495.3 (M+1); (ES−): 471.4 (M−1).

Scheme 134

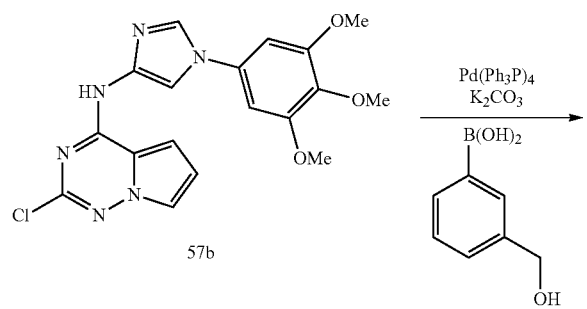

Scheme 135

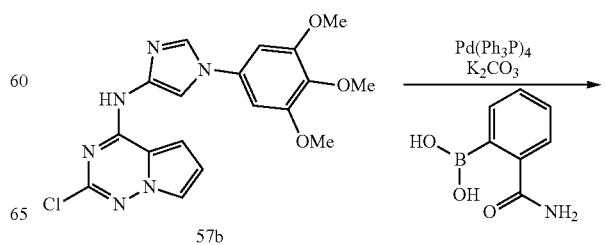

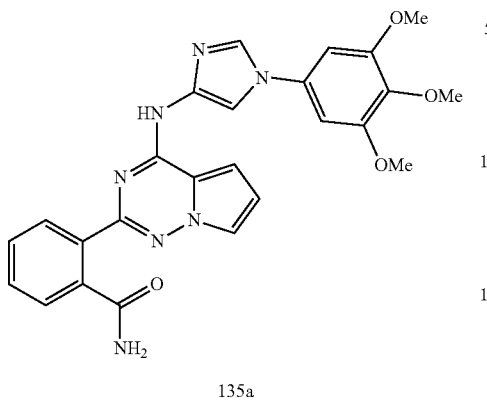

135a

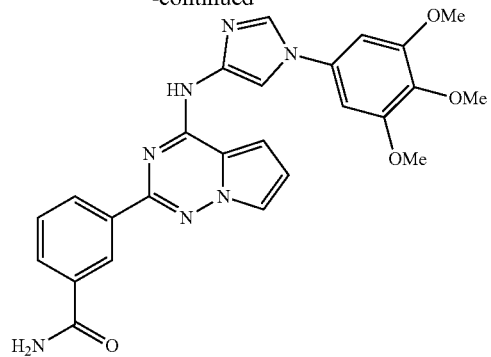

136a

Preparation of 2-(4-((1-(3,4,5-trimethoxyphenyl)-1H-imidazol-4-yl)amino)pyrrolo[2,1-f][1,2,4]triazin-2-yl)benzamide (135a)

Compound 135a was prepared from 2-chloro-N-(1-(3,4,5-trimethoxyphenyl)-1H-imidazol-4-yl)pyrrolo[2,1-f][1,2,4]triazin-4-amine (57b) (0.3 g, 0.75 mmol), using 2-carbamoylphenylboronic acid (185 mg, 1.12 mmol), Pd(Ph₃P)₄ (86 mg, 0.075 mmol), potassium carbonate (207 mg, 1.5 mmol) in 1,4-Dioxane (8 mL) and Water (2 mL) according to the procedure reported in step-3 of Scheme 77. This gave after workup, purification by flash column chromatography [(silica gel, 12 g) eluting with ethyl acetate/MeOH (9:1) in hexane from 0-70%] 2-(4-((1-(3,4,5-trimethoxyphenyl)-1H-imidazol-4-yl)amino)pyrrolo[2,1-f][1,2,4]triazin-2-yl)benzamide (135a) (26 mg, 7% yield) as an off white solid; $^1$H NMR (300 MHz, DMSO-d₆) δ 10.77 (s, 1H, D₂O exchangeable), 8.25-8.16 (m, 2H, D₂O exchangeable), 7.83-7.74 (m, 2H), 7.60 (s, 1H), 7.56-7.46 (m, 3H), 7.41-7.30 (m, 2H), 7.15 (s, 2H), 6.79-6.70 (m, 1H), 3.91 (s, 6H), 3.67 (s, 3H); MS (ES+): 486.3 (M+1); 508.3 (M+Na); HPLC purity; 95.32%

Preparation of 3-(4-((1-(3,4,5-trimethoxyphenyl)-1H-imidazol-4-yl)amino)pyrrolo[2,1-f][1,2,4]triazin-2-yl)benzamide (136a)

Compound 136a was prepared from 2-chloro-N-(1-(3,4,5-trimethoxyphenyl)-1H-imidazol-4-yl)pyrrolo[2,1-f][1,2,4]triazin-4-amine (57b) (0.3 g, 0.75 mmol), using 3-carbamoylphenylboronic acid (185 mg, 1.12 mmol), Pd(Ph₃P)₄ (86 mg, 0.075 mmol), potassium carbonate (207 mg, 1.5 mmol) in 1,4-dioxane (8 mL) and water (2 mL) according to the procedure reported in step-3 of Scheme 77. This gave after workup, 3-(4-((1-(3,4,5-trimethoxyphenyl)-1H-imidazol-4-yl)amino)pyrrolo[2,1-f][1,2,4]triazin-2-yl)benzamide (136a) (250 mg, 69% yield) as a white solid. $^1$H NMR (300 MHz, DMSO-d₆) δ 10.97 (s, 1H, D₂O exchangeable), 8.81 (d, J=2.4 Hz, 1H), 8.45 (d, J=7.9 Hz, 1H), 8.33-8.27 (m, 1H), 8.23-8.09 (m, 2H, D₂O exchangeable), 7.98 (d, J=8.0 Hz, 1H), 7.89-7.82 (m, 1H), 7.56 (t, J=7.8 Hz, 1H), 7.49-7.34 (m, 2H), 6.99 (s, 2H), 6.81-6.69 (m, 1H), 3.90 (s, 6H), 3.71 (s, 3H); MS (ES+): 508.3 (M+Na); (ES-): 484.4 (M-1); HPLC purity; 98.25%.

Scheme 137

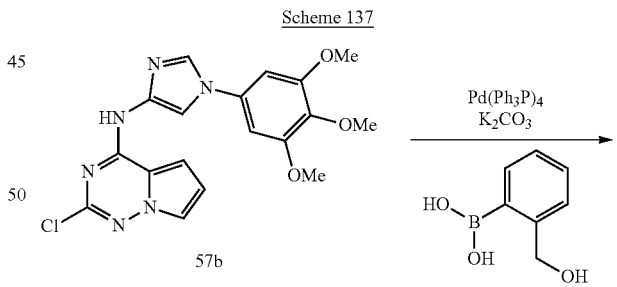

Scheme 136

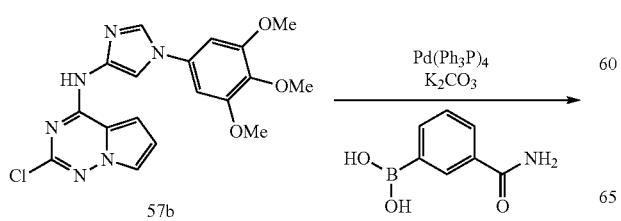

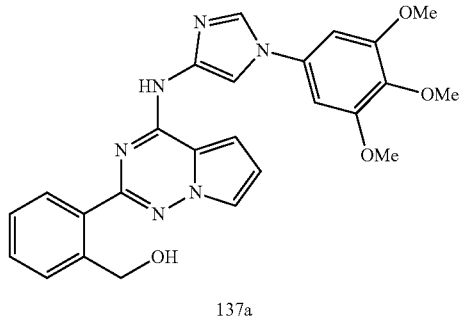

137a

Preparation of (2-(4-((1-(3,4,5-trimethoxyphenyl)-1H-imidazol-4-yl)amino)pyrrolo[2,1-f][1,2,4]triazin-2-yl)phenyl)methanol (137a)

Compound 137a was prepared from 2-chloro-N-(1-(3,4,5-trimethoxyphenyl)-1H-imidazol-4-yl)pyrrolo[2,1-f][1,2,4]triazin-4-amine (57b) (0.3 g, 0.75 mmol), using 2-(hydroxymethyl)phenylboronic acid (171 mg, 1.10 mmol), Pd(Ph$_3$P)$_4$ (86 mg, 0.075 mmol), potassium carbonate (207 mg, 1.5 mmol) in 1,4-dioxane (8 mL) and water (2 mL) according to the procedure reported in step-3 of Scheme 77. This gave after workup, purification by flash column chromatography [(silica gel, 12 g) eluting with ethyl acetate/MeOH (9:1) in hexane from 0-100%] (2-(4-((1-(3,4,5-trimethoxyphenyl)-1H-imidazol-4-yl)amino)pyrrolo[2,1-f][1,2,4]triazin-2-yl)phenyl)methanol (137a) (65 mg, 18% yield) as a white solid; $^1$H NMR (300 MHz, DMSO-d$_6$) δ 10.93 (s, 1H, D$_2$O exchangeable), 8.27 (s, 1H), 8.06 (s, 1H), 7.93 (d, J=7.6 Hz, 1H), 7.80 (s, 1H), 7.67 (d, J=7.7 Hz, 1H), 7.47 (t, J=7.5 Hz, 1H), 7.42-7.30 (m, 2H), 6.91 (s, 2H), 6.75 (t, J=3.5 Hz, 1H), 5.19 (t, J=5.6 Hz, 1H, D$_2$O exchangeable), 4.86 (d, J=5.5 Hz, 2H), 3.85 (s, 6H), 3.68 (s, 3H); MS (ES+): 495.3 (M+1); (ES−): 471.4 (M−1); HPLC purity; 97.31%.

Scheme 138

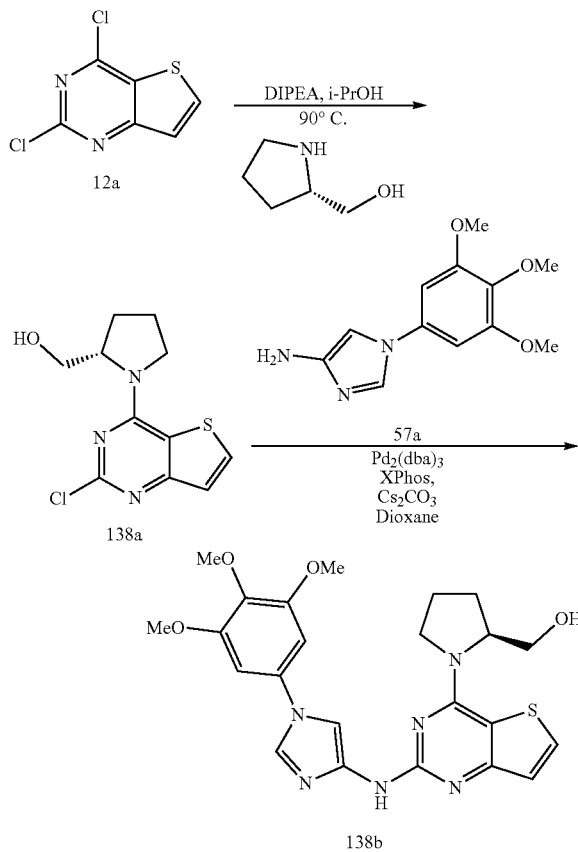

Preparation of (S)-(1-(2-((1-(3,4,5-trimethoxyphenyl)-1H-imidazol-4-yl)amino)thieno[3,2-d]pyrimidin-4-yl)pyrrolidin-2-yl)methanol (138b)

Step-1: Preparation of (S)-(1-(2-chlorothieno[3,2-d]pyrimidin-4-yl)pyrrolidin-2-yl)methanol (138a) Compound 138a was prepared from 2,4-dichlorothieno[3,2-d]pyrimidine (12a) (2 g, 9.75 mmol) in 2-Propanol (20 mL), (S)-pyrrolidin-2-ylmethanol (0.96 mL, 9.75 mmol), DIPEA (5.11 mL, 29.3 mmol) according to the procedure reported in step-1 of Scheme 96. This gave (S)-(1-(2-chlorothieno[3,2-d]pyrimidin-4-yl)pyrrolidin-2-yl)methanol (138a) (1.17 g, 45% yield) as a white solid; $^1$H NMR (300 MHz, DMSO-d$_6$): δ 8.27 (d, J=5.5 Hz, 1H), 7.34 (d, J=5.5 Hz, 1H), 4.89 (s, 1H), 4.40 (s, 1H), 3.92 (s, 2H), 3.68-3.56 (m, 1H), 3.56-3.42 (m, 1H), 2.20-1.85 (m, 4H). MS (ES+): 270.2 (M+1); MS (ES−): 268.2, 304.2 (M+Cl).

Step-2: Preparation of (S)-(1-(2-((1-(3,4,5-trimethoxyphenyl)-1H-imidazol-4-yl)amino)thieno[3,2-d]pyrimidin-4-yl)pyrrolidin-2-yl)methanol (138b)

Compound 138b was prepared from (S)-(1-(2-chlorothieno[3,2-d]pyrimidin-4-yl)pyrrolidin-2-yl)methanol (138a) (500 mg, 1.85 mmol), 1-(3,4,5-trimethoxyphenyl)-1H-imidazol-4-amine (57a) (508 mg, 2.32 mmol, free base), dicyclohexyl(2',4',6'-triisopropylbiphenyl-2-yl)phosphine (XPhos, 398 mg, 0.834 mmol), cesium carbonate (1.81 g, 5.56 mmol), Pd$_2$(dba)$_3$ (260 mg, 0.28 mmol) in anhydrous Dioxane (15 mL) according to the procedure reported in step-3 of Scheme 101. This gave after workup and purification by reverse phase flash column chromatography [(silica gel C-18, 24 g) eluting with acetonitrile and 0.1% HCl water] followed by lyophilization (S)-(1-(2-((1-(3,4,5-trimethoxyphenyl)-1H-imidazol-4-yl)amino)thieno[3,2-d]pyrimidin-4-yl)pyrrolidin-2-yl)methanol (138b) (410 mg, 46% yield) HCl salt as a white solid; $^1$H NMR (300 MHz, DMSO-d$_6$) δ 10.82-10.49 (m, 1H, D$_2$O exchangeable), 8.43 (d, J=5.5 Hz, 1H), 8.36 (s, 1H), 7.74 (s, 1H), 7.45 (d, J=5.5 Hz, 1H), 6.98 (s, 2H), 4.77-4.54 (m, 1H), 4.17-3.93 (m, 1H), 3.88 (s, 6H), 3.79-3.71 (m, 1H), 3.69 (s, 3H), 3.65-3.50 (m, 2H), 2.31-1.96 (m, 4H); MS (ES+) 483.3 (M+1), 505.3 (M+Na), (ES−) 517.3 (M+Cl); HPLC purity; 96.8%.

Scheme 139

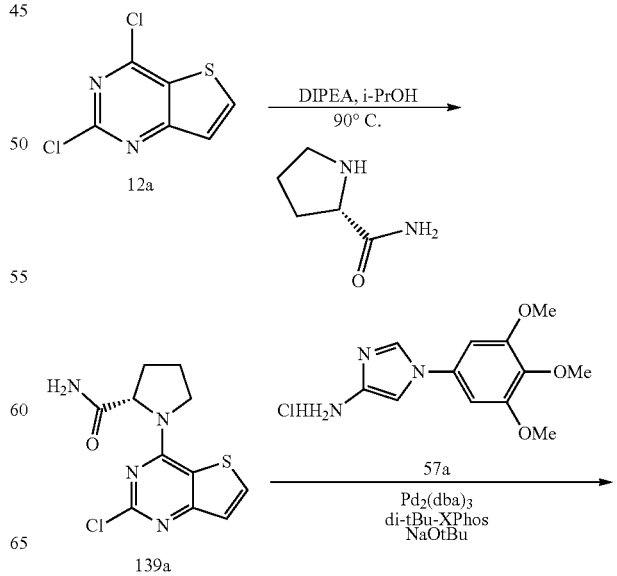

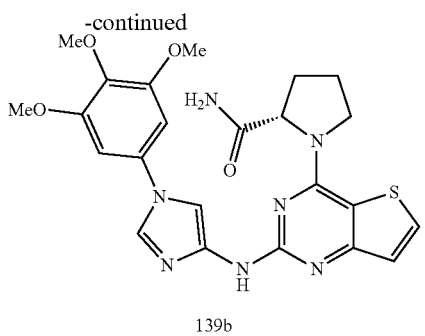

139b

Preparation of (S)-1-(2-((1-(3,4,5-trimethoxyphenyl)-1H-imidazol-4-yl)amino)thieno[3,2-d]pyrimidin-4-yl)pyrrolidine-2-carboxamide (139b)

Step-1: Preparation of (S)-1-(2-chlorothieno[3,2-d]pyrimidin-4-yl)pyrrolidine-2-carboxamide (139a)

Compound 139a was prepared from 2,4-dichlorothieno[3,2-d]pyrimidine (12a) (2 g, 9.75 mmol) in 2-Propanol (20 mL) was added (S)-pyrrolidine-2-carboxamide (1.11 g, 9.75 mmol), DIPEA (5.11 mL, 29.3 mmol) according to the procedure reported in step-1 of Scheme 96. This gave (S)-1-(2-chlorothieno[3,2-d]pyrimidin-4-yl)pyrrolidine-2-carboxamide (139a) (2.2 g, 80% yield) as a white solid; $^1$H NMR (300 MHz, DMSO-$d_6$): δ 8.29 (d, J=5.4 Hz, 1H), 7.55 (s, 1H), 7.36 (d, J=5.4 Hz, 1H), 7.04 (s, 1H), 4.58 (d, J=7.8 Hz, 1H), 4.25-3.87 (m, 2H), 2.35-1.67 (m, 4H). MS (ES−): 317.2 (M+Cl).

Step-2: Preparation of (S)-1-(2-((1-(3,4,5-trimethoxyphenyl)-1H-imidazol-4-yl)amino)thieno[3,2-d]pyrimidin-4-yl)pyrrolidine-2-carboxamide (139b)

Compound 139b was prepared from (S)-1-(2-chlorothieno[3,2-d]pyrimidin-4-yl)pyrrolidine-2-carboxamide (139a) (0.5 g, 1.85 mmol), 1-(3,4,5-trimethoxyphenyl)-1H-imidazol-4-amine hydrochloride (57a) (0.53 g, 1.85 mmol), di-tert-butyl(2',4',6'-triisopropylbiphenyl-2-yl)phosphine (0.094 g, 0.22 mmol), sodium 2-methylpropan-2-olate (1.07 g, 11.12 mmol), Pd$_2$(dba)$_3$ (102 mg, 0.111 mmol) in anhydrous Dioxane (15 mL) according to the procedure reported in step-3 of Scheme 101. This gave after workup and purification by reverse phase flash column chromatography [(silica gel C-18, 24 g) eluting with acetonitrile and 0.1% HCl water] followed by lyophilization (S)-1-(2-((1-(3,4,5-trimethoxyphenyl)-1H-imidazol-4-yl)amino)thieno[3,2-d]pyrimidin-4-yl)pyrrolidine-2-carboxamide (139b) (38 mg, 4% yield) as a white HCl salt; $^1$H NMR (300 MHz, DMSO-$d_6$) δ 10.54 (s, 1H), 8.45 (d, J=5.6 Hz, 1H), 8.31 (s, 1H), 7.71 (s, 1H), 7.62 (s, 1H), 7.44 (d, J=5.4 Hz, 2H), 7.29 (s, 1H), 7.11 (s, 2H), 4.88-4.76 (m, 1H), 4.45-4.30 (m, 1H), 4.11-3.96 (m, 1H), 3.92 (s, 6H), 3.68 (s, 3H), 2.21-1.99 (m, 4H); MS (ES+): 496.4 (M+1); MS (ES−): 494.3 (M−1).

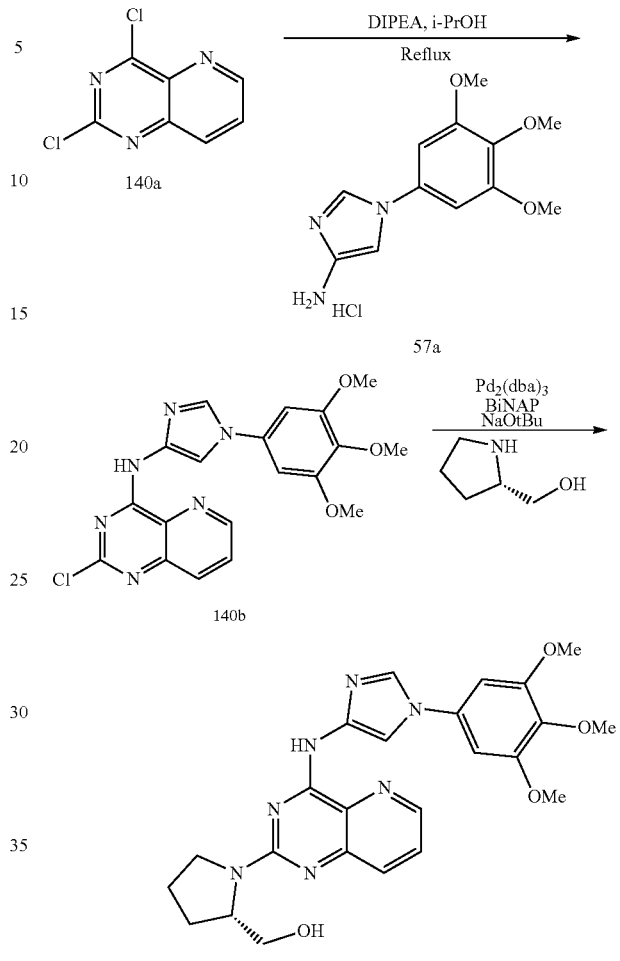

Preparation of (S)-(1-(4-((1-(3,4,5-trimethoxyphenyl)-1H-imidazol-4-yl)amino)pyrido[3,2-d]pyrimidin-2-yl)pyrrolidin-2-yl)methanol (140c)

Step-1: Preparation of 2-chloro-N-(1-(3,4,5-trimethoxyphenyl)-1H-imidazol-4-yl)pyrido[3,2-d]pyrimidin-4-amine (140b)

Compound 140b was prepared according to the procedure reported in Scheme 1 from 2,4-dichloropyrido[3,2-d]pyrimidine (140a) (0.5 g, 2.5 mmol, CAS #39551-54-7) in 2-Propanol (10 mL) using DIPEA (1.31 mL, 7.50 mmol) and 1-(3,4,5-trimethoxyphenyl)-1H-imidazol-4-amine hydrochloride (57a) (0.79 g, 2.75 mmol). This gave after workup and purification by flash column chromatography [Silica gel, (24 g) eluting with DCM in MeOH 0 to 30%], 2-chloro-N-(1-(3,4,5-trimethoxyphenyl)-1H-imidazol-4-yl)pyrido[3,2-d]pyrimidin-4-amine (140b) (0.58 g, 56% yield) as a yellow solid; $^1$H NMR (300 MHz, DMSO-$d_6$): δ 10.36 (s, 1H), 8.93 (dd, J=4.3, 1.5 Hz, 1H), 8.30-8.13 (m, 2H), 8.02-7.87 (m, 2H), 6.96 (s, 2H), 3.88 (s, 6H), 3.70 (s, 3H). MS (ES+): 435.3 (M+Na).

Step-2: Preparation of (S)-(1-(4-((1-(3,4,5-trimethoxyphenyl)-1H-imidazol-4-yl)amino)pyrido[3,2-d]pyrimidin-2-yl)pyrrolidin-2-yl)methanol (140c)

Compound 140c was prepared from 2-chloro-N-(1-(3,4,5-trimethoxyphenyl)-1H-imidazol-4-yl)pyrido[3,2-d]pyrimidin-4-amine (140b) (0.15 g, 0.36 mmol), (S)-pyrrolidin-2-ylmethanol (0.04 mL, 0.36 mmol), 2,2'-bis(diphenylphosphino)-1,1'-binaphthyl (BiNAP, 0.03 g, 0.04 mmol), sodium 2-methylpropan-2-olate (0.11 g, 1.09 mmol), Pd$_2$(dba)$_3$ (30 mg, 0.04 mmol) in degassed toluene (10 mL) according to the procedure reported in step-3 of Scheme 101. This gave after workup and purification by reverse phase flash column chromatography [silica (12 g), eluting with DMA 80 in CH$_2$Cl$_2$ from 0 to 30%] (S)-(1-(4-((1-(3,4,5-trimethoxyphenyl)-1H-imidazol-4-yl)amino)pyrido[3,2-d]pyrimidin-2-yl)pyrrolidin-2-yl)methanol (140c) (50 mg, 29% yield) as a yellow solid; $^1$H NMR (300 MHz, DMSO-d$_6$): δ (mixture of rotamers) δ 9.44 and 9.29 (2s, 1H), 8.45-8.42 and 8.42-8.41 (2m, 1H), 8.24 (s, 1H), 8.05 and 7.97 (2s, 1H), 7.75 and 7.73 (2s, 1H), 7.62 and 7.59 (2d, J=4.2 Hz, 1H), 6.97 and 6.95 (2s, 2H), 5.15 and 4.99 (2s, 1H), 4.40 and 4.24 (2s, 1H), 3.96-3.34 (m, 13H), 2.14-1.81 (m, 4H); MS (ES+): 478.3 (M+1); MS (ES−): 476.3 (M−1); 512.5 (M+Cl).

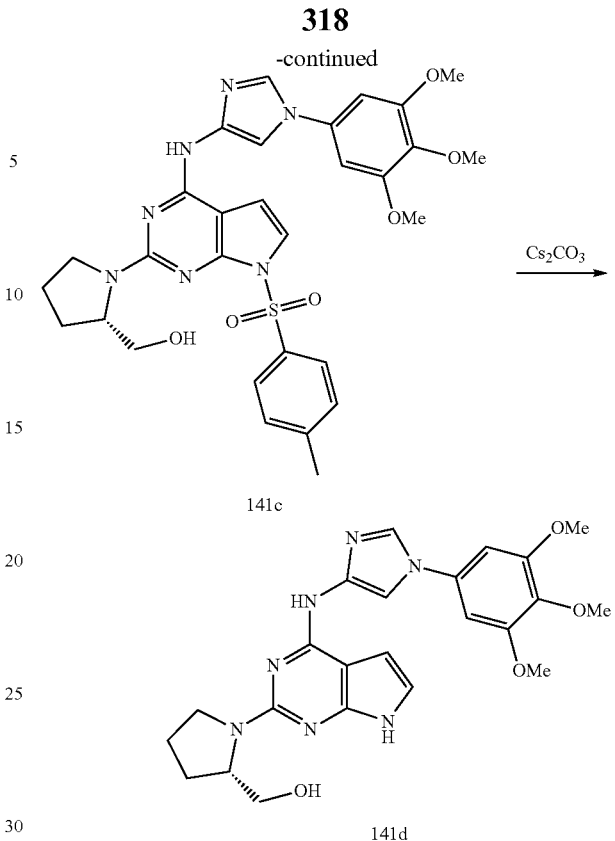

Preparation of (S)-(1-(4-((1-(3,4,5-trimethoxyphenyl)-1H-imidazol-4-yl)amino)-7H-pyrrolo[2,3-d]pyrimidin-2-yl)pyrrolidin-2-yl)methanol (141d)

Step-1: Preparation of 2-chloro-7-tosyl-N-(1-(3,4,5-trimethoxyphenyl)-1H-imidazol-4-yl)-7H-pyrrolo[2,3-d]pyrimidin-4-amine (141b)

Compound 141b was prepared according to the procedure reported in Scheme 1 from 2,4-dichloro-7-tosyl-7H-pyrrolo[2,3-d]pyrimidine (141a) (100 mg, 0.29 mmol, prepared according to procedure reported by Su, Qibin et al; *Journal of Medicinal Chemistry*, 57(1), 144-158; 2014) in 2-Propanol (5 mL) using DIPEA (0.15 mL, 0.88 mmol) and 1-(3,4,5-trimethoxyphenyl)-1H-imidazol-4-amine hydrochloride (57a) (93 mg, 0.29 mmol). This gave after filtration 2-chloro-7-tosyl-N-(1-(3,4,5-trimethoxyphenyl)-1H-imidazol-4-yl)-7H-pyrrolo[2,3-d]pyrimidin-4-amine (141b) (122 mg, 75% yield) as white solid; $^1$H NMR (300 MHz, DMSO-d$_6$) δ 10.92 (s, 1H), 8.16 (s, 1H), 8.01-7.92 (m, 2H), 7.81 (d, J=1.6 Hz, 1H), 7.66 (d, J=4.0 Hz, 1H), 7.47 (d, J=8.1 Hz, 2H), 7.23 (s, 1H), 6.90 (s, 2H), 3.86 (s, 6H), 3.69 (s, 3H), 2.37 (s, 3H); MS (ES+) 556.1 (M+1); 577.2 (M+Na).

Step-2: Preparation of (S)-(1-(7-tosyl-4-((1-(3,4,5-trimethoxyphenyl)-1H-imidazol-4-yl)amino)-7H-pyrrolo[2,3-d]pyrimidin-2-yl)pyrrolidin-2-yl)methanol (141c)

Compound 141c was prepared from 2-chloro-7-tosyl-N-(1-(3,4,5-trimethoxyphenyl)-1H-imidazol-4-yl)-7H-pyrrolo[2,3-d]pyrimidin-4-amine (141b) (150 mg, 0.27 mmol), DIPEA (0.14 mL, 0.81 mmol) and (S)-pyrrolidin-2-ylmethanol (82 mg, 0.81 mmol) in 2-Propanol (5 mL) according to

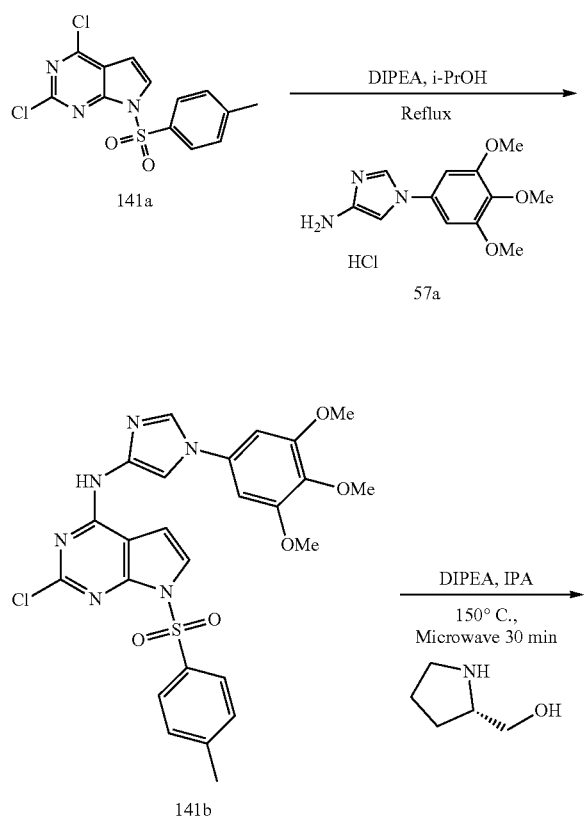

the procedure reported in Scheme 2. This gave after workup and purification by flash column chromatography [silica gel (24 g), eluting with ethyl acetate/MeOH (9:1) in hexane from 0-70%] (S)-(1-(7-tosyl-4-((1-(3,4,5-trimethoxyphenyl)-1H-imidazol-4-yl)amino)-7H-pyrrolo[2,3-d]pyrimidin-2-yl)pyrrolidin-2-yl)methanol (141c) (130 mg, 78% yield) as white solid; $^1$H NMR (300 MHz, DMSO-$d_6$) δ 10.25-10.07 (m, 1H, D$_2$O exchangeable), 8.18 (s, 1H), 8.02 (d, J=8.0 Hz, 2H), 8.00-7.80 (m, 1H), 7.44 (d, J=8.1 Hz, 2H), 7.20 (d, J=3.9 Hz, 1H), 7.05 (s, 1H), 6.91 (s, 2H), 4.98-4.76 (m, 1H, D$_2$O exchangeable), 4.34-4.04 (m, 1H), 3.86 (s, 6H), 3.80-3.71 (m, 2H), 3.67 (s, 3H), 3.64-3.55 (m, 1H), 3.47-3.37 (m, 1H), 2.37 (s, 3H), 2.10-1.83 (m, 4H); MS (ES$^+$) 642.3 (M+Na); (ES-): δ 18.4 (M-1).

Step-3: Preparation of (S)-(1-(4-((1-(3,4,5-trimethoxyphenyl)-1H-imidazol-4-yl)amino)-7H-pyrrolo[2,3-d]pyrimidin-2-yl)pyrrolidin-2-yl)methanol (141d)

To a solution of(S)-(1-(7-tosyl-4-((1-(3,4,5-trimethoxyphenyl)-1H-imidazol-4-yl)amino)-7H-pyrrolo[2,3-d]pyrimidin-2-yl)pyrrolidin-2-yl)methanol (141c) (650 mg, 1.05 mmol) in MeOH/THF (50 mL) was added Cs$_2$CO$_3$ (1025 mg, 3.15 mmol). The resulting mixture was heated at 50° C. overnight. The reaction mixture was cooled to room temperature, concentrated in vacuum and the resulting residue was dissolved in ethyl acetate, washed with water, brine, filtered and concentrated in vacuum. The residue was purified by chromatography [silica (24 g), eluting with ethyl acetate/MeOH (9:1) in hexane from 0-70%] then further purified by reverse phase column chromatography [(silica gel C-18 50 g), eluting with CH$_3$CN in water (containing 0.1% HCl) from 0-100%] to give (S)-(1-(4-((1-(3,4,5-trimethoxyphenyl)-1H-imidazol-4-yl)amino)-7H-pyrrolo[2,3-d]pyrimidin-2-yl)pyrrolidin-2-yl)methanol (141d) (320 mg, 66% yield) HCl salt as a white solid; $^1$H NMR (300 MHz, DMSO-$d_6$) δ 11.42 (s, 2H, D$_2$O exchangeable), 8.45 (s, 1H), 7.94 (s, 1H), 7.06-6.89 (m, 4H), 4.46-4.24 (m, 4H, 1H is D$_2$O exchangeable), 3.88 (s, 6H), 3.68 (s, 3H), 3.64-3.48 (m, 2H), 2.16-1.92 (m, 4H); MS (ES$^+$) 466.3 (M+1); (ES-) 464.6 (M-1); 500.3 (M+Cl); HPLC purity, 97.94%.

Scheme 142

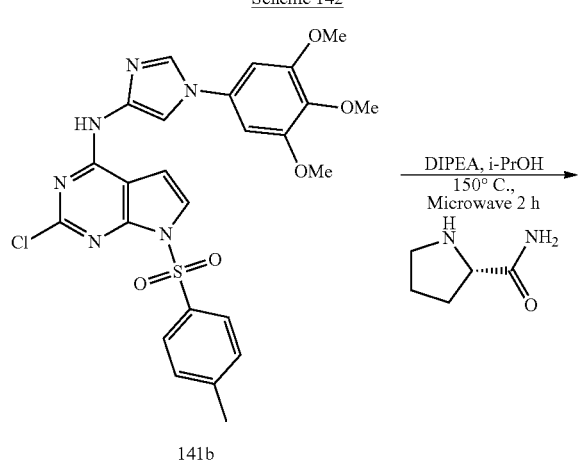

141b

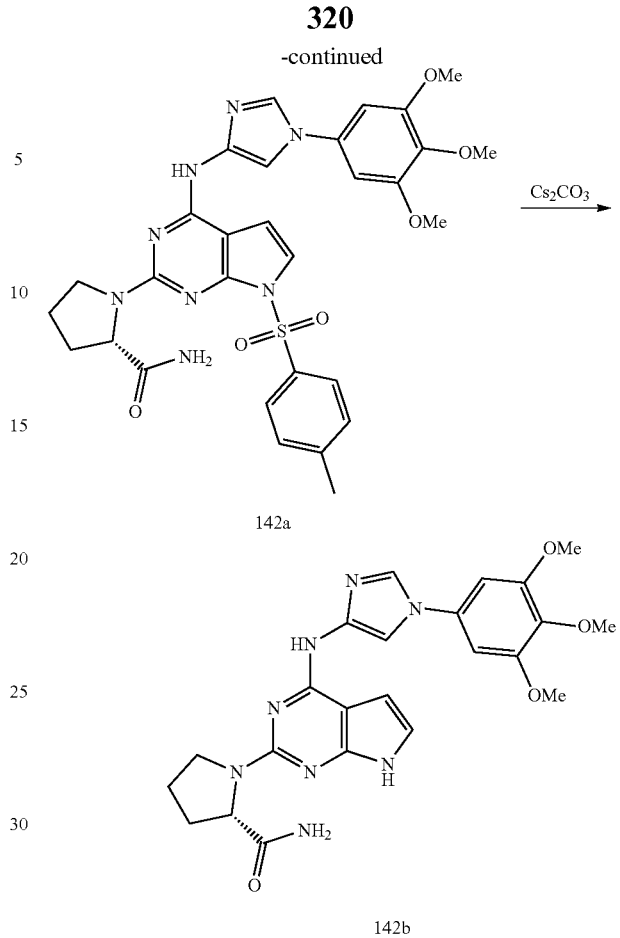

142a

142b

Preparation of (S)-1-(4-((1-(3,4,5-trimethoxyphenyl)-1H-imidazol-4-yl)amino)-7H-pyrrolo[2,3-d]pyrimidin-2-yl)pyrrolidine-2-carboxamide (142b)

Step-1: Preparation of (S)-1-(7-tosyl-4-((1-(3,4,5-trimethoxyphenyl)-1H-imidazol-4-yl)amino)-7H-pyrrolo[2,3-d]pyrimidin-2-yl)pyrrolidine-2-carboxamide (142a)

Compound 142a was prepared from 2-chloro-7-tosyl-N-(1-(3,4,5-trimethoxyphenyl)-1H-imidazol-4-yl)-7H-pyrrolo[2,3-d]pyrimidin-4-amine (141b) (150 mg, 0.27 mmol), DIPEA (0.14 mL, 0.81 mmol) and (S)-pyrrolidine-2-carboxamide (93 mg, 0.81 mmol) in 2-Propanol (5 mL) according to the procedure reported in Scheme 2. This gave after workup and purification by flash column chromatography [silica gel (24 g), eluting with ethyl acetate/MeOH (9:1) in hexane from 0-70%] (S)-1-(7-tosyl-4-((1-(3,4,5-trimethoxyphenyl)-1H-imidazol-4-yl)amino)-7H-pyrrolo[2,3-d]pyrimidin-2-yl)pyrrolidine-2-carboxamide (142a) (80 mg, 47% yield) as an off white solid; $^1$H NMR (300 MHz, DMSO-$d_6$) δ 10.31-9.92 (m, 1H, D$_2$O exchangeable), 8.24-8.10 (m, 1H), 8.03 (d, J=8.0 Hz, 2H), 7.90-7.72 (m, 1H), 7.45 (d, J=8.1 Hz, 2H), 7.26-7.15 (m, 1H), 7.15-6.83 (m, 4H), 4.57-4.33 (m, 1H), 3.90 (s, 6H), 3.68 (s, 3H), 3.59-3.46 (m, 1H), 2.37 (s, 3H), 2.05-1.90 (m, 3H), 2.27-2.11 (m, 1H), 1.26-1.11 (m, 2H); MS (ES+): δ 33.3 (M+1); 656.3 (M+Na); (ES-): δ 31.4 (M-1).

Step-2: Preparation of (S)-1-(4-((1-(3,4,5-trimethoxyphenyl)-1H-imidazol-4-yl)amino)-7H-pyrrolo[2,3-d]pyrimidin-2-yl)pyrrolidine-2-carboxamide (142b)

Compound 142b was prepared from (S)-1-(7-tosyl-4-((1-(3,4,5-trimethoxyphenyl)-1H-imidazol-4-yl)amino)-7H-pyrrolo[2,3-d]pyrimidin-2-yl)pyrrolidine-2-carboxamide (142a) (50 mg, 0.79 mmol), in MeOH/THF (3 mL) using $Cs_2CO_3$ (77 mg, 0.24 mmol) according to the procedure reported in step-3 of Scheme 141. This gave after work up and by flash column chromatography [silica (12 g), eluting with ethyl acetate/MeOH (9:1) in hexane from 0-70%](S)-1-(4-((1-(3,4,5-trimethoxyphenyl)-1H-imidazol-4-yl)amino)-7H-pyrrolo[2,3-d]pyrimidin-2-yl)pyrrolidine-2-carboxamide (142b) (28 mg, 74% yield) as a white solid; $^1$H NMR (300 MHz, DMSO-$d_6$) δ 11.03 (s, 1H, $D_2O$ exchangeable), 9.68 (s, 1H, $D_2O$ exchangeable), 8.14 (d, J=1.6 Hz, 1H), 7.96 (s, 1H), 7.14-6.97 (m, 3H), 6.91 (s, 1H), 6.81-6.68 (m, 2H), 4.47 (d, J=8.6 Hz, 1H), 3.92 (s, 7H), 3.69 (s, 3H), 3.64-3.50 (m, 1H), 2.29-2.09 (m, 1H), 2.04-1.81 (m, 3H); MS (ES+): 479.3 (M+1); (ES−): 477.4 (M−1); HPLC purity, 97.22%.

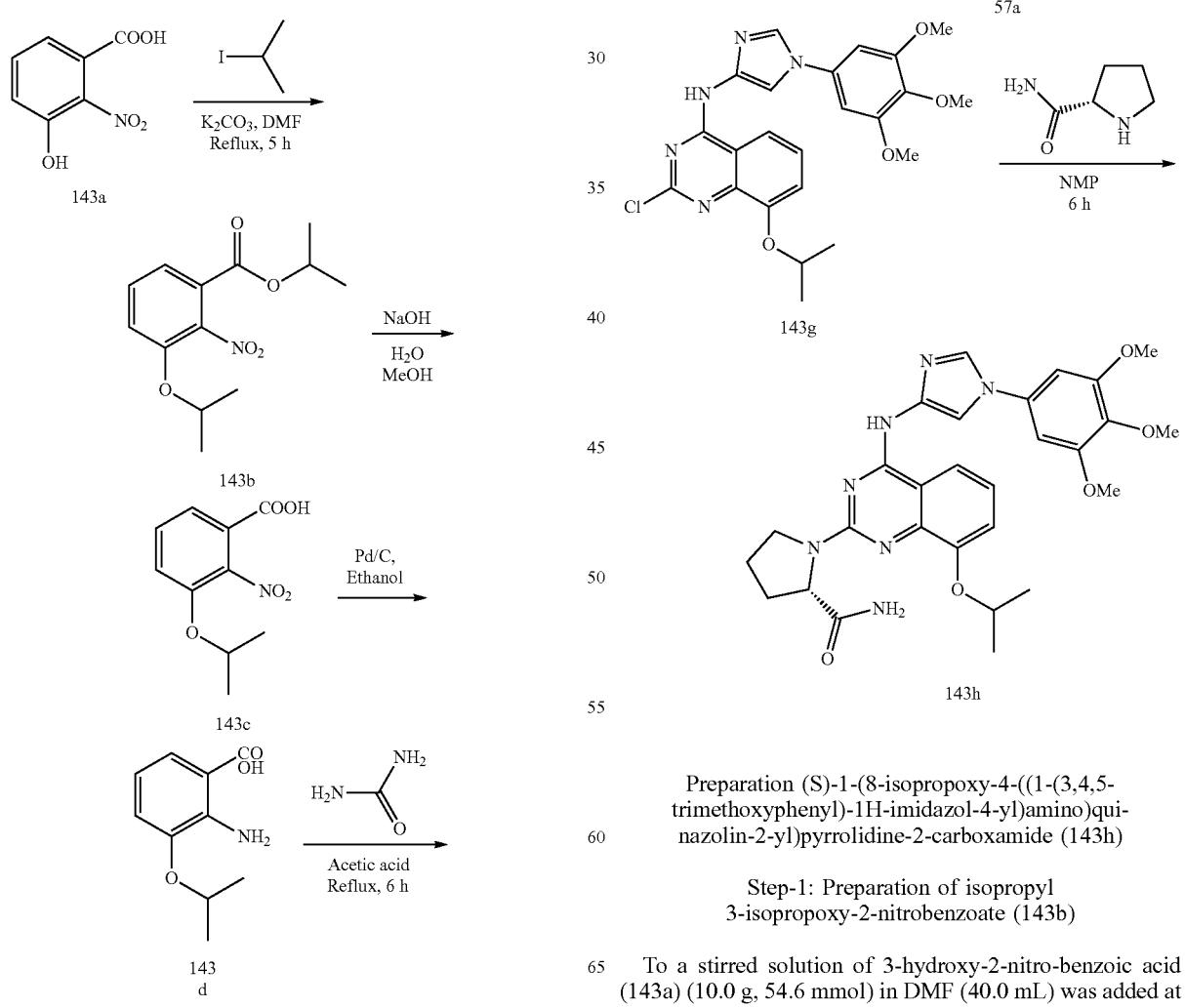

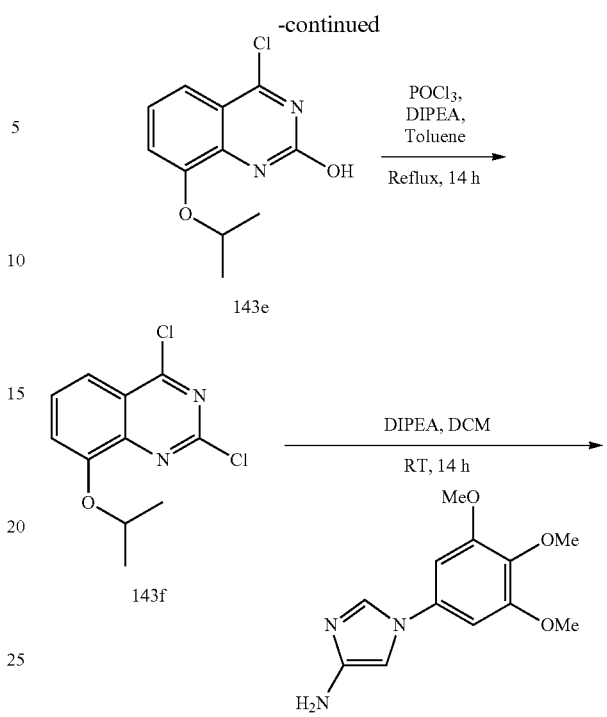

Preparation (S)-1-(8-isopropoxy-4-((1-(3,4,5-trimethoxyphenyl)-1H-imidazol-4-yl)amino)quinazolin-2-yl)pyrrolidine-2-carboxamide (143h)

Step-1: Preparation of isopropyl 3-isopropoxy-2-nitrobenzoate (143b)

To a stirred solution of 3-hydroxy-2-nitro-benzoic acid (143a) (10.0 g, 54.6 mmol) in DMF (40.0 mL) was added at room temperature potassium carbonate (30.14 g, 218 mmol)

and isopropyl iodide (13.09 mL, 77.04 mmol). The reaction mixture was stirred at reflux for 4 h and poured into ice-water with vigorous stirring. The aqueous layer was extracted with EtOAc (3×200 mL). The combined organic layers was washed with brine (50.0 mL), dried, filtered and concentrated under vacuum to get afford isopropyl 3-isopropoxy-2-nitrobenzoate (143b) (8 g, 55%) as a brown liquid, which was used as such without further purification; $^1$H NMR (300 MHz, DMSO-$d_6$): δ 7.90-7.59 (m, 2H), 7.53 (dd, J=7.0, 2.0 Hz, 1H), 5.09 (m, 1H), 4.95-4.57 (m, 1H), 1.26 (dd, J=6.1, 4.0 Hz, 12H); MS (ES+): 268 (M+1).

Step-2: Preparation of 3-isopropoxy-2-nitrobenzoic acid (143c)

To a stirred solution of isopropyl 3-isopropoxy-2-nitrobenzoate (143b) (8.0 g, 29.9 mmol) in methanol (32 mL) was added a solution of sodium hydroxide (5.9 g, 22.07 mmol) in water (32.0 mL) and stirred at room temperature for 5 h. The reaction mixture was acidified with 1 N HCl at 0° C. and the solid obtained was collected by filtration, dried in vacuum oven at 40° C. to get 3-isopropoxy-2-nitrobenzoic acid (143c) (5.5 g, 81%) as an off-white solid; $^1$H NMR (300 MHz, DMSO-$d_6$): δ 7.76-7.40 (m, 3H), 4.82 (m, 1H), 1.24 (d, J=6.0 Hz, 6H); MS (ES−): 224.0 (M−1).

Step-3: Preparation of 2-amino-3-isopropoxybenzoic acid (143d)

A solution of 3-isopropoxy-2-nitrobenzoic acid (143c) (5.5 g, 22.22 mmol) in ethanol (60 mL) was added 10% Pd/C (1.0 g, 0.94 mmol) and hydrogenated for 12 h at room temperature using a hydrogen balloon. The reaction mixture was filtered through a Celite bed to remove Pd/C. The filtrate was concentrated to dryness to furnish 2-amino-3-isopropoxybenzoic acid (143d) (3.5 g, 74%) as a yellowish solid; $^1$H NMR (300 MHz, DMSO-$d_6$): δ 7.32 (dd, J=8.2, 1.4 Hz, 1H), 6.97 (dd, J=8.0, 1.4 Hz, 1H), 6.48 (t, J=8.0 Hz, 1H), 4.55 (m, 1H), 1.28 (d, J=6.0 Hz, 6H); MS (ES−): 194.0 (M−1).

Step-4: Preparation of 8-isopropoxyquinazoline-2,4-diol (143e)

To a stirred solution of 2-amino-3-isopropoxybenzoic acid (143d) (3.5 g, 17.92 mmol) in acetic acid (96.25 mL) was added urea (14.99 g, 248.08 mmol) and heated at 110° C. for 5 h. The reaction mixture was cooled to room temperature and concentrated in vacuum to dryness. The residue was diluted with water (250 mL) and solid obtained was collected by filtration, dried in vacuum to afford 8-isopropoxyquinazoline-2,4-diol (143e) (1.8 g, 42%) as a brown solid; $^1$H NMR (300 MHz, DMSO-$d_6$): δ 11.29 (s, 1H), 10.38 (s, 1H), 7.44 (dd, J=7.9, 1.2 Hz, 1H), 7.36-7.26 (m, 1H), 7.11 (t, J=8.0 Hz, 1H), 4.72 (dt, J=12.0, 6.0 Hz, 1H), 1.31 (dd, J=6.1, 1.0 Hz, 6H); MS (ES−): 219.0 (M−1).

Step-5: Preparation of 2,4-dichloro-8-isopropoxyquinazoline (143f)

To a stirred solution of 8-isopropoxyquinazoline-2,4-diol (143e) (1.5 g, 6.81 mmol) in toluene (9 mL) at room temperature was added DIPEA (3.5 mL, 27.08 mmol), POCl$_3$ (9 mL) and heated at 90° C. for 12 h. The reaction mixture was poured into ice-water with vigorous stirring and the aqueous layer was extracted with EtOAc (2×100 mL). The combined organic extracts were washed with saturated sodium bicarbonate solution (50.0 mL), dried, filtered and concentrated under vacuum. The crude residue was purified by flash column chromatography [silica gel, eluting with ethyl acetate in n-hexane (0-5%)] to furnish 2,4-dichloro-8-isopropoxyquinazoline (143f) (0.8 g, 46%) as a yellowish solid; $^1$H NMR (300 MHz, DMSO-$d_6$): δ 7.84-7.74 (m, 2H), 7.67 (q, J=4.7 Hz, 1H), 4.91 (m, 1H), 1.39 (d, J=6.0 Hz, 6H).

Step-6: Preparation of 2-chloro-8-isopropoxy-N-(1-(3,4,5-trimethoxyphenyl)-1H-imidazol-4-yl)quinazolin-4-amine (143g)

Compound 143g was prepared according to the procedure reported in Scheme 1 from 2,4-dichloro-8-isopropoxyquinazoline (143f) (1.0 g, 3.88 mmol) in IPA (15 mL) using DIPEA (2.03 mL, 15.71 mmol) and 1-(3,4,5-trimethoxyphenyl)-1H-imidazol-4-ylamine (57a) (0.96 g, 3.88 mmol, free base). This gave after work up 2-chloro-8-isopropoxy-N-(1-(3,4,5-trimethoxyphenyl)-1H-imidazol-4-yl)quinazolin-4-amine (143g) (600 mg, 33%) as an off-white solid; $^1$H NMR (300 MHz, DMSO-$d_6$): δ $^1$H NMR (300 MHz, DMSO-$d_6$): δ 7.78 (dd, J=8.1, 1.6 Hz, 1H), 7.47-7.13 (m, 2H), 4.80 (dt, J=19.9, 5.9 Hz, 2H), 4.56 (t, J=5.6 Hz, 1H), 4.09-3.82 (m, 2H), 3.63 (dd, J=5.7, 4.0 Hz, 2H), 2.24-1.93 (m, 3H), 1.82 (td, J=8.8, 8.2, 3.9 Hz, 1H), 1.33 (dd, J=6.0, 2.4 Hz, 6H); MS (ES+): 470.0 (M+1); HPLC purity: 98.63%.

Step-7: Preparation of (S)-1-(8-isopropoxy-4-((1-(3,4,5-trimethoxyphenyl)-1H-imidazol-4-yl)amino)quinazolin-2-yl)pyrrolidine-2-carboxamide (143h)

Compound 143h was prepared according to the procedure reported in step-2 of Scheme 76 from 2-chloro-8-isopropoxy-N-(1-(3,4,5-trimethoxyphenyl)-1H-imidazol-4-yl)quinazolin-4-amine (143g) (350 mg, 0.74 mmol) and L-prolinamide (0.42 g, 3.71 mmol) in NMP (10 mL). This gave after workup and purification by flash chromatography (silica gel, eluting with 0-40% methanol in DCM) compound (143h) (0.06 g, 15%) as an off-white solid. The white solid was repurified by reverse phase flash column chromatography [(silica gel C-18, 24 g) eluting with acetonitrile and 0.1% HCl in water (0-50%)] to afford (S)-1-(8-isopropoxy-4-((1-(3,4,5-trimethoxyphenyl)-1H-imidazol-4-yl)amino)quinazolin-2-yl)pyrrolidine-2-carboxamide (143h) (60 mg) as a yellow HCl salt; $^1$H NMR (300 MHz, DMSO-$d_6$): δ 10.34 (s, 1H), 10.02 (s, 1H), 8.23 (s, 1H), 8.12 (d, J=8.2 Hz, 1H), 7.99 (s, 1H), 7.11 (d, J=8.9 Hz, 3H), 6.99 (q, J=8.6 Hz, 3H), 4.95-4.76 (m, 1H), 4.58 (d, J=7.6 Hz, 1H), 4.01-3.85 (m, 7H), 3.69 (s, 3H), 3.35-3.29 (m, 1H), 2.37-1.76 (m, 4H), 1.38-1.17 (m, 6H). MS (ES+): 570.3 (M+Na).

Scheme 144

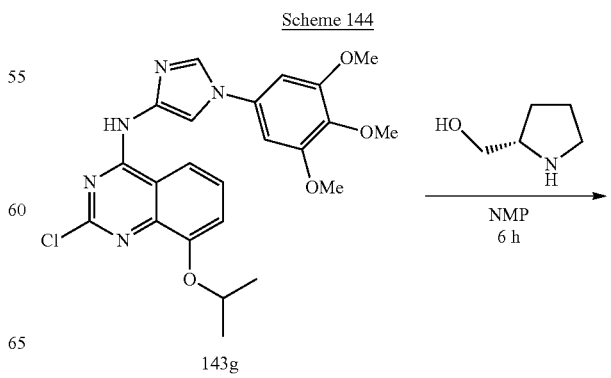

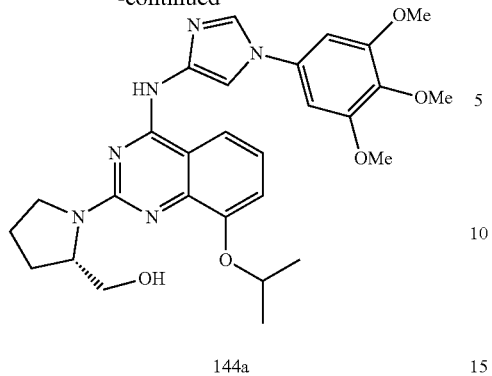

144a

Preparation (S)-(1-(8-isopropoxy-4-((1-(3,4,5-trimethoxyphenyl)-1H-imidazol-4-yl)amino)quinazolin-2-yl)pyrrolidin-2-yl)methanol (144a)

Compound 144a was prepared according to the procedure reported in step-2 of Scheme 76 from 2-chloro-8-isopropoxy-N-(1-(3,4,5-trimethoxyphenyl)-1H-imidazol-4-yl)quinazolin-4-amine (143g) (300 mg, 0.63 mmol) and (S)-pyrrolidin-2-ylmethanol (0.64 g, 6.38 mmol) in NMP (10 mL). This gave after workup and purification by flash chromatography (silica gel, eluting with 0-40% methanol in DCM) compound (144a) (70 mg, 20%) as an off-white solid. The solid was repurified by reverse phase flash column chromatography [(silica gel C-18, 24 g) eluting with acetonitrile and 0.1% HCl in water (0-50%)] to afford (S)-(1-(8-isopropoxy-4-((1-(3,4,5-trimethoxyphenyl)-1H-imidazol-4-yl)amino)quinazolin-2-yl)pyrrolidin-2-yl)methanol (144a) (80 mg) as a yellow HCl salt; $^1$H NMR (300 MHz, DMSO-d$_6$) (mixture of rotamers) δ 10.35 and 10.11 (2s, 1H), 8.26 and 8.13 (s, 2H), 8.09 and 8.06 (2s, 1H), 7.12 and 7.10 (2s, 1H), 7.06-6.89 (m, 4H), 4.87-4.61 (m, 1H), 4.23-3.46 (m, 14H), 2.29-1.60 (m, 4H), 1.31 and 1.27 (d, J=6.0 Hz, 6H); MS (ES+): 535.3 (M+1); MS (ES−): 533.4 (M−1). HPLC purity: 96.15%.

Scheme 145

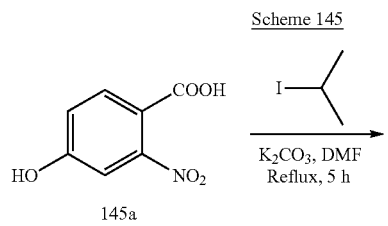

145a

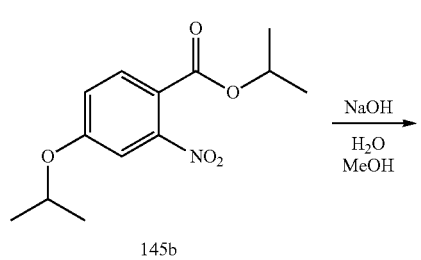

145b

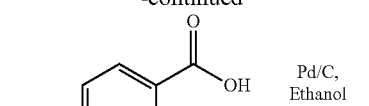

145c

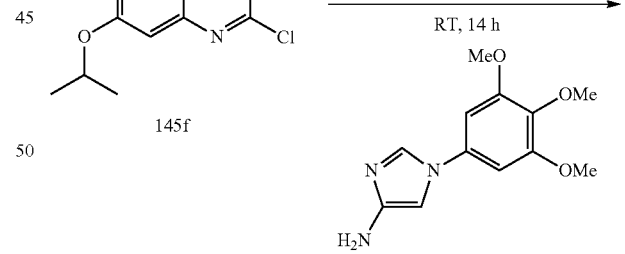

145d

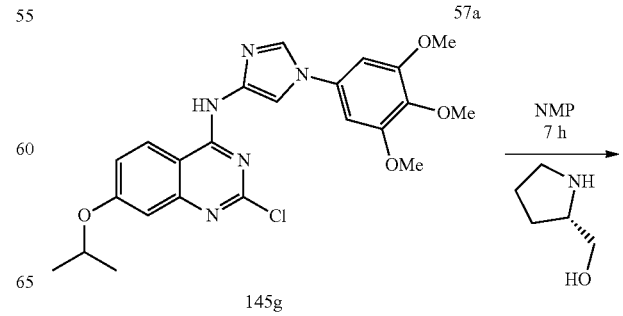

145e

145f

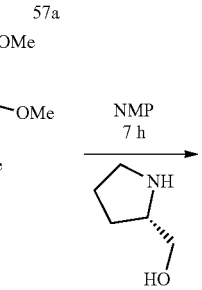

57a

145g

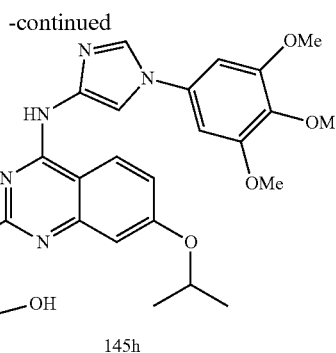

145h

Preparation (S)-(1-(7-isopropoxy-4-((1-(3,4,5-trimethoxyphenyl)-1H-imidazol-4-yl)amino)quinazolin-2-yl)pyrrolidin-2-yl)methanol (145h)

Step-1: Preparation of isopropyl 4-isopropoxy-2-nitrobenzoate (145b)

Compound 145b was prepared from 4-hydroxy-2-nitrobenzoic acid (145a) (10.0 g, 54.60 mmol) in DMF (40 mL) using potassium carbonate (30.14 g, 218 mmol) and isopropyl iodide (13.09 mL, 77.04 mmol) according to the procedure reported in step-1 of Scheme 143. This gave after workup isopropyl 4-isopropoxy-2-nitrobenzoate (145b) (8 g, 55%) as a brown liquid, which was used as such without further purification; $^1$H NMR (300 MHz, DMSO-$d_6$): δ 7.83-7.80 (d, 1H), 7.50-7.49 (d, 1H), 7.30-7.26 (m, 1H), 5.06 (m, 1H), 4.81 (m, 1H), 1.30-1.14 (d, 12H); MS ES (+): 268 (M+1).

Step-2: Preparation of 4-isopropoxy-2-nitrobenzoic acid (145c)

Compound 145c was prepared from isopropyl 4-isopropoxy-2-nitrobenzoate (145b) (8.0 g, 29.9 mmol) in methanol (32 mL) and water (32 mL) using sodium hydroxide (5.9 g, 22.07 mmol) according to the procedure reported in step-2 of Scheme 143. This gave after workup 4-isopropoxy-2-nitrobenzoic acid (145c) (5.5 g, 81%) as an off-white solid; $^1$H NMR (300 MHz, DMSO-$d_6$): δ 7.88-7.83 (d, 1H). 7.49-7.43 (d, 1H), 7.30-7.26 (m, 1H), 4.84-4.76 (m, 1H), 1.30-1.24 (d, 6H); MS (ES–): 224.0 (M–1).

Step-3: Preparation of 2-amino-4-isopropoxybenzoic acid (145d)

Compound 145d was prepared from 4-isopropoxy-2-nitrobenzoic acid (145c) according to the procedure reported in step-3 of Scheme 143. This gave after workup 2-amino-4-isopropoxybenzoic acid (145d) (3.5 g, 73%) as a yellow solid; $^1$H NMR (300 MHz, DMSO-$d_6$): δ 8.55-8.10 (d, 2H), 7.33-7.30 (d, 1H), 6.99-6.66 (d, 1H), 6.50-6.45 (m, 1H), 4.59-4.51 (m, 1H), 1.29-1.27 (d, 6H); MS ES (–): 194.0 (M–1).

Step-4: Preparation of 7-isopropoxyquinazoline-2,4-diol (145e)

Compound 145e was prepared from 2-amino-4-isopropoxybenzoic acid (145d) (3.5 g, 17.92 mmol) in acetic acid (96.25 mL) using urea (14.99 g, 248.08 mmol) according to the procedure reported in step-4 of Scheme 143. This gave 7-isopropoxyquinazoline-2,4-diol (145e) (1.8 g, 46%) as a brown solid; MS (ES–): 219.2 (M–1).

Step-5: Preparation of 2,4-dichloro-7-isopropoxyquinazoline (145f)

Compound 145f was prepared from 7-isopropoxyquinazoline-2, 4-diol (145e) (1.5 g, 6.81 mmol) in toluene (9 mL) using DIPEA (3.5 mL, 27.08 mmol) and POCl$_3$ (9 mL) according to the procedure reported in step-5 of Scheme 143. This gave after work up and purification by flash column chromatography [silica gel, eluting with ethyl acetate in n-hexane (0-5%)] 2,4-dichloro-7-isopropoxyquinazoline (145f) (0.8 g, 46%) as a yellow solid; $^1$H NMR (300 MHz, DMSO-$d_6$): δ 8.17-8.14 (d, 1H), 7.46-7.42 (m, 2H), 4.98-4.94 (m, 1H), 1.41-1.36 (d, 6H); MS (ES+): 258.0 (M+1).

Step-6: Preparation of 2-chloro-7-isopropoxy-N-(1-(3,4,5-trimethoxyphenyl)-1H-imidazol-4-yl)quinazolin-4-amine (145g)

Compound 145g was prepared according to the procedure reported in Scheme 1 from 2,4-dichloro-7-isopropoxyquinazoline (145f) (1.0 g, 3.88 mmol) in IPA (15 mL) using DIPEA (2.03 mL, 15.71 mmol) and 1-(3,4,5-trimethoxyphenyl)-1H-imidazol-4-ylamine (57a) (0.96 g, 3.88 mmol). This gave after work up 2-chloro-7-isopropoxy-N-(1-(3,4,5-trimethoxyphenyl)-1H-imidazol-4-yl)quinazolin-4-amine (145g) (0.6 g, 33%) as an off-white solid; $^1$H NMR (300 MHz, DMSO-$d_6$): δ 10.88 (s, 1H), 8.64-8.61 (d, 1H). 8.21-8.20 (d, 1H), 7.95 (s, 1H), 7.17-7.13 (m, 2H), 6.93 (s, 2H), 4.87-4.83 (m, 1H), 3.88 (s, 6H). 3.70 (s, 3H), 1.35-1.33 (d, 6H); MS (ES–): 468.0 (M–1).

Step-7: Preparation of (S)-(1-(7-isopropoxy-4-((1-(3,4,5-trimethoxyphenyl)-1H-imidazol-4-yl)amino)quinazolin-2-yl)pyrrolidin-2-yl)methanol (145h)

Compound 145h was prepared according to the procedure reported in step-2 of Scheme 76 from 2-chloro-7-isopropoxy-N-(1-(3,4,5-trimethoxyphenyl)-1H-imidazol-4-yl)quinazolin-4-amine (145g) (180 mg, 0.38 mmol) and (S)-pyrrolidin-2-ylmethanol (0.38 g, 3.75 mmol) in NMP (10 mL). This gave after workup and purification by flash chromatography (Silica gel, eluting with 0-40% methanol in DCM) compound (145h) (0.11 g, 54%) as an off-white solid. The white solid was repurified by reverse phase flash column chromatography [(silica gel C-18, 24 g) eluting with acetonitrile and 0.1% HCl in water (0-50%)] to afford (S)-(1-(7-isopropoxy-4-((1-(3,4,5-trimethoxyphenyl)-1H-imidazol-4-yl)amino)quinazolin-2-yl)pyrrolidin-2-yl)methanol (145h) (90 mg) HCl salt as a yellow solid; $^1$H NMR (300 MHz, DMSO-$d_6$): δ 8.29 (d, J=9.0 Hz, 1H), 8.21 (s, 1H), 8.03 (s, 1H), 6.94 (s, 2H), 6.84-6.61 (m, 2H), 4.73 (p, J=5.9 Hz, 1H), 4.55-4.14 (m, 2H), 3.88 (s, 6H), 3.70 (s, 3H), 3.57-3.18 (m, 3H), 2.06-1.94 (m, 4H), 1.32 (d, J=5.9 Hz, 6H). MS (ES+): 535.4 (M+1); MS (ES–): 533.4 (M–1).

Scheme 146

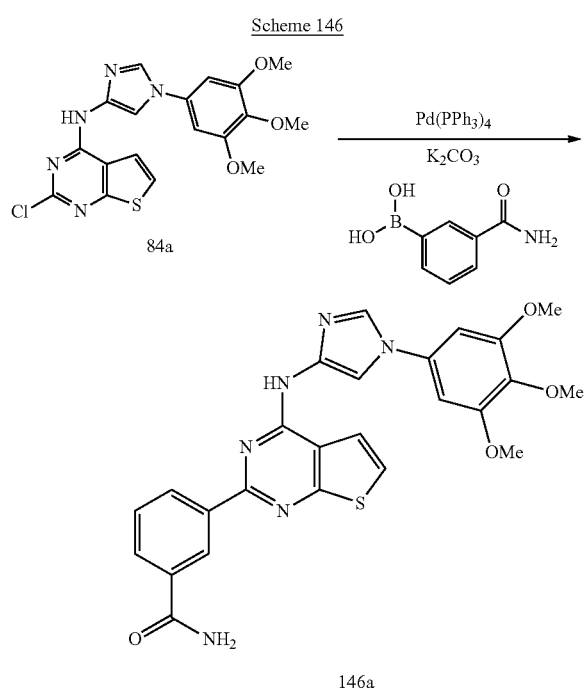

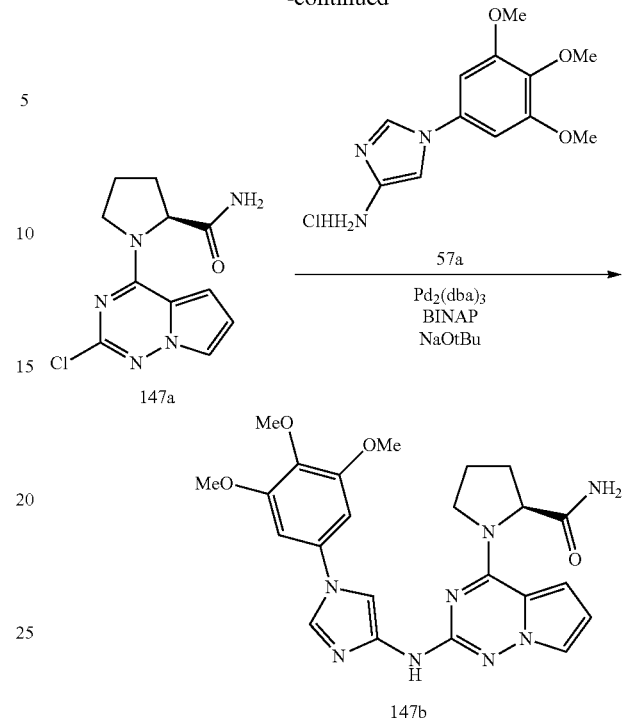

Preparation of 3-(4-((1-(3,4,5-trimethoxyphenyl)-1H-imidazol-4-yl)amino)thieno[2,3-d]pyrimidin-2-yl)benzamide (146a)

Compound 146a was prepared from 2-chloro-N-(1-(3,4,5-trimethoxyphenyl)-1H-imidazol-4-yl)thieno[2,3-d]pyrimidin-4-amine (84a) (150 mg, 0.36 mmol), using 3-carbamoylphenylboronic acid (89 mg, 0.54 mmol), Pd(Ph$_3$P)$_4$ (83 mg, 0.072 mmol) and potassium carbonate (99 mg, 0.72 mmol) in 1,4-Dioxane and Water (10 mL, 4:1) according to the procedure reported in step-3 of Scheme 77. This gave after workup and filtration followed by drying of solid, 3-(4-((1-(3,4,5-trimethoxyphenyl)-1H-imidazol-4-yl)amino)thieno[2,3-d]pyrimidin-2-yl)benzamide (146a) (85 mg, 47% yield) as a yellow solid; $^1$H NMR (300 MHz, DMSO-d6) δ 10.65 (s, 1H, D$_2$O exchangeable), 8.95 (s, 1H), 8.60 (d, J=7.9 Hz, 1H), 8.29 (s, 1H), 8.18 (s, 1H), 8.16-8.08 (m, 2H), 8.00 (d, J=7.7 Hz, 1H), 7.71 (d, J=5.9 Hz, 1H), 7.58 (t, J=7.7 Hz, 1H), 7.43 (s, 1H), 7.00 (s, 2H), 3.91 (s, 6H), 3.72 (s, 3H); MS (ES+): 525.3 (M+Na); (ES−): 501.2 (M−1).

Scheme 147

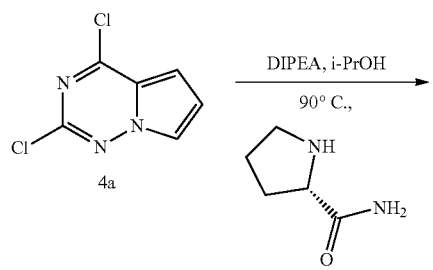

Preparation of (S)-1-(2-((1-(3,4,5-trimethoxyphenyl)-1H-imidazol-4-yl)amino)pyrrolo[2,1-f][1,2,4]triazin-4-yl)pyrrolidine-2-carboxamide (147b)

Step-1: Preparation of (S)-1-(2-chloropyrrolo[2,1-f][1,2,4]triazin-4-yl)pyrrolidine-2-carboxamide (147a) Compound 147a was prepared from 2,4-dichloropyrrolo[2,1-f][1,2,4]triazine (4a) (2 g, 9.75 mmol) in 2-Propanol (20 mL) was added (S)-pyrrolidine-2-carboxamide (1.21 g, 10.64 mmol), DIPEA (5.57 mL, 31.9 mmol) according to the procedure reported in step-1 of Scheme 96. This gave (S)-1-(2-chloropyrrolo[2,1-f][1,2,4]triazin-4-yl)pyrrolidine-2-carboxamide (147a) (2.2 g, 78% yield) as a white solid; $^1$H NMR (300 MHz, DMSO-d$_6$): δ 7.85-7.65 (m, 1H), 7.53 (s, 1H), 7.32 (s, 1H), 7.09-6.97 (m, 1H), 6.79-6.64 (m, 1H), 4.65 (dd, J=8.3, 2.9 Hz, 1H), 4.17-3.58 (m, 2H), 2.44-1.75 (m, 4H); MS (ES−): 300.3, 302.3 (M+Cl).

Step-2: Preparation of (S)-1-(2-((1-(3,4,5-trimethoxyphenyl)-1H-imidazol-4-yl)amino)pyrrolo[2,1-f][1,2,4]triazin-4-yl)pyrrolidine-2-carboxamide (147b)

Compound 147b was prepared from (S)-1-(2-chloropyrrolo[2,1-f][1,2,4]triazin-4-yl)pyrrolidine-2-carboxamide (147a) (0.3 g, 1.13 mmol), 1-(3,4,5-trimethoxyphenyl)-1H-imidazol-4-amine hydrochloride (57a) (0.5 g, 1.3 mmol), 2,2'-bis(diphenylphosphino)-1,1'-binaphthyl (BiNAP, 0.08 g, 0.14 mmol), sodium 2-methylpropan-2-olate (0.33 g, 3.39 mmol), Pd$_2$(dba)$_3$ (100 mg, 0.11 mmol) in anhydrous toluene (10 mL) according to the procedure reported in step-3 of Scheme 101. This gave after workup and purification by flash column chromatography [silica gel, (12 g) eluting with DMA 80 in CH$_2$Cl$_2$ from 0 to 30%], reverse phase flash column chromatography [(silica gel C-18, 24 g) eluting with acetonitrile and 0.1% HCl water] followed by lyophilization (S)-1-(2-((1-(3,4,5-trimethoxyphenyl)-1H-imidazol-4-yl)amino)pyrrolo[2,1-f][1,2,4]triazin-4-yl)pyrrolidine-2-carboxamide (147b) (0.04 g, 6% yield) HCl salt as a yellow solid; $^1$H NMR (300 MHz, DMSO-d$_6$): δ 8.88 (s, 1H), 7.84-7.47 (m, 2H), 7.47-6.78 (m, 5H), 6.69 (s, 1H), 6.65-6.59 (m, 1H), 4.91-4.78 (m, 1H), 4.47-4.02 (m, 1H), 3.74 (s, 9H), 3.26-2.88 (m, 1H), 2.36-1.56 (m, 4H). MS (ES+): 479.3 (M+1), 501.3 (M+Na); MS (ES-): 513.3 (M+Cl).

Scheme 148

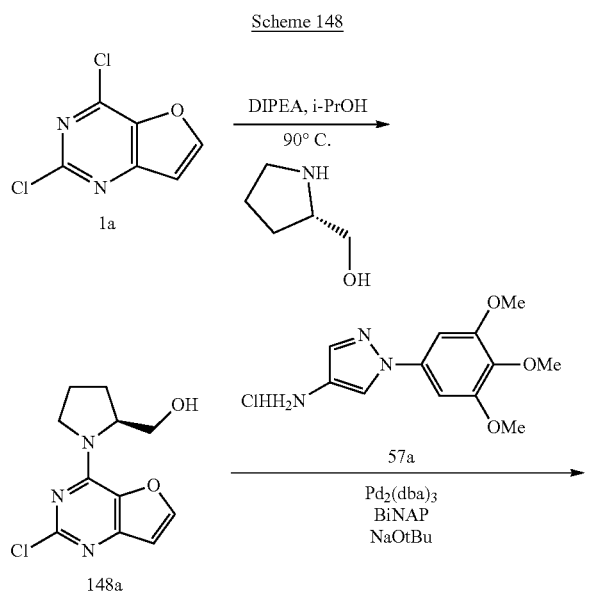

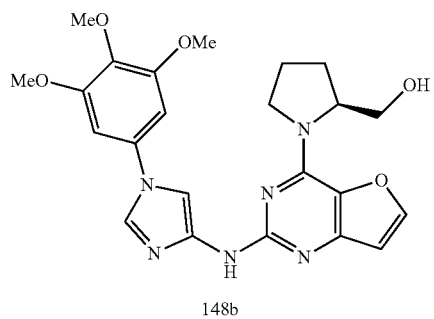

Preparation of (S)-(1-(2-((1-(3,4,5-trimethoxyphenyl)-1H-imidazol-4-yl)amino)furo[3,2-d]pyrimidin-4-yl)pyrrolidin-2-yl)methanol (148b)

Step-1: Preparation of (S)-(1-(2-chlorofuro[3,2-d]pyrimidin-4-yl)pyrrolidin-2-yl)methanol (148a) Compound 148a was prepared from 2,4-dichlorofuro[3,2-d]pyrimidine (1a) (3 g, 15.87 mmol) in 2-Propanol (30 mL) using (S)-pyrrolidin-2-ylmethanol (1.57 mL, 15.87 mmol), DIPEA (8.32 mL, 47.6 mmol) according to the procedure reported in step-1 of Scheme 96. This gave (S)-(1-(2-chlorofuro[3,2-d]pyrimidin-4-yl)pyrrolidin-2-yl)methanol (148a) (3.07 g, 76% yield) as a white solid; $^1$H NMR (300 MHz, DMSO-d$_6$): δ $^1$H NMR (300 MHz, DMSO-d$_6$) δ 8.22 (d, J=2.1 Hz, 1H), 6.90 (d, 1H), 4.58-4.19 (m, 1H), 4.03-3.74 (m, 1H), 3.58 (d, J=27.4 Hz, 3H), 1.98 (d, J=27.9 Hz, 4H).

Step-2: Preparation of (S)-(1-(2-((1-(3,4,5-trimethoxyphenyl)-1H-imidazol-4-yl)amino)furo[3,2-d]pyrimidin-4-yl)pyrrolidin-2-yl)methanol (148b)

Compound 148b was prepared from (S)-(1-(2-chlorofuro[3,2-d]pyrimidin-4-yl)pyrrolidin-2-yl)methanol (148a) (0.3 g, 1.18 mmol), 1-(3,4,5-trimethoxyphenyl)-1H-imidazol-4-amine hydrochloride (57a) (0.34 g, 1.18 mmol), 2,2'-bis(diphenylphosphino)-1,1'-binaphthyl (BiNAP, 0.09 g, 0.14 mmol), sodium 2-methylpropan-2-olate (0.34 g, 3.6 mmol), Pd$_2$(dba)$_3$ (0.10 g, 0.11 mmol) in anhydrous toluene (10 mL) according to the procedure reported in step-3 of Scheme 101. This gave after workup and purification by flash column chromatography [silica gel, (12 g) eluting with DMA 80 in CH$_2$Cl$_2$ from 0 to 30%], reverse phase flash column chromatography [(silica gel C-18, 24 g) eluting with acetonitrile and 0.1% HCl water] followed by lyophilization (S)-(1-(2-((1-(3,4,5-trimethoxyphenyl)-1H-imidazol-4-yl)amino)furo[3,2-d]pyrimidin-4-yl)pyrrolidin-2-yl)methanol (148b) (80 mg, 14% yield) HCl salt as a yellow solid; $^1$H NMR (300 MHz, DMSO-d$_6$): δ 10.85 (s, 1H), 8.81-8.66 (m, 1H), 8.37 (d, J=7.2 Hz, 1H), 7.96-7.82 (m, 1H), 7.08 (s, 1H), 7.03 (s, 2H), 4.62 (m, 1H), 4.20-3.42 (m, 13H), 2.26-1.86 (m, 4H); MS (ES+): 467.3 (M+1), 489.3 (M+Na); MS (ES-): 501.3 (M+Cl).

Scheme 149

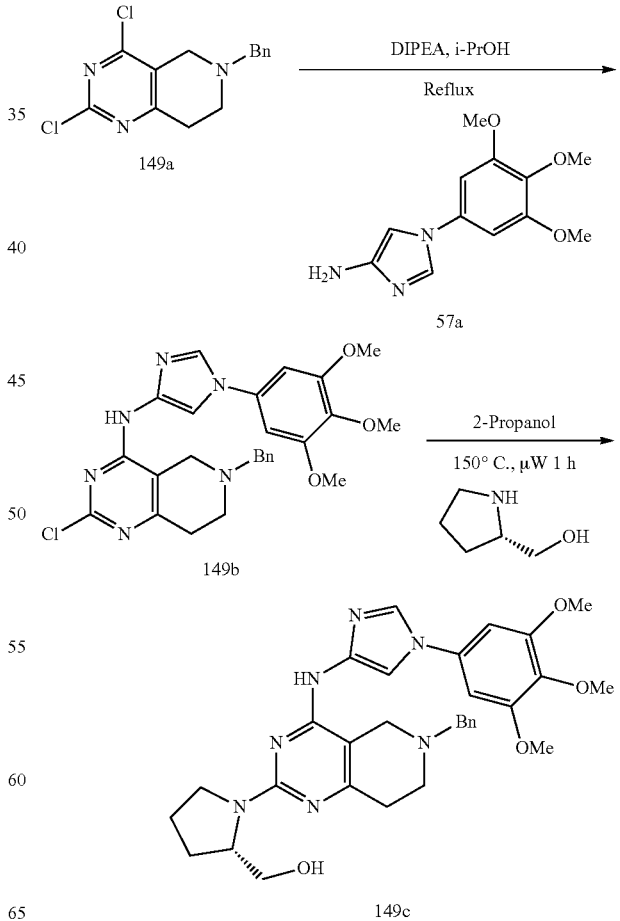

333

Preparation of (S)-(1-(6-benzyl-4-((1-(3,4,5-trimethoxyphenyl)-1H-imidazol-4-yl)amino)-5,6,7,8-tetrahydropyrido[4,3-d]pyrimidin-2-yl)pyrrolidin-2-yl)methanol (149c)

Step-1: Preparation of 6-benzyl-2-chloro-N-(1-(3,4,5-trimethoxyphenyl)-1H-imidazol-4-yl)-5,6,7,8-tetrahydropyrido[4,3-d]pyrimidin-4-amine (149b)

Compound 149b was prepared according to the procedure reported in Scheme 1 from 6-benzyl-2,4-dichloro-5,6,7,8-tetrahydropyrido[4,3-d]pyrimidine (149a) (1 g, 3.4 mmol) in 2-Propanol (15 mL) using DIPEA (2.38 mL, 13.6 mmol) and 1-(3,4,5-trimethoxyphenyl)-1H-imidazol-4-amine (57a) (1.17 g, 4.08 mmol). This gave 6-benzyl-2-chloro-N-(1-(3,4,5-trimethoxyphenyl)-1H-imidazol-4-yl)-5,6,7,8-tetrahydropyrido[4,3-d]pyrimidin-4-amine (149b) (320 mg, 19% yield) as a buff colored solid; $^1$H NMR (300 MHz, DMSO-d6) δ 9.57 (s, 1H), 8.14 (d, J=1.3 Hz, 1H), 7.77 (d, J=1.5 Hz, 1H), 7.37 (d, J=8.2 Hz, 4H), 7.29 (d, J=7.0 Hz, 1H), 6.94-6.83 (m, 2H), 3.86 (d, J=1.2 Hz, 6H), 3.73 (s, 2H), 3.68 (d, J=1.1 Hz, 3H), 3.51 (s, 2H), 2.72 (s, 4H); MS (ES+): 507.3 (M+1), (ES−): 541.4 (M+Cl).

Step-2: Preparation of (S)-(1-(6-benzyl-4-((1-(3,4,5-trimethoxyphenyl)-1H-imidazol-4-yl)amino)-5,6,7,8-tetrahydropyrido[4,3-d]pyrimidin-2-yl)pyrrolidin-2-yl)methanol (149c)

Compound 149c was prepared from 6-benzyl-2-chloro-N-(1-(3,4,5-trimethoxyphenyl)-1H-imidazol-4-yl)-5,6,7,8-tetrahydropyrido[4,3-d]pyrimidin-4-amine (149b) (120 mg, 0.24 mmol), (S)-pyrrolidin-2-ylmethanol (72 mg, 0.71 mmol) in 2-Propanol (2 mL) according to the procedure reported in Scheme 2. This gave after workup and purification by flash column chromatography [silica gel, (12 g), eluting with DMA 80 in dichloromethane (0 to 40%)], (S)-(1-(6-benzyl-4-((1-(3,4,5-trimethoxyphenyl)-1H-imidazol-4-yl)amino)-5,6,7,8-tetrahydropyrido[4,3-d]pyrimidin-2-yl)pyrrolidin-2-yl)methanol (149c) (131 mg, 97% yield) as a light brown solid; $^1$H NMR (300 MHz, DMSO-d$_6$) δ 8.67 (s, 1H, D$_2$O exchangeable), 8.15 (s, 1H), 7.91 (s, 1H), 7.51-7.09 (m, 5H), 6.90 (s, 2H), 5.31-4.80 (m, 1H, D$_2$O exchangeable), 4.13 (d, J=19.8 Hz, 1H), 3.86 (s, 7H), 3.79-3.51 (m, 8H), 3.45 (s, 2H), 2.64 (d, J=5.3 Hz, 2H), 2.61-2.50 (m, 2H), 2.03-1.75 (m, 4H); MS (ES+): 572.4 (M+1), 594.4 (M+Na), (ES−): 570.5 (M−1).

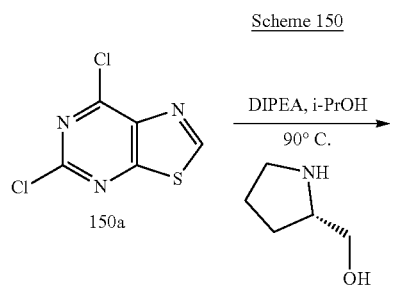

Scheme 150

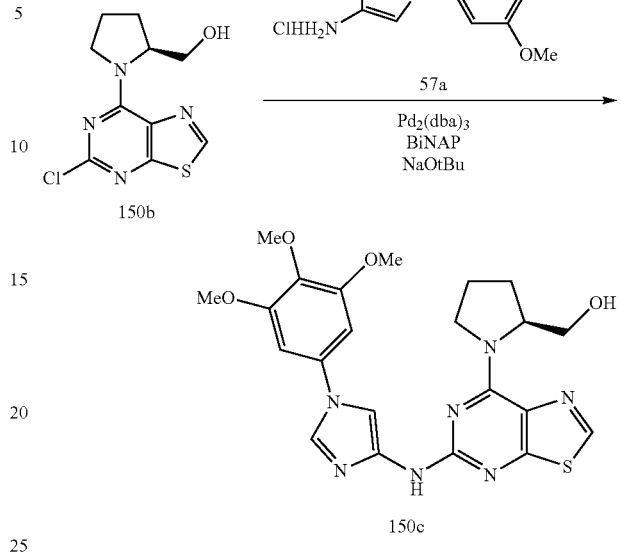

Preparation of (S)-(1-(5-((1-(3,4,5-trimethoxyphenyl)-1H-imidazol-4-yl)amino)thiazolo[5,4-d]pyrimidin-7-yl)pyrrolidin-2-yl)methanol (150c)

Step-1: Preparation of (S)-(1-(5-chlorothiazolo[5,4-d]pyrimidin-7-yl)pyrrolidin-2-yl)methanol (150b) Compound 150b was prepared from 5,7-dichlorothiazolo[5,4-d]pyrimidine (150a) (500 mg, 15.87 mmol; CAS #13479-88-4) in 2-Propanol (10 mL) using (S)-pyrrolidin-2-ylmethanol (0.24 mL, 2.43 mmol), DIPEA (1.27 mL, 7.28 mmol) according to the procedure reported in step-1 of Scheme 96. This gave after work up and purification by flash column chromatography [silica gel, (12 g) eluting with MeOH in CH$_2$Cl$_2$ from 0 to 30%] (S)-(1-(5-chlorothiazolo[5,4-d]pyrimidin-7-yl)pyrrolidin-2-yl)methanol (150b) (0.33 g, 50% yield) as a white solid; $^1$H NMR (300 MHz, DMSO-d$_6$): δ 9.17 (d, J=13.2 Hz, 1H), 5.04 (q, J=5.5, 5.0 Hz, 1H), 4.85 (t, J=5.7 Hz, 1H), 4.40 (dt, J=10.4, 4.6 Hz, 1H), 4.23-3.96 (m, 1H), 3.75-3.49 (m, 2H), 2.20-1.83 (m, 4H). MS (ES+): 293.2 (M+Na).

Step-2: Preparation of (S)-(1-(5-((1-(3,4,5-trimethoxyphenyl)-1H-imidazol-4-yl)amino)thiazolo[5,4-d]pyrimidin-7-yl)pyrrolidin-2-yl)methanol (150c)

Compound 150c was prepared from (S)-(1-(5-chlorothiazolo[5,4-d]pyrimidin-7-yl)pyrrolidin-2-yl)methanol (150b) (0.15 g, 0.55 mmol), 1-(3,4,5-trimethoxyphenyl)-1H-imidazol-4-amine hydrochloride (57a) (0.19 g, 0.67 mmol), 2,2'-bis(diphenylphosphino)-1,1'-binaphthyl (BiNAP, 0.04 g, 0.07 mmol), sodium 2-methylpropan-2-olate (0.16 g, 1.66 mmol), Pd$_2$(dba)$_3$ (0.05 g, 0.06 mmol) in anhydrous toluene (7 mL) according to the procedure reported in step-3 of Scheme 101. This gave after workup and purification by flash column chromatography [silica gel (12 g), eluting with DMA-80 in CH$_2$Cl$_2$ from 0 to 30%], reverse phase flash column chromatography [(silica gel C-18, 24 g) eluting with acetonitrile and 0.1% HCl water] followed by lyophilization (S)-(1-(5-((1-(3,4,5-trimethoxyphenyl)-1H-imidazol-4-yl)

amino)thiazolo[5,4-d]pyrimidin-7-yl)pyrrolidin-2-yl)
methanol (150c) (0.03 g, 10% yield) as a yellow solid; $^1$H
NMR (300 MHz, DMSO-d$_6$) δ 10.14 (s, 1H), 9.20 (s, 1H),
8.90 (s, 1H), 7.93 (s, 1H), 7.12 (s, 2H), 5.19-4.98 (m, 1H),
4.70-4.47 (m, 1H), 4.31-4.14 (m, 1H), 4.13-3.96 (m, 1H),
3.94-3.55 (m, 11H), 2.15-1.81 (m, 4H); MS (ES+): 484.3
(M+1); MS (ES−): 518.3 (M+Cl). HPLC purity: 95.61%.

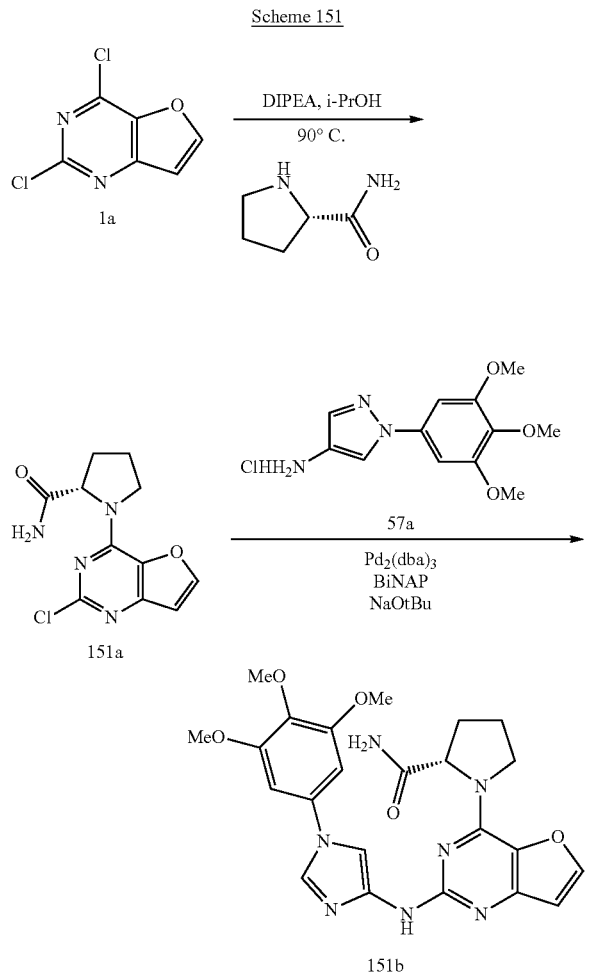

Preparation of (S)-1-(2-((1-(3,4,5-trimethoxyphe-
nyl)-1H-imidazol-4-yl)amino)furo[3,2-d]pyrimidin-
4-yl)pyrrolidine-2-carboxamide (151b)

Step-1: Preparation of (S)-1-(2-chlorofuro[3,2-d]pyrimi-
din-4-yl)pyrrolidine-2-carboxamide (151a) Compound 151a
was prepared from 2,4-dichlorofuro[3,2-d]pyrimidine (1a)
(800 mg, 4.23 mmol) in 2-Propanol (16 mL) using (S)-
pyrrolidine-2-carboxamide (482 mg, 4.23 mmol), DIPEA
(2.21 mL, 12.69 mmol) according to the procedure reported
in step-1 of Scheme 96. This gave (S)-1-(2-chlorofuro[3,2-
d]pyrimidin-4-yl)pyrrolidine-2-carboxamide (151a) (600
mg, 53% yield) as a white solid; $^1$H NMR (300 MHz,
DMSO-d$_6$) (mixture of rotamers) δ 8.33, 8.25 (2s, 1H), 7.58,
7.53 (2s, 1H), 7.13, 7.05 (2s, 1H), 6.96 (2s, 1H), 4.87, 4.52
(2d, J=8.4 Hz, 1H), 4.18-3.86 (m, 1H), 3.81-3.52 (m, 1H),
2.38-1.70 (m, 4H); MS (ES+): 267.3 (M+1), (ES−): 301.2,
303.2 (M+Cl).

Step-2: Preparation of (S)-1-(2-((1-(3,4,5-
trimethoxyphenyl)-1H-imidazol-4-yl)amino)furo[3,
2-d]pyrimidin-4-yl)pyrrolidine-2-carboxamide
(151b)

Compound 151b was prepared from (S)-1-(2-chlorofuro
[3,2-d]pyrimidin-4-yl)pyrrolidine-2-carboxamide (151a)
(0.3 g, 1.13 mmol), 1-(3,4,5-trimethoxyphenyl)-1H-imida-
zol-4-amine hydrochloride (57a) (0.32 g, 1.13 mmol), 2,2'-
bis(diphenylphosphino)-1,1'-binaphthyl (BiNAP, 100 mg,
0.11 mmol), sodium 2-methylpropan-2-olate (0.32 g, 3.37
mmol), Pd$_2$(dba)$_3$ (100 mg, 0.11 mmol) in anhydrous tolu-
ene (10 mL) according to the procedure reported in step-3 of
Scheme 101. This gave after workup and purification by
flash column chromatography [silica gel, (12 g) eluting with
DMA 80 in CH$_2$Cl$_2$ from 0 to 30%], reverse phase flash
column chromatography [(silica gel C-18, 24 g) eluting with
acetonitrile and 0.1% HCl water] followed by lyophilization
(S)-1-(2-((1-(3,4,5-trimethoxyphenyl)-1H-imidazol-4-yl)
amino)furo[3,2-d]pyrimidin-4-yl)pyrrolidine-2-carboxam-
ide (151b) (60 mg, 10% yield) as a yellow solid; $^1$H NMR
(300 MHz, DMSO-d$_6$) (mixture of two rotamers) δ 10.94
and 10.78 (2s, 1H), 8.79 and 8.68 (2s, 1H), 8.43 and 8.33
(2d, J=2.1 Hz, 1H), 7.94 and 7.79 (2s, 1H), 7.60 and 7.26
(2s, 1H), 7.21 and 7.14 (2s, 2H), 7.10 and 7.09 (2s, 1H),
7.07-7.02 (m, 1H), 5.09-5.01 and 4.80-4.68 (2m, 1H), 4.40-
4.26 (m, 1H), 4.12-3.99 (m, 1H), 3.92 and 3.88 (2s, 6H),
3.69 (s, 3H), 2.43-1.84 (m, 4H); MS (ES+): 480.3 (M+1);
MS (ES−): 478.4 (M−1).

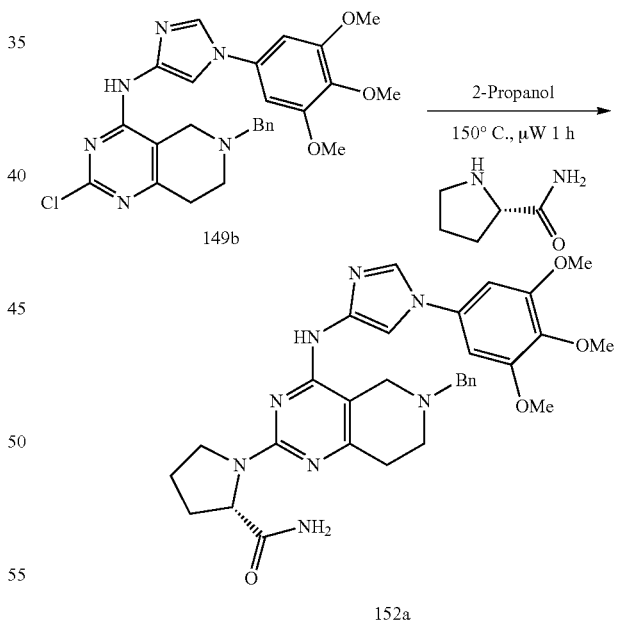

Preparation of (S)-1-(6-benzyl-4-(1-(3,4,5-
trimethoxyphenyl)-1H-imidazol-4-ylamino)-5,6,7,8-
tetrahydropyrido[4,3-d]pyrimidin-2-yl)pyrrolidine-2-
carboxamide (152a)

Compound 152a was prepared from 6-benzyl-2-chloro-
N-(1-(3,4,5-trimethoxyphenyl)-1H-imidazol-4-yl)-5,6,7,8-
tetrahydropyrido[4,3-d]pyrimidin-4-amine (149b) (120 mg, 0.24 mmol), (S)-pyrrolidine-2-carboxamide (81 mg, 0.71 mmol) in 2-Propanol (3 mL) according to the procedure reported in Scheme 2. This gave after workup and purification by flash column chromatography [silica gel, (12 g), eluting with DMA 80 in dichloromethane (0 to 40%)], (S)-1-(6-benzyl-4-(1-(3,4,5-trimethoxyphenyl)-1H-imidazol-4-ylamino)-5,6,7,8-tetrahydropyrido[4,3-d]pyrimidin-2-yl)pyrrolidine-2-carboxamide (152a) (90 mg, 65% yield) as a light yellow solid; $^1$H NMR (300 MHz, DMSO-d$_6$) δ 8.46 (s, 1H, D$_2$O exchangeable), 8.12 (s, 1H), 7.97-7.72 (m, 1H), 7.49-7.24 (m, 5H), 7.20-6.98 (m, 2H), 6.95-6.80 (m, 2H), 4.39 (d, J=8.6 Hz, 1H), 3.99-3.84 (m, 7H), 3.83-3.76 (m, 1H), 3.78-3.63 (m, 3H), 3.55-3.41 (m, 3H), 3.42-3.32 (m, 1H), 2.78-2.56 (m, 4H), 2.30-2.02 (m, 1H), 2.02-1.76 (m, 3H); MS (ES+): 585.4 (M+1), (ES−): 583.4 (M−1).

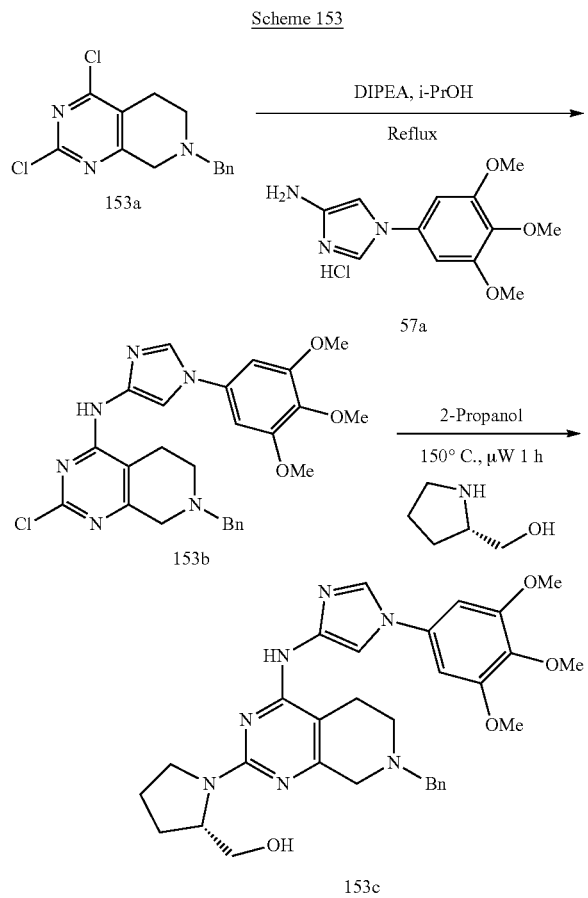

Scheme 153

Preparation of (S)-(1-(7-benzyl-4-((1-(3,4,5-trimethoxyphenyl)-1H-imidazol-4-yl)amino)-5,6,7,8-tetrahydropyrido[3,4-d]pyrimidin-2-yl)pyrrolidin-2-yl)methanol (153c)

Step-1: Preparation of 7-benzyl-2-chloro-N-(1-(3,4,5-trimethoxyphenyl)-1H-imidazol-4-yl)-5,6,7,8-tetrahydropyrido[3,4-d]pyrimidin-4-amine (153b)

Compound 153b was prepared according to the procedure reported in Scheme 1 from 7-benzyl-2,4-dichloro-5,6,7,8-tetrahydropyrido[3,4-d]pyrimidine (153a) (1 g, 3.4 mmol; CAS #1059735-34-0) in 2-Propanol (15 mL) using DIPEA (2.38 mL, 13.6 mmol) and 1-(3,4,5-trimethoxyphenyl)-1H-imidazol-4-amine hydrochloride (57a) (1.17 g, 4.08 mmol). This gave 7-benzyl-2-chloro-N-(1-(3,4,5-trimethoxyphenyl)-1H-imidazol-4-yl)-5,6,7,8-tetrahydropyrido[3,4-d]pyrimidin-4-amine (153b) (350 mg, 20% yield) as a buff colored solid; $^1$H NMR (300 MHz, DMSO-d$_6$) δ 9.56 (s, 1H), 8.15 (d, J=1.7 Hz, 1H), 7.78 (s, 1H), 7.45-7.23 (m, 5H), 6.90 (s, 2H), 3.86 (s, 6H), 3.68 (s, 3H), 3.67 (s, 2H), 3.39 (s, 2H), 2.78-2.68 (m, 2H), 2.68-2.58 (m, 2H); MS (ES+): 507.3 (M+1), 529.3 (M+Na), (ES−): 541.4 (M+Cl).

Step-2: Preparation of (S)-(1-(7-benzyl-4-((1-(3,4,5-trimethoxyphenyl)-1H-imidazol-4-yl)amino)-5,6,7,8-tetrahydropyrido[3,4-d]pyrimidin-2-yl)pyrrolidin-2-yl)methanol (153c)

Compound 153c was prepared from 7-benzyl-2-chloro-N-(1-(3,4,5-trimethoxyphenyl)-1H-imidazol-4-yl)-5,6,7,8-tetrahydropyrido[3,4-d]pyrimidin-4-amine (153b) (150 mg, 0.296 mmol), (S)-pyrrolidin-2-ylmethanol (90 mg, 0.89 mmol) in 2-Propanol (2 mL) according to the procedure reported in Scheme 2. This gave after workup and purification by flash column chromatography [silica gel (25 g), eluting with DMA 80 in dichloromethane (0 to 40%)], (S)-(1-(7-benzyl-4-((1-(3,4,5-trimethoxyphenyl)-1H-imidazol-4-yl)amino)-5,6,7,8-tetrahydropyrido[3,4-d]pyrimidin-2-yl)pyrrolidin-2-yl)methanol (153c) (110 mg, 65% yield) as an orange solid. $^1$H NMR (300 MHz, DMSO-d$_6$) δ 8.65 (s, 1H, D$_2$O exchangeable), 8.17 (s, 1H), 7.92 (s, 1H), 7.45-7.14 (m, 5H), 6.91 (s, 2H), 5.01 (s, 1H, D$_2$O exchangeable), 4.33-3.97 (m, 1H), 3.67 (s, 3H), 3.63 (s, 2H), 3.32 (d, J=1.7 Hz, 4H), 3.22 (s, 2H), 2.69 (q, J=5.6 Hz, 2H), 2.56 (d, J=5.5 Hz, 2H), 2.02-1.72 (m, 4H); MS (ES+) 572.4 (M+1), 594.5 (M+Na), (ES−): 570.4 (M−1), 606.6 (M+Cl).

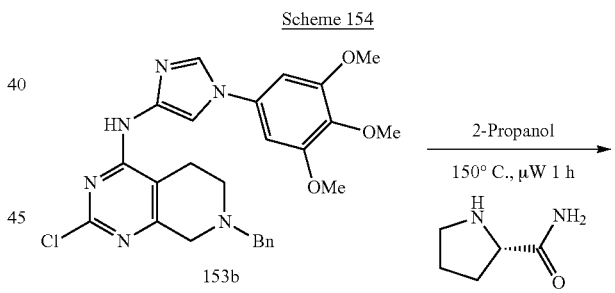

Scheme 154

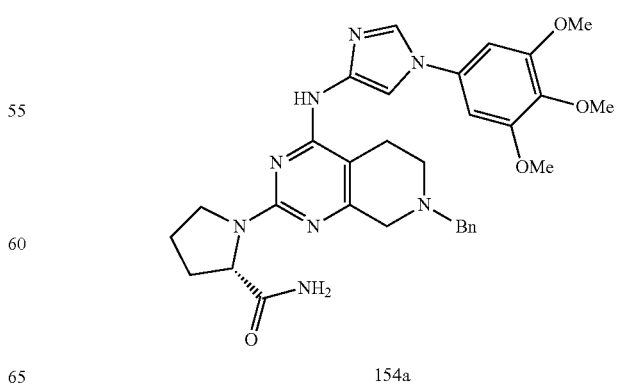

154a

Preparation of (S)-1-(7-benzyl-4-((1-(3,4,5-trimethoxyphenyl)-1H-imidazol-4-yl)amino)-5,6,7,8-tetrahydropyrido[3,4-d]pyrimidin-2-yl)pyrrolidine-2-carboxamide (154a)

Compound 154a was prepared from 7-benzyl-2-chloro-N-(1-(3,4,5-trimethoxyphenyl)-1H-imidazol-4-yl)-5,6,7,8-tetrahydropyrido[3,4-d]pyrimidin-4-amine (153b) (150 mg, 0.3 mmol), (S)-pyrrolidine-2-carboxamide (101 mg, 0.89 mmol) in 2-Propanol (4 mL) according to the procedure reported in Scheme 2. This gave after workup and purification by flash column chromatography [silica gel, (12 g), eluting with DMA 80 in dichloromethane (0 to 40%)], (S)-1-(7-benzyl-4-((1-(3,4,5-trimethoxyphenyl)-1H-imidazol-4-yl)amino)-5,6,7,8-tetrahydropyrido[3,4-d]pyrimidin-2-yl)pyrrolidine-2-carboxamide (154a) (100 mg, 58% yield) as an orange solid; $^1$H NMR (300 MHz, DMSO-$d_6$) δ 8.44 (s, 1H, $D_2O$ exchangeable), 8.14 (s, 1H), 7.85 (s, 1H), 7.42-7.23 (m, 5H), 7.08 (s, 2H), 6.90 (s, 2H), 4.36 (s, 1H), 3.91 (s, 6H), 3.83-3.74 (m, 1H), 3.68 (s, 3H), 3.66-3.55 (m, 2H), 3.55-3.35 (m, 1H), 3.23 (s, 2H), 2.69 (d, J=6.3 Hz, 2H), 2.57 (d, J=5.4 Hz, 2H), 2.15 (s, 1H), 1.91 (d, J=14.8 Hz, 3H); MS (ES+): 585.4 (M+1), 607.4 (M+Na), (ES−): 583.4 (M−1).

Preparation (S)-1-(4-((1-(3,4,5-trimethoxyphenyl)-1H-imidazol-4-yl)amino)thieno[2,3-d]pyrimidin-2-yl)pyrrolidine-2-carboxamide (155a)

Compound 155a was prepared according to the procedure reported in step-2 of Scheme 76 from 2-chloro-N-(1-(3,4,5-trimethoxyphenyl)-1H-imidazol-4-yl)thieno[2,3-d]pyrimidin-4-amine (84a) (800 mg, 1.91 mmol), (S)-pyrrolidine-2-carboxamide (2.18 g, 19.1 mmol) and DIPEA (0.627 mL, 3.59 mmol) in NMP (40 mL). This gave after workup and purification by flash chromatography (Silica gel, eluting with 0-10% methanol in DCM) compound (155a) (0.43 g, 44%) as an off-white solid. The solid was repurified by reverse phase flash column chromatography [(silica gel C-18, 24 g) eluting with acetonitrile and 0.1% HCl in water (0-50%)] to afford (S)-1-(4-((1-(3,4,5-trimethoxyphenyl)-1H-imidazol-4-yl)amino)thieno[2,3-d]pyrimidin-2-yl)pyrrolidine-2-carboxamide (155a) (232 mg) HCl salt as a white solid; $^1$H NMR (300 MHz, DMSO-$d_6$): δ 11.29 (s, 1H), 8.43 (s, 1H), 7.99 (d, J=5.8 Hz, 1H), 7.90 (s, 1H), 7.53 (s, 1H), 7.40 (d, J=5.7 Hz, 1H), 7.17 (s, 1H), 7.14 (s, 2H), 4.62 (d, J=8.6 Hz, 1H), 3.94 (s, 7H), 3.69 (s, 3H), 3.66-3.51 (m, 1H), 2.38-1.86 (m, 4H). MS (ES+): 496.3 (M+1); MS (ES−): 494.4 (M−1), 530.3 (M+Cl).

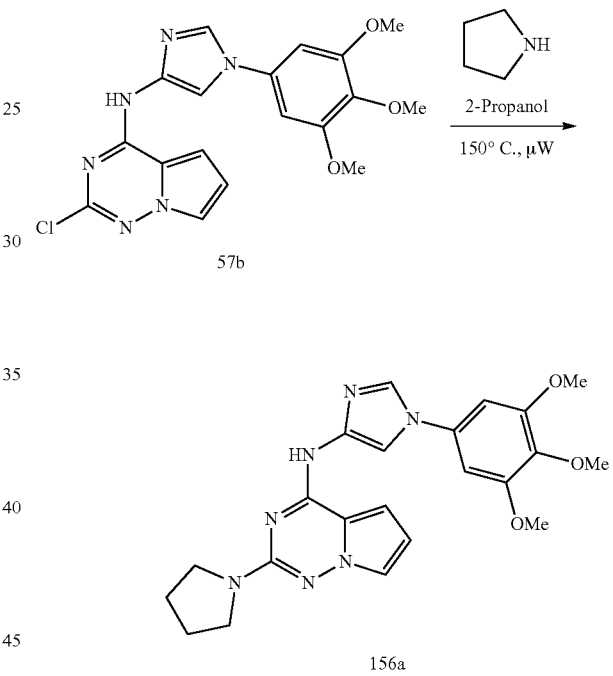

Scheme 156

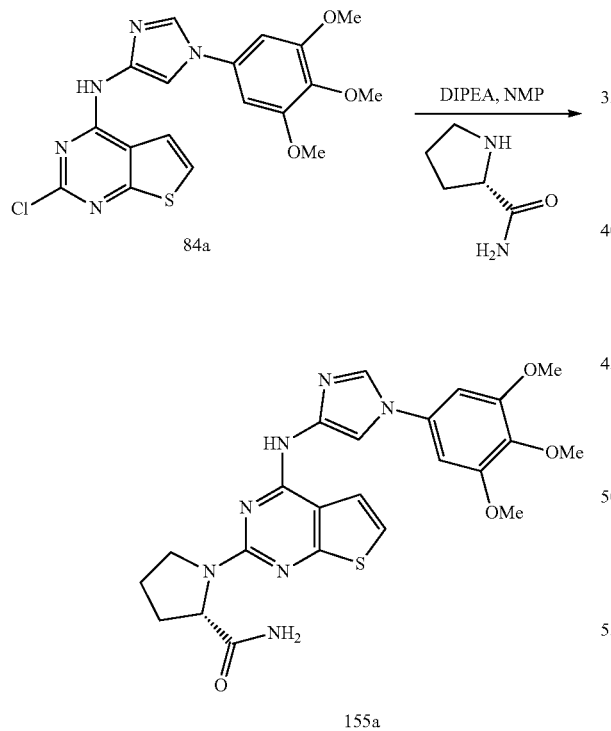

Scheme 155

Preparation of 2-(pyrrolidin-1-yl)-N-(1-(3,4,5-trimethoxyphenyl)-1H-imidazol-4-yl)pyrrolo[2,1-f][1,2,4]triazin-4-amine (156a)

Compound 156a was prepared from 2-chloro-N-(1-(3,4,5-trimethoxyphenyl)-1H-imidazol-4-yl)pyrrolo[2,1-f][1,2,4]triazin-4-amine (57b) (150 mg, 0.37 mmol), pyrrolidine (0.09 mL, 1.12 mmol) in 2-Propanol (5 mL) according to the procedure reported in Scheme 2. This gave after workup and purification by flash column chromatography [silica gel, (12 g), eluting with DMA 80 in dichloromethane (0 to 30%)], 2-(pyrrolidin-1-yl)-N-(1-(3,4,5-trimethoxyphenyl)-1H-imidazol-4-yl)pyrrolo[2,1-f][1,2,4]triazin-4-amine (156a) (0.03 g, 19% yield) as a yellow solid; $^1$H NMR (300 MHz, DMSO-$d_6$): δ 10.56 (s, 1H), 8.25 (s, 1H), 8.06 (s, 1H), 7.39 (t, J=1.9 Hz, 1H), 7.11 (dd, J=4.5, 1.7 Hz, 1H), 6.93 (s, 2H), 6.39 (dd, J=4.4, 2.4 Hz, 1H), 3.87 (s, 6H), 3.69 (s, 3H), 3.55 (d, J=6.2 Hz, 4H), 1.91 (q, J=3.5 Hz, 4H). MS (ES+): 436.4 (M+1).

Scheme 157

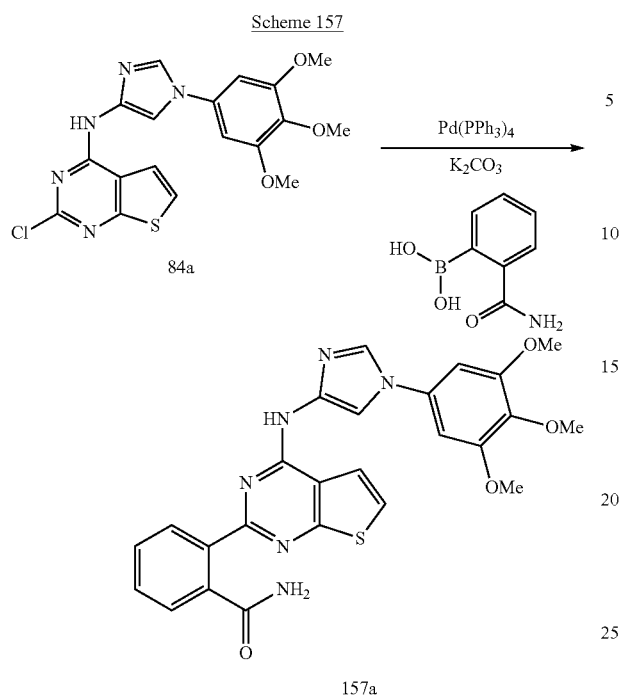

Preparation of 2-(4-((1-(3,4,5-trimethoxyphenyl)-1H-imidazol-4-yl)amino)thieno[2,3-d]pyrimidin-2-yl)benzamide (157a)

Compound 157a was prepared from 2-chloro-N-(1-(3,4,5-trimethoxyphenyl)-1H-imidazol-4-yl)thieno[2,3-d]pyrimidin-4-amine (84a) (150 mg, 0.36 mmol), using 2-carbamoylphenylboronic acid (89 mg, 0.54 mmol), Pd(Ph₃P)₄ (83 mg, 0.072 mmol) and potassium carbonate (99 mg, 0.72 mmol) in 1,4-Dioxane and Water (10 mL, 4:1) according to the procedure reported in step-3 of Scheme 77. This gave after workup and filtration followed by drying of solid, 2-(4-((1-(3,4,5-trimethoxyphenyl)-1H-imidazol-4-yl)amino)thieno[2,3-d]pyrimidin-2-yl)benzamide (157a) (23 mg, 13% yield) as an off white solid; $^1$H NMR (300 MHz, DMSO-$d_6$) δ 10.48 (s, 1H), 8.22 (d, J=1.5 Hz, 2H, D₂O exchangeable), 8.10 (d, J=6.0 Hz, 1H), 7.95-7.87 (m, 1H), 7.71-7.64 (m, 1H), 7.57-7.40 (m, 4H), 7.33-7.18 (m, 1H), 7.16 (s, 2H), 3.91 (s, 6H), 3.68 (s, 3H); MS (ES+): 503.3 (M+1); 525.2 (M+Na); (ES−) 501.3 (M−1).

Scheme 158

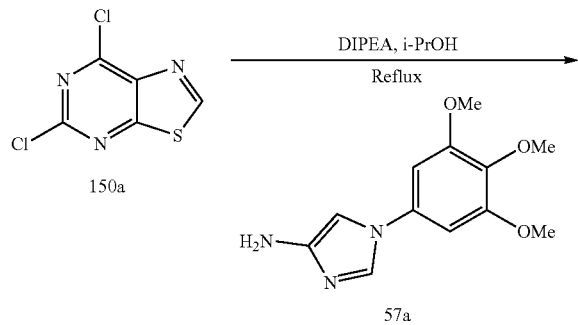

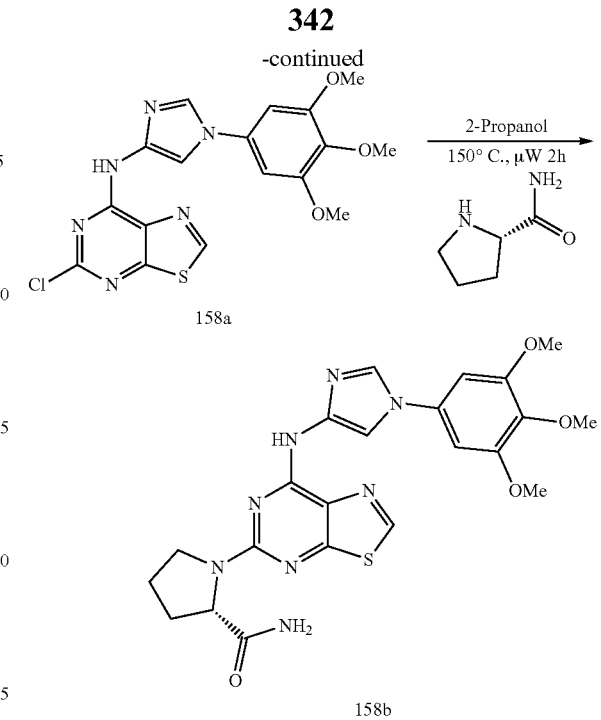

Preparation of (S)-1-(7-((1-(3,4,5-trimethoxyphenyl)-1H-imidazol-4-yl)amino)thiazolo[5,4-d]pyrimidin-5-yl)pyrrolidine-2-carboxamide (158b)

Step-1: Preparation of 5-chloro-N-(1-(3,4,5-trimethoxyphenyl)-1H-imidazol-4-yl)thiazolo[5,4-d]pyrimidin-7-amine (158a)

Compound 158a was prepared according to the procedure reported in Scheme 1 from 5,7-dichlorothiazolo[5,4-d]pyrimidine (150a) (0.3 g, 1.46 mmol) in 2-Propanol (10 mL) using DIPEA (0.76 mL, 4.37 mmol) and 1-(3,4,5-trimethoxyphenyl)-1H-imidazol-4-amine (57a) (0.46 g, 1.6 mmol, free base). This gave after workup and purification by flash column chromatography [silica gel, (40 g) eluting with methanol in DCM (0 to 30%)] 5-chloro-N-(1-(3,4,5-trimethoxyphenyl)-1H-imidazol-4-yl)thiazolo[5,4-d]pyrimidin-7-amine (158a) (0.41 g, 67% yield) as a brown solid; MS (ES+): 441.2 & 443.2 (M+Na); MS (ES−): 417.3 (M−1).

Step-2: Preparation of (S)-1-(7-((1-(3,4,5-trimethoxyphenyl)-1H-imidazol-4-yl)amino)thiazolo[5,4-d]pyrimidin-5-yl)pyrrolidine-2-carboxamide (158b)

Compound 158b was prepared from 5-chloro-N-(1-(3,4,5-trimethoxyphenyl)-1H-imidazol-4-yl)thiazolo[5,4-d]pyrimidin-7-amine (158a) (0.07 g, 0.16 mmol), (S)-pyrrolidine-2-carboxamide (0.05 g, 0.47 mmol) in 2-Propanol (5 mL) according to the procedure reported in Scheme 2. This gave after workup and purification by flash column chromatography [silica gel, (25 g), eluting with DMA 80 in dichloromethane (0 to 30%)], (S)-1-(7-((1-(3,4,5-trimethoxyphenyl)-1H-imidazol-4-yl)amino)thiazolo[5,4-d]pyrimidin-5-yl)pyrrolidine-2-carboxamide (158b) (0.04 g, 52% yield) as a yellow solid; $^1$H NMR (300 MHz, DMSO-$d_6$): (a mixture of two rotamers) δ 9.79 and 9.26 (2s, 1H), 8.85 and 8.52 (2s, 1H), 8.18 and 8.09 (2s, 1H), 7.90 (s, 1H), 7.46-6.79 (m, 4H), 4.56-4.37 and 4.36-4.29 (2m, 1H), 3.91 (s, 7H), 3.72 and 3.69 (2s, 3H), 3.62-3.48 (m, 1H), 2.37-1.83 (m, 4H). MS (ES+): 497.3 (M+1); MS (ES−): 531.3 (M+Cl).

Scheme 159

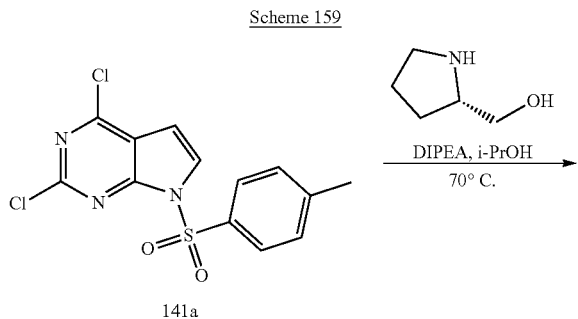

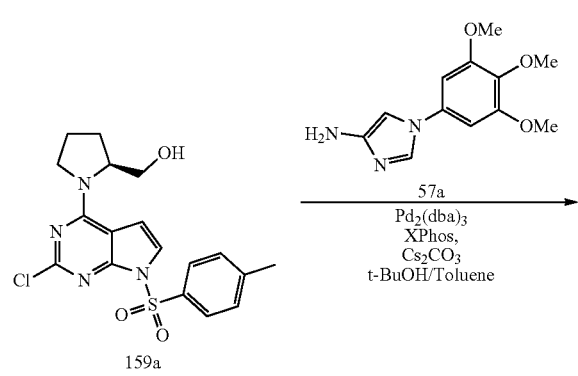

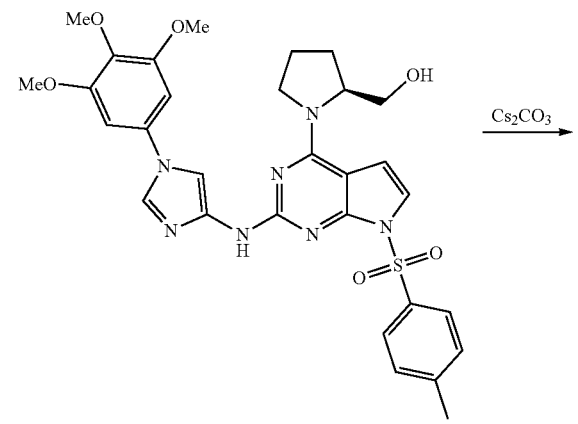

Preparation of (S)-(1-(2-((1-(3,4,5-trimethoxyphenyl)-1H-imidazol-4-yl)amino)-7H-pyrrolo[2,3-d]pyrimidin-4-yl)pyrrolidin-2-yl)methanol (159c)

Step-1: Preparation of (S)-(1-(2-chloro-7-tosyl-7H-pyrrolo[2,3-d]pyrimidin-4-yl)pyrrolidin-2-yl)methanol (159a)

Compound 159a was prepared from 2,4-dichloro-7-tosyl-7H-pyrrolo[2,3-d]pyrimidine (141a) (1 g, 2.92 mmol) in 2-Propanol (10 mL), (S)-pyrrolidin-2-ylmethanol (0.3 gm, 2.92 mmol), DIPEA (0.77 mL, 4.38 mmol) according to the procedure reported in step-1 of Scheme 96. This gave after workup and purification by flash column chromatography [silica (12 g), eluting with ethyl acetate/MeOH (9:1) in hexane from 0-70%] (S)-(1-(2-chloro-7-tosyl-7H-pyrrolo[2,3-d]pyrimidin-4-yl)pyrrolidin-2-yl)methanol (159a) (865 mg, 73% yield) as a white solid; $^1$H NMR (300 MHz, DMSO-d$_6$) δ 7.96 (d, J=8.2 Hz, 2H), 7.58 (s, 1H), 7.46 (d, J=8.1 Hz, 2H), 6.88 (s, 1H), 5.10-4.66 (m, 1H, D$_2$O exchangeable), 4.28 (s, 1H), 3.90-3.35 (m, 4H), 2.37 (s, 3H), 2.12-1.81 (m, 4H); MS (ES$^+$) 407.3 (M+1); (ES−) 441.2 (M+Cl).

Step-2: Preparation of (S)-(1-(7-tosyl-2-((1-(3,4,5-trimethoxyphenyl)-1H-imidazol-4-yl)amino)-7H-pyrrolo[2,3-d]pyrimidin-4-yl)pyrrolidin-2-yl)methanol (159b)

Compound 159b was prepared from (S)-(1-(2-chloro-7-tosyl-7H-pyrrolo[2,3-d]pyrimidin-4-yl)pyrrolidin-2-yl)methanol (159a) (620 mg, 1.52 mmol), 1-(3,4,5-trimethoxyphenyl)-1H-imidazol-4-amine (57a) (1085 mg, 3.05, free base), dicyclohexyl(2',4',6'-triisopropylbiphenyl-2-yl)phosphine (XPhos, 327 mg, 0.69 mmol), cesium carbonate (1241 mg, 3.81 mmol), Pd$_2$(dba)$_3$ (209 mg, 0.23 mmol) in toluene and t-BuOH (20 mL, 5:1) according to the procedure reported in step-3 of Scheme 101. This gave after workup and twice purification by flash column chromatography [silica (40 g), eluting with DMA80 in DCM from 0-60%], [silica (24 g), eluting with MeOH in DCM from 0-10%] (S)-(1-(7-tosyl-2-((1-(3,4,5-trimethoxyphenyl)-1H-imidazol-4-yl)amino)-7H-pyrrolo[2,3-d]pyrimidin-4-yl)pyrrolidin-2-yl)methanol (159b) (198 mg, 21% yield) as a brown solid; $^1$H NMR (300 MHz, DMSO-d$_6$) δ 9.33 (s, 1H, D$_2$O exchangeable), 8.68-8.24 (m, 1H), 8.21 (s, 1H), 8.04 (s, 2H), 7.36 (d, J=8.0 Hz, 2H), 7.25 (d, J=3.8 Hz, 1H), 6.97 (s, 2H), 6.72 (d, J=4.1 Hz, 1H), 5.04-4.55 (m, 1H, D$_2$O exchangeable), 4.56-4.15 (m, 1H), 3.82 (s, 6H), 3.78-3.71 (m, 1H), 3.67 (s, 3H), 3.64-3.47 (m, 3H), 2.30 (s, 3H), 2.13-1.77 (m, 4H); MS (ES+): δ 20.8 (M+1); 642.4 (M+Na); (ES−): 618.4 (M−1).

Step-3: Preparation of (S)-(1-(2-((1-(3,4,5-trimethoxyphenyl)-1H-imidazol-4-yl)amino)-7H-pyrrolo[2,3-d]pyrimidin-4-yl)pyrrolidin-2-yl)methanol (159c)

Compound 159c was prepared from (S)-(1-(7-tosyl-2-((1-(3,4,5-trimethoxyphenyl)-1H-imidazol-4-yl)amino)-7H-pyrrolo[2,3-d]pyrimidin-4-yl)pyrrolidin-2-yl)methanol (159b) (150 mg, 0.24 mmol) and Cs$_2$CO$_3$ (237 mg, 0.73 mmol) in MeOH/THF (5 mL, 3:2) according to the procedure reported in step-3 of Scheme 141. This gave after workup and purification by flash column chromatography [silica (12 g), eluting with ethyl acetate/MeOH (9:1) in hexane from 0-70%] followed by prep-HPLC [(silica gel C-18, 24 g) eluting with ACN in water (contains 0.1% HCl) from 0-100%], (S)-(1-(2-((1-(3,4,5-trimethoxyphenyl)-1H-imidazol-4-yl)amino)-7H-pyrrolo[2,3-d]pyrimidin-4-yl)pyrrolidin-2-yl)methanol (159c) (26 mg, 23% yield) as an off white solid; $^1$H NMR (300 MHz, DMSO-$d_6$) δ 12.00 (s, 1H, $D_2O$ exchangeable), 10.40 (s, 1H, $D_2O$ exchangeable), 8.37 (s, 1H), 7.67 (s, 1H), 7.16-7.03 (m, 1H), 6.97 (s, 2H), 6.72-6.62 (m, 1H), 4.73-4.38 (m, 2H, $D_2O$ exchangeable), 4.06-3.93 (m, 2H), 3.88 (s, 6H), 3.69 (s, 3H), 3.61-3.53 (m, 2H), 2.22-1.92 (m, 4H); MS (ES+): 466.3 (M+1), 488.4 (M+Na); (ES−): 464.4 (M−1), 500.3 (M+Cl).

Scheme 160

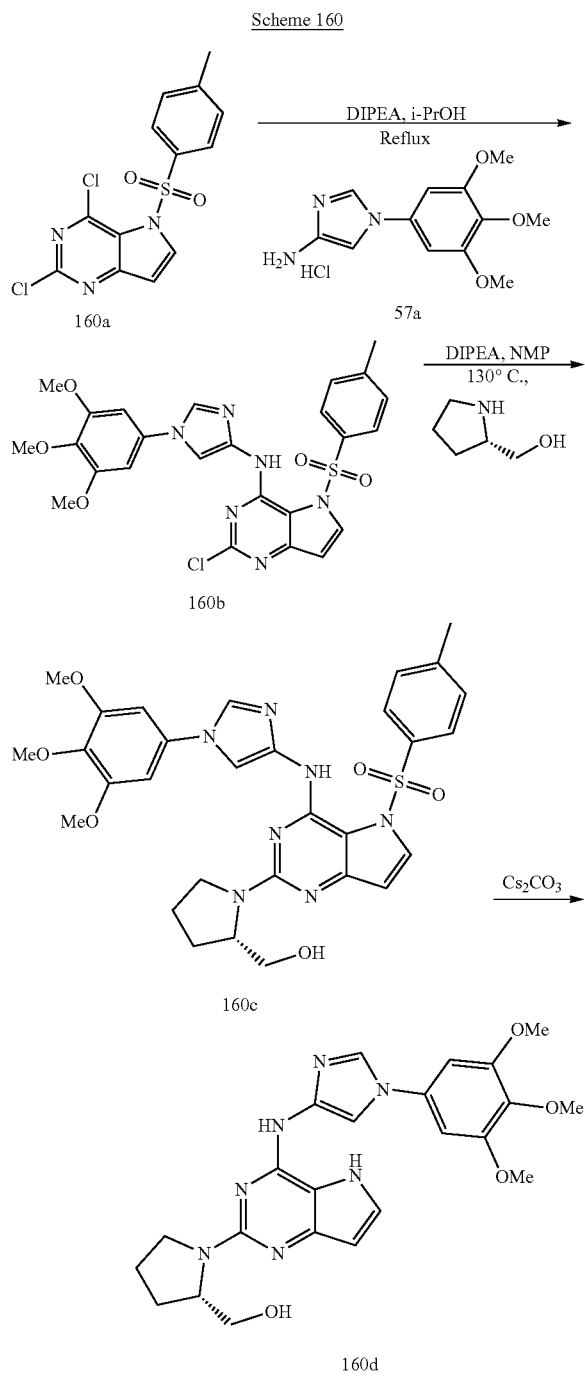

Preparation of (S)-(1-(4-((1-(3,4,5-trimethoxyphenyl)-1H-imidazol-4-yl)amino)-5H-pyrrolo[3,2-d]pyrimidin-2-yl)pyrrolidin-2-yl)methanol (160d)

Step-1: Preparation of 2-chloro-5-tosyl-N-(1-(3,4,5-trimethoxyphenyl)-1H-imidazol-4-yl)-5H-pyrrolo[3,2-d]pyrimidin-4-amine (160b)

Compound 160b was prepared according to the procedure reported in Scheme 1 from 2,4-dichloro-5-tosyl-5H-pyrrolo[3,2-d]pyrimidine (160a) (3 g, 8.77 mmol, prepared according to procedure reported by Su, Qibin et al; *Journal of Medicinal Chemistry*, 57(1), 144-158; 2014) in 2-Propanol (5 mL) using DIPEA (4.59 mL, 26.3 mmol) and 1-(3,4,5-trimethoxyphenyl)-1H-imidazol-4-amine hydrochloride (57a) (4.17 g, 13.15 mmol). This gave after filtration 2-chloro-5-tosyl-N-(1-(3,4,5-trimethoxyphenyl)-1H-imidazol-4-yl)-5H-pyrrolo[3,2-d]pyrimidin-4-amine (160b) (1.03 g, 21% yield) as white solid; $^1$H NMR (300 MHz, DMSO-$d_6$) δ 9.90 (s, 1H), 8.26 (d, J=3.7 Hz, 1H), 8.21 (d, J=1.6 Hz, 1H), 7.86-7.74 (m, 3H), 7.46 (d, J=8.1 Hz, 2H), 6.98-6.90 (m, 3H), 3.89 (s, 6H), 3.72 (s, 3H), 2.34 (s, 3H); MS (ES+): 555.2 (M+1); 577.2 (M+Na).

Step-2: Preparation of (S)-(1-(5-tosyl-4-((1-(3,4,5-trimethoxyphenyl)-1H-imidazol-4-yl)amino)-5H-pyrrolo[3,2-d]pyrimidin-2-yl)pyrrolidin-2-yl)methanol (160c)

Compound 160c was prepared from 2-chloro-5-tosyl-N-(1-(3,4,5-trimethoxyphenyl)-1H-imidazol-4-yl)-5H-pyrrolo[3,2-d]pyrimidin-4-amine (160b) (400 mg, 0.72 mmol), (S)-pyrrolidin-2-ylmethanol (219 mg, 2.16 mmol) and DIPEA (0.378 mL, 2.162 mmol) in NMP (5 mL) according to the procedure reported in step-2 of Scheme 76. This gave after workup and purification by flash column chromatography [silica gel (24 g), eluting with ethyl acetate/MeOH (9:1) in hexane from 0-70%] (S)-(1-(5-tosyl-4-((1-(3,4,5-trimethoxyphenyl)-1H-imidazol-4-yl)amino)-5H-pyrrolo[3,2-d]pyrimidin-2-yl)pyrrolidin-2-yl)methanol (160c) (166 mg, 37% yield) as an off white solid; $^1$H NMR (300 MHz, DMSO-$d_6$) δ 9.57 (s, 1H, $D_2O$ exchangeable), 8.22 (s, 1H), 7.88 (d, J=3.7 Hz, 2H), 7.68 (d, J=8.2 Hz, 2H), 7.41 (d, J=8.1 Hz, 2H), 6.95 (s, 2H), 6.64 (d, J=3.7 Hz, 1H), 4.93-4.80 (m, 1H, $D_2O$ exchangeable), 4.25 (s, 1H), 3.88 (s, 6H), 3.69 (s, 5H), 3.34-3.21 (m, 4H), 2.32 (s, 3H), 2.05-1.79 (m, 4H); MS (ES+): δ 20.4 (M+1); 642.3 (M+Na); (ES−): δ 18.3 (M−1).

Step-3: Preparation of (S)-(1-(4-((1-(3,4,5-trimethoxyphenyl)-1H-imidazol-4-yl)amino)-5H-pyrrolo[3,2-d]pyrimidin-2-yl)pyrrolidin-2-yl)methanol (160d)

Compound 160d was prepared from (S)-(1-(5-tosyl-4-((1-(3,4,5-trimethoxyphenyl)-1H-imidazol-4-yl)amino)-5H-pyrrolo[3,2-d]pyrimidin-2-yl)pyrrolidin-2-yl)methanol (160c) (120 mg, 0.19 mmol) and $Cs_2CO_3$ (189 mg, 0.58 mmol) in MeOH/THF (5 mL, 3:2) according to the procedure reported in step-3 of Scheme 141. This gave after workup and purification by flash column chromatography [silica (12 g), eluting with ethyl acetate/MeOH (9:1) in hexane from 0-100%] (S)-(1-(4-((1-(3,4,5-trimethoxyphenyl)-1H-imidazol-4-yl)amino)-5H-pyrrolo[3,2-d]pyrimidin- 2-yl)pyrrolidin-2-yl)methanol (160d) (38 mg, 42% yield) as a white solid; $^1$H NMR (300 MHz, DMSO-$d_6$) δ 10.62 (s, 1H, $D_2O$ exchange), 9.69 (s, 1H, $D_2O$ exchange), 8.18 (s, 1H), 7.97 (d, J=1.7 Hz, 1H), 7.34 (t, J=2.9 Hz, 1H), 6.93 (s, 2H), 6.10 (d, J=2.5 Hz, 1H), 4.27-4.15 (m, 1H), 3.87 (s, 6H), 3.78-3.62 (m, 5H), 3.62-3.51 (m, 1H), 3.40-3.32 (m, 2H), 1.95-1.89 (m, 4H); MS (ES+): 466.4 (M+1); (ES−): 464.4 (M−1).

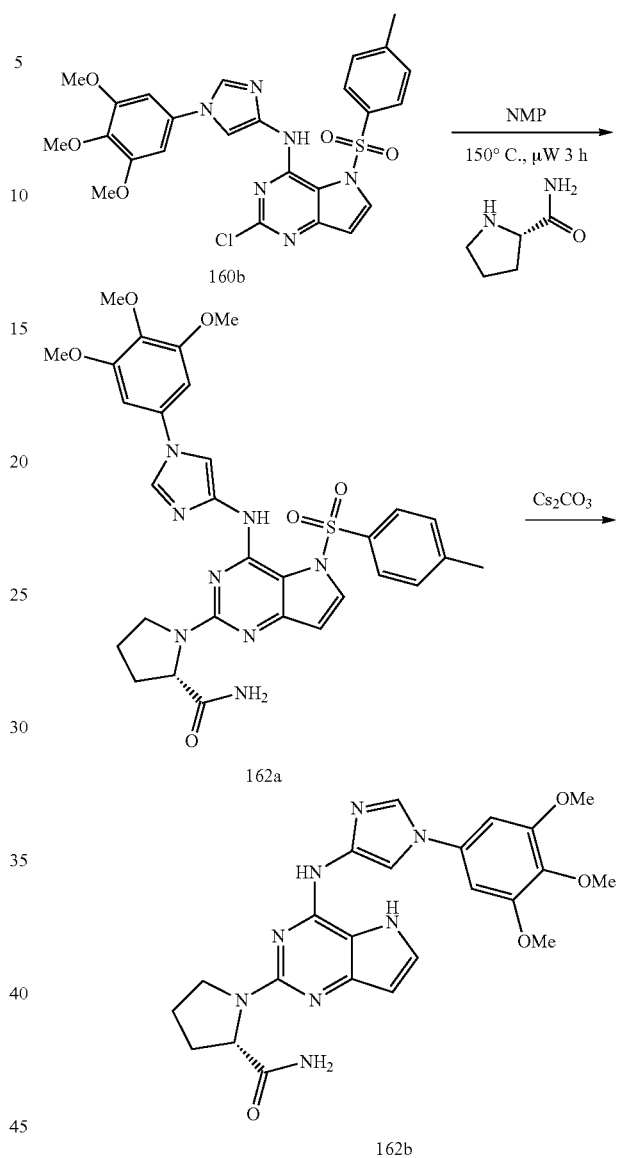

Scheme 161

Scheme 162

Preparation of (S)-1-(4-((1-(3,4,5-trimethoxyphenyl)-1H-imidazol-4-yl)amino)pyrido[3,2-d]pyrimidin-2-yl)pyrrolidine-2-carboxamide (161a)

Compound 161a was prepared from 2-chloro-N-(1-(3,4,5-trimethoxyphenyl)-1H-imidazol-4-yl)pyrido[3,2-d]pyrimidin-4-amine (140b) (0.06 g, 0.15 mmol), (S)-pyrrolidine-2-carboxamide (0.05 g, 0.47 mmol) in 2-Propanol (5 mL) according to the procedure reported in Scheme 2. This gave after workup and purification by flash column chromatography [silica (12 g), eluting with DMA-80 in $CH_2Cl_2$ from 0 to 30%] (S)-1-(4-((1-(3,4,5-trimethoxyphenyl)-1H-imidazol-4-yl)amino)pyrido[3,2-d]pyrimidin-2-yl)pyrrolidine-2-carboxamide (161a) (26 mg, 37% yield) as a yellow solid; $^1$H NMR (300 MHz, DMSO-$d_6$): (a mixture of two rotamers) δ 9.43 and 9.26 (2s, 1H), 8.47 and 8.46 (2s, 1H), 8.23 (s, 1H), 8.11 and 7.98 (2s, 1H), 7.83 and 7.80 (s, 1H), 7.71-7.59 (m, 1H), 7.37 and 7.28 (2s, 1H), 7.18-6.84 (m, 3H), 4.52 and 4.33 (2d, J=8.8 Hz, 1H), 3.94 and 3.89 (2s, 6H), 3.83-3.57 (m, 5H), 2.38-2.19 and 2.08-1.87 (2m, 4H); MS (ES+): 491.3 (M+1), MS (ES−): 525.3 (M+Cl).

Preparation of (S)-1-(4-((1-(3,4,5-trimethoxyphenyl)-1H-imidazol-4-yl)amino)-5H-pyrrolo[3,2-d]pyrimidin-2-yl)pyrrolidine-2-carboxamide (162b)

Step-1: Preparation of (S)-1-(5-tosyl-4-((1-(3,4,5-trimethoxyphenyl)-1H-imidazol-4-yl)amino)-5H-pyrrolo[3,2-d]pyrimidin-2-yl)pyrrolidine-2-carboxamide (162a)

Compound 162a was prepared from 2-chloro-5-tosyl-N-(1-(3,4,5-trimethoxyphenyl)-1H-imidazol-4-yl)-5H-pyrrolo[3,2-d]pyrimidin-4-amine (160b) (327 mg, 0.59 mmol), (S)-pyrrolidine-2-carboxamide (269 mg, 2.36 mmol) in NMP (5 mL) according to the procedure reported in Scheme 2. This gave after workup and twice purification by flash column chromatography [silica (12 g), eluting with ethyl acetate/ MeOH (9:1) in hexane from 0-70%]; [silica (12 g), eluting with MeOH in DCM from 0-20%] (S)-1-(5-tosyl-4-((1-(3, 4,5-trimethoxyphenyl)-1H-imidazol-4-yl)amino)-5H-pyrrolo[3,2-d]pyrimidin-2-yl)pyrrolidine-2-carboxamide (162a) (162 mg, 44% yield) as a white solid; ¹H NMR (300 MHz, DMSO-d₆) δ 9.60 (s, 1H, D₂O exchangeable), 8.20 (s, 1H), 8.00-7.77 (m, 2H), 7.68 (d, J=8.5 Hz, 2H), 7.41 (d, J=8.1 Hz, 2H), 7.30-6.80 (m, 4H; 2H, D₂O exchangeable), 6.68 (s, 1H), 4.51-4.30 (m, 1H), 4.04-3.74 (m, 8H), 3.69 (s, 3H), 2.32 (s, 3H), 2.24-2.06 (m, 1H), 2.01-1.79 (m, 3H); MS (ES+): δ 33.2 (M+1); 655.2 (M+Na); (ES−): δ 31.5 (M−1).

Step-2: Preparation of (S)-1-(4-((1-(3,4,5-trimethoxyphenyl)-1H-imidazol-4-yl)amino)-5H-pyrrolo[3,2-d]pyrimidin-2-yl)pyrrolidine-2-carboxamide (162b)

Compound 162b was prepared from (S)-1-(5-tosyl-4-((1-(3,4,5-trimethoxyphenyl)-1H-imidazol-4-yl)amino)-5H-pyrrolo[3,2-d]pyrimidin-2-yl)pyrrolidine-2-carboxamide (162a) (130 mg, 0.21 mmol) and Cs₂CO₃ (201 mg, 0.62 mmol) in MeOH/THF (5 mL, 3:2) according to the procedure reported in step-3 of Scheme 141. This gave after workup and purification twice by flash column chromatography [silica (12 g), eluting with ethyl acetate/MeOH (9:1) in hexane from 0-100%], [silica (12 g), eluting with DMA-80 in DCM from 0-60%], followed by conversion of free base to HCl salt using 1 N HCl (2 mL) in CH₃CN, (S)-1-(4-((1-(3,4,5-trimethoxyphenyl)-1H-imidazol-4-yl)amino)-5H-pyrrolo[3,2-d]pyrimidin-2-yl)pyrrolidine-2-carboxamide (162b) (30 mg, 31% yield) HCl salt as a white solid; ¹H NMR (300 MHz, DMSO-d₆) δ 12.52 (s, 1H, D₂O exchangeable), 12.02 (s, 1H, D₂O exchangeable), 11.14 (s, 1H, D₂O exchangeable), 8.29 (s, 1H), 7.84 (s, 1H), 7.67-7.59 (m, 1H), 7.56 (s, 1H, D₂O exchangeable), 7.26-7.16 (m, 1H, D₂O exchangeable), 7.12 (s, 2H), 6.41 (s, 1H), 4.61 (d, J=8.9 Hz, 2H), 4.52 (brs, 2H, D₂O exchangeable), 3.93 (s, 6H), 3.69 (s, 3H), 3.62-3.49 (m, 1H), 2.36-2.24 (m, 1H), 2.13-1.97 (m, 3H); MS (ES+): 479.4 (M+1), 501.3 (M+Na); (ES−): 513.3 (M+Cl).

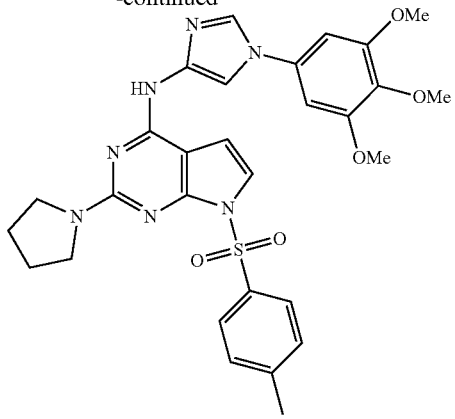

163a

Preparation of 2-(pyrrolidin-1-yl)-7-tosyl-N-(1-(3,4,5-trimethoxyphenyl)-1H-imidazol-4-yl)-7H-pyrrolo[2,3-d]pyrimidin-4-amine (163a)

Compound 163a was prepared from 2-chloro-7-tosyl-N-(1-(3,4,5-trimethoxyphenyl)-1H-imidazol-4-yl)-7H-pyrrolo[2,3-d]pyrimidin-4-amine (141b) (80 mg, 0.14 mmol), pyrrolidine (62 mg, 0.87 mmol) in 2-Propanol (5 mL) according to the procedure reported in Scheme 2. This gave after workup and purification by flash column chromatography [silica (12 g), eluting with ethyl acetate/MeOH (9:1) in hexane from 0-70%] 2-(pyrrolidin-1-yl)-7-tosyl-N-(1-(3,4,5-trimethoxyphenyl)-1H-imidazol-4-yl)-7H-pyrrolo[2,3-d]pyrimidin-4-amine (163a) (65 mg, 76% yield) as a white solid; ¹H NMR (300 MHz, DMSO-d₆) δ 10.15 (s, 1H, D₂O exchangeable), 8.18 (s, 1H), 8.05-7.96 (m, 3H), 7.43 (d, J=8.1 Hz, 2H), 7.18 (d, J=4.0 Hz, 1H), 7.02 (d, J=4.0 Hz, 1H), 6.89 (s, 2H), 3.85 (s, 6H), 3.75-3.50 (m, 7H), 2.36 (s, 3H), 2.02-1.87 (m, 4H); MS (ES+): 590.3 (M+1); 612.3 (M+Na); (ES−): 588.5 (M−1).

Scheme 164

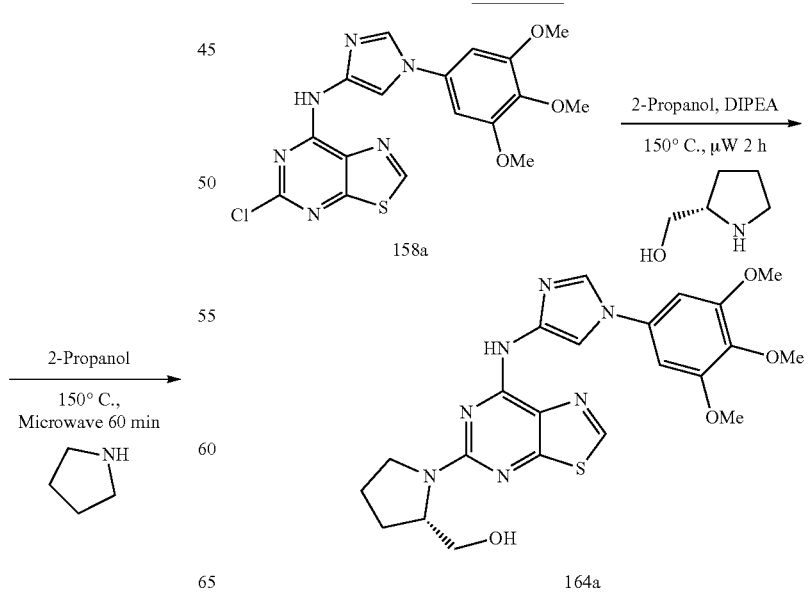

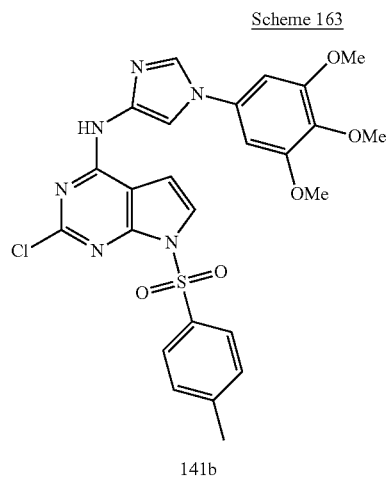

Scheme 163

141b

Preparation of (S)-(1-(7-((1-(3,4,5-trimethoxyphenyl)-1H-imidazol-4-yl)amino)thiazolo[5,4-d]pyrimidin-5-yl)pyrrolidin-2-yl)methanol (164a)

Compound 164a was prepared from 5-chloro-N-(1-(3,4,5-trimethoxyphenyl)-1H-imidazol-4-yl)thiazolo[5,4-d]pyrimidin-7-amine (158a) (120 mg, 0.29 mmol), (S)-pyrrolidin-2-ylmethanol (0.09 mL, 0.86 mmol), DIPEA (0.15 mL, 0.86 mmol) in 2-Propanol (5 mL) according to the procedure reported in Scheme 2. This gave after workup and purification by flash column chromatography [silica (12 g), eluting with DMA-80 in CH$_2$Cl$_2$ from 0 to 30%](S)-(1-(7-((1-(3,4,5-trimethoxyphenyl)-1H-imidazol-4-yl)amino)thiazolo[5,4-d]pyrimidin-5-yl)pyrrolidin-2-yl)methanol (164a) (31 mg, 23% yield) as a yellow solid; $^1$H NMR (300 MHz, DMSO-d$_6$) δ 9.84-9.29 (m, 1H), 8.80 (s, 1H), 8.19 (s, 1H), 8.10-7.78 (m, 1H), 6.96 (s, 2H), 5.08-4.61 (m, 1H), 4.46-4.05 (m, 1H), 4.01-3.22 (m, 13H), 2.11-1.78 (m, 4H); MS (ES+): 484.3 (M+1); MS (ES−): 482.3 (M−1); 518.2 (M+Cl). HPLC purity: 94.37%.

Scheme 165

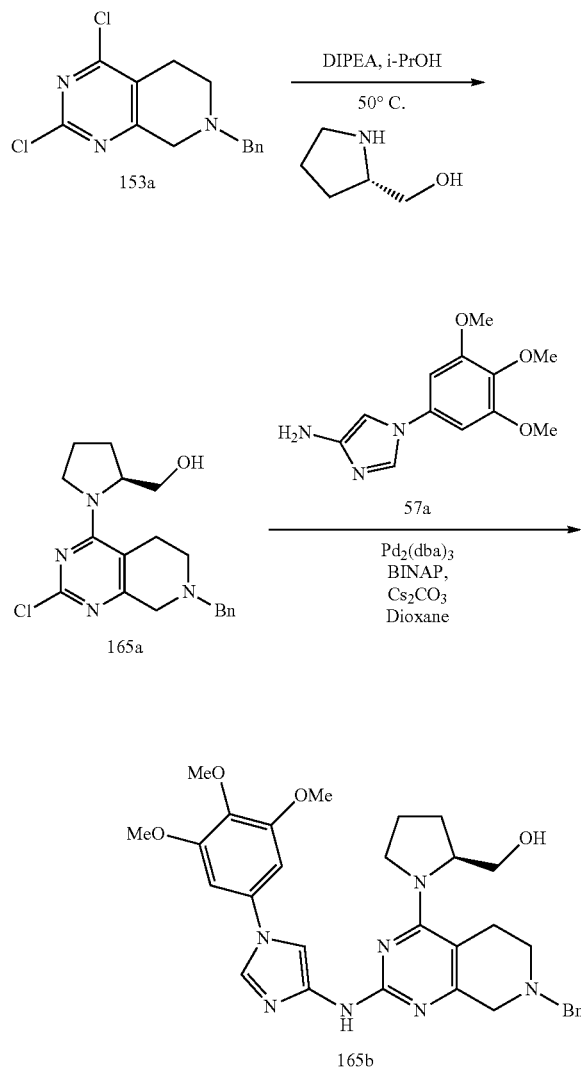

Preparation of (S)-(1-(7-benzyl-2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (165b)

Step-1: Preparation of (S)-(1-(7-benzyl-2-chloro-5,6,7,8-tetrahydropyrido[3,4-d]pyrimidin-4-yl)pyrrolidin-2-yl)methanol (165a)

Compound 165a was prepared from 7-benzyl-2,4-dichloro-5,6,7,8-tetrahydropyrido[3,4-d]pyrimidine (153a) (1 g, 3.4 mmol) in 2-Propanol (5 mL), (S)-pyrrolidin-2-ylmethanol (344 mg, 3.4 mmol), DIPEA (0.89 mL, 5.1 mmol) according to the procedure reported in step-1 of Scheme 96. This gave after workup and purification by flash column chromatography [silica (40 g), eluting with DMA-80 in dichloromethane] (S)-(1-(7-benzyl-2-chloro-5,6,7,8-tetrahydropyrido[3,4-d]pyrimidin-4-yl)pyrrolidin-2-yl)methanol (165a) (1.13 g, 93% yield) as a white solid; $^1$H NMR (300 MHz, DMSO-d$_6$) δ 7.45-7.17 (m, 5H), 4.71 (t, J=5.9 Hz, 1H, D$_2$O exchangeable), 4.40-4.23 (m, 1H), 3.76-3.56 (m, 4H), 3.56-3.42 (m, 2H), 3.43-3.26 (m, 1H), 3.21 (d, J=17.3 Hz, 1H), 3.03-2.78 (m, 2H), 2.76-2.57 (m, 1H), 2.41-2.24 (m, 1H), 1.99-1.83 (m, 3H), 1.81-1.69 (m, 1H).

Step-2: Preparation of (S)-(1-(7-benzyl-2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (165b)

Compound 165b was prepared from (S)-(1-(7-benzyl-2-chloro-5,6,7,8-tetrahydropyrido[3,4-d]pyrimidin-4-yl)pyrrolidin-2-yl)methanol (165a) (300 mg, 0.84 mmol), 1-(3,4,5-trimethoxyphenyl)-1H-imidazol-4-amine (57a) (313 mg, 1.25 mmol, free base), 2,2'-bis(diphenylphosphino)-1,1'-binaphthyl (BiNAP, 104 mg, 0.167 mmol), cesium carbonate (817 mg, 2.51 mmol) and Pd$_2$(dba)$_3$ (115 mg, 0.125 mmol) in 1,4-dioxane (10 mL) according to the procedure reported in step-3 of Scheme 101. This gave after workup and purification by flash column chromatography [silica (40 g), eluting with DMA-80 in CH$_2$Cl$_2$ from 0 to 30%] followed by reverse phase column chromatography [(silica gel C-18, 24 g) eluting with acetonitrile and 0.1% HCl water] (S)-(1-(7-benzyl-2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (165b) (235 mg, 49% yield) as a yellow solid; $^1$H NMR (300 MHz, DMSO-d$_6$) δ 12.74-11.60 (m, 1H, D$_2$O exchangeable), 10.20 (s, 1H, D$_2$O exchangeable), 8.71 (s, 1H), 7.88-7.59 (m, 3H), 7.59-7.36 (m, 3H), 7.02 (s, 2H), 4.58 (s, 1H), 4.50 (s, 2H), 4.33-4.03 (m, 2H), 3.87 (s, 6H), 3.69 (s, 3H), 3.67-3.53 (m, 2H), 3.53-3.39 (m, 2H), 3.39-3.22 (m, 2H), 3.26-2.92 (m, 1H), 2.11-1.76 (m, 4H); MS (ES+): 572.4 (M+1), 594.3 (M+Na).

Scheme 166

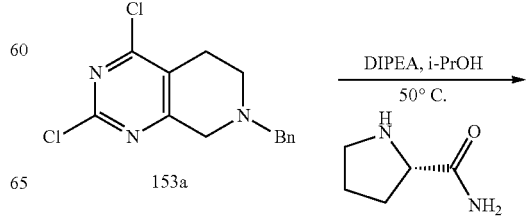

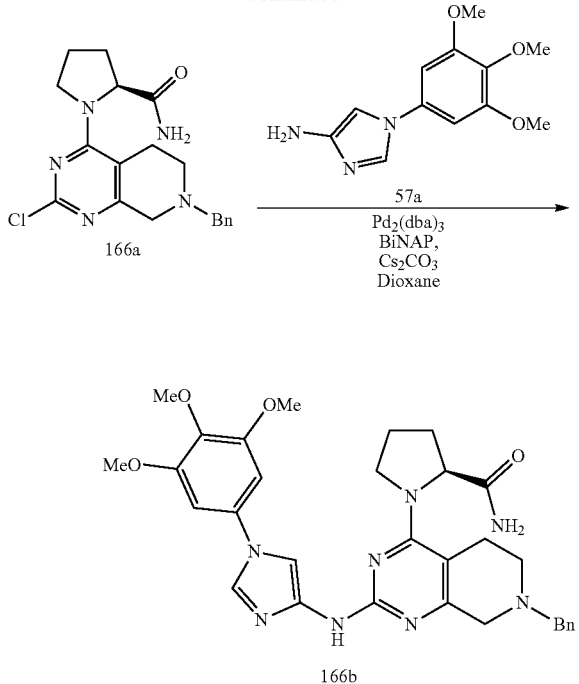

Preparation of (S)-1-(7-benzyl-2-((1-(3,4,5-trimethoxyphenyl)-1H-imidazol-4-yl)amino)-5,6,7,8-tetrahydropyrido[3,4-d]pyrimidin-4-yl)pyrrolidine-2-carboxamide (166b)

Step-1: Preparation of (S)-1-(7-benzyl-2-chloro-5,6,7,8-tetrahydropyrido[3,4-d]pyrimidin-4-yl)pyrrolidine-2-carboxamide (166a)

Compound 166a was prepared from 7-benzyl-2,4-dichloro-5,6,7,8-tetrahydropyrido[3,4-d]pyrimidine (153a) (1 g, 3.4 mmol) in 2-Propanol (5 mL), (S)-pyrrolidine-2-carboxamide (388 mg, 3.4 mmol), DIPEA (0.89 mL, 5.1 mmol) according to the procedure reported in step-1 of Scheme 96. This gave after workup and purification by flash column chromatography [silica (40 g), eluting with DMA-80 in dichloromethane] (S)-1-(7-benzyl-2-chloro-5,6,7,8-tetrahydropyrido[3,4-d]pyrimidin-4-yl)pyrrolidine-2-carboxamide (166a) (1.1 g, 87% yield) as a white solid; $^1$H NMR (300 MHz, DMSO-$d_6$) δ 7.43-7.24 (m, 6H), 6.94 (s, 1H), 4.60-4.46 (m, 1H), 3.97-3.70 (m, 2H), 3.63 (s, 2H), 3.49-3.23 (m, 2H), 2.98-2.84 (m, 3H), 2.78-2.60 (m, 1H), 2.21-2.04 (m, 1H), 1.96-1.72 (m, 3H).

Step-2: Preparation of (S)-1-(7-benzyl-2-((1-(3,4,5-trimethoxyphenyl)-1H-imidazol-4-yl)amino)-5,6,7,8-tetrahydropyrido[3,4-d]pyrimidin-4-yl)pyrrolidine-2-carboxamide (166b)

Compound 166b was prepared from (S)-1-(7-benzyl-2-chloro-5,6,7,8-tetrahydropyrido[3,4-d]pyrimidin-4-yl)pyrrolidine-2-carboxamide (166a) (400 mg, 1.07 mmol), 1-(3,4,5-trimethoxyphenyl)-1H-imidazol-4-amine (57a) (402 mg, 1.61, free base), 2,2'-bis(diphenylphosphino)-1,1'-binaphthyl (BiNAP, 134 mg, 0.21 mmol), cesium carbonate (1.05 g, 3.23 mmol) and Pd$_2$(dba)$_3$ (148 mg, 0.161 mmol) in 1,4-dioxane (10 mL) according to the procedure reported in step-3 of Scheme 101. This gave after workup and purification by flash column chromatography [silica (40 g), eluting with DMA-80 in CH$_2$Cl$_2$ from 0 to 30%] followed by reverse phase column chromatography [(silica gel C-18, 24 g) eluting with acetonitrile and 0.1% HCl water] (S)-1-(7-benzyl-2-((1-(3,4,5-trimethoxyphenyl)-1H-imidazol-4-yl)amino)-5,6,7,8-tetrahydropyrido[3,4-d]pyrimidin-4-yl)pyrrolidine-2-carboxamide (166b) (105 mg, 17% yield) light yellow solid; $^1$H NMR (300 MHz, DMSO-$d_6$) δ 12.25 (s, 1H, D$_2$O exchangeable), 10.11 (s, 1H, D$_2$O exchangeable), 8.91 (s, 1H), 7.89 (s, 1H, D$_2$O exchangeable), 7.74 (dd, J=6.5, 2.9 Hz, 2H), 7.63-7.44 (m, 5H), 7.24 (s, 2H), 7.11 (s, 1H, D$_2$O exchangeable), 4.74-4.59 (m, 1H), 4.51 (s, 2H), 4.36-3.97 (m, 4H), 3.91 (s, 6H), 3.82-3.47 (m, 5H), 3.47-3.00 (m, 4H), 2.38-2.11 (m, 1H), 2.08-1.69 (m, 3H); FREE BASE $^1$H NMR (300 MHz, DMSO-$d_6$) δ 8.59 (s, 1H), 8.03 (s, 1H), 7.72 (s, 1H), 7.39-7.24 (m, 5H), 7.21 (s, 1H), 7.10 (s, 2H), 6.92 (s, 1H), 4.72-4.58 (m, 1H), 4.07-3.89 (m, 2H), 3.90 (s, 6H), 3.67 (s, 3H), 3.62 (s, 2H), 3.42 (d, J=16.5 Hz, 1H), 3.16 (d, J=16.6 Hz, 1H), 2.87 (d, J=10.1 Hz, 2H), 2.46-2.34 (m, 1H), 2.29-2.07 (m, 1H), 1.99-1.72 (m, 4H); MS (ES+): 585.4 (M+1), (ES−): 619.5 (M+Cl).

Scheme 167

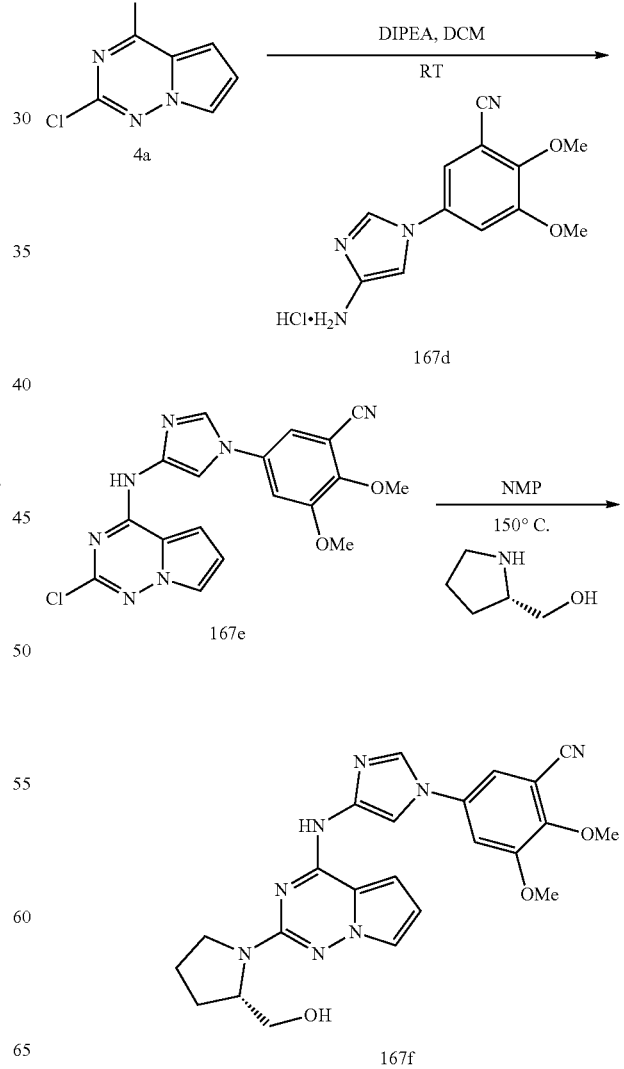

Preparation of (S)-5-(4-((2-(2-(hydroxymethyl)pyrrolidin-1-yl)pyrrolo[2,1-f][1,2,4]triazin-4-yl)amino)-1H-imidazol-1-yl)-2,3-dimethoxybenzonitrile (167f)

Step-1: Preparation of 5-(4-((2-chloropyrrolo[2,1-f][1,2,4]triazin-4-yl)amino)-1H-imidazol-1-yl)-2,3-dimethoxybenzonitrile (167e)

Compound 167e was prepared according to the procedure reported in Scheme 1 from 2,4-dichloropyrrolo[2,1-f][1,2,4]triazine (4a) (670 mg, 2.38 mmol) in DCM (20 mL) using DIPEA (1.38 g, 10.72 mmol) and 5-(4-amino-1H-imidazol-1-yl)-2,3-dimethoxybenzonitrile hydrochloride (167d) (1.0 g, 5.31 mmol). This gave after workup 5-(4-((2-chloropyrrolo[2,1-f][1,2,4]triazin-4-yl)amino)-1H-imidazol-1-yl)-2,3-dimethoxybenzonitrile (167e) (1.03 g, 21% yield) as an off white solid; $^1$H NMR (300 MHz, DMSO-$d_6$) δ 10.66 (s, 1H), 9.22 (m, 1H), 7.92 (s, 2H), 7.83 (s, 2H), 7.35-7.34 (s, 1H), 6.79 (s, 1H) 3.92 (s, 3H), 3.90 (s, 3H).

Step-2: Preparation of (S)-5-(4-((2-(2-(hydroxymethyl)pyrrolidin-1-yl)pyrrolo[2,1-f][1,2,4]triazin-4-yl)amino)-1H-imidazol-1-yl)-2,3-dimethoxybenzonitrile (167f)

Compound 167f was prepared from 5-(4-((2-chloropyrrolo[2,1-f][1,2,4]triazin-4-yl)amino)-1H-imidazol-1-yl)-2,3-dimethoxybenzonitrile (167e) (300 mg, 0.76 mmol), (S)-pyrrolidin-2-ylmethanol (770 mg, 7.58 mmol) in NMP (12 mL) according to the procedure reported in step-2 of Scheme 76. This gave after workup and purification by flash column chromatography [silica gel (24 g), eluting with methanol in ethyl acetate 0-10%] (S)-5-(4-((2-(2-(hydroxymethyl)pyrrolidin-1-yl)pyrrolo[2,1-f][1,2,4]triazin-4-yl)amino)-1H-imidazol-1-yl)-2,3-dimethoxybenzonitrile (167f) (50 mg, 14% yield) as a yellow solid; $^1$H NMR (300 MHz, DMSO-$d_6$) δ 9.66 (s, 1H), 7.92 (s, 2H), 7.45 (t, J=2.1 Hz, 1H), 6.97 (dd, J=4.5, 1.6 Hz, 1H), 6.48 (dd, J=4.5, 2.5 Hz, 1H), 4.64 (t, J=4.8 Hz, 1H), 4.12-4.01 (m, 1H), 3.91 (s, 3H), 3.88 (s, 3H), 3.66-3.56 (m, 1H), 3.55-3.38 (m, 3H), 2.08-1.74 (m, 4H).

Scheme 168

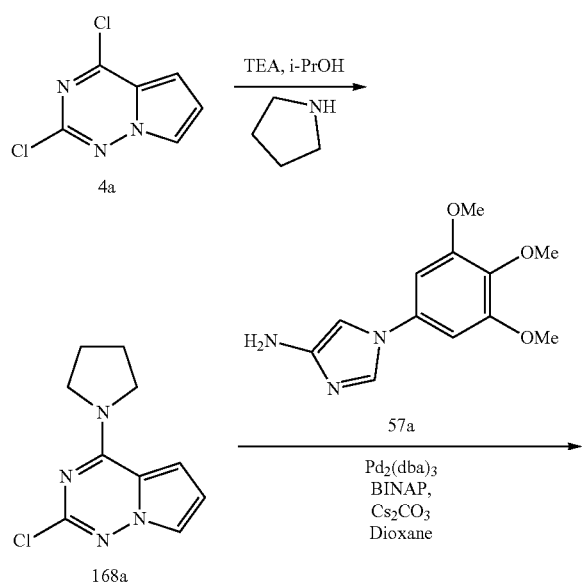

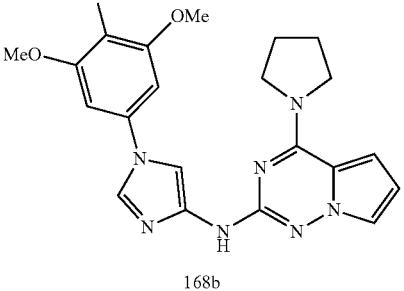

Preparation of 4-(pyrrolidin-1-yl)-N-(1-(3,4,5-trimethoxyphenyl)-1H-imidazol-4-yl)pyrrolo[2,1-f][1,2,4]triazin-2-amine (168b)

Step-1: Preparation of 2-chloro-4-(pyrrolidin-1-yl)pyrrolo[2,1-f][1,2,4]triazine (168a)

Compound 168a was prepared from 2,4-dichloropyrrolo[2,1-f][1,2,4]triazine (4a) (1.02 g, 5.44 mmol) in 2-Propanol (30 mL), pyrrolidine (0.49 mL, 5.98 mmol), TEA (1.52 mL, 10.87 mmol) according to the procedure reported in step-1 of Scheme 96. This gave after workup and purification by flash column chromatography [silica (40 g), eluting with DMA-80 in dichloromethane] 2-chloro-4-(pyrrolidin-1-yl)pyrrolo[2,1-f][1,2,4]triazine (168a) (550 mg, 45% yield) as a white solid; $^1$H NMR (300 MHz, DMSO-$d_6$) δ 7.69 (dd, J=2.7, 1.5 Hz, 1H), 6.96 (dd, J=4.6, 1.6 Hz, 1H), 6.66 (dd, J=4.6, 2.7 Hz, 1H), 3.93 (t, J=6.9 Hz, 2H), 3.64 (t, J=6.8 Hz, 2H), 2.05 (p, J=6.8 Hz, 2H), 1.90 (p, J=6.8 Hz, 2H).

Step-2: Preparation of 4-(pyrrolidin-1-yl)-N-(1-(3,4,5-trimethoxyphenyl)-1H-imidazol-4-yl)pyrrolo[2,1-f][1,2,4]triazin-2-amine (168b)

Compound 168b was prepared from 2-chloro-4-(pyrrolidin-1-yl)pyrrolo[2,1-f][1,2,4]triazine (168a) (0.5 g, 2.25 mmol), 1-(3,4,5-trimethoxyphenyl)-1H-imidazol-4-amine (57a) (840 mg, 3.37, free base), 2,2'-bis(diphenylphosphino)-1,1'-binaphthyl (BiNAP, 280 mg, 0.45 mmol), cesium carbonate (2195 mg, 6.74 mmol) and Pd$_2$(dba)$_3$ (308 mg, 0.34 mmol) in 1,4-dioxane (10 mL) according to the procedure reported in step-3 of Scheme 101. This gave after workup and purification twice by flash column chromatography [silica (40 g), eluting with DMA-80 in CH$_2$Cl$_2$ from 0 to 30%], [silica (25 g), eluting with (9:1) ethyl acetate/methanol in hexane from 0 to 100%], followed by reverse phase column chromatography [(silica gel C-18, 24 g) eluting with acetonitrile and 0.1% HCl water] 4-(pyrrolidin-1-yl)-N-(1-(3,4,5-trimethoxyphenyl)-1H-imidazol-4-yl)pyrrolo[2,1-f][1,2,4]triazin-2-amine (168b) (21 mg, 2% yield) as a white solid; $^1$H NMR (300 MHz, DMSO-$d_6$) δ 8.53 (s, 1H), 8.02 (d, J=1.6 Hz, 1H), 7.68 (d, J=1.6 Hz, 1H), 7.55 (t, J=2.0 Hz, 1H), 6.89 (s, 2H), 6.75 (dd, J=4.5, 1.6 Hz, 1H), 6.46 (dd, J=4.5, 2.5 Hz, 1H), 3.88 (s, 6H), 3.83-3.71 (m, 4H), 3.68 (s, 3H), 2.15-1.85 (m, 4H); MS (ES+): 436.3 (M+1), 458.3 (M+Na).

Scheme 169

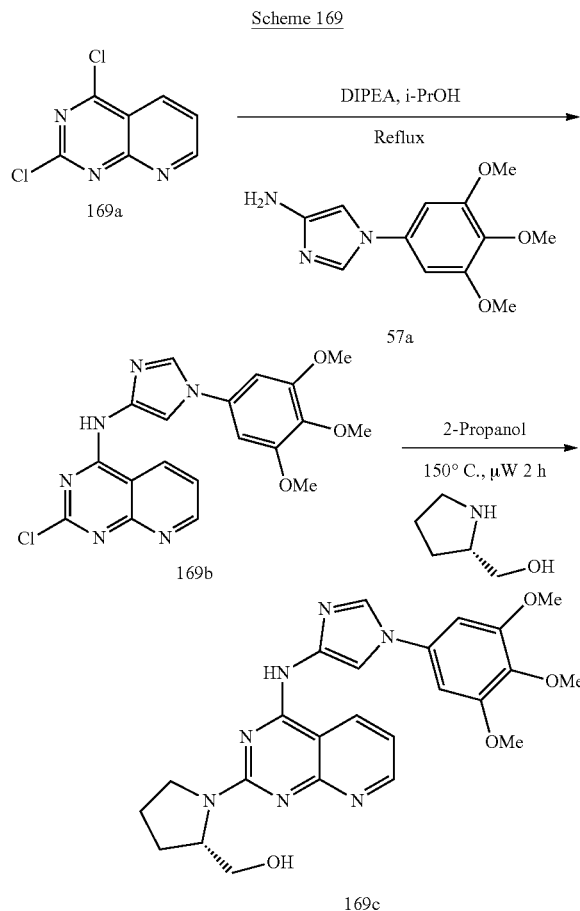

Preparation of (S)-(1-(4-((1-(3,4,5-trimethoxyphenyl)-1H-imidazol-4-yl)amino)pyrido[2,3-d]pyrimidin-2-yl)pyrrolidin-2-yl)methanol (169c)

Step-1: Preparation of 2-chloro-N-(1-(3,4,5-trimethoxyphenyl)-1H-imidazol-4-yl)pyrido[2,3-d]pyrimidin-4-amine (169b)

Compound 169b was prepared according to the procedure reported in Scheme 1 from 2,4-dichloropyrido[2,3-d]pyrimidine (169a) (0.5 g, 2.5 mmol; CAS #126728-20-9) in 2-Propanol (10 mL) using DIPEA (1.31 mL, 7.5 mmol) and 1-(3,4,5-trimethoxyphenyl)-1H-imidazol-4-amine (57a) (0.86 g, 3.0 mmol). This gave after workup and purification by flash column chromatography [silica gel, (40 g) eluting with methanol in DCM (0 to 30%)] 2-chloro-N-(1-(3,4,5-trimethoxyphenyl)-1H-imidazol-4-yl)pyrido[2,3-d]pyrimidin-4-amine (169b) (0.7 g, 68% yield) as a brown solid; MS (ES+): 435.7 (M+Na); MS (ES−): 411.3 & 413.3 (M−1).

Step-2: Preparation of (S)-(1-(4-((1-(3,4,5-trimethoxyphenyl)-1H-imidazol-4-yl)amino)pyrido[2,3-d]pyrimidin-2-yl)pyrrolidin-2-yl)methanol (169c)

Compound 169c was prepared from 2-chloro-N-(1-(3,4,5-trimethoxyphenyl)-1H-imidazol-4-yl)pyrido[2,3-d]pyrimidin-4-amine (169b) (0.15 g, 0.36 mmol), (S)-pyrrolidin-2-ylmethanol (0.11 mL, 1.09 mmol) in 2-Propanol (5 mL) according to the procedure reported in Scheme 2. This gave after workup and purification by flash column chromatography [silica gel, (25 g), eluting with DMA-80 in dichloromethane (0 to 30%)], (S)-(1-(4-((1-(3,4,5-trimethoxyphenyl)-1H-imidazol-4-yl)amino)pyrido[2,3-d]pyrimidin-2-yl)pyrrolidin-2-yl)methanol (169c) (06 mg, 35% yield) as a yellow solid; $^1$H NMR (300 MHz, DMSO-$d_6$): (as a mixture of two rotamers)$^1$H NMR (300 MHz, DMSO-$d_6$) δ 10.70 and 10.49 (s, 1H), 8.88 and 8.86 (2d, J=2.0 Hz, 1H), 8.71-8.63 (m, 1H), 8.32-8.23 (m, 1H), 8.13 and 8.04 (2s, 1H), 7.16-7.02 (m, 1H), 6.99 (s, 1H), 6.95 (s, 1H), 5.72-5.59 and 5.01-4.88 (2m, 1H), 4.54-4.40 and 4.33-4.17 (2m, 1H), 3.99-3.35 (m, 13H), 2.14-1.79 (m, 4H); MS (ES+): 478.3 (M+1); MS (ES−): 512.3 (M+Cl).

Scheme 170

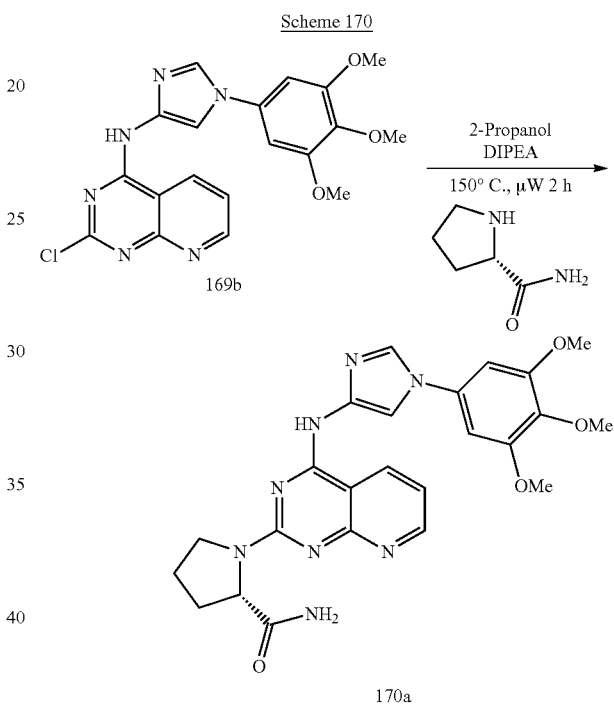

Preparation of (S)-1-(4-((1-(3,4,5-trimethoxyphenyl)-1H-imidazol-4-yl)amino)pyrido[2,3-d]pyrimidin-2-yl)pyrrolidine-2-carboxamide (170a)

Compound 170a was prepared from 2-chloro-N-(1-(3,4,5-trimethoxyphenyl)-1H-imidazol-4-yl)pyrido[2,3-d]pyrimidin-4-amine (169b) (0.15 g, 0.36 mmol), (S)-pyrrolidine-2-carboxamide (124 mg, 1.09 mmol), DIPEA (0.19 mL, 1.09 mmol) in 2-Propanol (5 mL) according to the procedure reported in Scheme 2. This gave after workup and purification by flash column chromatography [silica gel, (12 g), eluting with DMA-80 in dichloromethane (0 to 30%)], followed by reverse phase flash column chromatography [(silica gel, C-18, 24 g) eluting with acetonitrile and 0.1% HCl water] (S)-1-(4-((1-(3,4,5-trimethoxyphenyl)-1H-imidazol-4-yl)amino)pyrido[2,3-d]pyrimidin-2-yl)pyrrolidine-2-carboxamide (170a) (31 mg, 17% yield) HCl salt as a yellow solid; $^1$H NMR (300 MHz, DMSO-$d_6$) δ 11.93 (s, 1H), 9.60-9.20 (m, 1H), 9.01-7.93 (m, 2H), 7.63-7.45 (m, 2H), 7.30-7.11 (m, 3H), 7.00 (s, 1H), 4.82-4.68 (m, 1H), 4.12-3.81 (m, 7H), 3.79-3.64 (m, 4H), 2.40-1.88 (m, 4H);

MS (ES+): 491.3 (M+1), 513.3 (M+Na); MS (ES−): 489.4 (M−1), 525.4 (M+Cl). HPLC purity: 97.96%.

Scheme 171

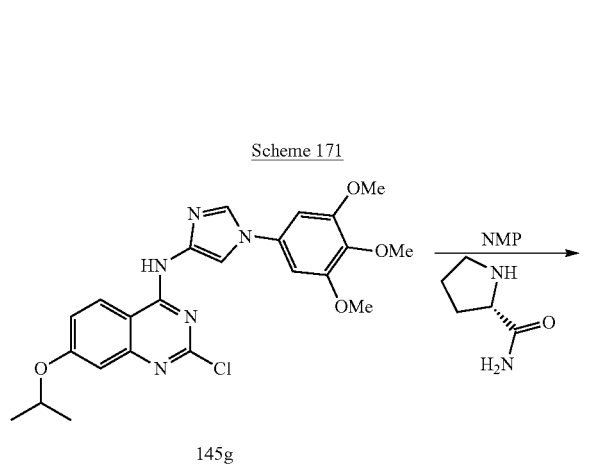

145g

171a

Preparation (S)-1-(7-isopropoxy-4-((1-(3,4,5-trimethoxyphenyl)-1H-imidazol-4-yl)amino)quinazolin-2-yl)pyrrolidine-2-carboxamide (171a)

Compound 171a was prepared according to the procedure reported in step-2 of Scheme 76 from 2-chloro-7-isopropoxy-N-(1-(3,4,5-trimethoxyphenyl)-1H-imidazol-4-yl)quinazolin-4-amine (145g) (300 mg, 0.63 mmol) and (S)-pyrrolidine-2-carboxamide (0.65 g, 5.75 mmol) in NMP (10 mL). This gave after workup and purification by flash chromatography. (Silica gel, eluting with 0-4% methanol in DCM) compound (171a) (0.28 g, 77%) as an off-white solid. The solid was repurified by reverse phase flash column chromatography [(silica gel C-18, 24 g) eluting with acetonitrile and 0.1% HCl in water (0-50%)] to afford (S)-1-(7-isopropoxy-4-((1-(3,4,5-trimethoxyphenyl)-1H-imidazol-4-yl)amino)quinazolin-2-yl)pyrrolidine-2-carboxamide (171a) (34 mg) HCl salt as a white solid; $^1$H NMR (300 MHz, DMSO-d$_6$): δ 12.31 (s, 1H), 11.37 (s, 1H), 8.66 (d, J=9.2 Hz, 1H), 8.36 (s, 1H), 7.89 (d, J=1.5 Hz, 1H), 7.71 (s, 1H), 7.60 (s, 1H), 7.22 (s, 1H), 7.13 (s, 2H), 7.08-6.94 (m, 1H), 4.80-4.68 (m, 1H), 4.14-4.00 (m, 1H), 3.94 (s, 7H), 3.69 (s, 4H), 2.38-1.94 (m, 4H), 1.37 (d, J=5.9 Hz, 6H); MS (ES+): 548.4 (M+1); MS (ES−): 582.4 (M+Cl). HPLC purity: 97.90%.

Scheme 172

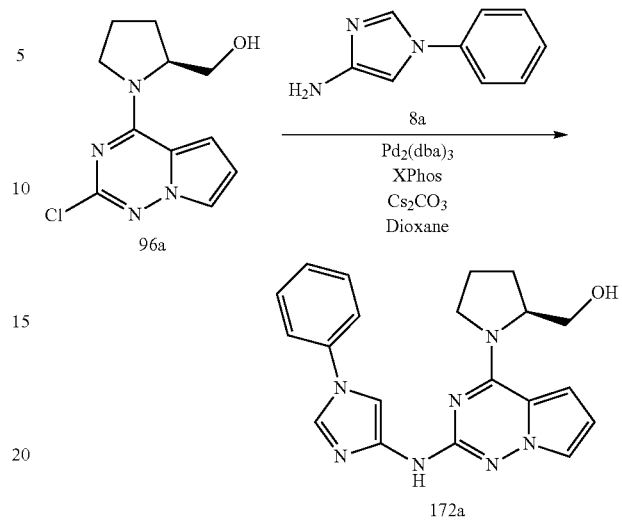

172a

Preparation of (S)-(1-(2-((1-phenyl-1H-imidazol-4-yl)amino)pyrrolo[2,1-f][1,2,4]triazin-4-yl)pyrrolidin-2-yl)methanol (172a)

Compound 172a was prepared from (S)-(1-(2-chloropyrrolo[2,1-f][1,2,4]triazin-4-yl)pyrrolidin-2-yl)methanol (96a) (0.91 g, 3.6 mmol), 1-phenyl-1H-imidazol-4-amine (8a) (860 mg, 5.40, free base), dicyclohexyl(2',4',6'-triisopropylbiphenyl-2-yl)phosphine (XPhos, 0.77 g, 1.62 mmol), cesium carbonate (3.52 g, 10.8 mmol) and Pd$_2$(dba)$_3$ (490 mg, 0.54 mmol) in 1,4-dioxane (30 mL) according to the procedure reported in step-3 of Scheme 101. This gave after workup and purification by flash column chromatography [silica (80 g), eluting with DMA-80 in CH$_2$Cl$_2$], followed by reverse phase column chromatography [(silica gel C-18, 24 g) eluting with acetonitrile and 0.1% HCl water] (S)-(1-(2-((1-phenyl-1H-imidazol-4-yl)amino)pyrrolo[2,1-f][1,2,4]triazin-4-yl)pyrrolidin-2-yl)methanol (172a) (370 mg, 27% yield) HCl salt as a white solid; $^1$H NMR (300 MHz, DMSO-d$_6$) δ 9.12 (s, 1H), 7.78 (s, 1H), 7.75 (s, 1H), 7.68-7.49 (m, 5H), 6.85 (d, J=4.6 Hz, 1H), 6.54 (s, 1H), 4.59-4.33 (m, 1H), 4.09-3.34 (m, 4H), 2.26-1.65 (m, 4H); MS (ES+): 376.3 (M+1), 398.3 (M+Na).

Scheme 173

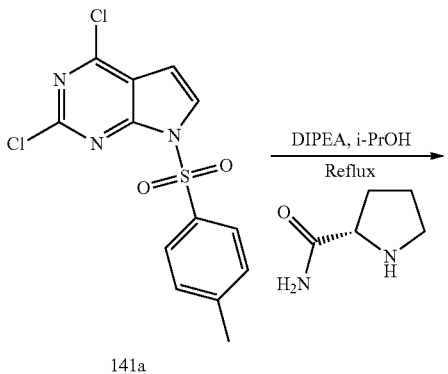

141a

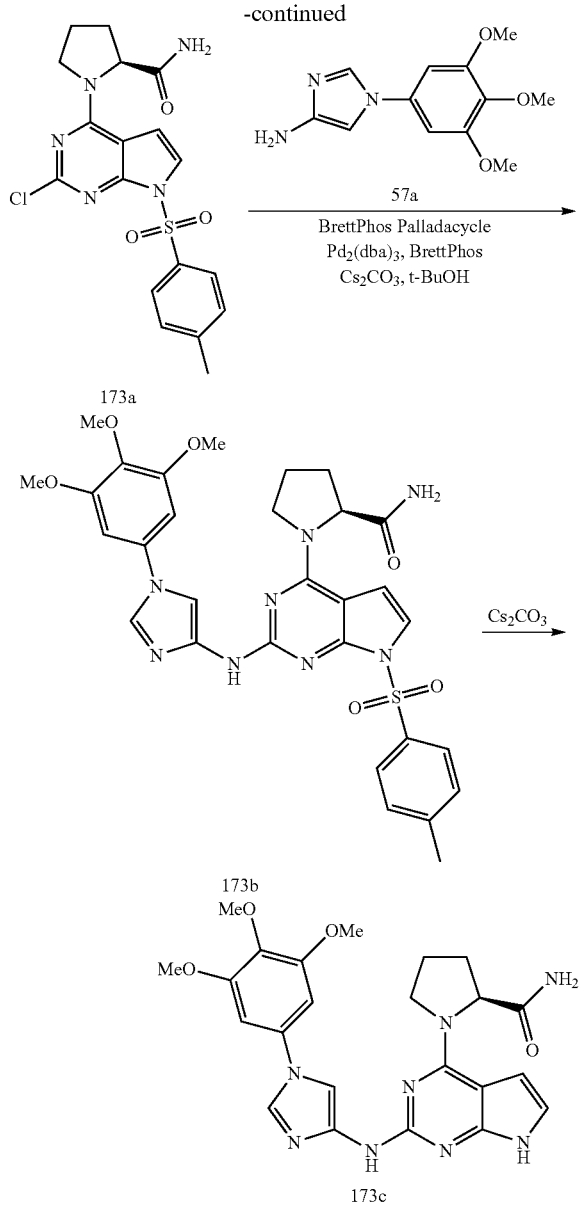

Preparation of (S)-1-(2-((1-(3,4,5-trimethoxyphenyl)-1H-imidazol-4-yl)amino)-7H-pyrrolo[2,3-d]pyrimidin-4-yl)pyrrolidine-2-carboxamide (173c)

Step-1: Preparation of (S)-1-(2-chloro-7-tosyl-7H-pyrrolo[2,3-d]pyrimidin-4-yl)pyrrolidine-2-carboxamide (173a)

Compound 173a was prepared from 2,4-dichloro-7-tosyl-7H-pyrrolo[2,3-d]pyrimidine (141a) (1.54 g, 4.5 mmol) in 2-Propanol (10 mL), (S)-pyrrolidine-2-carboxamide (0.51 g, 4.50 mmol), DIPEA (1.18 mL, 6.75 mmol) according to the procedure reported in step-1 of Scheme 96. This gave after workup and purification by flash column chromatography [silica (12 g), eluting with ethyl acetate/MeOH (9:1) in hexane from 0-70%] (S)-1-(2-chloro-7-tosyl-7H-pyrrolo[2,3-d]pyrimidin-4-yl)pyrrolidine-2-carboxamide (173a) (600 mg, 32% yield) as a white solid; MS (ES−): 418.4 (M−1), 454.2, 456.3 (M+Cl).

Step-2: Preparation of (S)-1-(7-tosyl-2-((1-(3,4,5-trimethoxyphenyl)-1H-imidazol-4-yl)amino)-7H-pyrrolo[2,3-d]pyrimidin-4-yl)pyrrolidine-2-carboxamide (173b)

Compound 173b was prepared from (S)-1-(2-chloro-7-tosyl-7H-pyrrolo[2,3-d]pyrimidin-4-yl)pyrrolidine-2-carboxamide (173a) (500 mg, 1.19 mmol), 1-(3,4,5-trimethoxyphenyl)-1H-imidazol-4-amine (57a) (848 mg, 2.38, free base), Pd$_2$(dba)$_3$ (109 mg, 0.12 mmol), BrettPhos (63.9 mg, 0.12 mmol), BrettPhos Palladacycle (64.8 mg, 0.071 mmol) and Cs$_2$CO$_3$ (776 mg, 2.38 mmol) in t-BuOH (15 mL) according to the procedure reported in step-3 of Scheme 101. This gave after workup and purification twice by flash column chromatography [silica (40 g), eluting with DMA 80 in CH$_2$Cl$_2$ from 0 to 50%]; [silica (24 g), eluting with EtOAc/MeOH (9:1) in hexane from 0-100%] (S)-1-(7-tosyl-2-((1-(3,4,5-trimethoxyphenyl)-1H-imidazol-4-yl)amino)-7H-pyrrolo[2,3-d]pyrimidin-4-yl)pyrrolidine-2-carboxamide (173b) (420 mg, 56% yield) as an off white solid; $^1$H NMR (300 MHz, DMSO-d$_6$) δ 9.52 (s, 1H, D$_2$O exchangeable), 8.65-8.34 (m, 1H), 8.34-8.17 (m, 1H), 8.14-7.88 (m, 2H), 7.36 (d, J=8.1 Hz, 3H, 1H is D$_2$O exchangeable), 7.26 (d, J=3.9 Hz, 1H), 7.15-6.91 (m, 3H, 1H is D$_2$O exchangeable), 6.84-6.68 (m, 1H), 4.72-4.51 (m, 1H), 3.84 (s, 6H), 3.70-3.62 (m, 5H), 2.30 (s, 3H), 2.12-1.87 (m, 4H); MS (ES+): δ 33.3 (M+1), 655.3 (M+Na).

Step-3: Preparation of (S)-1-(2-((1-(3,4,5-trimethoxyphenyl)-1H-imidazol-4-yl)amino)-7H-pyrrolo[2,3-d]pyrimidin-4-yl)pyrrolidine-2-carboxamide (173c)

Compound 173c was prepared from (S)-1-(7-tosyl-2-((1-(3,4,5-trimethoxyphenyl)-1H-imidazol-4-yl)amino)-7H-pyrrolo[2,3-d]pyrimidin-4-yl)pyrrolidine-2-carboxamide (173b) (220 mg, 0.35 mmol), in MeOH/THF (5 mL, 1:1) using Cs$_2$CO$_3$ (340 mg, 1.04 mmol) according to the procedure reported in step-3 of Scheme 141. This gave after work up and purification twice by flash column chromatography [silica (12 g), eluting with ethyl acetate/MeOH (9:1) in hexane from 0-100%], [silica (12 g), eluting with DMA-80 in DCM from 0-60%], free base of compound 173c. The free base was stirred for 30 min in CH$_3$CN in presence of HCl (1N, 2 mL) to afford after lyophilization (S)-1-(2-((1-(3,4,5-trimethoxyphenyl)-1H-imidazol-4-yl)amino)-7H-pyrrolo[2,3-d]pyrimidin-4-yl)pyrrolidine-2-carboxamide (173c) (39 mg, 23% yield) HCl salt as an off white solid; $^1$H NMR (300 MHz, DMSO-d$_6$) δ 12.24 (s, 1H, D$_2$O exchangeable), 10.75 and 10.33 (2s, 1H, D$_2$O exchangeable), 8.57 (s, 1H), 7.89-7.73 (m, 1H, D$_2$O exchangeable), 7.48 and 7.34 (2 bs, 1H, D$_2$O exchangeable), 7.21-6.94 (m, 4H, partially D$_2$O exchangeable), 6.70 and 6.49 (2 bs, 1H), 4.92-4.72 (m, 2H), 4.31-4.20 (m, 2H), 3.91 (s, 7H), 3.70 (s, 3H), 2.37-2.18 (m, 1H), 2.14-1.92 (m, 3H); MS (ES+): 479.4 (M+1), 501.3 (M+Na); (ES−): 513.4 (M+Cl).

Scheme 174

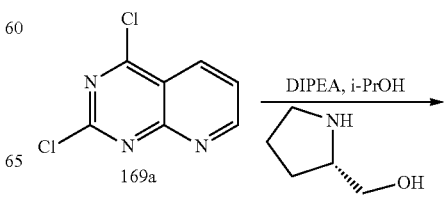

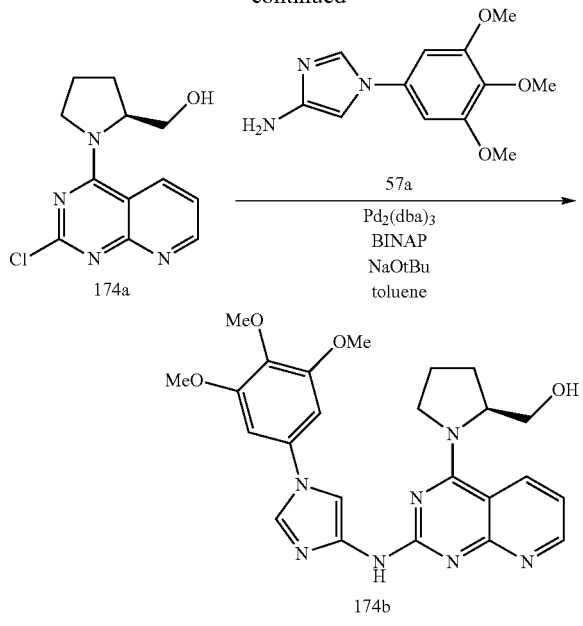

Preparation of (S)-(1-(2-((1-(3,4,5-trimethoxyphenyl)-1H-imidazol-4-yl)amino)pyrido[2,3-d]pyrimidin-4-yl)pyrrolidin-2-yl)methanol (174b)

Step-1: Preparation of (S)-(1-(2-chloropyrido[2,3-d]pyrimidin-4-yl)pyrrolidin-2-yl)methanol (174a)

Compound 174a was prepared from 2,4-dichloropyrido[2,3-d]pyrimidine (169a) (0.5 g, 2.5 mmol) in 2-Propanol (10 mL) using (S)-pyrrolidin-2-ylmethanol (0.25 mL, 2.5 mmol) and DIPEA (1.31 mL, 7.5 mmol) according to the procedure reported in step-1 of Scheme 96. This gave after workup and purification by flash column chromatography [silica (12 g), eluting with MeOH in dichloromethane] (S)-(1-(2-chloropyrido[2,3-d]pyrimidin-4-yl)pyrrolidin-2-yl)methanol (174a) (0.46 g, 70% yield) as a white solid; MS (ES+): 265.3 (M+1), 287.2 (M+Na); MS (ES−): 263.2 (M−1), 299.3 (M+Cl).

Step-2: Preparation of (S)-(1-(2-((1-(3,4,5-trimethoxyphenyl)-1H-imidazol-4-yl)amino)pyrido[2,3-d]pyrimidin-4-yl)pyrrolidin-2-yl)methanol (174b)

Compound 174b was prepared from (S)-(1-(2-chloropyrido[2,3-d]pyrimidin-4-yl)pyrrolidin-2-yl)methanol (174a) (0.25 g, 0.94 mmol), 1-(3,4,5-trimethoxyphenyl)-1H-imidazol-4-amine (57a) (280 mg, 1.13, free base), 2,2'-bis(diphenylphosphino)-1,1'-binaphthyl (BiNAP, 0.071 g, 0.113 mmol), sodium tert-butoxide (0.27 g, 2.83 mmol) and Pd$_2$(dba)$_3$ (90 mg, 0.09 mmol) in toluene (10 mL) according to the procedure reported in step-3 of Scheme 101. This gave after workup and purification by flash column chromatography [silica (12 g), eluting with DMA-80 in CH$_2$Cl$_2$ from 0 to 30%], followed by reverse phase column chromatography [(silica gel C-18, 24 g) eluting with acetonitrile and 0.1% HCl water] (S)-(1-(2-((1-(3,4,5-trimethoxyphenyl)-1H-imidazol-4-yl)amino)pyrido[2,3-d]pyrimidin-4-yl)pyrrolidin-2-yl)methanol (174b) (31 mg, 7% yield) HCl salt as a yellow solid; $^1$H NMR (300 MHz, DMSO-d$_6$) δ 10.29 (s, 1H), 8.81 (s, 1H), 8.56 (d, J=8.3 Hz, 1H), 8.16 (s, 1H), 7.73 (s, 1H), 7.24 (dd, J=8.1, 4.5 Hz, 1H), 6.94 (s, 2H), 5.17-4.88 (m, 1H), 4.88-4.66 (m, 1H), 4.17-3.55 (m, 13H), 2.21-1.84 (m, 4H); MS (ES+): 478.3 (M+1), 500.3 (M+Na). HPLC purity: 96.94%.

Scheme 175

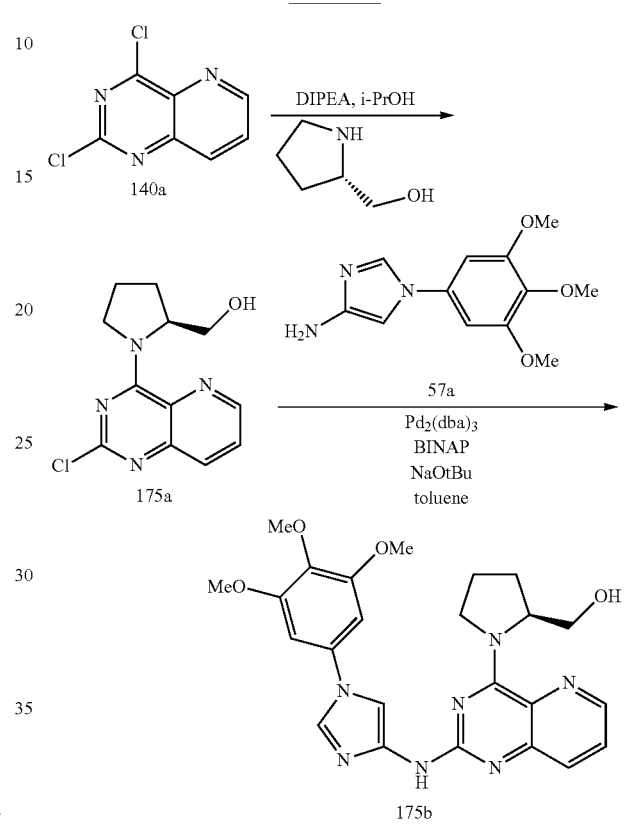

Preparation of (S)-(1-(2-((1-(3,4,5-trimethoxyphenyl)-1H-imidazol-4-yl)amino)pyrido[3,2-d]pyrimidin-4-yl)pyrrolidin-2-yl)methanol (175b)

Step-1: Preparation of (S)-(1-(2-chloropyrido[3,2-d]pyrimidin-4-yl)pyrrolidin-2-yl)methanol (175a) Compound 175a was prepared from 2,4-dichloropyrido[3,2-d]pyrimidine (140a) (0.3 g, 1.50 mmol) in 2-Propanol (10 mL) using (S)-pyrrolidin-2-ylmethanol (0.15 mL, 1.50 mmol) and DIPEA (0.79 mL, 4.50 mmol) according to the procedure reported in step-1 of Scheme 96. This gave after workup and purification by flash column chromatography [silica (12 g), eluting with MeOH in dichloromethane 0-30%] (S)-(1-(2-chloropyrido[3,2-d]pyrimidin-4-yl)pyrrolidin-2-yl)methanol (175a) (0.21 g, 53% yield) as a white solid; MS (ES+): 265.3 (M+1), 287.2 (M+Na); MS (ES−): 263.3 & 265.3 (M−1).

Step-2: Preparation of (S)-(1-(2-((1-(3,4,5-trimethoxyphenyl)-1H-imidazol-4-yl)amino)pyrido[3,2-d]pyrimidin-4-yl)pyrrolidin-2-yl)methanol (175b)

Compound 175b was prepared from (S)-(1-(2-chloropyrido[3,2-d]pyrimidin-4-yl)pyrrolidin-2-yl)methanol (175a) (0.2 g, 0.76 mmol), 1-(3,4,5-trimethoxyphenyl)-1H-imidazol-4-amine (57a) (280 mg, 1.13, free base), 2,2'-bis(diphenylphosphino)-1,1'-binaphthyl (BiNAP, 0.06 g, 0.09 mmol), sodium tert-butoxide (0.22 g, 2.27 mmol) and Pd$_2$(dba)$_3$ (70 mg, 0.08 mmol) in toluene (15 mL) according to the procedure reported in step-3 of Scheme 101. This gave after workup and purification by flash column chromatography [silica (12 g), eluting with DMA 80 in CH$_2$Cl$_2$ from 0 to 30%], followed by reverse phase column chromatography [(silica gel C-18, 24 g) eluting with acetonitrile and 0.1% HCl water] (S)-(1-(2-((1-(3,4,5-trimethoxyphenyl)-1H-imidazol-4-yl)amino)pyrido[3,2-d]pyrimidin-4-yl)pyrrolidin-2-yl)methanol (175b) (33 mg, 9% yield) HCl salt as a yellow solid; $^1$H NMR (300 MHz, DMSO-d$_6$) δ 10.82 (s, 1H), 8.77-8.68 (m, 1H), 8.34 (s, 1H), 8.04 (s, 1H), 7.89-7.79 (m, 1H), 7.77 (s, 1H), 7.00 (s, 1H), 6.96 (s, 1H), 4.85 (s, 1H), 4.63-4.46 (m, 1H), 4.46-4.31 (m, 1H), 4.18-3.99 (m, 1H), 3.89 (s, 6H), 3.87-3.75 (m, 1H), 3.75-3.59 (m, 4H), 2.34-1.84 (m, 4H); MS (ES+): 478.3 (M+1), 500.3 (M+Na); MS (ES−): 512.3 (M+Cl). HPLC purity: 97.16%.

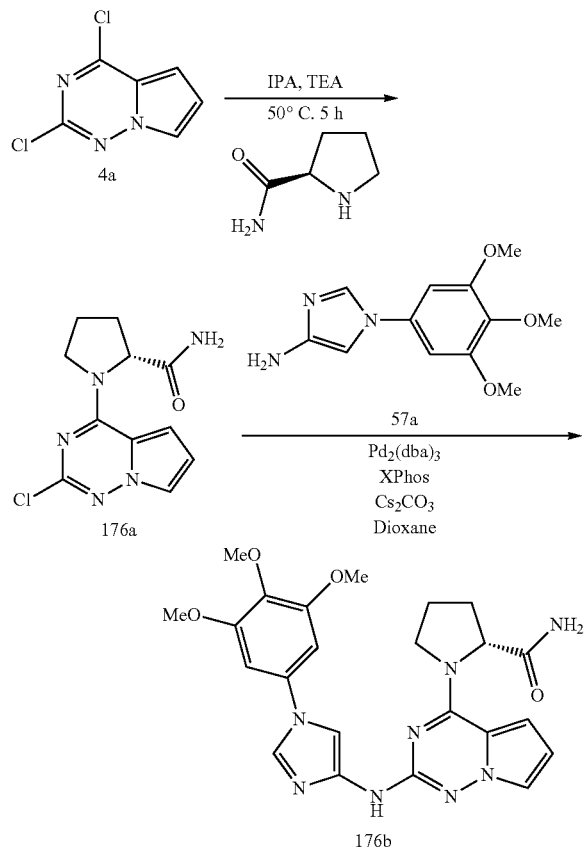

Scheme 176

Preparation of (R)-1-(2-((1-(3,4,5-trimethoxyphenyl)-1H-imidazol-4-yl)amino)pyrrolo[2,1-f][1,2,4]triazin-4-yl)pyrrolidine-2-carboxamide (176b)

Step-1: Preparation of (R)-1-(2-chloropyrrolo[2,1-f][1,2,4]triazin-4-yl)pyrrolidine-2-carboxamide (176a) Compound 176a was prepared from 2,4-dichloropyrrolo[2,1-f][1,2,4]triazine (4a) (3 g, 15.96 mmol) in 2-Propanol (10 mL) using (R)-pyrrolidine-2-carboxamide (2.0 g, 17.55 mmol) and TEA (4.45 mL, 31.9 mmol) according to the procedure reported in step-1 of Scheme 96. This gave after workup and purification by flash column chromatography [silica (80 g), eluting with 9:1 mixture of ethyl acetate and methanol in hexanes] (R)-1-(2-chloropyrrolo[2,1-f][1,2,4]triazin-4-yl)pyrrolidine-2-carboxamide (176a) (3.85 g, 91% yield) as a white solid; $^1$H NMR (300 MHz, DMSO-d$_6$) δ 7.83-7.62 (m, 1H), 7.41 (d, J=70.7 Hz, 1H), 7.01 (dd, J=4.6, 1.6 Hz, 1H), 6.74 (dd, J=19.1, 3.6 Hz, 1H), 6.70-6.57 (m, 1H), 5.01-4.51 (m, 1H), 4.22-3.56 (m, 2H), 2.43-1.72 (m, 4H).

Step-2: Preparation of (R)-1-(2-((1-(3,4,5-trimethoxyphenyl)-1H-imidazol-4-yl)amino)pyrrolo[2,1-f][1,2,4]triazin-4-yl)pyrrolidine-2-carboxamide (176b)

Compound 176b was prepared from (R)-1-(2-chloropyrrolo[2,1-f][1,2,4]triazin-4-yl)pyrrolidine-2-carboxamide (176a) (0.5 g, 1.88 mmol), 1-(3,4,5-trimethoxyphenyl)-1H-imidazol-4-amine (57a) (700 mg, 2.82 mmol, free base), dicyclohexyl(2',4',6'-triisopropylbiphenyl-2-yl)phosphine (XPhos, 0.40 g, 0.84 mmol), cesium carbonate (1.83 g, 5.65 mmol) and Pd$_2$(dba)$_3$ (250 mg, 0.28 mmol) in 1,4-dioxane (10 mL) according to the procedure reported in step-3 of Scheme 101. This gave after workup and purification by flash column chromatography [silica (80 g), eluting with DMA-80 in CH$_2$Cl$_2$], followed by reverse phase column chromatography [(silica gel C18, 150 g) eluting with acetonitrile and 0.1% HCl water] (R)-1-(2-((1-(3,4,5-trimethoxyphenyl)-1H-imidazol-4-yl)amino)pyrrolo[2,1-f][1,2,4]triazin-4-yl)pyrrolidine-2-carboxamide (176b) (394 mg, 43.8% yield) as awhite solid; $^1$H NMR (300 MHz, DMSO-d$_6$) δ 9.66-9.46, 9.46-9.27 (2m, 1H), 9.22 (s, 1H), 7.90, 7.85 (2s, 1H), 7.78-7.67, 7.67-7.57 (2m, 1H), 7.43 (s, 1H), 7.30-7.08 (m, 2H), 7.08-6.85 (m, 1H), 6.75-6.46 (m, 1H), 4.95-4.82, 4.75-4.59 (2m, 1H), 4.33-4.05 (m, 1H), 4.01-3.75 (m, 7H), 3.72 (s, 3H), 2.30-1.81 (m, 4H); $^1$H NMR (300 MHz, DMSO-d$_6$-D$_2$O) δ 9.11 (s, 1H), 7.72-7.55, 7.87-7.72 (2m, 1H), 7.18-7.05 (m, 2H), 6.91 (d, J=4.6 Hz, 1H), 6.73-6.50 (m, 2H), 4.74-4.61, 4.94-4.88 (2m, 1H), 4.25-4.13 (m, 1H), 4.01-3.93 (m, 1H), 3.91 (s, 6H), 3.73 (s, 3H), 2.32-1.91 (m, 4H); MS (ES+): 479.4 (M+1), 501.4 (M+Na), (ES−): 513.4 (M+Cl).

Scheme 177

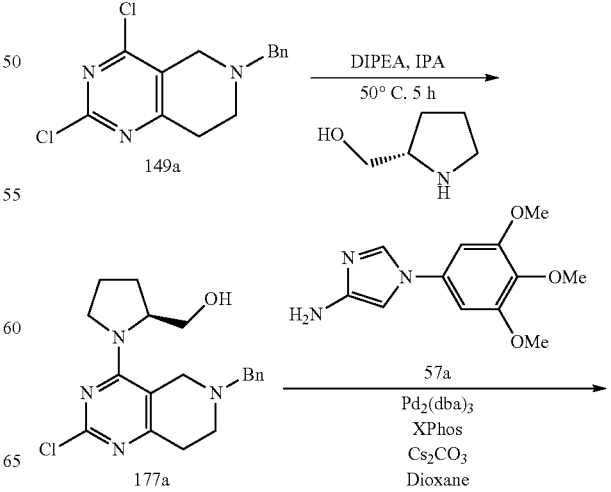

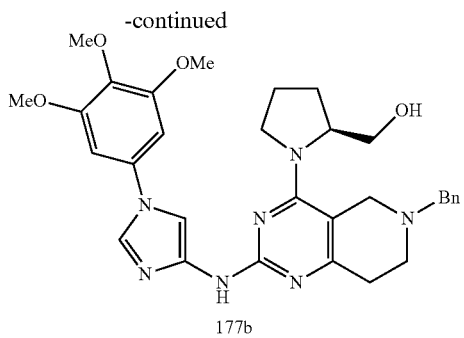

177b

Preparation of (S)-(1-(6-benzyl-2-((1-(3,4,5-trimethoxyphenyl)-1H-imidazol-4-yl)amino)-5,6,7,8-tetrahydropyrido[4,3-d]pyrimidin-4-yl)pyrrolidin-2-yl)methanol (177b)

Step-1: Preparation of (S)-(1-(6-benzyl-2-chloro-5,6,7,8-tetrahydropyrido[4,3-d]pyrimidin-4-yl)pyrrolidin-2-yl)methanol (177a)

Compound 177a was prepared from 6-benzyl-2,4-dichloro-5,6,7,8-tetrahydropyrido[4,3-d]pyrimidine (149a) (0.5 g, 1.7 mmol) in 2-Propanol (5 mL) using (S)-pyrrolidin-2-ylmethanol (172 mg, 1.7 mmol) and DIPEA (0.45 mL, 2.55 mmol) according to the procedure reported in step-1 of Scheme 96. This gave after workup and purification by flash column chromatography [silica (40 g), eluting with DMA 80 in chloroform (0 to 50%)] (S)-(1-(6-benzyl-2-chloro-5,6,7,8-tetrahydropyrido[4,3-d]pyrimidin-4-yl)pyrrolidin-2-yl)methanol (177a) (511 mg, 84% yield) as an oil; $^1$H NMR (300 MHz, DMSO-d$_6$) δ 7.40-7.18 (m, 5H), 4.79-4.63 (m, 1H, D$_2$O exchangeable), 4.37-4.18 (m, 1H), 3.78-3.64 (m, 2H), 3.65-3.49 (m, 4H), 3.52-3.34 (m, 2H), 2.89-2.72 (m, 1H), 2.72-2.54 (m, 2H), 2.47-2.32 (m, 1H), 1.97-1.79 (m, 3H), 1.78-1.63 (m, 1H).

Step-2: Preparation of (S)-(1-(6-benzyl-2-((1-(3,4,5-trimethoxyphenyl)-1H-imidazol-4-yl)amino)-5,6,7,8-tetrahydropyrido[4,3-d]pyrimidin-4-yl)pyrrolidin-2-yl)methanol (177b)

Compound 177b was prepared from (S)-(1-(6-benzyl-2-chloro-5,6,7,8-tetrahydropyrido[4,3-d]pyrimidin-4-yl)pyrrolidin-2-yl)methanol (177a) (0.33 g, 0.91 mmol), 1-(3,4,5-trimethoxyphenyl)-1H-imidazol-4-amine (57a) (340 mg, 1.36 mmol, free base), dicyclohexyl(2',4',6'-triisopropylbiphenyl-2-yl)phosphine (XPhos, 195 mg, 0.41 mmol), cesium carbonate (890 mg, 2.73 mmol) and Pd$_2$(dba)$_3$ (125 mg, 0.14 mmol) in 1,4-dioxane (10 mL) according to the procedure reported in step-3 of Scheme 101. This gave after workup and purification by flash column chromatography [silica (80 g), eluting with DMA 80 in CH$_2$Cl$_2$], followed by reverse phase column chromatography [(silica gel C-18, 24 g) eluting with acetonitrile and 0.1% HCl water] (S)-(1-(6-benzyl-2-((1-(3,4,5-trimethoxyphenyl)-1H-imidazol-4-yl)amino)-5,6,7,8-tetrahydropyrido[4,3-d]pyrimidin-4-yl)pyrrolidin-2-yl)methanol (177b) (140 mg, 27% yield) HCl salt as a yellow solid; $^1$H NMR (300 MHz, DMSO-d$_6$) δ 12.50-11.73 (m, 1H, D$_2$O exchangeable), 10.61-10.07 (m, 1H, D$_2$O exchangeable), 8.58-8.26 (m, 1H), 7.79-7.65 (m, 3H), 7.55-7.42 (m, 3H), 6.98 (s, 2H), 4.67-4.30 (m, 7H), 3.87 (s, 6H), 3.83-3.72 (m, 2H), 3.68 (s, 3H), 3.66-3.38 (m, 2H), 3.37-2.95 (m, 2H), 2.10-1.75 (m, 4H); $^1$H NMR (300 MHz, DMSO-d-D$_2$O) δ 8.45 (s, 1H), 7.71 (s, 1H), 7.68-7.59 (m, 2H), 7.57-7.47 (m, 3H), 6.96 (s, 2H), 4.65-4.36 (m, 7H), 3.87 (s, 6H), 3.70-3.68 (m, 4H), 3.67-3.56 (m, 1H), 3.57-3.40 (m, 2H), 3.11 (s, 2H), 2.14-1.79 (m, 4H); MS (ES+): 572.4 (M+1), 595.5 (M+Na), (ES−): 606.4 (M+Cl); HPLC purity: 98.17%.

Scheme 178

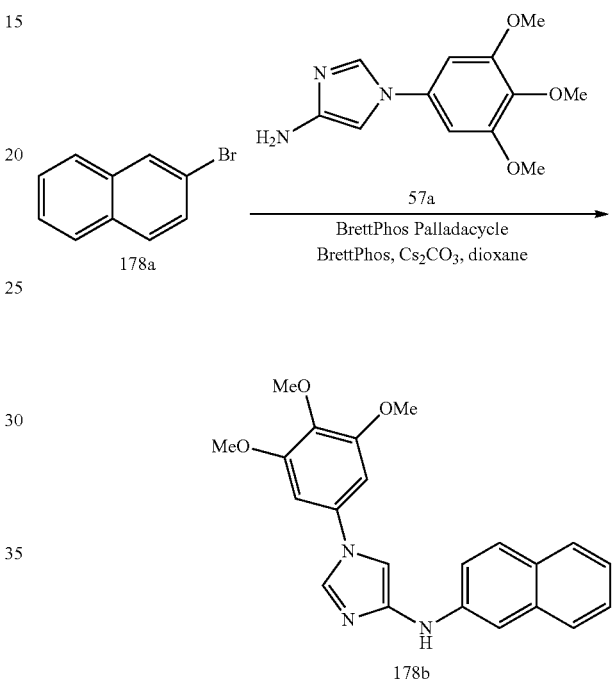

Preparation of N-(naphthalen-2-yl)-1-(3,4,5-trimethoxyphenyl)-1H-imidazol-4-amine (178b)

To a solution of 2-bromonaphthalene (178a) (100 mg, 0.48 mmol, in a 40 mL vial) in dioxane (5 mL) was added 1-(3,4,5-trimethoxyphenyl)-1H-imidazol-4-amine (57a) (181 mg, 0.72 mmol, free base), BrettPhos Palladacycle (22 mg, 0.024 mmol), BrettPhos (23 mg, 0.048 mmol) and Cs$_2$CO$_3$ (393 mg, 1.21 mmol). The reaction mixture was fully degassed with argon and heated at 95° C. for 12 h. The reaction mixture was diluted with EtOAc (120 mL), filtered to remove inorganic solids. The filtrate was washed with water, brine, dried, filtered and concentrated in vacuum. The residue obtained was purified twice by flash column chromatography [silica (12 g), eluting with DMA80 in DCM 0-60%] to furnish compound 178b as a free base. The free base was stirred for 30 min in CH$_3$CN in presence of HCl (1N, 2 mL) to afford after lyophilization N-(naphthalen-2-yl)-1-(3,4,5-trimethoxyphenyl)-1H-imidazol-4-amine (178b) (26 mg, 14% yield) HCl salt as an off white solid; $^1$H NMR (300 MHz, DMSO-d$_6$) δ 9.23 (s, 1H), 8.99 (brs, 1H, D$_2$O exchangeable), 8.02 (s, 1H, D$_2$O exchangeable), 7.87-7.70 (m, 3H), 7.45-7.40 (m, 1H), 7.40-7.33 (m, 2H), 7.33-7.22 (m, 2H), 7.16 (s, 2H), 3.90 (s, 6H), 3.72 (s, 3H); MS (ES$^+$) 376.3 (M+1); (ES−) 410.3 (M+Cl).

Scheme 179

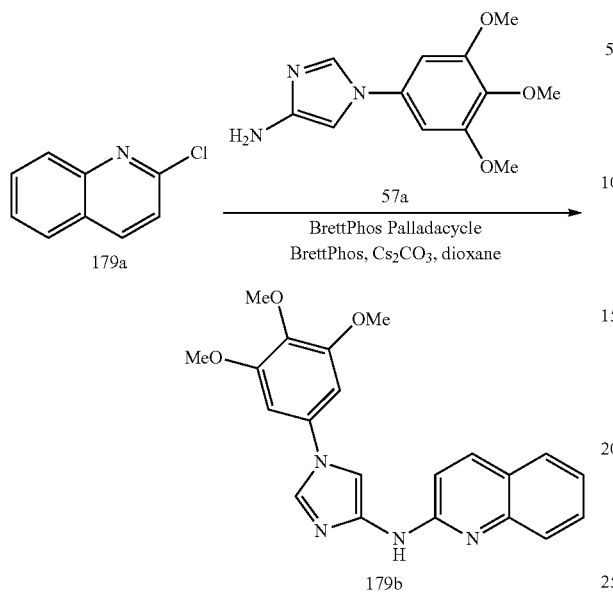

Preparation of N-(1-(3,4,5-trimethoxyphenyl)-1H-imidazol-4-yl)quinolin-2-amine (179b)

Compound 179b was prepared from 2-chloroquinoline (179a) (75 mg, 0.46 mmol) in dioxane (5 mL), 1-(3,4,5-trimethoxyphenyl)-1H-imidazol-4-amine (57a) (171 mg, 0.69 mmol), BrettPhos Palladacycle (21 mg, 0.023 mmol), BrettPhos (25 mg, 0.046 mmol) and $Cs_2CO_3$ (299 mg, 0.92 mmol) according to the procedure reported in Scheme 178. This gave after workup and purification by flash column chromatography [silica (24 g), eluting with EtOAc/MeOH (9:1) in hexane from 0-100%] N-(1-(3,4,5-trimethoxyphenyl)-1H-imidazol-4-yl)quinolin-2-amine (179b) (138 mg, 80% yield) as a yellow solid; $^1$H NMR (300 MHz, DMSO-$d_6$) δ 9.86 (s, 1H, $D_2O$ exchangeable), 8.21-8.15 (m, 1H), 8.13-8.06 (m, 1H), 7.98 (d, J=8.9 Hz, 1H), 7.82 (d, J=8.3 Hz, 1H), 7.69 (dd, J=8.1, 1.5 Hz, 1H), 7.62-7.51 (m, 1H), 7.29-7.18 (m, 1H), 7.14 (d, J=8.9 Hz, 1H), 6.95 (s, 2H), 3.91 (s, 6H), 3.70 (s, 3H); MS (ES+): 377.3 (M+1); 399.3 (M+Na); (ES−): 375.3 (M−1).

Scheme 180

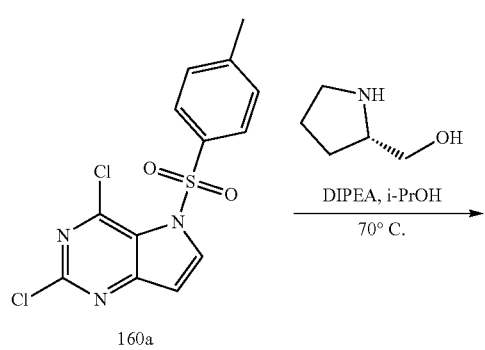

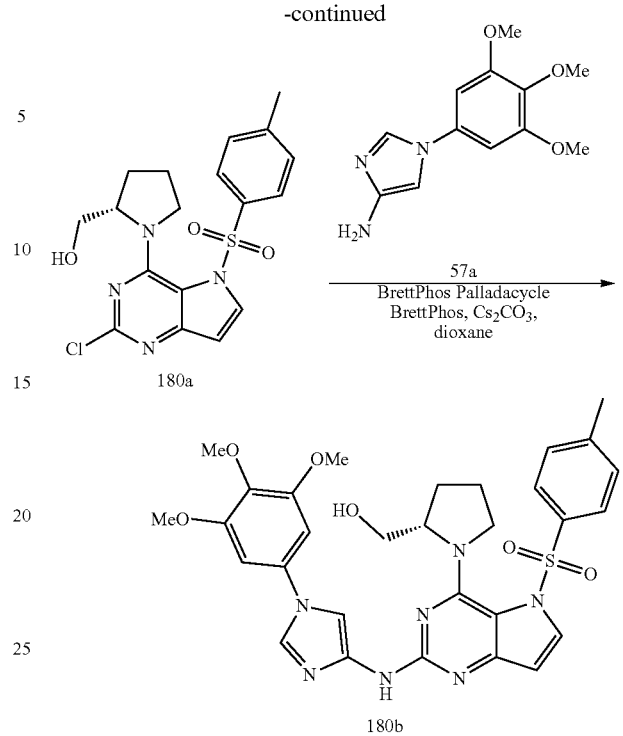

Preparation of (S)-(1-(5-tosyl-2-((1-(3,4,5-trimethoxyphenyl)-1H-imidazol-4-yl)amino)-5H-pyrrolo[3,2-d]pyrimidin-4-yl)pyrrolidin-2-yl)methanol (180b)

Step-1: Preparation of (S)-(1-(2-chloro-5-tosyl-5H-pyrrolo[3,2-d]pyrimidin-4-yl)pyrrolidin-2-yl)methanol (180a)

Compound 180a was prepared from 2,4-dichloro-5-tosyl-5H-pyrrolo[3,2-d]pyrimidine (160a) (1.23 g, 3.59 mmol) in IPA (15 mL), (S)-pyrrolidin-2-ylmethanol (0.36 g, 3.59 mmol), DIPEA (0.94 mL, 5.39 mmol) according to the procedure reported in step-1 of Scheme 96. This gave after workup and purification by flash column chromatography [silica (12 g), eluting with ethyl acetate/MeOH (9:1) in hexane from 0-70%] (S)-(1-(2-chloro-5-tosyl-5H-pyrrolo[3,2-d]pyrimidin-4-yl)pyrrolidin-2-yl)methanol (180a) (1.21 g, 83% yield) as a white solid; $^1$H NMR (300 MHz, DMSO-$d_6$) δ 7.88 (d, J=3.7 Hz, 1H), 7.47-7.36 (m, 2H), 7.33-7.23 (m, 2H), 6.67 (d, J=3.7 Hz, 1H), 4.80 (t, 1H, $D_2O$ exchangeable), 4.61-4.45 (m, 1H), 4.07-3.93 (m, 1H), 3.65-3.48 (m, 2H), 3.44-3.34 (m, 1H), 2.31 (s, 3H), 2.11-1.84 (m, 3H), 1.82-1.66 (m, 1H).

Step-2: Preparation of (S)-(1-(5-tosyl-2-((1-(3,4,5-trimethoxyphenyl)-1H-imidazol-4-yl)amino)-5H-pyrrolo[3,2-d]pyrimidin-4-yl)pyrrolidin-2-yl)methanol (180b)

Compound 180b was prepared from (S)-(1-(2-chloro-5-tosyl-5H-pyrrolo[3,2-d]pyrimidin-4-yl)pyrrolidin-2-yl)methanol (180a) (350 mg, 0.86 mmol) in dioxane (15 mL), 1-(3,4,5-trimethoxyphenyl)-1H-imidazol-4-amine (57a) (322 mg, 1.29 mmol), BrettPhos Palladacycle (39 mg, 0.043 mmol), BrettPhos (46 mg, 0.086 mmol) and $Cs_2CO_3$ (561 mg, 1.72 mmol) according to the procedure reported in Scheme 178. This gave after workup and twice purification by flash column chromatography [silica (40 g), eluting with DMA-80 in DCM from 0-60%], [silica (24 g), eluting with EtOAc/MeOH (9:1) in hexane from 0-100%] compound 180b as a free base. The free base was converted to HCl salt using 1 N HCl (2 mL) in acetonitrile to afford (S)-(1-(5-tosyl-2-((1-(3,4,5-trimethoxyphenyl)-1H-imidazol-4-yl)amino)-5H-pyrrolo[3,2-d]pyrimidin-4-yl)pyrrolidin-2-yl)methanol (180b) (75 mg, 14% yield) HCl salt as an off white solid; $^1$H NMR (300 MHz, DMSO-$d_6$) δ 13.32-12.00 (m, 1H, $D_2O$ exchangeable), 10.83-10.49 (m, 1H, $D_2O$ exchangeable), 8.52 (s, 1H), 8.05-7.88 (m, 2H), 7.77 (s, 1H), 7.48 (d, J=8.1 Hz, 2H), 7.09-6.96 (m, 3H), 4.84-4.57 (m, 1H), 4.28-4.08 (m, 1H), 3.98-3.83 (m, 8H), 3.72-3.62 (m, 5H), 2.39 (s, 3H), 2.13-1.91 (m, 4H); MS (ES+): δ 20.3 (M+1); (ES−): δ 18.4 (M−1).

Preparation of (S)-(1-(2-((1-(3,4,5-trimethoxyphenyl)-1H-imidazol-4-yl)amino)-5,6,7,8-tetrahydropyrido[4,3-d]pyrimidin-4-yl)pyrrolidin-2-yl)methanol (181d)

Step-1: Preparation of (S)-tert-butyl 2-chloro-4-(2-(hydroxymethyl)pyrrolidin-1-yl)-7,8-dihydropyrido[4,3-d]pyrimidine-6(5H)-carboxylate (181b)

Compound 181b was prepared from tert-butyl 2,4-dichloro-7,8-dihydropyrido[4,3-d]pyrimidine-6(5H)-carboxylate (181a) (2.0 g, 6.58 mmol, CAS #635698-56-5) in 2-Propanol (20 mL) using (S)-pyrrolidin-2-ylmethanol (0.67 g, 6.58 mmol) and DIPEA (1.72 mL, 9.86 mmol) according to the procedure reported in step-1 of Scheme 96. This gave after workup and purification by flash column chromatography [silica (40 g), eluting with DMA 80 in chloroform (0 to 50%)] (S)-tert-butyl 2-chloro-4-(2-(hydroxymethyl)pyrrolidin-1-yl)-7,8-dihydropyrido[4,3-d]pyrimidine-6(5H)-carboxylate (181b) (511 mg, 84% yield) as an oil; $^1$H NMR (300 MHz, DMSO-$d_6$) δ 4.79-4.71 (m, 1H, $D_2O$ exchangeable), 4.56 (m, 2H), 4.31 (dd, J=6.3, 3.9 Hz, 1H), 3.83-3.55 (m, 2H), 3.57-3.28 (m, 4H), 2.67 (t, J=6.1 Hz, 2H), 2.04-1.85 (m, 3H), 1.85-1.69 (m, 1H), 1.41 (s, 9H).

Step-2: Preparation of (S)-tert-butyl 4-(2-(hydroxymethyl)pyrrolidin-1-yl)-2-((1-(3,4,5-trimethoxyphenyl)-1H-imidazol-4-yl)amino)-7,8-dihydropyrido[4,3-d]pyrimidine-6(5H)-carboxylate (181c)

Compound 181c was prepared from (S)-tert-butyl 2-chloro-4-(2-(hydroxymethyl)pyrrolidin-1-yl)-7,8-dihydropyrido[4,3-d]pyrimidine-6(5H)-carboxylate (181b) (0.5 g, 1.36 mmol), 1-(3,4,5-trimethoxyphenyl)-1H-imidazol-4-amine (57a) (422 mg, 1.69 mmol, free base), dicyclohexyl (2',4',6'-triisopropylbiphenyl-2-yl)phosphine (XPhos, 0.29 g, 0.61 mmol), cesium carbonate (1.33 g, 4.07 mmol) and Pd$_2$(dba)$_3$ (186 mg, 0.2 mmol) in 1,4-dioxane (10 mL) according to the procedure reported in step-3 of Scheme 101. This gave after workup and purification by flash column chromatography [silica (80 g), eluting with DMA 80 in CH$_2$Cl$_2$], followed by reverse phase column chromatography [(silica gel C-18, 24 g) eluting with acetonitrile and 0.1% HCl water] (S)-tert-butyl 4-(2-(hydroxymethyl)pyrrolidin-1-yl)-2-((1-(3,4,5-trimethoxyphenyl)-1H-imidazol-4-yl)amino)-7,8-dihydropyrido[4,3-d]pyrimidine-6(5H)-carboxylate (181c) (350 mg, 44% yield) HCl salt as a white solid; $^1$H NMR (300 MHz, DMSO-$d_6$-$D_2O$) δ 8.33 (d, J=17.4 Hz, 1H), 7.74-7.56 (m, 1H), 6.94 (d, J=3.4 Hz, 2H), 4.80-4.44 (m, 3H), 3.93-3.84 (m, 8H), 3.84-3.71 (m, 2H), 3.69 (s, 3H), 3.65-3.22 (m, 2H), 2.89-2.71 (m, 2H), 2.21-1.79 (m, 4H), 1.43 (s, 9H); MS (ES+) 582.4 (M+1), 604.3 (M+Na), (ES−) 616.5 (M+Cl); HPLC purity: 90.07%.

Step-3: Preparation of (S)-(1-(2-((1-(3,4,5-trimethoxyphenyl)-1H-imidazol-4-yl)amino)-5,6,7,8-tetrahydropyrido[4,3-d]pyrimidin-4-yl)pyrrolidin-2-yl)methanol (181d)

Compound 181d was prepared by hydrolysis of Boc of (S)-tert-butyl 4-(2-(hydroxymethyl)pyrrolidin-1-yl)-2-((1-(3,4,5-trimethoxyphenyl)-1H-imidazol-4-yl)amino)-7,8-dihydropyrido[4,3-d]pyrimidine-6(5H)-carboxylate (181c) (260 mg, 0.45 mmol) in DCM using trifluoroacetic acid (0.69 mL, 8.94 mmol). This gave after purification by reverse phase column chromatography [(silica gel C-18, 100

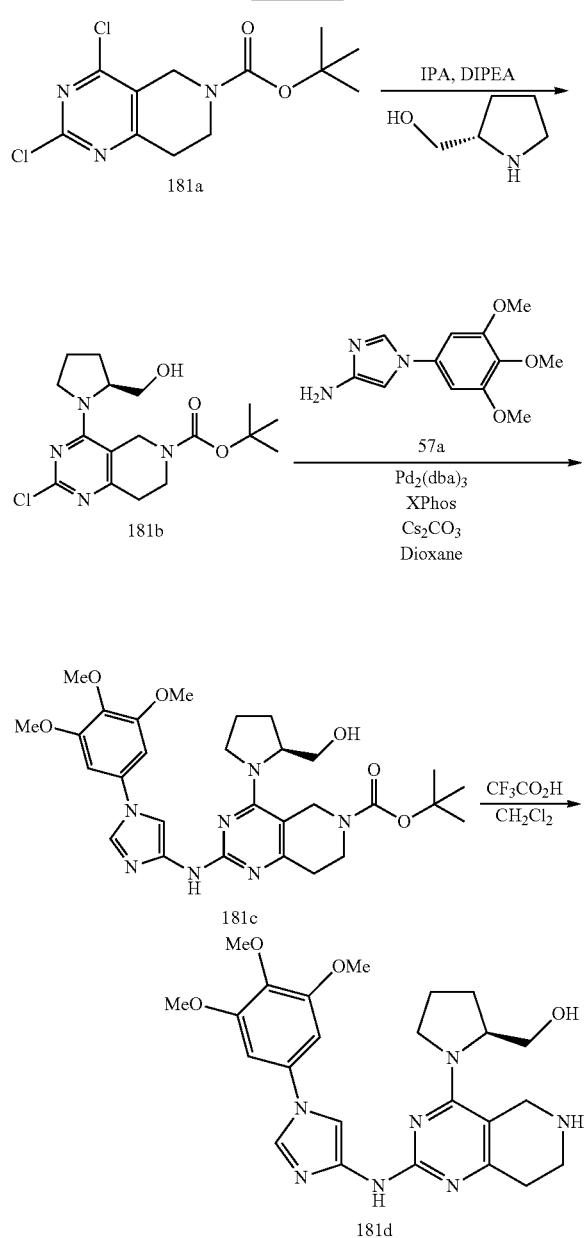

Scheme 181 g) eluting with 0.1% HCl and acetonitrile] (S)-(1-(2-((1-(3,4,5-trimethoxyphenyl)-1H-imidazol-4-yl)amino)-5,6,7,8-tetrahydropyrido [4,3-d]pyrimidin-4-yl)pyrrolidin-2-yl) methanol (181d) (95 mg, 44% yield) HCl salt as a white solid; $^1$H NMR (300 MHz, DMSO-$d_6$) δ 10.48-9.44 (m, 3H, $D_2O$ exchangeable), 8.41 (s, 1H), 7.70 (s, 1H), 6.97 (d, J=2.6 Hz, 2H), 4.74-4.47 (m, 2H), 4.47-4.22 (m, 2H), 3.87 (s, 6H), 3.68 (s, 3H), 3.69-3.54 (m, 4H), 3.55-3.36 (m, 2H), 3.36-3.16 (m, 1H), 3.12-2.95 (m, 2H), 2.14-1.71 (m, 4H); MS (ES+): 482.4 (M+1), 504.3 (M+Na), (ES−): 516.3 (M+Cl).

Scheme 182

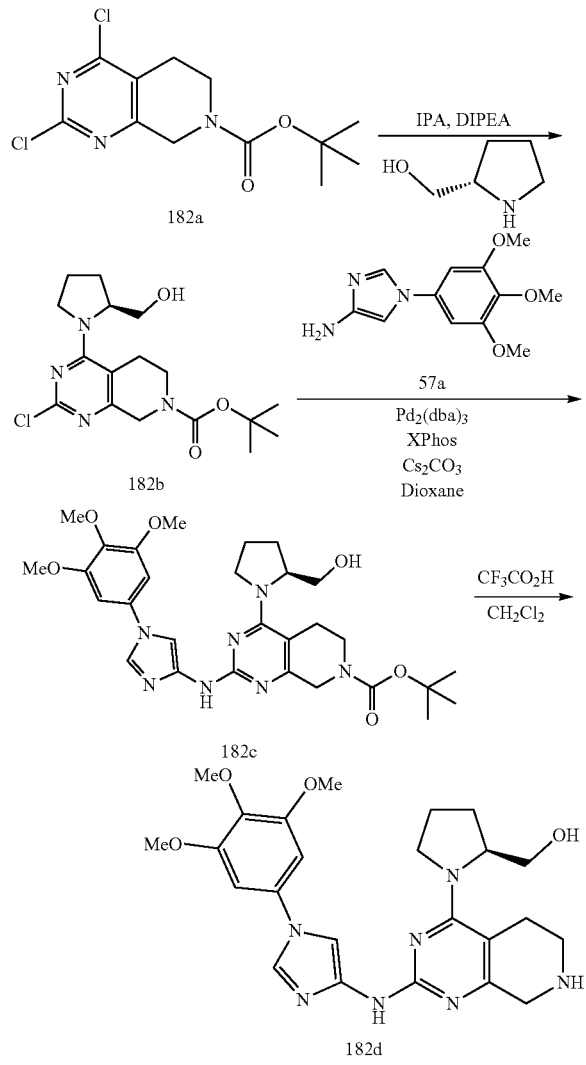

Preparation of (S)-(1-(2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (182d)

Step-1: Preparation of (S)-tert-butyl 2-chloro-4-(2-(hydroxymethyl)pyrrolidin-1-yl)-5,6-dihydropyrido[3,4-d]pyrimidine-7(8H)-carboxylate (182b)

Compound 182b was prepared from tert-butyl 2,4-dichloro-5,6-dihydropyrido[3,4-d]pyrimidine-7(8H)-carboxylate (182a) (2.0 g, 6.58 mmol, CAS #916420-27-4) in 2-Propanol (20 mL) using (S)-pyrrolidin-2-ylmethanol (0.67 g, 6.58 mmol) and DIPEA (1.72 mL, 9.86 mmol) according to the procedure reported in step-1 of Scheme 96. This gave after workup and purification by flash column chromatography [silica (40 g), eluting with DMA 80 in chloroform (0 to 50%)] (S)-tert-butyl 2-chloro-4-(2-(hydroxymethyl)pyrrolidin-1-yl)-5,6-dihydropyrido[3,4-d]pyrimidine-7(8H)-carboxylate (182b) (1.85 g, 76% yield) as an oil; $^1$H NMR (300 MHz, DMSO-$d_6$) δ 4.77-4.62 (m, 1H), 4.47 (d, J=18.7 Hz, 1H), 4.39-4.26 (m, 1H), 4.23-4.01 (m, 1H), 4.00-3.84 (m, 2H), 3.76-3.55 (m, 2H), 3.54-3.34 (m, 1H), 3.12-2.79 (m, 2H), 2.76-2.62 (m, 1H), 2.03-1.83 (m, 3H), 1.81-1.63 (m, 1H), 1.43 (s, 9H).

Step-2: Preparation of (S)-tert-butyl 4-(2-(hydroxymethyl)pyrrolidin-1-yl)-2-((1-(3,4,5-trimethoxyphenyl)-1H-imidazol-4-yl)amino)-5,6-dihydropyrido[3,4-d]pyrimidine-7(8H)-carboxylate (182c)

Compound 182c was prepared from (S)-tert-butyl 2-chloro-4-(2-(hydroxymethyl)pyrrolidin-1-yl)-5,6-dihydropyrido[3,4-d]pyrimidine-7(8H)-carboxylate (182b) (0.5 g, 1.36 mmol), 1-(3,4,5-trimethoxyphenyl)-1H-imidazol-4-amine (57a) (422 mg, 1.69 mmol, free base), dicyclohexyl (2',4',6'-triisopropylbiphenyl-2-yl)phosphine (XPhos, 290 mg, 0.61 mmol), cesium carbonate (1.33 g, 4.07 mmol) and $Pd_2(dba)_3$ (186 mg, 0.2 mmol) in 1,4-dioxane (10 mL) according to the procedure reported in step-3 of Scheme 101. This gave after workup and purification by flash column chromatography [silica (80 g), eluting with DMA-80 in $CH_2Cl_2$], followed by reverse phase column chromatography [(silica gel C-18, 24 g) eluting with acetonitrile and 0.1% HCl water] (S)-tert-butyl 4-(2-(hydroxymethyl)pyrrolidin-1-yl)-2-((1-(3,4,5-trimethoxyphenyl)-1H-imidazol-4-yl)amino)-5,6-dihydropyrido[3,4-d]pyrimidine-7(8H)-carboxylate (182c) (320 mg, 41% yield) HCl salt as a white solid; $^1$H NMR (300 MHz, DMSO-$d_6$-$D_2O$) δ 8.43 (s, 1H), 7.71 (s, 1H), 6.96 (s, 2H), 4.64-4.52 (m, 2H), 4.28-4.17 (m, 1H), 4.01-3.67 (m, 12H), 3.67-3.53 (m, 1H), 3.53-3.42 (m, 2H), 3.32-3.04 (m, 2H), 2.07-1.91 (m, 4H), 1.45 (s, 9H); MS (ES+): 582.4 (M+1), (ES−): δ 16.4 (M+Cl); HPLC purity: 90.76%.

Step-3: Preparation of (S)-(1-(2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (182d)

Compound 182d was prepared by hydrolysis of Boc of (S)-tert-butyl 4-(2-(hydroxymethyl)pyrrolidin-1-yl)-2-((1-(3,4,5-trimethoxyphenyl)-1H-imidazol-4-yl)amino)-5,6-dihydropyrido[3,4-d]pyrimidine-7(8H)-carboxylate (182c) (255 mg, 0.44 mmol) in DCM using trifluoroacetic acid (0.68 mL, 8.77 mmol) according to the procedure reported in Scheme 122. This gave after purification by reverse phase column chromatography [(silica gel C-18, 100 g) eluting with 0.1% HCl and acetonitrile] (S)-(1-(2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (182d) (155 mg, 73% yield) HCl salt as a white solid; $^1$H NMR (300 MHz, DMSO-$d_6$) δ 10.20 (s, 1H), 10.03-9.76 (m, 2H), 8.59 (s, 1H), 7.73 (s, 1H), 7.00 (s, 2H), 4.61 (s, 1H), 4.20 (s, 2H), 3.87 (s, 6H), 3.82-3.73 (m, 2H), 3.69 (s, 3H), 3.66-3.56 (m, 1H), 3.52-3.35 (m, 2H), 3.22-3.05 (m, 2H), 3.01-2.85 (m, 1H), 2.09-1.80 (m, 4H); MS (ES+): 482.4

(M+1), 504.4 (M+Na), (ES−): 516.4 (M+Cl); Analysis calculated for $C_{24}H_{31}N_7O_4(HCl)_3(H_2O)_4$: C, 43.48; H, 6.39; Cl, 16.04; N, 14.79. Found: C, 43.49; H, 6.22; Cl, 15.85; N, 14.56.

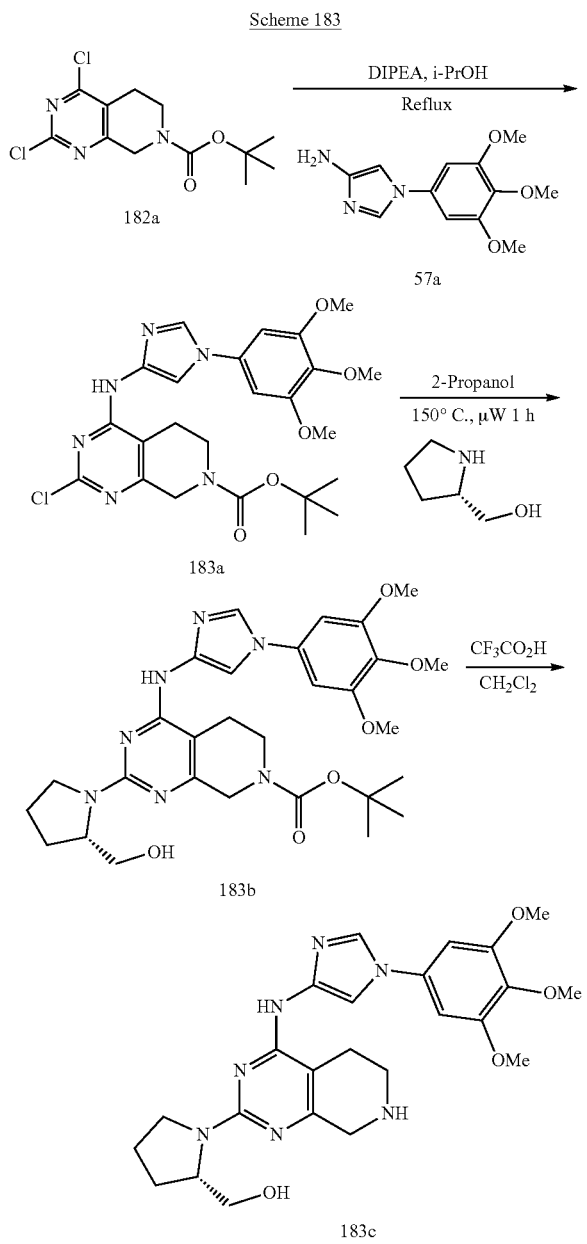

Preparation of (S)-(1-(4-((1-(3,4,5-trimethoxyphenyl)-1H-imidazol-4-yl)amino)-5,6,7,8-tetrahydropyrido[3,4-d]pyrimidin-2-yl)pyrrolidin-2-yl)methanol (183c)

Step-1: Preparation of tert-butyl 2-chloro-4-((1-(3,4, 5-trimethoxyphenyl)-1H-imidazol-4-yl)amino)-5,6-dihydropyrido[3,4-d]pyrimidine-7(8H)-carboxylate (183a)

Compound 183a was prepared from tert-butyl 2,4-dichloro-5,6-dihydropyrido[3,4-d]pyrimidine-7(8H)-carboxylate (182a) (1.0 g, 3.29 mmol) in 2-Propanol (15 mL) using DIPEA (2.3 mL, 13.15 mmol) and 1-(3,4,5-trimethoxyphenyl)-1H-imidazol-4-amine (57a) (0.98 g, 3.95 mmol). This gave after workup and purification by flash column chromatography [silica gel, (12 g) eluting with DMA-80 in DCM (0 to 80%)] tert-butyl 2-chloro-4-((1-(3,4,5-trimethoxyphenyl)-1H-imidazol-4-yl)amino)-5, 6-dihydropyrido[3,4-d]pyrimidine-7(8H)-carboxylate (183a) (0.87 g, 51% yield) as a buff solid; $^1$H NMR (300 MHz, DMSO-$d_6$) δ 9.65 (s, 1H, $D_2O$ exchangeable), 8.16 (d, J=1.5 Hz, 1H), 7.78 (d, J=1.6 Hz, 1H), 6.90 (s, 2H), 4.35 (s, 2H), 3.87 (s, 6H), 3.69 (s, 3H), 3.61 (t, J=5.8 Hz, 2H), 2.69-2.60 (m, 2H), 1.43 (s, 9H).

Step-2: Preparation of (S)-tert-butyl 2-(2-(hydroxymethyl)pyrrolidin-1-yl)-4-((1-(3,4,5-trimethoxyphenyl)-1H-imidazol-4-yl)amino)-5, 6-dihydropyrido[3,4-d]pyrimidine-7(8H)-carboxylate (183b)

Compound 183b was prepared from tert-butyl 2-chloro-4-((1-(3,4,5-trimethoxyphenyl)-1H-imidazol-4-yl)amino)-5,6-dihydropyrido[3,4-d]pyrimidine-7(8H)-carboxylate (183a) (0.4 g, 0.77 mmol), (S)-pyrrolidin-2-ylmethanol (235 mg, 2.32 mmol) in 2-Propanol (7 mL) according to the procedure reported in Scheme 2. This gave after workup and purification by flash column chromatography [silica gel, (40 g), eluting with DMA 80 in dichloromethane], (S)-tert-butyl 2-(2-(hydroxymethyl)pyrrolidin-1-yl)-4-((1-(3,4,5-trimethoxyphenyl)-1H-imidazol-4-yl)amino)-5,6-dihydropyrido[3,4-d]pyrimidine-7(8H)-carboxylate (183b) (0.41 g, 91% yield) as a white solid; $^1$H NMR (300 MHz, DMSO-$d_6$) δ 8.79 (s, 1H, $D_2O$ exchangeable), 8.18 (s, 1H), 7.93 (s, 1H), 6.92 (s, 2H), 5.26-4.70 (m, 1H, $D_2O$ exchangeable), 4.39-3.97 (m, 3H), 3.87 (s, 6H), 3.77-3.56 (m, 4H), 3.66-3.40 (m, 4H), 3.39-3.23 (m, 1H), 2.58-2.53 (m, 2H), 2.06-1.79 (m, 4H), 1.44 (s, 9H); MS (ES+): 582.4 (M+1), 604.3 (M+Na), (ES−): 580.4 (M−1); HPLC purity: 95.74%.

Step-3: Preparation of (S)-(1-(4-((1-(3,4,5-trimethoxyphenyl)-1H-imidazol-4-yl)amino)-5,6,7, 8-tetrahydropyrido[3,4-d]pyrimidin-2-yl)pyrrolidin-2-yl)methanol (183c)

Compound 183c was prepared by hydrolysis of Boc of (S)-tert-butyl 2-(2-(hydroxymethyl)pyrrolidin-1-yl)-4-((1-(3,4,5-trimethoxyphenyl)-1H-imidazol-4-yl)amino)-5,6-dihydropyrido[3,4-d]pyrimidine-7(8H)-carboxylate (183b) (363 mg, 0.624 mmol) in DCM (10 mL) using trifluoroacetic acid (0.96 mL, 12.48 mmol) according to the procedure reported in Scheme 122. This gave after purification by reverse phase column chromatography [(silica gel C-18, 100 g) eluting with 0.1% HCl and acetonitrile] (S)-(1-(4-((1-(3, 4,5-trimethoxyphenyl)-1H-imidazol-4-yl)amino)-5, 6,7,8-tetrahydropyrido[3,4-d]pyrimidin-2-yl)pyrrolidin-2-yl) methanol (183c) (210 mg, 70% yield) HCl salt as a white solid; $^1$H NMR (300 MHz, DMSO-d-$D_2O$) δ 8.27 (s, 1H), 7.91 (s, 1H), 6.89 (s, 2H), 4.47-4.31 (m, 1H), 4.21-4.10 (m, 2H), 3.86-3.80 (m, 6H), 3.66 (s, 3H), 3.65-3.45 (m, 2H), 3.45-3.31 (m, 4H), 2.82-2.69 (m, 2H), 2.09-1.85 (m, 4H); MS (ES+): 482.3 (M+1), 504.4 (M+Na), (ES−): 516.4 (M+Cl); HPLC: 99.46%; Analysis calculated for $C_{24}H_{31}N_7O_4(HCl)_{2.75}(H_2O)_3$: C, 45.33; H, 6.30; Cl, 15.33; N, 15.42. Found: C, 45.13; H, 6.18; Cl, 15.74; N, 15.22.

Scheme 184

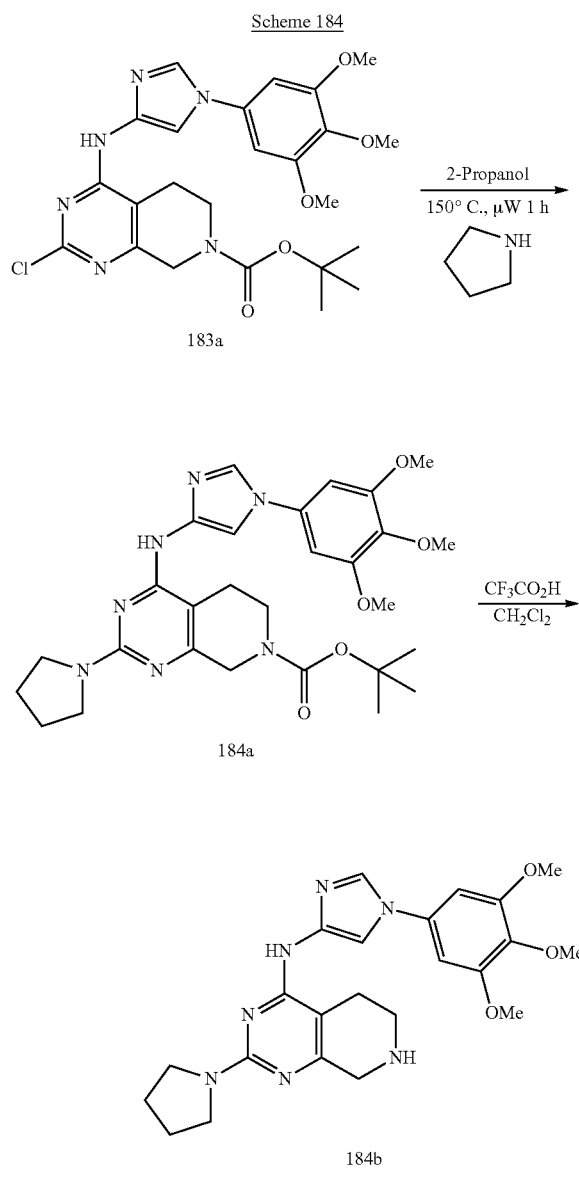

(184a) (0.18 g, 84% yield) as a white solid; $^1$H NMR (300 MHz, DMSO-$d_6$) δ 8.84 (s, 1H, $D_2O$ exchangeable), 8.18 (s, 1H), 8.01 (d, J=1.7 Hz, 1H), 6.89 (s, 2H), 4.20 (s, 2H), 3.86 (s, 6H), 3.68 (s, 3H), 3.56 (s, 6H), 2.61-2.40 (m, 2H), 1.98-1.81 (m, 4H), 1.43 (s, 9H); MS (ES+): 552.4 (M+1), 574.4 (M+Na); HPLC purity: 96.29%.

Step-2: Preparation of 2-(pyrrolidin-1-yl)-N-(1-(3,4,5-trimethoxyphenyl)-1H-imidazol-4-yl)-5,6,7,8-tetrahydropyrido[3,4-d]pyrimidin-4-amine (184b)

Compound 184b was prepared by hydrolysis of Boc of tert-butyl 2-(pyrrolidin-1-yl)-4-((1-(3,4,5-trimethoxyphenyl)-1H-imidazol-4-yl)amino)-5,6-dihydropyrido[3,4-d]pyrimidine-7(8H)-carboxylate (184a) (150 mg, 0.27 mmol) in DCM (10 mL) using trifluoroacetic acid (0.42 mL, 5.44 mmol) according to the procedure reported in Scheme 122. This gave after workup and purification by reverse phase column chromatography [(silica gel C-18, 100 g) eluting with 0.1% HCl and acetonitrile] 2-(pyrrolidin-1-yl)-N-(1-(3,4,5-trimethoxyphenyl)-1H-imidazol-4-yl)-5,6,7,8-tetrahydropyrido[3,4-d]pyrimidin-4-amine (184b) (91 mg, 74% yield) HCl salt as a white solid; $^1$H NMR (300 MHz, DMSO-$d_6$-$D_2O$) δ 10.61 (s, 1H, $D_2O$ exchangeable), 9.92 (s, 2H, $D_2O$ exchangeable), 8.39 (s, 1H), 8.02 (d, J=1.6 Hz, 1H), 6.95 (s, 2H), 4.29 (s, 2H), 3.87 (s, 6H), 3.69 (s, 3H), 3.70-3.52 (m, 2H), 3.47-3.31 (m, 4H), 2.91-2.78 (m, 2H), 1.99 (m, 4H); MS (ES+): 452.4 (M+1), (ES-): 486.4 (M+Cl); HPLC purity: 98.30%; Analysis calculated for $C_{23}H_{29}N_7O_3(HCl)_{2.5}(H_2O)_3$: C, 46.29; H, 6.33; Cl, 14.85; N, 16.43; Found: C, 46.70; H, 6.22; Cl, 14.74; N, 16.51.

Scheme 185

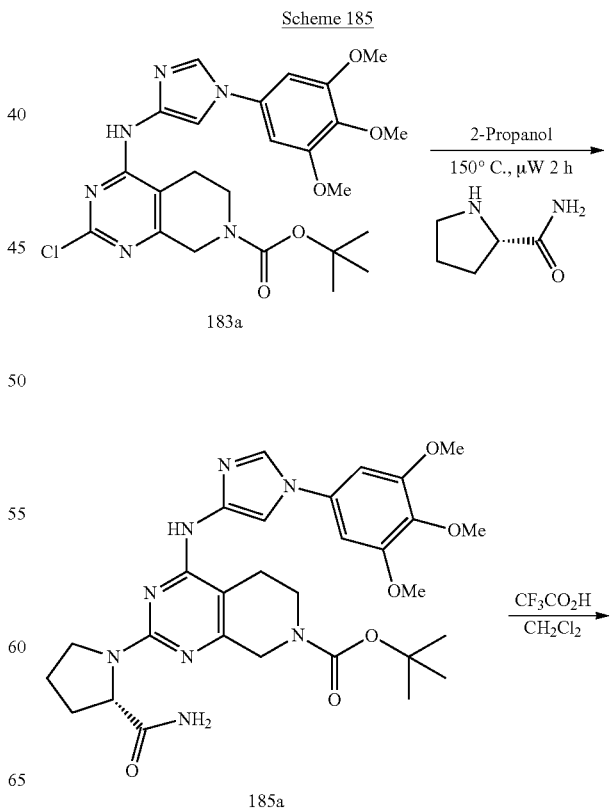

Preparation of 2-(pyrrolidin-1-yl)-N-(1-(3,4,5-trimethoxyphenyl)-1H-imidazol-4-yl)-5,6,7,8-tetrahydropyrido[3,4-d]pyrimidin-4-amine (184b)

Step-1: Preparation of tert-butyl 2-(pyrrolidin-1-yl)-4-((1-(3,4,5-trimethoxyphenyl)-1H-imidazol-4-yl)amino)-5,6-dihydropyrido[3,4-d]pyrimidine-7(8H)-carboxylate (184a)

Compound 184a was prepared from tert-butyl 2-chloro-4-((1-(3,4,5-trimethoxyphenyl)-1H-imidazol-4-yl)amino)-5,6-dihydropyrido[3,4-d]pyrimidine-7(8H)-carboxylate (183a) (0.2 g, 0.39 mmol), pyrrolidine (83 mg, 1.16 mmol) in 2-Propanol (3 mL) according to the procedure reported in Scheme 2. This gave after workup and purification by flash column chromatography [silica gel, (25 g), eluting with DMA 80 in dichloromethane], tert-butyl 2-(pyrrolidin-1-yl)-4-((1-(3,4,5-trimethoxyphenyl)-1H-imidazol-4-yl)amino)-5,6-dihydropyrido[3,4-d]pyrimidine-7(8H)-carboxylate

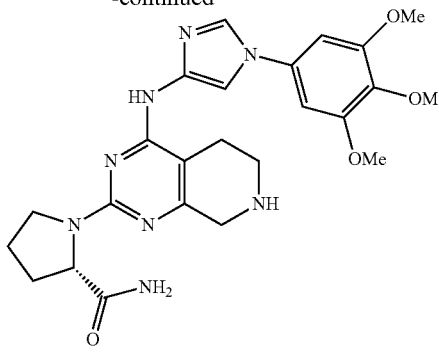

185b

Preparation of (S)-1-(4-((1-(3,4,5-trimethoxyphenyl)-1H-imidazol-4-yl)amino)-5,6,7,8-tetrahydropyrido[3,4-d]pyrimidin-2-yl)pyrrolidine-2-carboxamide (185b)

Step-1: Preparation of (S)-tert-butyl 2-(2-carbamoylpyrrolidin-1-yl)-4-((1-(3,4,5-trimethoxyphenyl)-1H-imidazol-4-yl)amino)-5, 6-dihydropyrido[3,4-d]pyrimidine-7(8H)-carboxylate (185a)

Compound 185a was prepared from tert-butyl 2-chloro-4-((1-(3,4,5-trimethoxyphenyl)-1H-imidazol-4-yl)amino)-5,6-dihydropyrido[3,4-d]pyrimidine-7(8H)-carboxylate (183a) (293 mg, 0.57 mmol), (S)-pyrrolidine-2-carboxamide (194 mg, 1.7 mmol) in 2-Propanol (7 mL) according to the procedure reported in Scheme 2. This gave after workup and purification by flash column chromatography [silica gel, (25 g), eluting with DMA 80 in dichloromethane], (S)-tert-butyl 2-(2-carbamoylpyrrolidin-1-yl)-4-((1-(3,4,5-trimethoxyphenyl)-1H-imidazol-4-yl)amino)-5,6-dihydropyrido[3,4-d]pyrimidine-7(8H)-carboxylate (185a) (0.29 g, 86% yield) as a white solid; $^1$H NMR (300 MHz, DMSO-$d_6$) δ 9.09-8.44 (m, 1H, D2O exchangeable), 8.15 (s, 1H), 7.99-7.71 (m, 1H), 7.29-6.75 (m, 4H), 4.45-4.34 (m, 1H), 4.33-4.10 (m, 2H), 3.91 (s, 6H), 3.68 (s, 3H), 3.57 (s, 2H), 3.41-3.27 (m, 2H), 2.62-2.44 (m, 2H), 2.30-2.07 (m, 1H), 2.02-1.76 (m, 3H), 1.43 (s, 9H); MS (ES+): 595.4 (M+1), 617.3 (M+Na); HPLC purity: 94.40%.

Step-2: Preparation of (S)-1-(4-((1-(3,4,5-trimethoxyphenyl)-1H-imidazol-4-yl)amino)-5,6,7,8-tetrahydropyrido[3,4-d]pyrimidin-2-yl)pyrrolidine-2-carboxamide (185b)

Compound 185b was prepared by hydrolysis of Boc of (S)-tert-butyl 2-(2-carbamoylpyrrolidin-1-yl)-4-((1-(3,4,5-trimethoxyphenyl)-1H-imidazol-4-yl)amino)-5,6-dihydropyrido[3,4-d]pyrimidine-7(8H)-carboxylate (185a) (260 mg, 0.44 mmol) in DCM (10 mL) using trifluoroacetic acid (0.674 mL, 8.74 mmol) according to the procedure reported in Scheme 122. This gave after workup and purification by reverse phase column chromatography [(silica gel C-18, 100 g) eluting with 0.1% HCl and acetonitrile] (S)-1-(4-((1-(3,4,5-trimethoxyphenyl)-1H-imidazol-4-yl)amino)-5,6,7,8-tetrahydropyrido[3,4-d]pyrimidin-2-yl)pyrrolidine-2-carboxamide (185b) (133 mg, 62% yield) HCl salt as a white solid; $^1$H NMR (300 MHz, DMSO-$d_6$-$D_2$O) δ 10.49-10.12 (m, 1H, D$_2$O exchangeable), 10.12-9.72 (m, 2H, D$_2$O exchangeable), 8.44 (s, 1H), 7.88 (s, 1H), 7.50 (s, 1H), 7.26-6.90 (m, 3H), 4.82-4.43 (m, 1H), 4.43-4.04 (m, 2H), 3.92 (s, 6H), 3.69 (s, 3H), 3.64-3.51 (m, 1H), 3.48-3.31 (m, 3H), 2.94-2.78 (m, 2H), 2.41-2.13 (m, 1H), 2.09-1.89 (m, 3H); MS (ES+): 495.3 (M+1), (ES−): 529.4 (M+Cl); HPLC: 96.21%; Analysis calculated for $C_{24}H_{30}N_9O_4(HCl)_{2.5}(H_2O)_{4.5}$: C, 43.23; H, 6.27; Cl, 13.29; N, 16.81. Found: C, 43.29; H, 6.11; Cl, 13.44; N, 16.37.

Scheme 186

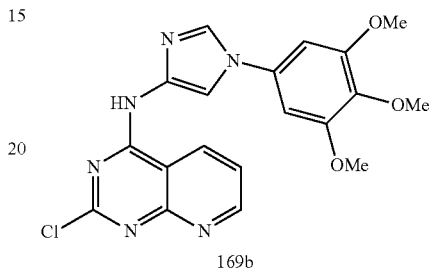

169b

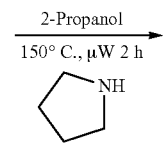

2-Propanol
150° C., μW 2 h

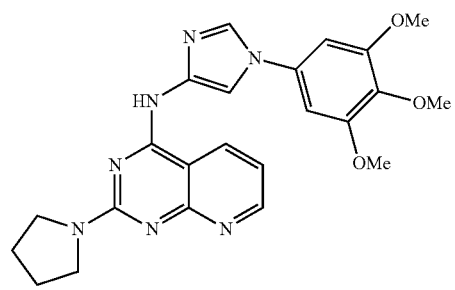

186a

Preparation of 2-(pyrrolidin-1-yl)-N-(1-(3,4,5-trimethoxyphenyl)-1H-imidazol-4-yl)pyrido[2,3-d]pyrimidin-4-amine (186a)

Compound 186a was prepared from 2-chloro-N-(1-(3,4,5-trimethoxyphenyl)-1H-imidazol-4-yl)pyrido[2,3-d]pyrimidin-4-amine (169b) (0.15 g, 0.36 mmol), pyrrolidine (0.09 mL, 1.09 mmol), DIPEA (0.19 mL, 1.09 mmol) in 2-Propanol (5 mL) according to the procedure reported in Scheme 2. This gave after workup and purification by flash column chromatography [silica gel, (12 g), eluting with DMA 80 in dichloromethane (0 to 30%)], followed by reverse phase flash column chromatography [(silica gel C-18, 24 g) eluting with acetonitrile and 0.1% HCl water 2-(pyrrolidin-1-yl)-N-(1-(3,4,5-trimethoxyphenyl)-1H-imidazol-4-yl)pyrido[2,3-d]pyrimidin-4-amine (186a) (43 mg, 26% yield) HCl salt as a yellow solid; $^1$H NMR (300 MHz, DMSO-$d_6$) δ 11.88 (s, 1H), 9.23 (d, J=8.0 Hz, 1H), 8.78 (d, J=5.0 Hz, 1H), 8.43 (s, 1H), 8.12 (s, 1H), 7.51 (dd, J=8.0, 5.0 Hz, 1H), 6.97 (s, 2H), 3.96 (t, J=6.6 Hz, 2H), 3.88 (s, 6H), 3.77-3.62 (m, 5H), 2.15-1.88 (m, 4H). MS (ES+): 448.3 (M+1); MS (ES−): 446.4 (M−1). HPLC purity: 98.41%.

Scheme 187

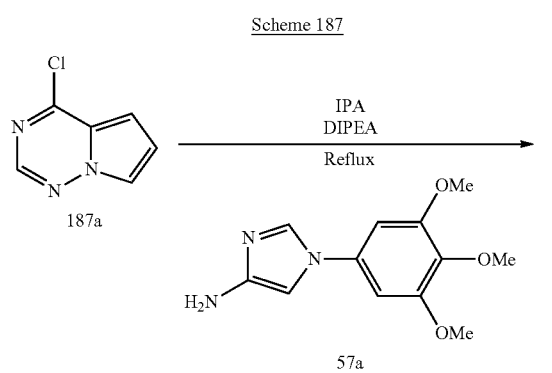

Preparation of N-(1-(3,4,5-trimethoxyphenyl)-1H-imidazol-4-yl)pyrrolo[2,1-f][1,2,4]triazin-4-amine (187b)

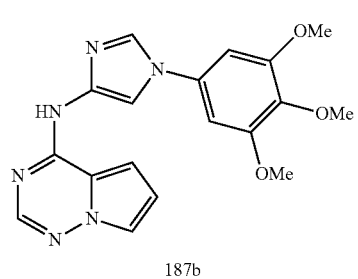

Compound 187b was prepared from 4-chloropyrrolo[2,1-f][1,2,4]triazine (187a) (0.1 g, 0.65 mmol; CAS #888720-29-4) in 2-Propanol (20 mL) using DIPEA (0.34 mL, 1.95 mmol) and 1-(3,4,5-trimethoxyphenyl)-1H-imidazol-4-amine (57a) (243 mg, 0.98 mmol). This gave after workup and purification by flash column chromatography [silica gel, (4 g) eluting with MeOH in DCM (0 to 30%)]; followed by reverse phase flash column chromatography [(silica gel C-18, 24 g) eluting with acetonitrile and 0.1% HCl water N-(1-(3,4,5-trimethoxyphenyl)-1H-imidazol-4-yl)pyrrolo[2,1-f][1,2,4]triazin-4-amine (187b) (36 mg, 15% yield) as a buff colored solid; $^1$H NMR (300 MHz, DMSO-$d_6$) δ 8.61 (s, 1H), 8.10 (s, 2H), 7.84 (s, 1H), 7.45 (s, 1H), 7.03 (s, 2H), 6.81 (s, 1H), 3.89 (s, 6H), 3.70 (s, 3H). MS (ES+): 367.3 (M+1); MS (ES−): 401.3 (M+Cl). HPLC purity: 99.62%.

Scheme 188

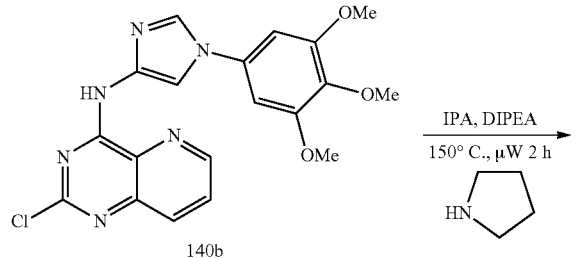

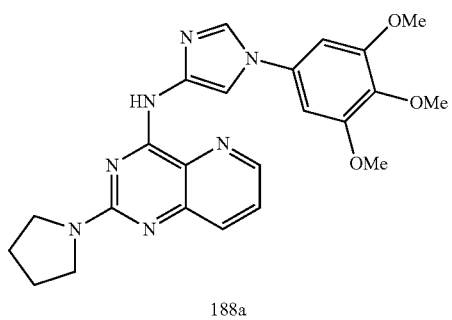

Preparation of 2-(pyrrolidin-1-yl)-N-(1-(3,4,5-trimethoxyphenyl)-1H-imidazol-4-yl)pyrido[3,2-d]pyrimidin-4-amine (188a)

Compound 188a was prepared from 2-chloro-N-(1-(3,4,5-trimethoxyphenyl)-1H-imidazol-4-yl)pyrido[3,2-d]pyrimidin-4-amine (140b) (80 mg, 0.19 mmol), pyrrolidine (0.05 mL, 0.58 mmol), DIPEA (0.1 mL, 0.58 mmol) in 2-Propanol (5 mL) according to the procedure reported in Scheme 2. This gave after workup and purification by flash column chromatography [silica gel, (12 g), eluting with DMA 80 in DCM 0 to 30%], 2-(pyrrolidin-1-yl)-N-(1-(3,4,5-trimethoxyphenyl)-1H-imidazol-4-yl)pyrido[3,2-d]pyrimidin-4-amine (188a) (46 mg, 53% yield) as a yellow solid; $^1$H NMR (300 MHz, DMSO-$d_6$) δ 9.34 (s, 1H), 8.40 (dd, J=4.2, 1.5 Hz, 1H), 8.22 (s, 1H), 8.05 (s, 1H), 7.72 (dd, J=8.6, 1.5 Hz, 1H), 7.58 (dd, J=8.5, 4.2 Hz, 1H), 6.93 (s, 2H), 3.87 (s, 6H), 3.83-3.75 (m, 2H), 3.70 (s, 3H), 3.65-3.45 (m, 2H), 2.03-1.83 (m, 4H). MS (ES+): 448.3 (M+1). HPLC purity: 97.56%.

Scheme 189

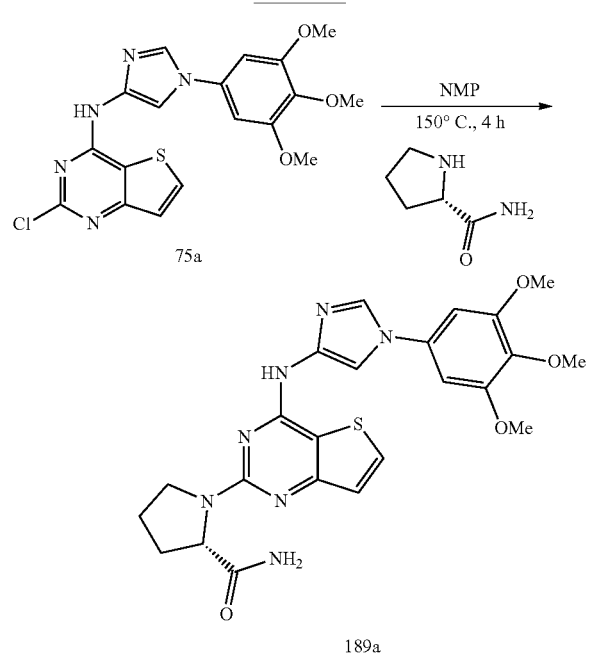

Preparation of (S)-1-(4-((1-(3,4,5-trimethoxyphenyl)-1H-imidazol-4-yl)amino)thieno[3,2-d]pyrimidin-2-yl)pyrrolidine-2-carboxamide (189a)

Compound 189a was prepared according to the procedure reported in step-2 of Scheme 76 from 2-chloro-N-(1-(3,4,5-trimethoxyphenyl)-1H-imidazol-4-yl)thieno[3,2-d]pyrimidin-4-amine (75a) (500 mg, 1.19 mmol) and (S)-pyrrolidine-2-carboxamide (273 mg, 2.39 mmol) in NMP (20 mL). This gave after workup and purification by flash chromatography (Silica gel, eluting with 0-10% methanol in ethyl acetate) compound (189a) (0.16 g, 27%) as a solid. The solid was repurified by reverse phase flash column chromatography [(Silica gel C-18, 24 g) eluting with acetonitrile and 0.1% HCl in water (0-50%)] to afford (S)-1-(4-((1-(3,4,5-trimethoxyphenyl)-1H-imidazol-4-yl)amino)thieno[3,2-d]pyrimidin-2-yl)pyrrolidine-2-carboxamide (189a) (69 mg) HCl salt as a yellow solid; $^1$H NMR (300 MHz, DMSO-d$_6$): δ 13.41 (s, 1H), 11.83 (s, 1H), 8.37 (s, 1H), 8.31 (d, J=5.4 Hz, 1H), 7.87 (s, 1H), 7.70-7.55 (m, 2H), 7.21 (s, 1H), 7.13 (s, 2H), 4.67 (d, J=8.7 Hz, 1H), 4.13-3.82 (m, 7H), 3.77-3.57 (m, 4H), 2.40-1.90 (m, 4H); MS (ES+): 496.3 (M+1); MS (ES−): 530.3 (M+Cl).

acetonitrile and 0.1% HCl water (0-50%) followed by lyophilization to afford (S)-1-(4-((1-(3,4,5-trimethoxyphenyl)-1H-imidazol-4-yl)amino)furo[3,2-d]pyrimidin-2-yl)pyrrolidine-2-carboxamide (190a) (40 mgs) HCl salt as a yellow solid; $^1$H NMR (300 MHz, DMSO-d): δ 11.84 (s, 1H), 8.53-8.34 (m, 2H), 7.90 (s, 1H), 7.59 (s, 1H), 7.19 (s, 1H), 7.16-7.03 (m, 3H), 4.61 (d, J=8.6 Hz, 1H), 4.08-3.83 (m, 7H), 3.74-3.54 (m, 4H), 2.40-1.87 (m, 4H); MS (ES+): 480.3 (M+1); MS (ES−): 514.3 (M+Cl). HPLC purity: 98.13%.

Scheme 191

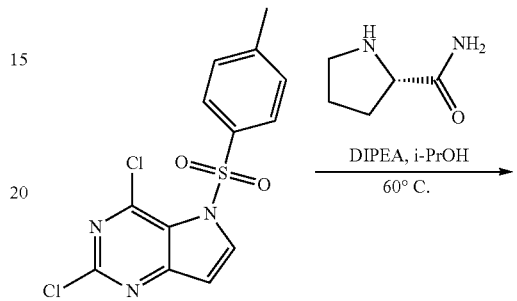

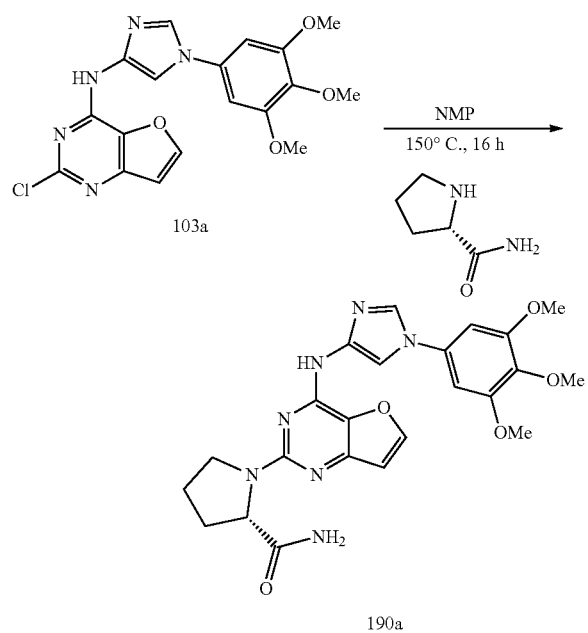

Scheme 190

Preparation of (S)-1-(4-((1-(3,4,5-trimethoxyphenyl)-1H-imidazol-4-yl)amino)furo[3,2-d]pyrimidin-2-yl)pyrrolidine-2-carboxamide (190a)

Compound 190a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (300 mg, 0.75 mmol) and (S)-pyrrolidine-2-carboxamide (0.85 g, 7.46 mmol) in NMP (20 mL). This gave after workup and purification by flash chromatography (silica gel, eluting with 0-10% methanol in ethyl acetate) compound 190a (90 mg, 24%) free base as a solid. This was re-purified by reverse phase flash column chromatography [silica gel C-18 column, (24 g) eluting with

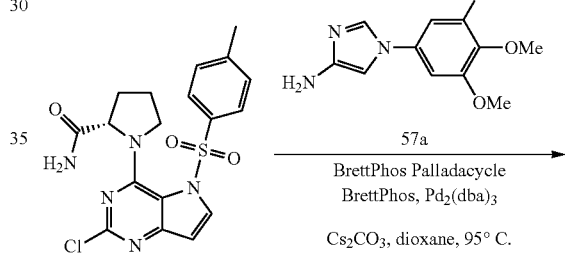

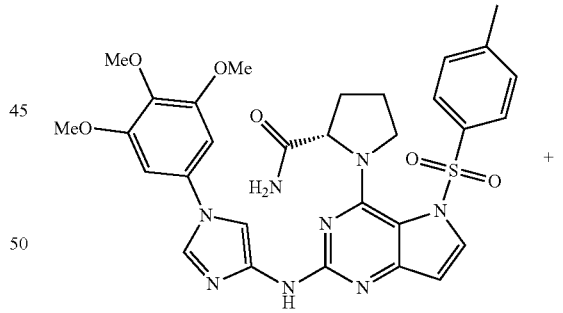

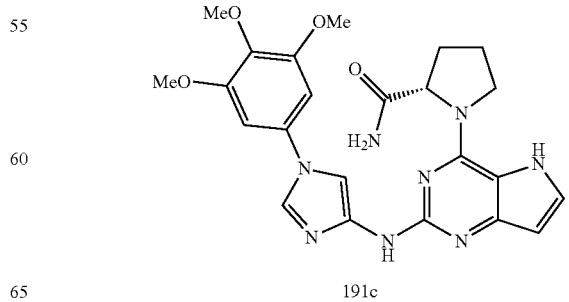

Preparation of (S)-1-(5-tosyl-2-((1-(3,4,5-trimethoxyphenyl)-1H-imidazol-4-yl)amino)-5H-pyrrolo[3,2-d]pyrimidin-4-yl)pyrrolidine-2-carboxamide (191b) and (S)-1-(2-((1-(3,4,5-trimethoxyphenyl)-1H-imidazol-4-yl)amino)-5H-pyrrolo[3,2-d]pyrimidin-4-yl)pyrrolidine-2-carboxamide (191c)

Step-1: Preparation of (S)-1-(2-chloro-5-tosyl-5H-pyrrolo[3,2-d]pyrimidin-4-yl)pyrrolidine-2-carboxamide (191a)

Compound 191a was prepared from 2,4-dichloro-5-tosyl-5H-pyrrolo[3,2-d]pyrimidine (160a) (1.91 g, 5.58 mmol) in IPA (15 mL), (S)-pyrrolidine-2-carboxamide (0.64 g, 5.58 mmol), DIPEA (1.46 mL, 8.38 mmol) according to the procedure reported in step-1 of Scheme 96. This gave after workup and purification by flash column chromatography [silica gel (12 g), eluting with ethyl acetate/MeOH (9:1) in hexane from 0-70%] (S)-1-(2-chloro-5-tosyl-5H-pyrrolo[3,2-d]pyrimidin-4-yl)pyrrolidine-2-carboxamide (191a) (1.6 g, 68% yield) as a white solid; $^1$H NMR (300 MHz, DMSO-$d_6$) δ 7.89 (d, J=3.7 Hz, 1H), 7.52-7.40 (m, 2H), 7.34-7.20 (m, 3H), 7.08 (s, 1H), 6.69 (d, J=3.7 Hz, 1H), 4.83 (s, 1H), 4.11-3.94 (m, 1H), 3.79-3.65 (m, 1H), 2.41-2.33 (m, 1H), 2.31 (s, 3H), 2.01-1.76 (m, 3H).

Step-2: Preparation of (S)-1-(5-tosyl-2-((1-(3,4,5-trimethoxyphenyl)-1H-imidazol-4-yl)amino)-5H-pyrrolo[3,2-d]pyrimidin-4-yl)pyrrolidine-2-carboxamide (191b) and (S)-1-(2-((1-(3,4,5-trimethoxyphenyl)-1H-imidazol-4-yl)amino)-5H-pyrrolo[3,2-d]pyrimidin-4-yl)pyrrolidine-2-carboxamide (191c)

Compound 191b and 191c was prepared from (S)-1-(2-chloro-5-tosyl-5H-pyrrolo[3,2-d]pyrimidin-4-yl)pyrrolidine-2-carboxamide (191a) (400 mg, 0.95 mmol) in tert-BuOH (15 mL), 1-(3,4,5-trimethoxyphenyl)-1H-imidazol-4-amine (57a) (261 mg, 1.05 mmol), BrettPhos Palladacycle (43 mg, 0.048 mmol), BrettPhos (77 mg, 0.14 mmol), Pd$_2$(dba)$_3$ (174 mgs, 0.19 mmol) and Cs$_2$CO$_3$ (621 mg, 1.91 mmol) according to the procedure reported in Scheme 178. This gave after workup and purification by flash column chromatography [silica (40 g), eluting with DMA80 in DCM from 0-60%], followed by reverse phase flash column chromatography [(silica gel C-18 column, 24 g) eluting with acetonitrile and 0.1% HCl water (0-50%)] and lyophilization (S)-1-(5-tosyl-2-((1-(3,4,5-trimethoxyphenyl)-1H-imidazol-4-yl)amino)-5H-pyrrolo[3,2-d]pyrimidin-4-yl)pyrrolidine-2-carboxamide (191b) (16 mg, 3% yield) HCl salt as a white solid; $^1$H NMR (300 MHz, DMSO-$d_6$) δ 12.49 (brs, 1H, D$_2$O exchangeable), 10.46 (s, 1H, 1H, D$_2$O exchangeable), 8.26 (s, 1H), 8.00 (d, J=8.0 Hz, 2H), 7.63 (s, 1H), 7.57-7.41 (m, 3H, 1H is D$_2$O exchangeable), 7.26-6.96 (m, 5H, 1H is D$_2$O exchangeable), 4.83-4.73 (m, 1H), 4.43-4.30 (m, 1H), 4.08-3.97 (m, 1H), 3.91 (s, 6H), 3.68 (s, 3H), 2.40 (s, 3H), 2.30-2.23 (m, 1H), 2.14-1.98 (m, 3H); MS (ES+): 633.3 (M+1); 655.3 (M+Na); (ES−): 631.4 (M−1); 667.3 (M+Cl), and (S)-1-(2-((1-(3,4,5-trimethoxyphenyl)-1H-imidazol-4-yl)amino)-5H-pyrrolo[3,2-d]pyrimidin-4-yl)pyrrolidine-2-carboxamide (191c) (15 mg, 3% yield) as a white solid; $^1$H NMR (300 MHz, DMSO-$d_6$) δ 12.58 (s, 1H, D$_2$O exchangeable), 11.97 (s, 1H, D$_2$O exchangeable), 10.21 (s, 1H, D$_2$O exchangeable), 8.29-8.20 (m, 1H), 7.71-7.66 (m, 1H), 7.63 (t, J=3.1 Hz, 1H, D$_2$O exchangeable), 7.56 (s, 1H), 7.23-7.16 (m, 1H, D$_2$O exchangeable), 7.10 (s, 2H), 6.51-6.40 (m, 1H), 4.85-4.72 (m, 1H), 4.40-4.30 (m, 1H), 3.92 (s, 6H), 3.76-3.73 (m, 2H), 3.69 (s, 3H), 2.31-2.23 (m, 1H), 2.15-2.02 (m, 3H); MS (ES+): 479.3 (M+1); 493.5 (M+Na); (ES−): 513.3 (M+Cl).

Scheme 192

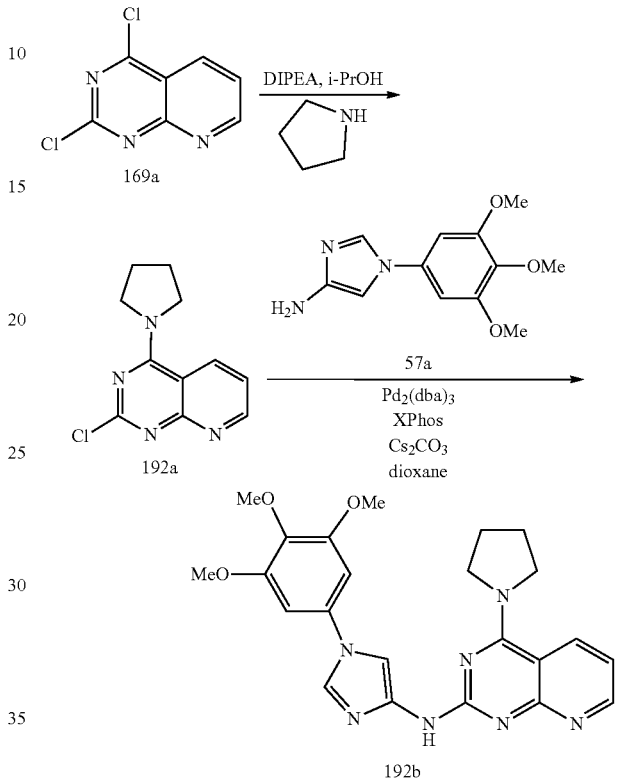

Preparation of 4-(pyrrolidin-1-yl)-N-(1-(3,4,5-trimethoxyphenyl)-1H-imidazol-4-yl)pyrido[2,3-d]pyrimidin-2-amine (192b)

Step-1: Preparation of 2-chloro-4-(pyrrolidin-1-yl)pyrido[2,3-d]pyrimidine (192a)

Compound 192a was prepared from 2,4-dichloropyrido[2,3-d]pyrimidine (169a) (0.5 g, 2.50 mmol) in 2-Propanol (10 mL) using pyrrolidine (0.21 mL, 2.5 mmol) and DIPEA (1.31 mL, 7.5 mmol) according to the procedure reported in step-1 of Scheme 96. This gave after workup and purification by flash column chromatography [silica gel (12 g), eluting with MeOH in dichloromethane 0 to 30%] 2-chloro-4-(pyrrolidin-1-yl)pyrido[2,3-d]pyrimidine (192a) (0.41 g, 70% yield) as a white solid; MS (ES+): 235.2 & 237.1 (M+1).

Step-2: Preparation of 4-(pyrrolidin-1-yl)-N-(1-(3,4,5-trimethoxyphenyl)-1H-imidazol-4-yl)pyrido[2,3-d]pyrimidin-2-amine (192b)

Compound 192b was prepared from 2-chloro-4-(pyrrolidin-1-yl)pyrido[2,3-d]pyrimidine (192a) (0.15 g, 0.64 mmol), 1-(3,4,5-trimethoxyphenyl)-1H-imidazol-4-amine (57a) (160 mg, 0.64 mmol, free base), dicyclohexyl(2',4',6'-triisopropylbiphenyl-2-yl)phosphine (XPhos, 180 mg, 0.38 mmol), Pd$_2$(dba)$_3$ (180 mg, 0.19 mmol) and cesium carbonate (630 mg, 1.92 mmol) in dioxane (5 mL) according to the procedure reported in step-1 of Scheme 96. This gave after workup and purification by flash column chromatography [silica (12 g), eluting with DMA-80 in CH$_2$Cl$_2$ from 0 to 30%], followed by reverse phase column chromatography [(silica gel C-18, 24 g) eluting with acetonitrile and 0.1% HCl water] 4-(pyrrolidin-1-yl)-N-(1-(3,4,5-trimethoxyphenyl)-1H-imidazol-4-yl)pyrido[2,3-d]pyrimidin-2-amine (192b) (50 mg, 16% yield) as a yellow solid; $^1$H NMR (300 MHz, DMSO-d$_6$): δ 10.86 (s, 1H), 9.06-8.64 (m, 2H), 8.59-8.13 (m, 1H), 7.98-7.66 (m, 1H), 7.64-7.31 (m, 1H), 6.96 (s, 2H), 4.47-3.25 (m, 13H), 2.26-1.81 (m, 4H). MS (ES+): 448.3 (M+1); MS (ES−): 446.0 (M−1).

Scheme 193

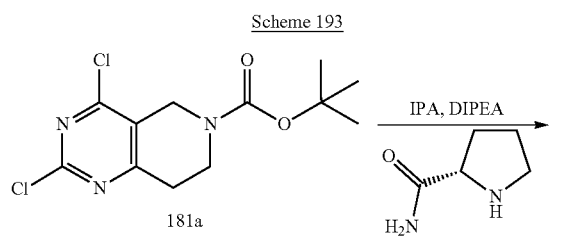

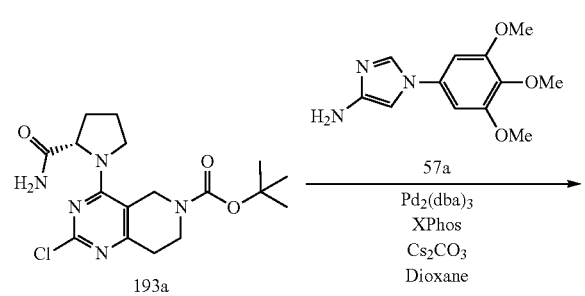

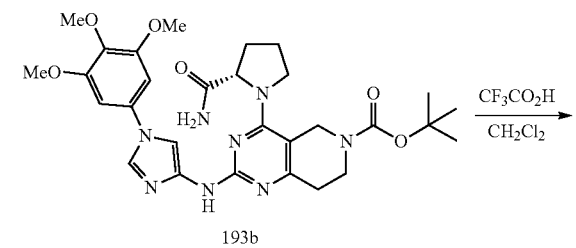

Preparation of (S)-1-(2-((1-(3,4,5-trimethoxyphenyl)-1H-imidazol-4-yl)amino)-5,6,7,8-tetrahydropyrido[4,3-d]pyrimidin-4-yl)pyrrolidine-2-carboxamide (193c)

Step-1: Preparation of (S)-tert-butyl 4-(2-carbamoylpyrrolidin-1-yl)-2-chloro-7,8-dihydropyrido[4,3-d]pyrimidine-6(5H)-carboxylate (193a)

Compound 193a was prepared from tert-butyl 2,4-dichloro-7,8-dihydropyrido[4,3-d]pyrimidine-6(5H)-carboxylate (181a) (2.0 g, 6.58 mmol) in 2-Propanol (20 mL) using (S)-pyrrolidine-2-carboxamide (0.75 g, 6.58 mmol) and DIPEA (1.72 mL, 9.86 mmol) according to the procedure reported in step-1 of Scheme 96. This gave after workup and purification by flash column chromatography [silica gel (40 g), eluting with DMA-80 in chloroform (0 to 50%)] (S)-tert-butyl 4-(2-carbamoylpyrrolidin-1-yl)-2-chloro-7,8-dihydropyrido[4,3-d]pyrimidine-6(5H)-carboxylate (193a) (1.8 g, 72% yield) as an oil; $^1$H NMR (300 MHz, DMSO-d$_6$) δ 7.43 (s, 1H), 6.95 (s, 1H), 4.75 (d, J=16.1 Hz, 1H), 4.61 (d, J=16.1 Hz, 1H), 4.50 (m, 1H), 3.92-3.70 (m, 2H), 3.69-3.41 (m, 2H), 2.67 (t, J=6.1 Hz, 2H), 2.13 (m, 1H), 1.88 (m, 3H), 1.42 (s, 9H).

Step-2: Preparation of (S)-tert-butyl 4-(2-carbamoylpyrrolidin-1-yl)-2-((1-(3,4,5-trimethoxyphenyl)-1H-imidazol-4-yl)amino)-7,8-dihydropyrido[4,3-d]pyrimidine-6(5H)-carboxylate (193b)

Compound 193b was prepared from (S)-tert-butyl 4-(2-carbamoylpyrrolidin-1-yl)-2-chloro-7,8-dihydropyrido[4,3-d]pyrimidine-6(5H)-carboxylate (193a) (0.52 g, 1.35 mmol), 1-(3,4,5-trimethoxyphenyl)-1H-imidazol-4-amine (57a) (422 mg, 1.69 mmol, free base), dicyclohexyl(2',4',6'-triisopropylbiphenyl-2-yl)phosphine (XPhos, 0.29 g, 0.61 mmol), cesium carbonate (1.33 g, 4.07 mmol) and Pd$_2$(dba)$_3$ (186 mg, 0.2 mmol) in 1,4-dioxane (10 mL) according to the procedure reported in step-3 of Scheme 101. This gave after workup and purification by flash column chromatography [silica gel (80 g), eluting with DMA 80 in CH$_2$Cl$_2$], followed by reverse phase column chromatography [(C18, 24 g) eluting with acetonitrile and 0.1% HCl water] (S)-tert-butyl 4-(2-carbamoylpyrrolidin-1-yl)-2-((1-(3,4,5-trimethoxyphenyl)-1H-imidazol-4-yl)amino)-7,8-dihydropyrido[4,3-d]pyrimidine-6(5H)-carboxylate (193b) (340 mg, 42% yield) HCl salt as a white solid; MS (ES+): 595.4 (M+1), (ES−): 593.5 (M−1).

Step-3: Preparation of (S)-1-(2-((1-(3,4,5-trimethoxyphenyl)-1H-imidazol-4-yl)amino)-5,6,7,8-tetrahydropyrido[4,3-d]pyrimidin-4-yl)pyrrolidine-2-carboxamide (193c)

Compound 193c was prepared by hydrolysis of Boc of (S)-tert-butyl 4-(2-carbamoylpyrrolidin-1-yl)-2-((1-(3,4,5-trimethoxyphenyl)-1H-imidazol-4-yl)amino)-7,8-dihydropyrido[4,3-d]pyrimidine-6(5H)-carboxylate (193b) (250 mg, 0.42 mmol) in DCM (5 mL) using trifluoroacetic acid (0.65 mL, 8.41 mmol) according to the procedure reported in Scheme 122. This gave after purification by reverse phase column chromatography [(silica gel C-18, 100 g) eluting with 0.1% HCl and acetonitrile] (S)-1-(2-((1-(3,4,5-trimethoxyphenyl)-1H-imidazol-4-yl)amino)-5,6,7,8-tetrahydropyrido[4,3-d]pyrimidin-4-yl)pyrrolidine-2-carboxamide (193c) (42 mg, 20% yield) HCl salt as a white solid; $^1$H NMR (300 MHz, DMSO-d$_6$) δ 10.30 (s, 2H, D$_2$O exchangeable), 9.72 (s, 1H, D₂O exchangeable), 8.49 (s, 1H), 7.86 (s, 1H), 7.66 (s, 1H), 7.20 (s, 2H), 4.72-4.57 (m, 2H), 4.44-4.27 (m, 1H), 4.19-4.02 (m, 1H), 3.91 (s, 6H), 3.85-3.69 (m, 1H), 3.69 (s, 3H), 3.52-3.37 (m, 1H), 3.36-3.19 (m, 1H), 3.11-2.95 (m, 2H), 2.34-2.21 (m, 1H), 2.11-1.78 (m, 3H); MS (ES+): 495.4 (M+1), (ES−): 529.4 (M+Cl).

Scheme 194

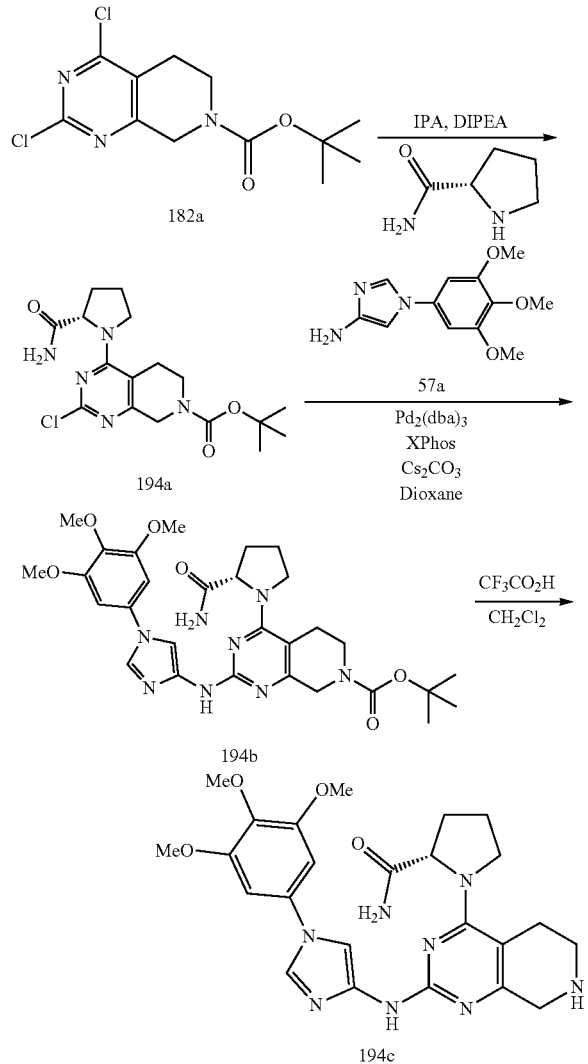

Preparation of (S)-1-(2-((1-(3,4,5-trimethoxyphenyl)-1H-imidazol-4-yl)amino)-5,6,7,8-tetrahydropyrido[3,4-d]pyrimidin-4-yl)pyrrolidine-2-carboxamide (194c)

Step-1: Preparation of (S)-tert-butyl 4-(2-carbamoylpyrrolidin-1-yl)-2-chloro-5,6-dihydropyrido[3,4-d]pyrimidine-7(8H)-carboxylate (194a)

Compound 194a was prepared from tert-butyl 2,4-dichloro-5,6-dihydropyrido[3,4-d]pyrimidine-7(8H)-carboxylate (182a) (2.0 g, 6.58 mmol) in 2-Propanol (20 mL) using (S)-pyrrolidine-2-carboxamide (0.75 g, 6.58 mmol) and DIPEA (1.72 mL, 9.86 mmol) according to the procedure reported in step-1 of Scheme 96. This gave after workup and purification by flash column chromatography [silica gel (40 g), eluting with DMA 80 in chloroform (0 to 50%)] (S)-tert-butyl 4-(2-carbamoylpyrrolidin-1-yl)-2-chloro-5,6-dihydropyrido[3,4-d]pyrimidine-7(8H)-carboxylate (194a) (0.51 g, 21% yield) as an oil; ¹H NMR (300 MHz, DMSO-d₆) δ 7.37 (s, 1H), 6.95 (s, 1H), 4.52 (m, 1H), 4.38 (d, J=18.6 Hz, 1H), 4.22 (d, J=18.9 Hz, 1H), 3.97-3.75 (m, 2H), 3.66 (m, 1H), 3.35-3.21 (m, 1H), 2.99-2.75 (m, 2H), 2.20-2.05 (m, 1H), 1.99-1.73 (m, 3H), 1.43 (s, 9H).

Step-2: Preparation of (S)-tert-butyl 4-(2-carbamoylpyrrolidin-1-yl)-2-((1-(3,4,5-trimethoxyphenyl)-1H-imidazol-4-yl)amino)-5,6-dihydropyrido[3,4-d]pyrimidine-7(8H)-carboxylate (194b)

Compound 194b was prepared from (S)-tert-butyl 4-(2-carbamoylpyrrolidin-1-yl)-2-chloro-5,6-dihydropyrido[3,4-d]pyrimidine-7(8H)-carboxylate (194a) (0.52 g, 1.35 mmol), 1-(3,4,5-trimethoxyphenyl)-1H-imidazol-4-amine (57a) (422 mg, 1.69 mmol, free base), dicyclohexyl(2',4',6'-triisopropylbiphenyl-2-yl)phosphine (XPhos, 29 mg, 0.61 mmol), cesium carbonate (1.33 g, 4.07 mmol) and Pd₂(dba)₃ (186 mg, 0.203 mmol) in 1,4-dioxane (10 mL) according to the procedure reported in step-3 of Scheme 101. This gave after workup and purification by flash column chromatography [silica gel (80 g), eluting with DMA-80 in CH₂Cl₂], (S)-tert-butyl 4-(2-carbamoylpyrrolidin-1-yl)-2-((1-(3,4,5-trimethoxyphenyl)-1H-imidazol-4-yl)amino)-5,6-dihydropyrido[3,4-d]pyrimidine-7(8H)-carboxylate (194b) (320 mg, 40% yield) as a white solid; ¹H NMR (300 MHz, DMSO-d₆) δ 10.13, 9.94 (2s, 1H, rotamers), 8.77, 8.42 (2s, 1H, rotamers), 7.86, 7.79 (2s, 1H, rotamers), 7.52 (s, 1H), 7.22 (s, 1H), 7.18-7.03 (m, 2H), 4.68 (m, 1H), 4.57 (d, J=18.7 Hz, 1H), 4.36 (d, J=18.5 Hz, 1H), 4.09 (d, J=49.7 Hz, 1H), 3.91 (s, 6H), 3.85-3.69 (m, 1H), 3.69 (m, 3H), 3.56-3.17 (m, 2H), 3.17-2.93 (m, 1H), 2.93-2.69 (m, 1H), 2.35-2.16 (m, 1H), 2.06-1.74 (m, 3H), 1.60 (s, 3H), 1.45 (s, 6H); MS (ES−): 593.5 (M−1), 629.4 (M+Cl).

Step-3: Preparation of (S)-1-(2-((1-(3,4,5-trimethoxyphenyl)-1H-imidazol-4-yl)amino)-5,6,7,8-tetrahydropyrido[3,4-d]pyrimidin-4-yl)pyrrolidine-2-carboxamide (194c)

Compound 194c was prepared by hydrolysis of Boc of (S)-tert-butyl 4-(2-carbamoylpyrrolidin-1-yl)-2-((1-(3,4,5-trimethoxyphenyl)-1H-imidazol-4-yl)amino)-5,6-dihydropyrido[3,4-d]pyrimidine-7(8H)-carboxylate (194b) (251 mg, 0.42 mmol) in DCM (5 mL) using trifluoroacetic acid (0.65 mL, 8.44 mmol) according to the procedure reported in Scheme 122. This gave after purification by reverse phase column chromatography [(silica gel C-18, 100 g) eluting with 0.1% HCl and acetonitrile] (S)-1-(2-((1-(3,4,5-trimethoxyphenyl)-1H-imidazol-4-yl)amino)-5,6,7,8-tetrahydropyrido[3,4-d]pyrimidin-4-yl)pyrrolidine-2-carboxamide (194c) (60 mg, 29% yield) HCl salt as a white solid; ¹H NMR (300 MHz, DMSO-d₆) δ 10.10 (s, 1H), 9.95 (s, 3H), 8.77 (s, 1H), 7.88 (s, 1H), 7.53 (s, 1H), 7.22 (s, 2H), 7.13 (s, 1H), 4.73-4.58 (m, 1H), 4.25-4.04 (m, 2H), 3.91 (s, 6H), 3.85-3.74 (m, 1H), 3.70 (s, 3H), 3.55-3.37 (m, 1H), 3.15 (d, J=27.5 Hz, 4H), 2.33-2.14 (m, 1H), 2.09-1.76 (m, 3H); MS (ES+): 495.4 (M+1), (ES−): 529.4.

Scheme 195

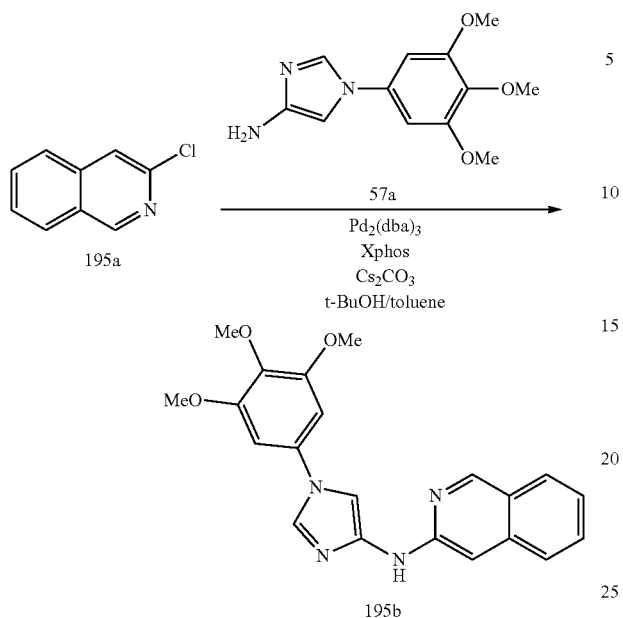

Preparation of N-(1-(3,4,5-trimethoxyphenyl)-1H-imidazol-4-yl)isoquinolin-3-amine (195b)

Compound 195b was prepared from 3-chloroisoquinoline (195a) (0.125 g, 0.76 mmol; CAS #19493-45-9), 1-(3,4,5-trimethoxyphenyl)-1H-imidazol-4-amine (57a) (190 mg, 0.76 mmol, free base), dicyclohexyl(2',4',6'-triisopropylbiphenyl-2-yl)phosphine (XPhos, 150 mg, 0.31 mmol), $Pd_2(dba)_3$ (140 mg, 0.195 mmol) and cesium carbonate (0.5 g, 1.53 mmol) in t-BuOH/toluene (12 mL, 1:3 ratio) according to the procedure reported in step-1 of Scheme 96. This gave after workup and purification by flash column chromatography [silica gel (24 g), eluting with EtOAc/MeOH (9:1) in hexane from 0-100%] followed by reverse phase column chromatography [(silica gel C-18, 50 g) eluting with acetonitrile and 0.1% HCl water] N-(1-(3,4,5-trimethoxyphenyl)-1H-imidazol-4-yl)isoquinolin-3-amine (195b) (22 mg, 8% yield) HCl salt as a yellow solid; $^1$H NMR (300 MHz, DMSO-$d_6$): δ 9.73 (s, 1H, $D_2O$ exchangeable), 9.11 (s, 1H), 9.08 (s, 1H), 8.04-7.93 (m, 2H), 7.78 (d, J=8.4 Hz, 1H), 7.69-7.59 (m, 1H), 7.43-7.35 (m, 1H), 7.27 (s, 1H), 7.12 (s, 2H), 3.90 (s, 6H), 3.72 (s, 3H); MS (ES+): 377.3 (M+1); 399.3 (M+Na); (ES-): 411.3 (M+Cl).

Scheme 196

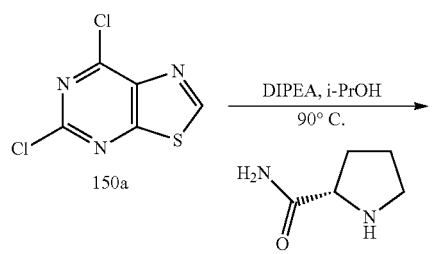

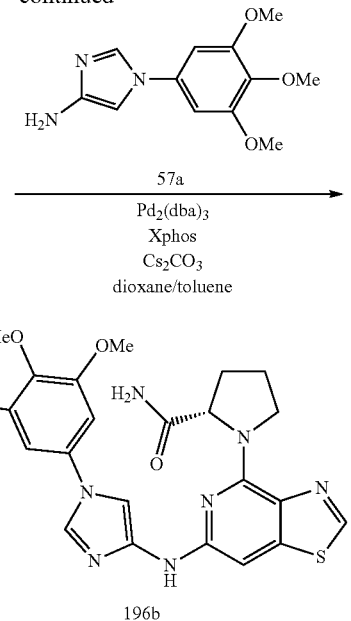

Preparation of (S)-1-(5-((1-(3,4,5-trimethoxyphenyl)-1H-imidazol-4-yl)amino)thiazolo[5,4-d]pyrimidin-7-yl)pyrrolidine-2-carboxamide (196b)

Step-1: Preparation of (S)-1-(5-chlorothiazolo[5,4-d]pyrimidin-7-yl)pyrrolidine-2-carboxamide (196a) Compound 196a was prepared from 5,7-dichlorothiazolo[5,4-d]pyrimidine (150a) (0.2 g, 0.97 mmol) in 2-Propanol (10 mL) using (S)-pyrrolidine-2-carboxamide (0.11 g, 0.97 mmol) and DIPEA (0.51 mL, 2.91 mmol) according to the procedure reported in step-1 of Scheme 96. This gave after workup and purification by flash column chromatography [silica gel (12 g), eluting with DCM in methanol (0 to 30%)] (S)-1-(5-chlorothiazolo[5,4-d]pyrimidin-7-yl)pyrrolidine-2-carboxamide (196a) (0.17 g, 61% yield) as a yellow solid; MS (ES+): 306.1 (M+Na); MS (ES-): 282.3 (M-1), 318.1 & 320.1 (M+Cl).

Step-2: Preparation of (S)-1-(5-((1-(3,4,5-trimethoxyphenyl)-1H-imidazol-4-yl)amino)thiazolo[5,4-d]pyrimidin-7-yl)pyrrolidine-2-carboxamide (196b)

Compound 196b was prepared from (S)-1-(5-chlorothiazolo[5,4-d]pyrimidin-7-yl)pyrrolidine-2-carboxamide (196a) (0.17 g, 0.6 mmol), 1-(3,4,5-trimethoxyphenyl)-1H-imidazol-4-amine (57a) (150 mg, 0.6 mmol, free base), dicyclohexyl(2',4',6'-triisopropylbiphenyl-2-yl)phosphine (XPhos, 0.17 g, 0.36 mmol), cesium carbonate (0.58 g, 1.79 mmol) and $Pd_2(dba)_3$ (160 mg, 0.18 mmol) in 1,4-dioxane (5 mL) and toluene (5 mL) according to the procedure reported in step-3 of Scheme 101. This gave after workup and purification by flash column chromatography [silica gel (12 g), eluting with DMA 80 in $CH_2Cl_2$], followed by reverse phase column chromatography [(silica gel C-18, 24 g) eluting with acetonitrile and 0.1% HCl water](S)-1-(5-((1-(3,4,5-trimethoxyphenyl)-1H-imidazol-4-yl)amino)thiazolo[5,4-d]pyrimidin-7-yl)pyrrolidine-2-carboxamide (196b) (10 mg, 4% yield) as a white solid; $^1$H NMR (300 MHz, DMSO-$d_6$): δ 10.01 (s, 1H), 9.23 (s, 1H), 9.04-8.67 (m, 1H), 7.96 (s, 1H), 7.53-6.81 (m, 4H), 4.77-4.03 (m, 3H), 4.02-3.50 (m, 9H), 2.32-1.83 (m, 4H). MS (ES+): 497.3 (M+1); MS (ES−): 495.3 (M−1).

Scheme 197

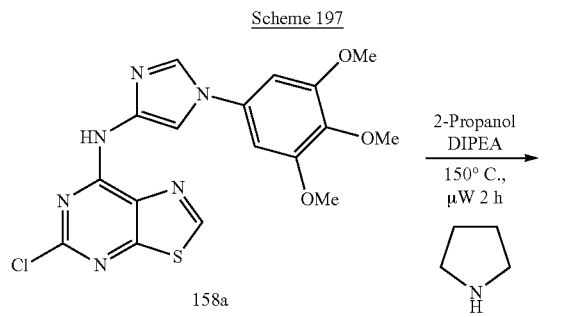

Preparation of 5-(pyrrolidin-1-yl)-N-(1-(3,4,5-trimethoxyphenyl)-1H-imidazol-4-yl)thiazolo[5,4-d]pyrimidin-7-amine (197a)

Compound 197a was prepared from 5-chloro-N-(1-(3,4,5-trimethoxyphenyl)-1H-imidazol-4-yl)thiazolo[5,4-d]pyrimidin-7-amine (158a) (0.15 g, 0.36 mmol), pyrrolidine (0.09 mL, 1.07 mmol), DIPEA (0.19 mL, 1.07 mmol) in 2-Propanol (5 mL) according to the procedure reported in Scheme 2. This gave after workup and purification by flash column chromatography [silica (12 g), eluting with DMA 80 in CH$_2$Cl$_2$ from 0 to 30%] 5-(pyrrolidin-1-yl)-N-(1-(3,4,5-trimethoxyphenyl)-1H-imidazol-4-yl)thiazolo[5,4-d]pyrimidin-7-amine (197a) (0.11 g, 68% yield) as a brown solid; $^1$H NMR (300 MHz, DMSO-d$_6$) δ 9.60 (s, 1H), 8.78 (s, 1H), 8.19 (s, 1H), 8.06 (s, 1H), 6.93 (s, 2H), 3.87 (s, 6H), 3.81-3.43 (m, 7H), 2.02-1.84 (m, 4H); MS (ES+): 454.3 (M+1); MS (ES−): 452.4 (M−1).

Scheme 198

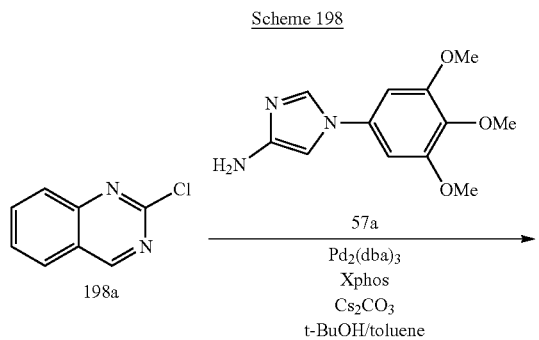

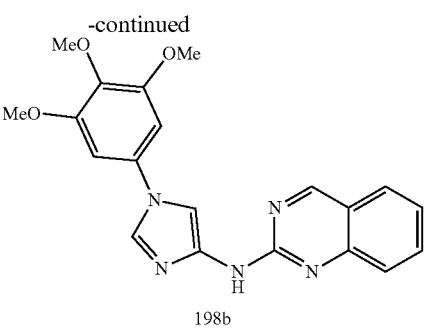

Preparation of N-(1-(3,4,5-trimethoxyphenyl)-1H-imidazol-4-yl)quinazolin-2-amine (198b)

Compound 198b was prepared from 2-chloroquinazoline (198a) (0.1 g, 0.61 mmol; CAS #6141-13-5), 1-(3,4,5-trimethoxyphenyl)-1H-imidazol-4-amine (57a) (151 mg, 0.61 mmol, free base), dicyclohexyl(2',4',6'-triisopropylbiphenyl-2-yl)phosphine (XPhos, 116 mg, 0.24 mmol), Pd$_2$(dba)$_3$ (111 mg, 0.12 mmol) and cesium carbonate (396 mg, 1.53 mmol) in t-BuOH/toluene (12 mL, 1:3 ratio) according to the procedure reported in step-1 of Scheme 96. This gave after workup and purification by flash column chromatography [silica gel (24 g), eluting with EtOAc/MeOH (9:1) in hexane from 0-100%] followed by reverse phase column chromatography [(silica gel C-18, 50 g) eluting with acetonitrile and 0.1% HCl water] N-(1-(3,4,5-trimethoxyphenyl)-1H-imidazol-4-yl)quinazolin-2-amine (198b) (13 mg, 6% yield) HCl salt as a yellow solid; $^1$H NMR (300 MHz, DMSO-d$_6$) δ 10.29 (s, 1H, D$_2$O exchangeable), 9.33 (s, 1H), 8.51 (s, 1H), 8.12 (s, 1H), 7.95 (d, J=8.0 Hz, 1H), 7.87-7.78 (m, 2H), 7.47-7.34 (m, 1H), 7.02 (s, 2H), 3.91 (s, 6H), 3.71 (s, 3H); MS (ES+): 378.3 (M+1); 400.3 (M+Na); (ES−): 376.3 (M−1).

Scheme 199

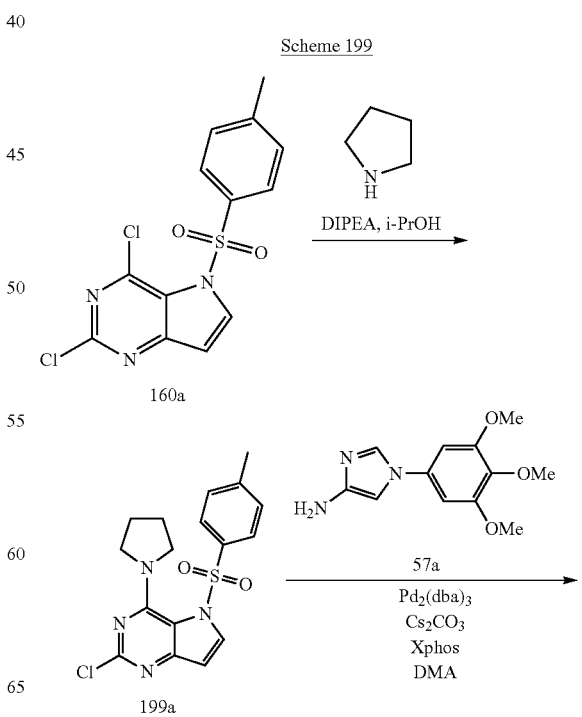

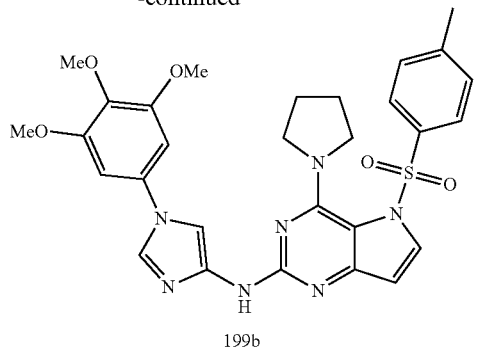

199b

Preparation of 4-(pyrrolidin-1-yl)-5-tosyl-N-(1-(3,4, 5-trimethoxyphenyl)-1H-imidazol-4-yl)-5H-pyrrolo [3,2-d]pyrimidin-2-amine (199b)

Step-1: Preparation of 2-chloro-4-(pyrrolidin-1-yl)- 5-tosyl-5H-pyrrolo[3,2-d]pyrimidine (199a)

Compound 199a was prepared from 2,4-dichloro-5-tosyl-5H-pyrrolo[3,2-d]pyrimidine (160a) (1.4 g, 4.09 mmol) in IPA (10 mL), pyrrolidine (290 mg, 4.09 mmol), DIPEA (1.07 mL, 6.14 mmol) according to the procedure reported in step-1 of Scheme 96. This gave after workup and purification by flash column chromatography [silica gel (12 g), eluting with ethyl acetate/MeOH (9:1) in hexane from 0-70%] 2-chloro-4-(pyrrolidin-1-yl)-5-tosyl-5H-pyrrolo[3, 2-d]pyrimidine (199a) (1.3 g, 84% yield) as a white solid; $^1$H NMR (300 MHz, DMSO-$d_6$) δ 7.95 (d, J=8.4 Hz, 2H), 7.56 (d, J=4.0 Hz, 1H), 7.45 (d, J=8.1 Hz, 2H), 6.87 (d, J=4.1 Hz, 1H), 3.78-3.63 (m, 2H), 3.60-3.45 (m, 2H), 2.37 (s, 3H), 2.07-1.92 (m, 2H), 1.92-1.78 (m, 2H).

Step-2: Preparation of 4-(pyrrolidin-1-yl)-5-tosyl-N- (1-(3,4,5-trimethoxyphenyl)-1H-imidazol-4-yl)-5H- pyrrolo[3,2-d]pyrimidin-2-amine (199b)

Compound 199b was prepared from 2-chloro-4-(pyrrolidin-1-yl)-5-tosyl-5H-pyrrolo[3,2-d]pyrimidine (199a) (350 mg, 0.93 mmol) in DMA (15 mL), 1-(3,4,5-trimethoxyphenyl)-1H-imidazol-4-amine (57a) (231 mg, 0.93 mmol), Pd$_2$(dba)$_3$ (170 mg, 0.19 mmol), X-Phos (177 mg, 0.37 mmol) and Cs$_2$CO$_3$ (756 mg, 2.32 mmol) according to the procedure reported in Scheme 178. This gave after workup and purification by flash column chromatography [silica gel (40 g), eluting with DMA-80 in DCM from 0-60%], 4-(pyrrolidin-1-yl)-5-tosyl-N-(1-(3,4,5-trimethoxyphenyl)-1H-imidazol-4-yl)-5H-pyrrolo[3,2-d]pyrimidin-2-amine (199b) (95 mg, 17% yield) free base as an off white solid. Free base (28 mg) was taken and mixed with 1% HCl for 1 h, excess HCl was then removed, and the residue was taken up with water/CH$_3$CN and lyophilized to give 4-(pyrrolidin-1-yl)-5-tosyl-N-(1-(3,4,5-trimethoxyphenyl)-1H-imidazol-4-yl)- 5H-pyrrolo[3,2-d]pyrimidin-2-amine (199b) (29 mg) HCl salt as an off white solid; $^1$H NMR (300 MHz, DMSO-$d_6$) δ 10.07 (s, 1H, D$_2$O exchangeable), 9.06 (s, 1H), 8.38 (s, 1H, D$_2$O exchangeable), 7.96 (d, J=8.0 Hz, 2H), 7.44-7.30 (m, 3H), 7.11 (s, 2H), 6.83 (d, J=4.0 Hz, 1H), 3.84 (s, 6H), 3.75-3.62 (m, 7H), 2.31 (s, 3H), 2.02-1.85 (m, 4H); MS (ES+): 590.3 (M+1); 612.3 (M+Na); (ES−): 588.3 (M−1).

Scheme 200

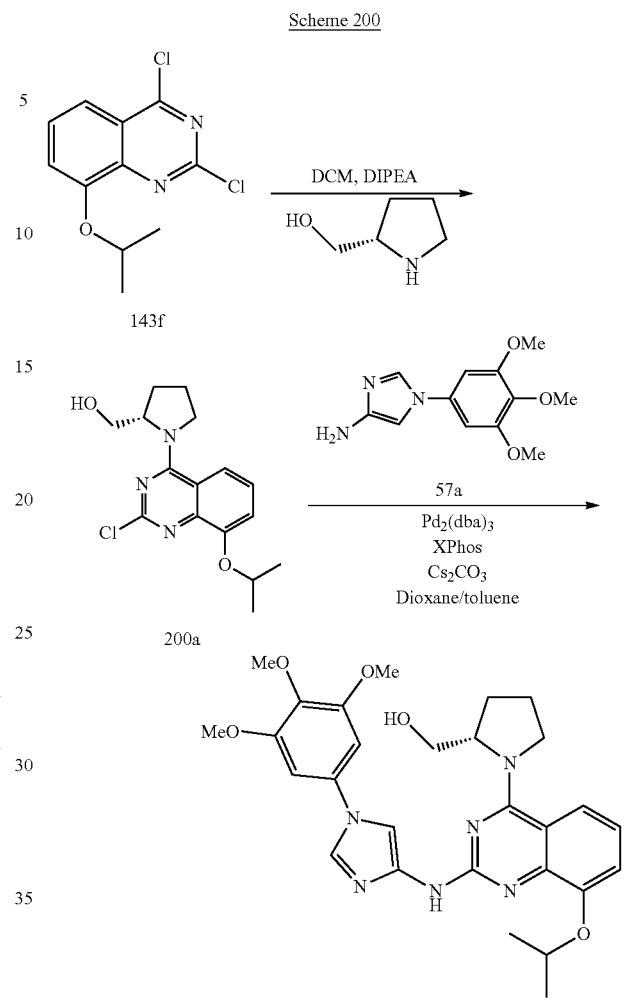

Preparation of (S)-(1-(8-isopropoxy-2-((1-(3,4,5-trimethoxyphenyl)-1H-imidazol-4-yl)amino)quinazolin-4-yl)pyrrolidin-2-yl)methanol (200b)

Step-1: Preparation of (S)-(1-(2-chloro-8-isopropoxyquinazolin-4-yl)pyrrolidin-2-yl)methanol (200a) Compound 200a was prepared from 2,4-dichloro-8-isopropoxyquinazoline (143f) (0.5 g, 1.95 mmol) in 2-DCM (10 mL) using (S)-pyrrolidin-2-ylmethanol (0.98 g, 9.76 mmol) and DIPEA (0.756 g, 5.85 mmol) according to the procedure reported in step-1 of Scheme 96. This gave after workup and purification by flash column chromatography [silica gel (25 g), eluting with DCM in methanol (0 to 30%)] (S)-(1-(2-chloro-8-isopropoxyquinazolin-4-yl)pyrrolidin-2-yl)methanol (200a) (0.6 g, 96% yield) as an off-white solid; MS (ES+): 322.3 (M+1), 344.3 (M+Na); MS (ES−): 320.3 (M−1).

Step-2: Preparation of (S)-(1-(8-isopropoxy-2-((1-(3,4,5-trimethoxyphenyl)-1H-imidazol-4-yl)amino) quinazolin-4-yl)pyrrolidin-2-yl)methanol (200b)

Compound 200b was prepared from (S)-(1-(2-chloro-8-isopropoxyquinazolin-4-yl)pyrrolidin-2-yl)methanol (200a)

(0.25 g, 0.78 mmol), 1-(3,4,5-trimethoxyphenyl)-1H-imidazol-4-amine (57a) (190 mg, 0.78 mmol, free base), dicyclohexyl(2',4',6'-triisopropylbiphenyl-2-yl)phosphine (XPhos, 220 mg, 0.47 mmol), cesium carbonate (0.76 g, 2.33 mmol) and $Pd_2(dba)_3$ (210 mg, 0.23 mmol) in 1,4-dioxane (5 mL) and toluene (5 mL) according to the procedure reported in step-3 of Scheme 101. This gave after workup and purification by flash column chromatography [silica gel (12 g), eluting with DMA-80 in $CH_2Cl_2$], followed by reverse phase column chromatography [(silica gel C-18, 24 g) eluting with acetonitrile and 0.1% HCl water] (S)-(1-(8-isopropoxy-2-((1-(3,4,5-trimethoxyphenyl)-1H-imidazol-4-yl)amino)quinazolin-4-yl)pyrrolidin-2-yl)methanol (200b) (50 mg, 11% yield) as a white solid; $^1$H NMR (300 MHz, DMSO-$d_6$) δ 13.78-13.65 and 11.98 (2m, 1H), 11.65 and 11.32 (2s, 1H), 8.51-8.32 (m, 1H), 7.85 (d, J=8.3 Hz, 1H), 7.57 (s, 1H), 7.49-7.29 (m, 2H), 7.00 (s, 2H), 4.90 (s, 1H), 4.29-4.04 (m, 1H), 3.99-3.49 (m, 13H), 2.27-1.86 (m, 4H), 1.56-1.29 (m, 6H); MS (ES+): 535.3 (M+1); MS (ES−): 569.4 (M+Cl). HPLC purity: 98.33%.

trimethoxyphenyl)-1H-imidazol-4-yl)-5,6,7,8-tetrahydropyrido[4,3-d]pyrimidin-2-amine (201b) (124 mg, 26% yield) HCl salt as a yellow solid; $^1$H NMR (300 MHz, DMSO-$d_6$) δ 11.79-11.52 (m, 1H, $D_2O$ exchangeable), 10.22 (s, 1H, $D_2O$ exchangeable), 8.83 (s, 1H), 8.40 (s, 1H), 7.90 (s, 1H), 7.75-7.60 (m, 2H), 7.58-7.43 (m, 3H), 7.03 (s, 2H), 4.58-4.33 (m, 2H), 4.23 (s, 2H), 3.88 (s, 6H), 3.70 (s, 3H), 3.54-3.19 (m, 3H), 3.19-2.95 (m, 1H); MS (ES+) 473.3 (M+1), (ES−) 507.2 (M+Cl); HPLC purity 98.29%0.

Scheme 202

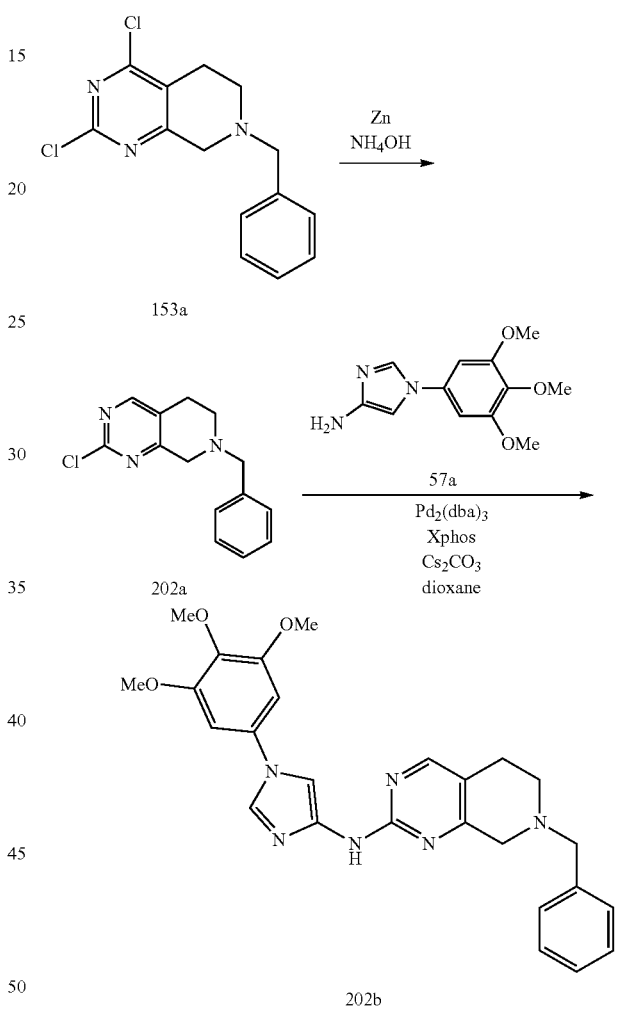

Scheme 201

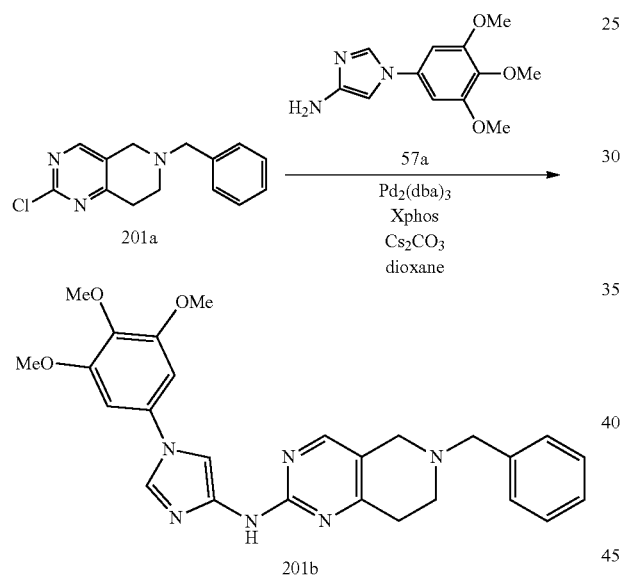

Preparation of 6-benzyl-N-(1-(3,4,5-trimethoxyphenyl)-1H-imidazol-4-yl)-5,6,7,8-tetrahydropyrido[4,3-d]pyrimidin-2-amine (201b)

Compound 201b was prepared from 6-benzyl-2-chloro-5,6,7,8-tetrahydropyrido[4,3-d]pyrimidine (201a) (0.26 g, 1.0 mmol, prepared according to the procedure reported by Sun, Hao-Peng et al; in European Journal of Medicinal Chemistry, 79, 399-412; 2014), 1-(3,4,5-trimethoxyphenyl)-1H-imidazol-4-amine (57a) (312 mg, 1.25, free base), dicyclohexyl(2',4',6'-triisopropylbiphenyl-2-yl)phosphine (XPhos, 215 mg, 0.45 mmol), $Pd_2(dba)_3$ (137 mg, 0.15 mmol) and cesium carbonate (978 mg, 3.0 mmol) in dioxane (10 mL) according to the procedure reported in step-1 of Scheme 96. This gave after workup and purification by flash column chromatography [silica gel (80 g), eluting with DMA-80 in dichloromethane] followed by reverse phase column chromatography [(silica gel C-18, 50 g) eluting with acetonitrile and 0.1% HCl water] 6-benzyl-N-(1-(3,4,5-

Preparation of 7-benzyl-N-(1-(3,4,5-trimethoxyphenyl)-1H-imidazol-4-yl)-5,6,7,8-tetrahydropyrido[3,4-d]pyrimidin-2-amine (202b)

Step-1: Preparation of 7-benzyl-2-chloro-5,6,7,8-tetrahydropyrido[3,4-d]pyrimidine (202a)

To a solution of 7-benzyl-2,4-dichloro-5,6,7,8-tetrahydropyrido[3,4-d]pyrimidine (153a) (2 g, 6.80 mmol) in ethanol (35 mL) was added zinc (3.56 g, 54.4 mmol) and ammonium hydroxide (4.73 mL, 34.0 mmol) and heated at 90° C. for 15 h. The reaction was cooled, filtered through Celite, and washed with ethyl acetate. The filtrate was concentrated and purified by flash column chromatography (silica gel, 25 g, eluting with 0 to100% ethyl acetate in hexanes) to afford 7-benzyl-2-chloro-5,6,7,8-tetrahydropyrido[3,4-d]pyrimidine (202a) (800 mg, 45% yield) as thick syrup; $^1$H NMR (300 MHz, Chloroform-d) δ 8.35 (d, J=3.1 Hz, 1H), 7.40-7.25 (m, 5H), 3.73 (s, 2H), 3.67 (s, 2H), 2.86 (d, J=5.4 Hz, 2H), 2.80 (t, J=5.5 Hz, 2H).

Step-2: Preparation of 7-benzyl-N-(1-(3,4,5-trimethoxyphenyl)-1H-imidazol-4-yl)-5,6,7,8-tetrahydropyrido[3,4-d]pyrimidin-2-amine (202b)

Compound 202b was prepared from 7-benzyl-2-chloro-5,6,7,8-tetrahydropyrido[3,4-d]pyrimidine (202a) (0.26 g, 1.0 mmol), 1-(3,4,5-trimethoxyphenyl)-1H-imidazol-4-amine (57a) (312 mg, 1.25 mmol, free base), dicyclohexyl (2',4',6'-triisopropylbiphenyl-2-yl)phosphine (XPhos, 215 mg, 0.45 mmol), Pd$_2$(dba)$_3$ (137 mg, 0.15 mmol) and cesium carbonate (977 mg, 3.0 mmol) in 1,4-dioxane (10 mL) according to the procedure reported in step-1 of Scheme 96. This gave after workup and purification by flash column chromatography [silica gel (80 g), eluting with DMA-80 in dichloromethane] followed by reverse phase column chromatography [(silica gel C-18, 50 g) eluting with acetonitrile and 0.1% HCl water] 7-benzyl-N-(1-(3,4,5-trimethoxyphenyl)-1H-imidazol-4-yl)-5,6,7,8-tetrahydropyrido[3,4-d]pyrimidin-2-amine (202b) (145 mg, 31% yield) HCl salt as a white solid; $^1$H NMR (300 MHz, DMSO-d$_6$) δ 11.76 (s, 1H, D$_2$O exchangeable), 10.18 (s, 1H, D$_2$O exchangeable), 8.74 (s, 1H), 8.46 (s, 1H), 7.85 (s, 1H), 7.70 (t, J=4.6 Hz, 2H), 7.55-7.41 (m, 3H), 7.00 (s, 2H), 4.48 (s, 2H), 4.34-4.11 (m, 2H), 3.88 (s, 6H), 3.70 (s, 3H), 3.45-3.06 (m, 3H), 3.02-2.86 (m, 1H); MS (ES+): 473.3 (M+1), (ES−): 507.3 (M+Cl); HPLC: 98.06%.

Preparation of (S)-1-(2-((1-(3,4,5-trimethoxyphenyl)-1H-imidazol-4-yl)amino)pyrido[2,3-d]pyrimidin-4-yl)pyrrolidine-2-carboxamide (203b)

Step-1: Preparation of (S)-1-(2-chloropyrido[2,3-d]pyrimidin-4-yl)pyrrolidine-2-carboxamide (203a)

Compound 203a was prepared from 2,4-dichloropyrido[2,3-d]pyrimidine (169a) (0.5 g, 2.50 mmol) in 2-Propanol (10 mL) using (S)-pyrrolidine-2-carboxamide (0.29 g, 2.5 mmol) and DIPEA (1.31 mL, 7.5 mmol) according to the procedure reported in step-1 of Scheme 96. This gave after workup and purification by flash column chromatography [silica gel (12 g), eluting with MeOH in dichloromethane 0 to 30%] (S)-1-(2-chloropyrido[2,3-d]pyrimidin-4-yl)pyrrolidine-2-carboxamide (203a) (0.51 g, 73% yield) as a white solid; MS (ES+): 278.2 & 280.2 (M+1).

Step-2: Preparation of (S)-1-(2-((1-(3,4,5-trimethoxyphenyl)-1H-imidazol-4-yl)amino)pyrido[2,3-d]pyrimidin-4-yl)pyrrolidine-2-carboxamide (203b)

Compound 203b was prepared from (S)-1-(2-chloropyrido[2,3-d]pyrimidin-4-yl)pyrrolidine-2-carboxamide (203a) (0.25 g, 0.9 mmol), 1-(3,4,5-trimethoxyphenyl)-1H-imidazol-4-amine (57a) (220 mg, 0.9 mmol, free base), dicyclohexyl(2',4',6'-triisopropylbiphenyl-2-yl)phosphine (XPhos, 280 mg, 0.54 mmol), Pd$_2$(dba)$_3$ (0.25 g, 0.27 mmol) and cesium carbonate (0.88 g, 2.7 mmol) in dioxane (5 mL) and toluene (5 mL) according to the procedure reported in step-1 of Scheme 96. This gave after workup and purification by flash column chromatography [silica (12 g), eluting with DMA −0 in CH$_2$Cl$_2$ from 0 to 30%], followed by reverse phase column chromatography [(silica gel C-18, 24 g) eluting with acetonitrile and 0.1% HCl water] (S)-1-(2-((1-(3,4,5-trimethoxyphenyl)-1H-imidazol-4-yl)amino)pyrido[2,3-d]pyrimidin-4-yl)pyrrolidine-2-carboxamide (203b) (30 mg, 6% yield) HCl salt as a white solid; $^1$H NMR (300 MHz, DMSO-d$_6$): δ 10.73 (s, 1H), 8.81 (s, 2H), 8.32 (s, 1H), 7.83 (s, 1H), 7.71-7.41 (m, 2H), 7.35-6.84 (m, 3H), 5.00-4.77 (m, 1H), 4.52-4.06 (m, 2H), 3.92 (s, 6H), 3.69 (s, 3H), 2.42-1.94 (m, 4H). MS (ES+): 591.3 (M+1), 513.3 (M+Na); MS (ES−): 525.3 (M+Cl).

Scheme 203

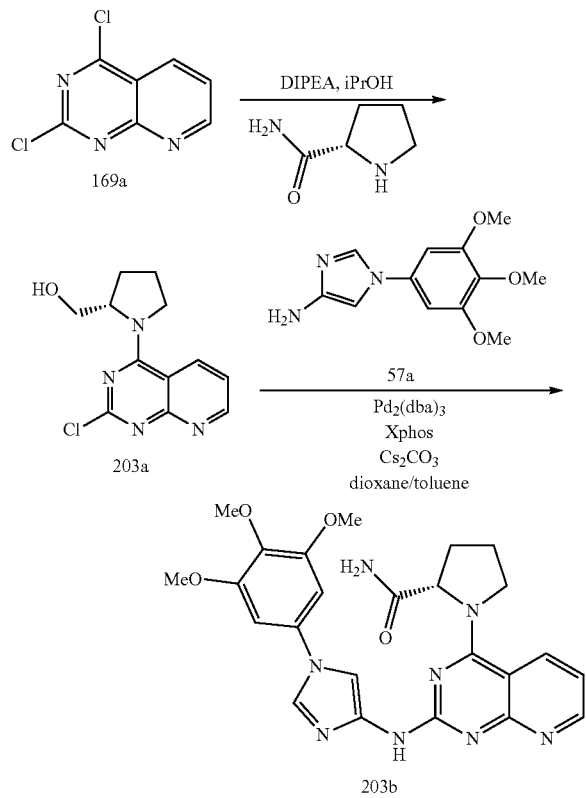

Scheme 204

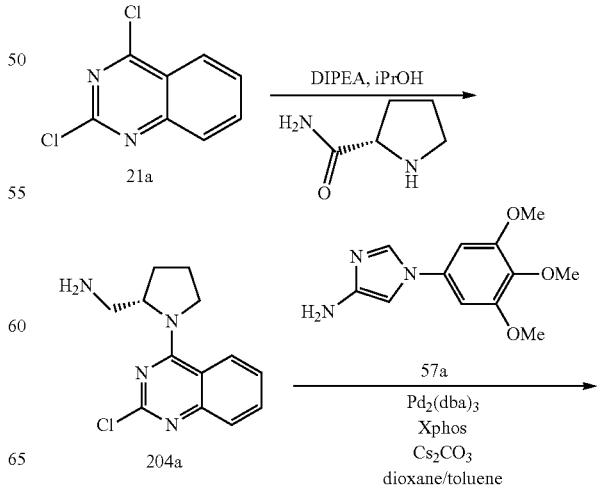

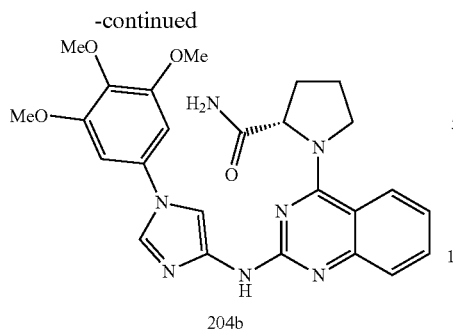

204b

Preparation of (S)-1-(2-((1-(3,4,5-trimethoxyphenyl)-1H-imidazol-4-yl)amino)quinazolin-4-yl)pyrrolidine-2-carboxamide (204b)

Step-1: Preparation of (S)-1-(2-chloroquinazolin-4-yl)pyrrolidine-2-carboxamide (204a)

Compound 204a was prepared from 2,4-dichloroquinazoline (21a) (0.5 g, 2.51 mmol) in 2-Propanol (10 mL) using (S)-pyrrolidine-2-carboxamide (0.29 g, 2.5 mmol) and DIPEA (1.31 mL, 7.5 mmol) according to the procedure reported in step-1 of Scheme 96. This gave after workup and purification by flash column chromatography [silica gel (12 g), eluting with MeOH in dichloromethane 0 to 30%] (S)-1-(2-chloroquinazolin-4-yl)pyrrolidine-2-carboxamide (204a) (0.27 g, 39% yield) as a white solid; MS (ES−): 311.2 & 313.2 (M+Cl).

Step-2: Preparation of (S)-1-(2-((1-(3,4,5-trimethoxyphenyl)-1H-imidazol-4-yl)amino)quinazolin-4-yl)pyrrolidine-2-carboxamide (204b)

Compound 204b was prepared from (S)-1-(2-chloroquinazolin-4-yl)pyrrolidine-2-carboxamide (204a) (0.25 g, 0.9 mmol), 1-(3,4,5-trimethoxyphenyl)-1H-imidazol-4-amine (57a) (230 mg, 0.9 mmol, free base), dicyclohexyl(2',4',6'-triisopropylbiphenyl-2-yl)phosphine (XPhos, 0.26 g, 0.54 mmol), Pd$_2$(dba)$_3$ (0.25 g, 0.27 mmol) and cesium carbonate (0.88 g, 2.7 mmol) in dioxane (5 mL) and toluene (5 mL) according to the procedure reported in step-1 of Scheme 96. This gave after workup and purification by flash column chromatography [silica gel (12 g), eluting with DMA-80 in CH$_2$Cl$_2$ from 0 to 30%], followed by reverse phase column chromatography [(silica gel C-18, 24 g) eluting with acetonitrile and 0.1% HCl water] (S)-1-(2-((1-(3,4,5-trimethoxyphenyl)-1H-imidazol-4-yl)amino)quinazolin-4-yl)pyrrolidine-2-carboxamide (204b) (0.03 g, 7% yield) HCl salt as a white solid; $^1$H NMR (300 MHz, DMSO-d$_6$) δ 10.68 (s, 1H), 8.68 (s, 1H), 8.39 (d, J=8.5 Hz, 1H), 7.94 (s, 1H), 7.89 (t, J=7.6 Hz, 1H), 7.71-7.54 (m, 2H), 7.49 (t, J=7.8 Hz, 1H), 7.36-7.10 (m, 3H), 4.93-4.83 (m, 1H), 4.54-4.38 (m, 1H), 4.31-4.14 (m, 1H), 3.92 (s, 6H), 3.70 (s, 3H), 2.42-1.86 (m, 4H); MS (ES+): 490.3 (M+1), 512.2 (M+Na); MS (ES−): 524.3 (M+Cl). HPLC purity: 95.00%.

Scheme 205

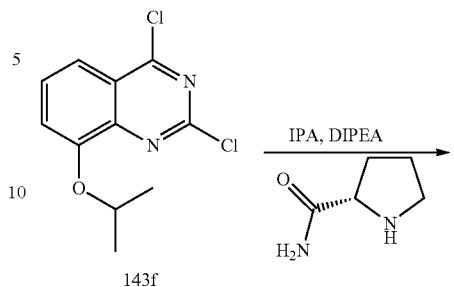

143f

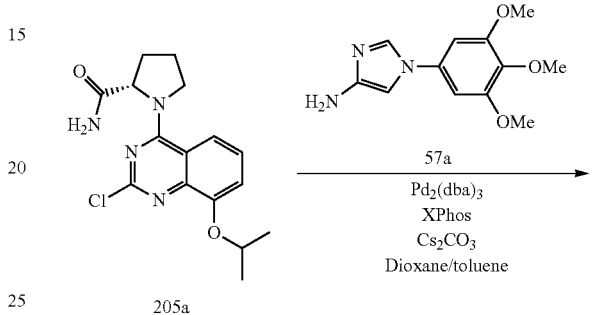

205a

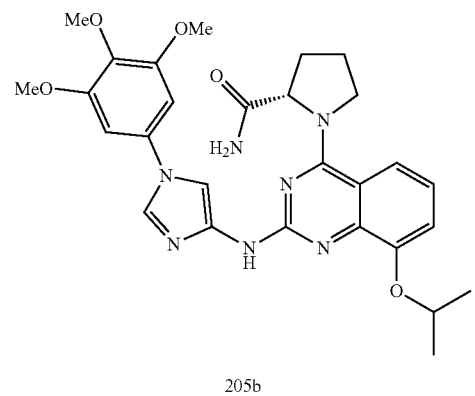

205b

Preparation of (S)-1-(8-isopropoxy-2-((1-(3,4,5-trimethoxyphenyl)-1H-imidazol-4-yl)amino)quinazolin-4-yl)pyrrolidine-2-carboxamide (205b)

Step-1: Preparation of (S)-1-(2-chloro-8-isopropoxyquinazolin-4-yl)pyrrolidine-2-carboxamide (205a) Compound 205a was prepared from 2,4-dichloro-8-isopropoxyquinazoline (143f) (0.50 g, 1.94 mmol) in 2-Propanol (10 mL) using (S)-pyrrolidine-2-carboxamide (1.1 g, 9.72 mmol) and DIPEA (0.75 g, 5.83 mmol) according to the procedure reported in step-1 of Scheme 96. This gave after workup and purification by flash column chromatography [silica gel (25 g), eluting with ethyl acetate in hexanes (10 to 80%)] (S)-1-(2-chloro-8-isopropoxyquinazolin-4-yl)pyrrolidine-2-carboxamide (205a) (0.615 g, 95%) as an off white solid; $^1$H NMR (300 MHz, DMSO-d$_6$): δ 7.82 (d, J=8.2 Hz, 1H), 7.55 (s, 1H), 7.46-7.21 (m, 2H), 7.04 (s, 1H), 4.78 (dt, J=15.0, 7.5 Hz, 2H), 4.07 (d, J=20.4 Hz, 2H), 2.10-1.72 (m, 4H), 1.33 (d, J=6.0 Hz, 6H); MS (ES+) 335.0 (M+1); HPLC purity: 99.1%.

Step-2: Preparation of (S)-1-(8-isopropoxy-2-((1-(3,4,5-trimethoxyphenyl)-1H-imidazol-4-yl)amino)quinazolin-4-yl)pyrrolidine-2-carboxamide (205b)

Compound 205b was prepared from (S)-1-(2-chloro-8-isopropoxyquinazolin-4-yl)pyrrolidine-2-carboxamide (205a) (0.25 g, 0.78 mmol), 1-(3,4,5-trimethoxyphenyl)-1H-imidazol-4-amine (57a) (190 mg, 0.78 mmol, free base), dicyclohexyl(2',4',6'-triisopropylbiphenyl-2-yl)phosphine (XPhos, 210 mg, 0.45 mmol), cesium carbonate (0.73 g, 2.24 mmol) and $Pd_2(dba)_3$ (210 mg, 0.23 mmol) in 1,4-dioxane (5 mL) and toluene (5 mL) according to the procedure reported in step-3 of Scheme 101. This gave after workup and purification by flash column chromatography [silica gel (12 g), eluting with DMA-80 in $CH_2Cl_2$], followed by reverse phase column chromatography [(silica gel C-18, 24 g) eluting with acetonitrile and 0.1% HCl water] (S)-1-(8-isopropoxy-2-((1-(3,4,5-trimethoxyphenyl)-1H-imidazol-4-yl)amino)quinazolin-4-yl)pyrrolidine-2-carboxamide (205b) (20 mg, 5% yield) as a white solid; $^1$H NMR (300 MHz, DMSO-$d_6$): δ 11.51 (s, 1H), 8.50-8.25 (m, 1H), 7.99-7.79 (m, 2H), 7.68-7.54 (m, 2H), 7.42 (d, J=8.6 Hz, 1H), 7.27-7.12 (m, 2H), 6.99 (s, 1H), 5.00-4.79 (m, 2H), 4.57-4.09 (m, 2H), 3.91 (s, 6H), 3.70 (s, 3H), 2.43-1.90 (m, 4H), 1.56-1.35 (m, 6H). MS (ES+): 548.3 (M+1), 570.4 (M+Na); MS (ES−): 582.3 (M+Cl); HPLC purity: 95.12%.

Preparation of (S)-4-(2-(trifluoromethyl)pyrrolidin-1-yl)-N-(1-(3,4,5-trimethoxyphenyl)-1H-imidazol-4-yl)pyrrolo[2,1-f][1,2,4]triazin-2-amine (206b)

Step-1: Preparation of (S)-2-chloro-4-(2-(trifluoromethyl)pyrrolidin-1-yl)pyrrolo[2,1-f][1,2,4]triazine (206a)

Compound 206a was prepared from 2,4-dichloropyrrolo[2,1-f][1,2,4]triazine (4a) (400 mg, 2.13 mmol) in IPA (40 mL), (S)-2-(trifluoromethyl)pyrrolidine (296 mg, 2.13 mmol), DIPEA (0.74 mL, 4.25 mmol) according to the procedure reported in step-1 of Scheme 96. This gave after workup and purification by flash column chromatography [silica (12 g), eluting with ethyl acetate in hexane from 0-50%] (S)-2-chloro-4-(2-(trifluoromethyl)pyrrolidin-1-yl)pyrrolo[2,1-f][1,2,4]triazine (206a) (590 mg, 95% yield) as a white solid; $^1$H NMR (300 MHz, DMSO-$d_6$) δ 7.88-7.80 (m, 1H), 7.14-7.05 (m, 1H), 6.82-6.74 (m, 1H), 5.48-5.33 (m, 1H), 4.16-4.08 (m, 1H), 4.09-3.95 (m, 1H), 2.23-2.09 (m, 4H); $^{19}$F NMR (282 MHz, DMSO) δ −71.87.

Step-2: Preparation of (S)-4-(2-(trifluoromethyl)pyrrolidin-1-yl)-N-(1-(3,4,5-trimethoxyphenyl)-1H-imidazol-4-yl)pyrrolo[2,1-f][1,2,4]triazin-2-amine (206b)

Compound 206b was prepared from (S)-2-chloro-4-(2-(trifluoromethyl)pyrrolidin-1-yl)pyrrolo[2,1-f][1,2,4]triazine (206a) (300 mg, 1.03 mmol) in toluene/t-BuOH (25 mL, Ratio: 5:2) using 1-(3,4,5-trimethoxyphenyl)-1H-imidazol-4-amine (57a) (309 mg, 1.24 mmol), $Pd_2(dba)_3$ (309 mg, 1.24 mmol), X-Phos (197 mg, 0.41 mmol) and $Cs_2CO_3$ (1177 mg, 3.61 mmol) according to the procedure reported in step-3 of Scheme 101. This gave after workup and purification twice by flash column chromatography [silica gel (40 g), eluting with DMA-80 in DCM from 0-100%] followed by [silica gel (12 g), eluting with EtOAc/MeOH (9:1) in hexane from 0-100%] free base of compound 206b. The free base was converted into HCl salt using 5% HCl, followed by lyophilization to give (S)-4-(2-(trifluoromethyl)pyrrolidin-1-yl)-N-(1-(3,4,5-trimethoxyphenyl)-1H-imidazol-4-yl)pyrrolo[2,1-f][1,2,4]triazin-2-amine (206b) (276 mg, 50% yield) HCl salt as a white solid; $^1$H NMR (300 MHz, DMSO-$d_6$) δ 9.49 (s, 1H, $D_2O$ exchangeable), 9.14 (s, 1H), 7.90 (s, 1H, $D_2O$ exchangeable), 7.73 (d, J=2.3 Hz, 1H), 7.11 (s, 2H), 6.99-6.91 (m, 1H), 6.66-6.56 (m, 1H), 5.58-5.44 (m, 1H), 4.20-4.06 (m, 1H), 4.06-3.94 (m, 1H), 3.90 (s, 6H), 3.72 (s, 3H), 2.23-2.09 (m, 4H); $^{19}$F NMR (282 MHz, DMSO) δ −71.95; MS (ES+): 504.3 (M+1), 526.3 (M+Na); (ES−): 538.3 (M+Cl).

Scheme 206

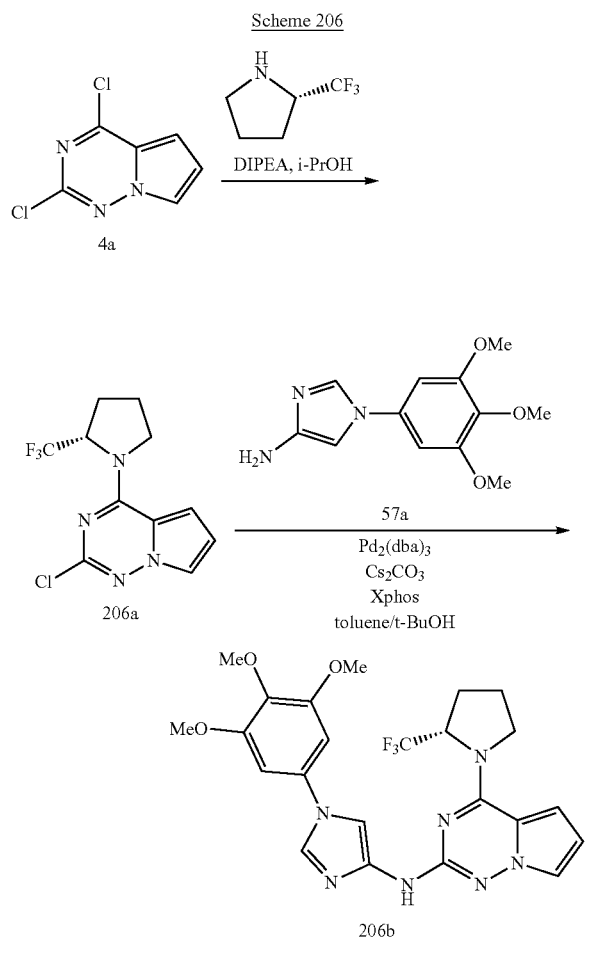

Scheme 207

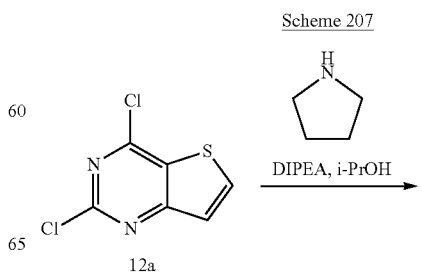

-continued

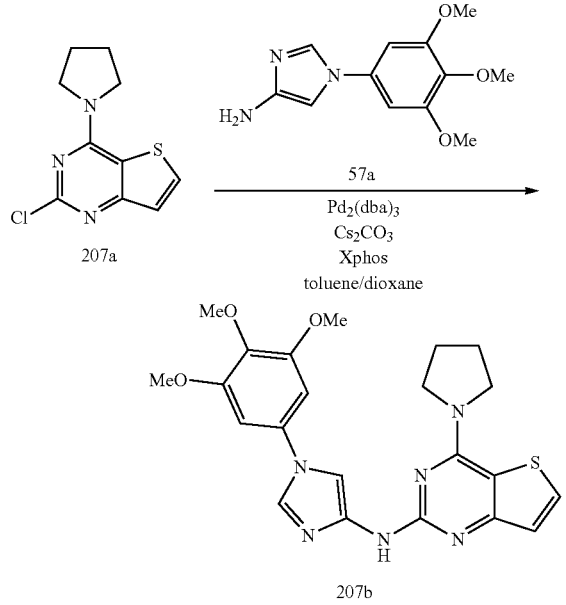

Preparation of 4-(pyrrolidin-1-yl)-N-(1-(3,4,5-trimethoxyphenyl)-1H-imidazol-4-yl)thieno[3,2-d]pyrimidin-2-amine (207b)

Step-1: Preparation of 2-chloro-4-(pyrrolidin-1-yl)thieno[3,2-d]pyrimidine (207a)

Compound 207a was prepared from 2,4-dichlorothieno[3,2-d]pyrimidine (12a) (1 g, 4.88 mmol) in IPA (10 mL), pyrrolidine (0.4 mL, 4.88 mmol), DIPEA (2.56 mL, 14.63 mmol) according to the procedure reported in step-1 of Scheme 96. This gave after workup and purification by flash column chromatography [silica gel (12 g), eluting with DCM and methanol (0 to 30%)] 2-chloro-4-(pyrrolidin-1-yl)thieno[3,2-d]pyrimidine (207a) (0.97 g, 83% yield) as a white solid; MS (ES+): 240.1 & 242.1 (M+1), 262.1 & 264.1 (M+Na).

Step-2: Preparation of 4-(pyrrolidin-1-yl)-N-(1-(3,4,5-trimethoxyphenyl)-1H-imidazol-4-yl)thieno[3,2-d]pyrimidin-2-amine (207b)

Compound 207b was prepared from 2-chloro-4-(pyrrolidin-1-yl)thieno[3,2-d]pyrimidine (207a) (400 mg, 1.67 mmol) in toluene/1,4-dioxane (10 mL, Ratio: 1:1) using 1-(3,4,5-trimethoxyphenyl)-1H-imidazol-4-amine (57a) (420 g, 1.67 mmol), Pd$_2$(dba)$_3$ (460 mg, 0.50 mmol), X-Phos (480 mg, 1.0 mmol) and Cs$_2$CO$_3$ (1630 mg, 5.01 mmol) according to the procedure reported in step-3 of Scheme 101. This gave after workup and purification by flash column chromatography [silica gel (12 g), eluting with DMA-80 in DCM from 0-100%] followed by reverse phase column chromatography [(silica gel C-18, 24 g) eluting with acetonitrile and 0.1% HCl water] 4-(pyrrolidin-1-yl)-N-(1-(3,4,5-trimethoxyphenyl)-1H-imidazol-4-yl)thieno[3,2-d]pyrimidin-2-amine (207b) (40 mg, 5% yield) HCl salt as an off white solid; $^1$H NMR (300 MHz, DMSO-d$_6$): δ 10.69 (s, 1H), 8.41 (d, J=5.5 Hz, 1H), 8.35 (s, 1H), 7.76 (s, 1H), 7.46 (d, J=5.5 Hz, 1H), 6.96 (s, 2H), 4.10-3.91 (m, 4H), 3.88 (s, 6H), 3.69 (s, 3H), 2.30-1.78 (m, 4H). MS (ES+): 453.3 (M+1), 475.3 (M+Na); MS (ES−): 487.4 (M+Cl).

Scheme 208

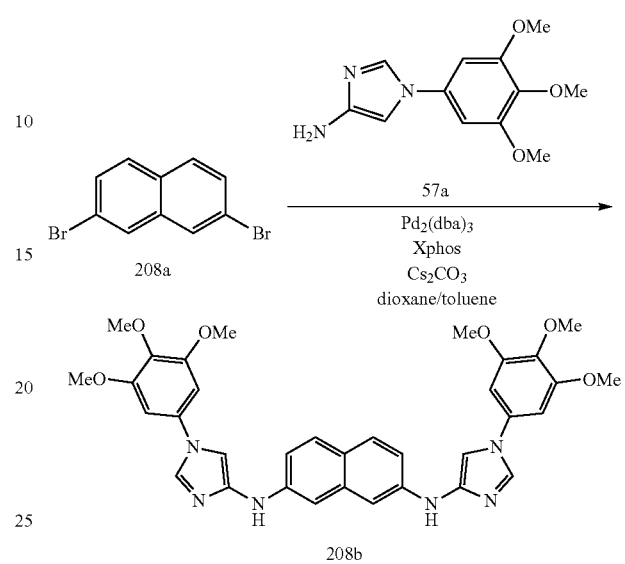

Preparation of N$^2$,N$^7$-bis(1-(3,4,5-trimethoxyphenyl)-1H-imidazol-4-yl)naphthalene-2,7-diamine (208b)

Compound 208b was prepared from 2,7-dibromonaphthalene (208a) (400 mg, 1.4 mmol, CAS #58556-75-5) in toluene/1,4-dioxane (25 mL, Ratio: 1:5) using 1-(3,4,5-trimethoxyphenyl)-1H-imidazol-4-amine (57a) (523 mg, 2.1 mmol), Pd$_2$(dba)$_3$ (128 mg, 0.14 mmol), X-Phos (200 mg, 0.42 mmol) and Cs$_2$CO$_3$ (912 mg, 2.8 mmol) according to the procedure reported in step-3 of Scheme 101. This gave after workup and purification by flash column chromatography [silica gel (12 g), eluting with DMA-80 in DCM from 0-100%] followed by reverse phase column chromatography [(silica gel C-18, 50 g) eluting with acetonitrile and 0.1% HCl water]N$^2$,N$^7$-bis(1-(3,4,5-trimethoxyphenyl)-1H-imidazol-4-yl)naphthalene-2,7-diamine (208b) (35 mg, 4% yield) HCl salt as a white solid; $^1$H NMR (300 MHz, DMSO-d$_6$) δ 8.97 (s, 2H), 8.76 (s, 2H, D$_2$O exchangeable), 7.89 (s, 2H, D$_2$O exchangeable), 7.68-7.58 (m, 2H), 7.25-7.20 (m, 2H), 7.14-7.01 (m, 6H), 3.87 (s, 12H), 3.71 (s, 6H); MS (ES+): 623.4 (M+1); 645.3 (M+Na); (ES−): 657.4 (M+Cl).

Scheme 209

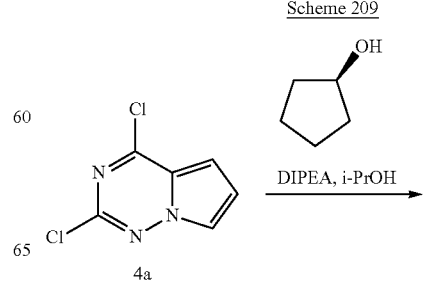

407

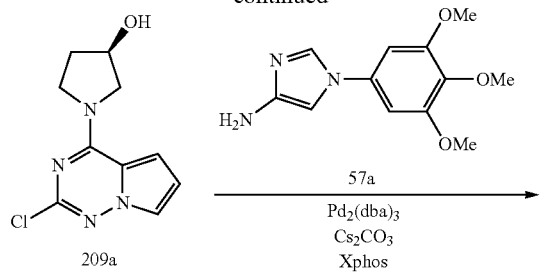

Preparation of (R)-1-(2-((1-(3,4,5-trimethoxyphenyl)-1H-imidazol-4-yl)amino)pyrrolo[2,1-f][1,2,4]triazin-4-yl)pyrrolidin-3-ol (209b)

Step-1: Preparation of (R)-1-(2-chloropyrrolo[2,1-f][1,2,4]triazin-4-yl)pyrrolidin-3-ol (209a)

Compound 209a was prepared from 2,4-dichloropyrrolo[2,1-f][1,2,4]triazine (4a) (520 mg, 2.77 mmol) in IPA (40 mL), (R)-pyrrolidin-3-ol (241 mg, 2.77 mmol), DIPEA (0.97 mL, 5.53 mmol) according to the procedure reported in step-1 of Scheme 96. This gave after workup and purification by flash column chromatography [silica gel (12 g), eluting with ethyl acetate in hexane from 0-50%] (R)-1-(2-chloropyrrolo[2,1-f][1,2,4]triazin-4-yl)pyrrolidin-3-ol (209a) (601 mg, 91% yield) as a white solid; $^1$H NMR (300 MHz, DMSO-$d_6$) δ 7.70 (t, J=2.0 Hz, 1H), 7.03-6.90 (m, 1H), 6.70-6.64 (m, 1H), 5.21-4.98 (m, 1H, D$_2$O exchangeable), 4.53-4.29 (m, 1H), 4.10-3.92 (m, 2H), 3.86-3.75 (m, 1H), 3.70-3.62 (m, 1H), 2.16-1.88 (m, 2H); MS (ES+): 239.3 (M+1); (ES−): 237.3 (M−1).

Step-2: Preparation of (R)-1-(2-((1-(3,4,5-trimethoxyphenyl)-1H-imidazol-4-yl)amino)pyrrolo[2,1-f][1,2,4]triazin-4-yl)pyrrolidin-3-ol (209b)

Compound 209b was prepared from (R)-1-(2-chloropyrrolo[2,1-f][1,2,4]triazin-4-yl)pyrrolidin-3-ol (209a) (300 mg, 1.26 mmol) in toluene/t-BuOH (25 mL, Ratio: 5:2) using 1-(3,4,5-trimethoxyphenyl)-1H-imidazol-4-amine (57a) (376 mg, 1.51 mmol), Pd$_2$(dba)$_3$ (173 mg, 0.19 mmol), X-Phos (240 mg, 0.50 mmol) and Cs$_2$CO$_3$ (1433 mg, 4.40 mmol) according to the procedure reported in step-3 of Scheme 101. This gave after workup and purification twice by flash column chromatography [silica gel (12 g), eluting with DMA-80 in DCM from 0-100%] followed by [silica gel (12 g), eluting with EtOAc/MeOH (9:1) in hexane from 0-100%] 110 mg free base of compound 209b. The free base was converted into HCl salt using 1 N HCl (1.0 mL) in CH$_3$CN (0.5 mL), followed by lyophilization to afford

408

(R)-1-(2-((1-(3,4,5-trimethoxyphenyl)-1H-imidazol-4-yl)amino)pyrrolo[2,1-f][1,2,4]triazin-4-yl)pyrrolidin-3-ol (209b) (40 mg, 7% yield) as an off white solid; $^1$H NMR (300 MHz, DMSO-$d_6$) δ 9.65 (s, 1H, D$_2$O exchangeable), 9.30 (s, 1H), 7.91 (s, 1H, D$_2$O exchangeable), 7.66 (t, J=1.9 Hz, 1H), 7.14 (s, 2H), 6.97-6.82 (m, 1H), 6.61-6.49 (m, 1H), 4.54-4.36 (m, 1H), 4.14-3.95 (m, 2H), 3.90 (s, 6H), 3.85-3.74 (m, 2H), 3.72 (s, 3H), 2.20-1.84 (m, 2H); MS (ES+): 452.9 (M+1); 475.4 (M+Na); (ES−): 486.3 (M+Cl).

Scheme 210

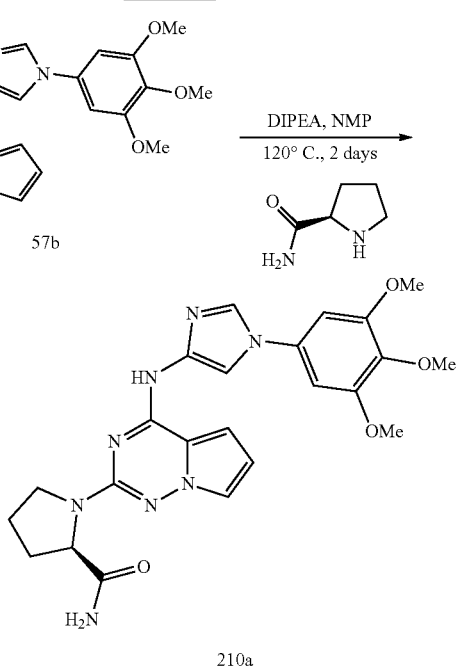

Preparation of (R)-1-(4-((1-(3,4,5-trimethoxyphenyl)-1H-imidazol-4-yl)amino)pyrrolo[2,1-f][1,2,4]triazin-2-yl)pyrrolidine-2-carboxamide (210a)

Compound 210a was prepared according to the procedure reported in step-2 of Scheme 76 from 2-chloro-N-(1-(3,4,5-trimethoxyphenyl)-1H-imidazol-4-yl)pyrrolo[2,1-f][1,2,4]triazin-4-amine (57b) (400 mg, 0.1 mmol), (R)-pyrrolidine-2-carboxamide (456 mg, 3.99 mmol) and DIPEA (0.52 mL, 2.99 mmol) in NMP (15 mL). This gave after workup and purification by flash chromatography (silica gel (24 g), eluting with DMA-80 in DCM from 0-60%) followed by reverse column chromatography [(silica gel C-18, 50 g), eluting with ACN in water (containing 0.1% HCl) from 0-100%] (R)-1-(4-((1-(3,4,5-trimethoxyphenyl)-1H-imidazol-4-yl)amino)pyrrolo[2,1-f][1,2,4]triazin-2-yl)pyrrolidine-2-carboxamide (210a) (196 mg, 41% yield) as a white solid; $^1$H NMR (300 MHz, DMSO-$d_6$) δ 10.73 (s, 1H, D$_2$O exchangeable), 8.57 (s, 1H), 7.98 (s, 1H), 7.47 (t, J=2.0 Hz, 1H), 7.26 (s, 1H, D$_2$O exchangeable), 7.18-7.09 (m, 3H), 7.02 (s, 1H, D$_2$O exchangeable), 6.49-6.39 (m, 1H), 4.40 (d, J=8.8 Hz, 1H), 3.93 (s, 6H), 3.83-3.73 (m, 1H), 3.69 (s, 3H), 3.53-3.39 (m, 1H), 2.27-2.12 (m, 1H), 2.01-1.85 (m, 3H); MS (ES+): 479.3 (M+1); (ES−): 477.3 (M−1); 513.3 (M+Cl).

Scheme 211

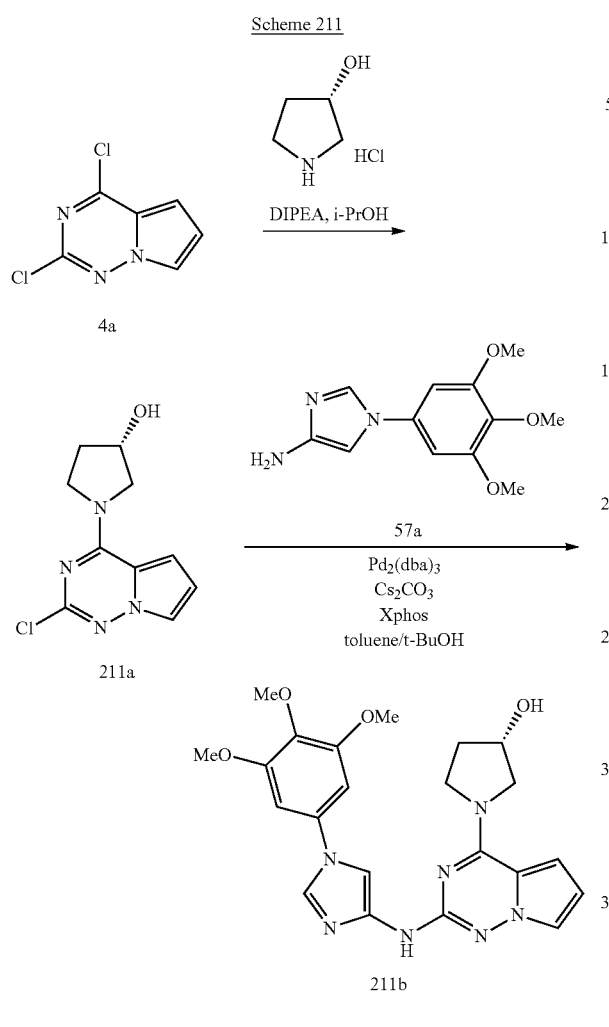

Preparation of (S)-1-(2-((1-(3,4,5-trimethoxyphenyl)-1H-imidazol-4-yl)amino)pyrrolo[2,1-f][1,2,4]triazin-4-yl)pyrrolidin-3-ol (211b)

Step-1: Preparation of (S)-1-(2-chloropyrrolo[2,1-f][1,2,4]triazin-4-yl)pyrrolidin-3-ol (211a)

Compound 211a was prepared from 2,4-dichloropyrrolo[2,1-f][1,2,4]triazine (4a) (520 mg, 2.77 mmol) in IPA (40 mL), (S)-pyrrolidin-3-ol hydrochloride (342 mg, 2.77 mmol), DIPEA (1.45 mL, 8.3 mmol) according to the procedure reported in step-1 of Scheme 96. This gave after workup and purification by flash column chromatography [silica gel (12 g), eluting with ethyl acetate in hexane from 0-50%] (S)-1-(2-chloropyrrolo[2,1-f][1,2,4]triazin-4-yl)pyrrolidin-3-ol (211a) (620 mg, 94% yield) as a white solid; $^1$H NMR (300 MHz, DMSO-$d_6$) δ 7.74-7.64 (m, 1H), 7.02-6.89 (m, 1H), 6.71-6.61 (m, 1H), 5.20-5.02 (m, 1H), 4.55-4.32 (m, 1H), 4.10-3.92 (m, 2H), 3.86-3.74 (m, 1H), 3.72-3.62 (m, 1H), 2.17-1.81 (m, 2H).

Step-2: Preparation of (S)-1-(2-((1-(3,4,5-trimethoxyphenyl)-1H-imidazol-4-yl)amino)pyrrolo[2,1-f][1,2,4]triazin-4-yl)pyrrolidin-3-ol (211b)

Compound 211b was prepared from (S)-1-(2-chloropyrrolo[2,1-f][1,2,4]triazin-4-yl)pyrrolidin-3-ol (211a) (300 mg, 1.26 mmol) in toluene/t-BuOH (25 mL, Ratio: 5:2) using 1-(3,4,5-trimethoxyphenyl)-1H-imidazol-4-amine (57a) (376 mg, 1.51 mmol), Pd$_2$(dba)$_3$ (173 mg, 0.19 mmol), X-Phos (240 mg, 0.50 mmol) and Cs$_2$CO$_3$ (1433 mg, 4.40 mmol) according to the procedure reported in step-3 of Scheme 101. This gave after workup and purification by flash column chromatography [silica gel (24 g), eluting with DMA80 in DCM from 0-100%] followed by reverse phase column chromatography [(silica gel C-18, 50 g) eluting with ACN in water containing 0.1% HCl) from 0-100%] (S)-1-(2-((1-(3,4,5-trimethoxyphenyl)-1H-imidazol-4-yl)amino)pyrrolo[2,1-f][1,2,4]triazin-4-yl)pyrrolidin-3-ol (211b) (135 mg, 24% yield) as a white solid; $^1$H NMR (300 MHz, DMSO-$d_6$) δ 9.68 (s, 1H, D$_2$O exchangeable), 9.31 (s, 1H), 7.93 (s, 1H, D$_2$O exchangeable), 7.66 (t, J=1.9 Hz, 1H), 7.14 (s, 2H), 6.89 (dd, J=21.4, 4.6 Hz, 1H), 6.61-6.50 (m, 1H), 5.04 (bs, 1H, D$_2$O exchangeable), 4.55-4.35 (m, 1H), 4.10-3.96 (m, 2H), 3.90 (s, 6H), 3.84-3.73 (m, 2H), 3.71 (s, 3H), 2.19-1.83 (m, 2H); MS (ES+): 452.3 (M+1); (ES-): 486.3 (M+Cl).

Scheme 212

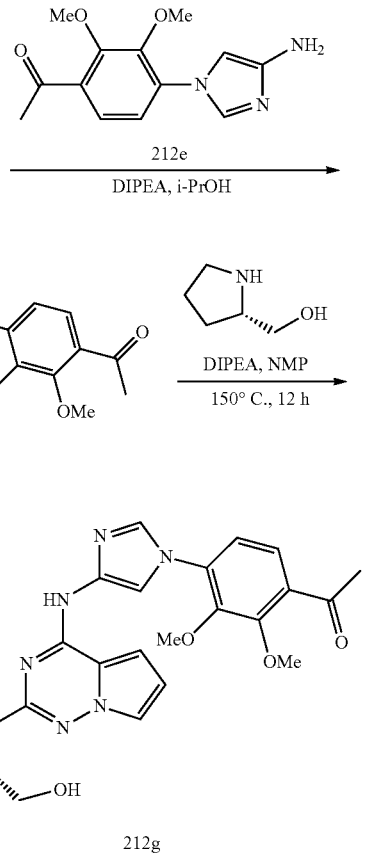

Preparation of (S)-1-(4-(4-((2-(2-(hydroxymethyl)pyrrolidin-1-yl)pyrrolo[2,1-f][1,2,4]triazin-4-yl)amino)-1H-imidazol-1-yl)-2,3-dimethoxyphenyl)ethanone (212g)

Step-1: Preparation of 1-(4-(4-((2-chloropyrrolo[2,1-f][1,2,4]triazin-4-yl)amino)-1H-imidazol-1-yl)-2,3-dimethoxyphenyl)ethanone (212f)

Compound 212f was prepared from 2,4-dichloropyrrolo[2,1-f][1,2,4]triazine (4a) (1.8 g, 9.57 mmol) in 2-Propanol (20 mL) using DIPEA (5.01 mL, 38.81 mmol) and 1-(4-(4-amino-1H-imidazol-1-yl)-2,3-dimethoxyphenyl)ethanone (212e) (1.29 g, 7.69 mmol). This gave after workup and purification by flash column chromatography [silica gel, (40 g) eluting with ethyl acetate in n-hexane (0-70%)] 1-(4-(4-((2-chloropyrrolo[2,1-f][1,2,4]triazin-4-yl)amino)-1H-imidazol-1-yl)-2,3-dimethoxyphenyl)ethanone (212f) (0.27 g, 7%) as an off white solid. $^1$H NMR (300 MHz, DMSO-$d_6$) δ 11.33 (s, 1H), 8.27 (d, J=1.6 Hz, 1H), 7.89 (d, J=1.6 Hz, 1H), 7.78 (dd, J=2.7, 1.5 Hz, 1H), 7.54 (d, J=2.6 Hz, 1H), 7.39 (s, 1H), 7.29 (d, J=2.6 Hz, 1H), 6.73 (dd, J=4.4, 2.6 Hz, 1H), 4.10-3.93 (m, 3H), 3.87 (d, J=0.8 Hz, 3H), 2.61 (d, J=0.8 Hz, 3H); MS (ES+): 413.0 (M+1).

Step-2: Preparation of (S)-1-(4-(4-((2-(2-(hydroxymethyl)pyrrolidin-1-yl)pyrrolo[2,1-f][1,2,4]triazin-4-yl)amino)-1H-imidazol-1-yl)-2,3-dimethoxyphenyl)ethanone (212g)

Compound 212g was prepared from 1-(4-(4-((2-chloropyrrolo[2,1-f][1,2,4]triazin-4-yl)amino)-1H-imidazol-1-yl)-2,3-dimethoxyphenyl)ethanone (212f) (0.4 g, 0.96 mmol), (S)-pyrrolidin-2-ylmethanol (0.60 g, 5.93 mmol) in NMP (10 mL) according to the procedure reported in step-2 of Scheme 76. This gave after workup and purification by flash column chromatography [silica gel, (40 g), eluting with ethyl acetate in hexane 0-100%] compound 212g (0.05 g, 11%) free base as an off white solid; The free base was repurified by reverse phase column chromatography [(silica gel C-18, 24 g), eluting with ACN in water (containing 0.1% HCl) from 0-100%] to afford (S)-1-(4-(4-((2-(2-(hydroxymethyl)pyrrolidin-1-yl)pyrrolo[2,1-f][1,2,4]triazin-4-yl)amino)-1H-imidazol-1-yl)-2,3-dimethoxyphenyl)ethanone (212g) (30 mg) HCl salt as an off-white solid; $^1$H NMR (300 MHz, DMSO-$d_6$): δ 10.59 (s, 1H), 8.38 (s, 1H), 8.02 (s, 1H), 7.52 (d, J=2.6 Hz, 1H), 7.45-7.33 (m, 2H), 7.13 (dd, J=4.5, 1.7 Hz, 1H), 6.41 (dd, J=4.5, 2.4 Hz, 1H), 4.27-4.13 (m, 1H), 3.97 (s, 3H), 3.85 (s, 3H), 3.78-3.66 (m, 1H), 3.62-3.27 (m, 3H), 2.59 (s, 3H), 2.15-1.78 (m, 4H). MS (ES+): 478.3 (M+1); MS (ES−): 512.3 (M+Cl).

Scheme 213

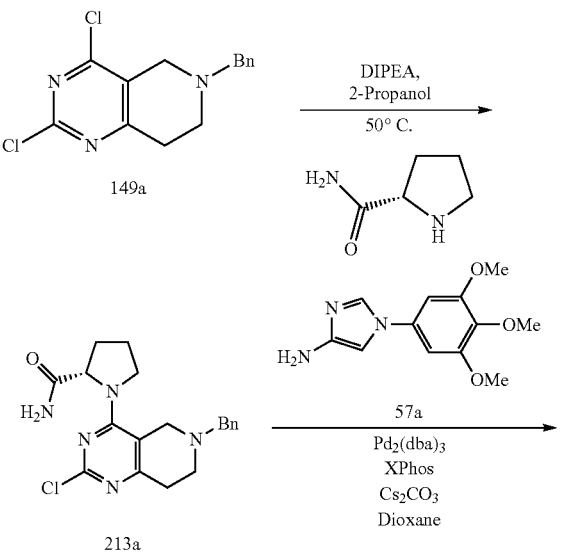

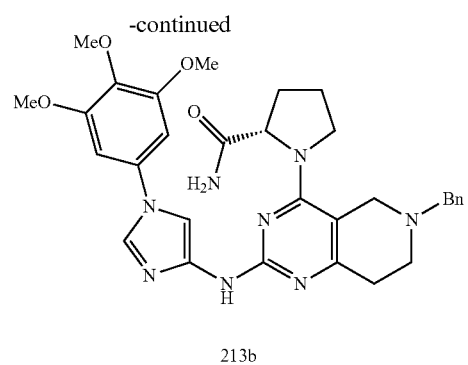

Preparation of (S)-1-(6-benzyl-2-((1-(3,4,5-trimethoxyphenyl)-1H-imidazol-4-yl)amino)-5,6,7,8-tetrahydropyrido[4,3-d]pyrimidin-4-yl)pyrrolidine-2-carboxamide (213b)

Step-1: Preparation of (S)-1-(6-benzyl-2-chloro-5,6,7,8-tetrahydropyrido[4,3-d]pyrimidin-4-yl)pyrrolidine-2-carboxamide (213a)

Compound 213a was prepared from 6-benzyl-2,4-dichloro-5,6,7,8-tetrahydropyrido[4,3-d]pyrimidine (149a) (0.5 g, 1.7 mmol) in 2-Propanol (5 mL) using (S)-pyrrolidine-2-carboxamide (194 mg, 1.7 mmol) and DIPEA (0.445 mL, 2.55 mmol) according to the procedure reported in step-1 of Scheme 96. This gave after workup and purification by flash column chromatography [silica gel (40 g), eluting with DMA 80 in chloroform (0 to 50%) (S)-1-(6-benzyl-2-chloro-5,6,7,8-tetrahydropyrido[4,3-d]pyrimidin-4-yl)pyrrolidine-2-carboxamide (213a) (496 mg, 78% yield) as a brown solid; 1H NMR (300 MHz, DMSO-$d_6$) δ 7.46-7.25 (m, 6H), 6.91 (s, 1H), 5.75 (s, 2H), 4.56-4.35 (m, 1H), 3.93-3.57 (m, 4H), 2.82-2.60 (m, 4H), 2.20-2.03 (m, 1H), 1.95-1.70 (m, 3H).

Step-2: Preparation of (S)-1-(6-benzyl-2-((1-(3,4,5-trimethoxyphenyl)-1H-imidazol-4-yl)amino)-5,6,7,8-tetrahydropyrido[4,3-d]pyrimidin-4-yl)pyrrolidine-2-carboxamide (213b)

Compound 213b was prepared from (S)-1-(6-benzyl-2-chloro-5,6,7,8-tetrahydropyrido[4,3-d]pyrimidin-4-yl)pyrrolidine-2-carboxamide (213a) (320 mg, 0.86 mmol), 1-(3,4,5-trimethoxyphenyl)-1H-imidazol-4-amine (57a) (268 mg, 1.08 mmol, free base), dicyclohexyl(2',4',6'-triisopropylbiphenyl-2-yl)phosphine (XPhos, 185 mg, 0.387 mmol), cesium carbonate (841 mg, 2.58 mmol) and Pd$_2$(dba)$_3$ (118 mg, 0.129 mmol) in 1,4-dioxane (15 mL) according to the procedure reported in step-3 of Scheme 101. This gave after workup and purification by flash column chromatography [silica gel (80 g), eluting with DMA 80 in CH$_2$Cl$_2$], followed by reverse phase column chromatography [(silica gel C-18, 24 g) eluting with acetonitrile and 0.1% HCl water] (S)-1-(6-benzyl-2-((1-(3,4,5-trimethoxyphenyl)-1H-imidazol-4-yl)amino)-5,6,7,8-tetrahydropyrido[4,3-d]pyrimidin-4-yl)pyrrolidine-2-carboxamide (213b) (125 mg, 25% yield) HCl salt as a white solid; $^1$H NMR (300 MHz, DMSO-$d_6$+D$_2$O) δ 8.50 (s, 1H), 7.78 (s, 1H), 7.60 (d, J=3.7 Hz, 2H), 7.56-7.41 (m, 3H), 7.12 (s, 2H), 4.76-4.51 (m, 3H), 4.49 (s, 2H), 3.87 (s, 6H), 3.81-3.63 (m, 5H), 3.43 (s, 2H), 3.11-2.98 (m, 2H), 2.35-2.14 (m, 1H), 2.08-1.75 (m, 3H); MS (ES+): 585.4 (M+1), (ES−): 619.4 (M+Cl); HPLC purity: 96.6%.

Scheme 214

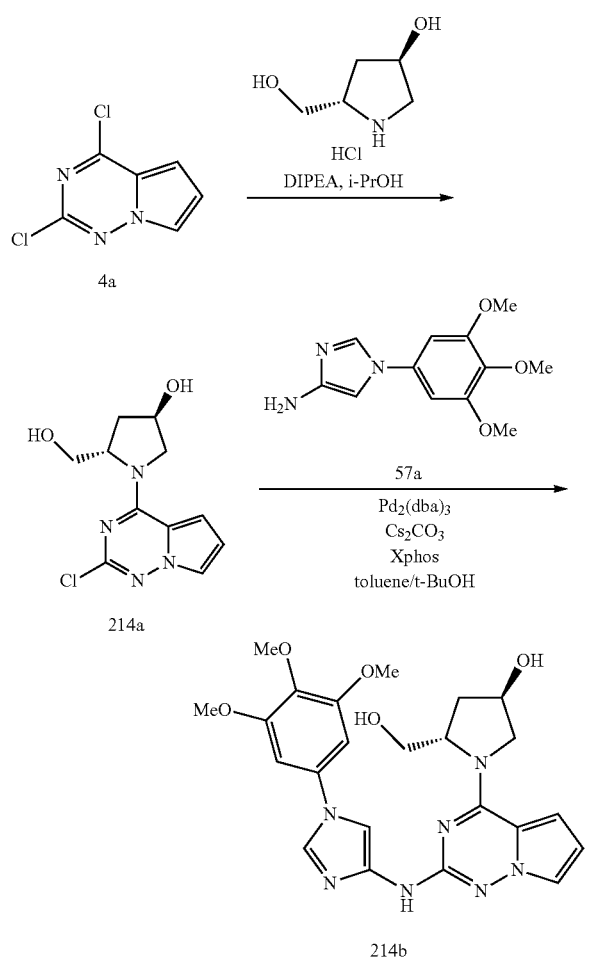

Preparation of (3R,5S)-5-(hydroxymethyl)-1-(2-((1-(3,4,5-trimethoxyphenyl)-1H-imidazol-4-yl)amino)pyrrolo[2,1-f][1,2,4]triazin-4-yl)pyrrolidin-3-ol (214b)

Step-1: Preparation of (3R,5S)-1-(2-chloropyrrolo[2,1-f][1,2,4]triazin-4-yl)-5-(hydroxymethyl)pyrrolidin-3-ol (214a)

Compound 214a was prepared from 2,4-dichloropyrrolo[2,1-f][1,2,4]triazine (4a) (400 mg, 2.13 mmol) in IPA (40 mL), (3R,5S)-5-(hydroxymethyl)pyrrolidin-3-ol hydrochloride (327 mg, 2.13 mmol), DIPEA (1.115 mL, 6.38 mmol) according to the procedure reported in step-1 of Scheme 96. This gave after workup and purification by flash column chromatography [silica gel (12 g), eluting with ethyl acetate in hexane from 0-50%] (3R,5S)-1-(2-chloropyrrolo[2,1-f][1,2,4]triazin-4-yl)-5-(hydroxymethyl)pyrrolidin-3-ol (214a) (425 mg, 74% yield) as a white solid; $^1$H NMR (300 MHz, DMSO-$d_6$) δ 7.75-7.67 (m, 1H), 6.97-6.86 (m, 1H), 6.73-6.61 (m, 1H), 5.14-5.00 (m, 1H, $D_2O$ exchangeable), 4.82 (t, J=5.8 Hz, 1H, $D_2O$ exchangeable), 4.56-4.40 (m, 2H), 4.08-3.95 (m, 1H), 3.91-3.75 (m, 2H), 3.66-3.46 (m, 1H), 2.35-2.12 (m, 1H), 2.09-1.88 (m, 1H).

Step-2: Preparation of (3R,5S)-5-(hydroxymethyl)-1-(2-((1-(3,4,5-trimethoxyphenyl)-1H-imidazol-4-yl)amino)pyrrolo[2,1-f][1,2,4]triazin-4-yl)pyrrolidin-3-ol (214b)

Compound 214b was prepared from (3R,5S)-1-(2-chloropyrrolo[2,1-f][1,2,4]triazin-4-yl)-5-(hydroxymethyl)pyrrolidin-3-ol (214a) (300 mg, 1.12 mmol) in toluene/t-BuOH (42 mL, Ratio: 5:2) using 1-(3,4,5-trimethoxyphenyl)-1H-imidazol-4-amine (57a) (334 mg, 1.34 mmol), $Pd_2(dba)_3$ (153 mg, 0.17 mmol), X-Phos (213 mg, 0.45 mmol) and $Cs_2CO_3$ (1273 mg, 3.91 mmol) according to the procedure reported in step-3 of Scheme 101. This gave after workup and purification by flash column chromatography [silica gel (24 g), eluting with DMA80 in DCM from 0-100%] followed by reverse phase flash column chromatography [(silica gel C-18 50 g), eluting with $CH_3CN$ in water (containing 0.1% HCl) from 0-100%](3R,5S)-5-(hydroxymethyl)-1-(2-((1-(3,4,5-trimethoxyphenyl)-1H-imidazol-4-yl)amino)pyrrolo[2,1-f][1,2,4]triazin-4-yl)pyrrolidin-3-ol (214b) (395 mg, 74% yield) HCl salt as a white solid; $^1$H NMR (300 MHz, DMSO-$d_6$) δ 9.59 (s, 1H, $D_2O$ exchangeable), 9.37 (s, 1H), 7.92 (bs, 1H, $D_2O$ exchangeable), 7.65 (s, 1H), 7.15 (s, 2H), 6.87-6.75 (m, 1H), 6.60-6.50 (m, 1H), 5.42 (brs, 2H, $D_2O$ exchangeable), 4.67-4.56 (m, 1H), 4.56-4.45 (m, 1H), 4.08-3.97 (m, 1H), 3.90 (s, 6H), 3.86-3.75 (m, 2H), 3.71 (s, 3H), 3.65-3.52 (m, 1H), 2.23-2.11 (m, 1H), 2.02-1.86 (m, 1H); MS (ES+): 482.3 (M+1); (ES−): 470.4 (M−1).

Scheme 215

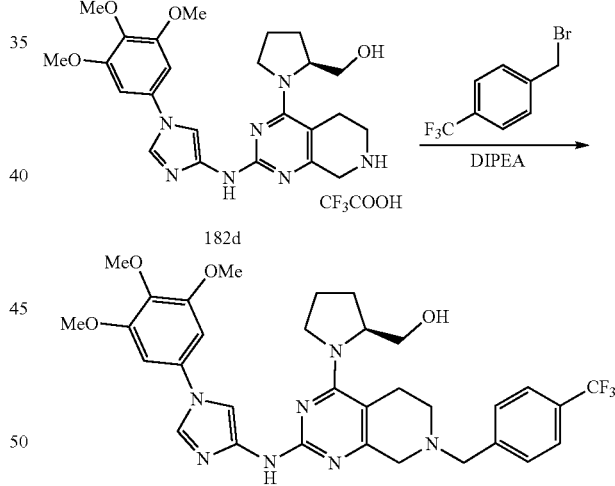

Preparation of (S)-(1-(7-(4-(trifluoromethyl)benzyl)-2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (215a)

To a stirred suspension of (S)-(1-(2-(1-(3,4,5-trimethoxyphenyl)-1H-imidazol-4-ylamino)-5,6,7,8-tetrahydropyrido[3,4-d]pyrimidin-4-yl)pyrrolidin-2-yl)methanol (182d) (119 mg, 0.2 mmol, 2,2,2-trifluoroacetate salt), 1-(bromomethyl)-4-(trifluoromethyl)benzene (96 mg, 0.4 mmol) in DCM (2.5 mL) was added DIPEA (0.14 mL, 0.8 mmol) and stirred at room temperature for 12 h. Reaction mixture was concentrated in vacuum, purified by flash column chromatography (silica gel, 24 g eluting with DMA-80 in dichloromethane) followed by purification by reverse phase column chromatography [(silica gel C-18, 25 g), eluting with 0.1% HCl and acetonitrile) to afford (S)-(1-(7-(4-(trifluoromethyl)benzyl)-2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (215a) (47 mg, 37% yield) HCl salt as a white solid; $^1$H NMR (300 MHz, DMSO-$d_6$) δ 10.20 (s, 1H, D$_2$O exchangeable), 8.67 (s, 1H), 7.96 (d, J=8.3 Hz, 2H), 7.88 (d, J=8.1 Hz, 2H), 7.74 (d, J=1.7 Hz, 1H), 7.01 (s, 2H), 4.68-4.46 (m, 5H), 4.31-4.01 (m, 2H), 3.87 (s, 6H), 3.69 (s, 3H), 3.67-3.55 (m, 2H), 3.53-3.36 (m, 2H), 3.37-3.16 (m, 2H), 3.13-2.90 (m, 1H), 2.10-1.78 (m, 4H); $^{19}$F NMR (282 MHz, DMSO-$d_6$) δ −61.19; MS (ES+): 640.4 (M+1), (ES−): 674.4 (M+Cl); HPLC purity: 96.4%.

Scheme 216

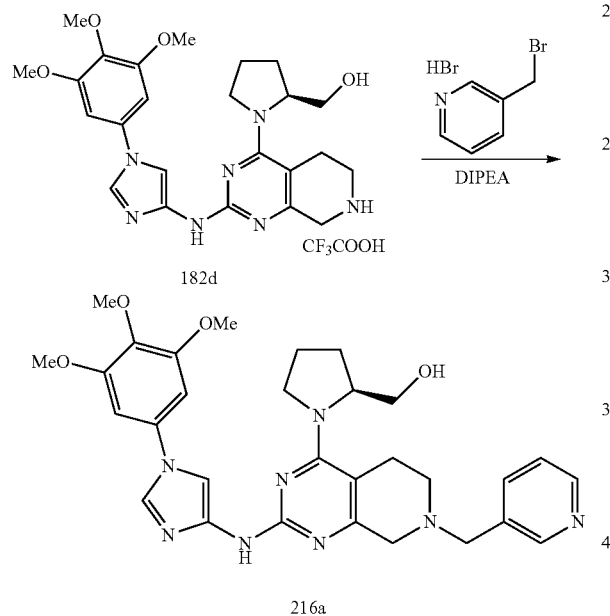

216a

Preparation of (S)-(1-(7-(pyridin-3-ylmethyl)-2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (216a)

To a stirred suspension of (S)-(1-(2-(1-(3,4,5-trimethoxyphenyl)-1H-imidazol-4-ylamino)-5,6,7,8-tetrahydropyrido[3,4-d]pyrimidin-4-yl)pyrrolidin-2-yl)methanol (182d) (119 mg, 0.2 mmol, 2,2,2-trifluoroacetate salt), 3-(bromomethyl)pyridine hydrobromide (101 mg, 0.4 mmol) in DCM (2.5 mL) was added DIPEA (0.14 mL, 0.8 mmol) and stirred at room temperature for 12 h. Reaction mixture was concentrated in vacuum, purified by flash column chromatography (silica gel, 24 g eluting with DMA 80 in dichloromethane) followed by purification by reverse phase column chromatography [(silica gel C-18, 25 g, eluting with 0.1% HCl and acetonitrile)] to afford (S)-(1-(7-(pyridin-3-ylmethyl)-2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (216a) (19 mg, 17% yield) HCl salt as a light yellow solid; $^1$H NMR (300 MHz, DMSO-$d_6$) δ 10.27 (s, 1H, D$_2$O exchangeable), 9.16 (s, 1H), 9.01-8.86 (m, 1H), 8.75 (d, J=7.9 Hz, 2H), 8.03 (s, 1H), 7.77 (s, 1H), 7.03 (s, 2H), 5.21-4.60 (m, 3H), 4.29-4.21 (m, 2H), 3.87 (s, 6H), 3.68 (s, 3H), 3.53-3.36 (m, 2H), 3.37-3.16 (m, 2H), 3.15-2.90 (m, 1H), 2.15-1.73 (m, 4H); MS (ES+): 573.4 (M+1), 595.4 (M+Na), (ES−): 607.4 (M+Cl); HPLC purity: 99.09%.

Scheme 217

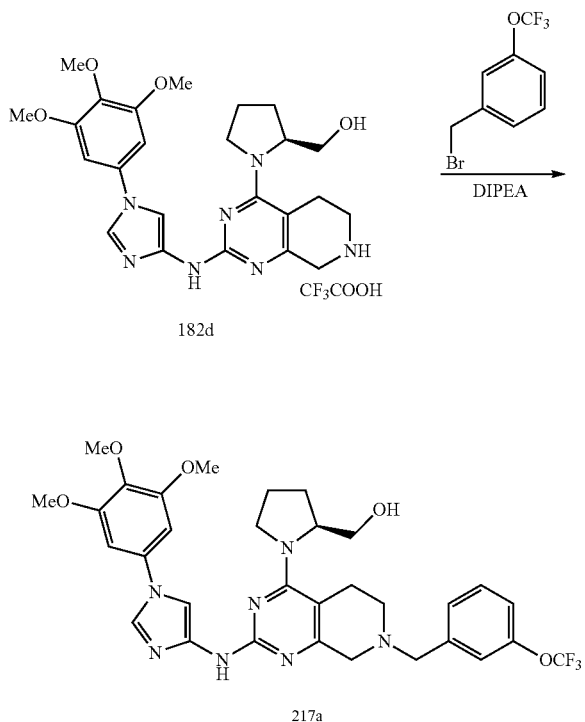

217a

Preparation of (S)-(1-(7-(3-(trifluoromethoxy)benzyl)-2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (217a)

To a stirred suspension of (S)-(1-(2-(1-(3,4,5-trimethoxyphenyl)-1H-imidazol-4-ylamino)-5,6,7,8-tetrahydropyrido[3,4-d]pyrimidin-4-yl)pyrrolidin-2-yl)methanol (182d) (119 mg, 0.2 mmol, 2,2,2-trifluoroacetate salt), 1-(bromomethyl)-3-(trifluoromethoxy)benzene (102 mg, 0.40 mmol) in DCM (2.5 mL) was added DIPEA (0.14 mL, 0.8 mmol) and stirred at room temperature for 12 h. Reaction mixture was concentrated in vacuum, purified by flash column chromatography (silica gel, 24 g eluting with DMA 80 in dichloromethane) followed by purification by reverse phase column chromatography [(silica gel C-18, 25 g, eluting with 0.1% HCl and acetonitrile] to afford (S)-(1-(7-(3-(trifluoromethoxy)benzyl)-2-((1-(3,4,5-trimethoxyphenyl)-1H-imidazol-4-yl)amino)-5,6,7,8-tetrahydropyrido[3,4-d]pyrimidin-4-yl)pyrrolidin-2-yl)methanol (217a) (55 mg, 42% yield) as a white solid; $^1$H NMR (300 MHz, DMSO-$d_6$) δ 10.17 (s, 1H, D$_2$O exchangeable), 8.68 (s, 1H), 7.77 (d, J=16.6 Hz, 3H), 7.64 (t, J=7.9 Hz, 1H), 7.50 (d, J=8.0 Hz, 1H), 7.01 (s, 2H), 4.67-4.47 (m, 2H), 4.48-4.00 (m, 2H), 3.87 (s, 6H), 3.69 (s, 3H), 3.67-3.54 (m, 1H), 3.52-3.36 (m, 1H), 3.37-3.08 (m, 1H), 3.11-2.78 (m, 1H), 1.94 (d, J=17.5

Hz, 4H); $^{19}$F NMR (282 MHz, DMSO-d$_6$) δ −56.66; MS (ES+): 656.4 (M+1), 678.3 (M+Na), 690.3 (M+Cl); HPLC purity 97.5%.

Scheme 218

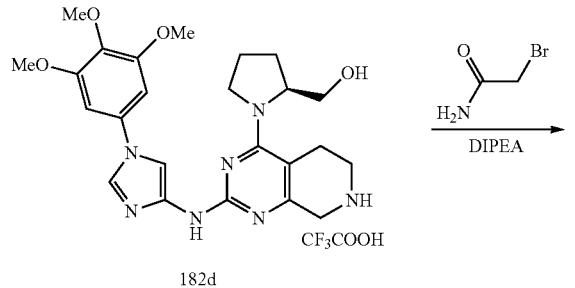

182d

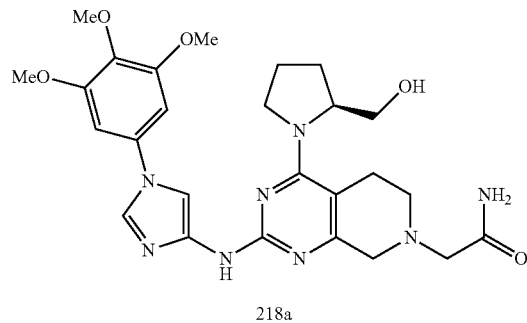

218a

Preparation of (S)-2-(4-(2-(hydroxymethyl)pyrrolidin-1-yl)-2-((1-(3,4,5-trimethoxyphenyl)-1H-imidazol-4-yl)amino)-5,6-dihydropyrido[3,4-d]pyrimidin-7(8H)-yl)acetamide (218a)

To a stirred suspension of (S)-(1-(2-(1-(3,4,5-trimethoxyphenyl)-1H-imidazol-4-ylamino)-5,6,7,8-tetrahydropyrido[3,4-d]pyrimidin-4-yl)pyrrolidin-2-yl)methanol (182d) (119 mg, 0.2 mmol, 2,2,2-trifluoroacetate salt), 2-bromoacetamide (55 mg, 0.4 mmol) in DCM (2.5 mL) was added DIPEA (0.14 mL, 0.8 mmol) and stirred at room temperature for 12 h. Reaction mixture was concentrated in vacuum, purified by flash column chromatography (silica gel, 24 g eluting with DMA 80 in dichloromethane) followed by purification by reverse phase column chromatography [(silica gel C-18, 25 g), eluting with 0.1% HCl and acetonitrile] to afford (S)-2-(4-(2-(hydroxymethyl)pyrrolidin-1-yl)-2-((1-(3,4,5-trimethoxyphenyl)-1H-imidazol-4-yl)amino)-5,6-dihydropyrido[3,4-d]pyrimidin-7(8H)-yl)acetamide (218a) (32 mg, 30% yield) HCl salt as a white solid; $^1$H NMR (300 MHz, DMSO-d$_6$) δ 10.16 (s, 1H, D$_2$O exchangeable), 8.68 (s, 1H), 8.10 (s, 1H, D$_2$O exchangeable), 7.77 (s, 1H, D$_2$O exchangeable), 7.74 (s, 1H), 7.02 (s, 2H), 4.68-4.45 (m, 1H), 4.39 (s, 2H), 4.29-3.99 (m, 3H), 3.88 (s, 6H), 3.87-3.71 (m, 1H), 3.69 (s, 3H), 3.67-3.49 (m, 2H), 3.49-3.27 (m, 2H), 3.27-3.10 (m, 1H), 3.09-2.91 (m, 1H), 2.07-1.81 (m, 4H); MS (ES+): 539.3 (M+1), 561.3 (M+Na), (ES−): 573.4 (M+Cl); HPLC purity: 98.3%.

Scheme 219

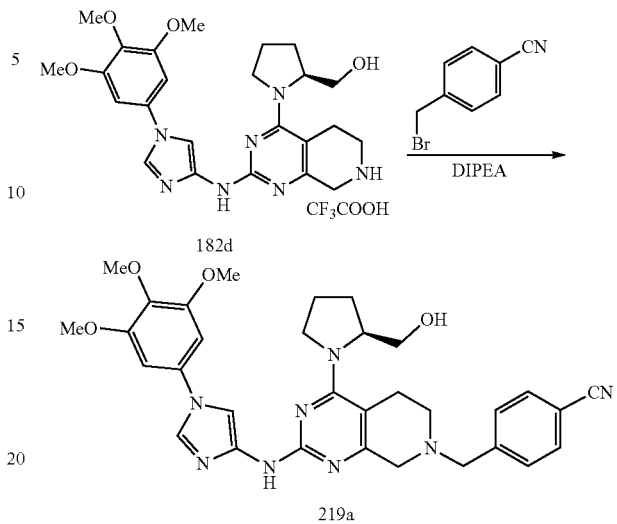

Preparation of (S)-4-((4-(2-(hydroxymethyl)pyrrolidin-1-yl)-2-((1-(3,4,5-trimethoxyphenyl)-1H-imidazol-4-yl)amino)-5,6-dihydropyrido[3,4-d]pyrimidin-7(8H)-yl)methyl)benzonitrile (219a)

To a stirred suspension of (S)-(1-(2-(1-(3,4,5-trimethoxyphenyl)-1H-imidazol-4-ylamino)-5,6,7,8-tetrahydropyrido[3,4-d]pyrimidin-4-yl)pyrrolidin-2-yl)methanol (182d) (119 mg, 0.2 mmol, 2,2,2-trifluoroacetate salt), 4-(bromomethyl)benzonitrile (78 mg, 0.4 mmol) in DCM (2.5 mL) was added DIPEA (0.14 mL, 0.8 mmol) and stirred at room temperature for 12 h. Reaction mixture was concentrated in vacuum, purified by flash column chromatography (silica gel, 24 g eluting with DMA-80 in dichloromethane) followed by purification by reverse phase column chromatography [(silica gel C-18 25 g), eluting with 0.1% HCl and acetonitrile] to afford (S)-4-((4-(2-(hydroxymethyl)pyrrolidin-1-yl)-2-((1-(3,4,5-trimethoxyphenyl)-1H-imidazol-4-yl)amino)-5,6-dihydropyrido[3,4-d]pyrimidin-7(8H)-yl)methyl)benzonitrile (219a) (52 mg, 44% yield) HCl salt as a white solid; $^1$H NMR (300 MHz, DMSO-d$_6$-D$_2$O) δ 8.78 (s, 1H), 8.01 (d, J=8.0 Hz, 2H), 7.92 (d, J=8.0 Hz, 2H), 7.77 (s, 1H), 7.03 (s, 2H), 4.70-4.49 (m, 3H), 4.33-4.09 (m, 2H), 3.88 (s, 6H), 3.87-3.70 (m, 1H), 3.66-3.56 (m, 2H), 3.55-3.37 (m, 2H), 3.37-3.23 (m, 2H), 3.19-2.98 (m, 1H), 1.94 (tt, J=18.8, 8.8 Hz, 4H); MS (ES+): 597.4 (M+1), (ES−): 631.4 (M+Cl); HPLC purity: 97.2%.

Scheme 220

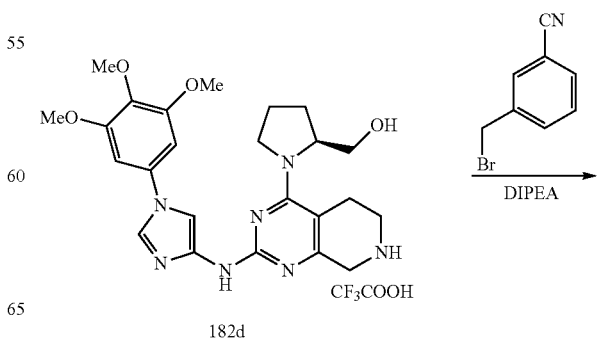

182d

-continued

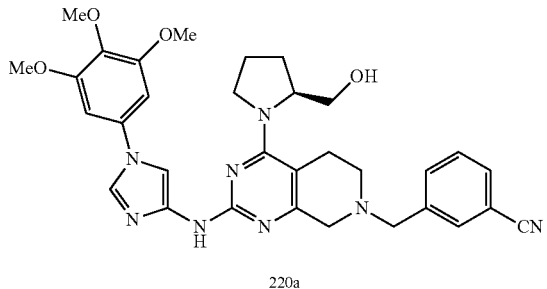

220a

Preparation of (S)-3-((4-(2-(hydroxymethyl)pyrrolidin-1-yl)-2-((1-(3,4,5-trimethoxyphenyl)-1H-imidazol-4-yl)amino)-5,6-dihydropyrido[3,4-d]pyrimidin-7(8H)-yl)methyl)benzonitrile (220a)

To a stirred suspension of (S)-(1-(2-(1-(3,4,5-trimethoxyphenyl)-1H-imidazol-4-ylamino)-5,6,7,8-tetrahydropyrido[3,4-d]pyrimidin-4-yl)pyrrolidin-2-yl)methanol (182d) (119 mg, 0.2 mmol, 2,2,2-trifluoroacetate salt), 3-(bromomethyl)benzonitrile (78 mg, 0.4 mmol) in DCM (2.5 mL) was added DIPEA (0.14 mL, 0.8 mmol) and stirred at room temperature for 12 h. Reaction mixture was concentrated in vacuum, purified by flash column chromatography (silica gel, 24 g eluting with DMA 80 in dichloromethane) followed by purification by reverse phase column chromatography [(silica gel C-18, 25 g), eluting with 0.1% HCl and acetonitrile] to afford (S)-3-((4-(2-(hydroxymethyl)pyrrolidin-1-yl)-2-((1-(3,4,5-trimethoxyphenyl)-1H-imidazol-4-yl)amino)-5,6-dihydropyrido[3,4-d]pyrimidin-7(8H)-yl)methyl)benzonitrile (220a) (56 mg, 47% yield) HCl salt as a white solid; $^1$H NMR (300 MHz, DMSO-$d_6$) δ 10.22 (s, 1H, D$_2$O exchangeable), 8.71 (s, 1H), 8.23 (s, 1H), 8.07 (d, J=7.8 Hz, 1H), 7.97 (d, J=7.7 Hz, 1H), 7.72 (dd, J=14.3, 6.1 Hz, 2H), 7.02 (s, 2H), 4.59-4.51 (m, 1H), 4.33-4.01 (m, 2H), 3.87 (s, 6H), 3.68 (s, 3H), 3.66-3.51 (m, 1H), 3.51-3.37 (m, 2H), 3.38-3.20 (m, 2H), 3.20-2.91 (m, 1H), 2.10-1.75 (m, 4H); MS (ES+) 597.5 (M+1); HPLC purity: 91.15%.

Scheme 221

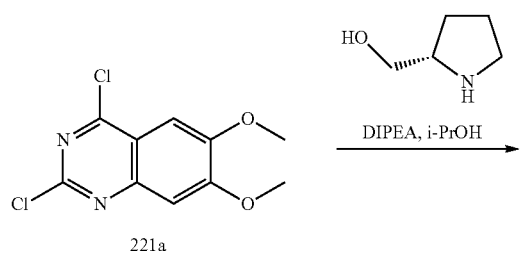

221a

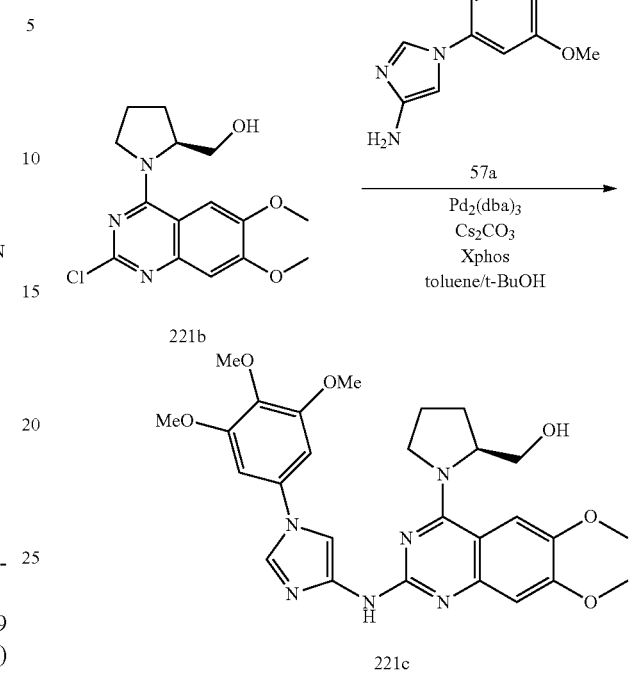

Preparation of (S)-(1-(6,7-dimethoxy-2-((1-(3,4,5-trimethoxyphenyl)-1H-imidazol-4-yl)amino)quinazolin-4-yl)pyrrolidin-2-yl)methanol (221c)

Step-1: Preparation of (S)-(1-(2-chloro-6,7-dimethoxyquinazolin-4-yl)pyrrolidin-2-yl)methanol (221b)

Compound 221b was prepared from 2,4-dichloro-6,7-dimethoxyquinazoline (221a) (1.0 g, 3.86 mmol; CAS #27631-29-4) in IPA (40 mL), (S)-pyrrolidin-2-ylmethanol (390 mg, 3.86 mmol), DIPEA (1.35 mL, 7.72 mmol) according to the procedure reported in step-1 of Scheme 96. This gave after workup and purification by flash column chromatography [silica gel (24 g), eluting with DMA-80 in DCM from 0-50%] (S)-(1-(2-chloro-6,7-dimethoxyquinazolin-4-yl)pyrrolidin-2-yl)methanol (221b) (1 g, 80% yield) as a white solid; $^1$H NMR (300 MHz, DMSO-$d_6$) δ 7.51 (s, 1H), 7.09 (s, 1H), 4.86 (t, J=5.5 Hz, 1H, D$_2$O exchangeable), 4.62-4.50 (m, 1H), 4.16-4.00 (m, 1H), 4.00-3.92 (m, 1H), 3.89 (s, 3H), 3.88 (s, 3H), 3.74-3.51 (m, 2H), 2.13-1.93 (m, 3H), 1.93-1.75 (m, 1H).

Step-2: Preparation of (S)-(1-(6,7-dimethoxy-2-((1-(3,4,5-trimethoxyphenyl)-1H-imidazol-4-yl)amino)quinazolin-4-yl)pyrrolidin-2-yl)methanol (221c)

Compound 221c was prepared from (S)-(1-(2-chloro-6,7-dimethoxyquinazolin-4-yl)pyrrolidin-2-yl)methanol (221b) (350 mg, 1.08 mmol) in toluene/t-BuOH (40 mL, Ratio: 5:2) using 1-(3,4,5-trimethoxyphenyl)-1H-imidazol-4-amine (57a) (323 mg, 1.30 mmol), Pd$_2$(dba)$_3$ (148 mg, 0.16 mmol), X-Phos (206 mg, 0.43 mmol) and Cs$_2$CO$_3$ (881 mg, 2.7 mmol) according to the procedure reported in step-3 of Scheme 101. This gave after workup and purification by flash column chromatography [silica gel (24 g), eluting with DMA-80 in DCM from 0-100%] followed by reverse phase flash column chromatography [(silica gel C-18 50 g), eluting with CH$_3$CN in water (containing 0.1% HCl) from 0-100%] (S)-(1-(6,7-dimethoxy-2-((1-(3,4,5-trimethoxyphenyl)-1H-imidazol-4-yl)amino)quinazolin-4-yl)pyrrolidin-2-yl)methanol (221c) (286 mg, 49% yield) as an off white solid; $^1$H NMR (300 MHz, Methanol-d$_4$) δ 8.81 (s, 1H), 7.81 (s, 1H), 7.66 (s, 1H), 7.19 (s, 1H), 7.01 (s, 2H), 4.80 (s, 1H), 4.31-4.16 (m, 2H), 4.01 (s, 3H), 3.94 (d, J=2.9 Hz, 9H), 3.86-3.79 (m, 5H), 2.29-1.96 (m, 4H); MS (ES+): 537.4 (M+1); (ES−): 535.4 (M−1); HPLC purity: 97.62%.

procedure reported in step-1 of Scheme 96. This gave after workup and purification by flash column chromatography [silica gel (12 g), eluting with EtOAc in hexane from 0-50%] (S)-2-(1-(2-chloropyrrolo[2,1-f][1,2,4]triazin-4-yl)pyrrolidin-2-yl)propan-2-ol (222a) (260 mg, 58% yield) as a white solid; $^1$H NMR (300 MHz, DMSO-d$_6$) δ 7.73 (s, 1H), 7.02 (d, J=4.5 Hz, 1H), 6.74-6.61 (m, 1H), 4.81 (s, 1H), 4.75-4.61 (m, 1H), 4.15-3.91 (m, 2H), 2.30-2.13 (m, 1H), 2.13-2.01 (m, 1H), 1.96-1.74 (m, 2H), 1.14 (s, 3H), 1.10 (s, 3H).

Step-2: Preparation of (S)-2-(1-(2-((1-(3,4,5-trimethoxyphenyl)-1H-imidazol-4-yl)amino)pyrrolo[2,1-f][1,2,4]triazin-4-yl)pyrrolidin-2-yl)propan-2-ol (222b)

Compound 222b was prepared from (S)-2-(1-(2-chloropyrrolo[2,1-f][1,2,4]triazin-4-yl)pyrrolidin-2-yl)propan-2-ol (222a) (250 mg, 0.89 mmol) in toluene/t-BuOH (40 mL, Ratio: 5:2) using 1-(3,4,5-trimethoxyphenyl)-1H-imidazol-4-amine (57a) (266 mg, 1.07 mmol), Pd$_2$(dba)$_3$ (122 mg, 0.13 mmol), X-Phos (170 mg, 0.36 mmol) and Cs$_2$CO$_3$ (725 mg, 2.23 mmol) according to the procedure reported in step-3 of Scheme 101. This gave after workup and purification by flash column chromatography [silica (24 g), eluting with DMA80 in DCM from 0-100%] followed by reverse phase flash column chromatography [(silica gel C-18 50 g), eluting with CH$_3$CN in water (containing 0.1% HCl) from 0-100%] (S)-2-(1-(2-((1-(3,4,5-trimethoxyphenyl)-1H-imidazol-4-yl)amino)pyrrolo[2,1-f][1,2,4]triazin-4-yl)pyrrolidin-2-yl)propan-2-ol (222b) (138 mg, 31% yield) as a white solid; $^1$H NMR (300 MHz, DMSO-d$_6$) δ 9.73 (s, 1H, D$_2$O exchangeable), 9.29 (s, 1H), 7.98-7.88 (m, 1H, D$_2$O exchangeable), 7.70 (s, 1H), 7.13 (s, 2H), 7.02-6.91 (m, 1H), 6.64-6.51 (m, 1H), 4.79 (d, J=7.6 Hz, 1H), 4.16-3.95 (m, 2H), 3.89 (s, 6H), 3.71 (s, 3H), 2.29-2.11 (m, 1H), 2.07-1.79 (m, 3H), 1.16 (s, 3H), 1.13 (s, 3H); MS (ES+): 494.4 (M+1); 516.4 (M+Na); (ES−): 528.4 (M+Cl).

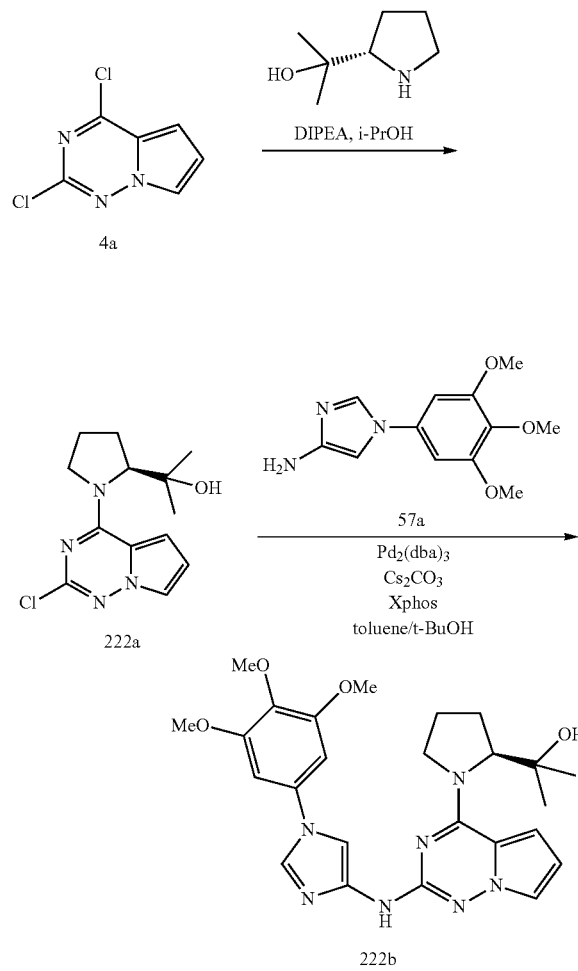

Preparation of (S)-2-(1-(2-((1-(3,4,5-trimethoxyphenyl)-1H-imidazol-4-yl)amino)pyrrolo[2,1-f][1,2,4]triazin-4-yl)pyrrolidin-2-yl)propan-2-ol (222b)

Step-1: Preparation of (S)-2-(1-(2-chloropyrrolo[2,1-f][1,2,4]triazin-4-yl)pyrrolidin-2-yl)propan-2-ol (222a)

Compound 222a was prepared from 2,4-dichloropyrrolo[1,2-f][1,2,4]triazine (4a) (300 mg, 1.6 mmol) in IPA (10 mL), (S)-2-(pyrrolidin-2-yl)propan-2-ol (206 mg, 1.6 mmol), DIPEA (0.56 mL, 3.19 mmol) according to the

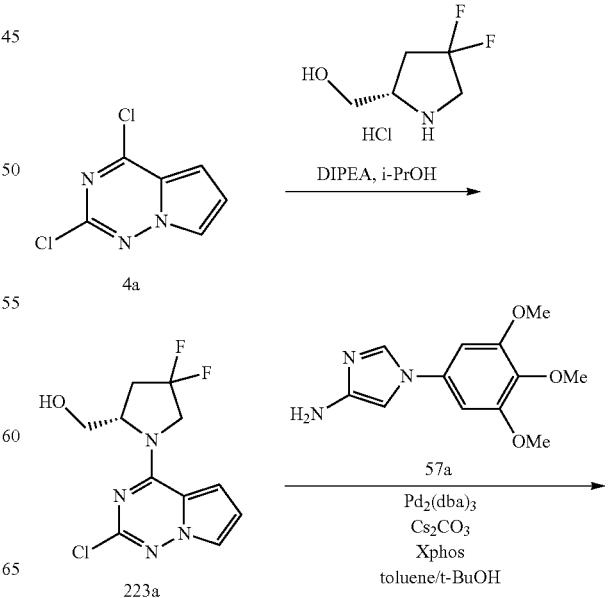

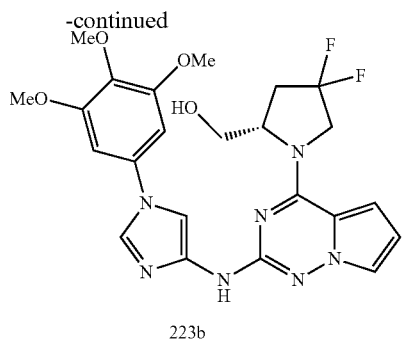

223b

Preparation of (S)-(4,4-difluoro-1-(2-((1-(3,4,5-trimethoxyphenyl)-1H-imidazol-4-yl)amino)pyrrolo[2,1-f][1,2,4]triazin-4-yl)pyrrolidin-2-yl)methanol (223b)

Step-1: Preparation of (S)-(1-(2-chloropyrrolo[2,1-f][1,2,4]triazin-4-yl)-4,4-difluoropyrrolidin-2-yl)methanol (223a)

Compound 223a was prepared from 2,4-dichloropyrrolo[2,1-f][1,2,4]triazine (4a) (1.30 g, 6.91 mmol) in IPA (10 mL), (S)-(4,4-difluoropyrrolidin-2-yl)methanol hydrochloride (1.2 g, 6.91 mmol), DIPEA (3.62 mL, 20.74 mmol) according to the procedure reported in step-1 of Scheme 96. This gave after workup and purification by flash column chromatography [silica (12 g), eluting with ethyl acetate in hexane from 0-50%] (S)-(1-(2-chloropyrrolo[2,1-f][1,2,4]triazin-4-yl)-4,4-difluoropyrrolidin-2-yl)methanol (223a) (1.5 g, 75% yield) as a white solid; $^1$H NMR (300 MHz, DMSO-$d_6$) δ 7.81 (s, 1H), 7.05 (s, 1H), 6.75 (s, 1H), 5.37-5.00 (m, 1H, D$_2$O exchangeable), 4.89-4.61 (m, 1H), 4.52-4.21 (m, 2H), 3.79-3.53 (m, 2H), 2.81-2.57 (m, 2H).

Step-2: Preparation of (S)-(4,4-difluoro-1-(2-((1-(3,4,5-trimethoxyphenyl)-1H-imidazol-4-yl)amino)pyrrolo[2,1-f][1,2,4]triazin-4-yl)pyrrolidin-2-yl)methanol (223b)

Compound 223b was prepared from (S)-(1-(2-chloropyrrolo[2,1-f][1,2,4]triazin-4-yl)-4,4-difluoropyrrolidin-2-yl)methanol (223a) (250 mg, 0.87 mmol) in toluene/t-BuOH (20 mL, Ratio: 5:2) using 1-(3,4,5-trimethoxyphenyl)-1H-imidazol-4-amine (57a) (259 mg, 0.87 mmol), Pd$_2$(dba)$_3$ (119 mg, 0.13 mmol), X-Phos (165 mg, 0.35 mmol) and Cs$_2$CO$_3$ (705 mg, 2.17 mmol) according to the procedure reported in step-3 of Scheme 101. This gave after workup and purification by flash column chromatography [silica gel (24 g), eluting with DMA-80 in DCM from 0-100%] followed by reverse phase flash column chromatography [(silica gel C-18 50 g), eluting with CH$_3$CN in water (containing 0.1% HCl) from 0-100%] (S)-(4,4-difluoro-1-(2-((1-(3,4,5-trimethoxyphenyl)-1H-imidazol-4-yl)amino)pyrrolo[2,1-f][1,2,4]triazin-4-yl)pyrrolidin-2-yl)methanol (223b) (233 mg, 54% yield) as a white solid; $^1$H NMR (300 MHz, DMSO-$d_6$) δ 9.57 (s, 1H, D$_2$O exchangeable), 9.25 (s, 1H), 7.92 (s, 1H, D$_2$O exchangeable), 7.69 (s, 1H), 7.13 (s, 2H), 6.94-6.85 (m, 1H), 6.63-6.53 (m, 1H), 4.80 (s, 1H), 4.52-4.20 (m, 2H), 3.89 (s, 6H), 3.77-3.64 (m, 5H), 2.78-2.54 (m, 2H); $^{19}$F NMR (282 MHz, DMSO) δ −95.62; MS (ES+): 502.3 (M+1); 524.3 (M+Na), (ES−): 536.3 (M+Cl); HPLC purity: 99.45%.

Scheme 224

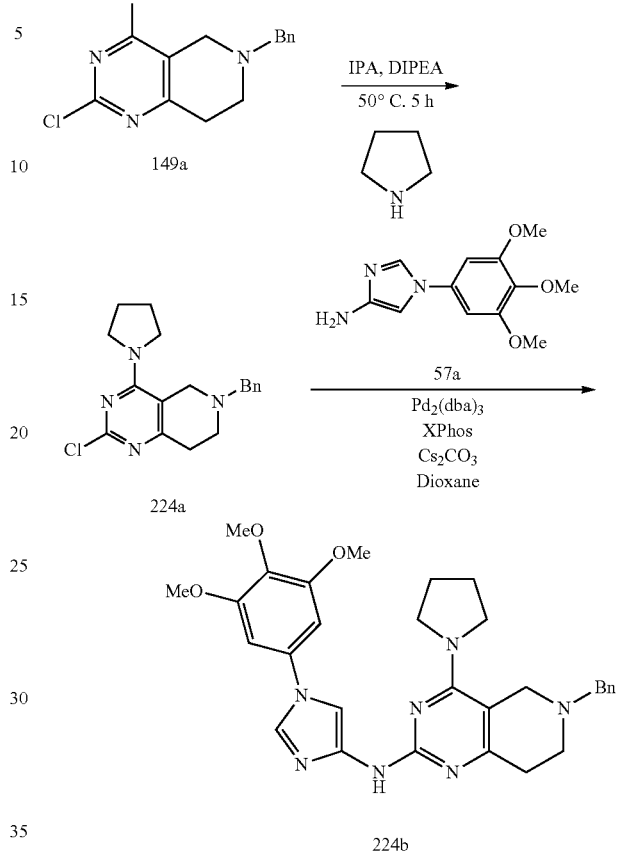

Preparation of 6-benzyl-4-(pyrrolidin-1-yl)-N-(1-(3,4,5-trimethoxyphenyl)-1H-imidazol-4-yl)-5,6,7,8-tetrahydropyrido[4,3-d]pyrimidin-2-amine (224b)

Step-1: Preparation of 6-benzyl-2-chloro-4-(pyrrolidin-1-yl)-5,6,7,8-tetrahydropyrido[4,3-d]pyrimidine (224a)

Compound 224a was prepared from 6-benzyl-2,4-dichloro-5,6,7,8-tetrahydropyrido[4,3-d]pyrimidine (149a) (0.5 g, 1.7 mmol) in 2-Propanol (5 mL) using pyrrolidine (0.121 g, 1.700 mmol) and DIPEA (0.89 mL, 5.1 mmol) according to the procedure reported in step-1 of Scheme 96. This gave after workup and purification by flash column chromatography [silica gel (40 g), eluting with (9:1) ethyl acetate/methanol in hexanes) 6-benzyl-2-chloro-4-(pyrrolidin-1-yl)-5,6,7,8-tetrahydropyrido[4,3-d]pyrimidine (224a) (430 mg, 77% yield) as a solid; $^1$H NMR (300 MHz, DMSO-$d_6$) δ 7.42-7.19 (m, 5H), 3.70-3.60 (m, 4H), 3.58-3.44 (m, 4H), 2.65 (s, 4H), 1.89-1.72 (m, 4H).

Step-2: Preparation of 6-benzyl-4-(pyrrolidin-1-yl)-N-(1-(3,4,5-trimethoxyphenyl)-1H-imidazol-4-yl)-5,6,7,8-tetrahydropyrido[4,3-d]pyrimidin-2-amine (224b)

Compound 224b was prepared from 6-benzyl-2-chloro-4-(pyrrolidin-1-yl)-5,6,7,8-tetrahydropyrido[4,3-d]pyrimidine (224a) (0.33 g, 1 mmol), 1-(3,4,5-trimethoxyphenyl)-

1H-imidazol-4-amine (57a) (287 mg, 1.15 mmol, free base), dicyclohexyl(2',4',6'-triisopropylbiphenyl-2-yl)phosphine (XPhos, 215 mg, 0.45 mmol), cesium carbonate (977 mg, 3 mmol) and Pd$_2$(dba)$_3$ (137 mg, 0.15 mmol) in 1,4-dioxane (15 mL) according to the procedure reported in step-3 of Scheme 101. This gave after workup and purification by flash column chromatography [silica gel (80 g), eluting with DMA-80 in CH$_2$Cl$_2$], followed by reverse phase column chromatography [(silica gel C-18, 24 g) eluting with acetonitrile and 0.1% HCl water]6-benzyl-4-(pyrrolidin-1-yl)-N-(1-(3,4,5-trimethoxyphenyl)-1H-imidazol-4-yl)-5,6,7,8-tetrahydropyrido[4,3-d]pyrimidin-2-amine (224b) (72 mg, 13% yield) HCl salt as a light yellow solid; $^1$H NMR (300 MHz, DMSO-d$_6$) δ 12.09 (s, 1H, D$_2$O exchangeable), 10.44 (s, 1H, D$_2$O exchangeable), 8.39 (s, 1H), 7.78-7.71 (m, 1H), 7.71-7.64 (m, 2H), 7.55-7.43 (m, 3H), 6.95 (s, 2H), 4.65-4.00 (m, 4H), 3.86 (s, 6H), 3.85-3.69 (m, 4H), 3.68 (s, 3H), 3.37-3.01 (m, 4H), 2.06-1.74 (m, 4H); MS (ES+): 542.4 (M+1), (ES−): 576.3 (M+Cl). HPLC purity: 95.59%.

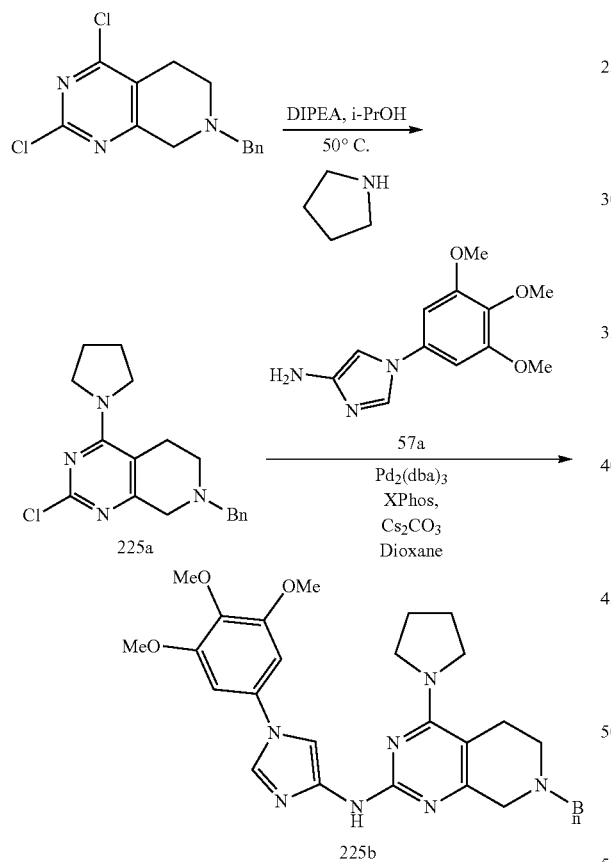

Scheme 225

225a

225b

Preparation of 7-benzyl-4-(pyrrolidin-1-yl)-N-(1-(3,4,5-trimethoxyphenyl)-1H-imidazol-4-yl)-5,6,7,8-tetrahydropyrido[3,4-d]pyrimidin-2-amine (225b)

Step-1: Preparation of 7-benzyl-2-chloro-4-(pyrrolidin-1-yl)-5,6,7,8-tetrahydropyrido[3,4-d]pyrimidine (225a)

Compound 225a was prepared from 7-benzyl-2,4-dichloro-5,6,7,8-tetrahydropyrido[3,4-d]pyrimidine (153a) (0.5 g, 1.7 mmol) in 2-Propanol (5 mL) using pyrrolidine (121 mg, 1.7 mmol) and DIPEA (0.89 mL, 5.1 mmol) according to the procedure reported in step-1 of Scheme 96. This gave after workup and purification by flash column chromatography [silica gel (40 g), eluting with DMA-80 in DCM] 7-benzyl-2-chloro-4-(pyrrolidin-1-yl)-5,6,7,8-tetrahydropyrido[3,4-d]pyrimidine (225a) (350 mg, 63% yield) as a white solid; $^1$H NMR (300 MHz, DMSO-d$_6$) δ 7.41-7.20 (m, 5H), 3.69-3.56 (m, 6H), 3.34 (m, 2H), 2.89 (t, J=5.8 Hz, 2H), 2.58 (t, J=5.6 Hz, 2H), 1.88-1.78 (m, 4H); MS (ES+) 329.3 (M+1), Step-2: Preparation of 7-benzyl-4-(pyrrolidin-1-yl)-N-(1-(3,4,5-trimethoxyphenyl)-1H-imidazol-4-yl)-5,6,7,8-tetrahydropyrido[3,4-d]pyrimidin-2-amine (225b)

Compound 225b was prepared from 7-benzyl-2-chloro-4-(pyrrolidin-1-yl)-5,6,7,8-tetrahydropyrido[3,4-d]pyrimidine (225a) (0.33 g, 1 mmol), 1-(3,4,5-trimethoxyphenyl)-1H-imidazol-4-amine (57a) (287 mg, 1.15 mmol, free base), dicyclohexyl(2',4',6'-triisopropylbiphenyl-2-yl)phosphine (XPhos, 215 mg, 0.45 mmol), cesium carbonate (977 mg, 3 mmol) and Pd$_2$(dba)$_3$ (137 mg, 0.15 mmol) in 1,4-dioxane (15 mL) according to the procedure reported in step-3 of Scheme 101. This gave after workup and purification by flash column chromatography [silica gel (80 g), eluting with DMA-80 in CH$_2$Cl$_2$], followed by reverse phase column chromatography [(silica gel C-18, 24 g) eluting with acetonitrile and 0.1% HCl water]7-benzyl-4-(pyrrolidin-1-yl)-N-(1-(3,4,5-trimethoxyphenyl)-1H-imidazol-4-yl)-5,6,7,8-tetrahydropyrido[3,4-d]pyrimidin-2-amine (225b) (115 mg, 21% yield) HCl salt as a white solid; $^1$H NMR (300 MHz, DMSO-d$_6$-D$_2$O) δ 8.45 (s, 1H), 7.71 (s, 1H), 7.64-7.55 (m, 2H), 7.54-7.45 (m, 3H), 6.92 (s, 2H), 4.50-4.30 (m, 2H), 4.15-3.97 (m, 2H), 3.85 (s, 6H), 3.83-3.74 (m, 4H), 3.67 (s, 3H), 3.58-3.41 (m, 2H), 3.20-3.08 (m, 2H), 1.95-1.83 (m, 4H); MS (ES+): 542.4 (M+1); HPLC purity: 96.69%.

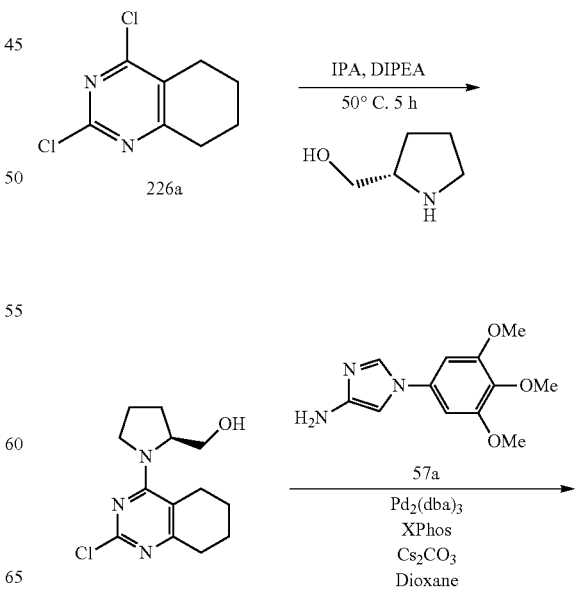

Scheme 226

226a

226b

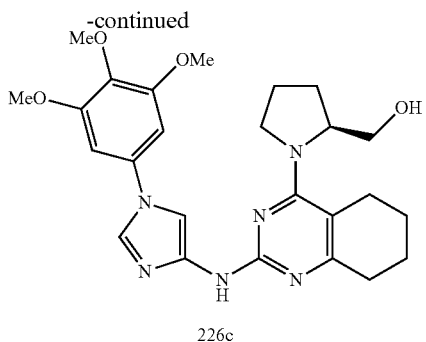

226c

Preparation of (S)-(1-(2-((1-(3,4,5-trimethoxyphenyl)-1H-imidazol-4-yl)amino)-5,6,7,8-tetrahydroquinazolin-4-yl)pyrrolidin-2-yl)methanol (226c)

Step-1: Preparation of (S)-(1-(2-chloro-5,6,7,8-tetrahydroquinazolin-4-yl)pyrrolidin-2-yl)methanol (226b)

Compound 226b was prepared from 2,4-dichloro-5,6,7,8-tetrahydroquinazoline (226a) (0.5 g, 2.46 mmol, CAS #1127-85-1) in 2-Propanol (5 mL) using (S)-pyrrolidin-2-ylmethanol (0.25 g, 2.46 mmol) and DIPEA (1.29 mL, 7.39 mmol) according to the procedure reported in step-1 of Scheme 96. This gave after workup and purification by flash column chromatography [silica gel (40 g), eluting with DMA-80 in chloroform (0 to 50%)] (S)-(1-(2-chloro-5,6,7,8-tetrahydroquinazolin-4-yl)pyrrolidin-2-yl)methanol (226b) (350 mg, 53% yield) as a white solid; $^1$H NMR (300 MHz, DMSO-$d_6$) δ 4.67 (t, J=5.7 Hz, 1H), 4.41-4.23 (m, 1H), 3.76-3.65 (m, 1H), 3.65-3.53 (m, 1H), 3.48 (m, 1H), 3.41-3.32 (m, 1H), 2.79-2.53 (m, 4H), 1.89 (m, 6H), 1.77-1.29 (m, 2H).

Step-2: Preparation of (S)-(1-(2-((1-(3,4,5-trimethoxyphenyl)-1H-imidazol-4-yl)amino)-5,6,7,8-tetrahydroquinazolin-4-yl)pyrrolidin-2-yl)methanol (226c)

Compound 226c was prepared from (S)-(1-(2-chloro-5,6,7,8-tetrahydroquinazolin-4-yl)pyrrolidin-2-yl)methanol (226b) (1.0 g, 3.73 mmol), 1-(3,4,5-trimethoxyphenyl)-1H-imidazol-4-amine (57a) (1.07 g, 4.29 mmol, free base), dicyclohexyl(2',4',6'-triisopropylbiphenyl-2-yl)phosphine (XPhos, 801 mg, 1.68 mmol), cesium carbonate (3.65 g, 11.2 mmol) and Pd$_2$(dba)$_3$ (513 mg, 0.56 mmol) in 1,4-dioxane (35 mL) according to the procedure reported in step-3 of Scheme 101. This gave after workup and purification by flash column chromatography [silica gel (80 g), eluting with DMA-80 in CH$_2$Cl$_2$], followed by reverse phase column chromatography [(silica gel C-18, 24 g) eluting with acetonitrile and 0.1% HCl water] (S)-(1-(2-((1-(3,4,5-trimethoxyphenyl)-1H-imidazol-4-yl)amino)-5,6,7,8-tetrahydroquinazolin-4-yl)pyrrolidin-2-yl)methanol (226c) (665 mg, 37% yield) HCl salt as a white solid; $^1$H NMR (300 MHz, DMSO-$d_6$) δ 12.93 (s, 1H, D$_2$O exchangeable), 10.14 (s, 1H), 8.33 (s, 1H, D$_2$O exchangeable), 7.64 (s, 1H), 6.96 (s, 2H), 4.65 (s, 1H), 4.01-3.90 (m, 2H), 3.90-3.78 (m, 6H), 3.67 (d, J=1.4 Hz, 3H), 3.57-3.38 (m, 2H), 2.84-2.57 (m, 4H), 2.07-1.74 (m, 6H), 1.72-1.39 (m, 2H); MS (ES+): 481.3 (M+1), (ES−): 515.3 (M+Cl); HPLC purity: 99.05%.

Scheme 227

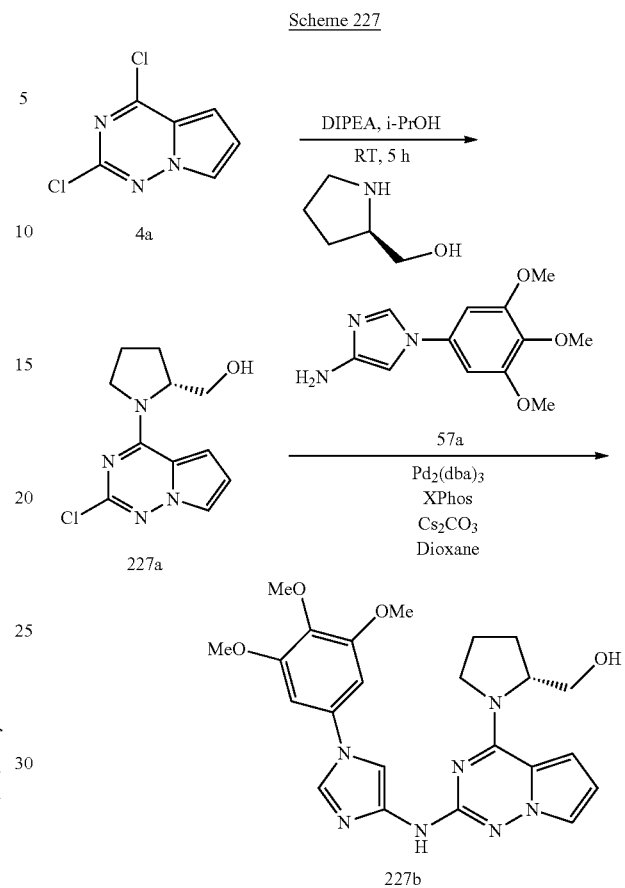

Preparation of (R)-(1-(2-((1-(3,4,5-trimethoxyphenyl)-1H-imidazol-4-yl)amino)pyrrolo[2,1-f][1,2,4]triazin-4-yl)pyrrolidin-2-yl)methanol (227b)

Step-1: Preparation of (R)-(1-(2-chloropyrrolo[2,1-f][1,2,4]triazin-4-yl)pyrrolidin-2-yl)methanol (227a) To a solution of 2,4-dichloropyrrolo[1,2-f][1,2,4]triazine (4a) (0.5 g, 2.7 mmol) in 2-Propanol (5 mL) was added (R)-pyrrolidin-2-ylmethanol (0.27 g, 2.66 mmol), DIPEA (1.39 mL, 8.00 mmol) and stirred at room temperature for 5 h. The solid obtained was collected by filtration, dried in vacuum to afford (R)-(1-(2-chloropyrrolo[2,1-f][1,2,4]triazin-4-yl)pyrrolidin-2-yl)methanol (227a) (0.43 g, 64% yield) as a white solid; $^1$H NMR (300 MHz, DMSO-$d_6$): δ 7.70 (dd, J=2.6, 1.4 Hz, 1H), 6.97 (dd, J=4.7, 1.6 Hz, 1H), 6.80-6.57 (m, 1H), 5.15 (t, J=5.7 Hz, 1H, D$_2$O exchangeable), 4.87 (t, J=5.7 Hz, 1H), 4.44 (d, J=17.8 Hz, 1H), 4.05-3.82 (m, 1H), 3.72-3.39 (m, 2H), 2.22-1.84 (m, 4H); MS (ES+): 253.3, (M+1); MS (ES−): 287.2 (M+Cl).

Step-2: Preparation of (R)-(1-(2-((1-(3,4,5-trimethoxyphenyl)-1H-imidazol-4-yl)amino)pyrrolo[2,1-f][1,2,4]triazin-4-yl)pyrrolidin-2-yl)methanol (227b)

Compound 227b was prepared from (R)-(1-(2-chloropyrrolo[2,1-f][1,2,4]triazin-4-yl)pyrrolidin-2-yl)methanol (227a) (253 mg, 1 mmol), 1-(3,4,5-trimethoxyphenyl)-1H-imidazol-4-amine (57a) (287 mg, 1.15 mmol, free base), dicyclohexyl(2',4',6'-triisopropylbiphenyl-2-yl)phosphine (XPhos, 215 mg, 0.45 mmol), cesium carbonate (977 mg, 3.0 mmol) and Pd$_2$(dba)$_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA-80 in CH$_2$Cl$_2$], followed by reverse phase column chromatography [(silica gel C18, 24 g) eluting with acetonitrile and 0.1% HCl water] (R)-(1-(2-((1-(3,4,5-trimethoxyphenyl)-1H-imidazol-4-yl)amino)pyrrolo[2,1-f][1,2,4]triazin-4-yl)pyrrolidin-2-yl)methanol (227b) (178 mg, 38% yield) HCl salt as a white solid; $^1$H NMR (300 MHz, DMSO-d$_6$) δ 9.35 (s, 1H, D$_2$O exchangeable), 9.00 (s, 1H), 7.84 (s, 1H), 7.61 (s, 1H), 7.08 (s, 2H), 6.85 (d, J=4.8 Hz, 1H), 6.54 (s, 1H), 4.67-4.36 (m, 1H), 4.11-3.93 (m, 2H), 3.89 (s, 6H), 3.71 (s, 3H), 3.71-3.60 (m, 2H), 3.61-3.31 (m, 2H), 2.21-1.81 (m, 4H); MS (ES+): 466.3 (M+1), 488.3 (M+Na), (ES−): 500.3 (M+Cl); HPLC purity: 98.29%.

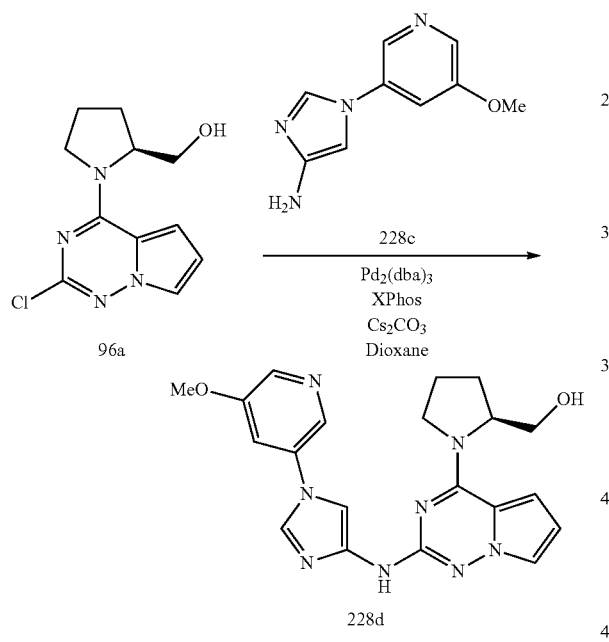

Scheme 228

Preparation of (S)-(1-(2-((1-(5-methoxypyridin-3-yl)-1H-imidazol-4-yl)amino)pyrrolo[2,1-f][1,2,4]triazin-4-yl)pyrrolidin-2-yl)methanol (228d)

Compound 228d was prepared from (S)-(1-(2-chloropyrrolo[2,1-f][1,2,4]triazin-4-yl)pyrrolidin-2-yl)methanol (96a) (253 mg, 1 mmol), 1-(5-methoxypyridin-3-yl)-1H-imidazol-4-amine (228c) (238 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and Pd$_2$(dba)$_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA 80 in CH$_2$Cl$_2$], followed by reverse phase column chromatography [(silica gel C-18, 24 g) eluting with acetonitrile and 0.1% HCl water](S)-(1-(2-((1-(5-methoxypyridin-3-yl)-1H-imidazol-4-yl)amino)pyrrolo[2,1-f][1,2,4]triazin-4-yl)pyrrolidin-2-yl)methanol (228d) (160 mg, 39% yield) HCl salt as a white solid; $^1$H NMR (300 MHz, DMSO-d$_6$) δ 9.46 (s, 1H, D$_2$O exchangeable), 9.02 (s, 1H), 8.68 (d, J=2.1 Hz, 1H), 8.43 (d, J=2.5 Hz, 1H), 7.97-7.86 (m, 2H), 7.68 (s, 1H), 6.88 (d, J=4.4 Hz, 1H), 6.55 (s, 1H), 4.53 (s, 1H), 3.96 (s, 3H), 3.95-3.78 (m, 2H), 3.74-3.36 (m, 2H), 2.23-1.80 (m, 4H); MS (ES+): 407.3 (M+1), 429.3 (M+Na), (ES−): 405.1 (M−1); HPLC purity: 99.51%.

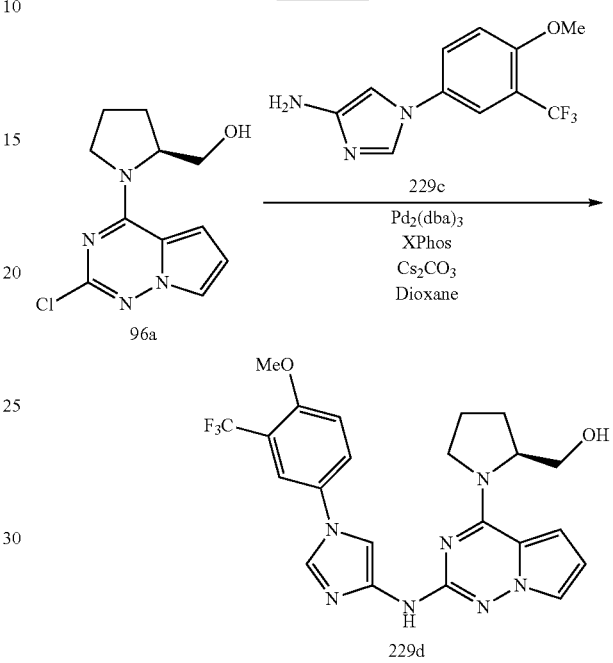

Scheme 229

Preparation of (S)-(1-(2-((1-(4-methoxy-3-(trifluoromethyl)phenyl)-1H-imidazol-4-yl)amino)pyrrolo[2,1-f][1,2,4]triazin-4-yl)pyrrolidin-2-yl)methanol (229d)

Compound 229d was prepared from (S)-(1-(2-chloropyrrolo[2,1-f][1,2,4]triazin-4-yl)pyrrolidin-2-yl)methanol (96a) (253 mg, 1 mmol), 1-(4-methoxy-3-(trifluoromethyl)phenyl)-1H-imidazol-4-amine (229c) (322 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and Pd$_2$(dba)$_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA-80 in CH$_2$Cl$_2$], followed by reverse phase column chromatography [(silica gel C-18, 24 g) eluting with acetonitrile and 0.1% HCl water] (S)-(1-(2-((1-(4-methoxy-3-(trifluoromethyl)phenyl)-1H-imidazol-4-yl)amino)pyrrolo[2,1-f][1,2,4]triazin-4-yl)pyrrolidin-2-yl)methanol (229d) (225 mg, 48% yield) HCl salt as a white solid; $^1$H NMR (300 MHz, DMSO-d$_6$) δ 9.38 (s, 1H), 8.97 (s, 1H), 8.07 (s, 1H), 8.04 (s, 2H), 7.81 (s, 1H), 7.62 (s, 1H), 7.49 (d, J=8.8 Hz, 1H), 6.85 (d, J=4.6 Hz, 1H), 6.54 (s, 1H), 4.50 (s, 1H), 3.98 (s, 3H), 3.96-3.71 (m, 2H), 3.67 (d, J=10.2 Hz, 1H), 3.58 (s, 1H), 2.23-1.82 (m, 4H); $^{19}$F NMR (282 MHz, DMSO-d$_6$) δ −61.08; MS (ES+): 474.3 (M+1), 496.2 (M+Na), (ES−): 508.3 (M+Cl); HPLC purity: 99.86%.

Scheme 230

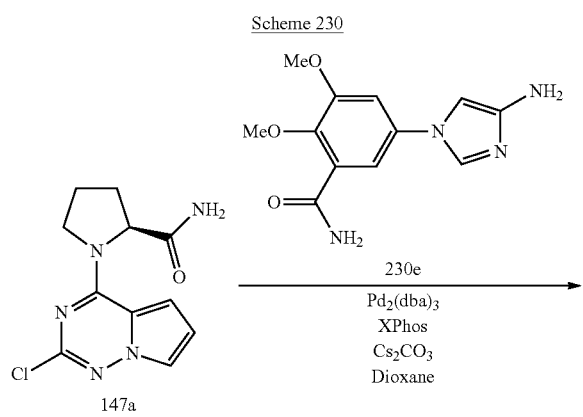

Scheme 231

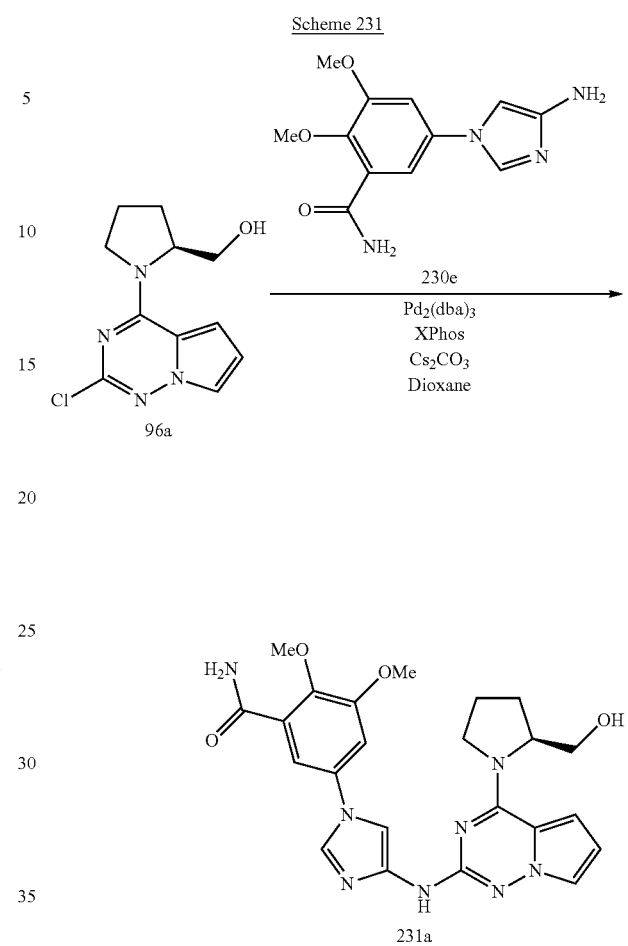

Preparation of (S)-1-(2-((1-(3-carbamoyl-4,5-dimethoxyphenyl)-1H-imidazol-4-yl)amino)pyrrolo[2,1-f][1,2,4]triazin-4-yl)pyrrolidine-2-carboxamide (230f)

Compound 230f was prepared from (S)-1-(2-chloropyrrolo[2,1-f][1,2,4]triazin-4-yl)pyrrolidine-2-carboxamide (147a) (400 mg, 1.5 mmol), 5-(4-amino-1H-imidazol-1-yl)-2,3-dimethoxybenzamide (230e) (550 mg, 2.10 mmol, free base), dicyclohexyl(2',4',6'-triisopropylbiphenyl-2-yl)phosphine (XPhos, 287 mg, 0.6 mmol), cesium carbonate (1470 mg, 4.51 mmol) and $Pd_2(dba)_3$ (206 mg, 0.225 mmol) in 1,4-dioxane (15 mL) according to the procedure reported in step-3 of Scheme 101. This gave after workup and purification by flash column chromatography [silica gel (20 g), eluting with methanol in $CH_2Cl_2$], (S)-1-(2-((1-(3-carbamoyl-4,5-dimethoxyphenyl)-1H-imidazol-4-yl)amino)pyrrolo[2,1-f][1,2,4]triazin-4-yl)pyrrolidine-2-carboxamide (230f) (80 mg, 12% yield) as an off-white solid; $^1$H NMR (300 MHz, DMSO-$d_6$): δ 8.58 (s, 1H), 8.06 (s, 1H), 7.82 (s, 1H), 7.66 (s, 2H), 7.63 (s, 1H), 7.58 (s, 1H), 7.49 (d, J=6.3 Hz, 1H), 7.43-7.31 (m, 1H), 7.30-7.00 (m, 1H), 6.90-6.73 (m, 1H), 6.71-6.42 (m, 1H), 4.85-4.66 (m, 1H), 4.18-4.09 (m, 1H), 3.98 (s, 3H), 3.87-3.72 (m, 4H), 2.20-1.93 (m, 4H). MS (ES+): 492.3 (M+1), 514.3 (M+Na); MS (ES−): 490.3 (M−1), 526.4 (M+Cl).

Preparation of (S)-5-(4-((4-(2-(hydroxymethyl)pyrrolidin-1-yl)pyrrolo[2,1-f][1,2,4]triazin-2-yl)amino)-1H-imidazol-1-yl)-2,3-dimethoxybenzamide (231a)

Compound 231a was prepared from (S)-(1-(2-chloropyrrolo[2,1-f][1,2,4]triazin-4-yl)pyrrolidin-2-yl)methanol (96a) (400 mg, 1.5 mmol), 5-(4-amino-1H-imidazol-1-yl)-2,3-dimethoxybenzamide (230e) (0.52 g, 2.21 mmol, free base), dicyclohexyl(2',4',6'-triisopropylbiphenyl-2-yl)phosphine (XPhos, 0.30 g, 0.63 mmol), cesium carbonate (1.54 g, 4.74 mmol) and $Pd_2(dba)_3$ (0.22 g, 0.24 mmol) in 1,4-dioxane (15 mL) according to the procedure reported in step-3 of Scheme 101. This gave after workup and purification by flash column chromatography [silica gel (20 g), eluting with 0-10% methanol in $CH_2Cl_2$], (S)-5-(4-((4-(2-(hydroxymethyl)pyrrolidin-1-yl)pyrrolo[2,1-f][1,2,4]triazin-2-yl)amino)-1H-imidazol-1-yl)-2,3-dimethoxybenzamide (231a) (80 mg, 11% yield) as an off-white solid; $^1$H NMR (300 MHz, DMSO-$d_6$): δ 8.63 (s, 1H), 8.06 (s, 1H), 7.79 (s, 1H), 7.65 (d, J=4.5 Hz, 2H), 7.59-7.53 (m, 1H), 7.39 (d, J=2.5 Hz, 1H), 7.33 (d, J=2.6 Hz, 1H), 6.76 (d, J=4.5 Hz, 1H), 6.47 (d, J=4.6 Hz, 1H), 4.79 (m, 1H), 4.52 (m, 1H), 3.96 (s, 3H), 3.80 (m, 7H), 2.21-1.79 (m, 4H); MS (ES+): 501.3 (M+Na); MS (ES−): 477.4 (M−1).

Scheme 232

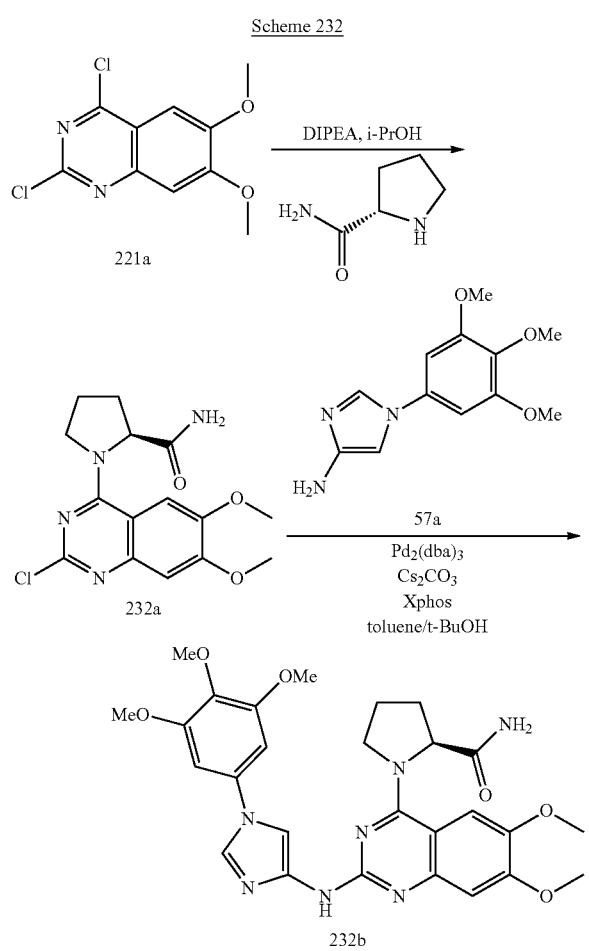

Preparation of (S)-1-(6,7-dimethoxy-2-((1-(3,4,5-trimethoxyphenyl)-1H-imidazol-4-yl)amino)quinazolin-4-yl)pyrrolidine-2-carboxamide (232b)

Step-1: Preparation of (S)-1-(2-chloro-6,7-dimethoxyquinazolin-4-yl)pyrrolidine-2-carboxamide (232a)

Compound 232a was prepared from 2,4-dichloro-6,7-dimethoxyquinazoline (221a) (1.0 g, 3.86 mmol) in IPA (40 mL), (S)-pyrrolidine-2-carboxamide (441 mg, 3.86 mmol), DIPEA (1.35 mL, 7.72 mmol) according to the procedure reported in step-1 of Scheme 96. This gave after workup and purification by flash column chromatography [silica gel (12 g), eluting with EtOAc in hexane from 0-50%] (S)-1-(2-chloro-6,7-dimethoxyquinazolin-4-yl)pyrrolidine-2-carboxamide (232a) (1.1 g, 85% yield) as a white solid; $^1$H NMR (300 MHz, DMSO-$d_6$) δ 7.59 (s, 1H), 7.51 (s, 1H), 7.11 (s, 2H), 4.83-4.67 (m, 1H), 4.20-4.09 (m, 1H), 4.09-3.98 (m, 1H), 3.90 (s, 3H), 3.89 (s, 3H), 2.31-2.15 (m, 1H), 2.06-1.80 (m, 3H).

Step-2: Preparation of (S)-1-(6,7-dimethoxy-2-((1-(3,4,5-trimethoxyphenyl)-1H-imidazol-4-yl)amino)quinazolin-4-yl)pyrrolidine-2-carboxamide (232b)

Compound 232b was prepared from (S)-1-(2-chloro-6,7-dimethoxyquinazolin-4-yl)pyrrolidine-2-carboxamide (232a) (350 mg, 1.04 mmol) in toluene/t-BuOH (40 mL, Ratio: 3:2) using 1-(3,4,5-trimethoxyphenyl)-1H-imidazol-4-amine (57a) (311 mg, 1.25 mmol, free base), Pd$_2$(dba)$_3$ (143 mg, 0.16 mmol), X-Phos (198 mg, 0.42 mmol) and Cs$_2$CO$_3$ (847 mg, 2.6 mmol) according to the procedure reported in step-3 of Scheme 101. This gave after workup and purification by flash column chromatography [silica gel (24 g), eluting with DMA-80 in DCM from 0-100%] followed by reverse phase flash column chromatography [(silica gel C-18, 50 g), eluting with CH$_3$CN in water (containing 0.1% HCl) from 0-100%] (S)-1-(6,7-dimethoxy-2-((1-(3,4,5-trimethoxyphenyl)-1H-imidazol-4-yl)amino)quinazolin-4-yl)pyrrolidine-2-carboxamide (232b) (23 mg, 4% yield) HCl salt as a white solid; $^1$H NMR (300 MHz, DMSO-$d_6$) δ 12.71 (s, 1H, D$_2$O exchangeable), 10.44 (s, 1H, D$_2$O exchangeable), 8.28 (s, 1H), 7.89-7.52 (m, 3H), 7.32-7.02 (m, 4H, 1H is D$_2$O exchangeable), 4.96-4.81 (m, 1H), 4.58-4.38 (m, 1H), 4.31-4.14 (m, 1H), 3.95 (s, 3H), 3.91 (s, 9H), 3.69 (s, 3H), 2.44-2.31 (m, 1H), 2.16-1.95 (m, 3H); MS (ES−): 548.8 (M−1): 584.4 (M+Cl).

Scheme 233

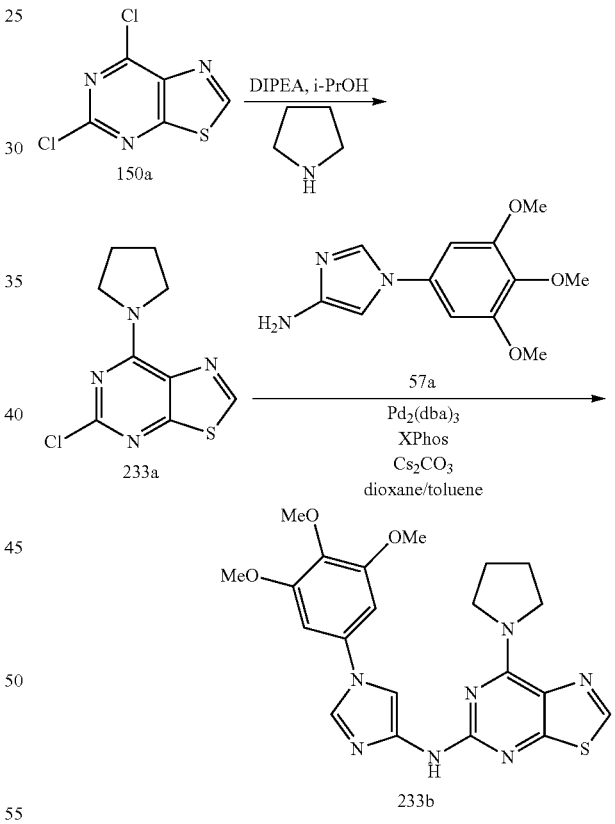

Preparation of 7-(pyrrolidin-1-yl)-N-(1-(3,4,5-trimethoxyphenyl)-1H-imidazol-4-yl)thiazolo[5,4-d]pyrimidin-5-amine (233b)

Step-1: Preparation of 5-chloro-7-(pyrrolidin-1-yl)thiazolo[5,4-d]pyrimidine (233a)

Compound 233a was prepared from 5,7-dichlorothiazolo[5,4-d]pyrimidine (150a) (0.5 g, 2.43 mmol) in 2-Propanol (20 mL) using pyrrolidine (0.2 mL, 2.43 mmol) and DIPEA (1.27 mL, 7.28 mmol) according to the procedure reported in step-1 of Scheme 96. This gave after workup and purification by flash column chromatography [silica gel (12 g), eluting with DCM in methanol (0 to 30%)] 5-chloro-7-(pyrrolidin-1-yl)thiazolo[5,4-d]pyrimidine (233a) (0.45 g, 77% yield) as a white solid; MS (ES+): 241.3 (M+1).

Step-2: Preparation of 7-(pyrrolidin-1-yl)-N-(1-(3,4,5-trimethoxyphenyl)-1H-imidazol-4-yl)thiazolo[5,4-d]pyrimidin-5-amine (233b)

Compound 233b was prepared from 5-chloro-7-(pyrrolidin-1-yl)thiazolo[5,4-d]pyrimidine (233a) (0.3 g, 1.25 mmol), 1-(3,4,5-trimethoxyphenyl)-1H-imidazol-4-amine (57a) (310 mg, 1.25 mmol, free base), dicyclohexyl(2',4',6'-triisopropylbiphenyl-2-yl)phosphine (XPhos, 0.36 g, 0.75 mmol), cesium carbonate (1.22 g, 3.74 mmol) and $Pd_2(dba)_3$ (0.34 g, 0.37 mmol) in 1,4-dioxane (5 mL) and toluene (5 mL) according to the procedure reported in step-3 of Scheme 101. This gave after workup and purification by flash column chromatography [silica gel (12 g), eluting with DMA-80 in $CH_2Cl_2$], followed by reverse phase column chromatography [(silica gel C-18, 24 g) eluting with acetonitrile and 0.1% HCl water] 7-(pyrrolidin-1-yl)-N-(1-(3,4,5-trimethoxyphenyl)-1H-imidazol-4-yl)thiazolo[5,4-d]pyrimidin-5-amine (233b) (20 mg, 3% yield) HCl salt as a white solid; $^1$H NMR (300 MHz, DMSO-$d_6$): δ 10.28 (s, 1H), 8.92 (s, 1H), 7.70-6.90 (m, 4H), 4.35-4.02 (m, 4H), 3.88 (s, 6H), 3.70 (s, 3H), 2.17-1.78 (m, 4H). MS (ES+): 454.3 (M+1).

(300 mg, 1.18 mmol), 1-(5-(4-amino-1H-imidazol-1-yl)-2,3-dimethoxyphenyl)ethanone (234d) (0.37 g, 1.42 mmol, free base), dicyclohexyl(2',4',6'-triisopropylbiphenyl-2-yl)phosphine (XPhos, 0.230 g, 0.47 mmol), cesium carbonate (1.16 g, 3.56 mmol) and $Pd_2(dba)_3$ (0.16 g, 0.18 mmol) in 1,4-dioxane (15 mL) according to the procedure reported in step-3 of Scheme 101. This gave after workup and purification by flash column chromatography [silica gel (20 g), eluting with 0-10% methanol in $CH_2Cl_2$] to afford compound (234e) (70 mg, 12% yield) free base as an off-white solid. The free base was repurified by reverse phase column chromatography [(silica gel C-18, 24 g), eluting with ACN in water (containing 0.1% HCl) from 0-100%] to afford (S)-1-(5-(4-((4-(2-(hydroxymethyl)pyrrolidin-1-yl)pyrrolo[2,1-f][1,2,4]triazin-2-yl)amino)-1H-imidazol-1-yl)-2,3-dimethoxyphenyl)ethanone (234e) (15 mg) HCl salt as a yellow solid; $^1$H NMR (300 MHz, DMSO-$d_6$): δ 9.60 (s, 1H), 9.27 (s, 1H), 7.89 (s, 1H), 7.68 (s, 1H), 7.65 (s, 1H), 7.50 (s, 1H), 7.03-6.79 (m, 1H), 6.65-6.48 (m, 1H), 4.73-4.29 (m, 1H), 4.17-3.28 (m, 10H), 2.61 (s, 3H), 2.23-1.81 (m, 4H). MS (ES+): 478.3 (M+1); MS (ES−): 512.3 (M+Cl).

Scheme 235

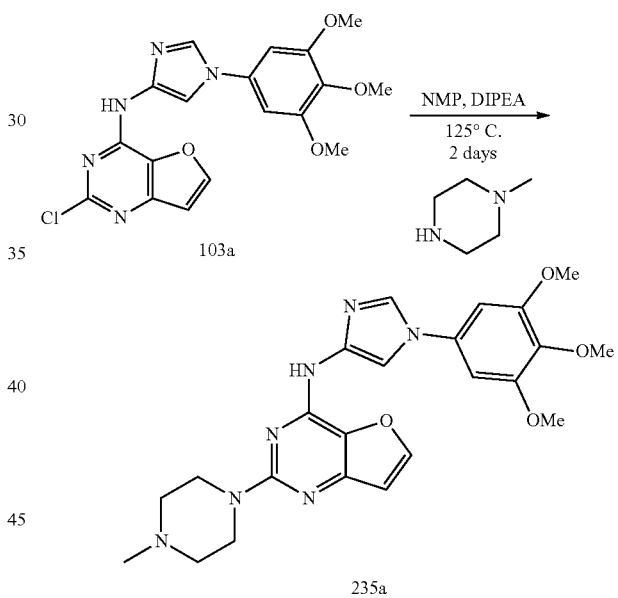

Preparation of 2-(4-methylpiperazin-1-yl)-N-(1-(3,4,5-trimethoxyphenyl)-1H-imidazol-4-yl)furo[3,2-d]pyrimidin-4-amine (235a)

Compound 235a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (300 mg, 0.75 mmol) and 1-methylpiperazine (299 mg, 2.99 mmol) in NMP (6 mL) using DIPEA (0.39 mL, 2.24 mmol) as base. This gave after workup compound 235a as a solid which was mixed with HCl (1%) in acetonitrile and lyophilized to give 2-(4-methylpiperazin-1-yl)-N-(1-(3,4,5-trimethoxyphenyl)-1H-imidazol-4-yl)furo[3,2-d]pyrimidin-4-amine (235a) (183 mg, 53% yield) HCl salt as an off white solid; $^1$H NMR (300 MHz, DMSO-$d_6$) δ 11.70 (s, 2H, $D_2O$ exchangeable), 8.88 (s, 1H), 8.40 (d, J=2.1 Hz, 1H), 8.17-7.99 (m, 1H, $D_2O$ exchangeable), Scheme 234

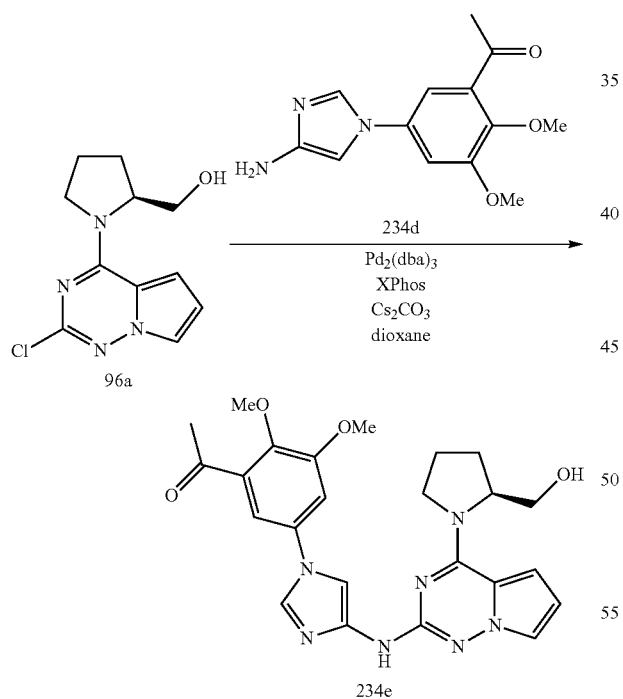

Preparation of (S)-1-(5-(4-((4-(2-(hydroxymethyl)pyrrolidin-1-yl)pyrrolo[2,1-f][1,2,4]triazin-2-yl)amino)-1H-imidazol-1-yl)-2,3-dimethoxyphenyl)ethanone (234e)

Compound 234e was prepared from (S)-(1-(2-chloropyrrolo[2,1-f][1,2,4]triazin-4-yl)pyrrolidin-2-yl)methanol (96a)

7.20-6.93 (m, 3H), 4.76 (d, J=14.0 Hz, 2H), 3.89 (s, 6H), 3.74-3.58 (m, 5H), 3.56-3.40 (m, 2H), 3.28-3.08 (m, 2H), 2.78 (d, J=4.1 Hz, 3H); MS (ES+) 466.3 (M+1); (ES−) 500.3 (M+Cl); HPLC purity, 95.54%.

Scheme 236

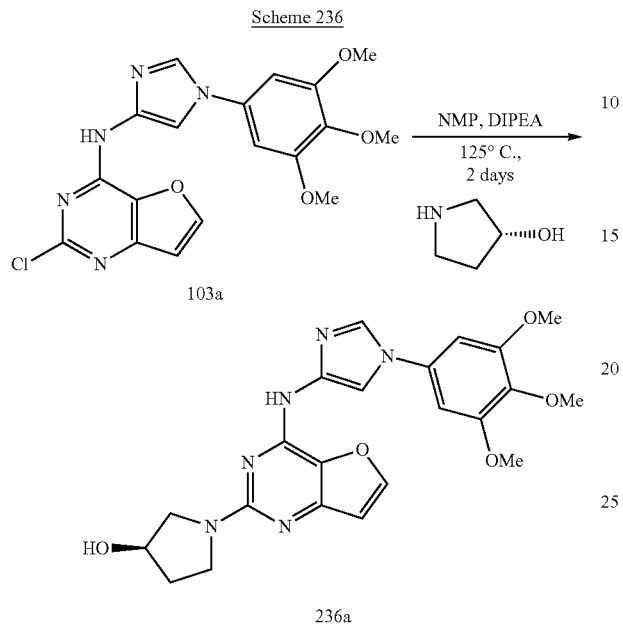

Preparation of (R)-1-(4-((1-(3,4,5-trimethoxyphenyl)-1H-imidazol-4-yl)amino)furo[3,2-d]pyrimidin-2-yl)pyrrolidin-3-ol (236a)

Compound 236a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (300 mg, 0.75 mmol) and (R)-pyrrolidin-3-ol (260 mg, 2.99 mmol) in NMP (6 mL) using DIPEA (0.78 mL, 4.48 mmol) as base. This gave after workup followed by purification by reverse column chromatography [(silica gel C-18, 50 g), eluting with acetonitrile in water (containing 0.1% HCl) from 0-100%] (R)-1-(4-((1-(3,4,5-trimethoxyphenyl)-1H-imidazol-4-yl)amino)furo[3,2-d]pyrimidin-2-yl)pyrrolidin-3-ol (236a) (59 mg, 18% yield) HCl salt as an off white solid; $^1$H NMR (300 MHz, DMSO-$d_6$) δ 13.33 (s, 1H, D$_2$O exchangeable), 11.96 (s, 1H, D$_2$O exchangeable), 8.45 (s, 1H), 8.35 (s, 1H), 8.08-7.95 (m, 1H), 7.05-6.99 (m, 1H), 6.99-6.91 (m, 2H), 4.51-4.45 (m, 4H), 3.88 (s, 6H), 3.78-3.63 (m, 5H), 2.20-1.81 (m, 2H); MS (ES+): 453.3 (M+1); (ES−): 451.6 (M−1); HPLC purity, 96.88%.

Scheme 237

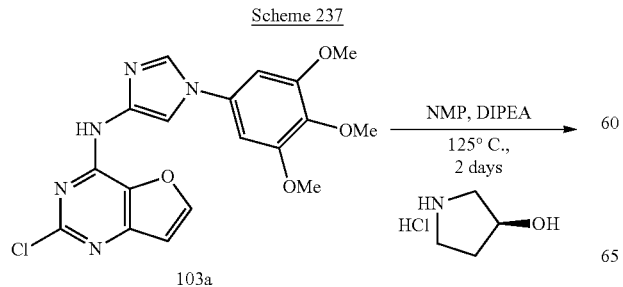

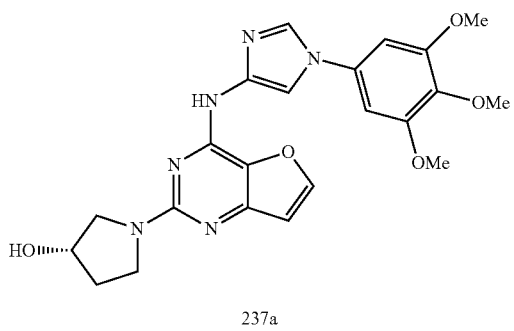

Preparation of (S)-1-(4-((1-(3,4,5-trimethoxyphenyl)-1H-imidazol-4-yl)amino)furo[3,2-d]pyrimidin-2-yl)pyrrolidin-3-ol (237a)

Compound 237a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (300 mg, 0.75 mmol) and (S)-pyrrolidin-3-ol hydrochloride (369 mg, 2.99 mmol) in NMP (6 mL) using DIPEA (0.78 mL, 4.48 mmol) as base. This gave after workup followed by purification by reverse column chromatography [(silica gel C-18, 50 g), eluting with acetonitrile in water (containing 0.1% HCl) from 0-100%] (S)-1-(4-((1-(3,4,5-trimethoxyphenyl)-1H-imidazol-4-yl)amino)furo[3,2-d]pyrimidin-2-yl)pyrrolidin-3-ol (237a) (43 mg, 13% yield) HCl salt as a white solid; $^1$H NMR (300 MHz, DMSO-$d_6$) δ 13.31 (s, 1H, D$_2$O exchangeable), 11.95 (s, 1H, D$_2$O exchangeable), 8.44 (s, 1H), 8.35 (s, 1H), 8.13-7.89 (m, 1H), 7.07-6.89 (m, 3H), 4.57-4.26 (m, 4H), 3.88 (s, 6H), 3.76-3.62 (m, 5H), 2.19-1.79 (m, 2H); MS (ES+): 453.3 (M+1); (ES−): 487.3 (M+Cl); HPLC purity, 96.60%.

Scheme 238

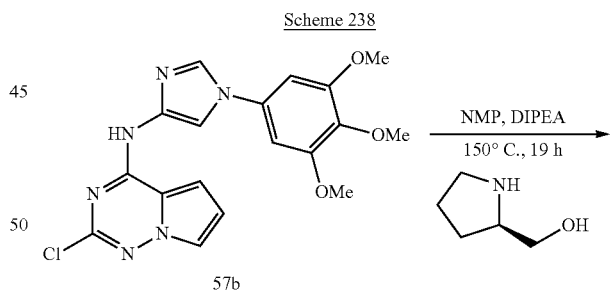

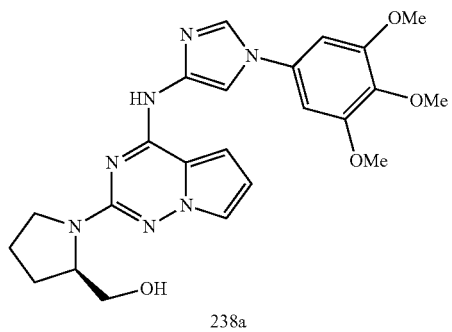

Preparation of (R)-(1-(4-((1-(3,4,5-trimethoxyphenyl)-1H-imidazol-4-yl)amino)pyrrolo[2,1-f][1,2,4]triazin-2-yl)pyrrolidin-2-yl)methanol (238a)

Compound 238a was prepared according to the procedure reported in step-2 of Scheme 76 from 2-chloro-N-(1-(3,4,5-trimethoxyphenyl)-1H-imidazol-4-yl)pyrrolo[1,2-f][1,2,4]triazin-4-amine (57b) (2 g, 4.99 mmol) and (R)-pyrrolidin-2-ylmethanol (1.97 mL, 19.96 mmol) in NMP (10 mL) using DIPEA (5.23 mL, 29.9 mmol) as base. This gave after workup and purification by flash column chromatography [silica (40 g), eluting with DMA 80 in CH$_2$Cl$_2$ from 0 to 30%] followed by reverse column chromatography [(silica gel C-18, 24 g), eluting with acetonitrile in water (containing 0.1% HCl) from 0-100%] (R)-(1-(4-((1-(3,4,5-trimethoxyphenyl)-1H-imidazol-4-yl)amino)pyrrolo[2,1-f][1,2,4]triazin-2-yl)pyrrolidin-2-yl)methanol (238a) (1.35 g, 58% yield) HCl salt as an off-white solid; $^1$H NMR (300 MHz, DMSO-d$_6$): δ 10.71 (s, 1H), 8.53 (s, 1H), 8.02 (d, J=1.5 Hz, 1H), 7.42 (d, J=2.1 Hz, 1H), 7.12 (dd, J=4.4, 1.6 Hz, 1H), 7.00 (t, J=1.2 Hz, 2H), 6.42 (ddd, J=4.5, 2.4, 1.3 Hz, 1H), 4.26-4.13 (m, 1H), 3.88 (s, 6H), 3.76-3.66 (m, 4H), 3.60-3.25 (m, 3H), 2.15-1.68 (m, 4H). MS (ES+): 466.3 (M+1), 488.3 (M+Na); MS (ES−): 464.2 (M−1), 500.3 (M+Cl). HPLC purity: 96.69%.

Scheme 239

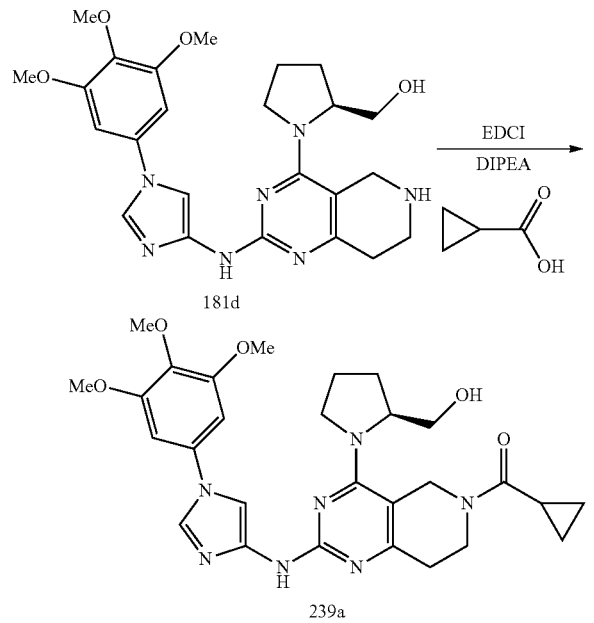

181d

239a

Preparation of (S)-cyclopropyl(4-(2-(hydroxymethyl)pyrrolidin-1-yl)-2-((1-(3,4,5-trimethoxyphenyl)-1H-imidazol-4-yl)amino)-7,8-dihydropyrido[4,3-d]pyrimidin-6(5H)-yl)methanone (239a)

To a solution of (S)-(1-(2-((1-(3,4,5-trimethoxyphenyl)-1H-imidazol-4-yl)amino)-5,6,7,8-tetrahydropyrido[4,3-d]pyrimidin-4-yl)pyrrolidin-2-yl)methanol (181d) (179 mg, 0.3 mmol), in dichloromethane (10 mL) was added cyclopropanecarboxylic acid (0.036 mL, 0.450 mmol), EDCI (86 mg, 0.450 mmol) and DIPEA (0.210 mL, 1.200 mmol). The solution was stirred at room temperature diluted with dichloromethane (50 mL), washed with brine (2×20 mL), dried, filtered, concentrated in vacuum. The residue obtained was purified by flash column chromatography (silica gel 25 g, eluting with DMA 80 in dichloromethane) followed by purification by reverse phase column chromatography [((silica gel C-18, 100 g), eluting with acetonitrile and 0.1% HCl in water] to afford (S)-cyclopropyl(4-(2-(hydroxymethyl)pyrrolidin-1-yl)-2-((1-(3,4,5-trimethoxyphenyl)-1H-imidazol-4-yl)amino)-7,8-dihydropyrido[4,3-d]pyrimidin-6(5H)-yl)methanone (239a) (95 mg, 58% yield) HCl salt as a light yellow solid; $^1$H NMR (300 MHz, DMSO-d$_6$) δ 13.23 (s, 1H, D$_2$O exchangeable), 10.27 (s, 1H, D$_2$O exchangeable), 8.43 (s, 1H), 7.70 (s, 1H), 6.98 (s, 2H), 5.15-4.78 (m, 2H), 4.78-4.39 (m, 2H), 4.27-4.07 (m, 1H), 3.87 (s, 6H), 3.84-3.55 (m, 5H), 3.55-3.39 (m, 2H), 2.97-2.65 (m, 2H), 2.22-2.01 (m, 1H), 2.01-1.80 (m, 4H), 0.85-0.63 (m, 4H); MS (ES+): 550.4 (M+1), (ES−): 584.3 (M+Cl); HPLC purity: 97.49.

Scheme 240

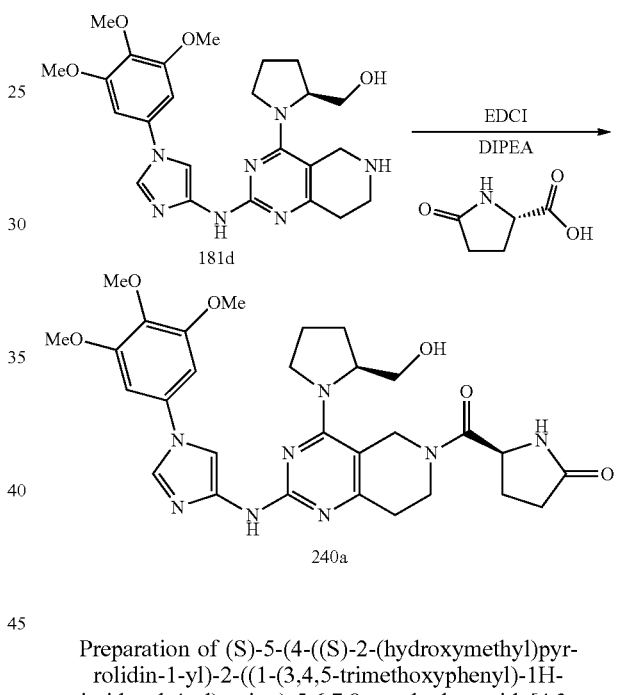

181d

240a

Preparation of (S)-5-(4-((S)-2-(hydroxymethyl)pyrrolidin-1-yl)-2-((1-(3,4,5-trimethoxyphenyl)-1H-imidazol-4-yl)amino)-5,6,7,8-tetrahydropyrido[4,3-d]pyrimidine-6-carbonyl)pyrrolidin-2-one (240a)

To a solution of (S)-(1-(2-((1-(3,4,5-trimethoxyphenyl)-1H-imidazol-4-yl)amino)-5,6,7,8-tetrahydropyrido[4,3-d]pyrimidin-4-yl)pyrrolidin-2-yl)methanol (181d) (179 mg, 0.3 mmol), in dichloromethane (10 mL) was added (S)-5-oxopyrrolidine-2-carboxylic acid (58.1 mg, 0.45 mmol), EDCI (86 mg, 0.45 mmol) and DIPEA (0.21 mL, 1.2 mmol). The solution was stirred at room temperature diluted with dichloromethane (50 mL), washed with brine (2×20 mL), dried, filtered, concentrated in vacuum. The residue obtained was purified by flash column chromatography (silica gel 25 g, eluting with DMA 80 in dichloromethane) followed by purification by reverse phase column chromatography [(silica gel C-18, 100 g), eluting with acetonitrile and 0.1% HCl in water] to afford (S)-5-(4-((S)-2-(hydroxymethyl)pyrrolidin-1-yl)-2-((1-(3,4,5-trimethoxyphenyl)-1H-imidazol-4-yl)amino)-5,6,7,8-tetrahydropyrido[4,3-d]pyrimidine-6-carbonyl)pyrrolidin-2-one (240a) (41 mg, 23% yield) HCl salt as a white solid; ¹H NMR (300 MHz, DMSO-d₆) δ 10.33 (s, 1H, D₂O exchangeable), 8.51 (s, 1H), 7.80 (d, J=32.8 Hz, 1H, D₂O exchangeable), 7.73 (s, 1H), 6.99 (s, 2H), 4.94 (d, J=15.7 Hz, 1H), 4.84-4.56 (m, 3H), 4.48 (d, J=15.6 Hz, 1H), 3.92-3.78 (m, 8H), 3.75-3.44 (m, 6H), 3.06-2.68 (m, 2H), 2.18-2.05 (m, 2H), 2.03-1.81 (m, 4H); MS (ES+): 593.4 (M+1), (ES-): 627.4 (M+Cl); HPLC purity: 94.07%.

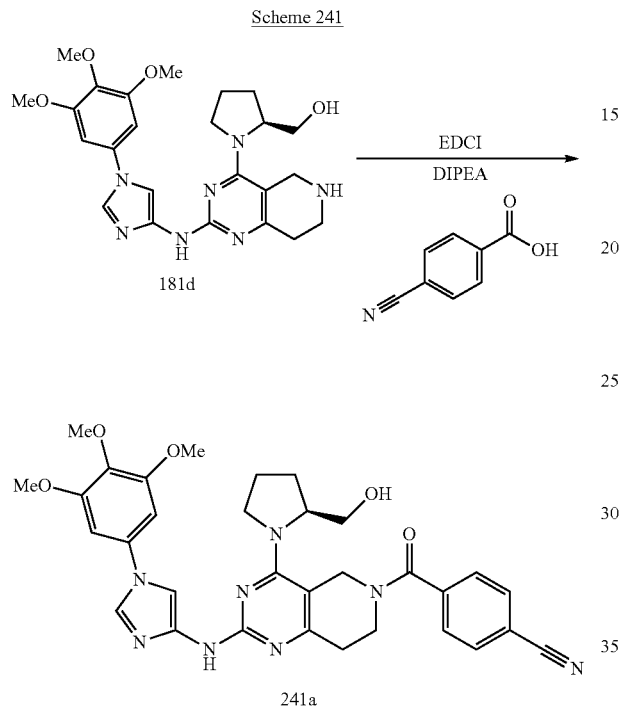

Scheme 241

181a

Preparation of (S)-4-(4-(2-(hydroxymethyl)pyrrolidin-1-yl)-2-((1-(3,4,5-trimethoxyphenyl)-1H-imidazol-4-yl)amino)-5,6,7,8-tetrahydropyrido[4,3-d]pyrimidine-6-carbonyl)benzonitrile (241a)

To a solution of (S)-(1-(2-((1-(3,4,5-trimethoxyphenyl)-1H-imidazol-4-yl)amino)-5,6,7,8-tetrahydropyrido[4,3-d]pyrimidin-4-yl)pyrrolidin-2-yl)methanol (181d) (179 mg, 0.3 mmol), in dichloromethane (10 mL) was added 4-cyanobenzoic acid (66 mg, 0.45 mmol), EDCI (86 mg, 0.45 mmol) and DIPEA (0.21 mL, 1.2 mmol). The solution was stirred at room temperature diluted with dichloromethane (50 mL), washed with brine (2×20 mL), dried, filtered, concentrated in vacuum. The residue obtained was purified by flash column chromatography (silica gel 25 g, eluting with DMA-80 in dichloromethane) followed by purification by reverse phase column chromatography [(silica gel C-18, 100 g), eluting with acetonitrile and 0.1% HCl water] to afford (S)-4-(4-(2-(hydroxymethyl)pyrrolidin-1-yl)-2-((1-(3,4,5-trimethoxyphenyl)-1H-imidazol-4-yl)amino)-5,6,7,8-tetrahydropyrido[4,3-d]pyrimidine-6-carbonyl)benzonitrile (241a) (61 mg, 33% yield) HCl salt as a white solid; ¹H NMR (300 MHz, DMSO-d₆) δ 10.31-9.94 (m, 1H, D₂O exchangeable), 8.31 (s, 1H), 7.98 (d, J=7.9 Hz, 2H), 7.78-7.56 (m, 3H), 6.96 (s, 2H), 5.23-4.87 (m, 1H), 4.87-4.57 (m, 2H), 4.01-3.73 (m, 7H), 3.75-3.66 (m, 3H), 2.12-1.64 (m, 4H), 3.87 (m, 7H), 3.69-3.21 (m, 4H), 3.05-2.61 (m, 2H); MS (ES+): 611.3 (M+1), 633.3 (M+Na), (ES-): 645.4 (M+Cl); HPLC purity: 90.45%.

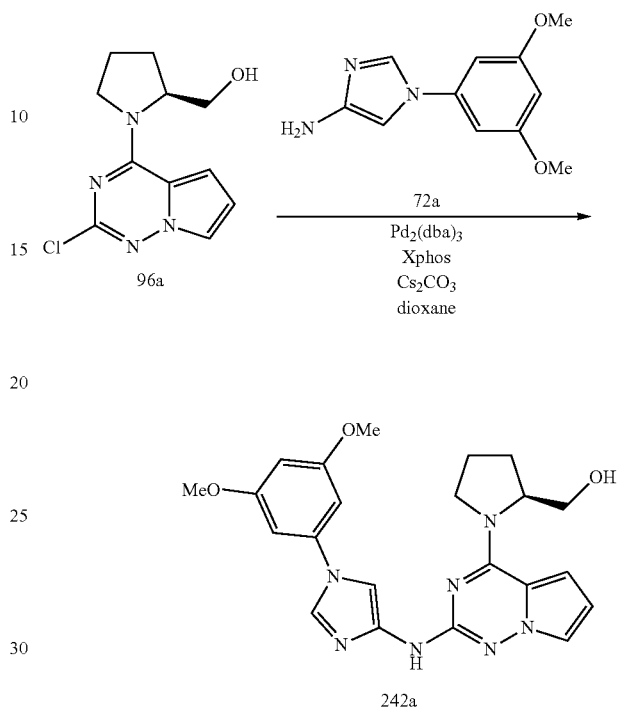

Scheme 242

242a

Preparation of (S)-(1-(2-((1-(3,5-dimethoxyphenyl)-1H-imidazol-4-yl)amino)pyrrolo[2,1-f][1,2,4]triazin-4-yl)pyrrolidin-2-yl)methanol (242a)

Compound 242a was prepared from (S)-(1-(2-chloropyrrolo[2,1-f][1,2,4]triazin-4-yl)pyrrolidin-2-yl)methanol (96a) (253 mg, 1.0 mmol), 1-(3,5-dimethoxyphenyl)-1H-imidazol-4-amine (72a) (274 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and Pd₂(dba)₃ (137 mg, 0.15 mmol) in 1,4-dioxane (15 mL) according to the procedure reported in step-3 of Scheme 101. This gave after workup and purification by flash column chromatography [silica gel (40 g), eluting with 0-100% (9:1) mixture of ethyl acetate and methanol in hexanes] compound (242a) free base as a solid. The free base was repurified by reverse phase column chromatography [(silica gel C-18, 100 g), eluting with ACN in water (containing 0.1% HCl) from 0-100%] to afford (S)-(1-(2-((1-(3,5-dimethoxyphenyl)-1H-imidazol-4-yl)amino)pyrrolo[2,1-f][1,2,4]triazin-4-yl)pyrrolidin-2-yl)methanol (242a) (230 mg, 53% yield) HCl salt as a white solid; ¹H NMR (300 MHz, DMSO-d₆) δ 9.37 (s, 1H, D₂O exchangeable), 9.03 (d, J=18.3 Hz, 1H), 7.84 (s, 1H), 7.64 (s, 1H), 7.00-6.93 (m, 2H), 6.85 (d, J=4.5 Hz, 1H), 6.63 (d, J=2.5 Hz, 1H), 6.53 (s, 1H), 4.58-4.40 (m, 1H), 3.85 (s, 6H), 3.68-3.32 (m, 4H), 2.09-1.79 (m, 4H); MS (ES+): 436.3 (M+1), 458.3 (M+Na); HPLC purity: 99.16%.

Scheme 243

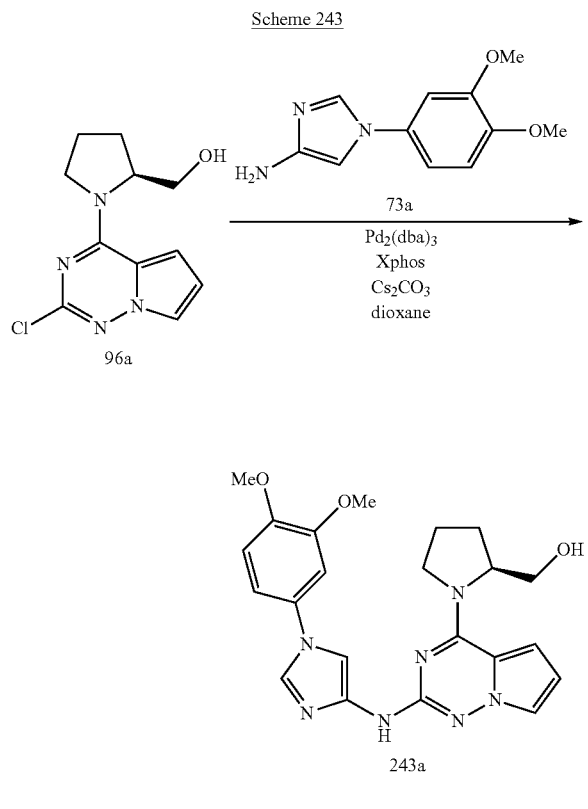

Preparation of (S)-(1-(2-((1-(3,4-dimethoxyphenyl)-1H-imidazol-4-yl)amino)pyrrolo[2,1-f][1,2,4]triazin-4-yl)pyrrolidin-2-yl)methanol (243a)

Compound 243a was prepared from (S)-(1-(2-chloropyrrolo[2,1-f][1,2,4]triazin-4-yl)pyrrolidin-2-yl)methanol (96a) (253 mg, 1.0 mmol), 1-(3,4-dimethoxyphenyl)-1H-imidazol-4-amine (73a) (274 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and Pd$_2$(dba)$_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA 80 in dichloromethane] compound (243a) free base as a solid. The free base was repurified by reverse phase column chromatography [(silica gel C-18, 100 g), eluting with ACN in water (containing 0.1% HCl) from 0-100%] to afford (S)-(1-(2-((1-(3,4-dimethoxyphenyl)-1H-imidazol-4-yl)amino)pyrrolo[2,1-f][1,2,4]triazin-4-yl)pyrrolidin-2-yl)methanol (243a) (160 mg, 37% yield) as a white HCl salt; $^1$H NMR (300 MHz, DMSO-d$_6$) δ 9.55-9.44 (m, 1H), 9.15 (s, 1H), 7.81 (s, 1H), 7.63 (s, 1H), 7.44-7.28 (m, 2H), 7.15 (d, J=8.6 Hz, 1H), 6.86 (d, J=4.7 Hz, 1H), 6.55 (s, 1H), 4.54-4.48 (m, 1H), 4.05-3.93 (m, 1H), 3.88 (s, 3H), 3.83 (s, 3H), 3.74-3.60 (m, 2H), 3.63-3.39 (m, 1H), 2.14-1.99 (m, 4H); MS (ES+): 436.3 (M+1), 458.3 (M+Na), (ES−): 470.3 (M+Cl); HPLC: 95.57%.

Scheme 244

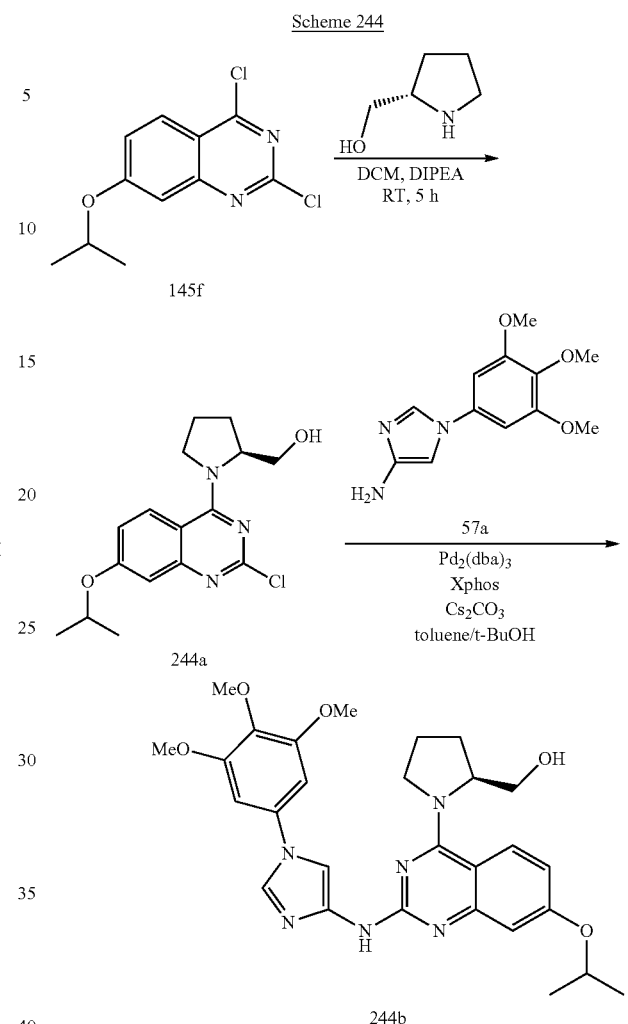

Preparation (S)-(1-(7-isopropoxy-2-((1-(3,4,5-trimethoxyphenyl)-1H-imidazol-4-yl)amino)quinazolin-4-yl)pyrrolidin-2-yl)methanol (244b)

Step-1: Preparation of(S)-(1-(2-chloro-7-isopropoxyquinazolin-4-yl)pyrrolidin-2-yl)methanol (244a)

Compound 244a was prepared according to the procedure reported in Scheme 1 from 2,4-dichloro-7-isopropoxyquinazoline (145f) (200 mg, 0.77 mmol) in DCM (10 mL) using DIPEA (0.4 mL, 3.09 mmol) and (S)-pyrrolidin-2-ylmethanol (0.39 gm, 3.85 mmol). This gave after work up and purification by flash column chromatography (silica gel, eluting with ethyl acetate in n-hexane 0-60%) (S)-(1-(2-chloro-7-isopropoxyquinazolin-4-yl)pyrrolidin-2-yl)methanol (244a) (0.15 g, 60%) as an off white solid; $^1$H NMR (300 MHz, DMSO-d$_6$): δ 8.15 (d, J=9.1 Hz, 1H), 7.15-6.87 (m, 2H), 4.82 (dt, J=8.0, 5.5 Hz, 2H), 4.55 (t, J=5.5 Hz, 1H), 4.11-3.74 (m, 1H), 3.61 (q, J=5.4, 4.4 Hz, 2H), 2.20-1.62 (m, 4H), 1.32 (dd, J=6.0, 2.2 Hz, 6H); MS (ES−): 320.0 (M−1).

Step-2: Preparation of (S)-(1-(7-isopropoxy-2-((1-(3,4,5-trimethoxyphenyl)-1H-imidazol-4-yl)amino)quinazolin-4-yl)pyrrolidin-2-yl)methanol (244b)

Compound 244b was prepared from (S)-(1-(2-chloro-7-isopropoxyquinazolin-4-yl)pyrrolidin-2-yl)methanol (244a) (500 mg, 1.55 mmol), 1-(3,4,5-trimethoxyphenyl)-1H-imidazol-4-amine (57a) (580 mg, 2.33 mmol, free base), dicyclohexyl(2',4',6'-triisopropylbiphenyl-2-yl)phosphine (XPhos, 290 mg, 0.6 mmol), cesium carbonate (2020 mg, 6.2 mmol) and $Pd_2(dba)_3$ (210 mg, 0.23 mmol) in toluene and t-BuOH (50 mL, ratio 5:2) according to the procedure reported in step-3 of Scheme 101. This gave after workup and purification by flash column chromatography [silica gel, eluting with methanol in dichloromethane 0-5%] (S)-(1-(7-isopropoxy-2-((1-(3,4,5-trimethoxyphenyl)-1H-imidazol-4-yl)amino)quinazolin-4-yl)pyrrolidin-2-yl)methanol (244b) (250 mg, 30% yield) free base as a white solid; $^1$H NMR (300 MHz, DMSO-$d_6$) δ 8.09 (d, J=1.5 Hz, 1H), 7.98 (d, J=9.3 Hz, 1H), 7.77 (s, 1H), 6.94 (s, 2H), 6.83-6.65 (m, 2H), 4.88 (s, 1H), 4.76 (dt, J=12.9, 6.5 Hz, 1H), 4.01 (s, 1H), 3.93-3.73 (m, 9H), 3.67 (d, J=9.8 Hz, 5H), 2.03 (s, 4H), 1.43-1.23 (m, 6H); MS (ES+): 535.4 (M+1), 557.7 (M+Na). HPLC purity: 87.35%.

Scheme 245

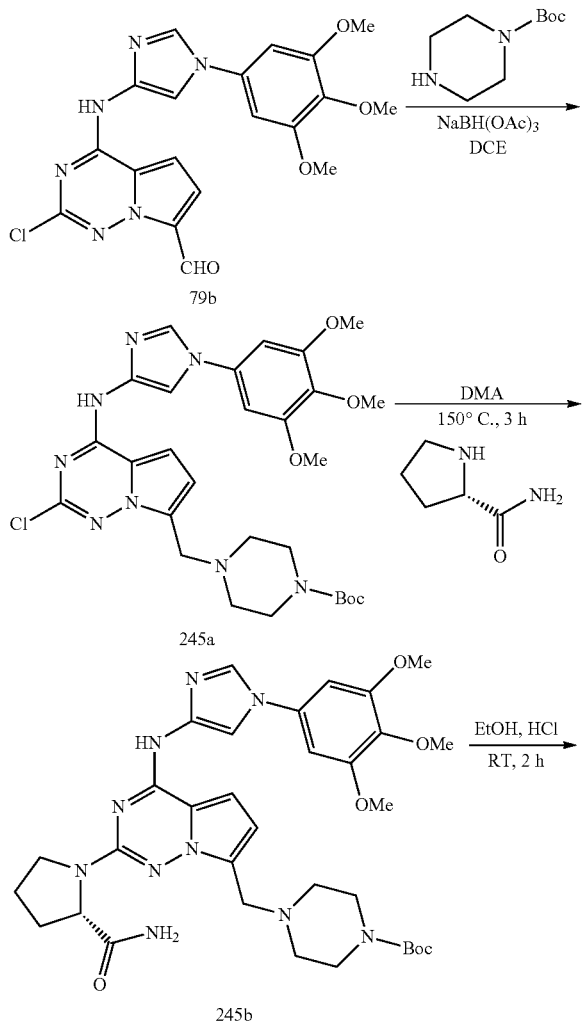

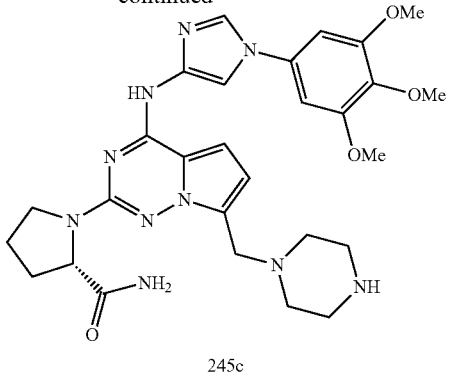

245c

Preparation of (S)-1-(7-(piperazin-1-ylmethyl)-4-((1-(3,4,5-trimethoxyphenyl)-1H-imidazol-4-yl)amino)pyrrolo[2,1-f][1,2,4]triazin-2-yl)pyrrolidine-2-carboxamide (245c)

Step-1: Preparation of tert-butyl 4-((2-chloro-4-((1-(3,4,5-trimethoxyphenyl)-1H-imidazol-4-yl)amino)pyrrolo[2,1-f][1,2,4]triazin-7-yl)methyl)piperazine-1-carboxylate (245a)

Compound 245a was prepared according to the procedure reported for reductive amination in step-1 of Scheme 105 from 2-chloro-4-(1-(3,4,5-trimethoxyphenyl)-1H-imidazol-4-ylamino)pyrrolo[1,2-f][1,2,4]triazine-7-carbaldehyde (79b) (2000 mg, 4.67 mmol) in dichloroethane (200 mL) using tert-butyl piperazine-1-carboxylate (1.3 mL, 5.13 mmol), acetic acid (0.54 mL) and NaBH(OAc)$_3$ (2.56 g, 12.1 mmol). This gave after workup and purification by flash column chromatography (silica gel, eluting with methanol in DCM from 0% to 15%) tert-butyl 4-((2-chloro-4-((1-(3,4,5-trimethoxyphenyl)-1H-imidazol-4-yl)amino)pyrrolo[2,1-f][1,2,4]triazin-7-yl)methyl)piperazine-1-carboxylate (245a) (1.2 g, 43% yield) as a brown solid; $^1$H NMR (300 MHz, DMSO-$d_6$): δ 11.22 (s, 1H), 8.20 (d, J=1.6 Hz, 1H), 7.88 (d, J=1.6 Hz, 1H), 7.40 (s, 1H), 6.93 (s, 2H), 6.66 (d, J=4.5 Hz, 1H), 3.88 (s, 9H), 3.81 (m, 2H), 3.70 (m, 4H), 2.38 (t, J=4.9 Hz, 4H), 1.38 (s, 9H); MS (ES+): 599.0 (M+1), MS (ES−): 597.3 (M−1).

Step 2: Preparation of (S)-tert-butyl 4-((2-(2-carbamoylpyrrolidin-1-yl)-4-((1-(3,4,5-trimethoxyphenyl)-1H-imidazol-4-yl)amino)pyrrolo[2,1-f][1,2,4]triazin-7-yl)methyl)piperazine-1-carboxylate (245b)

Compound 245b was prepared from tert-butyl 4-((2-chloro-4-((1-(3,4,5-trimethoxyphenyl)-1H-imidazol-4-yl)amino)pyrrolo[2,1-f][1,2,4]triazin-7-yl)methyl)piperazine-1-carboxylate (245a) (500 mg, 0.84 mmol), (S)-pyrrolidine-2-carboxamide (950 mg, 8.36 mmol) in DMA (30 mL) according to the procedure reported in step-2 of Scheme 76. This gave after workup and purification by flash column chromatography (Silica gel, eluting with methanol in DCM from 0% to 5%) (S)-tert-butyl 4-((2-(2-carbamoylpyrrolidin-1-yl)-4-((1-(3,4,5-trimethoxyphenyl)-1H-imidazol-4-yl)amino)pyrrolo[2,1-f][1,2,4]triazin-7-yl)methyl)piperazine-1-carboxylate (245b) (0.22 g, 39%) as a brown solid; $^1$H NMR (300 MHz, DMSO-$d_6$) δ 10.47 (s, 1H), 8.22 (d, J=1.4 Hz, 1H), 7.94 (s, 1H), 7.25 (s, 1H), 7.17 (d, J=4.3 Hz, 1H), 7.02 (d, J=15.2 Hz, 3H), 6.39 (s, 1H), 4.38 (d, J=8.4 Hz, 1H), 3.86 (d, J=35.0 Hz, 9H), 3.69 (s, 3H), 2.42 (s, 4H), 2.20 (s, 2H), 1.95 (s, 5H), 1.42 (d, J=8.9 Hz, 2H), 1.37 (s, 9H); MS: ES (+): 677.3 (M+1).

Step 3: Preparation of (S)-1-(7-(piperazin-1-ylmethyl)-4-((1-(3,4,5-trimethoxyphenyl)-1H-imidazol-4-yl)amino)pyrrolo[2,1-f][1,2,4]triazin-2-yl)pyrrolidine-2-carboxamide (245c)

To a stirred solution of (S)-tert-butyl 4-((2-(2-carbamoylpyrrolidin-1-yl)-4-((1-(3,4,5-trimethoxyphenyl)-1H-imidazol-4-yl)amino)pyrrolo[2,1-f][1,2,4]triazin-7-yl)methyl)piperazine-1-carboxylate (245b) (200 mg, 0.3 mmol) in ethanol (2.0 mL) was added 4N ethanolic HCl (2.0 mL, 8.0 mmol) and stirred at room temperature for 2 h. The reaction mixture was concentrated under reduced pressure and solid obtained was triturated with diethyl ether collected by filtration, dried in vacuum to afford (S)-1-(7-(piperazin-1-ylmethyl)-4-((1-(3,4,5-trimethoxyphenyl)-1H-imidazol-4-yl)amino)pyrrolo[2,1-f][1,2,4]triazin-2-yl)pyrrolidine-2-carboxamide (245c) (150 mg, 88%) as a brown solid; $^1$H NMR (300 MHz, DMSO-$d_6$): δ 12.46 (s, 1H), 11.21 (s, 1H), 10.39-9.72 (m, 2H), 8.80 (s, 1H), 7.32-7.03 (m, 4H), 6.77 (d, J=4.5 Hz, 1H), 4.69-4.47 (m, 2H), 4.46-4.20 (m, 1H), 4.01-3.08 (m, 19H), 2.36-1.74 (m, 4H). MS (ES+): 577.3 (M+1); MS (ES−): 611.2 (M+Cl).

Scheme 246

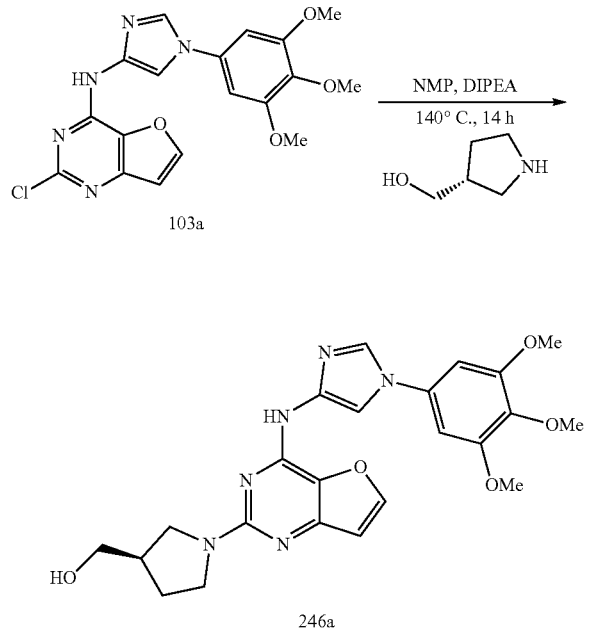

Preparation of (R)-(1-(4-((1-(3,4,5-trimethoxyphenyl)-1H-imidazol-4-yl)amino)furo[3,2-d]pyrimidin-2-yl)pyrrolidin-3-yl)methanol (246a)

Compound 246a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (350 mg, 0.87 mmol) and (R)-pyrrolidin-3-ylmethanol (352 mg, 3.48 mmol) in NMP (4 mL) using DIPEA (0.46 mL, 2.61 mmol) as base. This gave after workup Compound 246a free base as a white solid; $^1$H NMR (300 MHz, DMSO-$d_6$) δ 10.20 (s, 1H, $D_2O$ exchangeable), 8.20 (s, 1H), 8.07-8.00 (m, 2H), 6.91 (s, 2H), 6.73 (d, J=2.1 Hz, 1H), 4.71 (t, J=5.1 Hz, 1H, $D_2O$ exchangeable), 3.87 (s, 6H), 3.68 (s, 7H), 3.45-3.38 (m, 2H), 2.41-2.34 (m, 1H), 2.04-1.93 (m, 1H), 1.80-1.67 (m, 1H); MS (ES+): 489.3 (M+Na); (ES−): 465.3 (M−1); HPLC purity, 97.16%. The free base was converted to HCl salt by using reverse column chromatography [(silica gel C-18 50 g), eluting with acetonitrile in water (containing 0.1% HCl) from 0-100%] to afford (R)-(1-(4-((1-(3,4,5-trimethoxyphenyl)-1H-imidazol-4-yl)amino)furo[3,2-d]pyrimidin-2-yl)pyrrolidin-3-yl)methanol (246a) (160 mg, 37% yield) HCl salt as a white solid; $^1$H NMR (300 MHz, DMSO-$d_6$) δ 13.18 (s, 1H, $D_2O$ exchangeable), 11.95 (s, 1H, $D_2O$ exchangeable), 8.44 (s, 1H), 8.38-8.30 (m, 1H), 8.07-7.94 (m, 1H), 7.00 (s, 1H), 6.95 (s, 2H), 5.15 (s, 1H, $D_2O$ exchangeable), 4.04-3.77 (m, 8H), 3.75-3.60 (m, 5H), 3.55-3.31 (m, 3H), 2.22-1.69 (m, 2H); MS (ES+): 467.3 (M+1); (ES−): 501.2 (M+Cl); HPLC purity, 96.98%.

Scheme 247

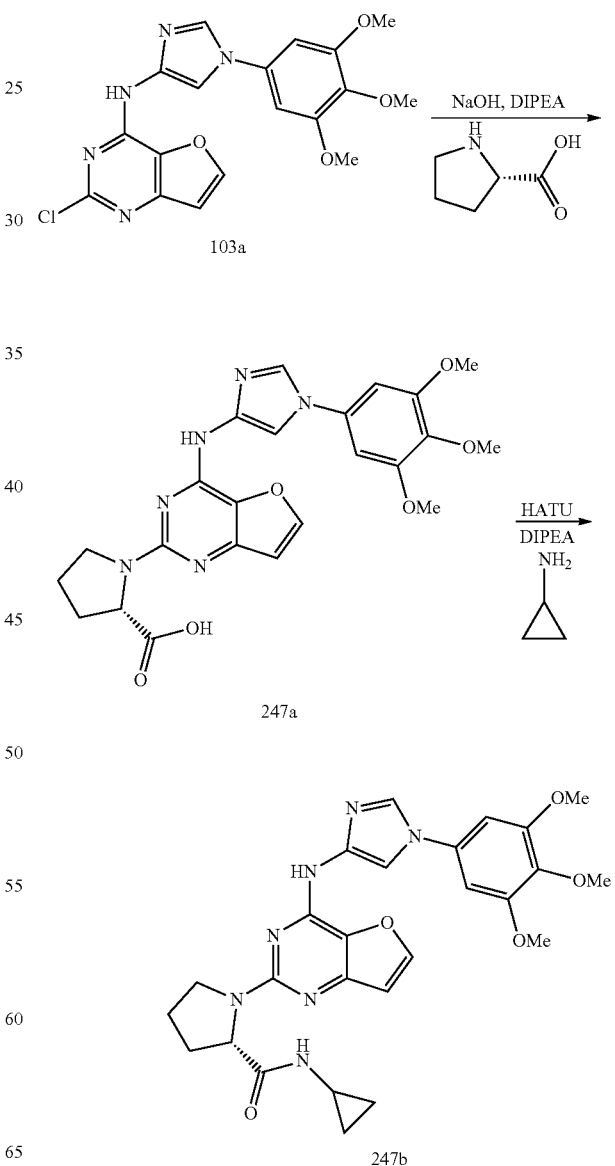

Preparation of (S)—N-cyclopropyl-1-(4-((1-(3,4,5-trimethoxyphenyl)-1H-imidazol-4-yl)amino)furo[3,2-d]pyrimidin-2-yl)pyrrolidine-2-carboxamide (247b)

Step-1: Preparation of (S)-1-(4-((1-(3,4,5-trimethoxyphenyl)-1H-imidazol-4-yl)amino)furo[3,2-d]pyrimidin-2-yl)pyrrolidine-2-carboxylic acid (247a)

To a solution of L-Proline (2.71 g, 23.52 mmol) and NaOH (0.94 g, 23.52 mmol) in dioxane/water (10 mL) was added (2-chloro-furo[3,2-d]pyrimidin-4-yl)-[1-(3,4,5-trimethoxy-phenyl)-1H-imidazol-4-yl]-amine (103a) (1.89 g, 4.7 mmol), DIPEA (1.23 mL, 7.06 mmol) and heated at reflux overnight. Additional NaOH (0.75 g, 18.82 mmol) in water (5 mL) was added to the reaction and heated at reflux for additional 8 h. The solid (starting material) was removed by filtration and filtrate was treated with HOAc (20 mL). The reaction mixture was and stirred at room temperature for 1 h and concentrated in vacuum to afford (S)-1-(4-((1-(3,4,5-trimethoxyphenyl)-1H-imidazol-4-yl)amino)furo[3,2-d]pyrimidin-2-yl)pyrrolidine-2-carboxylic acid (247a) (1.68 g, 74.3% yield), which was used in the next step without further purification; MS (ES+): 481.2 (M+1); (ES−): 479.3 (M−1).

Step-2: Preparation of (S)—N-cyclopropyl-1-(4-((1-(3,4,5-trimethoxyphenyl)-1H-imidazol-4-yl)amino)furo[3,2-d]pyrimidin-2-yl)pyrrolidine-2-carboxamide (247b)

To a solution of (S)-1-(4-((1-(3,4,5-trimethoxyphenyl)-1H-imidazol-4-yl)amino)furo[3,2-d]pyrimidin-2-yl)pyrrolidine-2-carboxylic acid (247a) (250 mg, 0.52 mmol) in DMF (10 mL) was added cyclopropanamine (36 mg, 0.62 mmol), DIPEA (0.18 mL, 1.04 mmol), HATU (237 mg, 0.62 mmol) and stirred at RT for 4 h. The reaction mixture was diluted with EtOAc, washed with water (3 xs), brine, dried, filtered and concentrated in vacuum. The residue obtained was purified by flash column chromatography [silica gel (24 g), eluting with DMA80 in DCM from 0-100%] followed by further purification by reverse phase column chromatography [(silica gel C-18, 50 g), eluting with ACN in water (containing 0.10% HCl) from 0-100%] to afford (S)—N-cyclopropyl-1-(4-((1-(3,4,5-trimethoxyphenyl)-1H-imidazol-4-yl)amino)furo[3,2-d]pyrimidin-2-yl)pyrrolidine-2-carboxamide (247b) (79 mg, 29% yield) HCl salt as an off white solid; $^1$H NMR (300 MHz, DMSO-d$_6$) δ 13.68 (bs, 1H, D$_2$O exchangeable), 11.88 (bs, 1H, D$_2$O exchangeable), 8.57 (s, 1H), 8.39 (s, 1H), 8.21-8.07 (m, 1H, D$_2$O exchangeable), 7.81 (s, 1H), 7.23-7.06 (m, 3H), 4.59 (d, J=8.6 Hz, 1H), 4.09-3.80 (m, 7H), 3.69 (s, 3H), 3.66-3.52 (m, 1H), 2.47-2.38 (m, 1H), 2.36-2.12 (m, 1H), 2.13-1.76 (m, 3H), 0.62-0.36 (m, 2H), 0.36-0.08 (m, 2H); MS (ES+): 520.3 (M+1); 542.3 (M+Na); (ES−): 518.4 (M−1); 554.3 (M+Cl); HPLC purity 97.27%.

Scheme 248

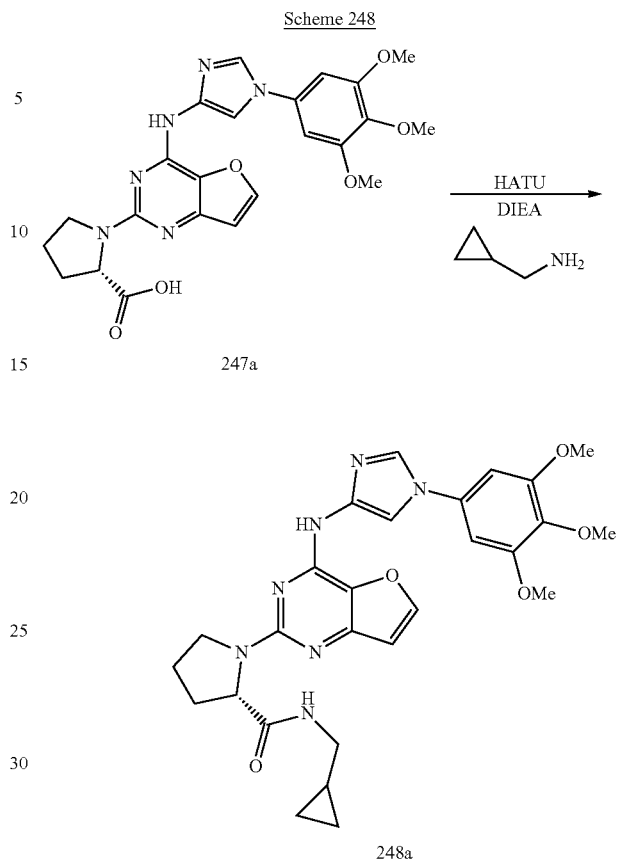

Preparation of (S)—N-(cyclopropylmethyl)-1-(4-((1-(3,4,5-trimethoxyphenyl)-1H-imidazol-4-yl)amino)furo[3,2-d]pyrimidin-2-yl)pyrrolidine-2-carboxamide (248a)

Compound 248a was prepared according to the procedure reported in Scheme 247 from (S)-1-(4-((1-(3,4,5-trimethoxyphenyl)-1H-imidazol-4-yl)amino)furo[3,2-d]pyrimidin-2-yl)pyrrolidine-2-carboxylic acid (247a) (160 mg, 0.33 mmol) in DMF (10 mL) using cyclopropylmethanamine (28.4 mg, 0.4 mmol), DIPEA (0.12 mL, 0.67 mmol), HATU (152 mg, 0.4 mmol). This gave after workup and purification by flash column chromatography [silica gel (24 g), eluting with DMA-80 in DCM from 0-100%] followed by further purification by reverse phase column chromatography [(silica gel C-18, 50 g), eluting with ACN in water (containing 0.1% HCl) from 0-100%] (S)—N-(cyclopropylmethyl)-1-(4-((1-(3,4,5-trimethoxyphenyl)-1H-imidazol-4-yl)amino)furo[3,2-d]pyrimidin-2-yl)pyrrolidine-2-carboxamide (248a) (45 mg, 25% yield) HCl salt as a white solid; $^1$H NMR (300 MHz, DMSO-d$_6$) δ 13.15 (s, 1H, D$_2$O exchangeable), 11.80 (s, 1H, D$_2$O exchangeable), 8.39 (d, J=2.1 Hz, 1H), 8.29 (s, 1H), 8.17-8.07 (m, 1H, D$_2$O exchangeable), 7.79 (s, 1H), 7.15-7.02 (m, 3H), 4.69 (d, J=8.5 Hz, 1H), 3.98-3.89 (m, 8H), 3.69 (s, 3H), 3.63-3.53 (m, 1H), 3.04-2.91 (m, 1H), 2.82-2.69 (m, 1H), 2.36-2.22 (m, 1H), 2.16-1.91 (m, 3H), 0.78-0.64 (m, 1H), 0.17-0.04 (m, 2H), −0.03-−0.11 (m, 2H); MS (ES+): 534.3 (M+1); (ES−): 532.3 (M−1); 568.2 (M+Cl); HPLC purity 98.3%.

Scheme 249

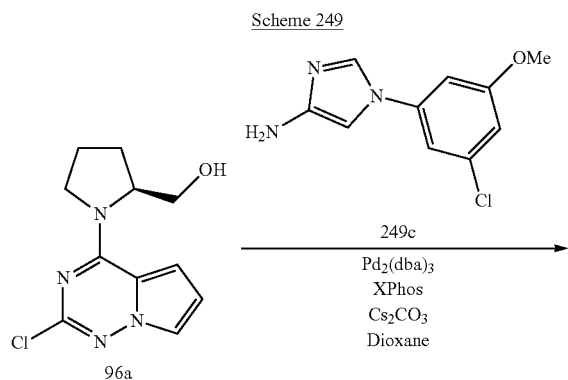

Scheme 250

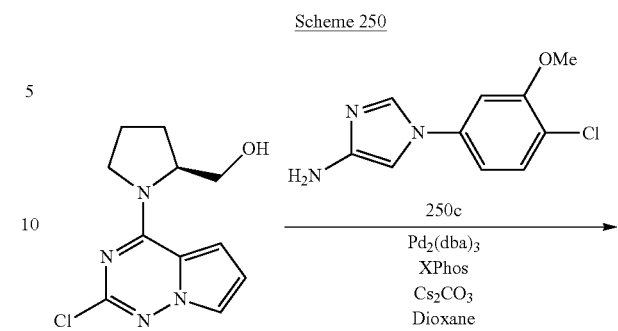

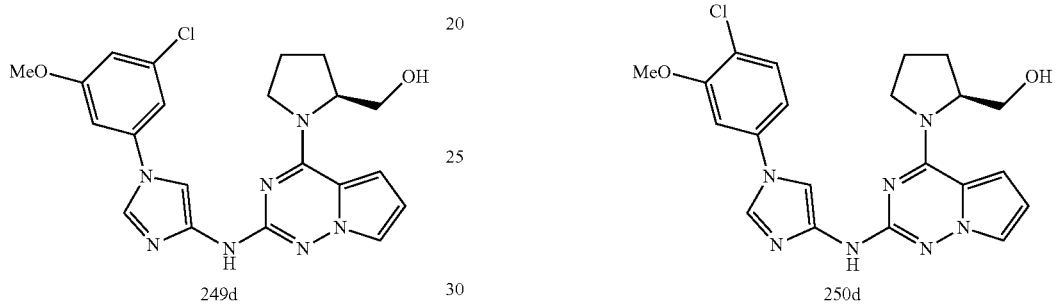

Preparation of (S)-(1-(2-((1-(3-chloro-5-methoxyphenyl)-1H-imidazol-4-yl)amino)pyrrolo[2,1-f][1,2,4]triazin-4-yl)pyrrolidin-2-yl)methanol (249d)

Compound 249d was prepared from (S)-(1-(2-chloropyrrolo[2,1-f][1,2,4]triazin-4-yl)pyrrolidin-2-yl)methanol (96a) (253 mg, 1.0 mmol), 1-(3-chloro-5-methoxyphenyl)-1H-imidazol-4-amine (249c) (280 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and $Pd_2(dba)_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA-80 in dichloromethane] compound (249d) free base as a solid. The free base was repurified by reverse phase column chromatography [(silica gel C-18, 100 g), eluting with ACN in water (containing 0.1% HCl) from 0-100%] to afford (S)-(1-(2-((1-(3-chloro-5-methoxyphenyl)-1H-imidazol-4-yl)amino)pyrrolo[2,1-f][1,2,4]triazin-4-yl)pyrrolidin-2-yl)methanol (249d) (30 mg, 7% yield) HCl salt as a white solid; $^1$H NMR (300 MHz, DMSO-$d_6$) δ 9.63-9.20 (m, 1H, $D_2O$ exchangeable), 8.99 (s, 1H), 7.86 (s, 1H), 7.68 (s, 1H), 7.55 (s, 1H), 7.38 (s, 1H), 7.17 (s, 1H), 6.88 (s, 1H), 6.55 (s, 1H), 4.66-4.38 (m, 1H), 4.08-3.91 (m, 1H), 3.89 (s, 3H), 3.75-3.61 (m, 2H), 3.64-3.37 (m, 1H), 2.23-1.86 (m, 4H), MS (ES+): 440.2 (M+1), 462.2 (M+Na), (ES−): 474.2 (M+Cl); HPLC purity: 98.71%.

Preparation of (S)-(1-(2-((1-(4-chloro-3-methoxyphenyl)-1H-imidazol-4-yl)amino)pyrrolo[2,1-f][1,2,4]triazin-4-yl)pyrrolidin-2-yl)methanol (250d)

Compound 250d was prepared from (S)-(1-(2-chloropyrrolo[2,1-f][1,2,4]triazin-4-yl)pyrrolidin-2-yl)methanol (96a) (253 mg, 1.0 mmol), 1-(4-chloro-3-methoxyphenyl)-1H-imidazol-4-amine (250c) (280 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and $Pd_2(dba)_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA 80 in dichloromethane] compound (250d) free base as a solid. The free base was repurified by reverse phase column chromatography [(silica gel C-18, 100 g), eluting with ACN in water (containing 0.1% HCl) from 0-100%] to afford (S)-(1-(2-((1-(4-chloro-3-methoxyphenyl)-1H-imidazol-4-yl)amino)pyrrolo[2,1-f][1,2,4]triazin-4-yl)pyrrolidin-2-yl)methanol (250d) (43 mg, 10% yield) HCl salt as a white solid; $^1$H NMR (300 MHz, DMSO-$d_6$) δ 9.39 (s, 1H, $D_2O$ exchangeable), 9.02 (s, 1H), 7.86 (s, 1H), 7.74-7.59 (m, 2H), 7.55 (d, J=2.4 Hz, 1H), 7.44-7.32 (m, 1H), 6.86 (d, J=4.6 Hz, 1H), 6.55 (s, 1H), 4.64-4.39 (m, 1H), 4.00 (s, 3H), 3.87 (s, 1H), 3.75-3.62 (m, 2H), 3.61-3.33 (m, 1H), 2.19-1.83 (m, 4H); MS (ES+): 440.3 (M+1), 462.2 (M+Na) (ES−): 474.2 (M+Cl); HPLC purity: 97.33%.

Scheme 251

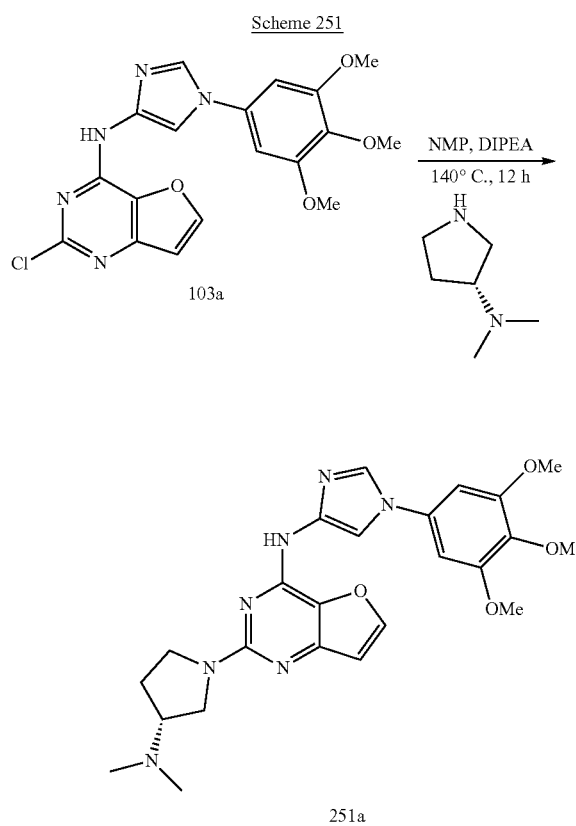

251a

Preparation of (R)-2-(3-(dimethylamino)pyrrolidin-1-yl)-N-(1-(3,4,5-trimethoxyphenyl)-1H-imidazol-4-yl)furo[3,2-d]pyrimidin-4-amine (251a)

Compound 251a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (422 mg, 1.05 mmol) and (R)—N,N-dimethylpyrrolidin-3-amine (600 mg, 5.25 mmol) in NMP (4 mL) using DIPEA (0.55 mL, 3.15 mmol) as base. This gave after workup by trituration of crude residue with MeOH (10 mL) followed by filtration and drying in vacuum compound 251a (160 mg, 32% yield) free base as an off white solid; $^1$H NMR (300 MHz, DMSO-$d_6$) δ 10.24 (s, 1H, $D_2O$ exchangeable), 8.16 (s, 1H), 8.08-7.98 (m, 2H), 6.92 (s, 2H), 6.78-6.70 (m, 1H), 3.92-3.78 (m, 8H), 3.68 (s, 3H), 3.61-3.46 (m, 1H), 3.31-3.16 (m, 1H), 2.83-2.66 (m, 1H), 2.17 (s, 6H), 2.13-2.03 (m, 1H), 1.86-1.72 (m, 1H); MS (ES+): 480.3 (M+1); (ES−): 514.3 (M+Cl); The free base was converted to HCl salt by using reverse column chromatography [(silica gel C-18, 50 g), eluting with acetonitrile in water (containing 0.1% HCl) from 0-100%] to afford (R)-2-(3-(dimethylamino)pyrrolidin-1-yl)-N-(1-(3,4,5-trimethoxyphenyl)-1H-imidazol-4-yl)furo[3,2-d]pyrimidin-4-amine (251a) (108 mg, 20% yield) HCl salt as a white solid; $^1$H NMR (300 MHz, DMSO-$d_6$) δ 12.23-11.64 (m, 2H, $D_2O$ exchangeable), 8.57 (s, 1H), 8.40 (d, J=2.1 Hz, 1H), 8.04 (s, 1H), 7.11-6.96 (m, 3H), 4.16-3.99 (m, 4H), 3.89 (s, 6H), 3.84-3.73 (m, 1H), 3.70 (s, 3H), 2.81 (s, 6H), 2.49-2.34 (m, 2H); MS (ES+) 480.3 (M+1); (ES−): 514.3 (M+Cl); MS (ES+): 480.3 (M+1); (ES−): 514.2 (M+Cl); HPLC purity: 96.58%.

Scheme 252

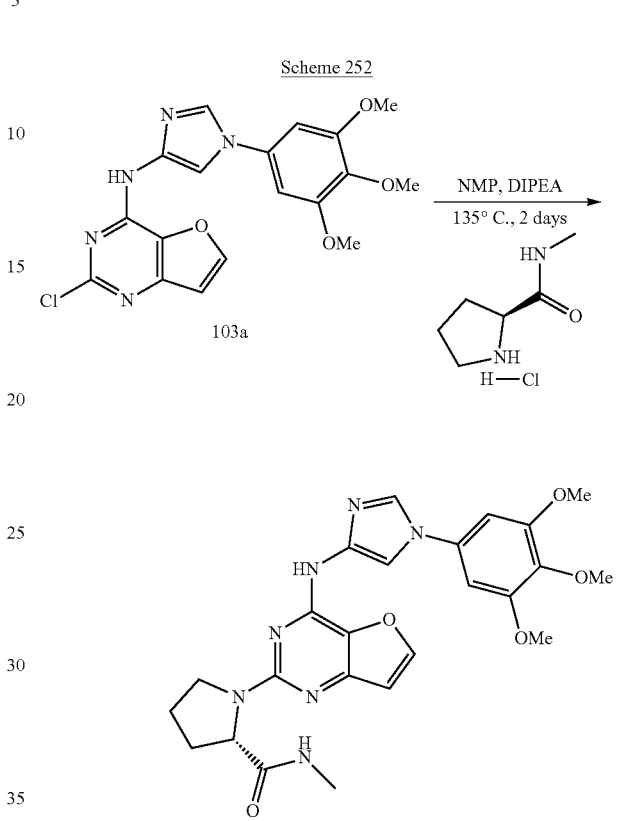

252a

Preparation of (S)—N-methyl-1-(4-((1-(3,4,5-trimethoxyphenyl)-1H-imidazol-4-yl)amino)furo[3,2-d]pyrimidin-2-yl)pyrrolidine-2-carboxamide (252a)

Compound 252a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (350 mg, 0.87 mmol) and (S)—N-methylpyrrolidine-2-carboxamide hydrochloride (574 mg, 3.48 mmol) in NMP (4 mL) using DIPEA (0.91 mL, 5.23 mmol) as base. This gave after workup by trituration of crude residue with MeOH (10 mL) followed by purification by reverse phase column chromatography [(silica gel C-18, 50 g), eluting with acetonitrile in water (containing 0.1% HCl) from 0-100%] (S)—N-methyl-1-(4-((1-(3,4,5-trimethoxyphenyl)-1H-imidazol-4-yl)amino)furo[3,2-d]pyrimidin-2-yl)pyrrolidine-2-carboxamide (252a) (245 mg, 57% yield) HCl salt as a white solid; $^1$H NMR (300 MHz, DMSO-$d_6$) δ 13.36 (s, 1H, $D_2O$ exchangeable), 11.84 (s, 1H, $D_2O$ exchangeable), 8.46-8.28 (m, 2H), 8.17-7.99 (m, 1H, $D_2O$ exchangeable), 7.73 (s, 1H), 7.19-7.01 (m, 3H), 4.66 (d, J=8.8 Hz, 1H), 4.00-3.88 (m, 7H), 3.69 (s, 3H), 3.64-3.51 (m, 1H), 2.50 (s, 3H), 2.35-2.17 (m, 1H), 2.15-1.86 (m, 3H); MS (ES+): 494.2 (M+Na); 516.2 (M+Na); (ES−): 528.2 (M+Cl); HPLC purity: 94.53%.

Scheme 253

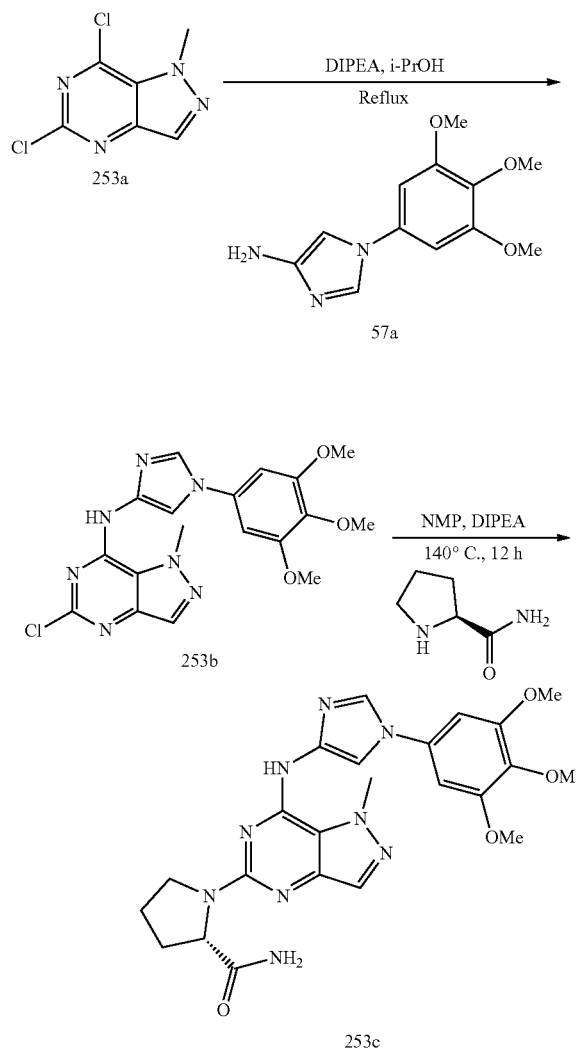

Preparation of (S)-1-(1-methyl-7-((1-(3,4,5-trimethoxyphenyl)-1H-imidazol-4-yl)amino)-1H-pyrazolo[4,3-d]pyrimidin-5-yl)pyrrolidine-2-carboxamide (253c)

Step-1: Preparation of 5-chloro-1-methyl-N-(1-(3,4,5-trimethoxyphenyl)-1H-imidazol-4-yl)-1H-pyrazolo[4,3-d]pyrimidin-7-amine (253b)

Compound 253b was prepared from 5,7-dichloro-1-methyl-1H-pyrazolo[4,3-d]pyrimidine (253a) (300 mg, 1.48 mmol) in 2-Propanol (50 mL) using DIPEA (0.77 mL, 4.43 mmol) and 1-(3,4,5-trimethoxyphenyl)-1H-imidazol-4-amine (57a) (387 mg, 1.55 mmol, free base) according to the procedure reported in Scheme 1. This gave after workup 5-chloro-1-methyl-N-(1-(3,4,5-trimethoxyphenyl)-1H-imidazol-4-yl)-1H-pyrazolo[4,3-d]pyrimidin-7-amine (253b) (320 mg, 52% yield) as a white solid; $^1$H NMR (300 MHz, DMSO-$d_6$) δ 9.87 (s, 1H), 8.26 (s, 1H), 8.07 (s, 1H), 7.95 (s, 1H), 6.95 (s, 2H), 4.38 (s, 3H), 3.88 (s, 6H), 3.69 (s, 3H); MS (ES+): 438.1 (M+Na); (ES−): 414.2 (M−1).

Step-2: Preparation of (S)-1-(1-methyl-7-((1-(3,4,5-trimethoxyphenyl)-1H-imidazol-4-yl)amino)-1H-pyrazolo[4,3-d]pyrimidin-5-yl)pyrrolidine-2-carboxamide (253c)

Compound 253c was prepared according to the procedure reported in step-2 of Scheme 76 from 5-chloro-1-methyl-N-(1-(3,4,5-trimethoxyphenyl)-1H-imidazol-4-yl)-1H-pyrazolo[4,3-d]pyrimidin-7-amine (253b) (300 mg, 0.72 mmol) and (S)-pyrrolidine-2-carboxamide (412 mg, 3.61 mmol) in NMP (10 mL) using DIPEA (0.38 mL, 2.16 mmol) as base. This gave after workup and purification by flash column chromatography [silica gel (24 g), eluting with DMA80 in DCM from 0-100%] followed by purification by reverse phase flash column chromatography [(silica gel C-18, 50 g), eluting with ACN in water (containing 0.1% HCl) from 0-100%] (S)-1-(1-methyl-7-((1-(3,4,5-trimethoxyphenyl)-1H-imidazol-4-yl)amino)-1H-pyrazolo[4,3-d]pyrimidin-5-yl)pyrrolidine-2-carboxamide (253c) (152 mg, 43% yield) HCl salt as a white solid; $^1$H NMR (300 MHz, DMSO-$d_6$) δ 12.75 (s, 1H, $D_2O$ exchangeable), 9.09 (s, 1H), 7.97 (s, 1H), 7.81 (s, 1H), 7.59 (s, 1H, $D_2O$ exchangeable), 7.23 (s, 2H), 7.17 (s, 1H, $D_2O$ exchangeable), 4.58 (d, J=8.8 Hz, 1H), 4.38 (s, 3H), 4.00-3.83 (m, 8H), 3.70 (s, 3H), 3.60-3.47 (m, 1H), 2.34-2.17 (m, 1H), 2.06-1.90 (m, 3H); MS (ES+): 494.3 (M+Na); 516.3 (M+Na); (ES−): 492.3 (M−1); 528.3 (M+Cl). HPLC purity, 98.77%

Scheme 254

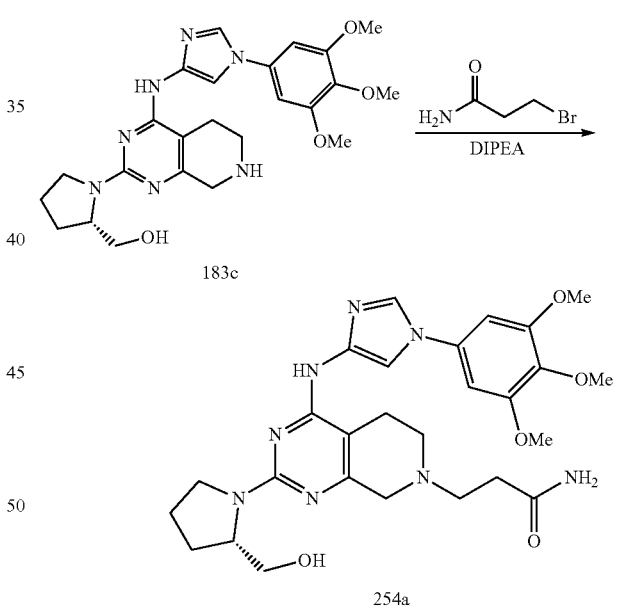

Preparation of (S)-3-(2-(2-(hydroxymethyl)pyrrolidin-1-yl)-4-((1-(3,4,5-trimethoxyphenyl)-1H-imidazol-4-yl)amino)-5,6-dihydropyrido[3,4-d]pyrimidin-7(8H)-yl)propanamide (254a)

To a stirred suspension of (S)-(1-(4-((1-(3,4,5-trimethoxyphenyl)-1H-imidazol-4-yl)amino)-5,6,7,8-tetrahydropyrido[3,4-d]pyrimidin-2-yl)pyrrolidin-2-yl)methanol (183c) (417 mg, 0.7 mmol), 3-bromopropanamide (213 mg, 1.4 mmol) in DCM (15 mL) was added DIPEA (0.489 mL, 2.80 mmol) and stirred at room temperature for 12 h.

Reaction mixture was concentrated in vacuum, purified by flash column chromatography (silica gel, 24 g eluting with DMA 80 in dichloromethane) followed by purification by reverse phase column chromatography [(silica gel C-18, 25 g), eluting with 0.1% aqueous HCl and acetonitrile) to afford (S)-3-(2-(2-(hydroxymethyl)pyrrolidin-1-yl)-4-((1-(3,4,5-trimethoxyphenyl)-1H-imidazol-4-yl)amino)-5,6-dihydropyrido[3,4-d]pyrimidin-7(8H)-yl)propanamide (254a) (95 mg, 25% yield) HCl salt as a white solid; $^1$H NMR (300 MHz, DMSO-d$_6$) δ 11.95 (s, 1H, D$_2$O exchangeable), 10.59 (s, 1H, D$_2$O exchangeable), 8.52 (s, 1H), 8.00 (s, 1H), 7.71 (s, 1H, D$_2$O exchangeable), 7.14 (s, 1H, D$_2$O exchangeable), 6.99 (s, 2H), 4.72-4.04 (m, 3H), 3.87 (s, 6H), 3.82-3.57 (m, 5H), 3.60-3.45 (m, 4H), 3.45-3.15 (m, 1H), 2.96 (s, 2H), 2.76 (s, 2H), 2.01 (s, 4H); MS (ES+): 553.4 (M+1), (ES−): 587.4 (M+Cl); HPLC purity: 93.71%.

[3,4-d]pyrimidin-2-yl)pyrrolidine-2-carboxamide (255a) (77 mg, 20% yield) HCl salt as a white solid; $^1$H NMR (300 MHz, DMSO-d$_6$) δ 12.32-11.60 (m, 1H, D$_2$O exchangeable), 10.43 (s, 1H, D$_2$O exchangeable), 8.59 (s, 1H), 7.90 (s, 1H), 7.72 (s, 1H, D$_2$O exchangeable), 7.54 (s, 1H, D$_2$O exchangeable), 7.27-6.96 (m, 4H, 2H D$_2$O exchangeable), 4.60-4.47 (m, 1H), 4.46-4.21 (m, 1H), 3.93 (s, 6H), 3.88-3.68 (m, 2H), 3.69 (s, 3H), 3.63-3.20 (m, 4H), 2.98 (s, 2H), 2.77 (s, 2H), 2.35-2.15 (m, 1H), 2.09-1.83 (m, 3H); MS (ES+): 566.4 (M+1), 588.3 (M+Na), (ES−): 600.3 (M+Cl); HPLC purity: 96.19%.

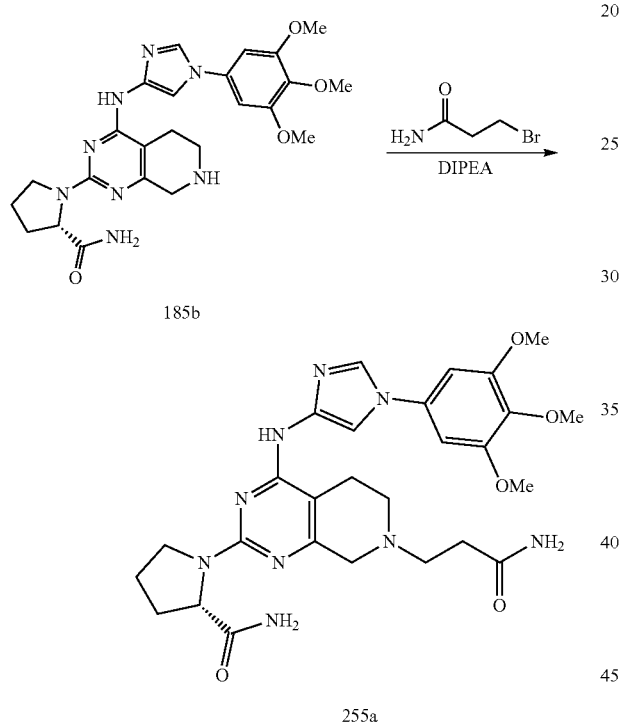

Scheme 255

185b

255a

Preparation of (S)-1-(7-(3-amino-3-oxopropyl)-4-((1-(3,4,5-trimethoxyphenyl)-1H-imidazol-4-yl)amino)-5,6,7,8-tetrahydropyrido[3,4-d]pyrimidin-2-yl)pyrrolidine-2-carboxamide (255a)

To a stirred suspension of (S)-1-(4-((1-(3,4,5-trimethoxyphenyl)-1H-imidazol-4-yl)amino)-5,6,7,8-tetrahydropyrido[3,4-d]pyrimidin-2-yl)pyrrolidine-2-carboxamide (185b) (426 mg, 0.7 mmol), 3-bromopropanamide (213 mg, 1.4 mmol) in DCM (15 mL) was added DIPEA (0.489 mL, 2.8 mmol) and stirred at room temperature for 12 h. Reaction mixture was concentrated in vacuum, purified by flash column chromatography (silica gel, 24 g eluting with DMA 80 in dichloromethane) followed by purification by reverse phase column chromatography [(silica gel C-18, 25 g), eluting with 0.1% aqueous HCl and acetonitrile) to afford (S)-1-(7-(3-amino-3-oxopropyl)-4-((1-(3,4,5-trimethoxyphenyl)-1H-imidazol-4-yl)amino)-5,6,7,8-tetrahydropyrido

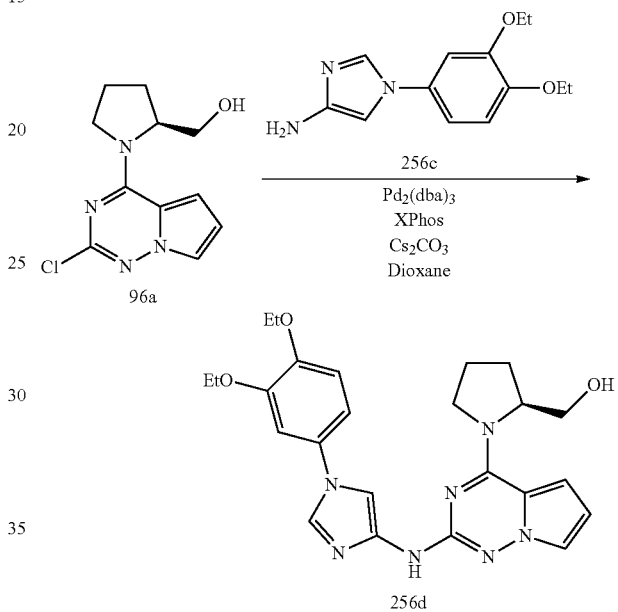

Scheme 256

96a

256d

Preparation of (S)-(1-(2-((1-(3,4-diethoxyphenyl)-1H-imidazol-4-yl)amino)pyrrolo[2,1-f][1,2,4]triazin-4-yl)pyrrolidin-2-yl)methanol (256d)

Compound 256d was prepared from (S)-(1-(2-chloropyrrolo[2,1-f][1,2,4]triazin-4-yl)pyrrolidin-2-yl)methanol (96a) (253 mg, 1.0 mmol), 1-(3,4-diethoxyphenyl)-1H-imidazol-4-amine (256c) (309 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and Pd$_2$(dba)$_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA 80 in dichloromethane] compound (256d) free base as a solid. The free base was repurified by reverse phase column chromatography [(silica gel C-18, 100 g), eluting with ACN in water (containing 0.1% HCl) from 0-100%] to afford (S)-(1-(2-((1-(3,4-diethoxyphenyl)-1H-imidazol-4-yl)amino)pyrrolo[2,1-f][1,2,4]triazin-4-yl)pyrrolidin-2-yl)methanol (256d) (205 mg, 44% yield) HCl salt as a white solid; $^1$H NMR (300 MHz, DMSO-d$_6$) δ 9.45 (s, 1H), 9.11 (s, 1H, D$_2$O exchangeable), 7.79 (s, 1H), 7.62 (s, 1H), 7.37 (d, J=2.5 Hz, 1H), 7.29 (d, J=8.3 Hz, 1H), 7.13 (d, J=8.8 Hz, 1H), 6.92-6.75 (m, 1H), 6.54 (s, 1H), 4.51 (s, 1H), 4.12 (dq, J=14.2, 7.0 Hz, 4H), 4.03-3.73 (m, 2H), 3.72-3.35

(m, 2H), 2.23-1.80 (m, 4H), 1.37 (q, J=6.6 Hz, 6H); MS (ES+): 464.3 (M+1), 486.3 (M+Na), (ES−): 498.3 (M+Cl); HPLC purity: 98.19%.

Scheme 257

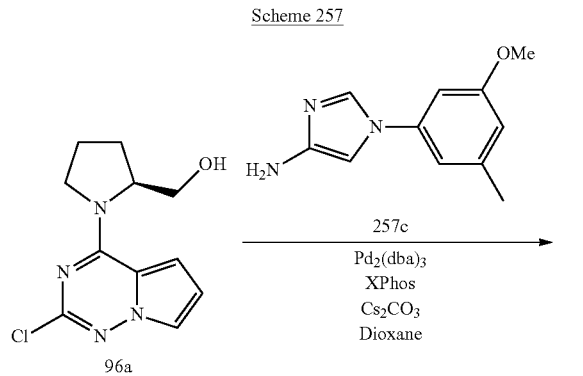

Scheme 258

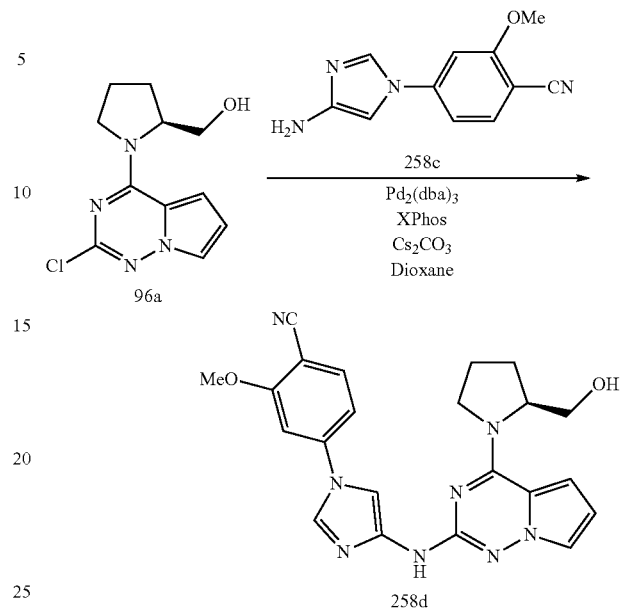

Preparation of (S)-4-(4-((4-(2-(hydroxymethyl)pyrrolidin-1-yl)pyrrolo[2,1-f][1,2,4]triazin-2-yl)amino)-1H-imidazol-1-yl)-2-methoxybenzonitrile (258d)

Compound 258d was prepared from (S)-(1-(2-chloropyrrolo[2,1-f][1,2,4]triazin-4-yl)pyrrolidin-2-yl)methanol (96a) (253 mg, 1.0 mmol), 4-(4-amino-1H-imidazol-1-yl)-2-methoxybenzonitrile (258c) (268 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and $Pd_2(dba)_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA 80 in dichloromethane] compound (258d) free base as a solid. The free base was repurified by reverse phase column chromatography [(silica gel C-18, 100 g), eluting with ACN in water (containing 0.1% HCl) from 0-100%] to afford (S)-4-(4-((4-(2-(hydroxymethyl)pyrrolidin-1-yl)pyrrolo[2,1-f][1,2,4]triazin-2-yl)amino)-1H-imidazol-1-yl)-2-methoxybenzonitrile (258d) (71 mg, 17% yield) HCl salt as a white solid; $^1$H NMR (300 MHz, DMSO-$d_6$) δ 9.35 (s, 1H, D$_2$O exchangeable), 8.89 (s, 1H), 8.06-7.79 (m, 2H), 7.67 (s, 1H), 7.59 (s, 1H), 7.52 (d, J=8.5 Hz, 1H), 6.89 (s, 1H), 6.55 (s, 1H), 4.64-4.45 (m, 1H), 4.06 (s, 3H), 4.05-3.31 (m, 4H), 2.24-1.80 (m, 4H); MS (ES+): 431.3 (M+1), 453.3 (M+Na), (ES−): 465.3 (M+Cl); HPLC purity: 98.56%.

Preparation of (S)-(1-(2-((1-(3-methoxy-5-methylphenyl)-1H-imidazol-4-yl)amino)pyrrolo[2,1-f][1,2,4]triazin-4-yl)pyrrolidin-2-yl)methanol (257d)

Compound 257d was prepared from (S)-(1-(2-chloropyrrolo[2,1-f][1,2,4]triazin-4-yl)pyrrolidin-2-yl)methanol (96a) (253 mg, 1.0 mmol), 1-(3-methoxy-5-methylphenyl)-1H-imidazol-4-amine (257c) (254 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and $Pd_2(dba)_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA 80 in dichloromethane]compound (257d) free base as a solid. The free base was repurified by reverse phase column chromatography [(silica gel C-18, 100 g), eluting with ACN in water (containing 0.1% HCl) from 0-100%] to afford (S)-(1-(2-((1-(3-methoxy-5-methylphenyl)-1H-imidazol-4-yl)amino)pyrrolo[2,1-f][1,2,4]triazin-4-yl)pyrrolidin-2-yl)methanol (257d) (200 mg, 48% yield) HCl salt as a white solid; $^1$H NMR (300 MHz, DMSO-$d_6$) δ 9.43 (s, 1H, D$_2$O exchangeable), 9.09 (s, 1H), 7.83 (s, 1H), 7.65 (s, 1H), 7.21 (d, J=9.4 Hz, 2H), 6.93 (s, 1H), 6.86 (d, J=4.5 Hz, 1H), 6.54 (s, 1H), 4.51 (s, 1H), 4.08-3.83 (m, 1H), 3.85 (s, 3H), 3.75-3.38 (m, 3H), 2.39 (s, 3H), 2.26-1.83 (m, 4H); MS (ES+): 420.3 (M+1), 442.3 (M+Na), (ES−): 454.3 (M+Cl); HPLC purity: 97.77%.

Scheme 259

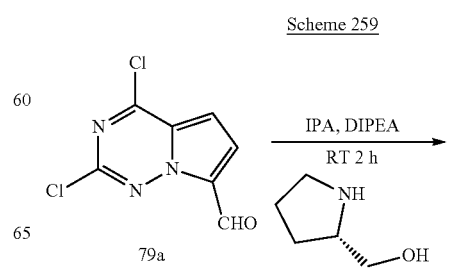

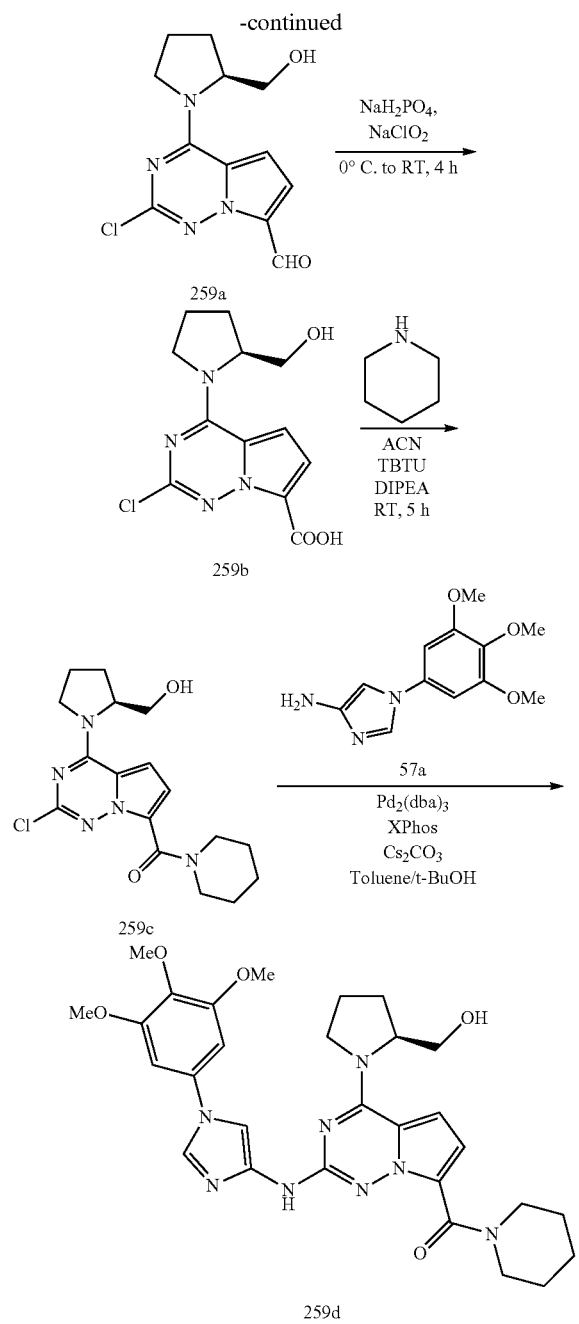

Preparation of (S)-(4-(2-(hydroxymethyl)pyrrolidin-1-yl)-2-((1-(3,4,5-trimethoxyphenyl)-1H-imidazol-4-yl)amino)pyrrolo[2,1-f][1,2,4]triazin-7-yl)(piperidin-1-yl)methanone (259d)

Step-1: Preparation of (S)-2-chloro-4-(2-(hydroxymethyl)pyrrolidin-1-yl)pyrrolo[2,1-f][1,2,4]triazine-7-carbaldehyde (259a)

To a solution of 2,4-dichloropyrrolo[1,2-f][1,2,4]triazine-7-carbaldehyde (79a) (0.4 g, 1.85 mmol) in 2-Propanol (10 mL) was added (S)-pyrrolidin-2-ylmethanol (0.18 mL, 1.85 mmol) and DIPEA (0.97 mL, 5.55 mmol). The mixture was stirred at room temp for 2 h and the solid obtained was collected by filtration, purified by flash column chromatog- raphy (silica gel 12 g, eluting with DCM and methanol 0 to 30%) to afford (S)-2-chloro-4-(2-(hydroxymethyl)pyrrolidin-1-yl)pyrrolo[1,2-f][1,2,4]triazine-7-carbaldehyde (259a) as a yellow solid; $^1$H NMR (300 MHz, DMSO-d$_6$) δ 9.09 (s, 1H), 7.47 (d, J=5.2 Hz, 1H), 6.86 (d, J=5.1 Hz, 1H), 5.44 (t, J=5.6 Hz, 1H), 4.50-4.40 (m, 1H), 4.10-3.86 (m, 2H), 3.78-3.68 (m, 1H), 3.59-3.45 (m, 1H), 2.27-2.02 (m, 3H), 1.93-1.78 (m, 1H).

Step-2: Preparation of (S)-2-chloro-4-(2-(hydroxymethyl)pyrrolidin-1-yl)pyrrolo[2,1-f][1,2,4]triazine-7-carboxylic acid (259b)

To a stirred solution of (S)-2-chloro-4-(2-(hydroxymethyl)pyrrolidin-1-yl)pyrrolo[2,1-f][1,2,4]triazine-7-carbaldehyde (259a) (2.0 g, 9.3 mmol) and in THF/water (66 mL, 8:2) were added 2-methyl-2-butene (5.4 g, 76.98 mmol) and sodium dihydrogen phosphate (9.2 g, 76.79 mmol) at room temperature. The reaction mixture was stirred at room temperature for 20 min, cooled to 0° C. and added NaClO$_2$ (3.3 g, 36.48 mmol). The reaction mixture was stirred at room temperature for 4 h and concentrated under reduce pressure. The residue obtained was acidified with 1 N HCl and the solid obtained was collected by filtration, washed with water, dried under vacuum to afford (S)-2-chloro-4-(2-(hydroxymethyl)pyrrolidin-1-yl)pyrrolo[2,1-f][1,2,4]triazine-7-carboxylic acid (259b) (2.0 g, 73%) as an off-white solid; $^1$H NMR (300 MHz, DMSO-d$_6$): δ 12.8 (S, 1H), 7.2 (m, 1H), 7.0 (m, 1H), 5.22 (s, 1H), 4.51-4.42 (m, 2H), 3.9 (m, 1H), 3.67-3.60 (m, 2H), 2.25-1.95 (m, 4H); MS: (ES+): 296.9 (M+1), (ES−): 295.1 (M−1).

Step-3: Preparation of (S)-(2-chloro-4-(2-(hydroxymethyl)pyrrolidin-1-yl)pyrrolo[2,1-f][1,2,4]triazin-7-yl)(piperidin-1-yl)methanone (259c)

To a stirred solution (S)-2-chloro-4-(2-(hydroxymethyl) pyrrolidin-1-yl)pyrrolo[2,1-f][1,2,4]triazine-7-carboxylic acid (259b) (1.0 g, 3.37 mmol) in acetonitrile (30 mL) was added TBTU (1.62 g, 5.05 mmol), DIPEA (1.0 g, 8.42 mmol) and piperidine (0.29 g, 3.37 mmol) sequentially at room temperature. The reaction mixture was stirred at room temperature for 5 h, diluted with water and extracted with ethyl acetate (3×50 mL). The organic layers were combined washed with brine, dried, filtered and concentrated under reduced pressure. The crude residue obtained was purified by flash column chromatography (silica gel, eluting with methanol in DCM 0 to 5%) to afford (S)-(2-chloro-4-(2-(hydroxymethyl)pyrrolidin-1-yl)pyrrolo[2,1-f][1,2,4]triazin-7-yl)(piperidin-1-yl)methanone (259c) (1.0 g, 82%) as an off-white solid; $^1$H NMR (300 MHz, DMSO-d$_6$) δ 7.04-7.02 (d, 1H), 6.77-6.76 (d, 1H), 4.8 (s, 1H), 4.5 (m, 1H), 4.01-3.9 (m, 2H), 3.6-3.5 (m, 4H), 3.1 (m, 2H), 2.05-1.94 (m, 4H), 1.58-1.39 (m, 6H); MS (ES+): 363.1 (M+1).

Step-4: Preparation of (S)-(4-(2-(hydroxymethyl)pyrrolidin-1-yl)-2-((1-(3,4,5-trimethoxyphenyl)-1H-imidazol-4-yl)amino)pyrrolo[2,1-f][1,2,4]triazin-7-yl)(piperidin-1-yl)methanone (259d)

Compound 259d was prepared from (S)-(2-chloro-4-(2-(hydroxymethyl)pyrrolidin-1-yl)pyrrolo[2,1-f][1,2,4]triazin-7-yl)(piperidin-1-yl)methanone (259c) (400 mg, 1.10 mmol) 1-(3,4,5-trimethoxyphenyl)-1H-imidazol-4-amine (57a) (411 mg, 1.65 mmol, free base), dicyclohexyl(2',4',6'-triisopropylbiphenyl-2-yl)phosphine (XPhos, 209 mg, 0.44 mmol), cesium carbonate (1000 mg, 3.08 mmol) and Pd$_2$(dba)$_3$ (151 mg, 0.17 mmol) in toluene/t-BuOH (56 mL, Ratio: 5:2) according to the procedure reported in step-3 of Scheme 101. This gave after workup and purification by flash column chromatography (silica gel, eluting with methanol in DCM 0-10%] followed by purification by reverse phase flash chromatography [(silica gel C-18, 24 g) eluting with acetonitrile and 0.1% HCl in water] (S)-(4-(2-(hydroxymethyl)pyrrolidin-1-yl)-2-((1-(3,4,5-trimethoxyphenyl)-1H-imidazol-4-yl)amino)pyrrolo[2,1-f][1,2,4]triazin-7-yl)(piperidin-1-yl)methanone (259d) (80 mgs, 11%) HCl salt as a brown solid; $^1$H NMR (300 MHz, DMSO-d$_6$): δ 9.80 (s, 1H), 9.38 (s, 1H), 7.95 (s, 1H), 7.14 (s, 2H), 6.92 (d, J=4.7 Hz, 1H), 6.75-6.60 (m, 1H), 4.68-4.28 (m, 1H), 4.10-2.91 (m, 18H), 2.30-1.72 (m, 4H), 1.65-1.17 (m, 6H). MS (ES+): 577.4 (M+1), 599.3 (M+Na); MS (ES−): 611.4 (M+Cl); HPLC purity: 95.17% nyl)-1H-imidazol-4-yl)furo[3,2-d]pyrimidin-4-amine (260a) (42 mg, 10% yield) as a white solid; $^1$H NMR (300 MHz, DMSO-d$_6$) δ 11.79 (s, 1H, D$_2$O exchangeable), 8.43-8.31 (m, 2H), 8.01 (s, 1H, D$_2$O exchangeable), 7.08-6.91 (m, 3H), 4.34-4.17 (m, 2H), 4.02-3.93 (m, 2H), 3.87 (s, 6H), 3.69 (s, 3H), 2.72-2.55 (m, 2H); $^{19}$F NMR (282 MHz, DMSO) δ −100.01; MS (ES+): 473.2 (M+1); HPLC purity: 94.94%.

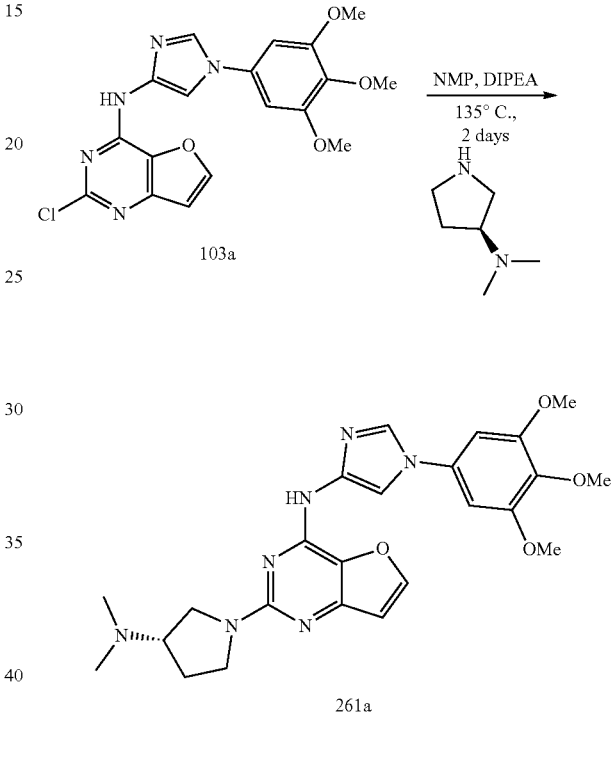

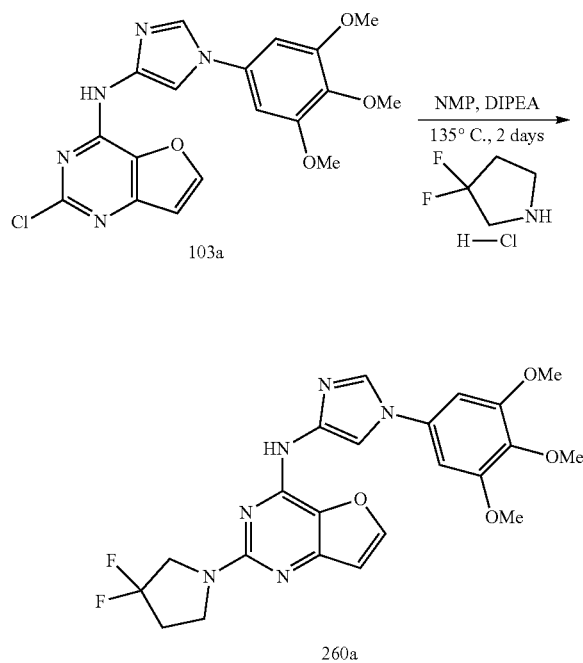

Preparation of 2-(3,3-difluoropyrrolidin-1-yl)-N-(1-(3,4,5-trimethoxyphenyl)-1H-imidazol-4-yl)furo[3,2-d]pyrimidin-4-amine (260a)

Compound 260a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (350 mg, 0.87 mmol) and 3,3-difluoropyrrolidine hydrochloride (500 mg, 3.48 mmol) in NMP (4 mL) using DIPEA (0.91 mL, 5.23 mmol) as base. This gave after workup by trituration of crude residue with MeOH (10 mL) followed by purification twice by reverse phase column chromatography [(silica gel C-18, 50 g), eluting with acetonitrile in water (containing 0.1% HCl) from 0-100%] 2-(3,3-difluoropyrrolidin-1-yl)-N-(1-(3,4,5-trimethoxyphe- Preparation of (S)-2-(3-(dimethylamino)pyrrolidin-1-yl)-N-(1-(3,4,5-trimethoxyphenyl)-1H-imidazol-4-yl)furo[3,2-d]pyrimidin-4-amine (261a)

Compound 261a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (350 mg, 0.87 mmol) and (S)—N,N-dimethylpyrrolidin-3-amine (398 mg, 3.48 mmol) in NMP (4 mL) using DIPEA (0.46 mL, 2.61 mmol) as base. This gave after workup by trituration of crude residue with MeOH (10 mL) followed by purification twice by reverse phase column chromatography [(silica gel C-18, 50 g), eluting with acetonitrile in water (containing 0.1% HCl) from 0-100%] (S)-2-(3-(dimethylamino)pyrrolidin-1-yl)-N-(1-(3,4,5-trimethoxyphenyl)-1H-imidazol-4-yl)furo[3,2-d]pyrimidin-4-amine (261a) (33 mg, 8% yield) as a white solid; $^1$H NMR (300 MHz, DMSO-d$_6$) δ 11.92 (s, 1H, D$_2$O exchangeable), 11.61 (s, 1H, D$_2$O exchangeable), 8.37 (d, J=8.7 Hz, 2H, 1H is D$_2$O exchangeable), 8.00 (s, 1H), 7.09-6.93 (m, 3H), 4.10-3.96 (m, 4H), 3.83-3.75 (m, 1H), 3.69 (s, 3H), 2.87-2.73 (m, 6H), 2.48-2.43 (m, 2H); MS (ES+): 480.2 (M+1); (ES−): 514.2 (M+Cl); HPLC purity: 95.36%.

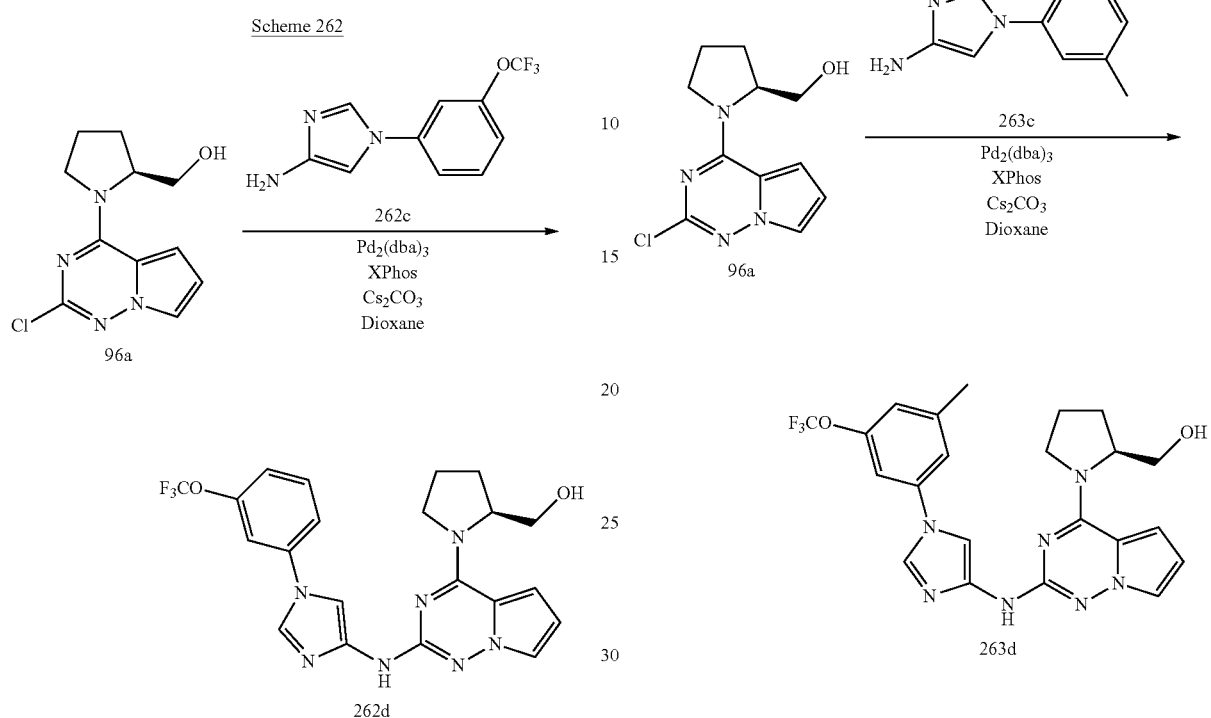

Scheme 262

Scheme 263

Preparation of (S)-(1-(2-((1-(3-(trifluoromethoxy)phenyl)-1H-imidazol-4-yl)amino)pyrrolo[2,1-f][1,2,4]triazin-4-yl)pyrrolidin-2-yl)methanol (262d)

Compound 262d was prepared from (S)-(1-(2-chloropyrrolo[2,1-f][1,2,4]triazin-4-yl)pyrrolidin-2-yl)methanol (96a) (253 mg, 1.0 mmol), 1-(3-(trifluoromethoxy)phenyl)-1H-imidazol-4-amine (262c) (304 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and Pd$_2$(dba)$_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA-80 in dichloromethane] compound (262d) free base as a solid. The free base was repurified by reverse phase column chromatography [(silica gel C-18, 50 g), eluting with ACN in water (containing 0.1% HCl) from 0-100%] to afford (S)-(1-(2-((1-(3-(trifluoromethoxy)phenyl)-1H-imidazol-4-yl)amino)pyrrolo[2,1-f][1,2,4]triazin-4-yl)pyrrolidin-2-yl)methanol (262d) (214 mg, 47% yield) HCl salt as a white solid; $^1$H NMR (300 MHz, DMSO-d$_6$) δ 9.84-9.52 (m, 1H, D$_2$O exchangeable), 9.12 (s, 1H), 8.04-7.84 (m, 3H), 7.74 (dd, J=14.6, 6.1 Hz, 2H), 7.52 (d, J=8.3 Hz, 1H), 6.92 (d, J=4.5 Hz, 1H), 6.57 (s, 1H), 4.09-3.75 (m, 1H), 3.75-3.51 (m, 2H), 3.51-3.29 (m, 1H), 2.25-1.86 (m, 4H); $^{19}$F NMR (282 MHz, DMSO-d$_6$) δ −56.78; MS (ES+): 460.2 (M+1), 482.2 (M+Na), (ES−) 494.2 (M+Cl); HPLC purity: 95.39%.

Preparation of (S)-(1-(2-((1-(3-methyl-5-(trifluoromethoxy)phenyl)-1H-imidazol-4-yl)amino)pyrrolo[2,1-f][1,2,4]triazin-4-yl)pyrrolidin-2-yl)methanol (263d)

Compound 263d was prepared from (S)-(1-(2-chloropyrrolo[2,1-f][1,2,4]triazin-4-yl)pyrrolidin-2-yl)methanol (96a) (253 mg, 1.0 mmol), 1-(3-methyl-5-(trifluoromethoxy)phenyl)-1H-imidazol-4-amine (263c) (322 mg, 1.25 mmol, free base), dicyclohexyl(2',4',6'-triisopropylbiphenyl-2-yl)phosphine (XPhos, 215 mg, 0.45 mmol), cesium carbonate (977 mg, 3.0 mmol) and Pd$_2$(dba)$_3$ (137 mg, 0.15 mmol) in 1,4-dioxane (15 mL) according to the procedure reported in step-3 of Scheme 101. This gave after workup and purification by flash column chromatography [silica gel (40 g), eluting with DMA 80 in dichloromethane] compound (263d) free base as a solid. The free base was repurified by reverse phase column chromatography [(silica gel C-18, 50 g), eluting with ACN in water (containing 0.1% HCl from 0-100%] to afford (S)-(1-(2-((1-(3-methyl-5-(trifluoromethoxy)phenyl)-1H-imidazol-4-yl)amino)pyrrolo[2,1-f][1,2,4]triazin-4-yl)pyrrolidin-2-yl)methanol (263d) (205 mg, 43% yield) HCl salt as a white solid; $^1$H NMR (300 MHz, DMSO-d$_6$) δ 9.87-9.37 (m, 1H, D$_2$O exchangeable), 9.06 (s, 1H), 7.87 (s, 1H), 7.81-7.64 (m, 3H), 7.36 (s, 1H), 6.91 (d, J=4.6 Hz, 1H), 6.57 (s, 1H), 4.59-4.50 (m, 1H), 4.08-3.76 (m, 1H), 3.75-3.51 (m, 2H), 3.51-3.33 (m, 1H), 2.47 (s, 3H), 2.27-1.86 (m, 4H); $^{19}$F NMR (282 MHz, DMSO-d$_6$) δ −56.66; MS (ES+): 474.2 (M+1), 496.2 (M+Na), (ES−): 508.2 (M+Cl); HPLC purity: 95.69%.

Scheme 264

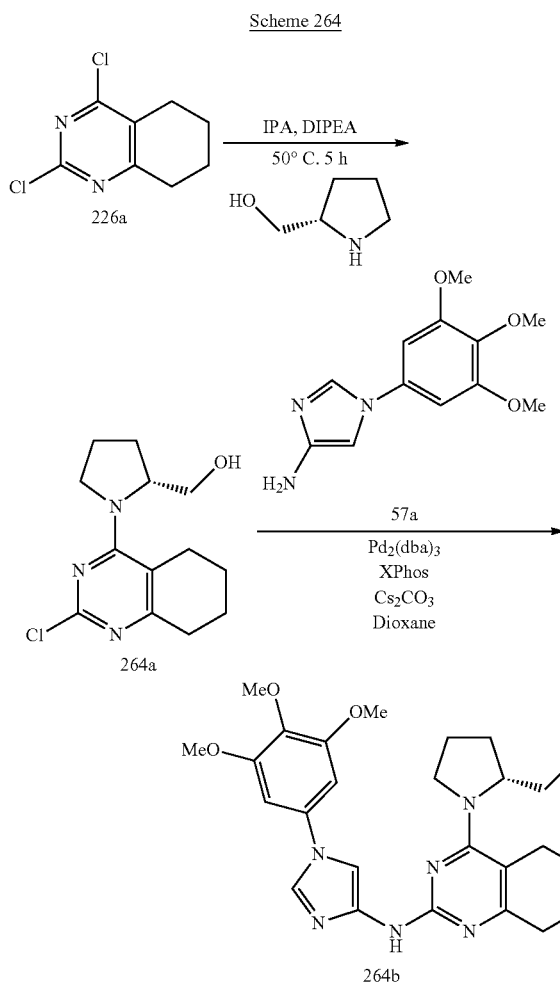

Preparation of (R)-(1-(2-((1-(3,4,5-trimethoxyphenyl)-1H-imidazol-4-yl)amino)-5,6,7,8-tetrahydroquinazolin-4-yl)pyrrolidin-2-yl)methanol (264b)

Step-1: Preparation of (R)-(1-(2-chloro-5,6,7,8-tetrahydroquinazolin-4-yl)pyrrolidin-2-yl)methanol (264a)

Compound 264a was prepared from 2,4-dichloro-5,6,7,8-tetrahydroquinazoline (226a) (0.5 g, 2.46 mmol, CAS #1127-85-1) in 2-Propanol (5 mL) using (R)-pyrrolidin-2-ylmethanol (0.25 g, 2.46 mmol) and DIPEA (1.29 mL, 7.39 mmol) according to the procedure reported in step-1 of Scheme 96. This gave after workup and purification by flash column chromatography [silica gel (40 g), eluting with DMA-80 in chloroform (0 to 50%) (R)-(1-(2-chloro-5,6,7,8-tetrahydroquinazolin-4-yl)pyrrolidin-2-yl)methanol (264a) (550 mg, 83% yield) as a white solid; $^1$H NMR (300 MHz, DMSO-$d_6$) δ 4.70 (t, J=5.7 Hz, 1H), 4.40-4.22 (m, 1H), 3.74-3.54 (m, 2H), 3.47 (m, 1H), 3.36 (m, 2H), 2.78-2.54 (m, 4H), 1.99-1.51 (m, 6H), 1.47-1.30 (m, 1H).

Step-2: Preparation of (R)-(1-(2-((1-(3,4,5-trimethoxyphenyl)-1H-imidazol-4-yl)amino)-5,6,7,8-tetrahydroquinazolin-4-yl)pyrrolidin-2-yl)methanol (264b)

Compound 264b was prepared from (R)-(1-(2-chloro-5,6,7,8-tetrahydroquinazolin-4-yl)pyrrolidin-2-yl)methanol (264a) (1.46 g, 5.45 mmol), 1-(3,4,5-trimethoxyphenyl)-1H-imidazol-4-amine (57a) (1.56 g, 6.27 mmol, free base), dicyclohexyl(2',4',6'-triisopropylbiphenyl-2-yl)phosphine (XPhos, 1.17 g, 2.45 mmol), cesium carbonate (5.33 g, 16.36 mmol) and Pd$_2$(dba)$_3$ (749 mg, 0.82 mmol) in 1,4-dioxane (40 mL) according to the procedure reported in step-3 of Scheme 101. This gave after workup and purification by flash column chromatography [silica gel (80 g), eluting with DMA 80 in CH$_2$Cl$_2$], followed by reverse phase column chromatography [(silica gel C-18, 24 g) eluting with acetonitrile and 0.1% HCl water] (R)-(1-(2-((1-(3,4,5-trimethoxyphenyl)-1H-imidazol-4-yl)amino)-5,6,7,8-tetrahydroquinazolin-4-yl)pyrrolidin-2-yl)methanol (264b) (799 mg, 32% yield) HCl salt as a white solid; $^1$H NMR (300 MHz, DMSO-$d_6$) δ 12.35 (s, 1H, D$_2$O exchangeable), 10.01 (s, 1H, D$_2$O exchangeable), 8.25 (s, 1H), 7.60 (s, 1H), 6.94 (d, J=1.1 Hz, 2H), 4.77-4.44 (m, 1H), 3.96-3.86 (m, 2H), 3.87 (d, J=1.0 Hz, 6H), 3.68 (s, 3H), 3.63-3.32 (m, 2H), 2.79-2.60 (m, 4H), 2.08-1.75 (m, 6H), 1.70-1.41 (m, 2H); MS (ES+): 481.4 (M+1), (ES−): 515.4 (M+Cl); HPLC purity: 96.8%.

Scheme 265

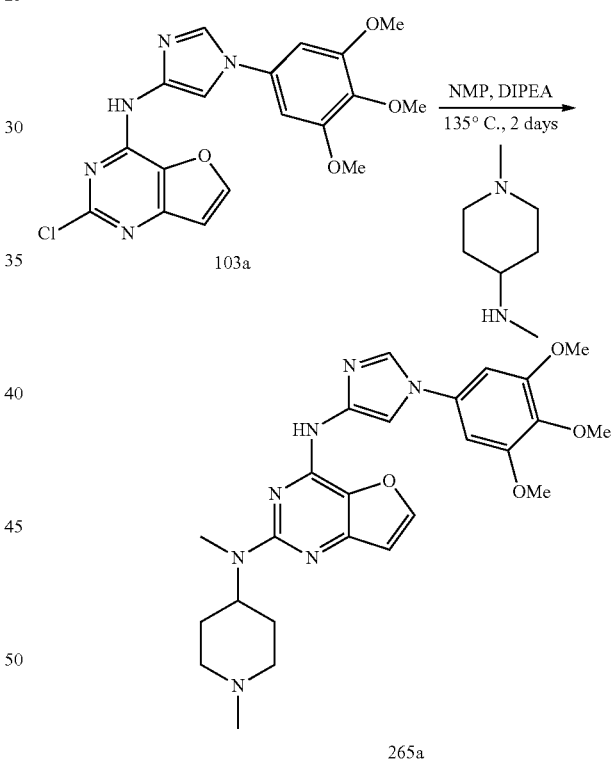

Preparation of N2-methyl-N2-(1-methylpiperidin-4-yl)-N4-(1-(3,4,5-trimethoxyphenyl)-1H-imidazol-4-yl)furo[3,2-d]pyrimidine-2,4-diamine (265a)

Compound 265a was prepared according to the procedure reported in step-2 of Scheme 76 from (2-chloro-furo[3,2-d]pyrimidin-4-yl)-[1-(3,4,5-trimethoxy-phenyl)-1H-imidazol-4-yl]-amine (103a) (350 mg, 0.87 mmol) and N,1-dimethylpiperidin-4-amine (893 mg, 6.97 mmol) in NMP (6 mL) using DIPEA (0.46 mL, 2.61 mmol) as base. This gave after workup and purification by flash column chromatography

[silica gel (24 g), eluting with DMA80 in DCM from 0-60%] followed by reverse phase column chromatography [(silica gel C-18, 50 g), eluting with acetonitrile in water (containing 0.1% HCl) from 0-100%] N2-methyl-N2-(1-methylpiperidin-4-yl)-N4-(1-(3,4,5-trimethoxyphenyl)-1H-imidazol-4-yl)furo[3,2-d]pyrimidine-2,4-diamine (265a) (103 mg, 24% yield) as an off white solid; $^1$H NMR (300 MHz, DMSO-d$_6$) δ 11.87 (s, 1H, D$_2$O exchangeable), 11.21 (s, 1H, D$_2$O exchangeable), 8.59 (s, 1H), 8.38 (s, 1H), 8.05 (s, 1H), 7.15-6.99 (m, 3H), 4.85-4.66 (m, 1H), 3.94-3.77 (m, 7H), 3.76-3.60 (m, 4H), 3.55-3.39 (m, 2H), 3.15 (s, 3H), 2.69-2.58 (m, 2H), 2.37-2.18 (m, 2H), 2.01-1.87 (m, 2H); MS (ES+): 494.3 (M+1); (ES−): 528.3 (M+Cl); HPLC purity: 91.01%.

Scheme 266

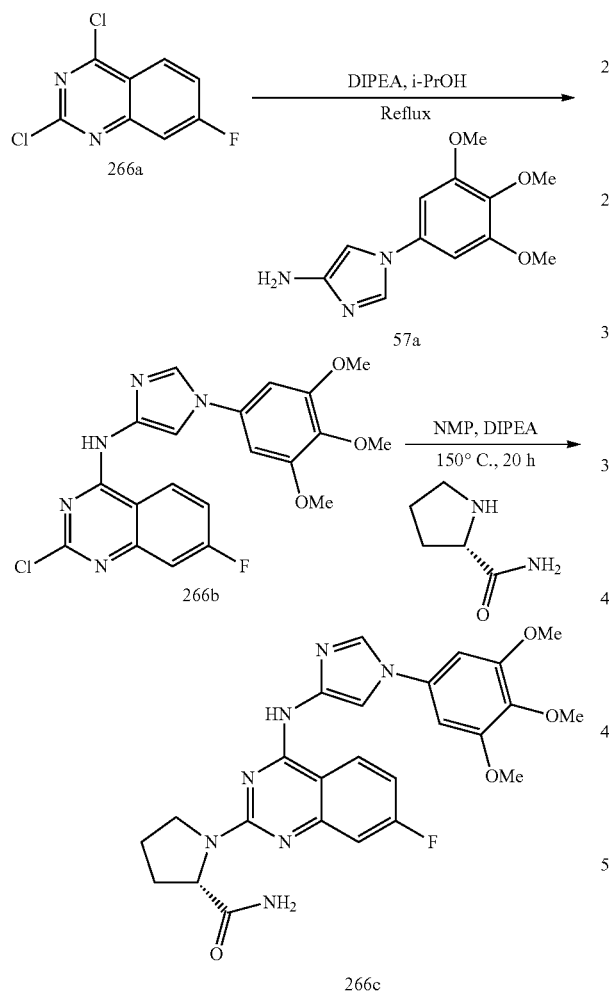

Preparation of (S)-1-(7-fluoro-4-((1-(3,4,5-trimethoxyphenyl)-1H-imidazol-4-yl)amino)quinazolin-2-yl)pyrrolidine-2-carboxamide (266c)

Step-1: Preparation of 2-chloro-7-fluoro-N-(1-(3,4,5-trimethoxyphenyl)-1H-imidazol-4-yl)quinazolin-4-amine (266b)

Compound 266b was prepared from 2,4-dichloro-7-fluoroquinazoline (266a) (500 mg, 2.3 mmol) in 2-Propanol (20 mL) using DIPEA (1.21 mL, 6.91 mmol) and 1-(3,4,5-trimethoxyphenyl)-1H-imidazol-4-amine (57a) (690 mg, 2.76 mmol, free base) according to the procedure reported in Scheme 1. This gave after workup 2-chloro-7-fluoro-N-(1-(3,4,5-trimethoxyphenyl)-1H-imidazol-4-yl)quinazolin-4-amine (266b) (0.91 g, 92% yield) as a brown solid; MS (ES+): 430.3 (M+1), 452.1 & 454.1 (M+Na); MS (ES−): 428.3 & 430.3 (M−1).

Step-2: Preparation of (S)-1-(7-fluoro-4-((1-(3,4,5-trimethoxyphenyl)-1H-imidazol-4-yl)amino)quinazolin-2-yl)pyrrolidine-2-carboxamide (266c)

Compound 266c was prepared according to the procedure reported in step-2 of Scheme 76 from 2-chloro-7-fluoro-N-(1-(3,4,5-trimethoxyphenyl)-1H-imidazol-4-yl)quinazolin-4-amine (266b) (300 mg, 0.7 mmol) and (S)-pyrrolidine-2-carboxamide (320 mg, 2.79 mmol) in NMP (10 mL) using DIPEA (0.73 mL, 4.19 mmol) as base. This gave after workup and purification by flash column chromatography [silica gel (12 g), eluting with DMA80 in DCM from 0-50%] followed by purification by reverse phase flash column chromatography [(silica gel C-18, 24 g), eluting with ACN in water (containing 0.1% HCl) from 0-100%] (S)-1-(7-fluoro-4-((1-(3,4,5-trimethoxyphenyl)-1H-imidazol-4-yl)amino)quinazolin-2-yl)pyrrolidine-2-carboxamide (266c) (220 mg, 62% yield) HCl salt as an yellow solid; $^1$H NMR (300 MHz, DMSO-d$_6$) δ 12.98 (s, 1H), 11.77 (s, 1H), 8.87 (dd, J=9.3, 5.7 Hz, 1H), 8.52 (s, 1H), 8.17 (d, J=10.0 Hz, 1H), 7.92 (s, 1H), 7.65 (s, 1H), 7.37 (dt, J=8.9, 5.1 Hz, 1H), 7.25 (s, 1H), 7.15 (s, 2H), 4.71 (d, J=8.6 Hz, 1H), 4.21-4.06 (m, 1H), 3.94 (s, 6H), 3.85-3.58 (m, 4H), 2.42-2.20 (m, 1H), 2.19-1.93 (m, 3H); $^{19}$F NMR (282 MHz, DMSO-d$_6$): δ −101.24; MS (ES+): 508.2 (M+1); MS (ES−): 506.3 (M−1). HPLC purity: 95.29%.

Scheme 267

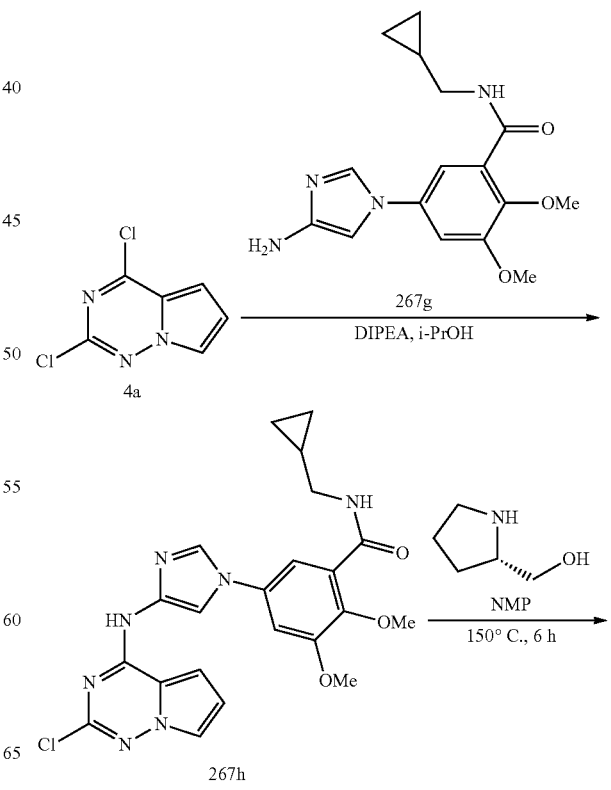

471

-continued

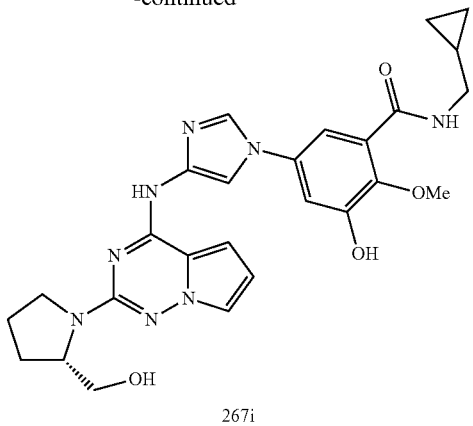

267i

Preparation of (S)—N-(cyclopropylmethyl)-3-hydroxy-5-(4-((2-(2-(hydroxymethyl)pyrrolidin-1-yl)pyrrolo[2,1-f][1,2,4]triazin-4-yl)amino)-1H-imidazol-1-yl)-2-methoxybenzamide (267i)

Step-1: Preparation of 5-(4-((2-chloropyrrolo[2,1-f][1,2,4]triazin-4-yl)amino)-1H-imidazol-1-yl)-N-(cyclopropylmethyl)-2,3-dimethoxybenzamide (267h)

Compound 267h was prepared from 2,4-dichloropyrrolo[2,1-f][1,2,4]triazine (4a) (400 mg, 2.12 mmol) in 2-Propanol (60 mL) using DIPEA (0.82 mL, 6.38 mmol) and 5-(4-amino-1H-imidazol-1-yl)-N-(cyclopropylmethyl)-2,3-dimethoxybenzamide (267g) (807 mg, 2.55 mmol) according to the procedure reported in Scheme 1. This gave after workup 5-(4-((2-chloropyrrolo[2,1-f][1,2,4]triazin-4-yl)amino)-1H-imidazol-1-yl)-N-(cyclopropylmethyl)-2,3-dimethoxybenzamide (267h) (0.35 g, 59%) as an off-white solid; $^1$H NMR (300 MHz, DMSO-$d_6$): δ 11.32 (s, 1H) 8.44 (s, 1H), 8.27 (s, 1H), 7.89-7.88 (s, 1H) 7.78 (s, 1H), 7.46-7.40 (d, 2H), 7.19 (s, 1H), 6.73 (s, 1H) 3.95 (s, 3H), 3.82 (s, 3H), 3.20-3.16 (m, 2H), 1.05-1.02 (m, 1H), 0.47-0.45 (m, 2H), 0.024-0.019 (m, 2H); MS (ES+): 468.0 (M+1), (ES−): 466.0 (M−1).

Step-2: Preparation of (S)—N-(cyclopropylmethyl)-3-hydroxy-5-(4-((2-(2-(hydroxymethyl)pyrrolidin-1-yl)pyrrolo[2,1-f][1,2,4]triazin-4-yl)amino)-1H-imidazol-1-yl)-2-methoxybenzamide (267i)

Compound 267i was prepared according to the procedure reported in step-2 of Scheme 76 from 5-(4-((2-chloropyrrolo[2,1-f][1,2,4]triazin-4-yl)amino)-1H-imidazol-1-yl)-N-(cyclopropylmethyl)-2,3-dimethoxybenzamide (267h) (300 mg, 0.64 mmol) and (S)-pyrrolidin-2-ylmethanol (650 mg, 6.14 mmol) in NMP (15 mL). This gave after workup and purification by flash column chromatography [silica gel (12 g), eluting with methanol in ethyl acetate (0-10%)] followed by purification by reverse phase flash column chromatography [(silica gel C-18, 24 g), eluting with ACN in water (containing 0.1% HCl) from 0-100%] (S)—N-(cyclopropylmethyl)-3-hydroxy-5-(4-((2-(2-(hydroxymethyl)pyrrolidin-1-yl)pyrrolo[2,1-f][1,2,4]triazin-4-yl)amino)-1H-imidazol-1-yl)-2-methoxybenzamide (267i) (20 mg) HCl salt as an off-white solid; $^1$H NMR (300 MHz, DMSO-$d_6$) δ 13.10 (s, 1H), 10.80 (s, 1H), 9.12 (t, J=5.5 Hz, 1H), 8.57 (s, 1H), 8.05 (s, 1H), 7.83 (d, J=2.2 Hz, 1H), 7.45 (s, 2H), 7.12 (d, J=4.4 Hz, 1H), 6.44 (dd, J=4.3, 2.4 Hz, 1H), 4.30-4.12 (m, 1H), 3.90 (s, 3H), 3.82-3.27 (m, 4H), 3.21 (t, J=6.3 Hz, 2H), 2.09-1.77 (m, 4H), 1.17-0.95 (m, 1H), 0.54-0.37 (m, 2H), 0.33-0.19 (m, 2H). MS (ES+): 519.3 (M+1), 541.2 (M+Na); MS (ES−): 517.3 (M−1); 553.3 (M+Cl).

Scheme 268

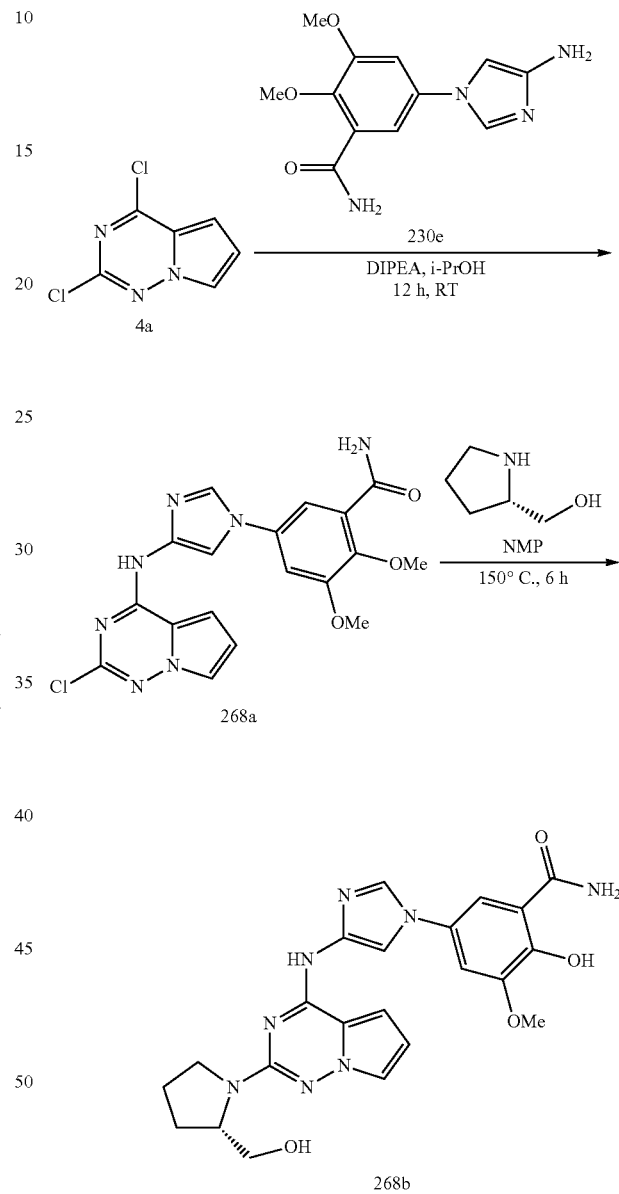

Preparation of (S)-2-hydroxy-5-(4-((2-(2-(hydroxymethyl)pyrrolidin-1-yl)pyrrolo[2,1-f][1,2,4]triazin-4-yl)amino)-1H-imidazol-1-yl)-3-methoxybenzamide (268b)

Step-1: Preparation of 5-(4-((2-chloropyrrolo[2,1-f][1,2,4]triazin-4-yl)amino)-1H-imidazol-1-yl)-2,3-dimethoxybenzamide (268a)

Compound 268a was prepared from 2,4-dichloropyrrolo[2,1-f][1,2,4]triazine (4a) (1000 mg, 5.31 mmol) in 2-Propanol (60 mL) using DIPEA (2.06, 15.95 mmol) and 5-(4-amino-1H-imidazol-1-yl)-2,3-dimethoxybenzamide (230e) (1.67 g, 6.38 mmol) according to the procedure reported in Scheme 1. This gave after workup 5-(4-((2-chloropyrrolo[2,1-f][1,2,4]triazin-4-yl)amino)-1H-imidazol-1-yl)-2,3-dimethoxybenzamide (268a) (0.5 g, 32%) as an off white solid; $^1$H NMR (300 MHz, DMSO-$d_6$): δ 11.31 (s, 1H), 8.28 (s, 1H), 7.86 (s, 1H), 7.67-7.54 (m, 2H), 7.58 (s, 1H), 7.45-7.40 (m, 3H), 6.72 (s, 1H), 3.95 (s, 3H), 3.86 (s, 3H); MS (ES+): 414.0 (M+1).

Step-2: Preparation of (S)-2-hydroxy-5-(4-((2-(2-(hydroxymethyl)pyrrolidin-1-yl)pyrrolo[2,1-f][1,2,4]triazin-4-yl)amino)-1H-imidazol-1-yl)-3-methoxybenzamide (268b)

Compound 268b was prepared according to the procedure reported in step-2 of Scheme 76 from 5-(4-((2-chloropyrrolo[2,1-f][1,2,4]triazin-4-yl)amino)-1H-imidazol-1-yl)-2,3-dimethoxybenzamide (268a) (500 mg, 1.2 mmol) and (S)-pyrrolidin-2-ylmethanol (1120 mg, 12.08 mmol) in NMP (15 mL). This gave after workup and purification by flash column chromatography [silica gel (12 g), eluting with methanol in ethyl acetate (0-10%)] Compound 268b free base (40 mg, 7%) as a solid. The solid was purified by reverse phase flash column chromatography [(silica gel C-18, 24 g), eluting with ACN in water (containing 0.1% HCl) from 0-100%] to afford (S)-2-hydroxy-5-(4-((2-(2-(hydroxymethyl)pyrrolidin-1-yl)pyrrolo[2,1-f][1,2,4]triazin-4-yl)amino)-1H-imidazol-1-yl)-3-methoxybenzamide (268b) (20 mg) HCl salt as an off-white solid; $^1$H NMR (300 MHz, DMSO-$d_6$) δ 10.78 (s, 1H), 8.50 (d, J=6.9 Hz, 2H), 8.17 (s, 1H), 8.02 (s, 1H), 7.79 (s, 1H), 7.44 (d, J=2.4 Hz, 2H), 7.12 (d, J=4.4 Hz, 1H), 6.48-6.38 (m, 1H), 4.27-4.13 (m, 1H), 3.89 (m, 3H), 3.76-3.25 (m, 1H), 3.58-3.46 (m, 1H), 3.44-3.25 (m, 2H), 2.06-1.80 (m, 4H); MS (ES+): 465.3 (M+1), 487.2 (M+Na); MS (ES−): 463.3 (M−1); 499.3 (M+Cl). HPLC purity: 81.95%.

Scheme 269

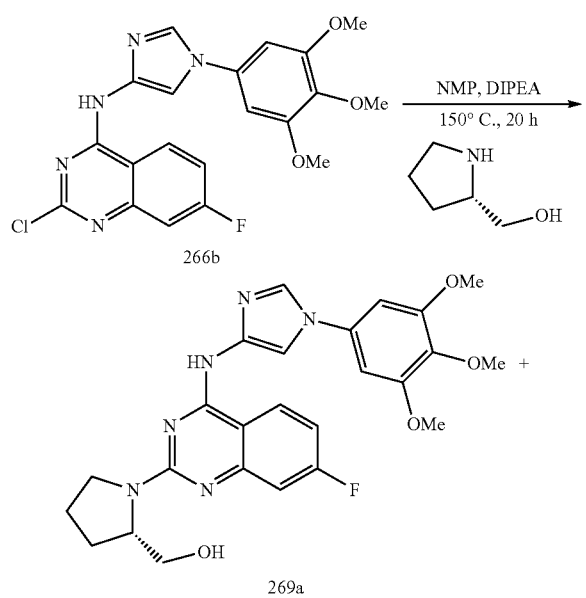

Preparation of (S)-(1-(7-fluoro-4-((1-(3,4,5-trimethoxyphenyl)-1H-imidazol-4-yl)amino)quinazolin-2-yl)pyrrolidin-2-yl)methanol (269a) and ((2S,2'S)-1,1'-(4-((1-(3,4,5-trimethoxyphenyl)-1H-imidazol-4-yl)amino)quinazoline-2,7-diyl)bis(pyrrolidine-2,1-diyl))dimethanol (269b)

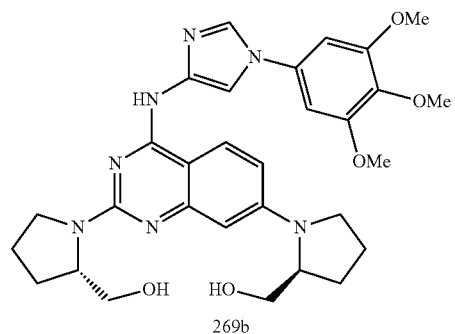

Compound 269a and 269b was prepared according to the procedure reported in step-2 of Scheme 76 from 2-chloro-7-fluoro-N-(1-(3,4,5-trimethoxyphenyl)-1H-imidazol-4-yl)quinazolin-4-amine (266b) (300 mg, 0.7 mmol) and (S)-pyrrolidin-2-ylmethanol (0.28 mL, 2.79 mmol) in NMP (15 mL) using DIPEA (0.73 mL, 4.19 mmol) as base. This gave after workup and purification twice by flash column chromatography [silica gel (12 g), eluting with DMA80 in DCM from 0-50%] followed by purification by reverse phase flash column chromatography [(silica gel C-18, 24 g), eluting with ACN in water (containing 0.1% HCl) from 0-100%] compound (269a) (0.09 g, 26%) HCl salt as a white solid and compound (269b) (0.02 g, 4% yield) HCl salt as a white solid.

Analytical data for (S)-(1-(7-fluoro-4-((1-(3,4,5-trimethoxyphenyl)-1H-imidazol-4-yl)amino)quinazolin-2-yl)pyrrolidin-2-yl)methanol (269a): $^1$H NMR (300 MHz, DMSO-$d_6$): δ 12.81 (s, 1H), 8.80 (td, J=9.6, 5.6 Hz, 1H), 8.56 (d, J=8.3 Hz, 1H), 8.21-7.97 (m, 2H), 7.41-7.25 (m, 1H), 7.02 (s, 1H), 6.95 (s, 1H), 4.80-4.40 (m, 1H), 4.09-3.30 (m, 13H), 2.24-1.83 (m, 4H). $^{19}$F NMR (282 MHz, DMSO-$d_6$): δ −101.53; MS (ES+): 495.2 (M+1); MS (ES−): 493.3 (M−1); HPLC purity: 99.43%.

Analytical data for ((2S,2'S)-1,1'-(4-((1-(3,4,5-trimethoxyphenyl)-1H-imidazol-4-yl)amino)quinazoline-2,7-diyl)bis(pyrrolidine-2,1-diyl))dimethanol (269b): $^1$H NMR (300 MHz, DMSO-$d_6$): δ 11.31 (s, 1H), 8.67 (d, J=10.0 Hz, 1H), 8.46 (d, J=9.0 Hz, 1H), 8.01 (s, 1H), 7.05 (q, J=17.0, 15.2 Hz, 3H), 6.79 (d, J=9.2 Hz, 1H), 4.64-4.39 (m, 1H), 4.00-3.72 (m, 8H), 3.72-3.03 (m, 10H), 2.20-1.76 (m, 8H). MS (ES+): 576.4 (M+1); MS (ES−): 610.4 (M+Cl). HPLC purity: 86.39%.

Scheme 270

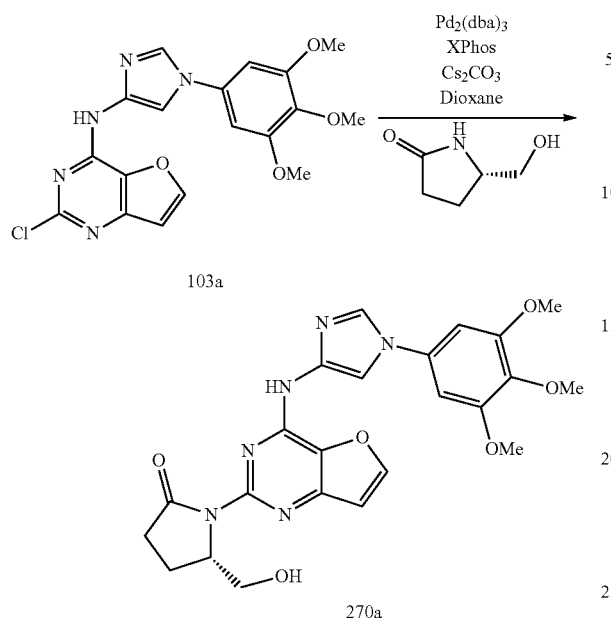

Preparation of (S)-5-(hydroxymethyl)-1-(4-((1-(3,4,5-trimethoxyphenyl)-1H-imidazol-4-yl)amino)furo[3,2-d]pyrimidin-2-yl)pyrrolidin-2-one (270a)

Compound 270a was prepared from 2-chloro-N-(1-(3,4,5-trimethoxyphenyl)-1H-imidazol-4-yl)furo[3,2-d]pyrimidin-4-amine (103a) (500 mg, 1.24 mmol), (S)-5-(hydroxymethyl)pyrrolidin-2-one (215 mg, 1.87 mmol), dicyclohexyl(2',4',6'-triisopropylbiphenyl-2-yl)phosphine (XPhos, 289 mg, 0.5 mmol), cesium carbonate (811 mg, 2.49 mmol) and Pd$_2$(dba)$_3$ (228 mg, 0.25 mmol) in 1,4-dioxane (20 mL) according to the procedure reported in step-3 of Scheme 101. This gave after workup and purification by flash column chromatography [silica gel (24 g), eluting with DMA 80 in DCM from 0-100%] compound (270a) free base as a solid. The free base was repurified by reverse phase column chromatography [(silica gel C-18, 50 g), eluting with ACN in water (containing 0.1% HCl) from 0-100%] to afford (S)-5-(hydroxymethyl)-1-(4-((1-(3,4,5-trimethoxyphenyl)-1H-imidazol-4-yl)amino)furo[3,2-d]pyrimidin-2-yl)pyrrolidin-2-one (270a) (142 mg, 24% yield) HCl salt as a white solid; $^1$H NMR (300 MHz, DMSO-d$_6$) δ 11.87 (s, 1H, D$_2$O exchangeable), 9.23 (s, 1H), 8.91-8.57 (m, 1H, D$_2$O exchangeable), 8.55-8.30 (m, 1H), 7.45-6.96 (m, 3H), 5.85 (s, 1H), 4.85-4.58 (m, 1H), 4.05-3.43 (m, 13H), 2.97-2.73 (m, 1H), 2.29-1.99 (m, 2H); MS (ES+): 481.3 (M+1); 503.2 (M+Na); (ES−): 479.2 (M−1), 515.3 (M+Cl); HPLC purity; 94.57%.

Scheme 271

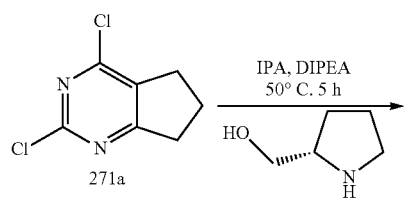

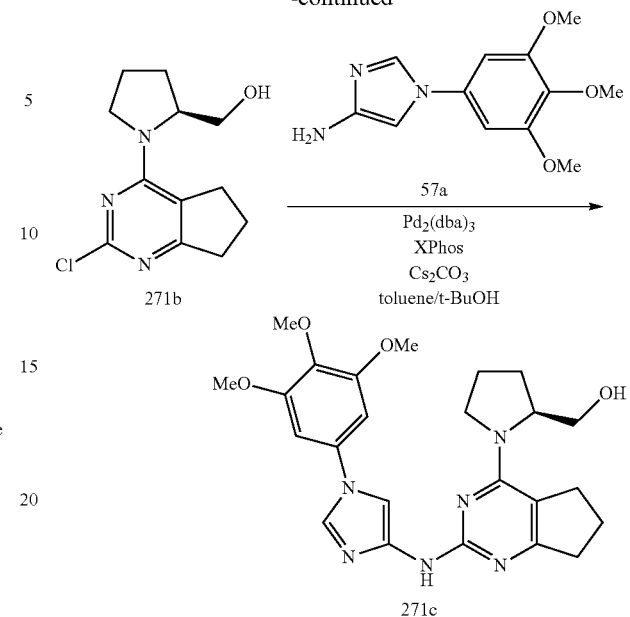

Preparation of (S)-(1-(2-((1-(3,4,5-trimethoxyphenyl)-1H-imidazol-4-yl)amino)-6,7-dihydro-5H-cyclopenta[d]pyrimidin-4-yl)pyrrolidin-2-yl)methanol (271c)

Step-1: Preparation of (S)-(1-(2-chloro-6,7-dihydro-5H-cyclopenta[d]pyrimidin-4-yl)pyrrolidin-2-yl)methanol (271b)

Compound 271b was prepared from 2,4-dichloro-6,7-dihydro-5H-cyclopenta[d]pyrimidine (271a) (0.25 g, 1.32 mmol, CAS #5466-43-3) in 2-Propanol (50 mL) using (S)-pyrrolidin-2-ylmethanol (0.13 g, 1.32 mmol) and DIPEA (0.46 mL, 2.64 mmol) according to the procedure reported in step-1 of Scheme 96. This gave after workup and purification by flash column chromatography [silica (12 g), eluting with EtOAc/MeOH (9:1) in hexane from 0-60%] (S)-(1-(2-chloro-6,7-dihydro-5H-cyclopenta[d]pyrimidin-4-yl)pyrrolidin-2-yl)methanol (271b) (286 mg, 85% yield) as a white solid; $^1$H NMR (300 MHz, DMSO-d$_6$) δ 4.91-4.73 (m, 1H, D$_2$O exchangeable), 4.28-4.14 (m, 1H), 3.81-3.40 (m, 3H), 3.32-3.27 (m, 1H), 3.17-2.95 (m, 2H), 2.75-2.60 (m, 2H), 2.02-1.73 (m, 6H); MS (ES+): 276.2 (M+Na); (ES−): 252.2 (M−1).

Step-2: Preparation of (S)-(1-(2-((1-(3,4,5-trimethoxyphenyl)-1H-imidazol-4-yl)amino)-6,7-dihydro-5H-cyclopenta[d]pyrimidin-4-yl)pyrrolidin-2-yl)methanol (271c)

Compound 271c was prepared from (S)-(1-(2-chloro-6,7-dihydro-5H-cyclopenta[d]pyrimidin-4-yl)pyrrolidin-2-yl)methanol (271b) (200 mg, 0.79 mmol), 1-(3,4,5-trimethoxyphenyl)-1H-imidazol-4-amine (57a) (196 mg, 0.79 mmol, free base), dicyclohexyl(2',4',6'-triisopropylbiphenyl-2-yl)phosphine (XPhos, 150 mg, 0.32 mmol), cesium carbonate (514 mg, 1.58 mmol) and Pd$_2$(dba)$_3$ (144 mg, 0.16 mmol) in toluene/t-BuOH (25 mL, Ratio: 5:2) according to the procedure reported in step-3 of Scheme 101. This gave after workup and purification by flash column chromatography

[silica gel (24 g), eluting with DMA-80 in DCM from 0-100%], followed by reverse phase column chromatography [(silica gel C-18, 50 g) eluting with acetonitrile and 0.1% HCl water] (S)-(1-(2-((1-(3,4,5-trimethoxyphenyl)-1H-imidazol-4-yl)amino)-6,7-dihydro-5H-cyclopenta[d]pyrimidin-4-yl)pyrrolidin-2-yl)methanol (271c) (130 mg, 35% yield) HCl salt as a white solid. $^1$H NMR (300 MHz, DMSO-$d_6$) δ 13.44 (s, 1H, $D_2O$ exchangeable), 10.44 (d, J=24.5 Hz, 1H, $D_2O$ exchangeable), 8.50 (s, 1H), 7.85-7.67 (m, 1H), 7.08-6.85 (m, 2H), 4.64-4.32 (m, 1H), 4.04-3.92 (m, 1H), 3.92-3.74 (m, 6H), 3.74-3.58 (m, 3H), 3.49-3.30 (m, 1H), 3.19-2.96 (m, 2H), 2.92-2.72 (m, 2H), 2.10-1.87 (m, 6H); MS (ES+): 467.3 (M+1); 489.3 (M+Na); (ES-): 501.3 (M+Cl); HPLC purity: 98.23%.

Scheme 272

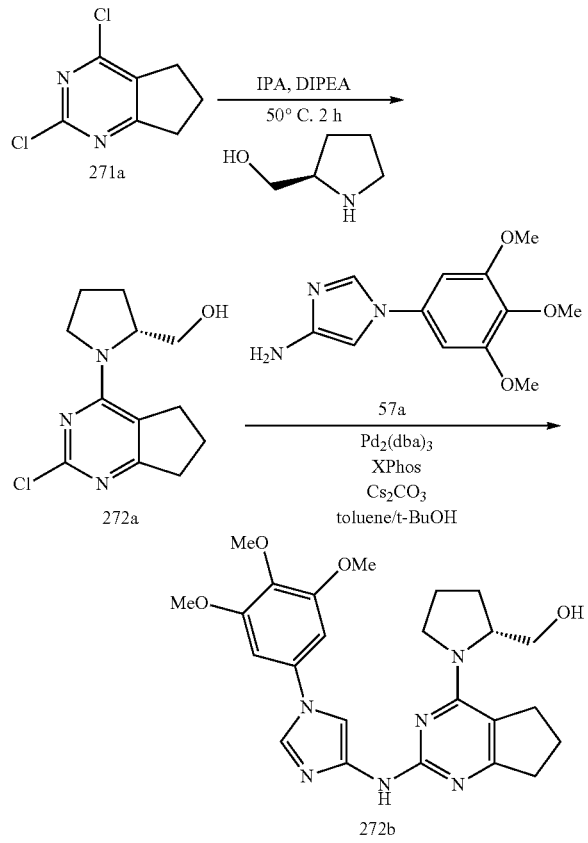

Preparation of (R)-(1-(2-((1-(3,4,5-trimethoxyphenyl)-1H-imidazol-4-yl)amino)-6,7-dihydro-5H-cyclopenta[d]pyrimidin-4-yl)pyrrolidin-2-yl)methanol (272b)

Step-1: Preparation of (R)-(1-(2-chloro-6,7-dihydro-5H-cyclopenta[d]pyrimidin-4-yl)pyrrolidin-2-yl)methanol (272a)

Compound 272a was prepared from 2,4-dichloro-6,7-dihydro-5H-cyclopenta[d]pyrimidine (271a) (0.25 g, 1.32 mmol) in 2-Propanol (50 mL) using (R)-pyrrolidin-2-yl-methanol (0.13 g, 1.32 mmol) and DIPEA (0.46 mL, 2.64 mmol) according to the procedure reported in step-1 of Scheme 96. This gave after workup and purification by flash column chromatography [silica gel (12 g), eluting with EtOAc/MeOH (9:1) in hexane from 0-60%] (R)-(1-(2-chloro-6,7-dihydro-5H-cyclopenta[d]pyrimidin-4-yl)pyrrolidin-2-yl)methanol (272a) (221 mg, 66% yield) as a white solid; $^1$H NMR (300 MHz, DMSO-$d_6$) δ 4.92-4.75 (m, 1H, $D_2O$ exchangeable), 4.29-4.15 (m, 1H), 3.78-3.42 (m, 3H), 3.32-3.22 (m, 1H), 3.14-2.97 (m, 2H), 2.75-2.58 (m, 2H), 2.01-1.79 (m, 6H); MS (ES+): 254.2 (M+1); (ES-): 252.3 (M-1).

Step-2: Preparation of (R)-(1-(2-((1-(3,4,5-trimethoxyphenyl)-1H-imidazol-4-yl)amino)-6,7-dihydro-5H-cyclopenta[d]pyrimidin-4-yl)pyrrolidin-2-yl)methanol (272b)

Compound 272b was prepared from (R)-(1-(2-chloro-6,7-dihydro-5H-cyclopenta[d]pyrimidin-4-yl)pyrrolidin-2-yl)methanol (272a) (200 mg, 0.79 mmol), 1-(3,4,5-trimethoxyphenyl)-1H-imidazol-4-amine (57a) (196 mg, 0.79 mmol, free base), dicyclohexyl(2',4',6'-triisopropylbiphenyl-2-yl)phosphine (XPhos, 150 mg, 0.32 mmol), cesium carbonate (514 mg, 1.58 mmol) and $Pd_2(dba)_3$ (144 mg, 0.16 mmol) in toluene/t-BuOH (25 mL, Ratio: 5:2) according to the procedure reported in step-3 of Scheme 101. This gave after workup and purification by flash column chromatography [silica gel (24 g), eluting with DMA-80 in DCM from 0-100%], followed by reverse phase column chromatography [(silica gel C-18, 50 g) eluting with acetonitrile and 0.1% HCl water] (R)-(1-(2-((1-(3,4,5-trimethoxyphenyl)-1H-imidazol-4-yl)amino)-6,7-dihydro-5H-cyclopenta[d]pyrimidin-4-yl)pyrrolidin-2-yl)methanol (272b) (137 mg, 37% yield) HCl salt as a white solid. $^1$H NMR (300 MHz, DMSO-$d_6$) δ 13.46 (s, 1H, $D_2O$ exchangeable), 10.68-10.17 (m, 1H, $D_2O$ exchangeable), 8.50 (s, 1H), 7.85-7.66 (m, 1H), 7.07-6.91 (m, 2H), 4.64-4.35 (m, 1H), 4.03-3.91 (m, 1H), 3.90-3.78 (m, 7H), 3.73-3.61 (m, 4H), 3.48-3.33 (m, 1H), 3.17-2.97 (m, 2H), 2.93-2.80 (m, 2H), 2.11-1.85 (m, 6H); MS (ES+): 467.3 (M+1); 489.3 (M+Na); (ES-): 501.3 (M+Cl); HPLC purity: 96.28%.

Scheme 273

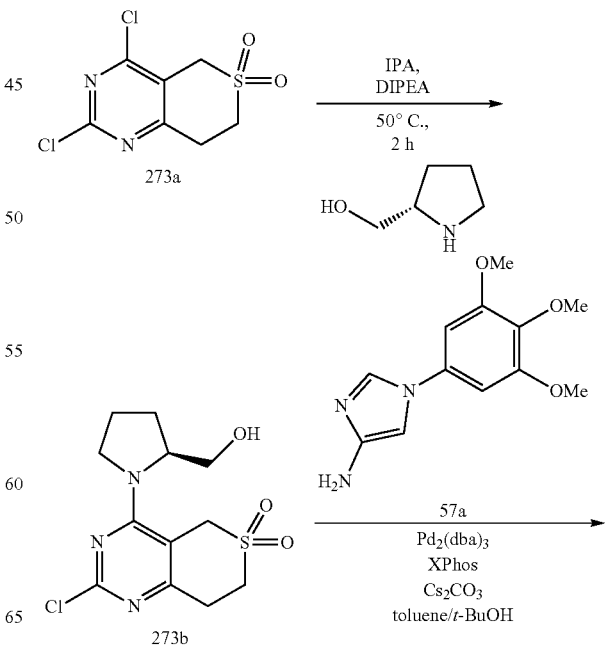

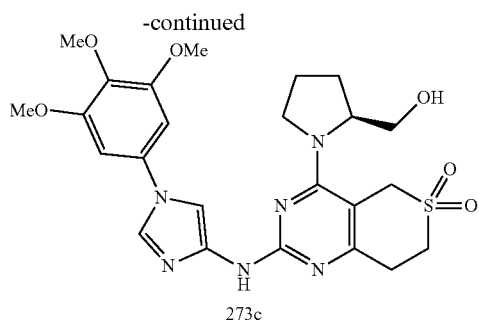

273c

Preparation of (S)-4-(2-(hydroxymethyl)pyrrolidin-1-yl)-2-((1-(3,4,5-trimethoxyphenyl)-1H-imidazol-4-yl)amino)-7,8-dihydro-5H-thiopyrano[4,3-d]pyrimidine 6,6-dioxide (273c)

Step-1: Preparation of (S)-2-chloro-4-(2-(hydroxymethyl)pyrrolidin-1-yl)-7,8-dihydro-5H-thiopyrano[4,3-d]pyrimidine 6,6-dioxide (273b)

Compound 273b was prepared from 2,4-dichloro-7,8-dihydro-5H-thiopyrano[4,3-d]pyrimidine 6,6-dioxide (273a) (0.2 g, 0.79 mmol, CAS #1187830-50-7) in 2-Propanol (50 mL) using (S)-pyrrolidin-2-ylmethanol (80 mg, 0.79 mmol) and DIPEA (0.28 mL, 1.58 mmol) according to the procedure reported in step-1 of Scheme 96. This gave after workup and purification by flash column chromatography [silica gel (12 g), eluting with EtOAc/MeOH (9:1) in hexane from 0-60%] (S)-2-chloro-4-(2-(hydroxymethyl)pyrrolidin-1-yl)-7,8-dihydro-5H-thiopyrano[4,3-d]pyrimidine 6,6-dioxide (273b) (234 mg, 93% yield) as a white solid; MS (ES+): 318.3 (M+1); 340.1 (M+Na); (ES−): 316.2 (M−1).

Step-2: Preparation of (S)-4-(2-(hydroxymethyl)pyrrolidin-1-yl)-2-((1-(3,4,5-trimethoxyphenyl)-1H-imidazol-4-yl)amino)-7,8-dihydro-5H-thiopyrano[4,3-d]pyrimidine 6,6-dioxide (273c)

Compound 273c was prepared from (S)-2-chloro-4-(2-(hydroxymethyl)pyrrolidin-1-yl)-7,8-dihydro-5H-thiopyrano[4,3-d]pyrimidine 6,6-dioxide (273b) (200 mg, 0.63 mmol), 1-(3,4,5-trimethoxyphenyl)-1H-imidazol-4-amine (57a) (157 mg, 0.63 mmol, free base), dicyclohexyl(2',4',6'-triisopropylbiphenyl-2-yl)phosphine (XPhos, 120 mg, 0.25 mmol), cesium carbonate (410 mg, 1.26 mmol) and Pd$_2$(dba)$_3$ (115 mg, 0.13 mmol) in toluene/t-BuOH (25 mL, Ratio: 5:2) according to the procedure reported in step-3 of Scheme 101. This gave after workup and purification by flash column chromatography [silica gel (24 g), eluting with DMA-80 in DCM from 0-100%], followed by reverse phase column chromatography [(silica gel C-18, 50 g) eluting with acetonitrile and 0.1% HCl water] (S)-4-(2-(hydroxymethyl)pyrrolidin-1-yl)-2-((1-(3,4,5-trimethoxyphenyl)-1H-imidazol-4-yl)amino)-7,8-dihydro-5H-thiopyrano[4,3-d]pyrimidine 6,6-dioxide (273c) (110 mg, 33% yield) HCl salt as a white solid. $^1$H NMR (300 MHz, DMSO-d$_6$) δ 10.32 (s, 1H, D$_2$O exchangeable), 8.47 (s, 1H), 7.70 (s, 1H), 6.98 (s, 2H), 4.73-4.57 (m, 2H), 4.47-4.34 (m, 1H), 3.93-3.72 (m, 9H), 3.71-3.59 (m, 5H), 3.57-3.46 (m, 3H), 3.36-3.13 (m, 2H), 2.05-1.78 (m, 4H); MS (ES+): 531.2 (M+1); (ES−): 565.2 (M+Cl); HPLC purity: 97.84%.

Scheme 274

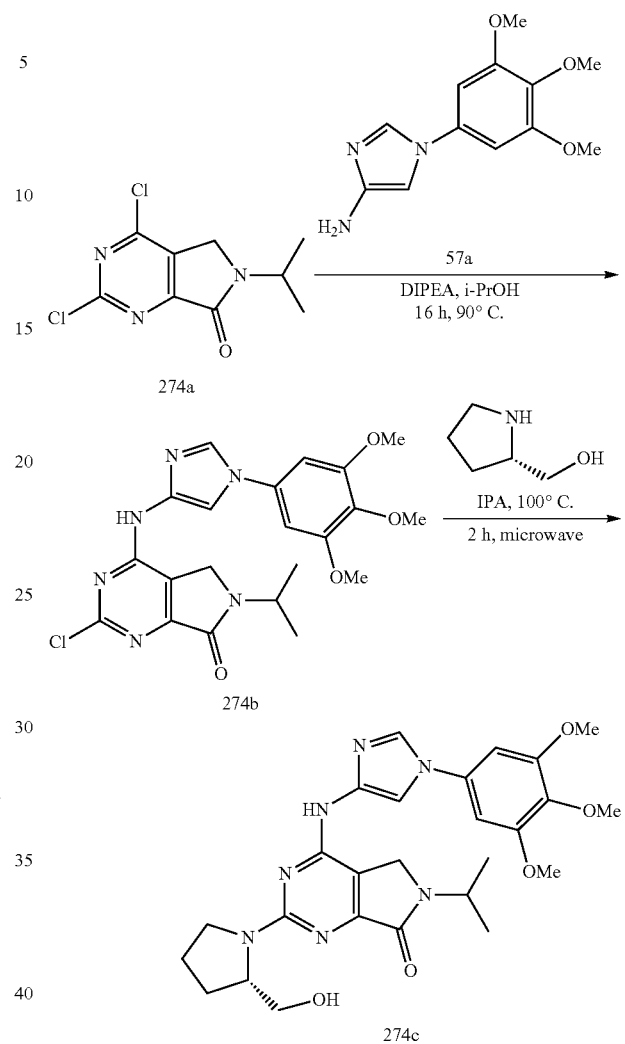

Preparation of (S)-2-(2-(hydroxymethyl)pyrrolidin-1-yl)-6-isopropyl-4-((1-(3,4,5-trimethoxyphenyl)-1H-imidazol-4-yl)amino)-5H-pyrrolo[3,4-d]pyrimidin-7(6H)-one (274c)

Step-1: Preparation of 2-chloro-6-isopropyl-4-((1-(3,4,5-trimethoxyphenyl)-1H-imidazol-4-yl)amino)-5H-pyrrolo[3,4-d]pyrimidin-7(6H)-one (274b)

Compound 274b was prepared from 2,4-dichloro-6-isopropyl-5H-pyrrolo[3,4-d]pyrimidin-7(6H)-one (274a) (200 mg, 0.813 mmol, CAS #1079649-94-7) in 2-Propanol (10 mL) using DIPEA (0.43 mL, 2.45 mmol) and 1-(3,4,5-trimethoxyphenyl)-1H-imidazol-4-amine (57a) (203 mg, 0.81 mmol, free base) according to the procedure reported in Scheme 1. This gave after workup 2-chloro-6-isopropyl-4-((1-(3,4,5-trimethoxyphenyl)-1H-imidazol-4-yl)amino)-5H-pyrrolo[3,4-d]pyrimidin-7(6H)-one (274b) (0.21 g, 56%) as a white solid; $^1$H NMR (300 MHz, DMSO-d$_6$) δ 10.97 (s, 1H), 8.18 (s, 1H), 7.83 (s, 1H), 6.92 (s, 2H), 4.50-4.29 (m, 3H), 3.87 (s, 6H), 3.69 (s, 3H), 1.23 (d, J=6.7 Hz, 6H).

Step-2: Preparation of (S)-2-(2-(hydroxymethyl)pyrrolidin-1-yl)-6-isopropyl-4-((1-(3,4,5-trimethoxyphenyl)-1H-imidazol-4-yl)amino)-5H-pyrrolo[3,4-d]pyrimidin-7(6H)-one (274c)

Compound 274c was prepared according to the procedure reported in Scheme 2 from 2-chloro-6-isopropyl-4-((1-(3,4,5-trimethoxyphenyl)-1H-imidazol-4-yl)amino)-5H-pyrrolo[3,4-d]pyrimidin-7(6H)-one (274b) (100 mg, 0.218 mmol) and (S)-pyrrolidin-2-ylmethanol (55 mg, 0.55 mmol) in 2-Propanol (1 mL). This gave after workup and purification by reverse phase flash column chromatography [(silica gel C-18, 50 g), eluting with ACN in water (containing 0.1% HCl) from 0-100%] (S)-2-(2-(hydroxymethyl)pyrrolidin-1-yl)-6-isopropyl-4-((1-(3,4,5-trimethoxyphenyl)-1H-imidazol-4-yl)amino)-5H-pyrrolo[3,4-d]pyrimidin-7(6H)-one (274c) (106 mg, 93% yield) HCl salt as a light yellow solid; $^1$H NMR (300 MHz, DMSO-$d_6$) δ 11.39 (d, J=22.6 Hz, 1H, $D_2O$ exchangeable), 8.39 (s, 1H), 7.99 (d, J=15.6 Hz, 1H), 6.97 (s, 2H), 4.40 (d, J=12.6 Hz, 5H, 1H $D_2O$ exchangeable), 3.87 (s, 6H), 3.68 (s, 4H), 3.66-3.51 (m, 2H), 3.55-3.36 (m, 1H), 2.00 (s, 4H), 1.25 (d, J=6.6 Hz, 6H); MS (ES+): 524.3 (M+1), 546.3 (M+Na), (ES−): 522.2 (M−1); HPLC purity: 96.16%.

C-18, 50 g), eluting with ACN in water (containing 0.1% HCl) from 0-100%] (R)-2-(2-(hydroxymethyl)pyrrolidin-1-yl)-6-isopropyl-4-((1-(3,4,5-trimethoxyphenyl)-1H-imidazol-4-yl)amino)-5H-pyrrolo[3,4-d]pyrimidin-7(6H)-one (275a) (86 mg, 88% yield) HCl salt as a light yellow solid; $^1$H NMR (300 MHz, DMSO-$d_6$) δ 11.55-11.18 (m, 1H, $D_2O$ exchangeable), 8.39 (s, 1H), 7.99 (d, J=15.9 Hz, 1H), 6.98 (s, 2H), 5.19-4.15 (m, 5H, 1H $D_2O$ exchangeable), 3.87 (s, 6H), 3.68 (s, 4H), 3.66-3.51 (m, 2H), 3.51-3.37 (m, 1H), 2.12-1.70 (m, 4H), 1.25 (d, J=6.7 Hz, 6H); MS (ES+): 524.3 (M+1), 546.4 (M+Na), (ES−): 522.3 (M−1); HPLC purity: 94.71%.

Scheme 276

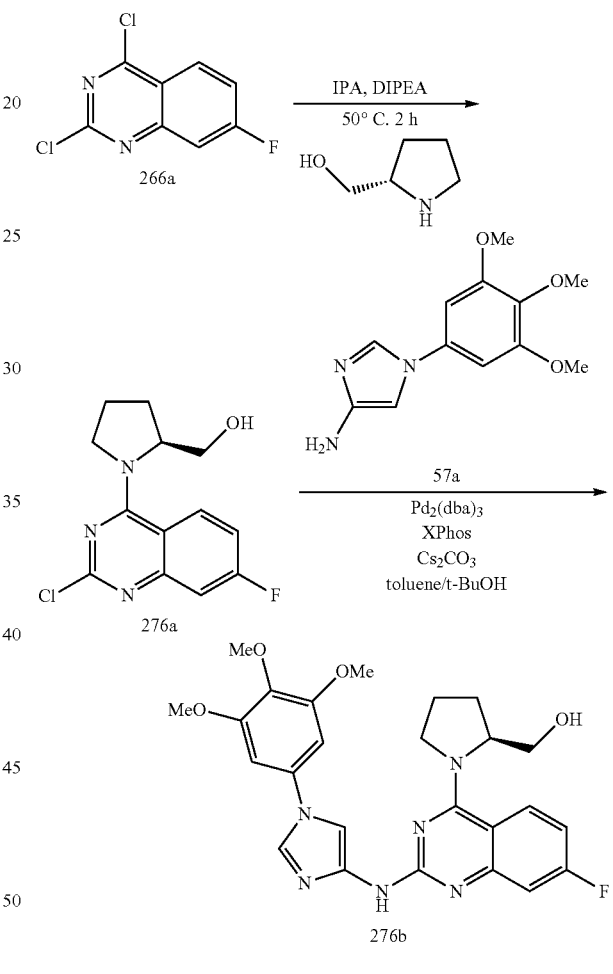

Scheme 275

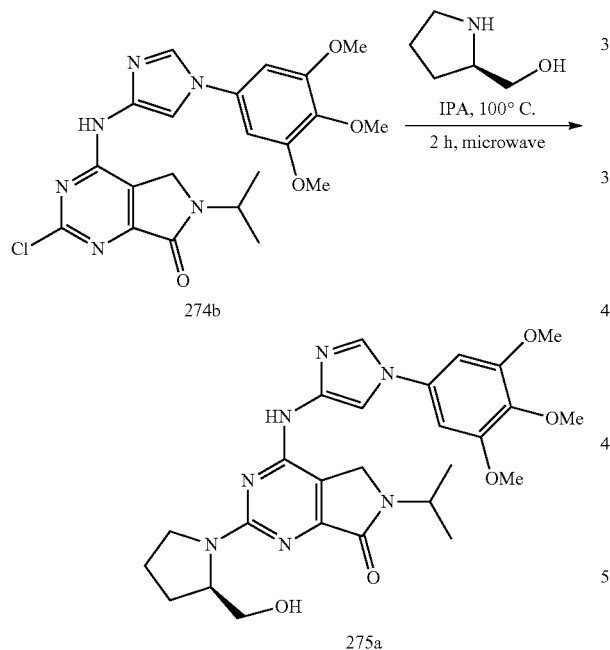

Preparation of (R)-2-(2-(hydroxymethyl)pyrrolidin-1-yl)-6-isopropyl-4-((1-(3,4,5-trimethoxyphenyl)-1H-imidazol-4-yl)amino)-5H-pyrrolo[3,4-d]pyrimidin-7(6H)-one (275a)

Compound 275a was prepared according to the procedure reported in Scheme 2 from 2-chloro-6-isopropyl-4-((1-(3,4,5-trimethoxyphenyl)-1H-imidazol-4-yl)amino)-5H-pyrrolo[3,4-d]pyrimidin-7(6H)-one (274b) (86 mg, 0.187 mmol) and (R)-pyrrolidin-2-ylmethanol (47 mg, 0.469 mmol) in 2-Propanol (1 mL). This gave after workup and purification by reverse phase flash column chromatography [(silica gel

Preparation of (S)-(1-(7-fluoro-2-((1-(3,4,5-trimethoxyphenyl)-1H-imidazol-4-yl)amino)quinazolin-4-yl)pyrrolidin-2-yl)methanol (276b)

Step-1: Preparation of (S)-(1-(2-chloro-7-fluoroquinazolin-4-yl)pyrrolidin-2-yl)methanol (276a)

Compound 276a was prepared from 2,4-dichloro-7-fluroquinazoline (266a) (0.4 g, 1.84 mmol) in 2-Propanol (10 mL) using (S)-pyrrolidin-2-ylmethanol (0.18 mL, 1.84 mmol) and DIPEA 5 (0.97 mL, 5.53 mmol) according to the procedure reported in step-1 of Scheme 96. This gave after workup and purification by flash column chromatography

[silica gel (12 g), eluting with DCM and methanol (0 to 30%)] (S)-(1-(2-chloro-7-fluoroquinazolin-4-yl)pyrrolidin-2-yl)methanol (276a) (0.467 g, 90% yield) as a yellow solid; MS (ES+): 282.2 (M+1); (ES−): 316.2 (M+Cl).

Step-2: Preparation of (S)-(1-(7-fluoro-2-((1-(3,4,5-trimethoxyphenyl)-1H-imidazol-4-yl)amino)quinazolin-4-yl)pyrrolidin-2-yl)methanol (276b)

Compound 276b was prepared from (S)-(1-(2-chloro-7-fluoroquinazolin-4-yl)pyrrolidin-2-yl)methanol (276a) (0.3 g, 1.07 mmol), 1-(3,4,5-trimethoxyphenyl)-1H-imidazol-4-amine (57a) (0.26 g, 1.07 mmol, free base), dicyclohexyl (2',4',6'-triisopropylbiphenyl-2-yl)phosphine (XPhos, 0.31 g, 0.64 mmol), cesium carbonate (1.041 g, 3.19 mmol) and Pd$_2$(dba)$_3$ (0.293 g, 0.319 mmol) in toluene/t-BuOH (40 mL, Ratio: 3:1) according to the procedure reported in step-3 of Scheme 101. This gave after workup and purification by flash column chromatography [silica gel (24 g), eluting with DMA80 in DCM from 0-50%], followed by reverse phase column chromatography [(silica gel C-18, 24 g) eluting with acetonitrile and 0.1% HCl water] (S)-(1-(7-fluoro-2-((1-(3,4,5-trimethoxyphenyl)-1H-imidazol-4-yl)amino)quinazolin-4-yl)pyrrolidin-2-yl)methanol (276b) (0.04 g, 8% yield) HCl salt as a white solid; $^1$H NMR (300 MHz, DMSO-d$_6$): δ 13.02 (s, 1H), 8.49-8.22 (m, 2H), 7.72 (s, 1H), 7.56-7.19 (m, 2H), 6.98 (s, 2H), 4.94-4.73 (m, 1H), 4.33-4.00 (m, 2H), 3.96-3.35 (m, 11H), 2.27-1.78 (m, 4H). $^{19}$F NMR (282 MHz, DMSO-d$_6$): δ −101.99; MS (ES+): 495.3 (M+1); MS (ES−): 529.3 (M+Cl). HPLC purity: 96.22%.

propoxy-N-(1-(3,4,5-trimethoxyphenyl)-1H-imidazol-4-yl)quinazolin-4-amine (145g) (300 mg, 0.63 mmol) and (R)-pyrrolidine-2-carboxamide (0.65 g, 5.7 mmol) in NMP (10 mL) using DIPEA (0.24 g, 1.91 mmol) as base. This gave after workup and purification by flash column chromatography [silica gel, eluting with DMA80 MeOH in DCM (0-4%)] Compound 277a (0.28 g, 81%) free base as an off-white solid; $^1$H NMR (300 MHz, DMSO-d$_6$) δ 12.48 (s, 1H), 11.46 (s, 1H), 8.66 (d, J=9.0 Hz, 1H), 8.48 (s, 1H), 7.91 (s, 1H), 7.79 (s, 1H), 7.62 (s, 1H), 7.22 (s, 1H), 7.15 (s, 2H), 7.07-6.96 (m, 1H), 4.88-4.60 (m, 2H), 4.16-4.02 (m, 1H), 3.94 (s, 6H), 3.83-3.55 (m, 4H), 2.40-1.74 (m, 4H), 1.37 (d, J=5.9 Hz, 6H); MS (ES+): 548.4 (M+1). The free base was converted to HCl salt using reverse phase flash column chromatography [(silica gel C-18, 24 g), eluting with ACN in water (containing 0.1% HCl) from 0-100%] to afford (R)-1-(7-isopropoxy-4-((1-(3,4,5-trimethoxyphenyl)-1H-imidazol-4-yl)amino)quinazolin-2-yl)pyrrolidine-2-carboxamide (277a) HCl salt as a yellow solid; $^1$H NMR (300 MHz, DMSO-d$_6$) δ 12.66 (s, 1H), 11.59 (s, 1H), 8.67 (d, J=9.0 Hz, 2H), 7.95 (s, 1H), 7.87 (s, 1H), 7.62 (s, 1H), 7.20 (s, 1H), 7.17 (s, 2H), 7.07-6.98 (m, 1H), 4.86-4.60 (m, 2H), 3.93 (s, 6H), 3.92-3.83 (m, 1H), 3.80-3.71 (m, 1H), 3.69 (s, 3H), 2.42-1.87 (m, 4H), 1.37 (dd, J=6.1, 2.1 Hz, 6H); MS (ES+): 548.4 (M+1); MS (ES−): 582.4 (M+Cl). HPLC purity: 93.76%.

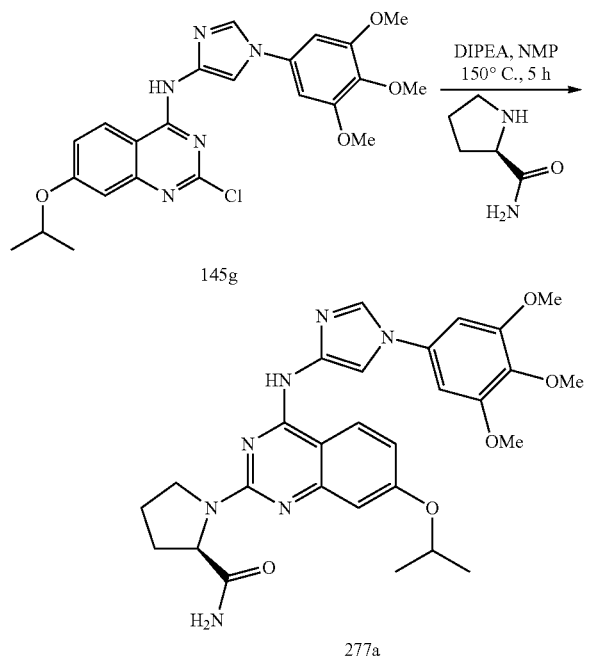

Preparation of (R)-1-(7-isopropoxy-4-((1-(3,4,5-trimethoxyphenyl)-1H-imidazol-4-yl)amino)quinazolin-2-yl)pyrrolidine-2-carboxamide (277a)

Compound 277a was prepared according to the procedure reported in step-2 of Scheme 76 from 2-chloro-7-iso-

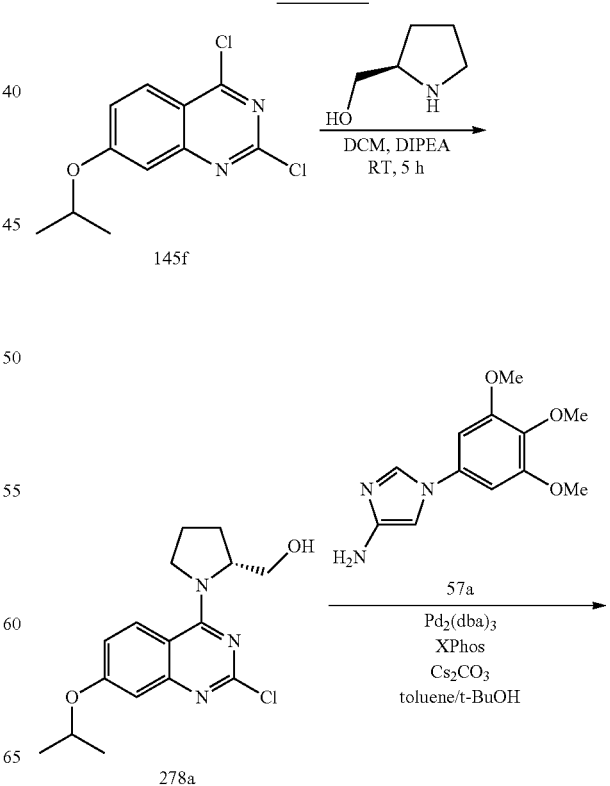

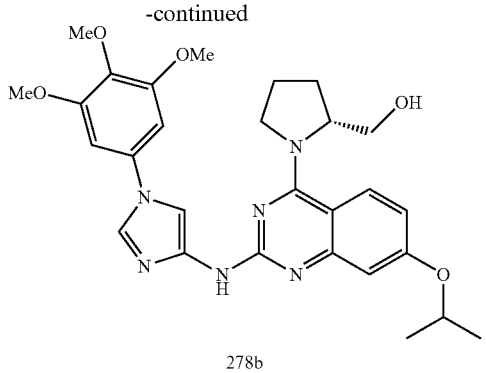

278b

Preparation (R)-(1-(7-isopropoxy-2-((1-(3,4,5-trimethoxyphenyl)-1H-imidazol-4-yl)amino)quinazolin-4-yl)pyrrolidin-2-yl)methanol (278b)

Step-1: Preparation of (R)-(1-(2-chloro-7-isopropoxyquinazolin-4-yl)pyrrolidin-2-yl)methanol (278a)

Compound 278a was prepared according to the procedure reported in Scheme 1 from 2,4-dichloro-7-isopropoxyquinazoline (145f) (200 mg, 0.77 mmol) in DCM (10 mL) using DIPEA (0.4 mL, 3.09 mmol) and (R)-pyrrolidin-2-ylmethanol (0.39 gm, 3.85 mmol). This gave after work up and purification by flash column chromatography (silica gel, eluting with ethyl acetate in n-hexane 0-60%) (R)-(1-(2-chloro-7-isopropoxyquinazolin-4-yl)pyrrolidin-2-yl)methanol (278a) (0.15 g, 60%) as an off white solid; $^1$H NMR (300 MHz, DMSO-$d_6$): δ 8.22-8.19 (d, 1H), 7.10-7.04 (m, 2H), 4.91-4.84 (m, 2H), 4.62-4.58 (m, 4H), 3.69-3.64 (m, 2H), 2.12-2.05 (m, 4H), 1.91-1.39 (d, 6H); MS (ES−): 320.0 (M−1).

Step-2: Preparation of (R)-(1-(7-isopropoxy-2-((1-(3,4,5-trimethoxyphenyl)-1H-imidazol-4-yl)amino) quinazolin-4-yl)pyrrolidin-2-yl)methanol (278b)

Compound 278b was prepared from (R)-(1-(2-chloro-7-isopropoxyquinazolin-4-yl)pyrrolidin-2-yl)methanol (278a) (500 mg, 1.55 mmol), 1-(3,4,5-trimethoxyphenyl)-1H-imidazol-4-amine (57a) (580 mg, 2.33 mmol, free base), dicyclohexyl(2′,4′,6′-triisopropylbiphenyl-2-yl)phosphine (XPhos, 290 mg, 0.6 mmol), cesium carbonate (2020 mg, 6.2 mmol) and Pd$_2$(dba)$_3$ (210 mg, 0.23 mmol) in toluene and t-BuOH (50 mL, ratio 5:2) according to the procedure reported in step-3 of Scheme 101. This gave after workup and purification by flash column chromatography [silica gel, eluting with methanol in dichloromethane 0-5%] compound (278b) (300 mg, 36% yield) free base as a white solid; $^1$H NMR (300 MHz, DMSO-$d_6$) δ −9.45 (s, 1H), 8.14 (s, 1H), 8.04 (m, 1H), 7.75 (s, 1H), 6.94-6.91 (m, 3H), 6.79-6.75 (m, 1H), 4.80-4.78 (s, 1H), 4.76-4.74 (m, 2H), 3.89-3.85 (s, 6H), 3.79-3.75 (m, 3H), 3.68 (m, 4H), 2.07-2.04 (d, 4H), 1.54-1.50 (d, 6H); MS (ES+) 535.0 (M+1); HPLC purity: 90.4%; The free base was repurified by reverse phase flash column chromatography [(silica gel C-18, 24 g) eluting with acetonitrile and 0.1% HCl in water] to afford (R)-(1-(7-isopropoxy-2-((1-(3,4,5-trimethoxyphenyl)-1H-imidazol-4-yl)amino)quinazolin-4-yl)pyrrolidin-2-yl)methanol (278b) (110 mgs) HCl salt as a yellow solid; $^1$H NMR (300 MHz, DMSO-$d_6$) δ 13.41 (s, 1H), 10.63 (s, 1H), 8.76 (s, 1H), 8.20 (d, J=9.4 Hz, 1H), 7.88 (s, 1H), 7.05 (s, 2H), 6.97 (dd, J=9.3, 2.4 Hz, 1H), 6.62 (s, 1H), 4.75 (dd, J=12.6, 6.5 Hz, 2H), 4.23-3.99 (m, 2H), 3.88 (s, 6H), 3.78-3.46 (m, 5H), 2.30-1.79 (m, 4H), 1.33 (dd, J=6.0, 1.6 Hz, 6H). MS (ES−): 569.3 (M+Cl). HPLC purity: 96.79%.

Scheme 279

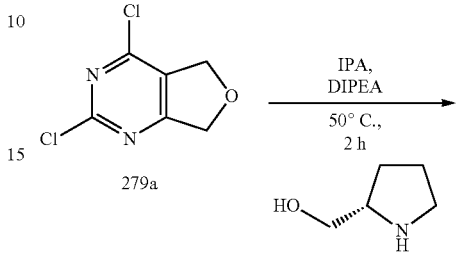

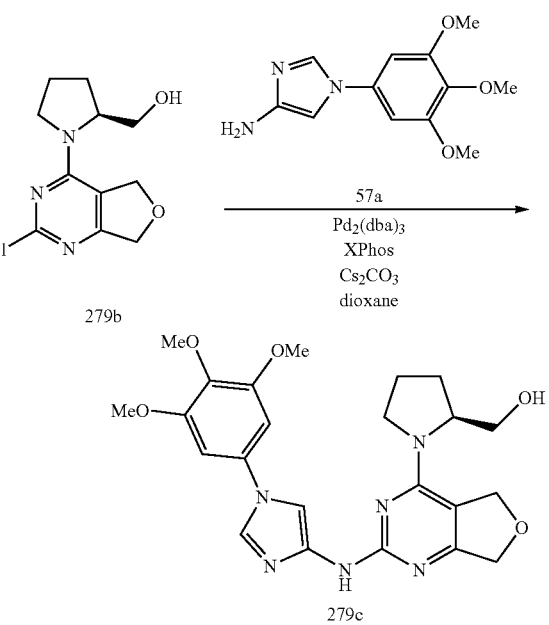

Preparation of (S)-(1-(2-((1-(3,4,5-trimethoxyphenyl)-1H-imidazol-4-yl)amino)-5,7-dihydrofuro[3,4-d]pyrimidin-4-yl)pyrrolidin-2-yl)methanol (279c)

Step-1: Preparation of (S)-(1-(2-chloro-5,7-dihydrofuro[3,4-d]pyrimidin-4-yl)pyrrolidin-2-yl)methanol (279b)

Compound 279b was prepared from 2,4-dichloro-5,7-dihydrofuro[3,4-d]pyrimidine (279a) (0.3 g, 1.57 mmol; CAS #848398-41-4) in 2-Propanol (5 mL) using (S)-pyrrolidin-2-ylmethanol (0.16 gm, 1.57 mmol) and DIPEA (0.823 mL, 4.71 mmol) according to the procedure reported in step-1 of Scheme 96. This gave after workup and purification by flash column chromatography [silica gel (40 g), eluting with DMA-80 in DCM] (S)-(1-(2-chloro-5,7-dihydrofuro[3,4-d]pyrimidin-4-yl)pyrrolidin-2-yl)methanol (279b) (374 mg, 93% yield) as a white solid; MS (ES+): 278.1 (M+Na).

Step-2: Preparation of (S)-(1-(2-((1-(3,4,5-trimethoxyphenyl)-1H-imidazol-4-yl)amino)-5,7-dihydrofuro[3,4-d]pyrimidin-4-yl)pyrrolidin-2-yl)methanol (279c)

Compound 279c was prepared from (S)-(1-(2-chloro-5,7-dihydrofuro[3,4-d]pyrimidin-4-yl)pyrrolidin-2-yl)methanol (279b) (256 mg, 1.0 mmol), 1-(3,4,5-trimethoxyphenyl)-1H-imidazol-4-amine (57a) (287 mg, 1.150 mmol, free base), dicyclohexyl(2',4',6'-triisopropylbiphenyl-2-yl)phosphine (XPhos, 215 mg, 0.45 mmol), cesium carbonate (977 mg, 3.0 mmol) and $Pd_2(dba)_3$ (137 mg, 0.15 mmol) in dioxane (15 mL) according to the procedure reported in step-3 of Scheme 101. This gave after workup and purification by flash column chromatography [silica gel (24 g), eluting with DMA80 in DCM], followed by reverse phase column chromatography [(silica gel C-18, 100 g) eluting with acetonitrile and 0.1% HCl water] (S)-(1-(2-((1-(3,4,5-trimethoxyphenyl)-1H-imidazol-4-yl)amino)-5,7-dihydrofuro[3,4-d]pyrimidin-4-yl)pyrrolidin-2-yl)methanol (279c) (140 mg, 30% yield) HCl salt as a light brown solid; $^1H$ NMR (300 MHz, DMSO-$d_6$) δ 10.66 (s, 1H), 8.53 (s, 1H), 7.77 (s, 1H), 6.99 (s, 2H), 5.42-5.12 (m, 2H), 5.06-4.81 (m, 2H), 4.70-4.28 (m, 1H), 3.87 (s, 6H), 3.86-3.70 (m, 1H), 3.69 (s, 3H), 3.64 (d, J=10.2 Hz, 1H), 3.55-3.28 (m, 2H), 2.13-1.82 (m, 4H); MS (ES+): 469.3 (M+1), (ES−): 503.3 (M+Cl); HPLC purity: 99.4%.

Preparation of (R)-(1-(2-((1-(3,4,5-trimethoxyphenyl)-1H-imidazol-4-yl)amino)-5,7-dihydrofuro[3,4-d]pyrimidin-4-yl)pyrrolidin-2-yl)methanol (280b)

Step-1: Preparation of (R)-(1-(2-chloro-5,7-dihydrofuro[3,4-d]pyrimidin-4-yl)pyrrolidin-2-yl)methanol (280a)

Compound 280a was prepared from 2,4-dichloro-5,7-dihydrofuro[3,4-d]pyrimidine (279a) (0.3 g, 1.57 mmol, CAS #848398-41-4) in 2-Propanol (5 mL) using (S)-pyrrolidin-2-ylmethanol (0.16 gm, 1.57 mmol) and DIPEA (0.823 mL, 4.71 mmol) according to the procedure reported in step-1 of Scheme 96. This gave after workup and purification by flash column chromatography [silica gel (40 g), eluting with DMA-80 in DCM] (R)-(1-(2-chloro-5,7-dihydrofuro[3,4-d]pyrimidin-4-yl)pyrrolidin-2-yl)methanol (280a) (368 mg, 92% yield) as a white solid; MS (ES+): 278.2 (M+Na), (ES−): 254.3.

Step-2: Preparation of (R)-(1-(2-((1-(3,4,5-trimethoxyphenyl)-1H-imidazol-4-yl)amino)-5,7-dihydrofuro[3,4-d]pyrimidin-4-yl)pyrrolidin-2-yl)methanol (280b)

Compound 280b was prepared from (R)-(1-(2-chloro-5,7-dihydrofuro[3,4-d]pyrimidin-4-yl)pyrrolidin-2-yl)methanol (280a) (256 mg, 1.0 mmol), 1-(3,4,5-trimethoxyphenyl)-1H-imidazol-4-amine (57a) (287 mg, 1.15 mmol, free base), dicyclohexyl(2',4',6'-triisopropylbiphenyl-2-yl)phosphine (XPhos, 215 mg, 0.45 mmol), cesium carbonate (977 mg, 3.0 mmol) and $Pd_2(dba)_3$ (137 mg, 0.15 mmol) in dioxane (15 mL) according to the procedure reported in step-3 of Scheme 101. This gave after workup and purification by flash column chromatography [silica gel (40 g), eluting with DMA-80 in DCM], followed by reverse phase column chromatography [(silica gel C-18, 100 g) eluting with acetonitrile and 0.1% HCl water](R)-(1-(2-((1-(3,4,5-trimethoxyphenyl)-1H-imidazol-4-yl)amino)-5,7-dihydrofuro[3,4-d]pyrimidin-4-yl)pyrrolidin-2-yl)methanol (280b) (135 mg, 29% yield) HCl salt as a light brown solid; $^1H$ NMR (300 MHz, DMSO-$d_6$) δ 10.65 (s, 1H), 8.52 (s, 1H), 7.76 (s, 1H), 6.99 (s, 2H), 5.41-5.07 (m, 2H), 5.03-4.74 (m, 2H), 4.64-4.37 (m, 1H), 3.87 (s, 6H), 3.86-3.68 (m, 1H), 3.69 (s, 3H), 3.69-3.57 (m, 1H), 3.56-3.29 (m, 2H), 2.09-1.83 (m, 4H); MS (ES+): 469.3 (M+1), (ES−): 503.3 (M+Cl); HPLC purity: 99.1%.

Scheme 280

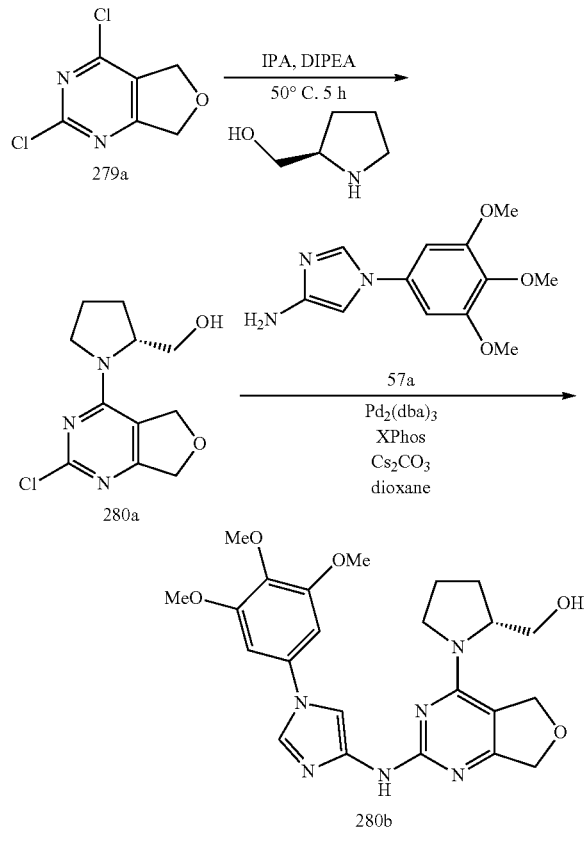

Scheme 281

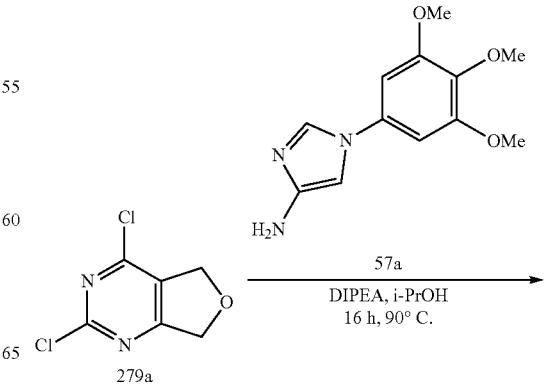

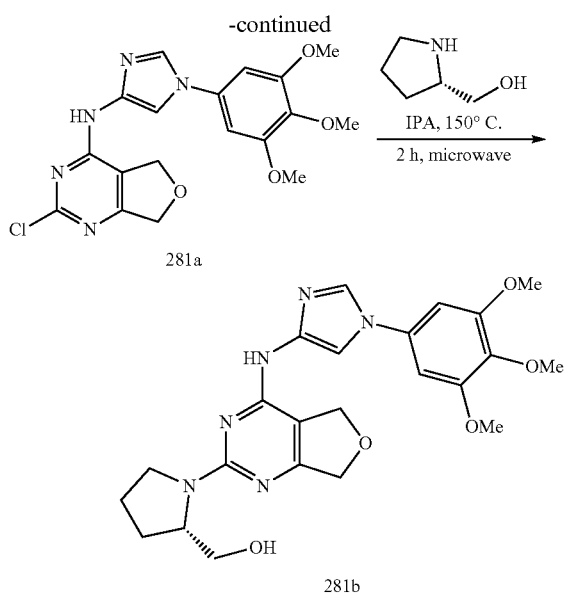

281a

281b

Preparation of (S)-(1-(4-((1-(3,4,5-trimethoxyphenyl)-1H-imidazol-4-yl)amino)-5,7-dihydrofuro[3,4-d]pyrimidin-2-yl)pyrrolidin-2-yl)methanol (281b)

Step-1: Preparation of 2-chloro-N-(1-(3,4,5-trimethoxyphenyl)-1H-imidazol-4-yl)-5,7-dihydrofuro[3,4-d]pyrimidin-4-amine (281a)

Compound 281a was prepared from 2,4-dichloro-5,7-dihydrofuro[3,4-d]pyrimidine (279a) (400 mg, 2.09 mmol) in 2-Propanol (10 mL) using DIPEA (1.1 mL, 6.28 mmol) and 1-(3,4,5-trimethoxyphenyl)-1H-imidazol-4-amine (57a) (522 mg, 2.09 mmol, free base) according to the procedure reported in Scheme 1. This gave after workup 2-chloro-N-(1-(3,4,5-trimethoxyphenyl)-1H-imidazol-4-yl)-5,7-dihydrofuro[3,4-d]pyrimidin-4-amine (281a) (545 mg, 64% yield) as a tan solid; $^1$H NMR (300 MHz, DMSO-$d_6$) δ 8.16 (s, 1H), 7.78 (s, 1H), 6.91 (s, 2H), 5.76 (s, 2H), 4.83 (s, 2H), 3.87 (s, 6H), 3.69 (s, 3H); MS (ES+): 404.1 (M+1); 426.3 (M+Na), (ES−): 402.3 (M−1)

Step-2: Preparation of (S)-(1-(4-((1-(3,4,5-trimethoxyphenyl)-1H-imidazol-4-yl)amino)-5,7-dihydrofuro[3,4-d]pyrimidin-2-yl)pyrrolidin-2-yl)methanol (281b)

Compound 281b was prepared according to the procedure reported in Scheme 2 from 2-chloro-N-(1-(3,4,5-trimethoxyphenyl)-1H-imidazol-4-yl)-5,7-dihydrofuro[3,4-d]pyrimidin-4-amine (281a) (200 mg, 0.5 mmol) and (S)-pyrrolidin-2-ylmethanol (125 mg, 1.24 mmol) in 2-Propanol (1 mL). This gave after workup and purification by reverse phase flash column chromatography [(silica gel C-18, 50 g), eluting with ACN in water (containing 0.1% HCl) from 0-100%] (S)-(1-(4-((1-(3,4,5-trimethoxyphenyl)-1H-imidazol-4-yl)amino)-5,7-dihydrofuro[3,4-d]pyrimidin-2-yl)pyrrolidin-2-yl)methanol (281b) (178 mg, 77% yield) HCl salt as a white solid; $^1$H NMR (300 MHz, DMSO-$d_6$) δ 11.15 (s, 1H), 8.32 (s, 1H), 7.92 (s, 1H), 6.95 (s, 2H), 4.96 (s, 4H), 4.56-4.39 (m, 1H), 4.37-3.89 (m, 2H), 3.87 (s, 6H), 3.68 (s, 3H), 3.57-3.38 (m, 2H), 2.16-1.89 (m, 4H); MS (ES+): 469.3 (M+1), (ES−): 503.3 (M+Cl); HPLC purity: 98.31%.

Scheme 282

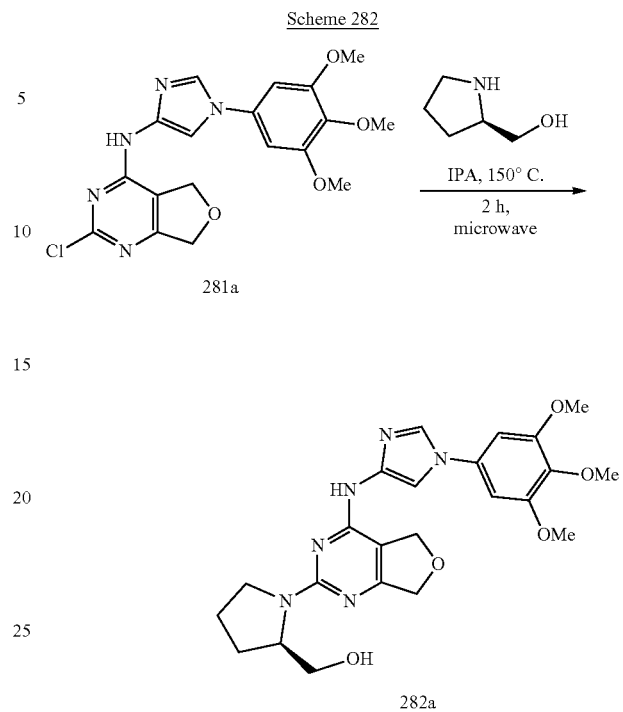

282a

Preparation of (R)-(1-(4-((1-(3,4,5-trimethoxyphenyl)-1H-imidazol-4-yl)amino)-5,7-dihydrofuro[3,4-d]pyrimidin-2-yl)pyrrolidin-2-yl)methanol (282a)

Compound 282a was prepared according to the procedure reported in Scheme 2 from 2-chloro-N-(1-(3,4,5-trimethoxyphenyl)-1H-imidazol-4-yl)-5,7-dihydrofuro[3,4-d]pyrimidin-4-amine (281a) (200 mg, 0.5 mmol) and (R)-pyrrolidin-2-ylmethanol (125 mg, 1.24 mmol) in 2-Propanol (1 mL). This gave after workup and purification by reverse phase flash column chromatography [(silica gel C-18, 50 g), eluting with ACN in water (containing 0.1% HCl) from 0-100%] (R)-(1-(4-((1-(3,4,5-trimethoxyphenyl)-1H-imidazol-4-yl)amino)-5,7-dihydrofuro[3,4-d]pyrimidin-2-yl)pyrrolidin-2-yl)methanol (282a) (125 mg, 54% yield) HCl salt as a white solid; $^1$H NMR (300 MHz, DMSO-$d_6$) δ 11.13 (s, 1H), 8.31 (s, 1H), 7.92 (s, 1H), 6.95 (s, 2H), 4.95 (s, 4H), 4.58-4.41 (m, 1H), 4.40-3.96 (m, 2H), 3.87 (s, 6H), 3.58-3.40 (m, 4H), 2.13-1.92 (m, 4H); MS (ES+): 469.3 (M+1), (ES−): 503.3 (M+Cl); HPLC: 98.2%.

Scheme 283

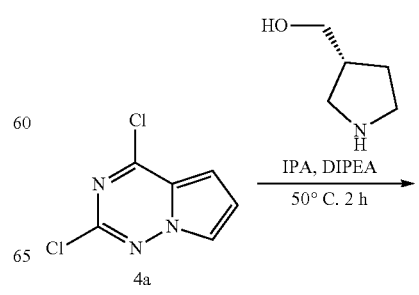

4a

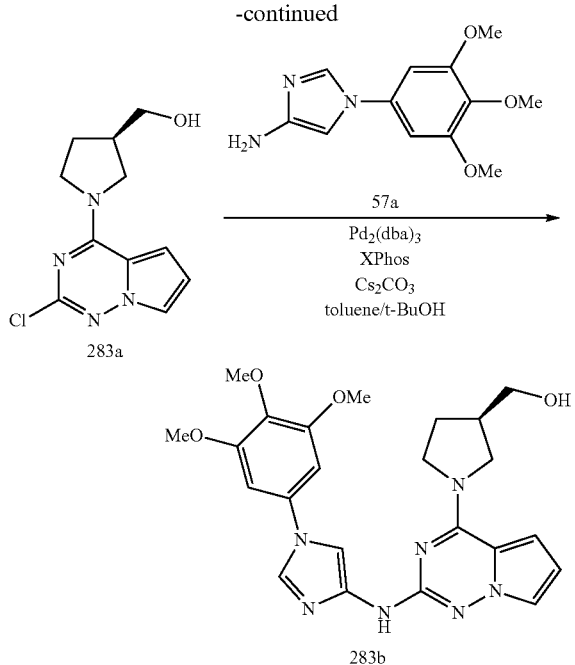

NMR (300 MHz, DMSO-$d_6$) δ 9.62 (s, 1H, $D_2O$ exchangeable), 9.25 (s, 1H), 7.90 (s, 1H, $D_2O$ exchangeable), 7.65 (t, J=2.0 Hz, 1H), 7.13 (s, 2H), 6.94-6.82 (m, 1H), 6.55 (s, 1H), 5.25 (s, 1H, $D_2O$ exchangeable), 4.07-3.81 (m, 9H), 3.75-3.65 (m, 4H), 3.60-3.36 (m, 3H), 2.20-1.67 (m, 2H); MS (ES+): 466.3 (M+1); (ES−): 500.2 (M+Cl); HPLC purity: 98.98%.

Scheme 284

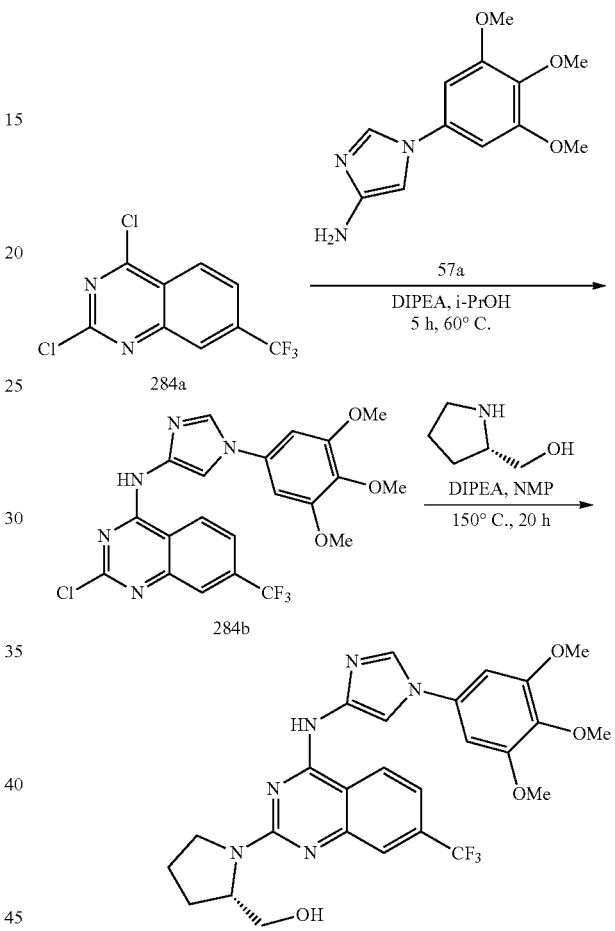

Preparation of (R)-(1-(2-(1-(3,4,5-trimethoxyphenyl)-1H-imidazol-4-ylamino)pyrrolo[1,2-f][1,2,4]triazin-4-yl)pyrrolidin-3-yl)methanol (283b)

Step-1: Preparation of (R)-(1-(2-chloropyrrolo[1,2-f][1,2,4]triazin-4-yl)pyrrolidin-3-yl)methanol (283a)

Compound 283a was prepared from 2,4-dichloropyrrolo [1,2-f][1,2,4]triazine (4a) (350 mg, 1.86 mmol) in 2-Propanol (10 mL) using (R)-pyrrolidin-3-ylmethanol (188 mg, 1.86 mmol) and DIPEA (0.98 mL, 5.58 mmol) according to the procedure reported in step-1 of Scheme 96. This gave after workup and purification by flash column chromatography [silica (24 g), EtOAc in hexane from 0-50%] (R)-(1-(2-chloropyrrolo[1,2-f][1,2,4]triazin-4-yl)pyrrolidin-3-yl)methanol (283a) (446 mg, 95% yield) as a yellow semi-solid; MS (ES+): 253.2 (M+1); (ES−): 287.2 (M+Cl).

Step-2: Preparation of (R)-(1-(2-(1-(3,4,5-trimethoxyphenyl)-1H-imidazol-4-ylamino)pyrrolo[1,2-f][1,2,4]triazin-4-yl)pyrrolidin-3-yl)methanol (283b)

Compound 283b was prepared from (R)-(1-(2-chloropyrrolo[1,2-f][1,2,4]triazin-4-yl)pyrrolidin-3-yl)methanol (283a) (430 mg, 1.7 mmol), 1-(3,4,5-trimethoxyphenyl)-1H-imidazol-4-amine (57a) (424 mg, 1.7 mmol, free base), dicyclohexyl(2',4',6'-triisopropylbiphenyl-2-yl)phosphine (XPhos, 324 mg, 0.68 mmol), cesium carbonate (1109 mg, 3.4 mmol) and $Pd_2(dba)_3$ (311 mg, 0.34 mmol) in toluene/t-BuOH (25 mL, Ratio: 5:2) according to the procedure reported in step-3 of Scheme 101. This gave after workup and purification by flash column chromatography [silica gel (24 g), eluting with DMA-80 in DCM 0-100%], followed by reverse phase column chromatography [(silica gel C-18, 50 g) eluting with acetonitrile and 0.1% HCl water] (R)-(1-(2-(1-(3,4,5-trimethoxyphenyl)-1H-imidazol-4-ylamino)pyrrolo[1,2-f][1,2,4]triazin-4-yl)pyrrolidin-3-yl)methanol (283b) (195 mg, 25% yield) HCl salt as a white solid. $^1H$

Preparation of (S)-(1-(7-(trifluoromethyl)-4-((1-(3,4,5-trimethoxyphenyl)-1H-imidazol-4-yl)amino)quinazolin-2-yl)pyrrolidin-2-yl)methanol (284c)

Step-1: Preparation of 2-chloro-7-(trifluoromethyl)-N-(1-(3,4,5-trimethoxyphenyl)-1H-imidazol-4-yl)quinazolin-4-amine (284b)

Compound 284b was prepared from 2,4-dichloro-7-(trifluoromethyl)quinazoline (284a) (500 mg, 1.872 mmol, CAS #396-02-1) in 2-Propanol (20 mL) using DIPEA (0.98 mL, 5.62 mmol) and 1-(3,4,5-trimethoxyphenyl)-1H-imidazol-4-amine (57a) (513 mg, 2.06 mmol, free base) according to the procedure reported in Scheme 1. This gave after workup 2-chloro-7-(trifluoromethyl)-N-(1-(3,4,5-trimethoxyphenyl)-1H-imidazol-4-yl)quinazolin-4-amine (284b) (741 mg, 82% yield) as a brown solid; $^1H$ NMR (300 MHz, DMSO-$d_6$) δ 11.45 (s, 1H), 8.99 (d, J=8.7 Hz, 1H), 8.24 (s, 1H), 8.03

(d, J=7.6 Hz, 2H), 7.90 (d, J=8.6 Hz, 1H), 6.95 (s, 2H), 3.88 (s, 6H), 3.70 (s, 3H); MS (ES+) 480.2 (M+1), 502.2 (M+Na); (ES−): 478.3 (M−1); 957.3 (2M−1)

Step-2: Preparation of (S)-(1-(7-(trifluoromethyl)-4-((1-(3,4,5-trimethoxyphenyl)-1H-imidazol-4-yl) amino)quinazolin-2-yl)pyrrolidin-2-yl)methanol (284c)

Compound 284c was prepared according to the procedure reported in step-2 of Scheme 76 from 2-chloro-7-(trifluoromethyl)-N-(1-(3,4,5-trimethoxyphenyl)-1H-imidazol-4-yl)quinazolin-4-amine (284b) (300 mg, 0.63 mmol) and (S)-pyrrolidin-2-ylmethanol (0.25 mL, 2.5 mmol), DIPEA (0.66 mL, 3.75 mmol) in NMP (10 mL). This gave after workup and purification by flash column chromatography [silica gel (12 g), eluting with DMA-80 in CH$_2$Cl$_2$ from 0 to 50%] followed by reverse phase flash column chromatography [(silica gel C-18, 24 g), eluting with ACN in water (containing 0.1% HCl) from 0-100%] (S)-(1-(7-(trifluoromethyl)-4-((1-(3,4,5-trimethoxyphenyl)-1H-imidazol-4-yl) amino)quinazolin-2-yl)pyrrolidin-2-yl)methanol (284c) (31 mg, 9% yield) HCl salt as a yellow solid; $^1$H NMR (300 MHz, DMSO-d$_6$): δ 12.86 (s, 1H), 8.95 (t, J=7.5 Hz, 1H), 8.75-8.60 (m, 1H), 8.48 (s, 1H), 8.10 (d, J=1.6 Hz, 1H), 7.77 (d, J=8.6 Hz, 1H), 7.02 (s, 1H), 6.97 (s, 1H), 4.84-4.50 (m, 1H), 4.13-3.43 (m, 13H), 2.22-1.94 (m, 4H). $^{19}$F NMR (282 MHz, DMSO-d$_6$): δ −62.17; MS (ES+): 545.3 (M+1); MS (ES−): 543.4 (M−1), 579.4 (M+Cl). HPLC purity: 91.18%.

yl)quinazolin-4-amine (284b) (300 mg, 0.63 mmol) and (S)-pyrrolidine-2-carboxamide (285 mg, 2.5 mmol), DIPEA (0.66 mL, 3.75 mmol) in NMP (10 mL). This gave after workup and purification by flash column chromatography [silica gel (12 g), eluting with DMA 80 in CH$_2$Cl$_2$ from 0 to 50%] followed by reverse phase flash column chromatography [(silica gel C-18, 24 g), eluting with ACN in water (containing 0.1% HCl) from 0-100%] (S)-1-(7-(trifluoromethyl)-4-((1-(3,4,5-trimethoxyphenyl)-1H-imidazol-4-yl) amino)quinazolin-2-yl)pyrrolidine-2-carboxamide (285a) (46 mg, 13% yield) HCl salt as a yellow solid; $^1$H NMR (300 MHz, DMSO-d$_6$) δ 13.06 (s, 1H), 9.00 (d, J=8.5 Hz, 1H), 8.74 (s, 1H), 8.46 (s, 1H), 7.95 (d, J=1.5 Hz, 1H), 7.81 (d, J=8.6 Hz, 1H), 7.63 (s, 1H), 7.26 (s, 1H), 7.14 (d, J=1.5 Hz, 2H), 4.75 (d, J=8.7 Hz, 1H), 4.22-4.07 (m, 1H), 3.94 (s, 6H), 3.86-3.73 (m, 1H), 3.69 (s, 3H), 2.44-1.87 (m, 4H); $^{19}$F NMR (282 MHz, DMSO-d$_6$): δ −62.16; MS (ES+): 558.3 (M+1), 580.3 (M+Na); MS (ES−): 556.3 (M−1), 592.4 (M+Cl). HPLC purity: 91.99%.

Scheme 286

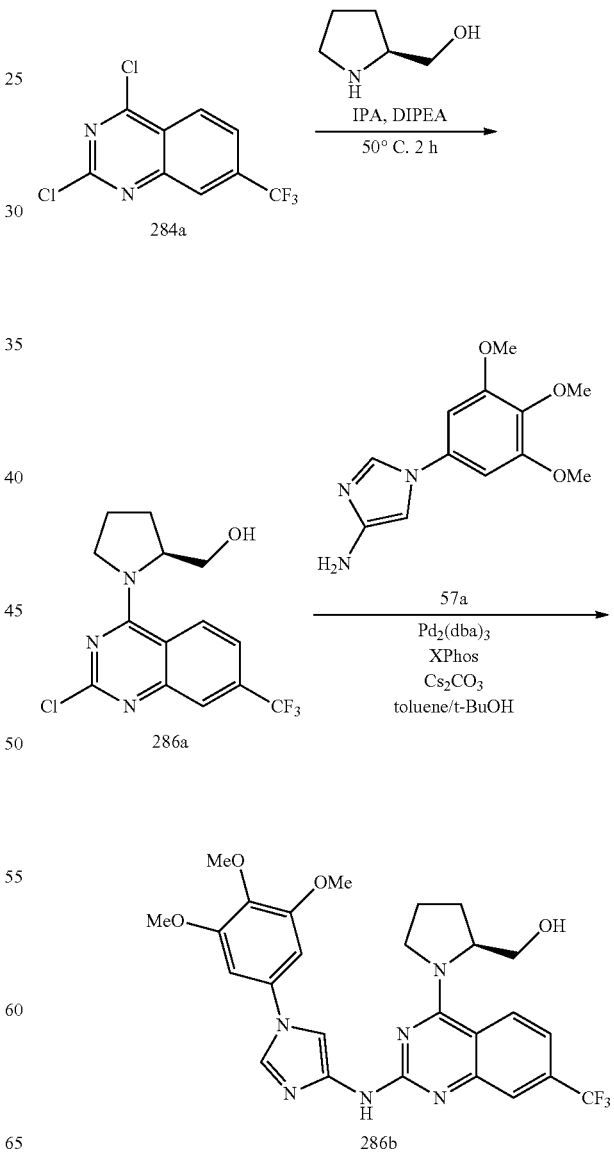

Scheme 285

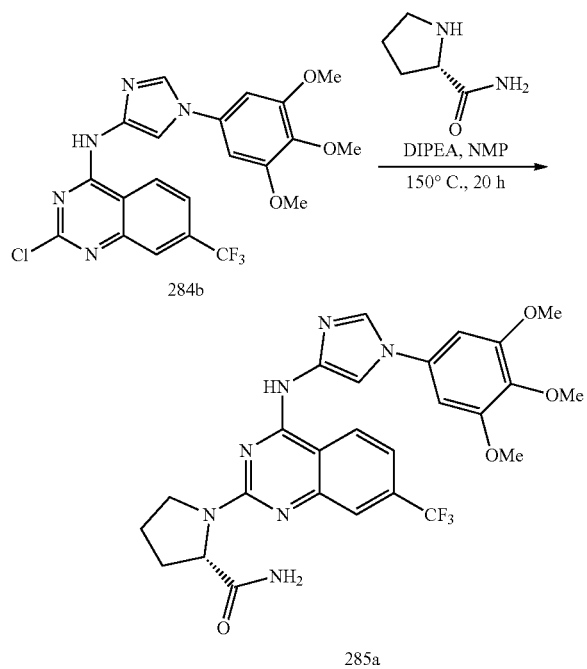

Preparation of (S)-1-(7-(trifluoromethyl)-4-((1-(3,4,5-trimethoxyphenyl)-1H-imidazol-4-yl)amino)quinazolin-2-yl)pyrrolidine-2-carboxamide (285a)

Compound 285a was prepared according to the procedure reported in step-2 of Scheme 76 from 2-chloro-7-(trifluoromethyl)-N-(1-(3,4,5-trimethoxyphenyl)-1H-imidazol-4-

Preparation of (S)-(1-(7-(trifluoromethyl)-2-((1-(3,4,5-trimethoxyphenyl)-1H-imidazol-4-yl)amino)quinazolin-4-yl)pyrrolidin-2-yl)methanol (286b)

Step-1: Preparation of (S)-(1-(2-chloro-7-(trifluoromethyl)quinazolin-4-yl)pyrrolidin-2-yl)methanol (286a)

Compound 286a was prepared from 2,4-dichloro-7-(trifluoromethyl)quinazoline (284a) (400 mg, 1.5 mmol) in 2-Propanol (15 mL) using (S)-pyrrolidin-3-ylmethanol (0.15 mL, 1.5 mmol) and DIPEA (0.79 mL, 4.49 mmol) according to the procedure reported in step-1 of Scheme 96. This gave after workup and purification by flash column chromatography [silica gel (12 g), DCM and methanol (0 to 30%)] (S)-(1-(2-chloro-7-(trifluoromethyl)quinazolin-4-yl)pyrrolidin-2-yl)methanol (286a) (0.41 g, 83% yield) as a yellow solid; $^1$H NMR (300 MHz, DMSO-d$_6$) δ 8.48 (d, J=8.8 Hz, 1H), 7.94 (d, J=1.9 Hz, 1H), 7.70 (dd, J=8.9, 2.0 Hz, 1H), 4.84 (t, J=5.8 Hz, 1H), 4.65-4.53 (m, 1H), 4.11-3.91 (m, 2H), 3.76-3.56 (m, 2H), 2.18-1.82 (m, 4H); MS (ES–): 330.2 (M–1).

Step-2: Preparation of (S)-(1-(7-(trifluoromethyl)-2-((1-(3,4,5-trimethoxyphenyl)-1H-imidazol-4-yl)amino)quinazolin-4-yl)pyrrolidin-2-yl)methanol (286b)

Compound 286b was prepared from (S)-(1-(2-chloro-7-(trifluoromethyl)quinazolin-4-yl)pyrrolidin-2-yl)methanol (286a) (300 mg, 0.9 mmol), 1-(3,4,5-trimethoxyphenyl)-1H-imidazol-4-amine (57a) (225 mg, 0.9 mmol, free base), dicyclohexyl(2',4',6'-triisopropylbiphenyl-2-yl)phosphine (XPhos, 259 mg, 0.54 mmol), cesium carbonate (884 mg, 2.7 mmol) and Pd$_2$(dba)$_3$ (248 mg, 0.27 mmol) in toluene/t-BuOH (40 mL, Ratio: 3:1) according to the procedure reported in step-3 of Scheme 101. This gave after workup and purification by flash column chromatography [silica gel (24 g), eluting with DMA-80 in DCM 0-50%], followed by reverse phase column chromatography [(silica gel C-18, 50 g) eluting with acetonitrile and 0.1% HCl in water] (S)-(1-(7-(trifluoromethyl)-2-((1-(3,4,5-trimethoxyphenyl)-1H-imidazol-4-yl)amino)quinazolin-4-yl)pyrrolidin-2-yl)methanol (286b) (178 mg, 36% yield) HCl salt as a yellow solid; $^1$H NMR (300 MHz, DMSO-d$_6$): δ 10.79 (s, 1H), 8.50 (d, J=9.2 Hz, 2H), 7.81 (s, 2H), 7.69 (d, J=8.7 Hz, 1H), 7.01 (s, 2H), 5.01-4.72 (m, 1H), 4.34-4.02 (m, 2H), 3.93-3.47 (m, 11H), 2.28-1.80 (m, 4H). $^{19}$F NMR (282 MHz, DMSO-d$_6$): δ –62.07; MS (ES+): 545.3 (M+1); MS (ES–): 543.4 (M–1), 579.4 (M+Cl). HPLC purity: 88.78%.

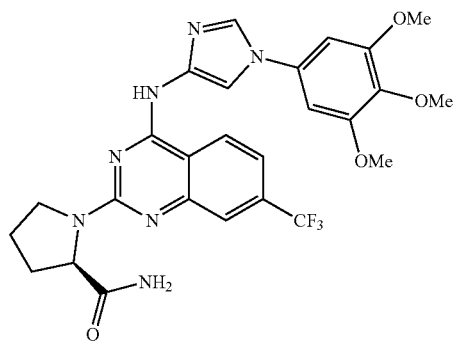

287a

Preparation of (R)-1-(7-(trifluoromethyl)-4-((1-(3,4,5-trimethoxyphenyl)-1H-imidazol-4-yl)amino)quinazolin-2-yl)pyrrolidine-2-carboxamide (287a)

Compound 287a was prepared according to the procedure reported in step-2 of Scheme 76 from 2-chloro-7-(trifluoromethyl)-N-(1-(3,4,5-trimethoxyphenyl)-1H-imidazol-4-yl)quinazolin-4-amine (284b) (100 mg, 0.208 mmol) and (R)-pyrrolidine-2-carboxamide (95 mg, 0.83 mmol), DIPEA (0.22 mL, 1.25 mmol) in NMP (4 mL). This gave after workup and purification by flash column chromatography [silica gel (12 g), eluting with DMA 80 in CH$_2$Cl$_2$ from 0 to 50%] followed by reverse phase flash column chromatography [(silica gel C-18, 24 g), eluting with ACN in water (containing 0.1% HCl) from 0-100%] (R)-1-(7-(trifluoromethyl)-4-((1-(3,4,5-trimethoxyphenyl)-1H-imidazol-4-yl)amino)quinazolin-2-yl)pyrrolidine-2-carboxamide (287a) (46 mg, 40% yield) HCl salt as a yellow solid; $^1$H NMR (300 MHz, DMSO-d$_6$): δ 12.88 (s, 1H), 8.99 (d, J=8.5 Hz, 1H), 8.65 (s, 1H), 8.41 (s, 1H), 7.97 (s, 1H), 7.81 (d, J=8.4 Hz, 1H), 7.62 (s, 1H), 7.27 (s, 1H), 7.14 (s, 2H), 4.76 (d, J=8.5 Hz, 1H), 4.20-4.09 (m, 1H), 3.94 (s, 6H), 3.83-3.73 (m, 1H), 3.69 (s, 3H), 2.39-1.95 (m, 4H). $^{19}$F NMR (282 MHz, DMSO-d$_6$): δ –62.17; MS (ES+): 558.3 (M+1); MS (ES–): 556.4 (M–1), 592.3 (M+Cl). HPLC purity: 98.63%.

Scheme 287

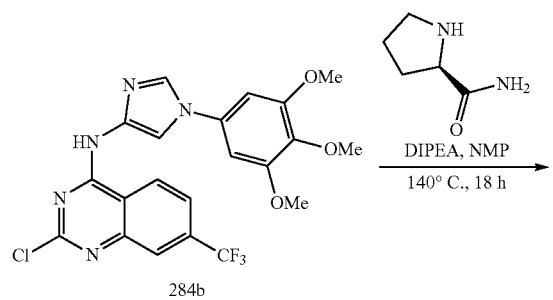

Scheme 288

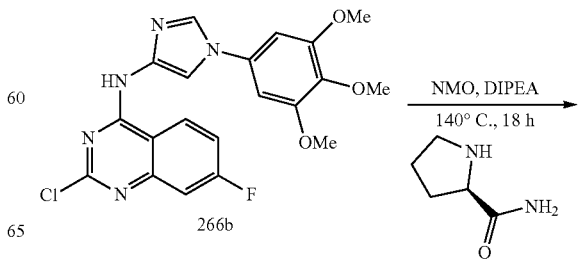

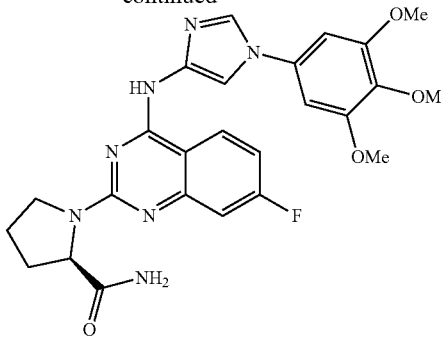

288a

Preparation of (R)-1-(7-fluoro-4-((1-(3,4,5-trimethoxyphenyl)-1H-imidazol-4-yl)amino)quinazolin-2-yl)pyrrolidine-2-carboxamide (288a)

Compound 288a was prepared according to the procedure reported in step-2 of Scheme 76 from 2-chloro-7-fluoro-N-(1-(3,4,5-trimethoxyphenyl)-1H-imidazol-4-yl)quinazolin-4-amine (266b) (1500 mg, 3.49 mmol) and (R)-pyrrolidine-2-carboxamide (1593 mg, 13.96 mmol) in NMP (10 mL) using DIPEA (3.66 mL, 20.94 mmol) as base. This gave after workup and purification by flash column chromatography [silica gel (12 g), eluting with DMA80 in DCM from 0-50%] followed by purification by reverse phase flash column chromatography [(silica gel C-18, 24 g), eluting with ACN in water (containing 0.1% HCl) from 0-100%] (R)-1-(7-fluoro-4-((1-(3,4,5-trimethoxyphenyl)-1H-imidazol-4-yl)amino)quinazolin-2-yl)pyrrolidine-2-carboxamide (288a) (192 mg, 11% yield) HCl salt as a light yellow solid; $^1$H NMR (300 MHz, DMSO-d$_6$): δ 13.05 (s, 1H), 8.87 (dd, J=9.3, 5.7 Hz, 1H), 8.59 (s, 1H), 8.19 (dt, J=10.1, 2.4 Hz, 1H), 7.98-7.87 (m, 1H), 7.64 (s, 1H), 7.37 (td, J=8.7, 2.6 Hz, 1H), 7.22 (s, 1H), 7.15 (t, J=1.4 Hz, 2H), 4.75-4.70 (m, 1H), 4.21-4.06 (m, 1H), 3.93 (d, J=1.4 Hz, 6H), 3.84-3.73 (m, 1H), 3.69 (d, J=1.4 Hz, 3H), 2.42-1.80 (m, 4H). $^{19}$F NMR (282 MHz, DMSO-d$_6$): δ −101.18; MS (ES+): 508.3 (M+1); MS (ES−): 506.3 (M−1), 542.3 (M+Cl). HPLC purity: 98.90%.

Scheme 289

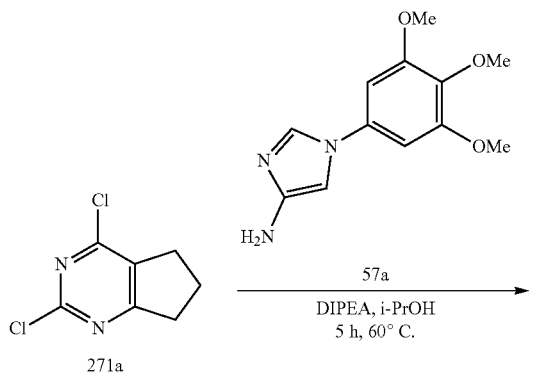

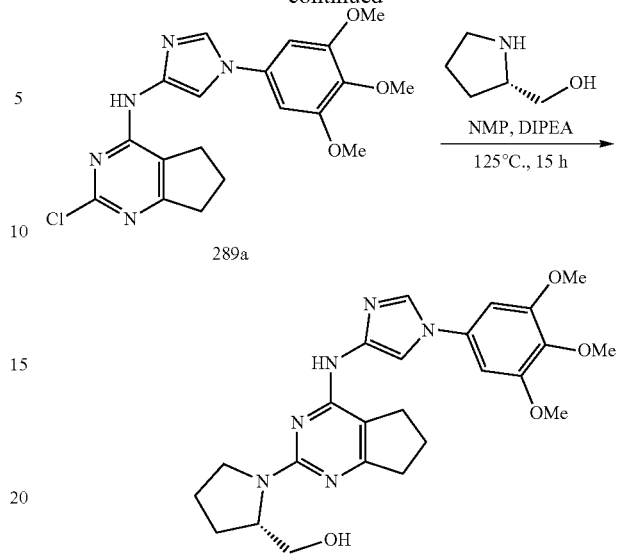

Preparation of (S)-(1-(4-((1-(3,4,5-trimethoxyphenyl)-1H-imidazol-4-yl)amino)-6,7-dihydro-5H-cyclopenta[d]pyrimidin-2-yl)pyrrolidin-2-yl)methanol (289b)

Step-1: Preparation of 2-chloro-N-(1-(3,4,5-trimethoxyphenyl)-1H-imidazol-4-yl)-6,7-dihydro-5H-cyclopenta[d]pyrimidin-4-amine (289a)

Compound 289a was prepared from 2,4-dichloro-6,7-dihydro-5H-cyclopenta[d]pyrimidine (271a) (1.7 g, 8.99 mmol) in 2-Propanol (50 mL) using DIPEA (4.71 mL, 27.0 mmol) and 1-(3,4,5-trimethoxyphenyl)-1H-imidazol-4-amine (57a) (2.35 g, 9.44 mmol, free base) according to the procedure reported in Scheme 1. This gave after workup 2-chloro-N-(1-(3,4,5-trimethoxyphenyl)-1H-imidazol-4-yl)-6,7-dihydro-5H-cyclopenta[d]pyrimidin-4-amine (289a) (1 g, 28% yield) as a yellow solid; $^1$H NMR (300 MHz, DMSO-d$_6$) δ 9.87 (s, 1H, D$_2$O exchangeable), 8.16-8.09 (m, 1H), 7.80-7.72 (m, 1H), 6.90 (s, 2H), 3.87 (s, 6H), 3.69 (s, 3H), 2.85-2.72 (m, 4H), 2.10-1.93 (m, 2H); MS (ES+): 402.1 (M+1), 424.1 (M+Na); (ES−): 400.2 (M−1), 436.1 (M+Cl).

Step-2: Preparation of (S)-(1-(4-((1-(3,4,5-trimethoxyphenyl)-1H-imidazol-4-yl)amino)-6,7-dihydro-5H-cyclopenta[d]pyrimidin-2-yl)pyrrolidin-2-yl)methanol (289b)

Compound 289b was prepared according to the procedure reported in step-2 of Scheme 76 from 2-chloro-N-(1-(3,4,5-trimethoxyphenyl)-1H-imidazol-4-yl)-6,7-dihydro-5H-cyclopenta[d]pyrimidin-4-amine (289a) (200 mg, 0.5 mmol) and (S)-pyrrolidin-2-ylmethanol (151 mg, 1.49 mmol), DIPEA (0.26 mL, 1.49 mmol) in NMP (3 mL). This gave after workup and purification by flash column chromatography [silica gel (12 g) eluting with DMA-80 in DCM from 0-50%], followed by reverse phase flash column chromatography [(silica gel C-18, 50 g), eluting with ACN in water (containing 0.1% HCl) from 0-100%] (S)-(1-(4-((1-(3,4,5-trimethoxyphenyl)-1H-imidazol-4-yl)amino)-6,7-dihydro-5H-cyclopenta[d]pyrimidin-2-yl)pyrrolidin-2-yl)methanol (289b) (122 mg, 53% yield) HCl salt as a white solid; $^1$H NMR (300 MHz, DMSO-$d_6$) δ 12.78 (s, 1H, D$_2$O exchangeable), 10.83 (s, 1H, D$_2$O exchangeable), 8.47 (d, J=1.5 Hz, 1H), 7.95 (s, 1H), 6.97 (s, 2H), 4.51-4.34 (m, 1H), 3.87 (s, 6H), 3.73-3.59 (m, 5H), 3.54-3.41 (m, 2H), 2.96 (t, J=7.8 Hz, 2H), 2.86-2.75 (m, 2H), 2.15-1.94 (m, 6H); MS (ES+): 467.3 (M+1); (ES−): 501.2 (M+Cl); HPLC purity, 98.77%

Scheme 290

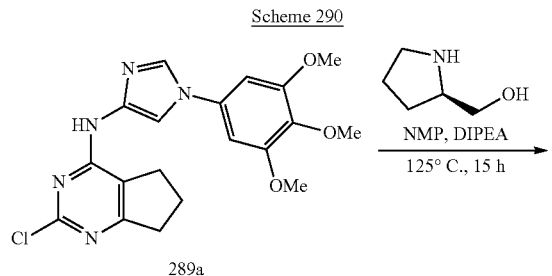

289a

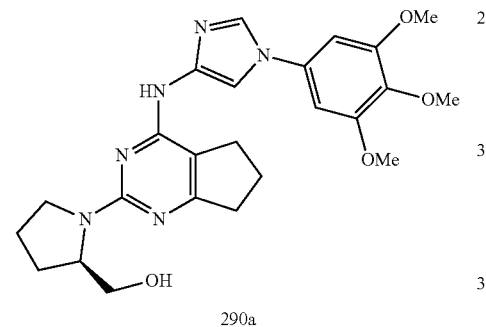

290a

Preparation of (R)-(1-(4-((1-(3,4,5-trimethoxyphenyl)-1H-imidazol-4-yl)amino)-6,7-dihydro-5H-cyclopenta[d]pyrimidin-2-yl)pyrrolidin-2-yl)methanol (290a)

Compound 290a was prepared according to the procedure reported in step-2 of Scheme 76 from 2-chloro-N-(1-(3,4,5-trimethoxyphenyl)-1H-imidazol-4-yl)-6,7-dihydro-5H-cyclopenta[d]pyrimidin-4-amine (289a) (200 mg, 0.5 mmol) and (R)-pyrrolidin-2-ylmethanol (151 mg, 1.49 mmol), DIPEA (0.26 mL, 1.49 mmol) in NMP (3 mL). This gave after workup and purification by flash column chromatography [silica gel (12 g) eluting with DMA-80 in DCM from 0-50%], followed by reverse phase flash column chromatography [(silica gel C-18, 50 g), eluting with ACN in water (containing 0.1% HCl) from 0-100%] (R)-(1-(4-((1-(3,4,5-trimethoxyphenyl)-1H-imidazol-4-yl)amino)-6,7-dihydro-5H-cyclopenta[d] pyrimidin-2-yl)pyrrolidin-2-yl)methanol (290a) (103 mg, 44% yield) HCl salt as a white solid; $^1$H NMR (300 MHz, DMSO-$d_6$) δ 13.11 (s, 1H, D$_2$O exchangeable), 10.99 (s, 1H, D$_2$O exchangeable), 8.79 (s, 1H), 7.98 (s, 1H), 7.32-6.50 (m, 2H, D$_2$O exchangeable, 1H), 4.41 (s, 1H), 3.87 (s, 6H), 3.82-3.71 (m, 2H), 3.68 (s, 3H), 3.53-3.36 (m, 2H), 3.09-2.89 (m, 2H), 2.85-2.63 (m, 2H), 2.22-1.84 (m, 6H); MS (ES+): 467.3 (M+1); (ES−): 501.2 (M+Cl); HPLC purity, 98.47%.

Scheme 291

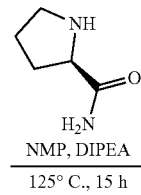

289a

291a

Preparation of (R)-1-(4-((1-(3,4,5-trimethoxyphenyl)-1H-imidazol-4-yl)amino)-6,7-dihydro-5H-cyclopenta[d]pyrimidin-2-yl)pyrrolidine-2-carboxamide (291a)

Compound 291a was prepared according to the procedure reported in step-2 of Scheme 76 from 2-chloro-N-(1-(3,4,5-trimethoxyphenyl)-1H-imidazol-4-yl)-6,7-dihydro-5H-cyclopenta[d]pyrimidin-4-amine (289a) (200 mg, 0.5 mmol) and (R)-pyrrolidine-2-carboxamide (227 mg, 1.99 mmol), DIPEA (0.26 mL, 1.49 mmol) in NMP (3 mL). This gave after workup and purification by flash column chromatography [silica gel (12 g) eluting with DMA-80 in DCM from 0-50%], followed by reverse phase flash column chromatography [(silica gel C-18, 50 g), eluting with ACN in water (containing 0.1% HCl) from 0-100%] (R)-1-(4-((1-(3,4,5-trimethoxyphenyl)-1H-imidazol-4-yl)amino)-6,7-dihydro-5H-cyclopenta[d]pyrimidin-2-yl)pyrrolidine-2-carboxamide (291a) (130 mg, 55% yield) HCl salt as a white solid; $^1$H NMR (300 MHz, DMSO-$d_6$) δ 13.30 (s, 1H, D$_2$O exchangeable), 10.95 (s, 1H, D$_2$O exchangeable), 8.77 (d, J=1.5 Hz, 1H), 8.04 (s, 1H, D$_2$O exchangeable), 7.88 (d, J=1.6 Hz, 1H), 7.60 (s, 1H, D$_2$O exchangeable), 7.22-7.11 (m, 3H), 4.59-4.50 (m, 1H), 4.00-3.85 (m, 1H), 3.92 (s, 6H), 3.68 (s, 3H), 3.64-3.53 (m, 1H), 3.06-2.96 (m, 2H), 2.87-2.76 (m, 2H), 2.30-2.20 (m, 1H), 2.17-1.91 (m, 5H); MS (ES+): 480.3 (M+1); (ES−): 514.2 (M+Cl); HPLC purity, 94.64%

Scheme 292

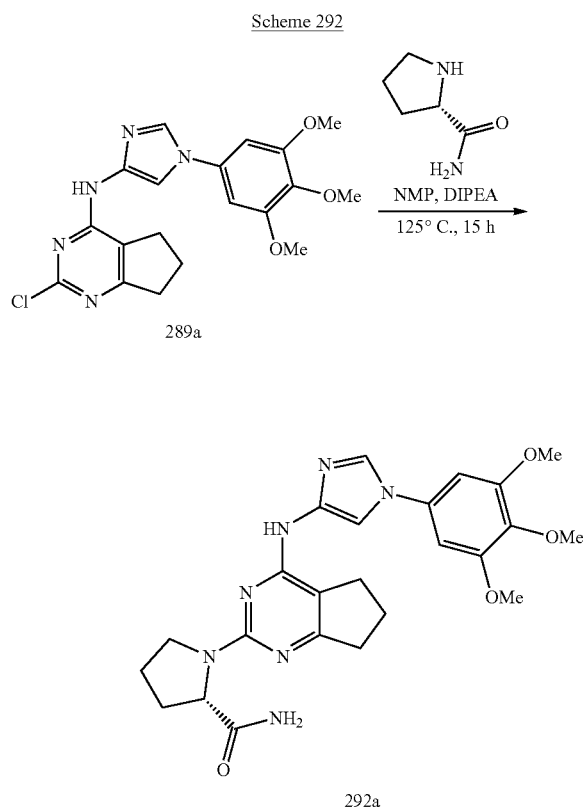

Preparation of (S)-1-(4-((1-(3,4,5-trimethoxyphenyl)-1H-imidazol-4-yl)amino)-6,7-dihydro-5H-cyclopenta[d]pyrimidin-2-yl)pyrrolidine-2-carboxamide (292a)

Compound 292a was prepared according to the procedure reported in step-2 of Scheme 76 from 2-chloro-N-(1-(3,4,5-trimethoxyphenyl)-1H-imidazol-4-yl)-6,7-dihydro-5H-cyclopenta[d]pyrimidin-4-amine (289a) (200 mg, 0.5 mmol) and (S)-pyrrolidine-2-carboxamide (227 mg, 1.99 mmol), DIPEA (0.26 mL, 1.49 mmol) in NMP (3 mL). This gave after workup and purification by flash column chromatography [silica gel (12 g) eluting with DMA-80 in DCM from 0-50%], followed by reverse phase flash column chromatography [(silica gel C-18, 50 g), eluting with ACN in water (containing 0.1% HCl) from 0-100%] (S)-1-(4-((1-(3,4,5-trimethoxyphenyl)-1H-imidazol-4-yl)amino)-6,7-dihydro-5H-cyclopenta[d]pyrimidin-2-yl)pyrrolidine-2-carboxamide (292a) (157 mg, 66% yield) HCl salt as a white solid; $^1$H NMR (300 MHz, DMSO-$d_6$) δ 13.35 (s, 1H, $D_2O$ exchangeable), 11.01 (s, 1H, $D_2O$ exchangeable), 8.88 (d, J=1.6 Hz, 1H), 8.22-8.04 (m, 1H, $D_2O$ exchangeable), 7.90 (d, J=1.7 Hz, 1H), 7.61 (s, 1H, $D_2O$ exchangeable), 7.18 (s, 3H), 4.60-4.52 (m, 1H), 4.02-3.95 (m, 1H), 3.92 (s, 6H), 3.68 (s, 3H), 3.64-3.54 (m, 1H), 3.08-2.96 (m, 2H), 2.88-2.75 (m, 2H), 2.32-2.20 (m, 1H), 2.17-1.89 (m, 5H); MS (ES+): 480.2 (M+1); (ES−): 514.2 (M+Cl); HPLC purity, 90.63%

Scheme 293

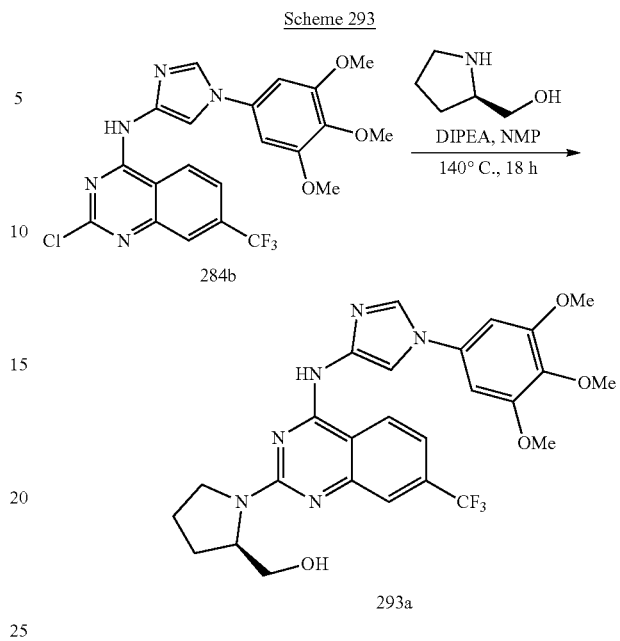

Preparation of (R)-(1-(7-(trifluoromethyl)-4-((1-(3,4,5-trimethoxyphenyl)-1H-imidazol-4-yl)amino)quinazolin-2-yl)pyrrolidin-2-yl)methanol (293a)

Compound 293a was prepared according to the procedure reported in step-2 of Scheme 76 from 2-chloro-7-(trifluoromethyl)-N-(1-(3,4,5-trimethoxyphenyl)-1H-imidazol-4-yl)quinazolin-4-amine (284b) (100 mg, 0.21 mmol) and (R)-pyrrolidin-2-ylmethanol (0.082 mL, 0.83 mmol), DIPEA (0.22 mL, 1.25 mmol) in NMP (3 mL). This gave after workup and purification by flash column chromatography [silica gel (12 g), eluting with DMA-80 in $CH_2Cl_2$ from 0 to 50%] followed by reverse phase flash column chromatography [(silica gel C-18, 24 g), eluting with ACN in water (containing 0.1% HCl) from 0-100%] (R)-(1-(7-(trifluoromethyl)-4-((1-(3,4,5-trimethoxyphenyl)-1H-imidazol-4-yl)amino)quinazolin-2-yl)pyrrolidin-2-yl)methanol (293a) (0.021 g, 19% yield) HCl salt as an off-white HCl salt; $^1$H NMR (300 MHz, DMSO-$d_6$) (a mixture of two rotamers) δ 12.69 (s, 1H), 12.06 and 11.92 (2s, 1H), 9.03-8.89 (m, 1H), 8.63 and 8.55 (2d, J=4.7 Hz, 1H), 8.48-8.39 (m, 1H), 8.10 and 8.09 (2s, 1H), 7.84-7.74 (m, 1H), 7.01 and 6.97 (2d, J=4.5 Hz, 2H), 4.83-4.53 (m, 1H), 4.16-3.44 (m, 13H), 2.24-1.79 (m, 4H). $^{19}$F NMR (282 MHz, DMSO-$d_6$): δ −62.16; MS (ES+): 545.3 (M+1); MS (ES−): 543.8 (M−1). HPLC purity: 98.81%.

Scheme 294

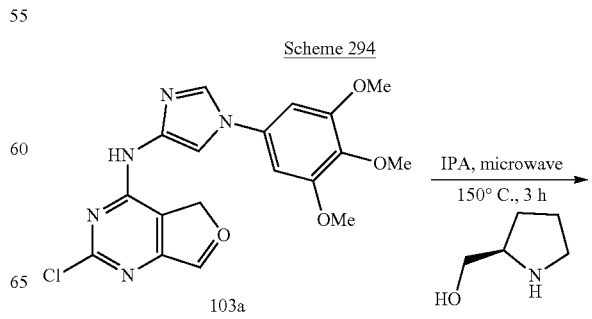

503

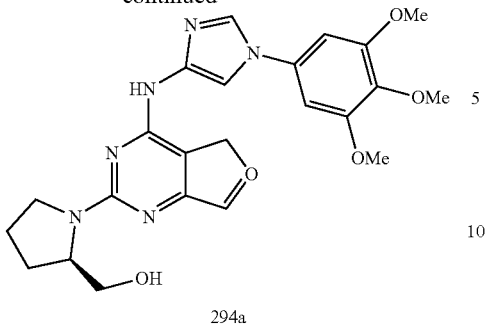

294a

Preparation of (R)-(1-(4-((1-(3,4,5-trimethoxyphenyl)-1H-imidazol-4-yl)amino)furo[3,2-d]pyrimidin-2-yl)pyrrolidin-2-yl)methanol (294a)

Compound 294a was prepared according to the procedure reported in Scheme 2 from (2-chloro-furo[3,2-d]pyrimidin-4-yl)-[1-(3,4,5-trimethoxy-phenyl)-1H-imidazol-4-yl]-amine (103a) (500 mg, 1.24 mmol) and (R)-pyrrolidin-2-ylmethanol (315 mg, 3.11 mmol) in 2-Propanol (2 mL). This gave after workup and purification by reverse phase flash column chromatography [(silica gel C-18 column, 100 g) eluting with acetonitrile and 0.1% HCl water] followed by lyophilization (R)-(1-(4-((1-(3,4,5-trimethoxyphenyl)-1H-imidazol-4-yl)amino)furo[3,2-d]pyrimidin-2-yl)pyrrolidin-2-yl)methanol (294a) (358 mg, 62%) HCl salt as a white solid; $^1$H NMR (300 MHz, DMSO-$d_6$) δ 13.18-12.46 (m, 1H, D$_2$O exchangeable), 12.08-11.66 (m, 1H, D$_2$O exchangeable), 8.36 (d, J=2.1 Hz, 1H), 8.34 (s, 1H), 7.97 (s, 1H), 6.99 (d, J=2.1 Hz, 1H), 6.97 (s, 2H), 4.56-4.41 (m, 1H), 3.87 (s, 6H), 3.68 (s, 3H), 3.60-3.40 (m, 4H), 2.17-1.87 (m, 4H); MS (ES+): 467.3 (M+1), (ES−): 501.2 (M+Cl); HPLC purity: 95.46%.

Scheme 295

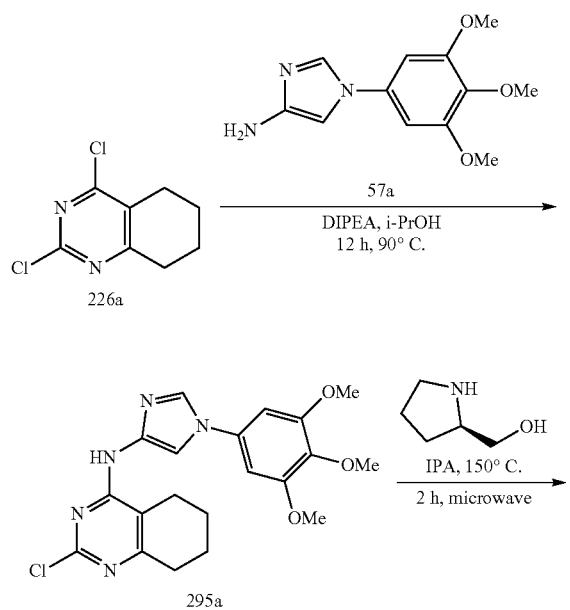

504

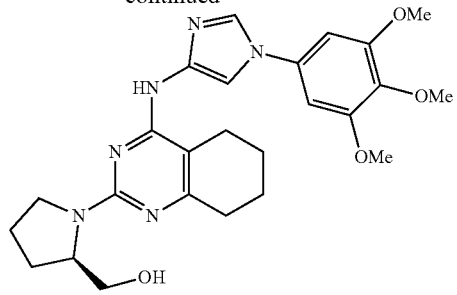

295b

Preparation of (R)-(1-(4-((1-(3,4,5-trimethoxyphenyl)-1H-imidazol-4-yl)amino)-5,6,7,8-tetrahydroquinazolin-2-yl)pyrrolidin-2-yl)methanol (295b)

Step-1: Preparation of 2-chloro-N-(1-(3,4,5-trimethoxyphenyl)-1H-imidazol-4-yl)-5,6,7,8-tetrahydroquinazolin-4-amine (295a)

Compound 295a was prepared from 2,4-dichloro-5,6,7,8-tetrahydroquinazoline (226a) (2 g, 9.85 mmol, CAS #1127-85-1) in 2-Propanol (50 mL) using DIPEA (5.16 mL, 29.5 mmol) and 1-(3,4,5-trimethoxyphenyl)-1H-imidazol-4-amine (57a) (2.58 g, 10.34 mmol, free base) according to the procedure reported in Scheme 1. This gave after workup 2-chloro-N-(1-(3,4,5-trimethoxyphenyl)-1H-imidazol-4-yl)-5,6,7,8-tetrahydroquinazolin-4-amine (295a) (1.64 g, 40% yield) as an off white solid; $^1$H NMR (300 MHz, DMSO-$d_6$) δ 9.33 (s, 1H), 8.16 (d, J=1.6 Hz, 1H), 7.78 (d, J=1.6 Hz, 1H), 6.90 (s, 2H), 3.87 (s, 6H), 3.69 (s, 3H), 2.67-2.53 (m, 4H), 1.84-1.66 (m, 4H).

Step-2: Preparation of (R)-(1-(4-((1-(3,4,5-trimethoxyphenyl)-1H-imidazol-4-yl)amino)-5,6,7,8-tetrahydroquinazolin-2-yl)pyrrolidin-2-yl)methanol (295b)

Compound 295b was prepared according to the procedure reported in Scheme 2 from 2-chloro-N-(1-(3,4,5-trimethoxyphenyl)-1H-imidazol-4-yl)-5,6,7,8-tetrahydroquinazolin-4-amine (295a) (300 mg, 0.721 mmol) and (R)-pyrrolidin-2-ylmethanol (182 mg, 1.8 mmol) in 2-Propanol (2 mL). This gave after workup and purification by reverse phase flash column chromatography [(silica gel C-18, 100 g), eluting with ACN in water (containing 0.1% HCl) from 0-100%] (R)-(1-(4-((1-(3,4,5-trimethoxyphenyl)-1H-imidazol-4-yl)amino)-5,6,7,8-tetrahydroquinazolin-2-yl)pyrrolidin-2-yl)methanol (295b) (250 mg, 72% yield) HCl salt as a white solid; $^1$H NMR (300 MHz, DMSO-$d_6$) δ 11.88-11.24 (m, 1H, D$_2$O exchangeable), 10.34-9.99 (m, 1H, D$_2$O exchangeable), 8.35 (s, 1H), 7.95 (s, 1H), 6.96 (s, 2H), 4.52-4.39 (m, 1H), 3.87 (s, 6H), 3.67 (s, 3H), 3.69-3.38 (m, 4H), 2.78-2.64 (m, 2H), 2.59-2.37 (m, 2H), 2.07-1.91 (m, 4H), 1.81-1.67 (m, 4H); MS (ES+): 481.3 (M+1), (ES−): 515.3 (M+Cl); HPLC purity: 95.66%.

Scheme 296

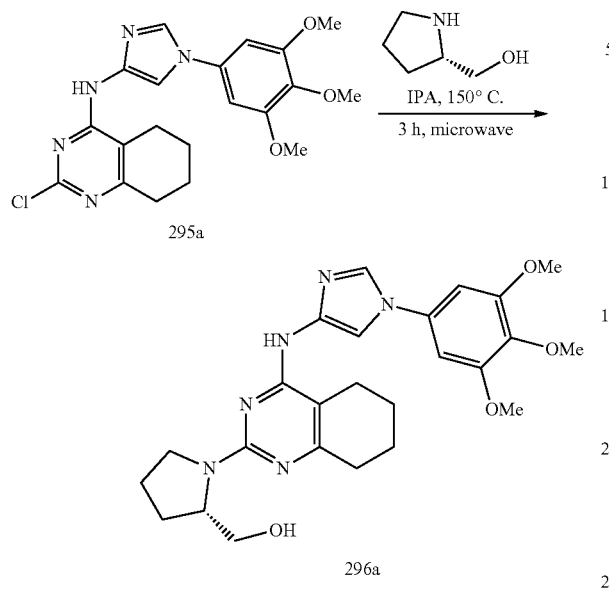

Preparation of (S)-(1-(4-((1-(3,4,5-trimethoxyphenyl)-1H-imidazol-4-yl)amino)-5,6,7,8-tetrahydroquinazolin-2-yl)pyrrolidin-2-yl)methanol (296a)

Compound 296a was prepared according to the procedure reported in Scheme 2 from 2-chloro-N-(1-(3,4,5-trimethoxyphenyl)-1H-imidazol-4-yl)-5,6,7,8-tetrahydroquinazolin-4-amine (295a) (300 mg, 0.72 mmol) and (S)-pyrrolidin-2-ylmethanol (182 mg, 1.8 mmol) in 2-Propanol (2 mL). This gave after workup and purification by reverse phase flash column chromatography [(silica gel C-18, 100 g), eluting with ACN in water (containing 0.1% HCl) from 0-100%] (S)-(1-(4-((1-(3,4,5-trimethoxyphenyl)-1H-imidazol-4-yl)amino)-5,6,7,8-tetrahydroquinazolin-2-yl)pyrrolidin-2-yl)methanol (296a) (245 mg, 71% yield) HCl salt as a white solid; $^1$H NMR (300 MHz, DMSO-d$_6$) δ 11.82-11.49 (m, 1H, D$_2$O exchangeable), 10.31

10.01 (m, 1H, D$_2$O exchangeable), 8.39 (s, 1H), 7.96 (s, 1H), 6.96 (s, 2H), 4.49-4.41 (m, 1H), 3.87 (s, 6H), 3.68 (s, 3H), 3.65-3.34 (m, 4H), 2.78-2.65 (m, 2H), 2.58-2.35 (m, 2H), 2.06-1.90 (m, 4H), 1.81-1.63 (m, 4H); MS (ES+) 481.3 (M+1), (ES−) 515.3 (M+Cl); HPLC purity: 98.7%.

Scheme 297

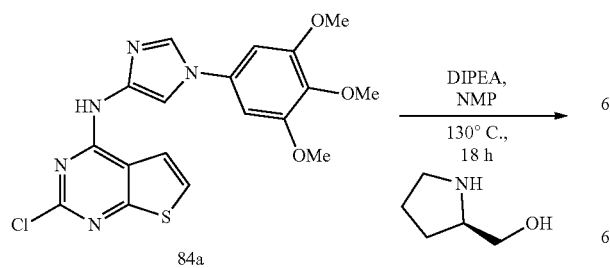

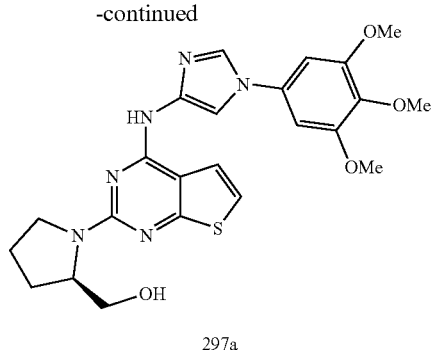

Preparation of (R)-(1-(4-((1-(3,4,5-trimethoxyphenyl)-1H-imidazol-4-yl)amino)thieno[2,3-d]pyrimidin-2-yl)pyrrolidin-2-yl)methanol (297a)

Compound 297a was prepared from 2-chloro-N-(1-(3,4,5-trimethoxyphenyl)-1H-imidazol-4-yl)thieno[2,3-d]pyrimidin-4-amine (84a) (500 mg, 1.2 mmol), (R)-pyrrolidin-2-ylmethanol (0.47 mL, 4.79 mmol), DIPEA (1.25 mL, 7.18 mmol) in NMP (5 mL) according to the procedure reported in step-2 of Scheme 76. This gave after workup and purification by flash column chromatography [silica gel (12 g), eluting with DMA 80 in CH$_2$Cl$_2$ from 0 to 50%] followed by reverse phase flash chromatography [(silica gel C-18, 24 g) eluting with acetonitrile and 0.1% HCl water] (R)-(1-(4-((1-(3,4,5-trimethoxyphenyl)-1H-imidazol-4-yl)amino)thieno[2,3-d]pyrimidin-2-yl)pyrrolidin-2-yl)methanol (297a) (295 mg, 51% yield) HCl salt as an off-white solid; $^1$H NMR (300 MHz, DMSO-d$_6$) δ 11.57 (s, 1H), 8.58 (s, 1H), 8.04 (s, 1H), 7.98 (d, J=5.7 Hz, 1H), 7.40 (d, J=5.7 Hz, 1H), 7.01 (s, 2H), 4.65-4.28 (m, 1H), 4.14-3.26 (m, 13H), 2.30-1.70 (m, 4H); MS (ES+): 483.2 (M+1); MS (ES−): 481.2 (M-1), 517.4 (M+Cl). HPLC purity: 97.27%.

Scheme 298

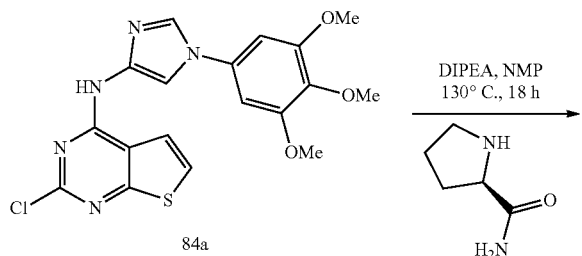

Preparation (R)-1-(4-((1-(3,4,5-trimethoxyphenyl)-1H-imidazol-4-yl)amino)thieno[2,3-d]pyrimidin-2-yl)pyrrolidine-2-carboxamide (298a)

Compound 298a was prepared according to the procedure reported in step-2 of Scheme 76 from 2-chloro-N-(1-(3,4,5-trimethoxyphenyl)-1H-imidazol-4-yl)thieno[2,3-d]pyrimidin-4-amine (84a) (500 mg, 1.2 mmol) and (R)-pyrrolidine-2-carboxamide (546 mg, 4.79 mmol), DIPEA (1.25 mL, 7.18 mmol) in NMP (5 mL). This gave after workup and purification by flash [silica gel (12 g), eluting with DMA 80 in CH$_2$Cl$_2$ from 0 to 50%] followed by purification by reverse phase flash column chromatography [(silica gel C-18, 24 g) eluting with acetonitrile and 0.1% HCl in water] (R)-1-(4-((1-(3,4,5-trimethoxyphenyl)-1H-imidazol-4-yl)amino)thieno[2,3-d]pyrimidin-2-yl)pyrrolidine-2-carboxamide (298a) (330 mg, 56% yield) HCl salt as a white solid; $^1$H NMR (300 MHz, DMSO-d$_6$): δ 11.42 (s, 1H), 8.49 (s, 1H), 8.00 (d, J=5.9 Hz, 1H), 7.91 (s, 1H), 7.58 (s, 1H), 7.42 (d, J=5.8 Hz, 1H), 7.20 (s, 1H), 7.15 (s, 2H), 4.81-4.48 (m, 1H), 4.13-3.78 (m, 7H), 3.79-3.43 (m, 4H), 2.39-1.80 (m, 4H). MS (ES+): 496.2 (M+1); MS (ES−): 494.3 (M−1), 530.3 (M+Cl). HPLC purity: 97.58%.

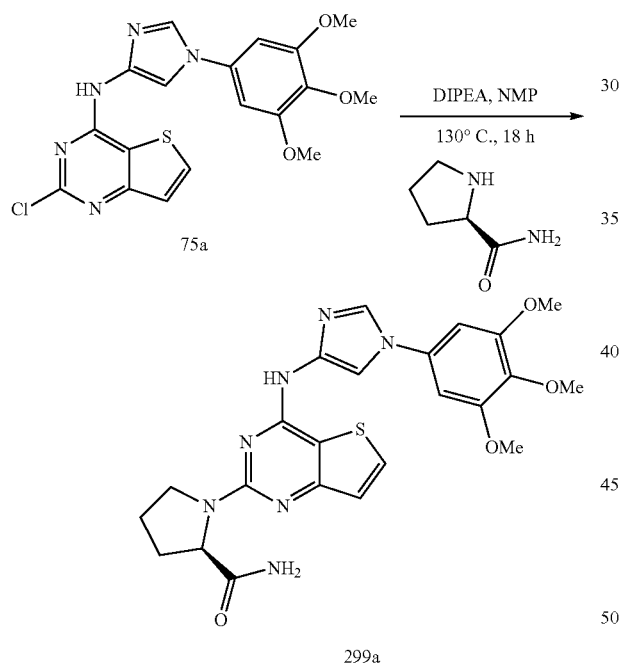

Scheme 299

Preparation of (R)-1-(4-((1-(3,4,5-trimethoxyphenyl)-1H-imidazol-4-yl)amino)thieno[3,2-d]pyrimidin-2-yl)pyrrolidine-2-carboxamide (299a)

Compound 299a was prepared according to the procedure reported in step-2 of Scheme 76 from 2-chloro-N-(1-(3,4,5-trimethoxyphenyl)-1H-imidazol-4-yl)thieno[3,2-d]pyrimidin-4-amine (75a) (500 mg, 1.2 mmol) and (R)-pyrrolidine-2-carboxamide (546 mg, 4.79 mmol), DIPEA (1.25 mL, 7.18 mmol) in NMP (5 mL). This gave after workup and purification by flash chromatography [silica gel (12 g), eluting with DMA 80 in CH$_2$Cl$_2$ from 0 to 50%] followed by purification by reverse phase flash column chromatography [(silica gel C-18, 24 g) eluting with acetonitrile and 0.1% HCl in water] (R)-1-(4-((1-(3,4,5-trimethoxyphenyl)-1H-imidazol-4-yl)amino)thieno[3,2-d]pyrimidin-2-yl)pyrrolidine-2-carboxamide (299a) (535 mg, 90% yield) HCl salt as a peach colored solid; $^1$H NMR (300 MHz, DMSO-d$_6$): δ 13.75 (s, 1H), 12.04 (s, 1H), 8.73 (s, 1H), 8.34 (d, J=5.4 Hz, 1H), 7.94 (s, 1H), 7.71 (d, J=5.4 Hz, 1H), 7.65 (s, 1H), 7.20 (s, 1H), 7.17 (s, 2H), 4.79-4.51 (m, 1H), 4.11-3.83 (m, 7H), 3.74-3.56 (m, 4H), 2.42-1.82 (m, 4H). MS (ES+): 496.2 (M+1); MS (ES−): 530.3 (M+Cl). HPLC purity: 95.76%.

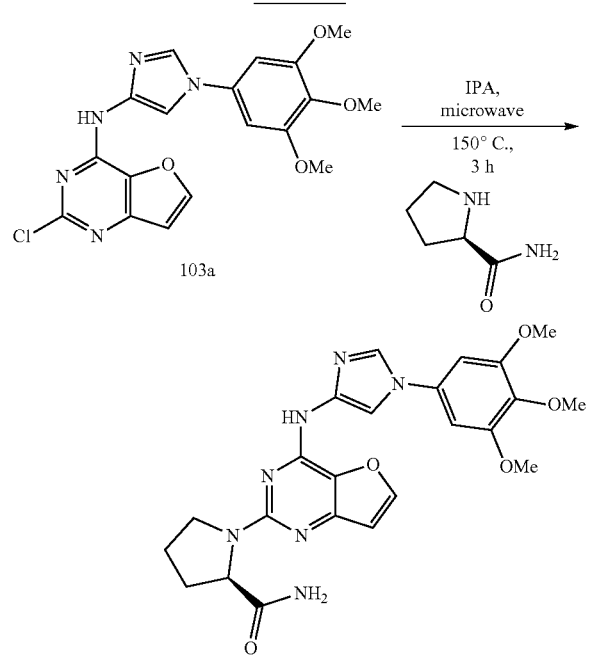

Scheme 300

Preparation of (R)-1-(4-((1-(3,4,5-trimethoxyphenyl)-1H-imidazol-4-yl)amino)furo[3,2-d]pyrimidin-2-yl)pyrrolidine-2-carboxamide (300a)

Compound 300a was prepared according to the procedure reported in Scheme 2 from (2-chloro-furo[3,2-d]pyrimidin-4-yl)-[1-(3,4,5-trimethoxy-phenyl)-1H-imidazol-4-yl]-amine (103a) (500 mg, 1.24 mmol) and (R)-pyrrolidine-2-carboxamide (355 mg, 3.11 mmol) in 2-Propanol (2 mL). This gave after workup and purification by reverse phase flash column chromatography [(silica gel C-18, 50 g) eluting with acetonitrile and 0.1% HCl in water] followed by lyophilization (R)-1-(4-((1-(3,4,5-trimethoxyphenyl)-1H-imidazol-4-yl)amino)furo[3,2-d]pyrimidin-2-yl)pyrrolidine-2-carboxamide (300a) (165 mg, 28% yield) HCl salt as a white solid; $^1$H NMR (300 MHz, DMSO-d$_6$) δ 13.68-12.81 (m, 1H, D$_2$O exchangeable), 11.88 (s, 1H, D$_2$O exchangeable), 8.40 (d, J=2.1 Hz, 1H), 7.86 (s, 1H), 7.62 (s, 1H, D$_2$O exchangeable), 7.25 (s, 1H, D$_2$O exchangeable), 7.13 (s, 2H), 7.09 (d, J=2.1 Hz, 1H), 4.62 (d, J=8.8 Hz, 1H), 3.94 (s, 6H), 3.69 (s, 3H), 3.65-3.50 (m, 2H), 2.37-2.22 (m, 1H), 2.17-1.95 (m, 3H); MS (ES+): 480.3 (M+1), 502.3 (M+Na), (ES−): 514.3 (M+Cl); HPLC purity: 94.9%.

Scheme 301

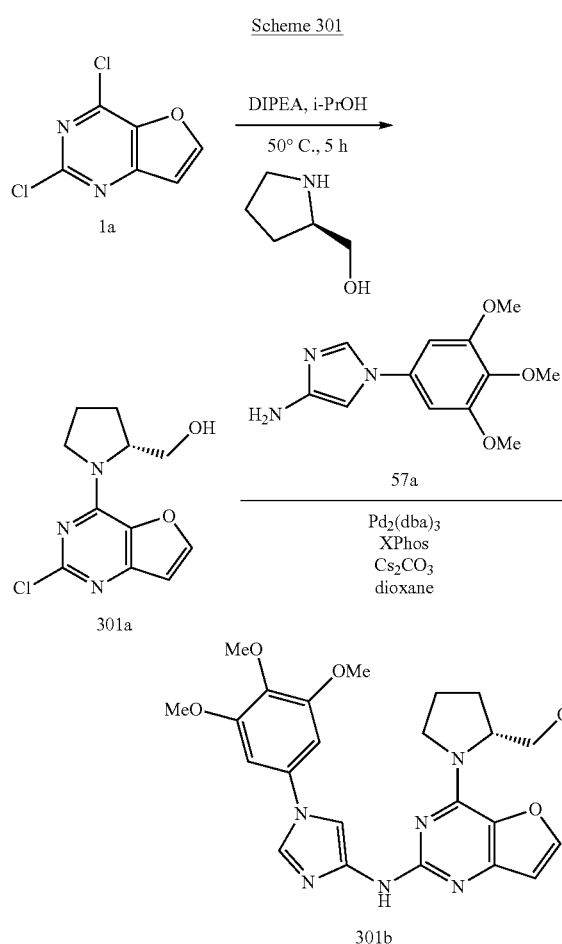

according to the procedure reported in step-3 of Scheme 101. This gave after workup and purification by flash column chromatography [silica gel, (80 g) eluting with DMA 80 in CH₂Cl₂], followed by reverse phase flash column chromatography [(silica gel C-18, 100 g) eluting with acetonitrile and 0.1% HCl water] (R)-(1-(2-((1-(3,4,5-trimethoxyphenyl)-1H-imidazol-4-yl)amino)furo[3,2-d]pyrimidin-4-yl)pyrrolidin-2-yl)methanol (301b) (125 mg, 19% yield) HCl salt as a white solid; ¹H NMR (300 MHz, DMSO-d₆) δ 10.92-10.79 (m, 1H, D₂O exchangeable), 10.82-10.67 (m, 1H, D₂O exchangeable), 8.49 (s, 1H), 8.43-8.30 (m, 1H), 7.79 (d, J=7.8 Hz, 1H), 7.07 (d, J=2.1 Hz, 1H), 6.99 (d, J=3.5 Hz, 2H), 4.62 (s, 1H), 4.15-3.88 (m, 2H), 3.88 (s, 6H), 3.68 (s, 3H), 3.65-3.46 (m, 2H), 2.22-1.89 (m, 4H); MS (ES+): 467.3 (M+1), 489.3 (M+Na), (ES-): 501.3 (M+Cl); HPLC purity: 97.5%.

Scheme 302

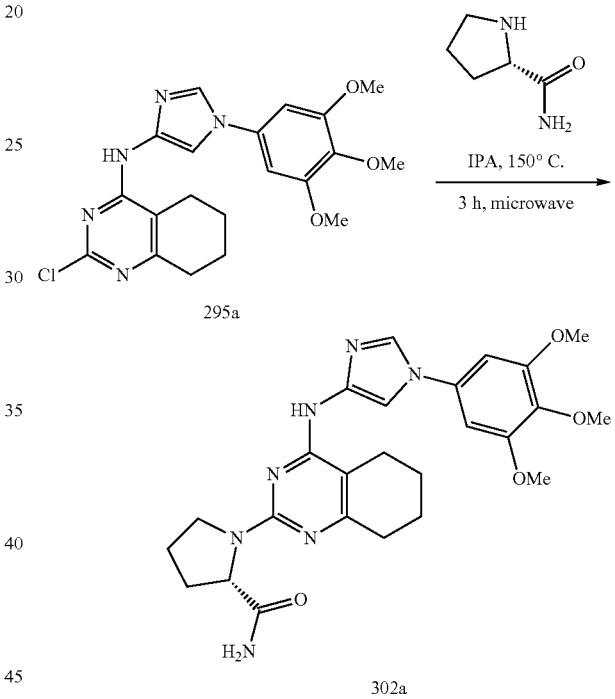

Preparation of (R)-(1-(2-((1-(3,4,5-trimethoxyphenyl)-1H-imidazol-4-yl)amino)furo[3,2-d]pyrimidin-4-yl)pyrrolidin-2-yl)methanol (301b)

Step-1: Preparation of (R)-(1-(2-chlorofuro[3,2-d]pyrimidin-4-yl)pyrrolidin-2-yl)methanol (301a) Compound 301a was prepared from 2,4-dichlorofuro[3,2-d]pyrimidine (1a) (500 mg, 2.65 mmol) in 2-Propanol (10 mL) using (R)-pyrrolidin-2-ylmethanol (281 mg, 2.78 mmol), DIPEA (1.39 mL, 7.94 mmol) according to the procedure reported in step-1 of Scheme 96. This gave (R)-(1-(2-chlorofuro[3,2-d]pyrimidin-4-yl)pyrrolidin-2-yl)methanol (301a) (360 mg, 54% yield) as a white solid; ¹H NMR (300 MHz, DMSO-d₆) δ 8.29 (d, J=2.2 Hz, 1H), 6.95 (d, J=2.3 Hz, 1H), 5.05-4.78 (m, 1H), 4.60-4.20 (m, 1H), 4.05-3.75 (m, 1H), 3.72-3.39 (m, 3H), 2.16-1.82 (m, 4H).

Step-2: Preparation of (R)-(1-(2-((1-(3,4,5-trimethoxyphenyl)-1H-imidazol-4-yl)amino)furo[3,2-d]pyrimidin-4-yl)pyrrolidin-2-yl)methanol (301b)

Compound 301b was prepared from (R)-(1-(2-chlorofuro[3,2-d]pyrimidin-4-yl)pyrrolidin-2-yl)methanol (301a) (0.35 g, 1.38 mmol), 1-(3,4,5-trimethoxyphenyl)-1H-imidazol-4-amine (57a) (395 mg, 1.59 mmol, free base), dicyclohexyl(2',4',6'-triisopropylbiphenyl-2-yl)phosphine (XPhos, 296 mg, 0.62 mmol), Pd₂(dba)3 (190 mg, 0.21 mmol) and cesium carbonate (1349 mg, 4.14 mmol) in dioxane (15 mL)

Preparation of (S)-1-(4-((1-(3,4,5-trimethoxyphenyl)-1H-imidazol-4-yl)amino)-5,6,7,8-tetrahydroquinazolin-2-yl)pyrrolidine-2-carboxamide (302a)

Compound 302a was prepared according to the procedure reported in Scheme 2 from 2-chloro-N-(1-(3,4,5-trimethoxyphenyl)-1H-imidazol-4-yl)-5,6,7,8-tetrahydroquinazolin-4-amine (295a) (300 mg, 0.72 mmol) and (S)-pyrrolidine-2-carboxamide (206 mg, 1.8 mmol) in 2-Propanol (2 mL). This gave after workup and purification by reverse phase flash column chromatography [(silica gel C-18, 100 g), eluting with ACN in water (containing 0.1% HCl) from 0-100%] (S)-1-(4-((1-(3,4,5-trimethoxyphenyl)-1H-imidazol-4-yl)amino)-5,6,7,8-tetrahydroquinazolin-2-yl)pyrrolidine-2-carboxamide (302a) (152 mg, 43% yield) HCl salt as a white solid; ¹H NMR (300 MHz, DMSO-d₆) δ 11.95-11.68 (m, 1H, D₂O exchangeable), 10.22-9.90 (m, 1H, D₂O exchangeable), 8.54-8.15 (m, 1H), 7.83 (s, 1H), 7.53 (s, 1H, D₂O exchangeable), 7.24 (s, 1H, D₂O exchangeable), 7.12 (s, 2H), 4.68-4.55 (m, 1H), 3.93 (s, 6H), 3.68 (s, 3H), 3.65-3.47 (m, 2H), 2.86-2.66 (m, 2H), 2.60-2.41 (m, 2H), 2.36-2.17 (m, 1H), 2.14-1.89 (m, 3H), 1.86-1.62 (m, 4H); MS (ES+): 494.3 (M+1), 516.3 (M+Na), (ES−): 528.4 (M+Cl); HPLC purity: 99.22%.

Scheme 303

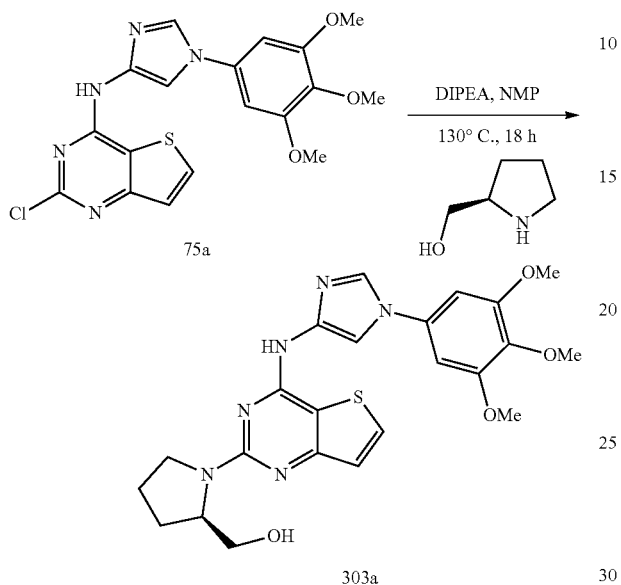

Preparation of (R)-(1-(4-((1-(3,4,5-trimethoxyphenyl)-1H-imidazol-4-yl)amino)thieno[3,2-d]pyrimidin-2-yl)pyrrolidin-2-yl)methanol (303a)

Compound 303a was prepared from 2-chloro-N-(1-(3,4,5-trimethoxyphenyl)-1H-imidazol-4-yl)thieno[3,2-d]pyrimidin-4-amine (75a) (500 mg, 1.2 mmol), (R)-pyrrolidin-2-ylmethanol (0.47 mL, 4.79 mmol), DIPEA (1.25 mL, 7.18 mmol) in NMP (5 mL) according to the procedure reported in step-2 of Scheme 76. This gave after workup and purification by flash column chromatography [silica gel (12 g), eluting with DMA-80 in CH$_2$Cl$_2$ from 0 to 50%] followed by reverse phase flash chromatography [(silica gel C-18, 24 g), eluting with acetonitrile and 0.1% HCl in water] (R)-(1-(4-((1-(3,4,5-trimethoxyphenyl)-1H-imidazol-4-yl)amino)thieno[3,2-d]pyrimidin-2-yl)pyrrolidin-2-yl)methanol (303a) (0.335 g, 58.0% yield) HCl salt as a white solid; $^1$H NMR (300 MHz, DMSO-d$_6$): δ 13.60 (s, 1H), 12.07 (s, 1H), 8.80 (s, 1H), 8.29 (d, J=5.4 Hz, 1H), 8.09 (s, 1H), 7.65 (d, J=5.4 Hz, 1H), 7.14-6.94 (m, 2H), 4.65-4.32 (m, 1H), 4.12-3.33 (m, 13H), 2.25-1.69 (m, 4H). MS (ES+): 483.3 (M+1); MS (ES−): 517.3 (M+Cl). HPLC purity: 97.38%.

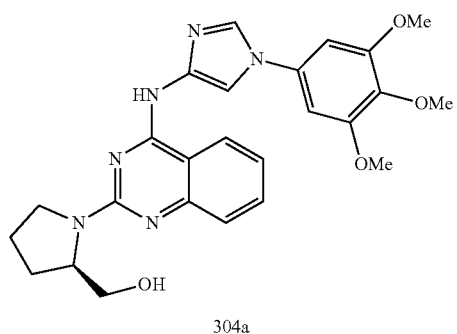

Preparation of (R)-(1-(4-((1-(3,4,5-trimethoxyphenyl)-1H-imidazol-4-yl)amino)quinazolin-2-yl)pyrrolidin-2-yl)methanol (304a)

Compound 304a was prepared from 2-chloro-N-(1-(3,4,5-trimethoxyphenyl)-1H-imidazol-4-yl)quinazolin-4-amine (86a) (370 mg, 0.9 mmol), (R)-pyrrolidin-2-ylmethanol (0.36 mL, 3.59 mmol), DIPEA (0.94 mL, 5.39 mmol) in NMP (5 mL) according to the procedure reported in step-2 of Scheme 76. This gave after workup and purification by flash column chromatography [silica gel (12 g), eluting with DMA-80 in CH$_2$Cl$_2$ from 0 to 50%], followed by purification by reverse phase flash chromatography [(silica gel C18, 24 g), eluting with acetonitrile and 0.1% HCl in water] (R)-(1-(4-((1-(3,4,5-trimethoxyphenyl)-1H-imidazol-4-yl)amino)quinazolin-2-yl)pyrrolidin-2-yl)methanol (304a) (195 mg, 46% yield) HCl salt as a brown solid; $^1$H NMR (300 MHz, DMSO-d$_6$) δ 12.59 (s, 1H), 11.92 (s, 1H), 9.00-8.58 (m, 1H), 8.37-7.98 (m, 2H), 7.83 (t, J=7.8 Hz, 1H), 7.58-7.29 (m, 1H), 7.06 (s, 2H), 7.00 (s, 1H), 4.81-4.41 (m, 1H), 4.12-3.35 (m, 13H), 2.30-1.65 (m, 4H); MS (ES+): 477.4 (M+1); MS (ES−): 511.4 (M+Cl). HPLC purity: 92.69%.

Scheme 305

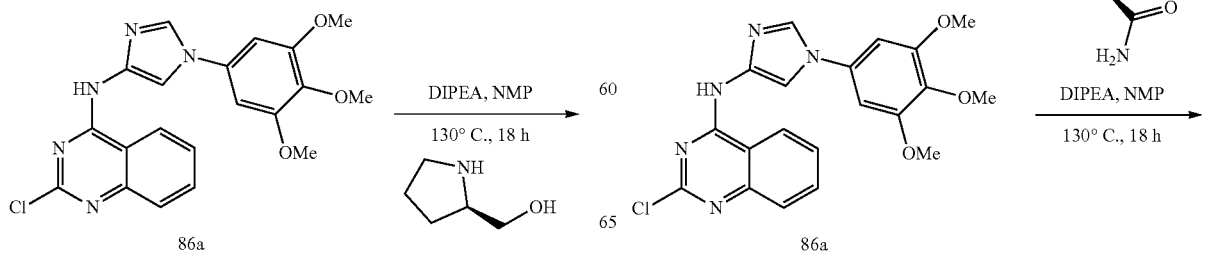

513

-continued

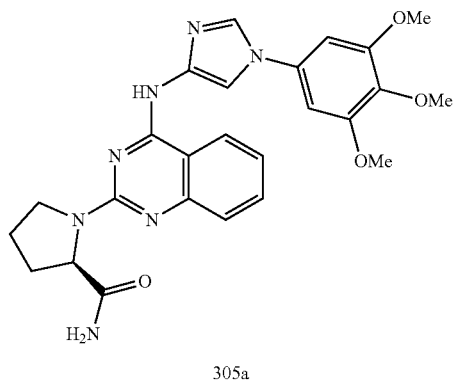

305a

Preparation (R)-1-(4-((1-(3,4,5-trimethoxyphenyl)-1H-imidazol-4-yl)amino)quinazolin-2-yl)pyrrolidine-2-carboxamide (305a)

Compound 305a was prepared according to the procedure reported in step-2 of Scheme 76 from 2-chloro-N-(1-(3,4,5-trimethoxyphenyl)-1H-imidazol-4-yl)quinazolin-4-amine (86a) (370 mg, 0.9 mmol) and (R)-pyrrolidine-2-carboxamide (410 mg, 3.59 mmol), DIPEA (0.94 mL, 5.39 mmol) in NMP (5 mL). This gave after workup and purification by flash chromatography [silica gel (12 g), eluting with DMA-80 in CH$_2$Cl$_2$ from 0 to 50%] followed by purification by reverse phase flash column chromatography [(silica gel C18 column, 24 g) eluting with acetonitrile and 0.1% HCl water] (R)-1-(4-((1-(3,4,5-trimethoxyphenyl)-1H-imidazol-4-yl)amino)quinazolin-2-yl)pyrrolidine-2-carboxamide (305a) (255 mg, 58.0% yield) HCl salt as a yellow solid; $^1$H NMR (300 MHz, DMSO-d$_6$): δ 12.69 (s, 1H), 11.78 (s, 1H), 8.78 (d, J=8.2 Hz, 1H), 8.62 (s, 1H), 8.22 (t, J=7.3 Hz, 1H), 8.00 (s, 1H), 7.87 (t, J=7.8 Hz, 1H), 7.65 (s, 1H), 7.48 (t, J=7.6 Hz, 1H), 7.25 (s, 1H), 7.16 (d, J=1.9 Hz, 2H), 4.73 (d, J=8.8 Hz, 1H), 4.18-4.03 (m, 1H), 3.94 (s, 6H), 3.82-3.72 (m, 1H), 3.69 (s, 3H), 2.40-1.72 (m, 4H). MS (ES+): 490.4 (M+1); MS (ES−): 524.4 (M+Cl). HPLC purity: 93.74%.

514

-continued

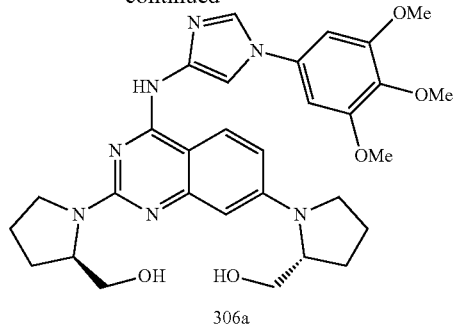

306a

Preparation of ((2R,2'R)-1,1'-(4-((1-(3,4,5-trimethoxyphenyl)-1H-imidazol-4-yl)amino)quinazoline-2,7-diyl)bis(pyrrolidine-2,1-diyl))dimethanol (306a)

Compound 306a was prepared according to the procedure reported in step-2 of Scheme 76 from 2-chloro-7-fluoro-N-(1-(3,4,5-trimethoxyphenyl)-1H-imidazol-4-yl)quinazolin-4-amine (266b) (300 mg, 0.47 mmol) and (R)-pyrrolidin-2-ylmethanol (0.18 mL, 1.86 mmol) in NMP (4 mL) using DIPEA (0.49 mL, 2.79 mmol) as base. This gave after workup and purification by flash column chromatography [silica gel (12 g), eluting with DMA 80 in CH$_2$Cl$_2$ from 0 to 50%] followed by purification by reverse phase flash column chromatography [(silica gel C18, 24 g), eluting with acetonitrile and 0.1% HCl in water] ((2R,2'R)-1,1'-(4-((1-(3,4,5-trimethoxyphenyl)-1H-imidazol-4-yl)amino)quinazoline-2,7-diyl)bis(pyrrolidine-2,1-diyl))dimethanol (306a) (62 mg, 23% yield) HCl salt as a yellow solid; $^1$H NMR (300 MHz, DMSO-d$_6$): δ 11.85 (2s, 1H), 11.42 (s, 1H), 8.85 (s, 1H), 8.48 (m, 1H), 8.09 (s, 1H), 7.27-6.95 (m, 3H), 6.81 (d, J=8.8 Hz, 1H), 4.65-4.32 (m, 1H), 4.09-2.95 (m, 18H), 2.27-1.57 (m, 8H). MS (ES+): 576.5 (M+1). HPLC purity: 93.12%.

Scheme 307

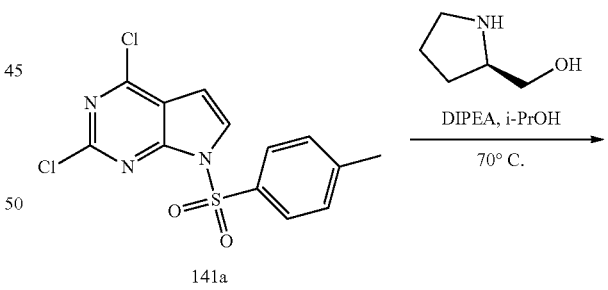

141a

Scheme 306

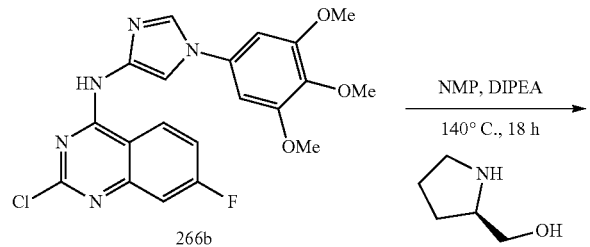

266b

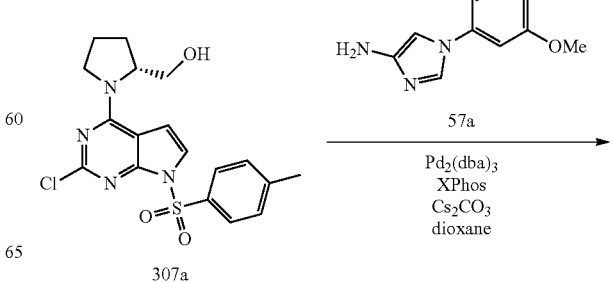

307a

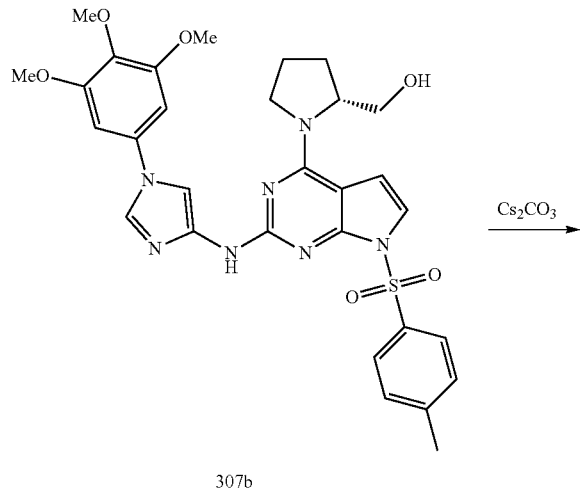

307b

307c

Preparation of (R)-(1-(2-((1-(3,4,5-trimethoxyphenyl)-1H-imidazol-4-yl)amino)-7H-pyrrolo[2,3-d]pyrimidin-4-yl)pyrrolidin-2-yl)methanol (307c)

Step-1: Preparation of (R)-(1-(2-chloro-7-tosyl-7H-pyrrolo[2,3-d]pyrimidin-4-yl)pyrrolidin-2-yl)methanol (307a)

Compound 307a was prepared from 2,4-dichloro-7-tosyl-7H-pyrrolo[2,3-d]pyrimidine (141a) (1 g, 2.92 mmol) in 2-Propanol (10 mL), (R)-pyrrolidin-2-ylmethanol (0.3 gm, 2.92 mmol), DIPEA (0.77 mL, 4.38 mmol) according to the procedure reported in step-1 of Scheme 96. This gave after workup and purification by flash column chromatography [silica gel (12 g), eluting with ethyl acetate/MeOH (9:1) in hexane from 0-70%] (R)-(1-(2-chloro-7-tosyl-7H-pyrrolo[2,3-d]pyrimidin-4-yl)pyrrolidin-2-yl)methanol (307a) (562 mg, 47% yield) as a white solid; $^1$H NMR (300 MHz, DMSO-$d_6$, mixture of rotamers) δ 8.06-7.89 (d, J=8.2 Hz, 2H), 7.62 (2s, 1H), 7.46 (d, J=8.2 Hz, 2H), 6.90 (2s, 1H), 4.94 (2s, 1H), 4.27 (m, 1H), 3.91-3.58 (m, 2H), 3.59-3.38 (m, 2H), 2.37 (s, 3H), 2.20-1.77 (m, 4H).

Step-2: Preparation of (R)-(1-(7-tosyl-2-((1-(3,4,5-trimethoxyphenyl)-1H-imidazol-4-yl)amino)-7H-pyrrolo[2,3-d]pyrimidin-4-yl)pyrrolidin-2-yl)methanol (307b)

Compound 307b was prepared from (R)-(1-(2-chloro-7-tosyl-7H-pyrrolo[2,3-d]pyrimidin-4-yl)pyrrolidin-2-yl)methanol (307a) (562 mg, 1.38 mmol), 1-(3,4,5-trimethoxyphenyl)-1H-imidazol-4-amine (57a) (396 mg, 1.59 mmol, free base), dicyclohexyl(2',4',6'-triisopropylbiphenyl-2-yl)phosphine (XPhos, 296 mg, 0.62 mmol), cesium carbonate (1349 mg, 4.14 mmol), $Pd_2(dba)_3$ (190 mg, 0.21 mmol) in dioxane (15 mL) according to the procedure reported in step-3 of Scheme 101. This gave after workup and purification by flash column chromatography [silica gel (80 g), eluting with DMA-80 in DCM from 0-60%], (R)-(1-(7-tosyl-2-((1-(3,4,5-trimethoxyphenyl)-1H-imidazol-4-yl)amino)-7H-pyrrolo[2,3-d]pyrimidin-4-yl)pyrrolidin-2-yl)methanol (307b) (215 mg, 25% yield) as a yellow solid; MS (ES+): 642.3 (M+Na), (ES−): 618.4 (M−1), 655.3 (M+Cl).

Step-3: Preparation of (R)-(1-(2-((1-(3,4,5-trimethoxyphenyl)-1H-imidazol-4-yl)amino)-7H-pyrrolo[2,3-d]pyrimidin-4-yl)pyrrolidin-2-yl)methanol (307c)

Compound 307c was prepared from (R)-(1-(7-tosyl-2-((1-(3,4,5-trimethoxyphenyl)-1H-imidazol-4-yl)amino)-7H-pyrrolo[2,3-d]pyrimidin-4-yl)pyrrolidin-2-yl)methanol (307b) (200 mg, 0.32 mmol) and $Cs_2CO_3$ (315 mg, 0.97 mmol) in MeOH/THF (10 mL, 3:2) according to the procedure reported in step-3 of Scheme 141. This gave after workup and purification by flash column chromatography [silica gel (24 g), eluting with ethyl acetate/MeOH (9:1) in hexane from 0-70%] followed by reverse phase prep-HPLC [(silica gel C-18, 100 g) eluting with $CH_3CN$ in water (containing 0.1% HCl) from 0-100%], (R)-(1-(2-((1-(3,4,5-trimethoxyphenyl)-1H-imidazol-4-yl)amino)-7H-pyrrolo[2,3-d]pyrimidin-4-yl)pyrrolidin-2-yl)methanol (307c) (45 mg, 30% yield) HCl salt as a white solid; $^1$H NMR (300 MHz, DMSO-$d_6$) δ 12.12 (s, 1H, $D_2O$ exchangeable), 10.73-10.32 (2s, 1H, $D_2O$ exchangeable), 8.43 (s, 1H), 7.72 (s, 1H), 7.21-7.06 (m, 1H), 6.99 (s, 2H), 6.69 (s, 1H), 4.68-4.38 (m, 1H), 4.08-3.92 (m, 1H), 3.89 (s, 6H), 3.89-3.75 (m, 1H), 3.69 (s, 3H), 3.67-3.38 (m, 2H), 2.23-1.89 (m, 4H); MS (ES+): 466.4 (M+1), 488.3 (M+Na), (ES−): 500.3 (M+Cl); HPLC purity: 98.79%.

Scheme 308

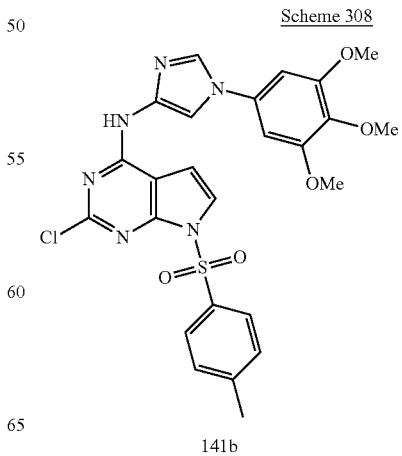

141b

IPA, 150° C.
Microwave 3 h

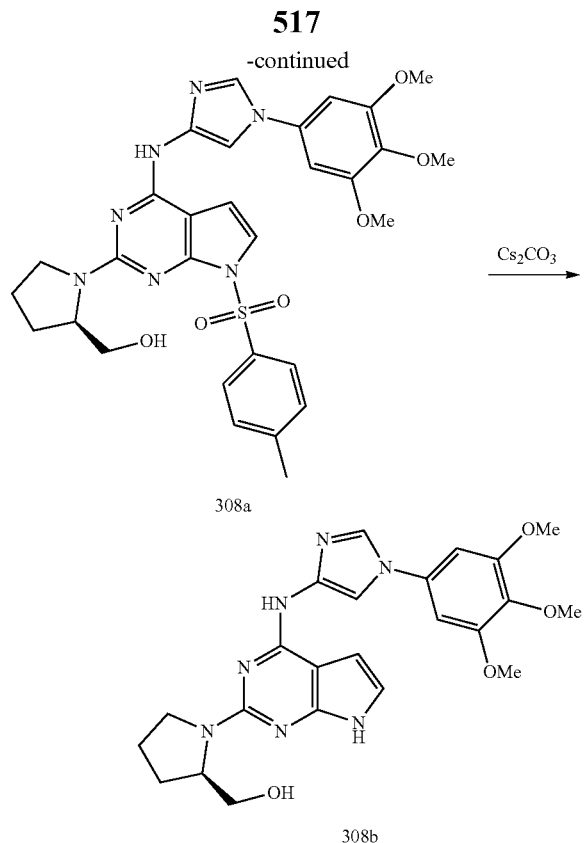

308a

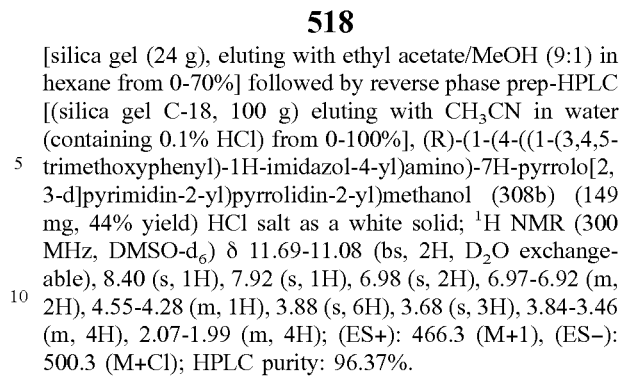

[silica gel (24 g), eluting with ethyl acetate/MeOH (9:1) in hexane from 0-70%] followed by reverse phase prep-HPLC [(silica gel C-18, 100 g) eluting with CH$_3$CN in water (containing 0.1% HCl) from 0-100%], (R)-(1-(4-((1-(3,4,5-trimethoxyphenyl)-1H-imidazol-4-yl)amino)-7H-pyrrolo[2,3-d]pyrimidin-2-yl)pyrrolidin-2-yl)methanol (308b) (149 mg, 44% yield) HCl salt as a white solid; $^1$H NMR (300 MHz, DMSO-d$_6$) δ 11.69-11.08 (bs, 2H, D$_2$O exchangeable), 8.40 (s, 1H), 7.92 (s, 1H), 6.98 (s, 2H), 6.97-6.92 (m, 2H), 4.55-4.28 (m, 1H), 3.88 (s, 6H), 3.68 (s, 3H), 3.84-3.46 (m, 4H), 2.07-1.99 (m, 4H); (ES+): 466.3 (M+1), (ES−): 500.3 (M+Cl); HPLC purity: 96.37%.

Scheme 309

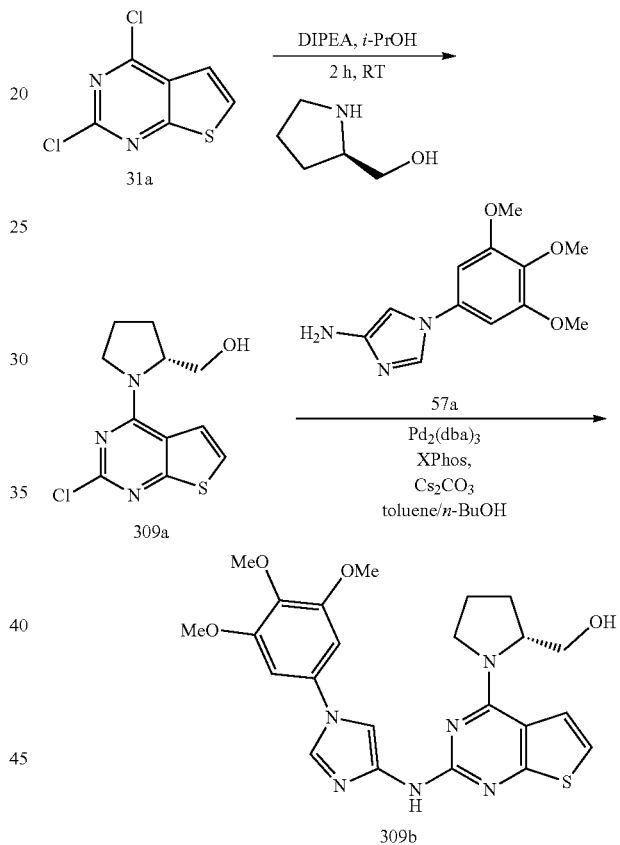

Preparation of (R)-(1-(2-((1-(3,4,5-trimethoxyphenyl)-1H-imidazol-4-yl)amino)thieno[2,3-d]pyrimidin-4-yl)pyrrolidin-2-yl)methanol (309b)

308b

Preparation of (R)-(1-(4-((1-(3,4,5-trimethoxyphenyl)-1H-imidazol-4-yl)amino)-7H-pyrrolo[2,3-d]pyrimidin-2-yl)pyrrolidin-2-yl)methanol (308b)

Step-1: Preparation of (R)-(1-(7-tosyl-4-((1-(3,4,5-trimethoxyphenyl)-1H-imidazol-4-yl)amino)-7H-pyrrolo[2,3-d]pyrimidin-2-yl)pyrrolidin-2-yl)methanol (308a)

Compound 308a was prepared from 2-chloro-7-tosyl-N-(1-(3,4,5-trimethoxyphenyl)-1H-imidazol-4-yl)-7H-pyrrolo[2,3-d]pyrimidin-4-amine (141b) (500 mg, 0.9 mmol), (R)-pyrrolidin-2-ylmethanol (273 mg, 2.7 mmol) in 2-Propanol (3 mL) according to the procedure reported in Scheme 2. This gave after workup and purification by flash column chromatography [silica gel (40 g), eluting with DMA-80 in dichloromethane] (R)-(1-(7-tosyl-4-((1-(3,4,5-trimethoxyphenyl)-1H-imidazol-4-yl)amino)-7H-pyrrolo[2,3-d]pyrimidin-2-yl)pyrrolidin-2-yl)methanol (308a) (460 mg, 82% yield) as a brown solid MS (ES+): 620.2 (M+1), (ES−): 654.2 (M+Cl).

Step-2: Preparation of (R)-(1-(4-((1-(3,4,5-trimethoxyphenyl)-1H-imidazol-4-yl)amino)-7H-pyrrolo[2,3-d]pyrimidin-2-yl)pyrrolidin-2-yl)methanol (308b)

Compound 308b was prepared from (R)-(1-(7-tosyl-4-((1-(3,4,5-trimethoxyphenyl)-1H-imidazol-4-yl)amino)-7H-pyrrolo[2,3-d]pyrimidin-2-yl)pyrrolidin-2-yl)methanol (308a) (450 mg, 0.73 mmol) and Cs$_2$CO$_3$ (710 mg, 2.18 mmol) in MeOH/THF (20 mL, 3:2) according to the procedure reported in step-3 of Scheme 141. This gave after workup and purification by flash column chromatography Step-1: Preparation of (R)-(1-(2-chlorothieno[2,3-d]pyrimidin-4-yl)pyrrolidin-2-yl)methanol (309a) Compound 309a was prepared from 2,4-dichlorothieno[2,3-d]pyrimidine (31a) (1 g, 4.88 mmol) in 2-Propanol (10 mL), (R)-pyrrolidin-2-ylmethanol (0.48 mL, 4.88 mmol), DIPEA (2.56 mL, 14.63 mmol) according to the procedure reported in step-1 of Scheme 96. This gave (R)-(1-(2-chlorothieno[2,3-d]pyrimidin-4-yl)pyrrolidin-2-yl)methanol (309a) (0.22 g, 17% yield) as a yellow solid; MS (ES−): 304.1 (M+Cl).

519

Step-2: Preparation of (R)-(1-(2-((1-(3,4,5-trimethoxyphenyl)-1H-imidazol-4-yl)amino)thieno[2,3-d]pyrimidin-4-yl)pyrrolidin-2-yl)methanol (309b)

Compound 309b was prepared from (R)-(1-(2-chlorothieno[2,3-d]pyrimidin-4-yl)pyrrolidin-2-yl)methanol (309a) (0.2 g, 0.74 mmol), 1-(3,4,5-trimethoxyphenyl)-1H-imidazol-4-amine (57a) (185 mg, 0.741 mmol), dicyclohexyl(2',4',6'-triisopropylbiphenyl-2-yl)phosphine (XPhos, 212 mg, 0.45 mmol), cesium carbonate (725 mg, 2.22 mmol), Pd$_2$(dba)$_3$ (204 mg, 0.22 mmol) in toluene/n-butanol (30 mL, Ratio: 2:1) according to the procedure reported in step-3 of Scheme 101. This gave after workup and purification by flash column chromatography [silica gel (24 g), eluting with DMA-80 in DCM from 0-50%] followed by reverse phase flash column chromatography [(silica gel C-18, 24 g) eluting with acetonitrile and 0.1% HCl in water] (R)-(1-(2-((1-(3,4,5-trimethoxyphenyl)-1H-imidazol-4-yl)amino)thieno[2,3-d]pyrimidin-4-yl)pyrrolidin-2-yl)methanol (309b) (52 mg, 15% yield) HCl salt as a yellow solid; $^1$H NMR (300 MHz, DMSO-d$_6$): δ 10.37 (s, 1H), 9.23 (s, 1H), 7.96 (s, 1H), 7.58 (d, J=6.1 Hz, 1H), 7.34 (d, J=6.0 Hz, 1H), 7.13 (s, 2H), 4.71-4.43 (m, 1H), 4.10-3.31 (m, 13H), 2.24-1.71 (m, 4H). MS (ES+): 483.3 (M+1); MS (ES-): 517.3 (M+Cl). HPLC purity: 98.16%.

520

Preparation of (R)-(1-(2-((1-(3,4,5-trimethoxyphenyl)-1H-imidazol-4-yl)amino)thieno[3,2-d]pyrimidin-4-yl)pyrrolidin-2-yl)methanol (310b)

Step-1: Preparation of (R)-(1-(2-chlorothieno[3,2-d]pyrimidin-4-yl)pyrrolidin-2-yl)methanol (310a) Compound 310a was prepared from 2,4-dichlorothieno[3,2-d]pyrimidine (12a) (1 g, 4.88 mmol) in 2-Propanol (10 mL), (R)-pyrrolidin-2-ylmethanol (0.48 mL, 4.88 mmol), DIPEA (2.56 mL, 14.63 mmol) according to the procedure reported in step-1 of Scheme 96. This gave (R)-(1-(2-chlorothieno[3,2-d]pyrimidin-4-yl)pyrrolidin-2-yl)methanol (310a) (780 mg, 59% yield) as a yellow solid; $^1$H NMR (300 MHz, DMSO-d$_6$) δ 8.26 (d, J=5.4 Hz, 1H), 7.33 (d, J=5.4 Hz, 1H), 4.89 (s, 1H), 4.50-4.30 (m, 1H), 4.09-3.73 (m, 2H), 3.61 (ddd, J=10.7, 5.7, 3.5 Hz, 1H), 3.49 (dt, J=11.2, 6.5 Hz, 1H), 2.16-2.03 (m, 2H), 1.97 (s, 2H); MS (ES-): 268 (M-1), 304.1 (M+Cl).

Step-2: Preparation of (R)-(1-(2-((1-(3,4,5-trimethoxyphenyl)-1H-imidazol-4-yl)amino)thieno[3,2-d]pyrimidin-4-yl)pyrrolidin-2-yl)methanol (310b)

Compound 310b was prepared from (R)-(1-(2-chlorothieno[3,2-d]pyrimidin-4-yl)pyrrolidin-2-yl)methanol (310a) (300 mg, 1.11 mmol), 1-(3,4,5-trimethoxyphenyl)-1H-imidazol-4-amine (57a) (277 mg, 1.11 mmol, free base), dicyclohexyl(2',4',6'-triisopropylbiphenyl-2-yl)phosphine (XPhos, 318 mg, 0.67 mmol), cesium carbonate (1087 mg, 3.34 mmol), Pd$_2$(dba)$_3$ (306 mg, 0.33 mmol) toluene/t-butanol (40 mL, Ratio: 3:1) according to the procedure reported in step-3 of Scheme 101. This gave after workup and purification by flash column chromatography [silica gel (40 g), eluting with DMA-80 in DCM from 0-100%] followed by reverse phase flash column chromatography [(silica gel C-18, 24 g) eluting with acetonitrile and 0.1% HCl water] (R)-(1-(2-((1-(3,4,5-trimethoxyphenyl)-1H-imidazol-4-yl)amino)thieno[3,2-d]pyrimidin-4-yl)pyrrolidin-2-yl)methanol (310b) (108 mg, 20% yield) HCl salt as a yellow solid; $^1$H NMR (300 MHz, DMSO-d$_6$) δ 10.71 (s, 1H), 8.67 (s, 1H), 8.43 (d, J=5.5 Hz, 1H), 7.86 (s, 1H), 7.43 (d, J=5.5 Hz, 1H), 7.02 (s, 2H), 4.79-4.48 (m, 1H), 4.15-3.92 (m, 2H), 3.88 (s, 6H), 3.79-3.69 (m, 1H), 3.68 (s, 3H), 3.55 (m, 1H), 2.36-1.79 (m, 4H); MS (ES+): 483.3 (M+1); MS (ES-): 517.3 (M+Cl). HPLC purity: 97.03%.

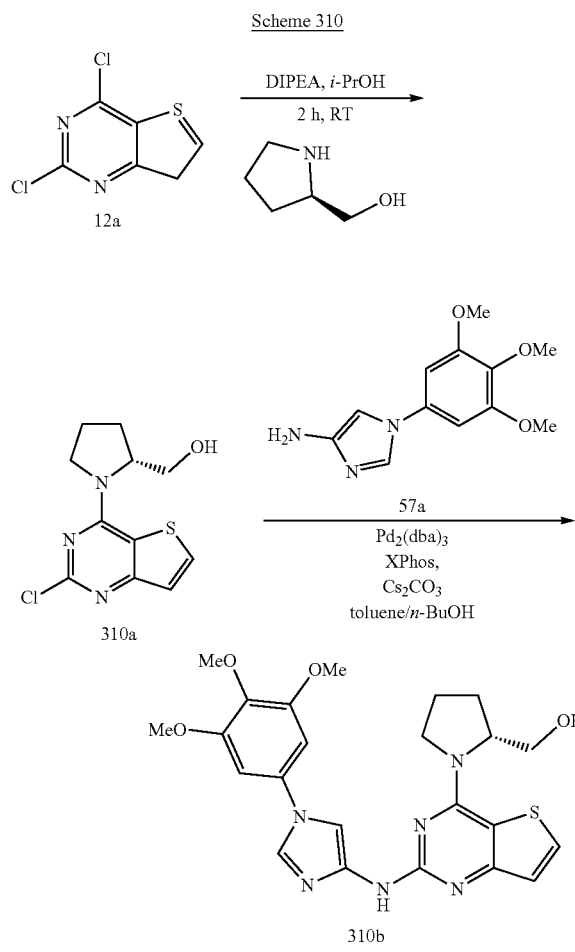

Scheme 310

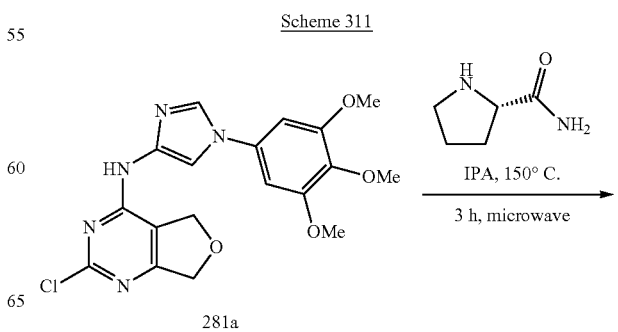

Scheme 311

-continued

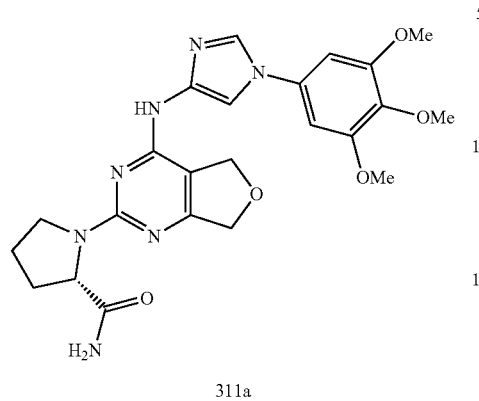

311a

Preparation of (S)-1-(4-((1-(3,4,5-trimethoxyphenyl)-1H-imidazol-4-yl)amino)-5,7-dihydrofuro[3,4-d]pyrimidin-2-yl)pyrrolidine-2-carboxamide (311a)

Compound 311a was prepared according to the procedure reported in Scheme 2 from 2-chloro-N-(1-(3,4,5-trimethoxyphenyl)-1H-imidazol-4-yl)-5,7-dihydrofuro[3,4-d]pyrimidin-4-amine (281a) (400 mg, 0.99 mmol) and (S)-pyrrolidine-2-carboxamide (339 mg, 2.97 mmol) in 2-Propanol (3 mL). This gave after workup and purification by reverse phase flash column chromatography [(silica gel C-18, 100 g), eluting with acetonitrile in water (containing 0.1% HCl) from 0-100%] (S)-1-(4-((1-(3,4,5-trimethoxyphenyl)-1H-imidazol-4-yl)amino)-5,7-dihydrofuro[3,4-d]pyrimidin-2-yl)pyrrolidine-2-carboxamide (311a) (315 mg, 66% yield) HCl salt as a light buff colored solid; $^1$H NMR (300 MHz, DMSO-$d_6$) δ 11.29 (s, 1H, $D_2O$ exchangeable), 8.47 (d, J=1.5 Hz, 1H), 7.83 (d, J=1.5 Hz, 1H), 7.64 (s, 1H, $D_2O$ exchangeable), 7.24 (s, 1H, $D_2O$ exchangeable), 7.13 (s, 2H), 5.07-4.91 (m, 4H), 4.57 (dd, J=9.0, 2.2 Hz, 1H), 3.93 (s, 6H), 3.93-3.82 (m, 1H), 3.69 (s, 3H), 3.63-3.49 (m, 1H), 2.39-2.16 (m, 1H), 2.14-1.88 (m, 3H); (ES+): 482.3 (M+1), (ES−): 516.3 (M+Cl), 997.5 (2M+Cl); HPLC purity: 98.35%.

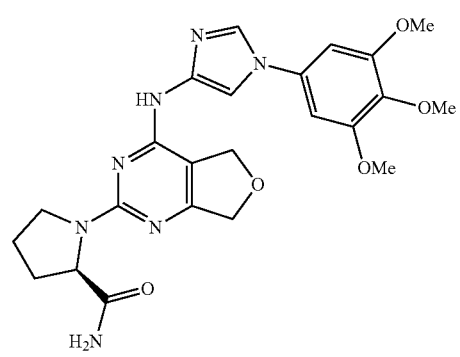

312a

Preparation of (R)-1-(4-((1-(3,4,5-trimethoxyphenyl)-1H-imidazol-4-yl)amino)-5,7-dihydrofuro[3,4-d]pyrimidin-2-yl)pyrrolidine-2-carboxamide (312a)

Compound 312a was prepared according to the procedure reported in Scheme 2 from 2-chloro-N-(1-(3,4,5-trimethoxyphenyl)-1H-imidazol-4-yl)-5,7-dihydrofuro[3,4-d]pyrimidin-4-amine (281a) (400 mg, 0.99 mmol) and (R)-pyrrolidine-2-carboxamide (339 mg, 2.97 mmol) in 2-Propanol (3.5 mL). This gave after workup and purification by reverse phase flash column chromatography [(silica gel C-18 100 g), eluting with acetonitrile in water (containing 0.1% HCl) from 0-100%] (R)-1-(4-((1-(3,4,5-trimethoxyphenyl)-1H-imidazol-4-yl)amino)-5,7-dihydrofuro[3,4-d]pyrimidin-2-yl)pyrrolidine-2-carboxamide (312a) (106 mg, 22% yield) HCl salt as a light buff colored solid; $^1$H NMR (300 MHz, DMSO-$d_6$) δ 11.23 (s, 1H, $D_2O$ exchangeable), 8.38 (s, 1H), 7.82 (d, J=1.5 Hz, 1H), 7.62 (s, 1H, $D_2O$ exchangeable), 7.24 (s, 1H, $D_2O$ exchangeable), 7.11 (s, 2H), 5.07-4.91 (m, 4H), 4.67-4.46 (m, 1H), 3.92 (s, 6H), 3.90-3.83 (m, 1H), 3.68 (s, 3H), 3.63-3.50 (m, 1H), 2.37-2.18 (m, 1H), 2.11-1.94 (m, 3H); (ES+): 482.3 (M+1), (ES−): 516.3 (M+Cl), 997.5 (2M+Cl); HPLC purity: 93.15%.

Scheme 312

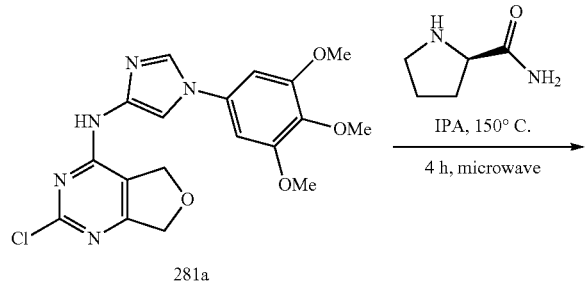

Scheme 313

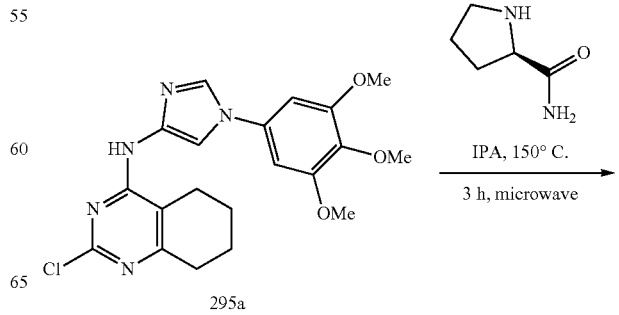

523

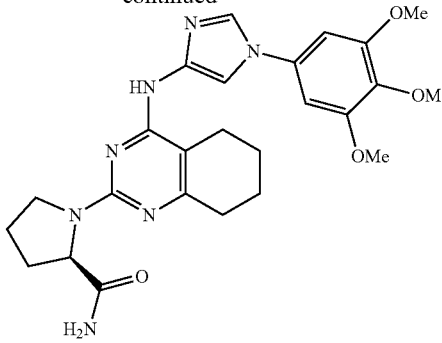

313a

Preparation of (R)-1-(4-((1-(3,4,5-trimethoxyphenyl)-1H-imidazol-4-yl)amino)-5,6,7,8-tetrahydroquinazolin-2-yl)pyrrolidine-2-carboxamide (313a)

Compound 313a was prepared according to the procedure reported in Scheme 2 from 2-chloro-N-(1-(3,4,5-trimethoxyphenyl)-1H-imidazol-4-yl)-5,6,7,8-tetrahydroquinazolin-4-amine (295a) (400 mg, 0.96 mmol) and (R)-pyrrolidine-2-carboxamide (329 mg, 2.89 mmol) in 2-Propanol (3 mL). This gave after workup and purification by reverse phase flash column chromatography [(silica gel C-18 (100 g), eluting with ACN in water (containing 0.1% HCl) from 0-100%] (R)-1-(4-((1-(3,4,5-trimethoxyphenyl)-1H-imidazol-4-yl)amino)-5,6,7,8-tetrahydroquinazolin-2-yl)pyrrolidine-2-carboxamide (313a) (286 mg, 60% yield) HCl salt as a white solid; $^1$H NMR (300 MHz, DMSO-$d_6$) δ 11.99 (s, 1H, D$_2$O exchangeable), 10.12 (s, 1H, D$_2$O exchangeable), 8.48 (s, 1H), 7.85 (s, 1H), 7.54 (s, 1H, D$_2$O exchangeable), 7.22 (s, 1H, D$_2$O exchangeable), 7.13 (s, 2H), 4.64-4.50 (m, 1H), 3.93 (s, 6H), 3.69 (s, 3H), 3.66-3.50 (m, 2H), 2.90-2.63 (m, 2H), 2.62-2.39 (m, 2H), 2.36-2.16 (m, 1H), 2.13-1.86 (m, 3H), 1.86-1.62 (m, 4H); MS (ES+): 494.3 (M+1), 516.3 (M+Na), (ES−): 528.3 (M+Cl); HPLC purity: 99.397%.

Scheme 314

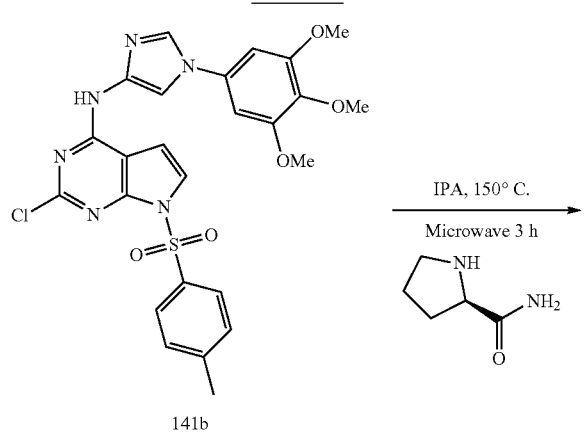

141b

524

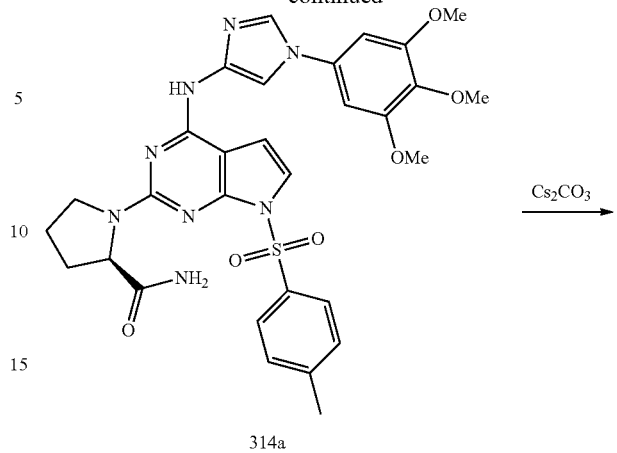

314a

314b

Preparation of (R)-1-(4-((1-(3,4,5-trimethoxyphenyl)-1H-imidazol-4-yl)amino)-7H-pyrrolo[2,3-d]pyrimidin-2-yl)pyrrolidine-2-carboxamide (314b)

Step-1: Preparation of (R)-1-(7-tosyl-4-((1-(3,4,5-trimethoxyphenyl)-1H-imidazol-4-yl)amino)-7H-pyrrolo[2,3-d]pyrimidin-2-yl)pyrrolidine-2-carboxamide (314a)

Compound 314a was prepared from 2-chloro-7-tosyl-N-(1-(3,4,5-trimethoxyphenyl)-1H-imidazol-4-yl)-7H-pyrrolo[2,3-d]pyrimidin-4-amine (141b) (500 mg, 0.9 mmol), (R)-pyrrolidine-2-carboxamide (308 mg, 2.7 mmol) in 2-Propanol (3 mL) according to the procedure reported in Scheme 2. This gave after workup and purification by flash column chromatography [silica gel (40 g), eluting with DMA-80 in dichloromethane] (R)-1-(7-tosyl-4-((1-(3,4,5-trimethoxyphenyl)-1H-imidazol-4-yl)amino)-7H-pyrrolo[2,3-d]pyrimidin-2-yl)pyrrolidine-2-carboxamide (314a) (430 mg, 75% yield) as a white solid; MS (ES+): 633.4 (M+1); (ES−): 631.4 (M−1)

Step-2: Preparation of (R)-1-(4-((1-(3,4,5-trimethoxyphenyl)-1H-imidazol-4-yl)amino)-7H-pyrrolo[2,3-d]pyrimidin-2-yl)pyrrolidine-2-carboxamide (314b)

Compound 314b was prepared from (R)-1-(7-tosyl-4-((1-(3,4,5-trimethoxyphenyl)-1H-imidazol-4-yl)amino)-7H-pyrrolo[2,3-d]pyrimidin-2-yl)pyrrolidine-2-carboxamide (314a) (421 mg, 0.67 mmol) and Cs$_2$CO$_3$ (650 mg, 2.0 mmol) in MeOH/THF (14 mL, 3:2) according to the procedure reported in step-3 of Scheme 141. This gave after workup and purification by flash column chromatography [silica gel (12 g), eluting with ethyl acetate/MeOH (9:1) in hexane from 0-70%] followed by reverse phase prep-HPLC [(silica gel C-18, 100 g) eluting with CH₃CN in water (containing 0.1% HCl) from 0-100%] (R)-1-(4-((1-(3,4,5-trimethoxyphenyl)-1H-imidazol-4-yl)amino)-7H-pyrrolo[2,3-d]pyrimidin-2-yl)pyrrolidine-2-carboxamide (314b) (88 mg, 28% yield) HCl salt as a white solid; ¹H NMR (300 MHz, DMSO-d₆) δ 11.33 (s, 1H, D₂O exchangeable), 11.17 (s, 1H, D₂O exchangeable), 8.34 (s, 1H), 7.83 (s, 1H), 7.54 (s, 1H, D₂O exchangeable), 7.23 (s, 1H, D₂O exchangeable), 7.12 (s, 2H), 7.00 (d, J=12.3 Hz, 2H), 4.66-4.56 (m, 1H), 3.93 (s, 6H), 3.69 (d, J=1.6 Hz, 3H), 3.66-3.48 (m, 2H), 2.37-2.23 (m, 1H), 2.16-1.92 (m, 3H); ¹H NMR (300 MHz, DMSO-d₆/D₂O) δ 11.39 (s, 1H), 8.34 (s, 1H), 7.83 (d, J=1.6 Hz, 1H), 7.11 (s, 2H), 7.01 (s, 2H), 4.61 (d, J=8.7 Hz, 1H), 3.93 (s, 6H), 3.69 (d, J=1.8 Hz, 3H), 3.62-3.37 (m, 2H), 2.31 (d, J=12.1 Hz, 1H), 2.05 (s, 3H); MS (ES+): 479.2 (M+1), (ES−): 513.3 (M+Cl), 991.5 (2M+Cl); HPLC purity: 98.43%.

Scheme 315

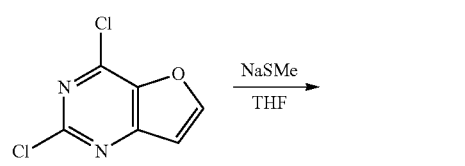

1a

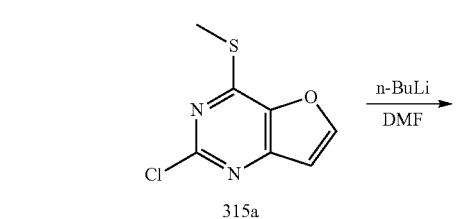

315a

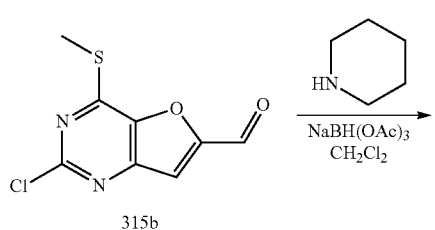

315b

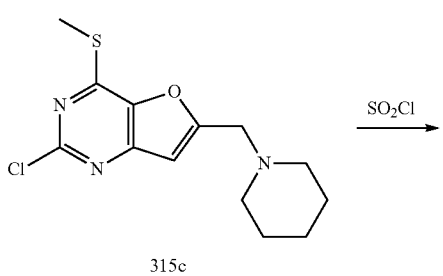

315c

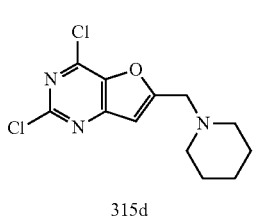

315d

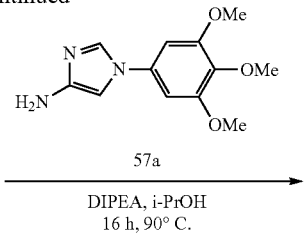

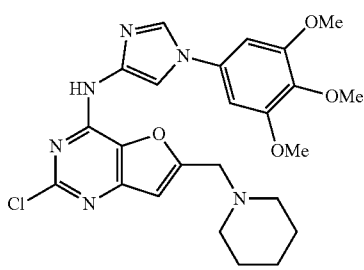

315e

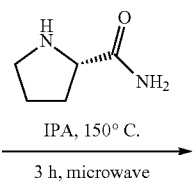

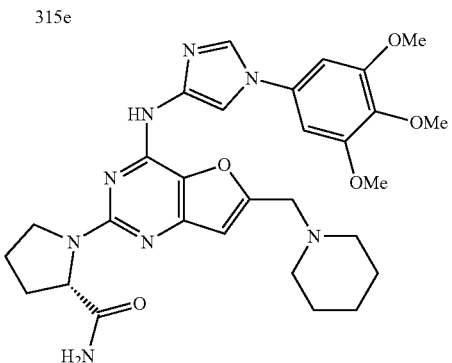

315f

Preparation of (S)-1-(6-(piperidin-1-ylmethyl)-4-((1-(3,4,5-trimethoxyphenyl)-1H-imidazol-4-yl)amino)furo[3,2-d]pyrimidin-2-yl)pyrrolidine-2-carboxamide (315f)

Step-1: Preparation of 2-chloro-4-(methylthio)furo[3,2-d]pyrimidine (315a)

Compound 315a was prepared from 2,4-dichlorofuro[3,2-d]pyrimidine (1a) (1 g, 5.29 mmol) and sodium thiomethoxide (385 mg, 5.29 mmol) in THF (20 mL) and DMF (2 mL) according to the procedure reported in step-1 of Scheme 70. This gave after workup and purification by flash column chromatography [silica gel, 24 g eluting with ethyl acetate in hexanes (0 to 20)]2-chloro-4-(methylthio)furo[3,2-d]pyrimidine (315a) (0.6 g, 56% yield); ¹H NMR (300 MHz, DMSO-d₆) δ 8.54 (d, J=2.2 Hz, 1H), 7.22 (d, J=2.2 Hz, 1H), 2.69 (s, 3H).

Step-2: Preparation of 2-chloro-4-(methylthio)furo[3,2-d]pyrimidine-6-carbaldehyde (315b)

Compound 315b was prepared from 2-chloro-4-(methylthio)furo[3,2-d]pyrimidine (315a) (583 mg, 2.91) according to the procedure reported in step-2 of Scheme 70. This gave after workup and purification by flash column chromatography [(silica gel, 40 g) eluting with ethyl acetate and hexanes] 2-chloro-4-(methylthio)furo[3,2-d]pyrimidine-6-carbaldehyde (315b) (403 mg, 61% yield) as a light red solid; $^1$H NMR (300 MHz, DMSO-d$_6$) δ 9.98 (s, 1H), 8.08 (s, 1H), 2.73 (s, 3H).

Step-3: Preparation of 2-chloro-4-(methylthio)-6-(piperidin-1-ylmethyl)furo[3,2-d]pyrimidine (315c)

Compound 315c was prepared according to the procedure reported for reductive amination in step-1 of Scheme 105 from 2-chloro-4-(methylthio) furo [3, 2-d] pyrimidine-6-carbaldehyde (315b) (400 mg, 1.75 mmol) in dichloromethane (10 mL) using piperidine (0.2 mL, 2.0 mmol), and NaBH(OAc)3 (556 mg, 2.62 mmol). This gave after workup and purification by flash column chromatography [(silica gel, 40 g) eluting with a (9:1) mixture of methanol/ethyl acetate in hexanes) 2-chloro-4-(methylthio)-6-(piperidin-1-ylmethyl)furo[3,2-d]pyrimidine (315c) (400 mg, 77% yield) as a red sticky material; $^1$H NMR (300 MHz, DMSO-d$_6$) δ 7.01 (s, 1H), 3.72 (s, 2H), 2.68 (s, 3H), 2.44-2.40 (m, 4H), 1.56-1.43 (m, 4H), 1.43-1.28 (m, 2H).

Step-4: Preparation of 2,4-dichloro-6-(piperidin-1-ylmethyl)furo[3,2-d]pyrimidine (315d)

Compound 315d was prepared from 2-chloro-4-(methylthio)-6-(piperidin-1-ylmethyl)furo[3,2-d]pyrimidine (315c) (390 mg, 1.31 mmol) according to the procedure reported in step-3 of Scheme 70. This gave after workup 2,4-dichloro-6-(piperidin-1-ylmethyl)furo[3,2-d]pyrimidine (315d) (0.32 g, 85% yield); $^1$H NMR (300 MHz, DMSO-d$_6$) δ 7.17 (s, 1H), 3.78 (s, 2H), 2.45 (t, J=5.1 Hz, 4H), 1.59-1.44 (m, 4H), 1.43-1.30 (m, 2H).

Step-5: Preparation of 2-chloro-6-(piperidin-1-ylmethyl)-N-(1-(3,4,5-trimethoxyphenyl)-1H-imidazol-4-yl)furo[3,2-d]pyrimidin-4-amine (315e)

Compound 315e was prepared from 2,4-dichloro-6-(piperidin-1-ylmethyl)furo[3,2-d]pyrimidine (315d) (320 mg, 1.12 mmol) in 2-Propanol (7 mL) using DIPEA (0.59 mL, 3.35 mmol) and 1-(3,4,5-trimethoxyphenyl)-1H-imidazol-4-amine (57a) (279 mg, 1.12 mmol) according to the procedure reported in Scheme 1. This gave after workup 2-chloro-6-(piperidin-1-ylmethyl)-N-(1-(3,4,5-trimethoxyphenyl)-1H-imidazol-4-yl)furo[3,2-d]pyrimidin-4-amine (315e) (132 mg, 24% yield) as a tan solid; $^1$H NMR (300 MHz, DMSO-d$_6$) δ 10.80 (s, 1H), 8.16 (d, J=1.5 Hz, 1H), 7.83 (d, J=1.6 Hz, 1H), 6.93 (s, 2H), 6.83 (s, 1H), 3.87 (s, 6H), 3.69 (s, 3H), 3.66 (s, 2H), 2.47-2.36 (m, 4H), 1.54-1.42 (m, 4H), 1.42-1.29 (m, 2H).

Step-6: Preparation of (S)-1-(6-(piperidin-1-ylmethyl)-4-((1-(3,4,5-trimethoxyphenyl)-1H-imidazol-4-yl)amino)furo[3,2-d]pyrimidin-2-yl)pyrrolidine-2-carboxamide (315f)

Compound 315f was prepared according to the procedure reported in Scheme 2 from 2-chloro-6-(piperidin-1-ylmethyl)-N-(1-(3,4,5-trimethoxyphenyl)-1H-imidazol-4-yl)furo[3,2-d]pyrimidin-4-amine (315e) (120 mg, 0.24 mmol) and (S)-pyrrolidine-2-carboxamide (82 mg, 0.72 mmol) in 2-Propanol (2 mL). This gave after workup and purification by reverse phase flash column chromatography [(silica gel C-18, 100 g), eluting with acetonitrile in water (containing 0.1% HCl) from 0-100%] (S)-1-(6-(piperidin-1-ylmethyl)-4-((1-(3,4,5-trimethoxyphenyl)-1H-imidazol-4-yl)amino)furo[3,2-d]pyrimidin-2-yl)pyrrolidine-2-carboxamide (315f) (50 mg, 36% yield) HCl salt as a white solid; $^1$H NMR (300 MHz, DMSO-d$_6$) δ 13.40 (s, 1H, D$_2$O exchangeable), 11.97 (s, 1H, D$_2$O exchangeable), 11.57 (s, 1H, D$_2$O exchangeable), 8.35 (s, 1H), 7.87 (s, 1H), 7.63 (s, 1H, D$_2$O exchangeable), 7.40 (s, 1H, D$_2$O exchangeable), 7.28 (s, 1H), 7.13 (s, 2H), 4.62 (m, 1H), 4.57 (m, 2H), 3.94 (s, 6H), 3.69 (s, 3H), 3.66-3.45 (m, 4H), 3.20-2.92 (m, 2H), 2.40-2.19 (m, 1H), 2.19-1.98 (m, 3H), 1.84 (m, 4H), 1.77-1.63 (m, 1H), 1.48-1.27 (m, 1H); MS (ES+): 577.4 (M+1), (ES−): 611.3 (M+Cl); HPLC purity: 95.99%.

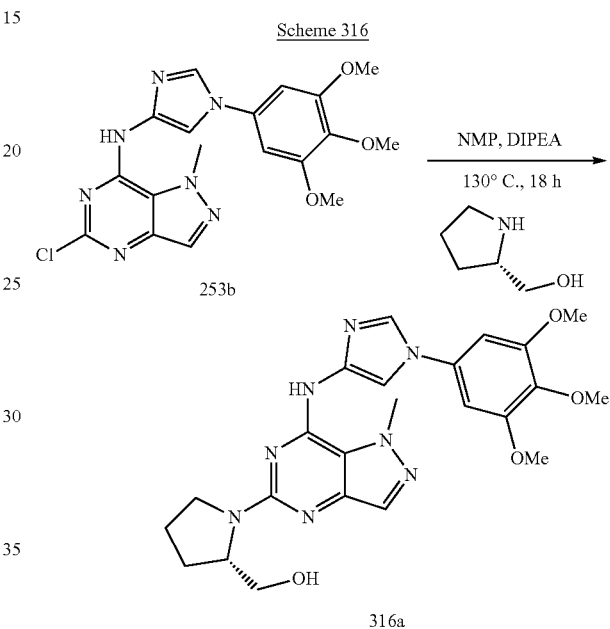

Scheme 316

Preparation of (S)-(1-(1-methyl-7-((1-(3,4,5-trimethoxyphenyl)-1H-imidazol-4-yl)amino)-1H-pyrazolo[4,3-d]pyrimidin-5-yl)pyrrolidin-2-yl)methanol (316a)

Compound 316a was prepared according to the procedure reported in step-2 of Scheme 76 from 5-chloro-1-methyl-N-(1-(3,4,5-trimethoxyphenyl)-1H-imidazol-4-yl)-1H-pyrazolo[4,3-d]pyrimidin-7-amine (253b) (200 mg, 0.48 mmol) and (S)-pyrrolidin-2-ylmethanol (0.19 mL, 1.92 mmol) in NMP (3 mL) using DIPEA (0.5 mL, 2.89 mmol) as base. This gave after workup and purification by flash column chromatography [silica gel (12 g), eluting with DMA-80 in DCM from 0-50%] followed by purification by reverse phase flash column chromatography [(silica gel C-18, 50 g), eluting with acetonitrile in water (containing 0.1% HCl) from 0-100%] of (S)-(1-(1-methyl-7-((1-(3,4,5-trimethoxyphenyl)-1H-imidazol-4-yl)amino)-1H-pyrazolo[4,3-d]pyrimidin-5-yl)pyrrolidin-2-yl)methanol (316a) (92 mg, 40% yield) HCl salt as a yellow solid; $^1$H NMR (300 MHz, DMSO-d$_6$) δ 12.79 (s, 1H), 8.90 (s, 1H), 8.08 (s, 1H), 7.79 (s, 1H), 7.06 (s, 2H), 4.56-4.39 (m, 1H), 4.37 (s, 3H), 4.05-3.90 (m, 1H), 3.89 (s, 6H), 3.89-3.69 (m, 1H), 3.69 (s, 3H), 3.66-3.41 (m, 2H), 2.23-1.72 (m, 4H); MS (ES+): 481.4 (M+1); MS (ES−): 479.4 (M−1), 515.3 (M+Cl). HPLC purity: 97.07%.

Scheme 317

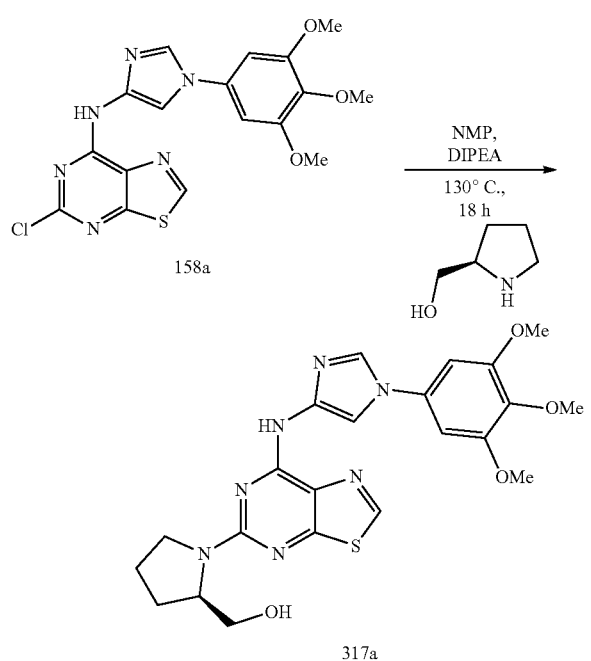

Preparation of (R)-(1-(7-((1-(3,4,5-trimethoxyphenyl)-1H-imidazol-4-yl)amino)thiazolo[5,4-d]pyrimidin-5-yl)pyrrolidin-2-yl)methanol (317a)

Compound 317a was prepared from 5-chloro-N-(1-(3,4,5-trimethoxyphenyl)-1H-imidazol-4-yl)thiazolo[5,4-d]pyrimidin-7-amine (158a) (400 mg, 0.96 mmol), (R)-pyrrolidin-2-ylmethanol (0.38 mL, 3.82 mmol), DIPEA (1.0 mL, 5.73 mmol) in NMP (3 mL) according to the procedure reported in step-2 of Scheme 76. This gave after workup and purification by flash column chromatography [silica gel (12 g), eluting with DMA-80 in CH₂Cl₂ from 0 to 50%] followed by reverse phase flash column chromatography [(silica gel C-18, 24 g) eluting with acetonitrile and 0.1% HCl in water] (R)-(1-(7-((1-(3,4,5-trimethoxyphenyl)-1H-imidazol-4-yl)amino)thiazolo[5,4-d]pyrimidin-5-yl)pyrrolidin-2-yl)methanol (317a) (0.065 g, 14% yield) HCl salt as a brown solid; ¹H NMR (300 MHz, DMSO-d₆) δ 11.06 (s, 1H), 9.22-9.08 (m, 1H), 8.99 (s, 1H), 8.21-8.07 (m, 1H), 7.11 (s, 2H), 4.50-4.12 (m, 1H), 3.89 (s, 6H), 3.84-3.71 (m, 1H), 3.70 (s, 3H), 3.68-3.47 (m, 3H), 3.42 (dd, J=10.5, 7.7 Hz, 1H), 2.22-1.74 (m, 4H); MS (ES+): 484.3 (M+1), 506.3 (M+Na); MS (ES−): 518.3 (M+Cl). HPLC purity: 91.19%.

Scheme 318

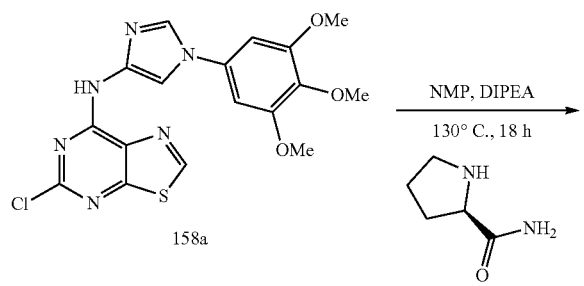

Preparation of (R)-1-(7-((1-(3,4,5-trimethoxyphenyl)-1H-imidazol-4-yl)amino)thiazolo[5,4-d]pyrimidin-5-yl)pyrrolidine-2-carboxamide (318a)

Compound 318a was prepared from 5-chloro-N-(1-(3,4,5-trimethoxyphenyl)-1H-imidazol-4-yl)thiazolo[5,4-d]pyrimidin-7-amine (158a) (400 mg, 0.96 mmol), (R)-pyrrolidine-2-carboxamide (436 mg, 3.82 mmol), DIPEA (1.0 mL, 5.73 mmol) in NMP (3 mL) according to the procedure reported in step-2 of Scheme 76. This gave after workup and purification by flash column chromatography [silica gel (12 g), eluting with DMA-80 in CH₂Cl₂ from 0 to 50%] followed by reverse phase flash column chromatography [(silica gel C-18, 24 g) eluting with acetonitrile and 0.1% HCl in water] (R)-1-(7-((1-(3,4,5-trimethoxyphenyl)-1H-imidazol-4-yl)amino)thiazolo[5,4-d]pyrimidin-5-yl)pyrrolidine-2-carboxamide (318a) (58 mg, 12% yield) HCl salt as a yellow solid; ¹H NMR (300 MHz, DMSO-d₆): (a mixture of two rotamers) 10.90 (2s, 1H), 9.31 (2s, 1H), 8.99 (2s, 1H), 8.15 (s, 1H), 7.43 (s, 1H), 7.26 (s, 2H), 7.12 (m, 1H), 4.50 (d, J=7.6 Hz, 1H), 3.94 (s, 6H), 3.90-3.82 (m, 1H), 3.71 (s, 3H), 3.67-3.49 (m, 1H), 2.38-1.77 (m, 4H); MS (ES+): 497.3 (M+1); MS (ES−): 495.3 (M−1), 531.3 (M+Cl). HPLC purity: 93.36%.

Scheme 319

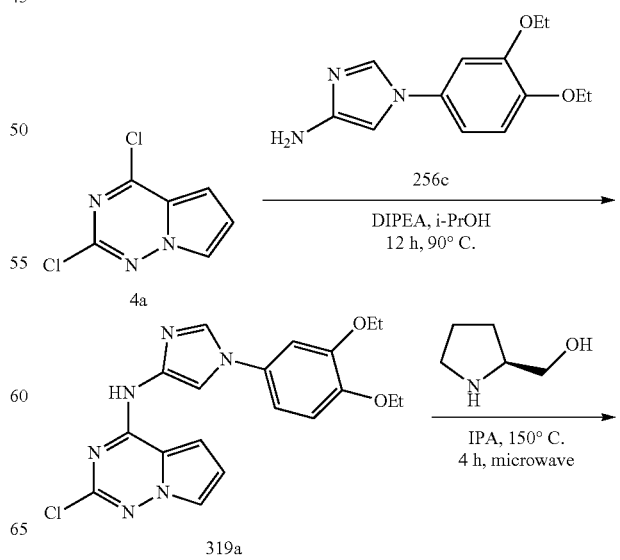

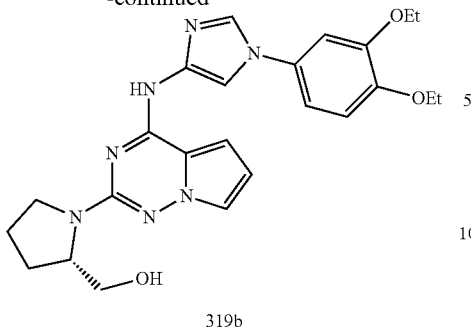

319b

Preparation of (S)-(1-(4-((1-(3,4-diethoxyphenyl)-1H-imidazol-4-yl)amino)pyrrolo[2,1-f][1,2,4]triazin-2-yl)pyrrolidin-2-yl)methanol (319b)

Step-1: Preparation of 2-chloro-N-(1-(3,4-diethoxyphenyl)-1H-imidazol-4-yl)pyrrolo[2,1-f][1,2,4]triazin-4-amine (319a)

Compound 319a was prepared from 2,4-dichloropyrrolo[2,1-f][1,2,4]triazine (4a) (350 mg, 1.86 mmol) in 2-Propanol (7 mL) using DIPEA (0.98 mL, 5.58 mmol) and 1-(3,4-diethoxyphenyl)-1H-imidazol-4-amine (256c) (460 mg, 1.86 mmol, free base) according to the procedure reported in Scheme 1. This gave after workup 2-chloro-N-(1-(3,4-diethoxyphenyl)-1H-imidazol-4-yl)pyrrolo[2,1-f][1,2,4]triazin-4-amine (319a) (320 mgs, 43%) as a tan solid; $^1$H NMR (300 MHz, DMSO-$d_6$) δ 11.32 (s, 1H), 8.15 (d, J=1.5 Hz, 1H), 7.83 (d, J=1.6 Hz, 1H), 7.77 (dd, J=2.6, 1.5 Hz, 1H), 7.42-7.35 (m, 1H), 7.23 (s, 1H), 7.09 (d, J=1.7 Hz, 2H), 6.72 (dd, J=4.5, 2.6 Hz, 1H), 4.15 (t, J=7.0 Hz, 2H), 4.07 (q, J=6.6 Hz, 2H), 1.41-1.36 (m, 3H), 1.36-1.30 (m, 3H).

Step-2: Preparation of (S)-(1-(4-((1-(3,4-diethoxyphenyl)-1H-imidazol-4-yl)amino)pyrrolo[2,1-f][1,2,4]triazin-2-yl)pyrrolidin-2-yl)methanol (319b)

Compound 319b was prepared according to the procedure reported in Scheme 2 from 2-chloro-N-(1-(3,4-diethoxyphenyl)-1H-imidazol-4-yl)pyrrolo[2,1-f][1,2,4]triazin-4-amine (319a) (250 mg, 0.63 mmol) and (S)-pyrrolidin-2-ylmethanol (0.19 mL, 1.88 mmol) in 2-Propanol (3 mL). This gave after workup and purification by flash column chromatography [(silica gel, 25 g) eluting DMA-80 in chloroform] compound 319b as a free base. The free base was re dissolved in acetonitrile (5 mL), HCl (1 N, 5 mL) and freeze-dried to afford (S)-(1-(4-((1-(3,4-diethoxyphenyl)-1H-imidazol-4-yl)amino)pyrrolo[2,1-f][1,2,4]triazin-2-yl)pyrrolidin-2-yl)methanol (319b) (131 mg, 45% yield) HCl salt as a white solid; $^1$H NMR (300 MHz, DMSO-$d_6$) δ 10.65 (s, 1H, D$_2$O exchangeable), 8.43 (s, 1H), 7.95 (d, J=1.6 Hz, 1H), 7.43 (t, J=2.1 Hz, 1H), 7.29-7.19 (m, 2H), 7.11 (dd, J=4.5, 1.7 Hz, 1H), 7.05 (d, J=8.6 Hz, 1H), 6.42 (dd, J=4.4, 2.5 Hz, 1H), 4.24-4.11 (m, 3H), 4.07 (m, 2H), 3.70 (dd, J=10.0, 3.6 Hz, 1H), 3.59-3.46 (m, 1H), 3.48-3.27 (m, 2H), 2.08-1.79 (m, 4H), 1.36 (q, J=6.9 Hz, 6H); MS (ES+): 464.4 (M+1), 486.4 (M+Na); HPLC purity: 98.47%.

Scheme 320

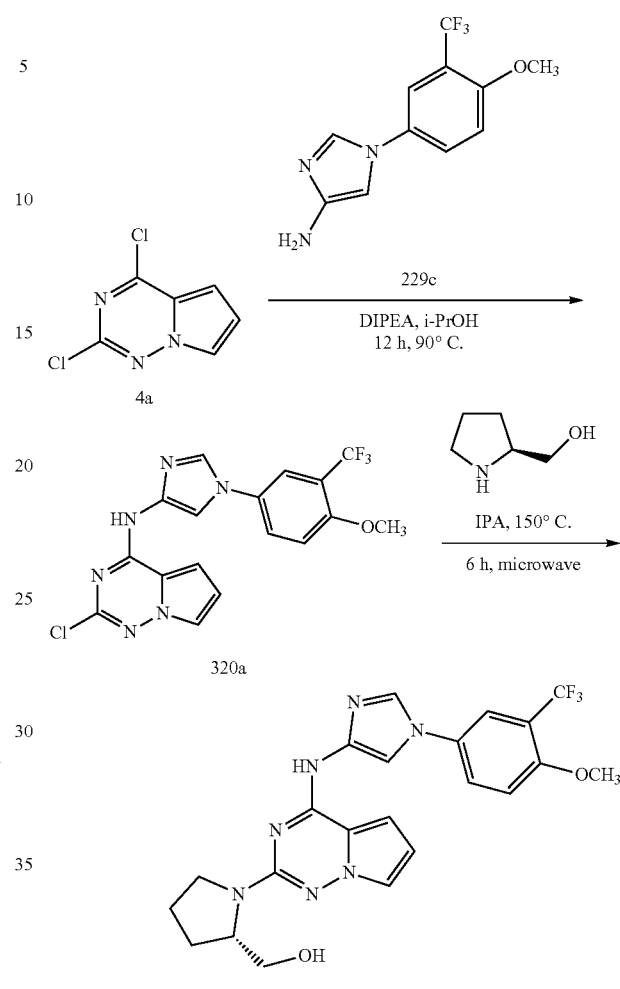

Preparation of (S)-(1-(4-((1-(4-methoxy-3-(trifluoromethyl)phenyl)-1H-imidazol-4-yl)amino)pyrrolo[2,1-f][1,2,4]triazin-2-yl)pyrrolidin-2-yl)methanol (320b)

Step-1: Preparation of 2-chloro-N-(1-(4-methoxy-3-(trifluoromethyl)phenyl)-1H-imidazol-4-yl)pyrrolo[2,1-f][1,2,4]triazin-4-amine (320a)

Compound 320a was prepared from 2,4-dichloropyrrolo[2,1-f][1,2,4]triazine (4a) (250 mg, 1.33 mmol) in 2-Propanol (5 mL) using DIPEA (0.7 mL, 3.99 mmol) and 1-(4-methoxy-3-(trifluoromethyl)phenyl)-1H-imidazol-4-amine (229c) (342 mg, 1.33 mmol, free base) according to the procedure reported in Scheme 1. This gave after workup 2-chloro-N-(1-(4-methoxy-3-(trifluoromethyl)phenyl)-1H-imidazol-4-yl)pyrrolo[2,1-f][1,2,4]triazin-4-amine (320a) (290 mg, 53% yield) as a tan solid; $^1$H NMR (300 MHz, DMSO-$d_6$) δ 11.33 (s, 1H), 8.23 (d, J=1.6 Hz, 1H), 7.96-7.90 (m, 1H), 7.88 (s, 2H), 7.77 (t, J=2.0 Hz, 1H), 7.46 (d, J=8.9 Hz, 1H), 7.40 (d, J=4.2 Hz, 1H), 6.72 (dd, J=4.4, 2.6 Hz, 1H), 3.96 (s, 3H).

Step-2: Preparation of (S)-(1-(4-((1-(4-methoxy-3-(trifluoromethyl)phenyl)-1H-imidazol-4-yl)amino)pyrrolo[2,1-f][1,2,4]triazin-2-yl)pyrrolidin-2-yl)methanol (320b)

Compound 320b was prepared according to the procedure reported in Scheme 2 from 2-chloro-N-(1-(4-methoxy-3-(trifluoromethyl)phenyl)-1H-imidazol-4-yl)pyrrolo[2,1-f][1,2,4]triazin-4-amine (320a) (200 mg, 0.49 mmol) and (S)-pyrrolidin-2-ylmethanol (0.14 mL, 1.47 mmol) in 2-Propanol (2 mL). This gave after workup and purification by flash column chromatography [(silica gel, 25 g) eluting DMA-80 in chloroform] followed by purification by reverse phase flash column chromatography [(silica gel C-18, 100 g) eluting with acetonitrile and 0.1% HCl in water] (S)-(1-(4-((1-(4-methoxy-3-(trifluoromethyl)phenyl)-1H-imidazol-4-yl)amino)pyrrolo[2,1-f][1,2,4]triazin-2-yl)pyrrolidin-2-yl)methanol (320b) (70 mg, 30% yield) HCl salt as a white solid; $^1$H NMR (300 MHz, DMSO-$d_6$) δ 10.66 (s, 1H, $D_2O$ exchangeable), 8.44 (s, 1H), 8.06-7.99 (m, 1H), 7.97 (d, J=1.5 Hz, 1H), 7.94 (d, J=2.5 Hz, 1H), 7.45-7.36 (m, 2H), 7.13 (dd, J=4.4, 1.5 Hz, 1H), 6.42 (dd, J=4.8, 2.2 Hz, 1H), 4.21-4.10 (m, 1H), 3.95 (s, 3H), 3.71 (dd, J=10.0, 3.5 Hz, 1H), 3.55-3.43 (m, 1H), 3.45-3.27 (m, 2H), 2.08-1.82 (m, 4H); $^{19}$F NMR (282 MHz, DMSO-$d_6$) δ −61.02; MS (ES$^+$), 474.3 (M+1), (ES$^-$), 508.3.3 (M+Cl); HPLC purity: 98.68%.

Preparation of (S)-(1-(4-((1-(5-methoxypyridin-3-yl)-1H-imidazol-4-yl)amino)pyrrolo[2,1-f][1,2,4]triazin-2-yl)pyrrolidin-2-yl)methanol (321b)

Step-1: Preparation of 2-chloro-N-(1-(5-methoxypyridin-3-yl)-1H-imidazol-4-yl)pyrrolo[2,1-f][1,2,4]triazin-4-amine (321a)

Compound 321a was prepared from 2,4-dichloropyrrolo[2,1-f][1,2,4]triazine (4a) (420 mg, 2.23 mmol) in 2-Propanol (10 mL) using DIPEA (1.17 mL, 6.7 mmol) and 1-(5-methoxypyridin-3-yl)-1H-imidazol-4-amine (228c) (425 mg, 2.23 mmol, free base) according to the procedure reported in Scheme 1. This gave after workup 2-chloro-N-(1-(5-methoxypyridin-3-yl)-1H-imidazol-4-yl)pyrrolo[2,1-f][1,2,4]triazin-4-amine (321a) (290 mg, 53% yield) as a tan solid; $^1$H NMR (300 MHz, DMSO-$d_6$) δ 11.37 (s, 1H), 8.53 (d, J=2.1 Hz, 1H), 8.37 (d, J=1.6 Hz, 1H), 8.35 (d, J=2.5 Hz, 1H), 7.99 (d, J=1.6 Hz, 1H), 7.79 (dd, J=2.6, 1.5 Hz, 1H), 7.76 (t, J=2.4 Hz, 1H), 7.40 (d, J=4.4 Hz, 1H), 6.73 (dd, J=4.5, 2.6 Hz, 1H), 3.94 (s, 3H).

Step-2: Preparation of (S)-(1-(4-((1-(5-methoxypyridin-3-yl)-1H-imidazol-4-yl)amino)pyrrolo[2,1-f][1,2,4]triazin-2-yl)pyrrolidin-2-yl)methanol (321b)

Compound 321b was prepared according to the procedure reported in Scheme 2 from 2-chloro-N-(1-(5-methoxypyridin-3-yl)-1H-imidazol-4-yl)pyrrolo[2,1-f][1,2,4]triazin-4-amine (321a) (300 mg, 0.88 mmol) and (S)-pyrrolidin-2-ylmethanol (0.35 mL, 3.51 mmol) in 2-Propanol (3 mL). This gave after workup and purification by flash column chromatography [(silica gel, 25 g) eluting DMA 80 in chloroform] compound 321b as a free base. The free base was re dissolved in acetonitrile (5 mL), HCl (1 N, 5 mL) and freeze-dried to afford (S)-(1-(4-((1-(5-methoxypyridin-3-yl)-1H-imidazol-4-yl)amino)pyrrolo[2,1-f][1,2,4]triazin-2-yl)pyrrolidin-2-yl)methanol (321b) (180 mg, 51% yield) HCl salt as a white solid; $^1$H NMR (300 MHz, DMSO-$d_6$) δ 10.70 (s, 1H, $D_2O$ exchangeable), 8.75-8.62 (m, 1H), 8.57-8.44 (m, 1H), 8.41-8.29 (m, 1H), 8.05 (s, 1H), 7.95-7.78 (m, 1H), 7.49-7.37 (m, 1H), 7.15 (dd, J=4.5, 1.6 Hz, 1H), 6.42 (dt, J=4.6, 1.7 Hz, 1H), 4.27-4.12 (m, 1H), 3.95 (s, 3H), 3.75 (dd, J=10.1, 3.5 Hz, 1H), 3.57-3.44 (m, 1H), 3.41-3.25 (m, 2H), 2.08-1.81 (m, 4H); MS (ES+): 407.3 (M+1), 429.3 (M+Na), 441.3 (M+Cl); HPLC purity: 98.89%.

Scheme 321

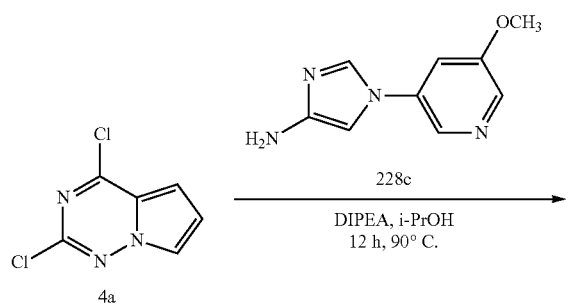

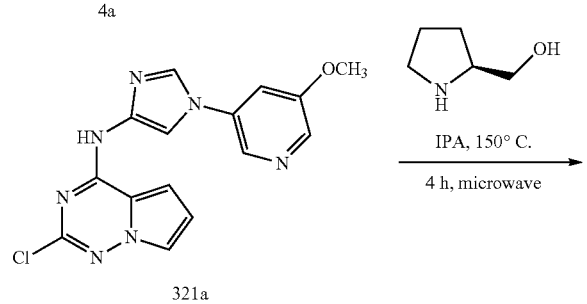

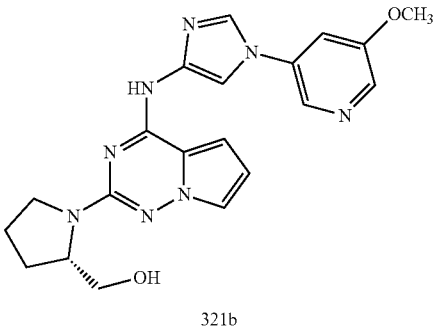

Scheme 322

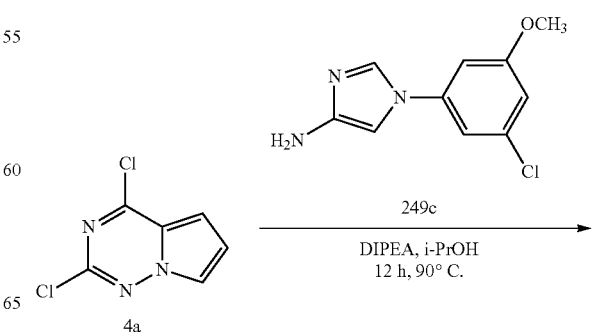

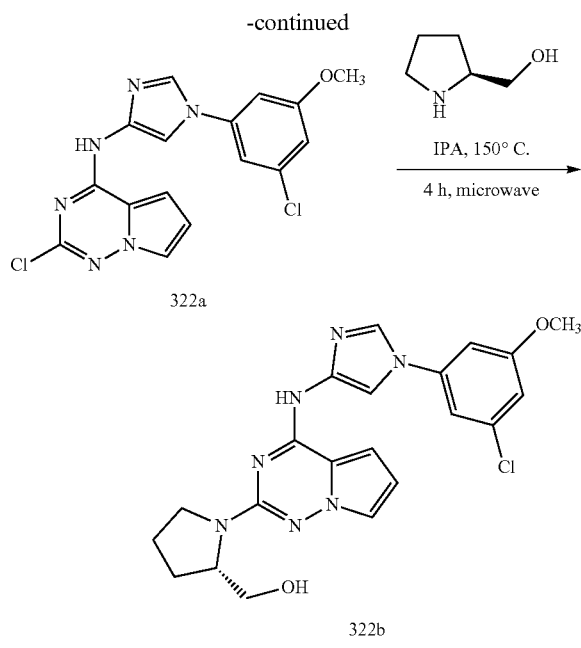

322a

322b

Preparation of (S)-(1-(4-((1-(3-chloro-5-methoxy-phenyl)-1H-imidazol-4-yl)amino)pyrrolo[2,1-f][1,2,4]triazin-2-yl)pyrrolidin-2-yl)methanol (322b)

Step-1: Preparation of 2-chloro-N-(1-(3-chloro-5-methoxyphenyl)-1H-imidazol-4-yl)pyrrolo[2,1-f][1,2,4]triazin-4-amine (322a)

Compound 322a was prepared from 2,4-dichloropyrrolo[2,1-f][1,2,4]triazine (4a) (350 mg, 1.86 mmol) in 2-Propanol (10 mL) using DIPEA (0.98 mL, 5.58 mmol) and 1-(3-chloro-5-methoxyphenyl)-1H-imidazol-4-amine (249c) (416 mg, 1.86 mmol, free base) according to the procedure reported in Scheme 1. This gave after workup 2-chloro-N-(1-(3-chloro-5-methoxyphenyl)-1H-imidazol-4-yl)pyrrolo[2,1-f][1,2,4]triazin-4-amine (322a) as a tan solid; $^1$H NMR (300 MHz, DMSO-$d_6$) δ 11.33 (s, 1H), 8.34 (d, J=1.5 Hz, 1H), 7.92 (d, J=1.5 Hz, 1H), 7.78 (q, J=1.5, 1.1 Hz, 1H), 7.39 (s, 2H), 7.23 (d, J=2.3 Hz, 1H), 7.09 (d, J=2.1 Hz, 1H), 6.73 (dd, J=4.3, 2.8 Hz, 1H), 3.87 (s, 3H).

Step-2: Preparation of (S)-(1-(4-((1-(3-chloro-5-methoxyphenyl)-1H-imidazol-4-yl)amino)pyrrolo[2,1-f][1,2,4]triazin-2-yl)pyrrolidin-2-yl)methanol (322b)

Compound 322b was prepared according to the procedure reported in Scheme 2 from 2-chloro-N-(1-(3-chloro-5-methoxyphenyl)-1H-imidazol-4-yl)pyrrolo[2,1-f][1,2,4]triazin-4-amine (322a) (250 mg, 0.67 mmol) and (S)-pyrrolidin-2-ylmethanol (0.26 mL, 2.67 mmol) in 2-Propanol (3 mL). This gave after workup and purification by flash column chromatography [(silica gel, 25 g) eluting DMA 80 in chloroform] compound 322b as a free base. The free base was re-dissolved in acetonitrile (5 mL), HCl (1 N, 5 mL) and freeze-dried to afford (S)-(1-(4-((1-(3-chloro-5-methoxyphenyl)-1H-imidazol-4-yl)amino)pyrrolo[2,1-f][1,2,4]triazin-2-yl)pyrrolidin-2-yl)methanol (322b) (96 mg, 33% yield) HCl salt as a white solid; $^1$H NMR (300 MHz, DMSO-$d_6$) δ 10.72 (s, 1H, D$_2$O exchangeable), 8.55 (d, J=1.5 Hz, 1H), 8.01 (d, J=1.6 Hz, 1H), 7.52 (t, J=1.9 Hz, 1H), 7.43 (t, J=2.0 Hz, 1H), 7.31 (t, J=2.1 Hz, 1H), 7.14 (dd, J=4.5, 1.7 Hz, 1H), 7.05 (t, J=1.9 Hz, 1H), 6.43 (dd, J=4.4, 2.4 Hz, 1H), 4.26-4.11 (m, 1H), 3.88 (s, 3H), 3.72 (dd, J=10.2, 3.6 Hz, 1H), 3.57-3.45 (m, 1H), 3.44-3.28 (m, 2H), 2.07-1.84 (m, 4H); (ES+): 440.3 (M+1), 462.3 (M+Na), 474.3 (M+Cl); HPLC purity: 99.39%.

Scheme 323

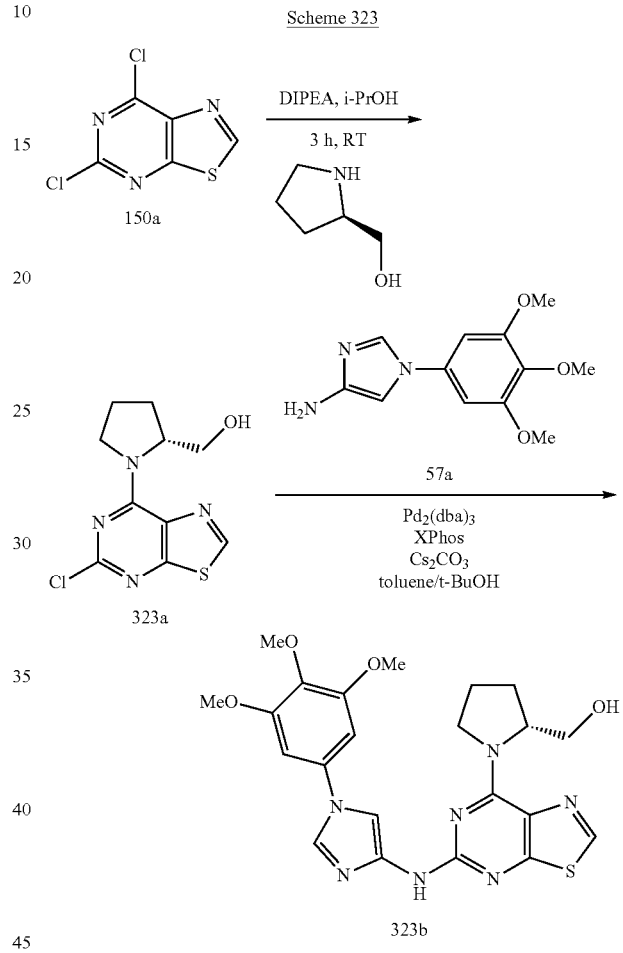

Preparation of (R)-(1-(5-((1-(3,4,5-trimethoxyphenyl)-1H-imidazol-4-yl)amino)thiazolo[5,4-d]pyrimidin-7-yl)pyrrolidin-2-yl)methanol (323b)

Step-1: Preparation of (R)-(1-(5-chlorothiazolo[5,4-d]pyrimidin-7-yl)pyrrolidin-2-yl)methanol (323a)

Compound 323a was prepared from 5,7-dichlorothiazolo[5,4-d]pyrimidine (150a) (500 mg, 15.87 mmol) in 2-Propanol (10 mL) using (R)-pyrrolidin-2-ylmethanol (0.24 mL, 2.43 mmol), DIPEA (1.27 mL, 7.28 mmol) according to the procedure reported in step-1 of Scheme 96. This gave after work up and purification by flash column chromatography [silica gel, (12 g) eluting with MeOH in CH$_2$Cl$_2$ from 0 to 30%] (R)-(1-(5-chlorothiazolo[5,4-d]pyrimidin-7-yl)pyrrolidin-2-yl)methanol (323a) (0.301 g, 46% yield) as a white solid; $^1$H NMR (300 MHz, DMSO-$d_6$) δ 9.18 (s, 1H), 5.16-4.96 (m, 1H), 4.94-4.63 (m, 1H), 4.52-3.87 (m, 2H), 3.79-3.20 (m, 2H), 2.53-1.69 (m, 6H); MS (ES-): 269.1 (M-1), 305.1 (M+Cl).

Step-2: Preparation of (R)-(1-(5-((1-(3,4,5-trimethoxyphenyl)-1H-imidazol-4-yl)amino)thiazolo[5,4-d]pyrimidin-7-yl)pyrrolidin-2-yl)methanol (323b)

Compound 323b was prepared from (R)-(1-(5-chlorothiazolo[5,4-d]pyrimidin-7-yl)pyrrolidin-2-yl)methanol (323a) (0.3 g, 1.11 mmol), 1-(3,4,5-trimethoxyphenyl)-1H-imidazol-4-amine (57a) (276 mg, 1.11 mmol), dicyclohexyl(2',4',6'-triisopropylbiphenyl-2-yl)phosphine (XPhos, 317 mg, 0.67 mmol), cesium carbonate (1083 mg, 3.32 mmol), Pd$_2$(dba)$_3$ (304 mg, 0.33 mmol) in Toluene (20 mL) and t-Butanol (10 mL) according to the procedure reported in step-3 of Scheme 101. This gave after workup and purification by flash column chromatography [silica gel, (12 g) eluting with DMA-80 in CH$_2$Cl$_2$ from 0 to 50%], reverse phase flash column chromatography [(silica gel C-18, 24 g) eluting with acetonitrile and 0.1% HCl in water] followed by lyophilization (R)-(1-(5-((1-(3,4,5-trimethoxyphenyl)-1H-imidazol-4-yl)amino)thiazolo[5,4-d]pyrimidin-7-yl)pyrrolidin-2-yl)methanol (323b) (128 mg, 24% yield) HCl salt as a yellow solid; $^1$H NMR (300 MHz, DMSO-d$_6$) δ 10.31 (bs, 1H), 9.39 (s, 1H), 8.93 (d, J=10.7 Hz, 1H), 7.98 (s, 1H), 7.15 (s, 2H), 5.27-4.99 (m, 1H), 4.72-4.41 (m, 1H), 4.31-4.10 (m, 1H), 4.10-3.93 (m, 1H), 3.89 (s, 6H), 3.70 (s, 3H), 3.69-3.55 (m, 1H), 3.54-3.36 (m, 1H), 2.32-1.82 (m, 4H); MS (ES−): 518.3 (M+Cl). HPLC purity: 97.15%.

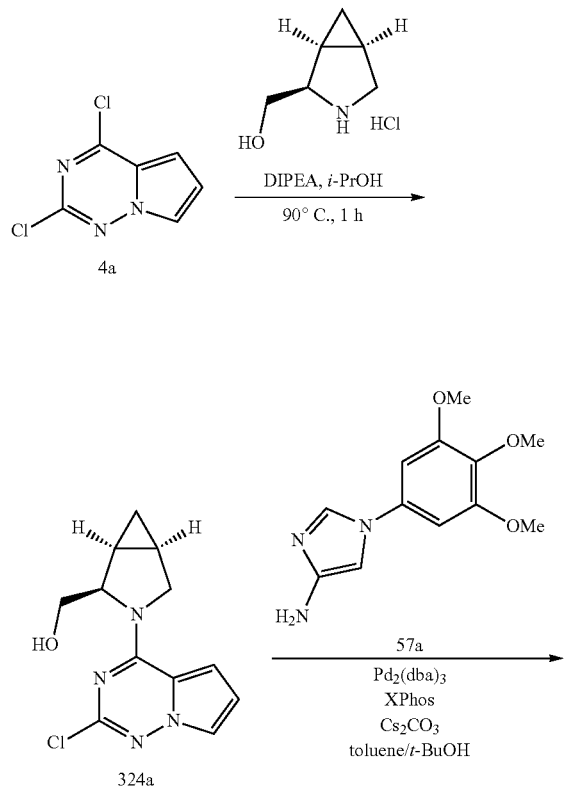

Scheme 324

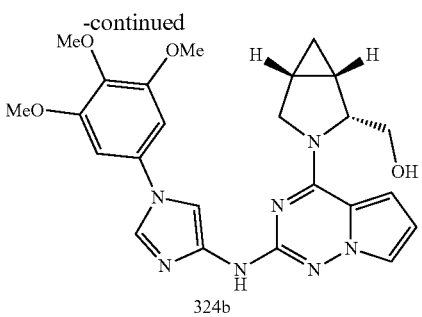

324b

Preparation of ((1S,2R,5R)-3-(2-((1-(3,4,5-trimethoxyphenyl)-1H-imidazol-4-yl)amino)pyrrolo[2,1-f][1,2,4]triazin-4-yl)-3-azabicyclo[3.1.0]hexan-2-yl)methanol (324b)

Step-1: Preparation of ((1S,2R,5R)-3-(2-chloropyrrolo[2,1-f][1,2,4]triazin-4-yl)-3-azabicyclo[3.1.0]hexan-2-yl)methanol (324a)

Compound 324a was prepared from 2,4-dichloropyrrolo[2,1-f][1,2,4]triazine (4a) (113 mg, 0.6 mmol) in 2-Propanol (4 mL) using (1S,2R,5R)-3-azabicyclo[3.1.0]hexan-2-ylmethanol hydrochloride (105 mg, 0.4 mmol), DIPEA (0.32 mL, 1.81 mmol) according to the procedure reported in step-1 of Scheme 96. This gave after work up ((1S,2R,5R)-3-(2-chloropyrrolo[2,1-f][1,2,4]triazin-4-yl)-3-azabicyclo[3.1.0]hexan-2-yl)methanol (324a) (105 mgs, 66% yield) as a white solid; $^1$H NMR (300 MHz, DMSO-d$_6$) δ 7.72 (dd, J=2.7, 1.4 Hz, 1H), 6.96 (dd, J=4.7, 1.5 Hz, 1H), 6.68 (dd, J=4.6, 2.7 Hz, 1H), 4.99 (t, J=5.7 Hz, 1H), 4.51-4.39 (m, 1H), 4.18-4.06 (m, 2H), 4.05-3.91 (m, 1H), 3.38-3.25 (m, 1H), 2.04-1.90 (m, 1H), 1.90-1.76 (m, 1H), 0.85-0.70 (m, 1H), 0.62 (q, J=4.5 Hz, 1H); MS (ES−): 263.2 (M−1); 299.2 (M+Cl).

Step-2: Preparation of ((1S,2R,5R)-3-(2-((1-(3,4,5-trimethoxyphenyl)-1H-imidazol-4-yl)amino)pyrrolo[2,1-f][1,2,4]triazin-4-yl)-3-azabicyclo[3.1.0]hexan-2-yl)methanol (324b)

Compound 324b was prepared from ((1S,2R,5R)-3-(2-chloropyrrolo[2,1-f][1,2,4]triazin-4-yl)-3-azabicyclo[3.1.0]hexan-2-yl)methanol (324a) (0.1 g, 0.38 mmol), 1-(3,4,5-trimethoxyphenyl)-1H-imidazol-4-amine (57a) (94 mg, 0.38 mmol), dicyclohexyl(2',4',6'-triisopropylbiphenyl-2-yl)phosphine (XPhos, 108 mg, 0.23 mmol), cesium carbonate (369 mg, 1.13 mmol), Pd$_2$(dba)$_3$ (104 mg, 0.11 mmol) in Toluene (10 mL) and t-Butanol (5 mL) according to the procedure reported in step-3 of Scheme 101. This gave after workup and purification by flash column chromatography [silica gel, (24 g) eluting with DMA-80 in CH$_2$Cl$_2$ from 0 to 50%], reverse phase flash column chromatography [(silica gel C-18, 24 g) eluting with acetonitrile and 0.1% HCl in water] followed by lyophilization ((1S,2R,5R)-3-(2-((1-(3,4,5-trimethoxyphenyl)-1H-imidazol-4-yl)amino)pyrrolo[2,1-f][1,2,4]triazin-4-yl)-3-azabicyclo[3.1.0]hexan-2-yl)methanol (324b) (55 mg, 31% yield) HCl salt as a white solid; $^1$H NMR (300 MHz, DMSO-d$_6$) δ 9.65 (s, 1H), 9.49 (s, 1H), 8.04-7.88 (m, 1H), 7.64 (d, J=2.3 Hz, 1H), 7.18 (s, 2H), 6.93-6.78 (m, 1H), 6.54 (dd, J=4.6, 2.5 Hz, 1H), 4.67-4.42 (m, 1H), 4.23-3.94 (m, 2H), 3.90 (s, 6H), 3.70 (s, 3H), 3.67-3.53 (m, 1H), 3.30 (t, J=9.1 Hz, 1H), 2.07-1.73

(m, 2H), 0.90-0.47 (m, 2H); MS (ES+): 478.4 (M+1), 500.3 (M+Na); MS (ES−): 512.4 (M+Cl). HPLC purity: 98.28%.

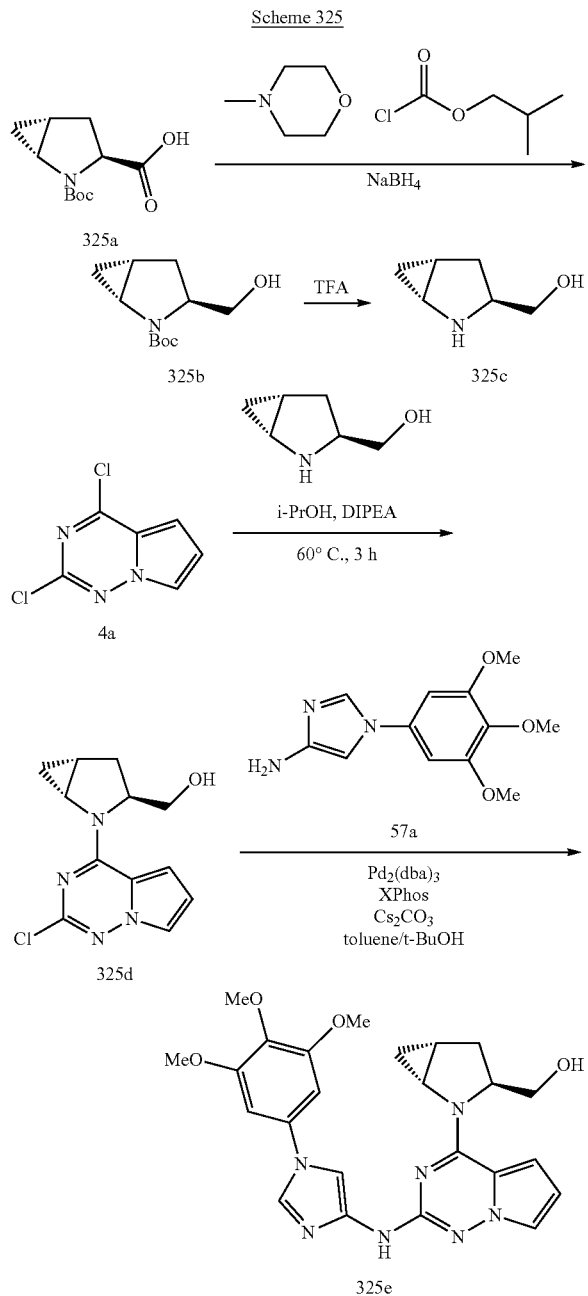

Scheme 325

325a 325b  325c

4a

325d

325e

Preparation of ((1R,3S,5R)-2-(2-((1-(3,4,5-trimethoxyphenyl)-1H-imidazol-4-yl)amino)pyrrolo[2,1-f][1,2,4]triazin-4-yl)-2-azabicyclo[3.1.0]hexan-3-yl)methanol (325e)

Step-1: Preparation of (1R,3S,5R)-tert-butyl 3-(hydroxymethyl)-2-azabicyclo[3.1.0]hexane-2-carboxylate (325b)

To the stirred solution of (1R,3S,5R)-2-(tert-butoxycarbonyl)-2-azabicyclo[3.1.0]hexane-3-carboxylic acid (325a) (100 mg, 0.44 mmol; CAS #197142-34-0) and N-methylmorpholine (0.05 mL, 0.44 mmol) in THF (5 mL) was added isobutyl chloroformate (0.06 mL, 0.44 mmol) at −5° C. After 10 min, the mixture was filtered over Celite and the precipitate was washed with THF (3×20 mL). The filtrate was cooled to 0° C. and a solution of NaBH$_4$ (25 mg, 0.66 mmol) in water (0.8 mL) was added carefully (a gas was released rapidly). After dilution with water (10 mL), the solution was washed with EtOAc (3×). The organic layers were collected, dried, filtered evaporated at reduced pressure to give (1R,3S,5R)-tert-butyl 3-(hydroxymethyl)-2-azabicyclo[3.1.0]hexane-2-carboxylate (325b) (100 mg) as a clear oil; MS (ES+): 236.2 (M+Na).

Step-2: Preparation of (1R,3S,5R)-2-azabicyclo[3.1.0]hexan-3-ylmethanol (325c)

To a solution of (1R,3S,5R)-tert-butyl 3-(hydroxymethyl)-2-azabicyclo[3.1.0]hexane-2-carboxylate (325b) (100 mg, 0.47 mmol) in DCM (6 mL) was added TFA (0.17 mL, 2.2 mmol) and stirred at RT for 2 h. Solvent was then removed in vacuum to furnish (1R,3S,5R)-2-azabicyclo[3.1.0]hexan-3-ylmethanol (325c) (100 mg, 100% yield) TFA salt as a clear oil, which was used in the next step without further purification.

Step-3: Preparation of ((1R,3S,5R)-2-(2-chloropyrrolo[2,1-f][1,2,4]triazin-4-yl)-2-azabicyclo[3.1.0]hexan-3-yl)methanol (325d)

To a solution of 2,4-dichloropyrrolo[1,2-f][1,2,4]triazine (4a) (83 mg, 0.44 mmol) in IPA (5 mL) was added (1R,3S,5R)-2-azabicyclo[3.1.0]hexan-3-ylmethanol TFA salt (325c) (100 mg, 0.44 mmol) and DIPEA (0.23 mL, 1.32 mmol). The resulting mixture was stirred for 3 h at 60° C., cooled to RT and concentrated in vacuum. The residue obtained was purified by flash column chromatography [silica gel (12 g), eluting with 0-60% EtOAc/MeOH (9:1) in hexane from 0-100%] to afford ((1R,3S,5R)-2-(2-chloropyrrolo[1,2-f][1,2,4]triazin-4-yl)-2-azabicyclo[3.1.0]hexan-3-yl)methanol (325d) (75 mg, 64% yield) as a semi-solid. $^1$H NMR (300 MHz, DMSO-d$_6$) δ 7.73 (t, J=2.0 Hz, 1H), 7.24-7.16 (m, 1H), 6.72-6.64 (m, 1H), 4.96 (t, J=5.8 Hz, 1H, D$_2$O exchangeable), 4.55-4.44 (m, 1H), 3.77-3.68 (m, 1H), 3.66-3.50 (m, 2H), 2.35-2.24 (m, 1H), 1.98-1.80 (m, 2H), 1.28-1.16 (m, 1H), 0.68-0.57 (m, 1H); MS (ES+): 265.2 (M+1); (ES−): 299.2, 301.2 (M+Cl).

Step-4: Preparation of ((1R,3S,5R)-2-(2-((1-(3,4,5-trimethoxyphenyl)-1H-imidazol-4-yl)amino)pyrrolo[2,1-f][1,2,4]triazin-4-yl)-2-azabicyclo[3.1.0]hexan-3-yl)methanol (325e)

Compound 325e was prepared from ((1R,3S,5R)-2-(2-chloropyrrolo[2,1-f][1,2,4]triazin-4-yl)-2-azabicyclo[3.1.0]hexan-3-yl)methanol (325d) (75 mg, 0.28 mmol), 1-(3,4,5-trimethoxyphenyl)-1H-imidazol-4-amine (57a) (78 mg, 0.31 mmol, free base), dicyclohexyl(2',4',6'-triisopropylbiphenyl-2-yl)phosphine (XPhos, 54 mg, 0.11 mmol), cesium carbonate (185 mg, 0.57 mmol), Pd$_2$(dba)$_3$ (52 mg, 0.06 mmol) in t-BuOH/toluene (10 mL, 3:1) according to the procedure reported in step-3 of Scheme 101. This gave after workup and purification by flash column chromatography [silica gel, (12 g) eluting with DMA-80 in CH$_2$Cl$_2$ from 0 to 100%], followed by reverse phase flash column chromatography [(silica gel C-18, 50 g) eluting with acetonitrile and 0.1% HCl in water] ((1R,3S,5R)-2-(2-((1-(3,4,5-trimethoxyphenyl)-1H-imidazol-4-yl)amino)pyrrolo[2,1-f][1,2,4]triazin- 4-yl)-2-azabicyclo[3.1.0]hexan-3-yl)methanol (325e) (15 mg, 11% yield) HCl salt as an off white solid; $^1$H NMR (300 MHz, DMSO-$d_6$) δ 9.63 (s, 1H, $D_2O$ exchangeable), 9.37 (s, 1H), 7.91 (d, J=1.8 Hz, 1H, $D_2O$ exchangeable), 7.69-7.62 (m, 1H), 7.18-7.06 (m, 3H), 6.60-6.51 (m, 1H), 4.65-4.60 (m, 2H), 3.89 (s, 6H), 3.71 (s, 3H), 3.67-3.56 (m, 3H), 2.31-2.18 (m, 1H), 1.96-1.78 (m, 2H), 1.27-1.13 (m, 1H), 0.58 (s, 1H); MS (ES+): 478.3 (M+1); (ES−): 512.4 (M+Cl); HPLC purity, 96.96%.

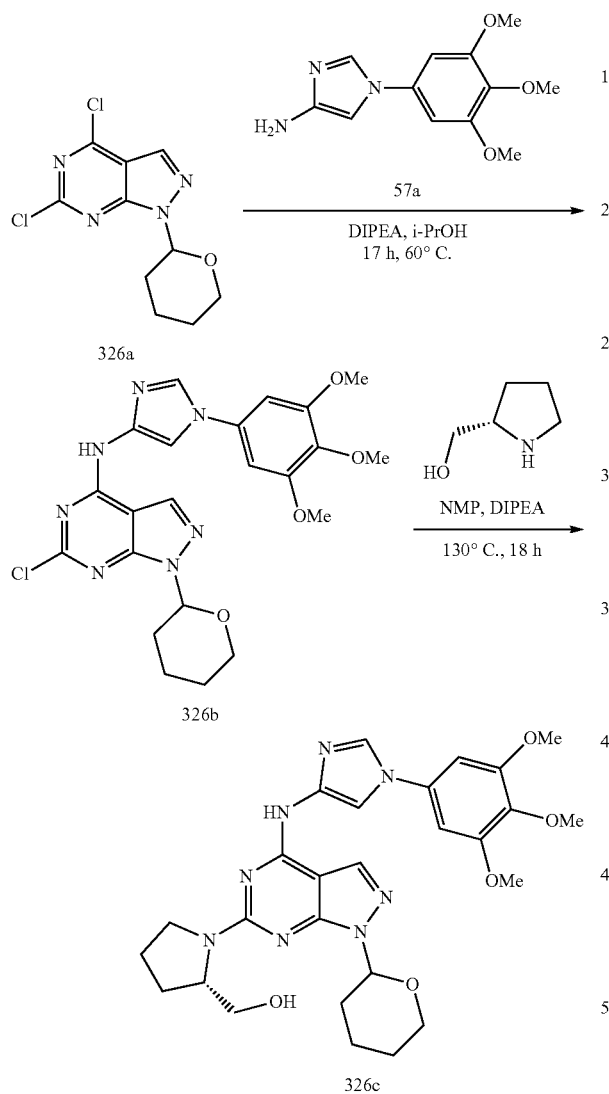

Preparation of ((2S)-1-(1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidin-2-yl)methanol (326c)

Step-1: Preparation of 6-chloro-1-(tetrahydro-2H-pyran-2-yl)-N-(1-(3,4,5-trimethoxyphenyl)-1H-imidazol-4-yl)-1H-pyrazolo[3,4-d]pyrimidin-4-amine (326b)

Compound 326b was prepared from 4,6-dichloro-1-(tetrahydro-2H-pyran-2-yl)-1H-pyrazolo[3,4-d]pyrimidine (326a) (500 mg, 1.83 mmol; prepared according to the procedure reported by Su, Qibin et al; in Journal of Medicinal Chemistry, 57(1), 144-158; 2014) in 2-Propanol (20 mL) using DIPEA (0.96 mL, 5.49 mmol) and 1-(3,4,5-trimethoxyphenyl)-1H-imidazol-4-amine (57a) (479 mg, 1.92 mmol, free base) according to the procedure reported in Scheme 1. This gave after workup 6-chloro-1-(tetrahydro-2H-pyran-2-yl)-N-(1-(3,4,5-trimethoxyphenyl)-1H-imidazol-4-yl)-1H-pyrazolo[3,4-d]pyrimidin-4-amine (326b) (660 mg, 74% yield) as a brown solid; $^1$H NMR (300 MHz, DMSO-$d_6$) δ 11.46 (s, 1H), 8.50 (s, 1H), 8.19 (s, 1H), 7.88 (s, 1H), 6.93 (s, 2H), 5.79 (d, J=10.0 Hz, 1H), 4.03-3.92 (m, 2H), 3.87 (s, 6H), 3.69 (s, 3H), 2.47-2.23 (m, 1H), 1.86 (m, 3H), 1.65-1.38 (m, 2H); MS (ES+): 486.3 (M+1), (ES−): 484.3 (M−1).

Step-2: Preparation of ((2S)-1-(1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidin-2-yl)methanol (326c)

Compound 326c was prepared according to the procedure reported in step-2 of Scheme 76 from 6-chloro-1-(tetrahydro-2H-pyran-2-yl)-N-(1-(3,4,5-trimethoxyphenyl)-1H-imidazol-4-yl)-1H-pyrazolo[3,4-d]pyrimidin-4-amine (326b) (200 mg, 0.41 mmol), (S)-pyrrolidin-2-ylmethanol (0.16 mL, 1.65 mmol) and DIPEA (0.43 mL, 2.47 mmol) in NMP (3 mL). This gave after workup and purification by flash column chromatography [(silica gel, 12 g) eluting with DMA-80 in chloroform 0 to 50%] ((2S)-1-(1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidin-2-yl)methanol (326c) (128 mg, 57% yield) as a white solid; $^1$H NMR (300 MHz, DMSO-$d_6$, mixture of rotamers) δ 10.57 (2s, 1H), 8.22 (s, 2H), 8.13-7.81 (2s, 1H), 6.95 (s, 2H), 5.84-5.52 (m, 1H), 4.98 (2s, 1H), 4.52-4.07 (2s, 1H), 3.99-3.90 (m, 1H), 3.87 (s, 6H), 3.85-3.71 (m, 1H), 3.68 (s, 3H), 3.64-3.38 (m, 4H), 2.46-2.32 (m, 1H), 1.88 (m, 6H), 1.54 (m, 2H); MS (ES+): 551.4 (M+1), 573.3 (M+Na); MS (ES−): 549.4 (M−1). HPLC purity: 96.22%.

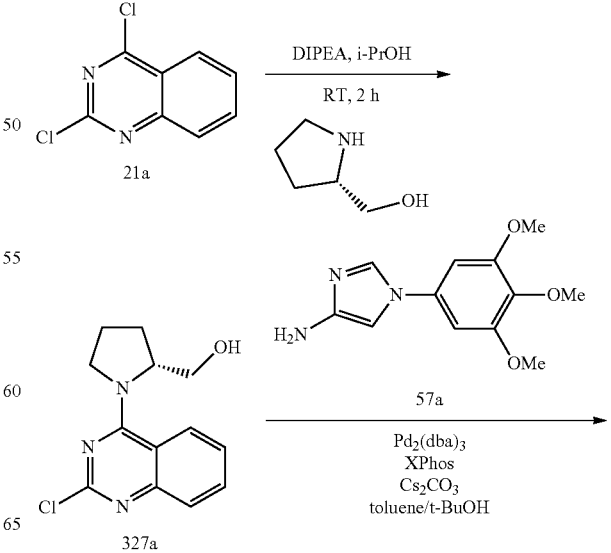

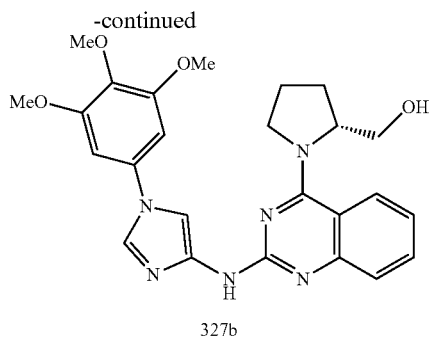

327b

Preparation of (R)-(1-(2-((1-(3,4,5-trimethoxyphenyl)-1H-imidazol-4-yl)amino)quinazolin-4-yl)pyrrolidin-2-yl)methanol (327b)

Step-1: Preparation of (R)-(1-(2-chloroquinazolin-4-yl)pyrrolidin-2-yl)methanol (327a)

Compound 327a was prepared from 2,4-dichloroquinazoline (21a) (1 g, 5.02 mmol) in 2-Propanol (10 mL) using (R)-pyrrolidin-2-ylmethanol (0.5 mL, 5.02 mmol), DIPEA (2.63 mL, 15.07 mmol) according to the procedure reported in step-1 of Scheme 96. This gave after workup and purification by flash column chromatography [silica gel, (12 g) eluting with DCM and methanol (0 to 30%)] (R)-(1-(2-chloroquinazolin-4-yl)pyrrolidin-2-yl)methanol (327a) (230 mg, 17% yield) as a yellow solid; MS (ES+): 264.3 (M+1); (ES−) 298.2 (M+Cl)

Step-2: Preparation of (R)-(1-(2-((1-(3,4,5-trimethoxyphenyl)-1H-imidazol-4-yl)amino)quinazolin-4-yl)pyrrolidin-2-yl)methanol (327b)

Compound 327b was prepared from (R)-(1-(2-chloroquinazolin-4-yl)pyrrolidin-2-yl)methanol (327a) (140 mg, 0.53 mmol), 1-(3,4,5-trimethoxyphenyl)-1H-imidazol-4-amine (57a) (132 mg, 0.53 mmol), dicyclohexyl(2',4',6'-triisopropylbiphenyl-2-yl)phosphine (XPhos, 152 mg, 0.32 mmol), cesium carbonate (519 mg, 1.59 mmol), Pd$_2$(dba)$_3$ (146 mg, 0.16 mmol) in Toluene (15 mL) and t-Butanol (5 mL) according to the procedure reported in step-3 of Scheme 101. This gave after workup and purification by flash column chromatography [silica gel, (12 g) eluting with DMA-80 in CH$_2$Cl$_2$ from 0 to 100%], reverse phase flash column chromatography [(silica gel C-18, 24 g) eluting with acetonitrile and 0.1% HCl in water] followed by lyophilization (R)-(1-(2-((1-(3,4,5-trimethoxyphenyl)-1H-imidazol-4-yl)amino)quinazolin-4-yl)pyrrolidin-2-yl)methanol (327b) (35 mg, 14% yield) HCl salt as a yellow solid; $^1$H NMR (300 MHz, DMSO-d$_6$) δ 13.40 (s, 1H), 10.61 (s, 1H), 8.50 (s, 1H), 8.30 (d, J=8.5 Hz, 1H), 7.86 (d, J=7.4 Hz, 1H), 7.81 (d, J=8.0 Hz, 1H), 7.67-7.50 (m, 1H), 7.49-7.38 (m, 1H), 7.01 (s, 2H), 4.98-4.72 (m, 1H), 4.29-4.04 (m, 1H), 3.88 (s, 6H), 3.81-3.72 (m, 3H), 3.68 (s, 3H), 2.22-1.88 (m, 4H); MS (ES+): 477.4 (M+1), 499.3 (M+Na); MS (ES−): 511.4 (M+Cl). HPLC purity: 94.57%.

Scheme 328

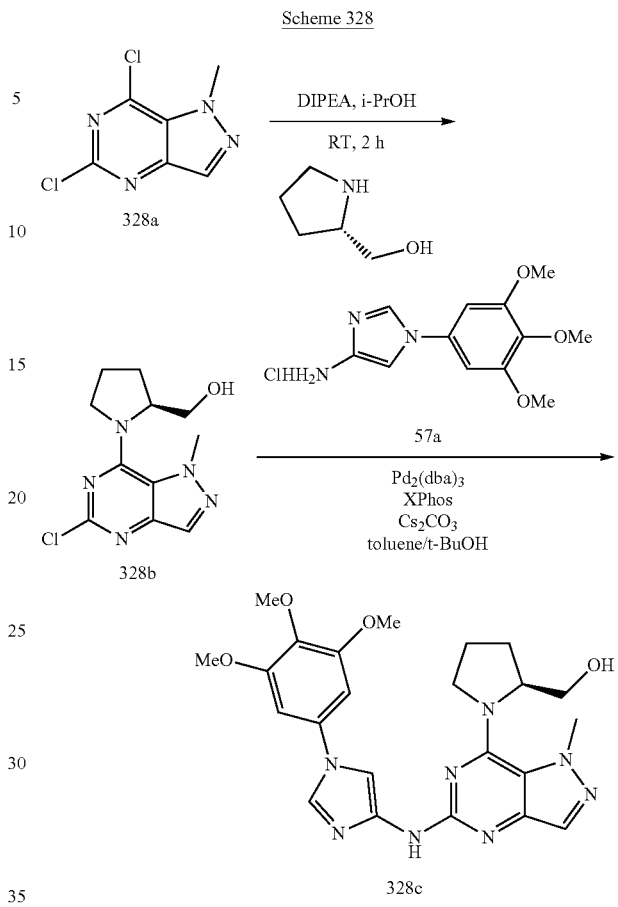

Preparation of (S)-(1-(1-methyl-5-((1-(3,4,5-trimethoxyphenyl)-1H-imidazol-4-yl)amino)-1H-pyrazolo[4,3-d]pyrimidin-7-yl)pyrrolidin-2-yl)methanol (328c)

Step-1: Preparation of (S)-(1-(5-chloro-1-methyl-1H-pyrazolo[4,3-d]pyrimidin-7-yl)pyrrolidin-2-yl)methanol (328b)

Compound 328b was prepared from 5,7-dichloro-1-methyl-1H-pyrazolo[4,3-d]pyrimidine (328a) (0.2 g, 0.99 mmol; CAS #939979-32-5) in 2-Propanol (10 mL) using (S)-pyrrolidin-2-ylmethanol (0.1 mL, 0.99 mmol), DIPEA (0.52 mL, 2.96 mmol) according to the procedure reported in step-1 of Scheme 96. This gave after workup and purification by flash column chromatography [silica gel, (12 g) eluting with DCM and methanol (0 to 30%)] (S)-(1-(5-chloro-1-methyl-1H-pyrazolo[4,3-d]pyrimidin-7-yl)pyrrolidin-2-yl)methanol (328b) (252 mg, 96% yield) as a white solid; MS (ES+): 268.2 (M+1); (ES−) 266.2 (M−1).

Step-2: Preparation of (S)-(1-(1-methyl-5-((1-(3,4,5-trimethoxyphenyl)-1H-imidazol-4-yl)amino)-1H-pyrazolo[4,3-d]pyrimidin-7-yl)pyrrolidin-2-yl)methanol (328c)

Compound 328c was prepared from (S)-(1-(5-chloro-1-methyl-1H-pyrazolo[4,3-d]pyrimidin-7-yl)pyrrolidin-2-yl)methanol (328b) (250 mg, 0.934 mmol), 1-(3,4,5- trimethoxyphenyl)-1H-imidazol-4-amine (57a) (233 mg, 0.93 mmol), dicyclohexyl(2',4',6'-triisopropylbiphenyl-2-yl)phosphine (XPhos, 267 mg, 0.56 mmol), cesium carbonate (913 mg, 2.8 mmol), Pd$_2$(dba)$_3$ (257 mg, 0.28 mmol) in Toluene (20 mL) and t-Butanol (10 mL) according to the procedure reported in step-3 of Scheme 101. This gave after workup and purification by flash column chromatography [silica gel, (12 g) eluting with DMA-80 in CH$_2$Cl$_2$ from 0 to 50%], reverse phase flash column chromatography [(silica gel C-18, 24 g) eluting with acetonitrile and 0.1% HCl in water] followed by lyophilization (S)-(1-(1-methyl-5-((1-(3,4,5-trimethoxyphenyl)-1H-imidazol-4-yl)amino)-1H-pyrazolo[4,3-d]pyrimidin-7-yl)pyrrolidin-2-yl)methanol (328c) (48 mg, 11% yield) HCl salt as a white solid; $^1$H NMR (300 MHz, DMSO-d$_6$) δ 10.78 (s, 1H), 8.36 (s, 1H), 7.96 (s, 1H), 7.68 (s, 1H), 6.97 (d, J=2.4 Hz, 2H), 4.90-4.60 (m, 1H), 4.21 (s, 3H), 4.12-4.00 (m, 1H), 3.99-3.90 (m, 1H), 3.88 (d, J=2.3 Hz, 6H), 3.85-3.69 (m, 1H), 3.68 (d, J=2.3 Hz, 3H), 3.67-3.37 (m, 1H), 2.18-1.91 (m, 4H), 1.87-1.69 (m, 1H); MS (ES+): 481.3 (M+1), 503.3 (M+Na); MS (ES−): 515.3 (M+Cl). HPLC purity: 98.00%.

phy [(silica gel C-18, 24 g) eluting with acetonitrile and 0.1% HCl in water] to afford (S)-(1-(4-((1-(3,4,5-trimethoxyphenyl)-1H-imidazol-4-yl)amino)-1H-pyrazolo[3,4-d]pyrimidin-6-yl)pyrrolidin-2-yl)methanol (329a) (34 mg, 80% yield) HCl salt as a white solid; $^1$H NMR (300 MHz, DMSO-d$_6$; mixture or rotamers) δ 12.63 (2s, 2H), 12.07 (s, 1H), 8.71 (s, 1H), 8.47 (s, 1H), 7.98 (2s, 1H), 6.98 (s, 2H), 4.69-4.27 (2m, 1H), 3.87 (s, 6H), 3.81-3.71 (m, 1H), 3.68 (s, 3H), 3.62-3.40 (m, 2H), 2.23-1.76 (m, 4H); MS (ES+): 467.3 (M+1); MS (ES−): 501.3 (M+Cl). HPLC purity: 92.77%.

Scheme 330

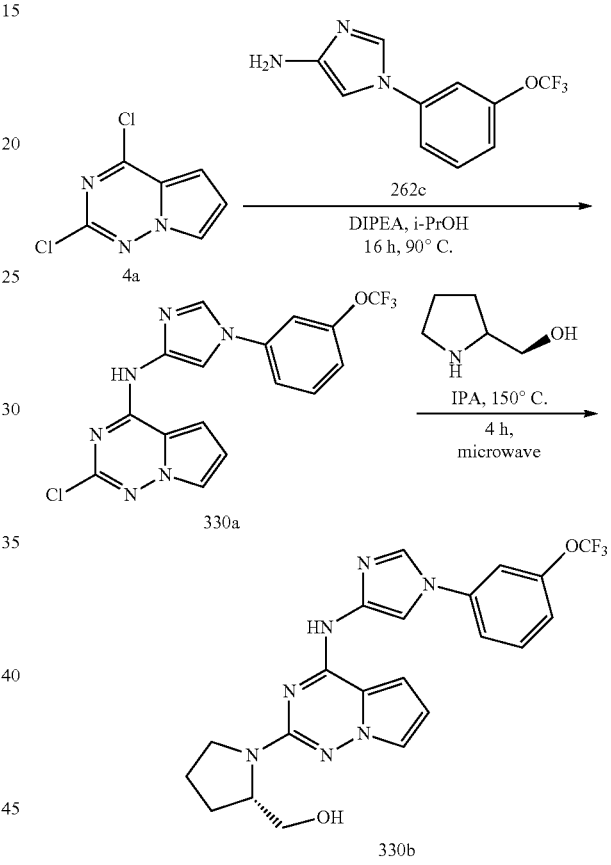

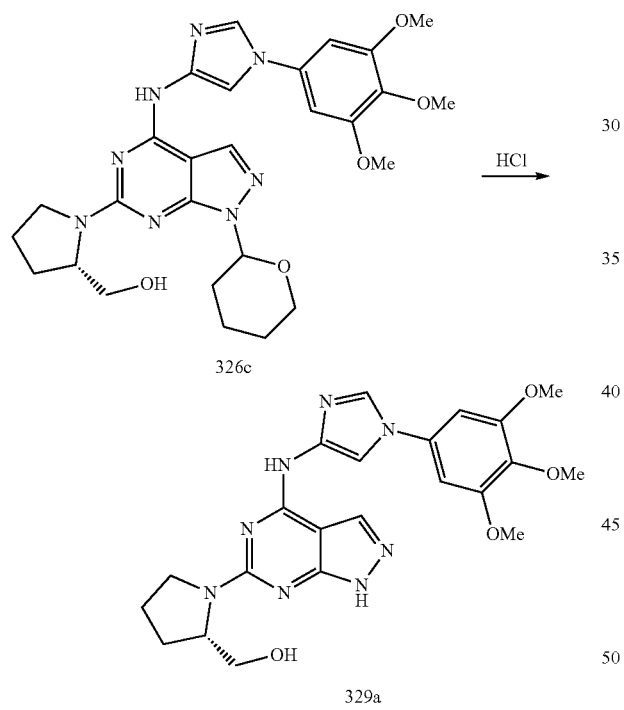

Scheme 329

326c

329a

Preparation of (S)-(1-(4-((1-(3,4,5-trimethoxyphenyl)-1H-imidazol-4-yl)amino)-1H-pyrazolo[3,4-d]pyrimidin-6-yl)pyrrolidin-2-yl)methanol (329a)

To a solution of ((2S)-1-(1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidin-2-yl)methanol (326c) (50 mg, 0.09 mmol) in MeOH (5 mL) was added hydrogen chloride (3 M in MeOH) (3.31 mg, 0.09 mmol) and heated at 90° C. for 2 h. The reaction mixture was concentrated in vacuum, purified by flash column chromatography [silica gel (12 g), eluting with DMA80 in DCM from 0-50%] and reverse phase flash column chromatogra- Preparation of (S)-(1-(4-((1-(3-(trifluoromethoxy)phenyl)-1H-imidazol-4-yl)amino)pyrrolo[2,1-f][1,2,4]triazin-2-yl)pyrrolidin-2-yl)methanol (330b)

Step-1: Preparation of 2-chloro-N-(1-(3-(trifluoromethoxy)phenyl)-1H-imidazol-4-yl)pyrrolo[2,1-f][1,2,4]triazin-4-amine (330a)

Compound 330a was prepared from 2,4-dichloropyrrolo[2,1-f][1,2,4]triazine (4a) (350 mg, 1.86 mmol) in 2-Propanol (10 mL) using DIPEA (0.98 mL, 5.58 mmol) and 1-(3-(trifluoromethoxy)phenyl)-1H-imidazol-4-amine (262c) (453 mg, 1.86 mmol) according to the procedure reported in Scheme 1. This gave after workup 2-chloro-N-(1-(3-(trifluoromethoxy)phenyl)-1H-imidazol-4-yl)pyrrolo[2,1-f][1,2,4]triazin-4-amine (330a) (0.29 g, 39% yield) as a tan solid; $^1$H NMR (300 MHz, DMSO-d$_6$) δ 11.37 (s, 1H), 8.37 (d, J=1.6 Hz, 1H), 7.97 (d, J=1.6 Hz, 1H), 7.79 (dd, J=2.7, 1.6 Hz, 2H), 7.77-7.66 (m, 2H), 7.42 (dt, J=6.6, 2.4 Hz, 2H), 6.73 (dd, J=4.5, 2.6 Hz, 1H); $^{19}$F NMR (282 MHz, DMSO-d$_6$) δ −56.76.

Step-2: Preparation of (S)-(1-(4-((1-(3-(trifluoromethoxy)phenyl)-1H-imidazol-4-yl)amino)pyrrolo[2,1-f][1,2,4]triazin-2-yl)pyrrolidin-2-yl)methanol (330b)

Compound 330b was prepared according to the procedure reported in Scheme 2 from 2-chloro-N-(1-(3-(trifluoromethoxy)phenyl)-1H-imidazol-4-yl)pyrrolo[2,1-f][1,2,4]triazin-4-amine (330a) (250 mg, 0.63 mmol) and (S)-pyrrolidin-2-ylmethanol (0.25 mL, 2.53 mmol) in 2-Propanol (3 mL). This gave after workup and purification by flash column chromatography [(silica gel, 25 g) eluting DMA-80 in chloroform] compound 330b as a free base. The free base was re-dissolved in acetonitrile (10 mL), HCl (1 N, 10 mL) and freeze-dried to afford (S)-(1-(4-((1-(3-(trifluoromethoxy)phenyl)-1H-imidazol-4-yl)amino)pyrrolo[2,1-f][1,2,4]triazin-2-yl)pyrrolidin-2-yl)methanol (330b) (43 mg, 15% yield) HCl salt as a white solid; $^{1}$H NMR (300 MHz, DMSO-d$_6$) δ 10.59 (s, 1H, D$_2$O exchangeable), 8.38 (s, 1H), 8.01 (s, 1H), 7.84 (d, J=6.0 Hz, 2H), 7.63 (t, J=8.4 Hz, 1H), 7.40 (t, J=2.1 Hz, 1H), 7.36 (d, J=8.5 Hz, 1H), 7.15 (dd, J=4.4, 1.7 Hz, 1H), 6.40 (dd, J=4.5, 2.4 Hz, 1H), 4.25-4.12 (m, 1H), 3.80-3.66 (m, 1H), 3.66-3.48 (m, 1H), 3.36-3.21 (m, 2H), 2.12-1.77 (m, 4H); $^{19}$F NMR (282 MHz, DMSO-d$_6$) δ −56.77; MS (ES+): 460.3 (M+1), 482.2 (M+Na), (ES−): 458.4 (M−1); HPLC purity: 99.17%.

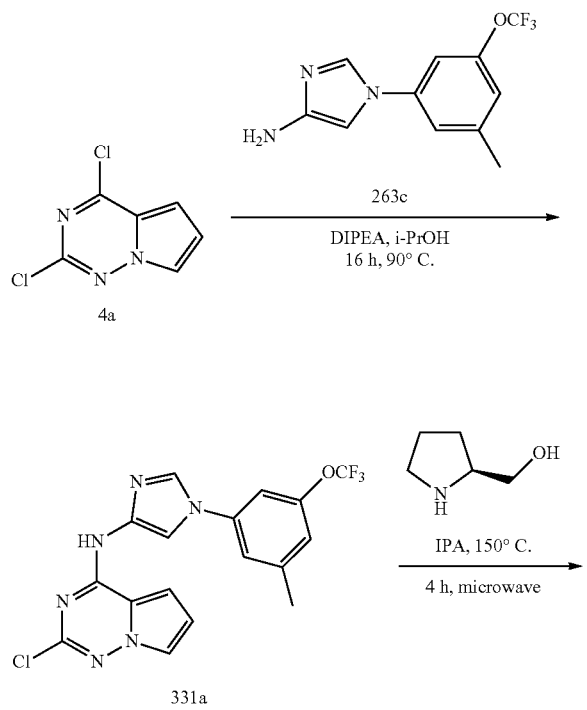

Scheme 331

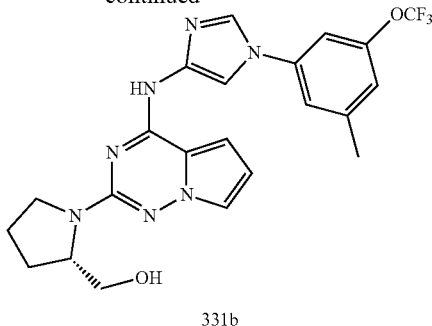

331b

Preparation of (S)-(1-(4-((1-(3-methyl-5-(trifluoromethoxy)phenyl)-1H-imidazol-4-yl)amino)pyrrolo[2,1-f][1,2,4]triazin-2-yl)pyrrolidin-2-yl)methanol (331b)

Step-1: Preparation of 2-chloro-N-(1-(3-methyl-5-(trifluoromethoxy)phenyl)-1H-imidazol-4-yl)pyrrolo[2,1-f][1,2,4]triazin-4-amine (331a)

Compound 331a was prepared from 2,4-dichloropyrrolo[2,1-f][1,2,4]triazine (4a) (285 mg, 1.52 mmol) in 2-Propanol (10 mL) using DIPEA (0.79 mL, 4.55 mmol) and 1-(3-methyl-5-(trifluoromethoxy)phenyl)-1H-imidazol-4-amine (263c) (0.93 g, 1.52 mmol) according to the procedure reported in Scheme 1. This gave after workup 2-chloro-N-(1-(3-methyl-5-(trifluoromethoxy)phenyl)-1H-imidazol-4-yl)pyrrolo[2,1-f][1,2,4]triazin-4-amine (331a) (312 mg, 50% yield) as a tan solid; $^{1}$H NMR (300 MHz, DMSO-d$_6$) δ 11.34 (s, 1H), 8.32 (d, J=1.6 Hz, 1H), 7.93 (d, J=1.6 Hz, 1H), 7.78 (dd, J=2.6, 1.5 Hz, 1H), 7.58 (s, 1H), 7.56 (s, 1H), 7.40 (d, J=4.5 Hz, 1H), 7.25 (d, J=2.2 Hz, 1H), 6.72 (dd, J=4.5, 2.6 Hz, 1H), 2.45 (s, 3H); $^{19}$F NMR (282 MHz, DMSO-d$_6$) δ −56.65.

Step-2: Preparation of (S)-(1-(4-((1-(3-methyl-5-(trifluoromethoxy)phenyl)-1H-imidazol-4-yl)amino)pyrrolo[2,1-f][1,2,4]triazin-2-yl)pyrrolidin-2-yl)methanol (331b)

Compound 331b was prepared according to the procedure reported in Scheme 2 from 2-chloro-N-(1-(3-methyl-5-(trifluoromethoxy)phenyl)-1H-imidazol-4-yl)pyrrolo[2,1-f][1,2,4]triazin-4-amine (331a) (250 mg, 0.61 mmol) and (S)-pyrrolidin-2-ylmethanol (0.24 mL, 2.45 mmol) in 2-Propanol (3 mL). This gave after workup and purification by flash column chromatography [(silica gel, 25 g) eluting DMA 80 in chloroform] compound 331b as a free base. The free base was re-dissolved in acetonitrile (10 mL), HCl (1 N, 10 mL) and freeze-dried to afford (S)-(1-(4-((1-(3-methyl-5-(trifluoromethoxy)phenyl)-1H-imidazol-4-yl)amino)pyrrolo[2,1-f][1,2,4]triazin-2-yl)pyrrolidin-2-yl)methanol (331b) (125 mg, 43% yield) HCl salt as a white solid; $^{1}$H NMR (300 MHz, DMSO-d$_6$) δ 10.64 (s, 1H, D$_2$O exchangeable), 8.44 (d, J=1.5 Hz, 1H), 8.01 (d, J=1.6 Hz, 1H), 7.72 (s, 1H), 7.64 (s, 1H), 7.45-7.37 (m, 1H), 7.24-7.19 (m, 1H), 7.15 (dd, J=4.5, 1.7 Hz, 1H), 6.41 (dd, J=4.4, 2.4 Hz, 1H), 4.26-4.12 (m, 1H), 3.76 (dd, J=10.1, 3.6 Hz, 1H), 3.48 (d, J=7.6 Hz, 1H), 3.43-3.27 (m, 2H), 2.42 (s, 3H), 2.13-1.80 (m, 4H); $^{19}$F NMR (282 MHz, DMSO-d$_6$) δ −56.67; MS (ES+): 474.3 (M+1), 496.3 (M+Na), (ES−): 508.3 (M+Cl); HPLC purity: 98.18%.

Scheme 332

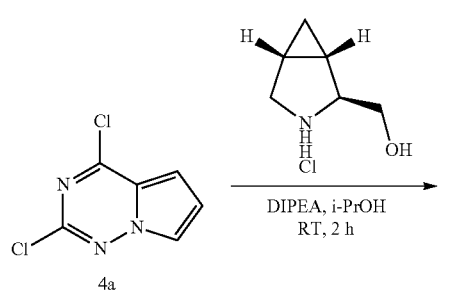

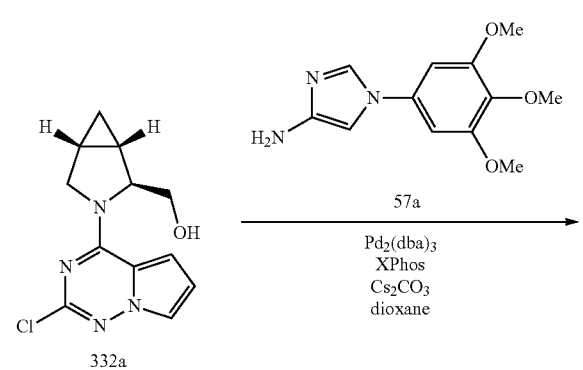

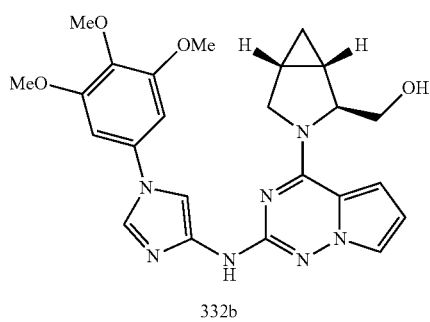

Preparation of ((1S,2S,5R)-3-(2-((1-(3,4,5-trimethoxyphenyl)-1H-imidazol-4-yl)amino)pyrrolo[2,1-f][1,2,4]triazin-4-yl)-3-azabicyclo[3.1.0]hexan-2-yl)methanol (332b)

Step-1: Preparation of ((1S,2S,5R)-3-(2-chloropyrrolo[2,1-f][1,2,4]triazin-4-yl)-3-azabicyclo[3.1.0]hexan-2-yl)methanol (332a)

Compound 324a was prepared from 2,4-dichloropyrrolo[2,1-f][1,2,4]triazine (4a) (113 mg, 0.6 mmol) in 2-Propanol (4 mL) using (1S,2S,5R)-3-azabicyclo[3.1.0]hexan-2-yl-methanol hydrochloride (90 mg, 0.6 mmol, CAS #1818847-65-2), DIPEA (0.32 mL, 1.81 mmol) according to the procedure reported in step-1 of Scheme 96. This gave after work ((1S,2S,5R)-3-(2-chloropyrrolo[2,1-f][1,2,4]triazin-4-yl)-3-azabicyclo[3.1.0]hexan-2-yl)methanol (332a) (117 mgs, 74% yield) as a white solid; $^1$H NMR (300 MHz, DMSO-$d_6$) δ 7.74-7.68 (m, 1H), 6.98-6.90 (m, 1H), 6.67 (dd, J=4.6, 2.6 Hz, 1H), 4.93 (t, J=5.8 Hz, 1H), 4.50 (dd, J=5.6, 3.1 Hz, 1H), 4.14-4.00 (m, 2H), 3.76-3.48 (m, 2H), 1.84-1.58 (m, 2H), 0.78-0.66 (m, 1H), 0.20-0.05 (m, 1H).

Step-2: Preparation of ((1S,2S,5R)-3-(2-((1-(3,4,5-trimethoxyphenyl)-1H-imidazol-4-yl)amino)pyrrolo[2,1-f][1,2,4]triazin-4-yl)-3-azabicyclo[3.1.0]hexan-2-yl)methanol (332b)

Compound 332b was prepared from ((1S,2S,5R)-3-(2-chloropyrrolo[2,1-f][1,2,4]triazin-4-yl)-3-azabicyclo[3.1.0]hexan-2-yl)methanol (332a) (110 mg, 0.42 mmol), 1-(3,4,5-trimethoxyphenyl)-1H-imidazol-4-amine (57a) (129 mg, 0.52 mmol, free base), dicyclohexyl(2',4',6'-triisopropylbiphenyl-2-yl)phosphine (XPhos, 89 mg, 0.19 mmol), cesium carbonate (406 mg, 1.25 mmol), Pd$_2$(dba)$_3$ (57 mg, 0.06 mmol) dioxane (15 mL) according to the procedure reported in step-3 of Scheme 101. This gave after workup and purification by flash column chromatography [silica gel, (24 g) eluting with DMA-80 in CH$_2$Cl$_2$ from 0 to 50%], reverse phase flash column chromatography [(silica gel C-18, 24 g) eluting with acetonitrile and 0.1% HCl in water] followed by lyophilization ((1S,2S,5R)-3-(2-((1-(3,4,5-trimethoxyphenyl)-1H-imidazol-4-yl)amino)pyrrolo[2,1-f][1,2,4]triazin-4-yl)-3-azabicyclo[3.1.0]hexan-2-yl)methanol (332b) (45 mg, 23% yield) HCl salt as a white solid; $^1$H NMR (300 MHz, DMSO-$d_6$) δ 9.47 (d, J=17.2 Hz, 1H, D$_2$O exchangeable), 9.14 (s, 1H), 7.85 (s, 1H), 7.62 (s, 1H), 7.11 (s, 2H), 6.83 (s, 1H), 6.54 (s, 1H), 4.63 (s, 1H), 4.54-4.16 (m, 1H), 4.09 (d, J=10.7 Hz, 1H), 3.90 (s, 6H), 3.71 (s, 3H), 3.69-3.35 (m, 2H), 1.96-1.55 (m, 2H), 0.83-0.67 (m, 1H), 0.21-0.05 (m, 1H); MS (ES+): 478.3 (M+1), 500.3 (M+Na), (ES−): 512.3 (M+Cl). HPLC purity: 99.35%.

Scheme 333

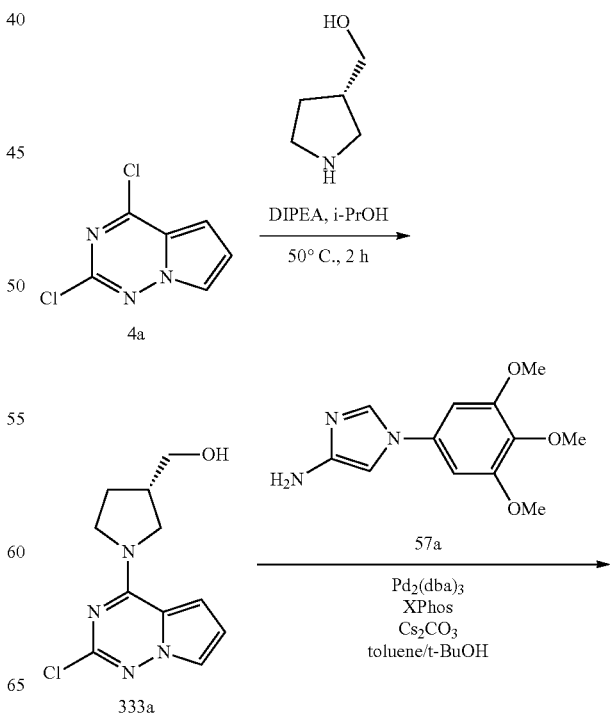

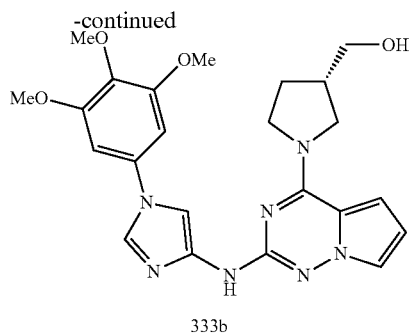

333b

Preparation of (S)-(1-(2-((1-(3,4,5-trimethoxyphenyl)-1H-imidazol-4-yl)amino)pyrrolo[2,1-f][1,2,4]triazin-4-yl)pyrrolidin-3-yl)methanol (333b)

Step-1: Preparation of (S)-(1-(2-chloropyrrolo[2,1-f][1,2,4]triazin-4-yl)pyrrolidin-3-yl)methanol (333a)

Compound 333a was prepared from 2,4-dichloropyrrolo[1,2-f][1,2,4]triazine (4a) (500 mg, 2.66 mmol) in 2-Propanol (10 mL) using (S)-pyrrolidin-3-ylmethanol (269 mg, 2.66 mmol) and DIPEA (1.39 mL, 7.98 mmol) according to the procedure reported in step-1 of Scheme 96. This gave after workup and purification by flash column chromatography [silica gel (12 g), EtOAc in hexane from 0-50%] (S)-(1-(2-chloropyrrolo[2,1-f][1,2,4]triazin-4-yl)pyrrolidin-3-yl)methanol (333a) (577 mg, 86% yield) as a white semi-solid; $^1$H NMR (300 MHz, DMSO-$d_6$) δ 7.70 (s, 1H), 7.02-6.79 (m, 1H), 6.73-6.55 (m, 1H), 4.90-4.63 (m, 1H, $D_2O$ exchangeable), 4.15-3.86 (m, 2H), 3.81-3.58 (m, 2H), 3.50-3.40 (m, 2H), 2.44-2.24 (m, 1H), 2.21-1.59 (m, 2H); MS (ES−): 251.1 (M−1), 287.1 (M+Cl).

Step-2: Preparation of (S)-(1-(2-((1-(3,4,5-trimethoxyphenyl)-1H-imidazol-4-yl)amino)pyrrolo[2,1-f][1,2,4]triazin-4-yl)pyrrolidin-3-yl)methanol (333b)

Compound 333b was prepared from (S)-(1-(2-chloropyrrolo[2,1-f][1,2,4]triazin-4-yl)pyrrolidin-3-yl)methanol (333a) (550 mg, 2.18 mmol), 1-(3,4,5-trimethoxyphenyl)-1H-imidazol-4-amine (57a) (651 mg, 2.61, free base), dicyclohexyl(2',4',6'-triisopropylbiphenyl-2-yl)phosphine (XPhos, 415 mg, 0.87 mmol), cesium carbonate (709 mg, 2.18 mmol) and $Pd_2(dba)_3$ (299 mg, 0.33 mmol) in toluene/t-BuOH (40 mL, Ratio: 3:2) according to the procedure reported in step-3 of Scheme 101. This gave after workup and purification by flash column chromatography [silica gel (40 g), eluting with DM80 in DCM 0-100%], followed by reverse phase column chromatography [(silica gel C-18, 50 g) eluting with acetonitrile and 0.1% HCl in water] (S)-(1-(2-((1-(3,4,5-trimethoxyphenyl)-1H-imidazol-4-yl)amino)pyrrolo[2,1-f][1,2,4]triazin-4-yl)pyrrolidin-3-yl)methanol (333b) (325 mg, 32% yield) HCl salt as a white solid. $^1$H NMR (300 MHz, DMSO-$d_6$) δ 9.65 (s, 1H, $D_2O$ exchangeable), 9.27 (s, 1H), 7.91 (d, J=1.8 Hz, 1H, $D_2O$ exchangeable), 7.66 (t, J=1.9 Hz, 1H), 7.14 (s, 2H), 6.89 (d, J=4.0 Hz, 1H), 6.56 (d, J=3.8 Hz, 1H), 4.04 (s, 9H), 3.76-3.63 (m, 4H), 3.59-3.39 (m, 2H), 2.48-2.31 (m, 1H), 2.22-1.67 (m, 2H); MS (ES+): 466.3 (M+1), (ES−): 500.3 (M+Cl); HPLC purity: 98.71%.

Scheme 334

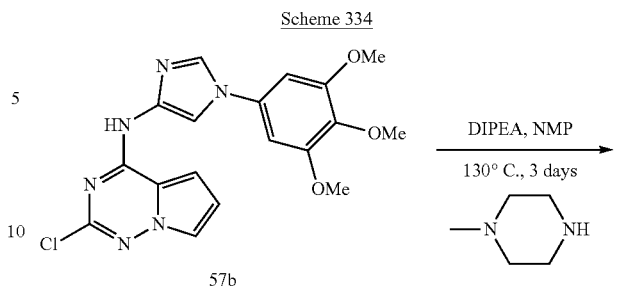

334a

Preparation of 2-(4-methylpiperazin-1-yl)-N-(1-(3,4,5-trimethoxyphenyl)-1H-imidazol-4-yl)pyrrolo[2,1-f][1,2,4]triazin-4-amine (334a)

Compound 334a was prepared according to the procedure reported in step-2 of Scheme 76 from 2-chloro-N-(1-(3,4,5-trimethoxyphenyl)-1H-imidazol-4-yl)pyrrolo[2,1-f][1,2,4]triazin-4-amine (57b) (200 mg, 0.5 mmol), 1-methylpiperazine (0.22 mL, 2.0 mmol) and DIPEA (0.52 mL, 2.99 mmol) in NMP (3 mL). This gave after workup and purification by flash chromatography (silica gel (12 g), eluting with DMA-80 in DCM from 0-50%) followed by reverse column chromatography [(silica gel C18, 20 g), eluting with acetonitrile and 0.1% HCl in water from 0-100%] 2-(4-methylpiperazin-1-yl)-N-(1-(3,4,5-trimethoxyphenyl)-1H-imidazol-4-yl)pyrrolo[2,1-f][1,2,4]triazin-4-amine (334a) (152 mg, 66% yield) HCl salt as a yellow solid; $^1$H NMR (300 MHz, DMSO-$d_6$): δ 11.35 (s, 1H), 11.13 (s, 1H), 9.00 (s, 1H), 8.06 (t, J=1.7 Hz, 1H), 7.55 (dt, J=2.5, 1.6 Hz, 1H), 7.23 (dd, J=4.4, 1.7 Hz, 1H), 7.10 (d, J=1.5 Hz, 2H), 6.55 (dd, J=4.5, 2.4 Hz, 1H), 4.42 (d, J=14.0 Hz, 2H), 3.89 (s, 6H), 3.70 (s, 3H), 3.38 (m, 4H), 3.19-2.97 (m, 2H), 2.75 (d, J=4.4 Hz, 3H). MS (ES+): 465.4 (M+1), 487.4 (M+Na); MS (ES−): 463.1 (M−1), 499.4 (M+Cl). HPLC purity: 98.64%.

Scheme 335

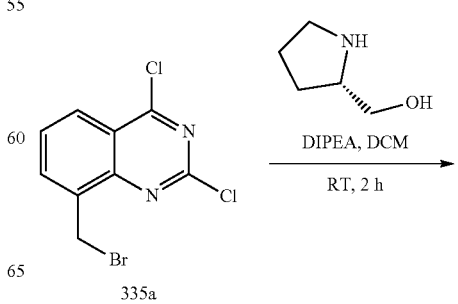

335a

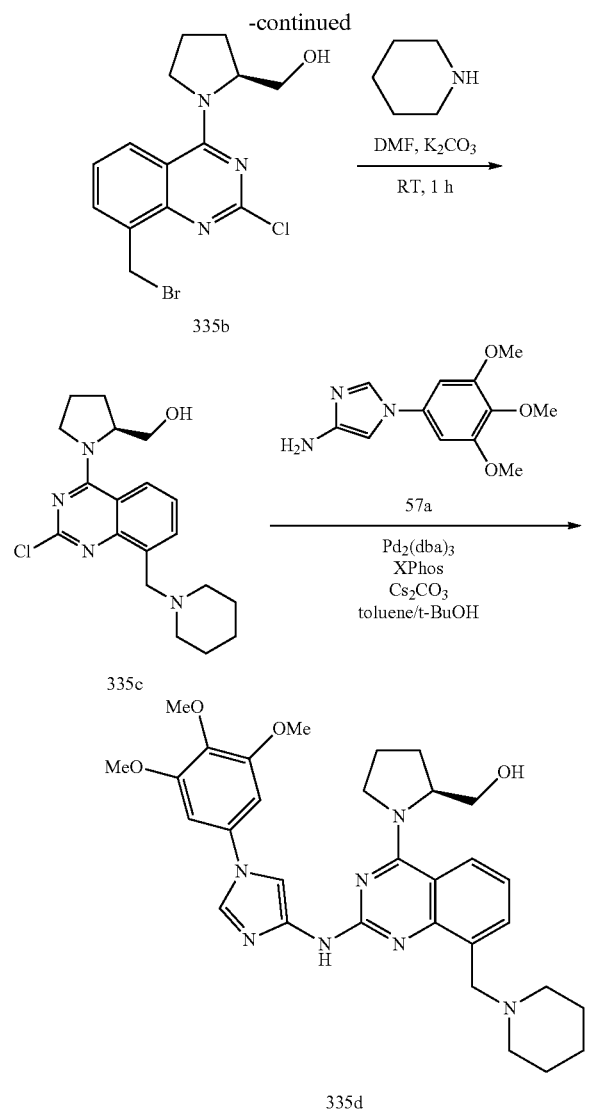

Preparation of (S)-(1-(8-(piperidin-1-ylmethyl)-2-((1-(3,4,5-trimethoxyphenyl)-1H-imidazol-4-yl)amino)quinazolin-4-yl)pyrrolidin-2-yl)methanol (335d)

Step-1: Preparation of (S)-(1-(8-(bromomethyl)-2-chloroquinazolin-4-yl)pyrrolidin-2-yl)methanol (335b)

Compound 335b was prepared from 8-(bromomethyl)-2,4-dichloroquinazoline (335a) (3.0 g, 10.27 mmol; CAS #: 192218-38-5; Prepared according to the procedure reported by Holmes, Jane L. et al; in Synthesis, 48(8), 1226-1234; 2016) in DCM (30 mL) using (S)-pyrrolidin-2-ylmethanol (0.5 g, 4.95 mmol) and DIPEA (3.9 g, 30.17 mmol) according to the procedure reported in step-1 of Scheme 96. This gave after workup and purification by flash column chromatography (silica gel, eluting with 0-100% EtOAc in n-hexane) (S)-(1-(8-(bromomethyl)-2-chloroquinazolin-4-yl)pyrrolidin-2-yl)methanol (335b) (1.4 g 38%) as a yellow solid; $^1$H NMR (300 MHz, DMSO-$d_6$): δ 8.22 (d, J=8.7, 1H), 7.92 (d, J=7.0, 1H), 7.43-7.41 (m, 1H), 5.74 (s, 1H), 5.03 (s, 2H), 4.56 (m, 1H), 4.15-3.82 (m, 2H), 3.76-3.56 (m, 2H), 2.03 (m, 3H), 1.85 (m, 1H).

Step-2: Preparation of (S)-(1-(2-chloro-8-(piperidin-1-ylmethyl)quinazolin-4-yl)pyrrolidin-2-yl)methanol (335c)

To a stirred solution of (S)-(1-(8-(bromomethyl)-2-chloroquinazolin-4-yl)pyrrolidin-2-yl)methanol (335b) (1.4 g, 3.92 mmol) in DMF (30 mL) at room temperature were added piperidine (0.4 g, 4.69 mmol) and $K_2CO_3$ (1.6 g, 11.55 mmol). The reaction mixture was stirred for 1 h at room temperature, quenched with water (300 mL) and extracted with EtOAc (3×100 mL). The combined organic extracts were concentrated and purified through silica gel column eluting with 10% MeOH in DCM to furnish (S)-(1-(2-chloro-8-(piperidin-1-ylmethyl)quinazolin-4-yl)pyrrolidin-2-yl)methanol (335c) (220 mg, 16%) as a yellow solid; $^1$H NMR (300 MHz, DMSO-$d_6$): δ 8.18 (d, J=8.0 Hz, 1H), 7.88 (d, J=7.2 Hz, 1H), 7.47 (m, 1H), 4.86 (d, J=5.8 Hz, 1H), 4.65-4.47 (m, 1H), 3.99 (m, 4H), 3.63 (m, 2H), 2.56 (m, 3H), 2.03 (d, m, 3H), 1.82 (m, 1H), 1.57 (m, 4H), 1.46-1.36 (m, 2H), 1.23 (m, 1H); MS (ES+): 361.3 (M+1), MS (ES−): 359.2 (M−1).

Step-3: Preparation of (S)-(1-(8-(piperidin-1-ylmethyl)-2-((1-(3,4,5-trimethoxyphenyl)-1H-imidazol-4-yl)amino)quinazolin-4-yl)pyrrolidin-2-yl)methanol (335d)

Compound 335d was prepared from (S)-(1-(2-chloro-8-(piperidin-1-ylmethyl)quinazolin-4-yl)pyrrolidin-2-yl)methanol (335c) (150 mg, 0.416 mmol), 1-(3,4,5-trimethoxyphenyl)-1H-imidazol-4-amine (57a) (104 mg, 0.42, free base), dicyclohexyl(2',4',6'-triisopropylbiphenyl-2-yl)phosphine (XPhos, 119 mg, 0.25 mmol), cesium carbonate (406 mg, 1.25 mmol) and $Pd_2(dba)_3$ (114 mg, 0.13 mmol) in toluene/t-BuOH (15 mL, Ratio: 2:1) according to the procedure reported in step-3 of Scheme 101. This gave after workup and purification by flash column chromatography [silica gel (24 g), eluting with DMA-80 in DCM from 0-50%], followed by reverse phase column chromatography [(silica gel C-18, 24 g) eluting with acetonitrile and 0.1% HCl in water] (S)-(1-(8-(piperidin-1-ylmethyl)-2-((1-(3,4,5-trimethoxyphenyl)-1H-imidazol-4-yl)amino)quinazolin-4-yl)pyrrolidin-2-yl)methanol (335d) (12 mg, 5% yield) HCl salt as a yellow solid. $^1$H NMR (300 MHz, DMSO-$d_6$) δ 10.94 (s, 1H), 10.72 (s, 1H), 8.44-8.31 (m, 2H), 8.22 (d, J=7.4 Hz, 1H), 7.75 (s, 1H), 7.49 (t, J=8.0 Hz, 1H), 6.99 (s, 2H), 5.09-4.41 (m, 5H), 4.32-4.03 (m, 2H), 3.89 (s, 6H), 3.68 (s, 3H), 3.53-3.10 (m, 4H), 2.22-1.86 (m, 4H), 1.85-1.62 (m, 6H); MS (ES+): 574.4 (M+1), 596.4 (M+Na); MS (ES−): 608.5 (M+Cl). HPLC purity: 92.95%; MS (ES+): 574.4 (M+1), 596.4 (M+Na); MS (ES−): 608.5 (M+Cl). HPLC purity: 92.95%.

Scheme 336

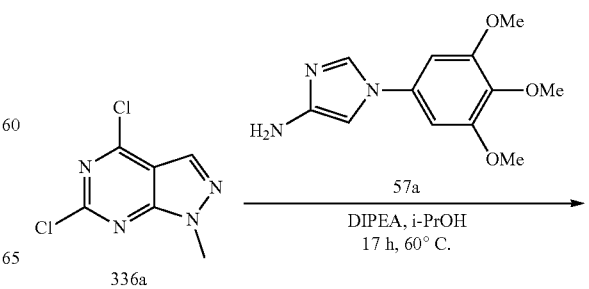

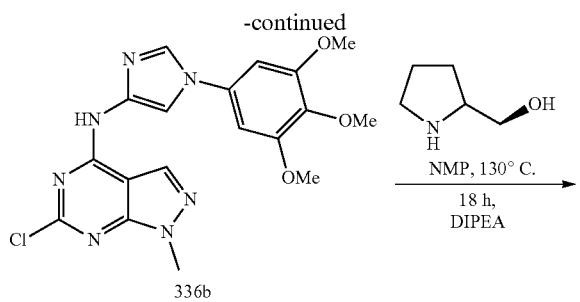

(336c) (117 mg, 51% yield) HCl salt as an off-white solid; $^1$H NMR (300 MHz, DMSO-d$_6$) δ 11.90 (2s, 1H), 8.83 (s, 1H), 8.30 (s, 1H), 8.00 (s, 1H), 7.05 (s, 2H), 4.36 (m, 2H), 4.06-3.89 (m, 1H), 3.88 (s, 6H), 3.85 (s, 3H), 3.81-3.71 (m, 1H), 3.69 (s, 3H), 3.66-3.32 (m, 1H), 2.20-1.77 (m, 4H); MS (ES+): 481.3 (M+1), 503.2 (M+Na); MS (ES−): 479.3 (M−1), 515.2 (M+Cl). HPLC purity: 99.23%.

Scheme 337

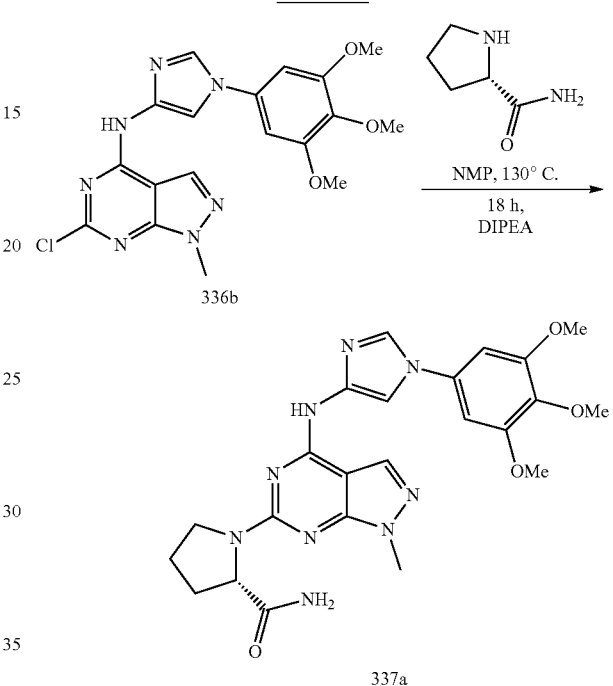

Preparation of (S)-(1-(1-methyl-4-((1-(3,4,5-trimethoxyphenyl)-1H-imidazol-4-yl)amino)-1H-pyrazolo[3,4-d]pyrimidin-6-yl)pyrrolidin-2-yl)methanol (336c)

Step-1: Preparation of 6-chloro-1-methyl-N-(1-(3,4,5-trimethoxyphenyl)-1H-imidazol-4-yl)-1H-pyrazolo[3,4-d]pyrimidin-4-amine (336b)

Compound 336b was prepared from 4,6-dichloro-1-methyl-1H-pyrazolo[3,4-d]pyrimidine (336a) (0.5 g, 2.463 mmol; CAS #98141-42-5) in 2-Propanol (20 mL) using DIPEA (1.29 mL, 7.39 mmol) and 1-(3,4,5-trimethoxyphenyl)-1H-imidazol-4-amine (57a) (645 mg, 2.59 mmol) according to the procedure reported in Scheme 1. This gave after workup 6-chloro-1-methyl-N-(1-(3,4,5-trimethoxyphenyl)-1H-imidazol-4-yl)-1H-pyrazolo[3,4-d]pyrimidin-4-amine (336b) (827 mg, 81% yield) as a brown solid; $^1$H NMR (300 MHz, DMSO-d$_6$) δ 11.40 (s, 1H), 8.42 (s, 1H), 8.19 (s, 1H), 7.88 (d, J=1.6 Hz, 1H), 6.93 (s, 2H), 3.90 (s, 3H), 3.87 (s, 6H), 3.69 (s, 3H); MS (ES+): 438.2 (M+Na); (ES−): 414.3 (M−1).

Step-2: Preparation of (S)-(1-(1-methyl-4-((1-(3,4,5-trimethoxyphenyl)-1H-imidazol-4-yl)amino)-1H-pyrazolo[3,4-d]pyrimidin-6-yl)pyrrolidin-2-yl)methanol (336c)

Compound 336c was prepared according to the procedure reported in step-2 of Scheme 76 from 6-chloro-1-methyl-N-(1-(3,4,5-trimethoxyphenyl)-1H-imidazol-4-yl)-1H-pyrazolo[3,4-d]pyrimidin-4-amine (336b) (200 mg, 0.48 mmol), (S)-pyrrolidin-2-ylmethanol (0.19 mL, 1.92 mmol) and DIPEA (0.5 mL, 2.89 mmol) in NMP (3 mL). This gave after workup and purification by flash column chromatography [(silica gel, 12 g) eluting DMA-80 in CH$_2$Cl$_2$ from 0 to 50%] followed by purification by reverse phase flash column chromatography [(silica gel C-18, 24 g) eluting with acetonitrile and 0.1% HCl in water] (S)-(1-(1-methyl-4-((1-(3,4,5-trimethoxyphenyl)-1H-imidazol-4-yl)amino)-1H-pyrazolo[3,4-d]pyrimidin-6-yl)pyrrolidin-2-yl)methanol Preparation of (S)-1-(1-methyl-4-((1-(3,4,5-trimethoxyphenyl)-1H-imidazol-4-yl)amino)-1H-pyrazolo[3,4-d]pyrimidin-6-yl)pyrrolidine-2-carboxamide (337a)

Compound 337a was prepared according to the procedure reported in step-2 of Scheme 76 from 6-chloro-1-methyl-N-(1-(3,4,5-trimethoxyphenyl)-1H-imidazol-4-yl)-1H-pyrazolo[3,4-d]pyrimidin-4-amine (336b) (200 mg, 0.48 mmol), (S)-pyrrolidine-2-carboxamide (220 mg, 1.92 mmol) and DIPEA (0.5 mL, 2.89 mmol) in NMP (3 mL). This gave after workup and purification by flash column chromatography [(silica gel, 12 g) eluting DMA-80 in CH$_2$Cl$_2$ from 0 to 50%] followed by purification by reverse phase flash column chromatography [(silica gel C-18, 24 g) eluting with acetonitrile and 0.1% HCl in water] ((S)-1-(1-methyl-4-((1-(3,4,5-trimethoxyphenyl)-1H-imidazol-4-yl)amino)-1H-pyrazolo[3,4-d]pyrimidin-6-yl)pyrrolidine-2-carboxamide (337a) (106 mg, 48% yield) HCl salt as an yellow solid; $^1$H NMR (300 MHz, DMSO-d$_6$, mixture of rotamers) δ 11.73 (2s, 1H), 9.02 (s, 1H), 8.28 (s, 1H), 8.05 (2s, 1H), 7.41 (2s, 1H), 7.24 (s, 1H), 7.06 (d, J=10.2 Hz, 2H), 4.52 (dd, J=8.5, 2.4 Hz, 1H), 3.93 (s, 6H), 3.90 (s, 2H), 3.87 (s, 3H), 3.75 (d, J=5.8 Hz, 1H), 3.70 (s, 3H), 2.40-1.79 (m, 4H); MS (ES+): 494.3 (M+1), 516.2 (M+Na); MS (ES−): 492.7 (M−1). HPLC purity: 97.68%.

Scheme 338

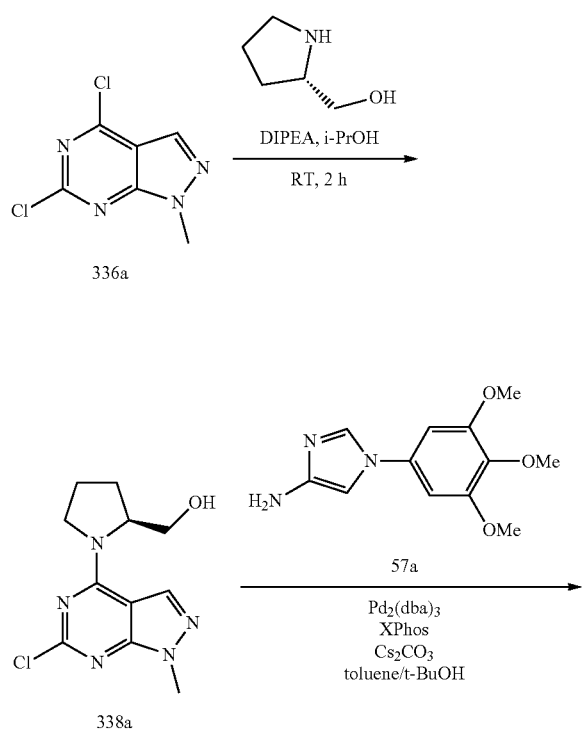

Preparation of (S)-(1-(1-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (338b)

Step-1: Preparation of (S)-(1-(6-chloro-1-methyl-1H-pyrazolo[3,4-d]pyrimidin-4-yl)pyrrolidin-2-yl)methanol (338a)

Compound 338a was prepared from 4,6-dichloro-1-methyl-1H-pyrazolo[3,4-d]pyrimidine (336a) (400 mg, 1.97 mmol) in 2-Propanol (10 mL) using (S)-pyrrolidin-3-yl-methanol (0.19 mL, 1.97 mmol) and DIPEA (1.0 mL, 5.91 mmol) according to the procedure reported in step-1 of Scheme 96. This gave after workup and purification by flash column chromatography [silica gel (12 g), eluting with DCM and methanol (0 to 30%)] (S)-(1-(6-chloro-1-methyl-1H-pyrazolo[3,4-d]pyrimidin-4-yl)pyrrolidin-2-yl)metha- nol (338a) (278 mg, 53% yield) as a white solid; MS (ES+): 268.2 (M+1); (ES−): 266.2 (M−1) 302.2 (M+Cl).

Step-2: Preparation of (S)-(1-(1-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (338b)

Compound 338b was prepared from (S)-(1-(6-chloro-1-methyl-1H-pyrazolo[3,4-d]pyrimidin-4-yl)pyrrolidin-2-yl)methanol (338a) (200 mg, 0.75 mmol), 1-(3,4,5-trimethoxyphenyl)-1H-imidazol-4-amine (57a) (186 mg, 0.745 mmol, free base), dicyclohexyl(2',4',6'-triisopropylbiphenyl-2-yl)phosphine (XPhos, 214 mg, 0.448 mmol), cesium carbonate (730 mg, 2.24 mmol) and Pd$_2$(dba)$_3$ (205 mg, 0.22 mmol) in toluene/t-BuOH (30 mL, Ratio: 2:1) according to the procedure reported in step-3 of Scheme 101. This gave after workup and purification by flash column chromatography [silica gel (24 g), eluting with DMA-80 in DCM from 0-50%], followed by reverse phase column chromatography [(silica gel C-18, 24 g) eluting with acetonitrile and 0.1% HCl in water] (S)-(1-(1-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (338b) (76 mg, 21% yield) HCl salt as a yellow solid; $^1$H NMR (300 MHz, DMSO-d$_6$) δ 10.34 (s, 1H), 9.07 (s, 1H), 8.12 (dm, 1H), 7.95 (m, 1H), 7.09 (s, 2H), 4.74-4.26 (m, 2H), 4.07-3.91 (m, 1H), 3.89 (s, 6H), 3.86 (s, 3H), 3.83-3.72 (m, 1H), 3.70 (s, 3H), 3.68-3.38 (m, 1H), 2.37-1.84 (m, 4H); MS (ES+): 481.4 (M+1); MS (ES−): 515.3 (M+Cl). HPLC purity: 98.33%.

Scheme 339

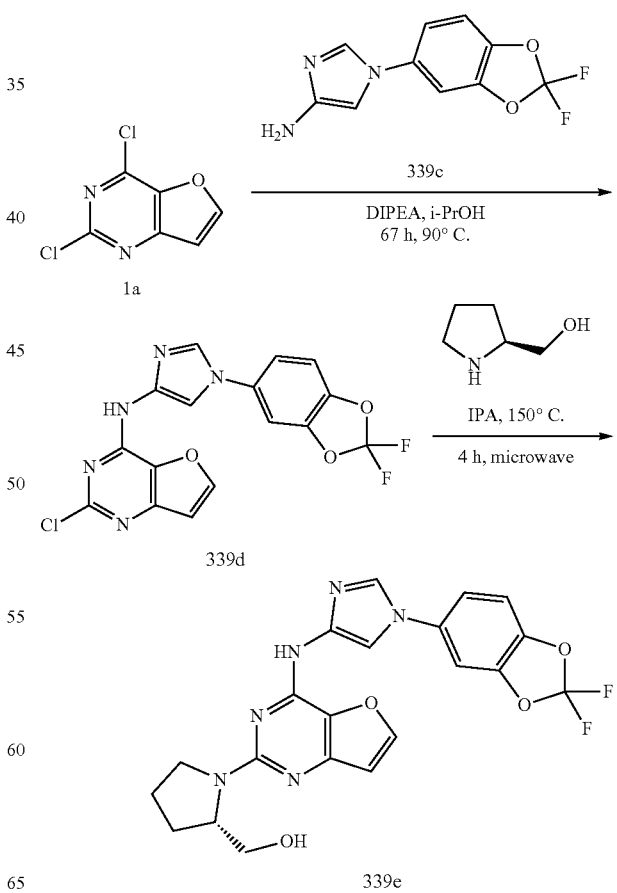

559
(S)-(1-(4-(1-(2,2-difluorobenzo[d][1,3]dioxol-5-yl)-1H-imidazol-4-ylamino)furo[3,2-d]pyrimidin-2-yl)pyrrolidin-2-yl)methanol (339e)

Step-1: Preparation of 2-chloro-N-(1-(2,2-difluorobenzo[d][1,3]dioxol-5-yl)-1H-imidazol-4-yl)furo[3,2-d]pyrimidin-4-amine (339d)

Compound 339d was prepared from 2,4-dichlorofuro[3,2-d]pyrimidine (1a) (324 mg, 1.71 mmol) in 2-Propanol (10 mL) using DIPEA (0.9 mL, 5.14 mmol) and 1-(2,2-difluorobenzo[d][1,3]dioxol-5-yl)-1H-imidazol-4-amine (339c) (410 mg, 1.71 mmol) according to the procedure reported in Scheme 1. This gave after workup 2-chloro-N-(1-(2,2-difluorobenzo[d][1,3]dioxol-5-yl)-1H-imidazol-4-yl)furo[3,2-d]pyrimidin-4-amine (339d) (268 mg, 40% yield) as a tan solid; $^1$H NMR (300 MHz, DMSO-d$_6$) δ 10.98 (s, 1H), 8.37 (d, J=2.1 Hz, 1H), 8.17 (d, J=1.6 Hz, 1H), 7.90 (d, J=2.2 Hz, 1H), 7.84 (d, J=1.6 Hz, 1H), 7.60 (d, J=8.6 Hz, 1H), 7.49 (dd, J=8.7, 2.2 Hz, 1H), 7.05 (d, J=2.1 Hz, 1H); $^{19}$F NMR (282 MHz, DMSO-d$_6$) δ -48.75.

Step-2: Preparation of (S)-(1-(4-(1-(2,2-difluorobenzo[d][1,3]dioxol-5-yl)-1H-imidazol-4-ylamino)furo[3,2-d]pyrimidin-2-yl)pyrrolidin-2-yl)methanol (339e)

Compound 339e was prepared according to the procedure reported in Scheme 2 from 2-chloro-N-(1-(2,2-difluorobenzo[d][1,3]dioxol-5-yl)-1H-imidazol-4-yl)furo[3,2-d]pyrimidin-4-amine (339d) (250 mg, 0.64 mmol), (S)-pyrrolidin-2-ylmethanol (0.25 mL, 2.55 mmol) in IPA (3 mL). This gave after workup and purification by flash column chromatography [(silica gel, 25 g) eluting DMA 80 in chloroform] compound 339e as a free base. The free base was dissolved in acetonitrile (10 mL), HCl (1 N, 10 mL) and freeze-dried to afford (S)-(1-(4-(1-(2,2-difluorobenzo[d][1,3]dioxol-5-yl)-1H-imidazol-4-ylamino)furo[3,2-d]pyrimidin-2-yl)pyrrolidin-2-yl)methanol (339e) (0.25 g, 86% yield) HCl salt as a white solid; $^1$H NMR (300 MHz, DMSO-d$_6$) δ 12.83 (s, 1H, D$_2$O exchangeable), 11.88 (s, 1H, D$_2$O exchangeable), 8.37 (d, J=2.1 Hz, 1H), 8.30 (s, 1H), 7.96 (s, 1H), 7.93 (s, 1H), 7.66-7.49 (m, 2H), 7.00 (d, J=2.1 Hz, 1H), 4.40 (s, 1H), 3.78-3.58 (m, 2H), 3.58-3.29 (m, 2H), 2.04 (d, J=28.2 Hz, 4H); $^{19}$F NMR (282 MHz, DMSO-d$_6$) δ -48.71; MS (ES+): 457.2 (M+1); (ES-) 491.3 (M+Cl); 947.5 (2M+Cl).

Scheme 340

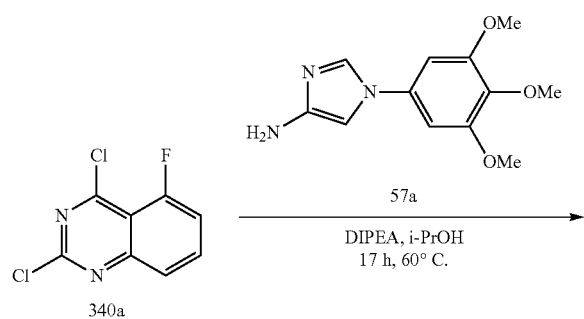

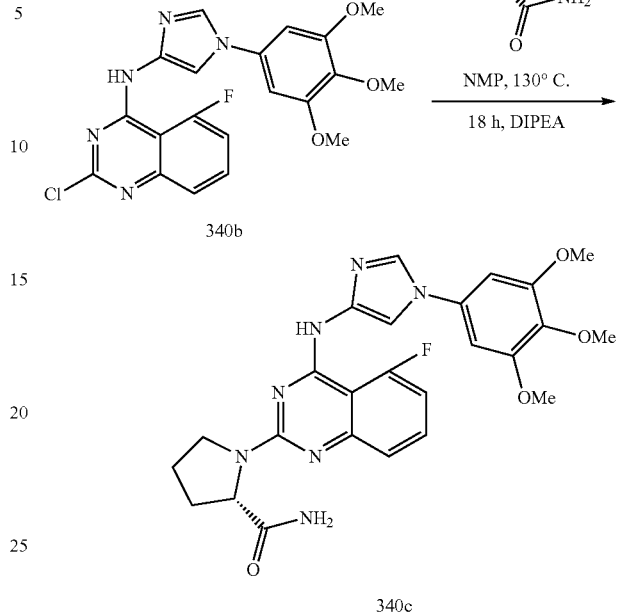

Preparation of (S)-1-(5-fluoro-4-((1-(3,4,5-trimethoxyphenyl)-1H-imidazol-4-yl)amino)quinazolin-2-yl)pyrrolidine-2-carboxamide (340c)

Step-1: Preparation of 2-chloro-5-fluoro-N-(1-(3,4,5-trimethoxyphenyl)-1H-imidazol-4-yl)quinazolin-4-amine (340b)

Compound 340b was prepared from 2,4-dichloro-5-fluoroquinazoline (340a) (500 mg, 2.3 mmol; CAS #87611-00-5) in 2-Propanol (20 mL) using DIPEA (1.21 mL, 6.91 mmol) and 1-(3,4,5-trimethoxyphenyl)-1H-imidazol-4-amine (57a) (603 mg, 2.42 mmol) according to the procedure reported in Scheme 1. This gave after workup 2-chloro-5-fluoro-N-(1-(3,4,5-trimethoxyphenyl)-1H-imidazol-4-yl)quinazolin-4-amine (340b) (734 mg, 74% yield) as a brown solid; $^1$H NMR (300 MHz, DMSO-d$_6$) δ 9.42 (d, J=13.5 Hz, 1H), 8.24 (d, J=1.5 Hz, 1H), 7.95 (d, J=1.6 Hz, 1H), 7.90 (td, J=8.2, 6.1 Hz, 1H), 7.60 (dd, J=8.4, 1.0 Hz, 1H), 7.50 (ddd, J=12.2, 8.1, 1.0 Hz, 1H), 6.95 (s, 2H), 3.88 (s, 6H), 3.70 (s, 3H); MS (ES+): 430.2 (M+1), 452.2 & 454.1 (M+Na); MS (ES-): 428.2 (M-1).

Step-2: Preparation of (S)-1-(5-fluoro-4-((1-(3,4,5-trimethoxyphenyl)-1H-imidazol-4-yl)amino)quinazolin-2-yl)pyrrolidine-2-carboxamide (340c)

Compound 340c was prepared according to the procedure reported in step-2 of Scheme 76 from 2-chloro-5-fluoro-N-(1-(3,4,5-trimethoxyphenyl)-1H-imidazol-4-yl)quinazolin-4-amine (340b) (200 mg, 0.47 mmol), (S)-pyrrolidine-2-carboxamide (0.212 g, 1.861 mmol) and DIPEA (0.488 mL, 2.79 mmol) in NMP (3 mL). This gave after workup and purification by flash column chromatography [(silica gel, 12 g) eluting DMA-80 in CH$_2$Cl$_2$ from 0 to 50%] followed by purification by reverse phase flash column chromatography [(silica gel C-18, 24 g) eluting with acetonitrile and 0.1%

HCl in water] (S)-1-(5-fluoro-4-((1-(3,4,5-trimethoxyphenyl)-1H-imidazol-4-yl)amino)quinazolin-2-yl)pyrrolidine-2-carboxamide (340c) (145 mg, 61% yield) HCl salt as an off-white solid; $^{1}$H NMR (300 MHz, DMSO-$d_6$) δ 13.09 (s, 1H), 9.95 (s, 1H), 8.65 (s, 1H), 8.18 (d, J=8.5 Hz, 1H), 7.96 (s, 1H), 7.94-7.80 (m, 1H), 7.68 (s, 1H), 7.39 (dd, J=12.4, 8.2 Hz, 1H), 7.28 (s, 1H), 7.16 (s, 2H), 4.70 (dd, J=8.9, 2.2 Hz, 1H), 4.20-4.03 (m, 1H), 3.93 (s, 6H), 3.88-3.73 (m, 1H), 3.69 (s, 3H), 2.41-1.88 (m, 4H); $^{19}$F NMR (282 MHz, DMSO-$d_6$) δ -109.40; MS (ES+): 508.3 (M+1); MS (ES-): 542.3 (M+Cl). HPLC purity: 98.48%.

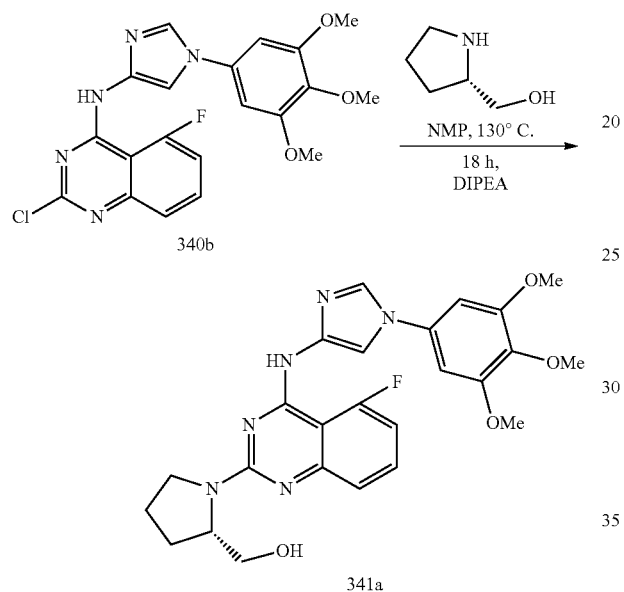

Scheme 341

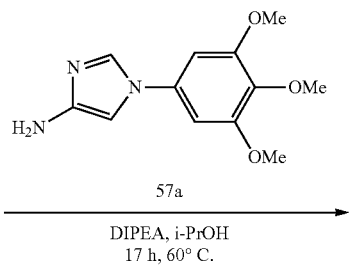

Scheme 342

Preparation of (S)-(1-(5-fluoro-4-((1-(3,4,5-trimethoxyphenyl)-1H-imidazol-4-yl)amino)quinazolin-2-yl)pyrrolidin-2-yl)methanol (341a)

Compound 341a was prepared according to the procedure reported in step-2 of Scheme 76 from 2-chloro-5-fluoro-N-(1-(3,4,5-trimethoxyphenyl)-1H-imidazol-4-yl)quinazolin-4-amine (340b) (200 mg, 0.47 mmol), (S)-pyrrolidin-2-ylmethanol (0.18 mL, 1.86 mmol) and DIPEA (0.49 mL, 2.79 mmol) in NMP (3 mL). This gave after workup and purification by flash column chromatography [(silica gel, 12 g) eluting DMA-80 in $CH_2Cl_2$ from 0 to 50%] followed by purification by reverse phase flash column chromatography [(silica gel C-18, 24 g) eluting with acetonitrile and 0.1% HCl in water] (S)-(1-(5-fluoro-4-((1-(3,4,5-trimethoxyphenyl)-1H-imidazol-4-yl)amino)quinazolin-2-yl)pyrrolidin-2-yl)methanol (341a) (110 mg, 48% yield) HCl salt as a yellow solid; $^{1}$H NMR (300 MHz, DMSO-$d_6$) δ 12.85 (s, 1H), 9.93 (brs, 1H), 8.61 (d, J=1.4 Hz, 1H), 8.18-8.02 (m, 2H), 7.93-7.78 (m, 1H), 7.42-7.26 (m, 1H), 7.03 (s, 1H), 6.99 (s, 1H), 4.86-4.47 (m, 1H), 4.12-3.90 (m, 1H), 3.88 (d, J=2.5 Hz, 6H), 3.68 (s, 3H), 3.67-3.60 (m, 1H), 2.13-1.98 (m, 4H); $^{19}$F NMR (282 MHz, DMSO-$d_6$): δ -109.73; MS (ES+): 495.3 (M+1), 517.3 (M+Na); MS (ES-): 529.3 (M+Cl). HPLC purity: 98.70%.

Preparation of (S)-(1-(4-((1-(3,4,5-trimethoxyphenyl)-1H-imidazol-4-yl)amino)-7,8-dihydro-5H-pyrano[4,3-d]pyrimidin-2-yl)pyrrolidin-2-yl)methanol (342c)

Step-1: Preparation of 2-chloro-N-(1-(3,4,5-trimethoxyphenyl)-1H-imidazol-4-yl)-7,8-dihydro-5H-pyrano[4,3-d]pyrimidin-4-amine (342b)

Compound 342b was prepared from 2,4-dichloro-7,8-dihydro-5H-pyrano[4,3-d]pyrimidine (342a) (120 mg, 0.585 mmol; CAS #944902-88-9) in 2-Propanol (10 mL) using DIPEA (0.31 mL, 1.76 mmol) and 1-(3,4,5-trimethoxyphenyl)-1H-imidazol-4-amine (57a) (153 mg, 0.62 mmol) according to the procedure reported in Scheme 1. This gave after workup 2-chloro-N-(1-(3,4,5-trimethoxyphenyl)-1H-imidazol-4-yl)-7,8-dihydro-5H-pyrano[4,3-d]pyrimidin-4-amine (342b) (62 mg, 25% yield) as a brown solid; MS (ES+): 418.2 (M+1); 440.2 (M+Na); (ES-): 416.2 (M-1).

Step-2: Preparation of (S)-(1-(4-((1-(3,4,5-trimethoxyphenyl)-1H-imidazol-4-yl)amino)-7,8-dihydro-5H-pyrano[4,3-d]pyrimidin-2-yl)pyrrolidin-2-yl)methanol (342c)

Compound 342c was prepared according to the procedure reported in step-2 of Scheme 76 from 2-chloro-N-(1-(3,4, 5-trimethoxyphenyl)-1H-imidazol-4-yl)-7,8-dihydro-5H-pyrano[4,3-d]pyrimidin-4-amine (342b) (55 mg, 0.13 mmol), (S)-pyrrolidin-2-ylmethanol (0.052 mL, 0.53 mmol) and DIPEA (0.14 mL, 0.79 mmol) in NMP (3 mL). This gave after workup and purification by flash column chromatography [(silica gel, 12 g) eluting DMA-80 in CH$_2$Cl$_2$ from 0 to 50%] followed by purification by reverse phase flash column chromatography [(silica gel, C18, 24 g) eluting with acetonitrile and 0.1% HCl in water] (S)-(1-(4-((1-(3,4,5-trimethoxyphenyl)-1H-imidazol-4-yl)amino)-7,8-dihydro-5H-pyrano[4,3-d]pyrimidin-2-yl)pyrrolidin-2-yl)methanol (342c) (35 mg, 55% yield) HCl salt as an off-white solid; $^1$H NMR (300 MHz, DMSO-d$_6$) δ 12.38 (s, 1H), 10.57 (s, 1H), 8.63 (s, 1H), 8.03 (s, 1H), 6.99 (s, 2H), 4.59 (s, 2H), 4.53-4.37 (m, 1H), 3.98-3.88 (m, 3H), 3.87 (s, 6H), 3.84-3.70 (m, 1H), 3.68 (s, 3H), 3.64-3.39 (m, 2H), 3.01-2.72 (m, 2H), 2.21-1.78 (m, 4H); MS (ES+): 483.3 (M+1); MS (ES−): 517.3 (M+Cl). HPLC purity: 93.78%.

Preparation of (S)-(1-(2-((1-(3,4,5-trimethoxyphenyl)-1H-imidazol-4-yl)amino)-7,8-dihydro-5H-pyrano[4,3-d]pyrimidin-4-yl)pyrrolidin-2-yl)methanol (343b)

Step-1: Preparation of (S)-(1-(2-chloro-7,8-dihydro-5H-pyrano[4,3-d]pyrimidin-4-yl)pyrrolidin-2-yl)methanol (343a)

Compound 343a was prepared from 2,4-dichloro-7,8-dihydro-5H-pyrano[4,3-d]pyrimidine (342a) (120 mg, 0.59 mmol) in 2-Propanol (10 mL) using (S)-pyrrolidin-3-yl-methanol (0.058 mL, 0.59 mmol) and DIPEA (0.31 mL, 1.76 mmol) according to the procedure reported in step-1 of Scheme 96. This gave after workup and purification by flash column chromatography [silica gel (12 g), eluting with DCM and methanol (0 to 30%)] (S)-(1-(2-chloro-7,8-dihydro-5H-pyrano[4,3-d]pyrimidin-4-yl)pyrrolidin-2-yl)methanol (343a) (0.151 g, 96% yield) as a white solid; MS (ES+): 270.2 (M+1); (ES−): 268.2 (M−1); 304.2 (M+Cl).

Step-2: Preparation of (S)-(1-(2-((1-(3,4,5-trimethoxyphenyl)-1H-imidazol-4-yl)amino)-7,8-dihydro-5H-pyrano[4,3-d]pyrimidin-4-yl)pyrrolidin-2-yl)methanol (343b)

Compound 343b was prepared from (S)-(1-(2-chloro-7,8-dihydro-5H-pyrano[4,3-d]pyrimidin-4-yl)pyrrolidin-2-yl)methanol (343a) (150 mg, 0.56 mmol), 1-(3,4,5-trimethoxyphenyl)-1H-imidazol-4-amine (57a) (139 mg, 0.56, free base), dicyclohexyl(2',4',6'-triisopropylbiphenyl-2-yl)phosphine (XPhos, 159 mg, 0.33 mmol), cesium carbonate (544 mg, 1.67 mmol) and Pd$_2$(dba)$_3$ (153 mg, 0.17 mmol) in toluene/t-BuOH (30 mL, Ratio: 2:1) according to the procedure reported in step-3 of Scheme 101. This gave after workup and purification by flash column chromatography [silica gel (24 g), eluting with DMA-80 in DCM from 0-50%], followed by reverse phase column chromatography [(silica gel C-18, 24 g) eluting with acetonitrile and 0.1% HCl in water] (S)-(1-(2-((1-(3,4,5-trimethoxyphenyl)-1H-imidazol-4-yl)amino)-7,8-dihydro-5H-pyrano[4,3-d]pyrimidin-4-yl)pyrrolidin-2-yl)methanol (343b) (0.119 g, 0.247 mmol, 44.3% yield) HCl salt as a yellow solid; $^1$H NMR (300 MHz, DMSO-d$_6$) δ 10.37 (s, 1H), 8.62 (s, 1H), 7.75 (s, 1H), 6.99 (s, 2H), 4.88-4.71 (m, 3H), 4.56 (s, 1H), 4.02-3.90 (m, 1H), 3.86 (s, 6H), 3.83-3.72 (m, 3H), 3.67 (s, 3H), 3.63-3.35 (m, 2H), 2.72 (m, 3H), 1.90 (m, 2H); MS (ES+): 483.4 (M+1), 505.3 (M+Na); MS (ES−): 517.3 (M+Cl). HPLC purity: 94.19%.

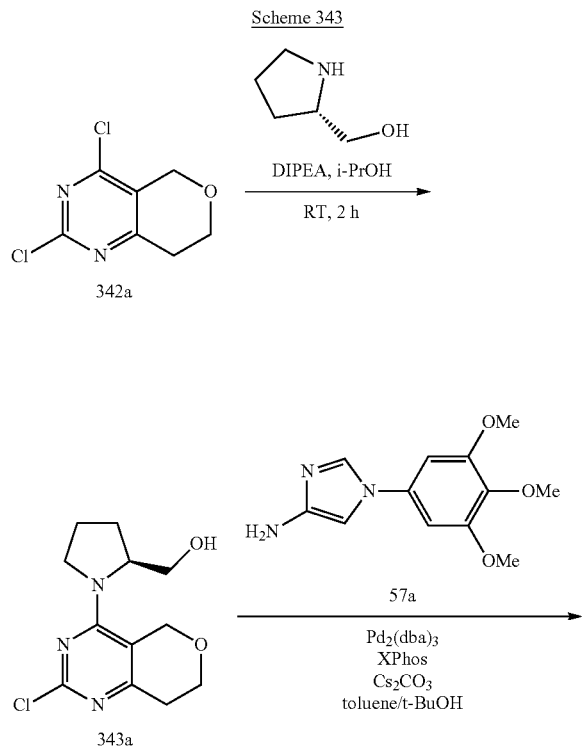

Scheme 343

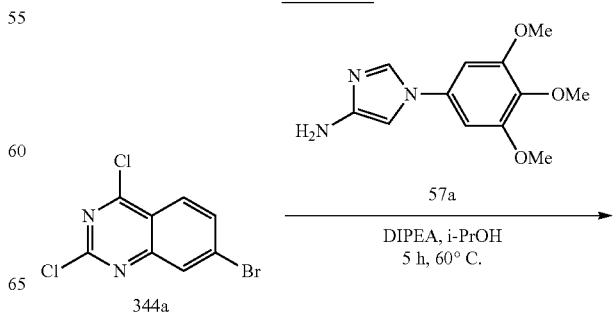

Scheme 344

-continued

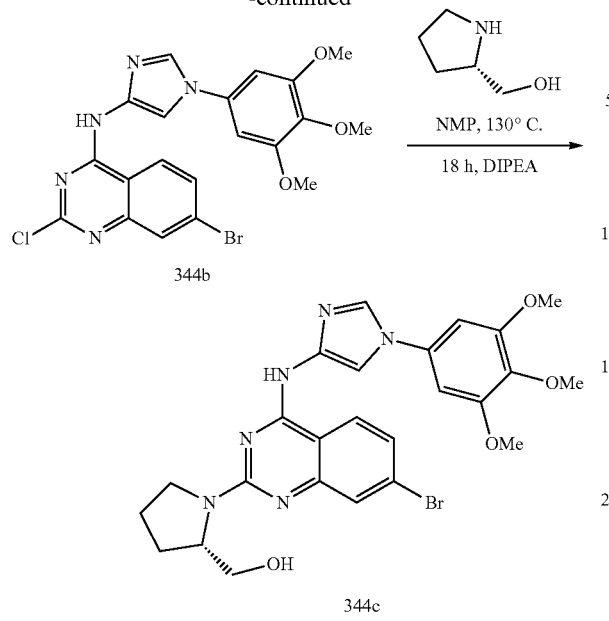

344b

344c

Preparation of (S)-(1-(7-bromo-4-((1-(3,4,5-trimethoxyphenyl)-1H-imidazol-4-yl)amino)quinazolin-2-yl)pyrrolidin-2-yl)methanol (344c)

Step-1: Preparation of 7-bromo-2-chloro-N-(1-(3,4,5-trimethoxyphenyl)-1H-imidazol-4-yl)quinazolin-4-amine (344b)

Compound 344b was prepared from 7-bromo-2,4-dichloroquinazoline (344a) (660 mg, 2.38 mmol; CAS #959237-68-4) in 2-Propanol (20 mL) using DIPEA (1.24 mL, 7.12 mmol) and 1-(3,4,5-trimethoxyphenyl)-1H-imidazol-4-amine (57a) (651 mg, 2.61 mmol) according to the procedure reported in Scheme 1. This gave after workup 7-bromo-2-chloro-N-(1-(3,4,5-trimethoxyphenyl)-1H-imidazol-4-yl)quinazolin-4-amine (344b) (890 mg, 76% yield) as a brown solid; $^1$H NMR (300 MHz, DMSO-$d_6$) δ 11.26 (s, 1H), 8.69 (d, J=8.9 Hz, 1H), 8.23 (d, J=1.5 Hz, 1H), 7.98 (d, J=1.6 Hz, 1H), 7.92 (d, J=2.0 Hz, 1H), 7.76 (dd, J=8.9, 2.0 Hz, 1H), 6.93 (s, 2H), 3.88 (s, 6H), 3.69 (s, 3H).

Step-2: Preparation of (S)-(1-(7-bromo-4-((1-(3,4,5-trimethoxyphenyl)-1H-imidazol-4-yl)amino)quinazolin-2-yl)pyrrolidin-2-yl)methanol (344c)

Compound 344c was prepared according to the procedure reported in step-2 of Scheme 76 from 7-bromo-2-chloro-N-(1-(3,4,5-trimethoxyphenyl)-1H-imidazol-4-yl)quinazolin-4-amine (344b) (0.3 g, 0.61 mmol), (S)-pyrrolidin-2-yl-methanol (0.24 mL, 2.45 mmol) and DIPEA (0.64 mL, 3.67 mmol) in NMP (3 mL). This gave after workup and purification by flash column chromatography [(silica gel, 12 g) eluting DMA-80 in $CH_2Cl_2$ from 0 to 50%] (S)-(1-(7-bromo-4-((1-(3,4,5-trimethoxyphenyl)-1H-imidazol-4-yl)amino)quinazolin-2-yl)pyrrolidin-2-yl)methanol (344c) (0.265 g, 78% yield) as a yellow solid; $^1$H NMR (300 MHz, DMSO-$d_6$) δ 10.47 (s, 1H), 8.42 (d, J=8.8 Hz, 1H), 8.27 (s, 1H), 8.07 (d, J=28.7 Hz, 1H), 7.45 (s, 1H), 7.19 (d, J=8.7 Hz, 1H), 6.96 (d, J=15.7 Hz, 2H), 5.26 (s, 1H), 4.95 (s, 1H), 4.52-4.14 (m, 2H), 3.88 (s, 6H), 3.85-3.67 (m, 1H), 3.68 (s, 3H), 3.65-3.25 (m, 1H), 2.11-1.81 (m, 4H); MS (ES+): 556.8 (M+1); MS (ES−): 553.4 & 555.3 (M−1). HPLC purity: 89.30%.

Scheme 345

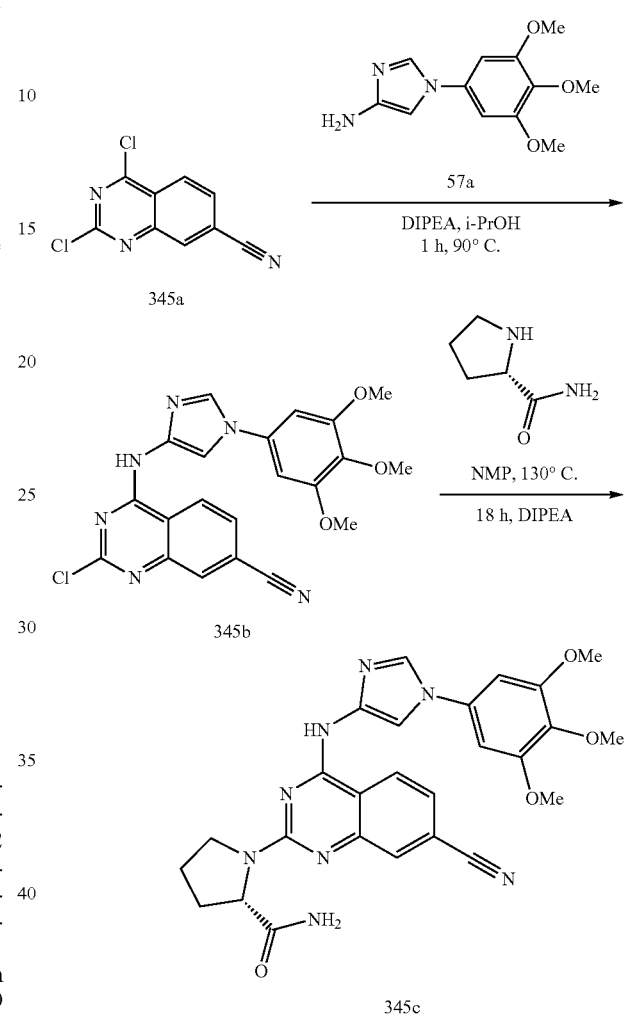

345a

345b

345c

Preparation of (S)-1-(7-cyano-4-((1-(3,4,5-trimethoxyphenyl)-1H-imidazol-4-yl)amino)quinazolin-2-yl)pyrrolidine-2-carboxamide (345c)

Step-1: Preparation of 2-chloro-4-((1-(3,4,5-trimethoxyphenyl)-1H-imidazol-4-yl)amino)quinazoline-7-carbonitrile (345b)

Compound 345b was prepared from 2,4-dichloroquinazoline-7-carbonitrile (345a) (500 mg, 2.23 mmol; CAS #864292-40-0) in 2-Propanol (15 mL) using DIPEA (1.17 mL, 6.7 mmol) and 1-(3,4,5-trimethoxyphenyl)-1H-imidazol-4-amine (57a) (556 mg, 2.23 mmol) according to the procedure reported in Scheme 1. This gave after workup 2-chloro-4-((1-(3,4,5-trimethoxyphenyl)-1H-imidazol-4-yl)amino)quinazoline-7-carbonitrile (345b) (818 mg, 84% yield) as a yellow solid; $^1$H NMR (300 MHz, DMSO-$d_6$): δ 11.48 (s, 1H), 8.90 (d, J=8.6 Hz, 1H), 8.26 (d, J=1.6 Hz, 2H), 8.01 (d, J=1.6 Hz, 1H), 7.95 (dd, J=8.5, 1.7 Hz, 1H), 6.94 (s, 2H), 3.88 (s, 6H), 3.70 (s, 3H). MS (ES+): 459.2 (M+Na); MS (ES−): 435.3 (M−1).

Step-2: Preparation of (S)-1-(7-cyano-4-((1-(3,4,5-trimethoxyphenyl)-1H-imidazol-4-yl)amino)quinazolin-2-yl)pyrrolidine-2-carboxamide (345c)

Compound 345c was prepared according to the procedure reported in step-2 of Scheme 76 from 2-chloro-4-((1-(3,4,5-trimethoxyphenyl)-1H-imidazol-4-yl)amino)quinazoline-7-carbonitrile (345b) (200 mg, 0.46 mmol), (S)-pyrrolidine-2-carboxamide (209 mg, 1.83 mmol) and DIPEA (0.48 mL, 2.75 mmol) in NMP (3 mL). This gave after workup and purification by flash column chromatography [(silica gel, 12 g) eluting DMA-80 in $CH_2Cl_2$ from 0 to 50%] followed by purification by reverse phase flash column chromatography [(silica gel C-18, 24 g) eluting with acetonitrile and 0.1% HCl in water] (S)-1-(7-cyano-4-((1-(3,4,5-trimethoxyphenyl)-1H-imidazol-4-yl)amino)quinazolin-2-yl)pyrrolidine-2-carboxamide (345c) (140 mg, 59% yield) HCl salt as a yellow solid; $^1$H NMR (300 MHz, DMSO-$d_6$) δ 13.23 (s, 1H), 11.88 (s, 1H), 8.91 (d, J=8.6 Hz, 1H), 8.81 (s, 1H), 8.63-8.48 (m, 1H), 7.94 (s, 1H), 7.86 (dd, J=8.5, 1.5 Hz, 1H), 7.66 (s, 1H), 7.27 (s, 1H), 7.15 (s, 2H), 4.73 (d, J=7.8 Hz, 1H), 4.23-3.99 (m, 1H), 3.93 (s, 6H), 3.88-3.72 (m, 1H), 3.69 (s, 3H), 2.41-1.83 (m, 4H); MS (ES+): 515.3 (M+1); MS (ES−): 513.4 (M−1), 549.4 (M+Cl). HPLC purity: 97.60%.

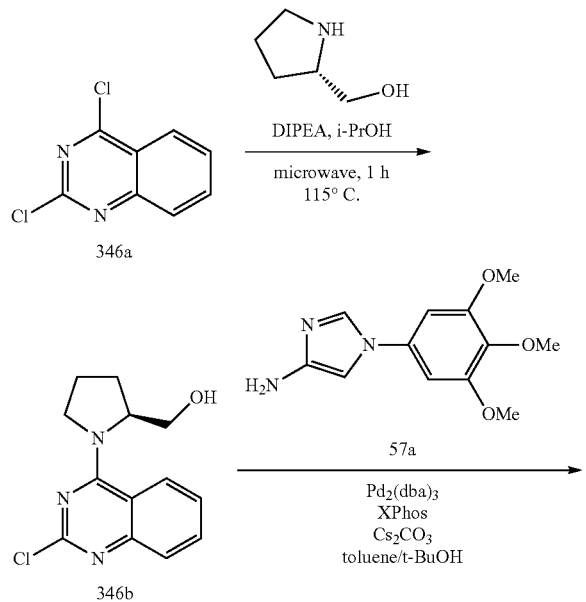

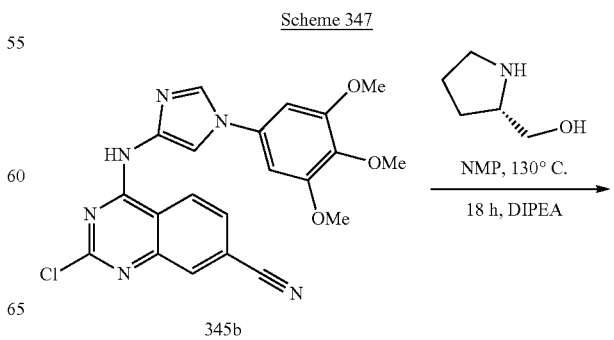

Preparation of (S)-(1-(3-((1-(3,4,5-trimethoxyphenyl)-1H-imidazol-4-yl)amino)isoquinolin-1-yl)pyrrolidin-2-yl)methanol (346c)

Step-1: Preparation of (S)-(1-(3-chloroisoquinolin-1-yl)pyrrolidin-2-yl)methanol (346b)

Compound 346b was prepared from 1,3-dichloroisoquinoline (346a) (1000 mg, 5.05 mmol; CAS #: 7742-73-6) in 2-Propanol (4 mL) using (S)-pyrrolidine-3-ylmethanol (560 mg, 5.55 mmol) and DIPEA (0.31 mL, 1.76 mmol) according to the procedure reported in Scheme 2. This gave after workup and purification by flash column chromatography [silica gel (12 g), eluting with EtOAc in hexane from 0-60%] (S)-(1-(3-chloroisoquinolin-1-yl)pyrrolidin-2-yl)methanol (346b) (1.15 g, 87% yield) as a yellow oil; $^1$H NMR (300 MHz, DMSO-$d_6$) δ 8.19 (d, J=8.6 Hz, 1H), 7.75-7.68 (m, 1H), 7.68-7.58 (m, 1H), 7.50-7.40 (m, 1H), 7.13 (s, 1H), 4.71 (t, J=5.6 Hz, 1H, $D_2O$ exchangeable), 4.58-4.45 (m, 1H), 4.08-3.93 (m, 1H), 3.77-3.59 (m, 2H), 3.56-3.47 (m, 1H), 2.13-1.87 (m, 3H), 1.80-1.63 (m, 1H); MS (ES+): 285.2 (M+Na); (ES−): 261.2 (M−1).

Step-2: Preparation of (S)-(1-(3-((1-(3,4,5-trimethoxyphenyl)-1H-imidazol-4-yl)amino)isoquinolin-1-yl)pyrrolidin-2-yl)methanol (346c)

Compound 346c was prepared from (S)-(1-(3-chloroisoquinolin-1-yl)pyrrolidin-2-yl)methanol (346b) (700 mg, 2.66 mmol), 1-(3,4,5-trimethoxyphenyl)-1H-imidazol-4-amine (57a) (731 mg, 2.93 mmol, free base), dicyclohexyl(2',4',6'-triisopropylbiphenyl-2-yl)phosphine (XPhos, 508 mg, 1.07 mmol), cesium carbonate (1736 mg, 5.33 mmol) and $Pd_2(dba)_3$ (487 mg, 0.53 mmol) in toluene/t-BuOH (10 mL, Ratio: 2:1) according to the procedure reported in step-3 of Scheme 101. This gave after workup and purification by flash column chromatography [silica gel (24 g), eluting with DMA-80 in DCM from 0-50%], followed by reverse phase column chromatography [(silica gel C-18, 24 g) eluting with acetonitrile and 0.1% HCl in water] (S)-(1-(3-((1-(3,4,5-trimethoxyphenyl)-1H-imidazol-4-yl)amino)isoquinolin-1-yl)pyrrolidin-2-yl)methanol (346c) (166 mg, 13% yield) HCl salt as a yellow solid; $^1$H NMR (300 MHz, DMSO-$d_6$) δ 10.08 (s, 1H, $D_2O$ exchangeable), 9.18 (d, J=1.7 Hz, 1H), 8.15 (d, J=8.7 Hz, 1H), 7.87 (d, J=1.8 Hz, 1H, $D_2O$ exchangeable), 7.67-7.49 (m, 2H), 7.28-7.18 (m, 1H), 7.14 (s, 2H), 6.58 (s, 1H, $D_2O$ exchangeable), 4.80-4.65 (m, 1H), 4.17-4.03 (m, 1H), 3.90 (s, 6H), 3.87-3.76 (m, 2H), 3.70 (s, 3H), 3.69-3.64 (m, 1H), 3.63-3.53 (m, 1H), 2.21-2.10 (m, 1H), 2.06-1.90 (m, 2H), 1.87-1.73 (m, 1H); MS (ES+): 476.3 (M+1), 485.3 (M+Na); (ES−): 474.4 (M−1); HPLC purity, 92.19%.

569

-continued

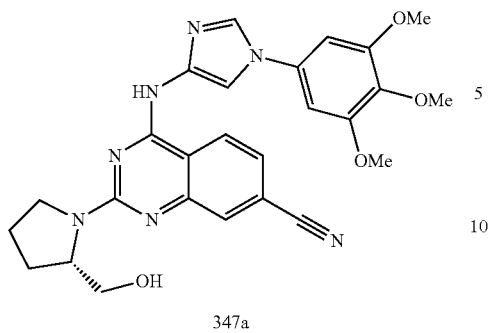

347a

Preparation of (S)-2-(2-(hydroxymethyl)pyrrolidin-1-yl)-4-((1-(3,4,5-trimethoxypentyl-1H-imidazol-4-yl)amino)quinazoline-7-carbonitrile (347a)

Compound 347a was prepared according to the procedure reported in step-2 of Scheme 76 from 2-chloro-4-((1-(3,4,5-trimethoxyphenyl)-1H-imidazol-4-yl)amino)quinazoline-7-carbonitrile (345b) (200 mg, 0.46 mmol), (S)-pyrrolidin-2-ylmethanol (0.18 mL, 1.83 mmol) and DIPEA (0.48 mL, 2.75 mmol) in NMP (3 mL). This gave after workup and purification by flash column chromatography [(silica gel, 12 g) eluting DMA-80 in CH$_2$Cl$_2$ from 0 to 50%] followed by purification by reverse phase flash column chromatography [(silica gel C-18, 24 g) eluting with acetonitrile and 0.1% HCl in water] (S)-2-(2-(hydroxymethyl)pyrrolidin-1-yl)-4-((1-(3,4,5-trimethoxyphenyl)-1H-imidazol-4-yl)amino)quinazoline-7-carbonitrile (347a) (81 mg, 35% yield) HCl salt as a yellow solid; $^1$H NMR (300 MHz, DMSO-d$_6$) δ 12.85 (s, 1H), 11.94 (s, 1H), 8.86 (t, J=8.1 Hz, 1H), 8.64 (d, J=12.5 Hz, 1H), 8.48 (s, 1H), 8.08 (s, 1H), 7.90-7.79 (m, 1H), 7.01 (s, 1H), 6.96 (s, 1H), 4.86-4.43 (m, 1H), 4.12-3.92 (m, 2H), 3.88 (s, 6H), 3.68 (s, 3H), 3.64-3.47 (m, 2H), 2.32-1.80 (m, 4H); MS (ES+): 502.4 (M+1); MS (ES−): 500.4 (M−1), 536.4 (M+Cl). HPLC purity: 97.21%.

570

-continued

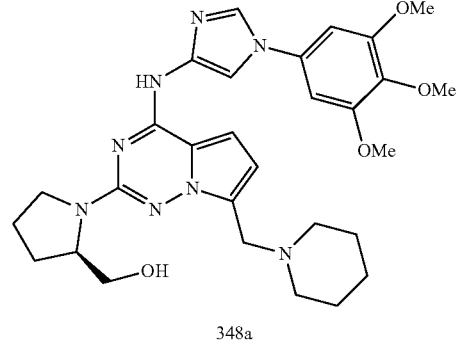

348a

Preparation of (R)-(1-(7-(piperidin-1-ylmethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (348a)

Compound 348a was prepared from 2-chloro-7-(piperidin-1-ylmethyl)-N-(1-(3,4,5-trimethoxyphenyl)-1H-imidazol-4-yl)pyrrolo[2,1-f][1,2,4]triazin-4-amine (105a) (500 mg, 1.01 mmol), (R)-pyrrolidin-2-ylmethanol (1001 mg, 10 mmol) in NMP (20 mL) according to the procedure reported in step-2 of Scheme 76. This gave after workup and purification by flash chromatography (Silica gel 40 g, eluting with MeOH in DCM from 0% to 10%) (R)-(1-(7-(piperidin-1-ylmethyl)-4-((1-(3,4,5-trimethoxyphenyl)-1H-imidazol-4-yl)amino)pyrrolo[2,1-f][1,2,4]triazin-2-yl)pyrrolidin-2-yl)methanol (348a) (200 mg, 35% yield) as a brown solid; $^1$H NMR (300 MHz, DMSO-d$_6$): δ 10.66 (s, 1H), 8.25 (s, 1H), 7.98 (s, 1H), 7.49-6.88 (m, 3H), 6.58 (s, 1H), 5.05-4.67 (m, 1H), 4.50-4.07 (m, 2H), 4.04-2.61 (m, 18H), 2.15-0.69 (m, 10H); MS (ES+): 498.2 (M+1); MS (ES−): 496.1 (M−1). HPLC: 85.92%; Hydrochloride salt of compound 348a was obtained by purification of crude reaction mixture from above step by reverse phase flash chromatography [(Silica gel C-18, 24 g) eluting with acetonitrile and 0.1% HCl in water] followed by lyophilization to afford compound 348a HCl salt as a yellow solid; $^1$H NMR (300 MHz, DMSO-d$_6$) δ 10.57 (s, 1H), 8.25 (s, 1H), 7.98 (s, 1H), 7.17 (d, J=4.5 Hz, 1H), 6.95 (s, 2H), 6.45 (s, 1H), 4.96-4.72 (m, 1H), 4.21 (s, 1H), 4.10-3.93 (m, 1H), 3.88 (s, 6H), 3.81-3.70 (m, 2H), 3.68 (s, 3H), 3.64-3.54 (m, 1H), 3.54-3.38 (m, 2H), 2.84-2.51 (m, 4H), 2.12-1.79 (m, 2H), 1.56 (s, 5H), 1.47-1.25 (m, 3H); MS (ES+): 563.5 (M+1); MS (ES−): 597.5 (M+Cl). HPLC purity: 93.73%.

Scheme 348

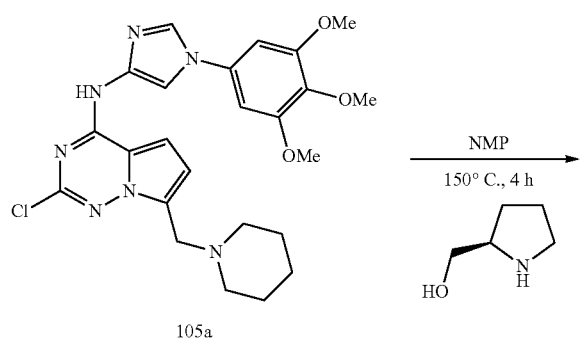

105a

Scheme 349

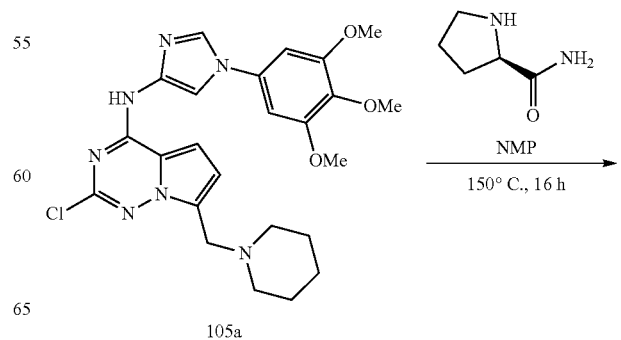

105a

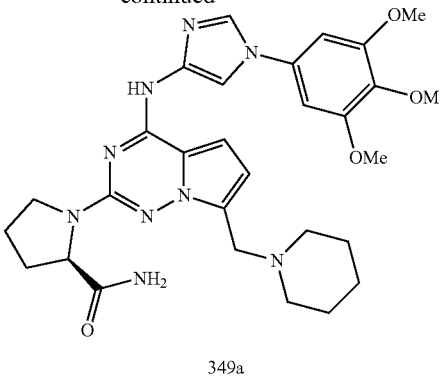

349a

Preparation of (R)-1-(7-(piperidin-1-ylmethyl)-4-((1-(3,4,5-trimethoxyphenyl)-1H-imidazol-4-yl)amino)pyrrolo[2,1-f][1,2,4]triazin-2-yl)pyrrolidine-2-carboxamide (349a)

Compound 349a was prepared from 2-chloro-7-(piperidin-1-ylmethyl)-N-(1-(3,4,5-trimethoxyphenyl)-1H-imidazol-4-yl)pyrrolo[2,1-f][1,2,4]triazin-4-amine (105a) (400 mg, 0.8 mmol), (R)-pyrrolidine-2-carboxamide (917 mg, 8.0 mmol) in NMP (20 mL) according to the procedure reported in step-2 of Scheme 76. This gave after workup and purification by flash chromatography (Silica gel, eluting with MeOH in DCM from 0% to 10%) (R)-1-(7-(piperidin-1-ylmethyl)-4-((1-(3,4,5-trimethoxyphenyl)-1H-imidazol-4-yl)amino)pyrrolo[2,1-f][1,2,4]triazin-2-yl)pyrrolidine-2-carboxamide (349a) (90 mg, 19.44%) free base as a brown solid; $^1$H NMR (300 MHz, DMSO-$d_6$) δ 11.04 (s, 1H), 10.75 (s, 1H), 8.65 (s, 1H), 8.03 (s, 1H), 7.47-6.91 (m, 5H), 6.77 (d, J=4.3 Hz, 1H), 4.51-4.31 (m, 3H), 4.01-3.55 (m, 11H), 3.32 (dd, J=32.2, 11.7 Hz, 2H), 2.94-2.69 (m, 2H), 2.33-1.18 (m, 10H); MS (ES+): 576.2 (M+1); HPLC purity; 83.51%. The free base was repurified by reverse phase flash chromatography [(Silica gel C-18, 24 g) eluting with acetonitrile and 0.1% HCl in water] followed by lyophilization to afford compound 349a HCl salt as a brown solid; $^1$H NMR (300 MHz, DMSO-$d_6$) δ 11.04 (s, 1H), 10.75 (s, 1H), 8.65 (s, 1H), 8.03 (s, 1H), 7.47-6.91 (m, 5H), 6.77 (d, J=4.3 Hz, 1H), 4.51-4.31 (m, 3H), 3.91 (s, 6H), 3.79 (m, 1H), 3.70 (s, 3H), 3.67-3.49 (m, 1H), 3.32 (m, 2H), 2.94-2.69 (m, 2H), 2.33-1.18 (m, 10H); MS (ES+): 576.3 (M+1); MS (ES–): 610.4 (M+Cl). HPLC purity: 91.36%.

Scheme 350

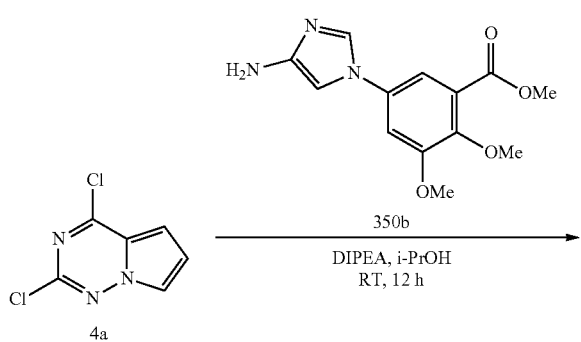

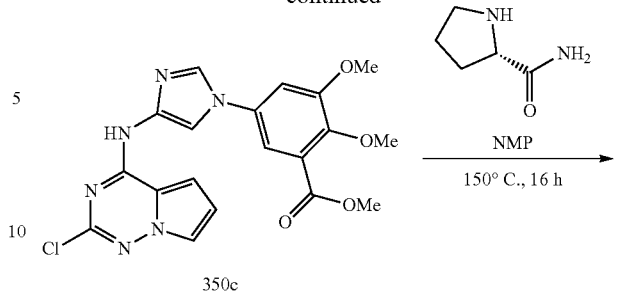

350c

Preparation of (S)-methyl 5-(4-((2-(2-carbamoylpyrrolidin-1-yl)pyrrolo[2,1-f][1,2,4]triazin-4-yl)amino)-1H-imidazol-1-yl)-2,3-dimethoxybenzoate (350d)

Step-1: Preparation of methyl 5-(4-((2-chloropyrrolo[2,1-f][1,2,4]triazin-4-yl)amino)-1H-imidazol-1-yl)-2,3-dimethoxybenzoate (350c)

Compound 350c was prepared from 2,4-dichloropyrrolo[2,1-f][1,2,4]triazine (4a) (1.5 g, 7.97 mmol) in 2-Propanol (45 mL) using DIPEA (3.09 g, 23.93 mmol) and methyl 5-(4-amino-1H-imidazol-1-yl)-2,3-dimethoxybenzoate (350b) (2.65 g, 9.57 mmol) according to the procedure reported in Scheme 1. This gave after workup methyl 5-(4-((2-chloropyrrolo[2,1-f][1,2,4]triazin-4-yl)amino)-1H-imidazol-1-yl)-2,3-dimethoxybenzoate (350c) (1.0 g, 29%) as an off-white solid; $^1$H NMR (300 MHz, DMSO-$d_6$): δ 11.32 (s, 1H), 8.26 (d, J=1.5 Hz, 1H), 7.88 (d, J=1.5 Hz, 1H), 7.77 (dd, J=2.6, 1.5 Hz, 1H), 7.54 (d, J=2.6 Hz, 1H), 7.49-7.23 (m, 2H), 6.72 (dd, J=4.5, 2.6 Hz, 1H), 3.96 (s, 3H), 3.87 (s, 3H), 3.80 (s, 3H); MS (ES+): 429.3 (M+1); MS (ES–): 427.1 (M–1).

Step-2: Preparation of (S)-methyl 5-(4-((2-(2-carbamoylpyrrolidin-1-yl)pyrrolo[2,1-f][1,2,4]triazin-4-yl)amino)-1H-imidazol-1-yl)-2,3-dimethoxybenzoate (350d)

Compound 350d was prepared according to the procedure reported in step-2 of Scheme 76 from methyl 5-(4-((2-chloropyrrolo[2,1-f][1,2,4]triazin-4-yl)amino)-1H-imidazol-1-yl)-2,3-dimethoxybenzoate (350c) (500 mg, 1.16 mmol), (S)-pyrrolidine-2-carboxamide (266 mg, 2.32 mmol) in NMP (10 mL). This gave after workup and purification by flash column chromatography [(silica gel, eluting with (0-5%) MeOH in ethyl acetate] (S)-methyl 5-(4-((2-(2-carbamoylpyrrolidin-1-yl)pyrrolo[2,1-f][1,2,4]triazin-4-yl)amino)-1H-imidazol-1-yl)-2,3-dimethoxybenzoate (350d) (35 mg, 6%) free base as an off-white solid; ¹H NMR (300 MHz, DMSO-d₆): δ 10.54 (s, 1H), 8.27 (d, J=1.5 Hz, 1H), 7.99 (s, 1H), 7.73 (d, J=2.6 Hz, 1H), 7.58-7.43 (m, 2H), 7.32-7.17 (m, 2H), 7.03 (s, 1H), 6.47 (m, 1H), 4.46 (m, 1H), 4.08 (s, 3H), 3.87 (s, 6H), 2.22 (m, 2H), 1.99 (m, 4H); MS (ES+): 507.3 (M+1), MS (ES−): 505.2 (M−1). The free base was converted to HCl salt by purification using reverse phase flash column chromatography [(silica gel C-18, 24 g) eluting with acetonitrile and 0.1% HCl in water] to afford (S)-methyl 5-(4-((2-(2-carbamoylpyrrolidin-1-yl)pyrrolo[2,1-f][1,2,4]triazin-4-yl)amino)-1H-imidazol-1-yl)-2,3-dimethoxybenzoate (350d) HCl salt as an off-white solid; ¹H NMR (300 MHz, DMSO-d₆) δ 10.51 (s, 1H), 8.29 (s, 1H), 7.96 (s, 1H), 7.69 (s, 1H), 7.51 (d, J=2.5 Hz, 1H), 7.43 (s, 1H), 7.22 (s, 1H), 7.19-7.11 (m, 1H), 6.96 (s, 1H), 6.43 (dd, J=4.4, 2.4 Hz, 1H), 4.41 (d, J=8.8 Hz, 1H), 4.04 (s, 3H), 4.00-3.88 (m, 1H), 3.86 (s, 3H), 3.80 (s, 3H), 3.55-3.40 (m, 1H), 2.30-1.85 (m, 4H); MS (ES+): 507.3 (M+1), 529.3 (M+Na); MS (ES−): 541.3 (M+Cl). HPLC purity: 97.50%.

Preparation of (S)-1-(4-((1-(3-(cyclopentylcarbamoyl)-4-hydroxy-5-methoxyphenyl)-1H-imidazol-4-yl)amino)pyrrolo[2,1-f][1,2,4]triazin-2-yl)pyrrolidine-2-carboxamide (351d)

Step-1: Preparation of 5-(4-((2-chloropyrrolo[2,1-f][1,2,4]triazin-4-yl)amino)-1H-imidazol-1-yl)-N-cyclopentyl-2,3-dimethoxybenzamide (351c)

Compound 351c was prepared from 2,4-dichloropyrrolo[2,1-f][1,2,4]triazine (4a) (500 mg, 2.65 mmol) in 2-Propanol (10 mL) using DIPEA (1.0 g, 7.95 mmol) and 5-(4-amino-1H-imidazol-1-yl)-N-cyclopentyl-2,3-dimethoxybenzamide (351b) (1.3 g, 3.93 mmol) according to the procedure reported in Scheme 1. This gave after workup methyl 5-(4-((2-chloropyrrolo[2,1-f][1,2,4]triazin-4-yl)amino)-1H-imidazol-1-yl)-N-cyclopentyl-2,3-dimethoxybenzamide (351c) (0.26 g, 20%) as a white solid; ¹H NMR (300 MHz, DMSO-d₆) δ 11.32 (s, 1H), 8.31-8.17 (m, 2H), 7.89 (d, J=1.6 Hz, 1H), 7.77 (dd, J=2.6, 1.5 Hz, 1H), 7.48-7.32 (m, 2H), 7.22 (d, J=2.6 Hz, 1H), 6.72 (dd, J=4.5, 2.6 Hz, 1H), 4.22 (m, 1H), 3.94 (s, 3H), 3.80 (s, 3H), 1.89 (m, 2H), 1.72-1.42 (m, 6H); MS (ES+): 482.1 (M+1); MS (ES−): 480.0 (M−1).

Step-2: Preparation of (S)-1-(4-((1-(3-(cyclopentylcarbamoyl)-4-hydroxy-5-methoxyphenyl)-1H-imidazol-4-yl)amino)pyrrolo[2,1-f][1,2,4]triazin-2-yl)pyrrolidine-2-carboxamide (351d)

Compound 351d was prepared according to the procedure reported in step-2 of Scheme 76 from 5-(4-((2-chloropyrrolo[2,1-f][1,2,4]triazin-4-yl)amino)-1H-imidazol-1-yl)-N-cyclopentyl-2,3-dimethoxybenzamide (351c) (250 mg, 0.52 mmol), (S)-pyrrolidine-2-carboxamide (590 mg, 5.16 mmol) in NMP (5 mL). This gave after workup and purification by flash column chromatography [(silica gel, eluting with MeOH in DCM (0-20%)] (S)-1-(4-((1-(3-(cyclopentylcarbamoyl)-4-hydroxy-5-methoxyphenyl)-1H-imidazol-4-yl)amino)pyrrolo[2,1-f][1,2,4]triazin-2-yl)pyrrolidine-2-carboxamide (351d) (160 mg, 57%) free base as an off-white solid; ¹H NMR (300 MHz, DMSO-d₆) δ 10.82 (s, 1H), 9.21 (d, J=7.0 Hz, 1H), 8.75 (s, 1H), 7.99 (d, J=2.4 Hz, 1H), 7.87 (s, 1H), 7.62 (s, 1H), 7.56 (d, J=2.3 Hz, 1H), 7.50 (t, J=1.9 Hz, 1H), 7.45 (s, 1H), 7.22-7.12 (m, 1H), 6.53-6.42 (m, 1H), 4.44-4.36 (m, 1H), 4.36-4.29 (m, 1H), 3.92 (s, 3H), 3.79-3.69 (m, 1H), 3.53-3.40 (m, 1H), 2.21-1.47 (m, 12H); MS (ES+): 546.2 (M+1); MS (ES−): 544.0 (M−1); HPLC: 95.8%. The free base was converted to HCl salt by purification using reverse phase flash column chromatography [(silica gel C-18, 24 g) eluting with acetonitrile and 0.1% HCl in water] to afford (S)-1-(4-((1-(3-(cyclopentylcarbamoyl)-4-hydroxy-5-methoxyphenyl)-1H-imidazol-4-yl)amino)pyrrolo[2,1-f][1,2,4]triazin-2-yl)pyrrolidine-2-carboxamide (351d) HCl salt as a white solid; ¹H NMR (300 MHz, DMSO-d₆) δ 10.82 (s, 1H), 9.21 (d, J=7.0 Hz, 1H), 8.75 (s, 1H), 7.99 (d, J=2.4 Hz, 1H), 7.87 (s, 1H), 7.62 (s, 1H), 7.56 (d, J=2.3 Hz, 1H), 7.50 (t, J=1.9 Hz, 1H), 7.45 (s, 1H), 7.22-7.12 (m, 1H), 6.53-6.42 (m, 1H), 4.44-4.36 (m, 1H), 4.36-4.29 (m, 1H), 3.92 (s, 3H), 3.79-3.69 (m, 1H), 3.53-3.40 (m, 1H), 2.21-1.47 (m, 12H); MS (ES+): 546.4 (M+1), 568.3 (M+Na); MS (ES−): 580.4 (M+Cl). HPLC purity: 94.02%.

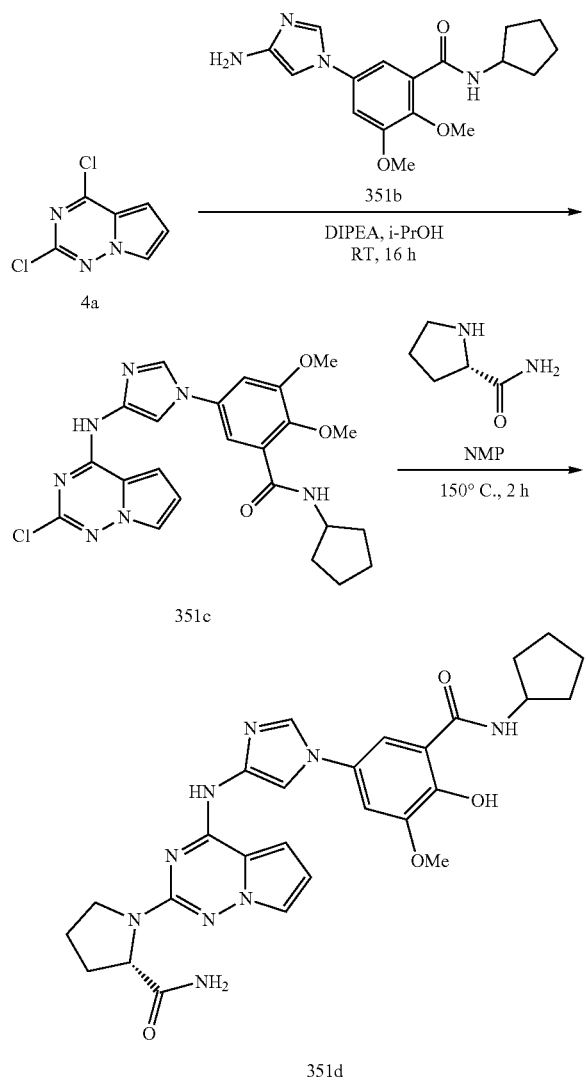

Scheme 351

Scheme 352

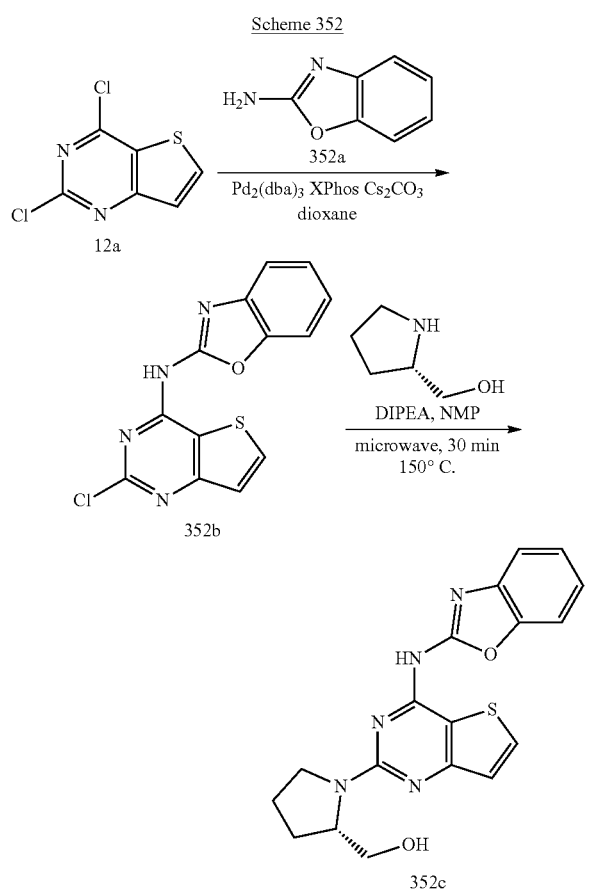

Preparation of (S)-(1-(4-(benzo[d]oxazol-2-ylamino)thieno[3,2-d]pyrimidin-2-yl)pyrrolidin-2-yl)methanol (352c)

Step-1: Preparation of N-(2-chlorothieno[3,2-d]pyrimidin-4-yl)benzo[d]oxazol-2-amine (352b)

Compound 352b was prepared from 2,4-dichlorothieno[3,2-d]pyrimidine (12a) (300 mg, 1.46 mmol), benzo[d]oxazol-2-amine (352a) (196 mg, 1.46 mmol, CAS #4570-41-6), dicyclohexyl(2',4',6'-triisopropylbiphenyl-2-yl)phosphine (XPhos, 209 mg, 0.44 mmol), cesium carbonate (715 mg, 2.19 mmol) and Pd$_2$(dba)$_3$ (201 mg, 0.22 mmol) in dioxane (20 mL) according to the procedure reported in step-3 of Scheme 101. This gave after workup and purification by flash column chromatography [silica (12 g), eluting with ethyl acetate/MeOH (9:1) in hexane from 0-50%] N-(2-chlorothieno[3,2-d]pyrimidin-4-yl)benzo[d]oxazol-2-amine (352b) (65 mg, 15% yield) as a yellow solid; $^1$H NMR (300 MHz, DMSO-d$_6$) δ 12.41 (s, 1H), 8.41-8.27 (m, 1H), 7.63-7.53 (m, 2H), 7.52-7.47 (m, 1H), 7.39-7.25 (m, 2H); MS (ES+) 303.1 (M+1); (ES−) 301.2 (M−1).

Step-2: Preparation of (S)-(1-(4-(benzo[d]oxazol-2-ylamino)thieno[3,2-d]pyrimidin-2-yl)pyrrolidin-2-yl)methanol (352c)

Compound 352c was prepared from N-(2-chlorothieno[3,2-d]pyrimidin-4-yl)benzo[d]oxazol-2-amine (352b) (60 mg, 0.2 mmol) in NMP (5 mL) using (S)-pyrrolidin-3-ylmethanol (40 mg, 0.4 mmol) and DIPEA (0.1 mL, 0.6 mmol) according to the procedure reported in Scheme 2. This gave after workup and purification by flash column chromatography [silica gel (12 g), eluting with ethyl acetate/MeOH (9:1) in hexane from 0-70%] (S)-(1-(4-(benzo[d]oxazol-2-ylamino)thieno[3,2-d]pyrimidin-2-yl)pyrrolidin-2-yl)methanol (352c) (10 mg, 14% yield) as a yellow solid; $^1$H NMR (300 MHz, DMSO-d$_6$) δ 13.69 (s, 1H, D$_2$O exchangeable), 8.13 (d, J=5.3 Hz, 1H), 7.52 (d, J=7.6 Hz, 2H), 7.40-7.12 (m, 3H), 5.45-4.58 (m, 1H, D$_2$O exchangeable), 4.36-4.15 (m, 1H), 3.82-3.45 (m, 4H), 2.19-1.92 (m, 4H); MS (ES+): 368.3 (M+1), 390.3 (M+Na); (ES−): 366.3 (M−1); HPLC purity 98.40%.

Scheme 353

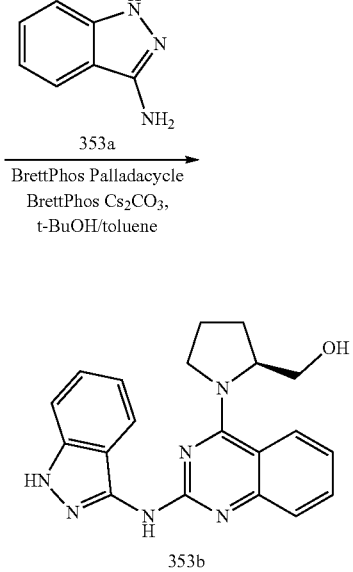

Preparation of (S)-(1-(2-((1H-indazol-3-yl)amino)quinazolin-4-yl)pyrrolidin-2-yl)methanol (353b)

To a solution of (S)-(1-(2-chloroquinazolin-4-yl)pyrrolidin-2-yl)methanol (115a) (300 mg, 1.14 mmol) in t-BuOH (5 mL) and toluene (4 mL) was added 1H-indazol-3-amine (353a) (303 mg, 2.28 mmol; CAS #874-05-5), BrettPhos Palladacycle (62 mg, 0.07 mmol), BrettPhos (73 mg, 0.14 mmol) and Cs$_2$CO$_3$ (741 mg, 2.28 mmol). The reaction mixture was fully degassed and filled with Ar, the resulting mixture was stirred at 100° C. for 2 days in an oil bath. The reaction mixture was diluted with EtOAc (120 mL) and filtered to remove inorganic solids. The filtrate was washed with water, brine, dried, filtered and concentrated in vacuum. The residue was purified by flash column chromatography [silica gel (40 g), eluting with DMA-80 in DCM from 0-60%] and reverse phase column [(silica gel C-18, 50 g), eluting with ACN in water (containing 0.1% HCl) from 0-100%] to afford (S)-(1-(2-((1H-indazol-3-yl)amino)quinazolin-4-yl)pyrrolidin-2-yl)methanol (353b) (39 mg, 10% yield) as a red solid; $^1$H NMR (300 MHz, DMSO-d$_6$) δ 13.13 (s, 1H, D$_2$O exchangeable), 11.49 (s, 1H, D$_2$O exchangeable), 8.32 (d, J=8.4 Hz, 1H), 8.07 (d, J=8.2 Hz, 1H), 7.87 (t, J=7.7 Hz, 1H), 7.78-7.69 (m, 1H), 7.60-7.40 (m, 3H), 7.17 (t, J=7.5

Hz, 1H), 4.78-4.54 (m, 1H), 4.22-4.11 (m, 2H), 3.89-3.69 (m, 2H), 3.63-3.46 (m, 1H), 2.22-1.84 (m, 4H); MS (ES+): 361.3 (M+1), 383.2 (M+Na); (ES-): 395.3; HPLC purity, 95.51%.

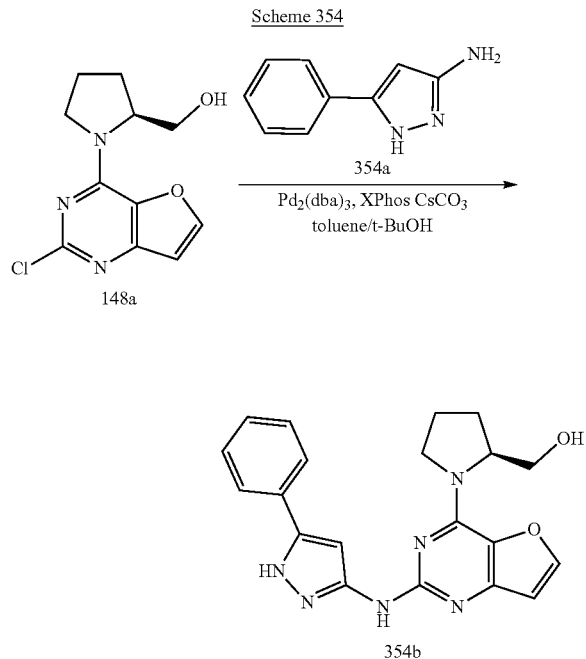

Scheme 354

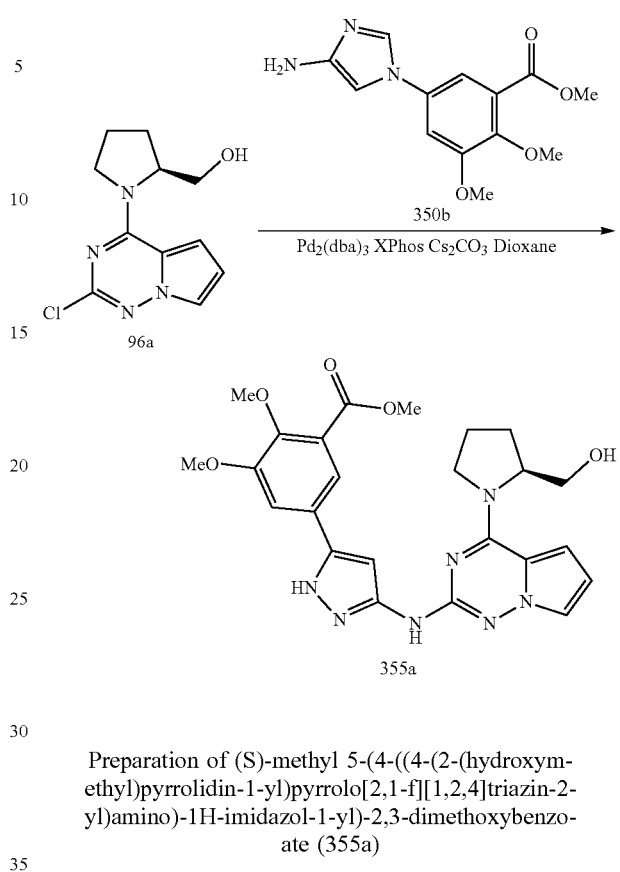

Scheme 355

Preparation of (S)-methyl 5-(4-((4-(2-(hydroxymethyl)pyrrolidin-1-yl)pyrrolo[2,1-f][1,2,4]triazin-2-yl)amino)-1H-imidazol-1-yl)-2,3-dimethoxybenzoate (355a)

Preparation of (S)-(1-(2-((5-phenyl-1H-pyrazol-3-yl)amino)furo[3,2-d]pyrimidin-4-yl)pyrrolidin-2-yl)methanol (354b)

To a degassed solution of dicyclohexyl(2',4',6'-triisopropylbiphenyl-2-yl)phosphine (169 mg, 0.36 mmol) in toluene (30 mL) and t-Butanol (10 mL) was added cesium carbonate (578 mg, 1.77 mmol) and Pd$_2$(dba)$_3$ (162 mg, 0.18 mmol). The resulting mixture was degassed and heated at 110° C. for 15 min. Then (S)-(1-(2-chlorofuro[3,2-d]pyrimidin-4-yl)pyrrolidin-2-yl)methanol (148a) (300 mg, 1.18 mmol) and 5-phenyl-1H-pyrazol-3-amine (354a) (94 mg, 0.59 mmol; CAS #1572-10-7) were added, degassed and filled with Ar. The resulting mixture was heated at 110° C. for 17 h. The reaction mixture was diluted with a mixture of EtOAc (100 mL) and methanol (10 mL), stirred for 10 mins, filtered to remove inorganic solids. The filtrate was concentrated in vacuum and the residue was purified by flash column chromatography [silica gel (12 g), eluting with DMA-80 in DCM from 0-100%] to afford (S)-(1-(2-((5-phenyl-1H-pyrazol-3-yl)amino)furo[3,2-d]pyrimidin-4-yl)pyrrolidin-2-yl)methanol (354b) (23 mg, 10% yield) as a white solid; $^1$H NMR (300 MHz, DMSO-d$_6$): δ 13.01 (s, 1H), 9.49 (s, 1H), 8.10 (d, J=2.1 Hz, 1H), 7.77 (d, J=7.7 Hz, 2H), 7.60-7.02 (m, 4H), 6.90-6.70 (m, 1H), 5.10-4.68 (m, 1H), 4.63-4.31 (m, 1H), 4.07-3.42 (m, 4H), 2.20-1.66 (m, 4H). MS (ES+): 377.2 (M+1); 399.1 (M+Na); MS (ES-): 375.3 (M-1); 411.2 (M+Cl). HPLC purity: 88.13%.

Compound 355a was prepared from (S)-(1-(2-chloropyrrolo[2,1-f][1,2,4]triazin-4-yl)pyrrolidin-2-yl)methanol (96a) (400 mg, 1.58 mmol), methyl 5-(4-amino-1H-imidazol-1-yl)-2,3-dimethoxybenzoate (350b) (610 mg, 2.21 mmol), dicyclohexyl(2',4',6'-triisopropylbiphenyl-2-yl)phosphine (XPhos, 330 mg, 0.71 mmol), cesium carbonate (1.54 g, 4.74 mmol) and Pd$_2$(dba)$_3$ (210 mg, 0.23 mmol) in 1,4-dioxane (10 mL) according to the procedure reported in step-3 of Scheme 101. This gave after workup and purification by flash column chromatography [silica gel, eluting with (0-5%) MeOH in ethyl acetate] compound 355a (40.0 mg, 5%) as an off-white solid; $^1$H NMR (300 MHz, DMSO-d$_6$): δ 9.13 (s, 1H), 8.74 (s, 1H), 7.78 (s, 1H), 7.59 (d, J=2.5 Hz, 2H), 7.49 (d, J=2.5 Hz, 1H), 6.83 (d, J=4.5 Hz, 1H), 6.52 (s, 1H), 4.59-4.43 (m, 1H), 4.03-3.76 (m, 10H), 3.76-3.42 (m, 3H), 2.32-1.74 (m, 4H); MS (ES+) 494.0 (M+1). The free base was converted to HCl salt by using reverse phase column chromatography [(silica gel C-18, 24 g) eluting with acetonitrile and 0.1% HCl in water] to afford (S)-methyl 5-(4-((4-(2-(hydroxymethyl)pyrrolidin-1-yl)pyrrolo[2,1-f][1,2,4]triazin-2-yl)amino)-1H-imidazol-1-yl)-2,3-dimethoxybenzoate (355a) HCl salt as an off-white; $^1$H NMR (300 MHz, DMSO-d$_6$): δ 9.13 (s, 1H), 8.74 (s, 1H), 7.78 (s, 1H), 7.59 (d, J=2.5 Hz, 2H), 7.49 (d, J=2.5 Hz, 1H), 6.83 (d, J=4.5 Hz, 1H), 6.52 (s, 1H), 4.59-4.43 (m, 1H), 4.03-3.76 (m, 1H), 3.97 (s, 3H), 3.87 (s, 3H), 3.81 (s, 3H), 3.76-3.42 (m, 3H), 2.32-1.74 (m, 4H). MS (ES+): 494.3 (M+1), 516.3 (M+Na); MS (ES-): 528.3 (M+Cl). HPLC purity: 98.18%.

Scheme 356

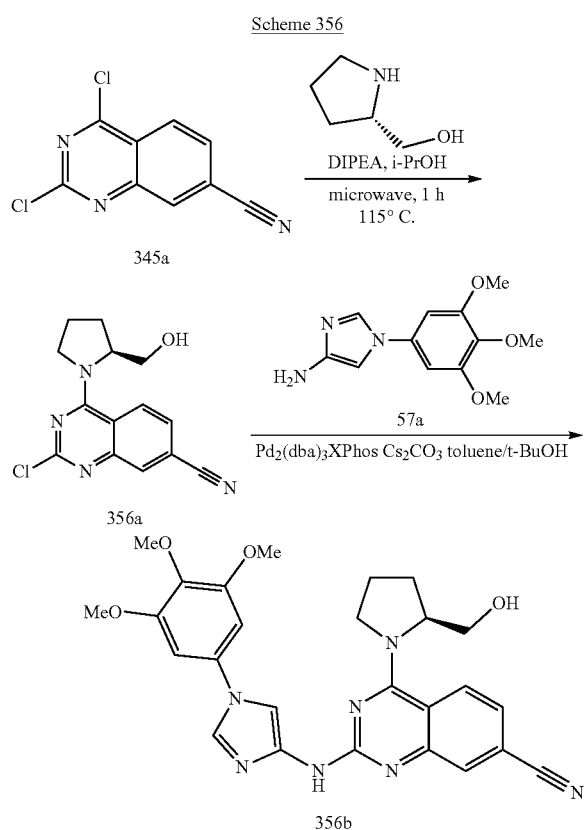

Preparation of (S)-4-(2-(hydroxymethyl)pyrrolidin-1-yl)-2-((1-(3,4,5-trimethoxyphenyl)-1H-imidazol-4-yl)amino)quinazoline-7-carbonitrile (356b)

Step-1: Preparation of (S)-2-chloro-4-(2-(hydroxymethyl)pyrrolidin-1-yl)quinazoline-7-carbonitrile (356a)

Compound 356a was prepared from 2,4-dichloroquinazoline-7-carbonitrile (345a) (400 mg, 1.79 mmol) in 2-Propanol (15 mL) using (S)-pyrrolidin-3-ylmethanol (0.18 mL, 1.79 mmol) and DIPEA (0.94 mL, 5.36 mmol) according to the procedure reported in Scheme 2. This gave after workup and purification by flash column chromatography [silica gel (12 g), eluting with DCM and methanol (0 to 50%)] (S)-2-chloro-4-(2-(hydroxymethyl)pyrrolidin-1-yl)quinazoline-7-carbonitrile (356a) (427 mg, 83% yield) as a yellow solid; $^1$H NMR (300 MHz, DMSO-d$_6$): δ 8.40 (d, J=8.8 Hz, 1H), 8.15 (d, J=1.8 Hz, 1H), 7.77 (dd, J=8.7, 1.8 Hz, 1H), 4.87 (t, J=5.9 Hz, 1H), 4.56 (d, J=6.6 Hz, 1H), 4.12-3.87 (m, 2H), 3.78-3.55 (m, 2H), 2.20-1.76 (m, 4H). MS (ES+): 289.2 (M+1); 311.2 (M+Na); MS (ES−): 287.2 (M−1).

Step-2: Preparation of (S)-4-(2-(hydroxymethyl)pyrrolidin-1-yl)-2-((1-(3,4,5-trimethoxyphenyl)-1H-imidazol-4-yl)amino)quinazoline-7-carbonitrile (356b)

Compound 356b was prepared from (S)-2-chloro-4-(2-(hydroxymethyl)pyrrolidin-1-yl)quinazoline-7-carbonitrile (356a) (300 mg, 1.04 mmol), 1-(3,4,5-trimethoxyphenyl)-1H-imidazol-4-amine (57a) (259 mg, 1.04 mmol), dicyclohexyl(2',4',6'-triisopropylbiphenyl-2-yl)phosphine (XPhos, 297 mg, 0.62 mmol), cesium carbonate (1016 mg, 3.12 mmol) and Pd$_2$(dba)$_3$ (285 mg, 0.31 mmol) in toluene/t-BuOH (40 mL, Ratio: 3:1) according to the procedure reported in step-3 of Scheme 101. This gave after workup and purification by flash column chromatography [silica gel (24 g), eluting with DMA-80 in DCM from 0-50%], followed by reverse phase column chromatography [(silica gel C-18, 24 g) eluting with acetonitrile and 0.1% HCl in water] (S)-4-(2-(hydroxymethyl)pyrrolidin-1-yl)-2-((1-(3,4,5-trimethoxyphenyl)-1H-imidazol-4-yl)amino)quinazoline-7-carbonitrile (356b) (91 mg, 18% yield) HCl salt as a yellow solid; $^1$H NMR (300 MHz, DMSO-d$_6$) δ 11.18 (s, 1H), 8.58-8.22 (m, 2H), 7.96 (s, 1H), 7.78 (dd, J=8.6, 1.6 Hz, 1H), 7.72 (s, 1H), 6.98 (s, 2H), 4.85 (s, 1H), 4.34-4.02 (m, 1H), 4.00-3.91 (m, 1H), 3.88 (s, 6H), 3.85-3.71 (m, 2H), 3.69 (s, 3H), 2.30-1.74 (m, 4H); MS (ES+): 502.3 (M+1); MS (ES−): 536.3 (M+Cl). HPLC purity: 94.11%.

Scheme 357

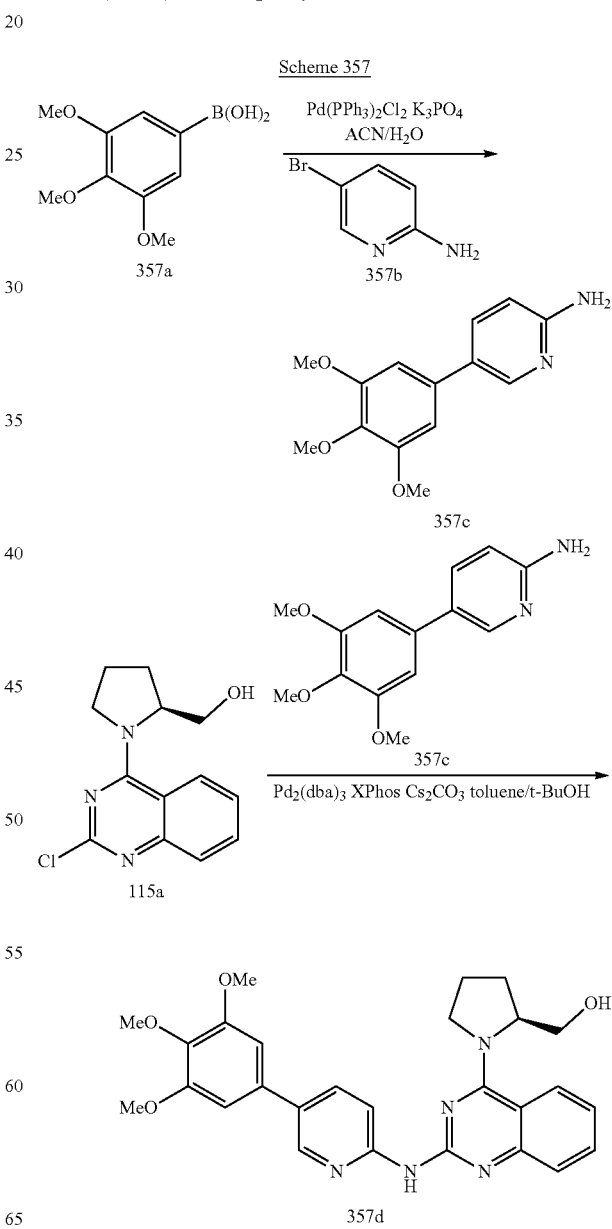

Preparation of (S)-(1-(2-((5-(3,4,5-trimethoxyphenyl)pyridin-2-yl)amino)quinazolin-4-yl)pyrrolidin-2-yl)methanol (357d)

Step-1: Preparation of 5-(3,4,5-trimethoxyphenyl)pyridin-2-amine (357c)

To a solution of 5-bromopyridin-2-amine (357b) (300 mg, 1.73 mmol) in ACN/H$_2$O (10 mL) was added 3,4,5-trimethoxyphenylboronic acid (357a) (551 mg, 2.6 mmol), Pd(PPh$_3$)$_2$Cl$_2$ (122 mg, 0.17 mmol) and K$_3$PO$_4$ (1.47 g, 6.94 mmol). The mixture was degassed, filled with Ar and heated 110° C. on microwave for 1 h. The mixture was diluted with EtOAc, washed with water, brine, dried filtered and concentrated in vacuum. The residue was purified by flash column chromatography [silica (12 g), eluting with DMA80 in DCM from 0-100%] to afford 5-(3,4,5-trimethoxyphenyl)pyridin-2-amine (357c) (125 mg, 28% yield) as a yellow solid; MS (ES+): 261.2 (M+1).

Step-2: Preparation of (S)-(1-(2-((5-(3,4,5-trimethoxyphenyl)pyridin-2-yl)amino)quinazolin-4-yl)pyrrolidin-2-yl)methanol (357d)

Compound 357d was prepared from (S)-(1-(2-chloroquinazolin-4-yl)pyrrolidin-2-yl)methanol (115a) (300 mg, 1.14 mmol), 5-(3,4,5-trimethoxyphenyl)pyridin-2-amine (357c) (296 mg, 1.14 mmol), dicyclohexyl(2',4',6'-triisopropylbiphenyl-2-yl)phosphine (XPhos, 325 mg, 0.68 mmol), cesium carbonate (1112 mg, 3.41 mmol) and Pd$_2$(dba)$_3$ (313 mg, 0.34 mmol) in toluene/t-BuOH (40 mL, Ratio: 3:1) according to the procedure reported in step-3 of Scheme 101. This gave after workup and purification by flash column chromatography [silica gel (24 g), eluting with DMA80 in DCM from 0-50%], followed by reverse phase column chromatography [(silica gel C-18, 24 g) eluting with acetonitrile and 0.1% HCl in water] (S)-(1-(2-((5-(3,4,5-trimethoxyphenyl)pyridin-2-yl)amino)quinazolin-4-yl)pyrrolidin-2-yl)methanol (357d) (208 mg, 38% yield) HCl salt as a yellow solid; $^1$H NMR (300 MHz, DMSO-d$_6$) δ 14.40 (s, 1H), 11.78 (s, 1H), 8.81 (d, J=2.4 Hz, 1H), 8.35 (d, J=8.5 Hz, 1H), 8.30 (dd, J=8.7, 2.5 Hz, 1H), 8.00-7.85 (m, 2H), 7.60 (d, J=8.7 Hz, 1H), 7.56-7.48 (m, 1H), 6.99 (s, 2H), 4.91-4.58 (m, 1H), 4.31-3.99 (m, 2H), 3.97-3.90 (m, 1H), 3.88 (s, 6H), 3.85-3.72 (m, 1H), 3.70 (s, 3H), 2.32-1.82 (m, 4H); MS (ES+): 488.4 (M+1); MS (ES−): 522.4 (M+Cl). HPLC purity: 96.38%.

Scheme 358

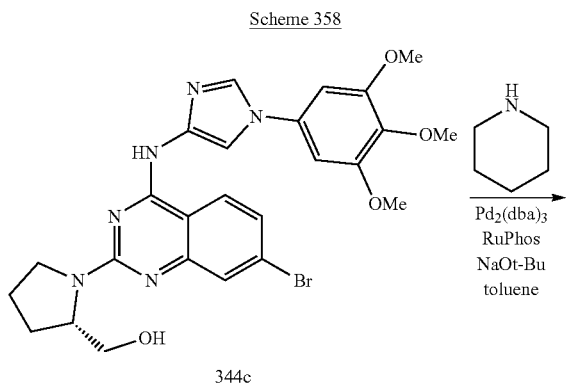

344c

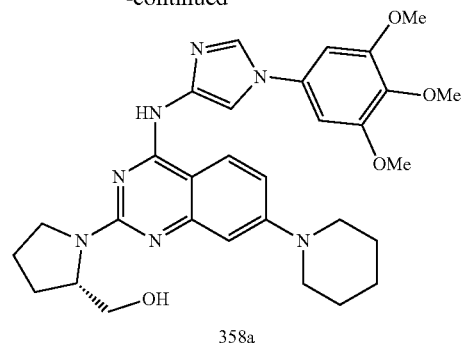

358a

Preparation of (S)-(1-(7-(piperidin-1-yl)-4-((1-(3,4,5-trimethoxyphenyl)-1H-imidazol-4-yl)amino)quinazolin-2-yl)pyrrolidin-2-yl)methanol (358a)

Compound 358a was prepared from (S)-(1-(7-bromo-4-((1-(3,4,5-trimethoxyphenyl)-1H-imidazol-4-yl)amino)quinazolin-2-yl)pyrrolidin-2-yl)methanol (344c) (300 mg, 0.54 mmol), piperidine (0.27 mL, 2.7 mmol), dicyclohexyl(2',6'-diisopropoxybiphenyl-2-yl)phosphine (RuPhos, 151 mg, 0.32 mmol), sodium 2-methylpropan-2-olate (260 mg, 2.7 mmol) and Pd$_2$(dba)$_3$ (148 mg, 0.16 mmol) in toluene (10 mL) according to the procedure reported in step-3 of Scheme 101. This gave after workup and purification by flash column chromatography [silica gel (24 g), eluting with DMA-80 in DCM from 0-50%], followed by reverse phase column chromatography [(silica gel C-18, 24 g) eluting with acetonitrile and 0.1% HCl in water] (S)-(1-(7-(piperidin-1-yl)-4-((1-(3,4,5-trimethoxyphenyl)-1H-imidazol-4-yl)amino)quinazolin-2-yl)pyrrolidin-2-yl)methanol (358a) (110 mg, 37% yield) HCl salt as a yellow solid; $^1$H NMR (300 MHz, DMSO-d$_6$) δ 12.09 (s, 1H), 11.48 (s, 1H), 9.02-8.74 (m, 1H), 8.47 (s, 1H), 8.07 (s, 1H), 7.70-7.38 (m, 1H), 7.26-6.92 (m, 3H), 4.76-4.24 (m, 1H), 3.88 (s, 6H), 3.83-3.74 (m, 2H), 3.69 (s, 3H), 3.45 (m, 4H), 2.27-1.76 (m, 4H), 1.78-1.28 (m, 6H); MS (ES+): 560.5 (M+1); MS (ES−): 598.5 (M−1). HPLC purity: 93.48%.

Scheme 359

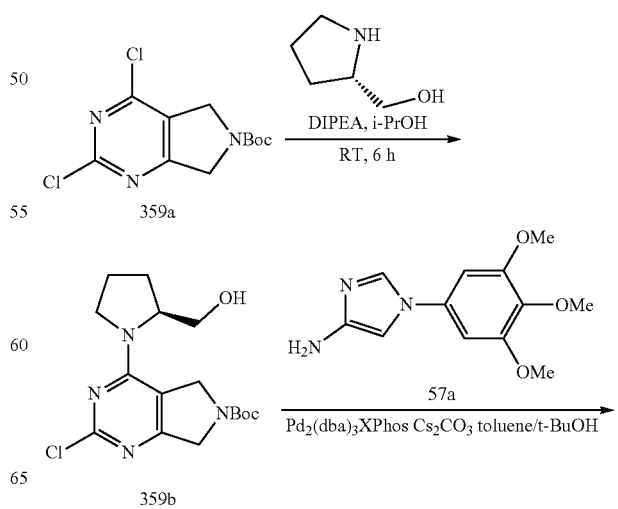

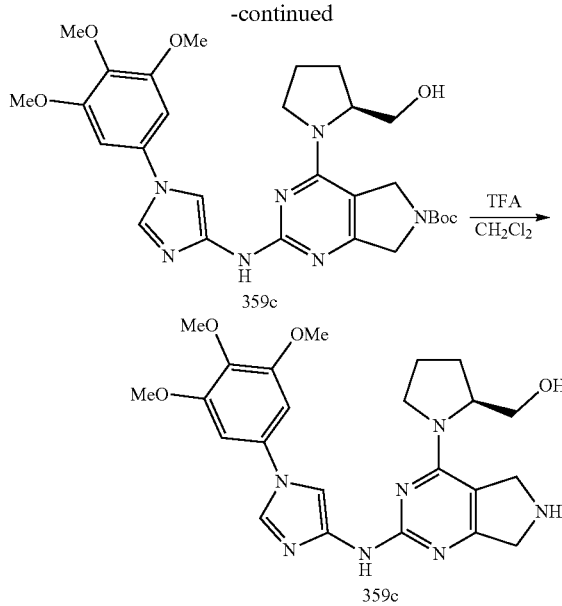

Preparation of (S)-(1-(2-(1-(3,4,5-trimethoxyphenyl)-1H-imidazol-4-ylamino)-6,7-dihydro-5H-pyrrolo[3,4-d]pyrimidin-4-yl)pyrrolidin-2-yl)methanol (359d)

Step-1: Preparation of (S)-tert-butyl 2-chloro-4-(2-(hydroxymethyl)pyrrolidin-1-yl)-5H-pyrrolo[3,4-d]pyrimidine-6(7H)-carboxylate (359b)

Compound 359b was prepared from tert-butyl 2,4-dichloro-5H-pyrrolo[3,4-d]pyrimidine-6(7H)-carboxylate (359a) (CAS #: 903129-71-5) (500 mg, 1.72 mmol) in 2-Propanol (10 mL) using (S)-pyrrolidin-2-ylmethanol (174 mg, 1.72 mmol) and DIPEA (0.6 mL, 3.45 mmol) according to the procedure reported in step-1 of Scheme 96. This gave after workup and purification by flash column chromatography [silica gel (24 g), eluting with eluting with EtOAc in hexane from 0-100%] (S)-tert-butyl 2-chloro-4-(2-(hydroxymethyl)pyrrolidin-1-yl)-5H-pyrrolo[3,4-d]pyrimidine-6(7H)-carboxylate (359b) (510 mg, 83% yield) as a white solid; $^1$H NMR (300 MHz, DMSO-$d_6$) δ 4.93-4.66 (m, 3H), 4.40-4.29 (m, 2H), 4.26-3.94 (m, 1H), 3.78-3.43 (m, 3H), 2.05-1.75 (m, 4H), 1.44 (s, 9H); MS (ES+): 355.3 (M+1); 377.2 (M+Na); (ES−): 353.3 (M−1).

Step-2, Preparation of (S)-tert-butyl 4-(2-(hydroxymethyl)pyrrolidin-1-yl)-2-(1-(3,4,5-trimethoxyphenyl)-1H-imidazol-4-ylamino)-5H-pyrrolo[3,4-d]pyrimidine-6(7H)-carboxylate (359c)

Compound 359c was prepared from (S)-tert-butyl 2-chloro-4-(2-(hydroxymethyl)pyrrolidin-1-yl)-5H-pyrrolo[3,4-d]pyrimidine-6(7H)-carboxylate (359b) (400 mg, 1.13 mmol), 1-(3,4,5-trimethoxyphenyl)-1H-imidazol-4-amine (57a) ((309 mg, 1.24 mmol), dicyclohexyl(2',4',6'-triisopropylbiphenyl-2-yl)phosphine (XPhos, 215 mg, 0.45 mmol), cesium carbonate (735 mg, 2.26 mmol) and Pd$_2$(dba)$_3$ (206 mg, 0.23 mmol) in t-BuOH/toluene (10 mL) according to the procedure reported in step-3 of Scheme 101. This gave after workup and twice purification by flash column chromatography [silica gel (24 g), eluting with DMA-80 in DCM from 0-100%](S)-tert-butyl 4-(2-(hydroxymethyl)pyrrolidin-1-yl)-2-(1-(3,4,5-trimethoxyphenyl)-1H-imidazol-4-ylamino)-5H-pyrrolo[3,4-d]pyrimidine-6(7H)-carboxylate (359c) (220 mg, 34% yield) as an off white solid; $^1$H NMR (300 MHz, DMSO-$d_6$) δ 9.16 (s, 1H, D$_2$O exchangeable), 8.07 (s, 1H), 7.66 (s, 1H), 6.90 (s, 2H), 5.00-4.87 (m, 1H, D$_2$O exchangeable), 4.80-4.61 (m, 2H), 4.30-4.22 (m, 2H), 3.86 (s, 6H), 3.81-3.72 (m, 1H), 3.66 (s, 3H), 3.65-3.53 (m, 2H), 3.33-3.20 (m, 2H), 2.02-1.85 (m, 4H), 1.45 (s, 9H); MS (ES+): 568.5 (M+1); 590.4 (M+Na); (ES−): 602.5 (M+Cl); HPLC purity: 95.97%.

Step-3: Preparation of (S)-(1-(2-(1-(3,4,5-trimethoxyphenyl)-1H-imidazol-4-ylamino)-6,7-dihydro-5H-pyrrolo[3,4-d]pyrimidin-4-yl)pyrrolidin-2-yl)methanol (359d)

Compound 359d was prepared by hydrolysis of (S)-tert-butyl 4-(2-(hydroxymethyl)pyrrolidin-1-yl)-2-(1-(3,4,5-trimethoxyphenyl)-1H-imidazol-4-ylamino)-5H-pyrrolo[3,4-d]pyrimidine-6(7H)-carboxylate (359c) (185 mg, 0.37 mmol) in DCM (20 mL) using trifluoroacetic acid (0.25 mL, 3.26 mmol) according to the procedure reported in Scheme 122. This gave after purification by reverse phase column chromatography [(silica gel C-18, 50 g), eluting with acetonitrile in water (containing 0.1% HCl) from 0-100%] (S)-(1-(2-(1-(3,4,5-trimethoxyphenyl)-1H-imidazol-4-ylamino)-6,7-dihydro-5H-pyrrolo[3,4-d]pyrimidin-4-yl)pyrrolidin-2-yl)methanol (359d) (85 mg, 56% yield) as a white solid; $^1$H NMR (300 MHz, DMSO-$d_6$) δ 10.40-10.19 (m, 3H, D$_2$O exchangeable), 8.96 (s, 1H), 7.89-7.78 (m, 1H, D$_2$O exchangeable), 7.06 (s, 2H), 4.77-4.61 (m, 2H), 4.35-4.24 (m, 2H), 3.87 (s, 6H), 3.84-3.74 (m, 1H), 3.69 (s, 3H), 3.65-3.59 (m, 1H), 3.43-3.32 (m, 1H), 2.06-1.80 (m, 4H); MS (ES+): 468.4 (M+1); (ES−): 502.4 (M+Cl); HPLC purity: 98.83%.

Scheme 360

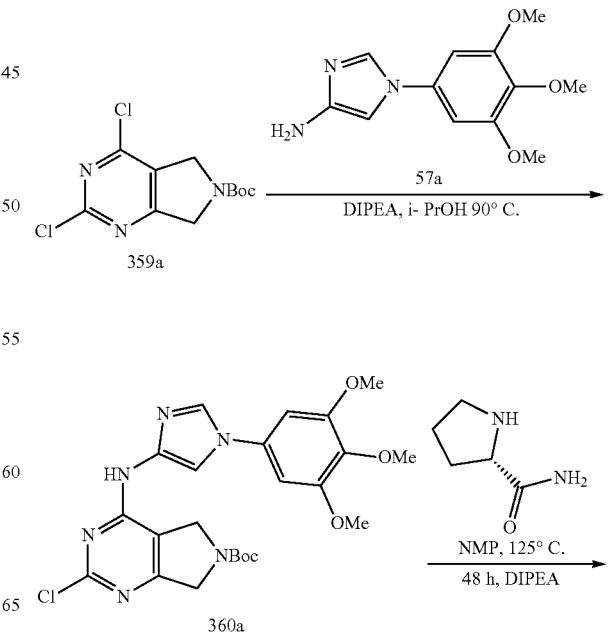

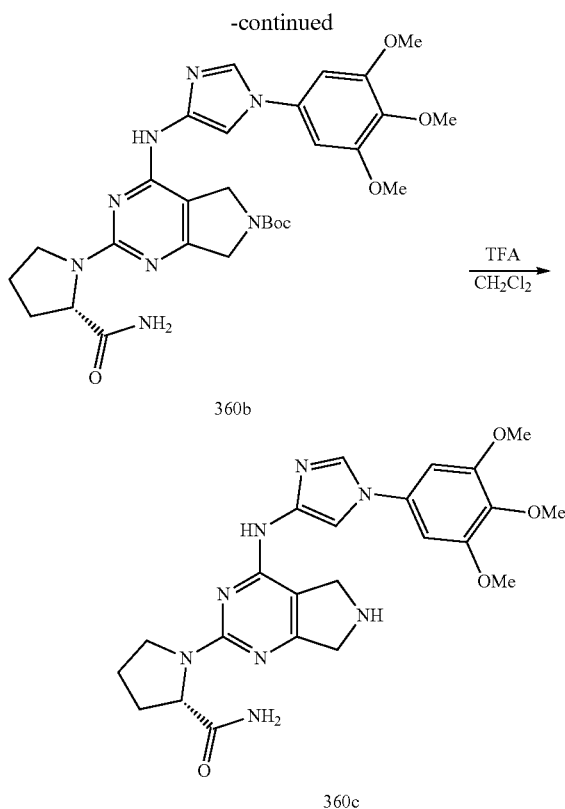

Preparation of (S)-1-(4-(1-(3,4,5-trimethoxyphenyl)-1H-imidazol-4-ylamino)-6,7-dihydro-5H-pyrrolo[3,4-d]pyrimidin-2-yl)pyrrolidine-2-carboxamide (360c)

Step-1: Preparation of tert-butyl 2-chloro-4-(1-(3,4,5-trimethoxyphenyl)-1H-imidazol-4-ylamino)-5H-pyrrolo[3,4-d]pyrimidine-6(7H)-carboxylate (360a)

Compound 360a was prepared from tert-butyl 2,4-dichloro-5H-pyrrolo[3,4-d]pyrimidine-6(7H)-carboxylate (359a) (1 g, 3.45 mmol) in 2-Propanol (15 mL) using DIPEA (1.2 mL, 6.89 mmol) and 1-(3,4,5-trimethoxyphenyl)-1H-imidazol-4-amine (57a) (860 mg, 3.45 mmol) according to the procedure reported in step-1 of Scheme 183. This gave after filtration tert-butyl 2-chloro-4-(1-(3,4,5-trimethoxyphenyl)-1H-imidazol-4-ylamino)-5H-pyrrolo[3,4-d]pyrimidine-6(7H)-carboxylate (360a) (1.4 g, 81% yield) as a white solid; $^1$H NMR (300 MHz, DMSO-d6) δ 10.55-10.26 (m, 1H, D2O exchangeable), 8.21-8.10 (m, 1H), 7.85-7.68 (m, 1H), 6.99-6.82 (m, 2H), 4.61-4.35 (m, 4H), 3.87 (s, 6H), 3.69 (s, 3H), 1.45 (s, 9H)); MS (ES+): 503.4 (M+1), 525.4 (M+Na); (ES−): 537.5 (M+Cl).

Step-2: Preparation of (S)-tert-butyl 2-(2-carbamoylpyrrolidin-1-yl)-4-(1-(3,4,5-trimethoxyphenyl)-1H-imidazol-4-ylamino)-5H-pyrrolo[3,4-d]pyrimidine-6(7H)-carboxylate (360b)

Compound 360b was prepared from tert-butyl 2-chloro-4-(1-(3,4,5-trimethoxyphenyl)-1H-imidazol-4-ylamino)-5H-pyrrolo[3,4-d]pyrimidine-6(7H)-carboxylate (360a) (275 mg, 0.547 mmol), (S)-pyrrolidine-2-carboxamide (250 mg, 2.187 mmol) and N-ethyl-N-isopropylpropan-2-amine (0.286 mL, 1.640 mmol) in N-Methyl-2-pyrrolidinone (5 mL) according to the procedure reported in step-2 of Scheme 76. This gave after workup and purification by flash column chromatography [silica gel (24 g), eluting with DMA80 in DCM from 0-60%] (S)-tert-butyl 2-(2-carbamoylpyrrolidin-1-yl)-4-(1-(3,4,5-trimethoxyphenyl)-1H-imidazol-4-ylamino)-5H-pyrrolo[3,4-d]pyrimidine-6(7H)-carboxylate (360b) (184 mg, 58% yield) as a white solid. MS (ES+): 581.4 (M+1), 603.4 (M+Na), (ES−): 579.5 (M−1).

Step-3: Preparation of (S)-1-(4-(1-(3,4,5-trimethoxyphenyl)-1H-imidazol-4-ylamino)-6,7-dihydro-5H-pyrrolo[3,4-d]pyrimidin-2-yl)pyrrolidine-2-carboxamide (360c)

Compound 360c was prepared by hydrolysis of (S)-tert-butyl 2-(2-carbamoylpyrrolidin-1-yl)-4-(1-(3,4,5-trimethoxyphenyl)-1H-imidazol-4-ylamino)-5H-pyrrolo[3,4-d]pyrimidine-6(7H)-carboxylate (360b) (184 mg, 0.32 mmol) in DCM (10 mL) using trifluoroacetic acid (0.49 mL, 6.34 mmol) according to the procedure reported in Scheme 122. This gave after purification by chromatography [silica gel (12 g), eluting with DMA80 in DCM from 0-100%] followed by reverse phase column chromatography [(silica gel C-18, 50 g), eluting with acetonitrile in water (containing 0.1% HCl) from 0-100%] (S)-1-(4-(1-(3,4,5-trimethoxyphenyl)-1H-imidazol-4-ylamino)-6,7-dihydro-5H-pyrrolo[3,4-d]pyrimidin-2-yl)pyrrolidine-2-carboxamide (360c) (122 mg, 80% yield) as a white solid; $^1$H NMR (300 MHz, DMSO-d$_6$) δ 11.25 (s, 1H, D$_2$O exchangeable), 10.71 (s, 1H, D$_2$O exchangeable), 10.57 (s, 1H, D$_2$O exchangeable), 8.52 (s, 1H), 7.86 (d, J=1.6 Hz, 1H, D$_2$O exchangeable), 7.59 (s, 1H, D$_2$O exchangeable), 7.22 (s, 1H), 7.14 (s, 2H), 4.60-4.39 (m, 6H), 3.93 (s, 6H), 3.90-3.85 (m, 1H), 3.69 (s, 3H), 3.65-3.52 (m, 1H), 2.36-2.19 (m, 1H), 2.07-1.90 (m, 3H); MS (ES+): 481.4 (M+1), 503.3 (M+Na); (ES−): 515.4 (M+Cl); HPLC purity: 99.27%.

Scheme 361

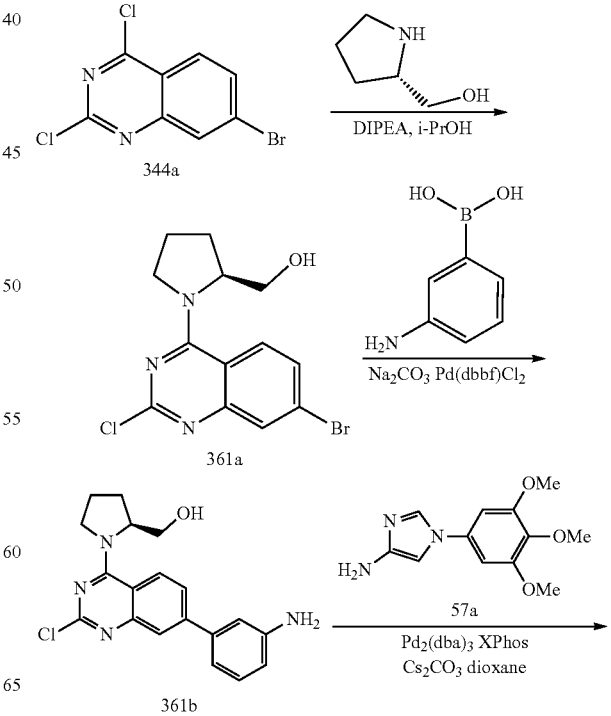

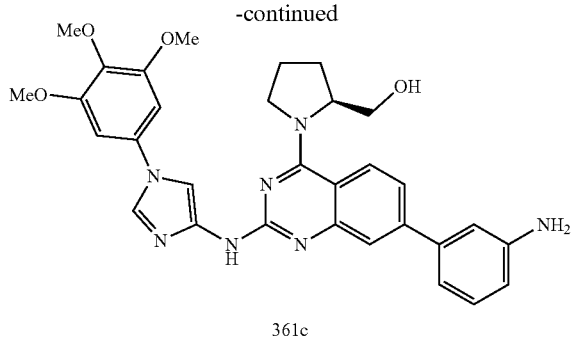

361c

Preparation of (S)-(1-(7-(3-aminophenyl)-2-((1-(3,4,5-trimethoxyphenyl)-1H-imidazol-4-yl)amino)quinazolin-4-yl)pyrrolidin-2-yl)methanol (361c)

Step-1: Preparation of (S)-(1-(7-bromo-2-chloroquinazolin-4-yl)pyrrolidin-2-yl)methanol (361a) Compound 361a was prepared from 7-bromo-2,4-dichloroquinazoline (344a) (3 g, 10.79 mmol) in 2-Propanol (20 mL) using (S)-pyrrolidin-2-ylmethanol (1.2 mL, 11.87 mmol), DIPEA (5.66 mL, 32.4 mmol) according to the procedure reported in step-1 of Scheme 96. This gave after work (S)-(1-(7-bromo-2-chloroquinazolin-4-yl)pyrrolidin-2-yl)methanol (361a) (2.5 g, 68% yield) as a white solid; $^1$H NMR (300 MHz, DMSO-$d_6$) δ 8.19 (d, J=9.1 Hz, 1H), 7.83 (d, J=2.2 Hz, 1H), 7.60 (dd, J=9.1, 2.2 Hz, 1H), 4.86 (t, J=5.8 Hz, 1H), 4.55 (s, 1H), 3.95 (dd, J=15.1, 7.6 Hz, 2H), 3.75-3.48 (m, 2H), 2.15-1.80 (m, 4H); MS (ES+): 364.1, 366.1 (M+Na), (ES-): 340.1, 342.1 (M-1).

Step-2: Preparation of (S)-(1-(7-(3-aminophenyl)-2-chloroquinazolin-4-yl)pyrrolidin-2-yl)methanol (361b)

Compound 361b was prepared from (S)-(1-(7-bromo-2-chloroquinazolin-4-yl)pyrrolidin-2-yl)methanol (361a) (500 mg, 1.46 mmol) using 3-aminophenylboronic acid (200 mg, 1.46 mmol Bis(triphenylphosphine)palladium(II) dichloride (51 mg, 0.073 mmol) and sodium carbonate (309 mg, 2.92 mmol) in toluene (15 mL), EtOH (7 mL) and water (3 mL) according to the procedure reported in step-3 of Scheme 77. This gave after workup and purification by flash column chromatography [silica gel, (24 g) eluting with DMA-80 in CH$_2$Cl$_2$ from 0 to 50%] (S)-(1-(7-(3-aminophenyl)-2-chloroquinazolin-4-yl)pyrrolidin-2-yl)methanol (361b) (365 mg, 71% yield) as a white solid; $^1$H NMR (300 MHz, DMSO-$d_6$) δ 8.32 (d, J=8.9 Hz, 1H), 7.75 (d, J=2.0 Hz, 1H), 7.68 (dd, J=8.8, 2.0 Hz, 1H), 7.16 (t, J=7.8 Hz, 1H), 6.98 (t, J=2.0 Hz, 1H), 6.93 (dt, J=7.5, 1.2 Hz, 1H), 6.65 (ddd, J=8.0, 2.3, 0.9 Hz, 1H), 5.29 (s, 2H), 4.88 (t, J=5.7 Hz, 1H), 4.58 (d, J=5.5 Hz, 1H), 4.13-3.90 (m, 2H), 3.66 (t, J=5.2 Hz, 2H), 2.16-1.78 (m, 4H); MS (ES+): 355.2 (M+1), 377.2 (M+Na), (ES-): 353.3 (M-1).

Step-3: Preparation of (S)-(1-(7-(3-aminophenyl)-2-((1-(3,4,5-trimethoxyphenyl)-1H-imidazol-4-yl)amino)quinazolin-4-yl)pyrrolidin-2-yl)methanol (361c)

Compound 361c was prepared from (S)-(1-(7-(3-aminophenyl)-2-chloroquinazolin-4-yl)pyrrolidin-2-yl)methanol (361b) (358 mg, 1.01 mmol), 1-(3,4,5-trimethoxyphenyl)-1H-imidazol-4-amine (57a) (314 mg, 1.26 mmol), dicyclohexyl(2',4',6'-triisopropylbiphenyl-2-yl)phosphine (XPhos, 216 mg, 0.45 mmol), cesium carbonate (986 mg, 3.03 mmol), Pd$_2$(dba)$_3$ (139 mg, 0.15 mmol) in dioxane (15 mL) according to the procedure reported in step-3 of Scheme 101. This gave after workup and purification by flash column chromatography [silica gel, (24 g) eluting with DMA-80 in CH$_2$Cl$_2$ from 0 to 50%] followed by reverse phase column chromatography [(silica gel C-18, 24 g) eluting with acetonitrile and 0.1% HCl in water] (S)-(1-(7-(3-aminophenyl)-2-((1-(3,4,5-trimethoxyphenyl)-1H-imidazol-4-yl)amino)quinazolin-4-yl)pyrrolidin-2-yl)methanol (361c) (60 mg, 10% yield) as a light yellow solid; $^1$H NMR (300 MHz, DMSO-$d_6$-D$_2$O) δ 8.35 (d, J=8.8 Hz, 1H), 8.28 (s, 1H), 7.91-7.73 (m, 1H), 7.70 (d, J=8.7 Hz, 2H), 7.51 (d, J=4.8 Hz, 2H), 7.43 (s, 1H), 7.17 (d, J=5.3 Hz, 1H), 6.92 (s, 2H), 4.92-4.67 (m, 1H), 4.24-4.06 (m, 2H), 4.03-3.91 (m, 1H), 3.84 (s, 6H), 3.81-3.65 (m, 1H), 3.66 (s, 3H), 2.24-1.84 (m, 4H); MS (ES+) 568.4 (M+1); HPLC purity: 96.68%.

Scheme 362

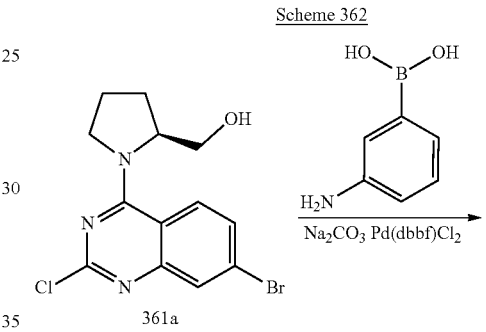

361a

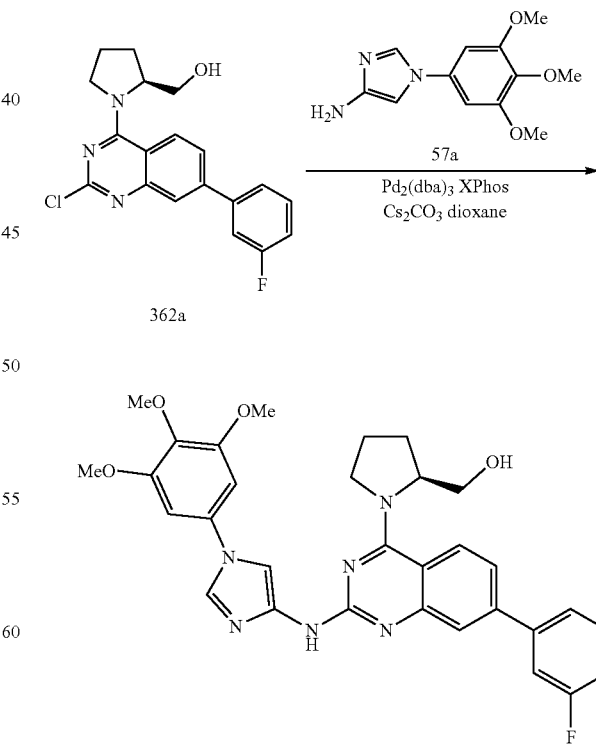

362a

362b

Preparation of (S)-(1-(7-(3-fluorophenyl)-2-((1-(3,4,5-trimethoxyphenyl)-1H-imidazol-4-yl)amino)quinazolin-4-yl)pyrrolidin-2-yl)methanol (362b)

Step-1: Preparation of (S)-(1-(2-chloro-7-(3-fluorophenyl)quinazolin-4-yl)pyrrolidin-2-yl)methanol (362a)

Compound 362a was prepared from (S)-(1-(7-bromo-2-chloroquinazolin-4-yl)pyrrolidin-2-yl)methanol (361a) (0.5 g, 1.459 mmol), using 3-fluorophenylboronic acid (204 mg, 1.46 mmol), Bis(triphenylphosphine)palladium(II) dichloride (51 mg, 0.073 mmol) and sodium carbonate (309 mg, 2.92 mmol) in toluene (15 mL), EtOH (7 mL) and water (3 mL) according to the procedure reported in step-3 of Scheme 77. This gave after workup and purification by flash column chromatography [silica gel, (24 g) eluting with DMA-80 in $CH_2Cl_2$ from 0 to 50%] (S)-(1-(2-chloro-7-(3-fluorophenyl)quinazolin-4-yl)pyrrolidin-2-yl)methanol (362a) (500 mg, 96% yield) as a white solid; $^1$H NMR (300 MHz, DMSO-$d_6$) δ 8.35 (d, J=8.9 Hz, 1H), 7.97 (d, J=2.0 Hz, 1H), 7.83 (dd, J=8.9, 2.1 Hz, 1H), 7.76-7.68 (m, 2H), 7.58 (td, J=8.2, 6.2 Hz, 1H), 7.35-7.25 (m, 1H), 4.89 (t, J=5.9 Hz, 1H), 4.59 (d, J=5.8 Hz, 1H), 4.16-3.86 (m, 2H), 3.66 (t, J=5.2 Hz, 2H), 2.18-1.73 (m, 4H); MS (ES+): 358.3 (M+1), 380.2 (M+Na), (ES−): 356.3 (M−1).

Step-2: Preparation of (S)-(1-(7-(3-fluorophenyl)-2-((1-(3,4,5-trimethoxyphenyl)-1H-imidazol-4-yl)amino)quinazolin-4-yl)pyrrolidin-2-yl)methanol (362b)

Compound 362b was prepared from (S)-(1-(2-chloro-7-(3-fluorophenyl)quinazolin-4-yl)pyrrolidin-2-yl)methanol (362a) (361 mg, 1.01 mmol), 1-(3,4,5-trimethoxyphenyl)-1H-imidazol-4-amine (57a) (314 mg, 1.261 mmol), dicyclohexyl(2',4',6'-triisopropylbiphenyl-2-yl)phosphine (XPhos, 216 mg, 0.454 mmol), cesium carbonate (986 mg, 3.03 mmol), $Pd_2(dba)_3$ (138 mg, 0.15 mmol) in dioxane (15 mL) according to the procedure reported in step-3 of Scheme 101. This gave after workup and purification by flash column chromatography [silica gel, (24 g) eluting with DMA-80 in $CH_2Cl_2$ from 0 to 50%], reverse phase column chromatography [(silica gel C-18, 24 g) eluting with acetonitrile and 0.1% HCl in water] (S)-(1-(7-(3-fluorophenyl)-2-((1-(3,4,5-trimethoxyphenyl)-1H-imidazol-4-yl)amino)quinazolin-4-yl)pyrrolidin-2-yl)methanol (362b) (115 mg, 20% yield) as a light yellow solid; $^1$H NMR (300 MHz, DMSO-$d_6$-$D_2O$) δ 8.34 (d, J=8.9 Hz, 1H), 8.28 (s, 1H), 8.08-7.78 (m, 1H), 7.77 (d, J=8.5 Hz, 1H), 7.63 (dd, J=20.3, 7.4 Hz, 4H), 7.32 (ddd, J=10.6, 6.3, 2.1 Hz, 1H), 6.93 (s, 2H), 4.81 (s, 1H), 4.31-4.02 (m, 2H), 3.90-3.83 (m, 1H), 3.85 (s, 6H), 3.79-3.67 (m, 1H), 3.66 (s, 3H), 2.23-1.84 (m, 4H); $^{19}$F NMR (282 MHz, DMSO-$d_6$) δ −112.13; MS (ES+): 571.4 (M+1), 593.4 (M+Na), (ES−): 605.4 (M+Cl); HPLC purity: 94.06%.

Scheme 363

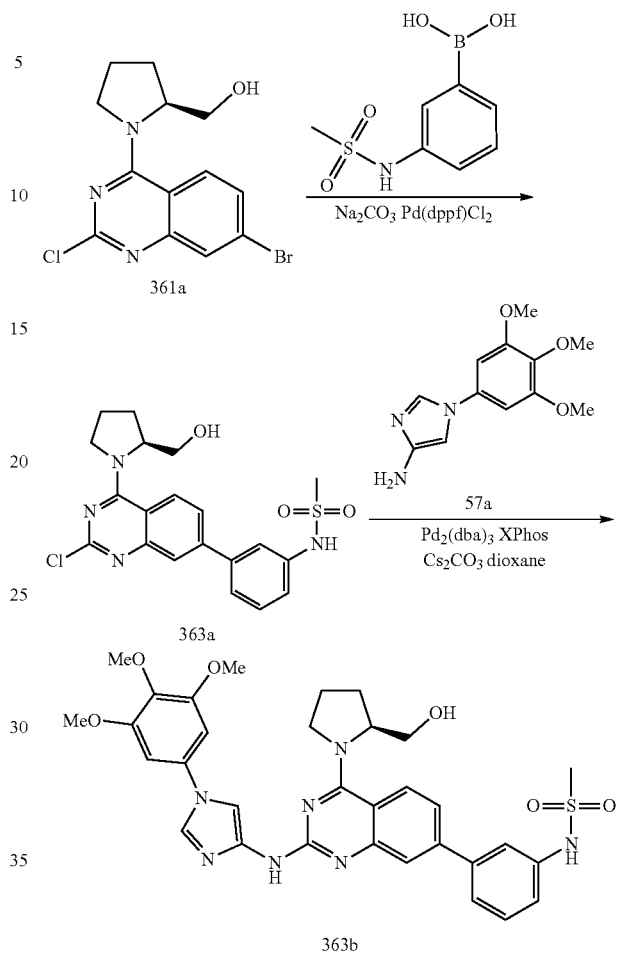

Preparation of (S)—N-(3-(4-(2-(hydroxymethyl)pyrrolidin-1-yl)-2-((1-(3,4,5-trimethoxyphenyl)-1H-imidazol-4-yl)amino)quinazolin-7-yl)phenyl)methanesulfonamide (363b)

Step-1: Preparation of (S)—N-(3-(2-chloro-4-(2-(hydroxymethyl)pyrrolidin-1-yl)quinazolin-7-yl)phenyl)methanesulfonamide (363a)

Compound 363a was prepared from (S)-(1-(7-bromo-2-chloroquinazolin-4-yl)pyrrolidin-2-yl)methanol (361a) (500 mg, 1.46 mmol), using (3-(methylsulfonamido)phenyl)boronic acid (314 mg, 1.46 mmol), Bis(triphenylphosphine)palladium(II) dichloride (51 mg, 0.073 mmol) and sodium carbonate (309 mg, 2.92 mmol) in toluene (15 mL), EtOH (7 mL) and water (3 mL) according to the procedure reported in step-3 of Scheme 77. This gave after workup and purification by flash column chromatography [silica gel, (24 g) eluting with DMA 80 in $CH_2Cl_2$ from 0 to 50%] (S)—N-(3-(2-chloro-4-(2-(hydroxymethyl)pyrrolidin-1-yl)quinazolin-7-yl)phenyl)methanesulfonamide (363a) (384 mg, 61% yield) as a white solid; $^1$H NMR (300 MHz, DMSO-$d_6$) δ 9.96 (s, 1H), 8.37 (d, J=8.9 Hz, 1H), 7.84 (d, J=2.0 Hz, 1H), 7.72 (dd, J=8.8, 2.0 Hz, 1H), 7.60 (d, J=2.0 Hz, 1H), 7.57 (dt, J=7.8, 1.4 Hz, 1H), 7.50 (t, J=7.8 Hz, 1H), 7.29 (ddd, J=7.9, 2.2, 1.2 Hz, 1H), 4.89 (t, J=5.7 Hz, 1H), 4.58 (d, J=5.7 Hz, 1H), 4.15-3.87 (m, 2H), 3.66 (t, J=5.2 Hz, 2H), 3.07 (s, 3H), 2.18-1.80 (m, 4H); MS (ES+): 433.2 (M+1), 455.2 (M+Na), (ES−): 431.3 (M−1).

Step-2: Preparation of (S)—N-(3-(4-(2-(hydroxymethyl)pyrrolidin-1-yl)-2-((1-(3,4,5-trimethoxyphenyl)-1H-imidazol-4-yl)amino)quinazolin-7-yl)phenyl)methanesulfonamide (363b)

Compound 363b was prepared from (S)—N-(3-(2-chloro-4-(2-(hydroxymethyl)pyrrolidin-1-yl)quinazolin-7-yl)phenyl)methanesulfonamide (363a) (390 mg, 0.9 mmol), 1-(3,4,5-trimethoxyphenyl)-1H-imidazol-4-amine (57a) (280 mg, 1.12 mmol), dicyclohexyl(2',4',6'-triisopropylbiphenyl-2-yl)phosphine (XPhos, 193 mg, 0.41 mmol), cesium carbonate (880 mg, 2.7 mmol), Pd$_2$(dba)$_3$ (124 mg, 0.14 mmol) in dioxane (15 mL) according to the procedure reported in step-3 of Scheme 101. This gave after workup and purification by flash column chromatography [silica gel, (24 g) eluting with DMA-80 in CH$_2$Cl$_2$ from 0 to 50%], reverse phase flash column chromatography [(silica gel C-18, 24 g) eluting with acetonitrile and 0.1% HCl in water] (S)—N-(3-(4-(2-(hydroxymethyl)pyrrolidin-1-yl)-2-((1-(3,4,5-trimethoxyphenyl)-1H-imidazol-4-yl)amino)quinazolin-7-yl)phenyl)methanesulfonamide (363b) (225 mg, 39% yield) as a light yellow solid; $^1$H NMR (300 MHz, DMSO-d$_6$) δ 13.27 (s, 1H, D$_2$O exchangeable), 10.57 (s, 1H, D$_2$O exchangeable), 10.07 (s, 1H, D$_2$O exchangeable), 8.38 (d, J=8.3 Hz, 2H), 7.74 (d, J=1.6 Hz, 1H), 7.70-7.62 (m, 1H), 7.59 (s, 1H), 7.51 (d, J=6.1 Hz, 2H), 7.40-7.29 (m, 2H), 6.99 (s, 2H), 4.87 (s, 1H), 4.34-4.12 (m, 2H), 3.88 (s, 6H), 3.86-3.69 (m, 2H), 3.68 (s, 3H), 3.07 (s, 3H), 2.27-1.90 (m, 4H); MS (ES+): 646.5 (M+1), (ES−): 644.4 (M−1), 680.5 (M+Cl); HPLC purity: 98.78%.

Scheme 364

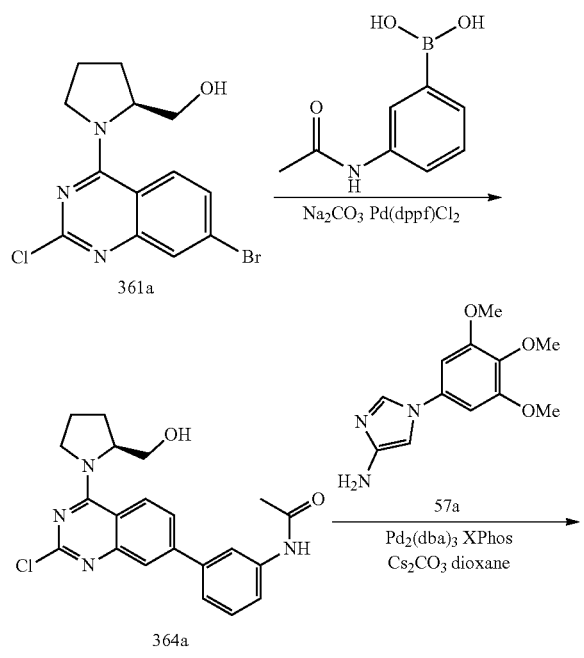

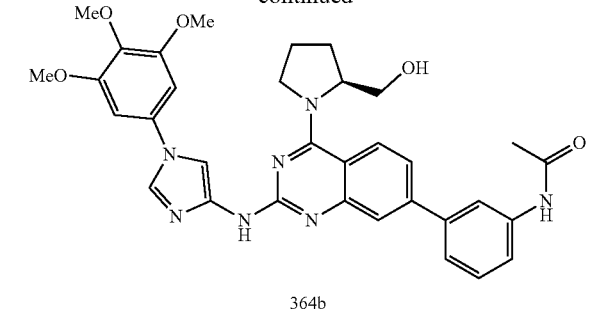

364b

Preparation of (S)—N-(3-(4-(2-(hydroxymethyl)pyrrolidin-1-yl)-2-((1-(3,4,5-trimethoxyphenyl)-1H-imidazol-4-yl)amino)quinazolin-7-yl)phenyl)acetamide (364b)

Step-1: Preparation of (S)—N-(3-(2-chloro-4-(2-(hydroxymethyl)pyrrolidin-1-yl)quinazolin-7-yl)phenyl)acetamide (364a)

Compound 364a was prepared from (S)-(1-(7-bromo-2-chloroquinazolin-4-yl)pyrrolidin-2-yl)methanol (361a) (500 mg, 1.46 mmol), using (3-acetamidophenyl)boronic acid (261 mg, 1.46 mmol), Bis(triphenylphosphine)palladium(II) dichloride (51 mg, 0.073 mmol) and sodium carbonate (309 mg, 2.92 mmol) in toluene (15 mL), EtOH (7 mL) and water (3 mL) according to the procedure reported in step-3 of Scheme 77. This gave after workup and purification by flash column chromatography [silica gel, (24 g) eluting with DMA-80 in CH$_2$Cl$_2$ from 0 to 50%] (S)—N-(3-(2-chloro-4-(2-(hydroxymethyl)pyrrolidin-1-yl)quinazolin-7-yl)phenyl)acetamide (364a) (381 mg, 66% yield) as a white solid; $^1$H NMR (300 MHz, DMSO-d$_6$) δ 10.12 (s, 1H), 8.37 (d, J=8.9 Hz, 1H), 8.10 (t, J=1.9 Hz, 1H), 7.81 (d, J=2.0 Hz, 1H), 7.71 (dd, J=8.9, 2.1 Hz, 1H), 7.62 (dt, J=7.4, 1.8 Hz, 1H), 7.53-7.41 (m, 2H), 5.77 (s, 1H), 4.89 (t, J=5.7 Hz, 1H), 4.66-4.54 (m, 1H), 4.14-3.93 (m, 1H), 3.66 (t, J=5.3 Hz, 2H), 2.09 (s, 3H), 2.11-1.80 (m, 4H); MS (ES+): 397.3, 399.2 (M+1), 419.3, 421.2 (M+Na), (ES−): 431.3, 433.3 (M+Cl).

Step-2: Preparation of (S)—N-(3-(4-(2-(hydroxymethyl)pyrrolidin-1-yl)-2-((1-(3,4,5-trimethoxyphenyl)-1H-imidazol-4-yl)amino)quinazolin-7-yl)phenyl)acetamide (364b)

Compound 364b was prepared from (S)—N-(3-(2-chloro-4-(2-(hydroxymethyl)pyrrolidin-1-yl)quinazolin-7-yl)phenyl)acetamide (364a) (357 mg, 0.9 mmol), 1-(3,4,5-trimethoxyphenyl)-1H-imidazol-4-amine (57a) (280 mg, 1.13 mmol), dicyclohexyl(2',4',6'-triisopropylbiphenyl-2-yl)phosphine (XPhos, 193 mg, 0.41 mmol), cesium carbonate (880 mg, 2.7 mmol), Pd$_2$(dba)$_3$ (124 mg, 0.14 mmol) in dioxane (15 mL) according to the procedure reported in step-3 of Scheme 101. This gave after workup and purification by flash column chromatography [silica gel, (24 g) eluting with DMA 80 in CH$_2$Cl$_2$ from 0 to 50%], reverse phase flash column chromatography [(silica gel C-18, 24 g) eluting with acetonitrile and 0.1% HCl in water] (S)—N-(3-(4-(2-(hydroxymethyl)pyrrolidin-1-yl)-2-((1-(3,4,5-trimethoxyphenyl)-1H-imidazol-4-yl)amino)quinazolin-7-yl)phenyl)acetamide (364b) (186 mg, 34% yield) as a light yellow solid; $^1$H NMR (300 MHz, DMSO-d$_6$) δ 13.21 (s, 1H, D$_2$O exchangeable), 10.56 (s, 1H, D$_2$O exchangeable), 10.31 (s, 1H, D$_2$O exchangeable), 8.36 (d, J=8.3 Hz, 2H), 8.10 (s, 1H), 7.71 (d, J=1.6 Hz, 1H), 7.65 (d, J=8.2 Hz, 3H), 7.45 (d, J=8.0 Hz, 2H), 6.98 (s, 2H), 5.04-4.67 (m, 1H), 4.32-4.06 (m, 2H), 3.88 (s, 6H), 3.88-3.71 (m, 2H), 3.68 (s, 3H), 2.31-1.85 (m, 7H); MS (ES+): 610.4 (M+1), (ES−): 644.5 (M+Cl); HPLC purity: 98.94%.

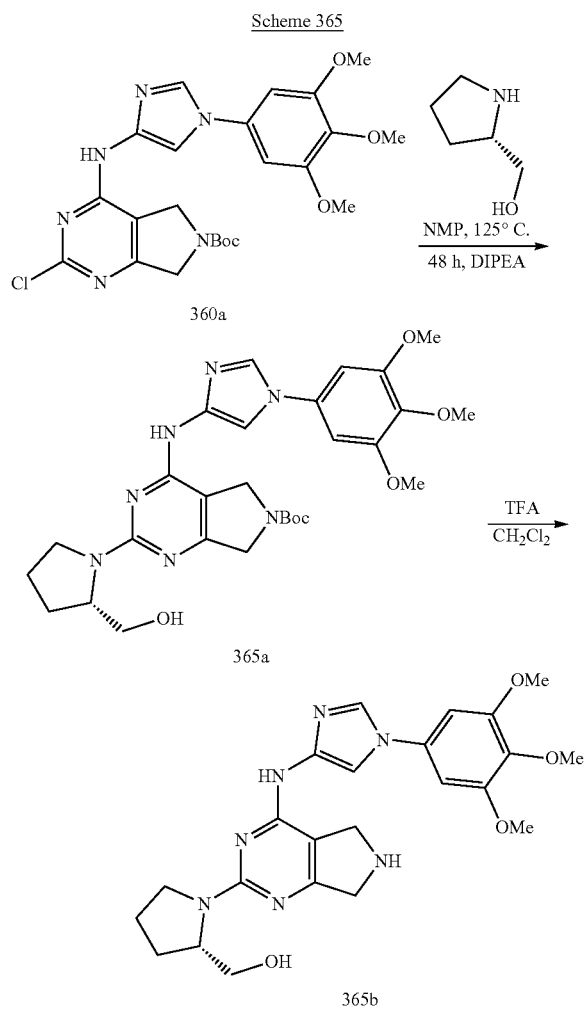

Scheme 365

Preparation of (S)-(1-(4-(1-(3,4,5-trimethoxyphenyl)-1H-imidazol-4-ylamino)-6,7-dihydro-5H-pyrrolo[3,4-d]pyrimidin-2-yl)pyrrolidin-2-yl)methanol (365b)

Step-1: Preparation of (S)-tert-butyl 2-(2-(hydroxymethyl)pyrrolidin-1-yl)-4-(1-(3,4,5-trimethoxyphenyl)-1H-imidazol-4-ylamino)-5H-pyrrolo[3,4-d]pyrimidine-6(7H)-carboxylate (365a)

Compound 365a was prepared from 2-chloro-4-(1-(3,4,5-trimethoxyphenyl)-1H-imidazol-4-ylamino)-5H-pyrrolo[3,4-d]pyrimidine-6(7H)-carboxylate (360a) (275 mg, 0.55 mmol), (S)-pyrrolidin-2-ylmethanol (221 mg, 2.19 mmol) and N-ethyl-N-isopropylpropan-2-amine (0.29 mL, 1.64 mmol) in N-methyl-2-pyrrolidinone (5 mL) according to the procedure reported in step-2 of Scheme 76. This gave after workup and purification by flash column chromatography [silica gel (24 g), eluting with DMA80 in DCM from 0-60%] (S)-tert-butyl 2-(2-(hydroxymethyl)pyrrolidin-1-yl)-4-(1-(3,4,5-trimethoxyphenyl)-1H-imidazol-4-ylamino)-5H-pyrrolo[3,4-d]pyrimidine-6(7H)-carboxylate (365a) (212 mg, 68% yield) as an off white solid; $^1$H NMR (300 MHz, DMSO-d$_6$) δ 9.71 (s, 1H, D$_2$O exchangeable), 8.17 (s, 1H), 8.00-7.77 (m, 1H), 6.92 (s, 2H), 4.90 (t, J=5.1 Hz, 1H, D$_2$O exchangeable), 4.43 (d, J=11.8 Hz, 2H), 4.27 (d, J=11.4 Hz, 2H), 4.16-3.99 (m, 1H), 3.87 (s, 6H), 3.80-3.57 (m, 5H), 3.34-3.18 (m, 2H), 2.04-1.83 (m, 4H), 1.46 (d, J=6.0 Hz, 9H); MS (ES+): 568.4 (M+1), 590.4 (M+Na).

Step-2: Preparation of (S)-(1-(4-(1-(3,4,5-trimethoxyphenyl)-1H-imidazol-4-ylamino)-6,7-dihydro-5H-pyrrolo[3,4-d]pyrimidin-2-yl)pyrrolidin-2-yl)methanol (365b)

Compound 365b was prepared by hydrolysis of (S)-tert-butyl 2-(2-(hydroxymethyl)pyrrolidin-1-yl)-4-(1-(3,4,5-trimethoxyphenyl)-1H-imidazol-4-ylamino)-5H-pyrrolo[3,4-d]pyrimidine-6(7H)-carboxylate (365a) (200 mg, 0.35 mmol) in DCM (10 mL) using trifluoroacetic acid (0.54 mL, 7.05 mmol) according to the procedure reported in Scheme 122. This gave after purification by flash column chromatography [silica gel (12 g), eluting with DMA-80 in DCM from 0-100%] and reverse phase column chromatography [(silica gel C-18 (50 g), eluting with acetonitrile in water (containing 0.1% HCl) from 0-100%] (S)-(1-(4-(1-(3,4,5-trimethoxyphenyl)-1H-imidazol-4-ylamino)-6,7-dihydro-5H-pyrrolo[3,4-d]pyrimidin-2-yl)pyrrolidin-2-yl)methanol (365b) (120 mg, 73% yield) as a white solid; $^1$H NMR (300 MHz, DMSO-d$_6$) δ 11.14 (s, 1H, D$_2$O exchangeable), 10.42 (s, 2H, D$_2$O exchangeable), 8.43 (s, 1H), 8.05-7.89 (m, 1H, D$_2$O exchangeable), 6.98 (s, 2H), 4.66-4.18 (m, 6H), 3.87 (s, 6H), 3.82-3.61 (m, 5H), 3.56-3.41 (m, 2H), 2.13-1.85 (m, 4H); MS (ES+): 468.4 (M+1); (ES−): 502.4 (M+Cl); HPLC purity: 99.73%

Scheme 366

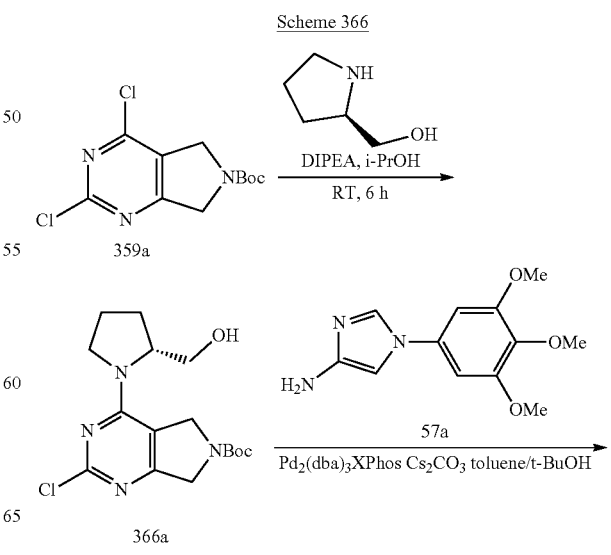

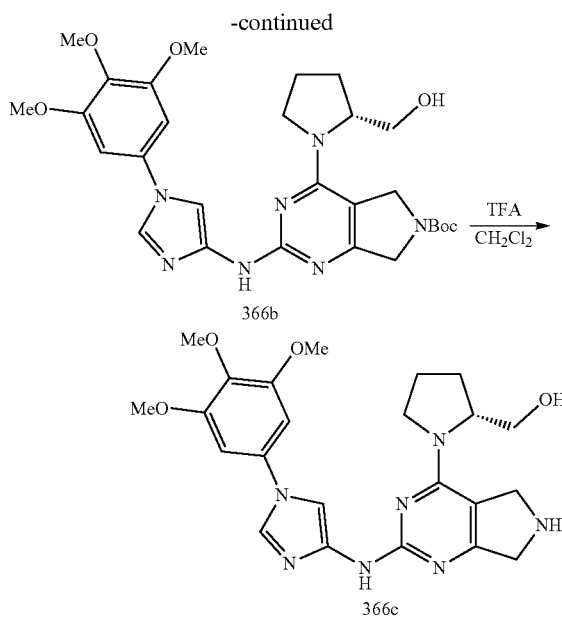

Preparation of (R)-(1-(2-(1-(3,4,5-trimethoxyphenyl)-1H-imidazol-4-ylamino)-6,7-dihydro-5H-pyrrolo[3,4-d]pyrimidin-4-yl)pyrrolidin-2-yl)methanol (366c)

Step-1: Preparation of (R)-tert-butyl 2-chloro-4-(2-(hydroxymethyl)pyrrolidin-1-yl)-5H-pyrrolo[3,4-d]pyrimidine-6(7H)-carboxylate (366a)

Compound 366a was prepared from tert-butyl 2,4-dichloro-5H-pyrrolo[3,4-d]pyrimidine-6(7H)-carboxylate (359a) (500 mg, 1.72 mmol) in 2-Propanol (10 mL) using (R)-pyrrolidin-2-ylmethanol (174 mg, 1.72 mmol) and DIPEA (0.60 mL, 3.45 mmol) according to the procedure reported in step-1 of Scheme 96. This gave after workup and purification by flash column chromatography [silica gel (24 g), eluting with eluting with EtOAc in hexane from 0-100%] (R)-tert-butyl 2-chloro-4-(2-(hydroxymethyl)pyrrolidin-1-yl)-5H-pyrrolo[3,4-d]pyrimidine-6(7H)-carboxylate (366a) (486 mg, 79% yield) as a white solid; $^1$H NMR (300 MHz, DMSO-d$_6$) δ 5.19-4.60 (m, 3H), 4.46-4.05 (m, 3H), 3.78-3.39 (m, 3H), 2.05-1.73 (m, 4H), 1.45 (s, 9H); MS (ES+): 355.3 (M+1), 377.2 (M+Na); (ES−): 353.3 (M−1). Step-2: Preparation of (R)-tert-butyl 4-(2-(hydroxymethyl)pyrrolidin-1-yl)-2-(1-(3,4,5-trimethoxyphenyl)-1H-imidazol-4-ylamino)-5H-pyrrolo[3,4-d]pyrimidine-6(7H)-carboxylate (366b)

Compound 366b was prepared from (R)-tert-butyl 2-chloro-4-(2-(hydroxymethyl)pyrrolidin-1-yl)-5H-pyrrolo[3,4-d]pyrimidine-6(7H)-carboxylate (366a) (400 mg, 1.13 mmol), 1-(3,4,5-trimethoxyphenyl)-1H-imidazol-4-amine (57a) (309 mg, 1.24 mmol), dicyclohexyl(2',4',6'-triisopropylbiphenyl-2-yl)phosphine (XPhos, 215 mg, 0.45 mmol), cesium carbonate (735 mg, 2.26 mmol) and Pd$_2$(dba)$_3$ (206 mg, 0.23 mmol) in t-BuOH/toluene (10 mL) according to the procedure reported in step-3 of Scheme 101. This gave after workup and twice purification by flash column chromatography [silica gel (24 g), eluting with DMA-80 in DCM from 0-100%](R)-tert-butyl 4-(2-(hydroxymethyl)pyrrolidin-1-yl)-2-(1-(3,4,5-trimethoxyphenyl)-1H-imidazol-4-ylamino)-5H-pyrrolo[3,4-d]pyrimidine-6(7H)-carboxylate (366b) (200 mg, 31% yield) as a yellow solid; $^1$H NMR (300 MHz, DMSO-d$_6$) δ 9.20 (s, 1H), 8.08 (s, 1H), 7.71-7.62 (m, 1H), 6.90 (s, 2H), 5.01-4.87 (m, 1H), 4.80-4.61 (m, 2H), 4.32-4.20 (m, 2H), 3.86 (s, 6H), 3.82-3.69 (m, 2H), 3.68-3.58 (m, 5H), 3.34-3.26 (m, 1H), 2.03-1.81 (m, 4H), 1.45 (s, 9H); MS (ES+): 568.4 (M+1), 590.4 (M+Na); (ES−): 566.5 (M−1).

Step-3: Preparation of (R)-(1-(2-(1-(3,4,5-trimethoxyphenyl)-1H-imidazol-4-ylamino)-6,7-dihydro-5H-pyrrolo[3,4-d]pyrimidin-4-yl)pyrrolidin-2-yl)methanol (366c)

Compound 366c was prepared by hydrolysis of (R)-tert-butyl 4-(2-(hydroxymethyl)pyrrolidin-1-yl)-2-(1-(3,4,5-trimethoxyphenyl)-1H-imidazol-4-ylamino)-5H-pyrrolo[3,4-d]pyrimidine-6(7H)-carboxylate (366b) (185 mg, 0.33 mmol) in DCM (20 mL) using trifluoroacetic acid (0.50 mL, 6.52 mmol) according to the procedure reported in Scheme 122. This gave after purification by reverse phase column chromatography [(silica gel C-18, 50 g), eluting with acetonitrile in water (containing 0.1% HCl) from 0-100%] (R)-(1-(2-(1-(3,4,5-trimethoxyphenyl)-1H-imidazol-4-ylamino)-6,7-dihydro-5H-pyrrolo[3,4-d]pyrimidin-4-yl)pyrrolidin-2-yl)methanol (366c) (108 mg, 71% yield) as a white solid; $^1$H NMR (300 MHz, DMSO-d$_6$) δ 10.24 (s, 3H, D$_2$O exchangeable), 9.00-8.80 (m, 1H), 7.84 (s, 1H, D$_2$O exchangeable), 7.06 (d, J=3.6 Hz, 2H), 4.77-4.60 (m, 2H), 4.53-4.38 (m, 1H), 4.37-4.18 (m, 2H), 3.88 (s, 6H), 3.84-3.74 (m, 1H), 3.74-3.51 (m, 5H), 3.45-3.33 (m, 1H), 2.08-1.81 (m, 4H); MS (ES+): 468.4 (M+1); (ES−): 467.2 (M−1).

Scheme 367

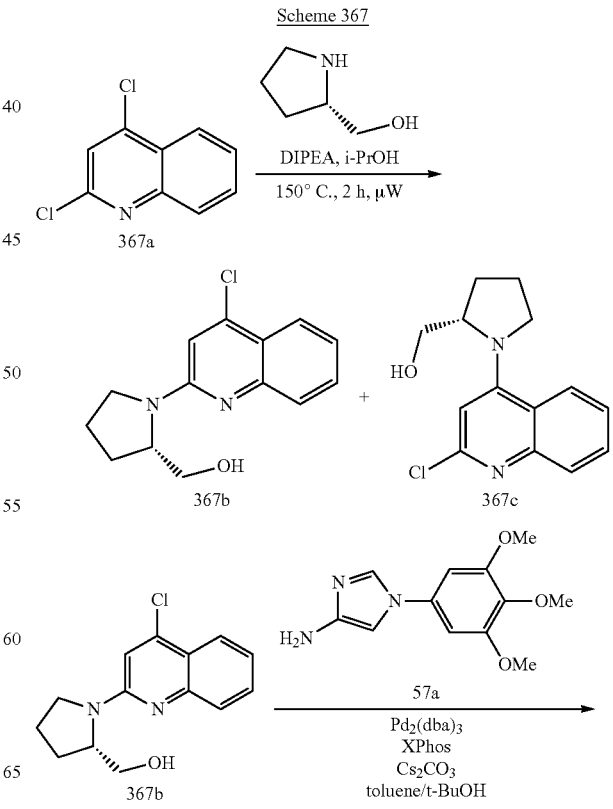

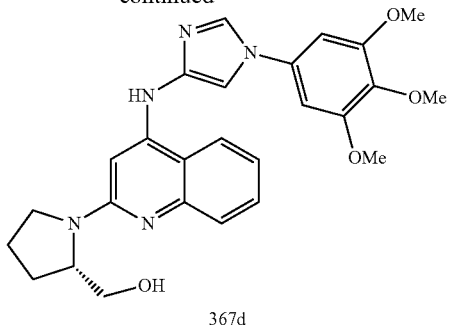

367d

Preparation of (S)-(1-(4-(1-(3,4,5-trimethoxyphenyl)-1H-imidazol-4-ylamino)quinolin-2-yl)pyrrolidin-2-yl)methanol (367d)

Step-1: Preparation of (S)-(1-(4-chloroquinolin-2-yl)pyrrolidin-2-yl)methanol (367b) and (S)-(1-(2-chloroquinolin-4-yl)pyrrolidin-2-yl)methanol (367c)

Compound 367b and compound 367c were prepared from 2,4-dichloroquinoline (367a, CAS Number 703-61-7) (1 g, 5.05 mmol) in 2-propanol (4 mL) using (S)-pyrrolidin-2-ylmethanol (0.56 g, 5.55 mmol) and DIPEA (1.32 mL, 7.57 mmol) by heating at 150° C. in a microwave for 2 h according to the procedure reported in step-1 of Scheme 96. This gave after workup and purification by flash column chromatography [silica gel (12 g), eluting with EtOAc in hexane from 0-60%] (S)-(1-(4-chloroquinolin-2-yl)pyrrolidin-2-yl)methanol (367b) (305 mg, 23% yield) as clear oil, $^1$H NMR (300 MHz, DMSO-$d_6$) δ 7.93-7.86 (m, 1H), 7.66-7.51 (m, 2H), 7.34-7.20 (m, 1H), 7.16 (s, 1H), 4.99 (t, J=5.7 Hz, 1H, $D_2O$ exchangeable), 4.18 (s, 1H), 3.67-3.51 (m, 2H), 3.50-3.37 (m, 2H), 2.04-1.86 (m, 4H); $^1$H NMR (600 MHz, DMSO-$d_6$) δ 7.90 (dd, J=8.2, 1.3 Hz, 1H), 7.61-7.54 (m, 2H), 7.28 (ddd, J=8.2, 6.4, 1.6 Hz, 1H), 7.16 (s, 1H), 4.97 (t, J=5.6 Hz, 1H), 4.18 (s, 1H), 3.64-3.53 (m, 2H), 3.49-3.35 (m, 2H), 2.05-1.96 (m, 2H), 1.96-1.88 (m, 2H); MS (ES+): 263.1 (M+1), 285.1 (M+Na); (ES−): 261.2 (M−1); and (S)-(1-(2-chloroquinolin-4-yl)pyrrolidin-2-yl)methanol (367c) (135 mg, 10% yield) as a white solid, $^1$H NMR (300 MHz, DMSO-$d_6$) δ 8.19 (dd, J=8.7, 1.4 Hz, 1H), 7.73 (dd, J=8.4, 1.6 Hz, 1H), 7.69-7.60 (m, 1H), 7.47-7.37 (m, 1H), 6.66 (s, 1H), 4.83 (t, J=5.7 Hz, 1H, $D_2O$ exchangeable), 4.21-4.10 (m, 1H), 4.03-3.90 (m, 1H), 3.69-3.48 (m, 2H), 3.46-3.37 (m, 1H), 2.24-2.10 (m, 1H), 2.05-1.87 (m, 2H), 1.82-1.62 (m, 1H); $^1$H NMR (600 MHz, DMSO-$d_6$) δ 8.18 (dd, J=8.6, 1.3 Hz, 1H), 7.73 (dd, J=8.4, 1.4 Hz, 1H), 7.65 (ddd, J=8.3, 6.8, 1.3 Hz, 1H), 7.42 (ddd, J=8.4, 6.8, 1.4 Hz, 1H), 6.65 (s, 1H), 4.80 (t, J=5.7 Hz, 1H), 4.21-4.11 (m, 1H), 3.99-3.90 (m, 1H), 3.65-3.57 (m, 1H), 3.57-3.49 (m, 1H), 3.44-3.35 (m, 1H), 2.23-2.12 (m, 1H), 2.02-1.86 (m, 2H), 1.79-1.69 (m, 1H); MS (ES+): 263.1 (M+1), 285.2 (M+Na); (ES−): 261.2 (M−1).

Step-2: Preparation of (S)-(1-(4-(1-(3,4,5-trimethoxyphenyl)-1H-imidazol-4-ylamino)quinolin-2-yl)pyrrolidin-2-yl)methanol (367d)

Compound 367d was prepared from (S)-(1-(4-chloroquinolin-2-yl)pyrrolidin-2-yl)methanol (367b) (638 mg, 2.43 mmol), 1-(3,4,5-trimethoxyphenyl)-1H-imidazol-4-amine (57a) (666 mg, 2.67 mmol), dicyclohexyl(2',4',6'-triisopropylbiphenyl-2-yl)phosphine (XPhos, 463 mg, 0.97 mmol), cesium carbonate (158 mg, 4.86 mmol) and $Pd_2(dba)_3$ (444 mg, 0.49 mmol) in t-BuOH/toluene (10 mL) according to the procedure reported in step-3 of Scheme 101. This gave after workup and purification by flash column chromatography [silica gel (24 g), eluting with DMA-80 in DCM from 0-100%] followed by reverse phase column chromatography [(silica gel C-18, 50 g), eluting with ACN in water (containing 0.1% HCl) from 0-100%] (S)-(1-(4-(1-(3,4,5-trimethoxyphenyl)-1H-imidazol-4-ylamino)quinolin-2-yl)pyrrolidin-2-yl)methanol (367d) (56 mg, 5% yield) as an off white solid; $^1$H NMR (300 MHz, DMSO-$d_6$) δ 11.91 (s, 1H, $D_2O$ exchangeable), 10.11 (s, 1H, $D_2O$ exchangeable), 8.60-8.48 (m, 2H), 8.19 (d, J=8.2 Hz, 1H, $D_2O$ exchangeable), 7.92 (s, 1H), 7.78 (t, J=7.8 Hz, 1H), 7.50 (t, J=7.8 Hz, 1H), 7.03 (s, 2H), 6.86 (s, 1H), 4.18-4.08 (m, 1H), 3.88 (s, 6H), 3.83-3.73 (m, 1H), 3.69 (s, 3H), 3.62-3.47 (m, 3H), 2.14-1.95 (m, 4H); MS (ES+): 476.4 (M+1); (ES−): 510.4 (M+Cl).

Scheme 368

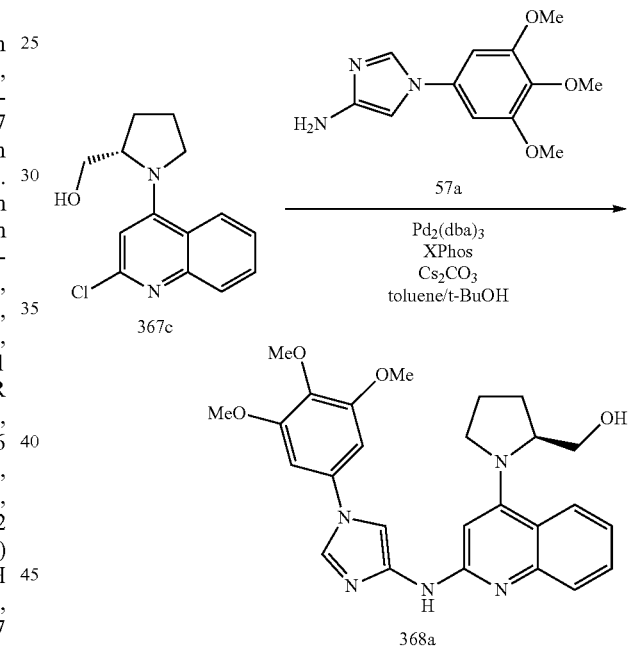

368a

Preparation of (S)-(1-(2-(1-(3,4,5-trimethoxyphenyl)-1H-imidazol-4-ylamino)quinolin-4-yl)pyrrolidin-2-yl)methanol (368a)

Compound 368a was prepared from (S)-(1-(2-chloroquinolin-4-yl)pyrrolidin-2-yl)methanol (367c) (320 mg, 1.22 mmol), 1-(3,4,5-trimethoxyphenyl)-1H-imidazol-4-amine (57a) (334 mg, 1.34 mmol), dicyclohexyl(2',4',6'-triisopropylbiphenyl-2-yl)phosphine (XPhos, 232 mg, 0.49 mmol), cesium carbonate (794 mg, 2.44 mmol) and $Pd_2(dba)_3$ (223 mg, 0.24 mmol) in t-BuOH/toluene (10 mL) according to the procedure reported in step-3 of Scheme 101. This gave after workup and purification by flash column chromatography [silica gel (24 g), eluting with DMA80 in DCM from 0-100%] followed by reverse phase flash column chromatography [(silica gel C-18, 50 g), eluting with ACN in water (containing 0.1% HCl) from 0-100%] (S)-(1-(2-(1-(3,4,5- trimethoxyphenyl)-1H-imidazol-4-ylamino)quinolin-4-yl)pyrrolidin-2-yl)methanol (368a) (73 mg, 13% yield) as an off white solid; $^1$H NMR (300 MHz, DMSO-d$_6$) δ 13.05 (s, 1H, D$_2$O exchangeable), 10.93 (s, 1H, D$_2$O exchangeable), 8.46 (s, 1H), 8.26 (d, J=8.5 Hz, 1H), 7.84-7.65 (m, 3H), 7.50-7.35 (m, 1H), 7.02 (s, 2H), 6.51 (s, 1H), 4.30-4.17 (m, 1H), 4.05-3.97 (m, 1H), 3.88 (s, 6H), 3.86-3.82 (m, 1H), 3.69 (s, 3H), 3.61-3.58 (m, 2H), 2.23-2.12 (m, 1H), 2.12-1.98 (m, 2H), 1.88-1.70 (m, 1H); MS (ES+): 476.4 (M+1); (ES−): 510.4 (M+Cl).

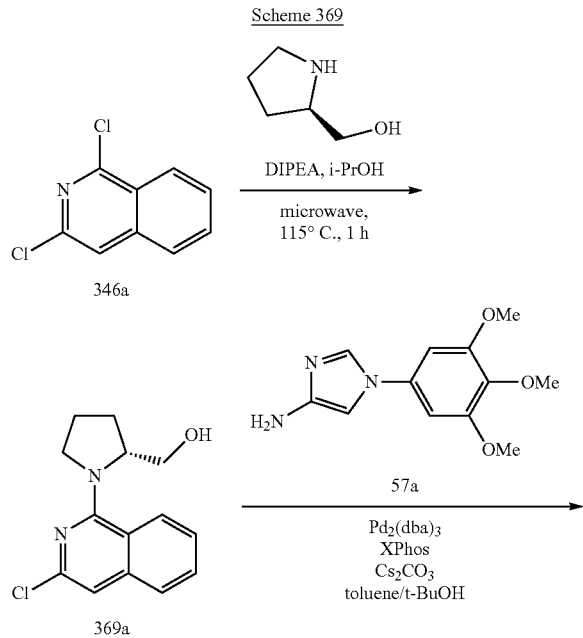

Scheme 369

Preparation of (R)-(1-(3-(1-(3,4,5-trimethoxyphenyl)-1H-imidazol-4-ylamino)isoquinolin-1-yl)pyrrolidin-2-yl)methanol (369b)

Step-1: Preparation of (R)-(1-(3-chloroisoquinolin-1-yl)pyrrolidin-2-yl)methanol (369a)

Compound 369a was prepared from 1,3-dichloroisoquinoline (346a) (1.5 g, 7.57 mmol) in 2-Propanol (6 mL) using (R)-pyrrolidin-2-ylmethanol (843 mg, 8.33 mmol) and DIPEA (1.98 mL, 11.36 mmol) according to the procedure reported in Scheme 2. This gave after workup and purification by flash column chromatography [silica gel (12 g), eluting with EtOAc in hexane from 0-60%] (R)-(1-(3-chloroisoquinolin-1-yl)pyrrolidin-2-yl)methanol (369a) (1.5 g, 75% yield) as a pink oil; $^1$H NMR (300 MHz, DMSO-d$_6$) δ 8.18 (d, J=8.5 Hz, 1H), 7.73-7.67 (m, 1H), 7.66-7.56 (m, 1H), 7.48-7.39 (m, 1H), 7.12 (s, 1H), 4.79-4.63 (m, 1H, D$_2$O exchangeable), 4.57-4.43 (m, 1H), 4.09-3.92 (m, 1H), 3.76-3.58 (m, 2H), 3.55-3.47 (m, 1H), 2.12-1.85 (m, 3H), 1.81-1.61 (m, 1H); MS (ES+): 263.1 (M+1), 285.1 (M+Na); (ES−): 261.2 (M−1).

Step-2: Preparation of (R)-(1-(3-(1-(3,4,5-trimethoxyphenyl)-1H-imidazol-4-ylamino)isoquinolin-1-yl)pyrrolidin-2-yl)methanol (369b)

Compound 369b was prepared from (R)-(1-(3-chloroisoquinolin-1-yl)pyrrolidin-2-yl)methanol (369a) (600 mg, 2.28 mmol), 1-(3,4,5-trimethoxyphenyl)-1H-imidazol-4-amine (57a) (626 mg, 2.51 mmol, free base), dicyclohexyl (2',4',6'-triisopropylbiphenyl-2-yl)phosphine (XPhos, 435 mg, 0.913 mmol), cesium carbonate (1.5 g, 4.57 mmol) and Pd$_2$(dba)$_3$ (418 mg, 0.46 mmol) in toluene/t-BuOH (10 mL, Ratio: 2:1) according to the procedure reported in step-3 of Scheme 101. This gave after workup and purification by flash column chromatography [silica gel (24 g), eluting with DMA-80 in DCM from 0-50%], followed by reverse phase column chromatography [(silica gel C-18, 24 g) eluting with acetonitrile and 0.1% HCl in water] (R)-(1-(3-(1-(3,4,5-trimethoxyphenyl)-1H-imidazol-4-ylamino)isoquinolin-1-yl)pyrrolidin-2-yl)methanol (369b) (93 mg, 9% yield) as a yellow solid; $^1$H NMR (300 MHz, DMSO-d$_6$) δ 10.12 (s, 1H, D$_2$O exchangeable), 9.20 (s, 1H), 8.15 (d, J=8.6 Hz, 1H), 7.89 (d, J=1.7 Hz, 1H, D$_2$O exchangeable), 7.64-7.51 (m, 2H), 7.28-7.18 (m, 1H), 7.14 (s, 2H), 6.58 (s, 1H, D$_2$O exchangeable), 4.79-4.67 (m, 1H), 4.16-4.04 (m, 1H), 3.90 (s, 6H), 3.88-3.76 (m, 2H), 3.70 (s, 3H), 3.68-3.64 (m, 1H), 3.62-3.56 (m, 1H), 2.21-2.09 (m, 1H), 2.06-1.91 (m, 2H), 1.89-1.73 (m, 1H); MS (ES+): 476.4 (M+1); (ES−): 474.5 (M−1), 510.3 (M+Cl).

Scheme 370

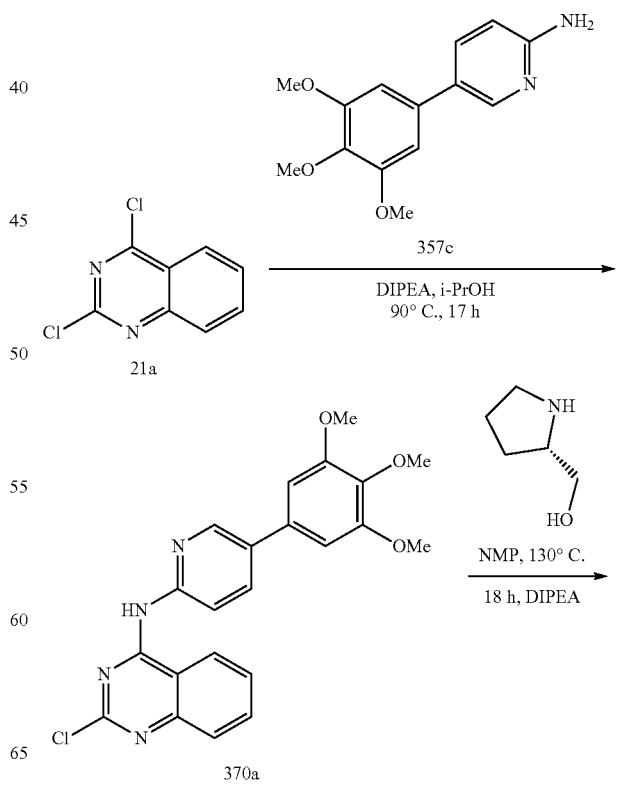

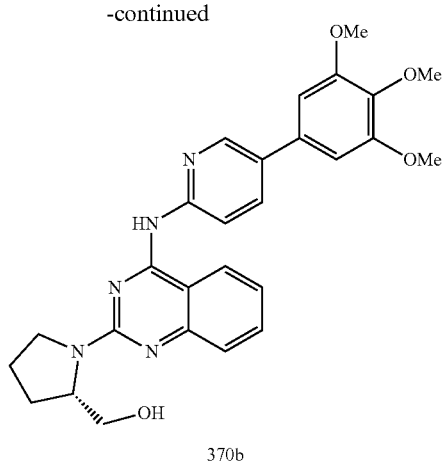

370b

Preparation of (S)-(1-(4-((5-(3,4,5-trimethoxyphenyl)pyridin-2-yl)amino)quinazolin-2-yl)pyrrolidin-2-yl)methanol (370b)

Step-1: Preparation of 2-chloro-N-(5-(3,4,5-trimethoxyphenyl)pyridin-2-yl)quinazolin-4-amine (370a)

Compound 370a was prepared from 2,4-dichloroquinazoline (21a) (310 mg, 1.54 mmol) in 2-Propanol (15 mL) using DIPEA (0.81 mL, 4.61 mmol) and 5-(3,4,5-trimethoxyphenyl)pyridin-2-amine (357c) (400 mg, 1.54 mmol) according to the procedure reported in step-1 of Scheme 183. This gave after workup and purification by flash column chromatography [silica gel (12 g), eluting with DMA 80 in $CH_2Cl_2$ from 0 to 50%] 2-chloro-N-(5-(3,4,5-trimethoxyphenyl)pyridin-2-yl)quinazolin-4-amine (370a) (480 mg, 74% yield) as a yellow solid; MS (ES+): 423.2 & 425.2 (M+1); MS (ES−): 421.3 & 423.2 (M−1).

Step-2: Preparation of (S)-(1-(4-((5-(3,4,5-trimethoxyphenyl)pyridin-2-yl)amino)quinazolin-2-yl)pyrrolidin-2-yl)methanol (370b)

Compound 370b was prepared from 2-chloro-N-(5-(3,4,5-trimethoxyphenyl)pyridin-2-yl)quinazolin-4-amine (370a) (180 mg, 0.43 mmol), (S)-pyrrolidin-2-ylmethanol (0.17 mL, 1.7 mmol) and N-ethyl-N-isopropylpropan-2-amine (0.45 mL, 2.55 mmol) in N-Methyl-2-pyrrolidinone (3 mL) according to the procedure reported in step-2 of Scheme 76. This gave after workup and purification by flash column chromatography [silica gel (12 g), eluting with DMA-80 in $CH_2Cl_2$ from 0 to 50%] followed by reverse phase column chromatography [(silica gel C-18, 24 g) eluting with acetonitrile and 0.1% HCl water] (S)-(1-(4-((5-(3,4,5-trimethoxyphenyl)pyridin-2-yl)amino)quinazolin-2-yl)pyrrolidin-2-yl)methanol (370b) (0.10 g, 48% yield) HCl salt as a yellow solid; $^1$H NMR (300 MHz, DMSO-$d_6$): δ 12.63 (s, 1H), 11.43 (s, 1H), 8.88 (d, J=2.8 Hz, 1H), 8.75 (d, J=8.2 Hz, 1H), 8.44-8.09 (m, 3H), 7.89 (ddd, J=8.4, 7.1, 1.2 Hz, 1H), 7.50 (t, J=7.7 Hz, 1H), 7.06 (d, J=2.6 Hz, 2H), 4.72-4.60 (m, 1H), 4.46-4.24 (m, 1H), 3.90 (s, 6H), 3.87-3.74 (m, 1H), 3.70 (s, 3H), 3.67-3.50 (m, 2H), 2.30-1.84 (m, 4H). MS (ES+): 488.3 (M+1); MS (ES−): 486.4 (M−1). HPLC purity: 97.17%.

Scheme 371

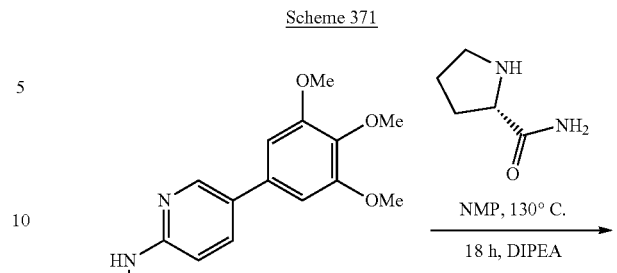

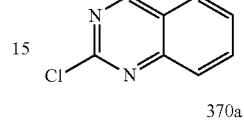

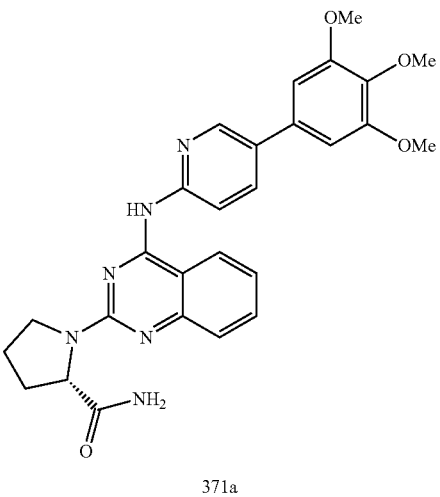

371a

Preparation of (S)-1-(4-((5-(3,4,5-trimethoxyphenyl)pyridin-2-yl)amino)quinazolin-2-yl)pyrrolidine-2-carboxamide (371a)

Compound 371a was prepared from 2-chloro-N-(5-(3,4,5-trimethoxyphenyl)pyridin-2-yl)quinazolin-4-amine (370a) (180 mg, 0.43 mmol), (S)-pyrrolidine-2-carboxamide (194 mg, 1.7 mmol) and N-ethyl-N-isopropylpropan-2-amine (0.45 mL, 2.55 mmol) in N-Methyl-2-pyrrolidinone (3 mL) according to the procedure reported in step-2 of Scheme 76. This gave after workup and purification by flash column chromatography [silica gel (12 g), eluting with DMA 80 in $CH_2Cl_2$ from 0 to 50%] followed by reverse phase column chromatography [(silica gel C-18, 24 g) eluting with acetonitrile and 0.1% HCl water] (S)-1-(4-((5-(3,4,5-trimethoxyphenyl)pyridin-2-yl)amino)quinazolin-2-yl)pyrrolidine-2-carboxamide (371a) (96 mg, 45% yield) HCl salt as a yellow solid; $^1$H NMR (300 MHz, DMSO-$d_6$) δ 12.89 (s, 1H), 8.87 (d, J=2.4 Hz, 1H), 8.76 (d, J=8.2 Hz, 1H), 8.29 (dd, J=8.7, 2.5 Hz, 1H), 8.21 (d, J=7.8 Hz, 1H), 8.15 (d, J=8.7 Hz, 1H), 7.92 (t, J=7.8 Hz, 1H), 7.79 (s, 1H), 7.52 (ddd, J=8.3, 7.1, 1.1 Hz, 1H), 7.30 (s, 1H), 7.04 (s, 2H), 4.66 (dd, J=8.4, 2.3 Hz, 1H), 4.00-3.92 (m, 1H), 3.90 (s, 6H), 3.86-3.75 (m, 1H), 3.71 (s, 3H), 2.40-1.87 (m, 4H); MS (ES+): 501.3 (M+1); MS (ES−): 499.4 (M−1); 535.4 (M+Cl). HPLC purity: 97.97%.

Scheme 372

Preparation of (R)-2-(2-(hydroxymethyl)pyrrolidin-1-yl)-4-((1-(3,4,5-trimethoxyphenyl)-1H-imidazol-4-yl)amino)quinazoline-7-carbonitrile (372a)

Compound 372a was prepared according to the procedure reported in step-2 of Scheme 76 from 2-chloro-4-((1-(3,4,5-trimethoxyphenyl)-1H-imidazol-4-yl)amino)quinazoline-7-carbonitrile (345b) (0.2 g, 0.46 mmol), (R)-pyrrolidin-2-ylmethanol (0.18 mL, 1.83 mmol) and DIPEA (0.48 mL, 2.75 mmol) in NMP (3 mL). This gave after workup and purification by flash column chromatography [(silica gel, 12 g) eluting DMA-80 in CH$_2$Cl$_2$ from 0 to 50%] followed by purification by reverse phase flash column chromatography [(silica gel C-18, 24 g) eluting with acetonitrile and 0.1% HCl in water] (R)-2-(2-(hydroxymethyl)pyrrolidin-1-yl)-4-((1-(3,4,5-trimethoxyphenyl)-1H-imidazol-4-yl)amino)quinazoline-7-carbonitrile (372a) (89 mg, 39% yield) HCl salt as a yellow solid; $^1$H NMR (300 MHz, DMSO-d$_6$) δ 12.95 (s, 1H), 12.02 (s, 1H), 8.94-8.81 (m, 1H), 8.74-8.65 (m, 1H), 8.51 (s, 1H), 8.18-7.99 (m, 1H), 7.93-7.75 (m, 1H), 7.01 (s, 1H), 6.95 (s, 1H), 4.84-4.48 (m, 1H), 3.88 (d, J=3.8 Hz, 6H), 3.68 (s, 3H), 3.64-3.40 (m, 1H), 2.29-1.84 (m, 4H); MS (ES+): 502.3 (M+1), 524.3 (M+Na); MS (ES−): 500.4 (M−1), 536.4 (M+Cl). HPLC purity: 97.92%.

Scheme 373

Preparation of (S)-1-(1,3-dimethyl-4-((1-(3,4,5-trimethoxyphenyl)-1H-imidazol-4-yl)amino)-1H-pyrazolo[3,4-d]pyrimidin-6-yl)pyrrolidine-2-carboxamide (373c)

Step-1: Preparation of 6-chloro-1,3-dimethyl-N-(1-(3,4,5-trimethoxyphenyl)-1H-imidazol-4-yl)-1H-pyrazolo[3,4-d]pyrimidin-4-amine (373b)

Compound 373b was prepared from 4,6-dichloro-1,3-dimethyl-1H-pyrazolo[3,4-d]pyrimidine (373a) (500 mg, 2.3 mmol, CAS #1072895-86-3) in 2-Propanol (15 mL) using DIPEA (1.21 mL, 6.91 mmol) and 1-(3,4,5-trimethoxyphenyl)-1H-imidazol-4-amine (57a) (0.57 g, 2.3 mmol) according to the procedure reported in step-1 of Scheme 183. This gave after filtration 6-chloro-1,3-dimethyl-N-(1-(3,4,5-trimethoxyphenyl)-1H-imidazol-4-yl)-1H-pyrazolo[3,4-d]pyrimidin-4-amine (373b) (0.67 g, 68% yield) as a brown solid; $^1$H NMR (300 MHz, DMSO-d$_6$) δ 9.61 (s, 1H), 8.24 (d, J=1.6 Hz, 1H), 7.90 (d, J=1.6 Hz, 1H), 6.94 (s, 2H), 3.87 (s, 6H), 3.81 (s, 3H), 3.69 (s, 3H), 2.60 (s, 3H). MS (ES+): 452.2 & 454.2 (M+Na); MS (ES−): 428.3 & 430.3 (M−1).

Step-2: Preparation of (S)-1-(1,3-dimethyl-4-((1-(3,4,5-trimethoxyphenyl)-1H-imidazol-4-yl)amino)-1H-pyrazolo[3,4-d]pyrimidin-6-yl)pyrrolidine-2-carboxamide (373c)

Compound 373c was prepared from 6-chloro-1,3-dimethyl-N-(1-(3,4,5-trimethoxyphenyl)-1H-imidazol-4-yl)-1H-pyrazolo[3,4-d]pyrimidin-4-amine (373b) (200 mg, 0.47 mmol), (S)-pyrrolidine-2-carboxamide (200 mg, 1.86 mmol) and N-ethyl-N-isopropylpropan-2-amine (0.49 mL, 2.79 mmol) in N-Methyl-2-pyrrolidinone (3 mL) according to the procedure reported in step-2 of Scheme 76. This gave after workup and purification by flash column chromatography [silica gel (12 g), eluting with DMA-80 in DCM from 0-50%] followed by purification by reverse phase flash column chromatography [(silica gel C-18, 24 g) eluting with acetonitrile and 0.1% HCl water] (S)-1-(1,3-dimethyl-4-((1-(3,4,5-trimethoxyphenyl)-1H-imidazol-4-yl)amino)-1H-pyrazolo[3,4-d]pyrimidin-6-yl)pyrrolidine-2-carboxamide (373c) (0.17 g, 72% yield) HCl salt as a white solid; $^1$H NMR (300 MHz, DMSO-d$_6$) δ 9.72 (2s, 1H), 9.29 (s, 1H), 8.13 (d, J=1.7 Hz, 1H), 7.12 (s, 2H), 4.46-4.12 (m, 1H), 3.89 (s, 6H), 3.82-3.72 (m, 1H), 3.71 (s, 3H), 3.70 (s, 3H), 3.68-3.60 (m, 1H), 3.58-3.27 (m, 1H), 2.60 (s, 3H), 2.17-1.77 (m, 4H); MS (ES+): 508.3 (M+1), 530.3 (M+Na); MS (ES−): 542.4 (M+Cl). HPLC purity: 96.64%.

Scheme 374

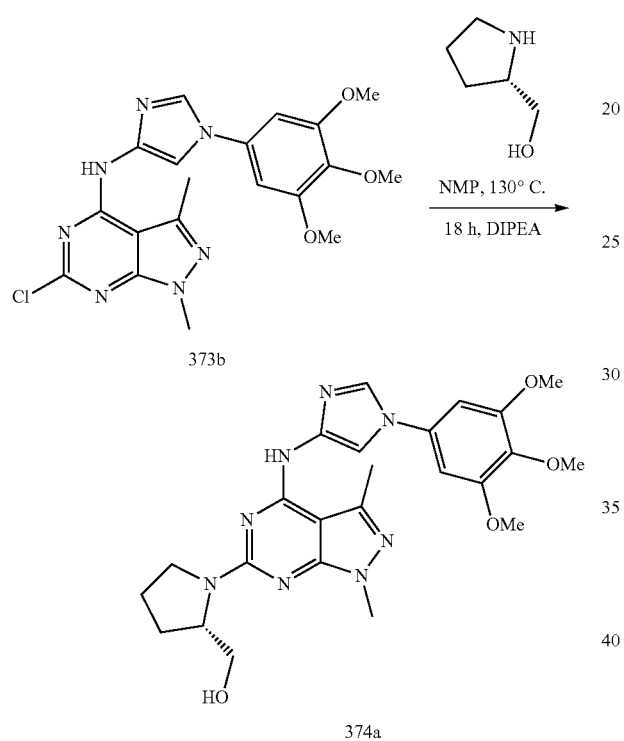

373b

374a

Preparation of (S)-(1-(1,3-dimethyl-4-((1-(3,4,5-trimethoxyphenyl)-1H-imidazol-4-yl)amino)-1H-pyrazolo[3,4-d]pyrimidin-6-yl)pyrrolidin-2-yl)methanol (374a)

Compound 374a was prepared from 6-chloro-1,3-dimethyl-N-(1-(3,4,5-trimethoxyphenyl)-1H-imidazol-4-yl)-1H-pyrazolo[3,4-d]pyrimidin-4-amine (373b) (200 mg, 0.47 mmol), (S)-pyrrolidin-2-ylmethanol (0.18 mL, 1.86 mmol) and N-ethyl-N-isopropylpropan-2-amine (0.49 mL, 2.79 mmol) in N-Methyl-2-pyrrolidinone (3 mL) according to the procedure reported in step-2 of Scheme 76. This gave after workup and purification by flash column chromatography [silica gel (12 g), eluting with DMA-80 in DCM from 0-50%] followed by purification by reverse phase flash column chromatography [(silica gel C-18, 24 g) eluting with acetonitrile and 0.1% HCl water] (S)-(1-(1,3-dimethyl-4-((1-(3,4,5-trimethoxyphenyl)-1H-imidazol-4-yl)amino)-1H-pyrazolo[3,4-d]pyrimidin-6-yl)pyrrolidin-2-yl)methanol (374a) (0.16 g, 68% yield) HCl salt as a white solid; $^1$H NMR (300 MHz, DMSO-d$_6$) δ 9.72 (s, 1H), 9.29 (s, 1H), 8.13 (d, J=1.7 Hz, 1H), 7.12 (s, 2H), 4.46-4.12 (m, 1H), 3.89 (s, 6H), 3.85-3.74 (m, 1H), 3.71 (s, 3H), 3.70 (s, 3H), 3.69-3.56 (m, 2H), 2.60 (s, 3H), 2.17-1.77 (m, 4H); MS (ES+): 495.4 (M+1), 517.4 (M+Na); MS (ES−): 529.4 (M+Cl). HPLC purity: 97.04%.

Scheme 375

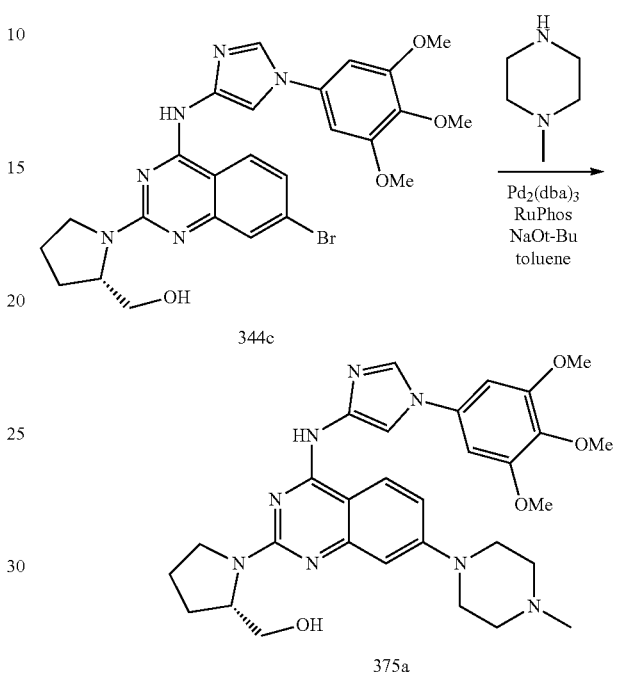

344c

375a

Preparation of (S)-(1-(7-(4-methylpiperazin-1-yl)-4-((1-(3,4,5-trimethoxyphenyl)-1H-imidazol-4-yl)amino)quinazolin-2-yl)pyrrolidin-2-yl)methanol (375a)

Compound 375a was prepared from (S)-(1-(7-bromo-4-((1-(3,4,5-trimethoxyphenyl)-1H-imidazol-4-yl)amino)quinazolin-2-yl)pyrrolidin-2-yl)methanol (344c) (150 mg, 0.27 mmol), 1-methylpiperazine (0.15 mL, 1.35 mmol), dicyclohexyl(2',6'-diisopropoxybiphenyl-2-yl)phosphine (RuPhos, 76 mg, 0.16 mmol), sodium 2-methylpropan-2-olate (130 mg, 1.35 mmol) and Pd$_2$(dba)$_3$ (74 mg, 0.08 mmol) in toluene (25 mL) according to the procedure reported in step-3 of Scheme 101. This gave after workup and purification by flash column chromatography [silica gel (24 g), eluting with DMA80 in DCM from 0-50%], followed by reverse phase column chromatography [(silica gel C-18, 24 g) eluting with acetonitrile and 0.1% HCl in water] (S)-(1-(7-(4-methylpiperazin-1-yl)-4-((1-(3,4,5-trimethoxyphenyl)-1H-imidazol-4-yl)amino)quinazolin-2-yl)pyrrolidin-2-yl)methanol (375a) (75 mg, 48% yield) HCl salt as a yellow solid; $^1$H NMR (300 MHz, DMSO-d$_6$) (a mixture of two rotamers) δ 12.24 and 12.20 (2s, 1H), 11.63-11.49 and 11.49-11.39 (2m, 1H), 8.66-8.52 (m, 2H), 8.05 and 8.04 (2s, 1H), 7.70 and 7.63 (2s, 1H), 7.21 and 7.18 (2s, 1H), 7.02 and 6.97 (2s, 2H), 4.63-4.47 (m, 1H), 4.09 and 4.04 (2s, 2H), 3.97-3.49 (m, 15H), 3.48-3.35 (m, 2H), 3.26-3.06 (m, 2H), 2.81 and 2.80 2 (s, 3H), 2.22-1.85 (m, 4H); MS (ES+): 575.5 (M+1); MS (ES−): 609.5 (M+Cl). HPLC purity: 94.27%.

Scheme 376

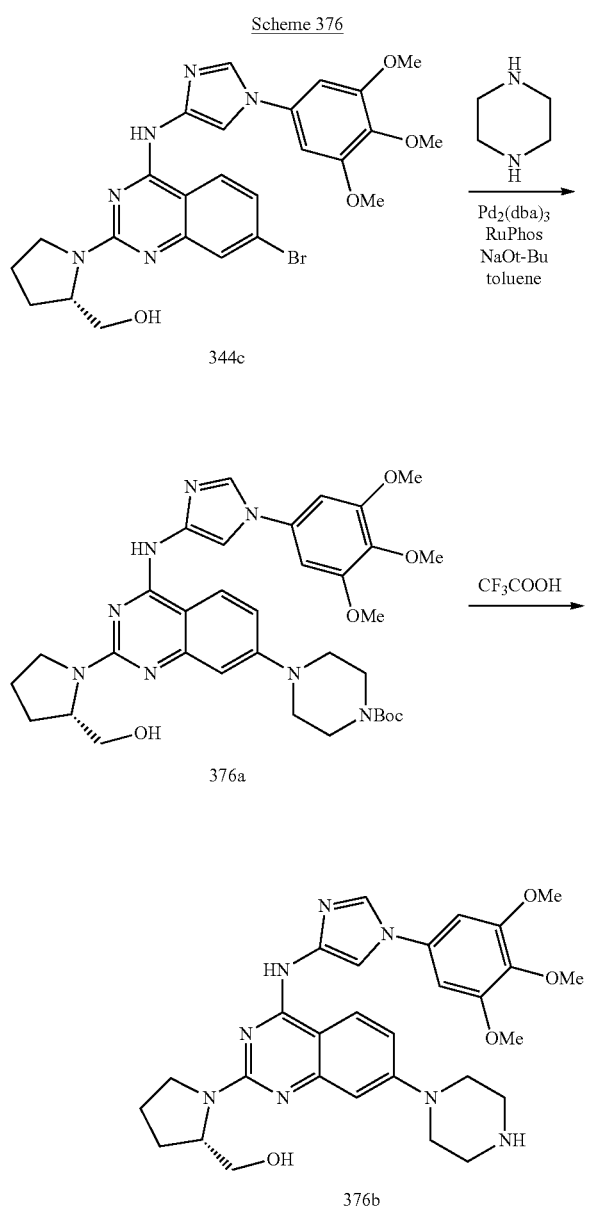

Preparation of (S)-1-(7-(piperazin-1-yl)-4-((1-(3,4,5-trimethoxyphenyl)-1H-imidazol-4-yl)amino)quinazolin-2-yl)pyrrolidin-2-yl)methanol (376b)

Step-1: Preparation of (S)-tert-butyl 4-(2-(2-(hydroxymethyl)pyrrolidin-1-yl)-4-((1-(3,4,5-trimethoxyphenyl)-1H-imidazol-4-yl)amino)quinazolin-7-yl)piperazine-1-carboxylate (376a)

Compound 376a was prepared from (S)-(1-(7-bromo-4-((1-(3,4,5-trimethoxyphenyl)-1H-imidazol-4-yl)amino)quinazolin-2-yl)pyrrolidin-2-yl)methanol (344c) (260 mg, 0.47 mmol), tert-butyl piperazine-1-carboxylate (0.44 g, 2.34 mmol), dicyclohexyl(2',6'-diisopropoxybiphenyl-2-yl)phosphine (RuPhos, 130 mg, 0.28 mmol), sodium 2-methylpropan-2-olate (230 mg, 2.34 mmol) and $Pd_2(dba)_3$ (130 mg, 0.14 mmol) in toluene (25 mL) according to the procedure reported in step-3 of Scheme 101. This gave after workup and purification by flash column chromatography [silica gel (24 g), eluting with DMA-80 in DCM from 0-50%], followed by reverse phase column chromatography [(silica gel C-18, 24 g) eluting with acetonitrile and 0.1% HCl in water] (S)-tert-butyl 4-(2-(2-(hydroxymethyl)pyrrolidin-1-yl)-4-((1-(3,4,5-trimethoxyphenyl)-1H-imidazol-4-yl)amino)quinazolin-7-yl)piperazine-1-carboxylate (376a) (60 mg, 20% yield) HCl salt as a yellow solid; $^1$H NMR (300 MHz, DMSO-$d_6$) δ 10.22 (s, 1H), 8.33 (d, J=9.1 Hz, 1H), 8.25 (s, 1H), 8.18-7.85 (m, 1H), 6.96 (s, 2H), 6.92-6.84 (m, 1H), 6.70-6.57 (m, 1H), 5.12-4.79 (m, 1H), 4.65-4.11 (m, 1H), 3.88 (s, 6H), 3.68 (s, 3H), 3.54-3.38 (m, 4H), 3.33-3.24 (m, 4H), 2.16-1.74 (m, 4H), 1.43 (s, 9H); MS (ES+): 661.5 (M+1); MS (ES−): 695.5 (M+Cl).

Step-2: Preparation of (S)-(1-(7-(piperazin-1-yl)-4-((1-(3,4,5-trimethoxyphenyl)-1H-imidazol-4-yl)amino)quinazolin-2-yl)pyrrolidin-2-yl)methanol (376b)

Compound 376b was prepared by hydrolysis of (S)-tert-butyl 4-(2-(2-(hydroxymethyl)pyrrolidin-1-yl)-4-((1-(3,4,5-trimethoxyphenyl)-1H-imidazol-4-yl)amino)quinazolin-7-yl)piperazine-1-carboxylate (376a) (50 mg, 0.08 mmol) in DCM (5 mL) using trifluoroacetic acid (0.29 mL, 3.78 mmol) according to the procedure reported in Scheme 122. This gave after workup and purification by flash column chromatography [silica gel (12 g), eluting with DMA-80 in DCM from 0-50%], followed by reverse phase column chromatography [(silica gel C-18, 24 g), eluting with acetonitrile in water (containing 0.1% HCl) from 0-100%] (S)-(1-(7-(piperazin-1-yl)-4-((1-(3,4,5-trimethoxyphenyl)-1H-imidazol-4-yl)amino)quinazolin-2-yl)pyrrolidin-2-yl)methanol (376b) (0.03 g, 68% yield) HCl salt as a yellow solid; $^1$H NMR (300 MHz, DMSO-$d_6$): (mixture of rotamers) δ 12.11 (2s, 1H), 11.36 (2s, 1H), 9.73-9.37 (m, 1H), 8.61-8.49 (m, 1H), 8.43 (2s, 1H), 8.14-7.93 (m, 1H), 7.72-7.42 (m, 1H), 7.22-7.12 (m, 1H), 7.00 (s, 1H), 6.96 (s, 1H), 4.67-4.47 (m, 1H), 3.88 (s, 6H), 3.76-3.69 (m, 1H), 3.68 (s, 3H), 3.67-3.44 (m, 4H), 3.35-3.06 (m, 4H), 2.29-1.79 (m, 4H); MS (ES+): 561.5 (M+1); MS (ES−): 595.5 (M+Cl). HPLC purity: 86.81%.

Scheme 377

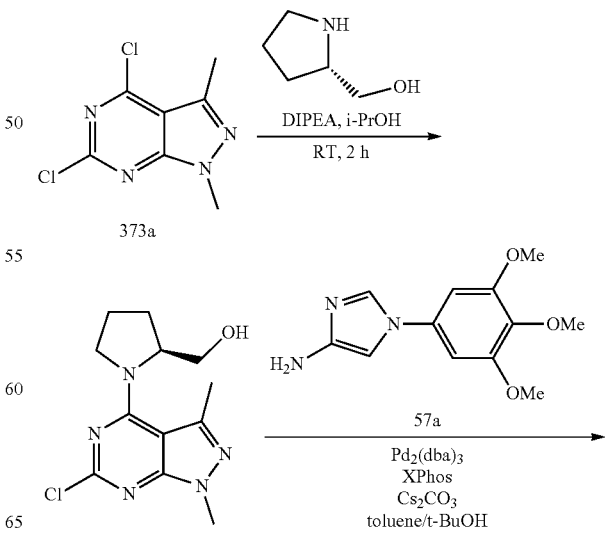

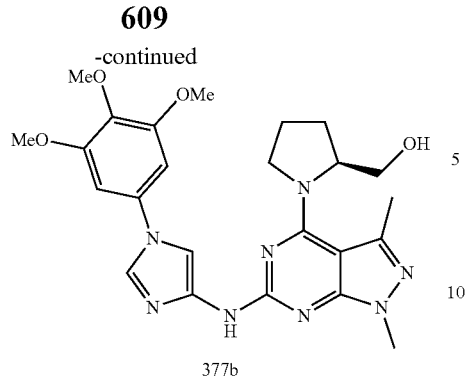

377b

Preparation of (S)-(1-(1,3-dimethyl-6-((1-(3,4,5-trimethoxyphenyl)-1H-imidazol-4-yl)amino)-1H-pyrazolo[3,4-d]pyrimidin-4-yl)pyrrolidin-2-yl)methanol (377b)

Step-1: Preparation of (S)-(1-(6-chloro-1,3-dimethyl-1H-pyrazolo[3,4-d]pyrimidin-4-yl)pyrrolidin-2-yl)methanol (377a)

Compound 377a was prepared from 4,6-dichloro-1,3-dimethyl-1H-pyrazolo[3,4-d]pyrimidine (373a) (400 mg, 1.84 mmol) in 2-Propanol (10 mL) using (S)-pyrrolidin-2-ylmethanol (180 mg, 1.84 mmol) and DIPEA (0.97 mL, 5.53 mmol) according to the procedure reported in step-1 of Scheme 96. This gave after workup and purification by flash column chromatography [silica gel (12 g), eluting with eluting with DCM and methanol (0 to 30%)] (S)-(1-(6-chloro-1,3-dimethyl-1H-pyrazolo[3,4-d]pyrimidin-4-yl)pyrrolidin-2-yl)methanol (377a) (490 mg, 94% yield) as a white solid; $^1$H NMR (300 MHz, DMSO-$d_6$) δ 4.94-4.73 (m, 1H), 4.56-4.33 (m, 1H), 3.85-3.78 (m, 1H), 3.77 (s, 3H), 3.76-3.68 (m, 1H), 3.67-3.45 (m, 2H), 2.55 (s, 3H), 2.17-1.78 (m, 4H); MS (ES+): 282.2 & 284.2 (M+1); MS (ES−): 316.2 & 318.2 (M+Cl).

Step-2: Preparation of (S)-(1-(1,3-dimethyl-6-((1-(3,4,5-trimethoxyphenyl)-1H-imidazol-4-yl)amino)-1H-pyrazolo[3,4-d]pyrimidin-4-yl)pyrrolidin-2-yl)methanol (377b)

Compound 377b was prepared from (S)-(1-(6-chloro-1,3-dimethyl-1H-pyrazolo[3,4-d]pyrimidin-4-yl)pyrrolidin-2-yl)methanol (377a) (300 mg, 1.07 mmol), 1-(3,4,5-trimethoxyphenyl)-1H-imidazol-4-amine (57a) (270 mg, 1.07 mmol), dicyclohexyl(2',4',6'-triisopropylbiphenyl-2-yl)phosphine (XPhos, 310 mg, 0.64 mmol), cesium carbonate (1040 mg, 3.19 mmol) and Pd$_2$(dba)$_3$ (290 mg, 0.32 mmol) in t-BuOH/toluene (30 mL, 2:1) according to the procedure reported in step-3 of Scheme 101. This gave after workup and purification by flash column chromatography [silica gel (24 g), eluting with DMA-80 in DCM from 0-50%] followed by purification by reverse phase column chromatography [(silica gel C-18, 24 g) eluting with acetonitrile and 0.1% HCl water] (S)-(1-(1,3-dimethyl-6-((1-(3,4,5-trimethoxyphenyl)-1H-imidazol-4-yl)amino)-1H-pyrazolo[3,4-d]pyrimidin-4-yl)pyrrolidin-2-yl)methanol (377b) (0.18 g, 33% yield) HCl salt as a white solid; $^1$H NMR (300 MHz, DMSO-$d_6$) δ 10.23 (s, 1H), 9.10 (s, 1H), 7.90 (s, 1H), 7.11 (s, 2H), 4.74-4.58 (m, 1H), 3.89 (s, 6H), 3.87-3.80 (m, 1H), 3.79 (s, 3H), 3.77-3.74 (m, 1H), 3.70 (s, 3H), 3.67-3.48 (m, 2H), 2.54 (s, 3H), 2.22-1.80 (m, 4H); MS (ES+): 495.4 (M+1), 517.4 (M+Na); MS (ES−): 529.4 (M+Cl). HPLC purity: 98.48%.

Scheme 378

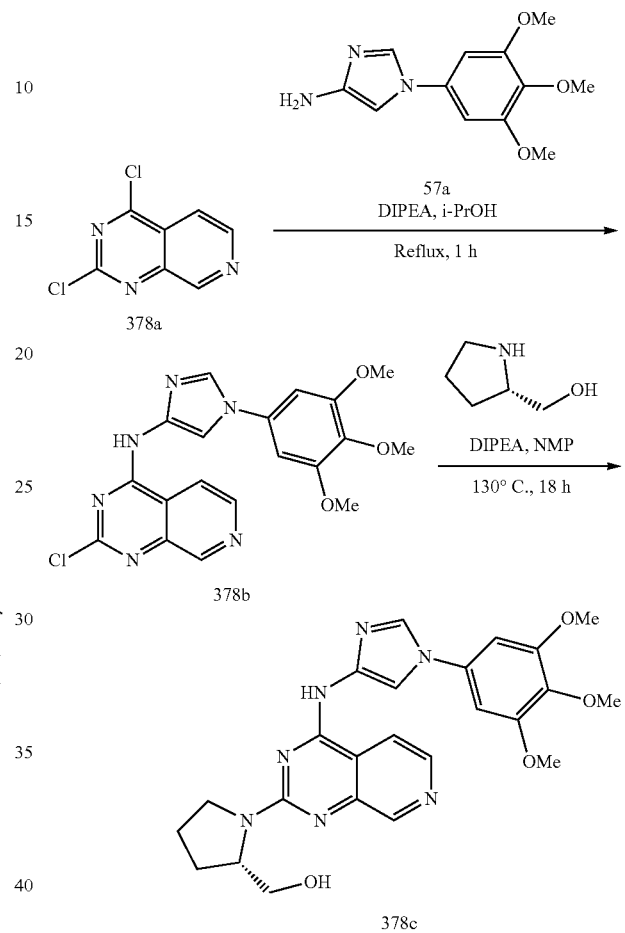

Preparation of (S)-(1-(4-((1-(3,4,5-trimethoxyphenyl)-1H-imidazol-4-yl)amino)pyrido[3,4-d]pyrimidin-2-yl)pyrrolidin-2-yl)methanol (378c)

Step-1: Preparation of 2-chloro-N-(1-(3,4,5-trimethoxyphenyl)-1H-imidazol-4-yl)pyrido[3,4-d]pyrimidin-4-amine (378b)

Compound 378b was prepared from 2,4-dichloropyrido[3,4-d]pyrimidine (378a) (500 mg, 2.5 mmol; CAS #908240-50-6) in 2-Propanol (15 mL) using DIPEA (1.31 mL, 7.5 mmol) and 1-(3,4,5-trimethoxyphenyl)-1H-imidazol-4-amine (57a) (623 mg, 2.5 mmol) according to the procedure reported in step-1 of Scheme 183. This gave after filtration 2-chloro-N-(1-(3,4,5-trimethoxyphenyl)-1H-imidazol-4-yl)pyrido[3,4-d]pyrimidin-4-amine (378b) (784 mg, 76% yield) as a brown solid; $^1$H NMR (300 MHz, DMSO-$d_6$) δ 11.58 (s, 1H), 9.08 (s, 1H), 8.68 (d, J=5.6 Hz, 1H), 8.62 (d, J=5.8 Hz, 1H), 8.26 (s, 1H), 8.02 (s, 1H), 6.94 (s, 2H), 3.88 (s, 6H), 3.70 (s, 3H); MS (ES+): 435.2 (M+Na); (ES−): 411.3 (M−1).

Step-2: Preparation of (S)-(1-(4-((1-(3,4,5-trimethoxyphenyl)-1H-imidazol-4-yl)amino)pyrido[3,4-d]pyrimidin-2-yl)pyrrolidin-2-yl)methanol (378c)

Compound 378c was prepared from 2-chloro-N-(1-(3,4,5-trimethoxyphenyl)-1H-imidazol-4-yl)pyrido[3,4-d]pyrimidin-4-amine (378b) (200 mg, 0.48 mmol), (S)-pyrrolidin-2-ylmethanol (0.19 mL, 1.94 mmol) and N-ethyl-N-isopropylpropan-2-amine (0.51 mL, 2.91 mmol) in NMP (3 mL) according to the procedure reported in step-2 of Scheme 76. This gave after workup and purification by flash column chromatography [silica gel (12 g), eluting with DMA 80 in $CH_2Cl_2$ from 0 to 50%], followed by purification using reverse phase flash column chromatography [(silica gel C-18, 24 g), eluting with acetonitrile and 0.1% HCl water] (S)-(1-(4-((1-(3,4,5-trimethoxyphenyl)-1H-imidazol-4-yl)amino)pyrido[3,4-d]pyrimidin-2-yl)pyrrolidin-2-yl)methanol (378c) (162 mg, 70% yield) HCl salt as a yellow HCl solid; $^1$H NMR (300 MHz, DMSO-$d_6$, mixture of rotamers) δ 9.55 (2s, 1H), 8.70-8.58 (m, 2H), 8.56 (s, 1H), 8.10 (s, 1H), 7.02 (s, 2H), 6.97 (s, 1H), 4.82-4.49 (m, 1H), 4.11-3.91 (m, 1H), 3.88 (s, 6H), 3.69 (s, 3H), 3.63-3.44 (m, 1H), 2.34-1.77 (m, 4H); MS (ES+): 478.4 (M+1); MS (ES-): 476.4 (M-1), 512.4 (M+Cl). HPLC purity: 97.94%.

mL) according to the procedure reported in step-2 of Scheme 76. This gave after workup and purification by flash column chromatography [silica gel (12 g), eluting with DMA-80 in $CH_2Cl_2$ from 0 to 50%], followed by purification using reverse phase flash column chromatography [(silica gel C-18, 24 g), eluting with acetonitrile and 0.1% HCl water] (S)-1-(4-((1-(3,4,5-trimethoxyphenyl)-1H-imidazol-4-yl)amino)pyrido[3,4-d]pyrimidin-2-yl)pyrrolidine-2-carboxamide (379a) (155 mg, 65% yield) HCl salt as a yellow HCl solid; $^1$H NMR (300 MHz, DMSO-$d_6$) δ 9.61 (s, 1H), 8.69 (d, J=5.7 Hz, 1H), 8.64 (d, J=5.5 Hz, 1H), 8.53 (s, 1H), 7.96 (s, 1H), 7.65 (s, 1H), 7.29 (s, 1H), 7.15 (s, 2H), 4.74 (d, J=7.7 Hz, 1H), 4.24-4.02 (m, 1H), 3.94 (s, 6H), 3.89-3.72 (m, 2H), 3.69 (s, 3H), 2.36-2.00 (m, 4H); MS (ES+): 491.4 (M+1), 513.3 (M+Na); MS (ES-): 489.4 (M-1), 525.4 (M+Cl); HPLC purity: 93.57%.

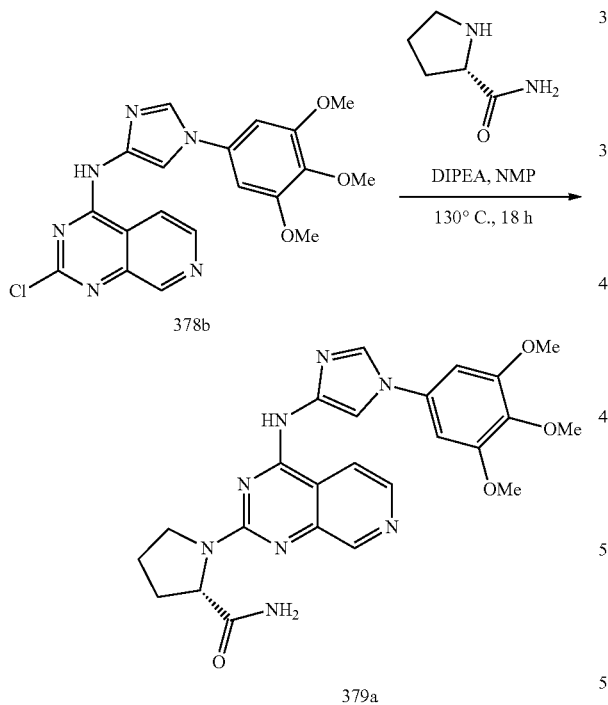

Scheme 379

Preparation of (S)-1-(4-((1-(3,4,5-trimethoxyphenyl)-1H-imidazol-4-yl)amino)pyrido[3,4-d]pyrimidin-2-yl)pyrrolidine-2-carboxamide (379a)

Compound 379a was prepared from 2-chloro-N-(1-(3,4,5-trimethoxyphenyl)-1H-imidazol-4-yl)pyrido[3,4-d]pyrimidin-4-amine (378b) (200 mg, 0.48 mmol), (S)-pyrrolidine-2-carboxamide (221 mg, 1.94 mmol) and N-ethyl-N-isopropylpropan-2-amine (0.51 mL, 2.91 mmol) in NMP (3

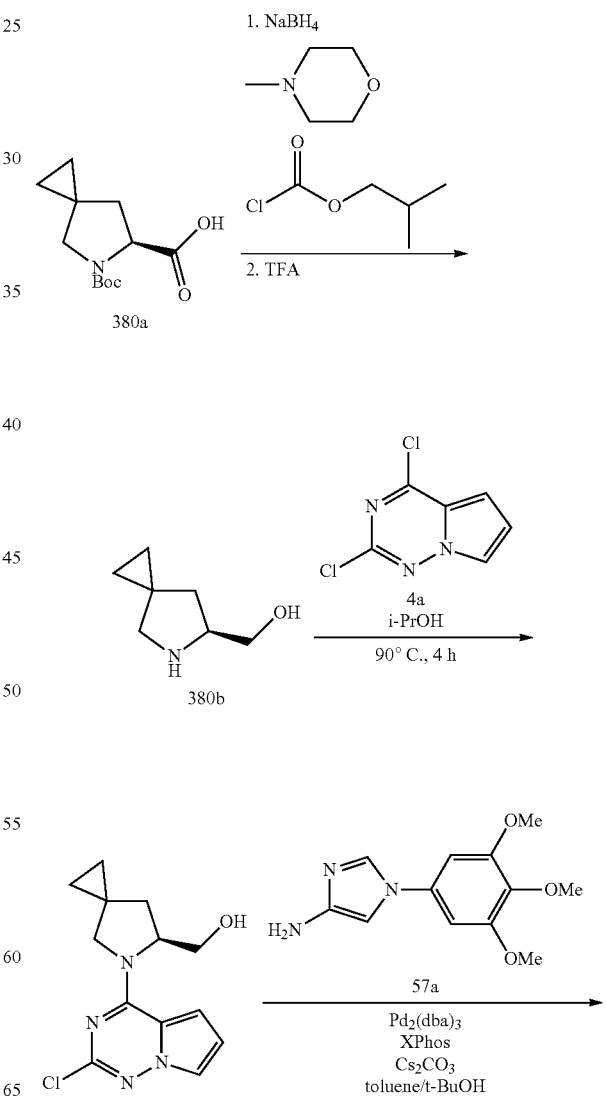

Scheme 380

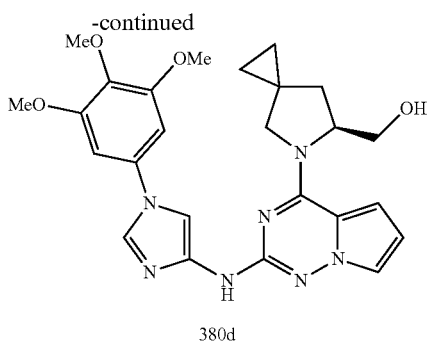

380d

Preparation of (S)-(5-(2-((1-(3,4,5-trimethoxyphenyl)-1H-imidazol-4-yl)amino)pyrrolo[2,1-f][1,2,4]triazin-4-yl)-5-azaspiro[2.4]heptan-6-yl)methanol (380d)

Step-1: Preparation of (S)-5-azaspiro[2.4]heptan-6-ylmethanol (380b)

Compound 380b was prepared from (S)-5-(tert-butoxycarbonyl)-5-azaspiro[2.4]heptane-6-carboxylic acid (380a) (500 mg, 2.07 mmol; CAS #1129634-44-1) according to the procedure reported in step-1 and step-2 of Scheme 325. This gave (S)-5-azaspiro[2.4]heptan-6-ylmethanol (380b) (488 mg, 98% yield) TFA salt as a clear oil. MS (ES+): 128.1 (M+1).

Step-2: Preparation of (S)-(5-(2-chloropyrrolo[2,1-f][1,2,4]triazin-4-yl)-5-azaspiro[2.4]heptan-6-yl)methanol (380c)

Compound 380c was prepared from 2,4-dichloropyrrolo[2,1-f][1,2,4]triazine (4a) (180 mg, 0.96 mmol) in 2-Propanol (5 mL) using (S)-5-azaspiro[2.4]heptan-6-ylmethanol (380b) (122 mg, 0.96 mmol) and DIPEA (0.5 mL, 2.88 mmol) according to the procedure reported in step-1 of Scheme 96. This gave after workup and purification by flash column chromatography [silica gel (12 g), eluting with eluting with 0-60% EtOAc/MeOH (9:1) in hexane from 0-100%] (S)-(5-(2-chloropyrrolo[2,1-f][1,2,4]triazin-4-yl)-5-azaspiro[2.4]heptan-6-yl)methanol (380c) (81 mg, 30% yield) as a white solid; MS (ES−): 277.2 (M−1).

Step-3: Preparation of (S)-(5-(2-((1-(3,4,5-trimethoxyphenyl)-1H-imidazol-4-yl)amino)pyrrolo[2,1-f][1,2,4]triazin-4-yl)-5-azaspiro[2.4]heptan-6-yl)methanol (380d)

Compound 380d was prepared from (S)-(5-(2-chloropyrrolo[2,1-f][1,2,4]triazin-4-yl)-5-azaspiro[2.4]heptan-6-yl)methanol (380c) (75 mg, 0.27 mmol), 1-(3,4,5-trimethoxyphenyl)-1H-imidazol-4-amine (57a) (67 mg, 0.27 mmol, free base), dicyclohexyl(2',4',6'-triisopropylbiphenyl-2-yl)phosphine (XPhos, 77 mg, 0.16 mmol), cesium carbonate (263 mg, 0.81 mmol), Pd$_2$(dba)$_3$ (74 mg, 0.08 mmol) in t-BuOH/toluene (30 mL, 2:1) according to the procedure reported in step-3 of Scheme 101. This gave after workup and purification by flash column chromatography [silica gel (12 g), eluting with DMA-80 in CH$_2$Cl$_2$ from 0 to 50%] followed by reverse phase flash column chromatography [(silica gel C-18, 24 g) eluting with acetonitrile and 0.1% HCl in water] (S)-(5-(2-((1-(3,4,5-trimethoxyphenyl)-1H-imidazol-4-yl)amino)pyrrolo[2,1-f][1,2,4]triazin-4-yl)-5-azaspiro[2.4]heptan-6-yl)methanol (380d) (0.025 g, 19% yield) HCl salt as a white solid; $^1$H NMR (300 MHz, DMSO-d$_6$) δ 9.58 (s, 1H), 9.30 (s, 1H), 7.89 (s, 1H), 7.63 (s, 1H), 7.14 (s, 2H), 6.96-6.68 (m, 1H), 6.68-6.31 (m, 1H), 4.78-4.38 (m, 1H), 4.08-3.93 (m, 1H), 3.89 (s, 6H), 3.71 (s, 3H), 3.65-3.34 (m, 3H), 2.28-2.01 (m, 1H), 1.92-1.61 (m, 1H), 0.86-0.45 (m, 4H); MS (ES+): 492.4 (M+1), 514.5 (M+Na); MS (ES−): 526.4 (M+Cl). HPLC purity: 97.29%.

Scheme 381

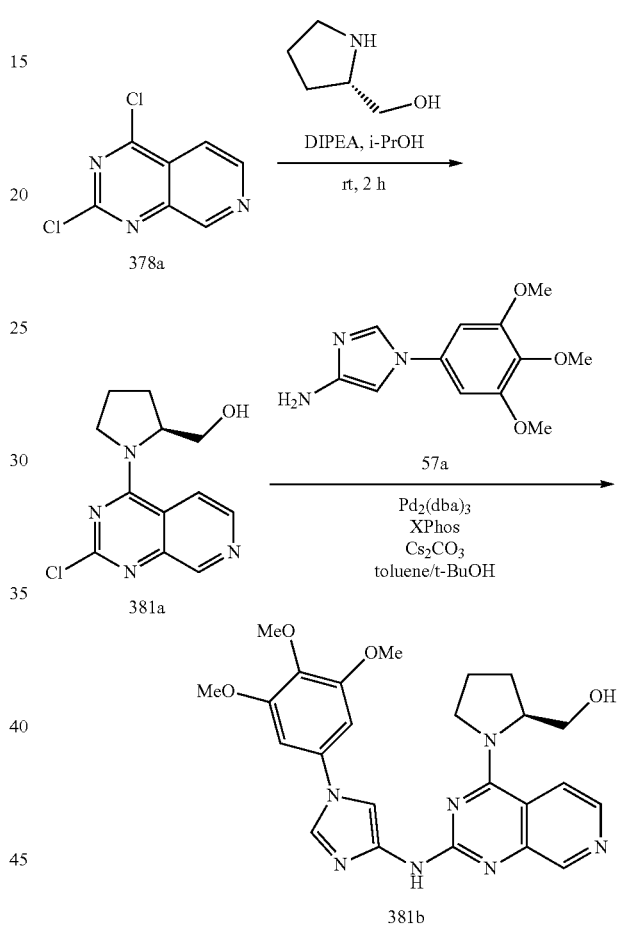

381b

Preparation of (S)-(1-(2-((1-(3,4,5-trimethoxyphenyl)-1H-imidazol-4-yl)amino)pyrido[3,4-d]pyrimidin-4-yl)pyrrolidin-2-yl)methanol (381b)

Step-1: Preparation of (S)-(1-(2-chloropyrido[3,4-d]pyrimidin-4-yl)pyrrolidin-2-yl)methanol (381a)

Compound 381a was prepared from 2,4-dichloropyrido[3,4-d]pyrimidine (378a) (400 mg, 1.84 mmol) in 2-Propanol (10 mL) using (S)-pyrrolidin-2-ylmethanol (0.2 mL, 2.0 mmol) and DIPEA (1.05 mL, 6.0 mmol) according to the procedure reported in step-1 of Scheme 96. This gave after workup and purification by flash column chromatography [silica gel (12 g), eluting with eluting with DCM and methanol (0 to 30%)] (S)-(1-(2-chloropyrido[3,4-d]pyrimidin-4-yl)pyrrolidin-2-yl)methanol (381a) (451 mg, 85% yield) as a white solid; $^1$H NMR (300 MHz, DMSO-d$_6$): δ

9.00 (s, 1H), 8.54 (d, J=5.8 Hz, 1H), 8.13 (d, J=5.9 Hz, 1H), 5.04-4.75 (m, 2H), 4.74-4.41 (m, 1H), 4.19-3.84 (m, 2H), 3.63 (m, 1H), 2.26-1.76 (m, 4H). MS (ES+): 265.2 (M+1); MS (ES−): 299.2 & 301.2 (M+Cl).

Step-2: Preparation of (S)-(1-(2-((1-(3,4,5-trimethoxyphenyl)-1H-imidazol-4-yl)amino)pyrido[3,4-d]pyrimidin-4-yl)pyrrolidin-2-yl)methanol (381b)

Compound 381b was prepared from (S)-(1-(2-chloropyrido[3,4-d]pyrimidin-4-yl)pyrrolidin-2-yl)methanol (381a) (300 mg, 1.13 mmol), 1-(3,4,5-trimethoxyphenyl)-1H-imidazol-4-amine (57a) (282 mg, 1.13 mmol), dicyclohexyl(2',4',6'-triisopropylbiphenyl-2-yl)phosphine (XPhos, 324 mg, 0.68 mmol), cesium carbonate (1108 mg, 3.4 mmol) and Pd$_2$(dba)$_3$ (311 mg, 0.34 mmol) in t-BuOH/toluene (30 mL, 2:1) according to the procedure reported in step-3 of Scheme 101. This gave after workup and purification by flash column chromatography [silica gel (24 g), eluting with DMA-80 in DCM from 0-50%] followed by purification by reverse phase column chromatography [(silica gel C-18, 24 g) eluting with acetonitrile and 0.1% HCl water](S)-(1-(2-((1-(3,4,5-trimethoxyphenyl)-1H-imidazol-4-yl)amino)pyrido[3,4-d]pyrimidin-4-yl)pyrrolidin-2-yl)methanol (381b) (102 mg, 19% yield) HCl salt as a yellow solid; $^1$H NMR (300 MHz, DMSO-d$_6$) δ 9.27-8.97 (m, 1H), 8.86 (s, 1H), 8.56 (d, J=5.7 Hz, 1H), 8.26 (s, 1H), 7.95 (s, 1H), 7.08 (s, 2H), 5.08-4.58 (m, 1H), 4.34-4.01 (m, 2H), 3.90 (s, 6H), 3.81-3.71 (m, 1H), 3.70 (s, 3H), 3.69-3.57 (m, 1H), 2.36-1.64 (m, 4H); MS (ES+): 478.4 (M+1); MS (ES−): 512.4 (M+Cl). HPLC purity: 95.00%.

(1-(3,4,5-trimethoxyphenyl)-1H-imidazol-4-yl)quinazolin-4-amine (344b) (1.5 g, 3.06 mmol), (R)-pyrrolidin-2-yl-methanol (1.21 mL, 12.23 mmol) and DIPEA (3.2 mL, 18.34 mmol) in NMP (5 mL). This gave after workup and purification by flash column chromatography [(silica gel, 40 g) eluting DMA-80 in CH$_2$Cl$_2$ from 0 to 50%] followed by purification by reverse phase column chromatography [(silica gel C-18, 50 g) eluting with acetonitrile and 0.1% HCl water] (R)-(1-(7-bromo-4-((1-(3,4,5-trimethoxyphenyl)-1H-imidazol-4-yl)amino)quinazolin-2-yl)pyrrolidin-2-yl)methanol (382a) (820 mg, 48% yield) HCl salt as an off-white solid; $^1$H NMR (300 MHz, DMSO-d$_6$) δ 12.66 (bs, 1H), 11.82 (bs, 1H), 8.71-8.58 (m, 1H), 8.58-8.49 (m, 1H), 8.47 (s, 1H), 8.05 (s, 1H), 7.69-7.47 (m, 1H), 7.01 (s, 1H), 6.95 (s, 1H), 4.73-4.47 (m, 1H), 3.88 (s, 6H), 3.84-3.78 (m, 1H), 3.68 (s, 3H), 3.67-3.60 (m, 1H), 3.59-3.43 (m, 2H), 2.26-1.81 (m, 4H); MS (ES+): 555.3 & 557.2 (M+1). HPLC purity: 97.42%.

Scheme 383

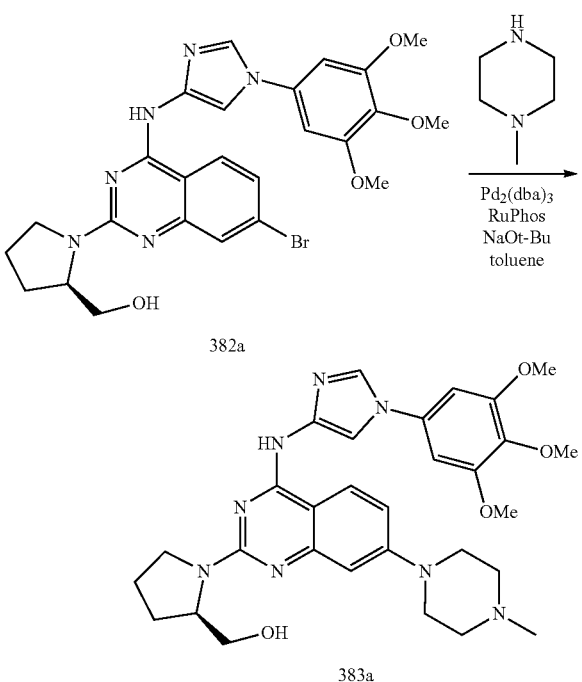

Preparation of (R)-(1-(7-(4-methylpiperazin-1-yl)-4-((1-(3,4,5-trimethoxyphenyl)-1H-imidazol-4-yl)amino)quinazolin-2-yl)pyrrolidin-2-yl)methanol (383a)

Compound 383a was prepared from (R)-(1-(7-bromo-4-((1-(3,4,5-trimethoxyphenyl)-1H-imidazol-4-yl)amino)quinazolin-2-yl)pyrrolidin-2-yl)methanol (382a) (150 mg, 0.27 mmol), 1-methylpiperazine (0.15 mL, 1.35 mmol), dicyclohexyl(2',6'-diisopropoxybiphenyl-2-yl)phosphine (RuPhos, 76 mg, 0.16 mmol), sodium 2-methylpropan-2-olate (130 mg, 1.35 mmol) and Pd$_2$(dba)$_3$ (74 mg, 0.08 mmol) in toluene (25 mL) according to the procedure reported in step-3 of Scheme 101. This gave after workup and purification by flash column chromatography [silica gel (24 g), eluting with DMA-80 in DCM from 0-50%], followed by reverse phase column chromatography [(silica gel C-18, 24

Scheme 382

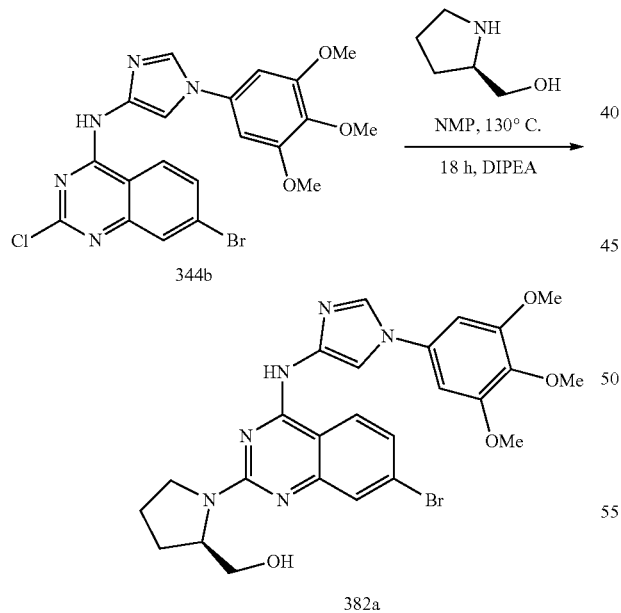

Preparation of (R)-(1-(7-bromo-4-((1-(3,4,5-trimethoxyphenyl)-1H-imidazol-4-yl)amino)quinazolin-2-yl)pyrrolidin-2-yl)methanol (382a)

Compound 382a was prepared according to the procedure reported in step-2 of Scheme 76 from 7-bromo-2-chloro-N- g) eluting with acetonitrile and 0.1% HCl in water] (R)-(1-(7-(4-methylpiperazin-1-yl)-4-((1-(3,4,5-trimethoxyphenyl)-1H-imidazol-4-yl)amino)quinazolin-2-yl)pyrrolidin-2-yl)methanol (383a) (24 mg, 16% yield) HCl salt as a yellow solid; $^1$H NMR (300 MHz, DMSO-$d_6$) δ 12.12 (s, 1H), 11.46 (s, 1H), 11.35 (s, 1H), 8.62-8.51 (m, 1H), 8.48 (s, 1H), 8.04 (s, 1H), 7.71-7.47 (m, 1H), 7.20 (d, J=9.2 Hz, 1H), 7.01 (s, 1H), 6.96 (s, 1H), 4.73-4.38 (m, 1H), 4.16-3.99 (m, 2H), 3.88 (s, 6H), 3.68 (s, 4H), 3.62-3.46 (m, 4H), 3.40 (t, J=13.0 Hz, 2H), 3.15 (q, J=10.7 Hz, 2H), 2.81 (d, J=4.5 Hz, 3H), 2.23-1.81 (m, 4H); MS (ES+): 575.5 (M+1); MS (ES−): 573.5 (M−1). HPLC purity: 97.91%.

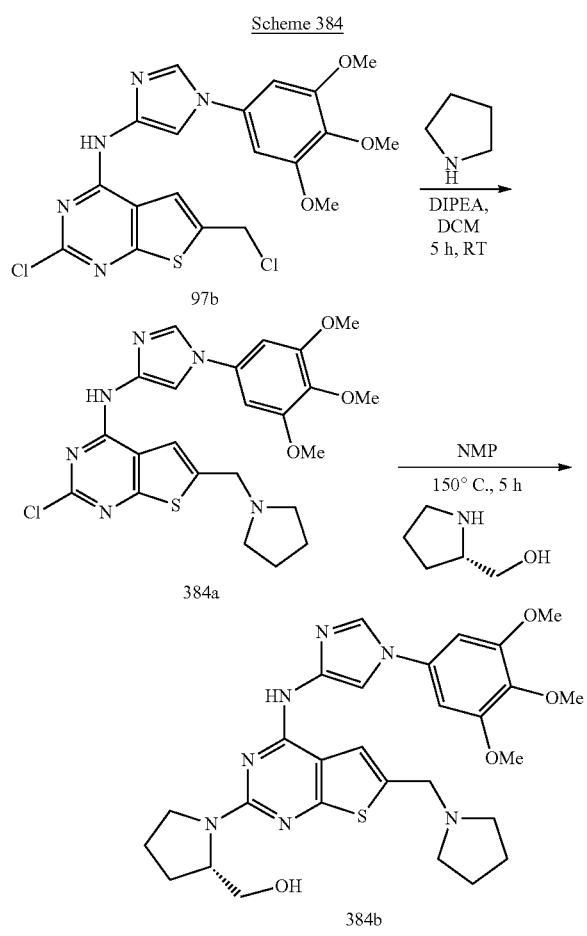

Scheme 384

Preparation of (S)-(1-(6-(pyrrolidin-1-ylmethyl)-4-((1-(3,4,5-trimethoxyphenyl)-1H-imidazol-4-yl)amino)thieno[2,3-d]pyrimidin-2-yl)pyrrolidin-2-yl)methanol (384b)

Step-1: Preparation of 2-chloro-6-(pyrrolidin-1-ylmethyl)-N-(1-(3,4,5-trimethoxyphenyl)-1H-imidazol-4-yl)thieno[2,3-d]pyrimidin-4-amine (384a)

Compound 384a was prepared from 2-chloro-6-(chloromethyl)-N-(1-(3,4,5-trimethoxyphenyl)-1H-imidazol-4-yl)thieno[2,3-d]pyrimidin-4-amine (97b) (500 mg, 1.07 mmol), DIPEA (410 mg, 3.21 mmol) and pyrrolidine (380 mg, 5.34 mmol) in DCM (15 mL) according to the procedure reported in step-3 of Scheme 97. This gave after workup and purification by flash column chromatography (silica gel, eluting with methanol in DCM 0-2%) 2-chloro-6-(pyrrolidin-1-ylmethyl)-N-(1-(3,4,5-trimethoxyphenyl)-1H-imidazol-4-yl)thieno[2,3-d]pyrimidin-4-amine (384a) (230 mgs, 43%) as a brown solid; $^1$H NMR (300 MHz, DMSO-$d_6$) δ 10.87 (2s, 1H), 8.18 (s, 1H), 7.88 (s, 2H), 6.93 (s, 2H), 3.88 (s, 6H), 3.70 (s, 3H), 2.61-2.53 (m, 2H), 1.79-1.55 (m, 4H), 1.34-1.15 (m, 4H); MS (ES+): 502.3 (M+1).

Step-2: Preparation of (S)-(1-(6-(pyrrolidin-1-ylmethyl)-4-((1-(3,4,5-trimethoxyphenyl)-1H-imidazol-4-yl)amino)thieno[2,3-d]pyrimidin-2-yl)pyrrolidin-2-yl)methanol (384b)

Compound 384b was prepared from 2-chloro-6-(pyrrolidin-1-ylmethyl)-N-(1-(3,4,5-trimethoxyphenyl)-1H-imidazol-4-yl)thieno[2,3-d]pyrimidin-4-amine (384a) (250 mg, 0.49 mmol), (S)-pyrrolidin-2-ylmethanol (490 mg, 4.85 mmol) in NMP (10 mL) according to the procedure reported in step-2 of Scheme 76. This gave after workup and purification by flash chromatography [silica gel, eluting with methanol in $CH_2Cl_2$ from 0 to 8%] (S)-(1-(6-(pyrrolidin-1-ylmethyl)-4-((1-(3,4,5-trimethoxyphenyl)-1H-imidazol-4-yl)amino)thieno[2,3-d]pyrimidin-2-yl)pyrrolidin-2-yl)methanol (384b) (140 mg, 50% yield) as a yellow solid; $^1$H NMR (300 MHz, DMSO-$d_6$) δ 10.09 (s, 1H), 8.21 (s, 1H), 7.98 (s, 1H), 7.69 (s, 1H), 6.95 (s, 2H), 5.01-4.76 (m, 1H), 4.48-4.00 (m, 5H), 3.88 (s, 6H), 3.68 (s, 3H), 2.83-2.55 (m, 6H), 1.97 (m, 4H), 1.76 (m, 4H); MS (ES+): 566.5 (M+1); 588.4 (M+Na); MS (ES−): 600.4 (M+Cl).

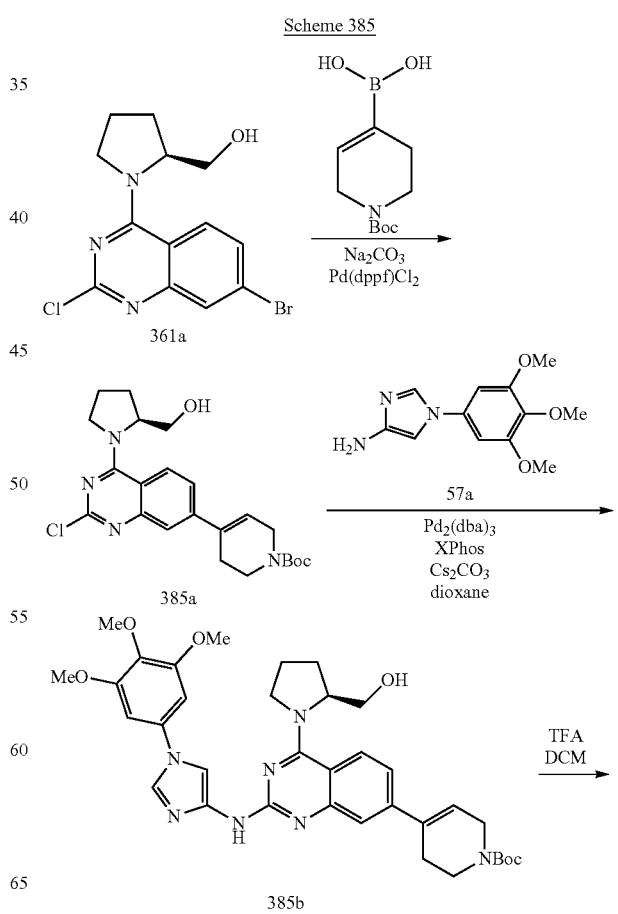

Scheme 385

619

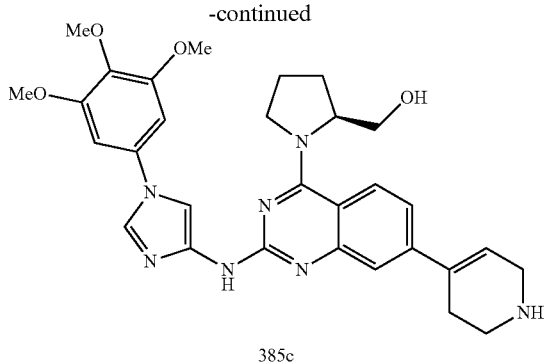

385c

Preparation of (S)-(1-(7-(1,2,3,6-tetrahydropyridin-4-yl)-2-((1-(3,4,5-trimethoxyphenyl)-1H-imidazol-4-yl)amino)quinazolin-4-yl)pyrrolidin-2-yl)methanol (385c)

Step-1: Preparation of (S)-tert-butyl 4-(2-chloro-4-(2-(hydroxymethyl)pyrrolidin-1-yl)quinazolin-7-yl)-5,6-dihydropyridine-1(2H)-carboxylate (385a)

Compound 385a was prepared from (S)-(1-(7-bromo-2-chloroquinazolin-4-yl)pyrrolidin-2-yl)methanol (361a) (500 mg, 1.46 mmol), using (1-(tert-butoxycarbonyl)-1,2,3,6-tetrahydropyridin-4-yl)boronic acid (331 mg, 1.46 mmol), Bis(triphenylphosphine)palladium(II) dichloride (51 mg, 0.073 mmol) and sodium carbonate (309 mg, 2.92 mmol) in toluene (15 mL), EtOH (7 mL) and water (3 mL) according to the procedure reported in step-3 of Scheme 77. This gave after workup and purification by flash column chromatography (S)-tert-butyl 4-(2-chloro-4-(2-(hydroxymethyl)pyrrolidin-1-yl)quinazolin-7-yl)-5,6-dihydropyridine-1(2H)-carboxylate (385a) (520 mg, 80% yield) as a white solid; $^1$H NMR (300 MHz, DMSO-$d_6$) δ 8.40-8.06 (m, 1H), 7.90-7.28 (m, 3H), 6.49 (s, 1H), 4.87 (s, 1H), 4.57 (s, 1H), 4.25-3.85 (m, 3H), 3.81-3.48 (m, 4H), 2.18-1.93 (m, 4H), 1.96-1.71 (m, 2H), 1.63-1.18 (m, 9H); MS (ES+): 445.4 (M+1), 467.3 (M+Na).

Step-2: Preparation of (S)-tert-butyl 4-(4-(2-(hydroxymethyl)pyrrolidin-1-yl)-2-((1-(3,4,5-trimethoxyphenyl)-1H-imidazol-4-yl)amino)quinazolin-7-yl)-5,6-dihydropyridine-1(2H)-carboxylate (385b)

Compound 385b was prepared from (S)-tert-butyl 4-(2-chloro-4-(2-(hydroxymethyl)pyrrolidin-1-yl)quinazolin-7-yl)-5,6-dihydropyridine-1(2H)-carboxylate (385a) (512 mg, 1.15 mmol), 1-(3,4,5-trimethoxyphenyl)-1H-imidazol-4-amine (57a) (358 mg, 1.44 mmol), dicyclohexyl(2',4',6'-triisopropylbiphenyl-2-yl)phosphine (XPhos, 247 mg, 0.52 mmol), cesium carbonate (1124 mg, 3.45 mmol), Pd$_2$(dba)$_3$ (158 mg, 0.17 mmol) in dioxane (15 mL) according to the procedure reported in step-3 of Scheme 101. This gave after workup and purification by flash column chromatography [silica gel, (40 g) eluting with DMA-80 in CH$_2$Cl$_2$ from 0 to 50%], reverse phase flash column chromatography [(silica gel C-18, 24 g) eluting with acetonitrile and 0.1% HCl in water] (S)-tert-butyl 4-(4-(2-(hydroxymethyl)pyrrolidin-1-yl)-2-((1-(3,4,5-trimethoxyphenyl)-1H-imidazol-4-yl)amino)quinazolin-7-yl)-5,6-dihydropyridine-1(2H)-carboxylate (385b) (400 mg, 53% yield) as a light yellow solid which was used as such for next step.

Step-3: Preparation of (S)-(1-(7-(1,2,3,6-tetrahydropyridin-4-yl)-2-((1-(3,4,5-trimethoxyphenyl)-1H-imidazol-4-yl)amino)quinazolin-4-yl)pyrrolidin-2-yl)methanol (385c)

Compound 385c was prepared by hydrolysis of (S)-tert-butyl 4-(4-(2-(hydroxymethyl)pyrrolidin-1-yl)-2-((1-(3,4,5-trimethoxyphenyl)-1H-imidazol-4-yl)amino)quinazolin-7-yl)-5,6-dihydropyridine-1(2H)-carboxylate (385b) (300 mg, 0.46 mmol) in DCM (10 mL) using trifluoroacetic acid (0.35 mL, 4.56 mmol) according to the procedure reported in Scheme 122. This gave after workup and purification by reverse phase column chromatography [(silica gel C-18, 24 g), eluting with acetonitrile in water (containing 0.1% HCl) from 0-100%] (S)-(1-(7-(1,2,3,6-tetrahydropyridin-4-yl)-2-((1-(3,4,5-trimethoxyphenyl)-1H-imidazol-4-yl)amino)quinazolin-4-yl)pyrrolidin-2-yl)methanol (385c) (108 mg, 43% yield) HCl salt as a yellow solid; $^1$H NMR (300 MHz, DMSO-$d_6$) δ 13.50-12.56 (m, 1H, D$_2$O exchangeable), 10.86-10.36 (m, 1H, D$_2$O exchangeable), 9.33 (s, 2H, D2O exchangeable), 8.39-8.22 (m, 2H), 7.71 (s, 1H), 7.64-7.41 (m, 2H), 6.98 (s, 2H), 6.52 (s, 1H), 5.49-5.02 (m, 1H, D$_2$O exchangeable), 5.02-4.59 (m, 1H), 4.33-4.01 (m, 2H), 3.88 (s, 6H), 3.89-3.72 (m, 2H), 3.68 (s, 3H), 3.55-3.27 (m, 4H), 2.74 (m, 2H), 2.06 (m, 4H); MS (ES+): 558.4 (M+1), (ES−): 592.4 (M+Cl); HPLC purity: 96.31%.

Scheme 386

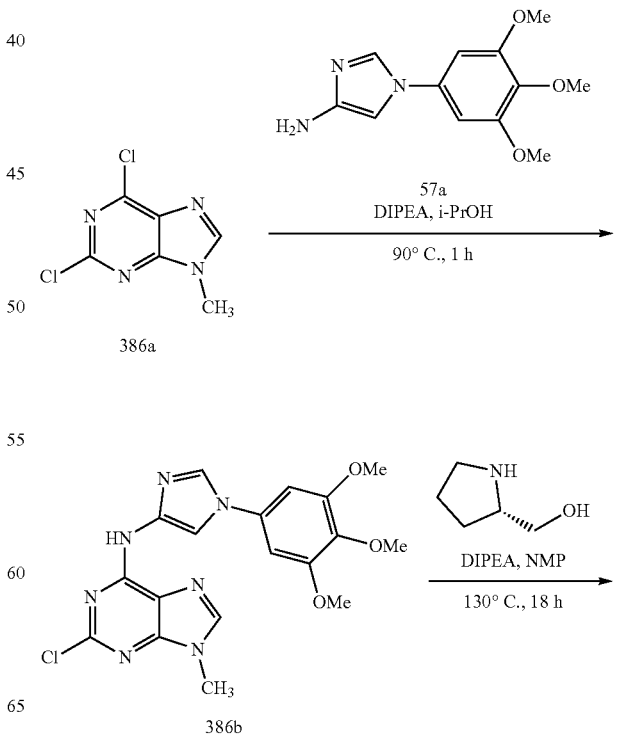

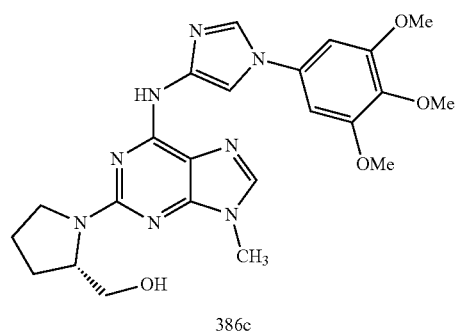

386c

Preparation of (S)-(1-(9-methyl-6-((1-(3,4,5-trimethoxyphenyl)-1H-imidazol-4-yl)amino)-9H-purin-2-yl)pyrrolidin-2-yl)methanol (386c)

Step-1: Preparation of 2-chloro-9-methyl-N-(1-(3,4,5-trimethoxyphenyl)-1H-imidazol-4-yl)-9H-purin-6-amine (386b)

Compound 386b was prepared from 2,6-dichloro-9-methyl-9H-purine (386a) (500 mg, 2.46 mmol; CAS #2382-10-7) in 2-Propanol (15 mL) using DIPEA (1.29 mL, 7.39 mmol) and 1-(3,4,5-trimethoxyphenyl)-1H-imidazol-4-amine (57a) (0.61 g, 2.46 mmol) according to the procedure reported in step-1 of scheme 183. This gave after filtration 2-chloro-9-methyl-N-(1-(3,4,5-trimethoxyphenyl)-1H-imidazol-4-yl)-9H-purin-6-amine (386b) (0.67 g, 65% yield) as a yellow solid; $^1$H NMR (300 MHz, DMSO-$d_6$): δ 10.57 (s, 1H), 8.26 (s, 1H), 8.18 (d, J=1.6 Hz, 1H), 7.86 (d, J=1.6 Hz, 1H), 6.93 (s, 2H), 3.88 (s, 6H), 3.75 (s, 3H), 3.69 (s, 3H); MS (ES+): 438.3, 440.2 (M+Na).

Step-2: Preparation of (S)-(1-(9-methyl-6-((1-(3,4,5-trimethoxyphenyl)-1H-imidazol-4-yl)amino)-9H-purin-2-yl)pyrrolidin-2-yl)methanol (386c)

Compound 386c was prepared from 2-chloro-9-methyl-N-(1-(3,4,5-trimethoxyphenyl)-1H-imidazol-4-yl)-9H-purin-6-amine (386b) (0.2 g, 0.48 mmol), (S)-pyrrolidin-2-ylmethanol (0.19 mL, 1.92 mmol), N-ethyl-N-isopropylpropan-2-amine (0.5 mL, 2.89 mmol) in NMP (3 mL) and heating at 130° C. for 18 h according to the procedure reported in scheme 2. This gave after workup and purification by flash column chromatography [silica gel (12 g), eluting with DMA 80 in CH$_2$Cl$_2$ from 0 to 50%], followed by purification using reverse phase flash column chromatography [(silica gel C-18, 24 g), eluting with acetonitrile and 0.1% HCl water] and lyophilization (S)-(1-(9-methyl-6-((1-(3,4,5-trimethoxyphenyl)-1H-imidazol-4-yl)amino)-9H-purin-2-yl)pyrrolidin-2-yl)methanol (386c) (0.13 g, 57% yield) as a white HCl salt; $^1$H NMR (300 MHz, DMSO-$d_6$): δ 10.98 (s, 1H), 9.09 (s, 1H), 8.72-8.59 (m, 1H), 8.00 (s, 1H), 7.01 (s, 2H), 4.43-4.22 (m, 1H), 4.22-4.02 (m, 1H), 3.88 (s, 6H), 3.78 (s, 3H), 3.75-3.71 (m, 1H), 3.68 (s, 4H), 3.65-3.25 (m, 1H), 2.20-1.71 (m, 4H). MS (ES+): 481.4 (M+1), 503.4 (M+Na). HPLC purity: 98.88%.

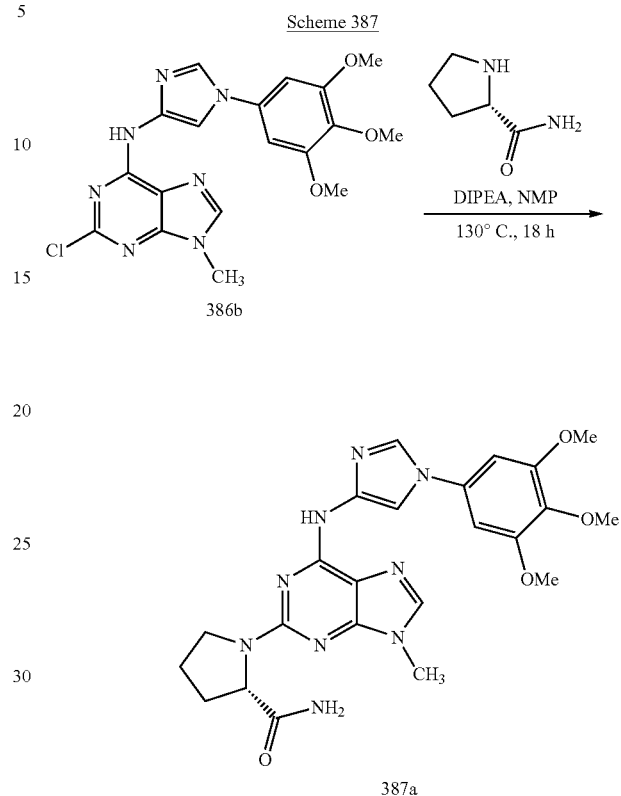

Scheme 387

386b

387a

Preparation of (S)-1-(9-methyl-6-((1-(3,4,5-trimethoxyphenyl)-1H-imidazol-4-yl)amino)-9H-purin-2-yl)pyrrolidine-2-carboxamide (387a)

Compound 387a was prepared from 2-chloro-9-methyl-N-(1-(3,4,5-trimethoxyphenyl)-1H-imidazol-4-yl)-9H-purin-6-amine (386b) (0.2 g, 0.48 mmol), (S)-pyrrolidine-2-carboxamide (0.22 g, 1.924 mmol), N-ethyl-N-isopropylpropan-2-amine (0.5 mL, 2.89 mmol) in NMP (3 mL) and heating at 130° C. for 18 h according to the procedure reported in scheme 2. This gave after workup and purification by flash column chromatography [silica gel (12 g), eluting with DMA 80 in CH$_2$Cl$_2$ from 0 to 50%], followed by purification using reverse phase flash column chromatography [(silica gel C-18, 24 g), eluting with acetonitrile and 0.1% HCl water] and lyophilization (S)-1-(9-methyl-6-((1-(3,4,5-trimethoxyphenyl)-1H-imidazol-4-yl)amino)-9H-purin-2-yl)pyrrolidine-2-carboxamide (387a) (0.13 g, 56% yield) HCl salt as a white solid; $^1$H NMR (300 MHz, DMSO-$d_6$): (a mixture of two rotamers) δ 11.12 and 10.94 (2s, 1H), 9.14 (s, 1H), 8.77 (s, 1H), 8.10 and 7.98 (2s, 1H), 7.26 (s, 1H), 7.50 (m, 2H), 7.20 (s, 1H), 7.11-6.88 (m, 2H), 4.46 (d, J=8.6 Hz, 1H), 3.93 and 3.88 (2s, 6H), 3.85 (m 1H), 3.81 and 3.75 (2s, 3H), 3.69 (s, 3H), 3.65-3.50 (m, 1H), 2.35-1.81 (m, 4H). MS (ES+): 494.4 (M+1); MS (ES−): 528.4 (M+Cl). HPLC purity: 99.17%.

623

Scheme 388

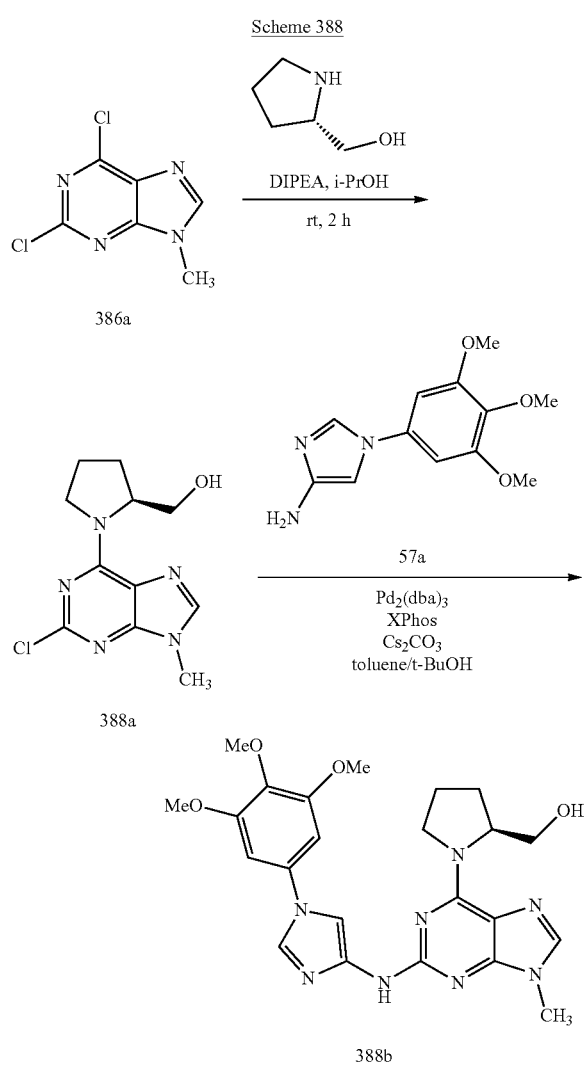

Preparation of (S)-(1-(9-methyl-2-((1-(3,4,5-trimethoxyphenyl)-1H-imidazol-4-yl)amino)-9H-purin-6-yl)pyrrolidin-2-yl)methanol (388b)

Step-1: Preparation of (S)-(1-(2-chloro-9-methyl-9H-purin-6-yl)pyrrolidin-2-yl)methanol (388a)

Compound 388a was prepared from 2,6-dichloro-9-methyl-9H-purine (386a) (400 mg, 1.97 mmol) in 2-Propanol (10 mL) using (S)-pyrrolidin-2-ylmethanol (0.2 mL, 2.0 mmol), DIPEA (1.03 mL, 5.91 mmol) and stirring at room temperature for 2 h according to the procedure reported in step-1 of scheme 96. This gave after workup and purification by flash column chromatography [silica gel (12 g), eluting with eluting with DCM and methanol (0 to 30%)](S)-(1-(2-chloro-9-methyl-9H-purin-6-yl)pyrrolidin-2-yl)methanol (388a) (0.40 g, 76% yield) as a white solid; $^1$H NMR (300 MHz, DMSO-$d_6$): δ 8.11 (d, J=8.8 Hz, 1H), 4.98-4.88 (m, 1H), 4.88-4.76 (m, 1H), 4.36-4.24 (m, 1H), 4.14-3.95 (m, 1H), 3.68 (s, 3H), 3.66-3.58 (m, 1H), 3.52-3.40 (m, 1H), 2.29-1.77 (m, 4H); MS (ES+): 268.2, 270.2 (M+1); MS (ES−): 302.2, 304.2 (M+Cl).

624

Step-2: Preparation of (S)-(1-(9-methyl-2-((1-(3,4,5-trimethoxyphenyl)-1H-imidazol-4-yl)amino)-9H-purin-6-yl)pyrrolidin-2-yl)methanol (388b)

Compound 388b was prepared from (S)-(1-(2-chloro-9-methyl-9H-purin-6-yl)pyrrolidin-2-yl)methanol (388a) (0.25 g, 0.93 mmol), 1-(3,4,5-trimethoxyphenyl)-1H-imidazol-4-amine (57a) (0.23 g, 0.93 mmol), dicyclohexyl(2',4',6'-triisopropylbiphenyl-2-yl)phosphine (XPhos, 0.27 g, 0.56 mmol), cesium carbonate (0.91 g, 2.80 mmol), Pd$_2$(dba)$_3$ (0.26 g, 0.28 mmol) in t-BuOH/toluene (15 mL, 2:1) and heating at 110° C. for 20 h according to the procedure reported in step-3 of scheme 101. This gave after workup and purification by flash column chromatography [silica gel (24 g), eluting with DMA-80 in DCM from 0-50%] followed by purification by reverse phase column chromatography [(silica gel C-18, 24 g) eluting with acetonitrile and 0.1% HCl water] and lyophilization (S)-(1-(9-methyl-2-((1-(3,4,5-trimethoxyphenyl)-1H-imidazol-4-yl)amino)-9H-purin-6-yl)pyrrolidin-2-yl)methanol (388b) (0.13 g, 29% yield) HCl salt as a white solid; $^1$H NMR (300 MHz, DMSO-$d_6$): δ 10.44 (s, 1H), 10.20 (s, 1H), 9.20-8.89 (m, 1H), 8.28-8.11 (m, 1H), 7.98-7.86 (m, 1H), 7.10 (s, 2H), 5.18-4.85 (m, 1H), 4.62-4.43 (m, 1H), 4.14 (d, J=9.1 Hz, 1H), 3.89 (m, 7H), 3.73 (s, 3H), 3.70 (s, 3H), 3.68-3.59 (m, 1H), 3.53 (d, J=8.5 Hz, 1H), 2.22-1.85 (m, 4H). MS (ES+): 481.5 (M+1), 503.4 (M+Na); MS (ES−): 515.4 (M+Cl). HPLC purity: 98.32%.

Scheme 389

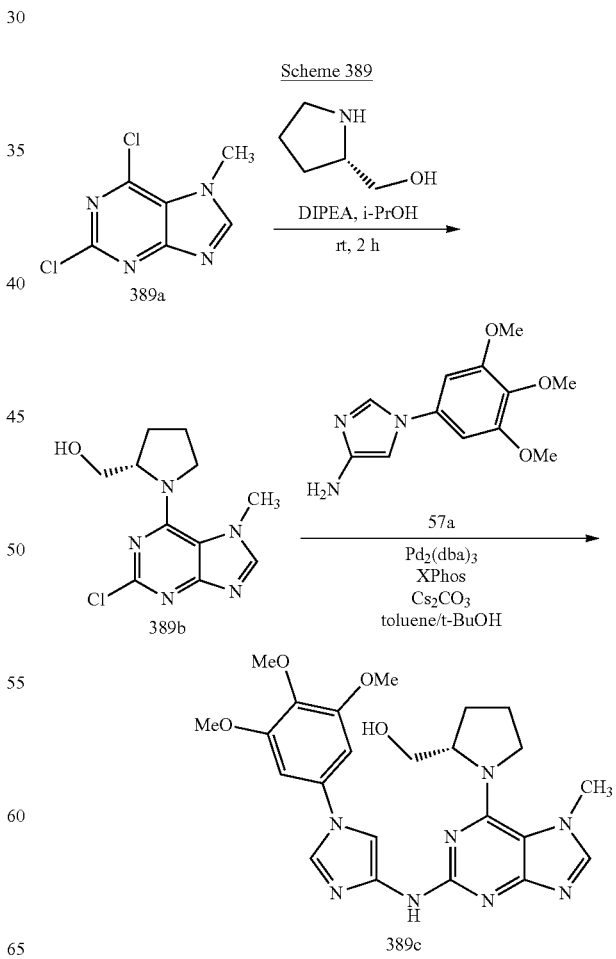

Preparation of (S)-(1-(7-methyl-2-((1-(3,4,5-trimethoxyphenyl)-1H-imidazol-4-yl)amino)-7H-purin-6-yl)pyrrolidin-2-yl)methanol (389c)

Step-1: Preparation of (S)-(1-(2-chloro-7-methyl-7H-purin-6-yl)pyrrolidin-2-yl)methanol (389b)

Compound 389b was prepared from 2,6-dichloro-7-methyl-7H-purine (389a) (400 mg, 1.97 mmol; CAS #: 2273-93-0) in 2-Propanol (10 mL) using (S)-pyrrolidin-2-ylmethanol (0.19 mL, 1.97 mmol), DIPEA (1.03 mL, 5.91 mmol) and stirring at room temperature for 2 h according to the procedure reported in step-1 of scheme 96. This gave after workup and purification by flash column chromatography [silica gel (12 g), eluting with eluting with DCM and methanol (0 to 30%)] (S)-(1-(2-chloro-7-methyl-7H-purin-6-yl)pyrrolidin-2-yl)methanol (389b) (0.41 g, 77% yield) as a white solid; $^1$H NMR (300 MHz, DMSO-$d_6$): δ 8.30 (s, 1H), 4.71 (dd, J=6.7, 5.3 Hz, 1H), 4.48 (m, 1H), 3.97 (s, 3H), 3.73 (dd, J=8.8, 5.5 Hz, 2H), 3.67-3.47 (m, 2H), 2.10-1.67 (m, 4H); MS (ES+): 268.2, 270.2 (M+1); MS (ES−): 302.2, 304.2 (M+Cl).

Step-2: Preparation of (S)-(1-(7-methyl-2-((1-(3,4,5-trimethoxyphenyl)-1H-imidazol-4-yl)amino)-7H-purin-6-yl)pyrrolidin-2-yl)methanol (389c)

Compound 389c was prepared from (S)-(1-(2-chloro-7-methyl-7H-purin-6-yl)pyrrolidin-2-yl)methanol (389b) (0.25 g, 0.93 mmol), 1-(3,4,5-trimethoxyphenyl)-1H-imidazol-4-amine (57a) (0.23 g, 0.93 mmol), dicyclohexyl(2',4',6'-triisopropylbiphenyl-2-yl)phosphine (XPhos, 0.13 g, 0.28 mmol), cesium carbonate (0.91 g, 2.80 mmol), Pd$_2$(dba)$_3$ (0.13 g, 0.14 mmol) in t-BuOH/toluene (15 mL, 2:1) and heating at 110° C. for 15 min according to the procedure reported in step-3 of scheme 101. This gave after workup and purification by flash column chromatography [silica gel (24 g), eluting with DMA-80 in DCM from 0-50%] followed by purification by reverse phase column chromatography [(silica gel C-18, 24 g) eluting with acetonitrile and 0.1% HCl water] and lyophilization (S)-(1-(7-methyl-2-((1-(3,4,5-trimethoxyphenyl)-1H-imidazol-4-yl)amino)-7H-purin-6-yl)pyrrolidin-2-yl)methanol (389c) (0.10 g, 21% yield) HCl salt as a white solid; $^1$H NMR (300 MHz, DMSO-$d_6$): δ 10.43 (s, 1H), 9.17 (s, 1H), 8.90 (s, 1H), 7.98 (s, 1H), 7.11 (d, J=2.2 Hz, 2H), 4.81-4.57 (m, 1H), 4.08 (s, 3H), 3.89 (m, 7H), 3.85-3.78 (m, 1H), 3.69 (s, 3H), 3.66-3.55 (m, 2H), 2.18-1.71 (m, 4H). MS (ES+): 481.4 (M+1), 503.3 (M+Na); MS (ES−): 515.4 (M+Cl). HPLC purity: 97.84%.

Scheme 390

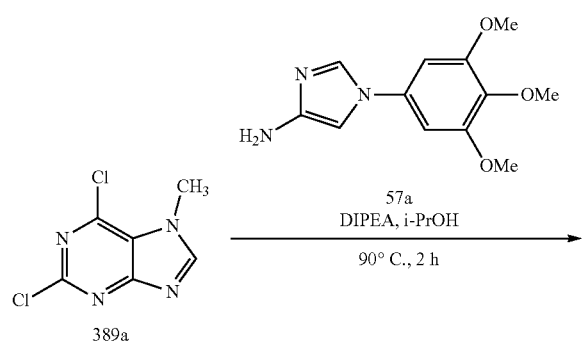

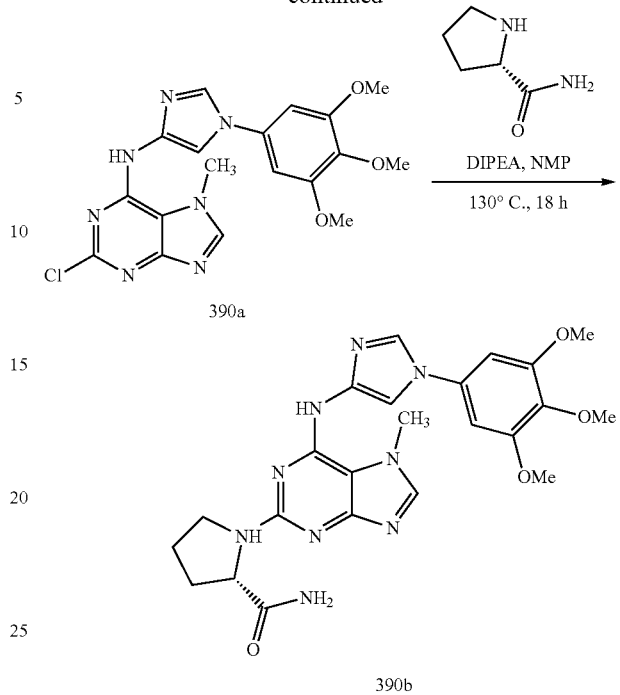

Preparation of (S)-1-(7-methyl-6-((1-(3,4,5-trimethoxyphenyl)-1H-imidazol-4-yl)amino)-7H-purin-2-yl)pyrrolidine-2-carboxamide (390b)

Step-1: Preparation of 2-chloro-7-methyl-N-(1-(3,4,5-trimethoxyphenyl)-1H-imidazol-4-yl)-7H-purin-6-amine (390a)

Compound 390a was prepared from 2,6-dichloro-7-methyl-7H-purine (389a) (500 mg, 2.46 mmol; CAS #2382-10-7) in 2-Propanol (15 mL) using DIPEA (1.29 mL, 7.39 mmol), 1-(3,4,5-trimethoxyphenyl)-1H-imidazol-4-amine (57a) (0.61 g, 2.46 mmol) and heating at 90° C. for 2 h according to the procedure reported in step-1 of scheme 183. This gave after filtration 2-chloro-7-methyl-N-(1-(3,4,5-trimethoxyphenyl)-1H-imidazol-4-yl)-7H-purin-6-amine (390a) (0.50 g, 49% yield) as a yellow solid; $^1$H NMR (300 MHz, DMSO-$d_6$): δ 9.44 (s, 1H), 8.34 (s, 1H), 8.22 (d, J=1.6 Hz, 1H), 7.88 (d, J=1.6 Hz, 1H), 6.93 (s, 2H), 4.15 (s, 3H), 3.87 (s, 6H), 3.69 (s, 3H); MS (ES+): 416.3, 418.2 (M+1); MS (ES−): 414.3 (M−1), 450.3, 452.3 (M+Cl).

Step-2: Preparation of (S)-1-(7-methyl-6-((1-(3,4,5-trimethoxyphenyl)-1H-imidazol-4-yl)amino)-7H-purin-2-yl)pyrrolidine-2-carboxamide (390b)

Compound 390b was prepared from 2-chloro-7-methyl-N-(1-(3,4,5-trimethoxyphenyl)-1H-imidazol-4-yl)-7H-purin-6-amine (390a) (0.2 g, 0.48 mmol), (S)-pyrrolidine-2-carboxamide (0.22 g, 1.92 mmol), N-ethyl-N-isopropylpropan-2-amine (0.5 mL, 2.89 mmol) in NMP (3 mL) and heating at 130° C. for 18 h according to the procedure reported in scheme 2. This gave after workup and purification by flash column chromatography [silica gel (12 g), eluting with DMA 80 in CH$_2$Cl$_2$ from 0 to 50%], followed by purification using reverse phase flash column chromatography [(silica gel C-18, 24 g) eluting with acetonitrile and 0.1% HCl water] and lyophilization (S)-1-(7-methyl-6-((1-(3,4,5-trimethoxyphenyl)-1H-imidazol-4-yl)amino)-7H-purin-2-yl)pyrrolidine-2-carboxamide (390b) (0.02 g, 9% yield) HCl salt as a brown solid; $^1$H NMR (300 MHz, DMSO-$d_6$): (a mixture of two rotamers): δ 10.01 (s, 1H), 8.82 and 8.74 (2s, 1H), 8.42 (s, 1H), 8.03 (s, 1H), 7.98 (s, 1H), 7.65 (s, 1H), 7.46 (s, 1H), 7.32 and 7.20 (2s, 1H), 7.13 and 7.05 (2s, 1H), 4.58 (d, J=9.0 Hz, 1H), 4.26 (s, 3H), 3.91 (s, 6H), 3.69 (s, 3H), 3.61-3.32 (m, 1H), 3.28-3.00 (m, 1H), 2.34-1.71 (m, 4H). MS (ES+): 494.4 (M+1), 516.3 (M+Na); MS (ES-): 492.3 (M-1), 528.4 (M+Cl). HPLC purity: 94.48%.

(57a) (0.15 g, 0.59 mmol) and heating at 90° C. for 1 h according to the procedure reported in step-1 of scheme 183. This gave after filtration 2-chloro-7-methyl-N-(1-(3,4,5-trimethoxyphenyl)-1H-imidazol-4-yl)quinazolin-4-amine (391b) (0.18 g, 72% yield) as a white solid; $^1$H NMR (300 MHz, DMSO-$d_6$): δ 11.01 (s, 1H), 8.63 (d, J=8.5 Hz, 1H), 8.23 (d, J=1.6 Hz, 1H), 7.99 (d, J=1.6 Hz, 1H), 7.52 (d, J=1.8 Hz, 1H), 7.44 (dd, J=8.5, 1.7 Hz, 1H), 6.94 (s, 2H), 3.88 (s, 6H), 3.70 (s, 3H), 2.49 (s, 3H). MS (ES+): 426.3 (M+1), 448.3 & 450.2 (M+Na); MS (ES-): 424.3 & 426.3 (M-1).

Step-2: Preparation of (S)-(1-(7-methyl-4-((1-(3,4,5-trimethoxyphenyl)-1H-imidazol-4-yl)amino)quinazolin-2-yl)pyrrolidin-2-yl)methanol (391c)

Compound 391c was prepared from 2-chloro-7-methyl-N-(1-(3,4,5-trimethoxyphenyl)-1H-imidazol-4-yl)quinazolin-4-amine (391b) (0.09 g, 0.21 mmol), (S)-pyrrolidin-2-ylmethanol (0.08 mL, 0.85 mmol), N-ethyl-N-isopropylpropan-2-amine (0.22 mL, 1.27 mmol) in NMP (3 mL) and heating at 130° C. for 18 h according to the procedure reported in scheme 2. This gave after workup and purification by flash column chromatography [silica gel (12 g), eluting with DMA 80 in CH$_2$Cl$_2$ from 0 to 50%], followed by purification using reverse phase flash column chromatography [(silica gel C-18, 24 g), eluting with acetonitrile and 0.1% HCl water] and lyophilization (S)-(1-(7-methyl-4-((1-(3,4,5-trimethoxyphenyl)-1H-imidazol-4-yl)amino)quinazolin-2-yl)pyrrolidin-2-yl)methanol (391c) (0.08 g, 78% yield) HCl salt as a white solid; $^1$H NMR (300 MHz, DMSO-$d_6$): (a mixture of two rotamers) δ 12.36 and 12.30 (2s, 1H), 11.69 and 11.59 (2s, 1H), 8.65-8.55 (m, 1H), 8.52 (m, 1H), 8.04 (s, 1H), 7.94-7.88 (m, 1H), 7.32-7.21 (m, 1H), 7.01 and 6.94 (2s, 2H), 6.02 (bs, 2H), 4.70-4.47 (m, 1H), 3.88 (m, 8H), 3.68 (m, 4H), 3.63-3.45 (m, 1H), 2.42 (s, 3H), 2.27-1.84 (m, 4H). MS (ES+): 491.5 (M+1); MS (ES-): 489.4 (M-1), 525.5 (M+Cl). HPLC purity: 99.54%.

Scheme 391

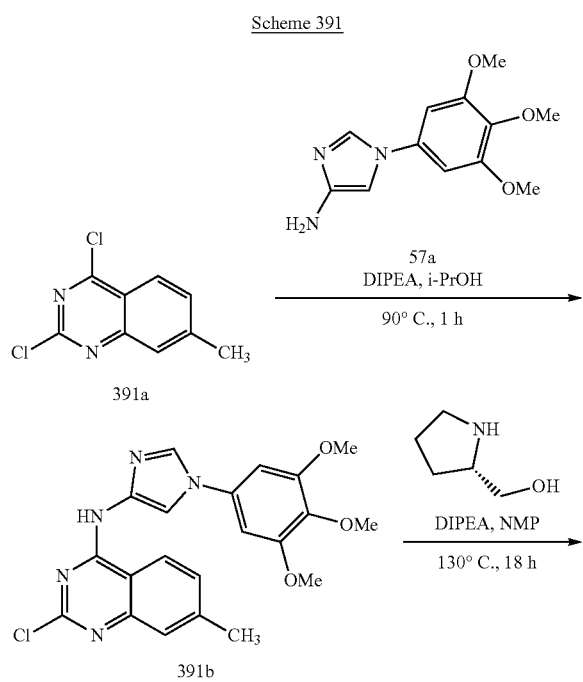

391a, 57a, 391b, 391c

Preparation of (S)-(1-(7-methyl-4-((1-(3,4,5-trimethoxyphenyl)-1H-imidazol-4-yl)amino)quinazolin-2-yl)pyrrolidin-2-yl)methanol (391c)

Step-1: Preparation of 2-chloro-7-methyl-N-(1-(3,4,5-trimethoxyphenyl)-1H-imidazol-4-yl)quinazolin-4-amine (391b)

Compound 391b was prepared from 2,4-dichloro-7-methylquinazoline (391a) (0.13 g, 0.59 mmol; CAS #25171-19-1) in 2-Propanol (10 mL) using DIPEA (0.31 mL, 1.76 mmol), 1-(3,4,5-trimethoxyphenyl)-1H-imidazol-4-amine Scheme 392

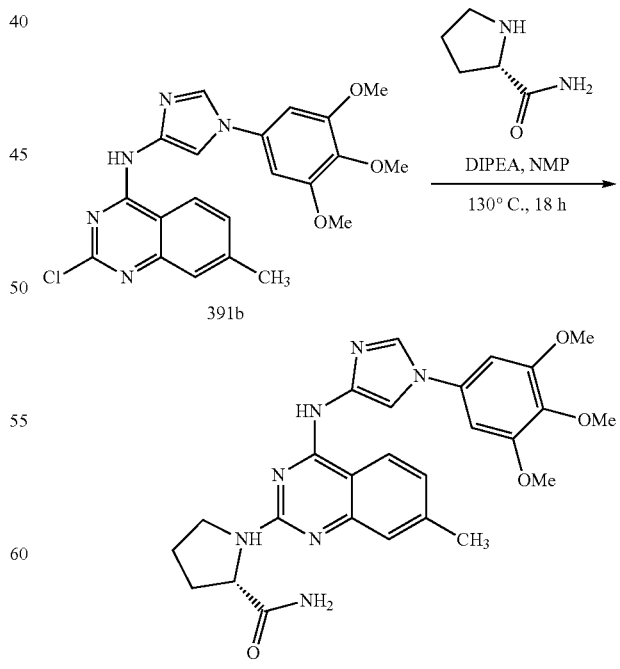

391b, 392a

Preparation of (S)-1-(7-methyl-4-((1-(3,4,5-trimethoxyphenyl)-1H-imidazol-4-yl)amino)quinazolin-2-yl)pyrrolidine-2-carboxamide (392a)

Compound 392a was prepared from 2-chloro-7-methyl-N-(1-(3,4,5-trimethoxyphenyl)-1H-imidazol-4-yl)quinazolin-4-amine (391b) (0.09 g, 0.21 mmol), (S)-pyrrolidine-2-carboxamide (0.10 g, 0.85 mmol), N-ethyl-N-isopropylpropan-2-amine (0.22 mL, 1.27 mmol) in NMP (3 mL) and heating at 130° C. for 18 h according to the procedure reported in scheme 2. This gave after workup and purification by flash column chromatography [silica gel (12 g), eluting with DMA 80 in CH$_2$Cl$_2$ from 0 to 50%], followed by purification using reverse phase flash column chromatography [(silica gel C-18, 24 g), eluting with acetonitrile and 0.1% HCl water] and lyophilization (S)-1-(7-methyl-4-((1-(3,4,5-trimethoxyphenyl)-1H-imidazol-4-yl)amino)quinazolin-2-yl)pyrrolidine-2-carboxamide (392a) (0.04 g, 37% yield) HCl salt as a white solid; $^1$H NMR (300 MHz, DMSO-d$_6$): δ 12.35 (s, 1H), 11.59 (s, 1H), 8.65 (d, J=8.4 Hz, 1H), 8.45 (s, 1H), 7.93 (s, 1H), 7.90 (s, 1H), 7.63 (s, 1H), 7.36-7.29 (m, 1H), 7.27 (s, 1H), 7.15 (s, 2H), 4.72 (d, J=8.3 Hz, 1H), 4.15-3.99 (m, 1H), 3.94 (s, 6H), 3.78-3.72 (m, 1H), 3.69 (s, 3H), 2.48 (s, 3H), 2.38-1.92 (m, 4H). MS (ES+): 504.4 (M+1); MS (ES−): 538.4 (M+Cl). HPLC purity: 89.25%.

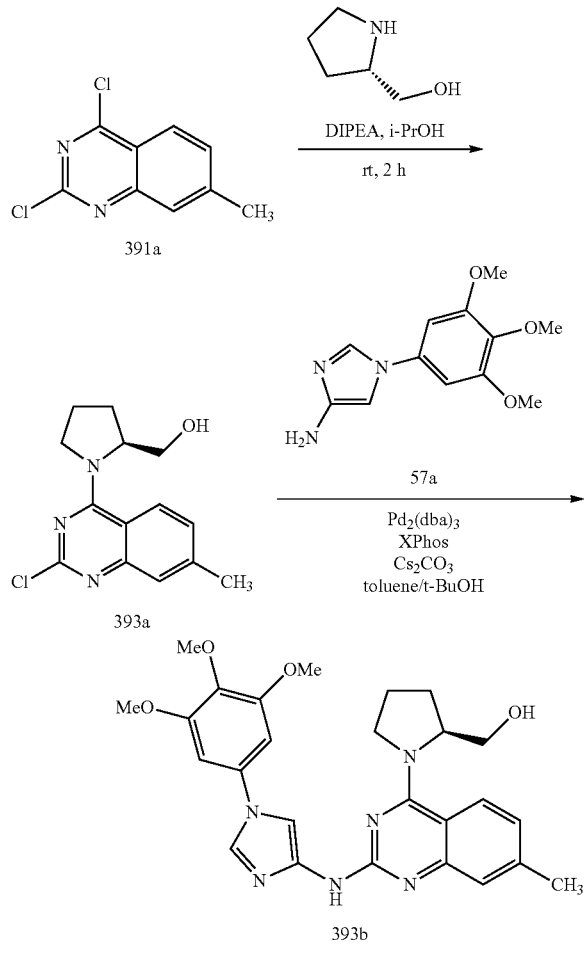

Scheme 393

Preparation of (S)-(1-(7-methyl-2-((1-(3,4,5-trimethoxyphenyl)-1H-imidazol-4-yl)amino)quinazolin-4-yl)pyrrolidin-2-yl)methanol (393b)

Step-1: Preparation of (S)-(1-(2-chloro-7-methylquinazolin-4-yl)pyrrolidin-2-yl)methanol (393a)

Compound 393a was prepared from 2,4-dichloro-7-methylquinazoline (391a) (0.13 g, 0.59 mmol) in 2-Propanol (10 mL) using (S)-pyrrolidin-2-ylmethanol (0.06 mL, 0.59 mmol), DIPEA (0.31 mL, 1.76 mmol) and stirring at room temperature for 2 h according to the procedure reported in step-1 of scheme 96. This gave after workup and purification by flash column chromatography [silica gel (12 g), eluting with eluting with DCM and methanol (0 to 30%)] (S)-(1-(2-chloro-7-methylquinazolin-4-yl)pyrrolidin-2-yl)methanol (393a) (0.08 g, 50% yield) as a white solid; $^1$H NMR (300 MHz, DMSO-d$_6$): δ 8.16 (d, J=8.7 Hz, 1H), 7.42 (d, J=1.5 Hz, 1H), 7.30 (dd, J=8.7, 1.9 Hz, 1H), 4.84 (t, J=5.7 Hz, 1H), 4.64-4.46 (m, 1H), 4.01 (t, J=8.8 Hz, 1H), 3.96-3.84 (m, 1H), 3.71-3.55 (m, 2H), 2.45 (s, 3H), 2.17-1.71 (m, 4H). MS (ES+): 278.2 & 280.2 (M+1); MS (ES−): 312.4 & 314.4 (M+Cl).

Step-2: Preparation of (S)-(1-(7-methyl-2-((1-(3,4,5-trimethoxyphenyl)-1H-imidazol-4-yl)amino)quinazolin-4-yl)pyrrolidin-2-yl)methanol (393b)

Compound 393b was prepared from (S)-(1-(2-chloro-7-methylquinazolin-4-yl)pyrrolidin-2-yl)methanol (393a) (0.08 g, 0.29 mmol), 1-(3,4,5-trimethoxyphenyl)-1H-imidazol-4-amine (57a) (0.07 g, 0.29 mmol), dicyclohexyl(2',4',6'-triisopropylbiphenyl-2-yl)phosphine (XPhos, 0.04 g, 0.09 mmol), cesium carbonate (0.28 g, 0.86 mmol), Pd$_2$(dba)$_3$ (0.04 g, 0.04 mmol) in t-BuOH/toluene (15 mL, 2:1) and heating at 110° C. for 15 min according to the procedure reported in step-3 of scheme 101. This gave after workup and purification by flash column chromatography [silica gel (24 g), eluting with DMA-80 in DCM from 0-50%] followed by purification by reverse phase column chromatography [(silica gel C-18, 24 g) eluting with acetonitrile and 0.1% HCl water] and lyophilization (S)-(1-(7-methyl-2-((1-(3,4,5-trimethoxyphenyl)-1H-imidazol-4-yl)amino)quinazolin-4-yl)pyrrolidin-2-yl)methanol (393b) (0.02 g, 16% yield) HCl salt as a yellow solid; $^1$H NMR (300 MHz, DMSO-d$_6$): δ 13.05 (s, 1H), 10.40 (s, 1H), 8.27 (s, 1H), 8.18 (d, J=8.7 Hz, 1H), 7.66 (s, 1H), 7.30 (s, 1H), 7.26 (d, J=8.7 Hz, 1H), 6.96 (s, 2H), 4.99-4.65 (m, 1H), 4.27-3.99 (m, 2H), 3.88 (s, 6H), 3.68 (s, 3H), 3.58-3.27 (m, 2H), 2.45 (s, 3H), 2.29-1.73 (m, 4H). MS (ES+): 491.5 (M+1); MS (ES−): 525.4 (M+Cl). HPLC purity: 93.25%.

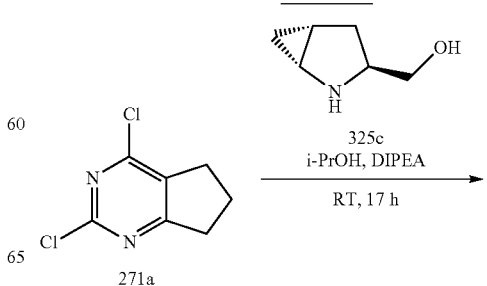

Scheme 394

-continued

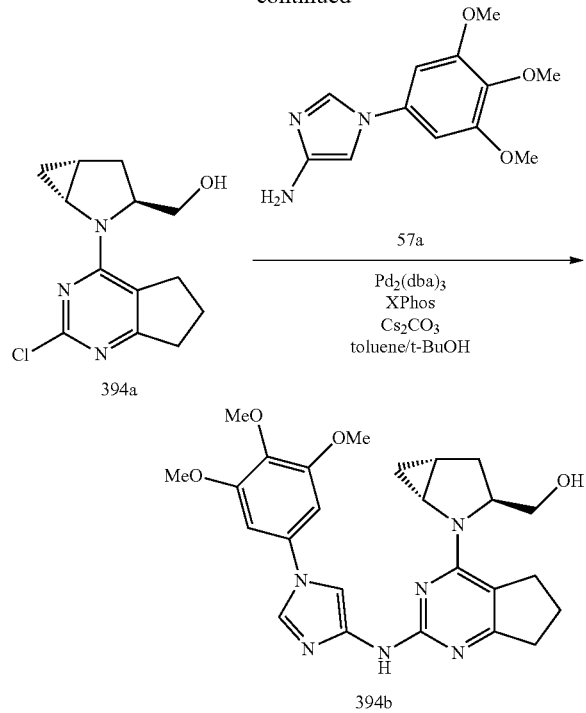

Preparation of ((1R,3S,5R)-2-(2-((1-(3,4,5-trimethoxyphenyl)-1H-imidazol-4-yl)amino)-6,7-dihydro-5H-cyclopenta[d]pyrimidin-4-yl)-2-azabicyclo[3.1.0]hexan-3-yl)methanol (394b)

Step-1: Preparation of ((1R,3S,5R)-2-(2-chloro-6,7-dihydro-5H-cyclopenta[d]pyrimidin-4-yl)-2-azabicyclo[3.1.0]hexan-3-yl)methanol (394a)

Compound 394a was prepared from 2,4-dichloro-6,7-dihydro-5H-cyclopenta[d]pyrimidine (271a) (0.20 g, 1.06 mmol) in 2-Propanol (10 mL) using (1R,3S,5R)-2-azabicyclo[3.1.0]hexan-3-ylmethanol (325c) (0.24 g, 1.06 mmol), DIPEA (0.55 mL, 3.17 mmol) and stirring at room temperature for 17 h according to the procedure reported in step-1 of scheme 96. This gave after workup and purification by flash column chromatography [silica gel (12 g), eluting with eluting with 0-80% EtOAc/MeOH (9:1) in hexane from 0-100%] ((1R,3S,5R)-2-(2-chloro-6,7-dihydro-5H-cyclopenta[d]pyrimidin-4-yl)-2-azabicyclo[3.1.0]hexan-3-yl)methanol (394a) (0.11 g, 37% yield) as a semi-solid; $^1$H NMR (300 MHz, DMSO-d$_6$) δ 4.87 (t, J=5.6 Hz, 1H), 4.34-4.25 (m, 1H), 3.59-3.49 (m, 2H), 3.43-3.33 (m, 1H), 3.18 (hept, J=7.9, 7.4 Hz, 2H), 2.71 (t, J=7.9 Hz, 2H), 2.25-2.15 (m, 1H), 1.96 (p, J=7.6 Hz, 2H), 1.87-1.69 (m, 2H), 0.96-0.86 (m, 1H), 0.52-0.45 (m, 1H); MS (ES+): 288.2 (M+Na); MS (ES−): 264.2 & 266.2 (M−1).

Step-2: Preparation of ((1R,3S,5R)-2-(2-((1-(3,4,5-trimethoxyphenyl)-1H-imidazol-4-yl)amino)-6,7-dihydro-5H-cyclopenta[d]pyrimidin-4-yl)-2-azabicyclo[3.1.0]hexan-3-yl)methanol (394b)

Compound 394b was prepared from ((1R,3S,5R)-2-(2-chloro-6,7-dihydro-5H-cyclopenta[d]pyrimidin-4-yl)-2-azabicyclo[3.1.0]hexan-3-yl)methanol (394a) (0.1 g, 0.38 mmol), 1-(3,4,5-trimethoxyphenyl)-1H-imidazol-4-amine (57a) (0.09 g, 0.38 mmol), dicyclohexyl(2',4',6'-triisopropylbiphenyl-2-yl)phosphine (XPhos, 0.11 g, 0.23 mmol), cesium carbonate (0.37 g, 1.13 mmol), Pd$_2$(dba)$_3$ (0.10 g, 0.11 mmol) in t-BuOH/toluene (20 mL, 3:1) heating at 110° C. for 20 h according to the procedure reported in step-3 of scheme 101. This gave after workup and purification by flash column chromatography [silica gel (12 g), eluting with DMA-80 in CH$_2$Cl$_2$ from 0 to 50%] followed by reverse phase flash column chromatography [(silica gel C-18, 24 g) eluting with acetonitrile and 0.1% HCl in water]((1R,3S,5R)-2-(2-((1-(3,4,5-trimethoxyphenyl)-1H-imidazol-4-yl)amino)-6,7-dihydro-5H-cyclopenta[d]pyrimidin-4-yl)-2-azabicyclo[3.1.0]hexan-3-yl)methanol (394b) (0.03 g, 14% yield) HCl salt as a yellow solid; $^1$H NMR (300 MHz, DMSO-d$_6$) δ 10.46 (s, 1H), 8.47 (s, 1H), 7.73 (s, 1H), 6.96 (s, 2H), 4.78-4.57 (m, 1H), 3.86 (s, 6H), 3.81-3.72 (m, 1H), 3.72-3.62 (m, 4H), 3.58-3.42 (m, 1H), 3.32-3.12 (m, 2H), 2.90 (t, J=8.0 Hz, 2H), 2.31-2.15 (m, 1H), 2.13-1.97 (m, 2H), 1.97-1.78 (m, 2H), 1.19-0.95 (m, 1H), 0.74-0.63 (m, 1H); MS (ES+): 479.5 (M+1); MS (ES−): 477.5 (M−1), 513.6 (M+Cl). HPLC purity: 95.09%.

Scheme 395

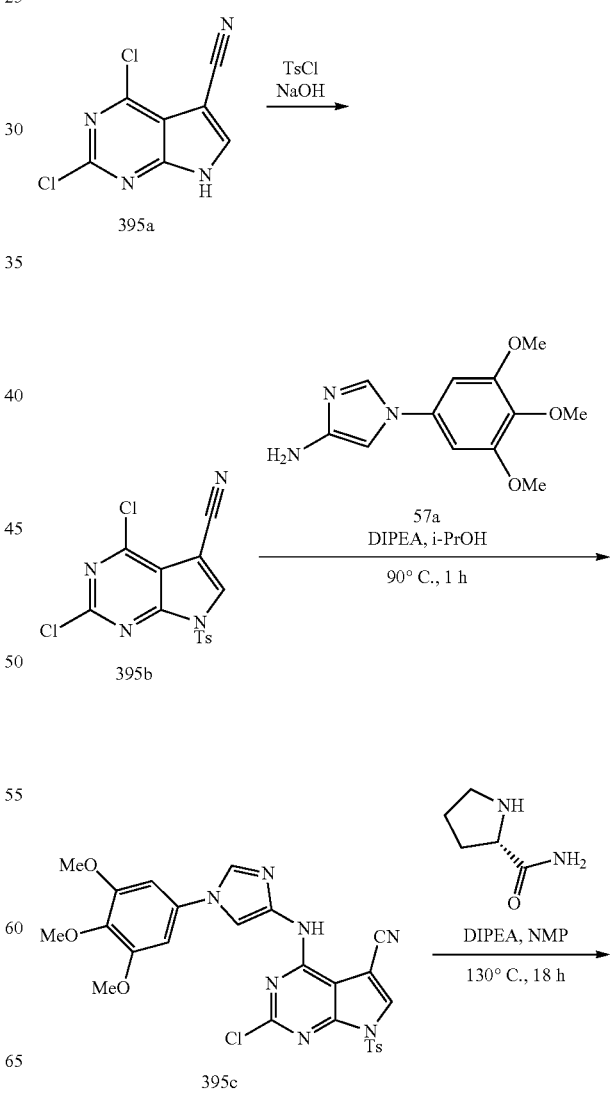

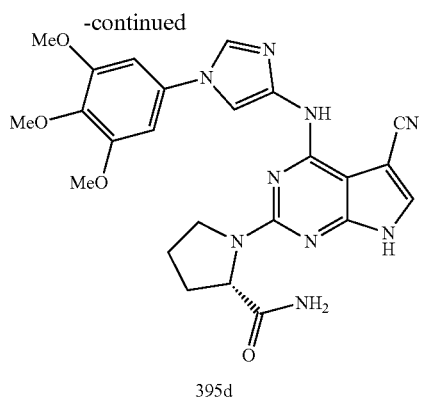

395d

Preparation of (S)-1-(5-cyano-4-((1-(3,4,5-trimethoxyphenyl)-1H-imidazol-4-yl)amino)-7H-pyrrolo[2,3-d]pyrimidin-2-yl)pyrrolidine-2-carboxamide (395d)

Step-1: Preparation of 2,4-dichloro-7-tosyl-7H-pyrrolo[2,3-d]pyrimidine-5-carbonitrile (395b)

To a solution of 2,4-dichloro-7H-pyrrolo[2,3-d]pyrimidine-5-carbonitrile (395a) (0.45 g, 2.11 mmol, CAS #1379367-43-7), tosyl chloride (0.44 g, 2.32 mmol), tetrabutylammonium hydrogen sulfate (0.04 g, 0.11 mmol) in DCM (20 mL) was added at room temperature sodium hydroxide (50% aq, 0.40 mL, 4.96 mmol). The reaction mixture stirred at room temperature for 30 min diluted with water and DCM. The organic layer was separated, dried, filtered and evaporated in vacuo to obtain 2,4-dichloro-7-tosyl-7H-pyrrolo[2,3-d]pyrimidine-5-carbonitrile (395b) (0.62 g, 79% yield) as a white solid. $^1$H NMR (300 MHz, DMSO-$d_6$): δ 9.20 (s, 1H), 8.10-8.06 (m, 2H), 7.55 (d, J=8.2 Hz, 2H), 2.41 (s, 3H).

Step-2: Preparation of 2-chloro-7-tosyl-4-((1-(3,4,5-trimethoxyphenyl)-1H-imidazol-4-yl)amino)-7H-pyrrolo[2,3-d]pyrimidine-5-carbonitrile (395c)

Compound 395c was prepared from 2,4-dichloro-7-tosyl-7H-pyrrolo[2,3-d]pyrimidine-5-carbonitrile (395b) (0.32 g, 0.86 mmol) in 2-Propanol (15 mL) using DIPEA (0.45 mL, 2.57 mmol), 1-(3,4,5-trimethoxyphenyl)-1H-imidazol-4-amine (57a) (0.21 g, 0.86 mmol) and heating at 90° C. for 1 h according to the procedure reported in step-1 of scheme 183. This gave after filtration 2-chloro-7-tosyl-4-((1-(3,4,5-trimethoxyphenyl)-1H-imidazol-4-yl)amino)-7H-pyrrolo[2,3-d]pyrimidine-5-carbonitrile (395c) (0.47 g, 94% yield) as a brown solid; $^1$H NMR (300 MHz, DMSO-$d_6$): δ 9.76 (s, 1H), 8.74 (s, 1H), 8.21 (s, 1H), 8.06 (d, J=8.0 Hz, 2H), 7.80 (d, J=7.3 Hz, 1H), 7.53 (d, J=8.1 Hz, 2H), 6.91 (d, J=6.8 Hz, 2H), 3.86 (s, 6H), 3.68 (s, 3H), 2.40 (s, 3H).

Step-3: Preparation of (S)-1-(5-cyano-4-((1-(3,4,5-trimethoxyphenyl)-1H-imidazol-4-yl)amino)-7H-pyrrolo[2,3-d]pyrimidin-2-yl)pyrrolidine-2-carboxamide (395d)

Compound 395d was prepared from 2-chloro-7-tosyl-4-((1-(3,4,5-trimethoxyphenyl)-1H-imidazol-4-yl)amino)-7H-pyrrolo[2,3-d]pyrimidine-5-carbonitrile (395c) (0.23 g, 0.40 mmol), (S)-pyrrolidine-2-carboxamide (0.18 g, 1.59 mmol), N-ethyl-N-isopropylpropan-2-amine (0.42 mL, 2.38 mmol) in NMP (3 mL) and heating at 130° C. for 18 h according to the procedure reported in scheme 2. This gave after workup and purification by flash column chromatography [silica gel (12 g), eluting with DMA 80 in $CH_2Cl_2$ from 0 to 50%], followed by purification using reverse phase flash column chromatography [(silica gel C-18, 24 g), eluting with acetonitrile and 0.1% HCl water] and lyophilization (S)-1-(5-cyano-4-((1-(3,4,5-trimethoxyphenyl)-1H-imidazol-4-yl)amino)-7H-pyrrolo[2,3-d]pyrimidin-2-yl)pyrrolidine-2-carboxamide (395d) (0.05 g, 23% yield) HCl salt as a yellow solid; $^1$H NMR (300 MHz, DMSO-d-$D_2$O): (a mixture of two rotamers) δ 9.32 and 9.19 (2s, 1H), 8.14 and 8.05 (2s, 1H), 7.94 and 7.89 (2d, J=2.7 Hz, 1H), 7.20 and 7.12 (2s, 2H), 4.61-4.48 and 4.47-4.29 (m, 1H), 3.90 and 3.83 (2s, 6H), 3.80-3.73 (m, 1H), 3.69 and 3.68 (2s, 3H), 3.57-3.39 (m, 1H), 2.33-1.80 (m, 4H). MS (ES+): 504.4 (M+1), 526.4 (M+Na); MS (ES−): 502.4 (M−1), 538.4 (M+Cl).

Scheme 396

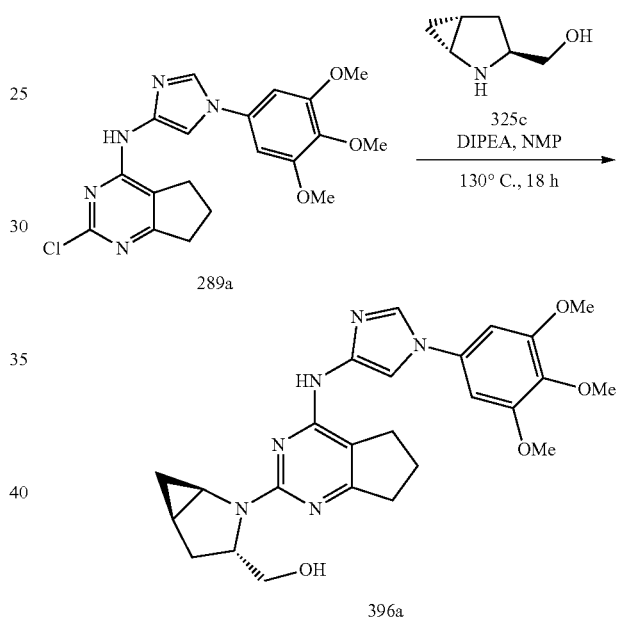

Preparation of ((1R,3S,5R)-2-(4-((1-(3,4,5-trimethoxyphenyl)-1H-imidazol-4-yl)amino)-6,7-dihydro-5H-cyclopenta[d]pyrimidin-2-yl)-2-azabicyclo[3.1.0]hexan-3-yl)methanol (396a)

Compound 396a was prepared from 2-chloro-N-(1-(3,4,5-trimethoxyphenyl)-1H-imidazol-4-yl)-6,7-dihydro-5H-cyclopenta[d]pyrimidin-4-amine (289a) (0.1 g, 0.25 mmol), (1R,3S,5R)-2-azabicyclo[3.1.0]hexan-3-ylmethanol (325c) (0.11 g, 1.00 mmol), N-ethyl-N-isopropylpropan-2-amine (0.26 mL, 1.49 mmol) in NMP (3 mL) and heating at 130° C. for 18 h according to the procedure reported in scheme 2. This gave after workup and purification by flash column chromatography [silica gel (12 g), eluting with DMA 80 in $CH_2Cl_2$ from 0 to 50%], followed by purification using reverse phase flash column chromatography [(silica gel C-18, 24 g), eluting with acetonitrile and 0.1% HCl water] and lyophilization ((1R,3S,5R)-2-(4-((1-(3,4,5-trimethoxyphenyl)-1H-imidazol-4-yl)amino)-6,7-dihydro-5H-cyclopenta[d]pyrimidin-2-yl)-2-azabicyclo[3.1.0]hexan-3-yl)

methanol (396a) (0.02 g, 13% yield) HCl salt as a brown solid; ¹H NMR (300 MHz, DMSO-d₆): δ 12.86 (s, 1H), 10.85 (s, 1H), 8.38 (s, 1H), 8.00 (s, 1H), 6.93 (s, 2H), 4.63-4.41 (m, 1H), 3.92-3.86 (m, 1H), 3.85 (s, 7H), 3.67 (s, 4H), 3.64-3.48 (m, 1H), 2.97 (t, J=7.7 Hz, 2H), 2.81 (t, J=7.4 Hz, 2H), 2.26-1.77 (m, 5H), 1.13-0.95 (m, 1H), 0.68-0.40 (m, 1H). MS (ES+): 479.4 (M+1); MS (ES−): 513.4 (M+Cl).

Scheme 397

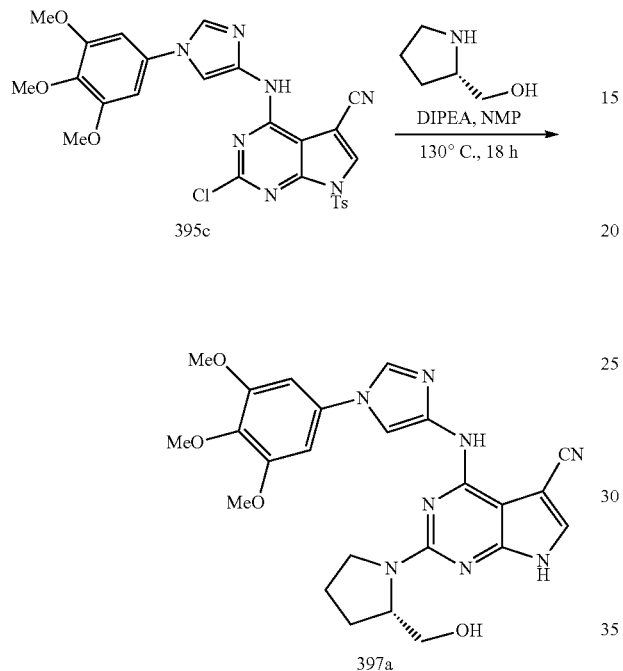

Preparation of (S)-2-(2-(hydroxymethyl)pyrrolidin-1-yl)-4-((1-(3,4,5-trimethoxyphenyl)-1H-imidazol-4-yl)amino)-7H-pyrrolo[2,3-d]pyrimidine-5-carbonitrile (397a)

Compound 397a was prepared from 2-chloro-7-tosyl-4-((1-(3,4,5-trimethoxyphenyl)-1H-imidazol-4-yl)amino)-7H-pyrrolo[2,3-d]pyrimidine-5-carbonitrile (395c) (0.23 g, 0.40 mmol), (S)-pyrrolidin-2-ylmethanol (0.16 mL, 1.59 mmol), N-ethyl-N-isopropylpropan-2-amine (0.42 mL, 2.38 mmol) in NMP (3 mL) and heating at 130° C. for 18 h according to the procedure reported in scheme 2. This gave after workup and purification by flash column chromatography [silica gel (12 g), eluting with DMA 80 in CH₂Cl₂ from 0 to 50%], followed by purification using reverse phase flash column chromatography [(silica gel C-18, 24 g), eluting with acetonitrile and 0.1% HCl water] and lyophilization (S)-2-(2-(hydroxymethyl)pyrrolidin-1-yl)-4-((1-(3,4,5-trimethoxyphenyl)-1H-imidazol-4-yl)amino)-7H-pyrrolo[2,3-d]pyrimidine-5-carbonitrile (397a) (0.02 g, 8% yield) HCl salt as a white solid; ¹H NMR (300 MHz, DMSO-d₆-D₂O): δ 12.39-12.19 (m, 1H), 8.61 (s, 1H), 8.37 (s, 1H), 8.01 (s, 1H), 7.88 (d, J=2.5 Hz, 1H), 7.01 (s, 2H), 4.41-4.02 (m, 1H), 3.96-3.80 (m, 7H), 3.69 (s, 3H), 3.59-3.25 (m, 1H), 2.14-1.78 (m, 4H). MS (ES+): 491.2 (M+1); MS (ES−): 489.4 (M−1). HPLC purity: 94.55%.

Scheme 398

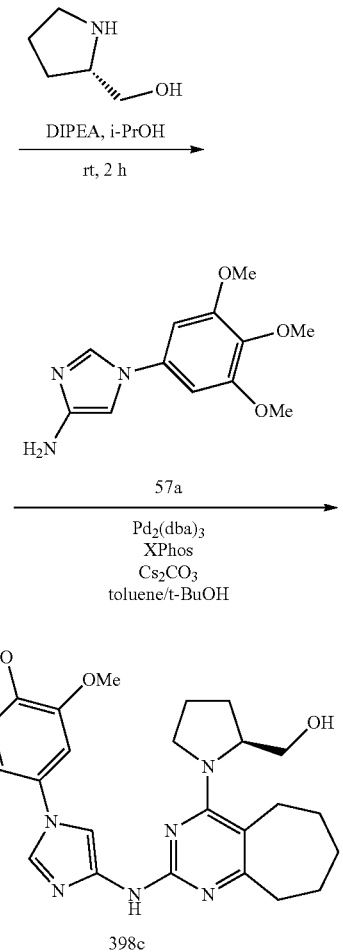

Preparation of (S)-(1-(2-((1-(3,4,5-trimethoxyphenyl)-1H-imidazol-4-yl)amino)-6,7,8,9-tetrahydro-5H-cyclohepta[d]pyrimidin-4-yl)pyrrolidin-2-yl)methanol (398c)

Step-1: Preparation of (S)-(1-(2-chloro-6,7,8,9-tetrahydro-5H-cyclohepta[d]pyrimidin-4-yl)pyrrolidin-2-yl)methanol (398b)

Compound 398b was prepared from 2,4-dichloro-6,7,8,9-tetrahydro-5H-cyclohepta[d]pyrimidine (398a) (0.12 g, 0.55 mmol; CAS #: 76780-96-6) in 2-Propanol (5 mL) using (S)-pyrrolidin-2-ylmethanol (0.06 mL, 0.55 mmol), DIPEA (0.29 mL, 1.66 mmol) and stirring at room temperature for 2 h according to the procedure reported in step-1 of scheme 96. This gave after workup and purification by flash column chromatography [silica gel (12 g), eluting with eluting with DCM and methanol (0 to 50%)] (S)-(1-(2-chloro-6,7,8,9-tetrahydro-5H-cyclohepta[d]pyrimidin-4-yl)pyrrolidin-2-yl)methanol (398b) (0.07 g, 46% yield) as a white solid; ¹H NMR (300 MHz, DMSO-d₆-D₂O): δ 4.35-4.21 (m, 1H), 3.73-3.58 (m, 1H), 3.58-3.49 (m, 1H), 3.44-3.30 (m, 2H), 2.90-2.54 (m, 4H), 2.06-1.38 (m, 10H). MS (ES+): 282.2 & 284.2 (M+1); MS (ES−): 316.3 & 318.2 (M+Cl).

Step-2: Preparation of (S)-(1-(2-((1-(3,4,5-trimethoxyphenyl)-1H-imidazol-4-yl)amino)-6,7,8,9-tetrahydro-5H-cyclohepta[d]pyrimidin-4-yl)pyrrolidin-2-yl)methanol (398c)

Compound 398c was prepared from (S)-(1-(2-chloro-6,7,8,9-tetrahydro-5H-cyclohepta[d]pyrimidin-4-yl)pyrrolidin-2-yl)methanol (398b) (0.07 g, 0.25 mmol), 1-(3,4,5-trimethoxyphenyl)-1H-imidazol-4-amine (57a) (0.06 g, 0.25 mmol), dicyclohexyl(2',4',6'-triisopropylbiphenyl-2-yl)phosphine (XPhos, 0.07 g, 0.15 mmol), cesium carbonate (0.24 g, 0.75 mmol), $Pd_2(dba)_3$ (0.07 g, 0.08 mmol) in t-BuOH/toluene (15 mL, 2:1) and heating at 110° C. for 15 min according to the procedure reported in step-3 of scheme 101. This gave after workup and purification by flash column chromatography [silica gel (24 g), eluting with DMA-80 in DCM from 0-50%] followed by purification by reverse phase column chromatography [(silica gel C-18, 24 g) eluting with acetonitrile and 0.1% HCl water] and lyophilization (S)-(1-(2-((1-(3,4,5-trimethoxyphenyl)-1H-imidazol-4-yl)amino)-6,7,8,9-tetrahydro-5H-cyclohepta[d]pyrimidin-4-yl)pyrrolidin-2-yl)methanol (398c) (0.02 g, 13% yield) HCl salt as a yellow solid; $^1$H NMR (300 MHz, DMSO-$d_6$-$D_2O$): δ 13.27 (s, 1H), 10.14 (s, 1H), 8.33 (s, 1H), 7.64 (s, 1H), 6.95 (d, J=1.9 Hz, 2H), 4.77-4.46 (m, 1H), 3.87 (m, 6H), 3.81-3.71 (m, 1H), 3.67 (s, 3H), 3.60-3.44 (m, 2H), 2.98-2.69 (m, 4H), 2.16-1.48 (m, 10H). MS (ES+): 495.5 (M+1); MS (ES−): 529.5 (M+Cl). HPLC purity: 91.95%.

Scheme 399

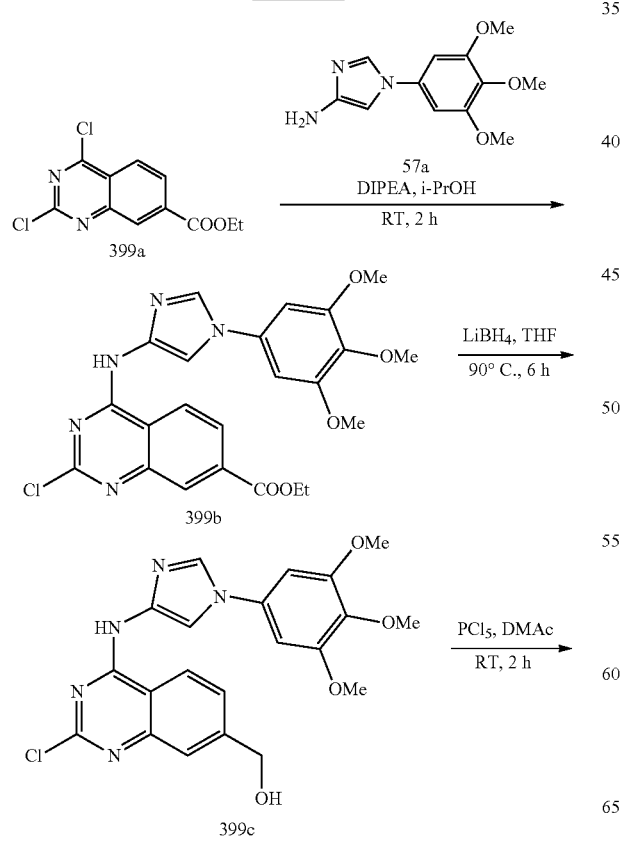

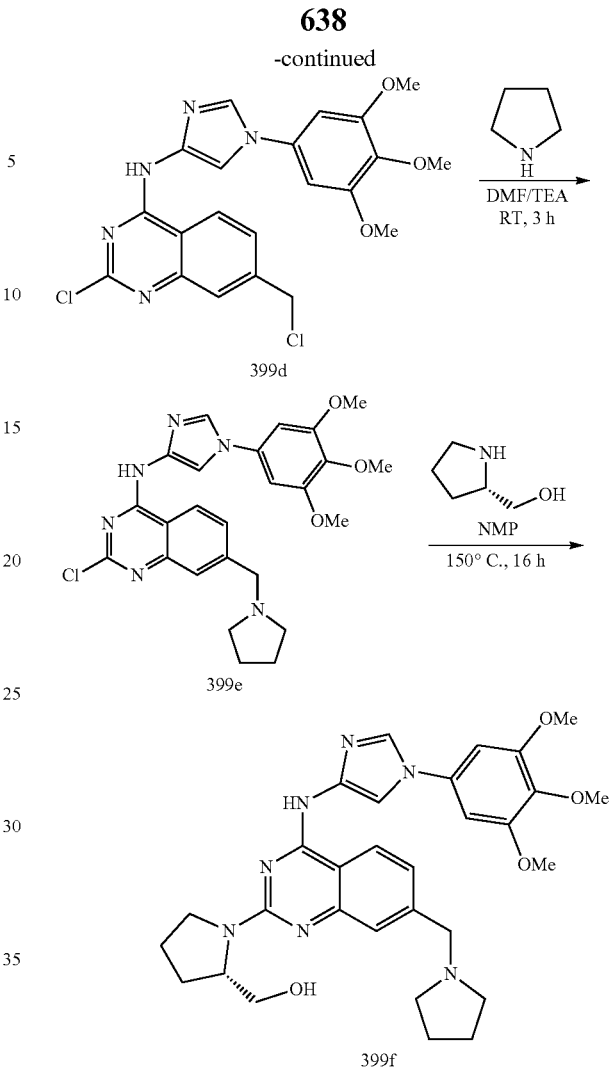

Preparation of (S)-(1-(7-(pyrrolidin-1-ylmethyl)-4-((1-(3,4,5-trimethoxyphenyl)-1H-imidazol-4-yl)amino)quinazolin-2-yl)pyrrolidin-2-yl)methanol (399f)

Step-1: Preparation of ethyl 2-chloro-4-((1-(3,4,5-trimethoxyphenyl)-1H-imidazol-4-yl)amino)quinazoline-7-carboxylate (399b)

Compound 399b was prepared from ethyl 2,4-dichloroquinazoline-7-carboxylate (399a) (4.0 g, 14.75 mmol; CAS #864291-31-6) in 2-Propanol (80 mL) using DIPEA (5.71 mL, 44.25 mmol), 1-(3,4,5-trimethoxyphenyl)-1H-imidazol-4-amine (57a) (3.67 g, 14.75 mmol) and stirring at room temperature for 2 h according to the procedure reported in step-1 of scheme 183. This gave after filtration ethyl 2-chloro-4-((1-(3,4,5-trimethoxyphenyl)-1H-imidazol-4-yl)amino)quinazoline-7-carboxylate (399b) (7.0 g, 98%) as a Brown solid; $^1$H NMR (300 MHz, DMSO-$d_6$) δ 11.38 (s, 1H), 8.90 (d, J=8.7 Hz, 1H), 8.22 (dd, J=13.0, 1.6 Hz, 1H), 8.17-7.85 (m, 2H), 6.95 (s, 2H), 4.52-4.14 (m, 2H), 3.88 (s, 6H), 3.71 (s, 3H), 1.58-1.21 (m, 3H); MS (ES+): 484.1 (M+1).

Step-2: Preparation of (2-chloro-4-((1-(3,4,5-trimethoxyphenyl)-1H-imidazol-4-yl)amino)quinazolin-7-yl)methanol (399c)

To a solution of ethyl 2-chloro-4-((1-(3,4,5-trimethoxyphenyl)-1H-imidazol-4-yl)amino)quinazoline-7-carboxylate (399b) (7.0 g, 14.46 mmol) in THF (420 mL) was added at 0° C. LiBH$_4$ (0.78 g, 36.16 mmol). The reaction mixture was heated at 90° C. for 6 h cooled to RT and concentrated in vacuum. The residue obtained was purified by flash column chromatography [silica gel, eluting with MeOH in DCM from (0%-10%)] to afford (2-chloro-4-((1-(3,4,5-trimethoxyphenyl)-1H-imidazol-4-yl)amino)quinazolin-7-yl)methanol (399c) (2.5 g, 39% yield) as an off-white solid; $^1$H NMR (300 MHz, DMSO-d$_6$) δ 11.03 (s, 1H), 8.69 (d, J=8.5 Hz, 1H), 8.22 (d, J=1.6 Hz, 1H), 7.99 (d, J=1.6 Hz, 1H), 7.78-7.46 (m, 2H), 6.95 (s, 2H), 5.51 (t, J=5.7 Hz, 1H), 4.69 (d, J=5.9 Hz, 2H), 3.88 (s, 6H), 3.70 (s, 3H); MS (ES+): 442.1 (M+1); MS (ES-): 440.0 (M-1).

Step-3: Preparation of 2-chloro-7-(chloromethyl)-N-(1-(3,4,5-trimethoxyphenyl)-1H-imidazol-4-yl)quinazolin-4-amine (399d)

To a stirred solution of (2-chloro-4-((1-(3,4,5-trimethoxyphenyl)-1H-imidazol-4-yl)amino)quinazolin-7-yl)methanol (399c) (1.0 g, 2.26 mmol) in N,N'-dimethylacetamide (DMAc) (20.0 mL) was added at RT phosphorus pentachloride (0.706 g, 3.39 mmol) and stirred at RT for 2 h. Reaction mixture was poured into water (600 mL) and aqueous phase was extracted with ethyl acetate (2×50 mL). The combined organic phase was filtered and concentrated under reduce pressure to afford 2-chloro-7-(chloromethyl)-N-(1-(3,4,5-trimethoxyphenyl)-1H-imidazol-4-yl)quinazolin-4-amine (399d) (1.04 g) which was taken as such for next step without further purification.

Step-4: Preparation of 2-chloro-7-(pyrrolidin-1-ylmethyl)-N-(1-(3,4,5-trimethoxyphenyl)-1H-imidazol-4-yl)quinazolin-4-amine (399e)

To a stirred solution of 2-chloro-7-(chloromethyl)-N-(1-(3,4,5-trimethoxyphenyl)-1H-imidazol-4-yl)quinazolin-4-amine (399d) (1.04 g, 2.25 mmol) in DMF (15.0 mL) was added TEA (6.65 mL) and pyrrolidine (0.24 g, 3.38 mmol) at RT. The resulting reaction mixture was stirred at room temperature for 3 h and poured into water (200 mL). The aqueous phase was extracted with ethyl acetate (2×200 mL). The combined organic phase was dried, filtered and concentrated under reduce pressure. The residue obtained was purified by flash column chromatography [silica gel, eluting with MeOH in DCM (0% to 10%)] to afford 2-chloro-7-(pyrrolidin-1-ylmethyl)-N-(1-(3,4,5-trimethoxyphenyl)-1H-imidazol-4-yl)quinazolin-4-amine (399e) (230 mg, 22%) as a light brown solid; $^1$H NMR (300 MHz, DMSO-d$_6$) δ 11.06 (s, 1H), 8.71 (d, J=8.8 Hz, 1H), 8.22 (d, J=1.6 Hz, 1H), 7.99 (d, J=1.7 Hz, 1H), 7.64-7.53 (m, 2H), 6.94 (s, 2H), 3.88 (s, 2H), 3.77 (s, 3H), 3.70 (s, 3H), 3.58 (m, 3H), 2.20 (m, 2H), 1.74 (m, 2H), 0.86 (s, 4H); MS (ES+): 495.0 (M+1); MS (ES-): 493.2 (M-1).

Step-5: Preparation of (S)-(1-(7-(pyrrolidin-1-ylmethyl)-4-((1-(3,4,5-trimethoxyphenyl)-1H-imidazol-4-yl)amino)quinazolin-2-yl)pyrrolidin-2-yl)methanol (399f)

Compound 399f was prepared from 2-chloro-7-(pyrrolidin-1-ylmethyl)-N-(1-(3,4,5-trimethoxyphenyl)-1H-imidazol-4-yl)quinazolin-4-amine (399e) (0.23 g, 0.464 mmol), (S)-pyrrolidin-2-ylmethanol (0.47 g, 4.64 mmol), in NMP (11.5 mL) and heating at 150° C. for 16 h according to the procedure reported in scheme 2. This gave after workup and purification by flash column chromatography (silica gel, eluting with MeOH in CH$_2$Cl$_2$ from 0 to 10%) (S)-(1-(7-(pyrrolidin-1-ylmethyl)-4-((1-(3,4,5-trimethoxyphenyl)-1H-imidazol-4-yl)amino)quinazolin-2-yl)pyrrolidin-2-yl)methanol (399f) (200 mg, 77%) as a brown solid; $^1$H NMR (300 MHz, DMSO-d$_6$) δ 12.71 (s, 1H), 12.11-11.63 (m, 2H), 8.85-8.71 (m, 1H), 8.59 (d, J=6.1 Hz, 1H), 8.33-8.20 (m, 1H), 8.11 (d, J=1.6 Hz, 1H), 7.85 (d, J=8.7 Hz, 1H), 7.03 (s, 1H), 6.98 (s, 1H), 4.76-4.55 (m, 1H), 4.51 (m, 2H), 4.12-3.78 (m, 7H), 3.68 (s, 3H), 3.61-3.45 (m, 1H), 3.45-3.28 (m, 2H), 3.17-2.99 (m, 2H), 2.79-2.65 (m, 1H), 2.27-1.60 (m, 8H); MS (ES+): 560.6 (M+1); MS (ES-): 594.6 (M+Cl).

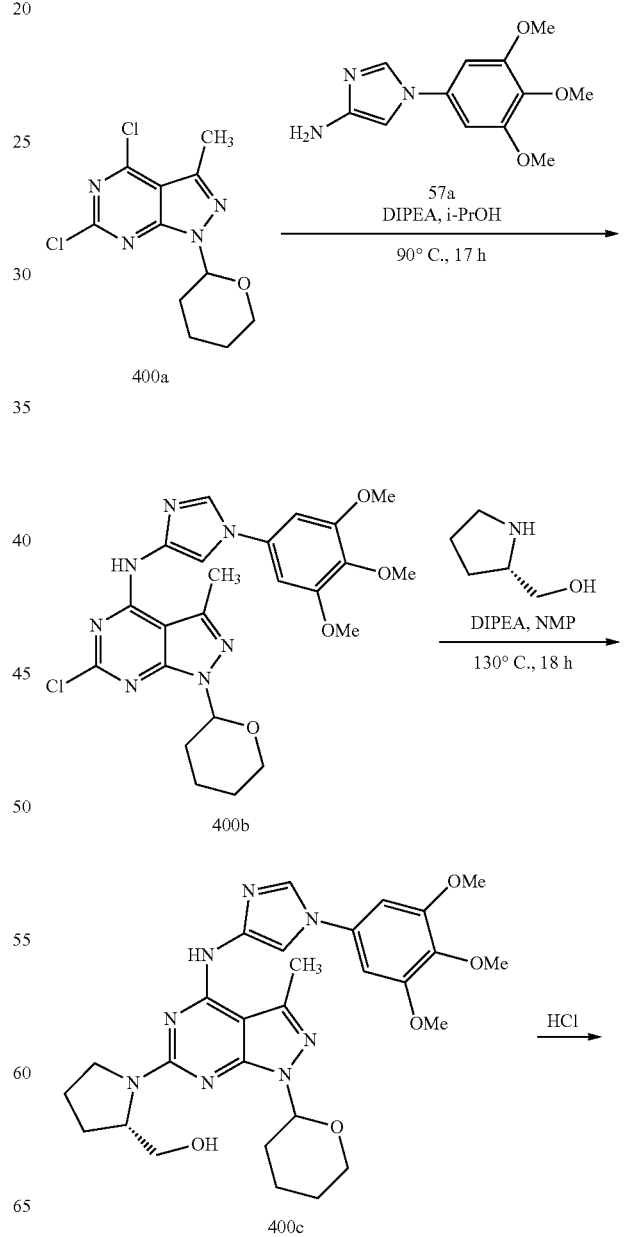

Scheme 400

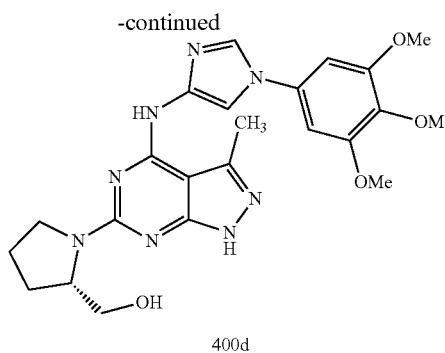

400d

Preparation of ((2S)-1-(3-methyl-1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidin-2-yl)methanol (400c) and (S)-(1-(3-methyl-4-((1-(3,4,5-trimethoxyphenyl)-1H-imidazol-4-yl)amino)-1H-pyrazolo[3,4-d]pyrimidin-6-yl)pyrrolidin-2-yl)methanol (400d)

Step-1: Preparation of 6-chloro-3-methyl-1-(tetrahydro-2H-pyran-2-yl)-N-(1-(3,4,5-trimethoxyphenyl)-1H-imidazol-4-yl)-1H-pyrazolo[3,4-d]pyrimidin-4-amine (400b)

Compound 400b was prepared from 4,6-dichloro-3-methyl-1-(tetrahydro-2H-pyran-2-yl)-1H-pyrazolo[3,4-d]pyrimidine (400a) (0.3 g, 1.05 mmol; CAS #1346447-97-9, prepared according to the procedure reported by Gray, Nathanael S. and Zhou, Wenjun in PCT Int. Appl., 2011140338) in 2-Propanol (15 mL) using DIPEA (0.55 mL, 3.13 mmol), 1-(3,4,5-trimethoxyphenyl)-1H-imidazol-4-amine (57a) (0.29 g, 1.15 mmol) and heating at 90° C. for 17 h according to the procedure reported in step-1 of scheme 183. This gave after workup and purification by flash column chromatography [silica (12 g), eluting with DMA 80 in CH$_2$Cl$_2$ from 0 to 50%] 6-chloro-3-methyl-1-(tetrahydro-2H-pyran-2-yl)-N-(1-(3,4,5-trimethoxyphenyl)-1H-imidazol-4-yl)-1H-pyrazolo[3,4-d]pyrimidin-4-amine (400b) (0.40 g, 77% yield) as an orange solid; $^1$H NMR (300 MHz, DMSO-d$_6$): δ 9.65 (s, 1H), 8.24 (d, J=1.5 Hz, 1H), 7.91 (d, J=1.5 Hz, 1H), 6.94 (s, 2H), 5.90-5.54 (m, 1H), 3.98-3.89 (m, 1H), 3.87 (s, 6H), 3.69 (s, 3H), 3.67-3.61 (m, 1H), 2.63 (s, 3H), 2.46-2.24 (m, 1H), 2.08-1.42 (m, 5H).

Step-2: Preparation of ((2S)-1-(3-methyl-1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidin-2-yl)methanol (400c)

Compound 400c was prepared from 6-chloro-3-methyl-1-(tetrahydro-2H-pyran-2-yl)-N-(1-(3,4,5-trimethoxyphenyl)-1H-imidazol-4-yl)-1H-pyrazolo[3,4-d]pyrimidin-4-amine (400b) (0.2 g, 0.40 mmol), (S)-pyrrolidin-2-ylmethanol (0.16 mL, 1.60 mmol), N-ethyl-N-isopropylpropan-2-amine (0.42 mL, 2.40 mmol) in NMP (3 mL) and heating at 130° C. for 18 h according to the procedure reported in scheme 2. This gave after workup and purification by flash column chromatography [silica gel (12 g), eluting with DMA 80 in CH$_2$Cl$_2$ from 0 to 50%], ((2S)-1-(3-methyl-1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidin-2-yl)methanol (400c) (0.09 g, 38% yield) free base as a yellow solid; $^1$H NMR (300 MHz, DMSO-d$_6$): δ 8.71 (s, 1H), 8.47 (s, 1H), 8.24 (s, 1H), 8.11-7.84 (m, 1H), 6.96 (s, 2H), 5.69-5.46 (m, 1H), 4.93 (t, J=5.1 Hz, 1H), 4.51-4.31 (m, 1H), 4.30-4.06 (m, 1H), 3.98-3.92 (m, 1H), 3.88 (s, 6H), 3.83-3.70 (m, 1H), 3.68 (s, 3H), 3.63-3.39 (m, 4H), 2.57 (s, 3H), 2.47-2.28 (m, 1H), 2.11-1.42 (m, 8H). MS (ES+): 565.5 (M+1); MS (ES−): 563.6 (M−1).

Step-3: Preparation of (S)-(1-(3-methyl-4-((1-(3,4,5-trimethoxyphenyl)-1H-imidazol-4-yl)amino)-1H-pyrazolo[3,4-d]pyrimidin-6-yl)pyrrolidin-2-yl)methanol (400d)

To a solution of ((2S)-1-(3-methyl-1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidin-2-yl)methanol (400c) (0.09 g, 0.16 mmol) in MeOH (5 mL) was added hydrogen chloride (3 M in MeOH) (1.59 mL, 4.78 mmol) and heated at 90° C. for 2 h. The reaction mixture was cooled to room temperature, extracted with ethyl acetate and concentrated in vacuum to furnish crude product. The crude residue was purified by flash column chromatography [silica gel (12 g), eluting with DMA80 in DCM from 0-50%] followed by reverse phase column chromatography (C18, 24 g) eluting with acetonitrile and 0.1% HCl water to afford (S)-(1-(3-methyl-4-((1-(3,4,5-trimethoxyphenyl)-1H-imidazol-4-yl)amino)-1H-pyrazolo[3,4-d]pyrimidin-6-yl)pyrrolidin-2-yl)methanol (400d) (0.06 g, 81% yield) HCl salt as a white solid; $^1$H NMR (300 MHz, DMSO-d$_6$): δ 10.33 (s, 1H), 10.17 (s, 1H), 8.57 (s, 1H), 8.03 (s, 1H), 7.02 (s, 2H), 4.60-4.27 (m, 1H), 3.97-3.91 (m, 1H), 3.88 (s, 6H), 3.84-3.71 (m, 1H), 3.68 (s, 3H), 3.66-3.57 (m, 1H), 3.57-3.41 (m, 1H), 2.78 (s, 3H), 2.21-1.78 (m, 4H). MS (ES+): 481.4 (M+1); MS (ES−): 515.5 (M+Cl) HPLC purity: 94.47%.

Scheme 401

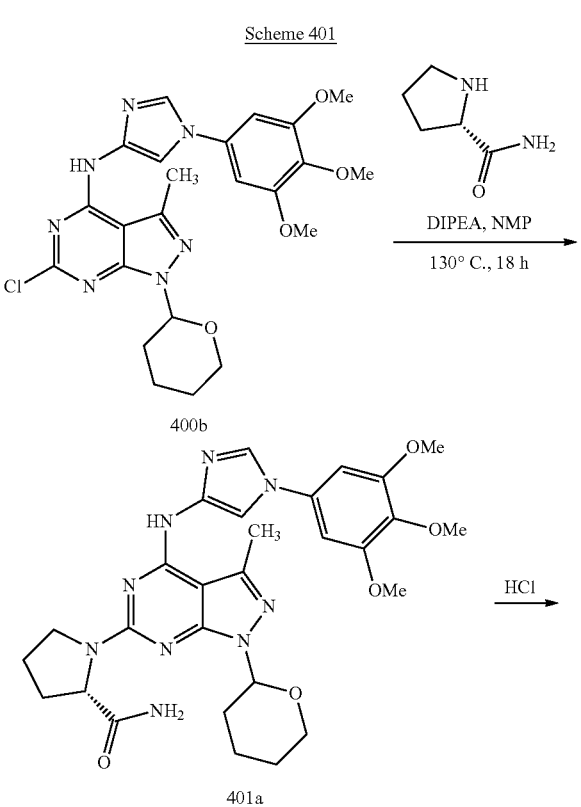

400b

401a

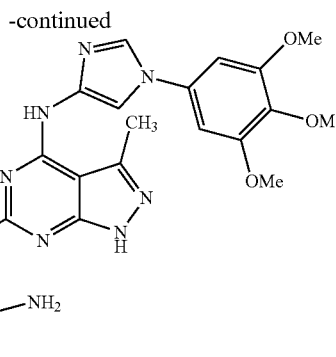

401b

Preparation of (2S)-1-(3-methyl-1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidine-2-carboxamide (401a) and (S)-1-(3-methyl-4-((1-(3,4,5-trimethoxyphenyl)-1H-imidazol-4-yl)amino)-1H-pyrazolo[3,4-d]pyrimidin-6-yl)pyrrolidine-2-carboxamide (401b)

Step-1: Preparation of (2S)-1-(3-methyl-1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidine-2-carboxamide (401a) Compound 401a was prepared from 6-chloro-3-methyl-1-(tetrahydro-2H-pyran-2-yl)-N-(1-(3,4,5-trimethoxyphenyl)-1H-imidazol-4-yl)-1H-pyrazolo[3,4-d]pyrimidin-4-amine (400b) (0.2 g, 0.40 mmol), (S)-pyrrolidine-2-carboxamide (0.18 g, 1.60 mmol), N-ethyl-N-isopropylpropan-2-amine (0.42 mL, 2.40 mmol) in NMP (3 mL) and heating at 130° C. for 18 h according to the procedure reported in scheme 2. This gave after workup and purification by flash column chromatography [silica gel (12 g), eluting with DMA 80 in CH$_2$Cl$_2$ from 0 to 50%] (2S)-1-(3-methyl-1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidine-2-carboxamide (401a) (0.10 g, 42% yield) free base as a yellow solid; $^1$H NMR (300 MHz, DMSO-d$_6$): (a mixture of two rotamers) δ 8.77 (s, 1H), 8.35 (d, J=5.6 Hz, 1H), 8.27 and 8.21 (2s, 1H), 8.11 and 7.90 (2s, 1H), 7.49-7.23 (m, 1H), 7.19 and 7.14 (2s, 1H), 6.98 (s, 1H), 6.93 (s, 1H), 5.71-5.49 (m, 1H), 4.62-4.35 (m, 1H), 3.92 (s, 7H), 3.89-3.83 (m, 2H), 3.68 (s, 3H), 3.63-3.46 (m, 2H), 2.58 (s, 3H), 2.46-2.07 (m, 1H), 2.07-1.82 (m, 4H), 1.82-1.40 (m, 4H). MS (ES+): 578.5 (M+1); MS (ES−): 576.6 (M−1). HPLC purity: 94.86%.

Step-2: Preparation of (S)-1-(3-methyl-4-((1-(3,4,5-trimethoxyphenyl)-1H-imidazol-4-yl)amino)-1H-pyrazolo[3,4-d]pyrimidin-6-yl)pyrrolidine-2-carboxamide (401b)

To a solution of (2S)-1-(3-methyl-1-(tetrahydro-2H-pyran-2-yl)-4-((1-(3,4,5-trimethoxyphenyl)-1H-imidazol-4-yl)amino)-1H-pyrazolo[3,4-d]pyrimidin-6-yl)pyrrolidine-2-carboxamide (401a) (0.05 g, 0.09 mmol) in MeOH (5 mL) was added hydrogen chloride (3 M in MeOH) (0.87 mL, 2.60 mmol) and heated at 90° C. for 2 h. The reaction mixture was cooled to room temperature, extracted with ethyl acetate and concentrated in vacuum to furnish crude product. The crude residue was purified by flash column chromatography [silica gel (12 g), eluting with DMA80 in DCM from 0-50%] followed by reverse phase column chromatography (C18, 24 g) eluting with acetonitrile and 0.1% HCl water to afford (S)-1-(3-methyl-4-((1-(3,4,5-trimethoxyphenyl)-1H-imidazol-4-yl)amino)-1H-pyrazolo[3,4-d]pyrimidin-6-yl)pyrrolidine-2-carboxamide (401b) (0.02 g, 56% yield) HCl salt as a white solid; $^1$H NMR (300 MHz, DMSO-d$_6$): δ 10.14 (s, 1H), 8.71 (s, 1H), 7.95 (s, 1H), 7.57 (s, 1H), 7.20 (s, 1H), 7.18 (s, 2H), 4.66 (m, 1H), 3.93 (s, 6H), 3.89-3.83 (m, 2H), 3.69 (s, 3H), 3.63-3.49 (m, 1H), 2.79 (s, 3H), 2.38-1.74 (m, 4H); MS (ES+): 494.4 (M+1), 516.4 (M+Na); MS (ES−): 528.5 (M+Cl).

Scheme 402

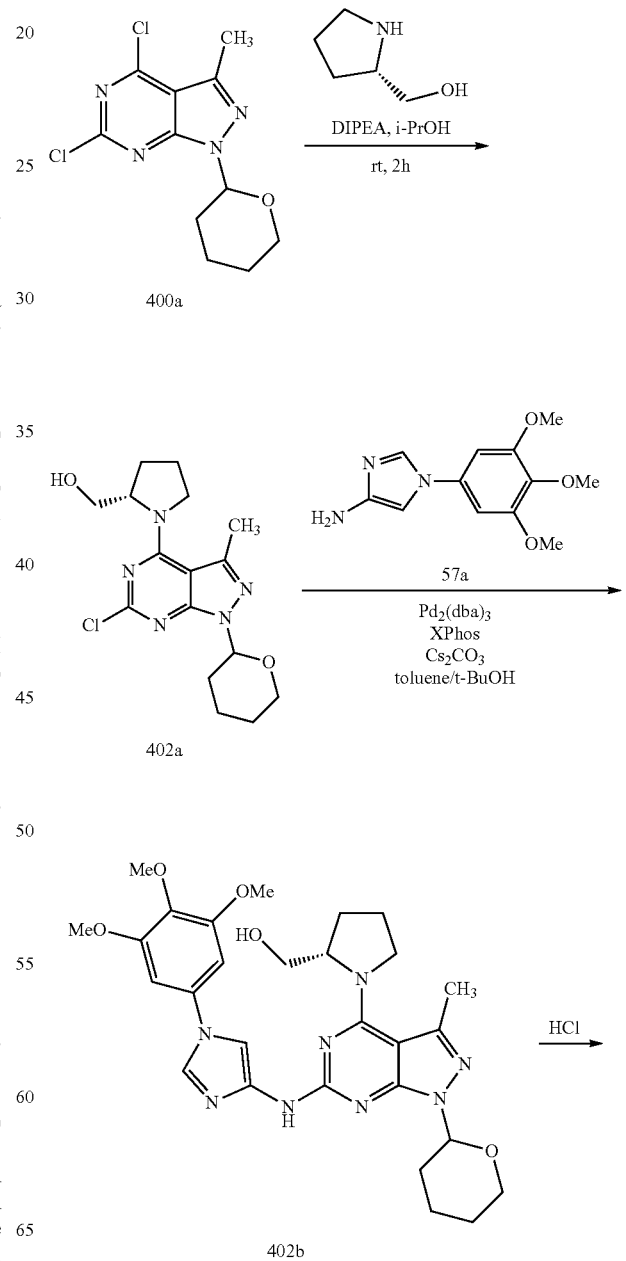

-continued

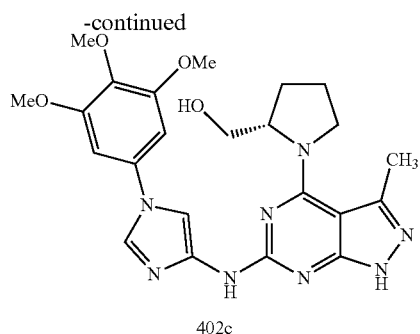

402c

Preparation of ((2S)-1-(3-methyl-1-(tetrahydro-2H-pyran-2-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (402b) and (S)-(1-(3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (402c)

Step-1: Preparation of ((2S)-1-(6-chloro-3-methyl-1-(tetrahydro-2H-pyran-2-yl)-1H-pyrazolo[3,4-d]pyrimidin-4-yl)pyrrolidin-2-yl)methanol (402a)

Compound 402a was prepared from 4,6-dichloro-3-methyl-1-(tetrahydro-2H-pyran-2-yl)-1H-pyrazolo[3,4-d]pyrimidine (400a) (0.2 g, 0.70 mmol) in 2-Propanol (5 mL) using (S)-pyrrolidin-2-ylmethanol (0.07 mL, 0.70 mmol), DIPEA (0.37 mL, 2.09 mmol) and stirring at room temperature for 2 h according to the procedure reported in step-1 of scheme 96. This gave after workup and purification by flash column chromatography [silica gel (12 g), eluting with hexane and ethyl acetate/methanol (9:1) (0 to 80%)] ((2S)-1-(6-chloro-3-methyl-1-(tetrahydro-2H-pyran-2-yl)-1H-pyrazolo[3,4-d]pyrimidin-4-yl)pyrrolidin-2-yl)methanol (402a) (0.17 g, 69% yield) as a white solid; $^1$H NMR (300 MHz, DMSO-$d_6$): δ 5.77-5.65 (m, 1H), 4.91-4.75 (m, 1H), 4.55-4.40 (m, 1H), 3.99-3.48 (m, 7H), 2.57 (s, 3H), 2.46-2.23 (m, 1H), 2.18-1.41 (m, 8H). MS (ES+): 352.3 & 354.3 (M+1); MS (ES−): 386.3 & 388.3 (M+Cl).

Step-2: Preparation of ((2S)-1-(3-methyl-1-(tetrahydro-2H-pyran-2-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (402b)

Compound 402b was prepared from ((2S)-1-(6-chloro-3-methyl-1-(tetrahydro-2H-pyran-2-yl)-1H-pyrazolo[3,4-d]pyrimidin-4-yl)pyrrolidin-2-yl)methanol (402a) (0.17 g, 0.47 mmol), 1-(3,4,5-trimethoxyphenyl)-1H-imidazol-4-amine (57a) (0.12 g, 0.47 mmol), dicyclohexyl(2',4',6'-triisopropylbiphenyl-2-yl)phosphine (XPhos, 0.13 g, 0.28 mmol), cesium carbonate (0.46 g, 1.41 mmol), Pd$_2$(dba)$_3$ (0.13 g, 0.14 mmol) in t-BuOH/toluene (20 mL, 3:1) and heating at 110° C. for 15 min according to the procedure reported in step-3 of scheme 101. This gave after workup and purification by flash column chromatography [silica gel (24 g), eluting with DMA-80 in DCM from 0-50%] followed by purification by reverse phase column chromatography [(silica gel C-18, 24 g) eluting with acetonitrile and 0.1% HCl water] and lyophilization ((2S)-1-(3-methyl-1-(tetrahydro-2H-pyran-2-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (402b) (0.10 g, 37% yield) HCl salt as a yellow solid; $^1$H NMR (300 MHz, DMSO-$d_6$): δ 9.16 (s, 1H), 9.14 (s, 1H), 8.10 (t, J=1.6 Hz, 1H), 7.74 (s, 1H), 6.96 (s, 2H), 5.88-5.65 (m, 1H), 4.97-4.73 (m, 1H), 4.72-4.50 (m, 1H), 3.99-3.93 (m, 1H), 3.89 (s, 6H), 3.84-3.69 (m, 5H), 3.68 (s, 3H), 3.63-3.41 (m, 1H), 2.51 (s, 3H), 2.47-2.18 (m, 1H), 2.17-1.36 (m, 8H). MS (ES+): 565.5 (M+1), 587.5 (M+Na).

Step-3: Preparation of (S)-(1-(3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (402c)

To a solution of ((2S)-1-(3-methyl-1-(tetrahydro-2H-pyran-2-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (402b) (0.06 g, 0.11 mmol) in MeOH (5 mL) was added hydrogen chloride (3 M in MeOH) (1.06 mL, 3.19 mmol) and heated at 90° C. for 2 h. The reaction mixture was cooled to room temperature, extracted with ethyl acetate and concentrated in vacuum to furnish crude product. The crude residue was purified by flash column chromatography [silica gel (12 g), eluting with DMA80 in DCM from 0-50%] followed by reverse phase column chromatography (C18, 24 g) eluting with acetonitrile and 0.1% HCl water and lyophilization to afford(S)-(1-(3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (402c) (0.04 g, 78% yield) HCl salt as a white solid; $^1$H NMR (300 MHz, DMSO-$d_6$): δ 10.59 (s, 1H), 8.63 (s, 1H), 7.80 (s, 1H), 7.01 (s, 2H), 4.86-4.58 (m, 1H), 4.02-3.91 (m, 3H), 3.88 (s, 6H), 3.68 (s, 3H), 3.65-3.51 (m, 1H), 2.70 (s, 3H), 2.23-1.87 (m, 4H). MS (ES+): 481.4 (M+1); MS (ES−): 515.5 (M+Cl) HPLC purity: 96.87%.

Scheme 403

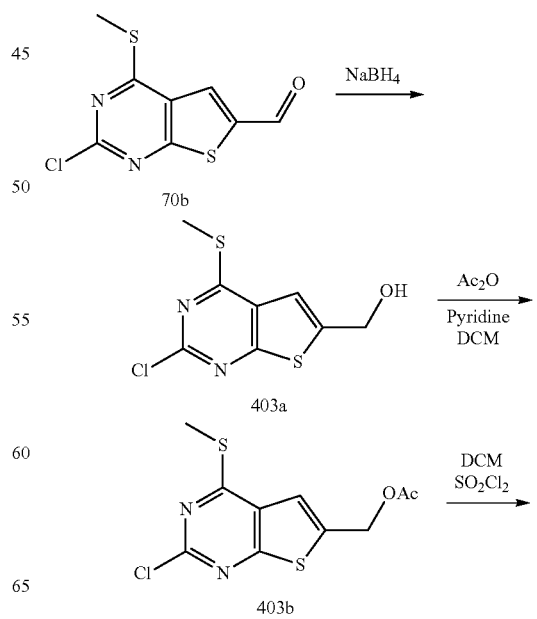

647
-continued

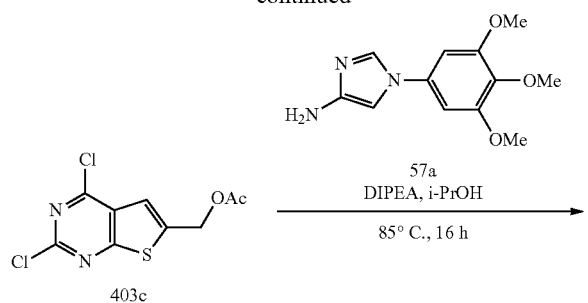

648
-continued

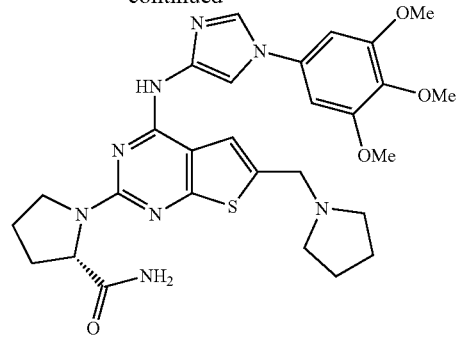

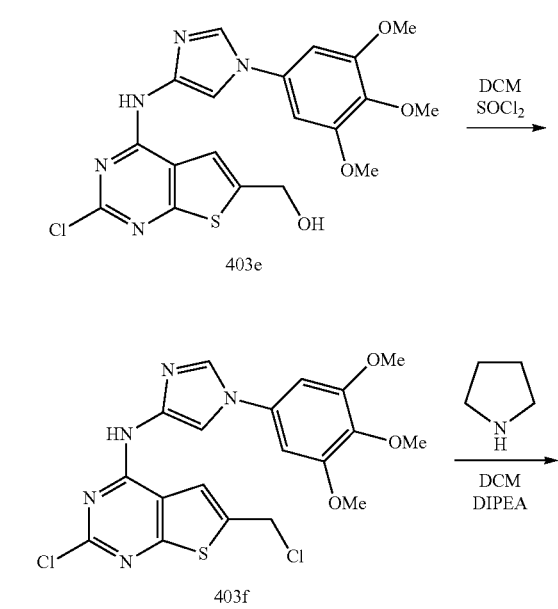

Preparation of (S)-1-(6-(pyrrolidin-1-ylmethyl)-4-((1-(3,4,5-trimethoxyphenyl)-1H-imidazol-4-yl)amino)thieno[2,3-d]pyrimidin-2-yl)pyrrolidine-2-carboxamide (403h)

Step-1: Preparation of (2-chloro-4-(methylthio)thieno[2,3-d]pyrimidin-6-yl)methanol (403a)

To a solution of 2-chloro-4-(methylthio)thieno[2,3-d]pyrimidine-6-carbaldehyde (70b) (40.0 g, 163.45 mmol) in THF (800 mL) was added cautiously at room temperature water (40.0 mL) and sodium borohydride (7.4 g, 195.76 mmol). The reaction mixture was stirred at room temperature for 3 h and quenched carefully with 1N HCl (500 mL). The aqueous layer was separated and extracted with ethyl acetate (3×600 mL). The combined organic extracts were washed with brine (500 mL), dried, filtered and concentrated under reduced pressure to afford (2-chloro-4-(methylthio)thieno[2,3-d]pyrimidin-6-yl)methanol (403a) (35.0 g, 87%) as a light yellow solid; $^1$H NMR (300 MHz, DMSO-$d_6$) δ 7.29 (t, J=1.3 Hz, 1H), 5.92 (s, 1H), 4.78 (d, J=1.3 Hz, 2H), 2.66 (s, 3H); MS (ES+): 247.2 (M+1).

Step-2: Preparation of (2-chloro-4-(methylthio)thieno[2,3-d]pyrimidin-6-yl)methyl acetate (403b)

To a stirred solution of (2-chloro-4-(methylthio)thieno[2,3-d]pyrimidin-6-yl)methanol (403a) (30.0 g, 121.5 mmol) in DCM (300.0 mL) was added at room temperature pyridine (30.0 mL) and acetic anhydride (90.0 mL). The reaction mixture was stirred at same temperature for 3 h and quenched with 1 N HCl (300.0 mL). The aqueous layer was separated and extracted with DCM (3×200.0 mL). The combined organic extracts were washed with brine, dried, filtered and concentrated under reduced pressure to afford (2-chloro-4-(methylthio)thieno[2,3-d]pyrimidin-6-yl)methyl acetate (403b) (28.0 g, 80% yield) as a light yellow solid; $^1$H NMR (300 MHz, DMSO-$d_6$) δ 7.58 (d, J=1.0 Hz, 1H), 5.39 (d, J=0.9 Hz, 2H), 2.68 (s, 3H), 2.10 (s, 3H); MS (ESI) 289.2 (M+1), MS (ES+): 287.1 (M−1).

Step-3: Preparation of (2,4-dichlorothieno[2,3-d]pyrimidin-6-yl)methyl acetate (403c)

To a stirred solution of (2-chloro-4-(methylthio)thieno[2,3-d]pyrimidin-6-yl)methyl acetate (403b) (20.0 g, 69.26 mmol) in DCM (400.0 mL) at 10° C. was added sulfuryl chloride (56.08 g, 415.53 mmol). The reaction mixture was stirred at room temperature for 2 h and quenched carefully by slow addition of saturated aqueous sodium bicarbonate solution (500.0 mL). The aqueous layer was separated and extracted with DCM (2×500.0 mL). The combined organic extracts were washed with brine, dried, filtered and concentrated under reduced pressure to afford (2,4-dichlorothieno[2,3-d]pyrimidin-6-yl)methyl acetate (403c) (16.0 g, 83% yield) as a light brown solid; $^1$H NMR (300 MHz, DMSO-$d_6$) δ 7.67 (d, J=1.0 Hz, 1H), 5.43 (d, J=1.0 Hz, 2H), 2.12 (s, 3H); MS (ES+): 277.0 (M+1).

Step-4: Preparation of (2-chloro-4-((1-(3,4,5-trimethoxyphenyl)-1H-imidazol-4-yl)amino)thieno[2,3-d]pyrimidin-6-yl)methyl acetate (403d)

Compound 403d was prepared from (2,4-dichlorothieno[2,3-d]pyrimidin-6-yl)methyl acetate (403c) (14.0 g, 50.51 mmol) in 2-Propanol (70 mL) using DIPEA (19.58 g, 151.55 mmol), 1-(3,4,5-trimethoxyphenyl)-1H-imidazol-4-amine (57a) (16.0 g, 64.18 mmol) and heating at 85° C. for 16 h according to the procedure reported in step-1 of scheme 183. This gave after filtration (2-chloro-4-((1-(3,4,5-trimethoxyphenyl)-1H-imidazol-4-yl)amino)thieno[2,3-d]pyrimidin-6-yl)methyl acetate (403d) (9.0 g, 37%) as an off white solid; $^1$H NMR (300 MHz, DMSO-$d_6$) δ 11.03 (s, 1H), 8.19 (d, J=1.6 Hz, 1H), 8.03 (s, 1H), 7.89 (d, J=1.6 Hz, 1H), 6.93 (s, 2H), 5.33 (s, 2H), 3.88 (s, 6H), 3.70 (s, 3H), 2.11 (s, 3H); MS (ES+): 488.4 (M-1).

Step-5: Preparation of (2-chloro-4-((1-(3,4,5-trimethoxyphenyl)-1H-imidazol-4-yl)amino)thieno[2,3-d]pyrimidin-6-yl)methanol (403e)

To a stirred solution of (2-chloro-4-((1-(3,4,5-trimethoxyphenyl)-1H-imidazol-4-yl)amino)thieno[2,3-d]pyrimidin-6-yl)methyl acetate (403d) (9.0 g, 18.36 mmol) in methanol (50 mL) was added at room temperature potassium carbonate (2.4 g, 17.36 mmol). The reaction mixture was stirred at room temperature for 5 h and concentrated under vacuum to dryness. The residue obtained was dissolved in DCM (250.0 mL) and filtered. The filtrate was diluted with water (250 mL) and extracted with DCM (3×300.0 mL). The combined organic extracts were washed with brine, dried, filtered and concentrated under reduced pressure to afford (2-chloro-4-((1-(3,4,5-trimethoxyphenyl)-1H-imidazol-4-yl)amino)thieno[2,3-d]pyrimidin-6-yl)methanol (403e) (5.0 g, 61% yield) as a light brown solid; $^1$H NMR (300 MHz, DMSO-$d_6$) δ: 8.18 (d, J=1.6 Hz, 1H), 7.88 (d, J=1.6 Hz, 2H), 7.82 (s, 1H), 6.92 (s, 2H), 5.81 (s, 1H), 4.71 (s, 2H), 3.87 (s, 6H), 3.69 (s, 3H); MS (ESI) 448.1 (M+1), MS (ES+): 446.4 (M-1).

Step-6: Preparation of 2-chloro-6-(chloromethyl)-N-(1-(3,4,5-trimethoxyphenyl)-1H-imidazol-4-yl)thieno[2,3-d]pyrimidin-4-amine (403f)

To a stirred solution of (2-chloro-4-((1-(3,4,5-trimethoxyphenyl)-1H-imidazol-4-yl)amino)thieno[2,3-d]pyrimidin-6-yl)methanol (403e) (5.0 g, 11.16 mmol) in DCM (500 mL) and DMF (50 mL) was added at 0° C. thionyl chloride (6.63 g, 55.80 mmol) and stirred at room temperature for 2 h. The reaction mixture was concentrated under vacuum and the residue obtained was triturated with ice water (50.0 mL). The solid obtained was collected by filtration, dried to furnish 2-chloro-6-(chloromethyl)-N-(1-(3,4,5-trimethoxyphenyl)-1H-imidazol-4-yl)thieno[2,3-d]pyrimidin-4-amine (403f) (4.5 g, 87%) as an off white solid; $^1$H NMR (300 MHz, DMSO-$d_6$) δ 11.12 (s, 1H), 8.74 (s, 1H), 8.03 (d, J=1.6 Hz, 1H), 7.82 (s, 1H), 7.03 (s, 2H), 4.74 (s, 2H), 3.88 (s, 6H), 3.71 (s, 3H); MS (ES+): 466.0 (M-1).

Step-7: Preparation of 2-chloro-6-(pyrrolidin-1-ylmethyl)-N-(1-(3,4,5-trimethoxyphenyl)-1H-imidazol-4-yl)thieno[2,3-d]pyrimidin-4-amine (403g)

To a stirred solution of 2-chloro-6-(chloromethyl)-N-(1-(3,4,5-trimethoxyphenyl)-1H-imidazol-4-yl)thieno[2,3-d]pyrimidin-4-amine (403f) (900 mg, 1.92 mmol) in DCM (13.5 mL) at room temperature was added pyrrolidine (204 mg, 2.88 mmol), DIPEA (748 mg, 5.76 mmol) and stirred at room temperature for 5 h. The reaction mass was poured into water (25.0 mL) and extracted with DCM (3×50.0 mL). The combined organic extracts were washed with brine, dried, filtered and concentrated under reduced pressure to afford crude product. The crude was crystallized using DCM and n-hexane to furnish 2-chloro-6-(pyrrolidin-1-ylmethyl)-N-(1-(3,4,5-trimethoxyphenyl)-1H-imidazol-4-yl)thieno[2,3-d]pyrimidin-4-amine (403g) (400 mg, 42%) as a brown solid; $^1$H NMR (300 MHz, DMSO-$d_6$) δ 10.86 (s, 1H), 8.31-8.13 (m, 1H), 7.98-7.69 (m, 1H), 6.92 (d, J=6.3 Hz, 3H), 3.88 (s, 9H), 3.76-3.61 (m, 4H), 1.74 (m, 4H), 1.23 (m, 2H); MS (ES+): 502.0 (M+1).

Step-8: Preparation of (S)-1-(6-(pyrrolidin-1-ylmethyl)-4-((1-(3,4,5-trimethoxyphenyl)-1H-imidazol-4-yl)amino)thieno[2,3-d]pyrimidin-2-yl)pyrrolidine-2-carboxamide (403h)

Compound 403h was prepared from 2-chloro-6-(pyrrolidin-1-ylmethyl)-N-(1-(3,4,5-trimethoxyphenyl)-1H-imidazol-4-yl)thieno[2,3-d]pyrimidin-4-amine (403g) (800 mg, 1.59 mmol), (S)-pyrrolidine-2-carboxamide (911 mg, 7.99 mmol), in NMP (16 mL) and heating at 150° C. for 5 h according to the procedure reported in scheme 2. This gave after workup and purification by reverse phase column chromatography [C18 (50 g), eluting with ACN in water (containing 0.1% HCl) from 0-100%] (S)-1-(6-(pyrrolidin-1-ylmethyl)-4-((1-(3,4,5-trimethoxyphenyl)-1H-imidazol-4-yl)amino)thieno[2,3-d]pyrimidin-2-yl)pyrrolidine-2-carboxamide (403h) HCl salt as an off-white solid; $^1$H NMR (300 MHz, DMSO-$d_6$; NMR shows rotamers) δ 11.33 (s, 2H), 8.53 (s, 1H), 8.12 (s, 1H), 7.92 (s, 1H), 7.51 (s, 1H), 7.16 (s, 2H), 4.60 (m, 3H), 3.94 (s, 6H), 3.69 (s, 3H), 3.44 (s, 2H), 3.11 (m, 4H), 2.30 (m, 2H), 2.11-1.83 (m, 8H); MS (ES+) 579.4 (M+1); MS (ES-) 613.4 (M+Cl).

Scheme 404

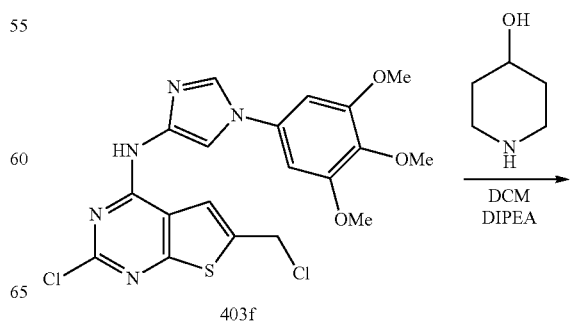

403f

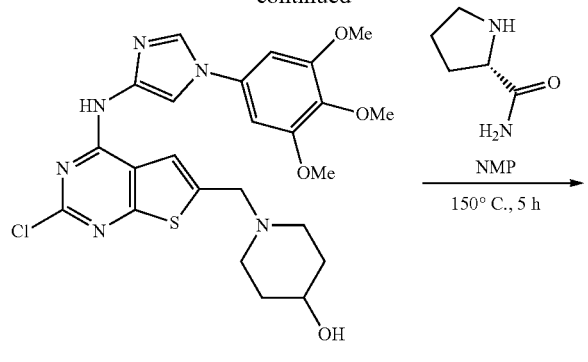

404a

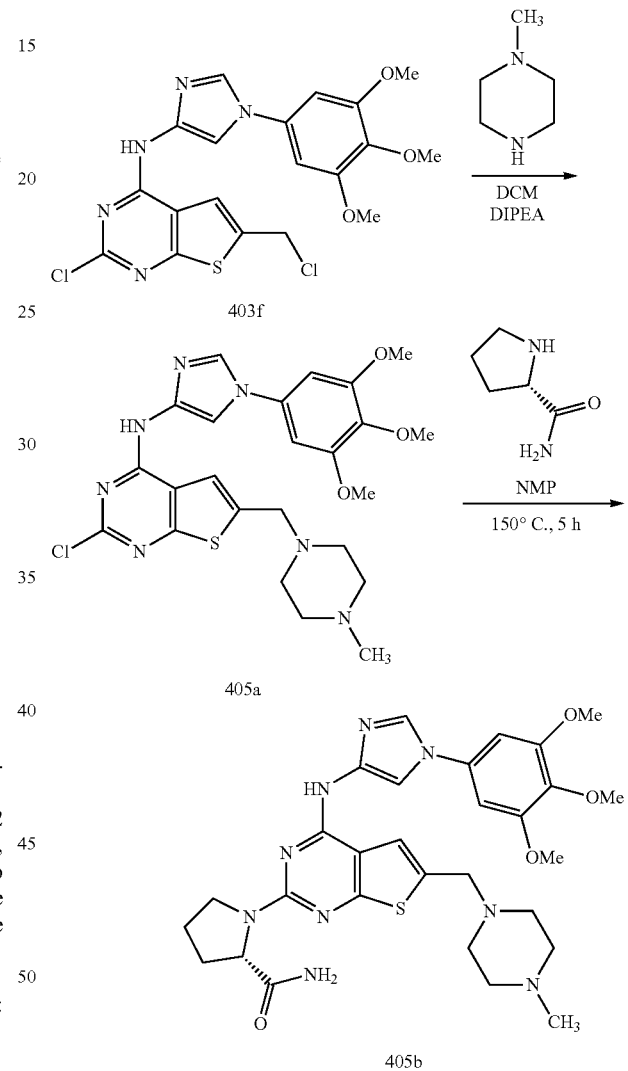

ACN in water (containing 0.1% HCl) from 0-100%] to afford (S)-1-(6-((4-hydroxypiperidin-1-yl)methyl)-4-((1-(3, 4,5-trimethoxyphenyl)-1H-imidazol-4-yl)amino)thieno[2,3-d]pyrimidin-2-yl)pyrrolidine-2-carboxamide (404b) HCl salt as an off-white solid; $^1$H NMR (300 MHz, DMSO-$d_6$; NMR shows rotamers) δ 11.25 (s, 1H), 10.91 (s, 2H), 8.48 (s, 1H), 8.15-8.05 (m, 1H), 7.91 (s, 1H), 7.47 (s, 1H), 7.15 (s, 2H), 4.66-4.49 (m, 3H), 3.90-3.77 (m, 7H), 3.69 (s, 3H), 3.65-2.87 (m, 6H), 2.35-1.56 (m, 8H); MS (ES+) 609.4 (M+1); MS (ES−) 643.5 (M+Cl).

Scheme 405

404b

Preparation of (S)-1-(6-((4-hydroxypiperidin-1-yl)methyl)-4-((1-(3,4,5-trimethoxyphenyl)-1H-imidazol-4-yl)amino)thieno[2,3-d]pyrimidin-2-yl)pyrrolidine-2-carboxamide (404b)

Step-1: Preparation of 1-((2-chloro-4-((1-(3,4,5-trimethoxyphenyl)-1H-imidazol-4-yl)amino)thieno[2,3-d]pyrimidin-6-yl)methyl)piperidin-4-ol (404a)

Compound 404a was prepared form 2-chloro-6-(chloromethyl)-N-(1-(3,4,5-trimethoxyphenyl)-1H-imidazol-4-yl)thieno[2,3-d]pyrimidin-4-amine (403f) (900 mg, 1.92 mmol) in DCM (13.5 mL) using piperidin-4-ol (292 mg, 2.89 mmol) and DIPEA (740 mg, 5.78 mmol) according to the procedure reported in step-7 of scheme 403. This gave after workup and crystallization using DCM and n-hexane 1-((2-chloro-4-((1-(3,4,5-trimethoxyphenyl)-1H-imidazol-4-yl)amino)thieno[2,3-d]pyrimidin-6-yl)methyl)piperidin-4-ol (404a) (900 mg, 88%) as a brown solid; MS (ES+): 531.0 (M+1).

Step-2: Preparation of (S)-1-(6-((4-hydroxypiperidin-1-yl)methyl)-4-((1-(3,4,5-trimethoxyphenyl)-1H-imidazol-4-yl)amino)thieno[2,3-d]pyrimidin-2-yl)pyrrolidine-2-carboxamide (404b)

Compound 404b was prepared from 1-((2-chloro-4-((1-(3,4,5-trimethoxyphenyl)-1H-imidazol-4-yl)amino)thieno[2,3-d]pyrimidin-6-yl)methyl)piperidin-4-ol (404a) (800 mg, 1.50 mmol), (S)-pyrrolidine-2-carboxamide (861 mg, 7.54 mmol), in NMP (12 mL) and heating at 150° C. for 5 h according to the procedure reported in scheme 2. This gave after workup compound 404b (430 mg, 47.0%) free base as an off white solid. The free base was purified by reverse phase column chromatography [C18 (50 g), eluting with Preparation of (S)-1-(6-((4-methylpiperazin-1-yl)methyl)-4-((1-(3,4,5-trimethoxyphenyl)-1H-imidazol-4-yl)amino)thieno[2,3-d]pyrimidin-2-yl)pyrrolidine-2-carboxamide (405b)

Step-1: Preparation of 2-chloro-6-((4-methylpiperazin-1-yl)methyl)-N-(1-(3,4,5-trimethoxyphenyl)-1H-imidazol-4-yl)thieno[2,3-d]pyrimidin-4-amine (405a)

Compound 405a was prepared form 2-chloro-6-(chloromethyl)-N-(1-(3,4,5-trimethoxyphenyl)-1H-imidazol-4-yl)

thieno[2,3-d]pyrimidin-4-amine (403f) (1.0 g, 2.14 mmol) in DCM (15 mL) using 1-methylpiperazine (322 mg, 3.21 mmol) and DIPEA (830 mg, 6.42 mmol) according to the procedure reported in step-7 of scheme 403. This gave after workup and crystallization using DCM and n-hexane 2-chloro-6-((4-methylpiperazin-1-yl)methyl)-N-(1-(3,4,5-trimethoxyphenyl)-1H-imidazol-4-yl)thieno[2,3-d]pyrimidin-4-amine (405a) (600 mg, 53%) as a brown solid; MS (ES+): 531.0 (M+1).

Step-2: Preparation of (S)-1-(6-((4-methylpiperazin-1-yl)methyl)-4-((1-(3,4,5-trimethoxyphenyl)-1H-imidazol-4-yl)amino)thieno[2,3-d]pyrimidin-2-yl)pyrrolidine-2-carboxamide (405b)

Compound 405b was prepared from 2-chloro-6-((4-methylpiperazin-1-yl)methyl)-N-(1-(3,4,5-trimethoxyphenyl)-1H-imidazol-4-yl)thieno[2,3-d]pyrimidin-4-amine (405a) (500 mg, 0.943 mmol), (S)-pyrrolidine-2-carboxamide (538 mg, 4.71 mmol), in NMP (10 mL) and heating at 150° C. for 5 h according to the procedure reported in scheme 2. This gave after workup compound 405b (430 mg, 75%) free base as an off white solid. The free base was purified by reverse phase column chromatography [C18 (50 g), eluting with ACN in water (containing 0.1% HCl) from 0-100%] to afford (S)-1-(6-((4-methylpiperazin-1-yl)methyl)-4-((1-(3,4,5-trimethoxyphenyl)-1H-imidazol-4-yl)amino)thieno[2,3-d]pyrimidin-2-yl)pyrrolidine-2-carboxamide (405b) HCl salt as an off-white solid; $^1$H NMR (300 MHz, DMSO-d$_6$; NMR shows rotamers) δ 11.56 (s, 1H), 11.26 (s, 1H), 8.49 (s, 1H), 8.05 (s, 1H), 7.91 (s, 1H), 7.51 (s, 1H), 7.16 (s, 2H), 4.66-4.54 (m, 1H), 4.46-4.01 (m, 4H), 3.93 (s, 6H), 3.90-3.81 (m, 2H), 3.69 (s, 3H), 3.64-3.54 (m, 2H), 3.50-3.04 (m, 4H), 2.81 (s, 3H), 2.38-2.16 (m, 1H), 2.10-1.92 (m, 3H); MS (ES+) 608.4 (M+1); MS (ES−) 642.4 (M+Cl).

Scheme 406

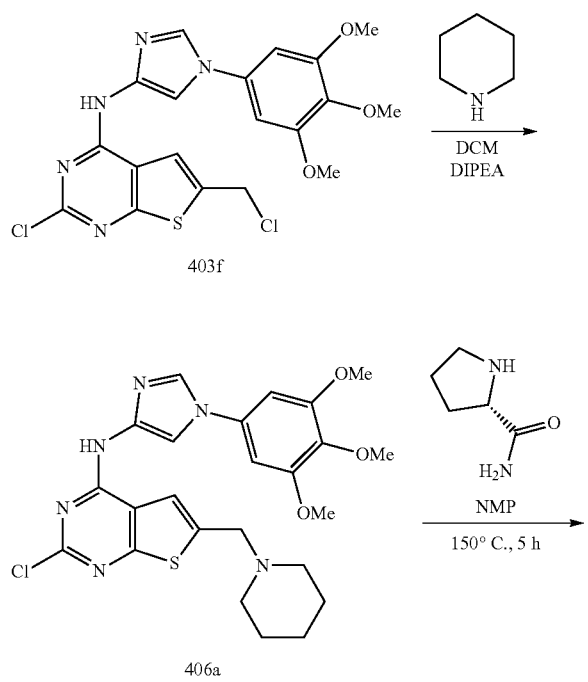

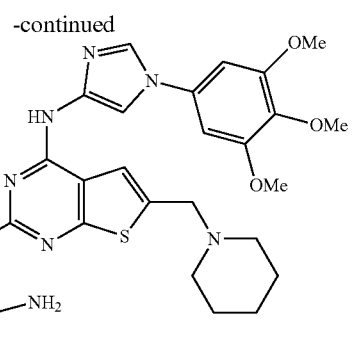

406b

Preparation of (S)-1-(6-(piperidin-1-ylmethyl)-4-((1-(3,4,5-trimethoxyphenyl)-1H-imidazol-4-yl)amino)thieno[2,3-d]pyrimidin-2-yl)pyrrolidine-2-carboxamide (406b)

Step-1: Preparation of 2-chloro-6-(piperidin-1-ylmethyl)-N-(1-(3,4,5-trimethoxyphenyl)-1H-imidazol-4-yl)thieno[2,3-d]pyrimidin-4-amine (406a)

Compound 406a was prepared form 2-chloro-6-(chloromethyl)-N-(1-(3,4,5-trimethoxyphenyl)-1H-imidazol-4-yl)thieno[2,3-d]pyrimidin-4-amine (403f) (0.9 g, 1.92 mmol) in DCM (13.5 mL) using 1-piperidine (246 mg, 2.89 mmol) and DIPEA (748 mg, 5.78 mmol) according to the procedure reported in step-7 of scheme 403. This gave after workup and crystallization using DCM and n-hexane 2-chloro-6-(piperidin-1-ylmethyl)-N-(1-(3,4,5-trimethoxyphenyl)-1H-imidazol-4-yl)thieno[2,3-d]pyrimidin-4-amine (406a) (550 mg, 55%) as a brown solid; $^1$H NMR (300 MHz, DMSO-d$_6$) δ 10.86 (s, 1H), 8.27-8.10 (m, 1H), 8.04-7.75 (m, 1H), 7.01-6.77 (m, 3H), 3.88 (s, 6H), 3.83 (m, 2H), 3.70 (s, 3H), 2.43 (m, 4H), 1.47 (m, 6H); MS (ES+): 514.9.0 (M+1), 512.6 (M−1).

Step-2: Preparation of (S)-1-(6-(piperidin-1-ylmethyl)-4-((1-(3,4,5-trimethoxyphenyl)-1H-imidazol-4-yl)amino)thieno[2,3-d]pyrimidin-2-yl)pyrrolidine-2-carboxamide (406b)

Compound 406b was prepared from 2-chloro-6-(piperidin-1-ylmethyl)-N-(1-(3,4,5-trimethoxyphenyl)-1H-imidazol-4-yl)thieno[2,3-d]pyrimidin-4-amine (406a) (550.0 mg, 1.06 mmol), (S)-pyrrolidine-2-carboxamide (609 mg, 5.33 mmol), in NMP (10 mL) and heating at 150° C. for 5 h according to the procedure reported in scheme 2. This gave after workup compound 406b (600 mg, 95%) free base as an off white solid. The free base was purified by reverse phase column chromatography [C18 (50 g), eluting with ACN in water (containing 0.1% HCl) from 0-100%] to afford (S)-1-(6-(piperidin-1-ylmethyl)-4-((1-(3,4,5-trimethoxyphenyl)-1H-imidazol-4-yl)amino)thieno[2,3-d]pyrimidin-2-yl)pyrrolidine-2-carboxamide (406b) HCl salt as an off-white solid; $^1$H NMR (300 MHz, DMSO-d$_6$/D2O, NMR shows rotamers) δ 8.42 (s, 1H), 8.05 (s, 1H), 7.91 (s, 1H), 7.13 (s, 2H), 4.59-4.40 (m, 3H), 3.93 (s, 6H), 3.87 (m, 2H), 3.68 (s, 3H), 3.02-2.84 (m, 4H), 2.35-2.10 (m, 1H), 2.06-1.57 (m, 8H), 1.37 (m, 1H); MS (ES+): 593.4 (M+1); MS (ES−): 627.5 (M+Cl).

Scheme 407

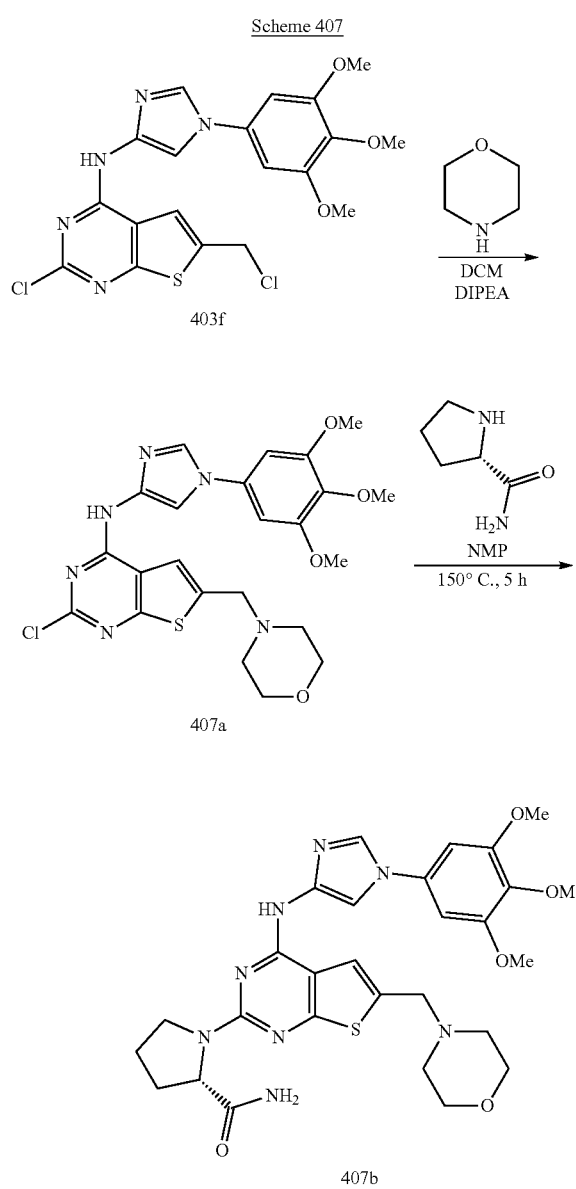

Preparation of (S)-1-(6-(morpholinomethyl)-4-((1-(3,4,5-trimethoxyphenyl)-1H-imidazol-4-yl)amino)thieno[2,3-d]pyrimidin-2-yl)pyrrolidine-2-carboxamide (407b)

Step-1: Preparation of 2-chloro-6-(morpholinomethyl)-N-(1-(3,4,5-trimethoxyphenyl)-1H-imidazol-4-yl)thieno[2,3-d]pyrimidin-4-amine (407a)

Compound 407a was prepared form 2-chloro-6-(chloromethyl)-N-(1-(3,4,5-trimethoxyphenyl)-1H-imidazol-4-yl)thieno[2,3-d]pyrimidin-4-amine (403f) (1.5 g, 3.21 mmol) in DCM (30 mL) using morpholine (420 mg, 4.82 mmol) and DIPEA (1.24 g, 9.63 mmol) according to the procedure reported in step-7 of scheme 403. This gave after workup and crystallization using DCM and n-hexane 2-chloro-6-(morpholinomethyl)-N-(1-(3,4,5-trimethoxyphenyl)-1H-imidazol-4-yl)thieno[2,3-d]pyrimidin-4-amine (407a) (1.5 g, 90%) as a brown solid; $^1$H NMR (300 MHz, DMSO-$d_6$) δ 10.88 (s, 1H), 8.19 (d, J=1.6 Hz, 1H), 7.88 (d, J=1.6 Hz, 1H), 6.92 (s, 2H), 3.87 (s, 6H), 3.74 (s, 2H), 3.69 (s, 3H), 3.60 (t, J=4.5 Hz, 4H), 2.47 (s, 4H); MS (ES+): 518.8 (M+1), 516.0 (M−1).

Step-2: Preparation of (S)-1-(6-(morpholinomethyl)-4-((1-(3,4,5-trimethoxyphenyl)-1H-imidazol-4-yl)amino)thieno[2,3-d]pyrimidin-2-yl)pyrrolidine-2-carboxamide (407b)

Compound 407b was prepared from 2-chloro-6-(morpholinomethyl)-N-(1-(3,4,5-trimethoxyphenyl)-1H-imidazol-4-yl)thieno[2,3-d]pyrimidin-4-amine (407a) (1.0 g, 1.93 mmol), (S)-pyrrolidine-2-carboxamide (1.1 g, 9.67 mmol), in NMP (10 mL) and heating at 150° C. for 5 h according to the procedure reported in scheme 2. This gave after workup compound 407b (800 mg, 70%) free base as an off white solid. The free base was purified by reverse phase column chromatography [C18 (50 g), eluting with ACN in water (containing 0.1% HCl) from 0-100%] to afford (S)-1-(6-(morpholinomethyl)-4-((1-(3,4,5-trimethoxyphenyl)-1H-imidazol-4-yl)amino)thieno[2,3-d]pyrimidin-2-yl)pyrrolidine-2-carboxamide (407b) HCl salt as an off-white solid; $^1$H NMR (300 MHz, DMSO-$d_6$/D$_2$O; NMR shows rotamers) δ 8.59 (s, 1H), 8.12 (s, 1H), 7.92 (s, 1H), 7.14 (s, 2H), 4.68-4.53 (m, 3H), 4.08-3.94 (m, 6H), 3.92 (s, 6H), 3.88-3.82 (m, 3H), 3.45-3.00 (m, 4H), 2.28 (m, 1H), 2.04 (m, 3H); MS (ES+): 595.4 (M+1), 617.4 (M+Na); MS (ES−): 629.4 (M+Cl); HPLC purity: 93.75%.

Scheme 408

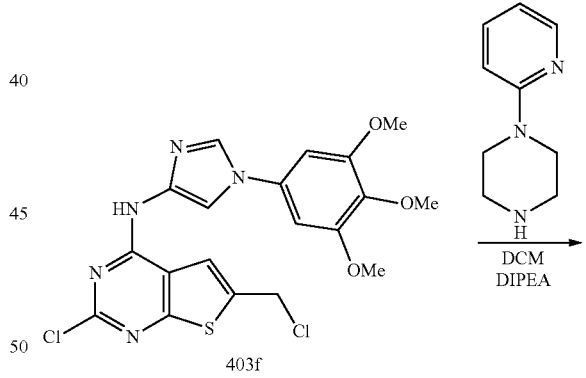

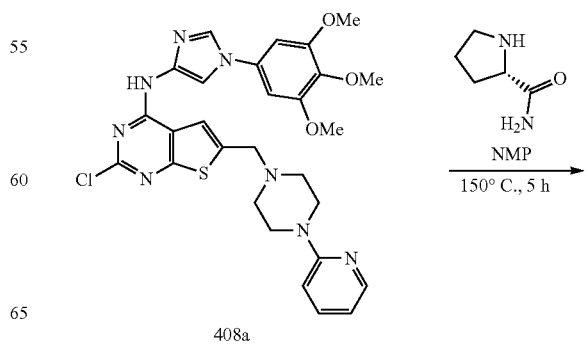

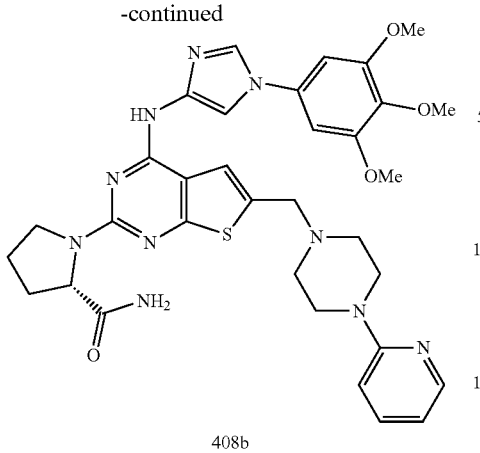

408b

Preparation of (S)-1-(6-((4-(pyridin-2-yl)piperazin-1-yl)methyl)-4-((1-(3,4,5-trimethoxyphenyl)-1H-imidazol-4-yl)amino)thieno[2,3-d]pyrimidin-2-yl)pyrrolidine-2-carboxamide (408b)

Step-1: Preparation of 2-chloro-6-((4-(pyridin-2-yl)piperazin-1-yl)methyl)-N-(1-(3,4,5-trimethoxyphenyl)-1H-imidazol-4-yl)thieno[2,3-d]pyrimidin-4-amine (408a)

Compound 408a was prepared form 2-chloro-6-(chloromethyl)-N-(1-(3,4,5-trimethoxyphenyl)-1H-imidazol-4-yl)thieno[2,3-d]pyrimidin-4-amine (403f) (800 mg, 1.71 mmol) in DCM (12 mL) using 1-(pyridin-2-yl)piperazine (420 mg, 2.57 mmol) and DIPEA (0.665 g, 5.14 mmol) according to the procedure reported in step-7 of scheme 403. This gave after workup and crystallization using DCM and n-hexane 2-chloro-6-((4-(pyridin-2-yl)piperazin-1-yl)methyl)-N-(1-(3,4,5-trimethoxyphenyl)-1H-imidazol-4-yl)thieno[2,3-d]pyrimidin-4-amine (408a) (800 mg, 79%) as a brown solid; MS (ES+): 593.0 (M+1).

Step-2: Preparation of (S)-1-(6-((4-(pyridin-2-yl)piperazin-1-yl)methyl)-4-((1-(3,4,5-trimethoxyphenyl)-1H-imidazol-4-yl)amino)thieno[2,3-d]pyrimidin-2-yl)pyrrolidine-2-carboxamide (408b)

Compound 408b was prepared from 2-chloro-6-((4-(pyridin-2-yl)piperazin-1-yl)methyl)-N-(1-(3,4,5-trimethoxyphenyl)-1H-imidazol-4-yl)thieno[2,3-d]pyrimidin-4-amine (408a) (0.8 g, 1.34 mmol), (S)-pyrrolidine-2-carboxamide (0.769 g, 6.74 mmol), in NMP (20 mL) and heating at 150° C. for 5 h according to the procedure reported in scheme 2. This gave after workup compound 408b (400 mg, 44%) free base as an off white solid. The free base was purified by reverse phase column chromatography [C18 (50 g), eluting with ACN in water (containing 0.1% HCl) from 0-100%] to afford (S)-1-(6-((4-(pyridin-2-yl)piperazin-1-yl)methyl)-4-((1-(3,4,5-trimethoxyphenyl)-1H-imidazol-4-yl)amino)thieno[2,3-d]pyrimidin-2-yl)pyrrolidine-2-carboxamide (408b) HCl salt as an off-white solid; $^1$H NMR (300 MHz, DMSO-$d_6$/D$_2$O) δ 8.17 (s, 1H), 8.09 (dd, J=5.1, 1.9 Hz, 1H), 7.70 (s, 1H), 7.51 (ddd, J=8.9, 7.0, 2.0 Hz, 1H), 7.23-7.04 (m, 2H), 7.01-6.87 (m, 1H), 6.81 (d, J=8.6 Hz, 1H), 6.63 (dd, J=7.1, 5.0 Hz, 1H), 4.55-4.33 (m, 1H), 4.02-3.76 (m, 6H), 3.67 (s, 6H), 3.46 (s, 3H), 3.45-3.34 (m, 6H), 2.22 (m, 1H), 1.93 (m, 3H); MS (ES+): 671.5 (M+1), 693.4 (M+Na); HPLC purity: 97.69%.

Scheme 409

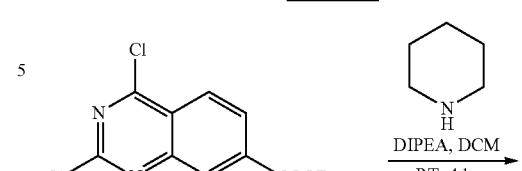

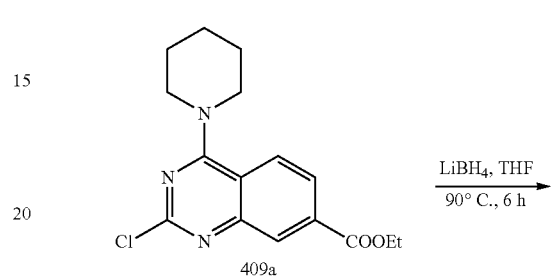

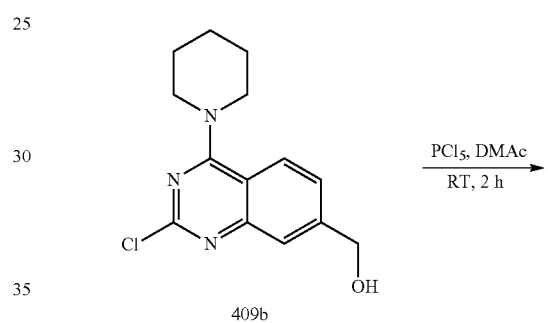

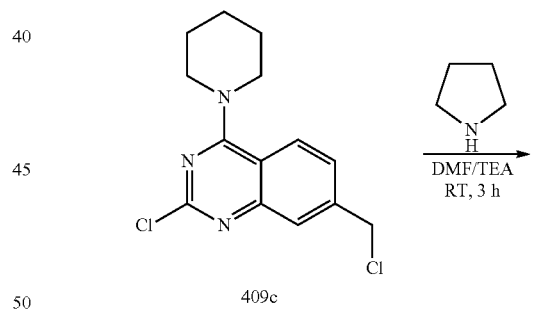

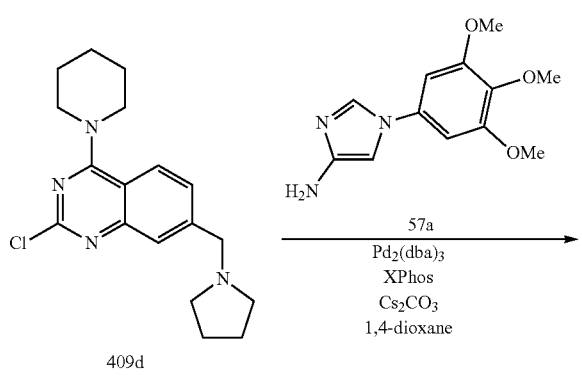

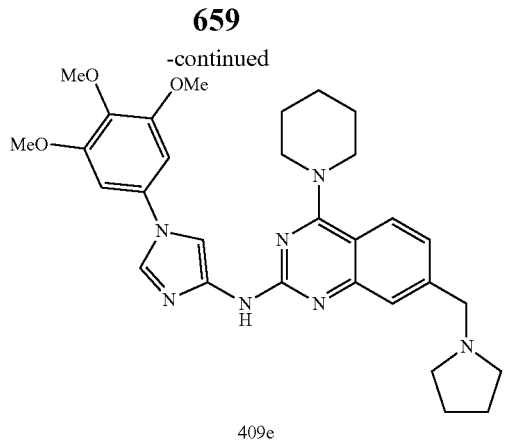

409e

Preparation of 4-(piperidin-1-yl)-7-(pyrrolidin-1-ylmethyl)-N-(1-(3,4,5-trimethoxyphenyl)-1H-imidazol-4-yl)quinazolin-2-amine (409e)

Step-1: Preparation of ethyl 2-chloro-4-(piperidin-1-yl)quinazoline-7-carboxylate (409a)

Compound 409a was prepared from ethyl 2,4-dichloroquinazoline-7-carboxylate (399a) (8.0 g, 29.5 mmol) in DCM (80 mL) using DIPEA (48.0 mL), piperidine (3.01 g, 35.41 mmol) and stirring at room temperature for 4 h according to the procedure reported in step-1 of scheme 183. This gave after workup ethyl 2-chloro-4-(piperidin-1-yl)quinazoline-7-carboxylate (409a) (8.0 g, 85%) as a white solid; $^1$H NMR (300 MHz, DMSO-$d_6$) δ 8.12 (d, J=1.6 Hz, 1H), 8.07 (d, J=8.7 Hz, 1H), 7.92 (dt, J=8.7, 1.3 Hz, 1H), 4.39 (q, J=7.0 Hz, 2H), 3.82 (s, 4H), 1.73 (s, 6H), 1.42-1.30 (m, 3H); MS (ES+): 320.0 (M+1).

Step-2: Preparation of (2-chloro-4-(piperidin-1-yl)quinazolin-7-yl)methanol (409b)

Compound 409b was prepared from ethyl 2-chloro-4-(piperidin-1-yl)quinazoline-7-carboxylate (409a) (8.0 g, 25.15 mmol,) in THF (400 mL) using LiBH$_4$ (1.369 g, 62.85 mmol) with heating at 90° C. for 6 h according to the procedure reported in step-2 of scheme 399. This gave after workup and purification by flash column chromatography [silica gel, eluting with MeOH in DCM from (0%-10%)] (2-chloro-4-(piperidin-1-yl)quinazolin-7-yl)methanol (409b) (6.0 g, 86% yield) as an off-white solid; $^1$H NMR (300 MHz, DMSO-$d_6$) δ 7.93 (d, J=8.8 Hz, 1H), 7.60 (s, 1H), 7.45 (d, J=8.4 Hz, 1H), 4.67 (s, 2H), 3.34 (s, 4H), 1.71 (s, 6H); MS (ES+): 278.0 (M+1).

Step-3: Preparation of 2-chloro-7-(chloromethyl)-4-(piperidin-1-yl)quinazoline (409c)

Compound 409c was prepared from (2-chloro-4-(piperidin-1-yl)quinazolin-7-yl)methanol (409b) (6.1 g, 22.1 mmol) in N,N'-dimethylacetamide (DMAc) (122 mL) using phosphorus pentachloride (6.90 g, 33.14 mmol) with stirring at room temperature for 2 h according to the procedure reported in step-3 of scheme 399. This gave after workup 2-chloro-7-(chloromethyl)-4-(piperidin-1-yl)quinazoline (409c) which was taken as such for next step without further purification.

Step-4: Preparation of 2-chloro-4-(piperidin-1-yl)-7-(pyrrolidin-1-ylmethyl)quinazoline (409d)

Compound 409d was prepared from 2-chloro-7-(chloromethyl)-4-(piperidin-1-yl)quinazoline (409c) 3.25 g, 11.01 mmol) in DMF (48.75 mL) using TEA (19.5 mL) and pyrrolidine (1.175 g, 16.52 mmol) with stirring at room temperature for 3 h according to the procedure reported in step-3 of scheme 399. This gave after workup and purification by flash column chromatography [silica gel, eluting with MeOH in DCM (0% to 10%)] 2-chloro-4-(piperidin-1-yl)-7-(pyrrolidin-1-ylmethyl)quinazoline (409d) (2.4 g, 66.11%) as a light brown solid; $^1$H NMR (300 MHz, DMSO-$d_6$) δ 7.91 (d, J=8.6 Hz, 1H), 7.57 (s, 1H), 7.47 (d, J=9.4 Hz, 1H), 3.77 (s, 4H), 3.72 (s, 2H), 2.47 (s, 4H), 1.71 (s, 10H); MS (ES+): 330.8 (M+1).

Step-5: Preparation of 4-(piperidin-1-yl)-7-(pyrrolidin-1-ylmethyl)-N-(1-(3,4,5-trimethoxyphenyl)-1H-imidazol-4-yl)quinazolin-2-amine (409e)

Compound 409e was prepared from 2-chloro-4-(piperidin-1-yl)-7-(pyrrolidin-1-ylmethyl)quinazoline (409d) (1.5 g, 4.53 mmol), 1-(3,4,5-trimethoxyphenyl)-1H-imidazol-4-amine (57a) (1.35 g, 5.43 mmol), dicyclohexyl(2',4',6'-triisopropylbiphenyl-2-yl)phosphine (XPhos, 0.9725 g, 2.03 mmol), cesium carbonate (4.43 g, 13.59 mmol), Pd$_2$(dba)$_3$ (0.623 g, 0.68 mmol) in 1,4-dioxane (11.5 mL) and heating at 85° C. for 16 h according to the procedure reported in step-3 of scheme 101. This gave after workup and purification by flash column chromatography [silica gel, eluting with MeOH in DCM (0% to 10%)] compound 409e (330 mg, 13.38%) free base as a brown solid. This was repurified by reverse phase column chromatography [(silica gel C-18, 24 g) eluting with acetonitrile and 0.1% HCl water] and lyophilized to furnish 4-(piperidin-1-yl)-7-(pyrrolidin-1-ylmethyl)-N-(1-(3,4,5-trimethoxyphenyl)-1H-imidazol-4-yl)quinazolin-2-amine (409e) HCl salt as a white solid; $^1$H NMR (300 MHz, DMSO-$d_6$) δ 13.46 (s, 1H), 11.54 (s, 1H), 10.66 (s, 1H), 8.35 (s, 1H), 8.05 (d, J=8.6 Hz, 1H), 7.82 (s, 2H), 7.75 (d, J=8.7 Hz, 1H), 7.71 (s, 1H), 6.97 (s, 2H), 4.53 (d, J=5.8 Hz, 2H), 4.16-3.97 (m, 4H), 3.88 (s, 6H), 3.69 (s, 3H), 3.45-3.30 (m, 1H), 3.17-2.91 (m, 3H), 2.14-1.39 (m, 10H); MS (ES+): 544.5 (M+1), MS (ES−): 578.6 (M+Cl); HPLC purity: 97.35%.

Scheme 410

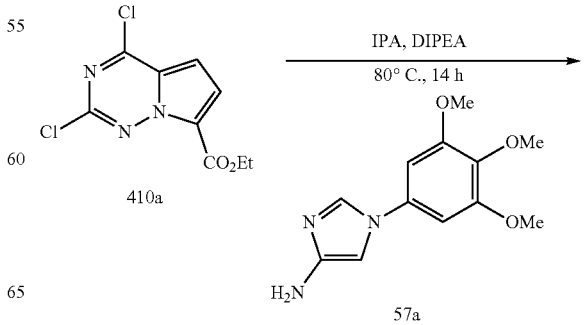

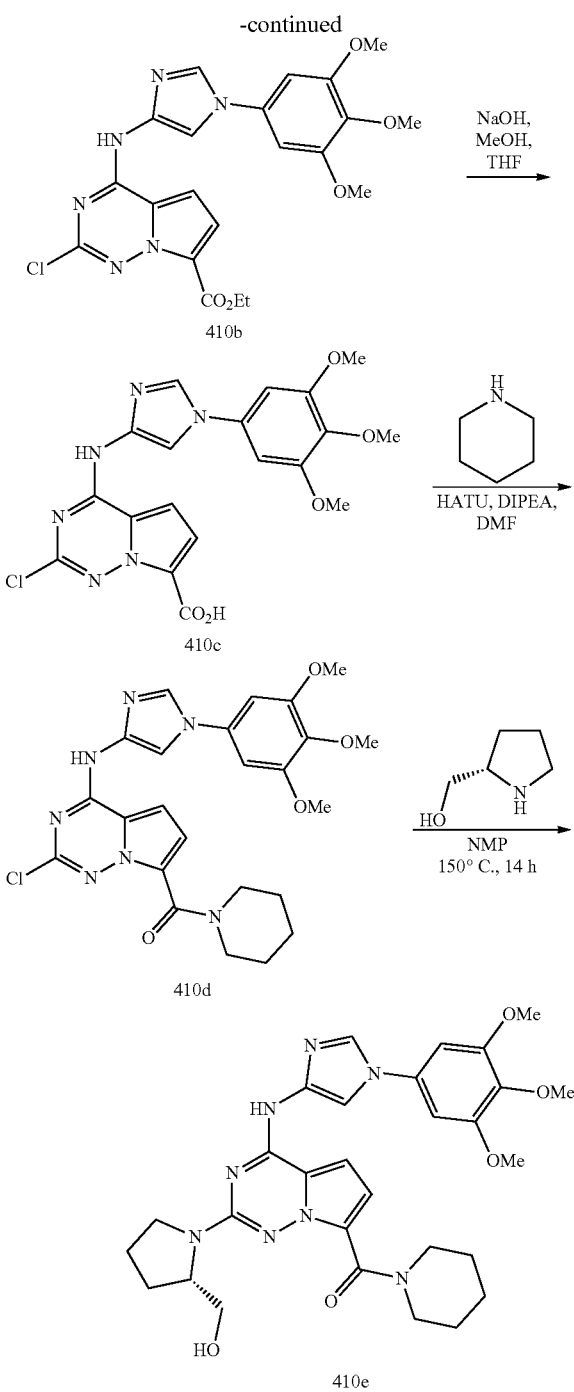

Preparation of (S)-(2-(2-(hydroxymethyl)pyrrolidin-1-yl)-4-((1-(3,4,5-trimethoxyphenyl)-1H-imidazol-4-yl)amino)pyrrolo[2,1-f][1,2,4]triazin-7-yl)(piperidin-1-yl)methanone (410e)

Step-1: Preparation of ethyl 2-chloro-4-((1-(3,4,5-trimethoxyphenyl)-1H-imidazol-4-yl)amino)pyrrolo[2,1-f][1,2,4]triazine-7-carboxylate (410b)

Compound 410b was prepared according to the procedure reported in scheme 1 from ethyl 2,4-dichloropyrrolo[2,1-f][1,2,4]triazine-7-carboxylate (410a) (1.0 g, 3.86 mmol; CAS #1363381-75-2) in 2-Propanol (20 mL) using DIPEA (1.2 g, 9.65 mmol) and 1-(3,4,5-trimethoxyphenyl)-1H-imidazol-4-amine (57a) (1.4 g, 5.79 mmol). This gave after workup and filtration ethyl 2-chloro-4-((1-(3,4,5-trimethoxyphenyl)-1H-imidazol-4-yl)amino)pyrrolo[2,1-f][1,2,4]triazine-7-carboxylate (410b) (1.6 g, 89%) as an off white solid.

Step 2: Preparation of 2-chloro-4-((1-(3,4,5-trimethoxyphenyl)-1H-imidazol-4-yl)amino)pyrrolo[2,1-f][1,2,4]triazine-7-carboxylic acid (410c)

To a solution of ethyl 2-chloro-4-((1-(3,4,5-trimethoxyphenyl)-1H-imidazol-4-yl)amino)pyrrolo[2,1-f][1,2,4]triazine-7-carboxylate (410b) (1.2 g, 2.54 mmol) in MeOH (12.0 mL) THF (12.0 mL) was added at room temperature a solution of —NaOH (2.03 g, 50.83 mmol) in water (12.0 mL). The reaction mixture was stirred for 4 h at 65° C., cooled to room temperature and poured into aqueous 1N HCl (15.0 mL). The solid obtained was collected by filtration dried in vacuum to furnish 2-chloro-4-((1-(3,4,5-trimethoxyphenyl)-1H-imidazol-4-yl)amino)pyrrolo[2,1-f][1,2,4]triazine-7-carboxylic acid (410c) (0.9 g, 79.78%) as an off white solid; $^1$H NMR (300 MHz, DMSO-$d_6$) δ 11.66 (s, 1H), 8.32 (s, 1H), 8.16 (d, J=1.7 Hz, 1H), 7.93 (d, J=1.5 Hz, 1H), 7.79 (s, 1H), 6.95 (s, 2H), 3.88 (s, 6H), 3.70 (s, 3H).

Step-3: Preparation of (2-chloro-4-((1-(3,4,5-trimethoxyphenyl)-1H-imidazol-4-yl)amino)pyrrolo[2,1-f][1,2,4]triazin-7-yl)(piperidin-1-yl)methanone (410d)

To a stirred solution of 2-chloro-4-((1-(3,4,5-trimethoxyphenyl)-1H-imidazol-4-yl)amino)pyrrolo[2,1-f][1,2,4]triazine-7-carboxylic acid (410c) (0.9 g, 2.02 mmol) in DMF (9.0 mL) was added at room temperature piperidine (0.340 g, 4.04 mmol), HATU (1.1 g, 3.03 mmol), DIPEA (0.65 g, 5.05 mmol) and stirred at room temperature for 14 h. The reaction mixture was poured into ice water (10.0 mL) and solid obtained was collected by filtration, dried in vacuum to furnish (2-chloro-4-((1-(3,4,5-trimethoxyphenyl)-1H-imidazol-4-yl)amino)pyrrolo[2,1-f][1,2,4]triazin-7-yl)(piperidin-1-yl)methanone (410d) (0.8 g, 77%) as an off white solid; $^1$H NMR (300 MHz, DMSO-$d_6$) δ 8.22 (s, 1H), 8.00-7.87 (m, 2H), 7.56 (s, 1H), 7.12 (s, 1H), 6.94 (s, 2H), 3.88 (s, 6H), 3.70 (s, 3H), 3.60 (m, 4H), 1.61 (m, 6H).

Step-4: Preparation of (S)-(2-(2-(hydroxymethyl)pyrrolidin-1-yl)-4-((1-(3,4,5-trimethoxyphenyl)-1H-imidazol-4-yl)amino)pyrrolo[2,1-f][1,2,4]triazin-7-yl)(piperidin-1-yl)methanone (410e)

Compound 410e was prepared from (2-chloro-4-((1-(3,4,5-trimethoxyphenyl)-1H-imidazol-4-yl)amino)pyrrolo[2,1-f][1,2,4]triazin-7-yl)(piperidin-1-yl)methanone (410d) (0.8 g, 1.56 mmol), (S)-pyrrolidin-2-ylmethanol (1.18 g, 11.66 mmol) in NMP (10 mL), heating at 150° C. for 14 h according to the procedure reported in scheme 2. This gave after workup and purification by flash column chromatography [silica gel, eluting with (0-10%) MeOH in DCM] (S)-(2-(2-(hydroxymethyl)pyrrolidin-1-yl)-4-((1-(3,4,5-trimethoxyphenyl)-1H-imidazol-4-yl)amino)pyrrolo[2,1-f][1,2,4]triazin-7-yl)(piperidin-1-yl)methanone (410e) (0.13 g, 14.4%) as an off white solid; $^1$H NMR (300 MHz, DMSO-$d_6$) δ 10.76 (s, 1H), 8.26 (d, J=1.6 Hz, 1H), 7.97 (d, J=1.7 Hz, 1H), 7.56 (d, J=1.8 Hz, 1H), 7.37 (d, J=1.8 Hz, 1H), 6.96 (s, 2H), 4.87 (t, J=5.1 Hz, 1H), 4.32-4.13 (m, 1H), 3.88 (s, 6H), 3.68 (s, 3H), 3.65-3.49 (m, 8H), 2.12-1.78 (m, 4H), 1.77-1.39 (m, 6H); MS (ES+): 577.4 (M+1); HPLC purity: 97.75%.

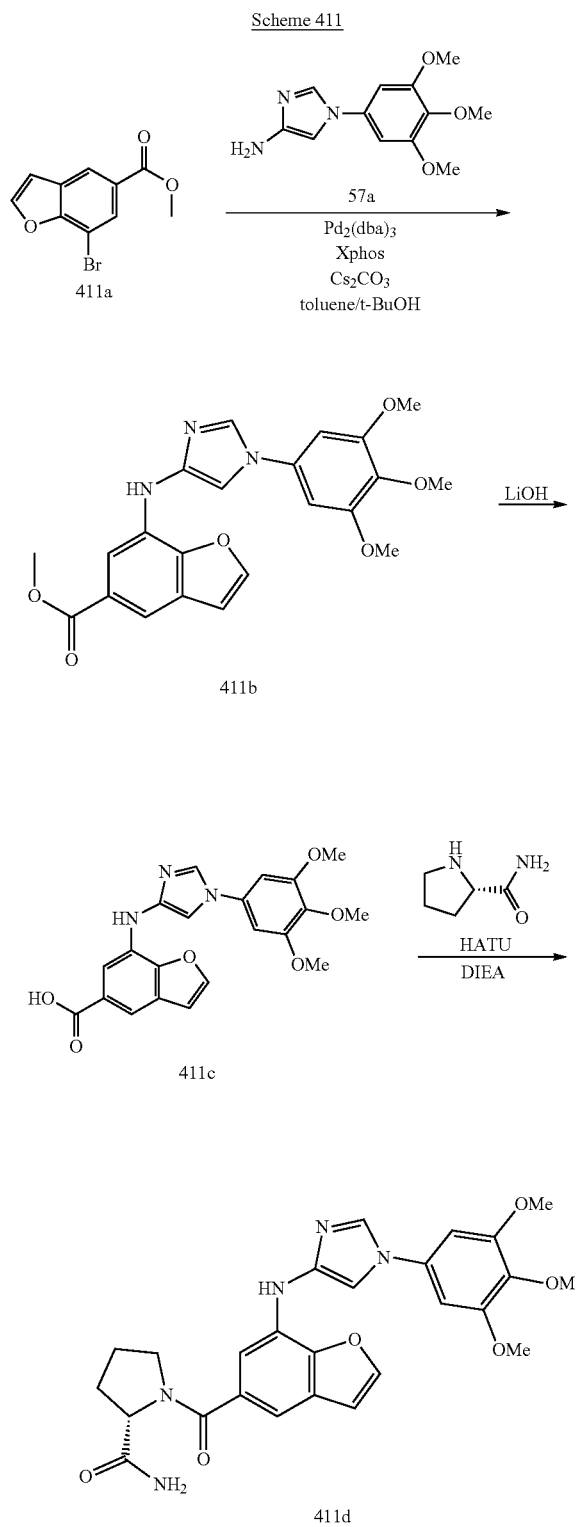

Preparation of (S)-1-(7-((1-(3,4,5-trimethoxyphenyl)-1H-imidazol-4-yl)amino)benzofuran-5-carbonyl)pyrrolidine-2-carboxamide (411d)

Step-1: Preparation of methyl 7-((1-(3,4,5-trimethoxyphenyl)-1H-imidazol-4-yl)amino)benzofuran-5-carboxylate (411b)

Compound 411b was prepared from methyl 7-bromobenzofuran-5-carboxylate (411a) (1 g, 3.92 mmol, CAS #286836-79-1), 1-(3,4,5-trimethoxyphenyl)-1H-imidazol-4-amine (57a) (0.98 g, 3.92 mmol), dicyclohexyl(2',4',6'-triisopropylbiphenyl-2-yl)phosphine (XPhos, 0.75 g, 1.57 mmol), cesium carbonate (2.55 g, 7.84 mmol), Pd$_2$(dba)$_3$ (0.72 g, 0.78 mmol) in toluene/t-BuOH (25 mL, Ratio: 5:2)) and heating at 90° C. for 12 h according to the procedure reported in step-3 of scheme 101. This gave after workup and purification by flash column chromatography [silica (24 g), eluting with DMA80 in DCM from 0-100%] followed by purification by reverse phase column chromatography [C18 steel column (250 mm×30 mm), eluting with ACN in water (containing 0.1% TFA) from 0-100%] methyl 7-((1-(3,4,5-trimethoxyphenyl)-1H-imidazol-4-yl)amino)benzofuran-5-carboxylate (411b) (230 mg, 13% yield) TFA salt as a white solid; $^1$H NMR (300 MHz, DMSO-d$_6$) δ 8.66-8.53 (m, 2H), 8.12 (d, J=2.2 Hz, 1H), 7.81-7.73 (m, 2H), 7.61 (s, 1H, D$_2$O exchangeable), 7.07 (d, J=2.1 Hz, 1H), 7.00 (s, 2H), 3.87 (s, 6H), 3.82 (s, 3H), 3.69 (s, 3H); $^{19}$F NMR (282 MHz, DMSO-d$_6$) δ −74.12; MS (ES+): 424.1 (M+1).

Step 2: Preparation of 7-((1-(3,4,5-trimethoxyphenyl)-1H-imidazol-4-yl)amino)benzofuran-5-carboxylic acid (411c)

To a solution of methyl 7-((1-(3,4,5-trimethoxyphenyl)-1H-imidazol-4-yl)amino)benzofuran-5-carboxylate (411b) (180 mg, 0.43 mmol) in MeOH/THF (6 mL) was added a solution of lithium hydroxide monohydrate (23 mg, 0.55 mmol) in water (2.0 mL). The resulting mixture was stirred at RT for 12 h and concentrated in vacuum. The residue obtained was acidified to PH~4 and the solid obtained was collected by filtration to afford on drying 7-((1-(3,4,5-trimethoxyphenyl)-1H-imidazol-4-yl)amino)benzofuran-5-carboxylic acid (411c) (80 mg, 46% yield) as a brown solid, 40 mg of this compound 411c was further purified by reverse phase column chromatography [C18 steel column (250 mm×30 mm), eluting with ACN in water (containing 0.1% HCl) from 0-100%] to furnish 7-((1-(3,4,5-trimethoxyphenyl)-1H-imidazol-4-yl)amino)benzofuran-5-carboxylic acid (411c) (20 mg) HCl salt as a white solid; $^1$H NMR (300 MHz, DMSO-d$_6$) δ 12.86 (s, 1H, D$_2$O exchangeable), 9.28 (s, 1H), 8.95 (s, 1H, D$_2$O exchangeable), 8.13 (d, J=2.2 Hz, 1H), 7.92 (d, J=1.7 Hz, 1H), 7.84 (d, J=1.5 Hz, 1H), 7.58 (d, J=1.5 Hz, 1H), 7.13 (s, 2H), 7.10 (d, J=2.2 Hz, 1H), 3.88 (s, 6H), 3.71 (s, 3H); MS (ES+): 410.1 (M+1); (ES−) 408.2 (M−1).

Step-3: Preparation of (S)-1-(7-((1-(3,4,5-trimethoxyphenyl)-1H-imidazol-4-yl)amino)benzofuran-5-carbonyl)pyrrolidine-2-carboxamide (411d)

Compound 411d was prepared from 7-((1-(3,4,5-trimethoxyphenyl)-1H-imidazol-4-yl)amino)benzofuran-5-carboxylic acid (411c) (30 mg, 0.073 mmol), using L-prolinamide (10.04 mg, 0.088 mmol) HATU (33.4 mg, 0.088 mmol), DIEA (0.038 mL, 0.22 mmol) in DMF (6 mL) according to the procedure reported in step-3 of scheme 410.

This gave after workup and purification by flash column chromatography [silica (24 g), eluting with DMA80 in DCM from 0 to 80%] followed by purification using reverse phase column chromatography [C18 steel column (250 mm×30 mm), eluting with ACN in water (containing 0.1% HCl) from 0-100%] (S)-1-(7-((1-(3,4,5-trimethoxyphenyl)-1H-imidazol-4-yl)amino)benzofuran-5-carbonyl)pyrrolidine-2-carboxamide (411d) (5 mg, 13% yield) HCl salt as a yellow solid; $^1$H NMR (300 MHz, DMSO-d$_6$) δ 11.85 and 9.52 (2s, 1H), 10.56 and 9.06 (2s, 1H, D$_2$O exchangeable), 8.22 and 8.11 2 (d, J=2.2 Hz, 1H), 8.05-7.95 (m, 1H), 7.52-7.33 (m, 2H), 7.26 (s, 1H), 7.21-7.09 (m, 2H), 7.07-6.86 (m, 3H), 4.42-4.29 (m, 1H), 3.88 and 3.79 (2s, 6H), 3.70 and 3.67 (2s, 3H), 3.63-3.44 (m, 2H), 2.26-2.04 (m, 1H), 1.91-1.69 (m, 3H); MS (ES$^+$) 506.2 (M+1); (ES−) 504.3 (M−1).

Scheme 412

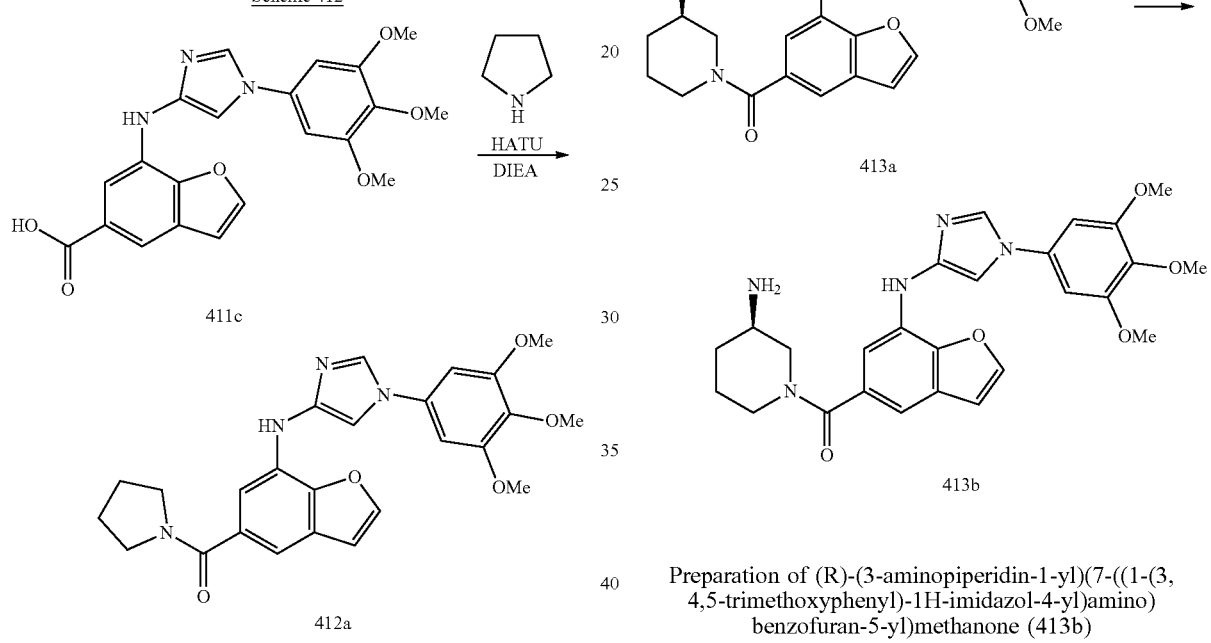

412a

Preparation of pyrrolidin-1-yl(7-((1-(3,4,5-trimethoxyphenyl)-1H-imidazol-4-yl)amino)benzofuran-5-yl)methanone (412a)

Compound 412a was prepared from 7-((1-(3,4,5-trimethoxyphenyl)-1H-imidazol-4-yl)amino)benzofuran-5-carboxylic acid (411c) (100 mg, 0.24 mmol), using pyrrolidine (20.85 mg, 0.29 mmol), HATU (111 mg, 0.29 mmol), DIEA (0.13 mL, 0.73 mmol) in DMF (6 mL) according to the procedure reported in step-3 of scheme 410. This gave after workup and purification by flash column chromatography [silica (24 g), eluting with DMA80 in DCM from 0 to 80%] followed by purification using reverse phase column chromatography [C18 (50 g), eluting with ACN in water (containing 0.1% HCl) from 0-100%] pyrrolidin-1-yl(7-((1-(3,4,5-trimethoxyphenyl)-1H-imidazol-4-yl)amino)benzofuran-5-yl)methanone (412a) (52 mg, 46% yield) HCl salt as a white solid; $^1$H NMR (300 MHz, DMSO-d$_6$) δ 9.23 (s, 1H), 8.87 (s, 1H, D$_2$O exchangeable), 8.10 (d, J=2.2 Hz, 1H), 7.90 (d, J=1.7 Hz, 1H, D$_2$O exchangeable), 7.33 (d, J=1.5 Hz, 1H), 7.12 (s, 3H), 7.01 (d, J=2.2 Hz, 1H), 3.88 (s, 6H), 3.70 (s, 3H), 3.47-3.40 (m, 4H), 1.92-1.72 (m, 4H); MS (ES+): 463.2 (M+1).

Scheme 413

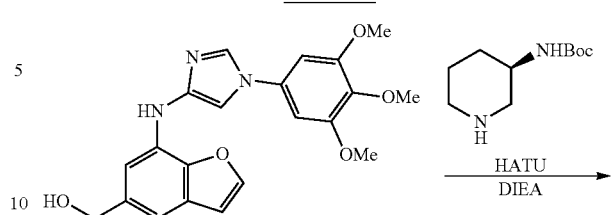

Preparation of (R)-(3-aminopiperidin-1-yl)(7-((1-(3,4,5-trimethoxyphenyl)-1H-imidazol-4-yl)amino)benzofuran-5-yl)methanone (413b)

Step-1: Preparation of (R)-tert-butyl (1-(7-((1-(3,4,5-trimethoxyphenyl)-1H-imidazol-4-yl)amino)benzofuran-5-carbonyl)piperidin-3-yl)carbamate (413a)

Compound 413a was prepared from 7-((1-(3,4,5-trimethoxyphenyl)-1H-imidazol-4-yl)amino)benzofuran-5-carboxylic acid (411c) (150 mg, 0.37 mmol), using (R)-tert-butyl piperidin-3-ylcarbamate (73.4 mg, 0.37 mmol), HATU (167 mg, 0.44 mmol), DIEA (0.19 mL, 1.10 mmol) in DMF (6 mL) according to the procedure reported in step-3 of scheme 410. This gave after workup and purification by flash column chromatography [silica (40 g), eluting with DMA80 in DCM from 0 to 30%] followed by [silica (40 g), eluting with EtOAc/MeOH (9:1) in hexane from 0 to 100%] (R)-tert-butyl (1-(7-((1-(3,4,5-trimethoxyphenyl)-1H-imidazol-4-yl)amino)benzofuran-5-carbonyl)piperidin-3-yl)carbamate (413a) (142 mg, 66% yield) as a white solid; MS (ES+): 592.3 (M+1); (ES−): 590.5 (M−1).

Step-2, preparation of (R)-(3-aminopiperidin-1-yl)(7-((1-(3,4,5-trimethoxyphenyl)-1H-imidazol-4-yl)amino)benzofuran-5-yl)methanone (413b)

To a solution of (R)-tert-butyl (1-(7-((1-(3,4,5-trimethoxyphenyl)-1H-imidazol-4-yl)amino)benzofuran-5- carbonyl)piperidin-3-yl)carbamate (413a) (140 mg, 0.24 mmol) in DCM (10 mL) was added TFA (0.37 mL, 4.73 mmol). The resulting mixture was stirred at room temperature for 2 h and concentrated in vacuum to dryness. The residue obtained was purified by reverse phase column chromatography [C18 steel column (250 mm×30 mm), eluting with ACN in water (containing 0.1% HCl) from 0-100%] to give (R)-(3-aminopiperidin-1-yl)(7-((1-(3,4,5-trimethoxyphenyl)-1H-imidazol-4-yl)amino)benzofuran-5-yl)methanone (413b) (50 mg, 43.0% yield) HCl salt as a white solid; $^1$H NMR (300 MHz, DMSO-$d_6$) δ 8.97 (s, 1H), 8.78 (s, 1H), 8.20 (s, 3H, $D_2O$ exchangeable), 8.10 (d, J=2.1 Hz, 1H), 7.80 (s, 1H, $D_2O$ exchangeable), 7.19 (s, 1H), 7.16-7.11 (m, 1H), 7.08 (s, 2H), 7.01 (d, J=2.2 Hz, 1H), 4.36-4.16 (m, 1H), 3.88 (s, 6H), 3.70 (s, 3H), 3.25-2.98 (m, 4H), 2.06-1.93 (m, 1H), 1.80-1.68 (m, 1H), 1.65-1.40 (m, 2H); MS (ES+): 492.2 (M+1).

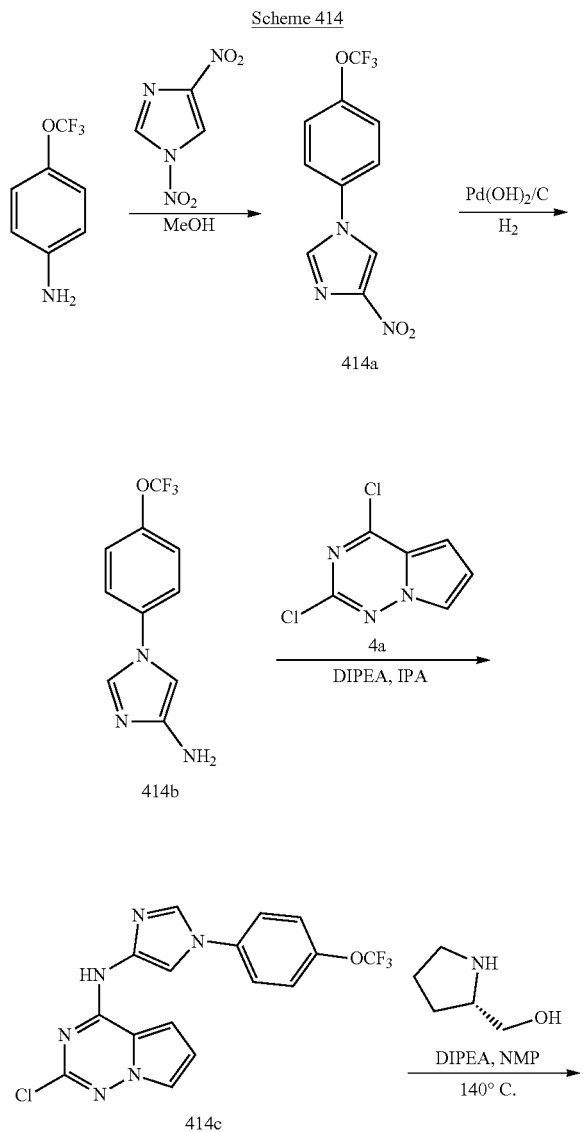

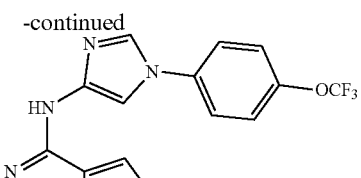

414d

Preparation of (S)-(1-(4-((1-(4-(trifluoromethoxy)phenyl)-1H-imidazol-4-yl)amino)pyrrolo[2,1-f][1,2,4]triazin-2-yl)pyrrolidin-2-yl)methanol (414d)

Step-1: Preparation of 4-nitro-1-(4-(trifluoromethoxy)phenyl)-1H-imidazole (414a)

Reaction of 1,4-dinitro-1H-imidazole (3.57 g, 22.58 mmol) with 4-(trifluoromethoxy)aniline (4 g, 22.58 mmol) as reported in step-2 of General scheme for preparation of 3-substituted-(4-amino-1H-imidazol-1-yl) gave after filtration 4-nitro-1-(4-(trifluoromethoxy)phenyl)-1H-imidazole (414a) (3.5 g, 57% yield) as a yellow solid; $^1$H NMR (300 MHz, DMSO-$d_6$) δ 9.05 (d, J=1.6 Hz, 1H), 8.51 (d, J=1.6 Hz, 1H), 8.00-7.97 (m, 1H), 7.97-7.93 (m, 1H), 7.67-7.64 (m, 1H), 7.64-7.60 (m, 1H); MS (ES+): 274.1 (M+1).

Step-2: Preparation of 1-(4-(trifluoromethoxy)phenyl)-1H-imidazol-4-amine (414b)

Reduction of nitro to amine of 4-nitro-1-(4-(trifluoromethoxy)phenyl)-1H-imidazole (414a) (4.1 g, 15.01 mmol) in MeOH (120 mL) using Palladium hydroxide on carbon, 20 wt. % loading (dry basis), matrix carbon, wet support (1.05 g, 1.50 mmol as reported in step-3 of General scheme for preparation of 3-substituted-(4-amino-1H-imidazol-1-yl) gave 1-(4-(trifluoromethoxy)phenyl)-1H-imidazol-4-amine (414b) (2.2 g, 60% yield) as a light yellow solid; MS (ES+): 244.1 (M+1).

Step-3: Preparation of 2-chloro-N-(1-(4-(trifluoromethoxy)phenyl)-1H-imidazol-4-yl)pyrrolo[2,1-f][1,2,4]triazin-4-amine (414c)

Compound 414c was prepared from 2,4-dichloropyrrolo[2,1-f][1,2,4]triazine (4a) (0.93 g, 4.93 mmol) in 2-Propanol (40 mL) using DIPEA (2.59 mL, 14.80 mmol), 1-(4-(trifluoromethoxy)phenyl)-1H-imidazol-4-amine (414b) (1.2 g, 4.93 mmol) and heating at reflux for 2 h according to the procedure reported in step-1 of scheme 183. This gave after workup and filtration 2-chloro-N-(1-(4-(trifluoromethoxy)phenyl)-1H-imidazol-4-yl)pyrrolo[2,1-f][1,2,4]triazin-4-amine (414c) (720 mg, 37% yield) as a yellow solid; $^1$H NMR (300 MHz, DMSO-$d_6$) δ 11.37 (s, 1H, $D_2O$ exchangeable), 8.32-8.25 (m, 1H), 7.96-7.88 (m, 1H), 7.85-7.74 (m, 3H), 7.64-7.53 (m, 2H), 7.41 (s, 1H), 6.76-6.67 (m, 1H); MS (ES+): 395.1 (M+1); (ES−): 393.2 (M−1).

Step-4: Preparation of (S)-(1-(4-((1-(4-(trifluoromethoxy)phenyl)-1H-imidazol-4-yl)amino)pyrrolo[2,1-f][1,2,4]triazin-2-yl)pyrrolidin-2-yl)methanol (414d)

Compound 414d was prepared from 2-chloro-N-(1-(4-(trifluoromethoxy)phenyl)-1H-imidazol-4-yl)pyrrolo[2,1-f]

[1,2,4]triazin-4-amine (414c) (500 mg, 1.27 mmol), (S)-pyrrolidin-2-ylmethanol 384 mg, 3.80 mmol), N-ethyl-N-isopropylpropan-2-amine (0.66 mL, 3.80 mmol) in NMP (5 mL) and heating at 140° C. overnight according to the procedure reported in scheme 2. This gave after workup and purification by flash column chromatography [silica (12 g), eluting with ethyl acetate/MeOH (9:1) in hexane from 0-70%] followed by reverse phase column chromatography [C18 steel column (250 mm×30 mm), eluting with ACN in water (containing 0.1% HCl) from 0-100%] (S)-(1-(4-((1-(4-(trifluoromethoxy)phenyl)-1H-imidazol-4-yl)amino)pyrrolo[2,1-f][1,2,4]triazin-2-yl)pyrrolidin-2-yl)methanol (414d) (110 mg, 19% yield) TFA salt as white solid; $^1$H NMR (300 MHz, DMSO-$d_6$) δ 10.84 (s, 1H, D$_2$O exchangeable), 8.61 (d, J=1.6 Hz, 1H), 8.02 (d, J=1.6 Hz, 1H), 7.99-7.90 (m, 2H), 7.55 (d, J=8.2 Hz, 2H), 7.49-7.42 (m, 1H), 7.16 (dd, J=4.4, 1.6 Hz, 1H), 6.49-6.40 (m, 1H), 5.36 (bs, 1H), 4.24-4.11 (m, 1H), 3.75 (dd, J=10.0, 3.6 Hz, 1H), 3.54-3.43 (m, 1H), 3.43-3.28 (m, 2H), 2.13-1.79 (m, 4H); $^{19}$F NMR (282 MHz, DMSO-$d_6$) δ −56.94; MS (ES+): 460.2 (M+1); (ES−): 458.3 (M−1).

Scheme 415

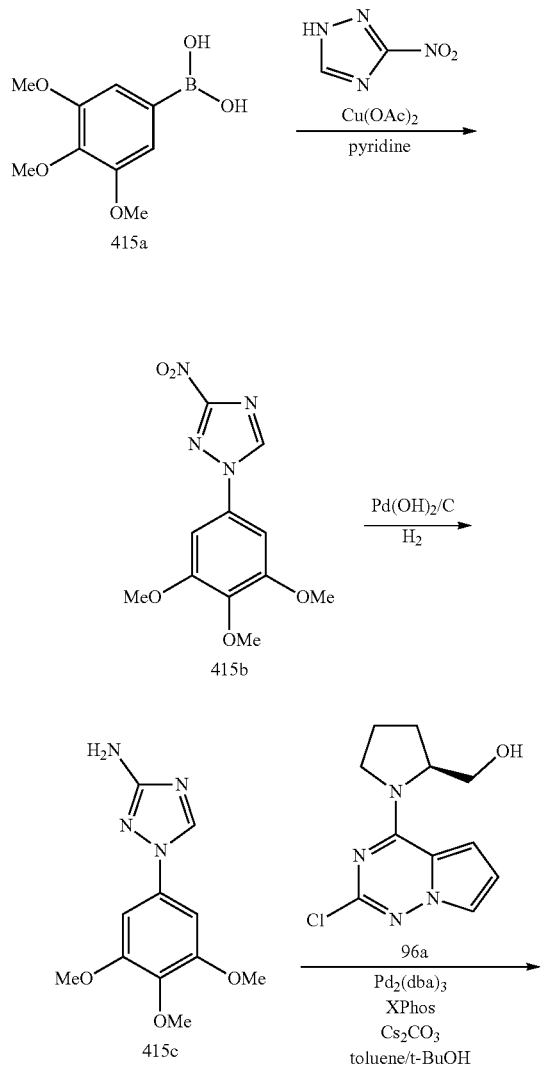

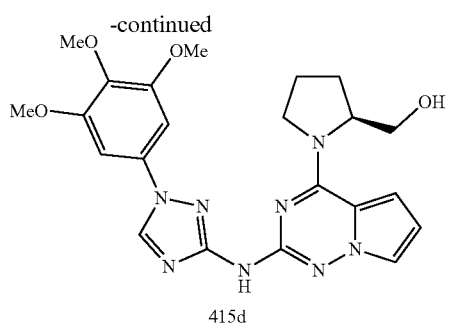

415d

Preparation of (S)-(1-(2-((1-(3,4,5-trimethoxyphenyl)-1H-1,2,4-triazol-3-yl)amino)pyrrolo[2,1-f][1,2,4]triazin-4-yl)pyrrolidin-2-yl)methanol (415d)

Step-1: Preparation of 3-nitro-1-(3,4,5-trimethoxyphenyl)-1H-1,2,4-triazole (415b)

To a solution of 3-nitro-1H-1,2,4-triazole (500 mg, 4.38 mmol; CAS #: 24807-55-4) in DCM (50 mL) was added copper (II) acetate (1194 mg, 6.58 mmol), 3,4,5-trimethoxyphenylboronic acid (415a) (1859 mg, 8.77 mmol; CAS #: 182163-96-8) and pyridine (0.71 mL, 8.77 mmol). The resulting mixture was stirred overnight under air atmosphere and concentrated in vacuum to dryness. The residue was taken up with EtOAc and filtered through a Celite pad, the filtrate was concentrated in vacuum and the obtained residue was purified by flash column chromatography [silica (12 g), eluting with EtOAc in hexane from 0-50%] to furnish 3-nitro-1-(3,4,5-trimethoxyphenyl)-1H-1,2,4-triazole (415b) (560 mg, 46% yield) as a white solid; MS (ES+): 281.1 (M+1).

Step-2: Preparation of 1-(3,4,5-trimethoxyphenyl)-1H-1,2,4-triazol-3-amine (415c)

A solution of 3-nitro-1-(3,4,5-trimethoxyphenyl)-1H-1,2,4-triazole (415b) (200 mg, 0.71 mmol) in MeOH (120 mL) was hydrogenated using Palladium hydroxide on carbon, 20 wt. % loading (dry basis), matrix carbon, wet support (50.1 mg, 0.071 mmol) for 6 h at atmospheric pressure. The reaction mixture was filtered through Celite and concentrated to afford 1-(3,4,5-trimethoxyphenyl)-1H-1,2,4-triazol-3-amine (415c) (165 mg, 92%) as a light yellow solid; $^1$H NMR (300 MHz, DMSO-$d_6$) δ 8.82 (s, 1H), 7.02 (s, 2H), 5.68 (s, 2H), 3.83 (s, 6H), 3.66 (s, 3H); MS (ES+): 251.1 (M+1).

Step-3: Preparation of (S)-(1-(2-((1-(3,4,5-trimethoxyphenyl)-1H-1,2,4-triazol-3-yl)amino)pyrrolo[2,1-f][1,2,4]triazin-4-yl)pyrrolidin-2-yl)methanol (415d)

Compound 415d was prepared from (S)-(1-(2-chloropyrrolo[2,1-f][1,2,4]triazin-4-yl)pyrrolidin-2-yl)methanol (96a) (160 mg, 0.63 mmol), 1-(3,4,5-trimethoxyphenyl)-1H-1,2,4-triazol-3-amine (415c) (158 mg, 0.63 mmol), dicyclohexyl(2',4',6'-triisopropylbiphenyl-2-yl)phosphine (XPhos, 121 mg, 0.25 mmol), cesium carbonate (516 mg, 1.58 mmol), Pd$_2$(dba)$_3$ (116 mg, 0.13 mmol) in toluene/t-BuOH (10 mL, Ratio: 5:2)) and heating at 110° C. overnight according to the procedure reported in step-3 of scheme 101. This gave after workup and purification by flash column chromatography [silica (40 g), eluting with DMA80 in DCM from 0-60%] (S)-(1-(2-((1-(3,4,5-trimethoxyphenyl)-1H-1,2,4-triazol-3-yl)amino)pyrrolo[2,1-f][1,2,4]triazin-4-yl)pyrrolidin-2-yl)methanol (415d) free base as an off white solid; 68 mg was taken and mixed with 1% HCl for 1 h, excess HCl was then removed, the residue was taken up with water/CH₃CN and lyophilized to give compound 415d HCl salt as a white solid; ¹H NMR (300 MHz, DMSO-d₆) δ 9.62 (s, 1H, D₂O exchangeable), 9.19 (s, 1H), 7.60-7.54 (m, 1H), 7.16 (s, 2H), 6.93 (d, J=4.1 Hz, 1H), 6.58 (s, 1H), 4.56 (s, 1H), 4.03-4.00 (m, 4H), 3.87 (s, 6H), 3.69 (s, 3H), 3.66-3.54 (m, 1H), 2.23-1.85 (m, 4H); MS (ES⁺) 467.2 (M+1); HPLC purity: 97.34%.

Scheme 416

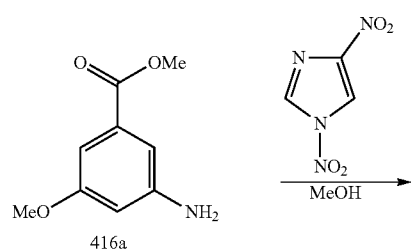

416a

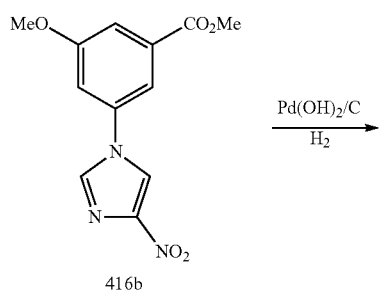

416b

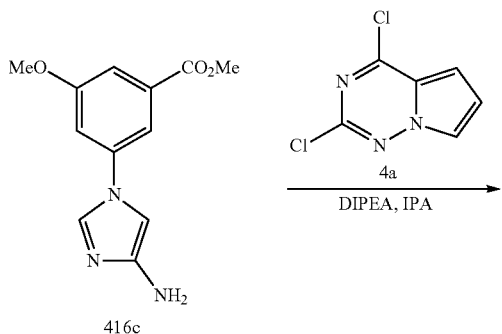

416c

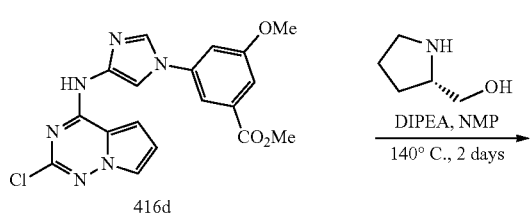

416d

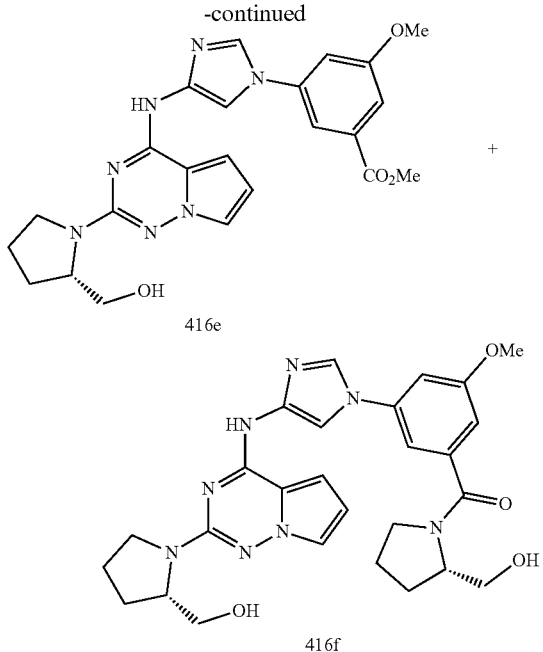

416e

416f

Preparation of (S)-methyl 3-(4-((2-(2-(hydroxymethyl)pyrrolidin-1-yl)pyrrolo[2,1-f][1,2,4]triazin-4-yl)amino)-1H-imidazol-1-yl)-5-methoxybenzoate (416e) and ((S)-2-(hydroxymethyl)pyrrolidin-1-yl) (3-(4-((2-((S)-2-(hydroxymethyl)pyrrolidin-1-yl) pyrrolo[2,1-f][1,2,4]triazin-4-yl)amino)-1H-imidazol-1-yl)-5-methoxyphenyl)methanone (416f)

Step-1: Preparation of methyl 3-methoxy-5-(4-nitro-1H-imidazol-1-yl)benzoate (416b)

Reaction of 1,4-dinitro-1H-imidazole (4.36 g, 27.6 mmol) with methyl 3-amino-5-methoxybenzoate (416a) (5 g, 27.6 mmol; CAS #217314-47-1) in MeOH (50 mL) as reported in step-2 of General scheme for preparation of 3-substituted-(4-amino-1H-imidazol-1-yl) gave after filtration methyl 3-methoxy-5-(4-nitro-1H-imidazol-1-yl)benzoate (416b) (6.75 g, 88% yield) as a yellow solid; ¹H NMR (300 MHz, DMSO-d₆) δ 9.14 (d, J=1.6 Hz, 1H), 8.60 (d, J=1.6 Hz, 1H), 7.91 (dd, J=2.1, 1.3 Hz, 1H), 7.70 (t, J=2.2 Hz, 1H), 7.52 (dd, J=2.4, 1.3 Hz, 1H), 3.92 (s, 3H), 3.90 (s, 3H).

Step-2: Preparation of methyl 3-(4-amino-1H-imidazol-1-yl)-5-methoxybenzoate (416c)

Reduction of nitro to amine of methyl 3-methoxy-5-(4-nitro-1H-imidazol-1-yl)benzoate (416b) (6.74 g, 24.31 mmol) in MeOH (120 mL) using Palladium hydroxide on carbon, 20 wt. % loading (dry basis), matrix carbon, wet support (1.707 g, 2.431 mmol) as reported in step-3 of General scheme for preparation of 3-substituted-(4-amino-1H-imidazol-1-yl) gave methyl 3-(4-amino-1H-imidazol-1-yl)-5-methoxybenzoate (416c) (5.6 g, 93% yield) as a light yellow semi-solid; ¹H NMR (300 MHz, DMSO-d₆) δ 7.98 (d, J=1.6 Hz, 1H), 7.62-7.54 (m, 1H), 7.40 (t, J=2.2 Hz, 1H), 7.36-7.29 (m, 1H), 6.72 (d, J=1.7 Hz, 1H), 4.47 (s, 2H), 3.88 (s, 3H), 3.88 (s, 3H).

Step-3: Preparation of methyl 3-(4-((2-chloropyrrolo[2,1-f][1,2,4]triazin-4-yl)amino)-1H-imidazol-1-yl)-5-methoxybenzoate (416d)

Compound 416d was prepared from 2,4-dichloropyrrolo [2,1-f][1,2,4]triazine (4a) (1.37 g, 7.28 mmol) in 2-Propanol (40 mL) using DIPEA (3.81 mL, 21.84 mmol), methyl 3-(4-amino-1H-imidazol-1-yl)-5-methoxybenzoate (416c) (1.8 g, 7.28 mmol) and heating at reflux for 2 h according to the procedure reported in step-1 of scheme 183. This gave after workup and filtration methyl 3-(4-((2-chloropyrrolo[2,1-f][1,2,4]triazin-4-yl)amino)-1H-imidazol-1-yl)-5-methoxybenzoate (416d) (1.5 g, 52% yield) as a yellow solid; $^1$H NMR (300 MHz, DMSO-d$_6$) δ 11.35 (s, 1H), 8.37 (d, J=1.6 Hz, 1H), 7.94 (d, J=1.6 Hz, 1H), 7.78 (dd, J=2.6, 1.5 Hz, 1H), 7.68 (dd, J=2.0, 1.3 Hz, 1H), 7.54 (t, J=2.2 Hz, 1H), 7.44 (dd, J=2.4, 1.3 Hz, 1H), 7.40 (d, J=4.3 Hz, 1H), 6.73 (dd, J=4.5, 2.6 Hz, 1H), 3.91 (d, J=2.3 Hz, 6H); MS (ES+): 399.1 (M+1); MS (ES−): 397.2 (M−1).

Step-4: Preparation of (S)-methyl 3-(4-((2-(2-(hydroxymethyl)pyrrolidin-1-yl)pyrrolo[2,1-f][1,2,4]triazin-4-yl)amino)-1H-imidazol-1-yl)-5-methoxybenzoate (416e) and ((S)-2-(hydroxymethyl)pyrrolidin-1-yl)(3-(4-((2-((S)-2-(hydroxymethyl)pyrrolidin-1-yl)pyrrolo[2,1-f][1,2,4]triazin-4-yl)amino)-1H-imidazol-1-yl)-5-methoxyphenyl)methanone (416f)

Compounds 416e and 416f were prepared from methyl 3-(4-((2-chloropyrrolo[2,1-f][1,2,4]triazin-4-yl)amino)-1H-imidazol-1-yl)-5-methoxybenzoate (416d) (1 g, 2.51 mmol), (S)-pyrrolidin-2-ylmethanol (0.76 g, 7.52 mmol), N-ethyl-N-isopropylpropan-2-amine (1.31 mL, 7.52 mmol) in NMP (15 mL) and heating at 140° C. for 2 days according to the procedure reported in scheme 2. This gave after workup and purification by flash column chromatography [silica (40 g), eluting with DMA80 in DCM from 0-70%] followed by reverse phase column chromatography [C18 steel column (250 mm×30 mm), eluting with ACN in water (containing 0.1% HCl) from 0-100%] (S)-methyl 3-(4-((2-(2-(hydroxymethyl)pyrrolidin-1-yl)pyrrolo[2,1-f][1,2,4]triazin-4-yl)amino)-1H-imidazol-1-yl)-5-methoxybenzoate (416e) (65 mg, 6% yield) HCl salt as a white solid and ((S)-2-(hydroxymethyl)pyrrolidin-1-yl)(3-(4-((2-((S)-2-(hydroxymethyl)pyrrolidin-1-yl)pyrrolo[2,1-f][1,2,4]triazin-4-yl)amino)-1H-imidazol-1-yl)-5-methoxyphenyl)methanone (416f) (125 mg, 9% yield) HCl salt as a white solid;

Data for compound 416e: $^1$H NMR (300 MHz, DMSO-d$_6$) δ 10.73 (s, 1H, D$_2$O exchangeable), 8.57 (d, J=1.6 Hz, 1H), 8.06 (d, J=1.6 Hz, 1H), 7.77 (t, J=1.7 Hz, 1H), 7.61 (t, J=2.2 Hz, 1H), 7.47-7.40 (m, 2H), 7.13 (dd, J=4.4, 1.7 Hz, 1H), 6.42 (dd, J=4.4, 2.4 Hz, 1H), 4.24-4.11 (m, 1H), 3.92 (s, 3H), 3.90 (s, 3H), 3.70 (dd, J=10.1, 3.7 Hz, 1H), 3.61-3.49 (m, 1H), 3.48-3.36 (m, 2H), 2.10-1.82 (m, 4H); MS (ES+): 464.4 (M+1); (ES−): 462.4 (M−1); Data for compound 416f: $^1$H NMR (300 MHz, DMSO-d$_6$) δ 10.83 (s, 1H, D$_2$O exchangeable), 8.69 (s, 1H), 8.04 (d, J=1.6 Hz, 1H, D$_2$O exchangeable), 7.49 (s, 1H), 7.46-7.43 (m, 1H), 7.43-7.37 (m, 1H), 7.14 (dd, J=4.5, 1.7 Hz, 1H), 7.09-6.96 (m, 1H), 6.51-6.38 (m, 1H), 4.23-4.06 (m, 2H), 3.88 (s, 3H), 3.70 (dd, J=10.0, 3.7 Hz, 1H), 3.67-3.55 (m, 2H), 3.53-3.43 (m, 2H), 3.40-3.02 (m, 3H), 2.04-1.67 (m, 8H); MS (ES+): 533.5 (M+1); (ES−): 531.5 (M−1).

Scheme 417

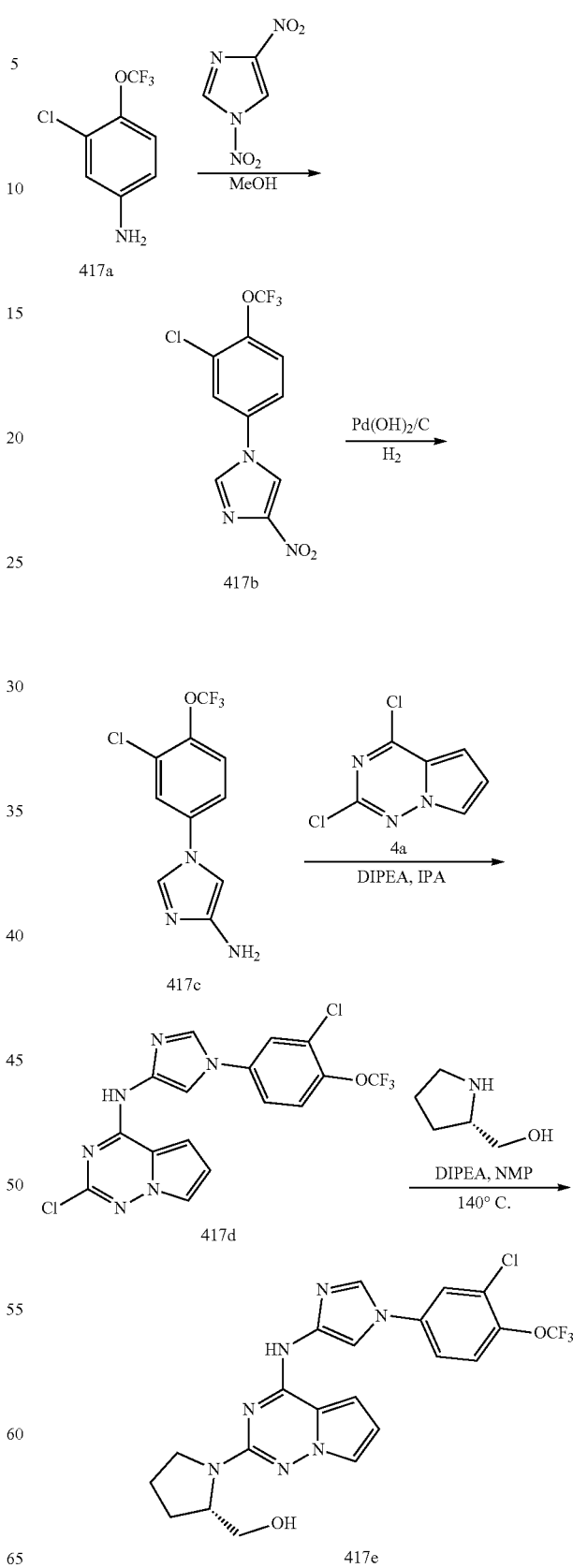

Preparation of (S)-(1-(4-((1-(3-chloro-4-(trifluoromethoxy)phenyl)-1H-imidazol-4-yl)amino)pyrrolo[2,1-f][1,2,4]triazin-2-yl)pyrrolidin-2-yl)methanol (417e)

Step-1: Preparation of 1-(3-chloro-4-(trifluoromethoxy)phenyl)-4-nitro-1H-imidazole (417b)

Reaction of 1,4-dinitro-1H-imidazole (3.74 g, 23.63 mmol) with 3-chloro-4-(trifluoromethoxy)aniline (417a) (5 g, 23.63 mmol) as reported in step-2 of General scheme for preparation of 3-substituted-(4-amino-1H-imidazol-1-yl) gave after filtration 1-(3-chloro-4-(trifluoromethoxy)phenyl)-4-nitro-1H-imidazole (417b) (6 g, 83% yield) as a yellow solid; $^1$H NMR (300 MHz, DMSO-$d_6$) δ 9.10 (d, J=1.6 Hz, 1H), 8.56 (d, J=1.6 Hz, 1H), 8.33 (d, J=2.7 Hz, 1H), 7.97 (dd, J=8.9, 2.7 Hz, 1H), 7.88-7.80 (m, 1H); $^{19}$F NMR (282 MHz, DMSO-$d_6$) δ −57.12; MS (ES+): 308.0 (M+1); (ES−): 342.1 (M+Cl).

Step-2: Preparation of 1-(3-chloro-4-(trifluoromethoxy)phenyl)-1H-imidazol-4-amine (417c)

Reduction of nitro to amine of 1-(3-chloro-4-(trifluoromethoxy)phenyl)-4-nitro-1H-imidazole (417b) (6 g, 19.51 mmol) in MeOH (120 mL) using Palladium hydroxide on carbon, 20 wt. % loading (dry basis), matrix carbon, wet support (1.370 g, 1.951 mmol) as reported in step-3 of General scheme for preparation of 3-substituted-(4-amino-1H-imidazol-1-yl) gave 1-(3-chloro-4-(trifluoromethoxy)phenyl)-1H-imidazol-4-amine (417c) (4.1 g, 76% yield) as a dark green oil; $^1$H NMR (300 MHz, DMSO-$d_6$) δ 8.08-7.92 (m, 2H), 7.75-7.57 (m, 2H), 6.75 (t, J=1.9 Hz, 1H), 4.55 (s, 2H); MS (ES+): 278.1 and 279.1 (M+1).

Step-3: Preparation of 2-chloro-N-(1-(3-chloro-4-(trifluoromethoxy)phenyl)-1H-imidazol-4-yl)pyrrolo[2,1-f][1,2,4]triazin-4-amine (417d)

Compound 417d was prepared from 2,4-dichloropyrrolo[2,1-f][1,2,4]triazine (4a) (1.17 g, 6.23 mmol) in 2-Propanol (40 mL) using DIPEA (3.26 mL, 18.69 mmol), 1-(3-chloro-4-(trifluoromethoxy)phenyl)-1H-imidazol-4-amine (417c) (1.73 g, 6.23 mmol) and heating at reflux for 2 h according to the procedure reported in step-1 of scheme 183. This gave after workup and filtration 2-chloro-N-(1-(3-chloro-4-(trifluoromethoxy)phenyl)-1H-imidazol-4-yl)pyrrolo[2,1-f][1,2,4]triazin-4-amine (417d) (2.1 g, 79% yield) as a yellow solid; MS (ES+): 429.0 and 430.1 (M+1); (ES−): 427.1 and 428.1 (M−1).

Step-4: Preparation of (S)-(1-(4-((1-(3-chloro-4-(trifluoromethoxy)phenyl)-1H-imidazol-4-yl)amino)pyrrolo[2,1-f][1,2,4]triazin-2-yl)pyrrolidin-2-yl)methanol (417e)

Compound 417e was prepared from 2-chloro-N-(1-(3-chloro-4-(trifluoromethoxy)phenyl)-1H-imidazol-4-yl)pyrrolo[2,1-f][1,2,4]triazin-4-amine (417d) (500 mg, 1.17 mmol), (S)-pyrrolidin-2-ylmethanol (354 mg, 3.50 mmol), N-ethyl-N-isopropylpropan-2-amine (0.61 mL, 3.50 mmol) in NMP (5 mL) and heating at 140° C. for 2 days according to the procedure reported in scheme 2. This gave after workup and purification by flash column chromatography [silica (24 g), eluting with DMA80 in DCM from 0-70%] followed by reverse phase column chromatography [C18 steel column (250 mm×30 mm), eluting with ACN in water (containing 0.1% HCl) from 0-100%] (S)-(1-(4-((1-(3-chloro-4-(trifluoromethoxy)phenyl)-1H-imidazol-4-yl)amino)pyrrolo[2,1-f][1,2,4]triazin-2-yl)pyrrolidin-2-yl)methanol (417e) (42 mg, 7% yield) HCl salt as an off white solid; $^1$H NMR (300 MHz, DMSO-$d_6$) δ 10.60 (s, 1H, D$_2$O exchangeable), 8.40 (d, J=1.5 Hz, 1H), 8.23 (d, J=2.7 Hz, 1H), 7.98 (d, J=1.6 Hz, 1H), 7.90 (dd, J=9.0, 2.7 Hz, 1H), 7.74-7.65 (m, 1H), 7.44-7.37 (m, 1H), 7.15 (dd, J=4.5, 1.7 Hz, 1H), 6.45-6.36 (m, 1H), 4.25-4.15 (m, 2H), 3.79 (dd, J=9.9, 3.4 Hz, 1H), 3.53-3.42 (m, 1H), 3.34 (t, J=9.5 Hz, 2H), 2.13-1.81 (m, 4H); $^{19}$F NMR (282 MHz, DMSO-$d_6$) δ −57.10; MS (ES+): 494.3 (M+1); (ES−): 492.3 (M−1).

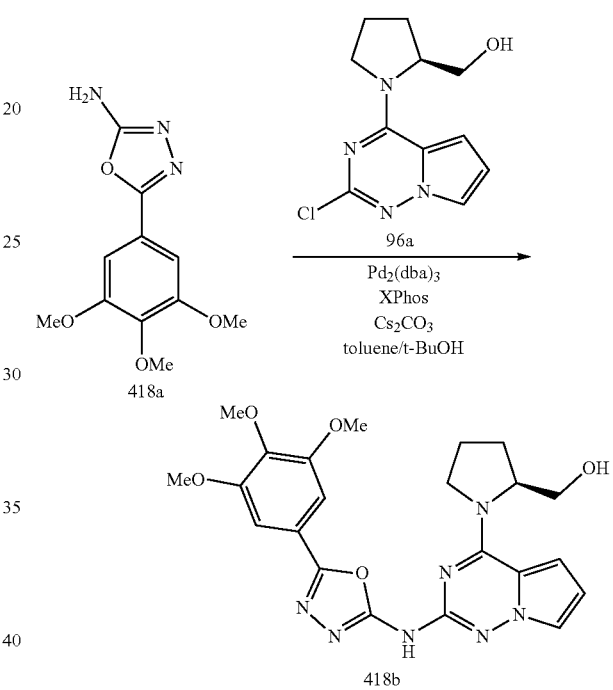

Scheme 418

Preparation of (S)-(1-(2-((5-(3,4,5-trimethoxyphenyl)-1,3,4-oxadiazol-2-yl)amino)pyrrolo[2,1-f][1,2,4]triazin-4-yl)pyrrolidin-2-yl)methanol (418b)

Compound 418b was prepared from (S)-(1-(2-chloropyrrolo[2,1-f][1,2,4]triazin-4-yl)pyrrolidin-2-yl)methanol (96a) (200 mg, 0.79 mmol), 5-(3,4,5-trimethoxyphenyl)-1,3,4-oxadiazol-2-amine (418a) (199 mg, 0.79 mmol; CAS #1673-43-4), dicyclohexyl(2',4',6'-triisopropylbiphenyl-2-yl)phosphine (XPhos, 151 mg, 0.32 mmol), cesium carbonate (645 mg, 1.98 mmol), Pd$_2$(dba)$_3$ (145 mg, 0.16 mmol) in toluene/t-BuOH (12 mL, Ratio: 5:1) and heating at 110° C. overnight according to the procedure reported in step-3 of scheme 101. This gave after workup and purification by flash column chromatography [silica (40 g), eluting with DMA80 in DCM from 0-60%] followed by reverse phase column chromatography [C18 steel column (250 mm×30 mm), eluting with ACN in water (containing 0.1% HCl) from 0-100%] (S)-(1-(2-((5-(3,4,5-trimethoxyphenyl)-1,3,4-oxadiazol-2-yl)amino)pyrrolo[2,1-f][1,2,4]triazin-4-yl)pyrrolidin-2-yl)methanol (418b) (133 mg, 36% yield) HCl salt as a white solid; $^1$H NMR (300 MHz, DMSO-$d_6$) δ 7.67 (s, 1H), 7.17 (s, 2H), 7.03-6.94 (m, 1H), 6.67-6.59 (m, 1H), 4.58-4.45 (m, 1H), 4.09-3.91 (m, 2H), 3.88 (s, 6H), 3.82-3.65 (m, 5H), 3.64-3.39 (m, 1H), 2.25-1.89 (m, 4H); MS (ES+): 468.3 (M+1); (ES−): 466.3 (M−1).

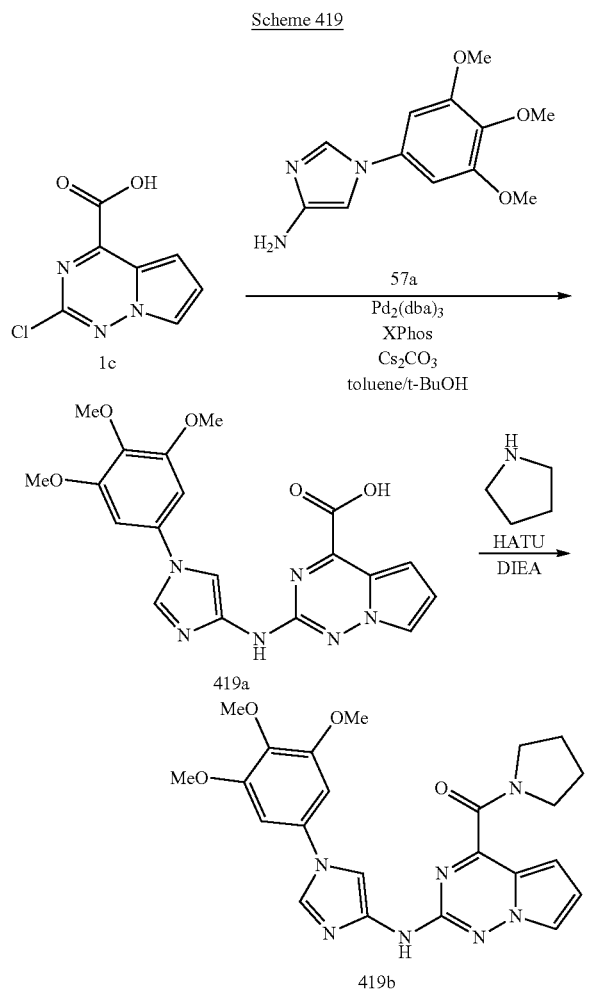

Scheme 419

Preparation of pyrrolidin-1-yl(2-((1-(3,4,5-trimethoxyphenyl)-1H-imidazol-4-yl)amino)pyrrolo[2,1-f][1,2,4]triazin-4-yl)methanone (419b)

Step-1: Preparation of 2-((1-(3,4,5-trimethoxyphenyl)-1H-imidazol-4-yl)amino)pyrrolo[2,1-f][1,2,4]triazine-4-carboxylic acid (419a)

Compound 419a was prepared from ethyl 2-chloropyrrolo[2,1-f][1,2,4]triazine-4-carboxylate (1c) (2 g, 8.86 mmol), 1-(3,4,5-trimethoxyphenyl)-1H-imidazol-4-amine (57a) (2.209 g, 8.86 mmol), dicyclohexyl(2',4',6'-triisopropylbiphenyl-2-yl)phosphine (XPhos, 1.27 g, 2.66 mmol), cesium carbonate (7.22 g, 22.16 mmol), Pd$_2$(dba)$_3$ (0.812 g, 0.886 mmol) in toluene/t-BuOH (10 mL, Ratio: 5:1) and heating at 110° C. overnight according to the procedure reported in step-3 of scheme 101. This gave after workup and purification by flash column chromatography [silica (40 g), eluting with MeOH in DCM from 0-40%] 2-((1-(3,4,5-trimethoxyphenyl)-1H-imidazol-4-yl)amino)pyrrolo[2,1-f][1,2,4]triazine-4-carboxylic acid (419a) (1.6 g, 44% yield) as a brown solid; MS (ES+): 411.1 (M+1); (ES−): 409.1 (M−1).

Step 2: Preparation of pyrrolidin-1-yl(2-((1-(3,4,5-trimethoxyphenyl)-1H-imidazol-4-yl)amino)pyrrolo[2,1-f][1,2,4]triazin-4-yl)methanone (419b)

Compound 419b was prepared from 2-((1-(3,4,5-trimethoxyphenyl)-1H-imidazol-4-yl)amino)pyrrolo[2,1-f][1,2,4]triazine-4-carboxylic acid (419a) (350 mg, 0.85 mmol), using pyrrolidine (72.8 mg, 1.02 mmol), HATU (389 mg, 1.02 mmol), DIEA (0.45 mL, 2.56 mmol) in DMF (6 mL) according to the procedure reported in step-3 of scheme 410. This gave after workup and purification by flash column chromatography [silica (24 g), eluting with DMA80 in DCM from 0 to 80%] followed by purification using reverse phase column chromatography [C18 (50 g), eluting with ACN in water (containing 0.1% HCl) from 0-100%] pyrrolidin-1-yl(2-((1-(3,4,5-trimethoxyphenyl)-1H-imidazol-4-yl)amino)pyrrolo[2,1-f][1,2,4]triazin-4-yl)methanone (419b) (42 mg, 11% yield) HCl salt as a yellow solid; $^1$H NMR (300 MHz, DMSO-d$_6$) δ 10.25 (s, 1H, D$_2$O exchangeable), 8.89 (s, 1H), 8.07 (t, J=1.9 Hz, 1H), 8.04 (s, 1H), 7.08 (s, 2H), 6.92-6.80 (m, 2H), 3.90 (s, 6H), 3.71 (s, 3H), 3.61-3.50 (m, 4H), 1.97-1.80 (m, 4H); MS (ES+) 464.0 (M+1).

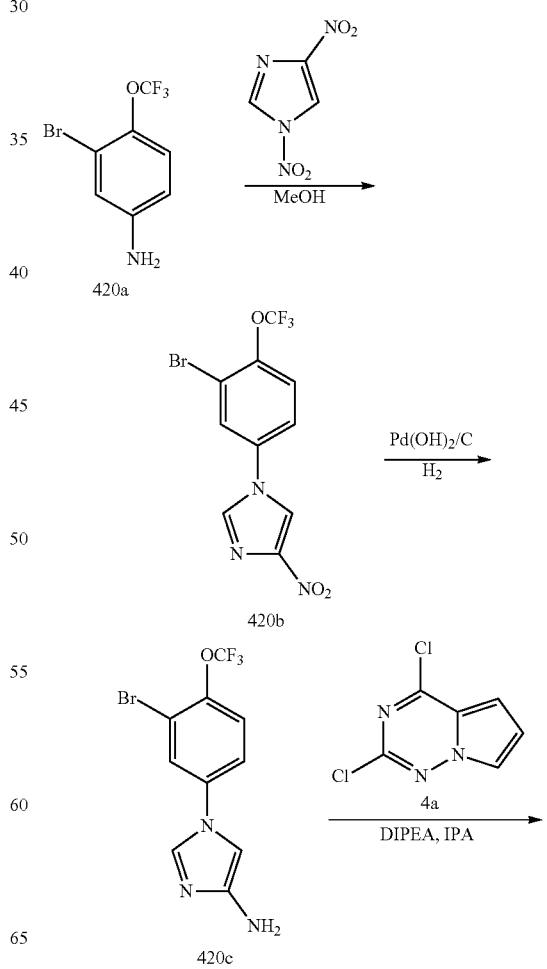

Scheme 420

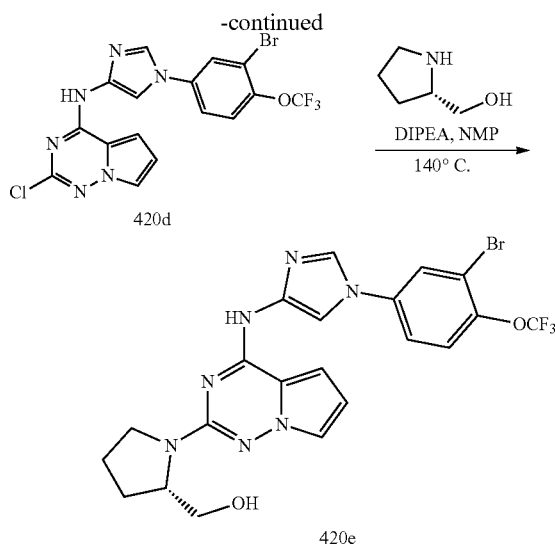

Preparation of (S)-(1-(4-((1-(3-bromo-4-(trifluoromethoxy)phenyl)-1H-imidazol-4-yl)amino)pyrrolo[2,1-f][1,2,4]triazin-2-yl)pyrrolidin-2-yl)methanol (420e)

Step-1: Preparation of 1-(3-bromo-4-(trifluoromethoxy)phenyl)-4-nitro-1H-imidazole (420b)

Reaction of 1,4-dinitro-1H-imidazole (3.09 g, 19.53 mmol) with 3-bromo-4-(trifluoromethoxy)aniline (420a) (5 g, 19.53 mmol) as reported in step-2 of General scheme for preparation of 3-substituted-(4-amino-1H-imidazol-1-yl) gave after filtration 1-(3-bromo-4-(trifluoromethoxy)phenyl)-4-nitro-1H-imidazole (420b) (4.2 g) as a yellow solid; MS (ES+): 352.0 and 353.0 (M+1).

Step-2: Preparation of 1-(3-bromo-4-(trifluoromethoxy)phenyl)-1H-imidazol-4-amine (420c)

Reduction of nitro to amine of 1-(3-bromo-4-(trifluoromethoxy)phenyl)-4-nitro-1H-imidazole (420b) (1.6 g, 4.54 mmol) in MeOH (120 mL) using Palladium hydroxide on carbon, 20 wt. % loading (dry basis), matrix carbon, wet support (0.319 g, 0.454 mmol) as reported in step-3 of General scheme for preparation of 3-substituted-(4-amino-1H-imidazol-1-yl) gave after workup and purification by flash column chromatography [silica (24 g), eluting with EtOAc in hexane from 0-100%] 1-(3-bromo-4-(trifluoromethoxy)phenyl)-1H-imidazol-4-amine (420c) (880 mg, 60% yield) as a brown solid; MS (ES+): 323.9 and 324.9 (M+1).

Step-3: Preparation of N-(1-(3-bromo-4-(trifluoromethoxy)phenyl)-1H-imidazol-4-yl)-2-chloropyrrolo[2,1-f][1,2,4]triazin-4-amine (420d)

Compound 420d was prepared from 2,4-dichloropyrrolo[2,1-f][1,2,4]triazine (4a) (350 mg, 1.86 mmol) in 2-Propanol (40 mL) using DIPEA (0.98 mL, 5.59 mmol), 1-(3-bromo-4-(trifluoromethoxy)phenyl)-1H-imidazol-4-amine (420c) (600 mg, 1.86 mmol) and heating at reflux for 2 h according to the procedure reported in step-1 of scheme 183. This gave after workup and filtration N-(1-(3-bromo-4-(trifluoromethoxy)phenyl)-1H-imidazol-4-yl)-2-chloropyrrolo[2,1-f][1,2,4]triazin-4-amine (420d) (465 mg, 53% yield) as a yellow solid; ¹H NMR (300 MHz, DMSO-d₆) δ 11.36 (s, 1H, D₂O exchangeable), 8.35 (d, J=1.6 Hz, 1H), 8.25 (d, J=2.6 Hz, 1H), 7.95 (d, J=1.6 Hz, 1H), 7.84-7.71 (m, 3H), 7.40 (d, J=4.3 Hz, 1H), 6.77-6.69 (m, 1H); ¹⁹F NMR (282 MHz, DMSO-d₆) δ −56.80; MS (ES⁺) 472.8 and 473.8 (M+1); MS (ES−) 470.7 and 471.8 (M−1).

Step-4: Preparation of (S)-(1-(4-((1-(3-bromo-4-(trifluoromethoxy)phenyl)-1H-imidazol-4-yl)amino)pyrrolo[2,1-f][1,2,4]triazin-2-yl)pyrrolidin-2-yl)methanol (420e)

Compound 420e was prepared from N-(1-(3-bromo-4-(trifluoromethoxy)phenyl)-1H-imidazol-4-yl)-2-chloropyrrolo[2,1-f][1,2,4]triazin-4-amine (420d) (315 mg, 0.67 mmol), (S)-pyrrolidin-2-ylmethanol (202 mg, 1.20 mmol), N-ethyl-N-isopropylpropan-2-amine (0.35 mL, 1.20 mmol) in NMP (5 mL) and heating at 140° C. for 3 h according to the procedure reported in scheme 2. This gave after workup and purification by flash column chromatography [silica (24 g), eluting with DMA80 in DCM from 0-70%] (S)-(1-(4-((1-(3-bromo-4-(trifluoromethoxy)phenyl)-1H-imidazol-4-yl)amino)pyrrolo[2,1-f][1,2,4]triazin-2-yl)pyrrolidin-2-yl)methanol (420e) (58 mg, 16% yield) as a white solid; ¹H NMR (300 MHz, DMSO-d₆) δ 10.56 (s, 1H, D₂O exchangeable), 8.36 (d, J=1.5 Hz, 1H), 8.30 (d, J=2.7 Hz, 1H), 7.97 (d, J=1.6 Hz, 1H), 7.92 (dd, J=8.9, 2.7 Hz, 1H), 7.66-7.60 (m, 1H), 7.43-7.36 (m, 1H), 7.15 (dd, J=4.5, 1.7 Hz, 1H), 6.43-6.36 (m, 1H), 4.98 (t, J=5.1 Hz, 1H, D₂O exchangeable), 4.26-4.12 (m, 1H), 3.84-3.72 (m, 1H), 3.55-3.43 (m, 1H), 3.34-3.25 (m, 2H), 2.11-1.78 (m, 4H); ¹⁹F NMR (282 MHz, DMSO-d₆) δ −56.77; MS (ES+): 539.8 and 540.8 (M+1); (ES−): 536.8 and 537.8 (M−1).

Scheme 421

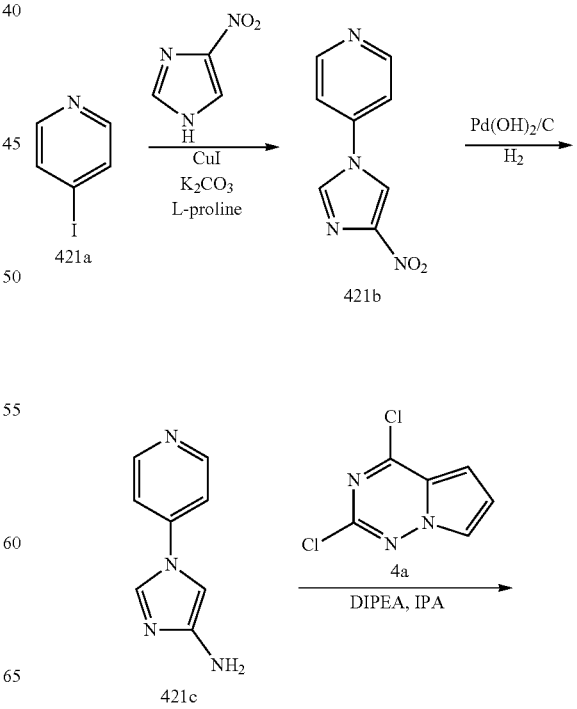

681

<br>-continued

421d

Preparation of (S)-(1-(4-((1-(pyridin-4-yl)-1H-imidazol-4-yl)amino)pyrrolo[2,1-f][1,2,4]triazin-2-yl)pyrrolidin-2-yl)methanol (421e)

Step-1: Preparation of 4-(4-nitro-1H-imidazol-1-yl)pyridine (421b)

A mixture of 4-iodopyridine (421a) (7.6 g, 37.1 mmol), L-proline (1.71 g, 14.83 mmol), copper(I) iodide (1.412 g, 7.41 mmol), 4-nitro-1H-imidazole (8.38 g, 74.1 mmol) and K$_2$CO$_3$ (10.25 g, 74.1 mmol) was degassed by vacuum/Ar-filled method (2×). Into the degassed mixture DMSO (10 mL) was added. The reaction mixture was again degassed, sealed and heated at 95° C. for 2 days, cooled to room temperature, diluted with water. The resulting mixture was extracted with dichloromethane (2×). The combined extracts were washed with water, dried, filtered and concentrated under reduced pressure. The residue was purified by chromatography [silica (24 g), eluting with EtOAc in hexane from 0-100%] to give 4-(4-nitro-1H-imidazol-1-yl)pyridine (421b) (550 mg, 8% yield) as a yellow solid; $^1$H NMR (300 MHz, DMSO-d$_6$) δ 9.23 (d, J=1.6 Hz, 1H), 8.79 (d, J=1.6 Hz, 1H), 8.77 (d, J=1.6 Hz, 1H), 8.74 (d, J=1.6 Hz, 1H), 7.95 (d, J=1.7 Hz, 1H), 7.94 (d, J=1.7 Hz, 1H); MS (ES+): 191.1 (M+1).

Step-2: Preparation of 1-(pyridin-4-yl)-1H-imidazol-4-amine (421c)

Reduction of nitro to amine of 4-(4-nitro-1H-imidazol-1-yl)pyridine (421b) (550 mg, 2.89 mmol) in MeOH (120 mL) using Palladium hydroxide on carbon, 20 wt. % loading (dry basis), matrix carbon, wet support (203 mg, 0.289 mmol) as reported in step-3 of General scheme for preparation of 3-substituted-(4-amino-1H-imidazol-1-yl) gave after workup and purification by flash column chromatography [silica (12 g), eluting with EtOAc in hexane from 0-100%] 1-(pyridin-4-yl)-1H-imidazol-4-amine (421c) (50 mg, 11% yield) as a yellow solid.

Step-3: Preparation of 2-chloro-N-(1-(pyridin-4-yl)-1H-imidazol-4-yl)pyrrolo[2,1-f][1,2,4]triazin-4-amine (421d)

Compound 421d was prepared from 2,4-dichloropyrrolo[2,1-f][1,2,4]triazine (4a) (470 mg, 2.50 mmol) in 2-Propanol (10 mL) using DIPEA (1.31 mL, 7.49 mmol), 1-(pyridin-

682

4-yl)-1H-imidazol-4-amine (421c) (400 mg, 2.50 mmol) and heating at reflux for 2 h according to the procedure reported in step-1 of scheme 183. This gave after workup and filtration 2-chloro-N-(1-(pyridin-4-yl)-1H-imidazol-4-yl)pyrrolo[2,1-f][1,2,4]triazin-4-amine (421d) (78 mg, 10% yield) as a yellow solid; MS (ES+): 311.9 (M+1).

Step-4: Preparation of (S)-(1-(4-((1-(pyridin-4-yl)-1H-imidazol-4-yl)amino)pyrrolo[2,1-f][1,2,4]triazin-2-yl)pyrrolidin-2-yl)methanol (421e)

Compound 421e was prepared from 2-chloro-N-(1-(pyridin-4-yl)-1H-imidazol-4-yl)pyrrolo[2,1-f][1,2,4]triazin-4-amine (421d) (50 mg, 0.160 mmol), (S)-pyrrolidin-2-yl-methanol (49 mg, 0.48 mmol), N-ethyl-N-isopropylpropan-2-amine (0.084 mL, 0.48 mmol) in NMP (5 mL) and heating at 140° C. for 2 h on microwave according to the procedure reported in scheme 2. This gave after workup and purification by flash column chromatography [silica (24 g), eluting with DMA80 in DCM from 0-70%] followed by purification by reverse phase column chromatography [C18 steel column (250 mm×30 mm), eluting with ACN in water (containing 0.1% HCl) from 0-100%] (S)-(1-(4-((1-(pyridin-4-yl)-1H-imidazol-4-yl)amino)pyrrolo[2,1-f][1,2,4]triazin-2-yl)pyrrolidin-2-yl)methanol (421e) (6.5 mg, 11% yield) as a yellow solid; $^1$H NMR (300 MHz, DMSO-d$_6$) δ 10.77 (s, 1H, D$_2$O exchangeable), 8.94 (s, 1H), 8.84 (s, 1H), 8.36 (s, 2H), 8.15 (s, 1H), 7.47-7.42 (m, 1H), 7.18 (dd, J=4.5, 1.7 Hz, 1H), 6.47-6.38 (m, 1H), 4.73-4.50 (m, 2H), 4.31-4.18 (m, 2H), 3.81 (dd, J=9.8, 3.4 Hz, 1H), 3.49 (dt, J=7.1, 3.7 Hz, 1H), 3.36 (t, J=9.5 Hz, 2H), 2.15-2.02 (m, 1H), 2.02-1.89 (m, 3H); MS (ES+): 377.1 (M+1); (ES-): 375.0 (M-1); HPLC purity: 95.24%.

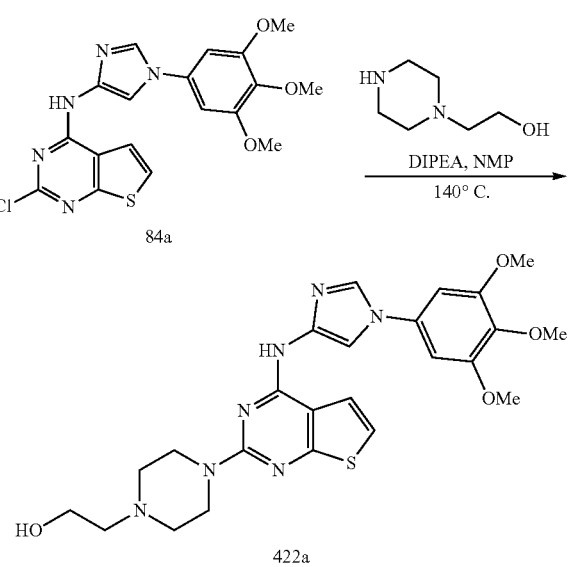

Scheme 422

Preparation of 2-(4-(4-((1-(3,4,5-trimethoxyphenyl)-1H-imidazol-4-yl)amino)thieno[2,3-d]pyrimidin-2-yl)piperazin-1-yl)ethanol (422a)

Compound 422a was prepared from 2-chloro-N-(1-(3,4,5-trimethoxyphenyl)-1H-imidazol-4-yl)thieno[2,3-d]pyrimidin-4-amine (84a) (400 mg, 0.96 mmol), 2-(piperazin- 1-yl)ethanol (150 mg, 1.15 mmol), N-ethyl-N-isopropylpropan-2-amine (0.33 mL, 1.91 mmol) in NMP (5 mL) and heating at 140° C. for 2 h according to the procedure reported in scheme 2. This gave after workup and purification by flash column chromatography [silica (24 g), eluting with DMA80 in DCM from 0-70%] followed by reverse phase column chromatography [C18 steel column (250 mm×30 mm), eluting with ACN in water (containing 0.1% HCl) from 0-100%]2-(4-(4-((1-(3,4,5-trimethoxyphenyl)-1H-imidazol-4-yl)amino)thieno[2,3-d]pyrimidin-2-yl)piperazin-1-yl)ethanol (422a) (250 mg, 51% yield) HCl salt as a white solid; $^1$H NMR (300 MHz, DMSO-d$_6$) δ 11.11 (s, 1H, D$_2$O exchangeable), 11.04 (s, 1H, D$_2$O exchangeable), 9.19 (s, 1H), 8.12 (d, J=1.7 Hz, 1H), 7.90 (d, J=6.0 Hz, 1H), 7.32 (d, J=6.0 Hz, 1H), 7.14 (s, 1H), 6.72 (s, 2H, D$_2$O exchangeable), 4.69 (d, J=14.0 Hz, 2H), 3.90 (s, 6H), 3.87-3.79 (m, 2H), 3.71 (s, 3H), 3.63-3.48 (m, 4H), 3.28-3.08 (m, 4H); MS (ES+): 512.2 (M+1); (ES−): 510.2 (M−1).

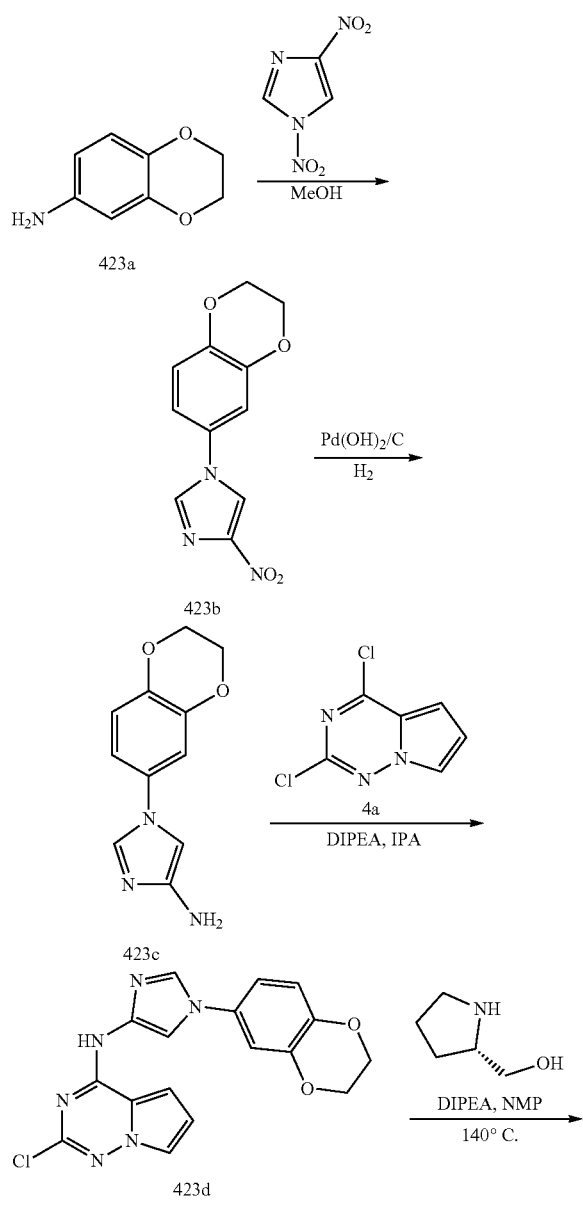
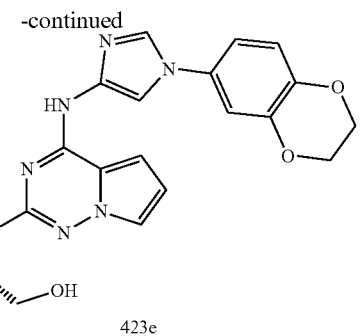

Preparation of (S)-(1-(4-((1-(2,3-dihydrobenzo[b][1,4]dioxin-6-yl)-1H-imidazol-4-yl)amino)pyrrolo[2,1-f][1,2,4]triazin-2-yl)pyrrolidin-2-yl)methanol (423e)

Step-1: Preparation of 1-(2,3-dihydrobenzo[b][1,4]dioxin-6-yl)-4-nitro-1H-imidazole (423b)

Reaction of 1,4-dinitro-1H-imidazole (2.091 g, 13.23 mmol) with 2,3-dihydrobenzo[b][1,4]dioxin-6-amine (423a) (2 g, 13.23 mmol) as reported in step-2 of General scheme for preparation of 3-substituted-(4-amino-1H-imidazol-1-yl) gave after filtration 1-(2,3-dihydrobenzo[b][1,4]dioxin-6-yl)-4-nitro-1H-imidazole (423b) (3 g, 92% yield) as a yellow solid; $^1$H NMR (300 MHz, DMSO-d$_6$) δ 8.90 (d, J=1.6 Hz, 1H), 8.37 (d, J=1.6 Hz, 1H), 7.39 (d, J=2.7 Hz, 1H), 7.26 (dd, J=8.7, 2.7 Hz, 1H), 7.04 (d, J=8.7 Hz, 1H), 4.35-4.27 (m, 4H); MS (ES+): 248.1 (M+1).

Step-2: Preparation of 1-(2,3-dihydrobenzo[b][1,4]dioxin-6-yl)-1H-imidazol-4-amine (423c)

Reduction of nitro to amine of 1-(2,3-dihydrobenzo[b][1,4]dioxin-6-yl)-4-nitro-1H-imidazole (423b) (1.75 g, 7.08 mmol) in MeOH (120 mL) using Palladium hydroxide on carbon, 20 wt. % loading (dry basis), matrix carbon, wet support (0.497 g, 0.708 mmol) as reported in step-3 of General scheme for preparation of 3-substituted-(4-amino-1H-imidazol-1-yl) gave 1-(2,3-dihydrobenzo[b][1,4]dioxin-6-yl)-1H-imidazol-4-amine (423c) (1.2 g, 78% yield) as a light yellow semi-solid; $^1$H NMR (300 MHz, DMSO-d$_6$) δ 7.70 (d, J=1.6 Hz, 1H), 7.05 (dd, J=2.5, 0.5 Hz, 1H), 6.99-6.94 (m, 1H), 6.91 (dd, J=8.6, 0.5 Hz, 1H), 6.54 (d, J=1.6 Hz, 1H), 4.34 (s, 2H, D$_2$O exchangeable), 4.28-4.24 (m, 4H); MS (ES+): 218.1 (M+1).

Step-3: Preparation of 2-chloro-N-(1-(2,3-dihydrobenzo[b][1,4]dioxin-6-yl)-1H-imidazol-4-yl)pyrrolo[2,1-f][1,2,4]triazin-4-amine (423d)

Compound 423d was prepared from 2,4-dichloropyrrolo[2,1-f][1,2,4]triazine (4a) (606 mg, 3.22 mmol) in 2-Propanol (40 mL) using DIPEA (1.69 mL, 9.67 mmol), 1-(2,3-dihydrobenzo[b][1,4]dioxin-6-yl)-1H-imidazol-4-amine (423c) (700 mg, 3.22 mmol) and heating at reflux for 2 h according to the procedure reported in step-1 of scheme 183. This gave after workup and filtration 2-chloro-N-(1-(2,3-dihydrobenzo[b][1,4]dioxin-6-yl)-1H-imidazol-4-yl)pyrrolo[2,1-f][1,2,4]triazin-4-amine (423d) (520 mg, 44% yield) as a yellow solid; $^1$H NMR (300 MHz, DMSO-d$_6$) δ 11.31 (s, 1H, D$_2$O exchangeable), 8.11 (d, J=1.6 Hz, 1H), 7.81 (d, J=1.6 Hz, 1H), 7.77 (dd, J=2.6, 1.5 Hz, 1H), 7.42-7.36 (m, 1H), 7.20 (d, J=2.4 Hz, 1H), 7.09 (dd, J=8.7, 2.5 Hz, 1H), 7.06-7.00 (m, 1H), 6.71 (dd, J=4.4, 2.6 Hz, 1H), 4.35-4.24 (m, 4H); MS (ES+): 369.1 (M+1).

Step-4: Preparation of (S)-(1-(4-((1-(2,3-dihydrobenzo[b][1,4]dioxin-6-yl)-1H-imidazol-4-yl)amino)pyrrolo[2,1-f][1,2,4]triazin-2-yl)pyrrolidin-2-yl)methanol (423e)

Compound 423e was prepared from 2-chloro-N-(1-(2,3-dihydrobenzo[b][1,4]dioxin-6-yl)-1H-imidazol-4-yl)pyrrolo[2,1-f][1,2,4]triazin-4-amine (423d) (400 mg, 1.09 mmol), (S)-pyrrolidin-2-ylmethanol (329 mg, 3.25 mmol), N-ethyl-N-isopropylpropan-2-amine (0.57 mL, 3.25 mmol) in NMP (5 mL) and heating at 140° C. for 100 mins according to the procedure reported in scheme 2. This gave after workup and purification by flash column chromatography [silica (24 g), eluting with DMA80 in DCM from 0-70%] (S)-(1-(4-((1-(2,3-dihydrobenzo[b][1,4]dioxin-6-yl)-1H-imidazol-4-yl)amino)pyrrolo[2,1-f][1,2,4]triazin-2-yl)pyrrolidin-2-yl)methanol (423e) (100 mg, 21% yield) as a white solid; $^1$H NMR (300 MHz, DMSO-$d_6$) δ 10.94 (s, 1H, D$_2$O exchangeable), 8.73 (d, J=1.6 Hz, 1H), 7.94 (d, J=1.7 Hz, 1H), 7.47 (dd, J=2.4, 1.6 Hz, 1H), 7.36 (d, J=2.7 Hz, 1H), 7.25 (dd, J=8.7, 2.7 Hz, 1H), 7.12 (dd, J=4.5, 1.7 Hz, 1H), 7.02 (d, J=8.7 Hz, 1H), 6.49-6.43 (m, 1H), 6.35-6.03 (m, 2H, D$_2$O exchangeable), 4.31 (s, 4H), 4.12 (dt, J=8.8, 3.7 Hz, 1H), 3.67 (dd, J=10.1, 3.8 Hz, 1H), 3.46 (d, J=7.3 Hz, 1H), 3.35 (dd, J=10.1, 8.1 Hz, 2H), 2.09-1.79 (m, 4H); MS (ES+): 434.0 (M+1); (ES−): 432.0 (M−1).

Scheme 424

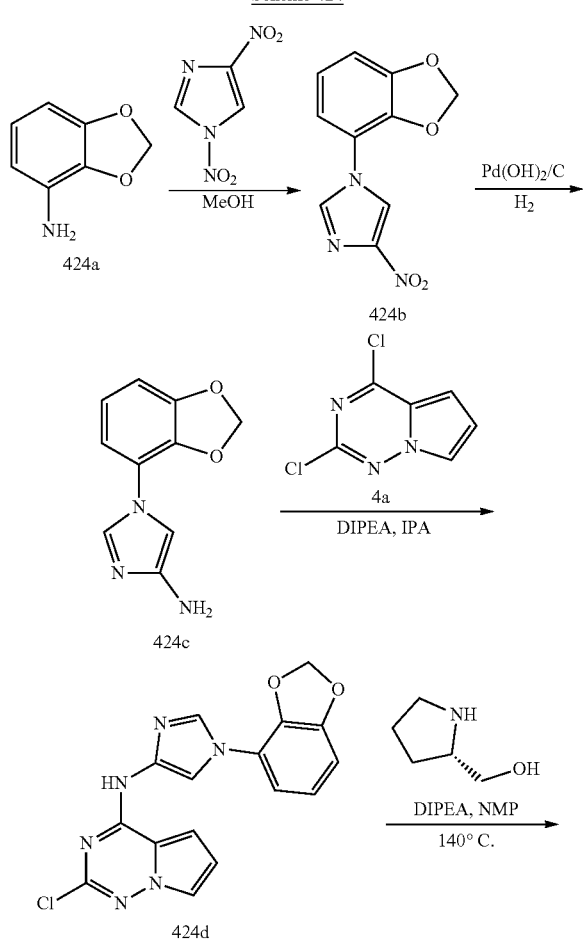

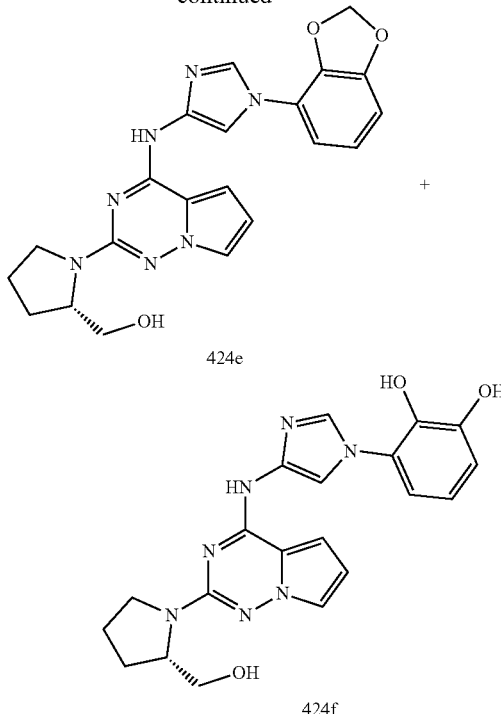

Preparation of (S)-(1-(4-((1-(benzo[d][1,3]dioxol-4-yl)-1H-imidazol-4-yl)amino)pyrrolo[2,1-f][1,2,4]triazin-2-yl)pyrrolidin-2-yl)methanol (424e) and (S)-3-(4-((2-(2-(hydroxymethyl)pyrrolidin-1-yl)pyrrolo[2,1-f][1,2,4]triazin-4-yl)amino)-1H-imidazol-1-yl)benzene-1,2-diol (424f)

Step-1: Preparation of 1-(benzo[d][1,3]dioxol-4-yl)-4-nitro-1H-imidazole (424b)

Reaction of 1,4-dinitro-1H-imidazole (1.15 g, 7.29 mmol) with benzo[d][1,3]dioxol-4-amine (424a) (1 g, 7.29 mmol) as reported in step-2 of General scheme for preparation of 3-substituted-(4-amino-1H-imidazol-1-yl) gave after filtration 1-(benzo[d][1,3]dioxol-4-yl)-4-nitro-1H-imidazole (424b) (1.4 g, 82% yield) as a yellow solid; $^1$H NMR (300 MHz, DMSO-$d_6$) S 8.84 (d, J=1.5 Hz, 1H), 8.37 (d, J=1.5 Hz, 1H), 7.30 (dd, J=7.5, 2.0 Hz, 1H), 7.14-6.98 (m, 2H), 6.20 (s, 2H).

Step-2: Preparation of 1-(benzo[d][1,3]dioxol-4-yl)-1H-imidazol-4-amine (424c)

Reduction of nitro to amine of 1-(benzo[d][1,3]dioxol-4-yl)-4-nitro-1H-imidazole (424b) (1.40 g, 6.0 mmol) in MeOH (120 mL) using Palladium hydroxide on carbon, 20 wt. % loading (dry basis), matrix carbon, wet support (0.42 g, 0.60 mmol) as reported in step-3 of General scheme for preparation of 3-substituted-(4-amino-1H-imidazol-1-yl) gave 1-(benzo[d][1,3]dioxol-4-yl)-1H-imidazol-4-amine (424c) (1.2 g, 98% yield) as a light yellow semi-solid; MS (ES+): 204.1 (M+1).

Step-3: Preparation of N-(1-(benzo[d][1,3]dioxol-4-yl)-1H-imidazol-4-yl)-2-chloropyrrolo[2,1-f][1,2,4]triazin-4-amine (424d)

Compound 424d was prepared from 2,4-dichloropyrrolo[2,1-f][1,2,4]triazine (4a) (666 mg, 3.54 mmol) in 2-Propanol (40 mL) using DIPEA (1.857 mL, 10.63 mmol), 1-(benzo[d][1,3]dioxol-4-yl)-1H-imidazol-4-amine (424c) (720 mg, 3.54 mmol) and heating at reflux for 2 h according to the procedure reported in step-1 of scheme 183. This gave after workup and filtration N-(1-(benzo[d][1,3]dioxol-4-yl)-1H-imidazol-4-yl)-2-chloropyrrolo[2,1-f][1,2,4]triazin-4-amine (424d) (450 mg, 36% yield) as a yellow solid.

Step-4: Preparation of (S)-(1-(4-((1-(benzo[d][1,3]dioxol-4-yl)-1H-imidazol-4-yl)amino)pyrrolo[2,1-f][1,2,4]triazin-2-yl)pyrrolidin-2-yl)methanol (424e) and (S)-3-(4-((2-(2-(hydroxymethyl)pyrrolidin-1-yl)pyrrolo[2,1-f][1,2,4]triazin-4-yl)amino)-1H-imidazol-1-yl)benzene-1,2-diol (424f)

Compounds 424e and 424f were prepared from N-(1-(benzo[d][1,3]dioxol-4-yl)-1H-imidazol-4-yl)-2-chloropyrrolo[2,1-f][1,2,4]triazin-4-amine (424d) (400 mg, 1.13 mmol), (S)-pyrrolidin-2-ylmethanol (342 mg, 3.38 mmol), N-ethyl-N-isopropylpropan-2-amine (0.59 mL, 3.38 mmol) in NMP (5 mL) and heating at 140° C. for 100 mins according to the procedure reported in scheme 2. This gave after workup and purification by flash column chromatography [silica (24 g), eluting with DMA80 in DCM from 0-70%] (S)-(1-(4-((1-(benzo[d][1,3]dioxol-4-yl)-1H-imidazol-4-yl)amino)pyrrolo[2,1-f][1,2,4]triazin-2-yl)pyrrolidin-2-yl)methanol (424e) (23 mg, 5% yield) as a white solid and (S)-3-(4-((2-(2-(hydroxymethyl)pyrrolidin-1-yl)pyrrolo[2,1-f][1,2,4]triazin-4-yl)amino)-1H-imidazol-1-yl)benzene-1,2-diol (424f) (27 mg, 6% yield) as a white solid; Data for compound 424e: $^1$H NMR (300 MHz, DMSO-$d_6$) δ 10.69 (s, 1H, $D_2O$ exchangeable), 8.32 (d, J=1.5 Hz, 1H), 8.11 (d, J=1.6 Hz, 1H), 7.41 (t, J=2.0 Hz, 1H), 7.31 (dd, J=7.4, 2.0 Hz, 1H), 7.13 (dd, J=4.4, 1.7 Hz, 1H), 7.05-6.92 (m, 2H), 6.41 (dd, J=4.4, 2.4 Hz, 1H), 6.18 (dd, J=8.8, 1.2 Hz, 2H), 4.14 (s, 1H), 3.67 (dd, J=10.2, 3.6 Hz, 1H), 3.61-3.49 (m, 1H), 3.48-3.29 (m, 2H), 2.13-1.80 (m, 4H); MS (ES+): 420.1 (M+1); (ES−): 418.1 (M−1); Data for compound 424f: $^1$H NMR (300 MHz, DMSO-$d_6$) δ 11.19-10.96 (m, 1H, $D_2O$ exchangeable), 10.37-9.27 (m, 1H, $D_2O$ exchangeable), 8.92-8.78 (m, 1H), 7.85 (d, J=1.7 Hz, 1H), 7.50 (dd, J=2.4, 1.6 Hz, 1H), 7.06 (dd, J=4.5, 1.6 Hz, 1H), 7.05-6.93 (m, 2H), 6.81 (t, J=8.0 Hz, 1H), 6.49 (dd, J=4.5, 2.5 Hz, 1H), 4.15-4.00 (m, 1H), 3.60 (dd, J=10.3, 4.0 Hz, 1H), 3.55-3.41 (m, 1H), 3.43-3.30 (m, 2H), 2.05-1.75 (m, 4H); MS (ES+): 408.1 (M+1); (ES−): 406.1 (M−1).

Scheme 425

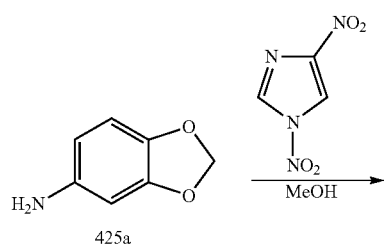

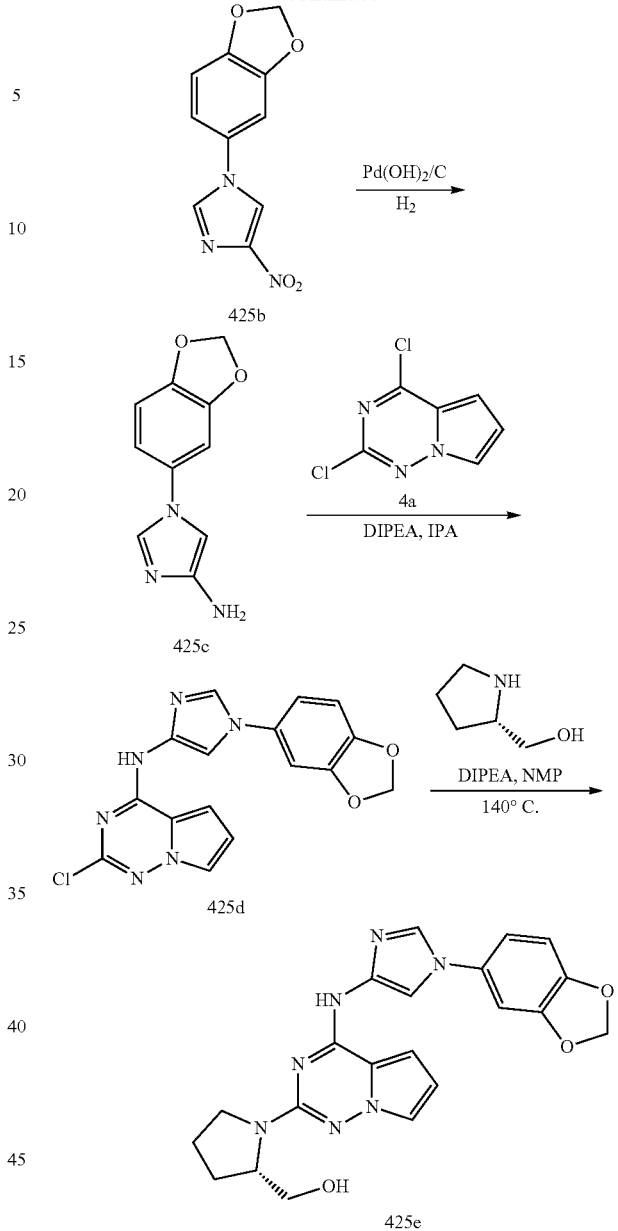

Preparation of (S)-(1-(4-((1-(benzo[d][1,3]dioxol-5-yl)-1H-imidazol-4-yl)amino)pyrrolo[2,1-f][1,2,4]triazin-2-yl)pyrrolidin-2-yl)methanol (425e)

Step-1: Preparation of 1-(benzo[d][1,3]dioxol-5-yl)-4-nitro-1H-imidazole (425b)

Reaction of 1,4-dinitro-1H-imidazole (3.46 g, 21.88 mmol) with benzo[d][1,3]dioxol-5-amine (425a) (3 g, 21.88 mmol) as reported in step-2 of General scheme for preparation of 3-substituted-(4-amino-1H-imidazol-1-yl) gave after filtration 1-(benzo[d][1,3]dioxol-5-yl)-4-nitro-1H-imidazole (425b) (3.2 g, 63% yield) as a yellow solid; $^1$H NMR (300 MHz, DMSO-$d_6$) δ 8.90 (d, J=1.6 Hz, 1H), 8.36 (d, J=1.6 Hz, 1H), 7.47 (d, J=2.2 Hz, 1H), 7.27 (dd, J=8.4, 2.3 Hz, 1H), 7.10 (d, J=8.4 Hz, 1H), 6.15 (s, 2H); MS (ES+): 234.1 (M+1).

Step-2: Preparation of 1-(benzo[d][1,3]dioxol-5-yl)-1H-imidazol-4-amine (425c)

Reduction of nitro to amine of 1-(benzo[d][1,3]dioxol-5-yl)-4-nitro-1H-imidazole (425b) (1.2 g, 5.15 mmol) in MeOH (120 mL) using Palladium hydroxide on carbon, 20 wt. % loading (dry basis), matrix carbon, wet support (0.36 g, 0.52 mmol) as reported in step-3 of General scheme for preparation of 3-substituted-(4-amino-1H-imidazol-1-yl) gave 1-(benzo[d][1,3]dioxol-5-yl)-1H-imidazol-4-amine (425c) (660 mg, 63% yield) as a light yellow semi-solid; MS (ES+): 204.1 (M+1).

Step-3: Preparation of N-(1-(benzo[d][1,3]dioxol-5-yl)-1H-imidazol-4-yl)-2-chloropyrrolo[2,1-f][1,2,4]triazin-4-amine (425d)

Compound 425d was prepared from 2,4-dichloropyrrolo[2,1-f][1,2,4]triazine (4a) (611 mg, 3.25 mmol) in 2-Propanol (40 mL) using DIPEA (1.70 mL, 9.74 mmol), 1-(benzo[d][1,3]dioxol-5-yl)-1H-imidazol-4-amine (425c) (660 mg, 3.25 mmol) and heating at reflux for 2 h according to the procedure reported in step-1 of scheme 183. This gave after workup and filtration N-(1-(benzo[d][1,3]dioxol-5-yl)-1H-imidazol-4-yl)-2-chloropyrrolo[2,1-f][1,2,4]triazin-4-amine (425d) (456 mg, 40% yield) as a yellow solid; MS (ES+): 355.0 (M+1).

Step-4: Preparation of (S)-(1-(4-((1-(benzo[d][1,3]dioxol-5-yl)-1H-imidazol-4-yl)amino)pyrrolo[2,1-f][1,2,4]triazin-2-yl)pyrrolidin-2-yl)methanol (425e)

Compound 425e was prepared from N-(1-(benzo[d][1,3]dioxol-5-yl)-1H-imidazol-4-yl)-2-chloropyrrolo[2,1-f][1,2,4]triazin-4-amine (425d) (400 mg, 1.13 mmol), (S)-pyrrolidin-2-ylmethanol (342 mg, 3.38 mmol), N-ethyl-N-isopropylpropan-2-amine (0.59 mL, 3.38 mmol) in NMP (5 mL) and heating at 140° C. for 50 mins according to the procedure reported in scheme 2. This gave after workup and purification by flash column chromatography [silica (24 g), eluting with DMA80 in DCM from 0-70%] followed by purification by reverse phase column chromatography [C18 steel column (250 mm×30 mm), eluting with ACN in water (containing 0.1% HCl) from 0-100%] (S)-(1-(4-((1-(benzo[d][1,3]dioxol-5-yl)-1H-imidazol-4-yl)amino)pyrrolo[2,1-f][1,2,4]triazin-2-yl)pyrrolidin-2-yl)methanol (425e) (122 mg, 26% yield) HCl salt as a white solid; $^1$H NMR (300 MHz, DMSO-$d_6$) δ 11.04 (s, 1H, $D_2O$ exchangeable), 8.78 (d, J=1.6 Hz, 1H), 7.95 (d, J=1.7 Hz, 1H), 7.52-7.43 (m, 2H), 7.27 (dd, J=8.4, 2.3 Hz, 1H), 7.13 (dd, J=4.5, 1.6 Hz, 1H), 7.07 (d, J=8.3 Hz, 1H), 6.50-6.44 (m, 1H), 6.15 (s, 2H), 4.25-4.02 (m, 1H), 3.68 (dd, J=10.1, 3.8 Hz, 1H), 3.54-3.43 (m, 1H), 3.40-3.29 (m, 2H), 2.16-1.77 (m, 4H); MS (ES+): 420.2 (M+1); (ES−): 418.1 (M−1).

Scheme 426

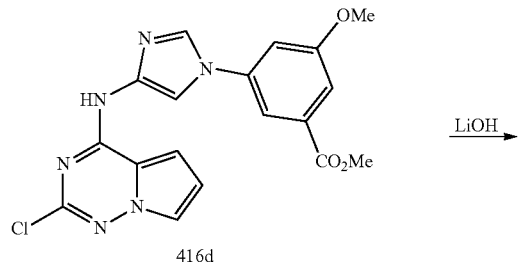

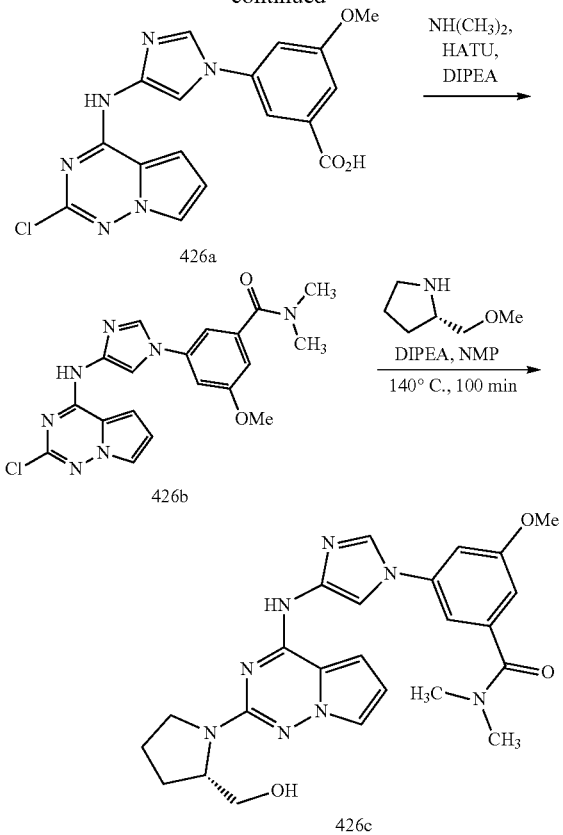

Preparation of (S)-3-(4-((2-(2-(hydroxymethyl)pyrrolidin-1-yl)pyrrolo[2,1-f][1,2,4]triazin-4-yl)amino)-1H-imidazol-1-yl)-5-methoxy-N,N-dimethylbenzamide (426c)

Step-1: Preparation of 3-(4-((2-chloropyrrolo[2,1-f][1,2,4]triazin-4-yl)amino)-1H-imidazol-1-yl)-5-methoxybenzoic acid (426a)

Compound 426a was prepared from methyl 3-(4-((2-chloropyrrolo[2,1-f][1,2,4]triazin-4-yl)amino)-1H-imidazol-1-yl)-5-methoxybenzoate (416d) (172 mg, 0.431 mmol) in MeOH/THF (6 mL) using a solution of lithium hydroxide monohydrate (42 mg, 1.0 mmol) in water (2 mL) according to the procedure reported in Step-2 of Scheme 411. This gave after workup 3-(4-((2-chloropyrrolo[2,1-f][1,2,4]triazin-4-yl)amino)-1H-imidazol-1-yl)-5-methoxybenzoic acid (426a) (166 mg, 100% yield) as a yellow solid. MS (ES+): 384.9 (M+1); MS (ES−): 382.9 (M−1).

Step-2: Preparation of 3-(4-((2-chloropyrrolo[2,1-f][1,2,4]triazin-4-yl)amino)-1H-imidazol-1-yl)-5-methoxy-N,N-dimethylbenzamide (426b)

Compound 426b was prepared from 3-(4-((2-chloropyrrolo[2,1-f][1,2,4]triazin-4-yl)amino)-1H-imidazol-1-yl)-5-methoxybenzoic acid (426a) (585 mg, 1.52 mmol), using 40% dimethylamine (370 mg, 3.28 mmol) HATU (699 mg, 1.838 mmol), DIPEA (0.8 mL, 4.58 mmol) in DMF (10 mL) according to the procedure reported in step-3 of scheme 410. This gave after workup and purification by flash column chromatography [silica (12 g), eluting with EA/MeOH 9:1 in DCM from 50 to 10%] 3-(4-((2-chloropyrrolo[2,1-f][1,2,4]triazin-4-yl)amino)-1H-imidazol-1-yl)-5-methoxy-N,N-dimethylbenzamide (426b) (453 mg, 72% yield) as a yellow solid. ¹H NMR (300 MHz, DMSO-d₆) δ 11.33 (s, 1H), 8.33 (d, J=1.6 Hz, 1H), 7.93 (d, J=1.6 Hz, 1H), 7.78 (dd, J=2.6, 1.5 Hz, 1H), 7.40 (s, 1H), 7.30 (t, J=2.2 Hz, 1H), 7.27-7.16 (m, 1H), 6.97 (dd, J=2.4, 1.2 Hz, 1H), 6.73 (dd, J=4.5, 2.6 Hz, 1H), 3.88 (s, 3H), 3.01 (s, 3H), 2.95 (s, 3H); MS (ES+): 412.1 (M+1).

Step-3: Preparation of (S)-3-(4-((2-(2-(hydroxymethyl)pyrrolidin-1-yl)pyrrolo[2,1-f][1,2,4]triazin-4-yl)amino)-1H-imidazol-1-yl)-5-methoxy-N,N-dimethylbenzamide (426c)

Compound 426c was prepared from 3-(4-((2-chloropyrrolo[2,1-f][1,2,4]triazin-4-yl)amino)-1H-imidazol-1-yl)-5-methoxy-N,N-dimethylbenzamide (426b) (453 mg, 1.100 mmol), (S)-pyrrolidin-2-ylmethanol (349 mg, 3.45 mmol), N-ethyl-N-isopropylpropan-2-amine (0.6 mL, 3.44 mmol) in NMP (6 mL) and heating at 140° C. for 100 min according to the procedure reported in scheme 2. This gave after workup and purification by flash column chromatography [silica (12 g), eluting with MeOH in DCM from 0-20%] followed by reverse phase column chromatography [C18 (RediSep 250×30 mm), eluting with ACN in water (containing 0.1% HCl) from 0-100%] (S)-3-(4-((2-(2-(hydroxymethyl)pyrrolidin-1-yl)pyrrolo[2,1-f][1,2,4]triazin-4-yl)amino)-1H-imidazol-1-yl)-5-methoxy-N,N-dimethylbenzamide (426c) (195 mg, 37% yield) HCl salt as white yellow solid. ¹H NMR (300 MHz, DMSO-d₆) δ 10.98 (s, 1H), 8.80 (d, J=1.6 Hz, 1H), 8.08 (d, J=1.7 Hz, 1H), 7.56-7.44 (m, 1H), 7.39 (dt, J=9.5, 1.9 Hz, 2H), 7.15 (dd, J=4.5, 1.6 Hz, 1H), 6.98 (dd, J=2.3, 1.2 Hz, 1H), 6.46 (dd, J=4.5, 2.4 Hz, 1H), 4.17 (s, 1H), 3.89 (s, 3H), 3.69 (dd, J=10.1, 3.8 Hz, 1H), 3.50 (d, J=7.0 Hz, 1H), 3.45-3.26 (m, 2H), 3.01 (s, 3H), 2.95 (s, 3H), 2.13-1.74 (m, 4H); MS (ES+): 477.2 (M+1); MS (ES−): 475.2 (M−1). HPLC purity 99.25%.

Scheme 427

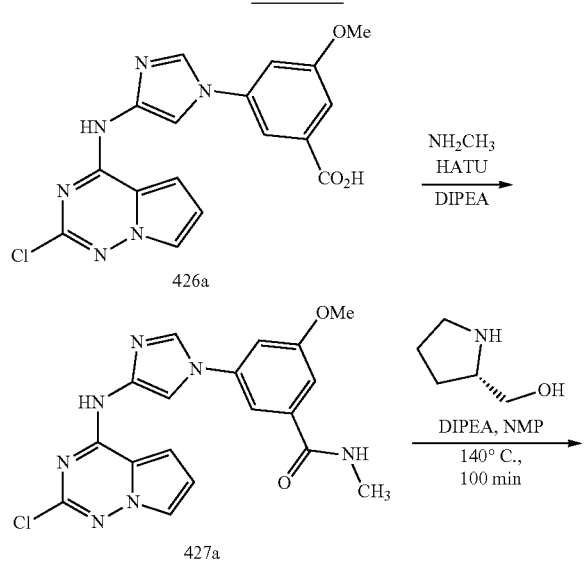

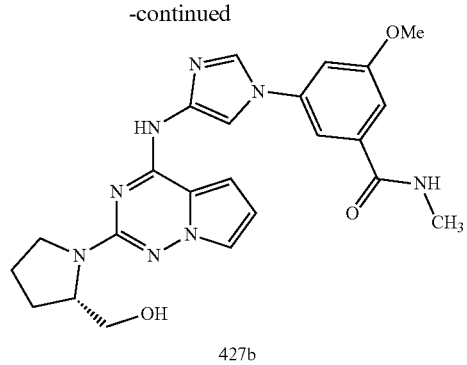

Preparation of (S)-3-(4-((2-(2-(hydroxymethyl)pyrrolidin-1-yl)pyrrolo[2,1-f][1,2,4]triazin-4-yl)amino)-1H-imidazol-1-yl)-5-methoxy-N-methylbenzamide (427b)

Step-1: Preparation of 3-(4-((2-chloropyrrolo[2,1-f][1,2,4]triazin-4-yl)amino)-1H-imidazol-1-yl)-5-methoxy-N-methylbenzamide (427a)

Compound 427a was prepared from 3-(4-((2-chloropyrrolo[2,1-f][1,2,4]triazin-4-yl)amino)-1H-imidazol-1-yl)-5-methoxybenzoic acid (426a) (585 mg, 1.52 mmol), using methanamine (2 M in THF, 1.6 mL, 3.20 mmol), HATU (708 mg, 1.862 mmol), DIPEA (0.8 mL, 4.58 mmol) in DMF (10 mL) according to the procedure reported in step-3 of scheme 410. This gave after workup and purification by flash column chromatography [silica (12 g), eluting with methanol in DCM from 0 to 20%] 3-(4-((2-chloropyrrolo[2,1-f][1,2,4]triazin-4-yl)amino)-1H-imidazol-1-yl)-5-methoxy-N-methylbenzamide (427a) (298 mg, 49% yield) as a yellow solid. ¹H NMR (300 MHz, DMSO-d₆) δ 11.35 (s, 1H), 8.63 (d, J=4.6 Hz, 1H), 8.32 (d, J=1.6 Hz, 1H), 7.95 (d, J=1.6 Hz, 1H), 7.78 (dd, J=2.6, 1.5 Hz, 1H), 7.64 (t, J=1.7 Hz, 1H), 7.41 (p, J=2.3 Hz, 3H), 6.73 (dd, J=4.5, 2.6 Hz, 1H), 3.90 (s, 3H), 2.82 (d, J=4.5 Hz, 3H); MS (ES+): 398.1 (M+1).

Step-2: Preparation of (S)-3-(4-((2-(2-(hydroxymethyl)pyrrolidin-1-yl)pyrrolo[2,1-f][1,2,4]triazin-4-yl)amino)-1H-imidazol-1-yl)-5-methoxy-N-methylbenzamide (427b)

Compound 427b was prepared from 3-(4-((2-chloropyrrolo[2,1-f][1,2,4]triazin-4-yl)amino)-1H-imidazol-1-yl)-5-methoxy-N-methylbenzamide (427a) (298 mg, 0.749 mmol), (S)-pyrrolidin-2-ylmethanol (277 mg, 2.74 mmol), N-ethyl-N-isopropylpropan-2-amine (0.45 mL, 2.58 mmol) in NMP (6 mL) and heating at 140° C. for 100 min according to the procedure reported in scheme 2. This gave after workup and purification by flash column chromatography [silica (12 g), eluting with MeOH in DCM from 0-20%] followed by reverse phase column chromatography [C18 (RediSep 250×30 mm), eluting with ACN in water (containing 0.1% HCl) from 0-100%] (S)-3-(4-((2-(2-(hydroxymethyl)pyrrolidin-1-yl)pyrrolo[2,1-f][1,2,4]triazin-4-yl)amino)-1H-imidazol-1-yl)-5-methoxy-N-methylbenzamide (427b) (111 mg, 32% yield) HCl salt as a white yellow solid. ¹H NMR (300 MHz, DMSO-d₆) δ 11.09 (s, 1H), 8.93 (d, J=1.6 Hz, 1H), 8.73 (q, J=4.4 Hz, 1H), 8.13 (d, J=1.6 Hz, 1H), 7.80 (t, J=1.6 Hz, 1H), 7.55-7.47 (m, 2H), 7.45 (dd, J=2.3, 1.2 Hz, 1H), 7.16 (dd, J=4.5, 1.7 Hz, 1H), 6.47 (dd, J=4.5, 2.4 Hz, 1H), 4.20 (s, 1H), 3.91 (s, 3H), 3.71 (dd, J=10.1, 3.9 Hz, 1H), 3.51 (d, J=7.7 Hz, 1H), 3.47-3.27 (m, 2H), 2.83 (d, J=4.3 Hz, 3H), 2.14-1.74 (m, 4H); MS (ES+): 463.2 (M+1); MS (ES−): 461.1 (M−1). HPLC purity 99.35%.

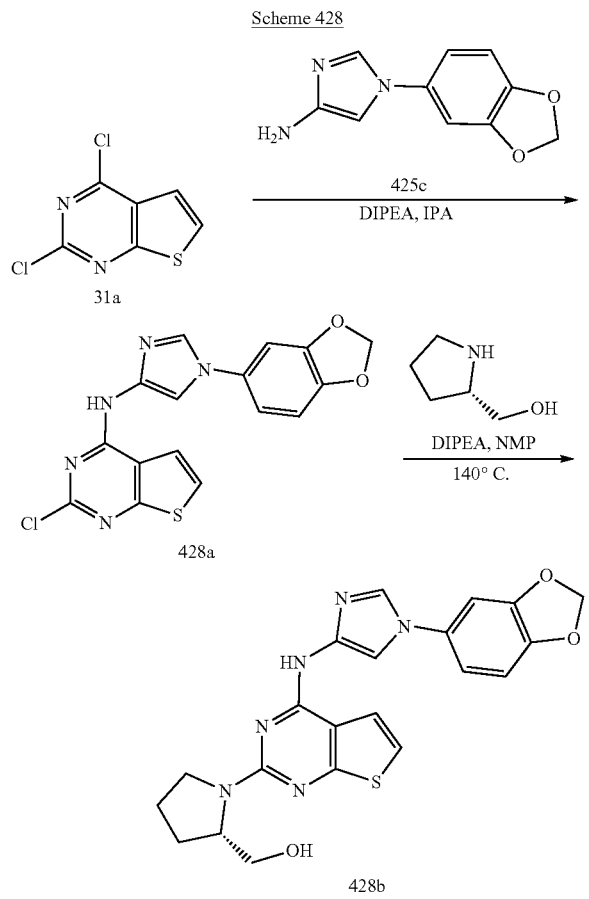

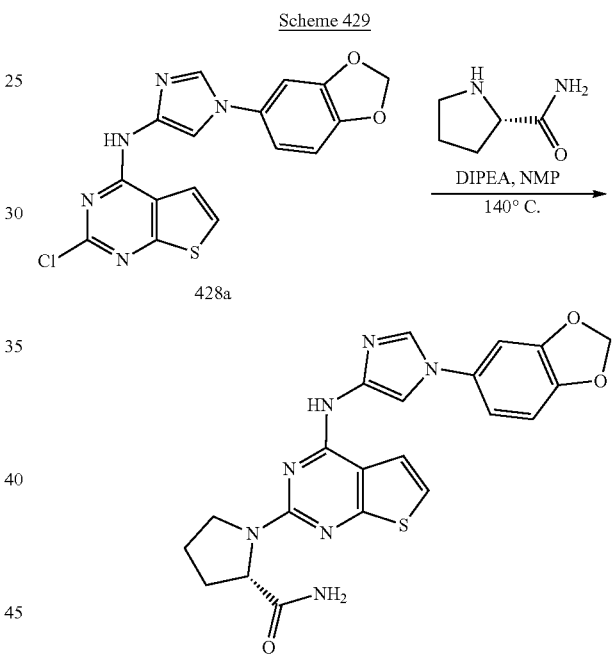

Preparation of (S)-(1-(4-((1-(benzo[d][1,3]dioxol-5-yl)-1H-imidazol-4-yl)amino)thieno[2,3-d]pyrimidin-2-yl)pyrrolidin-2-yl)methanol (428b)

Step-1: Preparation of N-(1-(benzo[d][1,3]dioxol-5-yl)-1H-imidazol-4-yl)-2-chlorothieno[2,3-d]pyrimidin-4-amine (428a)

Compound 428a was prepared from 2,4-dichlorothieno[2,3-d]pyrimidine (31a) (858 mg, 4.18 mmol) in 2-Propanol (40 mL) using DIPEA (2.19 mL, 12.55 mmol), 1-(benzo[d][1,3]dioxol-5-yl)-1H-imidazol-4-amine (425c) (850 mg, 4.18 mmol) and heating at reflux for 2 h according to the procedure reported in step-1 of scheme 183. This gave after workup and filtration N-(1-(benzo[d][1,3]dioxol-5-yl)-1H-imidazol-4-yl)-2-chlorothieno[2,3-d]pyrimidin-4-amine (428a) (330 mg, 21% yield) as a yellow solid; MS (ES+): 372.0 (M+1); (ES−): 370.0 (M−1).

Step-2: Preparation of (S)-(1-(4-((1-(benzo[d][1,3]dioxol-5-yl)-1H-imidazol-4-yl)amino)thieno[2,3-d]pyrimidin-2-yl)pyrrolidin-2-yl)methanol (428b)

Compound 428b was prepared from N-(1-(benzo[d][1,3]dioxol-5-yl)-1H-imidazol-4-yl)-2-chlorothieno[2,3-d]pyrimidin-4-amine (428a) (300 mg, 0.80 mmol), (S)-pyrrolidin-2-ylmethanol (245 mg, 2.42 mmol), N-ethyl-N-isopropylpropan-2-amine (0.42 mL, 2.42 mmol) in NMP (5 mL) and heating at 140° C. for 50 mins according to the procedure reported in scheme 2. This gave after workup and purification by flash column chromatography [silica (24 g), eluting with DMA80 in DCM from 0-70%] followed by purification by reverse phase column chromatography [C18 steel column (250 mm×30 mm), eluting with ACN in water (containing 0.1% HCl) from 0-100%] (S)-(1-(4-((1-(benzo[d][1,3]dioxol-5-yl)-1H-imidazol-4-yl)amino)thieno[2,3-d]pyrimidin-2-yl)pyrrolidin-2-yl)methanol (428b) (230 mg, 65% yield) HCl salt as a white solid; $^1$H NMR (300 MHz, DMSO-$d_6$) δ 11.47 (s, 1H, $D_2O$ exchangeable), 8.39 (s, 1H), 7.90 (d, J=5.8 Hz, 1H), 7.85 (s, 1H), 7.41-7.27 (m, 2H), 7.22-7.08 (m, 1H), 7.02-6.91 (m, 1H), 6.07 (s, 2H), 4.40-4.25 (m, 1H), 3.77-3.66 (m, 1H), 3.66-3.55 (m, 1H), 3.54-3.39 (m, 2H), 2.10-1.82 (m, 4H); MS (ES+): 437.1 (M+1); (ES−): 435.1 (M−1).

Preparation of (S)-1-(4-((1-(benzo[d][1,3]dioxol-5-yl)-1H-imidazol-4-yl)amino)thieno[2,3-d]pyrimidin-2-yl)pyrrolidine-2-carboxamide (429a)

Compound 429a was prepared from N-(1-(benzo[d][1,3]dioxol-5-yl)-1H-imidazol-4-yl)-2-chlorothieno[2,3-d]pyrimidin-4-amine (428a) (320 mg, 0.86 mmol), (S)-pyrrolidine-2-carboxamide (295 mg, 2.58 mmol), N-ethyl-N-isopropylpropan-2-amine (0.45 mL, 2.58 mmol) in NMP (5 mL) and heating at 140° C. for 50 mins according to the procedure reported in scheme 2. This gave after workup and purification by flash column chromatography [silica (24 g), eluting with DMA80 in DCM from 0-70%] followed by purification by reverse phase column chromatography [C18 steel column (250 mm×30 mm), eluting with ACN in water (containing 0.1% HCl) from 0-100%] (S)-1-(4-((1-(benzo[d][1,3]dioxol-5-yl)-1H-imidazol-4-yl)amino)thieno[2,3-d]

pyrimidin-2-yl)pyrrolidine-2-carboxamide (429a) (194 mg, 50% yield) HCl salt as a white solid; ¹H NMR (300 MHz, DMSO-d$_6$) δ 11.44 (s, 1H, D$_2$O exchangeable), 8.44 (s, 1H), 8.00 (d, J=5.9 Hz, 1H), 7.81 (s, 1H), 7.60 (s, 1H), 7.54 (d, J=2.3 Hz, 1H), 7.43 (d, J=5.8 Hz, 1H), 7.34-7.20 (m, 2H), 7.04 (d, J=8.4 Hz, 1H), 6.13 (s, 2H), 4.59 (d, J=8.5 Hz, 1H), 4.03-3.91 (m, 1H), 3.70-3.57 (m, 1H), 2.36-2.23 (m, 1H), 2.12-1.90 (m, 3H); MS (ES+): 450.1 (M+1), (ES−): 448.1 (M−1).

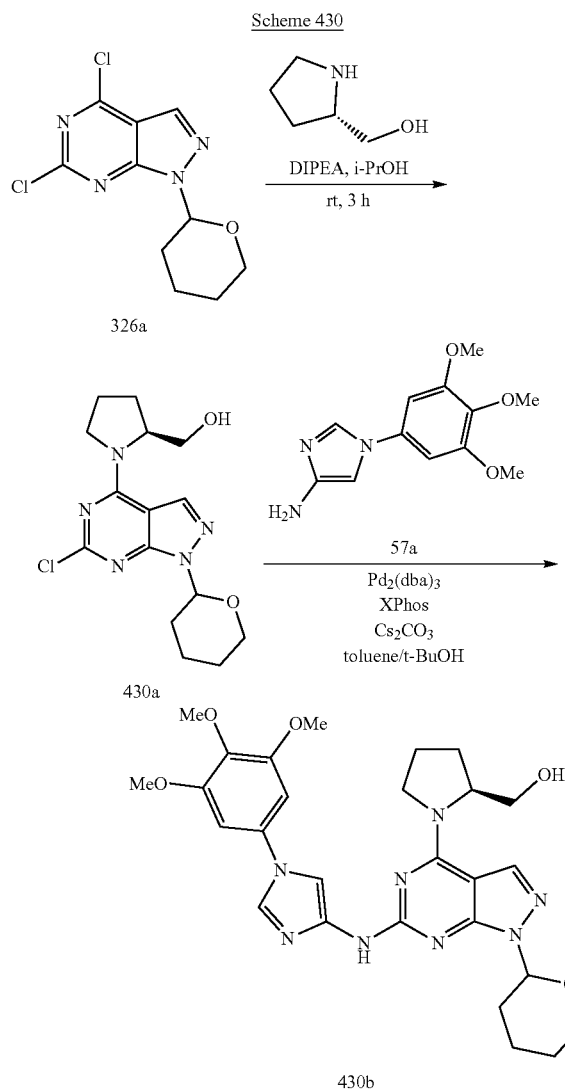

Scheme 430

Preparation of ((2S)-1-(1-(tetrahydro-2H-pyran-2-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (430b)

Step-1: Preparation of ((2S)-1-(6-chloro-1-(tetrahydro-2H-pyran-2-yl)-1H-pyrazolo[3,4-d]pyrimidin-4-yl)pyrrolidin-2-yl)methanol (430a)

Compound 430a was prepared from 4,6-dichloro-1-(tetrahydro-2H-pyran-2-yl)-1H-pyrazolo[3,4-d]pyrimidine (326a) (1 g, 3.66 mmol) in 2-Propanol (10 mL) using (S)-pyrrolidin-2-ylmethanol (0.361 mL, 3.66 mmol), DIPEA (1.92 mL, 10.98 mmol) and stirring at room temperature for 3 h according to the procedure reported in step-1 of scheme 96. This gave after workup and purification by flash column chromatography [silica gel, 12 g eluting with DCM and methanol (0 to 30%)] ((2S)-1-(6-chloro-1-(tetrahydro-2H-pyran-2-yl)-1H-pyrazolo[3,4-d]pyrimidin-4-yl)pyrrolidin-2-yl)methanol (430a) (650 mg, 53% yield) as a yellow solid; MS (ES+): 338.1 (M+1).

Step-2: Preparation of ((2S)-1-(1-(tetrahydro-2H-pyran-2-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (430b)

Compound 430b was prepared from ((2S)-1-(6-chloro-1-(tetrahydro-2H-pyran-2-yl)-1H-pyrazolo[3,4-d]pyrimidin-4-yl)pyrrolidin-2-yl)methanol (430a) (300 mg, 0.89 mmol), 1-(3,4,5-trimethoxyphenyl)-1H-imidazol-4-amine (57a) (221 mg, 0.89 mmol), dicyclohexyl(2',4',6'-triisopropylbiphenyl-2-yl)phosphine (XPhos, 169 mg, 0.36 mmol), cesium carbonate (723 mg, 2.22 mmol), Pd$_2$(dba)$_3$ (163 mg, 0.18 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA-80 in DCM from 0-50%] followed by purification by reverse phase column chromatography [(silica gel C-18, 24 g) eluting with acetonitrile and 0.1% HCl water] and lyophilization ((2S)-1-(1-(tetrahydro-2H-pyran-2-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (430b) (135 mg, 28% yield) HCl salt as a white solid. ¹H NMR (300 MHz, DMSO-d$_6$) δ 10.54-10.17 (m, 1H, D$_2$O exchangeable), 9.15 (s, 1H), 8.15 (d, J=2.7 Hz, 1H), 7.95 (d, J=7.2 Hz, 1H), 7.23-7.07 (m, 2H), 5.93-5.73 (m, 1H), 4.68-4.33 (m, 1H), 4.02-3.92 (m, 2H), 3.90 (s, 6H), 3.80-3.47 (m, 8H), 2.41-2.29 (m, 1H), 2.23-1.93 (m, 6H), 1.91-1.67 (m, 2H), 1.62-1.46 (m, 2H); MS (ES+): 551.3 (M+1).

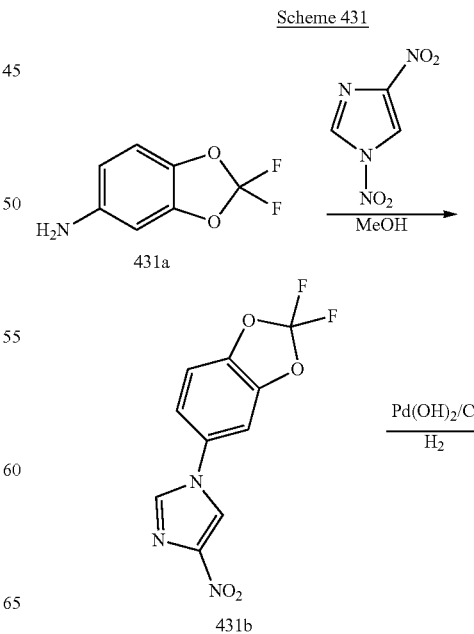

Scheme 431

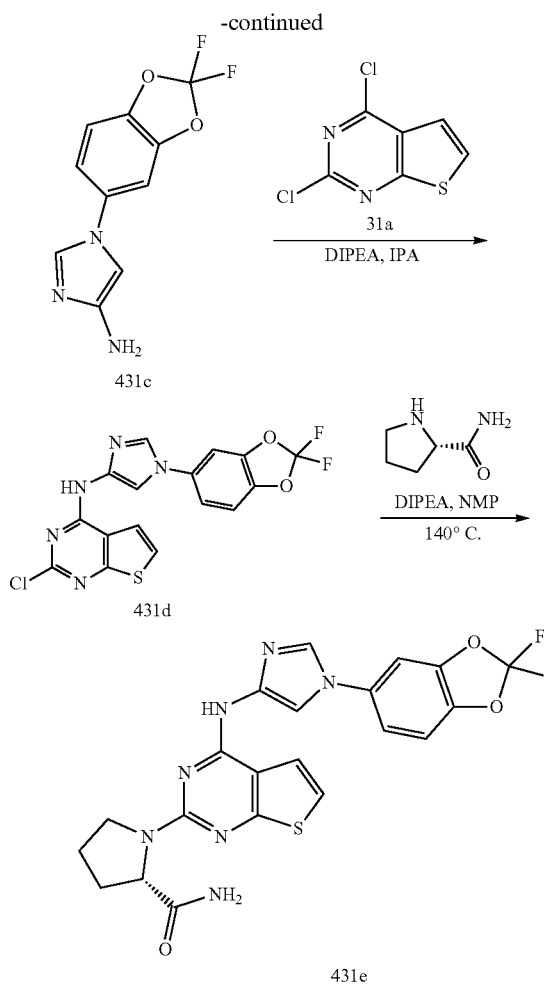

Preparation of (S)-1-(4-((1-(2,2-difluorobenzo[d][1,3]dioxol-5-yl)-1H-imidazol-4-yl)amino)thieno[2,3-d]pyrimidin-2-yl)pyrrolidine-2-carboxamide (431e)

Step-1: Preparation of 1-(2,2-difluorobenzo[d][1,3]dioxol-5-yl)-4-nitro-1H-imidazole (431b)

Reaction of 1,4-dinitro-1H-imidazole (4.57 g, 28.9 mmol) with 2,2-difluorobenzo[d][1,3]dioxol-5-amine (431a) (5 g, 28.9 mmol) as reported in step-2 of General scheme for preparation of 3-substituted-(4-amino-1H-imidazol-1-yl) gave after filtration 1-(2,2-difluorobenzo[d][1,3]dioxol-5-yl)-4-nitro-1H-imidazole (431b) (5.5 g, 71% yield) as a yellow solid; MS (ES+): 270.1 (M+1).

Step-2: Preparation of 1-(2,2-difluorobenzo[d][1,3]dioxol-5-yl)-1H-imidazol-4-amine (431c)

Reduction of nitro to amine of 1-(2,2-difluorobenzo[d][1,3]dioxol-5-yl)-4-nitro-1H-imidazole (431b) (2 g, 7.43 mmol) in MeOH (120 mL) using Palladium hydroxide on carbon, 20 wt. % loading (dry basis), matrix carbon, wet support (0.522 g, 0.743 mmol) as reported in step-3 of General scheme for preparation of 3-substituted-(4-amino-1H-imidazol-1-yl) gave 1-(2,2-difluorobenzo[d][1,3]dioxol-5-yl)-1H-imidazol-4-amine (431c) (560 mg, 32% yield) as a light yellow semi-solid; MS (ES+): 240.1 (M+1).

Step-3: Preparation of 2-chloro-N-(1-(2,2-difluorobenzo[d][1,3]dioxol-5-yl)-1H-imidazol-4-yl)thieno[2,3-d]pyrimidin-4-amine (431d)

Compound 431d was prepared from 2,4-dichlorothieno[2,3-d]pyrimidine (31a) (557 mg, 2.72 mmol) in 2-Propanol (40 mL) using DIPEA (1.42 mL, 8.15 mmol), 1-(2,2-difluorobenzo[d][1,3]dioxol-5-yl)-1H-imidazol-4-amine (431c) (650 mg, 2.72 mmol) and heating at reflux for 2 h according to the procedure reported in step-1 of scheme 183. This gave after workup and filtration 2-chloro-N-(1-(2,2-difluorobenzo[d][1,3]dioxol-5-yl)-1H-imidazol-4-yl)thieno[2,3-d]pyrimidin-4-amine (431d) (560 mg, 51% yield) as a yellow solid; $^1$H NMR (300 MHz, DMSO-$d_6$) δ 11.05 (s, 1H), 8.20 (d, J=1.6 Hz, 1H), 8.09-7.98 (m, 1H), 7.95-7.86 (m, 2H), 7.71 (d, J=5.9 Hz, 1H), 7.61 (d, J=8.6 Hz, 1H), 7.50 (dd, J=8.6, 2.2 Hz, 1H); $^{19}$F NMR (282 MHz, DMSO-$d_6$) δ −48.79 MS (ES+): 408.0 (M+1); (ES−): 406.0 (M−1).

Step-4: Preparation of (S)-1-(4-((1-(2,2-difluorobenzo[d][1,3]dioxol-5-yl)-1H-imidazol-4-yl)amino)thieno[2,3-d]pyrimidin-2-yl)pyrrolidine-2-carboxamide (431e)

Compound 431e was prepared from 2-chloro-N-(1-(2,2-difluorobenzo[d][1,3]dioxol-5-yl)-1H-imidazol-4-yl)thieno[2,3-d]pyrimidin-4-amine (431d) (250 mg, 0.61 mmol), (S)-pyrrolidine-2-carboxamide (210 mg, 1.84 mmol), N-ethyl-N-isopropylpropan-2-amine (0.32 mL, 1.84 mmol) in NMP (5 mL) and heating at 140° C. for 50 mins according to the procedure reported in scheme 2. This gave after workup and purification by flash column chromatography [silica (24 g), eluting with DMA80 in DCM from 0-70%] followed by purification by reverse phase column chromatography [C18 steel column (250 mm×30 mm), eluting with ACN in water (containing 0.1% HCl) from 0-100%] (S)-1-(4-((1-(2,2-difluorobenzo[d][1,3]dioxol-5-yl)-1H-imidazol-4-yl)amino)thieno[2,3-d]pyrimidin-2-yl)pyrrolidine-2-carboxamide (431e) (122 mg, 41% yield) HCl salt as a white solid; $^1$H NMR (300 MHz, DMSO-$d_6$) δ 11.34 (s, 1H, $D_2O$ exchangeable), 8.35 (d, J=1.5 Hz, 1H), 8.05 (d, J=2.3 Hz, 1H), 7.99 (d, J=5.8 Hz, 1H), 7.81 (d, J=1.6 Hz, 1H, $D_2O$ exchangeable), 7.72-7.62 (m, 2H), 7.57 (d, J=8.7 Hz, 1H), 7.41 (d, J=5.8 Hz, 1H), 7.32 (s, 1H), 4.65-4.57 (m, 1H), 4.02-3.92 (m, 1H), 3.68-3.55 (m, 1H), 2.40-2.23 (m, 1H), 2.13-1.93 (m, 3H); $^{19}$F NMR (282 MHz, DMSO-$d_6$) δ −48.77; MS (ES+): 486.1 (M+1); (ES−): 484.1 (M−1).

Scheme 432

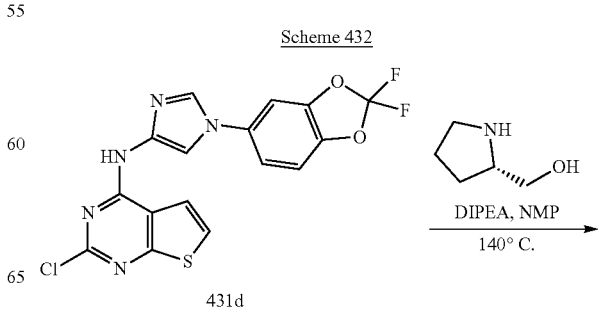

-continued

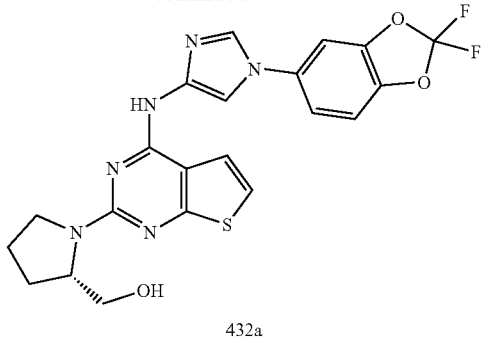

432a

Preparation of (S)-(1-(4-((1-(2,2-difluorobenzo[d][1,3]dioxol-5-yl)-1H-imidazol-4-yl)amino)thieno[2,3-d]pyrimidin-2-yl)pyrrolidin-2-yl)methanol (432a)

Compound 432a was prepared from 2-chloro-N-(1-(2,2-difluorobenzo[d][1,3]dioxol-5-yl)-1H-imidazol-4-yl)thieno[2,3-d]pyrimidin-4-amine (431d) (250 mg, 0.61 mmol), (S)-pyrrolidin-2-ylmethanol (186 mg, 1.84 mmol), N-ethyl-N-isopropylpropan-2-amine (0.32 mL, 1.84 mmol) in NMP (5 mL) and heating at 140° C. for 50 mins according to the procedure reported in scheme 2. This gave after workup and purification by flash column chromatography [silica (24 g), eluting with DMA80 in DCM from 0-70%] followed by purification by reverse phase column chromatography [C18 steel column (250 mm×30 mm), eluting with ACN in water (containing 0.1% HCl) from 0-100%] (S)-(1-(4-((1-(2,2-difluorobenzo[d][1,3]dioxol-5-yl)-1H-imidazol-4-yl)amino)thieno[2,3-d]pyrimidin-2-yl)pyrrolidin-2-yl)methanol (432a) (179 mg, 62% yield) HCl salt as a white solid; $^1$H NMR (300 MHz, DMSO-$d_6$) δ 11.44 (s, 1H, D$_2$O exchangeable), 8.37 (s, 1H), 8.04-7.87 (m, 3H), 7.67-7.51 (m, 2H), 7.40 (d, J=5.8 Hz, 1H), 4.48-4.37 (m, 2H), 3.79-3.69 (m, 2H), 3.59-3.44 (m, 2H), 2.18-1.91 (m, 4H); $^{19}$F NMR (282 MHz, DMSO-$d_6$) δ −48.73; MS (ES+): 473.1 (M+1); (ES−): 471.1 (M−1).

Scheme 433

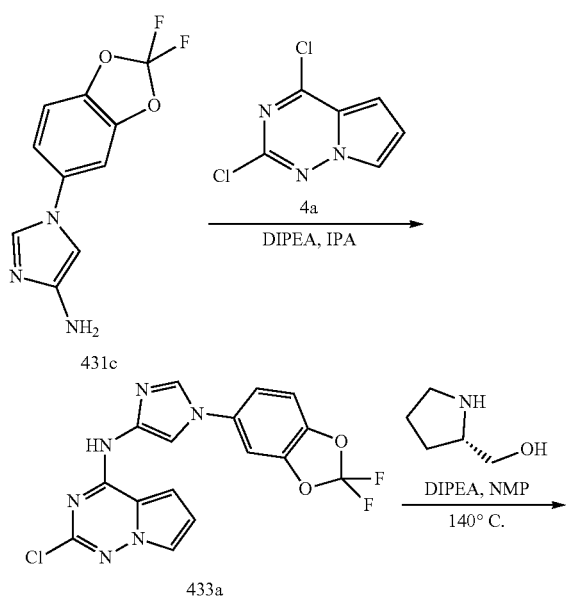

-continued

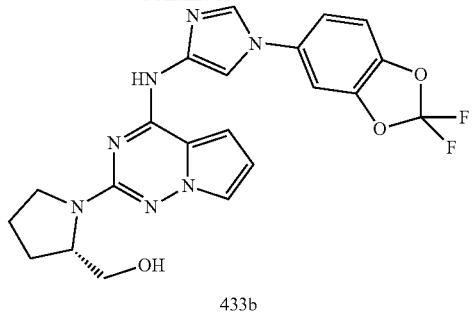

433b

Preparation of (S)-(1-(4-((1-(2,2-difluorobenzo[d][1,3]dioxol-5-yl)-1H-imidazol-4-yl)amino)pyrrolo[2,1-f][1,2,4]triazin-2-yl)pyrrolidin-2-yl)methanol (433b)

Step-1: Preparation of 2-chloro-N-(1-(2,2-difluorobenzo[d][1,3]dioxol-5-yl)-1H-imidazol-4-yl)pyrrolo[2,1-f][1,2,4]triazin-4-amine (433a)

Compound 433a was prepared from 2,4-dichloropyrrolo[2,1-f][1,2,4]triazine (4a) (519 mg, 2.76 mmol) in 2-Propanol (40 mL) using DIPEA (1.45 mL, 8.28 mmol), 1-(2,2-difluorobenzo[d][1,3]dioxol-5-yl)-1H-imidazol-4-amine (431c) (660 mg, 2.76 mmol) and heating at reflux for 2 h according to the procedure reported in step-1 of scheme 183. This gave after workup and filtration 2-chloro-N-(1-(2,2-difluorobenzo[d][1,3]dioxol-5-yl)-1H-imidazol-4-yl)pyrrolo[2,1-f][1,2,4]triazin-4-amine (433a) (630 mg, 58% yield) as a yellow solid; $^1$H NMR (300 MHz, DMSO-$d_6$) δ 11.35 (s, 1H), 8.21 (d, J=1.6 Hz, 1H), 7.91 (dd, J=6.8, 1.9 Hz, 2H), 7.78 (dd, J=2.6, 1.5 Hz, 1H), 7.60 (d, J=8.7 Hz, 1H), 7.50 (dd, J=8.7, 2.3 Hz, 1H), 7.44-7.36 (m, 1H), 6.73 (dd, J=4.5, 2.6 Hz, 1H); $^{19}$F NMR (282 MHz, DMSO-$d_6$) δ −48.78; MS (ES+): 391.1 (M+1); (ES−): 389.1 (M−1).

Step-2: Preparation of (S)-(1-(4-((1-(2,2-difluorobenzo[d][1,3]dioxol-5-yl)-1H-imidazol-4-yl)amino)pyrrolo[2,1-f][1,2,4]triazin-2-yl)pyrrolidin-2-yl)methanol (433b)

Compound 433b was prepared from 2-chloro-N-(1-(2,2-difluorobenzo[d][1,3]dioxol-5-yl)-1H-imidazol-4-yl)pyrrolo[2,1-f][1,2,4]triazin-4-amine (433a) (200 mg, 0.51 mmol), (S)-pyrrolidin-2-ylmethanol (155 mg, 1.54 mmol), N-ethyl-N-isopropylpropan-2-amine (0.29 mL, 1.54 mmol) in NMP (5 mL) and heating at 140° C. for 50 mins according to the procedure reported in scheme 2. This gave after workup and purification by flash column chromatography [silica (24 g), eluting with DMA80 in DCM from 0-70%] followed by purification by reverse phase column chromatography [C18 steel column (250 mm×30 mm), eluting with ACN in water (containing 0.1% HCl) from 0-100%] (S)-(1-(4-((1-(2,2-difluorobenzo[d][1,3]dioxol-5-yl)-1H-imidazol-4-yl)amino)pyrrolo[2,1-f][1,2,4]triazin-2-yl)pyrrolidin-2-yl)methanol (433b) (50 mg, 21% yield) HCl salt as a white solid; $^1$H NMR (300 MHz, DMSO-$d_6$) δ 10.77 (s, 1H, D$_2$O exchangeable), 8.47 (d, J=1.6 Hz, 1H), 7.98 (d, J=2.2 Hz, 1H), 7.96 (d, J=1.7 Hz, 1H), 7.66-7.60 (m, 1H), 7.59-7.54 (m, 1H), 7.45-7.41 (m, 1H), 7.14 (dd, J=4.5, 1.6 Hz, 1H), 6.45-6.38 (m, 1H), 4.22-4.11 (m, 1H), 3.75 (dd, J=10.1, 3.6 Hz, 1H), 3.53-3.42 (m, 1H), 3.39-3.26 (m, 2H), 2.11-2.00

(m, 1H), 1.99-1.84 (m, 3H); $^{19}$F NMR (282 MHz, DMSO-$d_6$) δ −48.73; MS (ES+): 456.1 (M+1); (ES−): 454.1 (M−1).

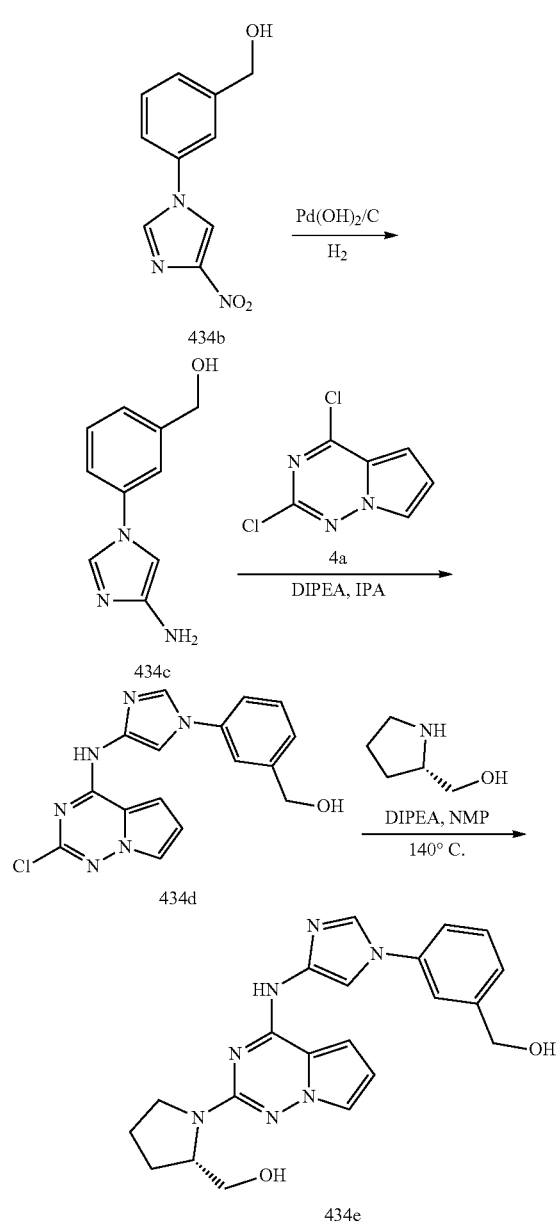

Scheme 434

Preparation of (S)-(1-(4-((1-(3-(hydroxymethyl)phenyl)-1H-imidazol-4-yl)amino)pyrrolo[2,1-f][1,2,4]triazin-2-yl)pyrrolidin-2-yl)methanol (434e)

Step-1: Preparation of (3-(4-nitro-1H-imidazol-1-yl)phenyl)methanol (434b)

Reaction of 1,4-dinitro-1H-imidazole (2.57 g, 16.24 mmol) with (3-aminophenyl)methanol (434a) (2 g, 16.24 mmol) as reported in step-2 of General scheme for preparation of 3-substituted-(4-amino-1H-imidazol-1-yl) gave after filtration (3-(4-nitro-1H-imidazol-1-yl)phenyl)methanol (434b) (2.4 g, 67% yield) as a yellow solid; MS (ES+): 220.0 (M+1).

Step-2: Preparation of (3-(4-amino-1H-imidazol-1-yl)phenyl)methanol (434c)

Reduction of nitro to amine of (3-(4-nitro-1H-imidazol-1-yl)phenyl)methanol (434b) (1.1 g, 5.02 mmol) in MeOH (40 mL) using Palladium hydroxide on carbon, 20 wt. % loading (dry basis), matrix carbon, wet support (0.35 g, 0.50 mmol) as reported in step-3 of General scheme for preparation of 3-substituted-(4-amino-1H-imidazol-1-yl) gave (3-(4-amino-1H-imidazol-1-yl)phenyl)methanol (434c) (745 mg, 78% yield) as a light yellow semi-solid; MS (ES+): 190.1 (M+1).

Step-3: Preparation of (3-(4-((2-chloropyrrolo[2,1-f][1,2,4]triazin-4-yl)amino)-1H-imidazol-1-yl)phenyl)methanol (434d)

Compound 434d was prepared from 2,4-dichloropyrrolo[2,1-f][1,2,4]triazine (4a) (745 mg, 3.96 mmol) in 2-Propanol (20 mL) using DIPEA (2.08 mL, 11.89 mmol), (3-(4-amino-1H-imidazol-1-yl)phenyl)methanol (434c) (750 mg, 3.96 mmol) and heating at reflux for 2 h according to the procedure reported in step-1 of scheme 183. This gave after workup and filtration (3-(4-((2-chloropyrrolo[2,1-f][1,2,4]triazin-4-yl)amino)-1H-imidazol-1-yl)phenyl)methanol (434d) (660 mg, 49% yield) as a yellow solid; MS (ES+): 341.1 (M+1); (ES−): 339.1 (M−1).

Step-4: Preparation of (S)-(1-(4-((1-(3-(hydroxymethyl)phenyl)-1H-imidazol-4-yl)amino)pyrrolo[2,1-f][1,2,4]triazin-2-yl)pyrrolidin-2-yl)methanol (434e)

Compound 434e was prepared from (3-(4-((2-chloropyrrolo[2,1-f][1,2,4]triazin-4-yl)amino)-1H-imidazol-1-yl)phenyl)methanol (434d) (250 mg, 0.73 mmol), (S)-pyrrolidin-2-ylmethanol (223 mg, 2.20 mmol), N-ethyl-N-isopropylpropan-2-amine (0.38 mL, 2.20 mmol) in NMP (5 mL) and heating at 140° C. for 50 mins according to the procedure reported in scheme 2. This gave after workup and purification by flash column chromatography [silica (24 g), eluting with DMA80 in DCM from 0-70%] followed by purification by reverse phase column chromatography [C18 steel column (250 mm×30 mm), eluting with ACN in water (containing 0.1% HCl) from 0-100%] (S)-(1-(4-((1-(3-(hydroxymethyl)phenyl)-1H-imidazol-4-yl)amino)pyrrolo[2,1-f][1,2,4]triazin-2-yl)pyrrolidin-2-yl)methanol (434e) (82 mg, 28% yield) HCl salt as a white solid; $^1$H NMR (300 MHz, DMSO-$d_6$) δ 10.95 (s, 1H, D$_2$O exchangeable), 8.75 (d, J=1.6 Hz, 1H), 8.04 (d, J=1.7 Hz, 1H), 7.70 (t, J=1.8 Hz, 1H), 7.68-7.61 (m, 1H), 7.51 (t, J=7.8 Hz, 1H), 7.47 (dd, J=2.4, 1.6 Hz, 1H), 7.40 (dt, J=7.7, 1.2 Hz, 1H), 7.13 (dd, J=4.5, 1.7 Hz, 1H), 6.45 (dd, J=4.5, 2.4 Hz, 1H), 4.59 (s, 2H), 4.15 (s, 1H), 3.71 (dd, J=10.1, 3.8 Hz, 1H), 3.58-3.45 (m, 1H), 3.37 (dd, J=10.2, 8.1 Hz, 2H), 2.07-1.84 (m, 4H); MS (ES+): 406.2 (M+1).

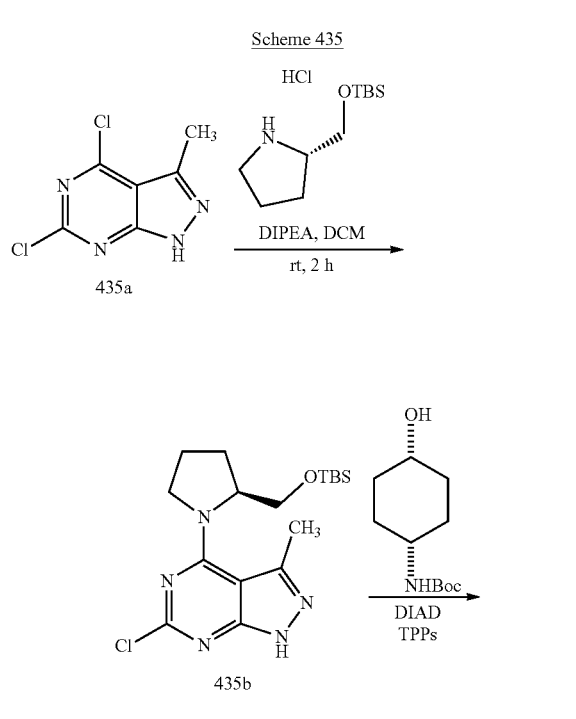

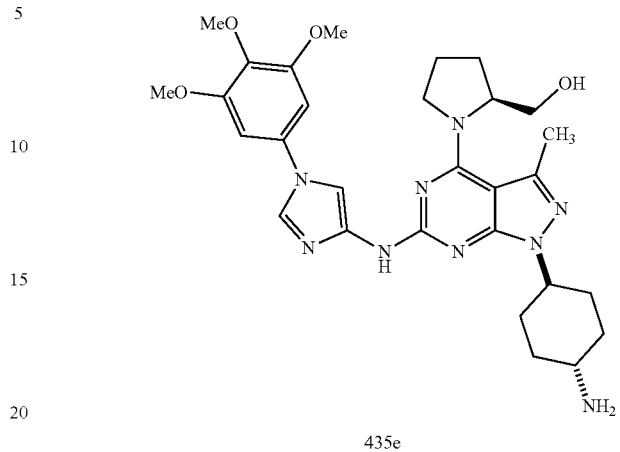

Preparation of ((S)-1-(1-((trans)-4-aminocyclohexyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (435e)

Step-1: Preparation of (S)-4-(2-(((tert-butyldimethylsilyl)oxy)methyl)pyrrolidin-1-yl)-6-chloro-3-methyl-1H-pyrazolo[3,4-d]pyrimidine (435b)

Compound 435b was prepared from 4,6-dichloro-3-methyl-1H-pyrazolo[3,4-d]pyrimidine (435a) (100 mg, 0.49 mmol; CAS #1211522-68-7) in DCM (5 mL) using (S)-2-((tert-butyldimethylsilyloxy)methyl)pyrrolidine hydrochloride (124 mg, 0.49 mmol; CAS #134756-75-5), DIPEA (0.26 mL, 1.48 mmol) and stirring at room temperature for 2 h according to the procedure reported in step-1 of scheme 96. This gave after workup and purification by flash column chromatography [silica (24 g), eluting with EtOAc in hexane from 0-70%] (S)-4-(2-(((tert-butyldimethylsilyl)oxy)methyl)pyrrolidin-1-yl)-6-chloro-3-methyl-1H-pyrazolo[3,4-d]pyrimidine (435b) as a white solid; MS (ES+): 382.2 (M+1); (ES−): 380.1 (M−1).

Step-2: Preparation of tert-butyl ((trans)-4-(4-((S)-2-(((tert-butyldimethylsilyl)oxy)methyl)pyrrolidin-1-yl)-6-chloro-3-methyl-1H-pyrazolo[3,4-d]pyrimidin-1-yl)cyclohexyl)carbamate (435c)

To a solution of (S)-4-(2-(((tert-butyldimethylsilyl)oxy)methyl)pyrrolidin-1-yl)-6-chloro-3-methyl-1H-pyrazolo[3,4-d]pyrimidine (435b) (150 mg, 0.39 mmol), triphenylphosphine (206 mg, 0.79 mmol), tert-butyl cis-4-hydroxycyclohexylcarbamate (127 mg, 0.59 mmol) in THF (3 mL) at 0° C. was added dropwise DIAD (0.12 mL, 0.59 mmol). The reaction mixture was stirred at RT overnight, concentrated in vacuum and the residue obtained was purified by flash column chromatography [silica (12 g), eluting with EtOAc in hexane from 0-60%] to furnish tert-butyl ((trans)-4-(4-((S)-2-(((tert-butyldimethylsilyl)oxy)methyl)pyrrolidin-1-yl)-6-chloro-3-methyl-1H-pyrazolo[3,4-d]pyrimidin-1-yl)cyclohexyl)carbamate (435c) (150 mg, 66% yield) as a white solid; $^1$H NMR (300 MHz, DMSO-d$_6$) δ 6.83 (d, J=7.9 Hz, 1H), 4.54-4.38 (m, 2H), 3.90-3.63 (m, 4H), 3.32-3.22 (m, 1H), 2.55 (s, 3H), 2.13-1.75 (m, 10H), 1.39 (s, 11H), 0.82 (s, 9H), −0.05 (s, 6H); MS (ES+): 579.3 (M+1).

Step-3: Preparation of tert-butyl ((trans)-4-(4-((S)-2-(((tert-butyldimethylsilyl)oxy)methyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclohexyl)carbamate (435d)

Compound 435d was prepared from tert-butyl ((trans)-4-(4-((S)-2-(((tert-butyldimethylsilyl)oxy)methyl)pyrrolidin-1-yl)-6-chloro-3-methyl-1H-pyrazolo[3,4-d]pyrimidin-1-yl)cyclohexyl)carbamate (435c) (220 mg, 0.38 mmol), 1-(3,4,5-trimethoxyphenyl)-1H-imidazol-4-amine (57a) (114 mg, 0.46 mmol), dicyclohexyl(2',4',6'-triisopropylbiphenyl-2-yl)phosphine (XPhos, 72.4 mg, 0.15 mmol), cesium carbonate (433 mg, 1.33 mmol), Pd$_2$(dba)$_3$ (70 mg, 0.076 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA-80 in DCM from 0-50%] tert-butyl ((trans)-4-(4-((S)-2-(((tert-butyldimethylsilyl)oxy)methyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclohexyl)carbamate (435d) (150 mg, 50% yield) as a yellow solid; MS (ES+): 792.4 (M+1).

Step-4: Preparation of ((S)-1-(1-((trans)-4-aminocyclohexyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (435e)

To a solution of tert-butyl ((trans)-4-(4-((S)-2-(((tert-butyldimethylsilyl)oxy)methyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclohexyl)carbamate (435d) (150 mg, 0.19 mmol) in DCM (15 mL) was added TFA (0.29 mL, 3.79 mmol) stirred at RT for 1 h and concentrated in vacuum to dryness. The residue obtained was dissolved in MeOH, added HCl (4N solution in dioxane, 0.95 mL, 3.79 mmol) and stirred at room temperature for 30 min. The reaction mixture was concentrated in vacuum and the residue obtained was purified by reverse phase column chromatography [C18 steel column (250 mm×30 mm), eluting with ACN in water (containing 0.1% HCl) from 0-100%] to afford ((S)-1-(1-((trans)-4-aminocyclohexyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (435e) (61 mg, 56% yield) HCl salt as a white solid; $^1$H NMR (300 MHz, DMSO-d$_6$) δ 10.18 (s, 1H, D$_2$O exchangeable), 9.11 (s, 1H), 8.35-8.19 (m, 3H, D$_2$O exchangeable), 7.84 (d, J=1.7 Hz, 1H), 7.11 (s, 2H), 4.70-4.62 (m, 1H), 4.55-4.45 (m, 2H), 3.89 (s, 6H), 3.85-3.79 (m, 2H), 3.70 (s, 3H), 3.65-3.62 (m, 1H), 3.56-3.44 (m, 2H), 3.20-3.07 (m, 1H), 2.54 (s, 3H), 2.14-2.05 (m, 3H), 2.01-1.88 (m, 7H), 1.73-1.54 (m, 2H); MS (ES+): 578.3 (M+1); (ES−): 612.3 (M+Cl).

Scheme 436

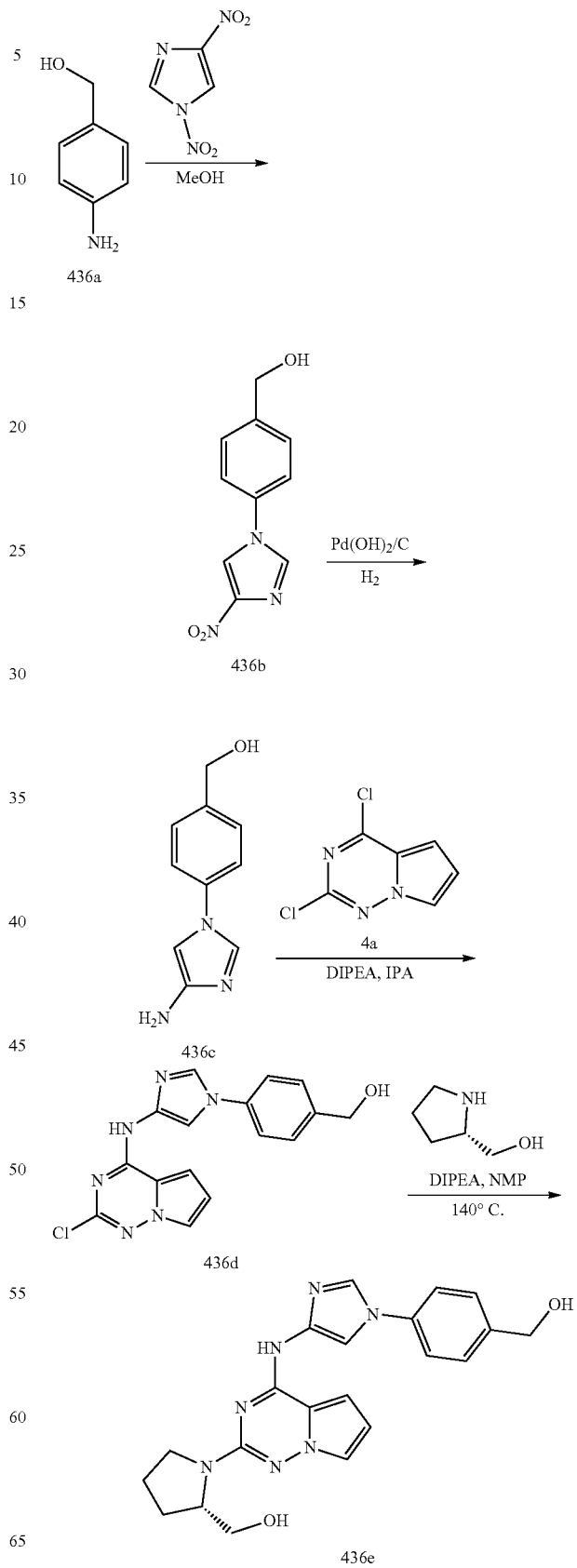

Preparation of (S)-(1-(4-((1-(4-(hydroxymethyl)phenyl)-1H-imidazol-4-yl)amino)pyrrolo[2,1-f][1,2,4]triazin-2-yl)pyrrolidin-2-yl)methanol (436e)

Step-1: Preparation of (4-(4-nitro-1H-imidazol-1-yl)phenyl)methanol (436b)

Reaction of 1,4-dinitro-1H-imidazole (2.182 g, 13.80 mmol) with (4-aminophenyl)methanol (436a) (1.7 g, 13.80 mmol) as reported in step-2 of General scheme for preparation of 3-substituted-(4-amino-1H-imidazol-1-yl) gave after filtration (4-(4-nitro-1H-imidazol-1-yl)phenyl)methanol (436b) (2.2 g, 73% yield) as a red solid; MS (ES+): 220.1 (M+1).

Step-2: Preparation of (4-(4-amino-1H-imidazol-1-yl)phenyl)methanol (436c)

Reduction of nitro to amine of (4-(4-nitro-1H-imidazol-1-yl)phenyl)methanol (436b) (800 mg, 3.65 mmol) in MeOH (50 mL) using Palladium hydroxide on carbon, 20 wt. % loading (dry basis), matrix carbon, wet support (256 mg, 0.37 mmol) as reported in step-3 of General scheme for preparation of 3-substituted-(4-amino-1H-imidazol-1-yl) gave (4-(4-amino-1H-imidazol-1-yl)phenyl)methanol (436c) (455 mg, 66% yield) as a light yellow semi-solid; $^1$H NMR (300 MHz, DMSO-$d_6$) δ 7.82 (d, J=1.7 Hz, 1H), 7.51-7.43 (m, 2H), 7.43-7.34 (m, 2H), 6.63 (d, J=1.7 Hz, 1H), 5.25 (t, J=5.7 Hz, 1H), 4.50 (d, J=4.9 Hz, 2H), 4.41 (s, 2H); MS (ES+) 190.1 (M+1).

Step-3: Preparation of (4-(4-((2-chloropyrrolo[2,1-f][1,2,4]triazin-4-yl)amino)-1H-imidazol-1-yl)phenyl)methanol (436d)

Compound 436d was prepared from 2,4-dichloropyrrolo[2,1-f][1,2,4]triazine (4a) (288 mg, 1.53 mmol) in 2-Propanol (40 mL) using DIPEA (0.803 mL, 4.60 mmol), (4-(4-amino-1H-imidazol-1-yl)phenyl)methanol (436c) (290 mg, 1.53 mmol) and heating at reflux for 2 h according to the procedure reported in step-1 of scheme 183. This gave after workup and filtration (4-(4-((2-chloropyrrolo[2,1-f][1,2,4]triazin-4-yl)amino)-1H-imidazol-1-yl)phenyl)methanol (436d) (334 mg, 64% yield) as a yellow solid; $^1$H NMR (300 MHz, DMSO-$d_6$) δ 11.34 (s, 1H), 8.23 (d, J=1.6 Hz, 1H), 7.90 (d, J=1.6 Hz, 1H), 7.77 (dd, J=2.6, 1.5 Hz, 1H), 7.67-7.57 (m, 2H), 7.55-7.46 (m, 2H), 7.40 (d, J=4.4 Hz, 1H), 6.72 (dd, J=4.5, 2.6 Hz, 1H), 5.32 (t, J=5.5 Hz, 1H), 4.56 (d, J=4.7 Hz, 2H); MS (ES+) 341.1 (M+1); (ES−) 339.0 (M−1).

Step-4: Preparation of (S)-(1-(4-((1-(4-(hydroxymethyl)phenyl)-1H-imidazol-4-yl)amino)pyrrolo[2,1-f][1,2,4]triazin-2-yl)pyrrolidin-2-yl)methanol (436e)

Compound 436e was prepared from (4-(4-((2-chloropyrrolo[2,1-f][1,2,4]triazin-4-yl)amino)-1H-imidazol-1-yl)phenyl)methanol (436d) (150 mg, 0.44 mmol), (S)-pyrrolidin-2-ylmethanol (134 mg, 1.32 mmol), N-ethyl-N-isopropylpropan-2-amine (0.23 mL, 1.32 mmol) in NMP (5 mL) and heating at 140° C. for 50 mins according to the procedure reported in scheme 2. This gave after workup and purification by flash column chromatography [silica (24 g), eluting with DMA80 in DCM from 0-70%] followed by purification by reverse phase column chromatography [C18 steel column (250 mm×30 mm), eluting with ACN in water (containing 0.1% HCl) from 0-100%] (S)-(1-(4-((1-(4-(hydroxymethyl)phenyl)-1H-imidazol-4-yl)amino)pyrrolo[2,1-f][1,2,4]triazin-2-yl)pyrrolidin-2-yl)methanol (436e) (86 mg, 48% yield) as a white solid; $^1$H NMR (300 MHz, DMSO-$d_6$) δ 10.92 (s, 1H, $D_2O$ exchangeable), 8.78-8.68 (m, 1H), 8.02 (d, J=1.7 Hz, 1H), 7.75 (d, J=8.3 Hz, 2H), 7.55-7.40 (m, 3H), 7.13 (dd, J=4.5, 1.7 Hz, 1H), 6.50-6.40 (m, 1H), 4.56 (s, 2H), 4.22-4.07 (m, 1H), 3.71 (dd, J=10.1, 3.8 Hz, 1H), 3.55-3.42 (m, 1H), 3.42-3.29 (m, 2H), 2.08-1.79 (m, 4H); MS (ES+): 406.2 (M+1).

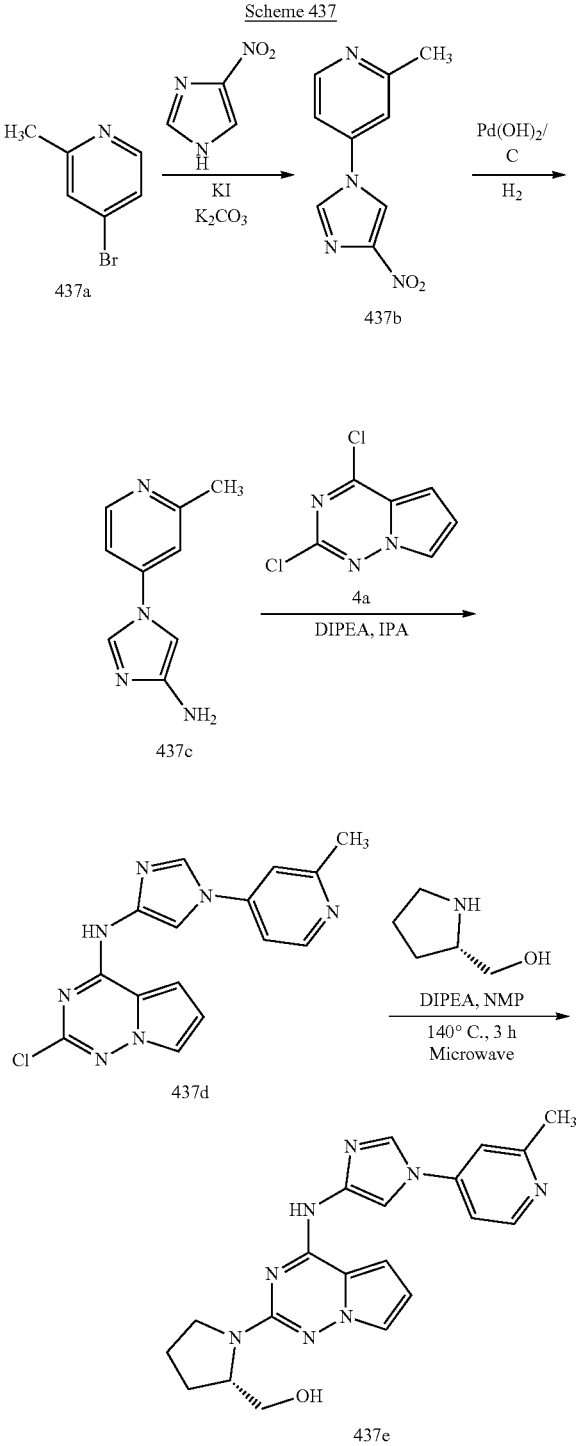

Scheme 437

Preparation of (S)-(1-(4-((1-(2-methylpyridin-4-yl)-1H-imidazol-4-yl)amino)pyrrolo[2,1-f][1,2,4]triazin-2-yl)pyrrolidin-2-yl)methanol (437e)

Step-1: Preparation of 2-methyl-4-(4-nitro-1H-imidazol-1-yl)pyridine (437b)

A solution of 4-bromo-2-methylpyridine (437a) (3.05 g, 17.73 mmol; CAS #22282-99-1), 4-nitro-1H-imidazole (1.97 g, 17.42 mmol; CAS #: 3034-38-6), potassium iodide (2.7 g, 16.26 mmol) and potassium carbonate (5.7 g, 41.2 mmol) in DMF (10 mL) was heated at 130° C. in a microwave reactor for 3 h. The reaction was diluted with water and extracted with EtOAc. The combined organic layers were washed with water, brine, dried, filtered and concentrated in vacuum. The residue obtained was purified by flash column chromatography [silica gel (80 g), eluting with ethyl acetate/methanol (9:1) in hexanes from 50-100%] to furnish 2-methyl-4-(4-nitro-1H-imidazol-1-yl)pyridine (437b) (1.36 g, 38% yield) as a yellow solid; $^1$H NMR (300 MHz, DMSO-$d_6$) δ 9.19 (d, J=1.6 Hz, 1H), 8.71 (d, J=1.6 Hz, 1H), 8.62 (d, J=5.5 Hz, 1H), 7.92-7.83 (m, 1H), 7.74 (ddd, J=5.6, 2.3, 0.6 Hz, 1H), 2.56 (s, 3H); MS (ES+): 205.1 (M+1).

Step-2: Preparation of 1-(2-methylpyridin-4-yl)-1H-imidazol-4-amine (437c)

Reduction of nitro to amine of 2-methyl-4-(4-nitro-1H-imidazol-1-yl)pyridine (437b) (1.36 g, 6.66 mmol) in MeOH (30 mL) using Palladium hydroxide on carbon, 20 wt. % loading (dry basis), matrix carbon, wet support (0.468 g, 0.666 mmol) as reported in step-3 of General scheme for preparation of 3-substituted-(4-amino-1H-imidazol-1-yl) gave after workup and purification by flash column chromatography [silica gel 24 g, eluting with MeOH/DCM from 0-20%] 1-(2-methylpyridin-4-yl)-1H-imidazol-4-amine (437c) (531 mg, 46% yield) as a yellow syrup; $^1$H NMR (300 MHz, DMSO-$d_6$) δ 8.41 (d, J=5.5 Hz, 1H), 8.13 (d, J=1.7 Hz, 1H), 7.49 (dt, J=2.3, 0.6 Hz, 1H), 7.40 (ddd, J=5.7, 2.3, 0.6 Hz, 1H), 6.76 (d, J=1.6 Hz, 1H), 4.59 (s, 2H), 2.48 (s, 3H); MS (ES+): 175.1 (M+1).

Step-3: Preparation of 2-chloro-N-(1-(2-methylpyridin-4-yl)-1H-imidazol-4-yl)pyrrolo[2,1-f][1,2,4]triazin-4-amine (437d)

Compound 437d was prepared from 2,4-dichloropyrrolo[2,1-f][1,2,4]triazine (4a) (341 mg, 1.81 mmol) in 2-Propanol (10 mL) using DIPEA (0.5 mL, 2.86 mmol), 1-(2-methylpyridin-4-yl)-1H-imidazol-4-amine (437c) (311 mg, 1.79 mmol) and heating at 90° C. for 3 h according to the procedure reported in step-1 of scheme 183. This gave after workup and filtration 2-chloro-N-(1-(2-methylpyridin-4-yl)-1H-imidazol-4-yl)pyrrolo[2,1-f][1,2,4]triazin-4-amine (437d) (349 mg, 60% yield) as yellow solid. $^1$H NMR (300 MHz, DMSO-$d_6$) δ 11.38 (s, 1H), 8.56 (d, J=5.6 Hz, 1H), 8.52 (d, J=1.6 Hz, 1H), 8.02 (d, J=1.6 Hz, 1H), 7.80 (dd, J=2.6, 1.5 Hz, 1H), 7.65 (d, J=2.1 Hz, 1H), 7.54 (dd, J=5.6, 2.2 Hz, 1H), 7.40 (s, 1H), 6.74 (dd, J=4.5, 2.6 Hz, 1H), 2.56 (s, 3H); MS (ES+): 326.1 (M+1).

Step-4: Preparation of (S)-(1-(4-((1-(2-methylpyridin-4-yl)-1H-imidazol-4-yl)amino)pyrrolo[2,1-f][1,2,4]triazin-2-yl)pyrrolidin-2-yl)methanol (437e)

Compound 437e was prepared from 2-chloro-N-(1-(2-methylpyridin-4-yl)-1H-imidazol-4-yl)pyrrolo[2,1-f][1,2,4]triazin-4-amine (437d) (145 mg, 0.445 mmol), (S)-pyrrolidin-2-ylmethanol (150 mg, 1.483 mmol), N-ethyl-N-isopropylpropan-2-amine (0.28 mL, 1.602 mmol) in NMP (5 mL) and heating at 140° C. for 3 h on microwave according to the procedure reported in scheme 2. This gave after workup and purification by flash column chromatography [silica (12 g), eluting with MeOH in DCM from 0-20%] followed by purification by reverse phase column chromatography [C18 (RediSep 250×30 mm), eluting with ACN in water (containing 0.1% HCl) from 0-100%] (S)-(1-(4-((1-(2-methylpyridin-4-yl)-1H-imidazol-4-yl)amino)pyrrolo[2,1-f][1,2,4]triazin-2-yl)pyrrolidin-2-yl)methanol (437e) (73 mg, 42% yield) as a yellow solid; $^1$H NMR (300 MHz, DMSO-$d_6$) δ 10.78 (s, 1H), 8.86 (d, J=1.5 Hz, 1H), 8.82 (d, J=6.7 Hz, 1H), 8.35 (d, J=2.3 Hz, 1H), 8.28 (dd, J=6.8, 2.4 Hz, 1H), 8.09 (d, J=1.6 Hz, 1H), 7.50-7.38 (m, 1H), 7.18 (dd, J=4.5, 1.7 Hz, 1H), 6.43 (dd, J=4.5, 2.4 Hz, 1H), 4.24 (s, 1H), 3.88-3.81 (m, 1H), 3.48 (d, J=9.7 Hz, 1H), 3.35 (t, J=8.2 Hz, 2H), 2.73 (s, 3H), 2.18-2.08 (m, 1H), 1.96 (m, 3H); MS (ES+): 391.2 (M+1); MS(ES−): 389.2 (M−1).

Scheme 438

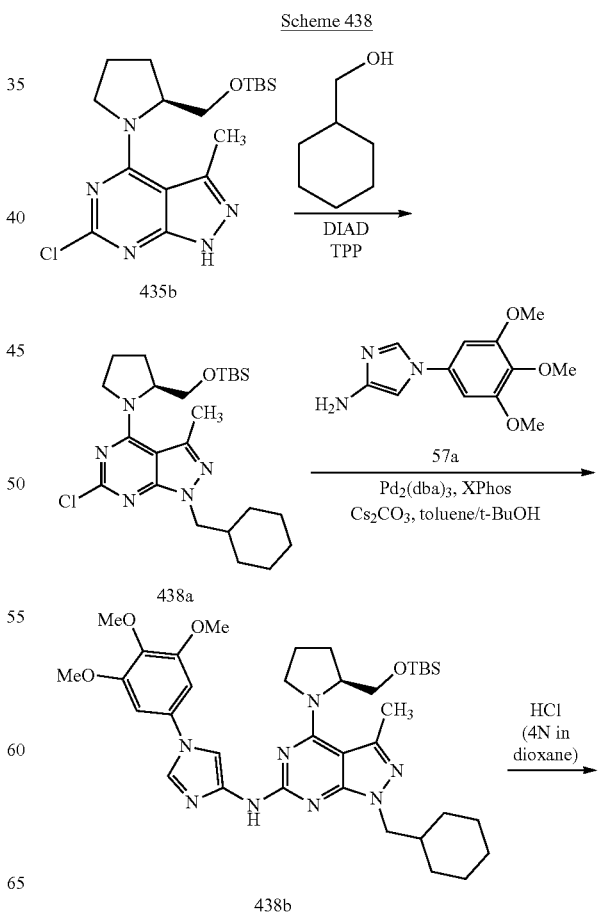

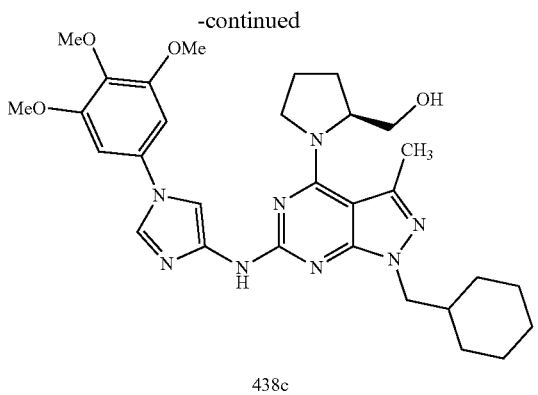

438c

Preparation of (S)-(1-(1-(cyclohexylmethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (438c)

Step-1: Preparation of (S)-4-(2-(((tert-butyldimethylsilyl)oxy)methyl)pyrrolidin-1-yl)-6-chloro-1-(cyclohexylmethyl)-3-methyl-1H-pyrazolo[3,4-d]pyrimidine (438a)

Compound 438a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF using triphenylphosphine (515 mg, 1.96 mmol), cyclohexylmethanol (224 mg, 1.96 mmol) and DIAD (0.38 mL, 1.96 mmol) according to the procedure reported in step-2 of scheme 435. This gave after workup and purification by flash column chromatography [silica (12 g), eluting with EtOAc in hexane from 0-60%](S)-4-(2-(((tert-butyldimethylsilyl)oxy)methyl)pyrrolidin-1-yl)-6-chloro-1-(cyclohexylmethyl)-3-methyl-1H-pyrazolo[3,4-d]pyrimidine (438a) (350 mg, 93% yield) as a clear oil; MS (ES+): 478.3 (M+1).

Step-2: Preparation of (S)-4-(2-(((tert-butyldimethylsilyl)oxy)methyl)pyrrolidin-1-yl)-1-(cyclohexylmethyl)-3-methyl-N-(1-(3,4,5-trimethoxyphenyl)-1H-imidazol-4-yl)-1H-pyrazolo[3,4-d]pyrimidin-6-amine (438b)

Compound 438b was prepared from (S)-4-(2-(((tert-butyldimethylsilyl)oxy)methyl)pyrrolidin-1-yl)-6-chloro-1-(cyclohexylmethyl)-3-methyl-1H-pyrazolo[3,4-d]pyrimidine (438a) (350 mg, 0.73 mmol), 1-(3,4,5-trimethoxyphenyl)-1H-imidazol-4-amine (57a) (219 mg, 0.88 mmol), dicyclohexyl(2',4',6'-triisopropylbiphenyl-2-yl)phosphine (XPhos, 140 mg, 0.29 mmol), cesium carbonate (835 mg, 2.56 mmol), Pd$_2$(dba)$_3$ (134 mg, 0.15 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA-80 in DCM from 0-50%] (S)-4-(2-(((tert-butyldimethylsilyl)oxy)methyl)pyrrolidin-1-yl)-1-(cyclohexylmethyl)-3-methyl-N-(1-(3,4,5-trimethoxyphenyl)-1H-imidazol-4-yl)-1H-pyrazolo[3,4-d]pyrimidin-6-amine (438b) (185 mg, 37% yield) as a yellow solid, MS (ES+): 691.4 (M+1).

Step-3: Preparation of (S)-(1-(1-(cyclohexylmethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (438c)

A solution of (S)-4-(2-(((tert-butyldimethylsilyl)oxy)methyl)pyrrolidin-1-yl)-1-(cyclohexylmethyl)-3-methyl-N-(1-(3,4,5-trimethoxyphenyl)-1H-imidazol-4-yl)-1H-pyrazolo[3,4-d]pyrimidin-6-amine (438b) (185 mg) in MeOH/DCM (10 mL) was added 4N HCl in dioxane (4 mL), stirred at room temperature for 10 min and concentrated in vacuum. The residue obtained was purified by reverse phase column chromatography [C18 steel column (250 mm×30 mm), eluting with ACN in water (containing 0.1% HCl) from 0-100%] to furnish (S)-(1-(1-(cyclohexylmethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (438c) (150 mg, 36% yield) HCl salt as a white solid; $^1$H NMR (300 MHz, DMSO-d$_6$) δ 10.11 (s, 1H, D$_2$O exchangeable), 8.95 (s, 1H), 7.85 (d, J=1.7 Hz, 1H, D$_2$O exchangeable), 7.09 (s, 2H), 4.76-4.57 (m, 2H), 4.04 (d, J=7.1 Hz, 2H), 3.89 (s, 6H), 3.70 (s, 3H), 3.67-3.52 (m, 1H), 2.55 (s, 3H), 2.14-1.82 (m, 6H), 1.69-1.48 (m, 6H), 1.22-0.93 (m, 6H); MS (ES+): 577.3 (M+1).

Scheme 439

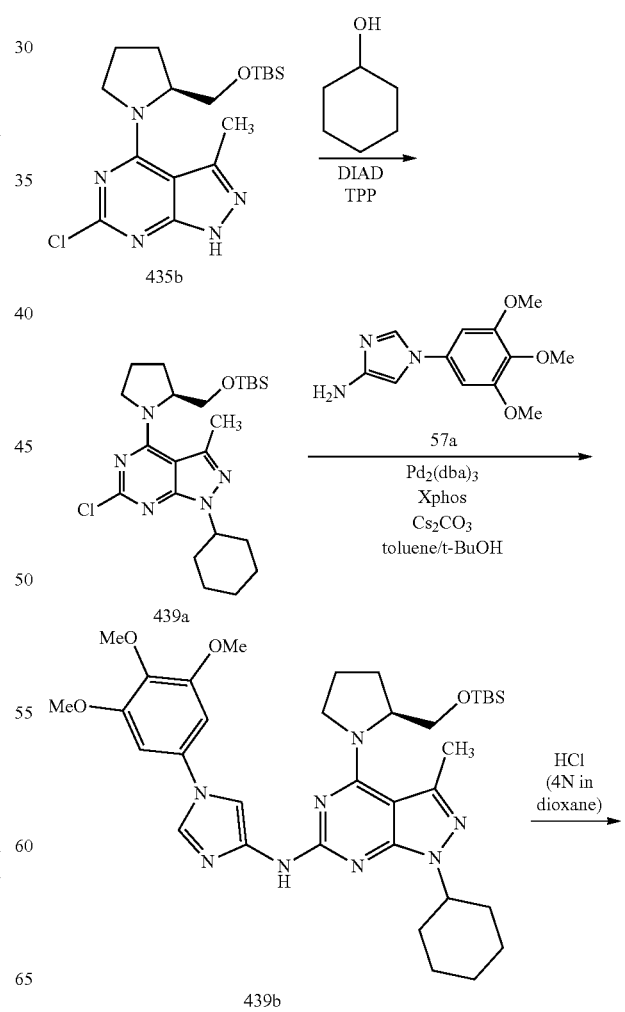

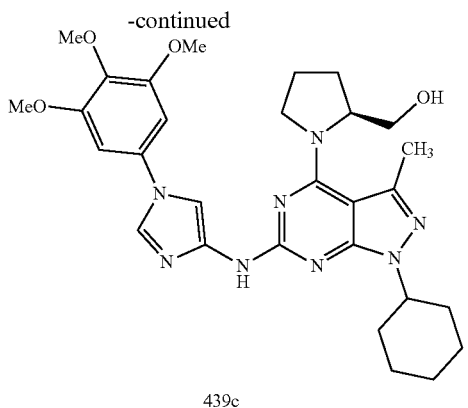

439c

Preparation of (S)-(1-(1-cyclohexyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (439c)

Step-1: Preparation of (S)-4-(2-(((tert-butyldimethylsilyl)oxy)methyl)pyrrolidin-1-yl)-6-chloro-1-cyclohexyl-3-methyl-1H-pyrazolo[3,4-d]pyrimidine (439a)

Compound 439a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF using triphenylphosphine (515 mg, 1.96 mmol), cyclohexanol (197 mg, 1.96 mmol), DIAD (0.38 mL, 1.96 mmol) and stirring at room temperature for 5 days according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-cyclohexyl-3-methyl-1H-pyrazolo[3,4-d]pyrimidine (439a) (300 mg, 82% yield) as a clear oil; MS (ES+): 464.2 (M+1).

Step-2: Preparation of(S)-4-(2-(((tert-butyldimethylsilyl)oxy)methyl)pyrrolidin-1-yl)-1-cyclohexyl-3-methyl-N-(1-(3,4,5-trimethoxyphenyl)-1H-imidazol-4-yl)-1H-pyrazolo[3,4-d]pyrimidin-6-amine (439b)

Compound 439b was prepared from (S)-4-(2-(((tert-butyldimethylsilyl)oxy)methyl)pyrrolidin-1-yl)-6-chloro-1-cyclohexyl-3-methyl-1H-pyrazolo[3,4-d]pyrimidine (439a) (300 mg, 0.65 mmol), 1-(3,4,5-trimethoxyphenyl)-1H-imidazol-4-amine (57a) (193 mg, 0.78 mmol), dicyclohexyl(2',4',6'-triisopropylbiphenyl-2-yl)phosphine (XPhos, 123 mg, 0.26 mmol), cesium carbonate (737 mg, 2.26 mmol), Pd$_2$(dba)$_3$ (118 mg, 0.13 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA80 in DCM from 0-60%] (S)-4-(2-(((tert-butyldimethylsilyl)oxy)methyl)pyrrolidin-1-yl)-1-cyclohexyl-3-methyl-N-(1-(3,4,5-trimethoxyphenyl)-1H-imidazol-4-yl)-1H-pyrazolo[3,4-d]pyrimidin-6-amine (439b) (142 mg, 33% yield) as a brown solid; MS (ES+): 677.4 (M+1).

Step-3: Preparation of (S)-(1-(1-cyclohexyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (439c)

A solution of (S)-4-(2-(((tert-butyldimethylsilyl)oxy)methyl)pyrrolidin-1-yl)-1-cyclohexyl-3-methyl-N-(1-(3,4,5-trimethoxyphenyl)-1H-imidazol-4-yl)-1H-pyrazolo[3,4-d]pyrimidin-6-amine (439b) (142 mg) in MeOH/DCM (10 mL) was added 4N HCl in dioxane (0.39 mL, 12.93 mmol), stirred at room temperature for 20 min and concentrated in vacuum. The residue obtained was purified by reverse phase column chromatography [C18 steel column (250 mm×30 mm), eluting with ACN in water (containing 0.1% HCl) from 0-100%] to afford (S)-(1-(1-cyclohexyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (439c) (94 mg, 26% yield) HCl salt as a white solid; $^1$H NMR (300 MHz, DMSO-d$_6$) δ 10.18 (s, 1H, D$_2$O exchangeable), 8.98 (s, 1H), 7.85 (d, J=1.7 Hz, 1H, D$_2$O exchangeable), 7.11 (s, 2H), 4.70-4.65 (m, 1H), 4.59-4.46 (m, 2H), 3.90 (s, 6H), 3.88-3.80 (m, 2H), 3.71 (s, 3H), 3.68-3.51 (m, 3H), 2.55 (s, 3H), 2.14-1.96 (m, 4H), 1.88-1.80 (m, 6H), 1.71-1.63 (m, 1H), 1.47-1.34 (m, 2H), 1.30-1.19 (m, 1H); MS (ES+) 563.3 (M+1).

Scheme 440

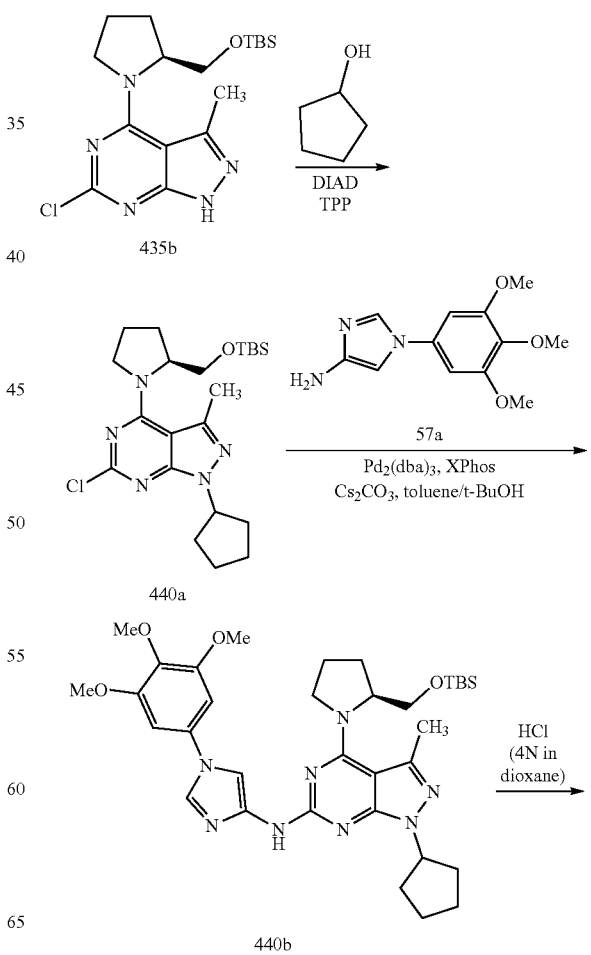

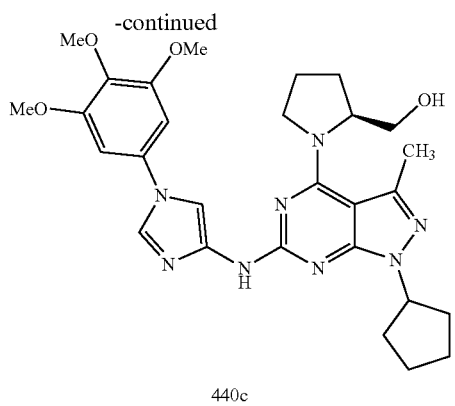

440c

Preparation of (S)-(1-(1-cyclopentyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (440c)

Step-1: Preparation of (S)-4-(2-(((tert-butyldimethylsilyl)oxy)methyl)pyrrolidin-1-yl)-6-chloro-1-cyclopentyl-3-methyl-1H-pyrazolo[3,4-d]pyrimidine (440a)

Compound 440a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF using triphenylphosphine (515 mg, 1.96 mmol), cyclopentanol (169 mg, 1.96 mmol), DIAD (0.38 mL, 1.96 mmol) and stirring at room temperature for 5 days according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-cyclopentyl-3-methyl-1H-pyrazolo[3,4-d]pyrimidine (440a) (300 mg, 85% yield) as a white solid; MS (ES+): 450.2 (M+1).

Step-2: Preparation of (S)-4-(2-(((tert-butyldimethylsilyl)oxy)methyl)pyrrolidin-1-yl)-1-cyclopentyl-3-methyl-N-(1-(3,4,5-trimethoxyphenyl)-1H-imidazol-4-yl)-1H-pyrazolo[3,4-d]pyrimidin-6-amine (440b)

Compound 440b was prepared from (S)-4-(2-(((tert-butyldimethylsilyl)oxy)methyl)pyrrolidin-1-yl)-6-chloro-1-cyclopentyl-3-methyl-1H-pyrazolo[3,4-d]pyrimidine (440a) (300 mg, 0.67 mmol), 1-(3,4,5-trimethoxyphenyl)-1H-imidazol-4-amine (57a) (199 mg, 0.80 mmol), dicyclohexyl(2',4',6'-triisopropylbiphenyl-2-yl)phosphine (XPhos, 127 mg, 0.27 mmol), cesium carbonate (760 mg, 2.33 mmol), Pd$_2$(dba)$_3$ (122 mg, 0.13 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA80 in DCM from 0-50%] (S)-4-(2-(((tert-butyldimethylsilyl)oxy)methyl)pyrrolidin-1-yl)-1-cyclopentyl-3-methyl-N-(1-(3,4,5-trimethoxyphenyl)-1H-imidazol-4-yl)-1H-pyrazolo[3,4-d]pyrimidin-6-amine (440b) which was used as such for next step; MS (ES+): 663.4 (M+1).

Step-3: Preparation of (S)-(1-(1-cyclopentyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (440c)

A solution of (S)-4-(2-(((tert-butyldimethylsilyl)oxy)methyl)pyrrolidin-1-yl)-1-cyclopentyl-3-methyl-N-(1-(3,4,5-trimethoxyphenyl)-1H-imidazol-4-yl)-1H-pyrazolo[3,4-d]pyrimidin-6-amine (440b) (from step-2 above) in MeOH/DCM (10 mL) was added 4N HCl in dioxane (0.393 mL, 12.93 mmol), stirred at room temperature for 20 min and concentrated in vacuum. The residue obtained was purified by reverse phase column chromatography [C18 steel column (250 mm×30 mm), eluting with ACN in water (containing 0.1% HCl) from 0-100%] to afford (S)-(1-(1-cyclopentyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (440c) (191 mg, 52% yield for 2 steps) HCl salt as a white solid; $^1$H NMR (300 MHz, DMSO-d$_6$) δ 10.25 (s, 1H, D$_2$O exchangeable), 9.03 (s, 1H), 7.88 (d, J=1.7 Hz, 1H), 7.10 (s, 3H), 5.15-5.01 (m, 1H), 4.76-4.63 (m, 1H), 3.90 (s, 6H), 3.88-3.78 (m, 2H), 3.71 (s, 3H), 2.56 (s, 3H), 2.13-1.78 (m, 12H), 1.71-1.56 (m, 2H); MS (ES+): 549.2 (M+1); HPLC purity: 98.78%.

Scheme 441

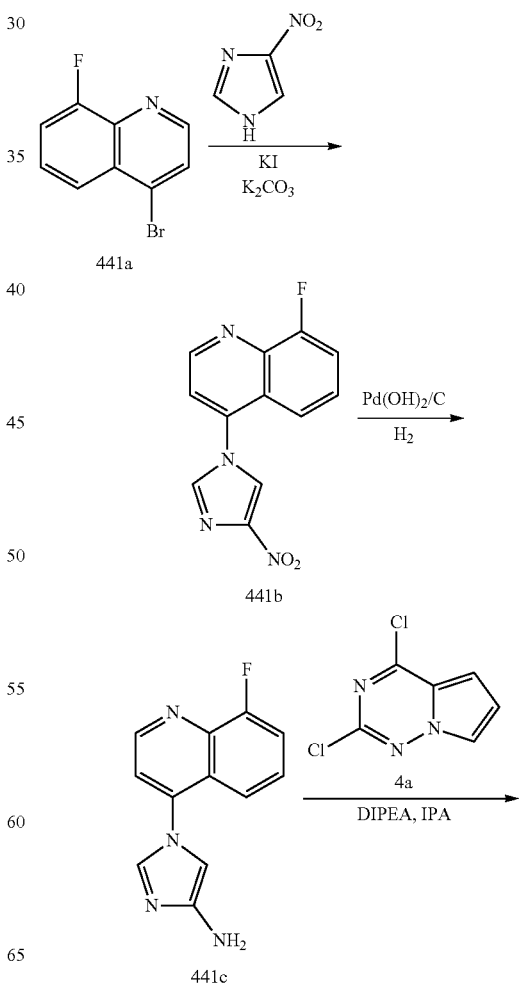

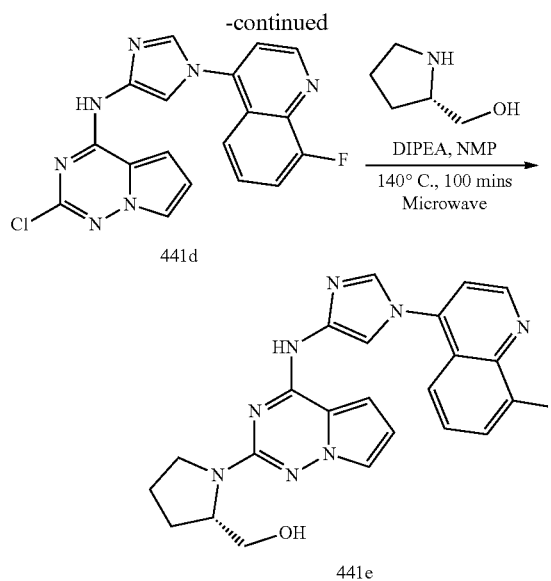

Preparation of (S)-(1-(4-((1-(8-fluoroquinolin-4-yl)-1H-imidazol-4-yl)amino)pyrrolo[2,1-f][1,2,4]triazin-2-yl)pyrrolidin-2-yl)methanol (441e)

Step-1: Preparation of 8-fluoro-4-(4-nitro-1H-imidazol-1-yl)quinoline (441b)

Compound 441b was prepared from 4-bromo-8-fluoroquinoline (441a) (1.08 g, 4.78 mmol; CAS #:927800-38-2) in DMF (8 mL) using 4-nitro-1H-imidazole (550 mg, 4.86 mmol), potassium iodide (811 mg, 4.89 mmol), potassium carbonate (2.2 g, 15.92 mmol) and heating at 100° C. in a microwave reactor for 2 h according to the procedure reported in step-1 of scheme 437. This gave after workup and purification by flash column chromatography [silica gel (40 g), eluting with ethyl acetate/methanol (9:1) in hex from 50-100%] 8-fluoro-4-(4-nitro-1H-imidazol-1-yl)quinoline (441b) (634 mg, 51% yield) as a yellow solid. $^1$H NMR (300 MHz, DMSO-d$_6$) δ 9.18 (d, J=4.6 Hz, 1H), 9.00 (d, J=1.5 Hz, 1H), 8.39 (d, J=1.5 Hz, 1H), 7.96 (d, J=4.5 Hz, 1H), 7.86-7.69 (m, 2H), 7.63 (dt, J=8.4, 1.0 Hz, 1H); $^{19}$F NMR (282 MHz, DMSO-d$_6$) δ −123.84. MS (ES+): 259.0 (M+1).

Step-2: Preparation of 1-(8-fluoroquinolin-4-yl)-1H-imidazol-4-amine (441c)

Reduction of nitro to amine of 8-fluoro-4-(4-nitro-1H-imidazol-1-yl)quinoline (441b) (630 mg, 2.44 mmol) in MeOH (30 mL) using Palladium hydroxide on carbon, 20 wt. % loading (dry basis), matrix carbon, wet support (241 mg, 0.343 mmol) as reported in step-3 of General scheme for preparation of 3-substituted-(4-amino-1H-imidazol-1-yl) gave after workup and purification by flash column chromatography [silica gel 24 g, eluting with MeOH/DCM from 0-20%] 1-(8-fluoroquinolin-4-yl)-1H-imidazol-4-amine (441c) (323 mg, 58% yield) as a yellow syrup. MS (ES+): 229.1 (M+1).

Step-3: Preparation of 2-chloro-N-(1-(8-fluoroquinolin-4-yl)-1H-imidazol-4-yl)pyrrolo[2,1-f][1,2,4]triazin-4-amine (441d)

Compound 441d was prepared from 2,4-dichloropyrrolo[2,1-f][1,2,4]triazine (4a) (267 mg, 1.42 mmol) in 2-Propanol (10 mL) using DIPEA (0.63 mL, 3.59 mmol), 1-(8-fluoroquinolin-4-yl)-1H-imidazol-4-amine (441c) (319 mg, 1.398 mmol) and heating at 90° C. for 3 h according to the procedure reported in step-1 of scheme 183. This gave after workup and filtration 2-chloro-N-(1-(8-fluoroquinolin-4-yl)-1H-imidazol-4-yl)pyrrolo[2,1-f][1,2,4]triazin-4-amine (441d) (223 mg, 42% yield) as a yellow solid. $^1$H NMR (300 MHz, DMSO-d$_6$) δ 11.52 (s, 1H), 9.12 (d, J=4.6 Hz, 1H), 8.21 (d, J=1.6 Hz, 1H), 7.95 (d, J=1.6 Hz, 1H), 7.87 (d, J=4.6 Hz, 1H), 7.83-7.69 (m, 4H), 7.44 (d, J=4.5 Hz, 1H), 6.75 (dd, J=4.5, 2.6 Hz, 1H); MS (ES+): 380.0 (M+1).

Step-4: Preparation of (S)-(1-(4-((1-(8-fluoroquinolin-4-yl)-1H-imidazol-4-yl)amino)pyrrolo[2,1-f][1,2,4]triazin-2-yl)pyrrolidin-2-yl)methanol (441e)

Compound 441e was prepared from 2-chloro-N-(1-(8-fluoroquinolin-4-yl)-1H-imidazol-4-yl)pyrrolo[2,1-f][1,2,4]triazin-4-amine (441d) (110 mg, 0.29 mmol), (S)-pyrrolidin-2-ylmethanol (195 mg, 1.93 mmol), N-ethyl-N-isopropylpropan-2-amine (0.212 mL, 1.215 mmol) in NMP (3 mL) and heating at 140° C. for 100 min in a microwave according to the procedure reported in scheme 2. This gave after workup and purification by reverse phase column chromatography [C18 (RediSep 250×30 mm), eluting with ACN in water (containing 0.1% HCl) from 0-100%] (S)-(1-(4-((1-(8-fluoroquinolin-4-yl)-1H-imidazol-4-yl)amino)pyrrolo[2,1-f][1,2,4]triazin-2-yl)pyrrolidin-2-yl)methanol (441e) (15 mg, 12% yield) as a yellow solid; $^1$H NMR (300 MHz, DMSO-d$_6$) δ 10.91 (s, 1H), 9.10 (d, J=4.6 Hz, 1H), 8.36 (d, J=1.5 Hz, 1H), 8.04 (d, J=1.6 Hz, 1H), 7.95-7.85 (m, 2H), 7.85-7.69 (m, 2H), 7.51-7.41 (m, 1H), 7.20 (dd, J=4.5, 1.7 Hz, 1H), 6.45 (dd, J=4.5, 2.4 Hz, 1H), 4.14-4.00 (m, 1H), 3.59 (dd, J=10.2, 3.6 Hz, 1H), 3.46 (t, J=8.4 Hz, 1H), 3.41-3.19 (m, 2H), 2.01-1.70 (m, 4H); $^{19}$F NMR (282 MHz, DMSO-d$_6$) δ −123.74. MS (ES+): 445.2 (M+1); MS(ES−): 443.1 (M−1). HPLC purity: 93.63%.

Scheme 442

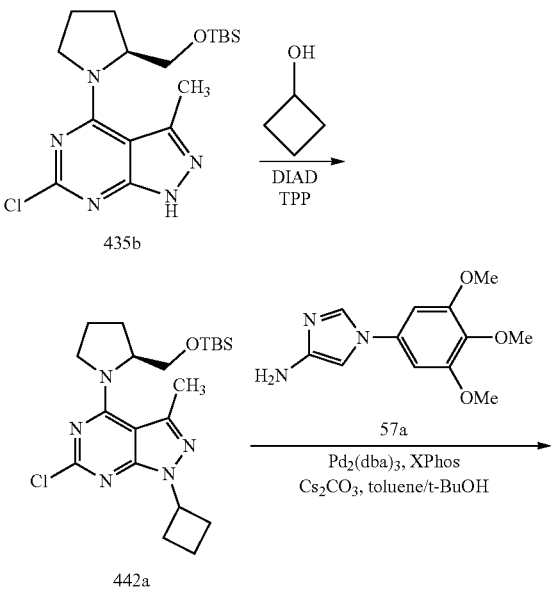

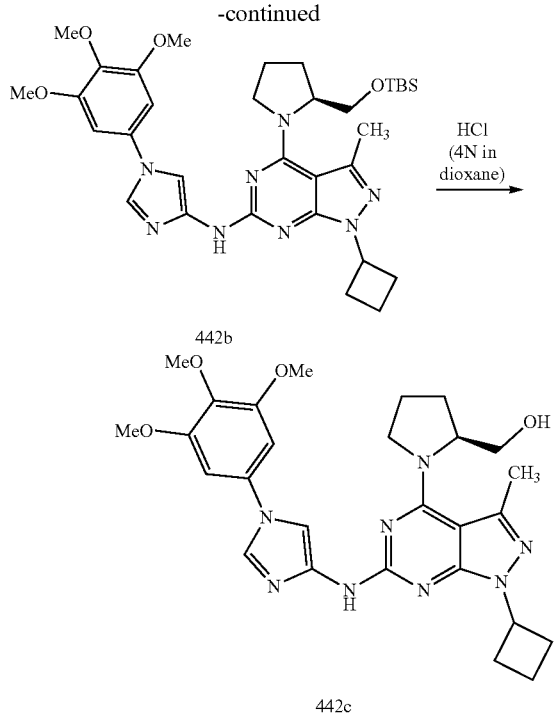

442b

442c

Preparation of (S)-(1-(1-cyclobutyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (442c)

Step-1: Preparation of (S)-4-(2-(((tert-butyldimethylsilyl)oxy)methyl)pyrrolidin-1-yl)-6-chloro-1-cyclobutyl-3-methyl-1H-pyrazolo[3,4-d]pyrimidine (442a)

Compound 442a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF using triphenylphosphine (515 mg, 1.96 mmol), cyclobutanol (142 mg, 1.96 mmol), DIAD (0.382 mL, 1.96 mmol) and stirring at room temperature for 5 days according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-cyclobutyl-3-methyl-1H-pyrazolo[3,4-d]pyrimidine (442a) (330 mg, 96% yield) as a clear oil; MS (ES+): 436.2 (M+1).

Step-2: Preparation of (S)-4-(2-(((tert-butyldimethylsilyl)oxy)methyl)pyrrolidin-1-yl)-1-cyclobutyl-3-methyl-N-(1-(3,4,5-trimethoxyphenyl)-1H-imidazol-4-yl)-1H-pyrazolo[3,4-d]pyrimidin-6-amine (442b)

Compound 442b was prepared from (S)-4-(2-(((tert-butyldimethylsilyl)oxy)methyl)pyrrolidin-1-yl)-6-chloro-1-cyclobutyl-3-methyl-1H-pyrazolo[3,4-d]pyrimidine (442a) (330 mg, 0.76 mmol), 1-(3,4,5-trimethoxyphenyl)-1H-imidazol-4-amine (57a) (226 mg, 0.91 mmol), dicyclohexyl(2',4',6'-triisopropylbiphenyl-2-yl)phosphine (XPhos, 144 mg, 0.30 mmol), cesium carbonate (863 mg, 2.65 mmol), Pd$_2$(dba)$_3$ (139 mg, 0.15 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA80 in DCM from 0-50%] (S)-4-(2-(((tert-butyldimethylsilyl)oxy)methyl)pyrrolidin-1-yl)-1-cyclobutyl-3-methyl-N-(1-(3,4,5-trimethoxyphenyl)-1H-imidazol-4-yl)-1H-pyrazolo[3,4-d]pyrimidin-6-amine (442b) as a white solid; MS (ES+): 649.3 (M+1).

Step-3: Preparation of (S)-(1-(1-cyclobutyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (442c)

A solution of (S)-4-(2-(((tert-butyldimethylsilyl)oxy)methyl)pyrrolidin-1-yl)-1-cyclobutyl-3-methyl-N-(1-(3,4,5-trimethoxyphenyl)-1H-imidazol-4-yl)-1H-pyrazolo[3,4-d]pyrimidin-6-amine (442b) (from step-2 above) in MeOH/DCM was added 4N HCl in dioxane (1.89 mL, 7.57 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (S)-(1-(1-cyclobutyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (442c) (140 mg, 35% yield) as a white solid; $^1$H NMR (300 MHz, DMSO-d$_6$) δ 10.17 (s, 1H, D$_2$O exchangeable), 9.04 (s, 1H), 7.89 (d, J=1.6 Hz, 1H), 7.11 (s, 2H), 5.26-5.13 (m, 1H), 4.71-4.62 (m, 1H), 3.90 (s, 6H), 3.87-3.77 (m, 2H), 3.70 (s, 3H), 3.66-3.53 (m, 2H), 2.70-2.58 (m, 2H), 2.57 (s, 3H), 2.41-2.28 (m, 2H), 2.20-1.95 (m, 4H), 1.95-1.66 (m, 4H); MS (ES+): 535.3 (M+1).

Scheme 443

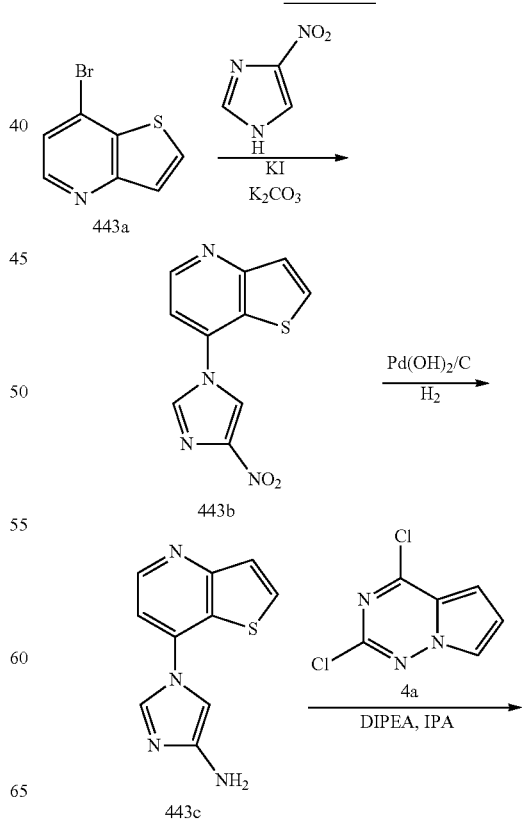

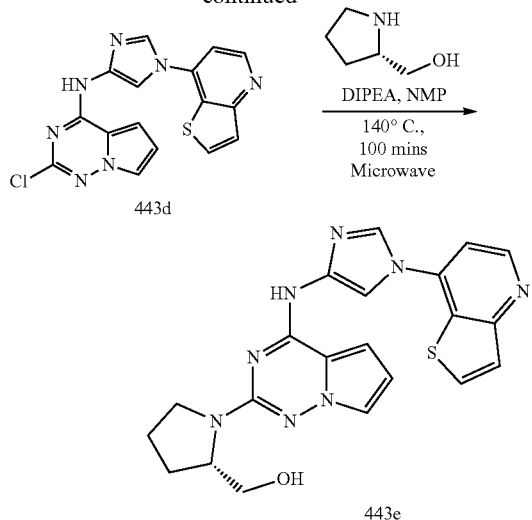

Preparation of (S)-(1-(4-((1-(thieno[3,2-b]pyridin-7-yl)-1H-imidazol-4-yl)amino)pyrrolo[2,1-f][1,2,4]triazin-2-yl)pyrrolidin-2-yl)methanol (443e)

Step-1: Preparation of 7-(4-nitro-1H-imidazol-1-yl)thieno[3,2-b]pyridine (443b)

Compound 443b was prepared from 7-bromothieno[3,2-b]pyridine (443a) (1 g, 5.90 mmol; CAS #: 69627-03-8) in DMF (5 mL) using 4-nitro-1H-imidazole (713 mg, 6.31 mmol), potassium iodide (1.032 g, 6.22 mmol), potassium carbonate (2.37 g, 17.15 mmol) and heating at 100° C. in a microwave reactor for 2 h according to the procedure reported in step-1 of scheme 437. This gave after workup 7-(4-nitro-1H-imidazol-1-yl)thieno[3,2-b]pyridine (443b) (420 mg, 29% yield) as a yellow solid. $^1$H NMR (300 MHz, DMSO-d$_6$) δ 9.08 (d, J=1.6 Hz, 1H), 8.90 (d, J=5.1 Hz, 1H), 8.59 (d, J=1.6 Hz, 1H), 8.37 (d, J=5.5 Hz, 1H), 7.83-7.72 (m, 2H); MS (ES+): 247.0 (M+1).

Step-2: Preparation of 1-(thieno[3,2-b]pyridin-7-yl)-1H-imidazol-4-amine (443c)

Reduction of nitro to amine of 7-(4-nitro-1H-imidazol-1-yl)thieno[3,2-b]pyridine (443b) (418 mg, 1.697 mmol) in MeOH (20 mL) using Palladium hydroxide on carbon, 20 wt. % loading (dry basis), matrix carbon, wet support (133 mg, 0.189 mmol) as reported in step-3 of General scheme for preparation of 3-substituted-(4-amino-1H-imidazol-1-yl) gave after workup and purification by flash column chromatography [silica gel 12 g, eluting with MeOH/DCM from 0-20%] 1-(thieno[3,2-b]pyridin-7-yl)-1H-imidazol-4-amine (443c) (137 mg, 37% yield) as a yellow solid. $^1$H NMR (300 MHz, DMSO-d$_6$) δ 8.71 (d, J=5.2 Hz, 1H), 8.26 (dd, J=5.6, 0.4 Hz, 1H), 8.04 (d, J=1.6 Hz, 1H), 7.67 (d, J=5.6 Hz, 1H), 7.54 (dd, J=5.2, 0.5 Hz, 1H), 6.85 (d, J=1.7 Hz, 1H), 4.73 (s, 2H); MS (ES+): 217.0 (M+1).

Step-3: Preparation of 2-chloro-N-(1-(thieno[3,2-b]pyridin-7-yl)-1H-imidazol-4-yl)pyrrolo[2,1-f][1,2,4]triazin-4-amine (443d)

Compound 443d was prepared from 2,4-dichloropyrrolo[2,1-f][1,2,4]triazine (4a) (121 mg, 0.644 mmol) in 2-Propanol (8 mL) using DIPEA (0.378 mL, 2.166 mmol), 1-(thieno[3,2-b]pyridin-7-yl)-1H-imidazol-4-amine (443c) (135 mg, 0.624 mmol) and heating at 90° C. for 3 h according to the procedure reported in step-1 of scheme 183. This gave after workup and filtration 2-chloro-N-(1-(thieno[3,2-b]pyridin-7-yl)-1H-imidazol-4-yl)pyrrolo[2,1-f][1,2,4]triazin-4-amine (443d) (181 mg, 79% yield) as an orange solid; $^1$H NMR (300 MHz, DMSO-d$_6$) δ 11.57 (s, 1H), 8.83 (d, J=5.1 Hz, 1H), 8.48 (d, J=1.7 Hz, 1H), 8.42-8.31 (m, 2H), 7.81 (dd, J=2.6, 1.5 Hz, 1H), 7.78-7.66 (m, 2H), 7.43 (s, 1H), 6.75 (dd, J=4.5, 2.6 Hz, 1H); MS (ES+): 368.0 (M+1), 390.0 (M+Na).

Step-4: Preparation of (S)-(1-(4-((1-(thieno[3,2-b]pyridin-7-yl)-1H-imidazol-4-yl)amino)pyrrolo[2,1-f][1,2,4]triazin-2-yl)pyrrolidin-2-yl)methanol (443e)

Compound 443e was prepared from 2-chloro-N-(1-(thieno[3,2-b]pyridin-7-yl)-1H-imidazol-4-yl)pyrrolo[2,1-f][1,2,4]triazin-4-amine (443d) (89 mg, 0.242 mmol), (S)-pyrrolidin-2-ylmethanol (157 mg, 1.552 mmol), N-ethyl-N-isopropylpropan-2-amine (0.165 mL, 0.944 mmol) in NMP (1.5 mL) and heating at 140° C. for 100 min in a microwave according to the procedure reported in scheme 2. This gave after workup and purification by reverse phase column chromatography [C18 (RediSep 250×30 mm), eluting with ACN in water (containing 0.1% HCl) from 0-100%] (S)-(1-(4-((1-(thieno[3,2-b]pyridin-7-yl)-1H-imidazol-4-yl)amino)pyrrolo[2,1-f][1,2,4]triazin-2-yl)pyrrolidin-2-yl)methanol (443e) (48 mg, 46% yield) HCl salt as a yellow solid. $^1$H NMR (300 MHz, DMSO-d$_6$) δ 10.83 (s, 1H), 8.91 (d, J=5.5 Hz, 1H), 8.59-8.39 (m, 2H), 8.25 (d, J=1.7 Hz, 1H), 7.90 (d, J=5.5 Hz, 1H), 7.81 (d, J=5.5 Hz, 1H), 7.49-7.37 (m, 1H), 7.20 (dd, J=4.5, 1.7 Hz, 1H), 6.44 (dd, J=4.5, 2.4 Hz, 1H), 4.16 (s, 1H), 3.68 (dd, J=10.2, 3.6 Hz, 1H), 3.58 (s, 1H), 3.53-3.41 (m, 1H), 3.35 (dd, J=10.2, 8.1 Hz, 1H), 2.10-1.77 (m, 4H); MS (ES+): 433.1 (M+1); MS (ES−): 431.1 (M−1).

Scheme 444

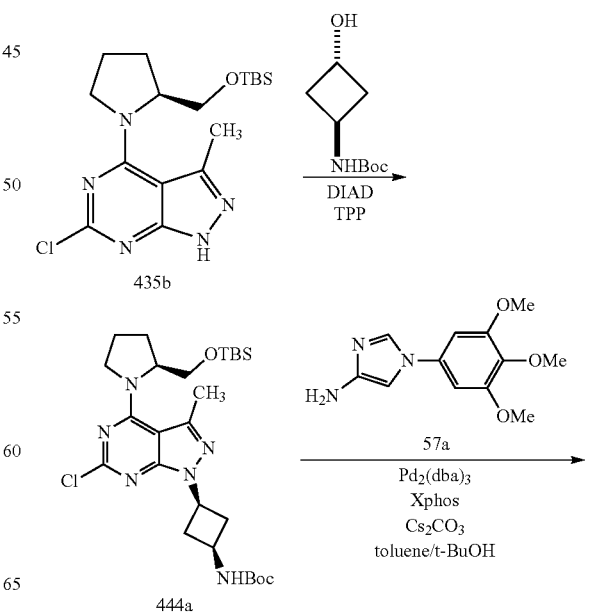

-continued

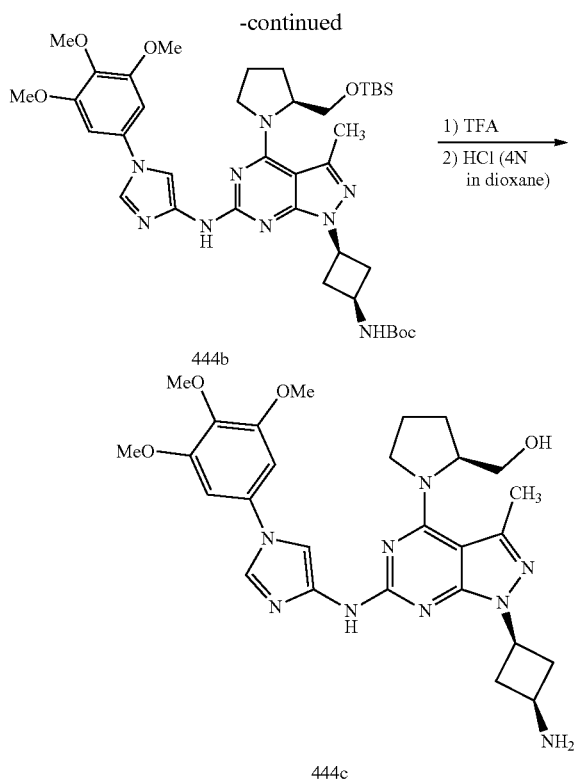

Preparation of ((S)-1-(1-(((cis)-3-aminocyclobutyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (444c)

Step-1: Preparation of tert-butyl ((cis)-3-(4-((S)-2-(((tert-butyldimethylsilyl)oxy)methyl)pyrrolidin-1-yl)-6-chloro-3-methyl-1H-pyrazolo[3,4-d]pyrimidin-1-yl)cyclobutyl)carbamate (444a)

Compound 444a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (350 mg, 0.92 mmol) in THF using triphenylphosphine (601 mg, 2.291 mmol), tert-butyl (trans)-3-hydroxycyclobutylcarbamate (429 mg, 2.29 mmol), DIAD (0.445 mL, 2.29 mmol) and stirring at room temperature overnight according to the procedure reported in step-2 of scheme 435. This gave after workup and purification by flash column chromatography [silica (12 g), eluting with EtOAc in hexane from 0-60%] tert-butyl ((cis)-3-(4-((S)-2-(((tert-butyldimethylsilyl)oxy)methyl)pyrrolidin-1-yl)-6-chloro-3-methyl-1H-pyrazolo[3,4-d]pyrimidin-1-yl)cyclobutyl)carbamate (444a) (430 mg, 85% yield) as a white solid; MS (ES+): 551.3 (M+1).

Step-2: Preparation of tert-butyl ((cis)-3-(4-((S)-2-(((tert-butyldimethylsilyl)oxy)methyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutyl)carbamate (444b)

Compound 444b was prepared from tert-butyl ((cis)-3-(4-((S)-2-(((tert-butyldimethylsilyl)oxy)methyl)pyrrolidin-1-yl)-6-chloro-3-methyl-1H-pyrazolo[3,4-d]pyrimidin-1-yl)cyclobutyl)carbamate (444a) (430 mg, 0.78 mmol), 1-(3,4,5-trimethoxyphenyl)-1H-imidazol-4-amine (57a) (233 mg, 0.96 mmol), dicyclohexyl(2',4',6'-triisopropylbiphenyl-2-yl)phosphine (XPhos, 149 mg, 0.31 mmol), cesium carbonate (890 mg, 2.73 mmol), $Pd_2(dba)_3$ (143 mg, 0.16 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA-80 in DCM from 0-50%] tert-butyl ((cis)-3-(4-((S)-2-(((tert-butyldimethylsilyl)oxy)methyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutyl)carbamate (444b) as a white solid; MS (ES+): 650.3 (M+1).

Step-3: Preparation of ((S)-1-(1-((cis)-3-aminocyclobutyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (444c)

To a solution of tert-butyl ((cis)-3-(4-((S)-2-(((tert-butyldimethylsilyl)oxy)methyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutyl)carbamate (444b) (from step-2 above) was dissolved in DCM/MeOH (10 mL, 1:1), was added TFA (1.202 mL, 15.60 mmol), HCl (4N in dioxane, 1.950 mL, 7.80 mmol) and stirred at room temperature for 20 min. The reaction mixture was concentrated in vacuum and the residue obtained was purified by reverse phase column chromatography [C18 steel column, eluting with ACN in water (containing 0.1% HCl) from 0-100%] to give ((S)-1-(1-((cis)-3-aminocyclobutyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (444c) (138 mg, 32% yield) as a white solid; $^1$H NMR (300 MHz, DMSO-$d_6$) δ 10.05 (s, 1H, $D_2O$ exchangeable), 9.11 (s, 1H), 8.50 (d, J=4.9 Hz, 3H, $D_2O$ exchangeable), 7.91 (d, J=1.7 Hz, 1H, $D_2O$ exchangeable), 7.13 (s, 2H), 5.09-4.99 (m, 1H), 4.69-4.62 (m, 1H), 3.91 (s, 6H), 3.87-3.76 (m, 2H), 3.71 (s, 3H), 3.68-3.49 (m, 4H), 2.78-2.70 (m, 4H), 2.59 (s, 3H), 2.09-1.89 (m, 4H); MS (ES$^+$) 550.3 (M+1).

Scheme 445

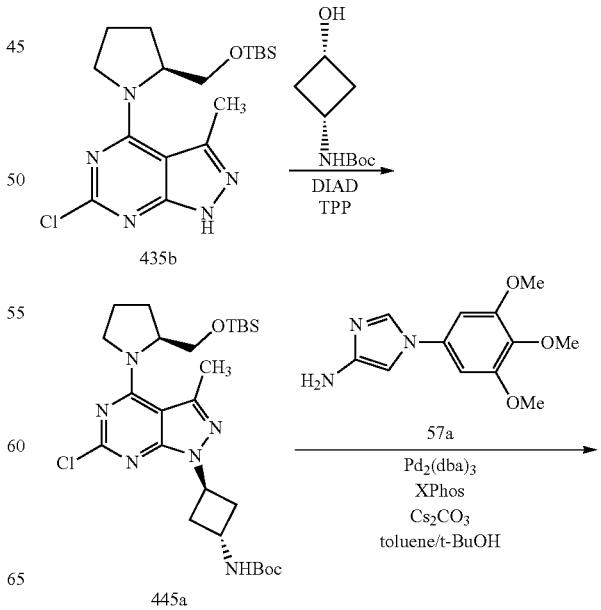

-continued

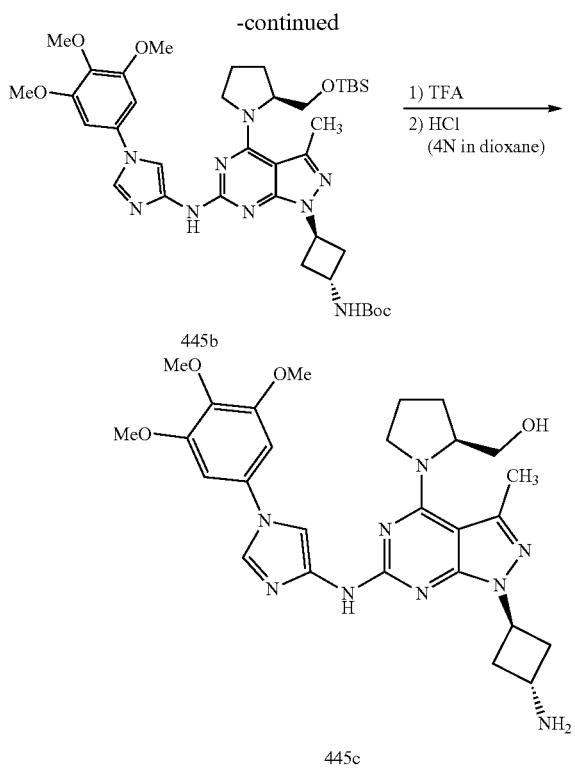

445b

445c

Preparation of ((S)-1-(1-(((trans)-3-aminocyclobutyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (445c)

Step-1: Preparation of tert-butyl ((trans)-3-(4-((S)-2-(((tert-butyldimethylsilyl)oxy)methyl)pyrrolidin-1-yl)-6-chloro-3-methyl-1H-pyrazolo[3,4-d]pyrimidin-1-yl)cyclobutyl)carbamate (445a)

Compound 445a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (350 mg, 0.92 mmol) in THF using triphenylphosphine (601 mg, 2.291 mmol), tert-butyl (cis)-3-hydroxycyclobutylcarbamate (429 mg, 2.29 mmol), DIAD (0.45 mL, 2.29 mmol) and stirring at room temperature overnight according to the procedure reported in step-2 of scheme 435. This gave after workup and purification by flash column chromatography [silica (12 g), eluting with EtOAc in hexane from 0-60%] tert-butyl ((trans)-3-(4-((S)-2-(((tert-butyldimethylsilyl)oxy)methyl)pyrrolidin-1-yl)-6-chloro-3-methyl-1H-pyrazolo[3,4-d]pyrimidin-1-yl)cyclobutyl)carbamate (445a) (475 mg, 94% yield) as a clear oil; MS (ES+): 551.3 (M+1).

Step-2: Preparation of tert-butyl ((trans)-3-(4-((S)-2-(((tert-butyldimethylsilyl)oxy)methyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutyl)carbamate (445b)

Compound 445b was prepared from tert-butyl ((trans)-3-(4-((S)-2-(((tert-butyldimethylsilyl)oxy)methyl)pyrrolidin-1-yl)-6-chloro-3-methyl-1H-pyrazolo[3,4-d]pyrimidin-1-yl)cyclobutyl)carbamate (445a) (475 mg, 0.86 mmol), 1-(3,4,5-trimethoxyphenyl)-1H-imidazol-4-amine (57a) (258 mg, 1.03 mmol), dicyclohexyl(2',4',6'-triisopropylbiphenyl-2-yl)phosphine (XPhos, 164 mg, 0.35 mmol), cesium carbonate (983 mg, 3.02 mmol), Pd$_2$(dba)$_3$ (158 mg, 0.17 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA-80 in DCM from 0-50%] tert-butyl ((trans)-3-(4-((S)-2-(((tert-butyldimethylsilyl)oxy)methyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutyl)carbamate (445b) as a white solid; MS (ES+): 764.3 (M+1).

Step-3: Preparation of ((S)-1-(1-(((trans)-3-aminocyclobutyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (445c)

To a solution of tert-butyl ((trans)-3-(4-((S)-2-(((tert-butyldimethylsilyl)oxy)methyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutyl)carbamate (445b) (from step-2 above) was dissolved in DCM/MeOH (10 mL, 1:1), was added TFA (0.66 mL, 8.62 mmol), HCl (4N in dioxane, 2.15 mL, 8.62 mmol) and stirred at room temperature for 20 min. The reaction mixture was concentrated in vacuum and the residue obtained was purified by reverse phase column chromatography [C18 steel column, eluting with ACN in water (containing 0.1% HCl) from 0-100%] to give ((S)-1-(1-(((trans)-3-aminocyclobutyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (445c) (110 mg, 23% yield) as a white solid; $^1$H NMR (300 MHz, DMSO-d$_6$) δ 10.07 (s, 1H, D$_2$O exchangeable), 9.21 (s, 1H), 8.62 (d, J=4.6 Hz, 3H, D$_2$O exchangeable), 7.88 (d, J=1.8 Hz, 1H, D$_2$O exchangeable), 7.13 (s, 2H), 5.68-5.48 (m, 1H), 4.69-4.59 (m, 2H), 4.00-3.93 (m, 1H), 3.90 (s, 6H), 3.87-3.76 (m, 2H), 3.71 (s, 3H), 3.66-3.61 (m, 1H), 3.56-3.48 (m, 1H), 2.87-2.76 (m, 2H), 2.74-2.64 (m, 2H), 2.59 (s, 3H), 2.10-1.88 (m, 4H); MS (ES$^+$) 550.3 (M+1).

Scheme 446

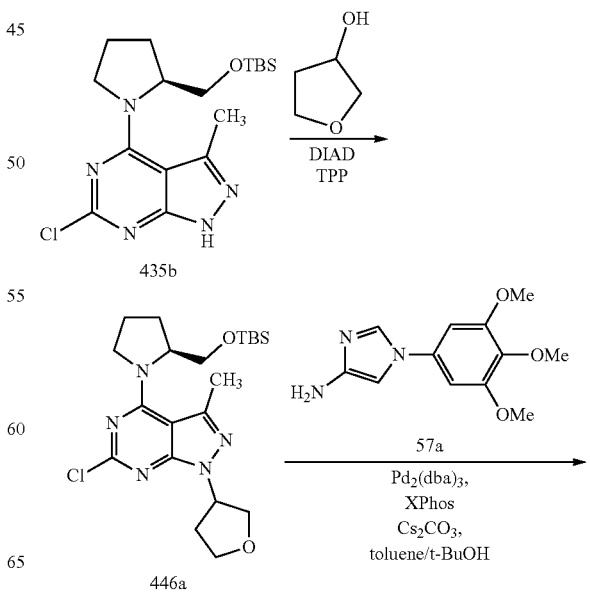

-continued

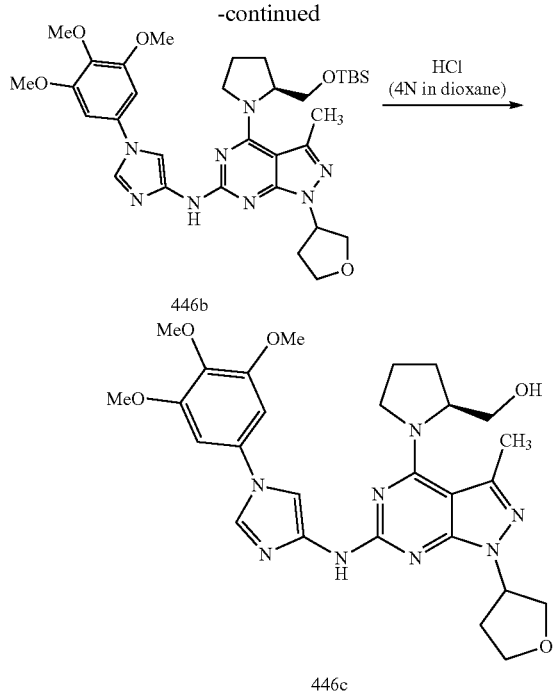

Preparation of ((2S)-1-(3-methyl-1-(tetrahydrofuran-3-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (446c)

Step-1: Preparation of 4-((S)-2-(((tert-butyldimethylsilyl)oxy)methyl)pyrrolidin-1-yl)-6-chloro-3-methyl-1-(tetrahydrofuran-3-yl)-1H-pyrazolo[3,4-d]pyrimidine (446a)

Compound 446a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF using triphenylphosphine (515 mg, 1.96 mmol), tetrahydrofuran-3-ol (173 mg, 1.96 mmol), DIAD (0.38 mL, 1.96 mmol) and stirring at room temperature overnight according to the procedure reported in step-2 of scheme 435. This gave after workup and purification by flash column chromatography [silica (12 g), eluting with EtOAc in hexane from 0-60%] 4-((S)-2-(((tert-butyldimethylsilyl)oxy)methyl)pyrrolidin-1-yl)-6-chloro-3-methyl-1-(tetrahydrofuran-3-yl)-1H-pyrazolo[3,4-d]pyrimidine (446a) (300 mg, 84% yield) as a clear oil; MS (ES+): 452.3 (M+1).

Step-2: Preparation of 4-((S)-2-(((tert-butyldimethylsilyl)oxy)methyl)pyrrolidin-1-yl)-3-methyl-1-(tetrahydrofuran-3-yl)-N-(1-(3,4,5-trimethoxyphenyl)-1H-imidazol-4-yl)-1H-pyrazolo[3,4-d]pyrimidin-6-amine (446b)

Compound 446b was prepared from 4-((S)-2-(((tert-butyldimethylsilyl)oxy)methyl)pyrrolidin-1-yl)-6-chloro-3-methyl-1-(tetrahydrofuran-3-yl)-1H-pyrazolo[3,4-d]pyrimidine (446a) (300 mg, 0.67 mmol), 1-(3,4,5-trimethoxyphenyl)-1H-imidazol-4-amine (57a) (199 mg, 0.80 mmol), dicyclohexyl(2',4',6'-triisopropylbiphenyl-2-yl)phosphine (XPhos, 127 mg, 0.27 mmol), cesium carbonate (760 mg, 2.33 mmol), Pd$_2$(dba)$_3$ (122 mg, 0.13 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA80 in DCM from 0-50%]4-((S)-2-(((tert-butyldimethylsilyl)oxy)methyl)pyrrolidin-1-yl)-3-methyl-1-(tetrahydrofuran-3-yl)-N-(1-(3,4,5-trimethoxyphenyl)-1H-imidazol-4-yl)-1H-pyrazolo[3,4-d]pyrimidin-6-amine (446b) as a white solid; MS (ES+): 665.3 (M+1).

Step-3: Preparation of ((2S)-1-(3-methyl-1-(tetrahydrofuran-3-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (446c)

A solution of 4-((S)-2-(((tert-butyldimethylsilyl)oxy)methyl)pyrrolidin-1-yl)-3-methyl-1-(tetrahydrofuran-3-yl)-N-(1-(3,4,5-trimethoxyphenyl)-1H-imidazol-4-yl)-1H-pyrazolo[3,4-d]pyrimidin-6-amine (446b) (from step-2 above) in MeOH/DCM (10 mL) was added 4N HCl in dioxane (1.66 mL, 6.64 mmol), stirred at room temperature for 20 min and concentrated in vacuum. The residue obtained was purified by reverse phase column chromatography [C18 steel column (250 mm×30 mm), eluting with ACN in water (containing 0.1% HCl) from 0-100%] ((2S)-1-(3-methyl-1-(tetrahydrofuran-3-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (446c) (132 mg, 36% yield) as a yellow solid; $^1$H NMR (300 MHz, DMSO-d$_6$) δ 10.35 (s, 1H, D$_2$O exchangeable), 9.20 (s, 1H), 7.98 (s, 1H, D$_2$O exchangeable), 7.13 (s, 2H), 5.42-5.31 (m, 4H), 4.71-4.63 (m, 1H), 4.10-3.98 (m, 2H), 3.95-3.86 (m, 8H), 3.85-3.78 (m, 2H), 3.70 (s, 3H), 3.66-3.53 (m, 2H), 2.55 (s, 3H), 2.39-2.23 (m, 2H), 2.12-1.88 (m, 4H); MS (ES+): 551.3 (M+1); (ES−): 549.2 (M−1).

Scheme 447

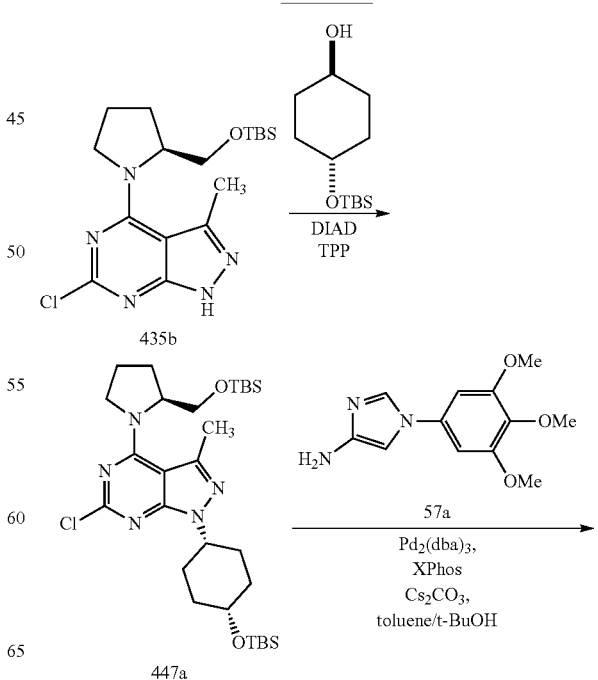

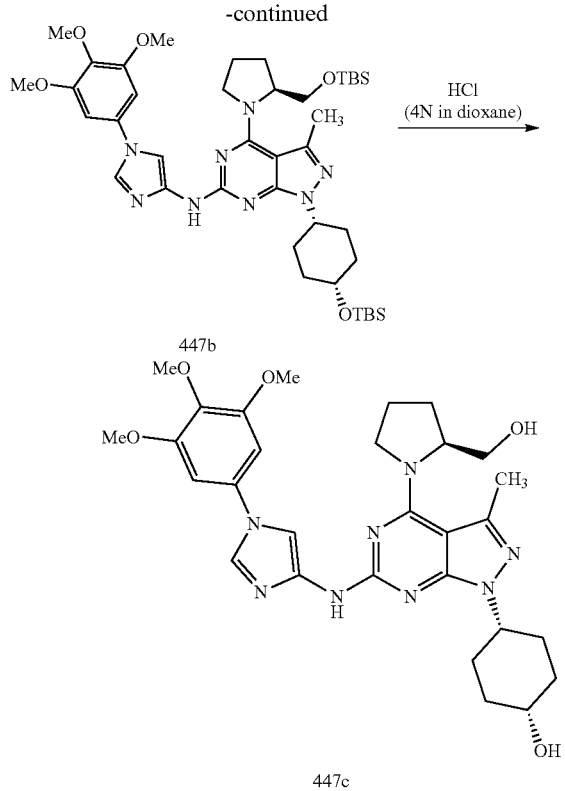

447b

447c

Preparation of (cis)-4-(4-((S)-2-(hydroxymethyl) pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclohexanol (447c)

Step-1: Preparation of 1-((cis)-4-((tert-butyldimethylsilyl)oxy)cyclohexyl)-4-((S)-2-(((tert-butyldimethylsilyl)oxy)methyl)pyrrolidin-1-yl)-6-chloro-3-methyl-1H-pyrazolo[3,4-d]pyrimidine (447a)

Compound 447a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF using triphenylphosphine (515 mg, 1.96 mmol), (trans)-4-(tert-butyldimethylsilyloxy)cyclohexanol (452 mg, 1.96 mmol; CAS #103202-63-7), DIAD (0.38 mL, 1.96 mmol) and stirring at room temperature overnight according to the procedure reported in step-2 of scheme 435. This gave after workup and purification by flash column chromatography [silica (12 g), eluting with EtOAc in hexane from 0-60%] 1-((cis)-4-((tert-butyldimethylsilyl)oxy)cyclohexyl)-4-((S)-2-(((tert-butyldimethylsilyl)oxy)methyl)pyrrolidin-1-yl)-6-chloro-3-methyl-1H-pyrazolo[3,4-d]pyrimidine (447a) (350 mg, 75% yield) as a clear oil; MS (ES+): 594.4 (M+1).

Step-2: Preparation of 1-((cis)-4-((tert-butyldimethylsilyl)oxy)cyclohexyl)-4-((S)-2-(((tert-butyldimethylsilyl)oxy)methyl)pyrrolidin-1-yl)-3-methyl-N-(1-(3,4,5-trimethoxyphenyl)-1H-imidazol-4-yl)-1H-pyrazolo[3,4-d]pyrimidin-6-amine (447b)

Compound 447b was prepared from 1-((cis)-4-((tert-butyldimethylsilyl)oxy)cyclohexyl)-4-((S)-2-(((tert-butyldimethylsilyl)oxy)methyl)pyrrolidin-1-yl)-6-chloro-3-methyl-1H-pyrazolo[3,4-d]pyrimidine (447a) (350 mg, 0.59 mmol), 1-(3,4,5-trimethoxyphenyl)-1H-imidazol-4-amine (57a) (176 mg, 0.71 mmol), dicyclohexyl(2',4',6'-triisopropylbiphenyl-2-yl)phosphine (XPhos, 112 mg, 0.24 mmol), cesium carbonate (672 mg, 2.06 mmol), Pd$_2$(dba)$_3$ (108 mg, 0.12 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA80 in DCM from 0-50%] 1-((cis)-4-((tert-butyldimethylsilyl)oxy)cyclohexyl)-4-((S)-2-(((tert-butyldimethylsilyl)oxy)methyl)pyrrolidin-1-yl)-3-methyl-N-(1-(3,4,5-trimethoxyphenyl)-1H-imidazol-4-yl)-1H-pyrazolo[3,4-d]pyrimidin-6-amine (447b) as a white solid; MS (ES+): 807.4 (M+1).

Step-3: Preparation of (cis)-4-(4-((S)-2-(hydroxymethyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclohexanol (447c)

To a solution of 1-((cis)-4-((tert-butyldimethylsilyl)oxy)cyclohexyl)-4-((S)-2-(((tert-butyldimethylsilyl)oxy)methyl)pyrrolidin-1-yl)-3-methyl-N-(1-(3,4,5-trimethoxyphenyl)-1H-imidazol-4-yl)-1H-pyrazolo[3,4-d]pyrimidin-6-amine (447b) (from above step-2) in MeOH/DCM (10 mL) was added 4N HCl in dioxane (0.15 mL, 0.59 mmol), stirred at room temperature for 20 min and concentrated in vacuum. The residue obtained was purified by reverse phase column chromatography [C18 steel column (250 mm×30 mm), eluting with ACN in water (containing 0.1% HCl) from 0-100%] to afford (cis)-4-(4-((S)-2-(hydroxymethyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclohexanol (447c) (106 mg, 31% yield) as a white solid; $^1$H NMR (300 MHz, DMSO-d$_6$) δ 10.25 (s, 1H, D$_2$O exchangeable), 9.00 (s, 1H), 7.85 (d, J=1.7 Hz, 1H, D$_2$O exchangeable), 7.10 (s, 2H), 4.72-4.64 (m, 1H), 4.60-4.49 (m, 1H), 3.92-3.82 (m, 10H), 3.70 (s, 3H), 3.66-3.53 (m, 2H), 2.56 (s, 3H), 2.32-2.19 (m, 2H), 2.09-1.90 (m, 4H), 1.86-1.75 (m, 2H), 1.63-1.53 (m, 4H); MS (ES+): 579.3 (M+1); (ES−): 613.3 (M+Cl).

Scheme 448

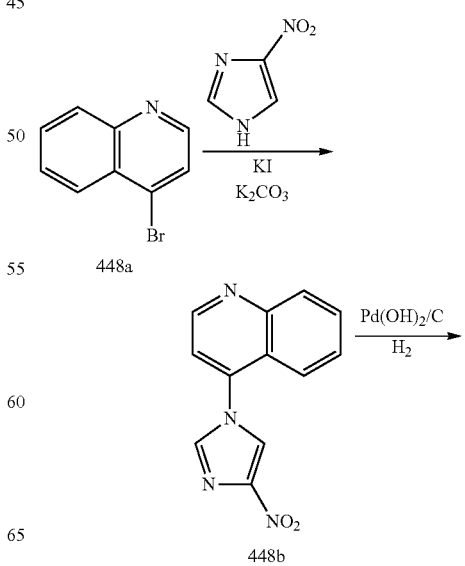

448a

448b

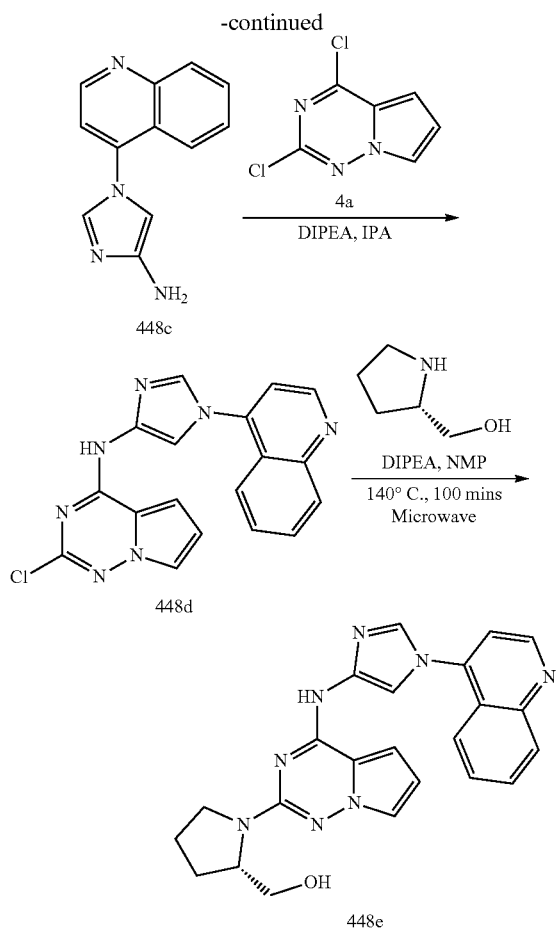

Preparation of (S)-(1-(4-((1-(quinolin-4-yl)-1H-imidazol-4-yl)amino)pyrrolo[2,1-f][1,2,4]triazin-2-yl)pyrrolidin-2-yl)methanol (448e)

Step-1: Preparation of 4-(4-nitro-1H-imidazol-1-yl)quinoline (448b)

Compound 448b was prepared from 4-bromoquinoline (448a) (1.1 g, 5.29 mmol; CAS #: 3964-04-3) in DMF (8 mL) using 4-nitro-1H-imidazole (0.588 g, 5.20 mmol), potassium iodide (0.86 g, 5.18 mmol), potassium carbonate (1.85 g, 13.39 mmol) and heating at 100° C. in a microwave reactor for 4 h according to the procedure reported in step-1 of scheme 437. This gave after workup 4-(4-nitro-1H-imidazol-1-yl)quinoline (448b) (745 mg, 60% yield) as a yellow solid. $^1$H NMR (300 MHz, DMSO-$d_6$) δ 9.13 (d, J=4.6 Hz, 1H), 9.00 (d, J=1.5 Hz, 1H), 8.39 (d, J=1.5 Hz, 1H), 8.23 (dt, J=8.5, 1.0 Hz, 1H), 7.94 (ddd, J=8.4, 5.9, 2.3 Hz, 1H), 7.84 (d, J=4.6 Hz, 1H), 7.82-7.72 (m, 2H); MS (ES+): 241.1 (M+1).

Step-2: Preparation of 1-(quinolin-4-yl)-1H-imidazol-4-amine (448c)

Reduction of nitro to amine of 4-(4-nitro-1H-imidazol-1-yl)quinoline (448b) (472 mg, 1.965 mmol) in MeOH (20 mL) using Palladium hydroxide on carbon, 20 wt. % loading (dry basis), matrix carbon, wet support (123 mg, 0.175 mmol) as reported in step-3 of General scheme for preparation of 3-substituted-(4-amino-1H-imidazol-1-yl) gave after workup and purification by flash column chromatography [silica gel 24 g, eluting with MeOH/DCM from 0-20%] 1-(quinolin-4-yl)-1H-imidazol-4-amine (448c) (244 mg, 59% yield) as a yellow syrup. $^1$H NMR (300 MHz, DMSO-$d_6$) δ 8.97 (d, J=4.7 Hz, 1H), 8.14 (ddd, J=8.4, 1.3, 0.6 Hz, 1H), 8.02 (ddd, J=8.4, 1.5, 0.7 Hz, 1H), 7.87 (ddd, J=8.4, 6.9, 1.4 Hz, 1H), 7.77-7.67 (m, 2H), 7.54 (d, J=4.7 Hz, 1H), 6.65 (d, J=1.6 Hz, 1H), 4.58 (s, 2H); MS (ES+): 211.1 (M+1).

Step-3: Preparation of 2-chloro-N-(1-(quinolin-4-yl)-1H-imidazol-4-yl)pyrrolo[2,1-f][1,2,4]triazin-4-amine (448d)

Compound 448d was prepared from 2,4-dichloropyrrolo[2,1-f][1,2,4]triazine (4a) (216 mg, 1.149 mmol) in 2-Propanol (8 mL) using DIPEA (0.408 mL, 2.337 mmol), 1-(quinolin-4-yl)-1H-imidazol-4-amine (448c) (239 mg, 1.137 mmol) and heating at 90° C. for 3 h according to the procedure reported in step-1 of scheme 183. This gave after workup and filtration 2-chloro-N-(1-(quinolin-4-yl)-1H-imidazol-4-yl)pyrrolo[2,1-f][1,2,4]triazin-4-amine (448d) (244 mg, 59% yield) as a yellow solid. $^1$H NMR (300 MHz, DMSO-$d_6$) δ 11.51 (s, 1H), 9.08 (d, J=4.6 Hz, 1H), 8.22 (dd, J=7.7, 1.4 Hz, 2H), 8.02-7.86 (m, 3H), 7.84-7.71 (m, 3H), 7.45 (d, J=4.2 Hz, 1H), 6.75 (dd, J=4.5, 2.6 Hz, 1H); MS (ES+): 362.1 (M+1), 384.1 (M+Na).

Step-4: Preparation of (S)-(1-(4-((1-(quinolin-4-yl)-1H-imidazol-4-yl)amino)pyrrolo[2,1-f][1,2,4]triazin-2-yl)pyrrolidin-2-yl)methanol (448e)

Compound 448e was prepared from 2-chloro-N-(1-(quinolin-4-yl)-1H-imidazol-4-yl)pyrrolo[2,1-f][1,2,4]triazin-4-amine (448d) (120 mg, 0.332 mmol), (S)-pyrrolidin-2-ylmethanol (189 mg, 1.87 mmol), N-ethyl-N-isopropylpropan-2-amine (0.3 mL, 1.72 mmol) in NMP (1.5 mL) and heating at 140° C. for 100 min in a microwave according to the procedure reported in scheme 2. This gave after workup and purification by reverse phase column chromatography [C18 (RediSep 250×30 mm), eluting with ACN in water (containing 0.1% HCl) from 0-100%] (S)-(1-(4-((1-(quinolin-4-yl)-1H-imidazol-4-yl)amino)pyrrolo[2,1-f][1,2,4]triazin-2-yl)pyrrolidin-2-yl)methanol (448e) (55 mg, 39% yield) as a yellow solid. $^1$H NMR (300 MHz, DMSO-$d_6$) δ 10.98 (s, 1H), 9.32 (d, J=5.5 Hz, 1H), 8.59-8.41 (m, 2H), 8.35 (d, J=8.5 Hz, 1H), 8.28-8.04 (m, 3H), 8.04-7.89 (m, 1H), 7.46 (t, J=2.1 Hz, 1H), 7.21 (dd, J=4.5, 1.7 Hz, 1H), 6.46 (dd, J=4.5, 2.4 Hz, 1H), 4.23-4.01 (m, 1H), 3.62 (dd, J=10.1, 3.6 Hz, 1H), 3.56-3.43 (m, 1H), 3.43-3.17 (m, 2H), 2.07-1.66 (m, 4H); MS (ES+): 427.2 (M+1); MS (ES−): 425.2 (M−1). HPLC purity 98.8%.

Scheme 449

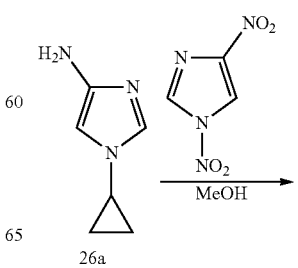

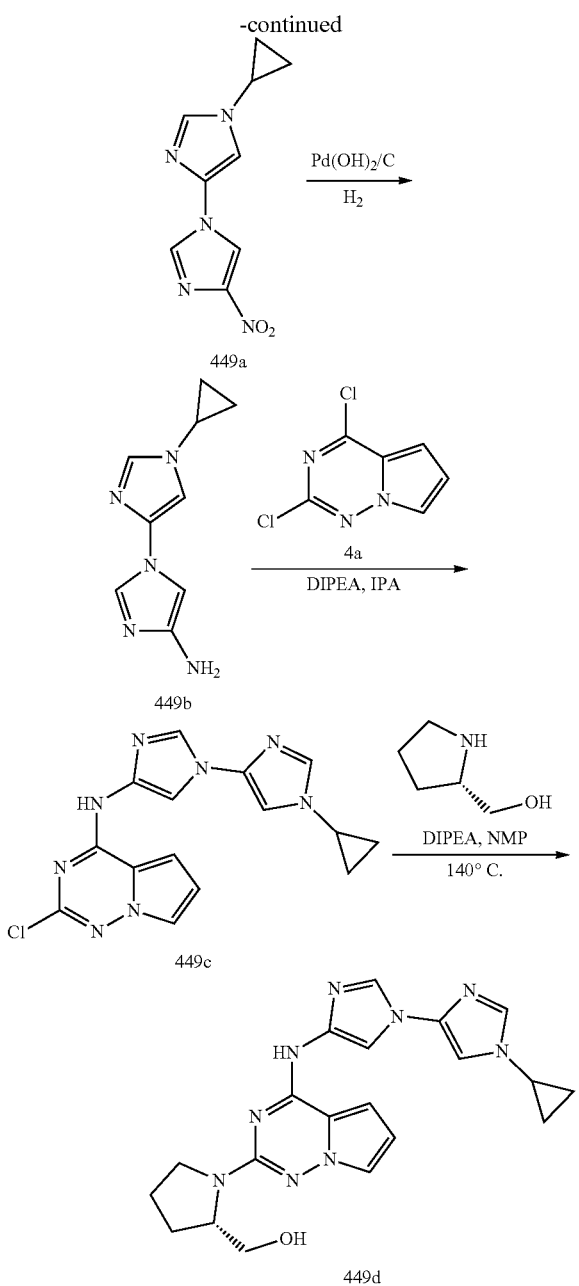

Preparation of (S)-(1-(4-((1'-cyclopropyl-1'H-[1,4'-biimidazol]-4-yl)amino)pyrrolo[2,1-f][1,2,4]triazin-2-yl)pyrrolidin-2-yl)methanol (449d)

Step-1: Preparation of 1'-cyclopropyl-4-nitro-1'H-1,4'-biimidazole (449a)

Reaction of 1,4-dinitro-1H-imidazole (2.29 g, 14.49 mmol) with 1-cyclopropyl-1H-imidazol-4-amine (26a) (1.91 g, 15.51 mmol) as reported in step-2 of General scheme for preparation of 3-substituted-(4-amino-1H-imidazol-1-yl) gave after work-up and purification by flash column chromatography [silica gel 24 g, eluting with ethyl acetate/MeOH (9:1) in hexanes from 50-100%] 1'-cyclopropyl-4-nitro-1'H-1,4'-biimidazole (449a) (2.33 g, 69% yield) as an orange solid. $^1$H NMR (300 MHz, DMSO-d$_6$) δ 8.71 (d, J=1.5 Hz, 1H), 8.28 (d, J=1.5 Hz, 1H), 7.85 (dd, J=1.6, 0.5 Hz, 1H), 7.77 (d, J=1.5 Hz, 1H), 3.66-3.56 (m, 1H), 1.02-0.99 (m, 4H); MS (ES+): 220.1 (M+1).

Step-2: Preparation of 1'-cyclopropyl-1'H-[1,4'-biimidazol]-4-amine (449b)

Reduction of nitro to amine of 1'-cyclopropyl-4-nitro-1'H-1,4'-biimidazole (449a) (749 mg, 3.42 mmol) in MeOH (30 mL) using Palladium hydroxide on carbon, 20 wt. % loading (dry basis), matrix carbon, wet support (255 mg, 0.363 mmol) as reported in step-3 of General scheme for preparation of 3-substituted-(4-amino-1H-imidazol-1-yl) gave work-up and purification by flash column chromatography [12 g, eluting with MeOH/DCM 0-20%] 1'-cyclopropyl-1'H-[1,4'-biimidazol]-4-amine (449b) (328 mg, 51% yield) as an dark oil. MS (ES+): 190.1 (M+1).

Step-3: Preparation of 2-chloro-N-(1'-cyclopropyl-1'H-[1,4'-biimidazol]-4-yl)pyrrolo[2,1-f][1,2,4]triazin-4-amine (449c)

Compound 449c was prepared from 2,4-dichloropyrrolo[2,1-f][1,2,4]triazine (4a) (330 mg, 1.755 mmol) in 2-Propanol (8 mL) using DIPEA (0.634 mL, 3.63 mmol), 1'-cyclopropyl-1'H-[1,4'-biimidazol]-4-amine (449b) (328 mg, 1.733 mmol) and heating at 90° C. for 3 h according to the procedure reported in step-1 of scheme 183. This gave after workup and filtration 2-chloro-N-(1'-cyclopropyl-1'H-[1,4'-biimidazol]-4-yl)pyrrolo[2,1-f][1,2,4]triazin-4-amine (449c) (185 mg, 31% yield) as a yellow solid. $^1$H NMR (300 MHz, DMSO-d$_6$) δ 11.29 (s, 1H), 8.03 (d, J=1.5 Hz, 1H), 7.85 (d, J=1.5 Hz, 1H), 7.81-7.71 (m, 2H), 7.60 (d, J=1.5 Hz, 1H), 7.38 (d, J=4.4 Hz, 1H), 6.71 (dd, J=4.4, 2.6 Hz, 1H), 3.59 (tt, J=7.2, 4.1 Hz, 1H), 1.12-0.89 (m, 4H); MS (ES+): 341.1 (M+1), 363.1 (M+Na).

Step-4: Preparation of (S)-(1-(4-((1'-cyclopropyl-1'H-[1,4'-biimidazol]-4-yl)amino)pyrrolo[2,1-f][1,2,4]triazin-2-yl)pyrrolidin-2-yl)methanol (449d)

Compound 449d was prepared from 2-chloro-N-(1'-cyclopropyl-1'H-[1,4'-biimidazol]-4-yl)pyrrolo[2,1-f][1,2,4]triazin-4-amine (449c) (90 mg, 0.264 mmol), (S)-pyrrolidin-2-ylmethanol (109 mg, 1.08 mmol), N-ethyl-N-isopropylpropan-2-amine (0.185 mL, 1.06 mmol) in NMP (1.5 mL) and heating at 140° C. for 120 mins in a microwave reactor according to the procedure reported in scheme 2. This gave after workup and purification by flash column chromatography [silica (24 g), eluting with DMA80 in DCM from 0-70%] followed by purification by reverse phase column chromatography [C18 (RediSep 250×30 mm), eluting with ACN in water (containing 0.1% HCl) from 0-100%] (S)-(1-(4-((1'-cyclopropyl-1'H-[1,4'-biimidazol]-4-yl)amino)pyrrolo[2,1-f][1,2,4]triazin-2-yl)pyrrolidin-2-yl)methanol (449d) (31 mg, 29% yield) as a yellow solid. $^1$H NMR (300 MHz, DMSO-d$_6$) δ 10.88 (s, 1H), 8.48 (d, J=1.5 Hz, 1H), 7.92 (dd, J=3.9, 1.5 Hz, 2H), 7.77 (d, J=1.5 Hz, 1H), 7.57-7.37 (m, 1H), 7.11 (dd, J=4.5, 1.7 Hz, 1H), 6.44 (dd, J=4.5, 2.4 Hz, 1H), 4.19-4.18 (m, 1H), 3.78 (dd, J=10.4, 3.6 Hz, 1H), 3.67-3.55 (m, 1H), 3.47 (t, J=8.3 Hz, 1H), 3.40-3.27 (m, 2H), 2.12-1.86 (m, 4H), 1.01 (m, 4H); MS (ES+): 406.2 (M+1); MS (ES−): 404.2 (M−1).

Scheme 450

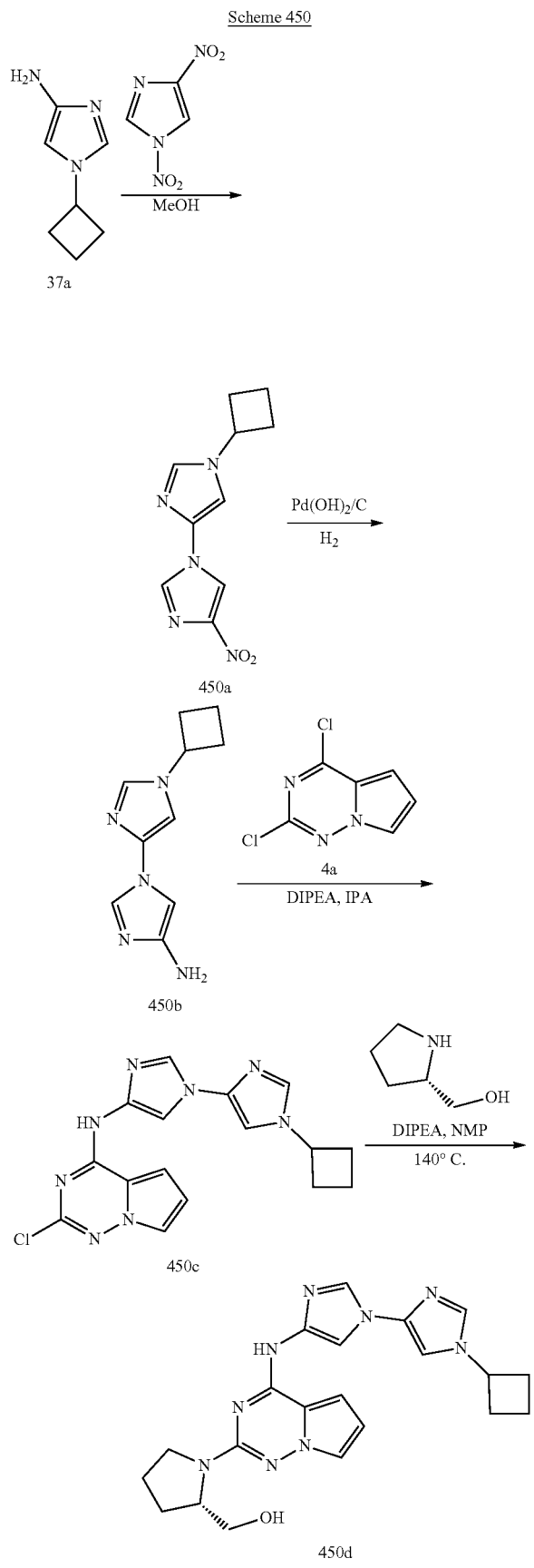

Preparation of (S)-(1-(4-((1'-cyclobutyl-1'H-[1,4'-biimidazol]-4-yl)amino)pyrrolo[2,1-f][1,2,4]triazin-2-yl)pyrrolidin-2-yl)methanol (450d)

Step-1: Preparation of 1'-cyclobutyl-4-nitro-1'H-1,4'-biimidazole (450a)

Reaction of 1,4-dinitro-1H-imidazole (960 mg, 6.07 mmol) with 1-cyclobutyl-1H-imidazol-4-amine (37a) (919 mg, 6.70 mmol) as reported in step-2 of General scheme for preparation of 3-substituted-(4-amino-1H-imidazol-1-yl) gave after work-up and purification by flash column chromatography [silica gel 24 g, eluting with ethyl acetate/MeOH (9:1) in hexanes from 50-100%] 1'-cyclobutyl-4-nitro-1'H-1,4'-biimidazole (450a) (1.03 g, 66% yield) as an orange solid; $^1$H NMR (300 MHz, DMSO-$d_6$) δ 8.71 (d, J=1.5 Hz, 1H), 8.29 (d, J=1.5 Hz, 1H), 7.92 (d, J=1.6 Hz, 1H), 7.87 (d, J=1.6 Hz, 1H), 4.78 (p, J=8.4 Hz, 1H), 2.47-2.27 (m, 4H), 1.93-1.65 (m, 2H).

Step-2: Preparation of 1'-cyclobutyl-1'H-[1,4'-biimidazol]-4-amine (450b)

Reduction of nitro to amine of 1'-cyclobutyl-4-nitro-1'H-1,4'-biimidazole (450a) (520 mg, 2.230 mmol) in MeOH (30 mL) using Palladium hydroxide on carbon, 20 wt. % loading (dry basis), matrix carbon, wet support (157 mg, 0.223 mmol) as reported in step-3 of General scheme for preparation of 3-substituted-(4-amino-1H-imidazol-1-yl) gave after work-up and purification by flash column chromatography [24 g, eluting with MeOH/DCM 0-20%] 1'-cyclobutyl-1'H-[1,4'-biimidazol]-4-amine (450b) (247 mg, 55% yield) as a yellow solid. $^1$H NMR (300 MHz, DMSO-$d_6$) δ 7.66 (d, J=1.6 Hz, 1H), 7.59 (d, J=1.5 Hz, 1H), 7.50 (d, J=1.6 Hz, 1H), 6.49 (d, J=1.6 Hz, 1H), 4.70 (p, J=8.4 Hz, 1H), 4.32 (s, 2H), 2.45-2.28 (m, 4H), 1.92-1.67 (m, 2H); MS (ES+): 204.1 (M+1).

Step-3: Preparation of 2-chloro-N-(1'-cyclobutyl-1'H-[1,4'-biimidazol]-4-yl)pyrrolo[2,1-f][1,2,4]triazin-4-amine (450c)

Compound 450c was prepared from 2,4-dichloropyrrolo[2,1-f][1,2,4]triazine (4a) (228 mg, 1.213 mmol) in 2-Propanol (8 mL) using DIPEA (0.422 mL, 2.414 mmol), 1'-cyclobutyl-1'H-[1,4'-biimidazol]-4-amine (450b) (245 mg, 1.205 mmol) and heating at 90° C. for 3 h according to the procedure reported in step-1 of scheme 183. This gave after workup and purification by flash column chromatography [24 g, eluting with MeOH/DCM 0-20%] 2-chloro-N-(1'-cyclobutyl-1'H-[1,4'-biimidazol]-4-yl)pyrrolo[2,1-f][1,2,4]triazin-4-amine (450c) (350 mg, 82% yield) as yellow foam; $^1$H NMR (300 MHz, DMSO-$d_6$) δ 11.29 (s, 1H), 8.03 (d, J=1.5 Hz, 1H), 7.85 (d, J=1.5 Hz, 1H), 7.82-7.72 (m, 3H), 7.39 (d, J=4.2 Hz, 1H), 6.71 (dd, J=4.4, 2.6 Hz, 1H), 4.77 (p, J=8.6 Hz, 1H), 2.47-2.36 (m, 4H), 1.90-1.72 (m, 2H); MS (ES+): 355.1 (M+1), 377.1 (M+Na).

Step-4: Preparation of (S)-(1-(4-((1'-cyclobutyl-1'H-[1,4'-biimidazol]-4-yl)amino)pyrrolo[2,1-f][1,2,4]triazin-2-yl)pyrrolidin-2-yl)methanol (450d)

Compound 450d was prepared from 2-chloro-N-(1'-cyclobutyl-1'H-[1,4'-biimidazol]-4-yl)pyrrolo[2,1-f][1,2,4]triazin-4-amine (450c) (100 mg, 0.282 mmol), (S)-pyrrolidin-2-ylmethanol (181 mg, 1.79 mmol), N-ethyl-N-isopropylpropan-2-amine (0.2 mL, 1.16 mmol) in NMP (1.5 mL) and heating at 140° C. for 100 mins in a microwave reactor according to the procedure reported in scheme 2. This gave after workup and purification by reverse phase column chromatography [C18 (RediSep 250×30 mm), eluting with ACN in water (containing 0.1% HCl) from 0-100%] (S)-(1-(4-((1'-cyclobutyl-1'H-[1,4'-biimidazol]-4-yl)amino)pyrrolo[2,1-f][1,2,4]triazin-2-yl)pyrrolidin-2-yl)methanol (450d) (42 mg, 36% yield) as a yellow solid. $^1$H NMR (300 MHz, DMSO-d$_6$) δ 11.09 (s, 1H), 8.65 (d, J=1.6 Hz, 1H), 8.00 (s, 2H), 7.96 (d, J=1.7 Hz, 1H), 7.48 (dd, J=2.4, 1.6 Hz, 1H), 7.12 (dd, J=4.4, 1.6 Hz, 1H), 6.47 (dd, J=4.5, 2.4 Hz, 1H), 4.79 (p, J=8.4 Hz, 1H), 4.17 (d, J=7.6 Hz, 1H), 3.78 (dd, J=10.4, 3.7 Hz, 1H), 3.47 (t, J=8.4 Hz, 1H), 3.42-3.27 (m, 2H), 2.48-2.29 (m, 4H), 2.16-1.71 (m, 6H); MS (ES+): 420.2 (M+1); MS(ES−): 418.2 (M−1).

Scheme 451

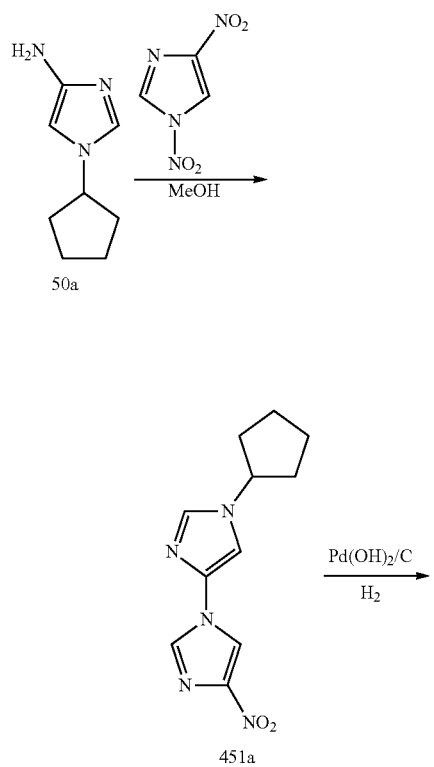

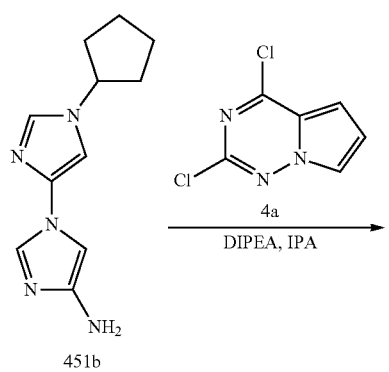

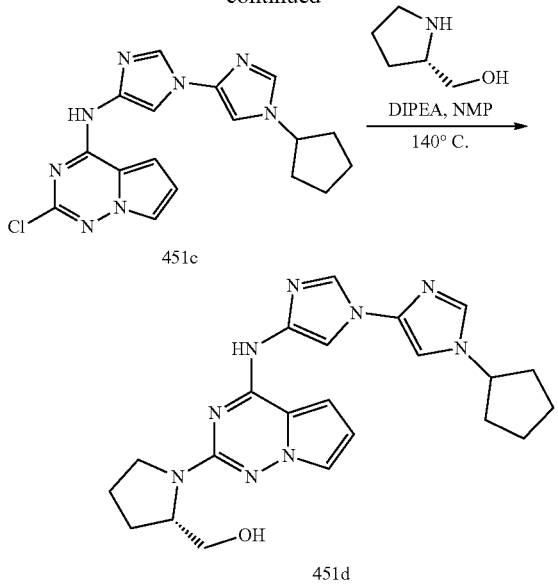

Preparation of (S)-(1-(4-((1'-cyclopentyl-1'H-[1,4'-biimidazol]-4-yl)amino)pyrrolo[2,1-f][1,2,4]triazin-2-yl)pyrrolidin-2-yl)methanol (451d)

Step-1: Preparation of 1'-cyclopentyl-4-nitro-1'H-1,4'-biimidazole (451a)

Reaction of 1,4-dinitro-1H-imidazole (691 mg, 4.37 mmol) with 1-cyclopentyl-1H-imidazol-4-amine (50a) (651 mg, 4.31 mmol) as reported in step-2 of General scheme for preparation of 3-substituted-(4-amino-1H-imidazol-1-yl) gave after work-up and purification by flash column chromatography [silica gel 24 g, eluting with ethyl acetate/MeOH (9:1) in hexanes from 50-100%] 1'-cyclopentyl-4-nitro-1'H-1,4'-biimidazole (451a) (637 mg, 60% yield) as an orange solid. $^1$H NMR (300 MHz, DMSO-d$_6$) δ 8.73 (d, J=1.5 Hz, 1H), 8.29 (d, J=1.5 Hz, 1H), 7.92-7.73 (m, 2H), 4.63 (p, J=6.7 Hz, 1H), 2.28-2.05 (m, 2H), 1.94-1.75 (m, 4H), 1.75-1.58 (m, 2H); MS (ES+): 248.1 (M+1).

Step-2: Preparation of 1'-cyclopentyl-1'H-[1,4'-biimidazol]-4-amine (451b)

Reduction of nitro to amine of 1'-cyclopentyl-4-nitro-1'H-1,4'-biimidazole (451a) (632 mg, 2.56 mmol) in MeOH (30 mL) using Palladium hydroxide on carbon, 20 wt. % loading (dry basis), matrix carbon, wet support (135 mg, 0.192 mmol) as reported in step-3 of General scheme for preparation of 3-substituted-(4-amino-1H-imidazol-1-yl) gave after work-up and purification by flash column chromatography [24 g, eluting with MeOH/DCM 0-20%] 1'-cyclopentyl-1'H-[1,4'-biimidazol]-4-amine (451b) (328 mg, 59% yield) as an yellow syrup; $^1$H NMR (300 MHz, DMSO-d$_6$) δ 7.63 (d, J=1.6 Hz, 1H), 7.59 (d, J=1.5 Hz, 1H), 7.38 (d, J=1.6 Hz, 1H), 6.49 (d, J=1.5 Hz, 1H), 4.55 (q, J=6.9 Hz, 1H), 4.31 (s, 2H), 2.11 (d, J=6.2 Hz, 2H), 1.86-1.73 (m, 4H), 1.65 (p, J=5.4, 3.7 Hz, 2H); MS (ES+): 218.1 (M+1).

Step-3: Preparation of 2-chloro-N-(1'-cyclopentyl-1'H-[1,4'-biimidazol]-4-yl)pyrrolo[2,1-f][1,2,4]triazin-4-amine (451c)

Compound 451c was prepared from 2,4-dichloropyrrolo[2,1-f][1,2,4]triazine (4a) (290 mg, 1.542 mmol) in 2-Propanol (8 mL) using DIPEA (0.324 mL, 1.857 mmol), 1'-cyclopentyl-1'H-[1,4'-biimidazol]-4-amine (451b) (323 mg, 1.487 mmol) and heating at 90° C. for 2.5 h according to the procedure reported in step-1 of scheme 183. This gave after workup and filtration 2-chloro-N-(1'-cyclopentyl-1'H-[1,4'-biimidazol]-4-yl)pyrrolo[2,1-f][1,2,4]triazin-4-amine (451c) (252 mg, 46% yield) as yellow solid. $^1$H NMR (300 MHz, DMSO-$d_6$) δ 11.28 (s, 1H), 8.03 (d, J=1.5 Hz, 1H), 7.85 (d, J=1.5 Hz, 1H), 7.80-7.72 (m, 2H), 7.64 (d, J=1.6 Hz, 1H), 7.39 (d, J=4.3 Hz, 1H), 6.71 (dd, J=4.5, 2.6 Hz, 1H), 4.60 (p, J=7.2 Hz, 1H), 2.26-2.07 (m, 2H), 1.83 (q, J=4.1, 2.5 Hz, 4H), 1.73-1.53 (m, 2H); MS (ES+): 369.1 (M+1).

Step-4: Preparation of (S)-(1-(4-((1'-cyclopentyl-1'H-[1,4'-biimidazol]-4-yl)amino)pyrrolo[2,1-f][1,2,4]triazin-2-yl)pyrrolidin-2-yl)methanol (451d)

Compound 451d was prepared from 2-chloro-N-(1'-cyclopentyl-1'H-[1,4'-biimidazol]-4-yl)pyrrolo[2,1-f][1,2,4]triazin-4-amine (451c) (102 mg, 0.277 mmol), (S)-pyrrolidin-2-ylmethanol (185 mg, 1.83 mmol), N-ethyl-N-isopropylpropan-2-amine (0.169 mL, 0.967 mmol) in NMP (1.5 mL) and heating at 140° C. for 100 mins in a microwave reactor according to the procedure reported in scheme 2. This gave after workup and purification by reverse phase column chromatography [C18 (RediSep 250×30 mm), eluting with ACN in water (containing 0.1% HCl) from 0-100%] (S)-(1-(4-((1'-cyclopentyl-1'H-[1,4'-biimidazol]-4-yl)amino)pyrrolo[2,1-f][1,2,4]triazin-2-yl)pyrrolidin-2-yl)methanol (451d) (64 mg, 53% yield) as a white solid; $^1$H NMR (300 MHz, DMSO-$d_6$) δ 10.88 (s, 1H), 8.49 (d, J=1.5 Hz, 1H), 7.95 (s, 2H), 7.83 (d, J=1.5 Hz, 1H), 7.53-7.36 (m, 1H), 7.11 (dd, J=4.5, 1.7 Hz, 1H), 6.45 (dd, J=4.5, 2.4 Hz, 1H), 4.61 (p, J=7.0 Hz, 1H), 4.15 (s, 1H), 3.80 (dd, J=10.4, 3.7 Hz, 1H), 3.47 (t, J=8.1 Hz, 1H), 3.34 (q, J=9.7, 8.3 Hz, 2H), 2.25-1.99 (m, 4H), 1.99-1.76 (m, 6H), 1.67 (qd, J=7.7, 6.7, 3.9 Hz, 2H); MS (ES+): 434.2 (M+1); MS (ES−): 432.2 (M−1).

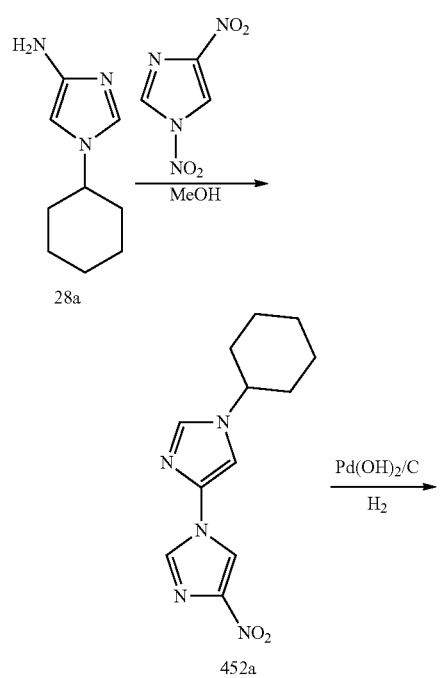

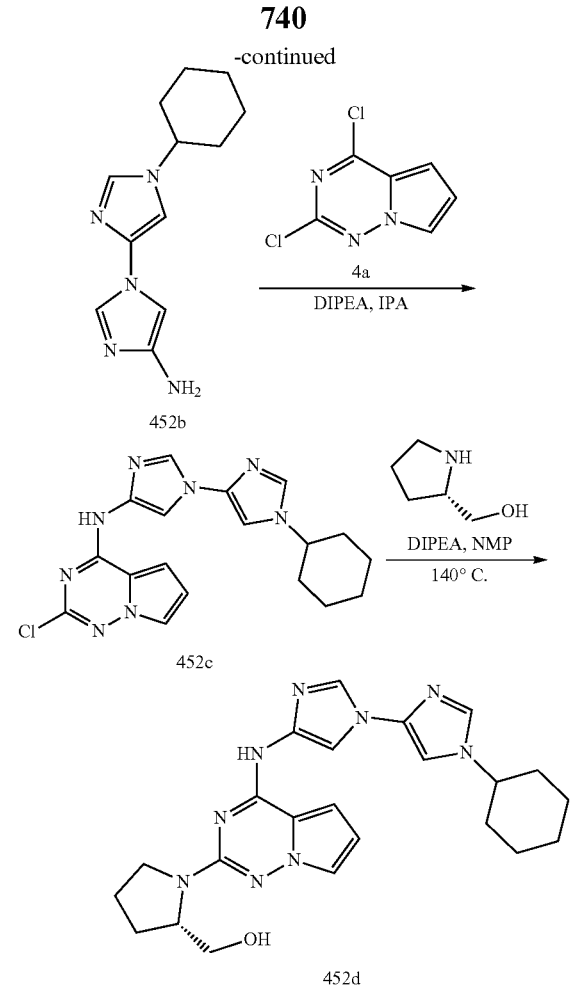

Preparation of (S)-(1-(4-((1'-cyclohexyl-1'H-[1,4'-biimidazol]-4-yl)amino)pyrrolo[2,1-f][1,2,4]triazin-2-yl)pyrrolidin-2-yl)methanol (452d)

Step-1: Preparation of 1'-cyclohexyl-4-nitro-1'H-1,4'-biimidazole (452a)

Reaction of 1,4-dinitro-1H-imidazole (550 mg, 3.48 mmol) with 1-cyclohexyl-1H-imidazol-4-amine (28a) (564 mg, 3.41 mmol) as reported in step-2 of General scheme for preparation of 3-substituted-(4-amino-1H-imidazol-1-yl) gave after work-up and purification by flash column chromatography [silica gel 24 g, eluting with ethyl acetate/MeOH (9:1) in hexanes from 50-100%] 1'-cyclohexyl-4-nitro-1'H-1,4'-biimidazole (452a) (650 mg, 73% yield) as an orange solid. $^1$H NMR (300 MHz, DMSO-$d_6$) δ 8.70 (d, J=1.5 Hz, 1H), 8.27 (d, J=1.5 Hz, 1H), 7.91-7.75 (m, 2H), 4.11 (tt, J=11.7, 3.8 Hz, 1H), 2.04 (d, J=12.2 Hz, 2H), 1.83 (d, J=13.1 Hz, 2H), 1.76-1.53 (m, 3H), 1.53-1.31 (m, 2H), 1.31-1.11 (m, 1H); MS (ES+): 262.1 (M+1).

Step-2: Preparation of 1'-cyclohexyl-1'H-[1,4'-biimidazol]-4-amine (452b)

Reduction of nitro to amine of 1'-cyclohexyl-4-nitro-1'H-1,4'-biimidazole (452a) (645 mg, 2.469 mmol) in MeOH (30 mL) using Palladium hydroxide on carbon, 20 wt. % loading (dry basis), matrix carbon, wet support (142 mg, 0.202 mmol) as reported in step-3 of General scheme for preparation of 3-substituted-(4-amino-1H-imidazol-1-yl) gave after work-up and purification by flash column chromatography [24 g, eluting with MeOH/DCM 0-20%] 1'-cyclohexyl-1'H-[1,4'-biimidazol]-4-amine (452b) (425 mg, 74% yield) as an yellow syrup. MS (ES+): 232.2 (M+1).

Step-3: Preparation of 2-chloro-N-(1'-cyclohexyl-1'H-[1,4'-biimidazol]-4-yl)pyrrolo[2,1-f][1,2,4]triazin-4-amine (452c)

Compound 452c was prepared from 2,4-dichloropyrrolo[2,1-f][1,2,4]triazine (4a) (342 mg, 1.82 mmol) in 2-Propanol (8 mL) using DIPEA (0.34 mL, 1.93 mmol), 1'-cyclohexyl-1'H-[1,4'-biimidazol]-4-amine (452b) (420 mg, 1.82 mmol) and heating at 90° C. for 4 h according to the procedure reported in step-1 of scheme 183. This gave after workup and filtration 2-chloro-N-(1'-cyclohexyl-1'H-[1,4'-biimidazol]-4-yl)pyrrolo[2,1-f][1,2,4]triazin-4-amine (452c) (184 mg, 27% yield) as a yellow solid. $^1$H NMR (300 MHz, DMSO-$d_6$) δ 11.29 (s, 1H), 8.01 (d, J=1.5 Hz, 1H), 7.84 (d, J=1.5 Hz, 1H), 7.76 (dd, J=3.5, 1.4 Hz, 2H), 7.65 (d, J=1.5 Hz, 1H), 7.39 (d, J=4.3 Hz, 1H), 6.71 (dd, J=4.5, 2.6 Hz, 1H), 4.09 (ddd, J=11.7, 7.9, 3.7 Hz, 1H), 2.04 (d, J=12.2 Hz, 2H), 1.83 (d, J=13.0 Hz, 2H), 1.77-1.58 (m, 3H), 1.40 (q, J=12.7 Hz, 2H), 1.24 (t, J=12.6 Hz, 1H); MS (ES+): 383.1 (M+1).

Step-4: Preparation of (S)-(1-(4-((1'-cyclohexyl-1'H-[1,4'-biimidazol]-4-yl)amino)pyrrolo[2,1-f][1,2,4]triazin-2-yl)pyrrolidin-2-yl)methanol (452d)

Compound 452d was prepared from 2-chloro-N-(1'-cyclohexyl-1'H-[1,4'-biimidazol]-4-yl)pyrrolo[2,1-f][1,2,4]triazin-4-amine (452c) (103 mg, 0.269 mmol), (S)-pyrrolidin-2-ylmethanol (165 mg, 1.63 mmol), N-ethyl-N-isopropylpropan-2-amine (0.207 mL, 1.12 mmol) in NMP (1.5 mL) and heating at 140° C. for 100 mins in a microwave reactor according to the procedure reported in scheme 2. This gave after workup and purification by reverse phase column chromatography [C18 (RediSep 250×30 mm), eluting with ACN in water (containing 0.1% HCl) from 0-100%] (S)-(1-(4-((1'-cyclohexyl-1'H-[1,4'-biimidazol]-4-yl)amino)pyrrolo[2,1-f][1,2,4]triazin-2-yl)pyrrolidin-2-yl)methanol (452d) (59 mg, 49% yield) as a white solid. $^1$H NMR (300 MHz, DMSO-$d_6$) δ 10.92 (s, 1H), 8.52 (d, J=1.5 Hz, 1H), 7.98 (d, J=1.5 Hz, 1H), 7.93 (d, J=1.6 Hz, 1H), 7.89 (d, J=1.5 Hz, 1H), 7.46 (t, J=2.1 Hz, 1H), 7.11 (dd, J=4.5, 1.6 Hz, 1H), 6.45 (dd, J=4.4, 2.4 Hz, 1H), 4.17-4.10 (m, 2H), 3.79 (dd, J=10.4, 3.6 Hz, 1H), 3.47 (t, J=8.4 Hz, 1H), 3.34 (t, J=9.7 Hz, 2H), 2.17-1.76 (m, 8H), 1.66 (m, 3H), 1.53-1.12 (m, 3H); MS (ES+): 448.2 (M+1); MS(ES−): 446.2 (M−1). HPLC purity 97.62%.

Scheme 453

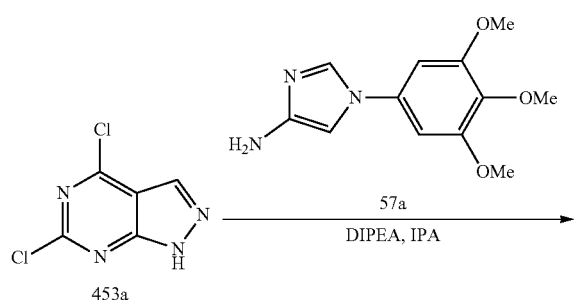

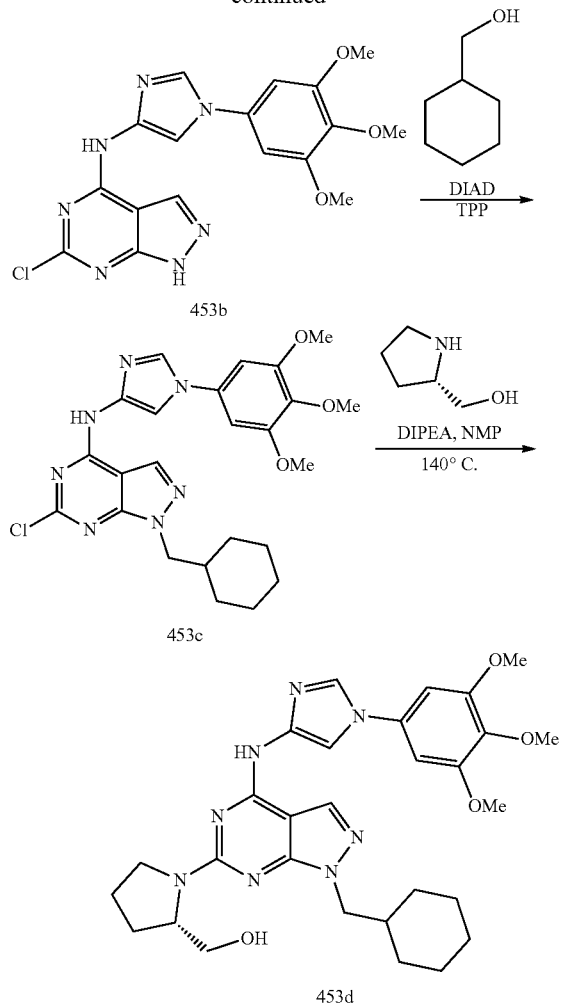

Preparation of (S)-(1-(1-(cyclohexylmethyl)-4-((1-(3,4,5-trimethoxyphenyl)-1H-imidazol-4-yl)amino)-1H-pyrazolo[3,4-d]pyrimidin-6-yl)pyrrolidin-2-yl)methanol (453d)

Step-1: Preparation of 6-chloro-N-(1-(3,4,5-trimethoxyphenyl)-1H-imidazol-4-yl)-1H-pyrazolo[3,4-d]pyrimidin-4-amine (453b)

Compound 453b was prepared from 4,6-dichloro-1H-pyrazolo[3,4-d]pyrimidine (453a) (455 mg, 2.41 mmol) in 2-Propanol (20 mL) using DIPEA (1.26 mL, 7.22 mmol), 1-(3,4,5-trimethoxyphenyl)-1H-imidazol-4-amine (57a) (600 mg, 2.41 mmol) and heating at reflux for 3 h according to the procedure reported in step-1 of scheme 183. This gave after workup and filtration 6-chloro-N-(1-(3,4,5-trimethoxyphenyl)-1H-imidazol-4-yl)-1H-pyrazolo[3,4-d]pyrimidin-4-amine (453b) (900 mg, 93% yield) as a yellow solid; MS (ES+): 402.1 (M+1).

Step-2: Preparation of 6-chloro-1-(cyclohexylmethyl)-N-(1-(3,4,5-trimethoxyphenyl)-1H-imidazol-4-yl)-1H-pyrazolo[3,4-d]pyrimidin-4-amine (453c)

Compound 453c was prepared from 6-chloro-N-(1-(3,4,5-trimethoxyphenyl)-1H-imidazol-4-yl)-1H-pyrazolo[3,4- d]pyrimidin-4-amine (453b) (300 mg, 0.75 mmol) in THF using triphenylphosphine (490 mg, 1.87 mmol), cyclohexylmethanol (213 mg, 1.87 mmol) and DIAD (0.36 mL, 1.87 mmol) according to the procedure reported in step-2 of scheme 435. This gave after workup and purification by flash column chromatography [silica (12 g), eluting with EtOAc in hexane from 0-60%] 6-chloro-1-(cyclohexylmethyl)-N-(1-(3,4,5-trimethoxyphenyl)-1H-imidazol-4-yl)-1H-pyrazolo[3,4-d]pyrimidin-4-amine (453c) (200 mg, 54% yield) as a white solid; MS (ES+): 498.2 (M+1).

Step-3: Preparation of (S)-(1-(1-(cyclohexylmethyl)-4-((1-(3,4,5-trimethoxyphenyl)-1H-imidazol-4-yl)amino)-1H-pyrazolo[3,4-d]pyrimidin-6-yl)pyrrolidin-2-yl)methanol (453d)

Compound 453d was prepared from 6-chloro-1-(cyclohexylmethyl)-N-(1-(3,4,5-trimethoxyphenyl)-1H-imidazol-4-yl)-1H-pyrazolo[3,4-d]pyrimidin-4-amine (453c) ((200 mg, 0.40 mmol), (S)-pyrrolidin-2-ylmethanol (61 mg, 0.60 mmol), N-ethyl-N-isopropylpropan-2-amine (0.21 mL, 1.21 mmol) in NMP (3 mL) and heating at 140° C. for 50 mins on a microwave reactor according to the procedure reported in scheme 2. This gave after workup and purification by reverse phase prep HPLC [C18 steel column, 250 mm×30 mm, eluting with ACN in water (containing 0.1% TFA) from 0-100%] (S)-(1-(1-(cyclohexylmethyl)-4-((1-(3,4,5-trimethoxyphenyl)-1H-imidazol-4-yl)amino)-1H-pyrazolo[3,4-d]pyrimidin-6-yl)pyrrolidin-2-yl)methanol (453d) (35 mg, 15% yield) TFA salt as a white solid; $^1$H NMR (300 MHz, DMSO-$d_6$) δ 10.86-10.52 (m, 1H, D$_2$O exchangeable), 8.35 (d, J=1.5 Hz, 1H), 8.17 (s, 1H), 8.09-7.90 (m, 1H), 6.97 (s, 2H), 4.38-4.15 (m, 2H), 4.00 (d, J=7.0 Hz, 2H), 3.88 (s, 6H), 3.82-3.72 (m, 2H), 3.69 (s, 3H), 3.62-3.30 (m, 2H), 2.08-1.82 (m, 5H), 1.71-1.45 (m, 5H), 1.27-1.07 (m, 3H), 1.05-0.89 (m, 2H); $^{19}$F NMR (282 MHz, DMSO-$d_6$) δ −74.47 (from TFA salt); MS (ES+): 563.3 (M+1); (ES−): 561.3 (M−1).

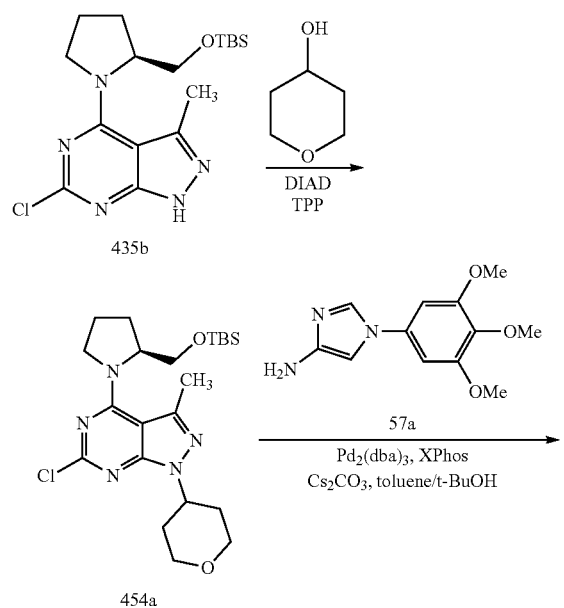

Scheme 454

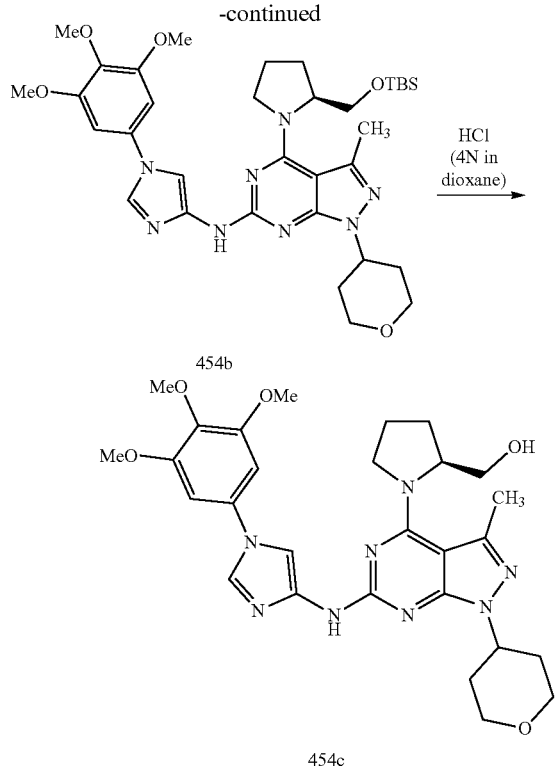

Preparation of (S)-(1-(3-methyl-1-(tetrahydro-2H-pyran-4-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (454c)

Step-1: Preparation of (S)-4-(2-(((tert-butyldimethylsilyl)oxy)methyl)pyrrolidin-1-yl)-6-chloro-3-methyl-1-(tetrahydro-2H-pyran-4-yl)-1H-pyrazolo[3,4-d]pyrimidine (454a)

Compound 454a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF using triphenylphosphine (515 mg, 1.96 mmol), tetrahydro-2H-pyran-4-ol (201 mg, 1.96 mmol), DIAD (0.38 mL, 1.96 mmol) and stirring at room temperature for 5 days according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-3-methyl-1-(tetrahydro-2H-pyran-4-yl)-1H-pyrazolo[3,4-d]pyrimidine (454a) (300 mg, 82% yield) as a clear oil; MS (ES+): 466.2 (M+1).

Step-2: Preparation of (S)-4-(2-(((tert-butyldimethylsilyl)oxy)methyl)pyrrolidin-1-yl)-3-methyl-1-(tetrahydro-2H-pyran-4-yl)-N-(1-(3,4,5-trimethoxyphenyl)-1H-imidazol-4-yl)-1H-pyrazolo[3,4-d]pyrimidin-6-amine (454b)

Compound 454b was prepared from (S)-4-(2-(((tert-butyldimethylsilyl)oxy)methyl)pyrrolidin-1-yl)-6-chloro-3-methyl-1-(tetrahydro-2H-pyran-4-yl)-1H-pyrazolo[3,4-d]pyrimidine (454a) (300 mg, 0.64 mmol), 1-(3,4,5- trimethoxyphenyl)-1H-imidazol-4-amine (57a) (193 mg, 0.78 mmol), dicyclohexyl(2',4',6'-triisopropylbiphenyl-2-yl)phosphine (XPhos, 123 mg, 0.26 mmol), cesium carbonate (737 mg, 2.26 mmol), $Pd_2(dba)_3$ (118 mg, 0.13 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA80 in DCM from 0-50%] (S)-4-(2-(((tert-butyldimethylsilyl)oxy)methyl)pyrrolidin-1-yl)-3-methyl-1-(tetrahydro-2H-pyran-4-yl)-N-(1-(3,4,5-trimethoxyphenyl)-1H-imidazol-4-yl)-1H-pyrazolo[3,4-d]pyrimidin-6-amine (454b) as a white solid; MS (ES+): 679.3 (M+1).

Step-3: Preparation of (S)-(1-(3-methyl-1-(tetrahydro-2H-pyran-4-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (454c)

A solution of (S)-4-(2-(((tert-butyldimethylsilyl)oxy)methyl)pyrrolidin-1-yl)-3-methyl-1-(tetrahydro-2H-pyran-4-yl)-N-(1-(3,4,5-trimethoxyphenyl)-1H-imidazol-4-yl)-1H-pyrazolo[3,4-d]pyrimidin-6-amine (454b) (from step-2 above) in MeOH/DCM (10 mL) was added 4N HCl in dioxane (0.16 mL, 0.64 mmol), stirred at room temperature for 20 min and concentrated in vacuum. The residue obtained was purified by reverse phase column chromatography [C18 steel column, eluting with ACN in water (containing 0.1% HCl) from 0-100%] (S)-(1-(3-methyl-1-(tetrahydro-2H-pyran-4-yl)-6-((1-(3,4,5-trimethoxyphenyl)-1H-imidazol-4-yl)amino)-1H-pyrazolo[3,4-d]pyrimidin-4-yl)pyrrolidin-2-yl)methanol (454c) (34 mg, 10% yield) HCl salt as a yellow solid; $^1H$ NMR (300 MHz, DMSO-$d_6$) δ 10.21 (s, 1H, $D_2O$ exchangeable), 9.10 (s, 1H), 7.88 (d, J=1.7 Hz, 1H, $D_2O$ exchangeable), 7.13 (s, 2H), 4.86-4.75 (m, 2H), 4.71-4.65 (m, 2H), 4.02-3.96 (m, 2H), 3.90 (s, 6H), 3.87-3.77 (m, 2H), 3.70 (s, 3H), 3.66-3.55 (m, 2H), 3.52-3.43 (m, 2H), 2.56 (s, 3H), 2.15-1.94 (m, 6H), 1.86-1.77 (m, 2H); MS (ES+): 565.3 (M+1); HPLC purity: 96.22%.

Scheme 455

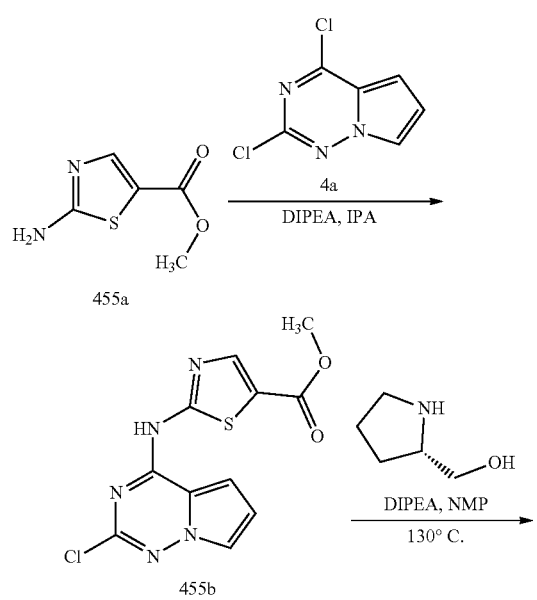

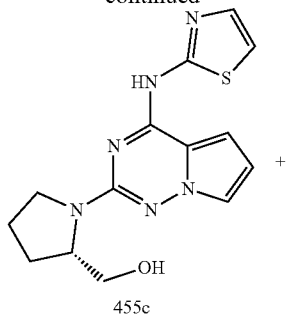

455c

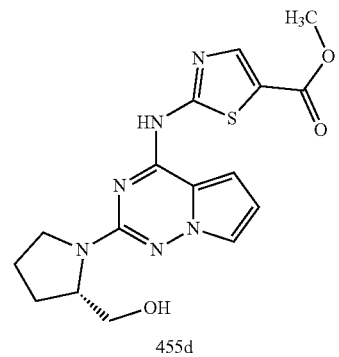

455d

Preparation of (S)-(1-(4-(thiazol-2-ylamino)pyrrolo[2,1-f][1,2,4]triazin-2-yl)pyrrolidin-2-yl)methanol (455c) and (S)-methyl 2-((2-(2-(hydroxymethyl)pyrrolidin-1-yl)pyrrolo[2,1-f][1,2,4]triazin-4-yl)amino)thiazole-5-carboxylate (455d)

Step-1: Preparation of methyl 2-((2-chloropyrrolo[2,1-f][1,2,4]triazin-4-yl)amino)thiazole-5-carboxylate (455b)

Compound 455b was prepared from 2,4-dichloropyrrolo[2,1-f][1,2,4]triazine (4a) (1.19 g, 6.32 mmol) in 2-Propanol (30 mL) using DIPEA (3.31 mL, 18.97 mmol), methyl 2-aminothiazole-5-carboxylate (455a) (1 g, 6.32 mmol; CAS #6633-61-0) and heating at 90° C. for 4 h according to the procedure reported in step-1 of scheme 183. This gave after workup and filtration methyl 2-((2-chloropyrrolo[2,1-f][1,2,4]triazin-4-yl)amino)thiazole-5-carboxylate (455b) (0.75 g, 38% yield) as a yellow solid; MS (ES-): 308.0 (M-1).

Step-2: Preparation of (S)-(1-(4-(thiazol-2-ylamino)pyrrolo[2,1-f][1,2,4]triazin-2-yl)pyrrolidin-2-yl)methanol (455c) and (S)-methyl 2-((2-(2-(hydroxymethyl)pyrrolidin-1-yl)pyrrolo[2,1-f][1,2,4]triazin-4-yl)amino)thiazole-5-carboxylate (455d)

Compounds 455c and 455d were prepared from methyl 2-((2-chloropyrrolo[2,1-f][1,2,4]triazin-4-yl)amino)thiazole-5-carboxylate (455b) (0.2 g, 0.65 mmol), (S)-pyrrolidin-2-ylmethanol (0.19 mL, 1.937 mmol), N-ethyl-N-isopropylpropan-2-amine (0.34 mL, 1.94 mmol) in NMP (3 mL) and heating at 130° C. for 60 mins according to the procedure reported in scheme 2. This gave after workup and purification by flash column chromatography [silica (12 g), eluting with MeOH in DCM from 0-20%] followed by reverse phase column chromatography [C18 (50 g), eluting with ACN in water (containing 0.1% HCl) from 0-100%] (S)-

(1-(4-(thiazol-2-ylamino)pyrrolo[2,1-f][1,2,4]triazin-2-yl)pyrrolidin-2-yl)methanol (455c) (10 mg, 5% yield) HCl salt as a yellow solid and (S)-methyl 2-((2-(2-(hydroxymethyl)pyrrolidin-1-yl)pyrrolo[2,1-f][1,2,4]triazin-4-yl)amino)thiazole-5-carboxylate (455d) (11 mg, 5% yield) HCl salt as a yellow solid; Data for Compound 455c: H NMR (300 MHz, DMSO-d$_6$) δ 12.24 (s, 1H), 7.55 (d, J=3.6 Hz, 1H), 7.51 (dd, J=2.4, 1.6 Hz, 1H), 7.28 (d, J=3.6 Hz, 1H), 7.19 (dd, J=4.5, 1.6 Hz, 1H), 6.48 (dd, J=4.5, 2.4 Hz, 1H), 4.30-4.13 (m, 1H), 3.72 (dd, J=10.2, 3.5 Hz, 1H), 3.58 (d, J=7.7 Hz, 1H), 3.54-3.43 (m, 1H), 3.36 (dd, J=10.2, 8.1 Hz, 1H), 2.11-1.86 (m, 4H); MS (ES+): 317.1 (M+1); MS (ES−): 315.1 (M−1); HPLC purity: 97.33%. Data for Compound 455d: $^1$H NMR (300 MHz, DMSO-d$_6$) δ 12.69 (s, 1H), 8.22 (s, 1H), 7.58 (dd, J=2.4, 1.6 Hz, 1H), 7.23 (dd, J=4.5, 1.6 Hz, 1H), 6.53 (dd, J=4.6, 2.4 Hz, 1H), 4.25-4.13 (m, 1H), 3.81 (s, 3H), 3.66 (dd, J=10.3, 3.3 Hz, 2H), 3.50 (td, J=11.7, 10.3, 6.6 Hz, 2H), 2.18-1.77 (m, 4H). MS (ES+): 375.1 (M+1); MS (ES−): 373.1 (M−1); HPLC purity: 92.43%.

Scheme 456

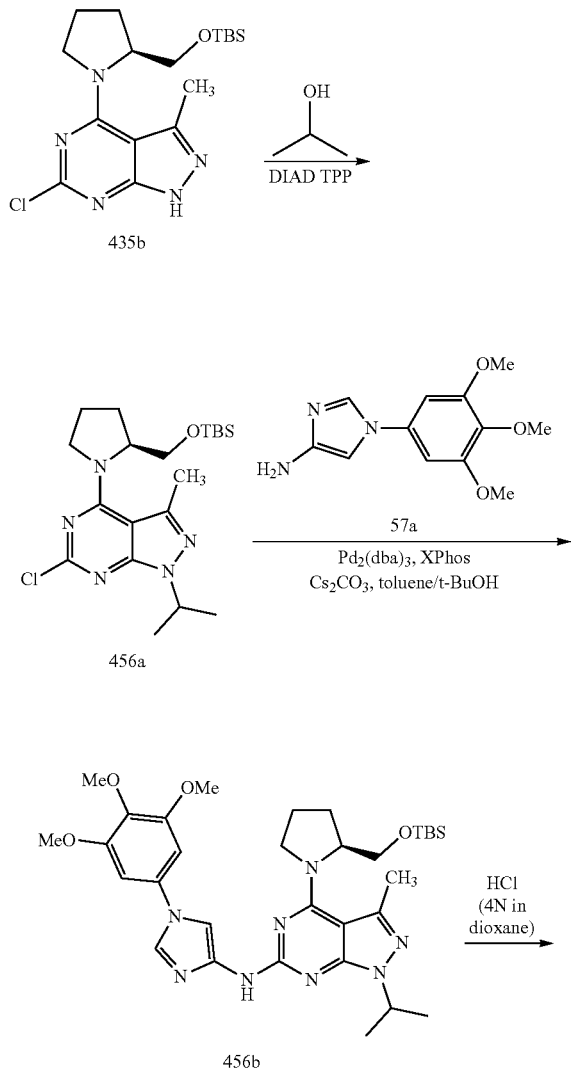

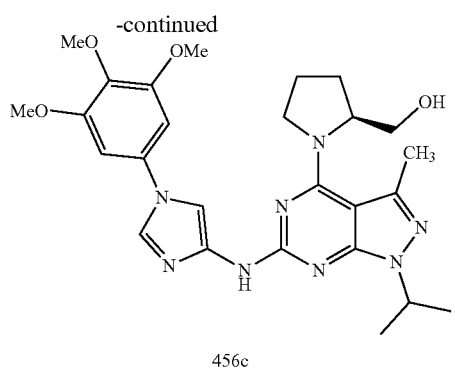

Preparation of (S)-(1-(1-isopropyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (456c)

Step-1: Preparation of (S)-4-(2-(((tert-butyldimethylsilyl)oxy)methyl)pyrrolidin-1-yl)-6-chloro-1-isopropyl-3-methyl-1H-pyrazolo[3,4-d]pyrimidine (456a)

Compound 456a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF (4 mL) using triphenylphosphine (515 mg, 1.96 mmol), propan-2-ol (118 mg, 1.96 mmol), DIAD (0.38 mL, 1.96 mmol) and stirring at room temperature overnight according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-isopropyl-3-methyl-1H-pyrazolo[3,4-d]pyrimidine (456a) (310 mg, 93% yield) as a clear oil; MS (ES+): 424.2 (M+1).

Step-2: Preparation of(S)-4-(2-(((tert-butyldimethylsilyl)oxy)methyl)pyrrolidin-1-yl)-1-isopropyl-3-methyl-N-(1-(3,4,5-trimethoxyphenyl)-1H-imidazol-4-yl)-1H-pyrazolo[3,4-d]pyrimidin-6-amine (456b)

Compound 456b was prepared from (S)-4-(2-(((tert-butyldimethylsilyl)oxy)methyl)pyrrolidin-1-yl)-6-chloro-1-isopropyl-3-methyl-1H-pyrazolo[3,4-d]pyrimidine (456a) (310 mg, 0.73 mmol), 1-(3,4,5-trimethoxyphenyl)-1H-imidazol-4-amine (57a) (219 mg, 0.88 mmol), dicyclohexyl(2',4',6'-triisopropylbiphenyl-2-yl)phosphine (XPhos, 139 mg, 0.29 mmol), cesium carbonate (834 mg, 2.56 mmol), Pd$_2$(dba)$_3$ (134 mg, 0.15 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA80 in DCM from 0-50%] (S)-4-(2-(((tert-butyldimethylsilyl)oxy)methyl)pyrrolidin-1-yl)-1-isopropyl-3-methyl-N-(1-(3,4,5-trimethoxyphenyl)-1H-imidazol-4-yl)-1H-pyrazolo[3,4-d]pyrimidin-6-amine (456b) as a white solid; MS (ES+): 637.4 (M+1).

Step-3: Preparation of (S)-(1-(1-isopropyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (456c)

To a solution of (S)-4-(2-(((tert-butyldimethylsilyl)oxy)methyl)pyrrolidin-1-yl)-1-isopropyl-3-methyl-N-(1-(3,4,5- trimethoxyphenyl)-1H-imidazol-4-yl)-1H-pyrazolo[3,4-d]pyrimidin-6-amine (456b) (from step-2 above) in MeOH/DCM (10 mL) was added 4N HCl in dioxane (1.83 mL, 7.31 mmol), stirred at room temperature for 20 min and concentrated in vacuum. The residue obtained was purified by reverse phase column chromatography [C18 steel column, eluting with ACN in water (containing 0.1% HCl) from 0-100%] to give (S)-(1-(1-isopropyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (456c) (115 mg, 30% yield) HCl salt as a white solid; $^1$H NMR (300 MHz, DMSO-$d_6$) δ 10.13 (s, 1H, $D_2O$ exchangeable), 9.01 (s, 1H), 7.86 (d, J=1.7 Hz, 1H), 7.09 (s, 2H), 4.96-4.86 (m, 1H), 4.70-4.61 (m, 1H), 3.89 (s, 6H), 3.87-3.78 (m, 2H), 3.70 (s, 3H), 3.67-3.52 (m, 2H), 2.55 (s, 3H), 2.13-1.87 (m, 4H), 1.45-1.38 (m, 6H); MS (ES+): 523.3 (M+1); (ES-): 557.1 (M+Cl); HPLC purity; 99.14%.

Scheme 457

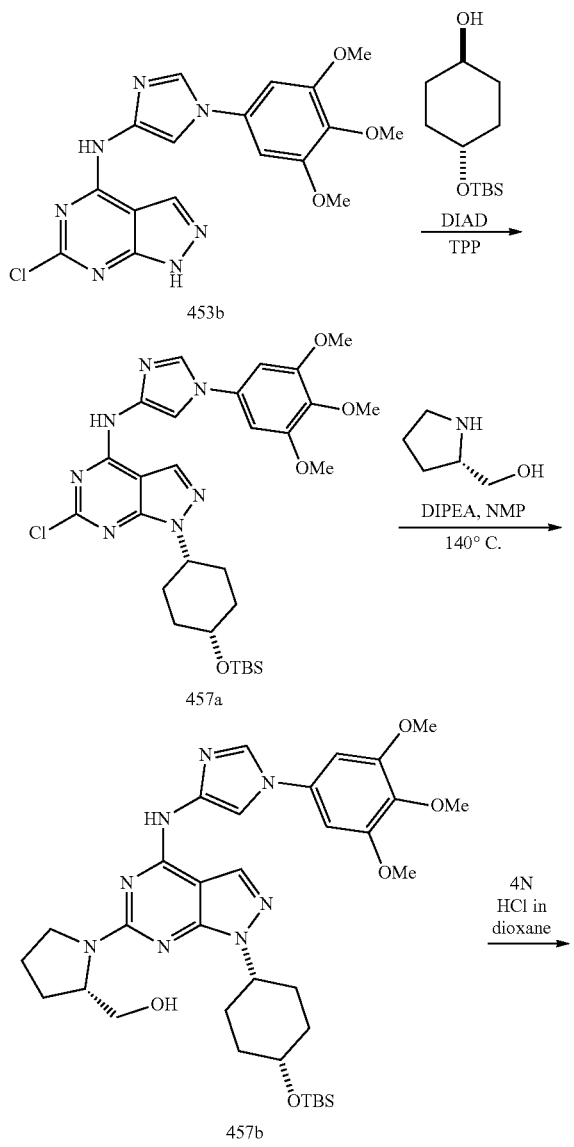

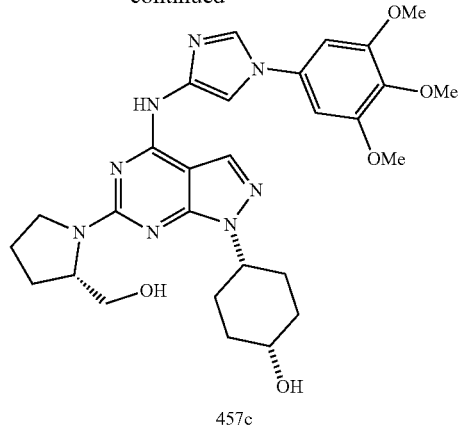

Preparation of (cis)-4-(6-((S)-2-(hydroxymethyl)pyrrolidin-1-yl)-4-((1-(3,4,5-trimethoxyphenyl)-1H-imidazol-4-yl)amino)-1H-pyrazolo[3,4-d]pyrimidin-1-yl)cyclohexanol (457c)

Step-1: Preparation of 1-((cis)-4-((tert-butyldimethylsilyl)oxy)cyclohexyl)-6-chloro-N-(1-(3,4,5-trimethoxyphenyl)-1H-imidazol-4-yl)-1H-pyrazolo[3,4-d]pyrimidin-4-amine (457a)

Compound 457a was prepared from 6-chloro-N-(1-(3,4,5-trimethoxyphenyl)-1H-imidazol-4-yl)-1H-pyrazolo[3,4-d]pyrimidin-4-amine (453b) (300 mg, 0.75 mmol) in THF using triphenylphosphine (587 mg, 2.24 mmol), (trans)-4-(tert-butyldimethylsilyloxy)cyclohexanol (516 mg, 2.24 mmol) and DIAD (0.44 mL, 2.24 mmol) according to the procedure reported in step-2 of scheme 435. This gave after workup and purification by flash column chromatography [silica (12 g), eluting with EtOAc in hexane from 0-60%] 1-((cis)-4-((tert-butyldimethylsilyl)oxy)cyclohexyl)-6-chloro-N-(1-(3,4,5-trimethoxyphenyl)-1H-imidazol-4-yl)-1H-pyrazolo[3,4-d]pyrimidin-4-amine (457a) (230 mg, 50% yield) as a yellow solid; MS (ES+): 614.2 (M+1).

Step-2: Preparation of ((S)-1-(1-((cis)-4-((tert-butyldimethylsilyl)oxy)cyclohexyl)-4-((1-(3,4,5-trimethoxyphenyl)-1H-imidazol-4-yl)amino)-1H-pyrazolo[3,4-d]pyrimidin-6-yl)pyrrolidin-2-yl)methanol (457b)

Compound 457b was prepared from 1-((cis)-4-((tert-butyldimethylsilyl)oxy)cyclohexyl)-6-chloro-N-(1-(3,4,5-trimethoxyphenyl)-1H-imidazol-4-yl)-1H-pyrazolo[3,4-d]pyrimidin-4-amine (457a) (230 mg, 0.37 mmol), (S)-pyrrolidin-2-ylmethanol (57 mg, 0.56 mmol), N-ethyl-N-isopropylpropan-2-amine (0.20 mL, 1.12 mmol) in NMP (3 mL) and heating at 140° C. for 50 mins on a microwave reactor according to the procedure reported in scheme 2. This gave after workup and purification by flash column chromatography [silica gel (24 g), eluting with DMA80 in DCM from 0-50%] ((S)-1-(1-((cis)-4-((tert-butyldimethylsilyl)oxy)cyclohexyl)-4-((1-(3,4,5-trimethoxyphenyl)-1H-imidazol-4-yl)amino)-1H-pyrazolo[3,4-d]pyrimidin-6-yl)pyrrolidin-2-yl)methanol (457b) as a white solid; MS (ES+): 679.4 (M+1).

Step-3: Preparation of (cis)-4-(6-((S)-2-(hydroxymethyl)pyrrolidin-1-yl)-4-((1-(3,4,5-trimethoxyphenyl)-1H-imidazol-4-yl)amino)-1H-pyrazolo[3,4-d]pyrimidin-1-yl)cyclohexanol (457c)

To a solution of ((S)-1-(1-((cis)-4-((tert-butyldimethylsilyl)oxy)cyclohexyl)-4-((1-(3,4,5-trimethoxyphenyl)-1H-imidazol-4-yl)amino)-1H-pyrazolo[3,4-d]pyrimidin-6-yl)pyrrolidin-2-yl)methanol (457b) (from step-2 above) in MeOH/DCM (10 mL) was added 4N HCl in dioxane (0.11 mL, 3.74 mmol), stirred at room temperature for 30 min and concentrated in vacuum. The residue obtained was purified by reverse phase column chromatography [C18 steel column, 250 mm×30 mm, eluting with ACN in water (containing 0.1% HCl) from 0-100%] to give (cis)-4-(6-((S)-2-(hydroxymethyl)pyrrolidin-1-yl)-4-((1-(3,4,5-trimethoxyphenyl)-1H-imidazol-4-yl)amino)-1H-pyrazolo[3,4-d]pyrimidin-1-yl)cyclohexanol (457c) (145 mg, 69% yield) HCl salt as a white solid; $^1$H NMR (300 MHz, DMSO-$d_6$) δ 11.92-11.23 (m, 1H, $D_2O$ exchangeable), 8.67 (s, 1H), 8.29 (s, 1H), 7.99 (s, 1H), 7.03 (s, 2H), 4.97 (s, 2H, $D_2O$ exchangeable), 4.65-4.51 (m, 1H), 4.44-4.28 (m, 1H), 3.89 (s, 6H), 3.81-3.66 (m, 6H), 3.64-3.35 (m, 2H), 2.39-2.20 (m, 2H), 2.08-1.89 (m, 4H), 1.85-1.73 (m, 2H), 1.68-1.53 (m, 4H); MS (ES+): 565.3 (M+1); (ES−): 563.3 (M−1); HPLC purity: 98.26%.

Scheme 458

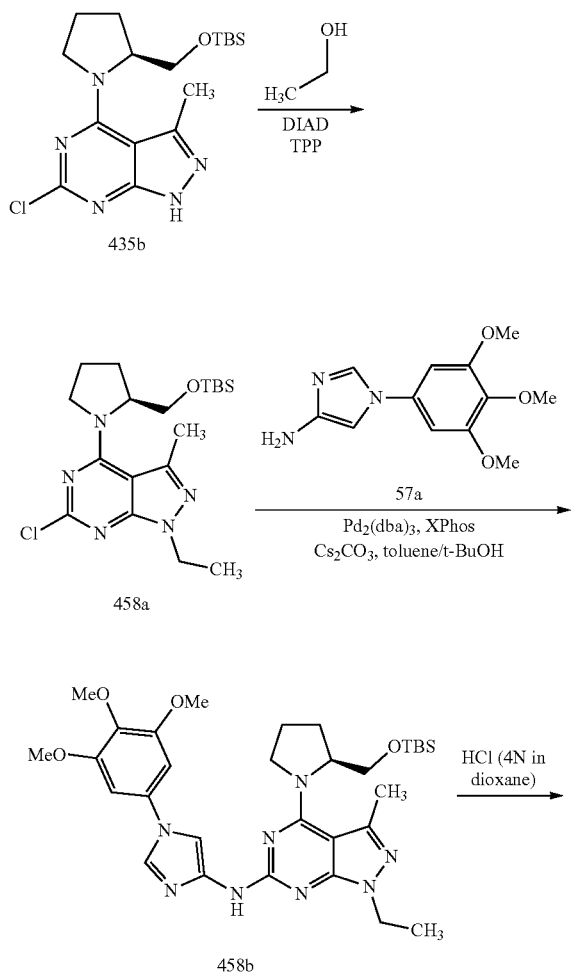

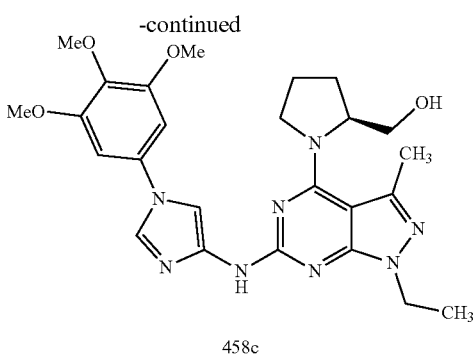

458c

Preparation of (S)-(1-(1-ethyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (458c)

Step-1: Preparation of (S)-4-(2-(((tert-butyldimethylsilyl)oxy)methyl)pyrrolidin-1-yl)-6-chloro-1-ethyl-3-methyl-1H-pyrazolo[3,4-d]pyrimidine (458a)

Compound 458a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF (4 mL) using triphenylphosphine (515 mg, 1.96 mmol), ethanol (90 mg, 1.96 mmol), DIAD (0.38 mL, 1.96 mmol) and stirring at room temperature overnight according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-ethyl-3-methyl-1H-pyrazolo[3,4-d]pyrimidine (458a) (300 mg, 93% yield) as a clear oil; MS (ES+): 410.2 (M+1).

Step-2: Preparation of (S)-4-(2-(((tert-butyldimethylsilyl)oxy)methyl)pyrrolidin-1-yl)-1-ethyl-3-methyl-N-(1-(3,4,5-trimethoxyphenyl)-1H-imidazol-4-yl)-1H-pyrazolo[3,4-d]pyrimidin-6-amine (458b)

Compound 458b was prepared from (S)-4-(2-(((tert-butyldimethylsilyl)oxy)methyl)pyrrolidin-1-yl)-6-chloro-1-ethyl-3-methyl-1H-pyrazolo[3,4-d]pyrimidine (458a) (300 mg, 0.73 mmol), 1-(3,4,5-trimethoxyphenyl)-1H-imidazol-4-amine (57a) (219 mg, 0.88 mmol), dicyclohexyl(2',4',6'-triisopropylbiphenyl-2-yl)phosphine (XPhos, 140 mg, 0.29 mmol), cesium carbonate (834 mg, 2.56 mmol), $Pd_2(dba)_3$ (134 mg, 0.15 mmol) in t-BuOH/toluene (25 mL, 4:1) and heating at 110° C. for 12 h according to the procedure reported in step-3 of scheme 101. This gave after workup and purification by flash column chromatography [silica gel (24 g), eluting with DMA80 in DCM from 0-50%] (S)-4-(2-(((tert-butyldimethylsilyl)oxy)methyl)pyrrolidin-1-yl)-1-ethyl-3-methyl-N-(1-(3,4,5-trimethoxyphenyl)-1H-imidazol-4-yl)-1H-pyrazolo[3,4-d]pyrimidin-6-amine (458b); MS (ES+): 623.3 (M+1).

Step-3: Preparation of (S)-(1-(1-ethyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (458c)

To a solution of (S)-4-(2-(((tert-butyldimethylsilyl)oxy)methyl)pyrrolidin-1-yl)-1-ethyl-3-methyl-N-(1-(3,4,5- trimethoxyphenyl)-1H-imidazol-4-yl)-1H-pyrazolo[3,4-d] pyrimidin-6-amine (458b) (from step-2 above) in MeOH/DCM (10 mL) was added 4N HCl in dioxane (1.83 mL, 7.31 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (S)-(1-(1-ethyl-3-methyl-6-((1-(3,4,5-trimethoxyphenyl)-1H-imidazol-4-yl)amino)-1H-pyrazolo [3,4-d]pyrimidin-4-yl)pyrrolidin-2-yl)methanol (458c) (78 mg, 21% yield) HCl salt as a white solid; $^1$H NMR (300 MHz, DMSO-$d_6$) δ 10.14 (s, 1H, D$_2$O exchangeable), 9.02 (s, 1H), 7.87 (d, J=1.8 Hz, 1H), 7.09 (s, 2H), 4.70-4.61 (m, 1H), 4.22 (q, J=7.2 Hz, 2H), 3.92-3.85 (m, 8H), 3.85-3.77 (m, 2H), 3.70 (s, 3H), 3.68-3.60 (m, 1H), 3.59-3.49 (m, 1H), 2.54 (s, 3H), 2.11-1.91 (m, 4H), 1.33 (t, J=7.2 Hz, 3H); MS (ES+): 509.3 (M+1); HPLC Purity: 97.14%.

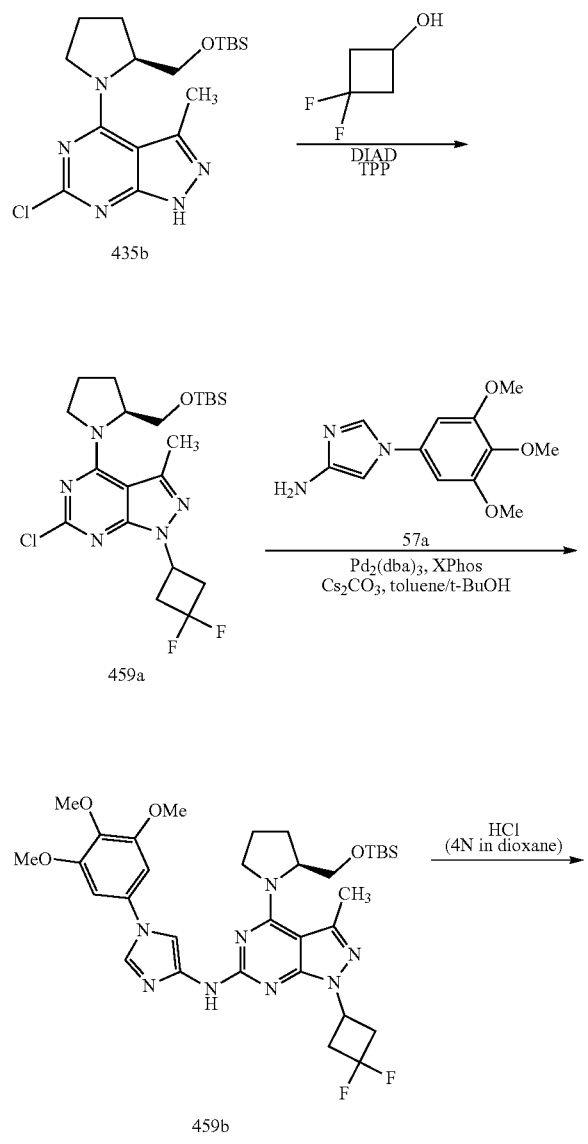

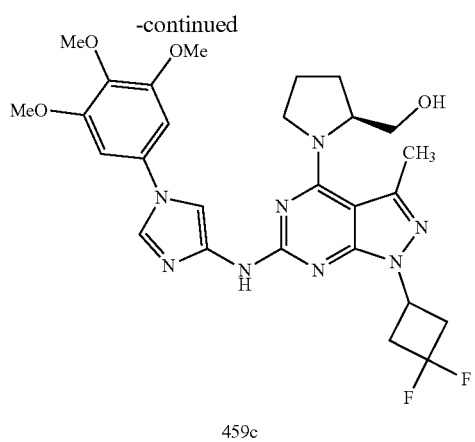

Preparation of (S)-(1-(1-(3,3-difluorocyclobutyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (459c)

Step-1: Preparation of (S)-4-(2-(((tert-butyldimethylsilyl)oxy)methyl)pyrrolidin-1-yl)-6-chloro-1-(3,3-difluorocyclobutyl)-3-methyl-1H-pyrazolo[3,4-d] pyrimidine (459a)

Compound 459a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF (4 mL) using triphenylphosphine (515 mg, 1.96 mmol), 3,3-difluorocyclobutanol (212 mg, 1.96 mmol), DIAD (0.38 mL, 1.96 mmol) and stirring at room temperature overnight according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-(3,3-difluorocyclobutyl)-3-methyl-1H-pyrazolo[3,4-d]pyrimidine (459a) (180 mg, 49% yield) as a clear oil; MS (ES+): 472.1 (M+1).

Step-2: Preparation of (S)-4-(2-(((tert-butyldimethylsilyl)oxy)methyl)pyrrolidin-1-yl)-1-(3,3-difluorocyclobutyl)-3-methyl-N-(1-(3,4,5-trimethoxyphenyl)-1H-imidazol-4-yl)-1H-pyrazolo[3,4-d] pyrimidin-6-amine (459b)

Compound 459b was prepared from (S)-4-(2-(((tert-butyldimethylsilyl)oxy)methyl)pyrrolidin-1-yl)-6-chloro-1-(3,3-difluorocyclobutyl)-3-methyl-1H-pyrazolo[3,4-d]pyrimidine (459a) (180 mg, 0.38 mmol), 1-(3,4,5-trimethoxyphenyl)-1H-imidazol-4-amine (57a) (114 mg, 0.46 mmol), dicyclohexyl(2',4',6'-triisopropylbiphenyl-2-yl) phosphine (XPhos, 73 mg, 0.15 mmol), cesium carbonate (435 mg, 1.34 mmol), Pd$_2$(dba)$_3$ (70 mg, 0.076 mmol) in t-BuOH/toluene (11 mL, 2.67:1) and heating at 110° C. for 12 h according to the procedure reported in step-3 of scheme 101. This gave after workup and purification by flash column chromatography [silica gel (24 g), eluting with DMA80 in DCM from 0-50%] (S)-4-(2-(((tert-butyldimethylsilyl)oxy)methyl)pyrrolidin-1-yl)-1-(3,3-difluorocyclobutyl)-3-methyl-N-(1-(3,4,5-trimethoxyphenyl)-1H-imidazol-4-yl)-1H-pyrazolo[3,4-d]pyrimidin-6-amine (459b); MS (ES+): 685.3 (M+1).

Step-3: Preparation of (S)-(1-(1-(3,3-difluorocyclobutyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (459c)

To a solution of (S)-4-(2-(((tert-butyldimethylsilyl)oxy)methyl)pyrrolidin-1-yl)-1-(3,3-difluorocyclobutyl)-3-methyl-N-(1-(3,4,5-trimethoxyphenyl)-1H-imidazol-4-yl)-1H-pyrazolo[3,4-d]pyrimidin-6-amine (459b) (from step-2 above) in MeOH/DCM (5 mL) was added 4N HCl in dioxane (0.953 mL, 3.81 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (S)-(1-(1-(3,3-difluorocyclobutyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (459c) (51 mg, 23% yield) HCl salt as a white solid; $^1$H NMR (300 MHz, DMSO-$d_6$) δ 10.04 (s, 1H, $D_2O$ exchangeable), 9.15 (s, 1H), 7.96 (s, 1H, $D_2O$ exchangeable), 7.13 (s, 2H), 5.28-5.15 (m, 1H), 4.69-4.58 (m, 1H), 3.90 (s, 6H), 3.86-3.75 (m, 2H), 3.71 (s, 3H), 3.67-3.59 (m, 1H), 3.59-3.50 (m, 1H), 3.26-3.10 (m, 4H), 2.58 (s, 3H), 2.09-1.87 (m, 4H); $^{19}$F NMR: (282 MHz, DMSO-$d_6$, Two pairs peaks were observed) δ −81.77, −82.47, −97.52, −98.21; MS (ES+): 571.3 (M+1); (ES−): 605.2 (M+Cl); HPLC purity: 99.71%.

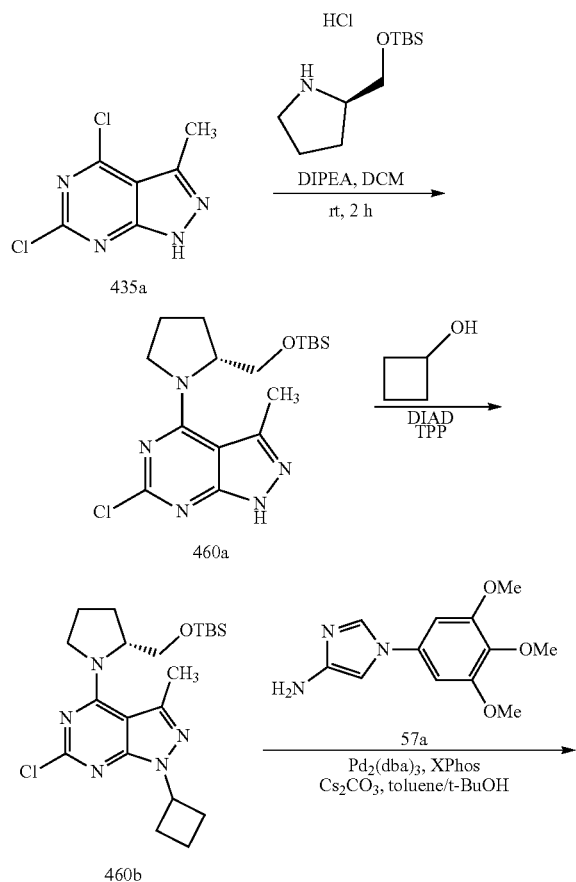

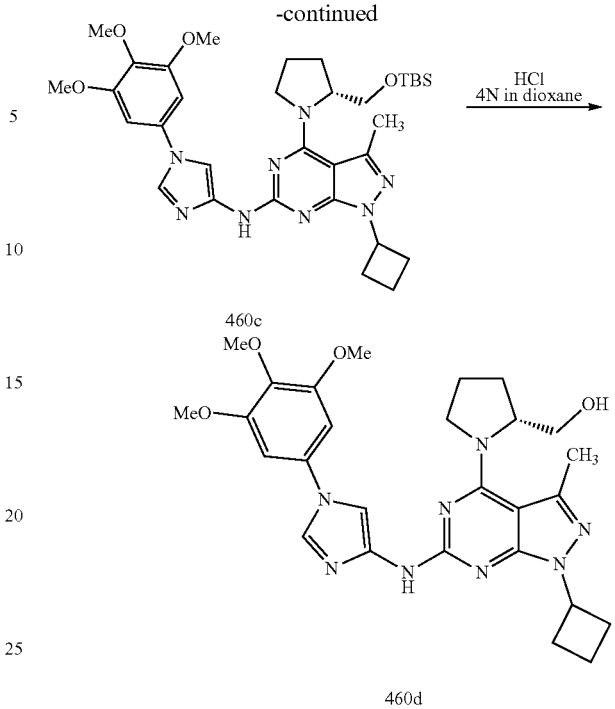

Preparation of (R)-(1-(1-cyclobutyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (460d)

Step-1: Preparation of (R)-4-(2-(((tert-butyldimethylsilyl)oxy)methyl)pyrrolidin-1-yl)-6-chloro-3-methyl-1H-pyrazolo[3,4-d]pyrimidine (460a)

Compound 460a was prepared from 4,6-dichloro-3-methyl-1H-pyrazolo[3,4-d]pyrimidine (435a) (lg, 4.93 mmol) in DCM (25 mL) using (R)-2-((tert-butyldimethylsilyloxy)methyl)pyrrolidine hydrochloride (1.24 g, 4.93 mmol; CAS #474774-33-9), DIPEA (2.58 mL, 14.78 mmol) and stirring at room temperature for 3 h according to the procedure reported in step-1 of scheme 96. This gave after workup and purification by flash column chromatography [silica (24 g), eluting with EtOAc in hexane from 0-70%] (R)-4-(2-(((tert-butyldimethylsilyl)oxy)methyl)pyrrolidin-1-yl)-6-chloro-3-methyl-1H-pyrazolo[3,4-d]pyrimidine (460a) (1.5 g, 80% yield) as a white solid; MS (ES+): 382.1 (M+1).

Step-2: Preparation of (R)-4-(2-(((tert-butyldimethylsilyl)oxy)methyl)pyrrolidin-1-yl)-6-chloro-1-cyclobutyl-3-methyl-1H-pyrazolo[3,4-d]pyrimidine (460b)

Compound 460b was prepared from (R)-4-(2-(((tert-butyldimethylsilyl)oxy)methyl)pyrrolidin-1-yl)-6-chloro-3-methyl-1H-pyrazolo[3,4-d]pyrimidine (460a) (350 mg, 0.92 mmol) in THF (4 mL) using triphenylphosphine (601 mg, 2.29 mmol), cyclobutanol (165 mg, 2.29 mmol), DIAD (0.445 mL, 2.29 mmol) and stirring at room temperature overnight according to the procedure reported in step-2 of scheme 435. This gave after workup and purification by flash column chromatography [silica (12 g), eluting with EtOAc in hexane from 0-60%] (R)-4-(2-(((tert-butyldimethylsilyl)oxy)methyl)pyrrolidin-1-yl)-6-chloro-1-cyclobutyl-3-methyl-1H-pyrazolo[3,4-d]pyrimidine (460b) (350 mg, 88% yield) as a clear oil; MS (ES+): 436.2 (M+1).

Step-3: Preparation of (R)-4-(2-(((tert-butyldimethylsilyl)oxy)methyl)pyrrolidin-1-yl)-1-cyclobutyl-3-methyl-N-(1-(3,4,5-trimethoxyphenyl)-1H-imidazol-4-yl)-1H-pyrazolo[3,4-d]pyrimidin-6-amine (460c)

Compound 460c was prepared from (R)-4-(2-(((tert-butyldimethylsilyl)oxy)methyl)pyrrolidin-1-yl)-6-chloro-1-cyclobutyl-3-methyl-1H-pyrazolo[3,4-d]pyrimidine (460b) (350 mg, 0.80 mmol), 1-(3,4,5-trimethoxyphenyl)-1H-imidazol-4-amine (57a) (240 mg, 0.96 mmol), dicyclohexyl(2',4',6'-triisopropylbiphenyl-2-yl)phosphine (XPhos, 153 mg, 0.32 mmol), cesium carbonate (915 mg, 2.81 mmol), Pd₂(dba)₃ (147 mg, 0.16 mmol) in t-BuOH/toluene (25 mL, 1:4) and heating at 110° C. for 12 h according to the procedure reported in step-3 of scheme 101. This gave after workup and purification by flash column chromatography [silica gel (24 g), eluting with DMA80 in DCM from 0-50%] (R)-4-(2-(((tert-butyldimethylsilyl)oxy)methyl)pyrrolidin-1-yl)-1-cyclobutyl-3-methyl-N-(1-(3,4,5-trimethoxyphenyl)-1H-imidazol-4-yl)-1H-pyrazolo[3,4-d]pyrimidin-6-amine (460c); MS (ES+): 649.3 (M+1).

Step-4: Preparation of (R)-(1-(1-cyclobutyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (460d)

To a solution of (R)-4-(2-(((tert-butyldimethylsilyl)oxy)methyl)pyrrolidin-1-yl)-1-cyclobutyl-3-methyl-N-(1-(3,4,5-trimethoxyphenyl)-1H-imidazol-4-yl)-1H-pyrazolo[3,4-d]pyrimidin-6-amine (460c) (from step-2 above) in MeOH/DCM (10 mL) was added 4N HCl in dioxane (2.01 mL, 8.03 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (R)-(1-(1-cyclobutyl-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (460d) (85 mg, 20% yield) HCl salt as a yellow solid; ¹H NMR (300 MHz, DMSO-d₆) δ 10.11 (s, 1H, D₂O exchangeable), 9.02 (s, 1H), 7.89 (d, J=1.7 Hz, 1H), 7.10 (s, 2H), 5.26-5.14 (m, 1H), 4.70-4.61 (m, 1H), 3.90 (s, 6H), 3.87-3.75 (m, 2H), 3.70 (s, 3H), 3.68-3.50 (m, 2H), 2.70-2.59 (m, 2H), 2.57 (s, 3H), 2.40-2.29 (m, 2H), 2.11-1.96 (m, 3H), 1.94-1.76 (m, 3H); MS (ES+): 535.3 (M+1); (ES-): 533.2 (M-1).

Scheme 461

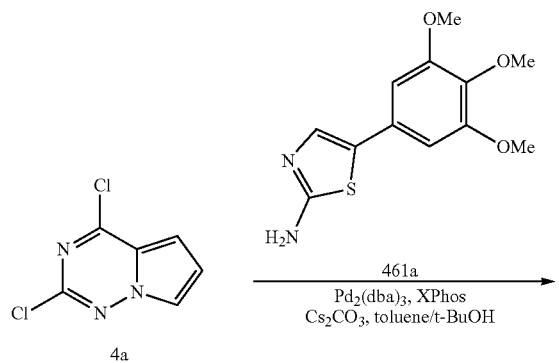

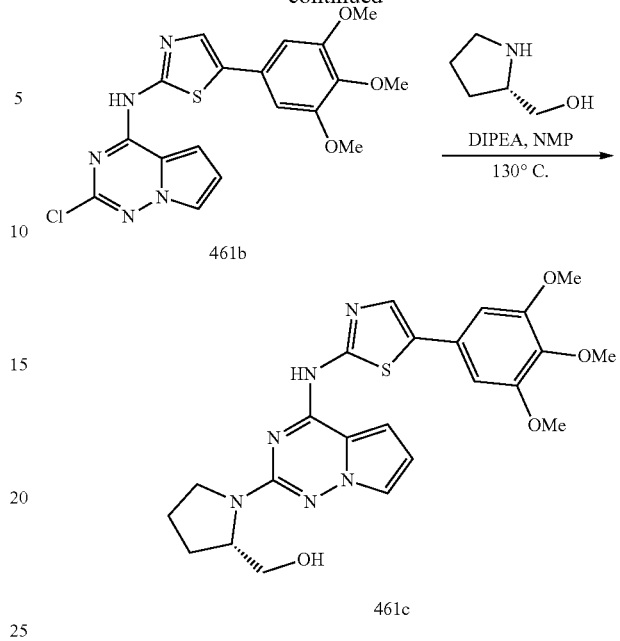

Preparation of (S)-(1-(4-((5-(3,4,5-trimethoxyphenyl)thiazol-2-yl)amino)pyrrolo[2,1-f][1,2,4]triazin-2-yl)pyrrolidin-2-yl)methanol (461c)

Step-1: Preparation of N-(2-chloropyrrolo[2,1-f][1,2,4]triazin-4-yl)-5-(3,4,5-trimethoxyphenyl)thiazol-2-amine (461b)

Compound 461b was prepared from 2,4-dichloropyrrolo[2,1-f][1,2,4]triazine (4a) (70.6 mg, 0.38 mmol), 5-(3,4,5-trimethoxyphenyl)thiazol-2-amine (461a) (50 mg, 0.98 mmol; CAS #1681084-05-8; prepared according to the procedure reported by Chen, Lijuan and Wei, Yuquan in Faming Zhuanli Shenqing, 104418821), dicyclohexyl(2',4',6'-triisopropylbiphenyl-2-yl)phosphine (XPhos, 36 mg, 0.075 mmol), cesium carbonate (214 mg, 0.66 mmol), Pd₂(dba)₃ (34.4 mg, 0.04 mmol) in t-BuOH/toluene (5 mL, 4:1) and heating at 110° C. for 12 h according to the procedure reported in step-3 of scheme 101. This gave after workup and purification by flash column chromatography [silica gel (4 g), eluting with MeOH in DCM from 0-50%] N-(2-chloropyrrolo[2,1-f][1,2,4]triazin-4-yl)-5-(3,4,5-trimethoxyphenyl)thiazol-2-amine (461b) (0.06 g, 70% yield) as a yellow solid; MS (ES+): 418.0, 420.0 (M+1); MS (ES-): 416.0, 418.1 (M-1).

Step-2: Preparation of (S)-(1-(4-((5-(3,4,5-trimethoxyphenyl)thiazol-2-yl)amino)pyrrolo[2,1-f][1,2,4]triazin-2-yl)pyrrolidin-2-yl)methanol (461c)

Compound 461c was prepared from N-(2-chloropyrrolo[2,1-f][1,2,4]triazin-4-yl)-5-(3,4,5-trimethoxyphenyl)thiazol-2-amine (461b) (0.12 g, 0.29 mmol), (S)-pyrrolidin-2-ylmethanol (0.09 mL, 0.862 mmol), N-ethyl-N-isopropylpropan-2-amine (0.150 mL, 0.862 mmol) in NMP (2 mL) and heating in a microwave reactor at 130° C. for 60 mins according to the procedure reported in scheme 2. This gave after workup and purification by flash column chromatography [silica (12 g), eluting with MeOH in DCM from 0-20%] followed by reverse phase column chromatography

[C18 (50 g), eluting with ACN in water (containing 0.1% HCl) from 0-100%] (S)-(1-(4-((5-(3,4,5-trimethoxyphenyl)thiazol-2-yl)amino)pyrrolo[2,1-f][1,2,4]triazin-2-yl)pyrrolidin-2-yl)methanol (461c) (0.01 g, 7% yield) HCl salt as a yellow solid; $^1$H NMR (300 MHz, DMSO-$d_6$) δ 7.99 (s, 1H), 7.53 (dd, J=2.4, 1.5 Hz, 1H), 7.20 (dd, J=4.5, 1.6 Hz, 1H), 7.01 (s, 2H), 6.50 (dd, J=4.5, 2.4 Hz, 1H), 4.46-4.29 (m, 1H), 3.88-3.86 (m, 1H), 3.84 (s, 6H), 3.67 (s, 3H), 3.52 (d, J=7.7 Hz, 1H), 3.45-3.27 (m, 2H), 2.19-1.82 (m, 4H); MS (ES+): 483.2 (M+1); MS (ES−): 481.2 (M−1).

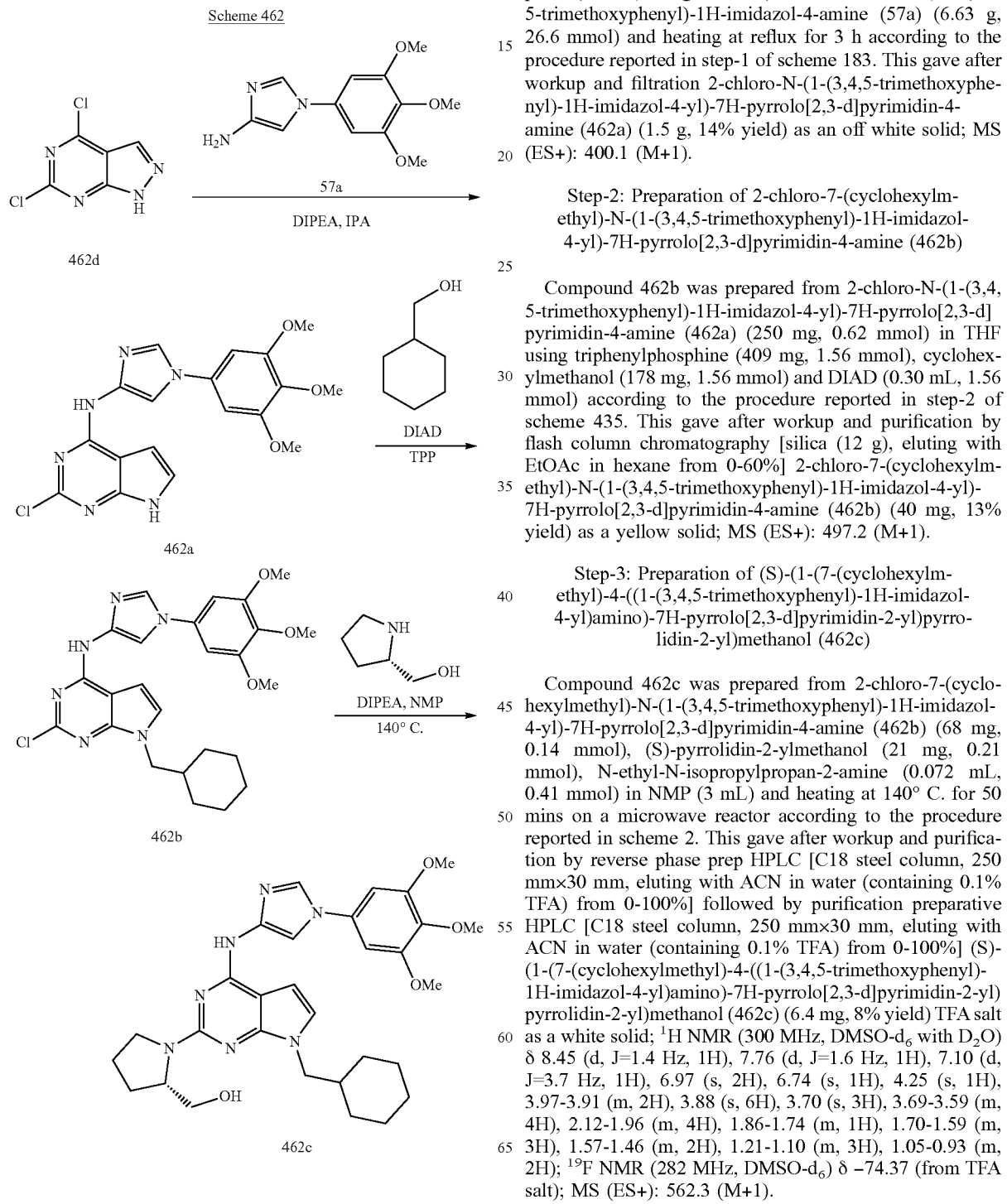

Scheme 462

Preparation of (S)-(1-(7-(cyclohexylmethyl)-4-((1-(3,4,5-trimethoxyphenyl)-1H-imidazol-4-yl)amino)-7H-pyrrolo[2,3-d]pyrimidin-2-yl)pyrrolidin-2-yl)methanol (462c)

Step-1: Preparation of 2-chloro-N-(1-(3,4,5-trimethoxyphenyl)-1H-imidazol-4-yl)-7H-pyrrolo[2,3-d]pyrimidin-4-amine (462a)

Compound 462a was prepared from 2,4-dichloro-7H-pyrrolo[2,3-d]pyrimidine (462d) (5 g, 26.6 mmol) in 2-Propanol (50 mL) using DIPEA (13.93 mL, 80 mmol), 1-(3,4,5-trimethoxyphenyl)-1H-imidazol-4-amine (57a) (6.63 g, 26.6 mmol) and heating at reflux for 3 h according to the procedure reported in step-1 of scheme 183. This gave after workup and filtration 2-chloro-N-(1-(3,4,5-trimethoxyphenyl)-1H-imidazol-4-yl)-7H-pyrrolo[2,3-d]pyrimidin-4-amine (462a) (1.5 g, 14% yield) as an off white solid; MS (ES+): 400.1 (M+1).

Step-2: Preparation of 2-chloro-7-(cyclohexylmethyl)-N-(1-(3,4,5-trimethoxyphenyl)-1H-imidazol-4-yl)-7H-pyrrolo[2,3-d]pyrimidin-4-amine (462b)

Compound 462b was prepared from 2-chloro-N-(1-(3,4,5-trimethoxyphenyl)-1H-imidazol-4-yl)-7H-pyrrolo[2,3-d]pyrimidin-4-amine (462a) (250 mg, 0.62 mmol) in THF using triphenylphosphine (409 mg, 1.56 mmol), cyclohexylmethanol (178 mg, 1.56 mmol) and DIAD (0.30 mL, 1.56 mmol) according to the procedure reported in step-2 of scheme 435. This gave after workup and purification by flash column chromatography [silica (12 g), eluting with EtOAc in hexane from 0-60%] 2-chloro-7-(cyclohexylmethyl)-N-(1-(3,4,5-trimethoxyphenyl)-1H-imidazol-4-yl)-7H-pyrrolo[2,3-d]pyrimidin-4-amine (462b) (40 mg, 13% yield) as a yellow solid; MS (ES+): 497.2 (M+1).

Step-3: Preparation of (S)-(1-(7-(cyclohexylmethyl)-4-((1-(3,4,5-trimethoxyphenyl)-1H-imidazol-4-yl)amino)-7H-pyrrolo[2,3-d]pyrimidin-2-yl)pyrrolidin-2-yl)methanol (462c)

Compound 462c was prepared from 2-chloro-7-(cyclohexylmethyl)-N-(1-(3,4,5-trimethoxyphenyl)-1H-imidazol-4-yl)-7H-pyrrolo[2,3-d]pyrimidin-4-amine (462b) (68 mg, 0.14 mmol), (S)-pyrrolidin-2-ylmethanol (21 mg, 0.21 mmol), N-ethyl-N-isopropylpropan-2-amine (0.072 mL, 0.41 mmol) in NMP (3 mL) and heating at 140° C. for 50 mins on a microwave reactor according to the procedure reported in scheme 2. This gave after workup and purification by reverse phase prep HPLC [C18 steel column, 250 mm×30 mm, eluting with ACN in water (containing 0.1% TFA) from 0-100%] followed by purification preparative HPLC [C18 steel column, 250 mm×30 mm, eluting with ACN in water (containing 0.1% TFA) from 0-100%] (S)-(1-(7-(cyclohexylmethyl)-4-((1-(3,4,5-trimethoxyphenyl)-1H-imidazol-4-yl)amino)-7H-pyrrolo[2,3-d]pyrimidin-2-yl)pyrrolidin-2-yl)methanol (462c) (6.4 mg, 8% yield) TFA salt as a white solid; $^1$H NMR (300 MHz, DMSO-$d_6$ with $D_2O$) δ 8.45 (d, J=1.4 Hz, 1H), 7.76 (d, J=1.6 Hz, 1H), 7.10 (d, J=3.7 Hz, 1H), 6.97 (s, 2H), 6.74 (s, 1H), 4.25 (s, 1H), 3.97-3.91 (m, 2H), 3.88 (s, 6H), 3.70 (s, 3H), 3.69-3.59 (m, 4H), 2.12-1.96 (m, 4H), 1.86-1.74 (m, 1H), 1.70-1.59 (m, 3H), 1.57-1.46 (m, 2H), 1.21-1.10 (m, 3H), 1.05-0.93 (m, 2H); $^{19}$F NMR (282 MHz, DMSO-$d_6$) δ −74.37 (from TFA salt); MS (ES+): 562.3 (M+1).

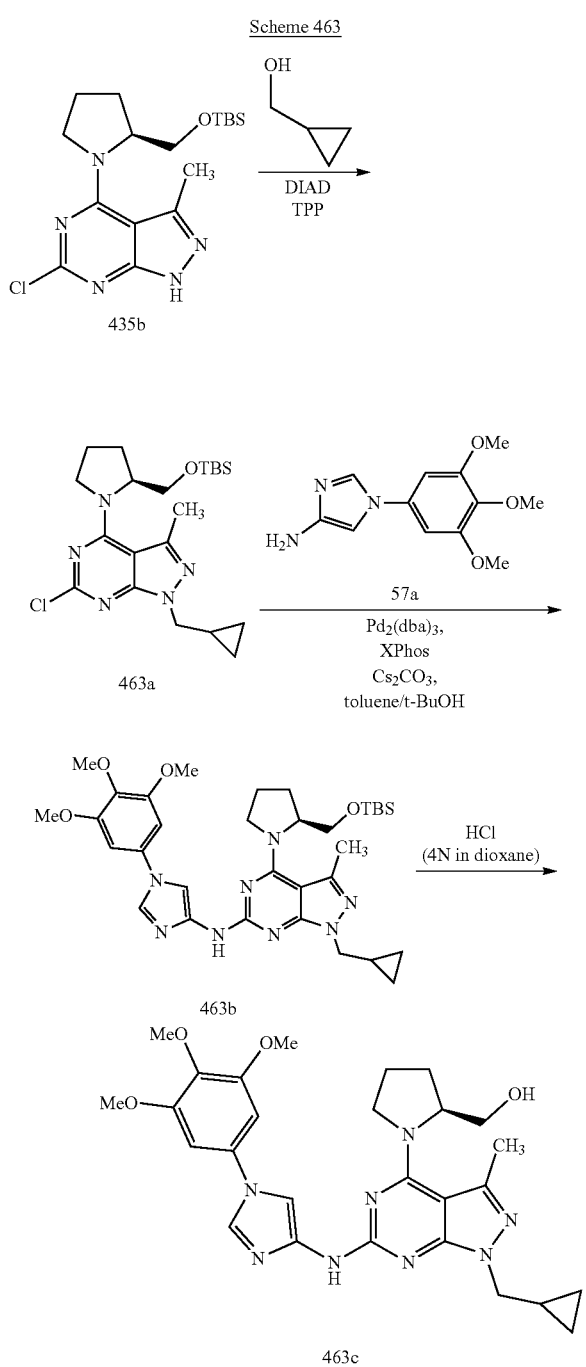

Scheme 463

Preparation of (S)-(1-(1-(cyclopropylmethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (463c)

Step-1: Preparation of (S)-4-(2-(((tert-butyldimethylsilyl)oxy)methyl)pyrrolidin-1-yl)-6-chloro-1-(cyclopropylmethyl)-3-methyl-1H-pyrazolo[3,4-d]pyrimidine (463a)

Compound 463a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF (4 mL) using triphenylphosphine (515 mg, 1.96 mmol), cyclopropylmethanol (142 mg, 1.96 mmol), DIAD (0.38 mL, 1.96 mmol) and stirring at room temperature overnight according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-(cyclopropylmethyl)-3-methyl-1H-pyrazolo[3,4-d]pyrimidine (463a) (300 mg, 88% yield) as a clear oil; MS (ES+): 436.2 (M+1).

Step-2: Preparation of (S)-4-(2-(((tert-butyldimethylsilyl)oxy)methyl)pyrrolidin-1-yl)-1-(cyclopropylmethyl)-3-methyl-N-(1-(3,4,5-trimethoxyphenyl)-1H-imidazol-4-yl)-1H-pyrazolo[3,4-d]pyrimidin-6-amine (463b)

Compound 463b was prepared from (S)-4-(2-(((tert-butyldimethylsilyl)oxy)methyl)pyrrolidin-1-yl)-6-chloro-1-(cyclopropylmethyl)-3-methyl-1H-pyrazolo[3,4-d]pyrimidine (463a) (300 mg, 0.69 mmol), 1-(3,4,5-trimethoxyphenyl)-1H-imidazol-4-amine (57a) (206 mg, 0.83 mmol), dicyclohexyl(2',4',6'-triisopropylbiphenyl-2-yl)phosphine (XPhos, 131 mg, 0.28 mmol), cesium carbonate (785 mg, 2.41 mmol), $Pd_2(dba)_3$ (126 mg, 0.14 mmol) in t-BuOH/toluene (25 mL, 1:4) and heating at 110° C. for 12 h according to the procedure reported in step-3 of scheme 101. This gave after workup and purification by flash column chromatography [silica gel (24 g), eluting with DMA80 in DCM from 0-50%] (S)-4-(2-(((tert-butyldimethylsilyl)oxy)methyl)pyrrolidin-1-yl)-1-(cyclopropylmethyl)-3-methyl-N-(1-(3,4,5-trimethoxyphenyl)-1H-imidazol-4-yl)-1H-pyrazolo[3,4-d]pyrimidin-6-amine (463b); MS (ES$^+$): δ 49.3 (M+1).

Step-3: Preparation of (S)-(1-(1-(cyclopropylmethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (463c)

To a solution of (S)-4-(2-(((tert-butyldimethylsilyl)oxy)methyl)pyrrolidin-1-yl)-1-(cyclopropylmethyl)-3-methyl-N-(1-(3,4,5-trimethoxyphenyl)-1H-imidazol-4-yl)-1H-pyrazolo[3,4-d]pyrimidin-6-amine (463b) (from step-2 above) in MeOH/DCM (10 mL) was added 4N HCl in dioxane (1.72 mL, 6.88 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (S)-(1-(1-(cyclopropylmethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (463c) (128 mg, 35% yield) HCl salt as a yellow solid; $^1$H NMR (300 MHz, DMSO-$d_6$) δ 10.39 (s, 1H, D$_2$O exchangeable), 9.05 (s, 1H), 7.89 (d, J=1.7 Hz, 1H, D$_2$O exchangeable), 7.09 (s, 2H), 4.75-4.65 (m, 1H), 4.09 (d, J=7.1 Hz, 2H), 3.95-3.83 (m, 8H), 3.70 (s, 3H), 3.66-3.53 (m, 2H), 2.56 (s, 3H), 2.15-1.86 (m, 4H), 1.32-1.20 (m, 1H), 0.51-0.43 (m, 2H), 0.43-0.37 (m, 2H); MS (ES+): 535.3 (M+1); HPLC purity: 98.43%.

Scheme 464

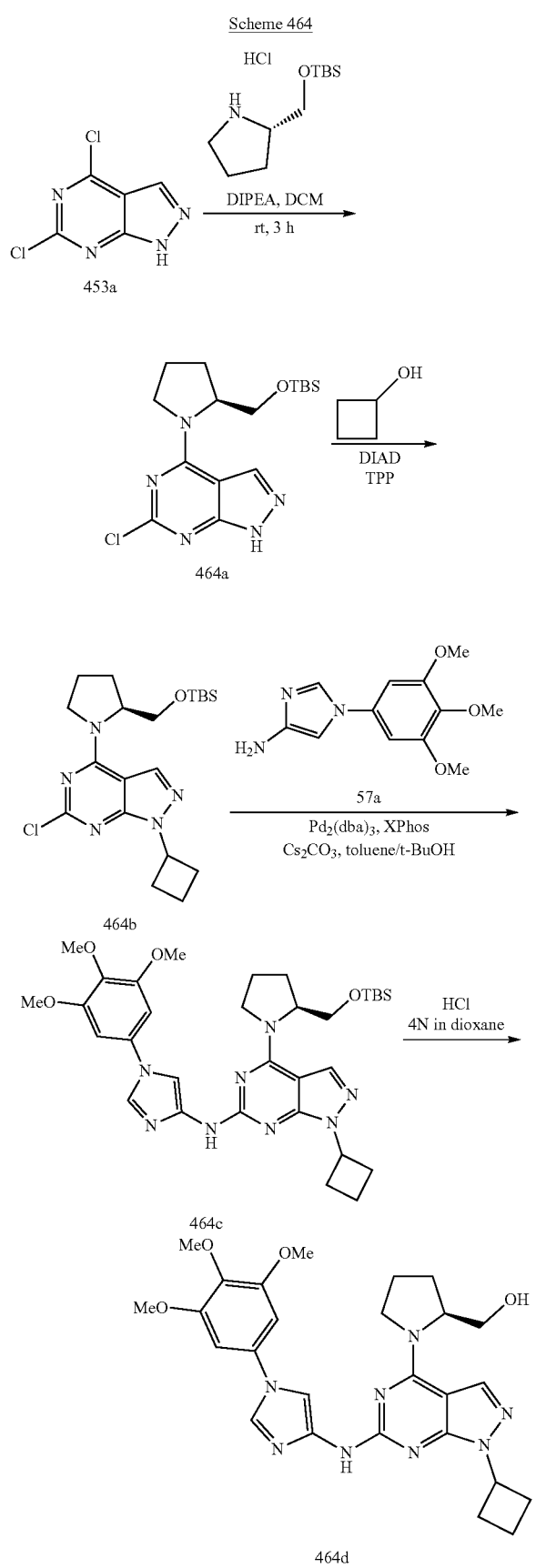

Preparation of (S)-(1-(1-cyclobutyl-6-((1-(3,4,5-trimethoxyphenyl)-1H-imidazol-4-yl)amino)-1H-pyrazolo[3,4-d]pyrimidin-4-yl)pyrrolidin-2-yl)methanol (464d)

Step-1: Preparation of (S)-4-(2-(((tert-butyldimethylsilyl)oxy)methyl)pyrrolidin-1-yl)-6-chloro-1H-pyrazolo[3,4-d]pyrimidine (464a)

Compound 464a was prepared from 4,6-dichloro-1H-pyrazolo[3,4-d]pyrimidine (453a) (5 g, 26.5 mmol) in DCM (25 mL) using (S)-2-((tert-butyldimethylsilyloxy)methyl)pyrrolidine hydrochloride (6.66 g, 26.5 mmol), DIPEA (13.86 mL, 79 mmol) and stirring at room temperature for 3 h according to the procedure reported in step-1 of scheme 96. This gave after workup and purification by flash column chromatography [silica (24 g), eluting with EtOAc in hexane from 0-70%] (S)-4-(2-(((tert-butyldimethylsilyl)oxy)methyl)pyrrolidin-1-yl)-6-chloro-1H-pyrazolo[3,4-d]pyrimidine (464a) (8 g, 82% yield) as a white solid; MS (ES+): 368.2 (M+1).

Step-2: Preparation of (S)-4-(2-(((tert-butyldimethylsilyl)oxy)methyl)pyrrolidin-1-yl)-6-chloro-1-cyclobutyl-1H-pyrazolo[3,4-d]pyrimidine (464b)

Compound 464b was prepared from (S)-4-(2-(((tert-butyldimethylsilyl)oxy)methyl)pyrrolidin-1-yl)-6-chloro-1H-pyrazolo[3,4-d]pyrimidine (464a) (350 mg, 0.95 mmol) in THF using triphenylphosphine (624 mg, 2.38 mmol), cyclobutanol (171 mg, 2.38 mmol), DIAD (0.46 mL, 2.38 mmol) and stirring at room temperature overnight according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-cyclobutyl-1H-pyrazolo[3,4-d]pyrimidine (464b) (300 mg, 75% yield) as a clear oil; MS (ES+): 422.2 (M+1).

Step-3: Preparation of (S)-4-(2-(((tert-butyldimethylsilyl)oxy)methyl)pyrrolidin-1-yl)-1-cyclobutyl-N-(1-(3,4,5-trimethoxyphenyl)-1H-imidazol-4-yl)-1H-pyrazolo[3,4-d]pyrimidin-6-amine (464c)

Compound 464c was prepared from (S)-4-(2-(((tert-butyldimethylsilyl)oxy)methyl)pyrrolidin-1-yl)-6-chloro-1-cyclobutyl-1H-pyrazolo[3,4-d]pyrimidine (464b) (300 mg, 0.71 mmol), 1-(3,4,5-trimethoxyphenyl)-1H-imidazol-4-amine (57a) (213 mg, 0.85 mmol), dicyclohexyl(2',4',6'-triisopropylbiphenyl-2-yl)phosphine (XPhos, 136 mg, 0.28 mmol), cesium carbonate (811 mg, 2.49 mmol), $Pd_2(dba)_3$ (130 mg, 0.14 mmol) in t-BuOH/toluene (25 mL, 1:4) and heating at 110° C. for 12 h according to the procedure reported in step-3 of scheme 101. This gave after workup and purification by flash column chromatography [silica gel (24 g), eluting with DMA80 in DCM from 0-50%] (S)-4-(2-(((tert-butyldimethylsilyl)oxy)methyl)pyrrolidin-1-yl)-1-cyclobutyl-N-(1-(3,4,5-trimethoxyphenyl)-1H-imidazol-4-yl)-1H-pyrazolo[3,4-d]pyrimidin-6-amine (464c); MS (ES+): 635.3 (M+1).

Step-4: Preparation of (S)-(1-(1-cyclobutyl-6-((1-(3,4,5-trimethoxyphenyl)-1H-imidazol-4-yl)amino)-1H-pyrazolo[3,4-d]pyrimidin-4-yl)pyrrolidin-2-yl)methanol (464d)

To a solution of (S)-4-(2-(((tert-butyldimethylsilyl)oxy)methyl)pyrrolidin-1-yl)-1-cyclobutyl-N-(1-(3,4,5- trimethoxyphenyl)-1H-imidazol-4-yl)-1H-pyrazolo[3,4-d]pyrimidin-6-amine (464c) (from step-3 above) in MeOH/DCM (10 mL) was added 4N HCl in dioxane (1.78 mL, 7.11 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (S)-(1-(1-cyclobutyl-6-((1-(3,4,5-trimethoxyphenyl)-1H-imidazol-4-yl)amino)-1H-pyrazolo[3,4-d]pyrimidin-4-yl)pyrrolidin-2-yl)methanol (464d) (174 mg, 47% yield) HCl salt as a white solid; $^1$H NMR (300 MHz, DMSO-d$_6$) δ 10.48-10.05 (m, 1H, D$_2$O exchangeable), 9.06 (s, 1H), 8.14 (s, 1H), 7.94 (d, J=6.9 Hz, 1H), 7.11 (d, J=2.6 Hz, 2H), 5.31-5.18 (m, 1H), 4.62-4.33 (m, 1H), 3.98-3.91 (m, 1H), 3.90 (s, 6H), 3.79-3.73 (m, 1H), 3.71 (s, 3H), 3.68-3.40 (m, 2H), 2.70-2.56 (m, 2H), 2.45-2.34 (m, 2H), 2.21-1.94 (m, 4H), 1.90-1.76 (m, 2H); MS (ES+): 521.3 (M+1); HPLC purity: 97.54%.

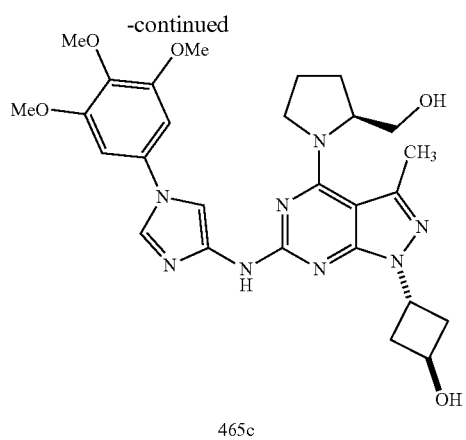

465c

Preparation of (trans)-3-(4-((S)-2-(hydroxymethyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutanol (465c)

Step-1: Preparation of 1-((trans)-3-((tert-butyldimethylsilyl)oxy)cyclobutyl)-4-((S)-2-(((tert-butyldimethylsilyl)oxy)methyl)pyrrolidin-1-yl)-6-chloro-3-methyl-1H-pyrazolo[3,4-d]pyrimidine (465a)

Compound 465a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF using triphenylphosphine (412 mg, 1.571 mmol), (cis)-3-(tert-butyldimethylsilyloxy)cyclobutanol (318 mg, 1.57 mmol; CAS #1408074-89-4), DIAD (0.31 mL, 1.57 mmol) and stirring at room temperature for overnight according to the procedure reported in step-2 of scheme 435. This gave after workup and purification by flash column chromatography [silica (12 g), eluting with EtOAc in hexane from 0-60%] 1-((trans)-3-((tert-butyldimethylsilyl)oxy)cyclobutyl)-4-((S)-2-(((tert-butyldimethylsilyloxy)methyl)pyrrolidin-1-yl)-6-chloro-3-methyl-1H-pyrazolo[3,4-d]pyrimidine (465a) (390 mg, 88% yield) as a clear oil; MS (ES+): 566.3 (M+1).

Step-2: Preparation of 1-((trans)-3-((tert-butyldimethylsilyl)oxy)cyclobutyl)-4-((S)-2-(((tert-butyldimethylsilyl)oxy)methyl)pyrrolidin-1-yl)-3-methyl-N-(1-(3,4,5-trimethoxyphenyl)-1H-imidazol-4-yl)-1H-pyrazolo[3,4-d]pyrimidin-6-amine (465b)

Compound 465b was prepared from 1-((trans)-3-((tert-butyldimethylsilyl)oxy)cyclobutyl)-4-((S)-2-(((tert-butyldimethylsilyl)oxy)methyl)pyrrolidin-1-yl)-6-chloro-3-methyl-1H-pyrazolo[3,4-d]pyrimidine (465a) (390 mg, 0.69 mmol), 1-(3,4,5-trimethoxyphenyl)-1H-imidazol-4-amine (57a) (206 mg, 0.83 mmol), dicyclohexyl(2',4',6'-triisopropylbiphenyl-2-yl)phosphine (XPhos, 131 mg, 0.28 mmol), cesium carbonate (785 mg, 2.41 mmol), Pd$_2$(dba)$_3$ (126 mg, 0.14 mmol) in t-BuOH/toluene (25 mL, 1:4) and heating at 110° C. for 12 h according to the procedure reported in step-3 of scheme 101. This gave after workup and purification by flash column chromatography [silica gel (24 g), eluting with DMA80 in DCM from 0-50%]1-((trans)-3-((tert-butyldimethylsilyl)oxy)cyclobutyl)-4-((S)-2-(((tert-butyldimethylsilyl)oxy)methyl)pyrrolidin-1-yl)-3-methyl-N-(1-(3,4,5-trimethoxyphenyl)-

Scheme 465

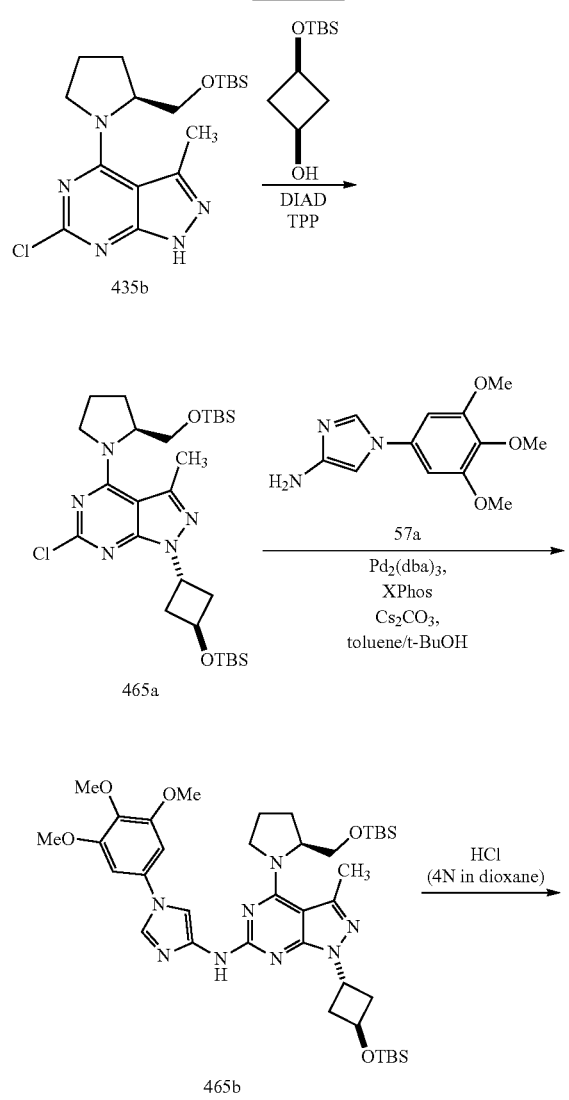

1H-imidazol-4-yl)-1H-pyrazolo[3,4-d]pyrimidin-6-amine (465b); MS (ES+): 779.4 (M+1).

Step-3: Preparation of (trans)-3-(4-((S)-2-(hydroxymethyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutanol (465c)

To a solution of 1-((trans)-3-((tert-butyldimethylsilyl)oxy)cyclobutyl)-4-((S)-2-(((tert-butyldimethylsilyl)oxy)methyl)pyrrolidin-1-yl)-3-methyl-N-(1-(3,4,5-trimethoxyphenyl)-1H-imidazol-4-yl)-1H-pyrazolo[3,4-d]pyrimidin-6-amine (465b) (from step-2 above) in MeOH/DCM was added 4N HCl in dioxane (1.722 mL, 6.89 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (trans)-3-(4-((S)-2-(hydroxymethyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutanol (465c) (107 mg, 28% yield) HCl salt as a white solid; $^1$H NMR (300 MHz, DMSO-$d_6$) δ 10.16 (s, 1H, $D_2O$ exchangeable), 9.07 (s, 1H), 7.87 (d, J=1.7 Hz, 1H), 7.10 (s, 2H), 5.36-5.27 (m, 1H), 4.70-4.61 (m, 1H), 4.54-4.46 (m, 1H), 3.90 (s, 6H), 3.87-3.75 (m, 2H), 3.70 (s, 3H), 3.67-3.48 (m, 2H), 2.77-2.62 (m, 2H), 2.57 (s, 3H), 2.41-2.28 (m, 2H), 2.13-1.85 (m, 4H); MS (ES+): 551.3 (M+1); HPLC purity: 98.70%.

Scheme 466

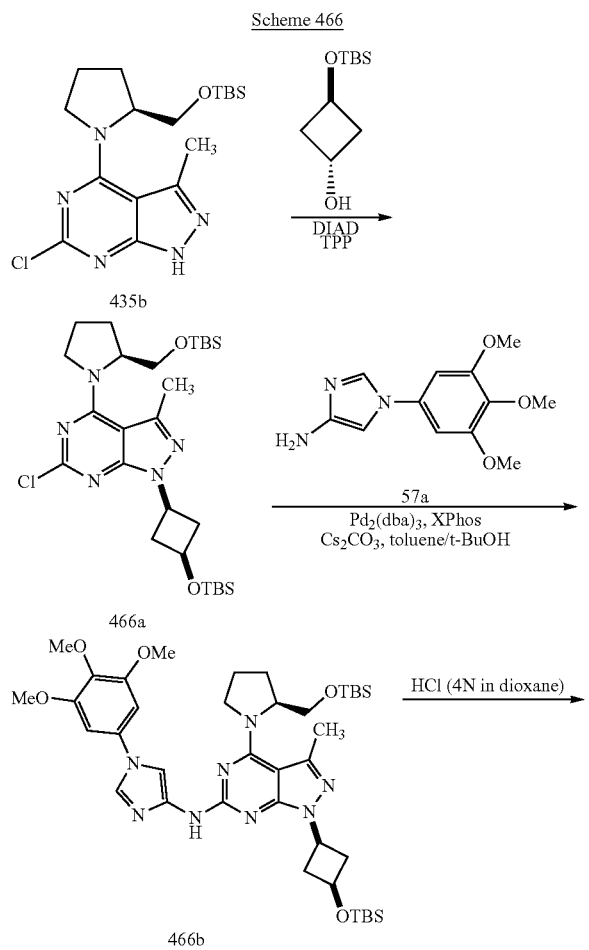

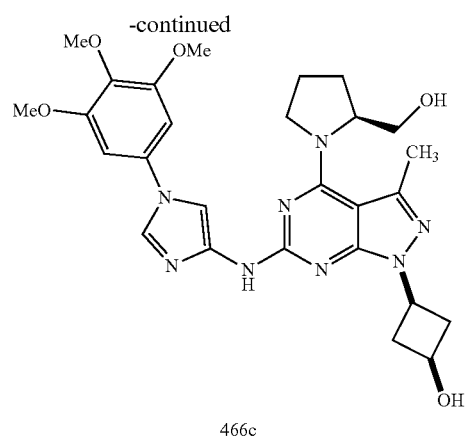

466c

Preparation of (cis)-3-(4-((S)-2-(hydroxymethyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutanol (466c)

Step-1: Preparation of 1-((cis)-3-((tert-butyldimethylsilyl)oxy)cyclobutyl)-4-((S)-2-(((tert-butyldimethylsilyl)oxy)methyl)pyrrolidin-1-yl)-6-chloro-3-methyl-1H-pyrazolo[3,4-d]pyrimidine (466a)

Compound 466a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (300 mg, 0.79 mmol) in THF using triphenylphosphine (412 mg, 1.571 mmol), (trans)-3-(tert-butyldimethylsilyloxy)cyclobutanol (318 mg, 1.57 mmol; CAS #1408075-44-4), DIAD (0.31 mL, 1.57 mmol) and stirring at room temperature for overnight according to the procedure reported in step-2 of scheme 435. This gave after workup and purification by flash column chromatography [silica (12 g), eluting with EtOAc in hexane from 0-60%] 1-((cis)-3-((tert-butyldimethylsilyl)oxy)cyclobutyl)-4-((S)-2-(((tert-butyldimethylsilyl)oxy)methyl)pyrrolidin-1-yl)-6-chloro-3-methyl-1H-pyrazolo[3,4-d]pyrimidine (466a) (380 mg, 85% yield) as a clear oil; MS (ES+): 566.3 (M+1).

Step-2: Preparation of 1-((cis)-3-((tert-butyldimethylsilyl)oxy)cyclobutyl)-4-((S)-2-(((tert-butyldimethylsilyl)oxy)methyl)pyrrolidin-1-yl)-3-methyl-N-(1-(3,4,5-trimethoxyphenyl)-1H-imidazol-4-yl)-1H-pyrazolo[3,4-d]pyrimidin-6-amine (466b)

Compound 466b was prepared from 1-((cis)-3-((tert-butyldimethylsilyl)oxy)cyclobutyl)-4-((S)-2-(((tert-butyldimethylsilyl)oxy)methyl)pyrrolidin-1-yl)-6-chloro-3-methyl-1H-pyrazolo[3,4-d]pyrimidine (466a) (380 mg, 0.671 mmol), 1-(3,4,5-trimethoxyphenyl)-1H-imidazol-4-amine (57a) (201 mg, 0.81 mmol), dicyclohexyl(2',4',6'-triisopropylbiphenyl-2-yl)phosphine (XPhos, 128 mg, 0.27 mmol), cesium carbonate (765 mg, 2.35 mmol), $Pd_2(dba)_3$ (123 mg, 0.13 mmol) in t-BuOH/toluene (25 mL, 1:4) and heating at 110° C. for 12 h according to the procedure reported in step-3 of scheme 101. This gave after workup and purification by flash column chromatography [silica gel (24 g), eluting with DMA80 in DCM from 0-50%] 1-((cis)-3-((tert-butyldimethylsilyl)oxy)cyclobutyl)-4-((S)-2-(((tert-butyldimethylsilyl)oxy)methyl)pyrrolidin-1- yl)-3-methyl-N-(1-(3,4,5-trimethoxyphenyl)-1H-imidazol-4-yl)-1H-pyrazolo[3,4-d]pyrimidin-6-amine (466b); MS (ES+): 779.4 (M+1).

Step-3: Preparation of (cis)-3-(4-((S)-2-(hydroxymethyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutanol (466c)

A solution of 1-((cis)-3-((tert-butyldimethylsilyl)oxy)cyclobutyl)-4-((S)-2-(((tert-butyldimethylsilyl)oxy)methyl)pyrrolidin-1-yl)-3-methyl-N-(1-(3,4,5-trimethoxyphenyl)-1H-imidazol-4-yl)-1H-pyrazolo[3,4-d]pyrimidin-6-amine (466b) (from step-2 above) in MeOH/DCM was added 4N HCl in dioxane (1.68 mL, 6.71 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (cis)-3-(4-((S)-2-(hydroxymethyl)pyrrolidin-1-yl)-3-methyl-6-((1-(3,4,5-trimethoxyphenyl)-1H-imidazol-4-yl)amino)-1H-pyrazolo[3,4-d]pyrimidin-1-yl)cyclobutanol (466c) (76 mg, 21% yield) HCl salt as a white solid; $^1$H NMR (300 MHz, DMSO-$d_6$) δ 10.12 (s, 1H, $D_2O$ exchangeable), 9.07 (s, 1H), 7.90 (d, J=1.7 Hz, 1H), 7.16-7.09 (m, 2H), 4.75-4.63 (m, 3H), 4.04-3.96 (m, 1H), 3.90 (s, 6H), 3.82-3.78 (m, 2H), 3.71 (s, 3H), 3.67-3.60 (m, 2H), 3.58-3.50 (m, 1H), 2.71-2.62 (m, 2H), 2.58 (s, 3H), 2.48-2.37 (m, 2H), 2.10-1.90 (m, 4H); MS (ES+): 551.3 (M+1); HPLC purity: 98.15%.

Scheme 467

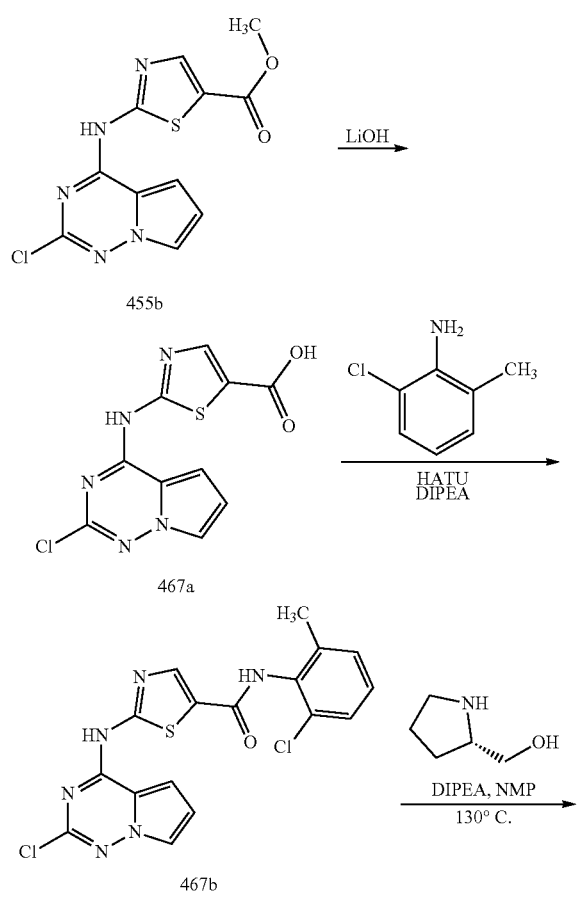

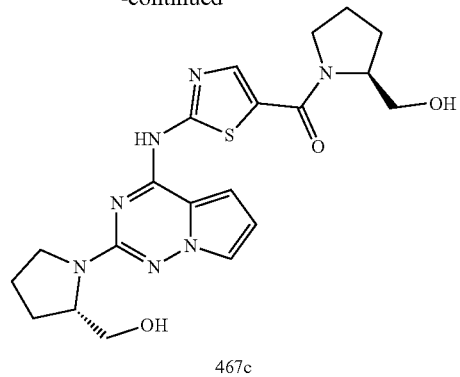

Preparation of ((S)-2-(hydroxymethyl)pyrrolidin-1-yl)(2-((2-((S)-2-(hydroxymethyl)pyrrolidin-1-yl)pyrrolo[2,1-f][1,2,4]triazin-4-yl)amino)thiazol-5-yl)methanone (467c)

Step-1: Preparation of 2-((2-chloropyrrolo[2,1-f][1,2,4]triazin-4-yl)amino)thiazole-5-carboxylic acid (467a)

To a solution of methyl 2-((2-chloropyrrolo[2,1-f][1,2,4]triazin-4-yl)amino)thiazole-5-carboxylate (455b) (0.11 g, 0.36 mmol) in THF/MeOH (6 mL, 1:1) was added a solution of lithium hydroxide hydrate (0.12 g, 2.84 mmol) in water (2 mL). The resulting mixture was stirred at RT for 23 h and evaporated in vacuum to dryness. The residue was dissolved in water, acidified to pH-4, and the solid obtained was collected by filtration, purified by reverse phase column chromatography [C18 (50 g), eluting with ACN in water (containing 0.1% HCl) from 0-100%] to furnish 2-((2-chloropyrrolo[2,1-f][1,2,4]triazin-4-yl)amino)thiazole-5-carboxylic acid (467a) (0.10 g, 95% yield) as a white solid; MS (ES+): 296.0, 298.0 (M+1); MS (ES−): 294.0, 296.0 (M−1).

Step-2: Preparation of N-(2-chloro-6-methylphenyl)-2-((2-chloropyrrolo[2,1-f][1,2,4]triazin-4-yl)amino)thiazole-5-carboxamide (467b)

Compound 467b was prepared from 2-((2-chloropyrrolo[2,1-f][1,2,4]triazin-4-yl)amino)thiazole-5-carboxylic acid (467a) (0.12 g, 0.41 mmol), using 2-chloro-6-methylaniline (0.07 mL, 0.61 mmol), HATU (0.46 g, 1.22 mmol), DIPEA (0.21 mL, 1.22 mmol) in DMF (4 mL) according to the procedure reported in step-3 of scheme 410. This gave after workup and purification by flash column chromatography [silica (12 g), eluting with ethyl acetate in hexane from 0 to 60%] N-(2-chloro-6-methylphenyl)-2-((2-chloropyrrolo[2,1-f][1,2,4]triazin-4-yl)amino)thiazole-5-carboxamide (467b) (0.05 g, 29% yield) as a yellow solid; MS (ES+): 420.9 (M+1).

Step-3: Preparation of ((S)-2-(hydroxymethyl)pyrrolidin-1-yl)(2-((2-((S)-2-(hydroxymethyl)pyrrolidin-1-yl)pyrrolo[2,1-f][1,2,4]triazin-4-yl)amino)thiazol-5-yl)methanone (467c)

Compound 467c was prepared from N-(2-chloro-6-methylphenyl)-2-((2-chloropyrrolo[2,1-f][1,2,4]triazin-4-yl)amino)thiazole-5-carboxamide (467b) (50 mg, 0.12 mmol), (S)-pyrrolidin-2-ylmethanol (0.04 mL, 0.36 mmol), N-ethyl-N-isopropylpropan-2-amine (0.06 mL, 0.36 mmol) in NMP (1 mL) and heating at 130° C. for 60 mins according to the procedure reported in scheme 2. This gave after workup and purification by flash column chromatography [silica (12 g), eluting with MeOH in DCM from 0-20%] followed by reverse phase column chromatography [C18 (50 g), eluting with ACN in water (containing 0.1% HCl) from 0-100%] ((S)-2-(hydroxymethyl)pyrrolidin-1-yl)(2-((2-((S)-2-(hydroxymethyl)pyrrolidin-1-yl)pyrrolo[2,1-f][1,2,4]triazin-4-yl)amino)thiazol-5-yl)methanone (467c) (12 mg, 23% yield) as a yellow solid; $^1$H NMR (300 MHz, DMSO-d$_6$) δ 12.43 (s, 1H), 8.01 (s, 1H), 7.56 (dd, J=2.4, 1.6 Hz, 1H), 7.21 (d, J=4.5 Hz, 1H), 6.51 (dd, J=4.5, 2.4 Hz, 1H), 4.26-4.09 (m, 2H), 3.85-3.27 (m, 8H), 2.14-1.77 (m, 8H); MS (ES+): 444.2 (M+1), 909.3 (2M+Na); MS (ES−): 442.2 (M−1). HPLC purity: 95.36%.

Scheme 468

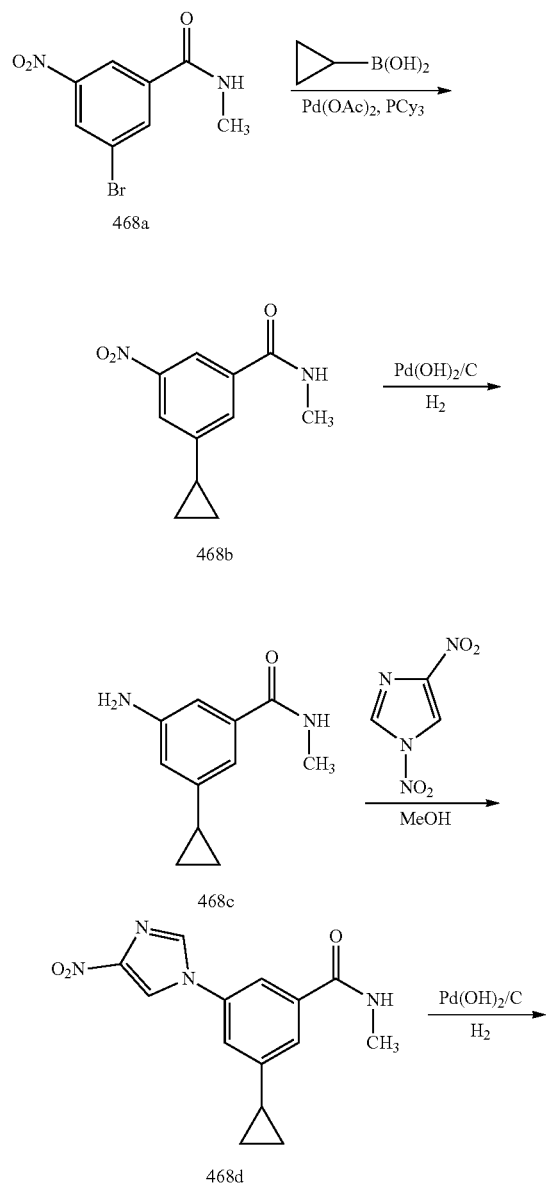

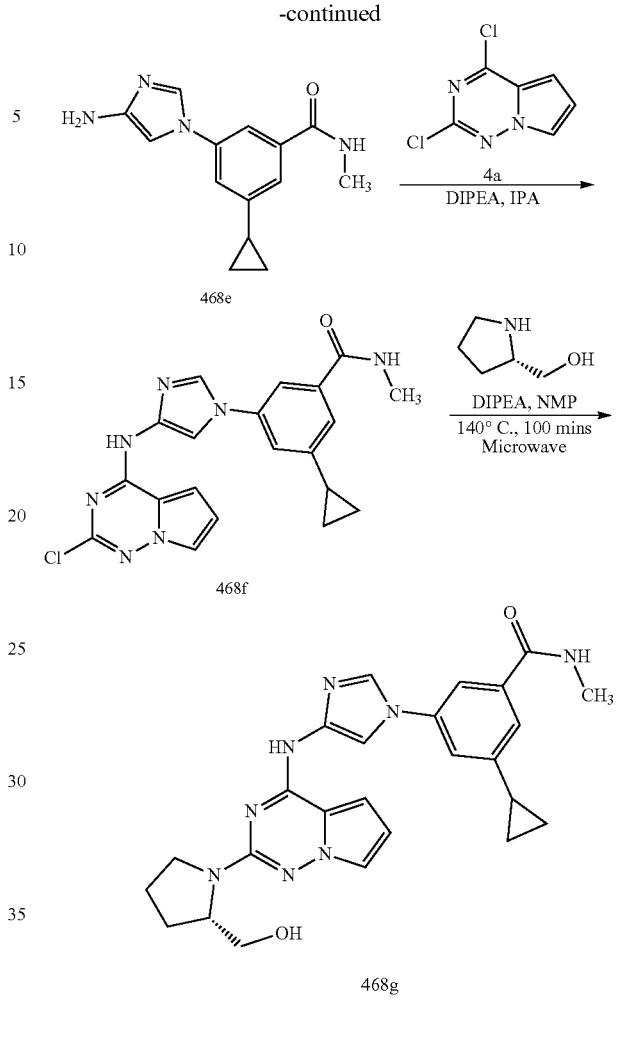

Preparation of (S)-3-cyclopropyl-5-(4-((2-(2-(hydroxymethyl)pyrrolidin-1-yl)pyrrolo[2,1-f][1,2,4]triazin-4-yl)amino)-1H-imidazol-1-yl)-N-methylbenzamide (468g)

Step-1: Preparation of 3-cyclopropyl-N-methyl-5-nitrobenzamide (468b)

To a solution of 3-bromo-N-methyl-5-nitrobenzamide (468a) (906 mg, 3.50 mmol; CAS #1375069-14-9), tricyclohexylphosphine (103 mg, 0.367 mmol), palladium (II) acetate (67 mg, 0.298 mmol) and cyclopropylboronic acid (423 mg, 4.92 mmol) in Toluene (12 mL) was added a solution of K$_3$PO$_4$ (2.57 g, 12.11 mmol) in water (1.2 mL). The mixture was degassed and filled with Argon and heated at 100° C. for 3 h. The solvent was removed in vacuo and the residue obtained was purified by flash column chromatography [silica (24 g), eluting with ethyl acetate in hexanes from 30-100%] to afford 3-cyclopropyl-N-methyl-5-nitrobenzamide (468b) (626 mg, 81% yield) as a yellow solid; $^1$H NMR (300 MHz, DMSO-d$_6$) δ 8.78 (d, J=5.1 Hz, 1H), 8.40 (dd, J=2.2, 1.5 Hz, 1H), 8.10 (t, J=1.9 Hz, 1H), 7.90 (t, J=1.7 Hz, 1H), 2.81 (d, J=4.5 Hz, 3H), 2.30-2.08 (m, 1H), 1.17-1.01 (m, 2H), 0.87 (m, 2H); MS (ES+): 221.1 (M+1).

Step-2: Preparation of 3-amino-5-cyclopropyl-N-methylbenzamide (468c)

Reduction of nitro to amine of 3-cyclopropyl-N-methyl-5-nitrobenzamide (468b) (623 mg, 2.83 mmol) in MeOH (30 mL) using Palladium hydroxide on carbon, 20 wt. % loading (dry basis), matrix carbon, wet support (122 mg, 0.174 mmol) as reported in step-3 of General scheme for preparation of 3-substituted-(4-amino-1H-imidazol-1-yl) gave 3-amino-5-cyclopropyl-N-methylbenzamide (468c) (538 mg, 2.83 mmol, 100% yield) as pale yellow oil, which was used in the next step without further purification; MS (ES+): 191.1 (M+1).

Step-3: Preparation of 3-cyclopropyl-N-methyl-5-(4-nitro-1H-imidazol-1-yl)benzamide (468d)

Reaction of 1,4-dinitro-1H-imidazole (500 mg, 3.16 mmol) with 3-amino-5-cyclopropyl-N-methylbenzamide (468c) (538 mg, 2.83 mmol) as reported in step-2 of General scheme for preparation of 3-substituted-(4-amino-1H-imidazol-1-yl) gave after filtration 3-cyclopropyl-N-methyl-5-(4-nitro-1H-imidazol-1-yl)benzamide (468d) (654 mg, 81% yield) as a yellow solid; $^1$H NMR (300 MHz, DMSO-$d_6$) δ 9.04 (dd, J=3.7, 1.6 Hz, 1H), 8.55-8.48 (m, 2H), 7.93 (dd, J=2.1, 1.5 Hz, 1H), 7.62 (dt, J=6.3, 1.7 Hz, 2H), 2.82 (dd, J=4.5, 1.9 Hz, 3H), 2.06 (m, 1H), 1.14-0.99 (m, 2H), 0.99-0.81 (m, 2H); MS (ES+): 287.1 (M+1).

Step-4: Preparation of 3-(4-amino-1H-imidazol-1-yl)-5-cyclopropyl-N-methylbenzamide (468e)

Reduction of nitro to amine of 3-cyclopropyl-N-methyl-5-(4-nitro-1H-imidazol-1-yl)benzamide (468d) (650 mg, 2.27 mmol) in MeOH (15 mL) using Palladium hydroxide on carbon, 20 wt. % loading (dry basis), matrix carbon, wet support (132 mg, 0.188 mmol) for 3.5 h as reported in step-3 of General scheme for preparation of 3-substituted-(4-amino-1H-imidazol-1-yl) gave 3-(4-amino-1H-imidazol-1-yl)-5-cyclopropyl-N-methylbenzamide (468e) (582 mg, 100% yield) as an yellow oil, which was used in the next step without further purification; $^1$H NMR (300 MHz, DMSO-$d_6$) δ 8.50 (d, J=5.0 Hz, 1H), 7.89 (d, J=1.6 Hz, 1H), 7.65 (t, J=1.8 Hz, 1H), 7.38 (d, J=1.8 Hz, 2H), 6.70 (d, J=1.6 Hz, 1H), 4.44 (s, 2H), 2.79 (d, J=4.5 Hz, 3H), 2.02 (m, 1H), 1.11-0.95 (m, 2H), 0.88-0.78 (m, 2H); MS (ES+): 257.1 (M+1).

Step-5: Preparation of 3-(4-((2-chloropyrrolo[2,1-f][1,2,4]triazin-4-yl)amino)-1H-imidazol-1-yl)-5-cyclopropyl-N-methylbenzamide (468f)

Compound 468f was prepared from 2,4-dichloropyrrolo[2,1-f][1,2,4]triazine (4a) (437 mg, 2.324 mmol) in 2-Propanol (12 mL) using DIPEA (0.405 mL, 2.321 mmol), 3-(4-amino-1H-imidazol-1-yl)-5-cyclopropyl-N-methylbenzamide (468e) (578 mg, 2.255 mmol) and heating at 90° C. for 3 h according to the procedure reported in step-1 of scheme 183. This gave after workup and filtration 3-(4-((2-chloropyrrolo[2,1-f][1,2,4]triazin-4-yl)amino)-1H-imidazol-1-yl)-5-cyclopropyl-N-methylbenzamide (468f) (323 mg, 35% yield) as a yellow solid; $^1$H NMR (300 MHz, DMSO-$d_6$) δ 11.34 (s, 1H), 8.61 (d, J=4.8 Hz, 2H), 8.31 (d, J=1.6 Hz, 1H), 7.93 (t, J=2.2 Hz, 1H), 7.84-7.74 (m, 2H), 7.54 (dt, J=5.1, 1.7 Hz, 2H), 7.41 (s, 1H), 6.73 (dd, J=4.5, 2.6 Hz, 1H), 2.87-2.78 (m, 3H), 2.17-2.02 (m, 1H), 1.11-1.02 (m, 2H), 0.92-0.84 (m, 2H); MS (ES+): 408.1 (M+1).

Step-6: Preparation of (S)-3-cyclopropyl-5-(4-((2-(2-(hydroxymethyl)pyrrolidin-1-yl)pyrrolo[2,1-f][1,2,4]triazin-4-yl)amino)-1H-imidazol-1-yl)-N-methylbenzamide (468g)

Compound 468g was prepared from 3-(4-((2-chloropyrrolo[2,1-f][1,2,4]triazin-4-yl)amino)-1H-imidazol-1-yl)-5-cyclopropyl-N-methylbenzamide (468f) (110 mg, 0.270 mmol), (S)-pyrrolidin-2-ylmethanol (171 mg, 1.69 mmol), N-ethyl-N-isopropylpropan-2-amine (0.176 mL, 1.01 mmol) in NMP (1.5 mL) and heating at 140° C. for 100 mins in a microwave reactor according to the procedure reported in scheme 2. This gave after workup and purification by reverse phase column chromatography [C18 steel column (250 mm×30 mm), eluting with ACN in water (containing 0.1% HCl) from 0-100%] (S)-3-cyclopropyl-5-(4-((2-(2-(hydroxymethyl)pyrrolidin-1-yl)pyrrolo[2,1-f][1,2,4]triazin-4-yl)amino)-1H-imidazol-1-yl)-N-methylbenzamide (468g) (35 mg, 28% yield) HCl salt as a yellow solid; $^1$H NMR (300 MHz, DMSO-$d_6$) δ 10.87 (s, 1H), 8.72 (d, J=1.6 Hz, 1H), 8.62 (q, J=4.5 Hz, 1H), 8.09 (d, J=1.7 Hz, 1H), 7.91 (t, J=1.8 Hz, 1H), 7.58 (dt, J=10.4, 1.7 Hz, 2H), 7.46 (t, J=2.1 Hz, 1H), 7.13 (dd, J=4.5, 1.7 Hz, 1H), 6.45 (dd, J=4.5, 2.4 Hz, 1H), 4.26-4.18 (m, 1H), 3.73 (dd, J=10.1, 3.8 Hz, 1H), 3.51 (d, J=7.6 Hz, 1H), 3.39 (dt, J=10.0, 6.9 Hz, 2H), 2.82 (d, J=4.4 Hz, 3H), 2.18-1.81 (m, 5H), 1.13-1.00 (m, 2H), 0.96-0.80 (m, 2H); MS (ES+): 473.2 (M+1); MS(ES-): 471.2 (M-1).

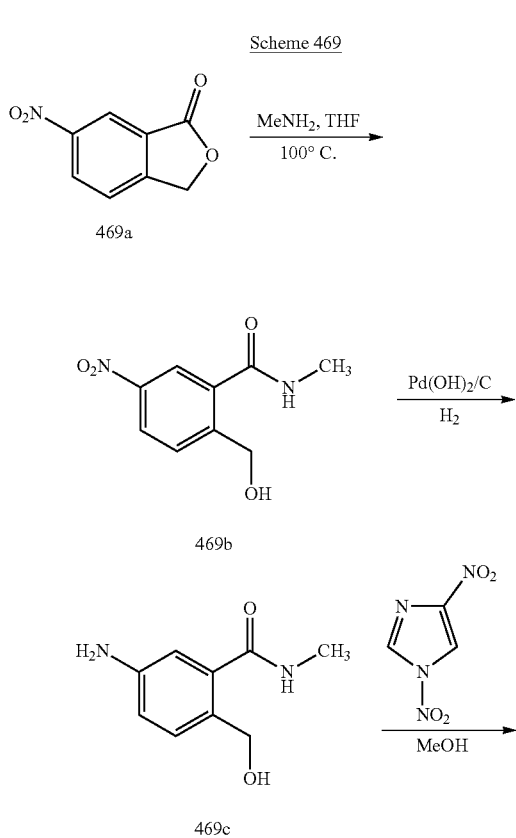

Scheme 469

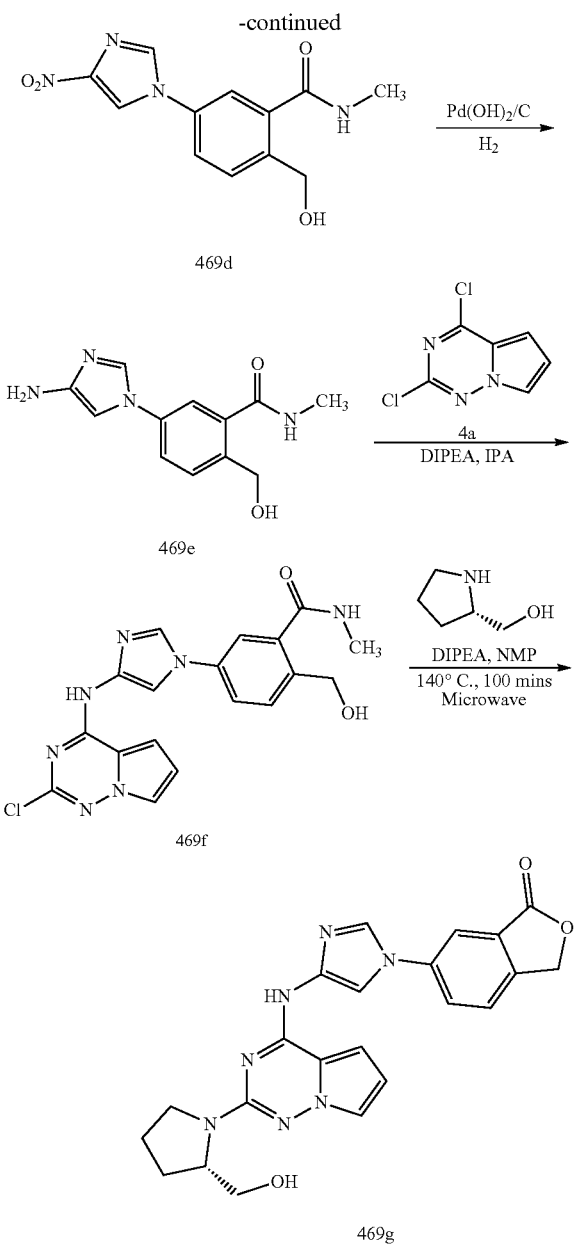

Preparation of (S)-6-(4-((2-(2-(hydroxymethyl)pyrrolidin-1-yl)pyrrolo[2,1-f][1,2,4]triazin-4-yl)amino)-1H-imidazol-1-yl)isobenzofuran-1(3H)-one (469g)

Step-1: Preparation of 2-(hydroxymethyl)-N-methyl-5-nitrobenzamide (469b)

To a solution of methanamine (2 M in THF, 3 mL, 6.00 mmol) was added 6-nitroisobenzofuran-1(3H)-one (469a) (300 mg, 1.675 mmol; CAS #610-93-5) and heated to 75° C. in a sealed tube for 12 h. The solvent was removed in vacuo to provide 2-(hydroxymethyl)-N-methyl-5-nitrobenzamide (469b) (352 mg, 100% yield) as yellow solid; $^1$H NMR (300 MHz, DMSO-$d_6$) δ 8.59 (s, 1H), 8.32 (dd, J=8.6, 2.4 Hz, 1H), 8.21 (d, J=2.4 Hz, 1H), 7.87 (d, J=8.6 Hz, 1H), 5.55 (s, 1H), 4.82-4.64 (m, 2H), 2.78 (d, J=4.6 Hz, 3H).

Step-2: Preparation of 5-amino-2-(hydroxymethyl)-N-methylbenzamide (469c)

Reduction of nitro to amine of 2-(hydroxymethyl)-N-methyl-5-nitrobenzamide (469b) (1.45 g, 6.90 mmol) in MeOH (30 mL) using Palladium hydroxide on carbon, 20 wt. % loading (dry basis), matrix carbon, wet support (226 mg, 0.322 mmol) as reported in step-3 of General scheme for preparation of 3-substituted-(4-amino-1H-imidazol-1-yl) gave after workup and purification by flash column chromatography [silica (24 g), eluting with MeOH/DCM 0-30%] 5-amino-2-(hydroxymethyl)-N-methylbenzamide (469c) (1.04 g, 84% yield) as an yellow syrup; $^1$H NMR (300 MHz, DMSO-$d_6$) δ 8.26 (d, J=4.8 Hz, 1H), 7.06 (d, J=8.1 Hz, 1H), 6.65 (d, J=2.4 Hz, 1H), 6.57 (dd, J=8.1, 2.4 Hz, 1H), 5.17 (s, 2H), 5.03 (t, J=5.7 Hz, 1H), 4.33 (d, J=5.7 Hz, 2H), 2.73 (d, J=4.6 Hz, 3H).

Step-3: Preparation of 2-(hydroxymethyl)-N-methyl-5-(4-nitro-1H-imidazol-1-yl)benzamide (469d)

Reaction of 1,4-dinitro-1H-imidazole (692 mg, 4.38 mmol) with 5-amino-2-(hydroxymethyl)-N-methylbenzamide (469c) (842 mg, 4.67 mmol) as reported in step-2 of General scheme for preparation of 3-substituted-(4-amino-1H-imidazol-1-yl) gave after filtration 2-(hydroxymethyl)-N-methyl-5-(4-nitro-1H-imidazol-1-yl)benzamide (469d) (779 mg, 64% yield) as an orange solid; $^1$H NMR (300 MHz, DMSO-$d_6$) δ 9.04 (d, J=1.6 Hz, 1H), 8.53 (d, J=1.6 Hz, 1H), 8.42 (d, J=4.8 Hz, 1H), 7.91-7.85 (m, 2H), 7.73 (dd, J=8.0, 0.8 Hz, 1H), 5.37 (t, J=5.6 Hz, 1H), 4.67 (d, J=5.6 Hz, 2H), 2.79 (d, J=4.6 Hz, 3H); MS (ES+): 277.1 (M+1).

Step-4: Preparation of 5-(4-amino-1H-imidazol-1-yl)-2-(hydroxymethyl)-N-methylbenzamide (469e)

Reduction of nitro to amine of 2-(hydroxymethyl)-N-methyl-5-(4-nitro-1H-imidazol-1-yl)benzamide (469d) (393 mg, 1.423 mmol) in MeOH (15 mL) using Palladium hydroxide on carbon, 20 wt. % loading (dry basis), matrix carbon, wet support (97 mg, 0.138 mmol) for 3.5 h as reported in step-3 of General scheme for preparation of 3-substituted-(4-amino-1H-imidazol-1-yl) gave 5-(4-amino-1H-imidazol-1-yl)-2-(hydroxymethyl)-N-methylbenzamide (469e) (350 mg, 100% yield) as a yellow foam, which was used in the next step without further purification; $^1$H NMR (300 MHz, DMSO-$d_6$) δ 8.42 (d, J=4.8 Hz, 1H), 7.88 (d, J=1.6 Hz, 1H), 7.59 (d, J=1.4 Hz, 2H), 7.54 (t, J=1.4 Hz, 1H), 6.69 (d, J=1.6 Hz, 1H), 5.26 (d, J=5.8 Hz, 1H), 4.59 (d, J=4.5 Hz, 2H), 4.44 (s, 2H), 2.77 (d, J=4.6 Hz, 3H). MS (ES+): 247.1 (M+1). Step-5: Preparation of 5-(4-((2-chloropyrrolo[2,1-f][1,2,4]triazin-4-yl)amino)-1H-imidazol-1-yl)-2-(hydroxymethyl)-N-methylbenzamide (469f)

Compound 469f was prepared from 2,4-dichloropyrrolo[2,1-f][1,2,4]triazine (4a) (267 mg, 1.42 mmol) in 2-Propanol (8 mL) using DIPEA (0.49 mL, 2.79 mmol), 5-(4-amino-1H-imidazol-1-yl)-2-(hydroxymethyl)-N-methylbenzamide (469e) (348 mg, 1.41 mmol) and heating at 90° C. for 3.5 h according to the procedure reported in step-1 of scheme 183. This gave after workup and filtration 5-(4-((2-chloropyrrolo[2,1-f][1,2,4]triazin-4-yl)amino)-1H-imidazol-1-yl)-2-(hydroxymethyl)-N-methylbenzamide (469f) (405 mg, 72.0% yield) as a yellow solid; $^1$H NMR (300 MHz, DMSO-$d_6$) δ 11.33 (s, 1H), 8.48 (d, J=4.8 Hz, 1H), 8.28 (d, J=1.6 Hz, 1H), 7.93 (d, J=1.6 Hz, 1H), 7.78 (dd, J=2.6, 1.6 Hz, 1H), 7.72 (d, J=1.6 Hz, 2H), 7.68 (t, J=1.4 Hz, 1H), 7.40 (s, 1H), 6.73 (dd, J=4.5, 2.6 Hz, 1H), 5.35 (t, J=5.7 Hz, 1H), 4.65 (d, J=5.0 Hz, 2H), 2.80 (d, J=4.6 Hz, 3H); MS (ES+): 398.1 (M+1).

Step-6: Preparation of (S)-6-(4-((2-(2-(hydroxymethyl)pyrrolidin-1-yl)pyrrolo[2,1-f][1,2,4]triazin-4-yl)amino)-1H-imidazol-1-yl)isobenzofuran-1(3H)-one (469g)

Compound 469g was prepared from 5-(4-((2-chloropyrrolo[2,1-f][1,2,4]triazin-4-yl)amino)-1H-imidazol-1-yl)-2-(hydroxymethyl)-N-methylbenzamide (469f) (123 mg, 0.309 mmol), (S)-pyrrolidin-2-ylmethanol (129 mg, 1.27 mmol), N-ethyl-N-isopropylpropan-2-amine (0.219 mL, 1.25 mmol) in NMP (1.5 mL) and heating at 140° C. for 100 mins in a microwave reactor according to the procedure reported in scheme 2. This gave after workup and purification by reverse phase column chromatography [C18 steel column (250 mm×30 mm), eluting with ACN in water (containing 0.1% HCl) from 0-100%] (S)-6-(4-((2-(2-(hydroxymethyl)pyrrolidin-1-yl)pyrrolo[2,1-f][1,2,4]triazin-4-yl)amino)-1H-imidazol-1-yl)isobenzofuran-1(3H)-one (469g) (22 mg, 17% yield) HCl salt as a yellow solid; $^1$H NMR (300 MHz, DMSO-$d_6$) δ 10.70 (s, 1H), 8.57 (s, 1H), 8.20 (d, J=13.6 Hz, 2H), 8.07 (s, 1H), 7.81 (d, J=7.6 Hz, 1H), 7.43 (s, 1H), 7.15 (s, 1H), 6.43 (s, 1H), 5.48 (s, 2H), 4.18 (s, 1H), 3.75 (d, J=8.6 Hz, 1H), 3.50 (s, 1H), 3.37 (t, J=9.0 Hz, 2H), 1.98 (m, 4H); MS (ES+): 432.1 (M+1); MS (ES−): 430.1 (M−1).

Scheme 470

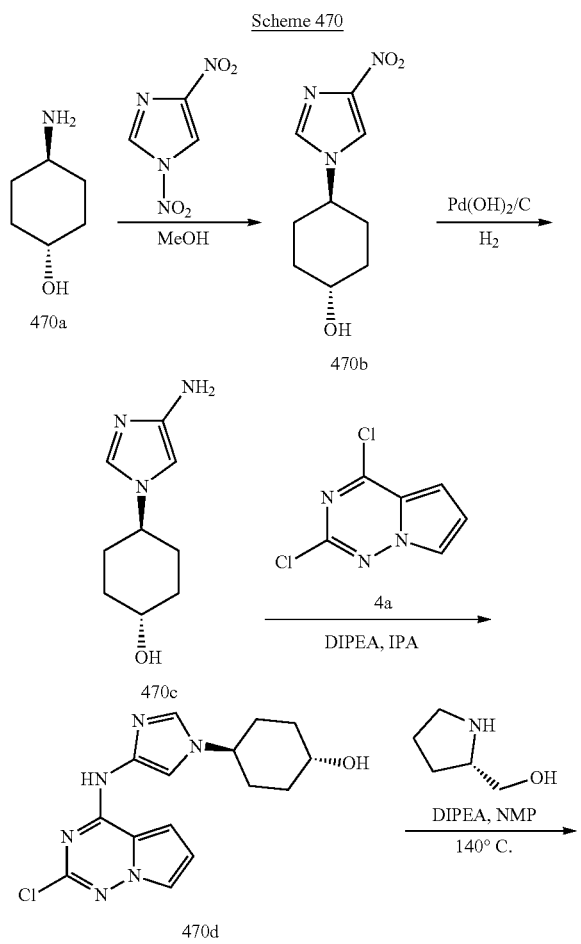

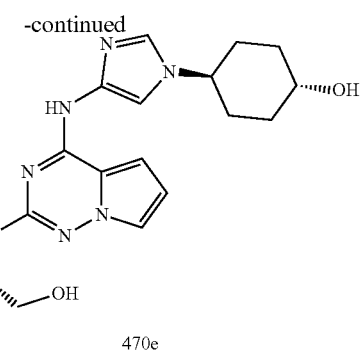

470e

Preparation of (trans)-4-(4-((2-((S)-2-(hydroxymethyl)pyrrolidin-1-yl)pyrrolo[2,1-f][1,2,4]triazin-4-yl)amino)-1H-imidazol-1-yl)cyclohexanol (470e)

Step-1: Preparation of (trans)-4-(4-nitro-1H-imidazol-1-yl)cyclohexanol (470b)

Reaction of 1,4-dinitro-1H-imidazole (1.08 g, 6.83 mmol) with (trans)-4-aminocyclohexanol (470a) (818 mg, 7.10 mmol; CAS #27489-62-9) as reported in step-2 of General scheme for preparation of 3-substituted-(4-amino-1H-imidazol-1-yl) gave after work-up and purification by flash column chromatography [silica gel 24 g, eluting with ethyl acetate/MeOH (9:1) in hexanes from 50-100%] (trans)-4-(4-nitro-1H-imidazol-1-yl)cyclohexanol (470b) (1.0 g, 69% yield) as a yellow solid; $^1$H NMR (300 MHz, DMSO-$d_6$) δ 8.50 (d, J=1.5 Hz, 1H), 7.94 (d, J=1.5 Hz, 1H), 4.72 (d, J=4.5 Hz, 1H), 4.16 (m, 1H), 3.48 (m, 1H), 2.06-1.85 (m, 4H), 1.85-1.68 (m, 2H), 1.30 (m, 2H); MS (ES+): 212.1 (M+1).

Step-2: Preparation of (trans)-4-(4-amino-1H-imidazol-1-yl)cyclohexanol (470c)

Reduction of nitro to amine of (trans)-4-(4-nitro-1H-imidazol-1-yl)cyclohexanol (470b) (536 mg, 2.54 mmol) in MeOH (20 mL) using Palladium hydroxide on carbon, 20 wt. % loading (dry basis), matrix carbon, wet support (110 mg, 0.157 mmol) as reported in step-3 of General scheme for preparation of 3-substituted-(4-amino-1H-imidazol-1-yl) gave (trans)-4-(4-amino-1H-imidazol-1-yl)cyclohexanol (470c) (460 mg, 100% yield) as a pale yellow oil which was used directly for next step without further purification; MS (ES+): 182.2 (M+1).

Step-3: Preparation of (trans)-4-(4-((2-chloropyrrolo[2,1-f][1,2,4]triazin-4-yl)amino)-1H-imidazol-1-yl)cyclohexanol (470d)

Compound 470d was prepared from 2,4-dichloropyrrolo[2,1-f][1,2,4]triazine (4a) (484 mg, 2.57 mmol) in 2-Propanol (10 mL) using DIPEA (1.3 mL, 7.44 mmol), (trans)-4-(4-amino-1H-imidazol-1-yl)cyclohexanol (470c) (460 mg, 2.54 mmol) and heating at 90° C. for 3 h according to the procedure reported in step-1 of scheme 183. This gave after workup and filtration (trans)-4-(4-((2-chloropyrrolo[2,1-f][1,2,4]triazin-4-yl)amino)-1H-imidazol-1-yl)cyclohexanol (470d) (563 mg, 67% yield) as a gray solid; $^1$H NMR (300 MHz, DMSO-$d_6$) δ 11.14 (s, 1H), 7.72 (dd, J=2.6, 1.6 Hz, 1H), 7.67 (d, J=1.6 Hz, 1H), 7.50 (d, J=1.5 Hz, 1H), 7.35 (dd, J=4.4, 1.6 Hz, 1H), 6.68 (dd, J=4.5, 2.6 Hz, 1H), 4.70

(d, J=4.4 Hz, 1H), 4.08 (m, 1H), 3.51 (d, J=4.0 Hz, 1H), 1.97 (m, 4H), 1.85-1.60 (m, 2H), 1.33 (m, 2H); MS (ES+): 333.1 (M+1).

Step-4: Preparation of (trans)-4-(4-((2-((S)-2-(hydroxymethyl)pyrrolidin-1-yl)pyrrolo[2,1-f][1,2,4]triazin-4-yl)amino)-1H-imidazol-1-yl)cyclohexanol (470e)

Compound 470e was prepared from (trans)-4-(4-((2-chloropyrrolo[2,1-f][1,2,4]triazin-4-yl)amino)-1H-imidazol-1-yl)cyclohexanol (470d) (117 mg, 0.352 mmol), (S)-pyrrolidin-2-ylmethanol (174 mg, 1.72 mmol), N-ethyl-N-isopropylpropan-2-amine (0.196 mL, 1.12 mmol) in NMP (1.5 mL) and heating at 140° C. for 100 mins in a microwave reactor according to the procedure reported in scheme 2. This gave after workup and purification by reverse phase column chromatography [C18 (RediSep 250×30 mm), eluting with ACN in water (containing 0.1% HCl) from 0-100%] (trans)-4-(4-((2-((S)-2-(hydroxymethyl)pyrrolidin-1-yl)pyrrolo[2,1-f][1,2,4]triazin-4-yl)amino)-1H-imidazol-1-yl)cyclohexanol (470e) (55 mg, 39% yield) HCl salt as a yellow solid; $^1$H NMR (300 MHz, DMSO-$d_6$, $D_2O$ exchange) δ 8.92 (s, 1H), 7.76 (d, J=1.7 Hz, 1H), 7.52 (t, J=2.1 Hz, 1H), 6.93 (d, J=4.5 Hz, 1H), 6.54 (dd, J=4.6, 2.4 Hz, 1H), 4.41-4.25 (m, 1H), 4.13-4.03 (m, 1H), 3.66-3.48 (m, 2H), 3.48-3.39 (m, 1H), 3.39-3.25 (m, 2H), 2.18-2.04 (m, 2H), 2.04-1.78 (m, 8H), 1.50-1.21 (m, 2H); MS (ES+): 398.2 (M+1); MS (ES−): 396.2 (M−1).

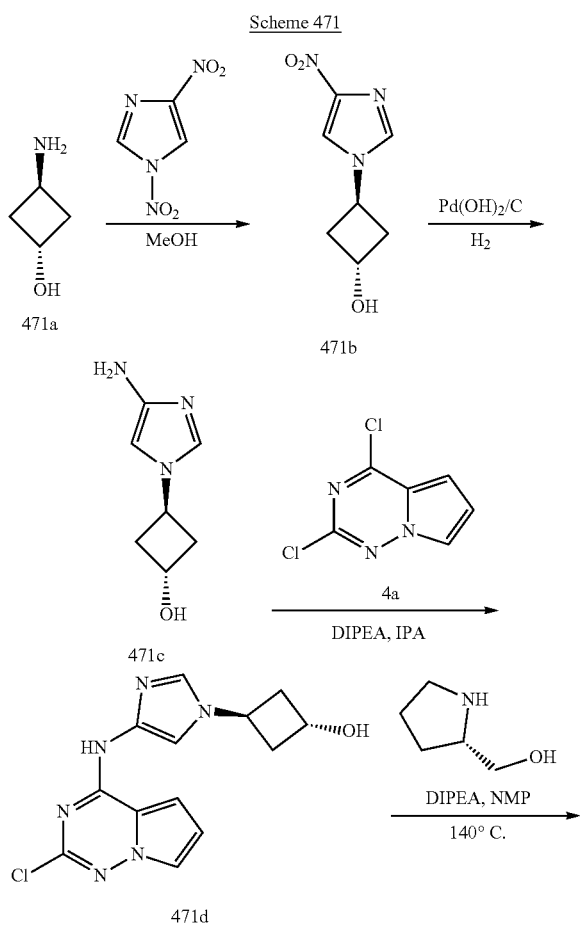

Scheme 471

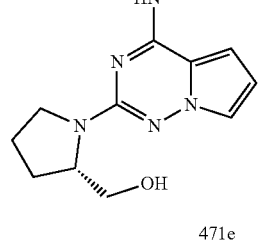

471e

Preparation of (trans)-3-(4-((2-((S)-2-(hydroxymethyl)pyrrolidin-1-yl)pyrrolo[2,1-f][1,2,4]triazin-4-yl)amino)-1H-imidazol-1-yl)cyclobutanol (471e)

Step-1: Preparation of (trans)-3-(4-nitro-1H-imidazol-1-yl)cyclobutanol (471b)

Reaction of 1,4-dinitro-1H-imidazole (726 mg, 4.59 mmol) with (trans)-3-aminocyclobutanol hydrochloride (471a) (560 mg, 4.53 mmol; CAS #1205037-95-1) using DIEA (0.865 mL, 4.95 mmol) in MeOH (20 mL) as reported in step-2 of General scheme for preparation of 3-substituted-(4-amino-1H-imidazol-1-yl) gave after work-up and purification by flash column chromatography [silica gel 24 g, eluting with ethyl acetate/MeOH (9:1) in hexanes from 50-100%] (trans)-3-(4-nitro-1H-imidazol-1-yl)cyclobutanol (471b) (696 mg, 84% yield) as a yellow solid; $^1$H NMR (300 MHz, DMSO-$d_6$) δ 8.57 (d, J=1.5 Hz, 1H), 7.99 (d, J=1.5 Hz, 1H), 5.30 (d, J=4.7 Hz, 1H), 4.97 (m, 1H), 4.40 (m, 1H), 2.71-2.57 (m, 2H), 2.45-2.32 (m, 2H).

Step-2: Preparation of (trans)-3-(4-amino-1H-imidazol-1-yl)cyclobutanol (471c)

Reduction of nitro to amine of (trans)-3-(4-nitro-1H-imidazol-1-yl)cyclobutanol (471b) (390 mg, 2.129 mmol in MeOH (20 mL) using Palladium hydroxide on carbon, 20 wt. % loading (dry basis), matrix carbon, wet support (110 mg, 0.157 mmol) as reported in step-3 of General scheme for preparation of 3-substituted-(4-amino-1H-imidazol-1-yl) gave (trans)-3-(4-amino-1H-imidazol-1-yl)cyclobutanol (471c) (326 mg, 100% yield) as an pale yellow oil which was used directly for next step without further purification; MS (ES+): 154.1 (M+1).

Step-3: Preparation of (trans)-3-(4-((2-chloropyrrolo[2,1-f][1,2,4]triazin-4-yl)amino)-1H-imidazol-1-yl)cyclobutanol (471d)

Compound 471d was prepared from 2,4-dichloropyrrolo[2,1-f][1,2,4]triazine (4a) (414 mg, 2.202 mmol) in 2-Propanol (8 mL) using DIPEA (1.0 mL, 5.73 mmol), (trans)-3-(4-amino-1H-imidazol-1-yl)cyclobutanol (471c) (326 mg, 2.128 mmol) and heating at 90° C. for 3 h according to the procedure reported in step-1 of scheme 183. This gave after workup and filtration (trans)-3-(4-((2-chloropyrrolo[2,1-f][1,2,4]triazin-4-yl)amino)-1H-imidazol-1-yl)cyclobutanol (471d) (446 mg, 69% yield) as a yellow solid; $^1$H NMR (300 MHz, DMSO-$d_6$) δ 11.17 (s, 1H), 7.82-7.69 (m, 2H), 7.52 (d, J=1.6 Hz, 1H), 7.36 (d, J=4.3 Hz, 1H), 6.69 (dd, J=4.4, 2.6 Hz, 1H), 5.31 (d, J=5.0 Hz, 1H), 4.88 (m, 1H), 4.56-4.36 (m, 1H), 2.62-2.54 (m, 2H), 2.41 (m, 2H); MS (ES+): 305.1 (M+1).

Step-4: Preparation of (trans)-3-(4-((2-((S)-2-(hydroxymethyl)pyrrolidin-1-yl)pyrrolo[2,1-f][1,2,4]triazin-4-yl)amino)-1H-imidazol-1-yl)cyclobutanol (471e)

Compound 471e was prepared from (trans)-3-(4-((2-chloropyrrolo[2,1-f][1,2,4]triazin-4-yl)amino)-1H-imidazol-1-yl)cyclobutanol (471d) (109 mg, 0.358 mmol), (S)-pyrrolidin-2-ylmethanol (171 mg, 1.69 mmol), N-ethyl-N-isopropylpropan-2-amine (0.261 mL, 1.49 mmol) in NMP (1.5 mL) and heating at 140° C. for 170 mins in a microwave reactor according to the procedure reported in scheme 2. This gave after workup and purification by reverse phase column chromatography [C18 (RediSep 250×30 mm), eluting with ACN in water (containing 0.1% HCl) from 0-100%] (trans)-3-(4-((2-((S)-2-(hydroxymethyl)pyrrolidin-1-yl)pyrrolo[2,1-f][1,2,4]triazin-4-yl)amino)-1H-imidazol-1-yl)cyclobutanol (471e) (51 mg, 39% yield) HCl salt as a yellow solid; $^1$H NMR (300 MHz, DMSO-$d_6$, $D_2O$ exchange) δ 9.02 (d, J=1.4 Hz, 1H), 7.77 (d, J=1.8 Hz, 1H), 7.52 (t, J=2.0 Hz, 1H), 6.96 (dd, J=4.5, 1.5 Hz, 1H), 6.54 (dd, J=4.5, 2.4 Hz, 1H), 5.20-5.03 (m, 1H), 4.51-4.34 (m, 1H), 4.18-4.04 (m, 1H), 3.60 (dd, J=10.3, 4.2 Hz, 1H), 3.54-3.41 (m, 1H), 3.41-3.25 (m, 2H), 2.83-2.66 (m, 2H), 2.52-2.38 (m, 2H), 2.06-1.75 (m, 4H); MS (ES+): 370.2 (M+1); MS (ES−): 368.2 (M−1).

Scheme 472

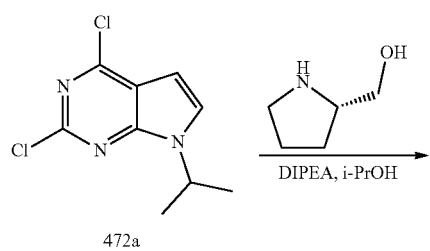

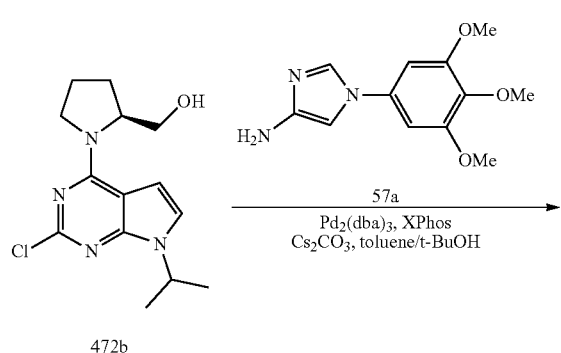

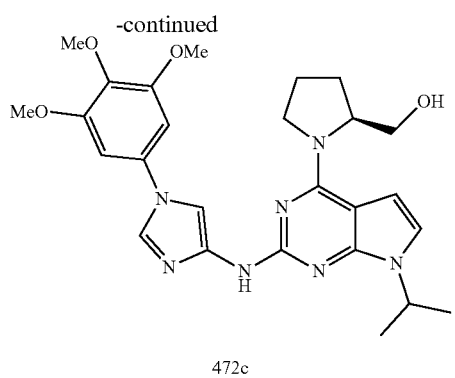

472c

Preparation of (S)-(1-(7-isopropyl-2-((1-(3,4,5-trimethoxyphenyl)-1H-imidazol-4-yl)amino)-7H-pyrrolo[2,3-d]pyrimidin-4-yl)pyrrolidin-2-yl)methanol (472c)

Step-1: Preparation of (S)-(1-(2-chloro-7-isopropyl-7H-pyrrolo[2,3-d]pyrimidin-4-yl)pyrrolidin-2-yl)methanol (472b)

Compound 472b was prepared from 2,4-dichloro-7-isopropyl-7H-pyrrolo[2,3-d]pyrimidine (472a) (200 mg, 0.87 mmol; CAS #1227635-12-2) in IPA (5 mL) using (S)-pyrrolidin-2-ylmethanol (88 mg, 0.87 mmol), DIPEA (0.46 mL, 2.61 mmol) and stirring at room temperature for 3 h according to the procedure reported in step-1 of scheme 96. This gave after workup and purification by flash column chromatography [silica (12 g), eluting with EtOAc in hexane from 0-70%] (S)-(1-(2-chloro-7-isopropyl-7H-pyrrolo[2,3-d]pyrimidin-4-yl)pyrrolidin-2-yl)methanol (472b) (200 mg, 78% yield) as clear oil; $^1$H NMR (300 MHz, DMSO-$d_6$) δ 7.35 (s, 1H), 6.62 (d, J=3.7 Hz, 1H), 4.88-4.74 (m, 1H), 4.37-4.25 (m, 1H), 3.91-3.52 (m, 3H), 3.48-3.35 (m, 1H), 2.13-1.78 (m, 4H), 1.46-1.29 (m, 6H); MS (ES+): 295.1 (M+1).

Step-2: Preparation of (S)-(1-(7-isopropyl-2-((1-(3,4,5-trimethoxyphenyl)-1H-imidazol-4-yl)amino)-7H-pyrrolo[2,3-d]pyrimidin-4-yl)pyrrolidin-2-yl)methanol (472c)

Compound 472c was prepared from (S)-(1-(2-chloro-7-isopropyl-7H-pyrrolo[2,3-d]pyrimidin-4-yl)pyrrolidin-2-yl)methanol (472b) (200 mg, 0.68 mmol), 1-(3,4,5-trimethoxyphenyl)-1H-imidazol-4-amine (57a) (203 mg, 0.81 mmol), dicyclohexyl(2',4',6'-triisopropylbiphenyl-2-yl)phosphine (XPhos, 129 mg, 0.27 mmol), cesium carbonate (774 mg, 2.38 mmol), $Pd_2(dba)_3$ (124 mg, 0.14 mmol) in t-BuOH/toluene (15 mL, 1:4) and heating at 110° C. for 12 h according to the procedure reported in step-3 of scheme 101. This gave after workup and purification by flash column chromatography [silica gel (24 g), eluting with DMA80 in DCM from 0-50%] (S)-(1-(7-isopropyl-2-((1-(3,4,5-trimethoxyphenyl)-1H-imidazol-4-yl)amino)-7H-pyrrolo[2,3-d]pyrimidin-4-yl)pyrrolidin-2-yl)methanol (472c) (95 mg, 28% yield) as a white solid; $^1$H NMR (300 MHz, DMSO-$d_6$) δ 10.98-10.34 (m, 1H, $D_2O$ exchangeable), 8.57 (s, 1H), 7.81 (s, 1H, $D_2O$ exchangeable), 7.32 (s, 1H), 7.00 (s, 2H), 6.75 (d, J=3.7 Hz, 1H), 4.95-4.78 (m, 1H), 4.75-4.42 (m, 1H), 4.06-3.94 (m, 1H), 3.89 (s, 6H), 3.84-3.71 (m, 1H), 3.70 (s, 3H), 3.65-3.54 (m, 2H), 2.22-1.95 (m, 4H), 1.49-1.43 (m, 6H); MS (ES+): 508.3 (M+1); HPLC purity: 98.94%.

Scheme 473

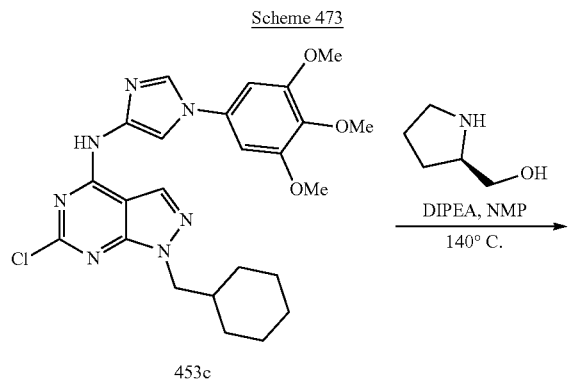

453c

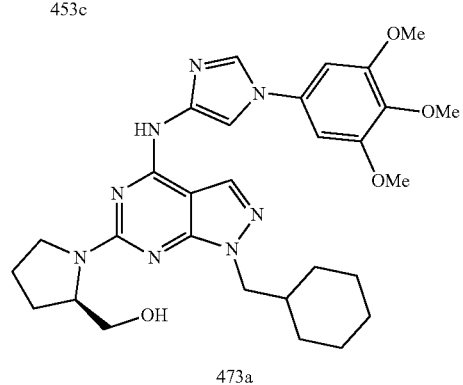

473a

Preparation of (R)-(1-(1-(cyclohexylmethyl)-4-((1-(3,4,5-trimethoxyphenyl)-1H-imidazol-4-yl)amino)-1H-pyrazolo[3,4-d]pyrimidin-6-yl)pyrrolidin-2-yl)methanol (473a)

Compound 473a was prepared from 6-chloro-1-(cyclohexylmethyl)-N-(1-(3,4,5-trimethoxyphenyl)-1H-imidazol-4-yl)-1H-pyrazolo[3,4-d]pyrimidin-4-amine (453c) (330 mg, 0.663 mmol), (R)-pyrrolidin-2-ylmethanol (134 mg, 1.325 mmol), N-ethyl-N-isopropylpropan-2-amine (0.347 mL, 1.988 mmol) in NMP (3 mL) and heating at 140° C. for 50 mins on a microwave reactor according to the procedure reported in scheme 2. This gave after workup and purification by flash column chromatography [silica gel (12 g), eluting with DMA80 in DCM from 0-50%] followed by reverse phase column chromatography [C18 steel column, eluting with ACN in water (containing 0.1% HCl) from 0-100%] and reverse phase prep HPLC [C18 steel column, 250 mm×30 mm, eluting with ACN in water (containing 0.1% TFA) from 0-100%] (R)-(1-(1-(cyclohexylmethyl)-4-((1-(3,4,5-trimethoxyphenyl)-1H-imidazol-4-yl)amino)-1H-pyrazolo[3,4-d]pyrimidin-6-yl)pyrrolidin-2-yl)methanol (473a) (69 mg, 19% yield) TFA salt as a white solid; $^1$H NMR (300 MHz, DMSO-$d_6$) δ 11.49 (m, 1H, D$_2$O exchangeable), 8.68 (s, 1H), 8.26 (s, 1H), 8.00 (s, 1H), 7.02 (s, 2H), 5.20 (brs, 1H, D$_2$O exchangeable), 4.44-4.19 (m, 1H), 4.15-3.99 (m, 2H), 3.88 (s, 6H), 3.77-3.64 (m, 5H), 3.62-3.29 (m, 2H), 2.07-1.82 (m, 5H), 1.70-1.40 (m, 5H), 1.20-1.07 (m, 3H), 1.06-0.90 (m, 2H); $^{19}$F NMR (282 MHz, DMSO-$d_6$) δ −74.69 (from TFA salt); MS (ES+): 563.3 (M+1); HPLC purity: 98.67%.

Scheme 474

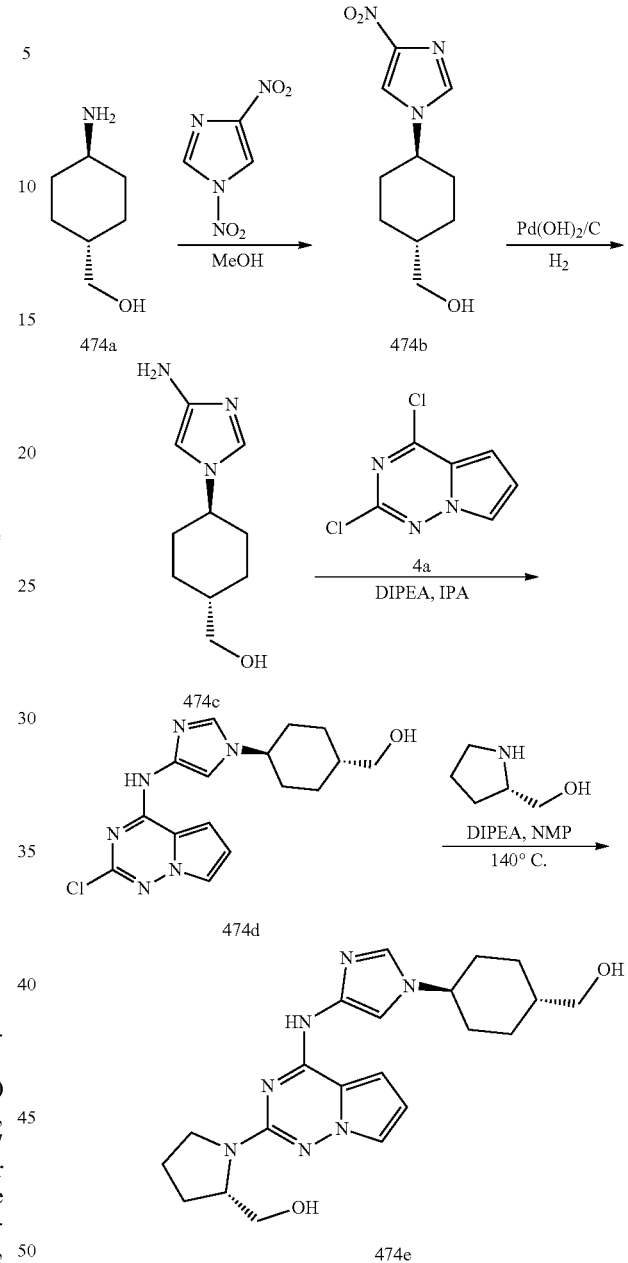

Preparation of ((S)-1-(4-((1-(((trans)-4-(hydroxymethyl)cyclohexyl)-1H-imidazol-4-yl)amino)pyrrolo[2,1-f][1,2,4]triazin-2-yl)pyrrolidin-2-yl)methanol (474e)

Step-1: Preparation of ((trans)-4-(4-nitro-1H-imidazol-1-yl)cyclohexyl)methanol (474b)

Reaction of 1,4-dinitro-1H-imidazole (1 g, 6.33 mmol) with ((trans)-4-aminocyclohexyl)methanol hydrochloride (474a) (1.07 g, 6.46 mmol; CAS #1504-49-0) using DIEA (1.1 mL, 6.30 mmol) in MeOH (20 mL) as reported in step-2 of General scheme for preparation of 3-substituted-(4-amino-1H-imidazol-1-yl) gave after work-up and purification by flash column chromatography [silica gel 24 g, eluting with ethyl acetate/MeOH (9:1) in hexanes from 50-100%] ((trans)-4-(4-nitro-1H-imidazol-1-yl)cyclohexyl)methanol (474b) (961 mg, 67% yield) as a yellow solid; $^1$H NMR (300 MHz, DMSO-d$_6$, D$_2$O exchange) δ 8.50 (s, 1H), 7.94 (s, 1H), 4.13 (m, 1H), 3.26 (d, J=6.2 Hz, 2H), 2.13-1.94 (m, 2H), 1.94-1.60 (m, 4H), 1.45 (t, J=10.2 Hz, 1H), 1.07 (m, 2H).

Step-2: Preparation of ((trans)-4-(4-amino-1H-imidazol-1-yl)cyclohexyl)methanol (474c)

Reduction of nitro to amine of ((trans)-4-(4-nitro-1H-imidazol-1-yl)cyclohexyl)methanol (474b) (400 mg, 1.776 mmol) in MeOH (20 mL) using Palladium hydroxide on carbon, 20 wt. % loading (dry basis), matrix carbon, wet support (125 mg, 0.178 mmol) as reported in step-3 of General scheme for preparation of 3-substituted-(4-amino-1H-imidazol-1-yl) gave ((trans)-4-(4-amino-1H-imidazol-1-yl)cyclohexyl)methanol (474c) (347 mg, 100% yield) as a yellow oil which was used directly for next step without further purification. MS (ES+): 196.1 (M+1).

Step-3: Preparation of ((trans)-4-(4-((2-chloropyrrolo[2,1-f][1,2,4]triazin-4-yl)amino)-1H-imidazol-1-yl)cyclohexyl)methanol (474d)

Compound 474d was prepared from 2,4-dichloropyrrolo[2,1-f][1,2,4]triazine (4a) (355 mg, 1.888 mmol) in 2-Propanol (10 mL) using DIPEA (0.9 mL, 5.15 mmol), ((trans)-4-(4-amino-1H-imidazol-1-yl)cyclohexyl)methanol (474c) (347 mg, 1.777 mmol) and heating at 90° C. for 3 h according to the procedure reported in step-1 of scheme 183. This gave after workup and purification by flash column chromatography [silica gel (12 g), eluting with MeOH in DCM from 0-20%] ((trans)-4-(4-((2-chloropyrrolo[2,1-f][1,2,4]triazin-4-yl)amino)-1H-imidazol-1-yl)cyclohexyl)methanol (474d) (518 mg, 84% yield) as a yellow foam. $^1$H NMR (300 MHz, DMSO-d$_6$) δ 11.14 (s, 1H), 7.72 (dd, J=2.6, 1.6 Hz, 1H), 7.68 (d, J=1.5 Hz, 1H), 7.51 (d, J=1.5 Hz, 1H), 7.35 (d, J=4.3 Hz, 1H), 6.68 (dd, J=4.4, 2.6 Hz, 1H), 4.49 (t, J=5.3 Hz, 1H), 4.12-4.02 (m, 1H), 3.26 (m, 2H), 2.07 (m, 2H), 1.87 (m, 2H), 1.78-1.57 (m, 2H), 1.45 (s, 1H), 1.17-0.97 (m, 2H); MS (ES+): 347.2 (M+1).

Step-4: Preparation of ((S)-1-(4-((1-((trans)-4-(hydroxymethyl)cyclohexyl)-1H-imidazol-4-yl)amino)pyrrolo[2,1-f][1,2,4]triazin-2-yl)pyrrolidin-2-yl)methanol (474e)

Compound 474e was prepared from ((trans)-4-(4-((2-chloropyrrolo[2,1-f][1,2,4]triazin-4-yl)amino)-1H-imidazol-1-yl)cyclohexyl)methanol (474d) (120 mg, 0.346 mmol), (S)-pyrrolidin-2-ylmethanol (206 mg, 2.04 mmol), N-ethyl-N-isopropylpropan-2-amine (0.211 mL, 1.21 mmol) in NMP (1.5 mL) and heating at 140° C. for 150 mins in a microwave reactor according to the procedure reported in scheme 2. This gave after workup and purification by reverse phase column chromatography [C18 (RediSep 250× 30 mm), eluting with ACN in water (containing 0.1% HCl) from 0-100%] ((S)-1-(4-((1-((trans)-4-(hydroxymethyl)cyclohexyl)-1H-imidazol-4-yl)amino)pyrrolo[2,1-f][1,2,4]triazin-2-yl)pyrrolidin-2-yl)methanol (474e) (71 mg, 50% yield) HCl salt as a white solid; $^1$H NMR (300 MHz, DMSO-d$_6$, D$_2$O exchange) δ 8.94 (s, 1H), 7.78 (s, 1H), 7.52 (s, 1H), 6.95 (s, 1H), 6.52 (t, J=3.1 Hz, 1H), 4.40-4.19 (m, 1H), 4.07 (s, 1H), 3.64 (s, 1H), 3.43 (s, 1H), 3.39-3.21 (m, 4H), 2.24-2.04 (m, 2H), 2.04-1.69 (m, 8H), 1.47 (s, 1H), 1.10 (m, 2H); MS (ES+): 412.2 (M+1); MS (ES−): 410.2 (M−1). HPLC purity: 97.50%.

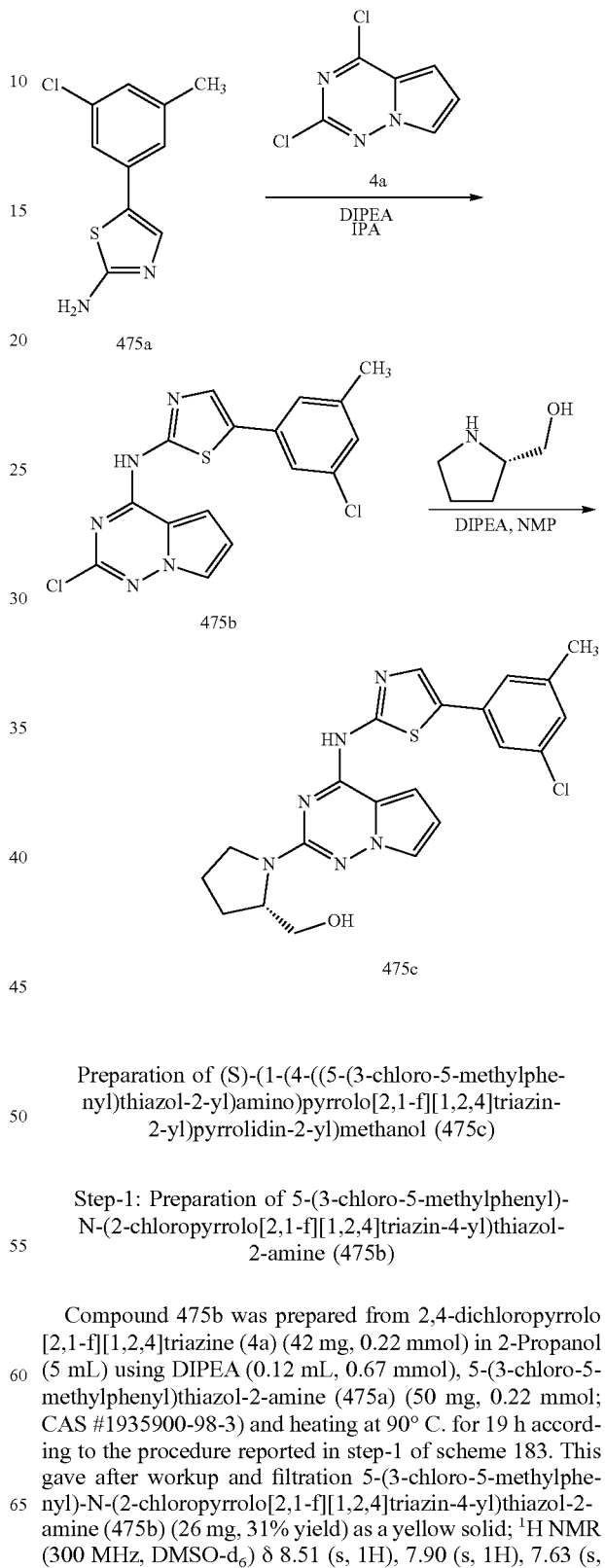

Scheme 475

Preparation of (S)-(1-(4-((5-(3-chloro-5-methylphenyl)thiazol-2-yl)amino)pyrrolo[2,1-f][1,2,4]triazin-2-yl)pyrrolidin-2-yl)methanol (475c)

Step-1: Preparation of 5-(3-chloro-5-methylphenyl)-N-(2-chloropyrrolo[2,1-f][1,2,4]triazin-4-yl)thiazol-2-amine (475b)

Compound 475b was prepared from 2,4-dichloropyrrolo[2,1-f][1,2,4]triazine (4a) (42 mg, 0.22 mmol) in 2-Propanol (5 mL) using DIPEA (0.12 mL, 0.67 mmol), 5-(3-chloro-5-methylphenyl)thiazol-2-amine (475a) (50 mg, 0.22 mmol; CAS #1935900-98-3) and heating at 90° C. for 19 h according to the procedure reported in step-1 of scheme 183. This gave after workup and filtration 5-(3-chloro-5-methylphenyl)-N-(2-chloropyrrolo[2,1-f][1,2,4]triazin-4-yl)thiazol-2-amine (475b) (26 mg, 31% yield) as a yellow solid; $^1$H NMR (300 MHz, DMSO-d$_6$) δ 8.51 (s, 1H), 7.90 (s, 1H), 7.63 (s, 1H), 7.48 (s, 1H), 7.35 (s, 1H), 7.30-7.23 (m, 1H), 6.73 (s, 1H), 6.35 (d, J=4.4 Hz, 1H), 2.40 (s, 3H); MS (ES+): 377.0 (M+1).

Step-2: Preparation of (S)-(1-(4-((5-(3-chloro-5-methylphenyl)thiazol-2-yl)amino)pyrrolo[2,1-f][1,2,4]triazin-2-yl)pyrrolidin-2-yl)methanol (475c)

Compound 475c was prepared from 5-(3-chloro-5-methylphenyl)-N-(2-chloropyrrolo[2,1-f][1,2,4]triazin-4-yl)thiazol-2-amine (475b) (25 mg, 0.07 mmol), (S)-pyrrolidin-2-ylmethanol (0.02 mL, 0.20 mmol), N-ethyl-N-isopropylpropan-2-amine (0.04 mL, 0.20 mmol) in NMP (1.5 mL) and heating at 150° C. for 30 mins in a microwave reactor according to the procedure reported in scheme 2. This gave after workup and purification by flash column chromatography [silica (12 g), eluting with MeOH in DCM from 0-20%] followed by reverse phase column chromatography [C18 (50 g), eluting with ACN in water (containing 0.1% HCl) from 0-100%] (S)-(1-(4-((5-(3-chloro-5-methylphenyl)thiazol-2-yl)amino)pyrrolo[2,1-f][1,2,4]triazin-2-yl)pyrrolidin-2-yl)methanol (475c) (12 mg, 41% yield) HCl salt as a yellow solid; $^1$H NMR (300 MHz, DMSO-d$_6$) δ 12.30 (s, 1H), 8.07 (s, 1H), 7.70 (s, 1H), 7.63 (s, 1H), 7.54 (dd, J=2.4, 1.6 Hz, 1H), 7.21 (s, 1H), 7.17 (d, J=2.0 Hz, 1H), 6.50 (dd, J=4.5, 2.4 Hz, 1H), 4.43-4.30 (m, 1H), 3.87 (m, 1H), 3.58-3.44 (m, 1H), 3.36 (m, 2H), 2.34-2.31 (m, 3H), 2.22-1.83 (m, 4H); MS (ES+): 441.1, 443.1 (M+1); MS (ES−): 439.1, 441.1 (M−1).

(0.07 g, 0.08 mmol) in t-BuOH/toluene (12 mL, 1:4) and heating at 110° C. for 21 h according to the procedure reported in step-3 of scheme 101. This gave after workup and purification by flash column chromatography [silica gel (12 g), eluting with DMA80 in DCM from 0-50%] followed by reverse phase column chromatography [C18 steel column, eluting with ACN in water (containing 0.1% HCl) from 0-100%] (S)-(1-(2-((5-(3,4,5-trimethoxyphenyl)thiazol-2-yl)amino)pyrrolo[2,1-f][1,2,4]triazin-4-yl)pyrrolidin-2-yl)methanol (476a) (0.04 g, 20% yield) HCl salt as a yellow solid; $^1$H NMR (300 MHz, DMSO-d$_6$) δ 7.88 (s, 1H), 7.69-7.60 (m, 1H), 6.95 (d, J=5.1 Hz, 2H), 6.86 (s, 1H), 6.61 (dd, J=4.6, 2.6 Hz, 1H), 4.83-4.69 (m, 1H), 4.05 (m, 1H), 3.96-3.87 (m, 1H), 3.84 (s, 7H), 3.67 (s, 3H), 3.51 (m, 1H), 2.30-1.84 (m, 4H); MS (ES+): 483.1 (M+1); MS (ES−): 481.1 (M−1). HPLC purity: 98.89%.

Scheme 476

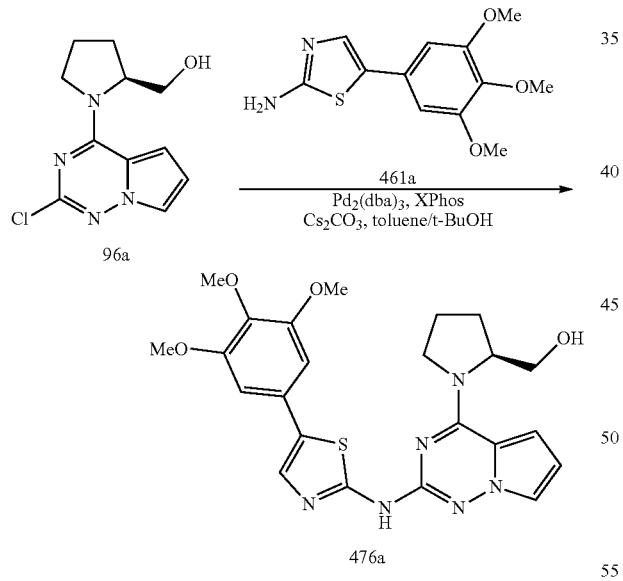

476a

Preparation of (S)-(1-(2-((5-(3,4,5-trimethoxyphenyl)thiazol-2-yl)amino)pyrrolo[2,1-f][1,2,4]triazin-4-yl)pyrrolidin-2-yl)methanol (476a)

Compound 476a was prepared from (S)-(1-(2-chloropyrrolo[2,1-f][1,2,4]triazin-4-yl)pyrrolidin-2-yl)methanol (96a) (200 mg, 0.68 mmol), 5-(3,4,5-trimethoxyphenyl)thiazol-2-amine (461a) (203 mg, 0.81 mmol), dicyclohexyl(2',4',6'-triisopropylbiphenyl-2-yl)phosphine (XPhos, 0.08 g, 0.16 mmol), cesium carbonate (0.451 g, 1.385 mmol), Pd$_2$(dba)$_3$ Scheme 477

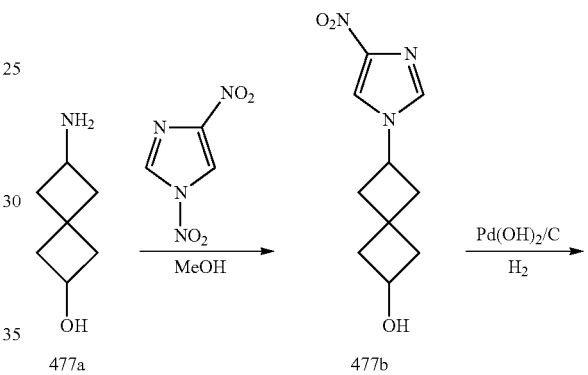

477a     477b

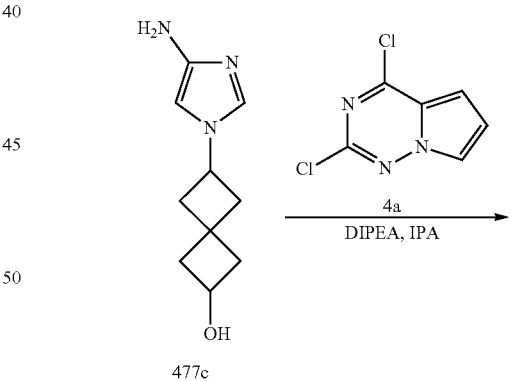

477c

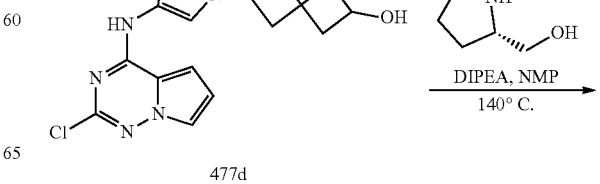

477d

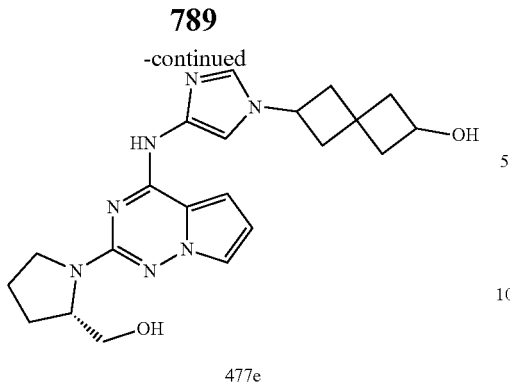

477e

Preparation of (S)-6-(4-((2-(2-(hydroxymethyl)pyrrolidin-1-yl)pyrrolo[2,1-f][1,2,4]triazin-4-yl)amino)-1H-imidazol-1-yl)spiro[3.3]heptan-2-ol (477e)

Step-1: Preparation of 6-(4-nitro-1H-imidazol-1-yl)spiro[3.3]heptan-2-ol (477b)

Reaction of 1,4-dinitro-1H-imidazole (485 mg, 3.07 mmol) with 6-aminospiro[3.3]heptan-2-ol (477a) (502 mg, 3.07 mmol; CAS #1820979-19-8) using DIPEA (0.6 mL, 3.44 mmol) in MeOH (20 mL) as reported in step-2 of General scheme for preparation of 3-substituted-(4-amino-1H-imidazol-1-yl) gave after work-up and purification by flash column chromatography [silica gel 24 g, eluting with ethyl acetate/MeOH (9:1) in hexanes from 50-100%] 6-(4-nitro-1H-imidazol-1-yl)spiro[3.3]heptan-2-ol (477b) (587 mg, 86% yield) as a yellow solid; $^1$H NMR (300 MHz, DMSO-$d_6$, $D_2O$ exchange) δ 8.50 (d, J=1.5 Hz, 1H), 7.91 (d, J=1.5 Hz, 1H), 4.71 (p, J=8.4 Hz, 1H), 4.00 (p, J=7.3 Hz, 1H), 2.42 (m, 5H), 2.27 (m, 1H), 1.90 (m, 2H).

Step-2: Preparation of 6-(4-amino-1H-imidazol-1-yl)spiro[3.3]heptan-2-ol (477c)

Reduction of nitro to amine of 6-(4-nitro-1H-imidazol-1-yl)spiro[3.3]heptan-2-ol (477b) (295 mg, 1.322 mmol) in MeOH (20 mL) using Palladium hydroxide on carbon, 20 wt. % loading (dry basis), matrix carbon, wet support (92 mg, 0.131 mmol) as reported in step-3 of General scheme for preparation of 3-substituted-(4-amino-1H-imidazol-1-yl) gave 6-(4-amino-1H-imidazol-1-yl)spiro[3.3]heptan-2-ol (477c) (255 mg, 100% yield) as a yellow oil which was used directly for next step without further purification; MS (ES+): 194.1 (M+1).

Step-3: Preparation of 6-(4-((2-chloropyrrolo[2,1-f][1,2,4]triazin-4-yl)amino)-1H-imidazol-1-yl)spiro[3.3]heptan-2-ol (477d)

Compound 477d was prepared from 2,4-dichloropyrrolo[2,1-f][1,2,4]triazine (4a) (251 mg, 1.335 mmol) in 2-Propanol (10 mL) using DIPEA (0.6 mL, 3.44 mmol), 6-(4-amino-1H-imidazol-1-yl)spiro[3.3]heptan-2-ol (477c) (255 mg, 1.320 mmol) and heating at 90° C. for 3 h according to the procedure reported in step-1 of scheme 183. This gave after workup and filtration 6-(4-((2-chloropyrrolo[2,1-f][1,2,4]triazin-4-yl)amino)-1H-imidazol-1-yl)spiro[3.3]heptan-2-ol (477d) (345 mg, 76% yield) as a yellow solid; $^1$H NMR (300 MHz, DMSO-$d_6$) δ 11.13 (s, 1H), 7.72 (dd, J=2.6, 1.5 Hz, 1H), 7.68 (d, J=1.6 Hz, 1H), 7.49 (d, J=1.6 Hz, 1H), 7.35 (d, J=4.4 Hz, 1H), 6.68 (dd, J=4.5, 2.6 Hz, 1H), 4.96 (d, J=6.3 Hz, 1H), 4.65 (p, J=8.2 Hz, 1H), 4.00 (p, J=7.3 Hz, 1H), 2.59-2.48 (m, 1H), 2.48-2.38 (m, 2H), 2.38-2.22 (m, 3H), 2.01-1.83 (m, 2H); MS (ES+): 345.1 (M+1).

Step-4: Preparation of (S)-6-(4-((2-(2-(hydroxymethyl)pyrrolidin-1-yl)pyrrolo[2,1-f][1,2,4]triazin-4-yl)amino)-1H-imidazol-1-yl)spiro[3.3]heptan-2-ol (477e)

Compound 477e was prepared from 6-(4-((2-chloropyrrolo[2,1-f][1,2,4]triazin-4-yl)amino)-1H-imidazol-1-yl)spiro[3.3]heptan-2-ol (477d) (109 mg, 0.316 mmol), (S)-pyrrolidin-2-ylmethanol (151 mg, 1.49 mmol), N-ethyl-N-isopropylpropan-2-amine (0.196 mL, 1.12 mmol) in NMP (1.5 mL) and heating at 140° C. for 220 mins in a microwave reactor according to the procedure reported in scheme 2. This gave after workup and purification by reverse phase column chromatography [C18 (RediSep 250×30 mm), eluting with ACN in water (containing 0.1% HCl) from 0-100%] (S)-6-(4-((2-(2-(hydroxymethyl)pyrrolidin-1-yl)pyrrolo[2,1-f][1,2,4]triazin-4-yl)amino)-1H-imidazol-1-yl)spiro[3.3]heptan-2-ol (477e) HCl salt as a white solid; MS (ES+): 410.2 (M+1); MS (ES−): 408.2 (M−1). HPLC purity: 97.68%. (72 mg, 57% yield) HCl salt as a light brown solid; $^1$H NMR (300 MHz, DMSO-$d_6$, $D_2O$ exchange) δ 8.88 (s, 1H), 7.73 (d, J=1.7 Hz, 1H), 7.52 (t, J=2.0 Hz, 1H), 6.91 (dd, J=4.6, 1.5 Hz, 1H), 6.55 (dd, J=4.5, 2.5 Hz, 1H), 4.84 (p, J=8.3 Hz, 1H), 4.12-3.99 (m, 2H), 3.60 (dd, J=10.3, 4.3 Hz, 1H), 3.53-3.26 (m, 3H), 2.65-2.56 (m, 1H), 2.52-2.39 (m, 4H), 2.37-2.21 (m, 1H), 2.07-1.78 (m, 6H); MS (ES+): 410.2 (M+1); MS(ES−): 408.2 (M−1). HPLC purity 97.68%.

Scheme 478

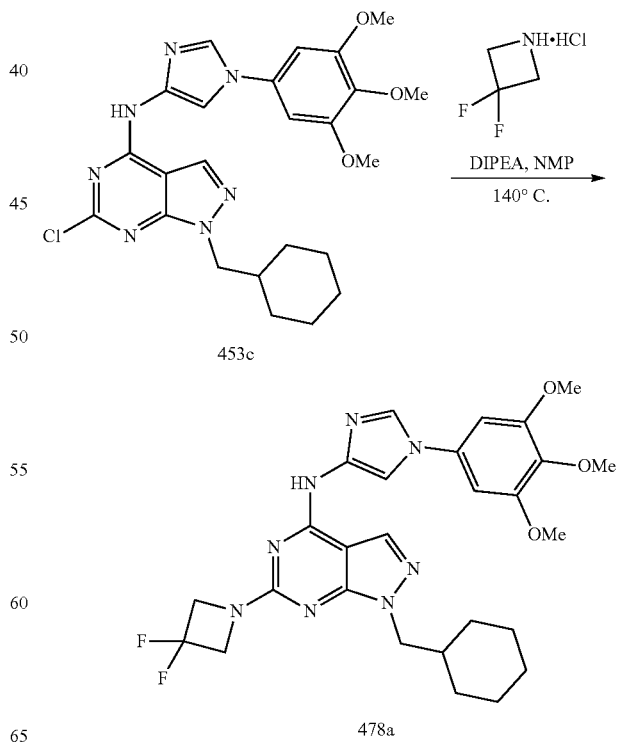

453c

478a

Preparation of 1-(cyclohexylmethyl)-6-(3,3-difluoroazetidin-1-yl)-N-(1-(3,4,5-trimethoxyphenyl)-1H-imidazol-4-yl)-1H-pyrazolo[3,4-d]pyrimidin-4-amine (478a)

Compound 478a was prepared from 6-chloro-1-(cyclohexylmethyl)-N-(1-(3,4,5-trimethoxyphenyl)-1H-imidazol-4-yl)-1H-pyrazolo[3,4-d]pyrimidin-4-amine (453c) (200 mg, 0.40 mmol), 3,3-difluoroazetidine hydrochloride (156 mg, 1.21 mmol), N-ethyl-N-isopropylpropan-2-amine (0.21 mL, 1.21 mmol) in NMP (3 mL) and heating at 140° C. for 50 mins on a microwave reactor according to the procedure reported in scheme 2. This gave after workup and purification by flash column chromatography [silica gel (12 g), eluting with DMA80 in DCM from 0-50%] followed by reverse phase column chromatography [C18 steel column, eluting with ACN in water (containing 0.1% HCl) from 0-100%] 1-(cyclohexylmethyl)-6-(3,3-difluoroazetidin-1-yl)-N-(1-(3,4,5-trimethoxyphenyl)-1H-imidazol-4-yl)-1H-pyrazolo[3,4-d]pyrimidin-4-amine (478a) (40 mg, 18% yield) HCl salt as a white solid; $^1$H NMR (300 MHz, DMSO-$d_6$) δ 11.07 (s, 1H, $D_2O$ exchangeable), 8.65 (s, 1H), 8.24 (s, 1H), 8.04 (d, J=1.6 Hz, 1H), 7.03 (s, 2H), 4.64-4.55 (m, 4H), 4.03 (d, J=7.1 Hz, 2H), 3.88 (s, 6H), 3.69 (s, 3H), 1.99-1.83 (m, 1H), 1.69-1.54 (m, 3H), 1.53-1.42 (m, 2H), 1.21-1.08 (m, 3H), 1.04-0.87 (m, 2H); $^{19}$F NMR (282 MHz, DMSO-$d_6$) δ −99.29; MS (ES+): 555.2 (M+1); HPLC purity: 95.99%; Analysis calculated for $C_{27}H_{32}F_2N_8O_3$.(HCl). 1.75 ($H_2O$): C, 52.09; H, 5.91; Cl, 5.69; N, 18.00. Found: C, 52.19; H, 5.86; Cl, 5.48; N, 17.87.

Scheme 479

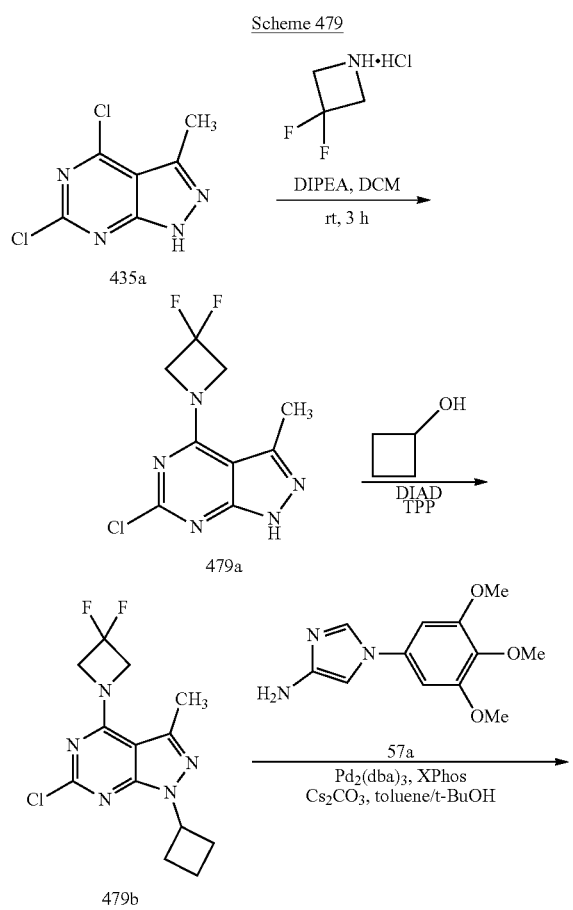

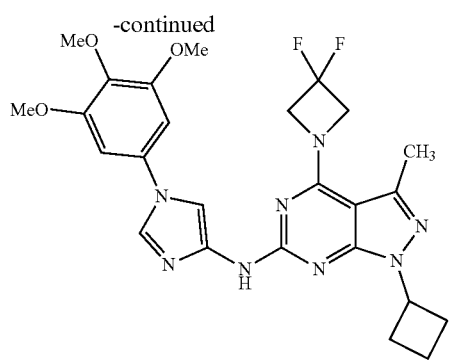

479c

Preparation of 1-cyclobutyl-4-(3,3-difluoroazetidin-1-yl)-3-methyl-N-(1-(3,4,5-trimethoxyphenyl)-1H-imidazol-4-yl)-1H-pyrazolo[3,4-d]pyrimidin-6-amine (479c)

Step-1: Preparation of 6-chloro-4-(3,3-difluoroazetidin-1-yl)-3-methyl-1H-pyrazolo[3,4-d]pyrimidine (479a)

Compound 479a was prepared from 4,6-dichloro-3-methyl-1H-pyrazolo[3,4-d]pyrimidine (435a) (549 mg, 2.70 mmol) in DCM (5 mL) using 3,3-difluoroazetidine hydrochloride (350 mg, 2.70 mmol), DIPEA (1.42 mL, 8.11 mmol) and stirring at room temperature for 3 h according to the procedure reported in step-1 of scheme 96. This gave after workup and purification by flash column chromatography [silica (12 g), eluting with EtOAc in hexane from 0-70%] 6-chloro-4-(3,3-difluoroazetidin-1-yl)-3-methyl-1H-pyrazolo[3,4-d]pyrimidine (479a) (612 mg, 87% yield) as a white solid; $^1$H NMR (300 MHz, DMSO-$d_6$) δ 13.42 (s, 1H), 4.85 (t, J=12.4 Hz, 4H), 2.49 (s, 3H); MS (ES+): 260.0 (M+1).

Step-2: Preparation of 6-chloro-1-cyclobutyl-4-(3,3-difluoroazetidin-1-yl)-3-methyl-1H-pyrazolo[3,4-d]pyrimidine (479b)

Compound 479b was prepared from 6-chloro-4-(3,3-difluoroazetidin-1-yl)-3-methyl-1H-pyrazolo[3,4-d]pyrimidine (479a) (300 mg, 1.16 mmol) in THF (4 mL) using triphenylphosphine (758 mg, 2.89 mmol), cyclobutanol (208 mg, 2.89 mmol), DIAD (0.56 mL, 2.89 mmol) and stirring at room temperature overnight according to the procedure reported in step-2 of scheme 435. This gave after workup and purification by flash column chromatography [silica (12 g), eluting with EtOAc in hexane from 0-60%] 6-chloro-1-cyclobutyl-4-(3,3-difluoroazetidin-1-yl)-3-methyl-1H-pyrazolo[3,4-d]pyrimidine (479b) (170 mg, 47% yield) as clear oil; MS (ES+): 314.1 (M+1).

Step-3: Preparation of 1-cyclobutyl-4-(3,3-difluoroazetidin-1-yl)-3-methyl-N-(1-(3,4,5-trimethoxyphenyl)-1H-imidazol-4-yl)-1H-pyrazolo[3,4-d]pyrimidin-6-amine (479c)

Compound 479c was prepared from 6-chloro-1-cyclobutyl-4-(3,3-difluoroazetidin-1-yl)-3-methyl-1H-pyrazolo[3,4-d]pyrimidine (479b) (270 mg, 0.86 mmol), 1-(3,4, 5-trimethoxyphenyl)-1H-imidazol-4-amine (57a) (257 mg, 1.03 mmol), dicyclohexyl(2',4',6'-triisopropylbiphenyl-2-yl) phosphine (XPhos, 164 mg, 0.34 mmol), cesium carbonate (915 mg, 2.81 mmol), Pd$_2$(dba)$_3$ (147 mg, 0.16 mmol) in t-BuOH/toluene (11 mL, 1:2.67) and heating at 110° C. for 12 h according to the procedure reported in step-3 of scheme 101. This gave after workup and purification by flash column chromatography [silica gel (12 g), eluting with DMA80 in DCM from 0-50%] followed by reverse phase column chromatography [C18 steel column, eluting with ACN in water (containing 0.1% HCl) from 0-100%] 1-cyclobutyl-4-(3,3-difluoroazetidin-1-yl)-3-methyl-N-(1-(3,4,5-trimethoxyphenyl)-1H-imidazol-4-yl)-1H-pyrazolo[3,4-d]pyrimidin-6-amine (479c) (2.5 mg, 1% yield) HCl salt as a white solid; $^1$H NMR (300 MHz, DMSO-d$_6$) δ 9.99 (s, 1H, D$_2$O exchangeable), 9.06 (s, 1H), 7.99 (s, 1H), 7.12 (s, 2H), 5.27-5.14 (m, 1H), 4.86 (t, J=12.5 Hz, 4H), 3.90 (s, 6H), 3.71 (s, 3H), 2.67-2.58 (m, 2H), 2.49 (s, 3H), 2.39-2.30 (m, 2H), 1.87-1.77 (m, 2H); $^{19}$F NMR (282 MHz, DMSO-d$_6$) δ –99.17; MS (ES+): 527.2 (M+1); HPLC purity: 93.08%.

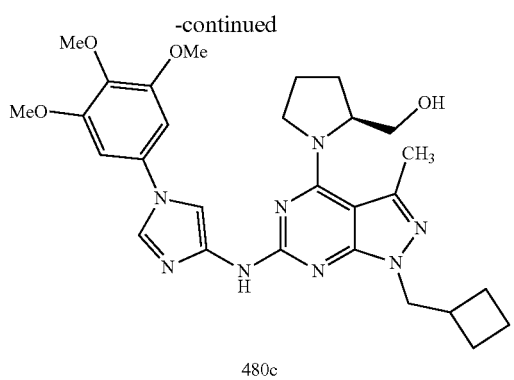

480c

Preparation of (S)-(1-(1-(cyclobutylmethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (480c)

Step-1: Preparation of(S)-4-(2-(((tert-butyldimethylsilyl)oxy)methyl)pyrrolidin-1-yl)-6-chloro-1-(cyclobutylmethyl)-3-methyl-1H-pyrazolo[3,4-d]pyrimidine (480a)

Compound 480a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (350 mg, 0.92 mmol) in THF (4 mL) using triphenylphosphine (601 mg, 2.29 mmol), cyclobutylmethanol (197 mg, 2.29 mmol), DIAD (0.445 mL, 2.291 mmol) and stirring at room temperature overnight according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-(cyclobutylmethyl)-3-methyl-1H-pyrazolo[3,4-d]pyrimidine (480a) (275 mg, 67% yield) as a clear oil; MS (ES+): 450.2 (M+1).

Step-2: Preparation of(S)-4-(2-(((tert-butyldimethylsilyl)oxy)methyl)pyrrolidin-1-yl)-1-(cyclobutylmethyl)-3-methyl-N-(1-(3,4,5-trimethoxyphenyl)-1H-imidazol-4-yl)-1H-pyrazolo[3,4-d]pyrimidin-6-amine (480b)

Compound 480b was prepared from (S)-4-(2-(((tert-butyldimethylsilyl)oxy)methyl)pyrrolidin-1-yl)-6-chloro-1-(cyclobutylmethyl)-3-methyl-1H-pyrazolo[3,4-d]pyrimidine (480a) (275 mg, 0.61 mmol), 1-(3,4,5-trimethoxyphenyl)-1H-imidazol-4-amine (57a) (183 mg, 0.73 mmol), dicyclohexyl(2',4',6'-triisopropylbiphenyl-2-yl) phosphine (XPhos, 117 mg, 0.24 mmol), cesium carbonate (697 mg, 2.14 mmol), Pd$_2$(dba)$_3$ (112 mg, 0.122 mmol) in t-BuOH/toluene (11 mL, 1:2.67) and heating at 110° C. for 12 h according to the procedure reported in step-3 of scheme 101. This gave after workup and purification by flash column chromatography [silica gel (24 g), eluting with DMA80 in DCM from 0-50%] followed by reverse phase column chromatography [C18 steel column, eluting with ACN in water (containing 0.1% HCl) from 0-100%] (S)-4-(2-(((tert-butyldimethylsilyl)oxy)methyl)pyrrolidin-1-yl)-1-(cyclobutylmethyl)-3-methyl-N-(1-(3,4,5-trimethoxyphenyl)-1H-imidazol-4-yl)-1H-pyrazolo[3,4-d]pyrimidin-6-amine (480b), MS (ES+): 663.3 (M+1).

Scheme 480

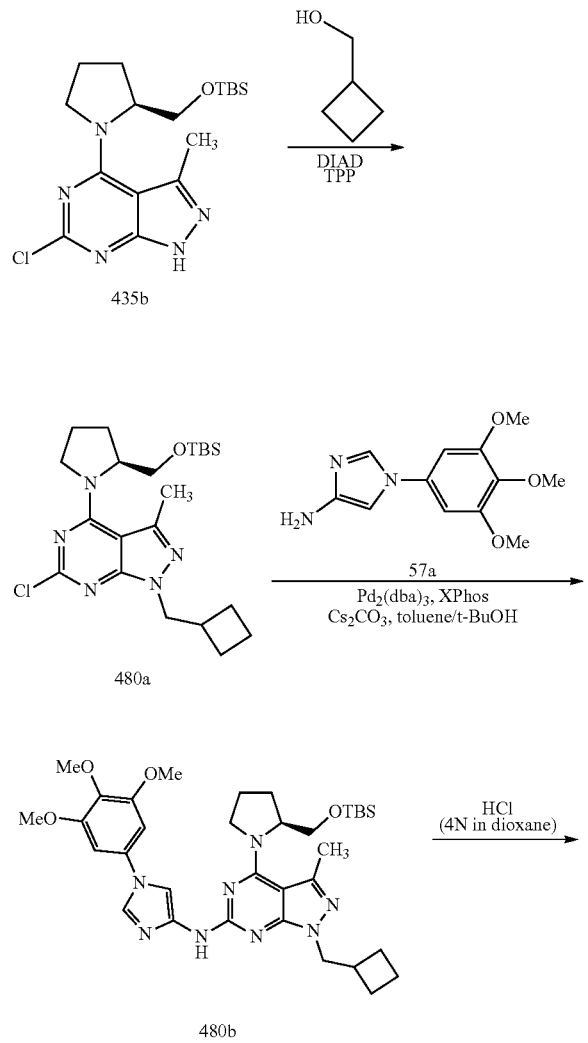

Step-3: Preparation of (S)-(1-(1-(cyclobutylmethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (480c)

To a solution of (S)-4-(2-(((tert-butyldimethylsilyl)oxy)methyl)pyrrolidin-1-yl)-1-(cyclobutylmethyl)-3-methyl-N-(1-(3,4,5-trimethoxyphenyl)-1H-imidazol-4-yl)-1H-pyrazolo[3,4-d]pyrimidin-6-amine (480b) (from step-2 above) in MeOH/DCM (10 mL) was added 4N HCl in dioxane (2.29 mL, 9.16 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (S)-(1-(1-(cyclobutylmethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (480c) (21 mg, 6% yield) HCl salt as a yellow solid; $^1$H NMR (300 MHz, DMSO-$d_6$) δ 10.35 (s, 1H, $D_2O$ exchangeable), 9.06 (s, 1H), 7.90 (d, J=1.7 Hz, 1H, $D_2O$ exchangeable), 7.10 (s, 2H), 5.58 (brs, 1H, $D_2O$ exchangeable), 4.74-4.63 (m, 1H), 4.24 (d, J=7.1 Hz, 2H), 3.89 (s, 6H), 3.87-3.76 (m, 2H), 3.70 (s, 3H), 3.64-3.51 (m, 2H), 2.85-2.72 (m, 1H), 2.54 (s, 3H), 2.09-1.89 (m, 6H), 1.85-1.76 (m, 4H); MS (ES$^+$) 549.3 (M+1); HPLC, purity: 95.90%; Analysis calculated for $C_{28}H_{36}N_8O_4$·2.5 (HCl) ·3.25 ($H_2O$): C, 48.16; H, 6.50; Cl, 12.69; N, 16.05. Found: C, 48.30; H, 6.26; Cl, 12.50; N, 16.05.

Scheme 481

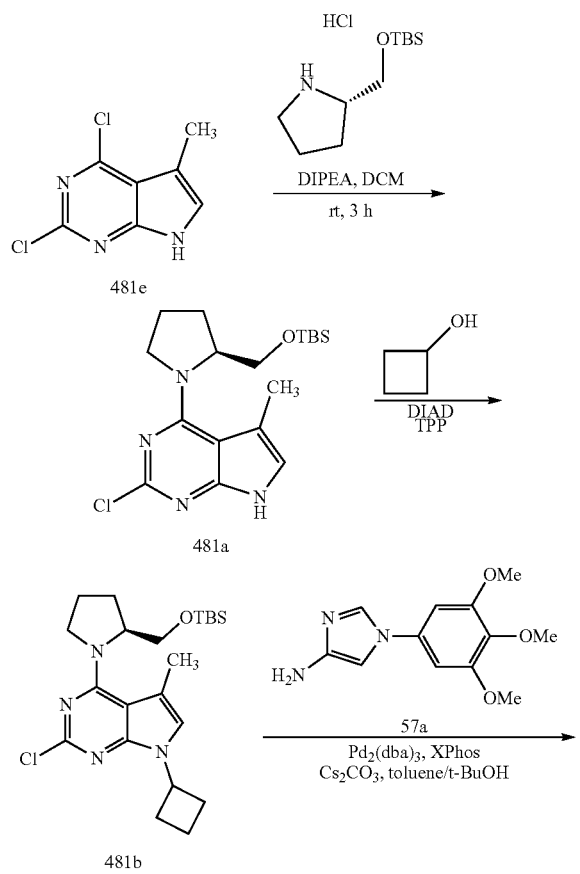

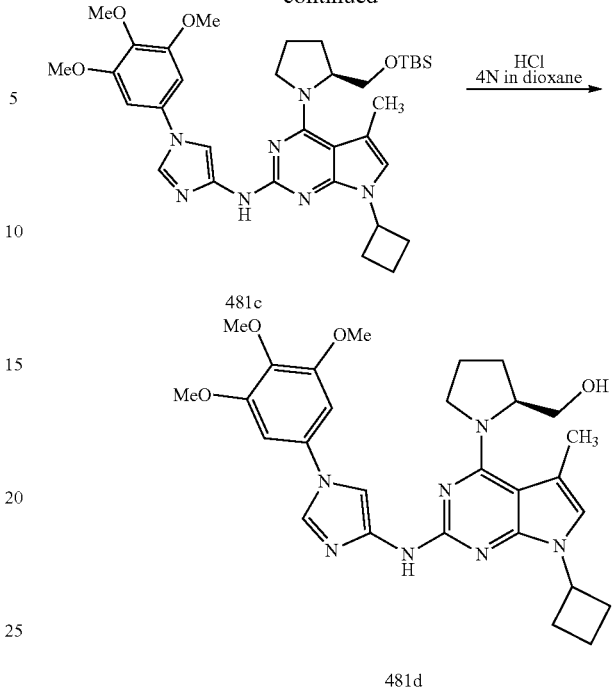

Preparation of (S)-(1-(7-cyclobutyl-5-methyl-2-((1-(3,4,5-trimethoxyphenyl)-1H-imidazol-4-yl)amino)-7H-pyrrolo[2,3-d]pyrimidin-4-yl)pyrrolidin-2-yl)methanol (481d)

Step-1: Preparation of (S)-4-(2-(((tert-butyldimethylsilyl)oxy)methyl)pyrrolidin-1-yl)-2-chloro-5-methyl-7H-pyrrolo[2,3-d]pyrimidine (481a)

Compound 481a was prepared from 2,4-dichloro-5-methyl-7H-pyrrolo[2,3-d]pyrimidine (481e) (2 g, 9.90 mmol; CAS #1060815-86-2) in DCM (30 mL) using (S)-2-((tert-butyldimethylsilyloxy)methyl)pyrrolidine hydrochloride (2.49 g, 9.90), DIPEA (5.19 mL, 29.7 mmol) and stirring at room temperature for 3 h according to the procedure reported in step-1 of scheme 96. This gave after workup and purification by flash column chromatography [silica (24 g), eluting with EtOAc in hexane from 0-70%] (S)-4-(2-(((tert-butyldimethylsilyl)oxy)methyl)pyrrolidin-1-yl)-2-chloro-5-methyl-7H-pyrrolo[2,3-d]pyrimidine (481a) (2.6 g, 69% yield) as a white solid; MS (ES+): 381.2 (M+1).

Step-2: Preparation of (S)-4-(2-(((tert-butyldimethylsilyl)oxy)methyl)pyrrolidin-1-yl)-2-chloro-7-cyclobutyl-5-methyl-7H-pyrrolo[2,3-d]pyrimidine (481b)

Compound 481b was prepared from (S)-4-(2-(((tert-butyldimethylsilyl)oxy)methyl)pyrrolidin-1-yl)-2-chloro-5-methyl-7H-pyrrolo[2,3-d]pyrimidine (481a) (400 mg, 1.05 mmol) in THF (4 mL) using triphenylphosphine (826 mg, 3.15 mmol), cyclobutanol (227 mg, 3.15 mmol), DIAD (0.612 mL, 3.15 mmol) and stirring at room temperature overnight according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-2-chloro-7-cyclobutyl-5-methyl-7H-pyrrolo[2,3-d]pyrimidine (481b) (77 mg, 17% yield) as a clear oil; MS (ES+): 435.2 (M+1).

Step-3: Preparation of (S)-4-(2-(((tert-butyldimethylsilyl)oxy)methyl)pyrrolidin-1-yl)-7-cyclobutyl-5-methyl-N-(1-(3,4,5-trimethoxyphenyl)-1H-imidazol-4-yl)-7H-pyrrolo[2,3-d]pyrimidin-2-amine (481c)

Compound 481c was prepared from (S)-4-(2-(((tert-butyldimethylsilyl)oxy)methyl)pyrrolidin-1-yl)-2-chloro-7-cyclobutyl-5-methyl-7H-pyrrolo[2,3-d]pyrimidine (481b) (77 mg, 0.177 mmol), 1-(3,4,5-trimethoxyphenyl)-1H-imidazol-4-amine (57a) (52.9 mg, 0.21 mmol), dicyclohexyl(2',4',6'-triisopropylbiphenyl-2-yl)phosphine (XPhos, 33.7 mg, 0.071 mmol), cesium carbonate (202 mg, 0.62 mmol), Pd₂(dba)₃ (32.4 mg, 0.035 mmol) in t-BuOH/toluene (13 mL, 1:2.7) and heating at 110° C. for 12 h according to the procedure reported in step-3 of scheme 101. This gave after workup and purification by flash column chromatography [silica gel (24 g), eluting with DMA80 in DCM from 0-50%] (S)-4-(2-(((tert-butyldimethylsilyl)oxy)methyl)pyrrolidin-1-yl)-7-cyclobutyl-5-methyl-N-(1-(3,4,5-trimethoxyphenyl)-1H-imidazol-4-yl)-7H-pyrrolo[2,3-d]pyrimidin-2-amine (481c); MS (ES+): 648.4 (M+1).

Step-4: Preparation of (S)-(1-(7-cyclobutyl-5-methyl-2-((1-(3,4,5-trimethoxyphenyl)-1H-imidazol-4-yl)amino)-7H-pyrrolo[2,3-d]pyrimidin-4-yl)pyrrolidin-2-yl)methanol (481d)

To a solution of (S)-4-(2-(((tert-butyldimethylsilyl)oxy)methyl)pyrrolidin-1-yl)-7-cyclobutyl-5-methyl-N-(1-(3,4,5-trimethoxyphenyl)-1H-imidazol-4-yl)-7H-pyrrolo[2,3-d]pyrimidin-2-amine (481c) (from step-2 above) in MeOH/DCM (10 mL) was added 4N HCl in dioxane (0.44 mL, 1.77 mmol), stirred at room temperature for 20 min and concentrated in vacuum. The residue obtained was purified by reverse phase column chromatography [C18 steel column, eluting with ACN in water (containing 0.1% HCl) from 0-100%] followed by preparative HPLC [C18 steel column, eluting with ACN in water (containing 0.1% TFA) from 0-100%] to give (S)-(1-(7-cyclobutyl-5-methyl-2-((1-(3,4,5-trimethoxyphenyl)-1H-imidazol-4-yl)amino)-7H-pyrrolo[2,3-d]pyrimidin-4-yl)pyrrolidin-2-yl)methanol (481d) (3 mg, 3% yield) TFA salt as a white solid; $^1$H NMR (300 MHz, DMSO-d₆) δ 10.02 (s, 1H, D₂O exchangeable), 8.54 (s, 1H), 7.68 (s, 1H, D₂O exchangeable), 7.24 (s, 1H), 7.01 (s, 2H), 5.14-5.03 (m, 1H), 4.65-4.55 (m, 1H), 3.89 (s, 6H), 3.83-3.78 (m, 2H), 3.69 (s, 3H), 3.65-3.63 (m, 2H), 2.44-2.37 (m, 4H), 2.33 (s, 3H), 2.11-2.05 (m, 2H), 2.01-1.89 (m, 2H), 1.85-1.76 (m, 2H); $^{19}$F NMR (282 MHz, DMSO-d₆) δ -73.95 (From TFA salt); MS (ES+) 534.2 (M+1); HPLC purity: 96.07%.

Scheme 482

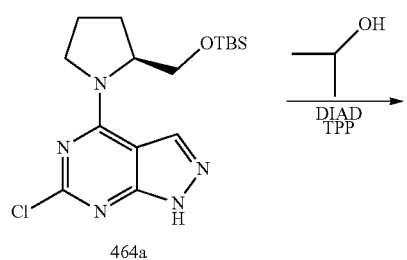

464a

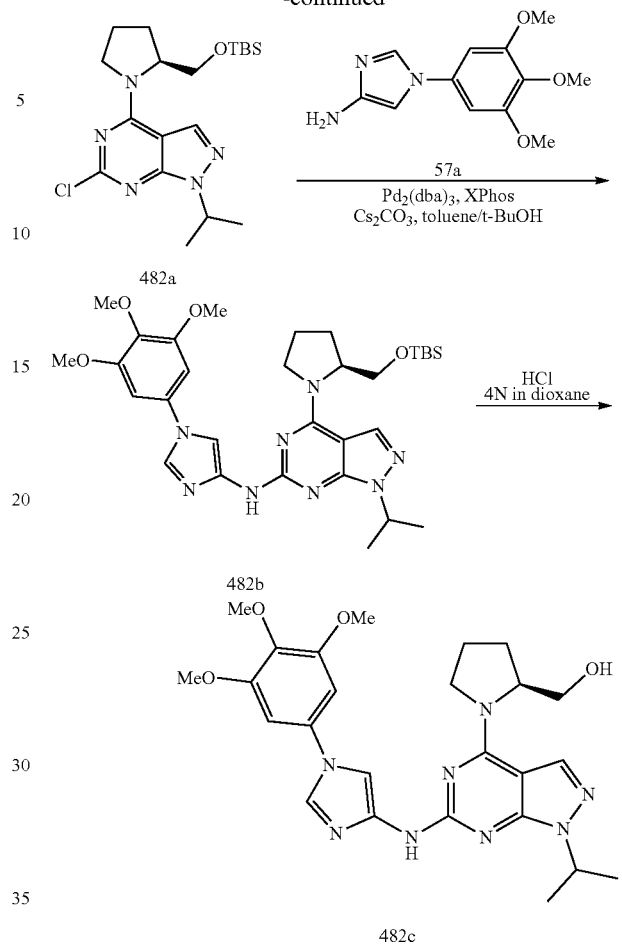

Preparation of (S)-(1-(1-isopropyl-6-((1-(3,4,5-trimethoxyphenyl)-1H-imidazol-4-yl)amino)-1H-pyrazolo[3,4-d]pyrimidin-4-yl)pyrrolidin-2-yl)methanol (482c)

Step-1: Preparation of (S)-4-(2-(((tert-butyldimethylsilyl)oxy)methyl)pyrrolidin-1-yl)-6-chloro-1-isopropyl-1H-pyrazolo[3,4-d]pyrimidine (482a)

Compound 482a was prepared from (S)-4-(2-(((tert-butyldimethylsilyl)oxy)methyl)pyrrolidin-1-yl)-6-chloro-1H-pyrazolo[3,4-d]pyrimidine (464a) (350 mg, 0.95 mmol) in THF using triphenylphosphine (624 mg, 2.378 mmol), propan-2-ol (143 mg, 2.38 mmol), DIAD (0.46 mL, 2.38 mmol) and stirring at room temperature overnight according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-isopropyl-1H-pyrazolo[3,4-d]pyrimidine (482a) (320 mg, 82% yield) as a clear oil; MS (ES+): 410.2 (M+1).

Step-2: Preparation of (S)-4-(2-(((tert-butyldimethylsilyl)oxy)methyl)pyrrolidin-1-yl)-1-isopropyl-N-(1-(3,4,5-trimethoxyphenyl)-1H-imidazol-4-yl)-1H-pyrazolo[3,4-d]pyrimidin-6-amine (482b)

Compound 482b was prepared from (S)-4-(2-(((tert-butyldimethylsilyl)oxy)methyl)pyrrolidin-1-yl)-6-chloro-1- isopropyl-1H-pyrazolo[3,4-d]pyrimidine (482a) (320 mg, 0.78 mmol), 1-(3,4,5-trimethoxyphenyl)-1H-imidazol-4-amine (57a) (233 mg, 0.94 mmol), dicyclohexyl(2',4',6'-triisopropylbiphenyl-2-yl)phosphine (XPhos, 149 mg, 0.31 mmol), cesium carbonate (890 mg, 2.73 mmol), Pd$_2$(dba)$_3$ (143 mg, 0.16 mmol) in t-BuOH/toluene (13 mL, 1:2.7) and heating at 110° C. for 12 h according to the procedure reported in step-3 of scheme 101. This gave after workup and purification by flash column chromatography [silica gel (24 g), eluting with DMA80 in DCM from 0-50%](S)-4-(2-(((tert-butyldimethylsilyl)oxy)methyl)pyrrolidin-1-yl)-1-isopropyl-N-(1-(3,4,5-trimethoxyphenyl)-1H-imidazol-4-yl)-1H-pyrazolo[3,4-d]pyrimidin-6-amine (482b) as a yellow solid; MS (ES+): 623.3 (M+1).

Step-3: Preparation of (S)-(1-(1-isopropyl-6-((1-(3,4,5-trimethoxyphenyl)-1H-imidazol-4-yl)amino)-1H-pyrazolo[3,4-d]pyrimidin-4-yl)pyrrolidin-2-yl)methanol (482c)

To a solution of (S)-4-(2-(((tert-butyldimethylsilyl)oxy)methyl)pyrrolidin-1-yl)-1-isopropyl-N-(1-(3,4,5-trimethoxyphenyl)-1H-imidazol-4-yl)-1H-pyrazolo[3,4-d]pyrimidin-6-amine (482b) (from step-2 above) in MeOH/DCM (10 mL) was added 4N HCl in dioxane (2.93 mL, 11.71 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (S)-(1-(1-isopropyl-6-((1-(3,4,5-trimethoxyphenyl)-1H-imidazol-4-yl)amino)-1H-pyrazolo[3,4-d]pyrimidin-4-yl)pyrrolidin-2-yl)methanol (482c) (140 mg, 35% yield) HCl salt as a white solid; $^1$H NMR (300 MHz, DMSO-d$_6$) δ 10.62-10.11 (m, 1H, D$_2$O exchangeable), 9.01 (s, 1H), 8.21-8.07 (m, 1H, D$_2$O exchangeable), 7.96-7.86 (m, 1H), 7.15-7.03 (m, 2H), 5.04-4.89 (m, 1H), 4.67-4.34 (m, 1H), 4.03-3.83 (m, 8H), 3.82-3.73 (m, 1H), 3.71 (s, 3H), 3.66-3.44 (m, 2H), 2.23-1.91 (m, 4H), 1.51-1.40 (m, 6H); MS (ES+): 509.3 (M+1); (ES−): 543.3 (M+Cl); HPLC purity: 99.64%.

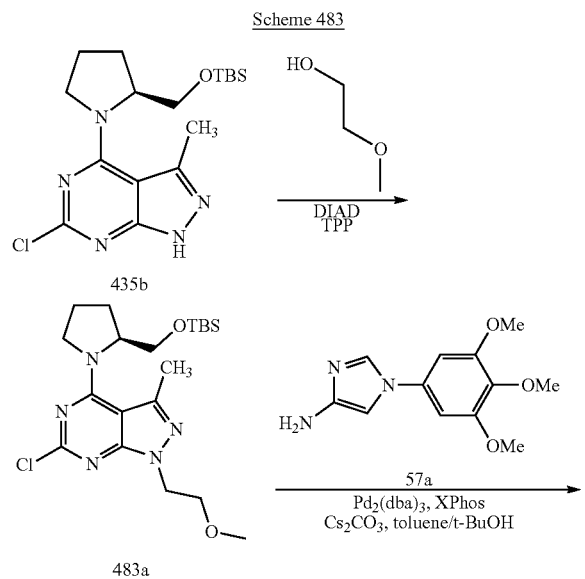

Scheme 483

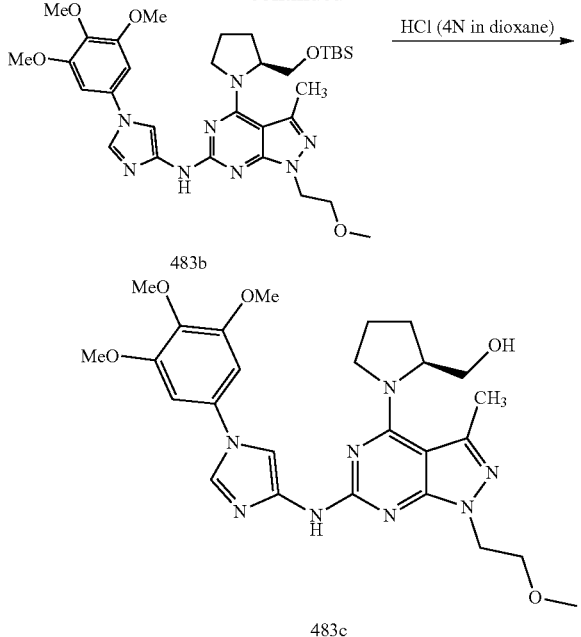

Preparation of (S)-(1-(1-(2-methoxyethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (483c)

Step-1: Preparation of (S)-4-(2-(((tert-butyldimethylsilyl)oxy)methyl)pyrrolidin-1-yl)-6-chloro-1-(2-methoxyethyl)-3-methyl-1H-pyrazolo[3,4-d]pyrimidine (483a)

Compound 483a was prepared from (S)-4-(2-(((tert-butyldimethylsilyl)oxy)methyl)pyrrolidin-1-yl)-6-chloro-3-methyl-1H-pyrazolo[3,4-d]pyrimidine (435b) (380 mg, 0.99 mmol) in THF (4 mL) using triphenylphosphine (652 mg, 2.49 mmol), 2-methoxyethanol (189 mg, 2.49 mmol), DIAD (0.484 mL, 2.487 mmol) and stirring at room temperature overnight according to the procedure reported in step-2 of scheme 435. This gave after workup and purification by flash column chromatography [silica (12 g), eluting with EtOAc in hexane from 0-60%] (S)-4-(2-(((tert-butyldimethylsilyl)oxy)methyl)pyrrolidin-1-yl)-6-chloro-1-(2-methoxyethyl)-3-methyl-1H-pyrazolo[3,4-d]pyrimidine (483a) (400 mg, 91% yield) as a clear oil; MS (ES+): 440.2 (M+1).

Step-2: Preparation of(S)-4-(2-(((tert-butyldimethylsilyl)oxy)methyl)pyrrolidin-1-yl)-1-(2-methoxyethyl)-3-methyl-N-(1-(3,4,5-trimethoxyphenyl)-1H-imidazol-4-yl)-1H-pyrazolo[3,4-d]pyrimidin-6-amine (483b)

Compound 483b was prepared from (S)-4-(2-(((tert-butyldimethylsilyl)oxy)methyl)pyrrolidin-1-yl)-6-chloro-1-(2-methoxyethyl)-3-methyl-1H-pyrazolo[3,4-d]pyrimidine (483a) (400 mg, 0.91 mmol), 1-(3,4,5-trimethoxyphenyl)-1H-imidazol-4-amine (57a) (295 mg, 1.18 mmol), dicyclohexyl(2',4',6'-triisopropylbiphenyl-2-yl)phosphine (XPhos, 173 mg, 0.364 mmol), cesium carbonate (1037 mg, 3.18 mmol), Pd$_2$(dba)$_3$ (166 mg, 0.18 mmol) in t-BuOH/toluene (11 mL, 1:2.67) and heating at 110° C. for 12 h according to the procedure reported in step-3 of scheme 101. This gave after workup and purification by flash column chromatography [silica gel (12 g), eluting with DMA80 in DCM from 0-50%] (S)-4-(2-(((tert-butyldimethylsilyl)oxy)methyl)pyrrolidin-1-yl)-1-(2-methoxyethyl)-3-methyl-N-(1-(3,4,5-trimethoxyphenyl)-1H-imidazol-4-yl)-1H-pyrazolo[3,4-d]pyrimidin-6-amine (483b) as a yellow solid; MS (ES+): 653.3 (M+1).

Step-3: Preparation of (S)-(1-(1-(2-methoxyethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (483c)

To a solution of (S)-4-(2-(((tert-butyldimethylsilyl)oxy)methyl)pyrrolidin-1-yl)-1-(2-methoxyethyl)-3-methyl-N-(1-(3,4,5-trimethoxyphenyl)-1H-imidazol-4-yl)-1H-pyrazolo[3,4-d]pyrimidin-6-amine (483b) (from step-2 above) in MeOH/DCM (10 mL) was added 4N HCl in dioxane (2.27 mL, 9.09 mmol), stirred at room temperature for 20 min and concentrated in vacuum. The residue obtained was purified by reverse phase column chromatography [C18 steel column, eluting with ACN in water (containing 0.1% HCl) from 0-100%] to furnish (S)-(1-(1-(2-methoxyethyl)-3-methyl-6-((1-(3,4,5-trimethoxyphenyl)-1H-imidazol-4-yl)amino)-1H-pyrazolo[3,4-d]pyrimidin-4-yl)pyrrolidin-2-yl)methanol (483c) (99 mg, 20% yield) HCl salt as a white solid; $^1$H NMR (300 MHz, DMSO-$d_6$) δ 10.34 (s, 1H, D$_2$O exchangeable), 9.10 (s, 1H), 7.98-7.88 (m, 1H, D$_2$O exchangeable), 7.10 (s, 2H), 4.69 (t, J=5.3 Hz, 1H), 4.36 (t, J=5.5 Hz, 2H), 3.95-3.81 (m, 8H), 3.75-3.71 (m, 2H), 3.70 (s, 3H), 3.66-3.52 (m, 2H), 3.20 (s, 3H), 2.55 (s, 3H), 2.15-1.86 (m, 4H); MS (ES+): 539.3 (M+1); (ES-): 573.2 (M+Cl); HPLC purity: 99.40%.

Preparation of 1-(cyclohexylmethyl)-6-(3-fluoroazetidin-1-yl)-N-(1-(3,4,5-trimethoxyphenyl)-1H-imidazol-4-yl)-1H-pyrazolo[3,4-d]pyrimidin-4-amine (484a)

Compound 484a was prepared from 6-chloro-1-(cyclohexylmethyl)-N-(1-(3,4,5-trimethoxyphenyl)-1H-imidazol-4-yl)-1H-pyrazolo[3,4-d]pyrimidin-4-amine (453c) (200 mg, 0.40 mmol), 3-fluoroazetidine hydrochloride (134 mg, 1.21 mmol), N-ethyl-N-isopropylpropan-2-amine (0.42 mL, 2.41 mmol) in NMP (3 mL) and heating at 140° C. for 50 mins on a microwave reactor according to the procedure reported in scheme 2. This gave after workup and purification by flash column chromatography [silica gel (12 g), eluting with DMA80 in DCM from 0-50%] followed by reverse phase column chromatography [C18 steel column, eluting with ACN in water (containing 0.1% HCl) from 0-100%] 1-(cyclohexylmethyl)-6-(3-fluoroazetidin-1-yl)-N-(1-(3,4,5-trimethoxyphenyl)-1H-imidazol-4-yl)-1H-pyrazolo[3,4-d]pyrimidin-4-amine (484a) (49 mg, 23% yield) HCl salt as a white solid; $^1$H NMR (300 MHz, DMSO-$d_6$) δ 11.05 (s, 1H, D$_2$O exchangeable), 8.53 (s, 1H), 8.22 (s, 1H), 8.02 (d, J=1.7 Hz, 1H, D$_2$O exchangeable), 7.00 (s, 2H), 5.65-5.34 (m, 1H), 4.58-4.46 (m, 2H), 4.32-4.26 (m, 2H), 4.05 (d, J=7.1 Hz, 2H), 3.88 (s, 6H), 3.69 (s, 3H), 1.94-1.82 (m, 1H), 1.68-1.55 (m, 3H), 1.52-1.44 (m, 2H), 1.19-1.09 (m, 3H), 1.05-0.91 (m, 2H); $^{19}$F NMR (282 MHz, DMSO-$d_6$) δ -179.71; MS (ES+): 537.2 (M+1); (ES-): 535.2 (M-1); HPLC purity: 96.91%.

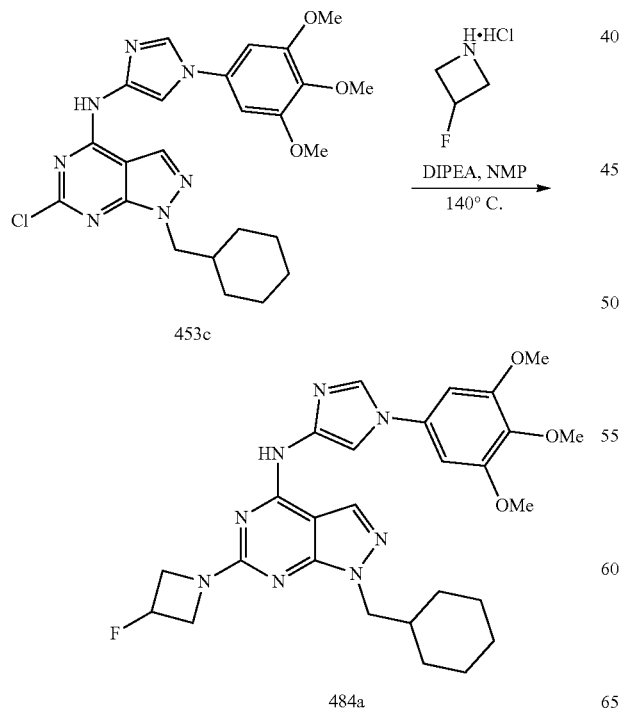

Scheme 484

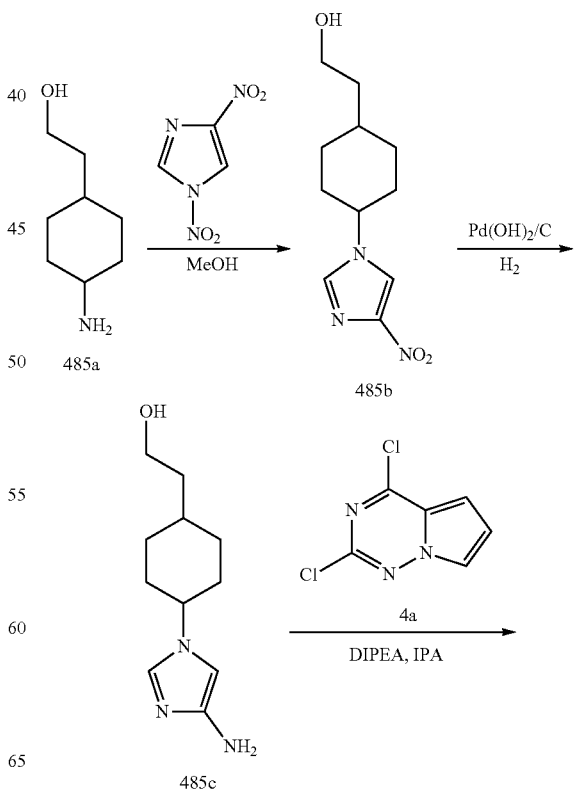

Scheme 485

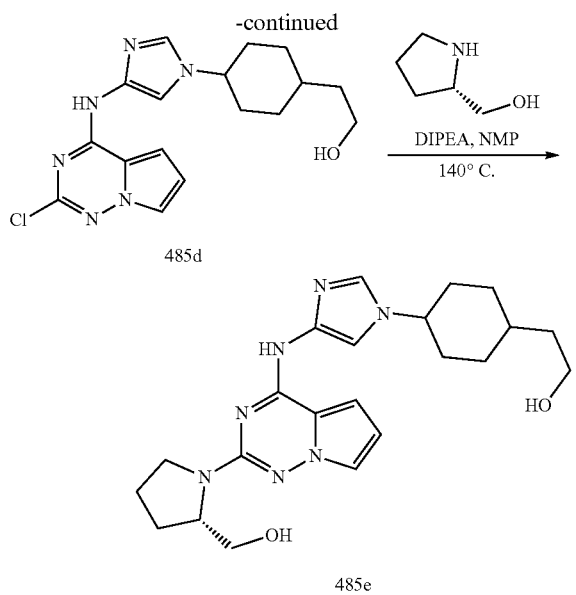

Preparation of (S)-2-(4-(4-((2-(2-(hydroxymethyl)
pyrrolidin-1-yl)pyrrolo[2,1-f][1,2,4]triazin-4-yl)
amino)-1H-imidazol-1-yl)cyclohexyl)ethanol (485e)

Step-1: Preparation of 2-(4-(4-nitro-1H-imidazol-1-yl)cyclohexyl)ethanol (485b)

Reaction of 1,4-dinitro-1H-imidazole (1.02 g, 6.45 mmol) with 2-(4-aminocyclohexyl)ethanol (485a) (1.03 g, 7.19 mmol; CAS #857831-26-6) in MeOH (20 mL) as reported in step-2 of General scheme for preparation of 3-substituted-(4-amino-1H-imidazol-1-yl) gave after work-up and purification by flash column chromatography [silica gel (24 g), eluting with ethyl acetate/MeOH (9:1) in hexanes from 50-100%]2-(4-(4-nitro-1H-imidazol-1-yl)cyclohexyl)ethanol (485b) (1.17 g, 76% yield) as a yellow syrup. $^1$H NMR (300 MHz, DMSO-d$_6$) δ 8.55 (dd, J=16.5, 1.5 Hz, 1H), 7.97 (dd, J=8.8, 1.5 Hz, 1H), 4.38 (td, J=5.0, 2.3 Hz, 1H), 4.17 (m, 1H), 3.45 (m, 2H), 2.10-1.92 (m, 2H), 1.77 (m, 4H), 1.62-1.33 (m, 4H), 1.15-0.96 (m, 1H).

Step-2: Preparation of 2-(4-(4-amino-1H-imidazol-1-yl)cyclohexyl)ethanol (485c)

Reduction of nitro to amine of 2-(4-(4-nitro-1H-imidazol-1-yl)cyclohexyl)ethanol (485b) (410 mg, 1.714 mmol) in MeOH (20 mL) using Palladium hydroxide on carbon, 20 wt. % loading (dry basis), matrix carbon, wet support (116 mg, 0.165 mmol) as reported in step-3 of General scheme for preparation of 3-substituted-(4-amino-1H-imidazol-1-yl) gave 2-(4-(4-amino-1H-imidazol-1-yl)cyclohexyl)ethanol (485c) (359 mg, 100% yield) as a yellow oil which was used directly for next step without further purification. MS (ES+): 210.1 (M+1).

Step-3: Preparation of 2-(4-(4-((2-chloropyrrolo[2,1-f][1,2,4]triazin-4-yl)amino)-1H-imidazol-1-yl)cyclohexyl)ethanol (485d)

Compound 485d was prepared from 2,4-dichloropyrrolo[2,1-f][1,2,4]triazine (4a) (340 mg, 1.808 mmol) in 2-Propanol (10 mL) using DIPEA (0.9 mL, 5.15 mmol), 2-(4-(4-amino-1H-imidazol-1-yl)cyclohexyl)ethanol (485c) (359 mg, 1.715 mmol) and heating at 90° C. for 4 h according to the procedure reported in step-1 of scheme 183. This gave after workup and purification by flash column chromatography [silica gel (12 g), eluting with MeOH in DCM (0-20%)] 2-(4-(4-((2-chloropyrrolo[2,1-f][1,2,4]triazin-4-yl)amino)-1H-imidazol-1-yl)cyclohexyl)ethanol (485d) (531 mg, 86% yield) as a yellow foam. $^1$H NMR (300 MHz, DMSO-d$_6$) δ 11.15 (s, 1H), 7.76-7.64 (m, 2H), 7.57-7.48 (m, 1H), 7.40-7.31 (m, 1H), 6.72-6.64 (m, 1H), 4.44-4.31 (m, 1H), 4.18-3.99 (m, 1H), 3.46 (qd, J=6.5, 2.7 Hz, 2H), 2.05 (d, J=11.8 Hz, 1H), 2.00-1.73 (m, 4H), 1.73-1.57 (m, 2H), 1.52 (q, J=6.7 Hz, 2H), 1.37 (q, J=6.5 Hz, 1H), 1.12 (t, J=12.2 Hz, 1H); MS (ES+): 361.1 (M+1).

Step-4: Preparation of (S)-2-(4-(4-((2-(2-(hydroxymethyl)pyrrolidin-1-yl)pyrrolo[2,1-f][1,2,4]triazin-4-yl)amino)-1H-imidazol-1-yl)cyclohexyl)ethanol (485e)

Compound 485e was prepared from 2-(4-(4-((2-chloropyrrolo[2,1-f][1,2,4]triazin-4-yl)amino)-1H-imidazol-1-yl)cyclohexyl)ethanol (485d) (118 mg, 0.327 mmol), (S)-pyrrolidin-2-ylmethanol (157 mg, 1.552 mmol), N-ethyl-N-isopropylpropan-2-amine (0.207 mL, 1.184 mmol) in NMP (1.5 mL) and heating at 140° C. for 150 mins in a microwave reactor according to the procedure reported in scheme 2. This gave after workup and purification by flash column chromatography [silica gel (12 g), eluting with MeOH in DCM (0-20%)] followed by reverse phase column chromatography [C18 (RediSep 250×30 mm), eluting with ACN in water (containing 0.1% HCl) from 0-100%] (S)-2-(4-(4-((2-(2-(hydroxymethyl)pyrrolidin-1-yl)pyrrolo[2,1-f][1,2,4]triazin-4-yl)amino)-1H-imidazol-1-yl)cyclohexyl)ethanol (485e) (52 mg, 37% yield) as a white solid; $^1$H NMR (300 MHz, DMSO-d$_6$) δ 8.85 (d, J=12.9 Hz, 1H), 7.72 (d, J=6.3 Hz, 1H), 7.48 (t, J=1.9 Hz, 1H), 6.87 (d, J=4.5 Hz, 1H), 6.51 (dt, J=4.2, 1.8 Hz, 1H), 4.41-4.15 (m, 1H), 4.04 (t, J=6.5 Hz, 1H), 3.56 (dt, J=10.2, 4.9 Hz, 1H), 3.50-3.23 (m, 5H), 2.09 (d, J=11.3 Hz, 1H), 2.03-1.67 (m, 9H), 1.67-1.30 (m, 4H), 1.08 (q, J=12.3 Hz, 1H); MS (ES+): 426.2 (M+1); MS (ES-): 424.2 (M-1).

Scheme 486

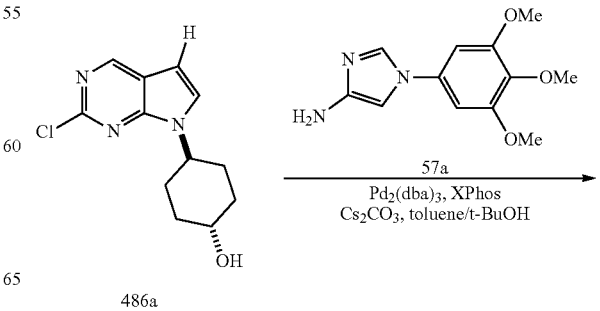

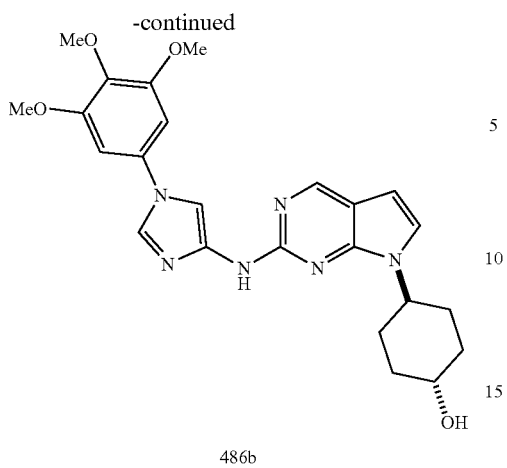

486b

Preparation of (trans)-4-(2-((1-(3,4,5-trimethoxyphenyl)-1H-imidazol-4-yl)amino)-7H-pyrrolo[2,3-d]pyrimidin-7-yl)cyclohexanol (486b)

Compound 486b was prepared from (trans)-4-(2-chloro-7H-pyrrolo[2,3-d]pyrimidin-7-yl)cyclohexanol (486a) (389 mg, 1.55 mmol; CAS #1621619-12-2), 1-(3,4,5-trimethoxyphenyl)-1H-imidazol-4-amine (57a) (462 mg, 1.85 mmol), dicyclohexyl(2',4',6'-triisopropylbiphenyl-2-yl)phosphine (XPhos, 295 mg, 0.62 mmol), cesium carbonate (1762 mg, 5.41 mmol), Pd$_2$(dba)$_3$ (283 mg, 0.31 mmol) in t-BuOH/toluene (11 mL, 1:2.67) and heating at 110° C. for 12 h according to the procedure reported in step-3 of scheme 101. This gave after workup and purification by flash column chromatography [silica gel (12 g), eluting with DMA80 in DCM from 0-50%] followed by reverse phase column chromatography [C18 steel column, eluting with ACN in water (containing 0.1% HCl) from 0-100%] (trans)-4-(2-((1-(3,4,5-trimethoxyphenyl)-1H-imidazol-4-yl)amino)-7H-pyrrolo[2,3-d]pyrimidin-7-yl)cyclohexanol (486b) (48 mg, 7% yield) HCl salt as a white solid; $^1$H NMR (300 MHz, DMSO-d$_6$) δ 10.69 (s, 1H, D$_2$O exchangeable), 8.89 (s, 1H), 8.82-8.72 (m, 1H), 7.87 (d, J=1.7 Hz, 1H), 7.66 (d, J=3.9 Hz, 1H), 7.09 (s, 2H), 6.66 (d, J=3.8 Hz, 1H), 4.68-4.51 (m, 2H), 3.90 (s, 6H), 3.70 (s, 3H), 3.60-3.47 (m, 1H), 2.00-1.85 (m, 6H), 1.46-1.27 (m, 2H); MS (ES+): 465.2 (M+1); HPLC purity: 98.24%.

Part 2: Synthesis of 3-substituted-(4-amino-1H-imidazol-1-yl) Reagents

General Scheme for Preparation of 3-substituted-(4-amino-1H-imidazol-1-yl)

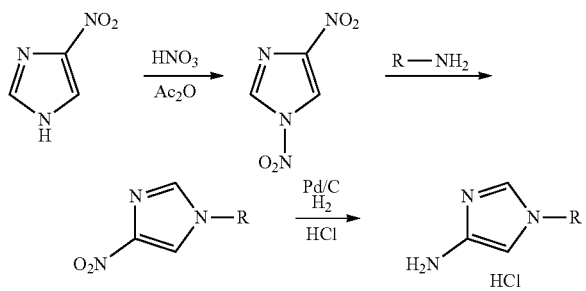

Step-1: Preparation of 1,4-dinitroimidazole 1,4-dinitroimidazole was prepared according to the procedure reported By Wuellner, Guido et al in PCT Int. Appl., 2010021409, 25 Feb. 2010 or as reported by Huibin Zhang et al; in Chem Biol Drug Des 2015; 85: 79-90.

Note: 1,4-Dinitroimidazole is a highly energetic, semi-stable substance and should be stored in a freezer at all times when it is not in use. Thermodynamic measurements have shown that it can potentially generate enough energy at 35° C. under adiabatic conditions to violently explode, extreme caution should be exercised at all times using this material.

Step-2 preparation of 3-substituted-(4-nitro-1H-imidazol-1-yl)

1,4-dinitro-1H-imidazole (1 mmol) was added to a solution of amine (1 mmol) in MeOH (5 mL) at room temperature and stirred for 16 h. The solid obtained was collected by filtration to afford 3-substituted-(4-nitro-1H-imidazol-1-yl) as a solid.

Step-3 preparation of 3-substituted-(4-amino-1H-imidazol-1-yl)

A solution of 3-substituted-(4-nitro-1H-imidazol-1-yl) (1 mmol) in methanol (5 mL) was hydrogenated using 10% Palladium on Carbon as catalyst at 15 psi until the reaction was complete (2-16 h). Reaction mixture was filtered and concentrated to afford 3-substituted-(4-amino-1H-imidazol-1-yl) as oil or a solid which was used directly for next step without further purification. The oily residue or solid of 3-substituted-(4-nitro-1H-imidazol-1-yl) was dissolved in 3 M HCl in methanol stirred for 1 h and concentrated in vacuum to afford 3-substituted-(4-amino-1H-imidazol-1-yl) as a HCl salt.

Preparation of 1-cyclopropyl-1H-imidazol-4-amine (26a)

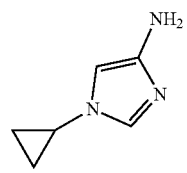

26a

Reaction of 1,4-dinitro-1H-imidazole (2 g, 12.65 mmol) with cyclopropylamine (0.89 mL, 12.65 mmol) as reported in step-2 of General scheme for preparation of 3-substituted-(4-amino-1H-imidazol-1-yl) gave after purification by flash column chromatography (silica gel, eluting with 1:1 hexanes-ethyl acetate) 1-cyclopropyl-4-nitro-1H-imidazole (1.75 g, 90% yield); $^1$H NMR (300 MHz, DMSO-d$_6$) δ 8.45 (d, J=1.5 Hz, 1H), 7.95 (d, J=1.5 Hz, 1H), 3.66 (tt, J=7.5, 3.9 Hz, 1H), 1.17-1.05 (m, 2H), 1.05-0.90 (m, 2H); MS (ES+): 154.2 (M+1), 176.2 (M+Na).

Reduction of nitro to amine of 1-cyclopropyl-4-nitro-1H-imidazole (1.75 g, 11.43 mmol) as reported in step-3 of General scheme for preparation of 3-substituted-(4-amino-1H-imidazol-1-yl) gave 1-cyclopropyl-1H-imidazol-4- amine (26a) (1.41 g, 100% yield) as an oil residue which was used directly for next step without further purification; MS (ES+): 124.2 (M+1).

Preparation of 1-cyclohexyl-1H-imidazol-4-amine (28a)

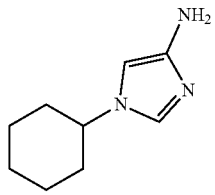

Reaction of 1,4-dinitro-1H-imidazole (2 g, 12.65 mmol) with cyclohexylamine (1.45 mL, 12.65 mmol) as reported in step-2 of General scheme for preparation of 3-substituted-(4-amino-1H-imidazol-1-yl) gave after purification by flash column chromatography (silica gel, eluting with 1:1 hexanes-ethyl acetate) 1-cyclohexyl-4-nitro-1H-imidazole (1.38, 56% yield); $^1$H NMR (300 MHz, DMSO-$d_6$) δ 8.57-8.46 (m, 1H), 8.02-7.89 (m, 1H), 4.26-4.00 (m, 1H), 2.06-1.94 (m, 2H), 1.88-1.76 (m, 2H), 1.75-1.67 (m, 2H), 1.67-1.59 (m, 1H), 1.48-1.10 (m, 3H); MS (ES+): 196.2 (M+1), 218.3 (M+Na).

Reduction of nitro to amine of 1-cyclohexyl-4-nitro-1H-imidazole (1.38 g, 7.07 mmol) as reported in step-3 of General scheme for preparation of 3-substituted-(4-amino-1H-imidazol-1-yl) gave 1-cyclohexyl-1H-imidazol-4-amine (1.22 g, 104% yield) as an light yellow oil; $^1$H NMR (300 MHz, DMSO-$d_6$) δ 8.54 (d, J=1.9 Hz, 1H), 6.71 (d, J=1.9 Hz, 1H), 4.10 (tt, J=11.8, 3.8 Hz, 1H), 2.06-1.91 (m, 2H), 1.81 (d, J=10.9 Hz, 2H), 1.75-1.51 (m, 3H), 1.47-1.03 (m, 3H); MS (ES+): 166.3 (M+1).

Preparation of 1-(2-fluorophenyl)-1H-imidazol-4-amine (36a)

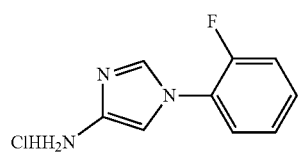

Reaction of 1,4-dinitro-1H-imidazole (2 g, 12.65 mmol) with 3-fluoroaniline (1.41 g, 12.65 mmol) as reported in step-2 of General scheme for preparation of 3-substituted-(4-amino-1H-imidazol-1-yl) gave after filtration 1-(2-fluorophenyl)-4-nitro-1H-imidazole (1.96 g, 75% yield) as a pale-off white solid; $^1$H NMR (300 MHz, DMSO-$d_6$) δ 9.07 (d, J=1.5 Hz, 1H), 8.55 (d, J=1.7 Hz, 1H), 7.84 (dt, J=10.2, 2.3 Hz, 1H), 7.75-7.68 (m, 1H), 7.68-7.58 (m, 1H), 7.41-7.29 (m, 1H); $^{19}$F NMR (282 MHz, DMSO-$d_6$) δ −110.55.

Reduction of nitro to amine of 1-(2-fluorophenyl)-4-nitro-1H-imidazole (1 g, 4.83 mmol) as reported in step-3 of General scheme for preparation of 3-substituted-(4-amino-1H-imidazol-1-yl) gave 1-(2-fluorophenyl)-1H-imidazol-4-amine hydrochloride (36a) (1.22 g) as an light yellow oil, which was converted to HCl salt.

Preparation of 1-cyclobutyl-1H-imidazol-4-amine hydrochloride (37a)

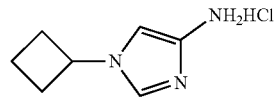

Reaction of 1,4-dinitro-1H-imidazole (1.11 g, 7.03 mmol) with 3-cyclobutanamine (0.5 g, 7.03 mmol) as reported in step-2 of General scheme for preparation of 3-substituted-(4-amino-1H-imidazol-1-yl) gave after filtration 1-cyclobutyl-4-nitro-1H-imidazole (0.88 g, 75% yield) as pink solid; $^1$H NMR (300 MHz, DMSO-$d_6$) δ 8.61 (d, J=1.5 Hz, 1H), 7.98 (d, J=1.5 Hz, 1H), 4.93-4.67 (m, 1H), 2.48-2.35 (m, 4H), 1.90-1.69 (m, 2H); MS (ES+): 168.2 (M+1), 190.2 (M+Na).

Reduction of nitro to amine of 1-cyclobutyl-4-nitro-1H-imidazole (875 mg, 5.23 mmol) as reported in step-3 of General scheme for preparation of 3-substituted-(4-amino-1H-imidazol-1-yl) gave 1-cyclobutyl-1H-imidazol-4-amine as an light yellow oil, which was converted to HCl salt to afford 1-cyclobutyl-1H-imidazol-4-amine hydrochloride (37a) (1.15 g) as light yellow colored solid; $^1$H NMR (300 MHz, DMSO-$d_6$) δ 8.60 (d, J=1.8 Hz, 1H), 6.75 (d, J=1.9 Hz, 1H), 4.75 (p, J=8.5 Hz, 1H), 2.46-2.27 (m, 4H), 1.89-1.65 (m, 2H); $^1$H NMR (300 MHz, DMSO-$d_6$/D$_2$O) δ 8.54 (s, 1H), 4.73 (p, J=8.5 Hz, 1H), 2.46-2.21 (m, 4H), 1.92-1.62 (m, 2H); MS (ES+): 138.2 (M+1); HPLC purity: 97.65%.

Preparation of 11-(quinolin-3-yl)-1H-imidazol-4-amine hydrochloride (38a)

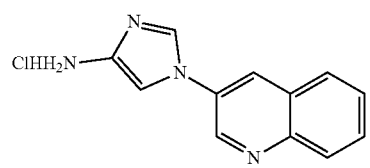

Reaction of 1,4-dinitro-1H-imidazole (0.5 g, 3.16 mmol) with quinolin-3-amine (801 mg, 3.16 mmol) as reported in step-2 of General scheme for preparation of 3-substituted-(4-amino-1H-imidazol-1-yl) gave after filtration 3-(4-nitro-1H-imidazol-1-yl)quinoline (595 mg, 78% yield) as a brown solid; $^1$H NMR (300 MHz, DMSO-$d_6$) δ 9.36 (d, J=2.7 Hz, 1H), 9.21 (d, J=1.5 Hz, 1H), 8.87 (dd, J=2.7, 0.8 Hz, 1H), 8.67 (d, J=1.6 Hz, 1H), 8.14 (dd, J=8.4, 1.1 Hz, 1H), 8.06 (dd, J=8.0, 1.5 Hz, 1H), 7.95-7.82 (m, 1H), 7.81-7.69 (m, 1H).

Reduction of nitro to amine of 3-(4-nitro-1H-imidazol-1-yl)quinoline (595 mg, 2.48 mmol) as reported in step-3 of General scheme for preparation of 3-substituted-(4-amino-1H-imidazol-1-yl) gave 1-(quinolin-3-yl)-1H-imidazol-4-amine as an light yellow oil, which was converted to HCl salt to afford 1-(quinolin-3-yl)-1H-imidazol-4-amine hydrochloride (38a) (866 mg) as light yellow colored solid, which was used directly for next step without further purification.

Preparation of 1-(pyridin-3-yl)-1H-imidazol-4-amine (39a)

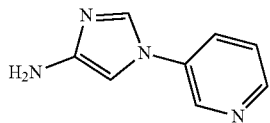

Reaction of 1,4-dinitro-1H-imidazole (1.418 g, 8.97 mmol) with pyridin-3-amine (844 mg, 8.97 mmol) as reported in step-2 of General scheme for preparation of 3-substituted-(4-amino-1H-imidazol-1-yl) gave after filtration 3-(4-nitro-1H-imidazol-1-yl)pyridine (588 mg, 35% yield) as a solid. The filtrate was evaporated and purified by flash column chromatography (silica gel, eluting with DCM-80 in DCM from 0-100%) to afford 3-(4-nitro-1H-imidazol-1-yl)pyridine (377 mg, 22% yield); $^1$H NMR (300 MHz, DMSO-$d_6$) δ 9.09 (d, J=1.6 Hz, 1H), 9.06 (dd, J=2.8, 0.8 Hz, 1H), 8.69 (dd, J=4.8, 1.4 Hz, 1H), 8.55 (d, J=1.6 Hz, 1H), 8.26 (ddd, J=8.3, 2.8, 1.4 Hz, 1H), 7.65 (ddd, J=8.3, 4.7, 0.8 Hz, 1H); MS (ES+): 191.2 (M+1), 213.2 (M+Na); MS (ES−): 189.1 (M−1); HPLC purity: 98.87%.

Reduction of nitro to amine of 3-(4-nitro-1H-imidazol-1-yl)pyridine (588 mg, 3.09 mmol) as reported in step-3 of General scheme for preparation of 3-substituted-(4-amino-1H-imidazol-1-yl) gave 1-(pyridin-3-yl)-1H-imidazol-4-amine (39a) (509 mg, 103% yield) as a light yellow oil; $^1$H NMR (300 MHz, DMSO-$d_6$) δ 8.85 (d, J=2.7 Hz, 1H), 8.46 (dd, J=4.7, 1.4 Hz, 1H), 8.01-7.95 (m, 2H), 7.58-7.41 (m, 1H), 6.73 (d, J=1.7 Hz, 1H), 4.53 (s, 2H); MS (ES+): 161.2 (M+1), 183.2 (M+Na); MS (ES−): 195.0 (M+Cl).

Preparation of 1-(3-fluorophenyl)-1H-imidazol-4-amine hydrochloride (44a)

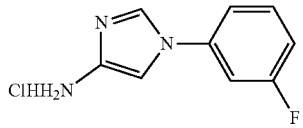

Reaction of 1,4-dinitro-1H-imidazole (2 g, 12.65 mmol) with 3-fluoroaniline (1.41 g, 12.65 mmol) as reported in step-2 of General scheme for preparation of 3-substituted-(4-amino-1H-imidazol-1-yl) gave after filtration 1-(3-fluorophenyl)-4-nitro-1H-imidazole (1.96 g, 75% yield) as a pale-off white solid; $^1$H NMR (300 MHz, DMSO-$d_6$) δ 9.07 (d, J=1.5 Hz, 1H), 8.55 (d, J=1.7 Hz, 1H), 7.84 (dt, J=10.2, 2.3 Hz, 1H), 7.75-7.68 (m, 1H), 7.68-7.58 (m, 1H), 7.41-7.29 (m, 1H); $^{19}$F NMR (282 MHz, DMSO-$d_6$) δ −110.55.

Reduction of nitro to amine of 1-(3-fluorophenyl)-4-nitro-1H-imidazole (1 g, 4.83 mmol) as reported in step-3 of General scheme for preparation of 3-substituted-(4-amino-1H-imidazol-1-yl) gave 1-(3-fluorophenyl)-1H-imidazol-4-amine (1.03 g, 100% yield) as an light yellow oil, which was converted to HCl salt to afford 1-(3-fluorophenyl)-1H-imidazol-4-amine hydrochloride (44a) as a yellow solid; $^1$H NMR (300 MHz, DMSO-d6) δ 8.85 (s, 1H), 7.82-7.71 (m, 1H), 7.69-7.56 (m, 2H), 7.45 (s, 1H), 7.40-7.25 (m, 1H); MS (ES+): 178.2 (M+1).

Preparation of 1-(3-(4-amino-1H-imidazol-1-yl)phenyl)ethanone (47a)

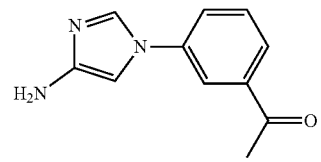

Reaction of 1,4-dinitro-1H-imidazole (0.5 g, 3.16 mmol) with 1-(3-aminophenyl)ethanone (0.428 g, 3.16 mmol) as reported in step-2 of General scheme for preparation of 3-substituted-(4-amino-1H-imidazol-1-yl) gave after filtration 1-(3-(4-nitro-1H-imidazol-1-yl)phenyl)ethanone (610 mg, 83% yield) as a red solid; $^1$H NMR (300 MHz, DMSO-$d_6$) δ 9.15 (d, J=1.6 Hz, 1H), 8.60 (d, J=1.6 Hz, 1H), 8.33 (t, J=1.9 Hz, 1H), 8.12-8.05 (m, 1H), 8.05-7.99 (m, 1H), 7.74 (t, J=7.9 Hz, 1H), 2.68 (s, 3H); MS (ES+): 232.2 (M+1), 254.3 (M+Na); MS (ES−): 230.2 (M−1).

Reduction of nitro to amine of 1-(3-(4-nitro-1H-imidazol-1-yl)phenyl)ethanone (273 mg, 1.18 mmol) as reported in step-3 of General scheme for preparation of 3-substituted-(4-amino-1H-imidazol-1-yl) gave 1-(3-(4-amino-1H-imidazol-1-yl)phenyl)ethanone (47a) (238 mg, 100% yield) as a pink solid, which was used as such for next step without further purification; MS (ES+): 202.2 (M+1), 224.2 (M+Na); MS (ES−): 200.1 (M−1).

Preparation of 4-(4-amino-1H-imidazol-1-yl)phenol (48a)

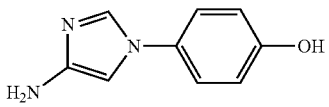

Reaction of 1,4-dinitro-1H-imidazole (500 mg, 3.16 mmol) with 4-aminophenol (345 mg, 3.16 mmol) as reported in step-2 of General scheme for preparation of 3-substituted-(4-amino-1H-imidazol-1-yl) gave after filtration 4-(4-nitro-1H-imidazol-1-yl)phenol (536 mg, 83% yield) as a red solid; $^1$H NMR (300 MHz, DMSO-$d_6$) δ 9.96 (s, 1H), 8.94-8.74 (m, 1H), 8.40-8.20 (m, 1H), 7.56 (d, J=8.8 Hz, 2H), 6.91 (d, J=8.9 Hz, 2H); $^1$H NMR (300 MHz, DMSO-$d_6$/D$_2$O) δ 8.76 (d, J=1.6 Hz, 1H), 8.23 (d, J=1.6 Hz, 1H), 7.52 (d, J=8.9 Hz, 2H), 6.90 (d, J=8.9 Hz, 1H); MS (ES+): 206.2 (M+1); 239.3 (M+Na); MS (ES−): 204.2 (M−1), 240.2 (M+Cl); HPLC purity: 99.58%.

Reduction of nitro to amine of 4-(4-nitro-1H-imidazol-1-yl)phenol (536 mg, 2.61 mmol) as reported in step-3 of General scheme for preparation of 3-substituted-(4-amino-1H-imidazol-1-yl) gave 4-(4-amino-1H-imidazol-1-yl)phenol (48a) (458 mg, 100% yield) as a pink solid, which was used as such for next step without further purification; MS (ES+): 176.2 (M+1); MS (ES−): 174.1 (M−1).

Preparation of
1-(4-chlorophenyl)-1H-imidazol-4-amine (49a)

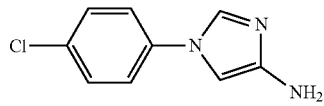

49a

Reaction of 1,4-dinitro-1H-imidazole (0.5 g, 3.16 mmol) with 4-chloroaniline (404 mg, 3.16 mmol) as reported in step-2 of General scheme for preparation of 3-substituted-(4-amino-1H-imidazol-1-yl) gave after filtration 1-(4-chlorophenyl)-4-nitro-1H-imidazole (513 mg, 73% yield) as a red solid; $^1$H NMR (300 MHz, DMSO-$d_6$) δ 9.02 (d, J=1.6 Hz, 1H), 8.49 (d, J=1.6 Hz, 1H), 7.90-7.80 (m, 2H), 7.71-7.61 (m, 2H); MS (ES+): 224.2 (M+1), 246.2 (M+Na); MS (ES−): 222.1 (M−1).

Reduction of nitro to amine of 1-(4-chlorophenyl)-4-nitro-1H-imidazole (536 mg, 2.4 mmol) as reported in step-3 of General scheme for preparation of 3-substituted-(4-amino-1H-imidazol-1-yl) gave 1-(4-chlorophenyl)-1H-imidazol-4-amine (49a) (464 mg, 100% yield) as a light yellow oil, which was used as such for next step without further purification; MS (ES+): 194.2 (M+1), 216.2 (M+Na).

Preparation of 1-cyclopentyl-1H-imidazol-4-amine hydrochloride (50a)

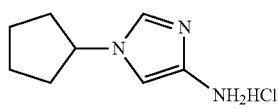

50a

Reaction of 1,4-dinitro-1H-imidazole (1 g, 6.33 mmol) with cyclopentanamine (539 mg, 6.33 mmol) as reported in step-2 of General scheme for preparation of 3-substituted-(4-amino-1H-imidazol-1-yl) gave after filtration 1-cyclopentyl-4-nitro-1H-imidazole (860 mg, 75% yield) as a pink solid; $^1$H NMR (300 MHz, DMSO-$d_6$) δ 8.50 (d, J=1.5 Hz, 1H), 7.95 (d, J=1.5 Hz, 1H), 4.63 (p, J=7.2 Hz, 1H), 2.28-2.05 (m, 2H), 1.95-1.65 (m, 4H), 1.68-1.49 (m, 2H); MS (ES+): 182.2 (M+1), 204.3 (M+Na); MS (ES−): 180.2 (M−1), 217.2 (M+Cl).

Reduction of nitro to amine of 1-cyclopentyl-4-nitro-1H-imidazole (875 mg, 4.83 mmol) as reported in step-3 of General scheme for preparation of 3-substituted-(4-amino-1H-imidazol-1-yl) gave 1-cyclopentyl-1H-imidazol-4-amine as an light yellow oil, which was converted to HCl salt to afford 1-cyclopentyl-1H-imidazol-4-amine hydrochloride (50a) (831 mg, 92% yield) as light yellow solid; $^1$H NMR (300 MHz, DMSO-$d_6$) δ 8.56 (d, J=1.9 Hz, 1H), 6.65 (d, J=1.9 Hz, 1H), 4.76-4.45 (m, 1H), 2.26-1.99 (m, 2H), 2.01-1.44 (m, 6H); MS (ES+): 152.2 (M+1).

Preparation of
1-(4-methoxyphenyl)-1H-imidazol-4-amine (55a)

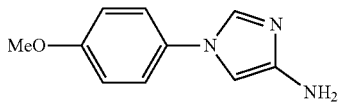

55a

Reaction of 1,4-dinitro-1H-imidazole (0.5 g, 3.16 mmol) with 4-methoxyaniline (390 mg, 3.16 mmol) as reported in step-2 of General scheme for preparation of 3-substituted-(4-amino-1H-imidazol-1-yl) gave after filtration 1-(4-methoxyphenyl)-4-nitro-1H-imidazole (593 mg, 86% yield) as a pink solid; $^1$H NMR (300 MHz, DMSO-$d_6$) δ 8.91 (d, J=1.6 Hz, 1H), 8.38 (d, J=1.6 Hz, 1H), 7.78-7.59 (m, 2H), 7.12 (d, J=9.0 Hz, 2H), 3.82 (s, 3H); MS (ES+): 220.3 (M+1); 242.3 (M+Na); MS (ES−): 218.2 (M−1).

Reduction of nitro to amine of 1-(4-methoxyphenyl)-4-nitro-1H-imidazole (592 mg, 2.7 mmol) as reported in step-3 of General scheme for preparation of 3-substituted-(4-amino-1H-imidazol-1-yl) gave 1-(4-methoxyphenyl)-1H-imidazol-4-amine (55a) (511 mg, 100% yield) as a pink solid, which was used directly for next step without further purification; MS (ES+): 190.3 (M+1); 212.3 (M+Na).

Preparation of
1-(3-methoxyphenyl)-1H-imidazol-4-amine (56a)

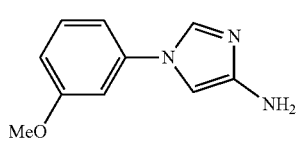

56a

Reaction of 1,4-dinitro-1H-imidazole (0.5 g, 3.16 mmol) with 3-methoxyaniline (390 mg, 3.16 mmol) as reported in step-2 of General scheme for preparation of 3-substituted-(4-amino-1H-imidazol-1-yl) gave after filtration 1-(3-methoxyphenyl)-4-nitro-1H-imidazole (522 mg, 75% yield) as a yellow solid; $^1$H NMR (300 MHz, DMSO-$d_6$) δ 9.05 (d, J=1.6 Hz, 1H), 8.52 (d, J=1.6 Hz, 1H), 7.48 (t, J=8.1 Hz, 1H), 7.44-7.34 (m, 2H), 7.12-6.95 (m, 1H), 3.85 (s, 3H); MS (ES+): 220.3 (M+1); 242.3 (M+Na); MS (ES−): 218.2 (M−1).

Reduction of nitro to amine of 1-(3-methoxyphenyl)-4-nitro-1H-imidazole (522 mg, 2.38 mmol) as reported in step-3 of General scheme for preparation of 3-substituted-(4-amino-1H-imidazol-1-yl) gave 1-(3-methoxyphenyl)-1H-imidazol-4-amine (56a) (451 mg, 100% yield) as an light yellow oil, which was used directly for next step without further purification; MS (ES+): 190.2 (M+1); 212.3 (M+Na).

Preparation of
1-(3,4,5-trimethoxyphenyl)-1H-imidazol-4-amine
(57a)

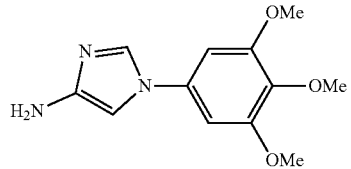 [SMILES: COc1cc(-n2cnc(N)c2)cc(OC)c1OC]

Reaction of 1,4-dinitro-1H-imidazole (500 mg, 3.16 mmol) with 3,4,5-trimethoxyaniline (924 mg, 3.16 mmol) as reported in step-2 of General scheme for preparation of 3-substituted-(4-amino-1H-imidazol-1-yl) gave after filtration 4-nitro-1-(3,4,5-trimethoxyphenyl)-1H-imidazole (854 mg, 97% yield) as a yellow solid; $^1$H NMR (300 MHz, DMSO-$d_6$) δ 9.07 (d, J=1.6 Hz, 1H), 8.51 (d, J=1.6 Hz, 1H), 7.13 (s, 2H), 3.87 (s, 6H), 3.69 (s, 3H); MS (ES+): 302.3 (M+Na); MS (ES−): 278.2 (M−1).

Reduction of nitro to amine of 4-nitro-1-(3,4,5-trimethoxyphenyl)-1H-imidazole (411 mg, 1.47 mmol) as reported in step-3 of General scheme for preparation of 3-substituted-(4-amino-1H-imidazol-1-yl) gave 1-(3,4,5-trimethoxyphenyl)-1H-imidazol-4-amine (57a) (309 mg, 84% yield) as a light yellow oil which was used as such without further purification; $^1$H NMR (300 MHz, DMSO-$d_6$) δ 7.83 (d, J=1.6 Hz, 1H), 6.79 (s, 2H), 6.68 (d, J=1.6 Hz, 1H), 4.38 (s, 2H), 3.83 (s, 6H), 3.65 (s, 3H); MS (ES+): 250.3 (M+1), 272.3 (M+Na).

Preparation of 3-(4-amino-1H-imidazol-1-yl)cyclobutanecarbonitrile (59a)

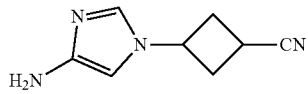

Reaction of 1,4-dinitro-1H-imidazole (298 mg, 1.89 mmol) with 3-aminocyclobutanecarbonitrile hydrochloride (250 mg, 1.89 mmol) as reported in step-2 of General scheme for preparation of 3-substituted-(4-amino-1H-imidazol-1-yl) gave after filtration 3-(4-nitro-1H-imidazol-1-yl)cyclobutanecarbonitrile (150 mg, 41% yield) as yellow solid; $^1$H NMR (300 MHz, DMSO-$d_6$) δ 8.77 (d, J=1.5 Hz, 1H), 8.03 (d, J=1.5 Hz, 1H), 4.94-4.69 (m, 1H), 3.32-3.13 (m, 1H), 3.00-2.73 (m, 4H); MS (ES−): 227.2 (M+Cl).

Reduction of nitro to amine of 3-(4-nitro-1H-imidazol-1-yl)cyclobutanecarbonitrile (150 mg, 0.78 mmol) as reported in step-3 of General scheme for preparation of 3-substituted-(4-amino-1H-imidazol-1-yl) gave 3-(4-amino-1H-imidazol-1-yl)cyclobutanecarbonitrile (59a) (127 mg, 100% yield) as a pink solid, which was used as such for next step without further purification; MS (ES+): 163.2 (M+1), 185.2 (M+Na).

Preparation of 1-(1H-indol-6-yl)-1H-imidazol-4-amine (65a)

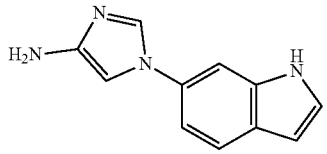

Reaction of 1,4-dinitro-1H-imidazole (500 mg, 3.16 mmol) with 1H-indol-6-amine (418 mg, 3.16 mmol) as reported in step-2 of General scheme for preparation of 3-substituted-(4-amino-1H-imidazol-1-yl) gave after filtration 6-(4-nitro-1H-imidazol-1-yl)-1H-indole (532 mg, 74% yield); $^1$H NMR (300 MHz, DMSO-$d_6$) δ 11.51 (s, 1H), 8.96 (d, J=1.6 Hz, 1H), 8.42 (d, J=1.5 Hz, 1H), 7.77-7.74 (m, 1H), 7.71 (d, J=8.5 Hz, 1H), 7.51 (dd, J=3.1, 2.5 Hz, 1H), 7.35 (dd, J=8.4, 2.1 Hz, 1H), 6.65-6.37 (m, 1H); MS (ES+): 229.3 (M+1), 251.3 (M+Na); MS (ES−): 227.2 (M−1), 263.2 (M+Cl); HPLC purity: 97.84%.

Reduction of nitro to amine of 6-(4-nitro-1H-imidazol-1-yl)-1H-indole (270 mg, 1.17 mmol) as reported in step-3 of General scheme for preparation of 3-substituted-(4-amino-1H-imidazol-1-yl) gave 1-(1H-indol-6-yl)-1H-imidazol-4-amine (65a) (231 mg, 100% yield) as a pink solid, which was used as such for next step without further purification; MS (ES+): 199.2 (M+1); MS (ES−): 197.2 (M−1), 233.2 (M+Cl).

Preparation of 1-(1H-indol-5-yl)-1H-imidazol-4-amine (67a)

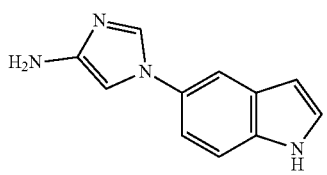

Reaction of 1,4-dinitro-1H-imidazole (500 mg, 3.16 mmol) with 1H-indol-5-amine (418 mg, 3.16 mmol) as reported in step-2 of General scheme for preparation of 3-substituted-(4-amino-1H-imidazol-1-yl) gave after filtration 5-(4-nitro-1H-imidazol-1-yl)-1H-indole (67a) (668 mg, 93% yield); $^1$H NMR (300 MHz, DMSO-$d_6$) δ 11.44 (s, 1H), 8.91 (d, J=1.6 Hz, 1H), 8.38 (d, J=1.5 Hz, 1H), 7.92 (d, J=2.2 Hz, 1H), 7.56 (d, J=8.7 Hz, 1H), 7.52 (t, J=2.8 Hz, 1H), 7.43 (dd, J=8.7, 2.2 Hz, 1H), 6.54 (ddd, J=3.0, 2.0, 0.9 Hz, 1H); MS (ES+): 229.3 (M+1); MS (ES−): 227.1 (M−1), 263.2 (M+Cl).

Reduction of nitro to amine of 5-(4-nitro-1H-imidazol-1-yl)-1H-indole (287 mg, 1.26 mmol) as reported in step-3 of General scheme for preparation of 3-substituted-(4-amino-1H-imidazol-1-yl) gave 1-(1H-indol-5-yl)-1H-imidazol-4-amine (67a) (231 mg, 100% yield) as a pink solid, which was used as such for next step without further purification; MS (ES+): 199.2 (M+1), 221.2 (M+Na); MS (ES−): 197.2 (M−1), 233.1.1 (M+Cl).

Preparation of 1-(1H-pyrazol-3-yl)-1H-imidazol-4-amine (71a)

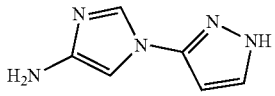

Reaction of 1,4-dinitro-1H-imidazole (0.5 g, 3.16 mmol) with 1H-pyrazol-3-amine (342 mg, 4.11 mmol) as reported in step-2 of General scheme for preparation of 3-substituted-(4-amino-1H-imidazol-1-yl) gave after filtration 3-(4-nitro-1H-imidazol-1-yl)-1H-pyrazole (410 mg, 72% yield) as a yellow solid; $^1$H NMR (300 MHz, DMSO-$d_6$) δ 13.21 (s, 1H, $D_2O$ exchangeable), 8.86 (d, J=1.5 Hz, 1H), 8.41 (d, J=1.5 Hz, 1H), 7.95 (dd, J=2.5, 1.7 Hz, 1H), 6.78 (t, J=2.2 Hz, 1H); MS (ES+): 202.2 (M+Na); MS (ES−): 178.1 (M−1).

Reduction of nitro to amine of 3-(4-nitro-1H-imidazol-1-yl)-1H-pyrazole (410 mg, 2.29 mmol) as reported in step-3 of General scheme for preparation of 3-substituted-(4-amino-1H-imidazol-1-yl) gave 1-(1H-pyrazol-3-yl)-1H-imidazol-4-amine (71a) (341 mg, 100% yield) as a pink solid, which was used as such for next step without further purification; MS (ES+): 150.2 (M+1), 172.2 (M+Na); MS (ES−): 148.1 (M−1).

Preparation of 1-(3,5-dimethoxyphenyl)-1H-imidazol-4-amine (72a)

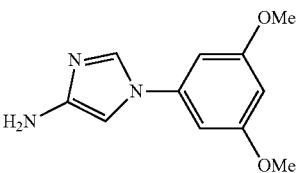

Reaction of 1,4-dinitro-1H-imidazole (1 g, 6.33 mmol) with 3,5-dimethoxyaniline (969 mg, 6.33 mmol) as reported in step-2 of General scheme for preparation of 3-substituted-(4-amino-1H-imidazol-1-yl) gave after filtration 1-(3,5-dimethoxyphenyl)-4-nitro-1H-imidazole (860 mg, 55% yield) as a yellow solid; $^1$H NMR (300 MHz, DMSO-$d_6$) δ 9.07 (d, J=1.6 Hz, 1H), 8.53 (d, J=1.6 Hz, 1H), 7.02 (d, J=2.2 Hz, 2H), 6.59 (t, J=2.2 Hz, 1H), 3.83 (s, 6H); MS (ES+): 250.3 (M+1), 272.3 (M+Na); MS (ES−): 248.2 (M−1).

Reduction of nitro to amine of 1-(3,5-dimethoxyphenyl)-4-nitro-1H-imidazole (415 mg, 1.67 mmol) as reported in step-3 of General scheme for preparation of 3-substituted-(4-amino-1H-imidazol-1-yl) gave 1-(3,5-dimethoxyphenyl)-1H-imidazol-4-amine (72a) (365 mg, 100% yield) as a yellow solid, which was used as such for next step without further purification; MS (ES+): 220.2 (M+1), 242.2 (M+Na).

Preparation of 1-(3,4-dimethoxyphenyl)-1H-imidazol-4-amine (73a)

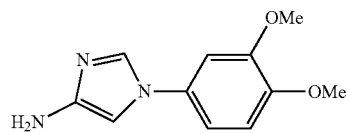

Reaction of 1,4-dinitro-1H-imidazole (1 g, 6.33 mmol) with 3,4-dimethoxyaniline (969 mg, 6.33 mmol) as reported in step-2 of General scheme for preparation of 3-substituted-(4-amino-1H-imidazol-1-yl) gave after filtration 1-(3,4-dimethoxyphenyl)-4-nitro-1H-imidazole (1.38 g, 87% yield) as a yellow solid; $^1$H NMR (300 MHz, DMSO-$d_6$) δ 8.98 (d, J=1.6 Hz, 1H), 8.42 (d, J=1.6 Hz, 1H), 7.39 (d, J=2.6 Hz, 1H), 7.31 (dd, J=8.6, 2.6 Hz, 1H), 7.10 (d, J=8.7 Hz, 1H), 3.86 (s, 3H), 3.81 (s, 3H); MS (ES+): 250.3 (M+1), 272.3 (M+Na); MS (ES−): 248.2 (M−1).

Reduction of nitro to amine of 1-(3,4-dimethoxyphenyl)-4-nitro-1H-imidazole (415 mg, 1.67 mmol) as reported in step-3 of General scheme for preparation of 3-substituted-(4-amino-1H-imidazol-1-yl) gave 1-(3,4-dimethoxyphenyl)-1H-imidazol-4-amine (73a) (365 mg, 100% yield) as a yellow solid, which was used as such for next step without further purification; MS (ES+): 220.3 (M+1), 242.3 (M+Na).

Preparation of 1-(quinolin-5-yl)-1H-imidazol-4-amine (76a)

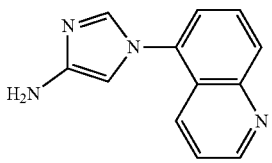

Reaction of 1,4-dinitro-1H-imidazole (2.19 g, 13.87 mmol) with quinolin-5-amine (2.0 g, 13.87 mmol) as reported in step-2 of General scheme for preparation of 3-substituted-(4-amino-1H-imidazol-1-yl) gave after filtration 5-(4-nitro-1H-imidazol-1-yl)quinoline (1.6 g, 53% yield) as a yellow solid; $^1$H NMR (300 MHz, DMSO-$d_6$): δ 9.062-9.057 (s, 1H), 8.92-8.91 (s, 1H), 8.28-8.26 (d, 2H), 8.077-8.073 (d, 1H), 7.98-7.88 (m, 2H), 7.67-7.66 (d, 1H); MS (ES+): 241.0 (M+1).

Reduction of nitro to amine of 5-(4-nitro-1H-imidazol-1-yl)quinoline (1.0 g, 4.16 mmol) as reported in step-3 of General scheme for preparation of 3-substituted-(4-amino-1H-imidazol-1-yl) gave 1-(quinolin-5-yl)-1H-imidazol-4-amine (76a) (800 mg, 92% yield) as a solid, which was used as such for next step without further purification.

817

Preparation of 1'-methyl-1'H-[1,4'-biimidazol]-4-amine (81a)

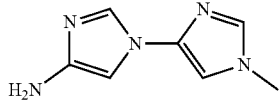

Reaction of 1,4-dinitro-1H-imidazole (500 mg, 3.16 mmol) with 1-methyl-1H-imidazol-4-amine hydrochloride (423 mg, 3.16 mmol) as reported in step-2 of General scheme for preparation of 3-substituted-(4-amino-1H-imidazol-1-yl) gave after filtration 1'-methyl-4-nitro-1'H-1,4'-biimidazole (192 mg, 31% yield) as a blue solid; $^1$H NMR (300 MHz, DMSO-$d_6$) δ 8.72 (d, J=1.5 Hz, 1H), 8.29 (d, J=1.5 Hz, 1H), 7.76-7.69 (m, 1H), 7.65 (d, J=1.5 Hz, 1H), 3.72 (s, 3H); MS (ES+): 194.2 (M+1), 216.2 (M+Na).

Reduction of nitro to amine of 1'-methyl-4-nitro-1'H-1,4'-biimidazole (190 mg, 0.99 mmol) as reported in step-3 of General scheme for preparation of 3-substituted-(4-amino-1H-imidazol-1-yl) gave 1'-methyl-1'H-[1,4'-biimidazol]-4-amine (81a) (162 mg, 100% yield) as a pink solid, which was used as such for next step without further purification; MS (ES+): 164.2 (M+1), 186.2 (M+Na).

Preparation of 1-(3,5-difluorophenyl)-1H-imidazol-4-amine (83a)

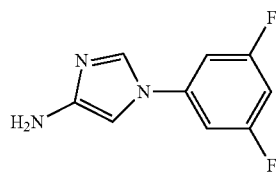

Reaction of 1,4-dinitro-1H-imidazole (1 g, 6.33 mmol) with 3,5-difluoroaniline (0817 mg, 6.33 mmol) as reported in step-2 of General scheme for preparation of 3-substituted-(4-amino-1H-imidazol-1-yl) gave after filtration 1-(3,5-difluorophenyl)-4-nitro-1H-imidazole (860 mg, 60% yield) as a pale off-white solid; $^1$H NMR (300 MHz, DMSO-$d_6$) δ 9.16-9.06 (m, 1H), 8.63-8.53 (m, 1H), 7.96-7.66 (m, 2H), 7.54-7.35 (m, 1H); $^{19}$F NMR (282 MHz, DMSO-$d_6$) δ −107.26; MS (ES−): 224.2 (M−1).

Reduction of nitro to amine of 1-(3,5-difluorophenyl)-4-nitro-1H-imidazole (437 mg, 1.94 mmol) as reported in step-3 of General scheme for preparation of 3-substituted-(4-amino-1H-imidazol-1-yl) gave 1-(3,5-difluorophenyl)-1H-imidazol-4-amine (83a) (379 mg, 100% yield) as a yellow solid, which was used as such for next step without further purification; MS (ES+): 196.2 (M+1), 218.2 (M+Na).

818

Preparation of 4-(4-amino-1H-imidazol-1-yl)benzamide hydrochloride (93a)

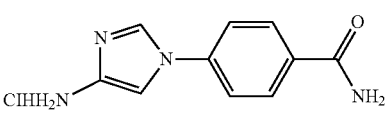

Reaction of 1,4-dinitro-1H-imidazole (1.5 g, 9.5 mmol) with 4-aminobenzamide (1.29 g, 9.5 mmol) as reported in step-2 of General scheme for preparation of 3-substituted-(4-amino-1H-imidazol-1-yl) gave after filtration 4-(4-nitro-1H-imidazol-1-yl)benzamide (1.65 g, 75% yield) as a reddish solid.

Reduction of nitro to amine of 4-(4-nitro-1H-imidazol-1-yl)benzamide (1.65 g, 7.11 mmol) as reported in step-3 of General scheme for preparation of 3-substituted-(4-amino-1H-imidazol-1-yl) gave after conversion to HCl salt using 3 M HCl in methanol 4-(4-amino-1H-imidazol-1-yl)benzamide hydrochloride (93a) (680 mg, 40% yield) as light yellow solid, which was used as such for next step without further purification. MS (ES+): 203.2 (M+1), 225.2 (M+Na).

Preparation of 3-(4-amino-1H-imidazol-1-yl)benzamide hydrochloride (94a)

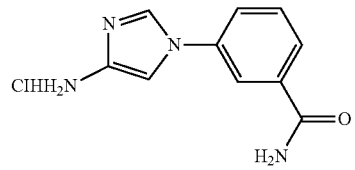

Reaction of 1,4-dinitro-1H-imidazole (1.5 g, 9.5 mmol) with 3-aminobenzamide (1.29 g, 9.5 mmol) as reported in step-2 of General scheme for preparation of 3-substituted-(4-amino-1H-imidazol-1-yl) gave afterfiltration 3-(4-nitro-1H-imidazol-1-yl)benzamide (1.85 g, 84% yield) as a reddish solid.

Reduction of nitro to amine of 3-(4-nitro-1H-imidazol-1-yl)benzamide (1.85 g, 7.97 mmol) as reported in step-3 of General scheme for preparation of 3-substituted-(4-amino-1H-imidazol-1-yl) gave after conversion to HCl salt using 3 M HCl in methanol 3-(4-amino-1H-imidazol-1-yl)benzamide hydrochloride (94a) (3.05 g) as light yellow solid, which was used as such for next step without further purification. MS (ES+): 203.3 (M+1), 225.3 (M+Na). MS (ES−): 201.2 (M−1).

Preparation of 1-(4-(4-amino-1H-imidazol-1-yl)phenyl)ethanone hydrochloride (95a)

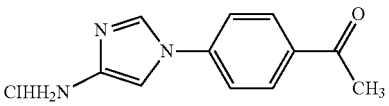

Reaction of 1,4-dinitro-1H-imidazole (1.5 g, 9.5 mmol) with 1-(4-aminophenyl)ethanone (1.28 g, 9.49 mmol) as reported in step-2 of General scheme for preparation of 3-substituted-(4-amino-1H-imidazol-1-yl) gave after filtration 1-(4-(4-nitro-1H-imidazol-1-yl)phenyl)ethanone (620 mg, 28% yield) as a reddish solid.

Reduction of nitro to amine of 1-(4-(4-nitro-1H-imidazol-1-yl)phenyl)ethanone (620 mg, 0.27 mmol) as reported in step-3 of General scheme for preparation of 3-substituted-(4-amino-1H-imidazol-1-yl) gave after conversion to HCl salt using 3 M HCl in methanol 1-(4-(4-amino-1H-imidazol-1-yl)phenyl)ethanone hydrochloride (95a) (770 mg) as light yellow solid, which was used as such for next step without further purification. MS (ES+): 202.3 (M+1), 224.3 (M+Na).

Preparation of
4-(4-amino-1H-imidazol-1-yl)benzonitrile
hydrochloride (116a)

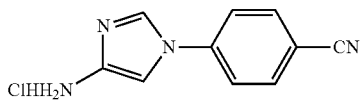

116a

Reaction of 1,4-dinitro-1H-imidazole (1.5 g, 9.5 mmol) with 4-aminobenzonitrile (1.12 g, 9.5 mmol) as reported in step-2 of General scheme for preparation of 3-substituted-(4-amino-1H-imidazol-1-yl) gave after filtration 4-(4-nitro-1H-imidazol-1-yl)benzonitrile (310 mg, 15% yield) as a reddish solid.

Reduction of nitro to amine of 4-(4-nitro-1H-imidazol-1-yl)benzonitrile (310 mg, 1.45 mmol) as reported in step-3 of General scheme for preparation of 3-substituted-(4-amino-1H-imidazol-1-yl) gave after conversion to HCl salt using 3 M HCl in methanol 4-(4-amino-1H-imidazol-1-yl)benzonitrile hydrochloride (116a) (403 mg) as a solid, which was used as such for next step without further purification.

Preparation of 1-(5-(4-amino-1H-imidazol-1-yl)-2-methoxyphenyl)ethanone hydrochloride (123a)

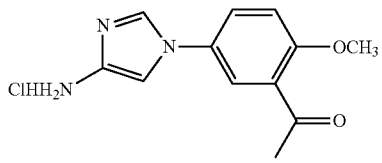

123a

Reaction of 1,4-dinitro-1H-imidazole (470 mg, 2.98 mmol) with 1-(5-amino-2-methoxyphenyl)ethanone hydrochloride (600 mg, 2.98 mmol; prepared according to the procedure reported by Mattes, Kenneth et al; in PCT Int. Appl., 2001046170, 28 Jun. 2001) as reported in step-2 of General scheme for preparation of 3-substituted-(4-amino-1H-imidazol-1-yl) gave after filtration 1-(2-methoxy-5-(4-nitro-1H-imidazol-1-yl)phenyl)ethanone (380 mg, 49% yield) as a red solid, which was used as such for next step without further purification; MS (ES−): 260.4 (M−1).

Reduction of nitro to amine of 1-(2-methoxy-5-(4-nitro-1H-imidazol-1-yl)phenyl)ethanone (380 g, 1.46 mmol) as reported in step-3 of General scheme for preparation of 3-substituted-(4-amino-1H-imidazol-1-yl) gave after conversion to HCl salt using 3 M HCl in methanol 1-(5-(4-amino-1H-imidazol-1-yl)-2-methoxyphenyl)ethanone hydrochloride (123a) (403 mg, 100% yield) as a yellow solid, which was used as such for next step without further purification. MS (ES+): 232.3 (M+1).

Preparation of 3-(4-amino-1H-imidazol-1-yl)-5-methoxybenzamide (125a)

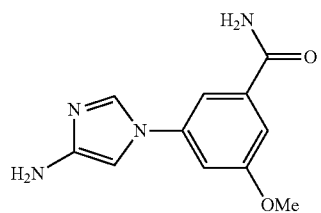

125a

Reaction of 1,4-dinitro-1H-imidazole (0.33 g, 2.11 mmol) with 3-amino-5-methoxybenzamide (350 mg, 2.11 mmol; prepared according to the procedure reported by Priestley, Eldon Scott and Zhang, Xiaojun; in PCT Int. Appl., 2007146719, 21 Dec. 2007) as reported in step-2 of General scheme for preparation of 3-substituted-(4-amino-1H-imidazol-1-yl) gave after filtration 3-methoxy-5-(4-nitro-1H-imidazol-1-yl)benzamide (450 mg, 82% yield) as a red solid, which was used as such for next step without further purification; MS (ES+): 285.3 (M+Na).

Reduction of nitro to amine of 3-methoxy-5-(4-nitro-1H-imidazol-1-yl)benzamide (450 mg, 1.72 mmol) as reported in step-3 of General scheme for preparation of 3-substituted-(4-amino-1H-imidazol-1-yl) gave 3-(4-amino-1H-imidazol-1-yl)-5-methoxybenzamide (125a) (400 mg, 100%) as a white solid, which was used as such for next step without further purification.

Preparation of
1-(3,4-difluorophenyl)-1H-imidazol-4-amine (128a)

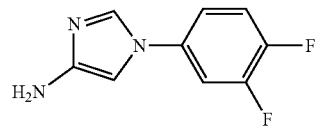

128a

Reaction of 1,4-dinitro-1H-imidazole (1.39 g, 8.79 mmol) with 3,4-difluoroaniline (1.14 g, 8.79 mmol) as reported in step-2 of General scheme for preparation of 3-substituted-(4-amino-1H-imidazol-1-yl) gave after filtration 1-(3,4-difluorophenyl)-4-nitro-1H-imidazole (901 mg, 46% yield) as a pale off-white solid; $^1$H NMR (300 MHz, DMSO-$d_6$) δ 9.03 (d, J=1.6 Hz, 1H), 8.49 (d, J=1.6 Hz, 1H), 8.19-8.03 (m, 1H), 7.81-7.66 (m, 2H); $^{19}$F NMR (282 MHz, DMSO-$d_6$) δ −135.17-−135.67 (m), −138.10-−138.52 (m); $^{19}$F CPD NMR (282 MHz, DMSO-$d_6$) δ −135.44 (d, J=22.7 Hz), −138.33 (d, J=22.8 Hz).

Reduction of nitro to amine of 1-(3,4-difluorophenyl)-4-nitro-1H-imidazole (440 mg, 1.95 mmol) as reported in step-3 of General scheme for preparation of 3-substituted-(4-amino-1H-imidazol-1-yl) gave 1-(3,4-difluorophenyl)-

1H-imidazol-4-amine (128a) (380 mg, 100% yield) as a yellow solid, which was used as such for next step without further purification; MS (ES+): 196.2 (M+1), 218.2 (M+Na).

Preparation of 5-(4-amino-1H-imidazol-1-yl)-2,3-dimethoxybenzonitrile hydrochloride (167d)

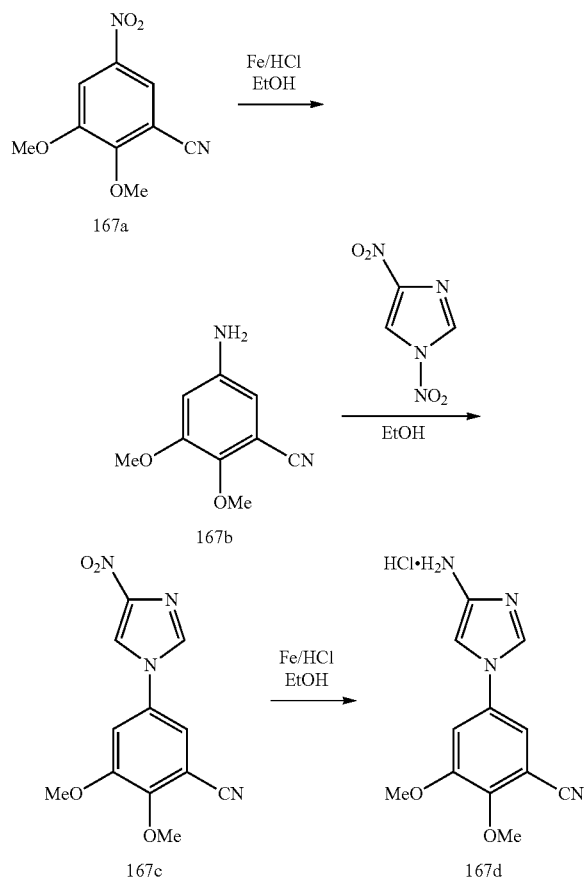

Step-1: Preparation of 5-amino-2,3-dimethoxybenzonitrile (167b)

To a stirred solution of 2,3-dimethoxy-5-nitro-benzonitrile (167a) (2.0 g, 9.61 mmol, prepared according to the procedure reported by Shackelford, Scott A. et al; in Journal of Organic Chemistry, 68(2), 267-275; 2003) in EtOH (50 mL) at room temperature was added Fe (4.2 g, 76.90 mmol) and heated at 75° C. for 3 h. The reaction mixture was concentrated under reduced pressure, quenched with aqueous ammonia (100 mL) and extracted with ethyl acetate (3×100 mL). The combined organic layers were washed with brine (100 mL), dried, filtered and concentrated under reduced pressure to afford 5-amino-2,3-dimethoxybenzonitrile (167b) (1.2 g, 70%) as an off-white solid; THNMR (300 MHz, DMSO-$d_6$): δ 6.58 (s, 1H), 6.30 (s, 1H), 5.34 (s, 2H), 3.76 (s, 3H), 3.71 (s, 3H).

Step-2: Preparation of 2,3-dimethoxy-5-(4-nitro-1H-imidazol-1-yl)benzonitrile (167c)

Reaction of 1,4-dinitro-1H-imidazole (1.06 g, 6.74 mmol) with 5-amino-2,3-dimethoxybenzonitrile (167b) (1.2 g, 6.74 mmol) as reported in step-2 of General scheme for preparation of 3-substituted-(4-amino-1H-imidazol-1-yl) gave after filtration 2,3-dimethoxy-5-(4-nitro-1H-imidazol-1-yl)benzonitrile (167c) (1.0 g, 54%) as an off-white solid; $^1$H NMR (300 MHz, DMSO-$d_6$): δ 9.09 (s, 1H), 8.52 (s, 1H), 7.86-7.82 (2s, 2H), 3.98 (2s, 6H).

Step-3: 5-(4-amino-1H-imidazol-1-yl)-2,3-dimethoxybenzonitrile hydrochloride (167d)

Reduction of nitro to amine of 2,3-dimethoxy-5-(4-nitro-1H-imidazol-1-yl)benzonitrile (167c) (1.0 g, 3.64 mmol) as reported in step-1 of this scheme, using Fe (1.6 g, 17.91 mmol) and conc. HCl (40 mL) in ethanol (50 mL) gave 5-(4-amino-1H-imidazol-1-yl)-2,3-dimethoxybenzonitrile hydrochloride (167d) (1.0 g, 98%) as an off-white solid; $^1$H NMR (300 MHz, DMSO-$d_6$): δ 10.49 (s, 1H), 7.84-7.78 (m, 3H), 7.24 (s, 1H), 6.18 (s, 1H), 3.92 (s, 3H), 3.90 (s, 3H).

Preparation of 1-(4-(4-amino-1H-imidazol-1-yl)-2,3-dimethoxyphenyl)ethanone (212e)

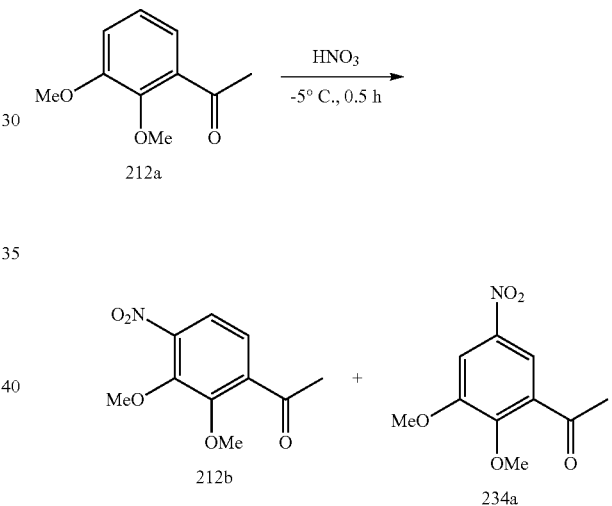

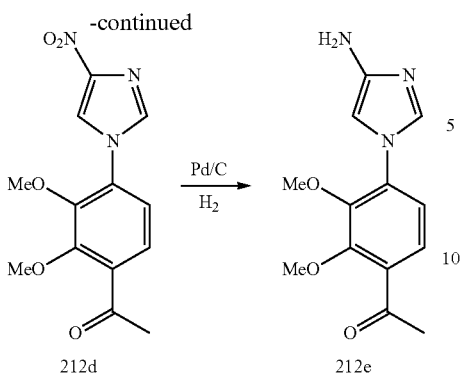

Step-1: Preparation of 1-(2,3-dimethoxy-4-nitrophenyl)ethanone (212b) and 1-(2,3-dimethoxy-5-nitrophenyl)ethanone (234a)

To a stirred solution of 1-(2,3-dimethoxyphenyl)ethan-1-one (212a) (6.0 g, 33.29 mmol) at −5° C. in DCM was added HNO$_3$ (12.59 g, 199 mmol) stirred at −5° C. for 0.5 h, poured into ice water (500 mL) and extracted with ethyl acetate (3×200 mL). The organic layers were combined washed with saturated aqueous NaHCO$_3$ solution (3×100 mL), dried, filtered, and concentrated under reduced pressure. The crude residue was purified by flash column chromatography [silica gel, with ethyl acetate in n-hexane (0-25%)] to afford 1-(2,3-dimethoxy-5-nitrophenyl)ethanone (234a) (2.0 g, 19%) as a yellow solid; $^1$H NMR (300 MHz, DMSO-d): δ 7.99 (q, J=2.8 Hz, 2H), 3.98 (d, J=4.9 Hz, 6H), 2.60 (s, 3H); MS (ES+): 226.0 (M+1) and 1-(2,3-dimethoxy-4-nitrophenyl)ethanone (212b) (1.8 g, 17%) as a yellow solid; $^1$H NMR (300 MHz, DMSO-d$_6$): δ 8.04 (dd, J=9.2, 1.1 Hz, 1H), 7.31 (dd, J=9.3, 1.2 Hz, 1H), 3.97 (d, J=1.3 Hz, 3H), 3.74 (d, J=1.2 Hz, 3H), 2.48 (d, J=1.3 Hz, 3H); MS (ES+): 226.0 (M+1).

Step-2: Preparation of 1-(4-amino-2,3-dimethoxyphenyl)ethanone (212c)

To a solution of 1-(2,3-dimethoxy-4-nitrophenyl)ethanone (212b) (3.0 g, 13.32 mmol) in EtOH (60 ml) was added Pd/C (0.63 g, 5.32 mmol) and hydrogenated at room temperature for 12 h. The reaction mixture was filter through Celite and filtrate was concentrated under reduced pressure to afford 1-(4-amino-2,3-dimethoxyphenyl)ethanone (212c) which was used as such in next step; MS (ES+): 196 (M+1).

Step-3: Preparation of 1-(2,3-dimethoxy-4-(4-nitro-1H-imidazol-1-yl)phenyl)ethanone (212d)

Reaction of 1,4-dinitro-1H-imidazole (2.42 g, 15.37 mmol) with 1-(4-amino-2,3-dimethoxyphenyl)ethanone (212c) (3.0 g, 15.37 mmol) as reported in step-2 of General scheme for preparation of 3-substituted-(4-amino-1H-imidazol-1-yl) gave after filtration 1-(2,3-dimethoxy-4-(4-nitro-1H-imidazol-1-yl)phenyl)ethanone (212d) (2.5 g, 56%) as yellow solid; $^1$H NMR (300 MHz, DMSO-d$_6$) δ 9.07 (d, J=1.5 Hz, 1H), 8.51 (d, J=1.5 Hz, 1H), 7.66 (d, J=2.7 Hz, 1H), 7.51 (d, J=2.6 Hz, 1H), 3.97 (s, 3H), 3.86 (s, 3H), 2.60 (s, 3H); MS (ES+): 292.0 (M+1).

Step-4: Preparation of 1-(4-(4-amino-1H-imidazol-1-yl)-2,3-dimethoxyphenyl)ethanone (212e)

Reduction of nitro to amine of 1-(2,3-dimethoxy-4-(4-nitro-1H-imidazol-1-yl)phenyl)ethanone (212d) (1.2 g, 4.12 mmol) as reported in step-3 of General scheme for preparation of 3-substituted-(4-amino-1H-imidazol-1-yl) gave 1-(4-(4-amino-1H-imidazol-1-yl)-2,3-dimethoxyphenyl)ethanone (212e) (100% yield) as a solid, which was used as such for next step without further purification.

Preparation of 1-(5-methoxypyridin-3-yl)-1H-imidazol-4-amine (228c)

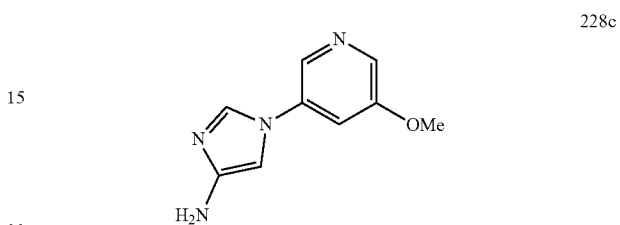

Reaction of 1,4-dinitro-1H-imidazole (2.55 g, 16.11 mmol) with 5-methoxypyridin-3-amine (2 g, 16.11 mmol; CAS #64436-92-6) as reported in step-2 of General scheme for preparation of 3-substituted-(4-amino-1H-imidazol-1-yl) gave after filtration 3-methoxy-5-(4-nitro-1H-imidazol-1-yl)pyridine (2 g, 9.08 mmol, 56% yield) as yellow solid; $^1$H NMR (300 MHz, DMSO-d$_6$) δ 9.09 (d, J=1.8 Hz, 1H), 8.64 (d, J=2.1 Hz, 1H), 8.54 (d, J=1.7 Hz, 1H), 8.39 (d, J=2.5 Hz, 1H), 7.88 (d, J=2.3 Hz, 1H), 3.92 (s, 3H).

Reduction of nitro to amine of 3-methoxy-5-(4-nitro-1H-imidazol-1-yl)pyridine (1 g, 4.54 mmol) as reported in step-3 of General scheme for preparation of 3-substituted-(4-amino-1H-imidazol-1-yl) gave 1-(5-methoxypyridin-3-yl)-1H-imidazol-4-amine (228c) (853 mg, 99% yield) as a light yellow solid; $^1$H NMR (300 MHz, DMSO-d$_6$) δ 8.44 (d, J=2.1 Hz, 1H), 8.19 (d, J=2.5 Hz, 1H), 8.00 (d, J=1.6 Hz, 1H), 7.59 (t, J=2.4 Hz, 1H), 6.77 (d, J=1.6 Hz, 1H), 4.52 (s, 2H, D$_2$O exchangeable), 3.90 (s, 3H).

Preparation of 1-(4-methoxy-3-(trifluoromethyl)phenyl)-1H-imidazol-4-amine (229c)

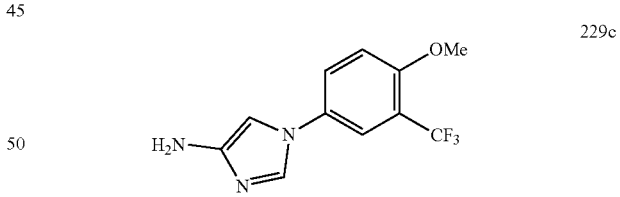

Reaction of 1,4-dinitro-1H-imidazole (4.13 g, 26.2 mmol) with 4-methoxy-3-(trifluoromethyl)aniline (5 g, 26.2 mmol; CAS #393-15-7) as reported in step-2 of General scheme for preparation of 3-substituted-(4-amino-1H-imidazol-1-yl) gave after filtration 1-(4-methoxy-3-(trifluoromethyl)phenyl)-4-nitro-1H-imidazole (3.5 g, 47% yield) as a white solid; 10 $^1$H NMR (300 MHz, DMSO-d$_6$) δ 9.04 (t, J=1.2 Hz, 1H), 8.47 (d, J=1.5 Hz, 1H), 8.09 (s, 1H), 8.07 (m, 1H), 7.54-7.42 (m, 1H), 3.97 (s, 3H).

Reduction of nitro to amine of 1-(4-methoxy-3-(trifluoromethyl)phenyl)-4-nitro-1H-imidazole (1 g, 3.48 mmol) as reported in step-3 of General scheme for preparation of 3-substituted-(4-amino-1H-imidazol-1-yl) gave 1-(4-methoxy-3-(trifluoromethyl)phenyl)-1H-imidazol-4-amine (229c) (800 mg, 89% yield) as a light yellow solid; $^1$H NMR (300 MHz, DMSO-d$_6$) δ 7.86 (d, J=1.6 Hz, 1H), 7.80 (dd, J=9.0, 2.8 Hz, 1H), 7.73 (d, J=2.8 Hz, 1H), 7.36 (d, J=9.0 Hz, 1H), 6.68 (d, J=1.6 Hz, 1H), 4.44 (s, 2H), 3.92 (s, 3H); $^{19}$F NMR (282 MHz, DMSO-d$_6$) δ −60.99.

Preparation of 5-(4-amino-1H-imidazol-1-yl)-2,3-dimethoxybenzamide (230e)

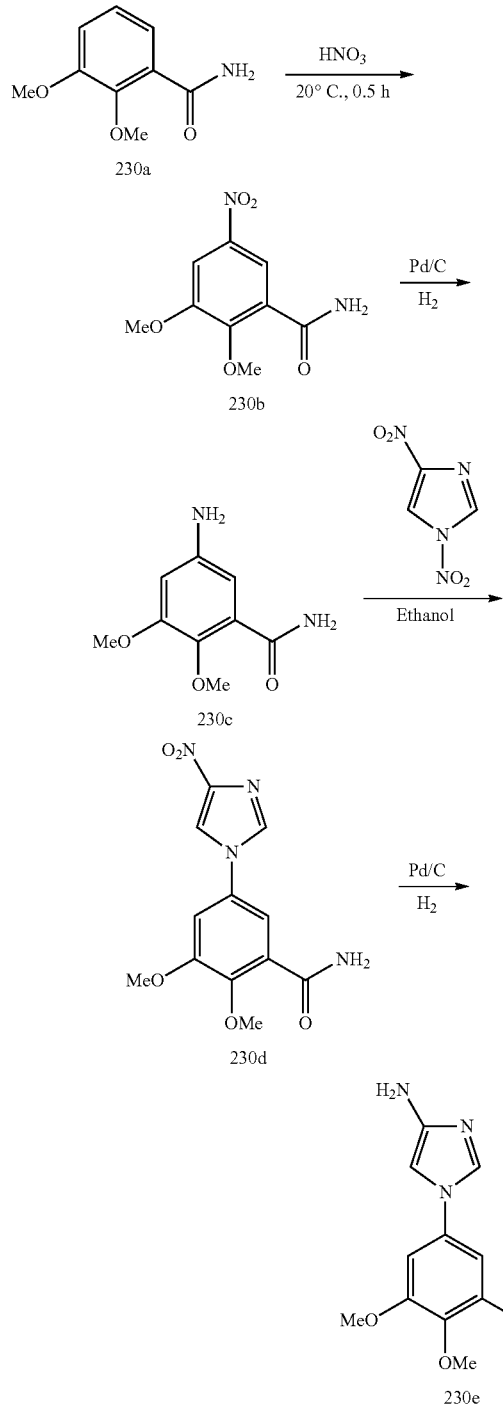

Step-1: Preparation of 2,3-dimethoxy-5-nitro-benzamide (230b)

To a stirred solution of 2,3-dimethoxy-benzamide (230a) (20 g, 110.38 mmol; CAS #1521-39-7) in acetic anhydride (140 mL) was added dropwise 70% HNO$_3$ (13.91 g, 154.53 mmol) at 15° C. The reaction mixture was stirred at 15-25° C. for 1 h and poured into ice water (1000 mL). The solid obtained was collected by filtration to get 2,3-dimethoxy-5-nitro-benzamide (230b) (15 g, 60%) as a yellow solid; $^1$H NMR (300 MHz, DMSO-d$_6$) δ 8.03-8.02 (d, 1H). 7.92-7.91 (d, 1H), 7.87 (s, 1H), 7.80 (s, 1H), 3.97 (s, 3H), 3.92 (s, 3H); MS (ES+): 227.0 (M+1).

Step-2: Preparation of 5-amino-2,3-dimethoxy-benzamide (230c)

To a solution of 2,3-dimethoxy-5-nitro-benzamide (230b) (15 g, 66.31 mmol) in EtOH (500 mL) was added Pd/C (3.4 g, 13.19 mmol) and hydrogenated at room temperature for 12 h. The reaction mixture was filtered through Celite and filtrate was concentrated under reduced pressure to afford 5-amino-2,3-dimethoxy-benzamide (230c) which was used as such in next step.

Step-3: Preparation of 2,3-dimethoxy-5-(4-nitro-imidazol-1-yl)-benzamide (230d)

Reaction of 1,4-dinitro-1H-imidazole (8.21 g, 52.02 mmol) with 5-amino-2,3-dimethoxy-benzamide (230c) (10 g, 52.02 mmol) as reported in step-2 of General scheme for preparation of 3-substituted-(4-amino-1H-imidazol-1-yl) gave after filtration 2,3-dimethoxy-5-(4-nitro-imidazol-1-yl)-benzamide (230d) (8 g, 61%) as a yellow solid; $^1$H NMR (300 MHz, DMSO-d$_6$): δ 9.06-9.05 (s, 1H). 8.51-8.50 (s, 1H), 7.77 (d, 1H), 7.69 (d, 1H), 7.58-7.57 (s, 1H), 7.54-7.53 (s, 1H), 3.95 (s, 3H), 3.82 (s, 3H); MS (ES+): 293.0 (M+1).

Step-4: Preparation of 5-(4-amino-1H-imidazol-1-yl)-2,3-dimethoxybenzamide (230e)

Reduction of nitro to amine of 2,3-dimethoxy-5-(4-nitro-imidazol-1-yl)-benzamide (230d) (2 g, 6.84 mmol) as reported in step-3 of General scheme for preparation of 3-substituted-(4-amino-1H-imidazol-1-yl) gave after purification by flash column chromatography [silica gel, eluting with methanol in ethyl acetate (0-5%)] 5-(4-amino-1H-imidazol-1-yl)-2,3-dimethoxybenzamide (230e) (600 mg, 34%) as an off-white solid; $^1$H NMR (300 MHz, DMSO-d$_6$): δ 8.28-8.27 (s, 1H). 8.05-8.04 (s, 1H), 7.78-7.75 (d, 2H), 7.64-7.60 (d, 2H), 7.38 (s, 1H), 7.34 (s, 1H), 3.94 (s, 3H), 3.84 (s, 3H); MS: ES+(M+1) 263.1.

Preparation of 1-(5-(4-amino-1H-imidazol-1-yl)-2,3-dimethoxyphenyl)ethanone (234d)

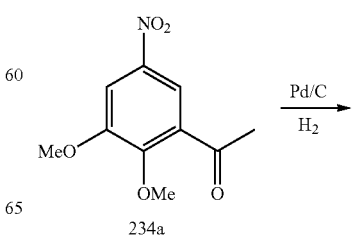

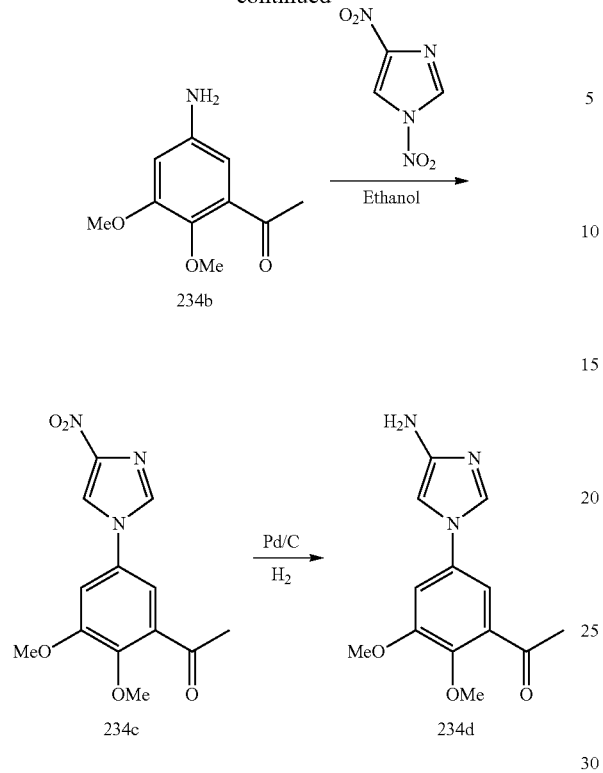

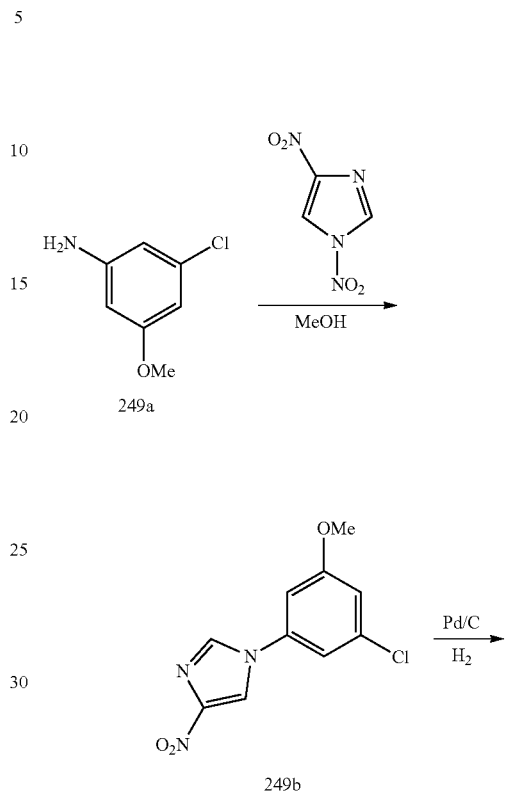

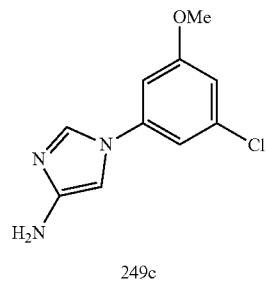

Step-1: Preparation of 1-(5-amino-2,3-dimethoxyphenyl)ethanone (234b)

To a solution of 1-(2,3-dimethoxy-5-nitrophenyl)ethanone (234a) (3 g, 13.32 mmol) in EtOH (60 mL) was added Pd/C (0.63 g, 5.32 mmol) and hydrogenated at room temperature for 12 h. The reaction mixture was filtered through Celite and filtrate was concentrated under reduced pressure to afford 1-(5-amino-2,3-dimethoxyphenyl)ethanone (234b) which was used as such in next step; MS (ES+): 196 (M+1).

Step-2: Preparation of 1-(2,3-dimethoxy-5-(4-nitro-1H-imidazol-1-yl)phenyl)ethanone (234c)

Reaction of 1,4-dinitro-1H-imidazole (1.62 g, 10.25 mmol) with 1-(5-amino-2,3-dimethoxyphenyl)ethanone (234b) (2 g, 10.25 mmol) as reported in step-2 of General scheme for preparation of 3-substituted-(4-amino-1H-imidazol-1-yl) gave after filtration 1-(2,3-dimethoxy-5-(4-nitro-1H-imidazol-1-yl)phenyl)ethanone (234c) (800 mg, 27%) as yellow solid; $^1$H NMR (300 MHz, DMSO-$d_6$) δ 8.58 (d, J=1.5 Hz, 1H), 7.97 (d, J=1.5 Hz, 1H), 7.47-7.13 (m, 2H), 3.93 (s, 3H), 3.84 (s, 3H), 2.45 (s, 3H); MS (ES+): 292.0 (M+1).

Step-4: Preparation of 1-(5-(4-amino-1H-imidazol-1-yl)-2,3-dimethoxyphenyl)ethanone (234d)

Reduction of nitro to amine of 1-(2,3-dimethoxy-5-(4-nitro-1H-imidazol-1-yl)phenyl)ethanone (234c) (800 mg, 2.74 mmol) as reported in step-3 of General scheme for preparation of 3-substituted-(4-amino-1H-imidazol-1-yl) gave 1-(5-(4-amino-1H-imidazol-1-yl)-2,3-dimethoxyphenyl)ethanone (234d) (300 mg, 34% yield) as a solid, which was used as such for next step without further purification.

Preparation of 1-(3-chloro-5-methoxyphenyl)-1H-imidazol-4-amine (249c)

Reaction of 1,4-dinitro-1H-imidazole (2.01 g, 12.69 mmol) with 3-chloro-5-methoxyaniline (249a) (2 g, 12.69 mmol; CAS #10272-06-7) as reported in step-2 of General scheme for preparation of 3-substituted-(4-amino-1H-imidazol-1-yl) gave after filtration 1-(3-chloro-5-methoxyphenyl)-4-nitro-1H-imidazole (249b) (2.48 g, 77% yield) as a red solid; $^1$H NMR (300 MHz, DMSO-$d_6$) δ 9.11 (d, J=1.6 Hz, 1H), 8.57 (d, J=1.6 Hz, 1H), 7.61 (t, J=1.8 Hz, 1H), 7.44 (d, J=2.2 Hz, 1H), 7.17 (t, J=1.9 Hz, 1H), 3.88 (s, 3H).

Reduction of nitro to amine of 1-(3-chloro-5-methoxyphenyl)-4-nitro-1H-imidazole (249b) (500 mg, 1.97 mmol) as reported in step-3 of General scheme for preparation of 3-substituted-(4-amino-1H-imidazol-1-yl) gave 1-(3-chloro-5-methoxyphenyl)-1H-imidazol-4-amine (249c) (430 g, 98% yield) as a brown oil which was used as such without further purification; MS (ES+): 224.1 (M+1).

Preparation of 1-(4-chloro-3-methoxyphenyl)-1H-imidazol-4-amine (250c)

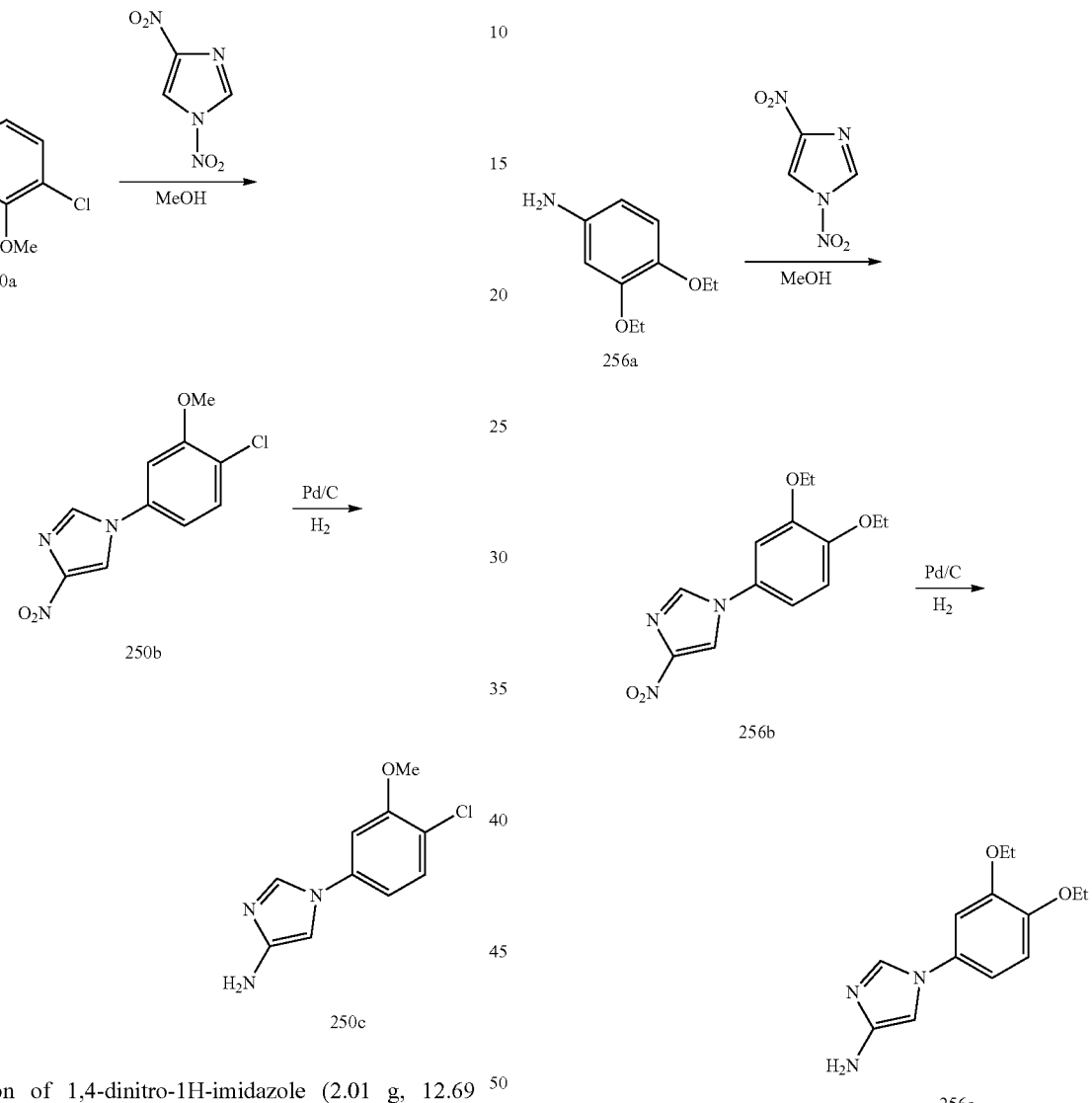

Reaction of 1,4-dinitro-1H-imidazole (2.01 g, 12.69 mmol) with 4-chloro-3-methoxyaniline (250a) (2 g, 12.69 mmol; CAS #13726-14-2) as reported in step-2 of General scheme for preparation of 3-substituted-(4-amino-1H-imidazol-1-yl) gave after filtration 1-(4-chloro-3-methoxyphenyl)-4-nitro-1H-imidazole (250b) (2.64 g, 82% yield) as a buff colored solid; $^1$H NMR (300 MHz, DMSO-d$_6$) δ 9.11 (s, 1H), 8.55 (s, 1H), 7.65 (d, J=8.5 Hz, 1H), 7.59 (d, J=2.6 Hz, 1H), 7.42 (dd, J=8.4, 2.6 Hz, 1H), 3.97 (s, 3H).

Reduction of nitro to amine of 1-(4-chloro-3-methoxyphenyl)-4-nitro-1H-imidazole (250b) (1 g, 3.94 mmol) as reported in step-3 of General scheme for preparation of 3-substituted-(4-amino-1H-imidazol-1-yl) gave 1-(4-chloro-3-methoxyphenyl)-1H-imidazol-4-amine (250c) (430 mg, 98% yield) as a light yellow solid which was used as such without further purification; $^1$H NMR (300 MHz, DMSO-d$_6$) δ 7.93 (d, J=1.6 Hz, 1H), 7.47 (d, J=8.5 Hz, 1H), 7.27 (d, J=2.4 Hz, 1H), 7.11 (dd, J=8.6, 2.4 Hz, 1H), 6.71 (d, J=1.7 Hz, 1H), 4.46 (s, 2H), 3.93 (s, 3H).

Preparation of 1-(3,4-diethoxyphenyl)-1H-imidazol-4-amine (256c)

Reaction of 1,4-dinitro-1H-imidazole (1.744 g, 11.04 mmol) with 3,4-diethoxyaniline (256a) (2 g, 11.04 mmol; CAS #39052-12-5) as reported in step-2 of General scheme for preparation of 3-substituted-(4-amino-1H-imidazol-1-yl) gave after filtration 1-(3,4-diethoxyphenyl)-4-nitro-1H-imidazole (256b) as a yellow colored solid; $^1$H NMR (300 MHz, DMSO-d$_6$) δ 8.97 (d, J=1.6 Hz, 1H), 8.42 (d, J=1.6 Hz, 1H), 7.38 (d, J=2.6 Hz, 1H), 7.28 (dd, J=8.5, 2.5 Hz, 1H), 7.10 (d, J=8.7 Hz, 1H), 4.11 (dq, J=17.4, 6.9 Hz, 4H), 1.35 (td, J=6.9, 5.3 Hz, 6H).

Reduction of nitro to amine of 1-(3,4-diethoxyphenyl)-4-nitro-1H-imidazole (256b) (1 g, 3.61 mmol) as reported in step-3 of General scheme for preparation of 3-substituted-(4-amino-1H-imidazol-1-yl) gave 1-(3,4-diethoxyphenyl)-

1H-imidazol-4-amine (256c) (844 mg, 95% yield) as a brown solid; ¹H NMR (300 MHz, DMSO-$d_6$) δ 7.73 (d, J=1.6 Hz, 1H), 7.08 (d, J=2.1 Hz, 1H), 6.97 (d, J=2.9 Hz, 2H), 6.59 (d, J=1.6 Hz, 1H), 4.35 (s, 2H), 4.05 (dq, J=21.4, 7.0 Hz, 4H), 1.41-1.23 (m, 6H); MS (ES+) 248.3 (M+1), 270.3 (M+Na).

Preparation of 1-(3-methoxy-5-methylphenyl)-1H-imidazol-4-amine (257c)

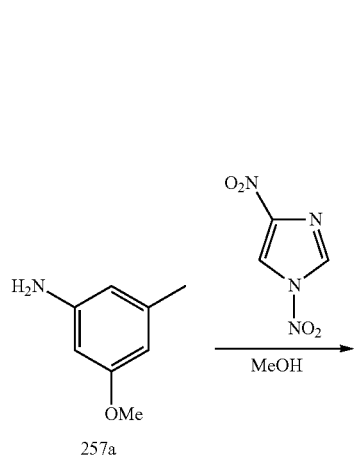

Reaction of 1,4-dinitro-1H-imidazole (1.74 g, 11.04 mmol) with 3-methoxy-5-methylaniline (257a) (2 g, 14.58 mmol; CAS #66584-31-4) as reported in step-2 of General scheme for preparation of 3-substituted-(4-amino-1H-imidazol-1-yl) gave after filtration 1-(3-methoxy-5-methylphenyl)-4-nitro-1H-imidazole (257b) as a yellow colored solid; ¹H NMR (300 MHz, DMSO-$d_6$) δ 9.02 (d, J=1.6 Hz, 1H), 8.49 (d, J=1.5 Hz, 1H), 7.25 (s, 1H), 7.22 (d, J=2.4 Hz, 1H), 6.88 (s, 1H), 3.83 (s, 3H), 2.35 (s, 3H).

Reduction of nitro to amine of 1-(3-methoxy-5-methylphenyl)-4-nitro-1H-imidazole (257b) (1 g, 4.29 mmol) as reported in step-3 of General scheme for preparation of 3-substituted-(4-amino-1H-imidazol-1-yl) gave 1-(3-methoxy-5-methylphenyl)-1H-imidazol-4-amine (257c) (826 mg, 95% yield) as a brown syrup; ¹H NMR (300 MHz, DMSO-$d_6$) δ 7.84 (d, J=1.6 Hz, 1H), 6.93 (s, 1H), 6.88 (d, J=2.2 Hz, 1H), 6.66 (s, 1H), 6.63 (d, J=1.6 Hz, 1H), 4.40 (s, 2H), 3.78 (s, 3H), 2.31 (s, 3H); MS (ES+): 204.3 (M+1).

Preparation of 4-(4-amino-1H-imidazol-1-yl)-2-methoxybenzonitrile (258c)

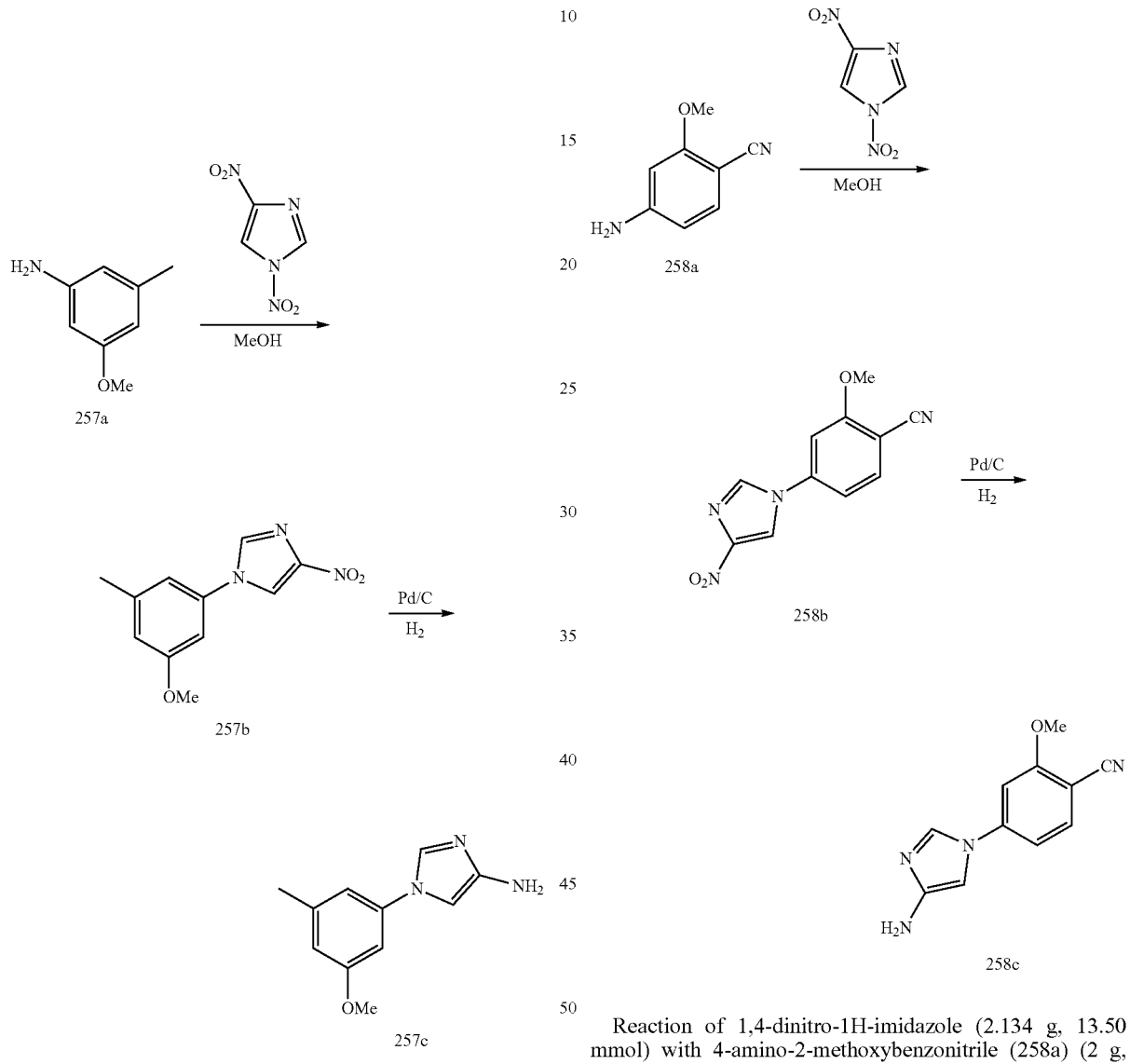

Reaction of 1,4-dinitro-1H-imidazole (2.134 g, 13.50 mmol) with 4-amino-2-methoxybenzonitrile (258a) (2 g, 13.5 mmol; CAS #7251-09-4) as reported in step-2 of General scheme for preparation of 3-substituted-(4-amino-1H-imidazol-1-yl) gave after filtration 2-methoxy-4-(4-nitro-1H-imidazol-1-yl)benzonitrile (258b) as a yellow colored solid; ¹H NMR (300 MHz, DMSO-$d_6$) δ 9.23 (s, 1H), 8.68 (s, 1H), 8.00 (d, J=8.4 Hz, 1H), 7.70 (s, 1H), 7.65-7.52 (m, 1H), 4.04 (s, 3H).

Reduction of nitro to amine of 2-methoxy-4-(4-nitro-1H-imidazol-1-yl)benzonitrile (258b) (1 g, 4.09 mmol) as reported in step-3 of General scheme for preparation of 3-substituted-(4-amino-1H-imidazol-1-yl) gave 4-(4-amino-1H-imidazol-1-yl)-2-methoxybenzonitrile (258c) (600 mg, 68% yield) as a brown syrup; ¹H NMR (300 MHz, DMSO-$d_6$) δ 8.13 (d, J=1.5 Hz, 1H), 7.78 (d, J=8.3 Hz, 1H), 7.34 (d, J=1.9 Hz, 1H), 7.27 (dd, J=8.4, 2.0 Hz, 1H), 6.82 (d, J=1.5 Hz, 1H), 4.59 (s, 2H), 3.99 (s, 3H).

833
Preparation of 1-(3-(trifluoromethoxy)phenyl)-1H-imidazol-4-amine (262c)

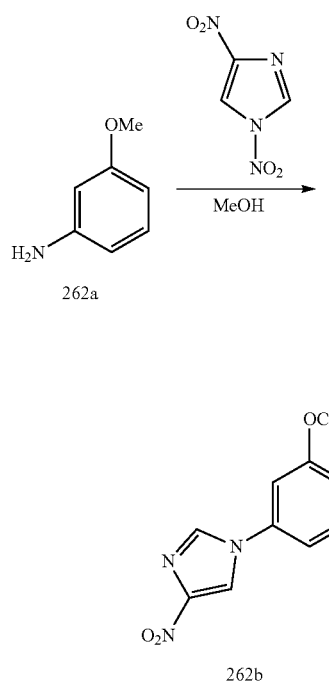

Reaction of 1,4-dinitro-1H-imidazole (1.785 g, 11.29 mmol) with 3-(trifluoromethoxy)aniline (262a) (2 g, 11.29 mmol; CAS #1535-73-5) as reported in step-2 of General scheme for preparation of 3-substituted-(4-amino-1H-imidazol-1-yl) gave after filtration 4-nitro-1-(3-(trifluoromethoxy)phenyl)-1H-imidazole (262b) as a yellow colored solid; $^1$H NMR (300 MHz, DMSO-$d_6$) δ 9.12 (d, J=1.6 Hz, 1H), 8.58 (d, J=1.6 Hz, 1H), 7.99 (s, 1H), 7.91 (dd, J=8.1, 2.1 Hz, 1H), 7.74 (t, J=8.2 Hz, 1H), 7.52 (d, J=8.2 Hz, 1H).

Reduction of nitro to amine of 4-nitro-1-(3-(trifluoromethoxy)phenyl)-1H-imidazole (262b) (1 g, 3.66 mmol) as reported in step-3 of General scheme for preparation of 3-substituted-(4-amino-1H-imidazol-1-yl) gave 1-(3-(trifluoromethoxy)phenyl)-1H-imidazol-4-amine (262c) as a brown syrup; $^1$H NMR (300 MHz, DMSO-$d_6$) δ 8.13 (d, J=1.5 Hz, 1H), 7.78 (d, J=8.3 Hz, 1H), 7.34 (d, J=1.9 Hz, 1H), 7.27 (dd, J=8.4, 2.0 Hz, 1H), 6.82 (d, J=1.5 Hz, 1H), 4.59 (s, 2H).

834
Preparation of 1-(3-methyl-5-(trifluoromethoxy)phenyl)-1H-imidazol-4-amine (263c)

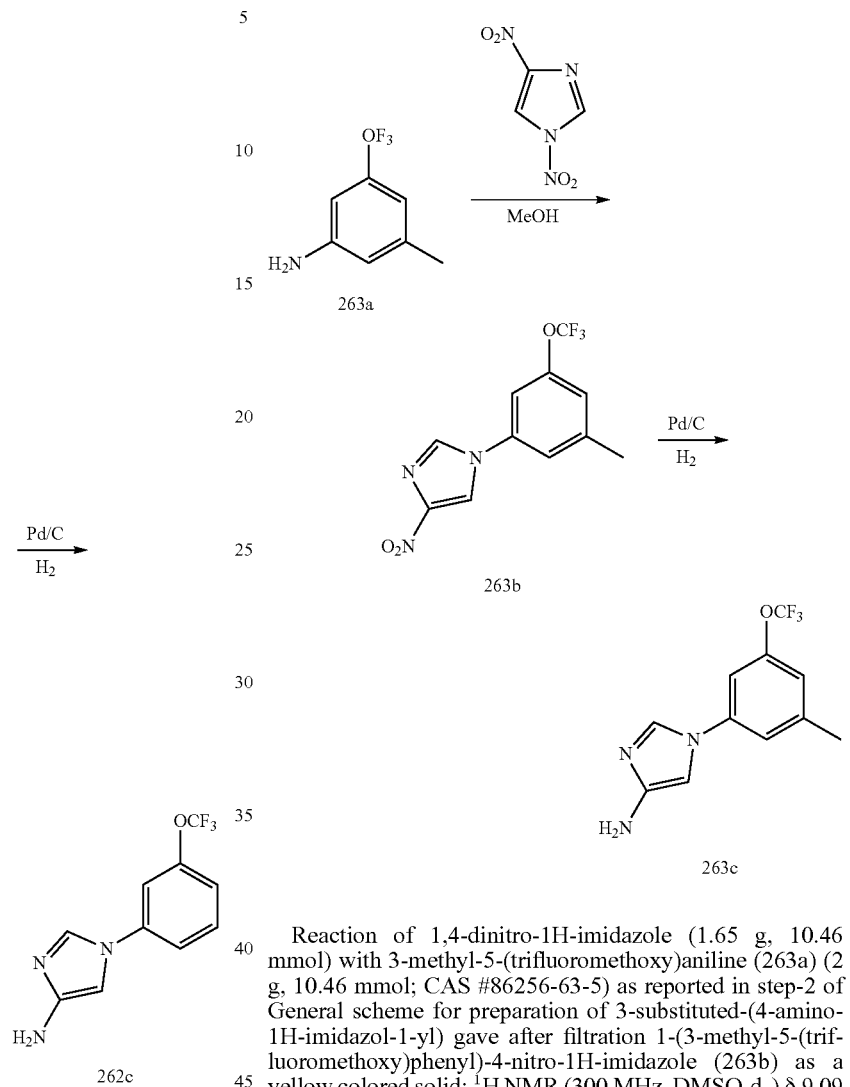

Reaction of 1,4-dinitro-1H-imidazole (1.65 g, 10.46 mmol) with 3-methyl-5-(trifluoromethoxy)aniline (263a) (2 g, 10.46 mmol; CAS #86256-63-5) as reported in step-2 of General scheme for preparation of 3-substituted-(4-amino-1H-imidazol-1-yl) gave after filtration 1-(3-methyl-5-(trifluoromethoxy)phenyl)-4-nitro-1H-imidazole (263b) as a yellow colored solid; $^1$H NMR (300 MHz, DMSO-$d_6$) δ 9.09 (d, J=1.6 Hz, 1H), 8.56 (d, J=1.6 Hz, 1H), 7.79 (s, 2H), 7.36 (s, 1H), 2.44 (s, 3H).

Reduction of nitro to amine of 1-(3-methyl-5-(trifluoromethoxy)phenyl)-4-nitro-1H-imidazole (263b) (1 g, 3.48 mmol) as reported in step-3 of General scheme for preparation of 3-substituted-(4-amino-1H-imidazol-1-yl) gave 1-(3-methyl-5-(trifluoromethoxy)phenyl)-1H-imidazol-4-amine (263c) as a brown syrup.

Preparation of 5-(4-amino-1H-imidazol-1-yl)-N-(cyclopropylmethyl)-2,3-dimethoxybenzamide (267g)

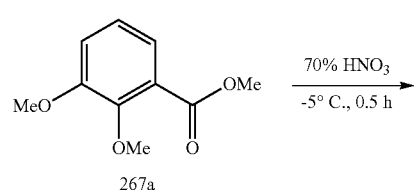

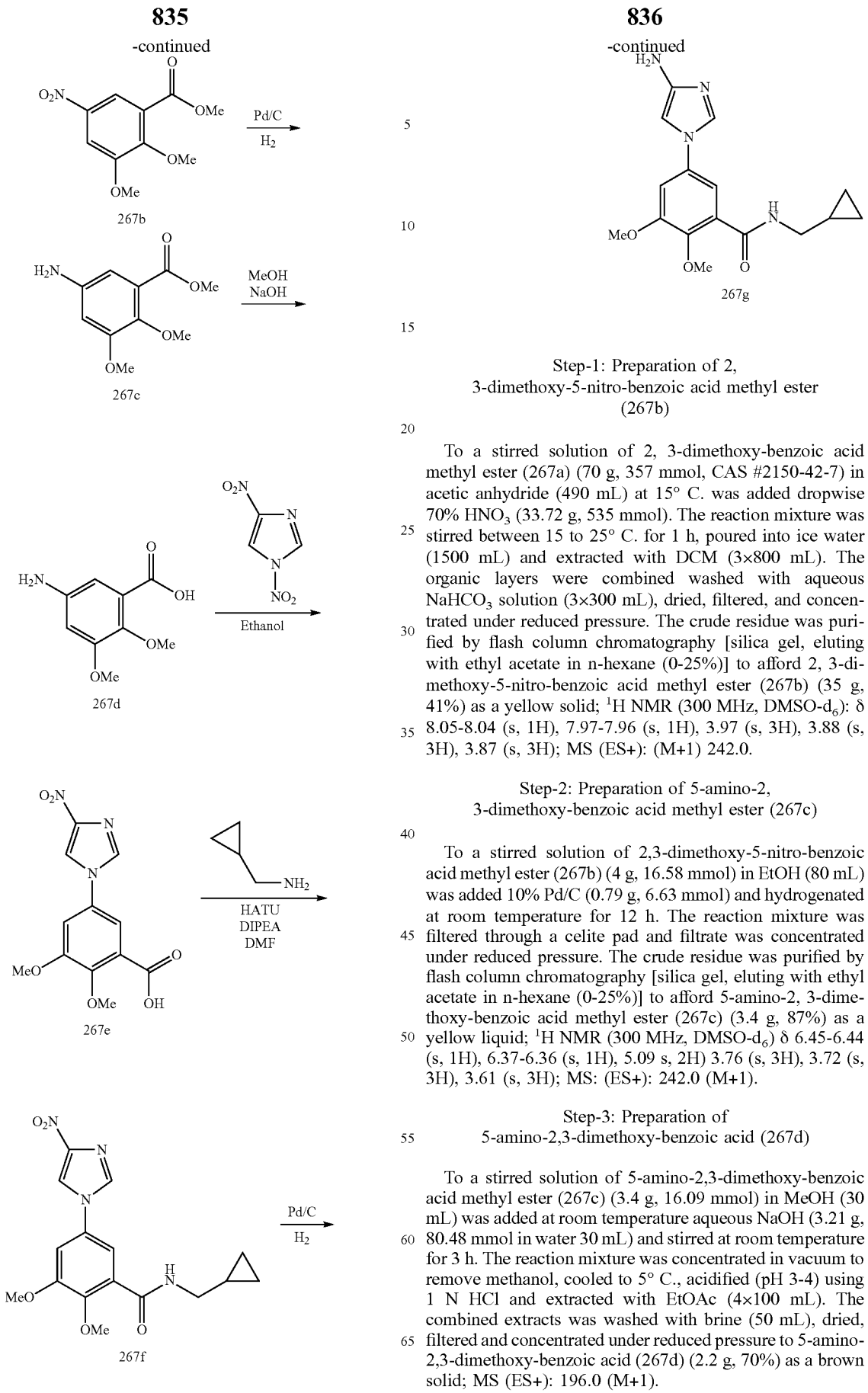

Step-1: Preparation of 2, 3-dimethoxy-5-nitro-benzoic acid methyl ester (267b)

To a stirred solution of 2, 3-dimethoxy-benzoic acid methyl ester (267a) (70 g, 357 mmol, CAS #2150-42-7) in acetic anhydride (490 mL) at 15° C. was added dropwise 70% $HNO_3$ (33.72 g, 535 mmol). The reaction mixture was stirred between 15 to 25° C. for 1 h, poured into ice water (1500 mL) and extracted with DCM (3×800 mL). The organic layers were combined washed with aqueous $NaHCO_3$ solution (3×300 mL), dried, filtered, and concentrated under reduced pressure. The crude residue was purified by flash column chromatography [silica gel, eluting with ethyl acetate in n-hexane (0-25%)] to afford 2, 3-dimethoxy-5-nitro-benzoic acid methyl ester (267b) (35 g, 41%) as a yellow solid; $^1$H NMR (300 MHz, DMSO-$d_6$): δ 8.05-8.04 (s, 1H), 7.97-7.96 (s, 1H), 3.97 (s, 3H), 3.88 (s, 3H), 3.87 (s, 3H); MS (ES+): (M+1) 242.0.

Step-2: Preparation of 5-amino-2, 3-dimethoxy-benzoic acid methyl ester (267c)

To a stirred solution of 2,3-dimethoxy-5-nitro-benzoic acid methyl ester (267b) (4 g, 16.58 mmol) in EtOH (80 mL) was added 10% Pd/C (0.79 g, 6.63 mmol) and hydrogenated at room temperature for 12 h. The reaction mixture was filtered through a celite pad and filtrate was concentrated under reduced pressure. The crude residue was purified by flash column chromatography [silica gel, eluting with ethyl acetate in n-hexane (0-25%)] to afford 5-amino-2, 3-dimethoxy-benzoic acid methyl ester (267c) (3.4 g, 87%) as a yellow liquid; $^1$H NMR (300 MHz, DMSO-$d_6$) δ 6.45-6.44 (s, 1H), 6.37-6.36 (s, 1H), 5.09 s, 2H) 3.76 (s, 3H), 3.72 (s, 3H), 3.61 (s, 3H); MS: (ES+): 242.0 (M+1).

Step-3: Preparation of 5-amino-2,3-dimethoxy-benzoic acid (267d)

To a stirred solution of 5-amino-2,3-dimethoxy-benzoic acid methyl ester (267c) (3.4 g, 16.09 mmol) in MeOH (30 mL) was added at room temperature aqueous NaOH (3.21 g, 80.48 mmol in water 30 mL) and stirred at room temperature for 3 h. The reaction mixture was concentrated in vacuum to remove methanol, cooled to 5° C., acidified (pH 3-4) using 1 N HCl and extracted with EtOAc (4×100 mL). The combined extracts was washed with brine (50 mL), dried, filtered and concentrated under reduced pressure to 5-amino-2,3-dimethoxy-benzoic acid (267d) (2.2 g, 70%) as a brown solid; MS (ES+): 196.0 (M+1).

Step-4: Preparation of 2,3-dimethoxy-5-(4-nitro-imidazol-1-yl)-benzoic acid (267e)

To a stirred solution of 5-amino-2,3-dimethoxy-benzoic acid (267d) (2.2 g, 11.15 mmol) in EtOH (50 mL) was added 1,4-dinitro-1H-imidazole (1.76 g, 11.15 mmol) and stirred at room temperature for 5 h. The solid obtained was collected by filtration, dried in vacuum to afford 2,3-dimethoxy-5-(4-nitro-imidazol-1-yl)-benzoic acid (267e) (1.7 g, 52%) as a yellow solid; $^1$H NMR (300 MHz, DMSO-$d_6$) δ 12.94 (s, 1H) 9.05 (s, 1H), 8.49 (s, 1H), 7.61-7.60 (s, 1H), 7.55-7.54 (s, 1H), 3.94 (s, 3H), 3.83 (s, 3H); MS (ES+): 294.0 (M+1); (ES−): 292 (M−1).

Step-5: Preparation of N-cyclopropylmethyl-2,3-dimethoxy-5-(4-nitro-imidazol-1-yl)-benzamide (267f)

To a solution of 2,3-dimethoxy-5-(4-nitro-imidazol-1-yl)-benzoic acid (267e) (1.7 g, 5.79 mmol) in DMF (30.0 mL) at room temperature was added cyclopropyl-methylamine (500 mg, 6.95 mmol), HATU (2.7 g, 6.95 mmol), DIPEA (2.24 g, 17.37 mmol) and stirred at room temperature for 2 h. The reaction mixture was poured into ice-water (100 mL) and extracted with EtOAc (3×80 mL). The combined organic phases were washed with brine (100 mL), dried, filtered, and concentrated under reduced pressure. The crude residue was purified by flash column chromatography [silica gel, eluting with ethyl acetate in n-hexane (0-70%)] to afford N-cyclopropylmethyl-2,3-dimethoxy-5-(4-nitro-imidazol-1-yl)-benzamide (267f) (1.1 g, 55%) as a yellow solid; $^1$H NMR (300 MHz, DMSO-$d_6$): δ 8.81-8.80 (s, 1H), 8.25 (s, 1H), 8.15 (s, 1H), 7.33 (s, 1H), 7.24 (s, 1H), 3.70 (s, 3H), 3.57 (s, 3H), 2.92-2.91 (m, 2H), 0.92-0.90 (m, 1H), 0.21-0.015 (m, 2H), 0.004-0.0 (m, 2H); MS (ES): 347.0 (M+1), (ES−): 345.0 (M−1).

Step-6: Preparation of 5-(4-amino-imidazol-1-yl)-N-cyclopropylmethyl-2,3-dimethoxy-benzamide (267g)

To a solution of N-cyclopropylmethyl-2,3-dimethoxy-5-(4-nitro-imidazol-1-yl)-benzamide (267f) (1.1 g, 3.17 mmol) in IPA (60 mL) was added 10% Pd/C (0.15 g, 1.27 mmol) and hydrogenated under balloon pressure for 12 h. The reaction mixture was filtered through a celite pad and filtrate was concentrated under reduced pressure to afford 5-(4-amino-imidazol-1-yl)-N-cyclopropylmethyl-2,3-dimethoxy-benzamide (267g) (100% yield) which was used as such in next step. MS (ES+): 317.0 (M+1), (ES−): 315.0 (M−1).

Preparation of 1-(2,2-difluorobenzo[d][1,3]dioxol-5-yl)-1H-imidazol-4-amine (339c)

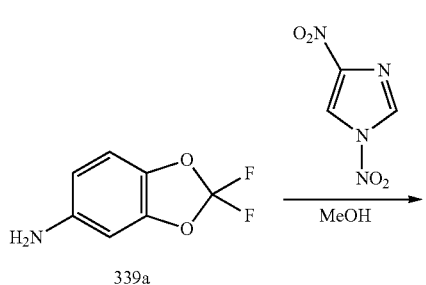

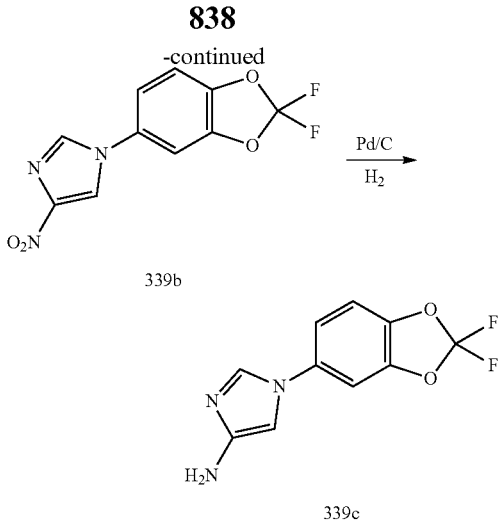

Step-1: Preparation of 1-(2,2-difluorobenzo[d][1,3]dioxol-5-yl)-4-nitro-1H-imidazole (339b)

Reaction of 1,4-dinitro-1H-imidazole (913 mg, 5.78 mmol) with 2,2-difluorobenzo[d][1,3]dioxol-5-amine (339a) (1 g, 5.78 mmol; CAS #1544-85-0) as reported in step-2 of General scheme for preparation of 3-substituted-(4-amino-1H-imidazol-1-yl) gave after filtration 1-(2,2-difluorobenzo[d][1,3]dioxol-5-yl)-4-nitro-1H-imidazole (339b) (491 mg, 31.6% yield) as a yellow solid; $^1$H NMR (300 MHz, DMSO-$d_6$) δ 8.99 (d, J=1.6 Hz, 1H), 8.45 (d, J=1.6 Hz, 1H), 8.04 (dd, J=1.9, 0.8 Hz, 1H), 7.68 (t, J=1.4 Hz, 2H).

Step-2: Preparation of 1-(2,2-difluorobenzo[d][1,3]dioxol-5-yl)-1H-imidazol-4-amine (339c)

Reduction of nitro to amine of 1-(2,2-difluorobenzo[d][1,3]dioxol-5-yl)-4-nitro-1H-imidazole (339b) (484 mg, 1.8 mmol) as reported in step-3 of General scheme for preparation of 3-substituted-(4-amino-1H-imidazol-1-yl) gave 1-(2,2-difluorobenzo[d][1,3]dioxol-5-yl)-1H-imidazol-4-amine (339c) (420 mg, 98% yield) as a white solid; $^1$H NMR (300 MHz, DMSO-$d_6$) δ 7.83 (d, J=1.6 Hz, 1H), 7.75 (d, J=2.2 Hz, 1H), 7.49 (d, J=8.6 Hz, 1H), 7.37 (dd, J=8.7, 2.3 Hz, 1H), 6.64 (d, J=1.6 Hz, 1H), 4.47 (s, 2H).

Preparation of methyl 5-(4-amino-1H-imidazol-1-yl)-2,3-dimethoxybenzoate (350b)

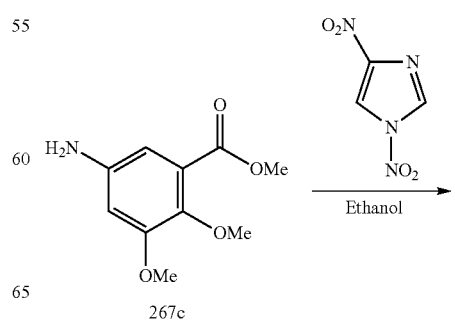

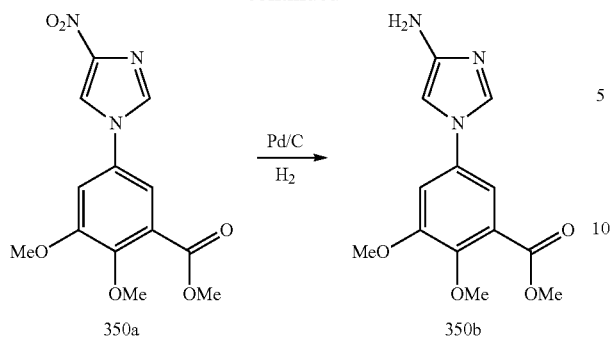

Step-1: Preparation of methyl 2,3-dimethoxy-5-(4-nitro-1H-imidazol-1-yl)benzoate (350a)

Reaction of 1,4-dinitro-1H-imidazole (3.74 g, 23.67 mmol) with methyl 5-amino-2,3-dimethoxybenzoate (267c) (5 g, 23.67 mmol) as reported in step-2 of General scheme for preparation of 3-substituted-(4-amino-1H-imidazol-1-yl) gave after filtration methyl 2,3-dimethoxy-5-(4-nitro-1H-imidazol-1-yl)benzoate (350a) (4 g, 55%) as a brown solid; $^1$H NMR (300 MHz, DMSO-$d_6$): δ 9.06 (d, J=1.6 Hz, 1H), 8.50 (d, J=1.6 Hz, 1H), 7.67 (d, J=2.7 Hz, 1H), 7.59 (d, J=2.7 Hz, 1H), 3.96 (s, 3H), 3.86 (s, 3H), 3.81 (s, 3H); MS (ES+): 308.1 (M+1).

Step-2: Preparation of methyl 5-(4-amino-1H-imidazol-1-yl)-2,3-dimethoxybenzoate (350b)

Reduction of nitro to amine of methyl 2,3-dimethoxy-5-(4-nitro-1H-imidazol-1-yl)benzoate (350a) (4 g, 13.01 mmol) as reported in step-3 of General scheme for preparation of 3-substituted-(4-amino-1H-imidazol-1-yl) gave methyl 5-(4-amino-1H-imidazol-1-yl)-2,3-dimethoxybenzoate (350b) (3.61 g, 100%) as brown oily mass; $^1$H NMR (300 MHz, DMSO-$d_6$) δ 7.80 (dd, J=7.3, 2.1 Hz, 1H), 7.68-7.34 (m, 2H), 7.35-7.25 (m, 1H), 7.18 (d, J=2.6 Hz, 1H), 6.62 (d, J=1.6 Hz, 1H), 3.86 (s, 3H), 3.81-3.75 (m, 6H); MS (ES+): 278.4 (M+1).

Preparation of 5-(4-amino-1H-imidazol-1-yl)-N-cyclopentyl-2,3-dimethoxybenzamide (351b)

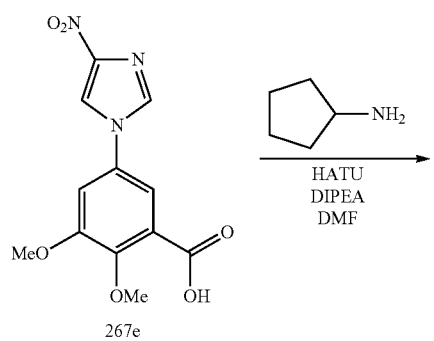

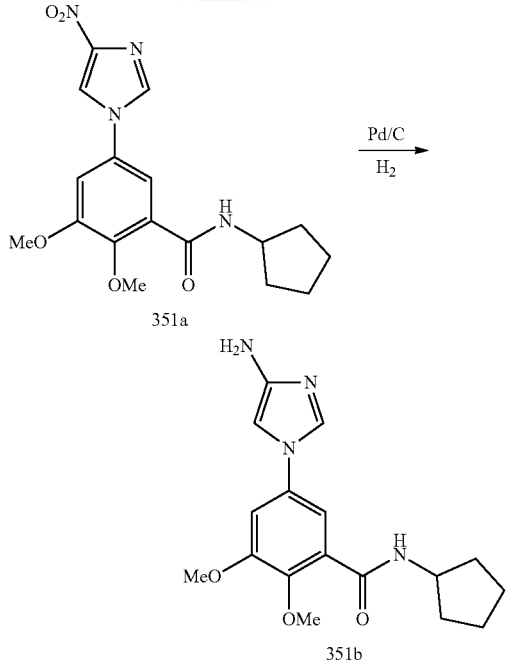

Step-1: Preparation of N-cyclopentyl-2,3-dimethoxy-5-(4-nitro-1H-imidazol-1-yl)benzamide (351a)

To a stirred solution of 2,3-dimethoxy-5-(4-nitro-1H-imidazol-1-yl)benzoic acid (267e) (1.5 g, 5.11 mmol) in DMF (30.0 mL) at RT were added cyclopentylamine (0.52 g, 6.13 mmol), HATU (1.5 g, 6.13 mmol) and DIPEA (1.98 g, 15.33 mmol). The reaction mixture was stirred at RT for 5 h, poured in ice water (150 mL) and extracted with ethyl acetate (3×100 mL). The combined organic extracts were washed with brine (2×100 mL), water (100 mL), dried, filtered and concentrated in vacuum. The crude residue was purified by silica gel column chromatography eluting with 80.0% ethyl acetate in n-hexane to furnish N-cyclopentyl-2,3-dimethoxy-5-(4-nitro-1H-imidazol-1-yl)benzamide (351a) (1.2 g, 66%) as an off-white solid; $^1$H NMR (300 MHz, DMSO-$d_6$): δ 9.05 (s, 1H), 8.50 (d, J=1.5 Hz, 1H), 8.24 (s, 1H), 7.55 (s, 1H), 7.43 (s, 1H), 4.26-4.13 (m, 1H), 3.94 (s, 3H), 3.79 (s, 3H), 2.02-1.83 (m, 2H), 1.77 (m, 3H), 1.43 (m, 3H); MS (ES+): 361.0 (M+1), MS (ES-): 359.3 (M-1).

Step-2: Preparation of 5-(4-amino-1H-imidazol-1-yl)-N-cyclopentyl-2,3-dimethoxybenzamide (351b)

Reduction of nitro to amine of N-cyclopentyl-2,3-dimethoxy-5-(4-nitro-1H-imidazol-1-yl)benzamide (351a) (1.0 g, 2.77 mmol) as reported in step-3 of General scheme for preparation of 3-substituted-(4-amino-1H-imidazol-1-yl) gave 5-(4-amino-1H-imidazol-1-yl)-N-cyclopentyl-2,3-dimethoxybenzamide (351b) (900 mg, 100%) as a brown oily mass; MS (ES+): 331.3 (M+1).

Part 3: Biological Assay Data

Biochemical assays to measure the inhibitory effects of the compounds were performed by ThermoFisher Scientific (Life Technologies). ALK2 inhibition was tested using LanthaScreen™ Eu Kinase Binding Assay screening protocol. Values generated from the enzymatic assay are shown in table below.

TABLE 1

Measured Ki ($IC_{50}$) Value for Compounds. One (+) is used to denote compounds with an $IC_{50}$ value of less than 0.1 micromolar concentration; Two (++) indicate compounds with an $IC_{50}$ value between 0.1 and 1 micromolar concentration; Three (+++) indicate compounds with an $IC_{50}$ value greater than 1 micromolar concentration.

| Compound | $IC_{50}$ |
|---|---|
| 1b | +++ |
| 2a | ++ |
| 3a | +++ |
| 4c | + |
| 4b | +++ |
| 5a | + |
| 6a | ++ |
| 7a | +++ |
| 8c | + |
| 9a | ++ |
| 10a | + |
| 11a | + |
| 12c | + |
| 13a | + |
| 14b | + |
| 15a | + |
| 16b | + |
| 17a | ++ |
| 18a | + |
| 19a | + |
| 20a | ++ |
| 21c | + |
| 22c | + |
| 23c | + |
| 24b | ++ |
| 25c | + |
| 26c | ++ |
| 27a | ++ |
| 28c | ++ |
| 29a | ++ |
| 30a | ++ |
| 31c | + |
| 32a | + |
| 33a | + |
| 34a | +++ |
| 35a | ++ |
| 36c | + |
| 37c | + |
| 38c | + |
| 39c | + |
| 40a | + |
| 41c | + |
| 42b | + |
| 43a | + |
| 44c | + |
| 45d | ++ |
| 46a | ++ |
| 47c | + |
| 48c | + |
| 49c | + |
| 50c | + |
| 51a | ++ |
| 52a | ++ |
| 53b | ++ |
| 54a | + |
| 55c | + |
| 56c | + |
| 57c | + |
| 58b | + |
| 59c | ++ |
| 60b | + |
| 61b | + |
| 62b | ++ |
| 63a | + |
| 64a | + |
| 65c | ++ |

TABLE 1-continued

Measured Ki ($IC_{50}$) Value for Compounds. One (+) is used to denote compounds with an $IC_{50}$ value of less than 0.1 micromolar concentration; Two (++) indicate compounds with an $IC_{50}$ value between 0.1 and 1 micromolar concentration; Three (+++) indicate compounds with an $IC_{50}$ value greater than 1 micromolar concentration.

| Compound | $IC_{50}$ |
|---|---|
| 66c | + |
| 67c | + |
| 68a | + |
| 69a | + |
| 70f | + |
| 71c | + |
| 72c | + |
| 73c | + |
| 74a | +++ |
| 75b | + |
| 76c | + |
| 77d | |
| 78f | + |
| 79d | + |
| 80a | ++ |
| 81c | +++ |
| 82a | + |
| 83c | + |
| 84b | + |
| 85b | + |
| 86b | + |
| 87c | ++ |
| 88a | + |
| 89a | ++ |
| 90a | + |
| 91a | + |
| 92d | ++ |
| 93c | + |
| 94c | + |
| 95c | + |
| 96b | + |
| 97d | + |
| 98a | + |
| 99b | + |
| 100e | |
| 101c | + |
| 102b | + |
| 103b | + |
| 104b | + |
| 105b | + |
| 106b | + |
| 107a | + |
| 108b | + |
| 109a | + |
| 110a | + |
| 111b | + |
| 112b | + |
| 113b | + |
| 114b | + |
| 115b | + |
| 116c | ++ |
| 117a | + |
| 118b | + |
| 119c | + |
| 120a | + |
| 121b | + |
| 122a | + |
| 123c | + |
| 124a | + |
| 125c | + |
| 126c | + |
| 127b | + |
| 128c | + |
| 129b | + |
| 130a | + |
| 131a | + |
| 132b | + |
| 133b | + |
| 134a | + |
| 135a | + |
| 136a | + |
| 137a | + |

TABLE 1-continued

Measured Ki (IC$_{50}$) Value for Compounds. One (+) is used to denote compounds with an IC$_{50}$ value of less than 0.1 micromolar concentration; Two (++) indicate compounds with an IC$_{50}$ value between 0.1 and 1 micromolar concentration; Three (+++) indicate compounds with an IC$_{50}$ value greater than 1 micromolar concentration.

| Compound | IC$_{50}$ |
| --- | --- |
| 138b | + |
| 139b | ++ |
| 140c | + |
| 141c | + |
| 142a | + |
| 141d | + |
| 143h | + |
| 144a | + |
| 145h | + |
| 146a | + |
| 147b | +++ |
| 148b | + |
| 149c | ++ |
| 150c | + |
| 151b | ++ |
| 152a | ++ |
| 153c | + |
| 154a | + |
| 155a | + |
| 156a | + |
| 142b | + |
| 157a | + |
| 158b | + |
| 159b | +++ |
| 160c | +++ |
| 161a | ++ |
| 162a | ++ |
| 163a | ++ |
| 164a | + |
| 165b | + |
| 166b | + |
| 159c | + |
| 160d | + |
| 167f | +++ |
| 168b | ++ |
| 169c | + |
| 170a | + |
| 352c | +++ |
| 171a | + |
| 162b | + |
| 172a | ++ |
| 173b | +++ |
| 174b | + |
| 175b | + |
| 176b | ++ |
| 353a | +++ |
| 177b | + |
| 178b | ++ |
| 173c | + |
| 179b | + |
| 180b | + |
| 181c | + |
| 182c | + |
| 183b | + |
| 184a | + |
| 185a | + |
| 186a | + |
| 187b | + |
| 188a | + |
| 183c | + |
| 189a | + |
| 190a | + |
| 184b | + |
| 185b | + |
| 191b | + |
| 192b | + |
| 191c | + |
| 181d | + |
| 193c | + |
| 182d | + |
| 194c | + |
| 195b | + |
| 196b | + |
| 197a | + |
| 198b | ++ |
| 199b | +++ |
| 200b | + |
| 201b | + |
| 202b | + |
| 203b | ++ |
| 204b | ++ |
| 205b | ++ |
| 206b | + |
| 207b | + |
| 208b | + |
| 209b | + |
| 210a | + |
| 211b | + |
| 212g | + |
| 213b | + |
| 214b | + |
| 215a | + |
| 216a | + |
| 217a | + |
| 218a | + |
| 219a | + |
| 220a | + |
| 221c | + |
| 222b | + |
| 223b | + |
| 224b | + |
| 225b | + |
| 226c | + |
| 227b | ++ |
| 228d | ++ |
| 229d | ++ |
| 230f | +++ |
| 231a | ++ |
| 232b | |
| 233b | ++ |
| 234e | ++ |
| 235a | + |
| 247b | + |
| 236a | + |
| 237a | + |
| 248a | + |
| 238a | + |
| 239a | + |
| 240a | + |
| 241a | + |
| 242a | ++ |
| 243a | ++ |
| 244b | + |
| 245c | + |
| 246a | + |
| 249d | ++ |
| 250d | +++ |
| 251a | + |
| 252a | + |
| 253c | +++ |
| 354b | +++ |
| 254a | + |
| 255a | + |
| 256d | +++ |
| 257d | ++ |
| 258d | +++ |
| 259d | + |
| 260a | + |
| 261a | + |
| 262d | +++ |
| 263d | +++ |
| 264b | + |
| 265a | + |
| 266c | + |

TABLE 1-continued

Measured Ki (IC$_{50}$) Value for Compounds. One (+) is used to denote compounds with an IC$_{50}$ value of less than 0.1 micromolar concentration; Two (++) indicate compounds with an IC$_{50}$ value between 0.1 and 1 micromolar concentration; Three (+++) indicate compounds with an IC$_{50}$ value greater than 1 micromolar concentration.

| Compound | IC$_{50}$ |
| --- | --- |
| 267i | ++ |
| 268b | + |
| 269b | + |
| 270a | + |
| 271c | + |
| 272b | + |
| 273c | + |
| 274c | + |
| 275a | + |
| 269a | + |
| 276b | + |
| 277a | + |
| 350d | + |
| 355a | + |
| 279c | + |
| 280b | + |
| 281b | + |
| 282a | + |
| 348a | + |
| 351d | +++ |
| 283b | + |
| 284c | + |
| 285a | + |
| 286b | + |
| 287a | + |
| 288a | + |
| 289b | + |
| 290a | + |
| 291a | + |
| 292a | + |
| 349a | + |
| 293a | + |
| 294a | + |
| 295b | + |
| 296a | + |
| 297a | + |
| 298a | + |
| 299a | + |
| 300a | + |
| 301b | + |
| 302a | + |
| 303a | + |
| 304a | + |
| 305a | + |
| 306a | + |
| 307c | + |
| 308b | + |
| 309b | + |
| 310b | + |
| 311a | + |
| 312a | + |
| 313a | + |
| 314b | + |
| 315f | + |
| 316a | ++ |
| 317a | + |
| 318a | + |
| 319b | ++ |
| 320b | + |
| 321b | + |
| 322b | + |
| 323b | + |
| 324b | ++ |
| 325e | + |
| 326c | + |
| 327b | + |
| 328c | + |
| 329a | + |
| 330b | + |
| 331b | + |
| 332b | + |
| 333b | + |
| 334a | + |
| 335d | + |
| 278b | + |
| 336c | + |
| 337a | + |
| 338b | + |
| 339e | ++ |
| 340c | ++ |
| 341a | + |
| 342c | + |
| 343b | + |
| 344c | + |
| 345c | + |
| 346c | ++ |
| 347a | + |
| 356b | + |
| 357d | +++ |
| 358a | + |
| 370b | +++ |
| 371a | +++ |
| 369b | ++ |
| 367b | +++ |
| 368a | ++ |
| 372a | + |
| 359c | + |
| 373c | +++ |
| 374a | ++ |
| 359d | + |
| 360c | + |
| 365b | + |
| 361c | + |
| 366c | + |
| 362b | + |
| 375a | + |
| 363b | + |
| 376b | + |
| 364b | + |
| 377b | + |
| 365a | + |
| 378c | + |
| 379a | + |
| 366b | + |
| 380d | + |
| 381b | + |
| 382a | + |
| 383a | + |
| 384b | + |
| 385c | + |
| 386c | + |
| 387a | + |
| 388b | + |
| 389c | + |
| 390b | +++ |
| 391c | + |
| 392a | + |
| 393b | ++ |
| 394b | + |
| 395d | +++ |
| 396a | + |
| 397a | ++ |
| 398c | + |
| 399f | + |
| 400d | ++ |
| 401b | +++ |
| 400c | ++ |
| 401a | +++ |
| 402b | + |
| 402c | + |
| 403h | + |
| 404b | + |
| 405b | + |
| 406b | + |

TABLE 1-continued

Measured Ki (IC$_{50}$) Value for Compounds. One (+) is used to denote compounds with an IC$_{50}$ value of less than 0.1 micromolar concentration; Two (++) indicate compounds with an IC$_{50}$ value between 0.1 and 1 micromolar concentration; Three (+++) indicate compounds with an IC$_{50}$ value greater than 1 micromolar concentration.

| Compound | IC$_{50}$ |
|---|---|
| 407b | + |
| 408b | + |
| 409e | + |
| 410e | + |
| 411d | ++ |
| 411c | ++ |
| 411b | ++ |
| 412a | ++ |
| 413b | ++ |
| 414d | ++ |
| 415d | ++ |
| 416e | + |
| 416f | ++ |
| 417e | +++ |
| 418b | +++ |
| 419b | ++ |
| 420e | +++ |
| 421e | + |
| 422a | + |
| 423e | ++ |
| 424e | + |
| 424f | ++ |
| 425e | + |
| 426c | + |
| 427b | + |
| 428b | + |
| 429a | ++ |
| 430b | + |
| 431e | +++ |
| 432a | ++ |
| 433b | ++ |
| 434e | + |
| 435e | + |
| 436e | + |
| 437e | + |
| 438c | + |
| 439c | + |
| 440c | + |
| 441e | + |
| 442c | + |
| 443e | + |
| 444c | + |
| 445c | + |
| 446c | + |
| 447c | + |
| 448e | + |
| 449d | + |
| 450d | ++ |
| 451d | ++ |
| 452d | ++ |
| 455c | ++ |
| 455d | +++ |
| 453d | + |
| 454c | + |
| 457c | + |
| 456c | + |
| 458c | + |
| 459c | + |
| 460d | + |
| 461c | + |
| 462c | + |
| 463c | + |
| 464d | + |
| 465c | + |
| 466c | + |
| 467c | +++ |
| 468g | +++ |
| 469g | ++ |
| 470e | ++ |
| 472c | + |
| 471e | + |
| 474e | + |
| 475c | +++ |
| 476a | + |

What is claimed is:

1. A compound represented by formula (I) or formula (II):

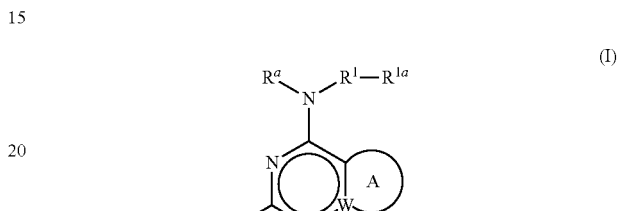

(I)

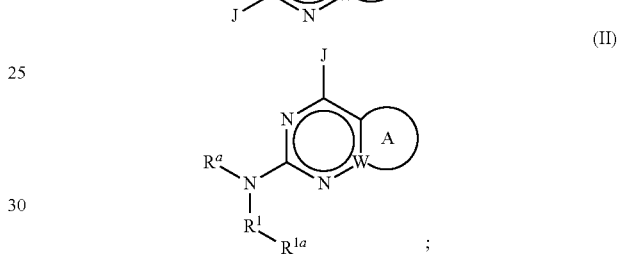

(II)

or a pharmaceutically acceptable salt thereof;
wherein:
A is a fused aromatic ring, heteroaromatic ring, partially unsaturated cycloalkyl ring, or partially unsaturated heterocycloalkyl ring optionally substituted by one or more occurrences of $R^4$;
W is C or N;
$R^a$ represents H or alkyl;
—$R^1$-$R^{1a}$ represents

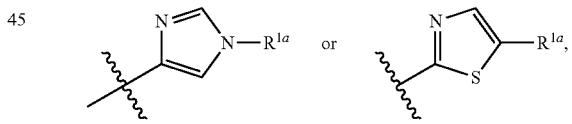

wherein $R^{1a}$ represents optionally substituted heteroaryl;
J represents halo, —$OR^2$, —$NR^2R^3$, —C(O)O(alkyl), —C(O)OH, or aryl, wherein aryl is optionally substituted by one or more occurrences of $R^{2a}$;
$R^2$ represents optionally substituted alkyl, aralkyl, heteroaralkyl, cycloalkyl, heterocycloalkyl, (cycloalkyl)alkyl, (heterocycloalkyl)alkyl, or hydroxyalkyl;
$R^3$ represents H or alkyl; or
$R^2$ and $R^3$, taken together, form a heterocycloalkyl ring, optionally substituted by one or more occurrences of $R^{2a}$;
$R^{2a}$, independently for each occurrence, represents halo, hydroxyl, —C(O)H, oxo, —$NH_2$, —C(O)$NH_2$, —C(O)OH, —C(O)$R^5$, —C(O)O$R^5$, —C(O)NH($R^5$), or optionally substituted alkyl, alkoxyl, hydroxyalkyl, heteroaryl, aryl, aryloxy, heteroaryloxy, arylalkyloxy, heteroarylalkyloxy, or —N(alkyl)$_2$;

or any two geminal or vicinal occurrences of $R^{2a}$, taken together, may form a spiro or fused cycloalkyl ring;

$R^4$, independently for each occurrence, represents halo, cyano, or optionally substituted alkyl, alkenyl, haloalkyl, hydroxyalkyl, aminoalkyl, alkoxy, aryl, aralkyl, heteroaryl, heteroaralkyl, heterocycloalkyl, heterocycloalkenyl, (heterocycloalkyl)alkyl, cycloalkyl, (cycloalkyl)alkyl, halocycloalkyl, hydroxycycloalkyl, aminocycloalkyl, aryloxy, heteroaryloxy, arylalkyloxy, heteroarylalkyloxy, —CH$_2$C(O)NH$_2$, —C(O)R$^5$, —C(O)OR$^5$, or —S(O)$_2$R$^5$;

$R^5$, independently for each occurrence, represents optionally substituted alkyl, aralkyl, aryl, heteroaralkyl, heteroaryl, cycloalkyl, heterocycloalkyl, (cycloalkyl)alkyl, or (heterocycloalkyl)alkyl; and $R^x$ and $R^y$ each independently represent H, alkyl, aralkyl, heteroaralkyl, aryl, heteroaryl, cycloalkyl, heterocycloalkyl, (cycloalkyl)alkyl, (heterocycloalkyl)alkyl, or hydroxyalkyl.

2. The compound of claim 1, wherein the compound is represented by formula (Ia) or formula (IIa):

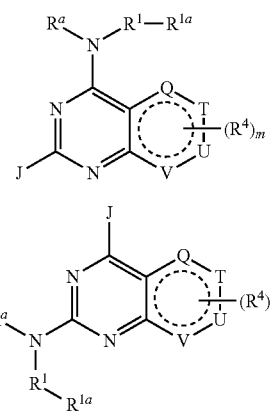

wherein:

valence permitting, Q, T, U, and V each independently represent CH, CH$_2$, N, NH, O, or SO$_2$, wherein any hydrogen of a CH, CH$_2$, or NH group is optionally replaced by an occurrence of $R^4$;

$R^4$, independently for each occurrence, represents halo, cyano, or optionally substituted alkyl, alkenyl, haloalkyl, hydroxyalkyl, aminoalkyl, alkoxy, aryl, aralkyl, heteroaryl, heteroaralkyl, heterocycloalkyl, heterocycloalkenyl, (heterocycloalkyl)alkyl, cycloalkyl, (cycloalkyl)alkyl, halocycloalkyl, hydroxycycloalkyl, aminocycloalkyl, aryloxy, heteroaryloxy, arylalkyloxy, heteroarylalkyloxy, —CH$_2$C(O)NH$_2$, —C(O)R$^5$, —C(O)OR$^5$, or —S(O)$_2$R$^5$; and m is an integer from 0-4, as permitted by valence.

3. The compound of claim 2, wherein the compound is represented by formula (Ib) or (IIb):

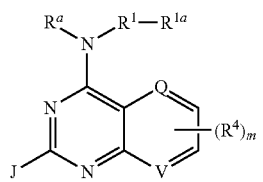

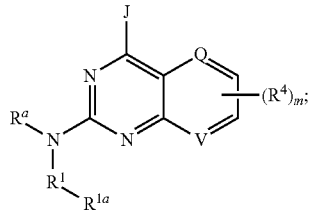

wherein Q represents CH or N; and V represents CH or N.

4. The compound of claim 2, wherein the compound is represented by formula (Ic) or (IIc):

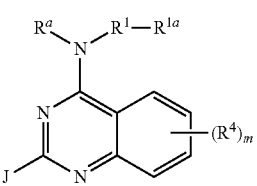

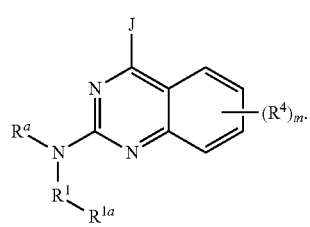

5. The compound of claim 2, wherein the compound is represented by formula (Id) or (IId):

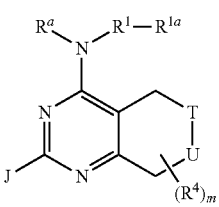

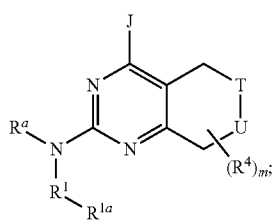

wherein T represents CH$_2$, NH, O, or SO$_2$; and U represents CH$_2$, NH, O, or SO$_2$.

6. The compound of claim 2, wherein the compound is represented by formula (Ie) or (IIe):

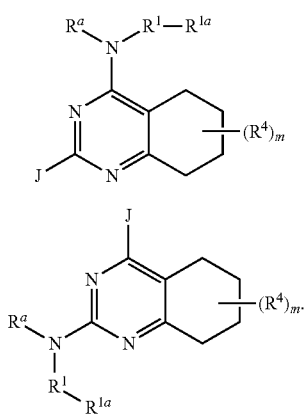

(Ie)

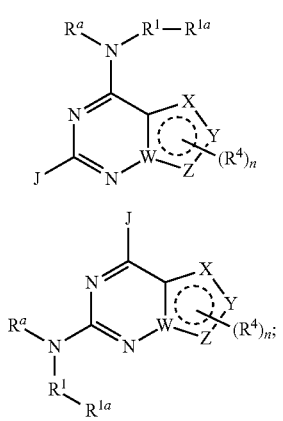

(IIe)

7. The compound of claim 3, wherein the compound is represented by formula (Ib) or (IIb); and wherein Q is N; and V is CH; or wherein Q is CH; and V is N.

8. The compound of claim 5, wherein the compound is represented by formula (Id) or (IId); and wherein T is NH; and U is CH$_2$; or wherein T is CH$_2$; and U is NH.

9. The compound of claim 1, wherein the compound is represented by formula (Ij) or formula (IIj):

(Ij)

(IIj)

wherein:

W is C or N;

valence permitting, X, Y, and Z each independently represent CH, CH$_2$, CO, N, NH, O, S, or SO$_2$, wherein any hydrogen of a CH, CH$_2$, or NH group is optionally replaced by an occurrence of R$^4$;

R$^4$, independently for each occurrence, represents cyano, halo, or optionally substituted alkyl, alkenyl, haloalkyl, hydroxyalkyl, aminoalkyl, alkoxy, aryl, aralkyl, heteroaryl, heteroaralkyl, heterocycloalkyl, heterocycloalkenyl, (heterocycloalkyl)alkyl, cycloalkyl, (cycloalkyl)alkyl, halocycloalkyl, hydroxycycloalkyl, aminocycloalkyl, aryloxy, heteroaryloxy, arylalkyloxy, heteroarylalkyloxy, —CH$_2$C(O)NH$_2$, —C(O)R$^5$, —C(O)OR$^5$, or —S(O)$_2$R$^5$; and n is an integer from 0-4, as permitted by valence.

10. The compound of claim 9, wherein the compound is represented by formula (Ik) or (IIk):

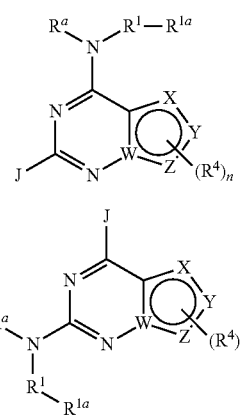

(Ik)

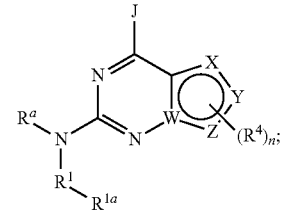

(IIk)

wherein X, Y, and Z each independently represent CH, N, NH, O, S, or SO$_2$.

11. The compound of claim 10, wherein the compound is represented by formula (Ik') or (IIk'):

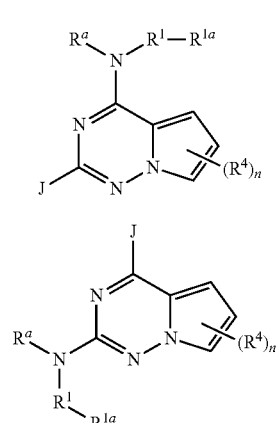

(Ik')

(IIk')

12. The compound of claim 10, wherein the compound is represented by formula (Ik") or (IIk"):

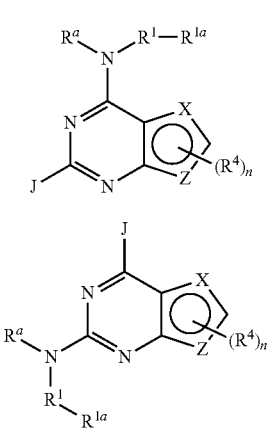

(Ik")

(IIk")

wherein at least one of X and Z is selected from the group consisting of O, N, NH, and S.

13. The compound of claim 12, wherein
(a) one of X and Z is selected from the group consisting of O, NH, and S; and the other of X and Z is CH;
(b) X is selected from the group consisting of O, NH, and S;
(c) Z is selected from the group consisting of O, NH, and S;
(d) each of X and Z are selected from the group consisting of O, N, NH, and S; or
(e) one of X and Z is N and the other of X and Z is NH.

14. The compound of claim 10, wherein the compound is represented by formula (In) or (IIn):

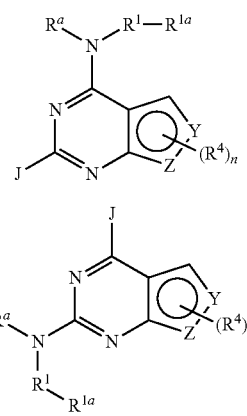

wherein each of Y and Z are selected from the group consisting of O, N, NH, and S.

15. The compound of claim 14, wherein Y is N and Z is NH.

16. The compound of claim 9, wherein the compound is represented by formula (Im) or (IIm):

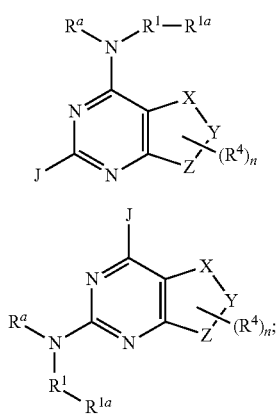

wherein X, Y, and Z each independently represent $CH_2$, CO, NH, O, S, or $SO_2$.

17. The compound of claim 16, wherein
(a) each of X, Y, and Z is $CH_2$; or
(b) one of X, Y, and Z is NH or O.

18. The compound of claim 1, wherein $R^4$, if present, is selected from the group consisting of optionally substituted alkyl, hydroxyalkyl, aminoalkyl, alkoxy, aryl, aralkyl, and (heterocycloalkyl)alkyl.

19. The compound of claim 1, wherein $R^a$ is H.

20. The compound of claim 1, wherein —$R^1$-$R^{1a}$ represents

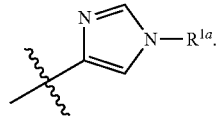

21. The compound of claim 1, wherein $R^{1a}$ is optionally substituted quinoline.

22. The compound of claim 1, wherein J is aryl, optionally substituted by one or more occurrences of $R^{2a}$.

23. The compound of claim 1, wherein J is —$NR^2R^3$.

24. The compound of claim 23, wherein $R^2$ and $R^3$, taken together, form a heterocycloalkyl ring, optionally substituted by one or more occurrences of $R^{2a}$.

25. The compound of claim 24, wherein $R^2$ and $R^3$, taken together, form a pyrrolidine ring, optionally substituted by one or more occurrences of $R^{2a}$.

26. The compound of claim 22, wherein $R^{2a}$, independently for each occurrence, represents —$C(O)NH_2$, —$C(O)R^5$, hydroxyalkyl, heteroaryl, or aryl.

27. The compound of claim 22, wherein $R^{2a}$ is —$C(O)NH_2$.

28. The compound of claim 22, wherein $R^{2a}$ is hydroxyalkyl.

29. The compound of claim 1, selected from the following table:

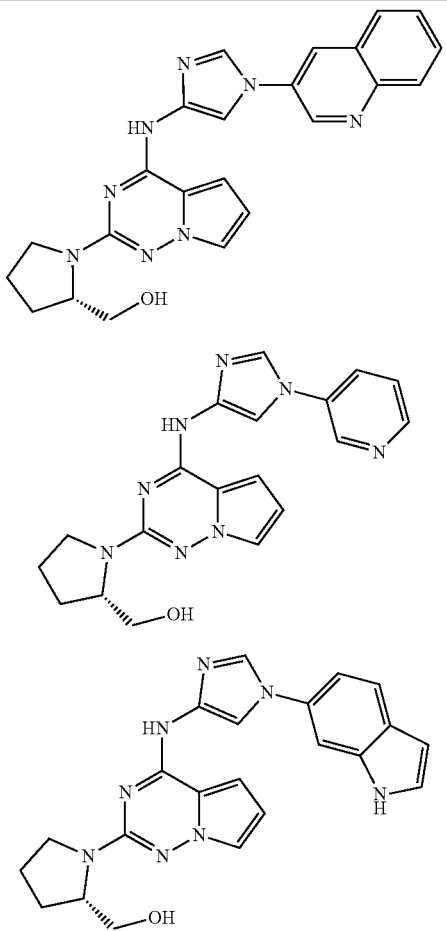

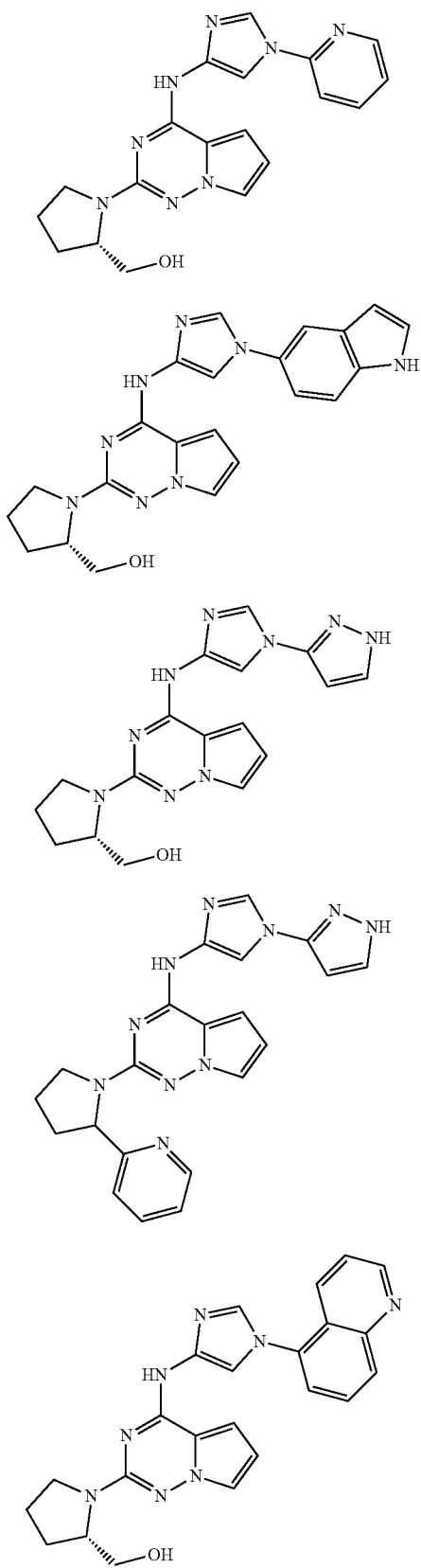
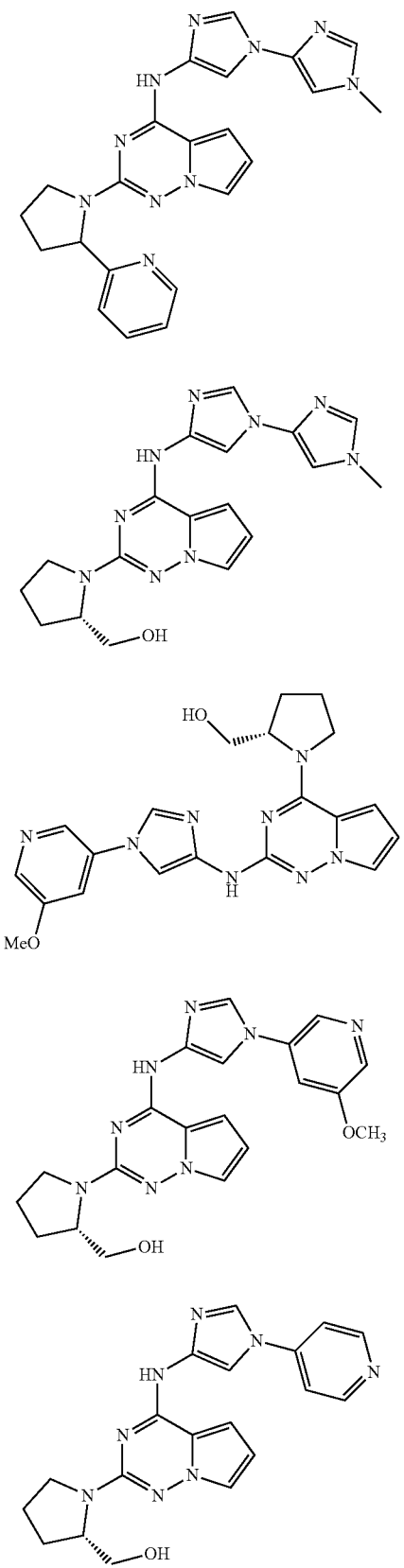

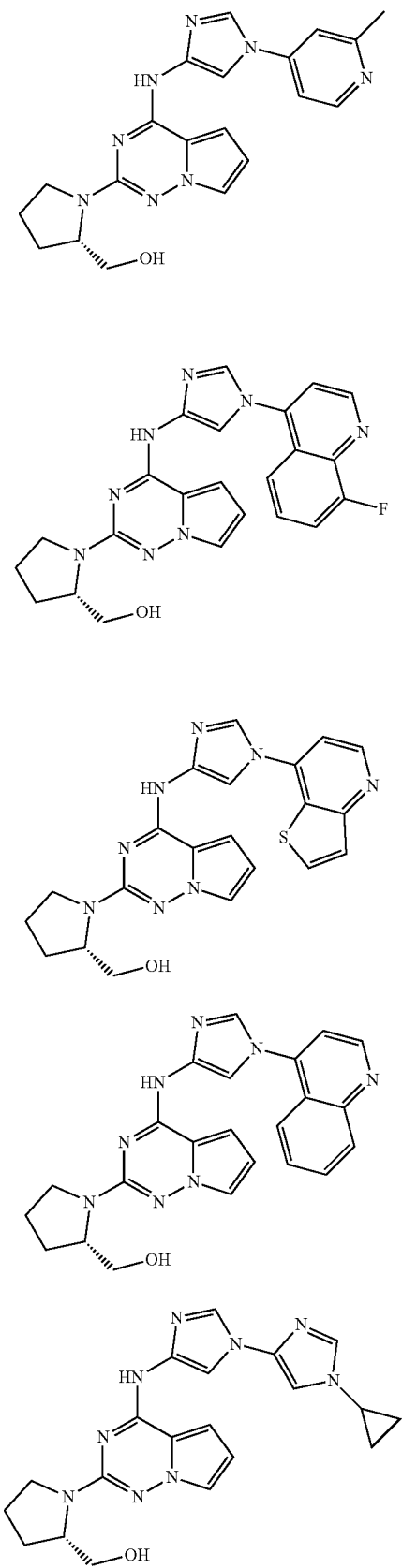

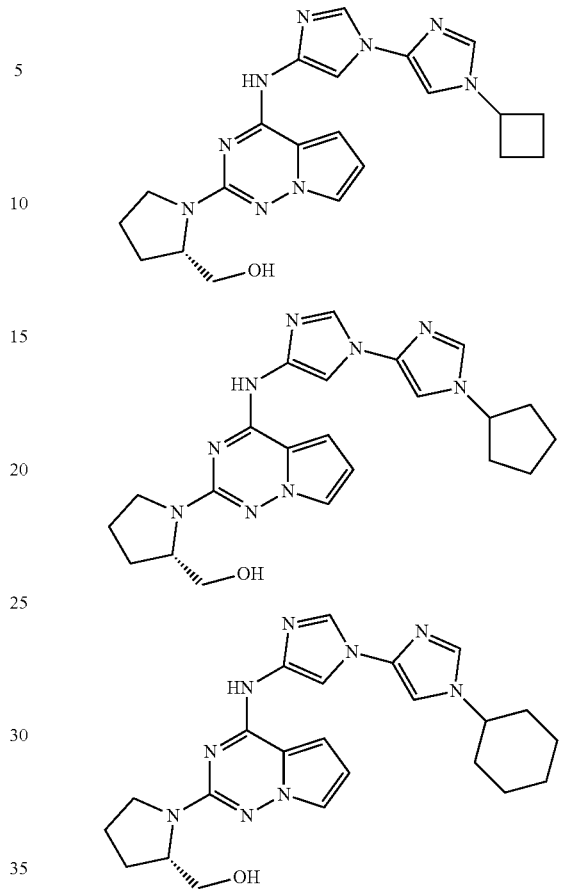

30. A pharmaceutical composition, comprising a compound of claim 1, or a pharmaceutically acceptable salt thereof; and a pharmaceutically acceptable excipient.

31. A method of inhibiting ALK2 kinase, comprising administering to a subject in need thereof an effective amount of a compound of claim 1, or a pharmaceutically acceptable salt thereof.

32. A method of treating fibrodysplasia ossificans progressiva, comprising administering to a subject in need thereof a therapeutically effective amount of a compound of claim 1, or a pharmaceutically acceptable salt thereof.

33. A method of treating a glioma, comprising administering to a subject in need thereof a therapeutically effective amount of a compound of claim 1, or a pharmaceutically acceptable salt thereof.

34. The method of claim 33, wherein the glioma is diffuse intrinsic pontine glioma.

35. The compound of claim 24, wherein $R^{2a}$, independently for each occurrence, represents —C(O)NH$_2$, —C(O)R$^5$, hydroxyalkyl, heteroaryl, or aryl.

36. The compound of claim 25, wherein $R^{2a}$, independently for each occurrence, represents —C(O)NH$_2$, —C(O)R$^5$, hydroxyalkyl, heteroaryl, or aryl.

37. The compound of claim 1, wherein the optional substituents are selected from halogen, haloalkyl, hydroxyl, carbonyl, carboxyl, alkoxycarbonyl, formyl, acyl, thiocarbonyl, thioester, thioacetate, thioformate, alkoxyl, alkenyloxy, alkynyloxy, phosphoryl, phosphate, phosphonate, phosphinate, amino, alkylamino, dialkylamino, amido, amidine, imine, cyano, nitro, azido, sulfhydryl, alkylthio, sulfate, sulfonate, sulfamoyl, sulfonamido, sulfonyl, silyl, silyloxy, heterocycloalkyl, cycloalkyl, alkyl, alkenyl, alkynyl, aryl, heteroaryl, arylalkyl, and heteroarylalkyl.

* * * * *

UNITED STATES PATENT AND TRADEMARK OFFICE
CERTIFICATE OF CORRECTION

PATENT NO. : 12,054,492 B2
APPLICATION NO. : 18/168055
DATED : August 6, 2024
INVENTOR(S) : Pravin L. Kotian et al.

It is certified that error appears in the above-identified patent and that said Letters Patent is hereby corrected as shown below:

In the Claims

In Claim 1, at Column 849, Lines 11-18:
"$R^5$, independently for each occurrence, represents optionally substituted alkyl, aralkyl, aryl, heteroaralkyl, heteroaryl, cycloalkyl, heterocycloalkyl, (cycloalkyl)alkyl, or (heterocycloalkyl)alkyl; and
$R^x$ and $R^y$ each independently represent H, alkyl, aralkyl, heteroaralkyl, aryl, heteroaryl, cycloalkyl, heterocycloalkyl, (cycloalkyl)alkyl, (heterocycloalkyl)alkyl, or hydroxyalkyl."

Should read:
--$R^5$, independently for each occurrence, represents optionally substituted alkyl, aralkyl, aryl, heteroaralkyl, heteroaryl, cycloalkyl, heterocycloalkyl, (cycloalkyl)alkyl, or (heterocycloalkyl)alkyl.--

In Claim 5, at Column 850, Lines 64-65:
"wherein T represents $CH_2$, NH, 0, or $SO_2$; and U represents $CH_2$, NH, 0, or $SO_2$."

Should read:
--wherein T represents $CH_2$, NH, O, or $SO_2$; and U represents $CH_2$, NH, O, or $SO_2$.--

Signed and Sealed this
Thirty-first Day of December, 2024

Derrick Brent
*Acting Director of the United States Patent and Trademark Office*